US012570675B2

(12) United States Patent
Jung et al.

(10) Patent No.: US 12,570,675 B2
(45) Date of Patent: Mar. 10, 2026

(54) BORONIC ACID COMPOUNDS

(71) Applicant: LG CHEM, LTD., Seoul (KR)

(72) Inventors: Cheol Kyu Jung, Daejeon (KR); Seung Wan Kang, Daejeon (KR); Byung Gyu Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 469 days.

(21) Appl. No.: 18/256,831

(22) PCT Filed: Dec. 10, 2021

(86) PCT No.: PCT/IB2021/061585
§ 371 (c)(1),
(2) Date: Jun. 9, 2023

(87) PCT Pub. No.: WO2022/123530
PCT Pub. Date: Jun. 16, 2022

(65) Prior Publication Data

US 2024/0101579 A1 Mar. 28, 2024

(30) Foreign Application Priority Data

Dec. 10, 2020 (KR) ........................ 10-2020-0171958

(51) Int. Cl.
*C07F 5/02* (2006.01)
*A61K 31/69* (2006.01)
*A61P 35/00* (2006.01)

(52) U.S. Cl.
CPC .............. *C07F 5/025* (2013.01); *A61K 31/69* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,780,454 A | 7/1998 | Adams et al. |
| 6,066,730 A | 5/2000 | Adams et al. |
| 6,083,903 A | 7/2000 | Adams et al. |
| 2002/0173488 A1 | 11/2002 | Adams et al. |
| 2003/0199561 A1 | 10/2003 | Adams et al. |
| 2004/0167332 A1 | 8/2004 | Adams et al. |
| 2006/0084691 A1 | 4/2006 | Piperdi |
| 2006/0122390 A1 | 6/2006 | Adams et al. |
| 2007/0282100 A1 | 12/2007 | Adams et al. |
| 2008/0132678 A1 | 6/2008 | Adams et al. |
| 2009/0099132 A1 | 4/2009 | Olhava et al. |
| 2009/0247731 A1 | 10/2009 | Adams et al. |
| 2011/0306560 A1 | 12/2011 | Adams et al. |
| 2013/0310320 A1 | 11/2013 | Adams et al. |
| 2015/0072942 A1 | 3/2015 | Adams et al. |
| 2018/0243442 A1 | 8/2018 | Lam et al. |

FOREIGN PATENT DOCUMENTS

| | | | |
|---|---|---|---|
| CN | 1168633 A | 12/1997 |
| CN | 106008572 A | 10/2016 |
| CN | 107151255 A | 9/2017 |
| JP | H10-510245 A | 10/1998 |
| JP | 2003-509502 A | 3/2003 |
| KR | 10-2007-0083719 A | 8/2007 |
| KR | 10-1471274 B1 | 12/2014 |
| WO | 96-13266 A1 | 5/1996 |
| WO | 2017031084 A1 | 2/2017 |
| WO | 2020-020858 A1 | 1/2020 |

OTHER PUBLICATIONS

International Search Report issued for International Application No. PCT/IB2021/061585 Mar. 18, 2022, 9 pages.
Ladi et al., Design and Evaluation of Highly-Selective Human Immunoproteasome Inhibitors Revels a Compensatory Process that Preserves Immune Cell Viability, Journal of Medical Chemistry, 2019, vol. 62, No. 15, pp. 7032-7041.
Database Caplus [Online], Jan. 1, 2017, University of California et al., "Nanoparticles comprising poly (vinylalcohol) for use in tumor detection and photodynamic and photothermal therapy—WO 2017031084A1," XP093146316, 2 pages.
Extended European search report issued on Apr. 8, 2024 for the European Patent Application No. 21902856.0, 7 pages.

*Primary Examiner* — Juliet C Switzer
*Assistant Examiner* — Dawanna Shar-Day White
(74) *Attorney, Agent, or Firm* — ROTHWELL, FIGG, ERNST & MANBECK, P.C.

(57) ABSTRACT

The present invention relates to a compound represented by Formula 1, a pharmaceutically acceptable salt thereof, or an isomer thereof, and a pharmaceutical composition for treating or preventing proteasome-mediated diseases, comprising the same as an active ingredient.

18 Claims, No Drawings

BOROINC ACID COMPOUNDS

TECHNICAL FIELD

This application is a 35 U.S.C. 371 National Phase Entry Application from PCT/IB2021/061585 filed on Dec. 10, 2021, which claims the benefit of priority based on Korean Patent Application No. 10-2020-0171958, filed on Dec. 10, 2020, the entire disclosures of which are incorporated as part of the specification in their entirety.

The present invention relates to boronic acid compounds.

BACKGROUND ART

Proteasomes are a part of the intracellular machinery and degrade damaged or unnecessary proteins through the ubiquitin-proteasome pathway, thereby playing a significant role in cell function and growth. Proteasome inhibitors inhibit proteasomes so as to induce the excessive accumulation of abnormal proteins in cancer cells and induce the apoptosis of cancer cells.

Cancer cells are more sensitively affected by proteasome inhibitors than normal cells. Thus, by inhibiting the hydrolytic activity of the proteasomes, anticancer effects may be expected. In particular, the proteasome inhibitor selectively binds to and inhibits the chymotrypsin-like activity over the caspase-like activity within the proteasome to reduce side effects and effectively treat cancer.

The anticancer effects of this proteasome inhibitor were confirmed on hematologic malignancy, and Velcade has been marketed as a drug utilizing the proteasome inhibitor. However, side effects, such as drug resistance, have also been reported. Accordingly, research on a combined treatment method with this drug and an epidermal growth factor receptor (EGFR) kinase inhibitor (Korean Laid-open Patent No. 10-2007-0083719), a marker composition for diagnosing resistance to this drug (Korean Registration Patent No. 10-1471274), or the like, has been continuously performed. However, there are still needs to develop alternative substances with fewer side effects.

As a proteasome inhibitor drug, Carfilzomib selectively binds to the chymotrypsin-like activity over the caspase-like activity within the proteasome, but due to its irreversible binding, has a limitation in terms of utility.

Accordingly, the present inventors have continued research on a compound that selectively and reversibly binds to and inhibits the chymotrypsin-like activity, confirmed that a novel boronic acid compound selectively and reversibly binds to the chymotrypsin-like activity, and completed the present invention.

PRIOR ART DOCUMENTS

Patent Documents (Patent Document 1) Korean Laid-open Patent No. 10-2007-0083719 (Aug. 24, 2007)

(Patent Document 2) Korean Registration Patent No. 10-1471274 (Dec. 3, 2014)

DISCLOSURE OF THE INVENTION

Technical Problem

An object of the present invention is to provide a compound which may selectively and reversibly bind to and inhibit the chymotrypsin-like activity within the proteasome.

Technical Solution

An aspect of the present invention provides a compound represented by the following Formula 1, a pharmaceutically acceptable salt thereof, or an isomer thereof:

[Formula 1]

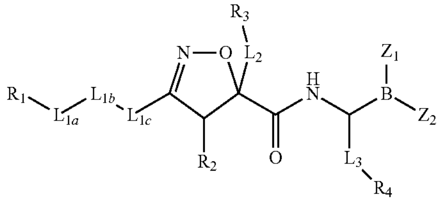

in the above formula, $R_1$ represents alkyl, cycloalkyl, aryl, heteroaryl, heterocycloalkyl, or a fused-bicyclo ring;

$R_2$ represents hydrogen or alkyl;

$R_3$ represents hydrogen, alkyl, cycloalkyl, aryl, or heteroaryl, or $R_2$ and $R_3$ may be combined with each other to form a 3- to 6-membered aliphatic ring, where $L_2$ is absent;

$R_4$ represents alkyl, cycloalkyl, or aryl;

$L_{1a}$ represents $(CH_2)_l$ (where l is an integer of 0 to 3) or $C(CH_2CH_2)$;

$L_{1b}$ is a direct linkage, or represents (C=O)NH, NH(C=O), NH, $(CH_2)_mO$ (where m is an integer of 0 to 3), $(C{=}O)N(CH_3)$, or $S(O_2)NH$;

$L_{1c}$ represents $(CH_2)_n$ (where n is an integer of 0 to 3), $CHR_5$, or $CR_6R_7$, where $R_5$, $R_6$, and $R_7$ are each independently C1-C4 heteroalkyl having 1 to 3 heteroatoms selected from the group consisting of O, N, and S, or C1-C4 alkyl;

$L_2$ represents $(CH_2)_o$ (where o is an integer of 0 to 3), $(CH_2)_pO$ (where p is an integer of 1 to 3), $CHR_8$, $CX_1X_2$, or $C(CH_2CH_2)$, where $R_8$ is OH, halogen, or C1-C3 alkyl, and $X_1$ and $X_2$ are each independently halogen;

$L_3$ represents $(CH_2)_q$ (where q is an integer of 0 to 3) or $CHR_9$, where $R_9$ is C1-C3 alkyl; and $Z_1$ and $Z_2$ are each independently OH or $OR_{10}$, $R_{10}$ represents alkyl, cycloalkyl, aryl, heteroaryl, or heterocycloalkyl, or in the case where $Z_1$ and $Z_2$ are $OR_{10}$, the two $R_{10}$ together may form a C2-C20 cyclic boric acid ester having a saturated, unsaturated, or optionally fused-bicyclo ring, where the cyclic boric acid ester may be substituted with hydroxyl, substituted or unsubstituted alkyl, cycloalkyl, alkoxy, aryl, aryloxy, or heteroaryl or heterocycloalkyl containing in the ring 1 or 2 heteroatoms selected from N, O, and S atoms.

Another aspect of the present invention provides a pharmaceutical composition for inhibiting the chymotrypsin-like activity within the proteasome, the composition comprising: the compound of Formula 1, the pharmaceutically acceptable salt thereof, or the isomer thereof, and a pharmaceutically acceptable carrier.

Advantageous Effects

The boronic acid compound of the present invention may selectively and reversibly bind to and inhibit chymotrypsin-like activity over the caspase-like activity within the proteasome.

Since the boronic acid compound of the present invention has excellent selectivity for proteasome activity in cancer cells being targeted, serious side effects may be minimized. In addition, since the boronic acid compound of the present invention binds reversibly, it is detached thereafter, and the proteasome function can be restored. In this regard, there are advantages in high development potential and utilization.

MODE FOR CARRYING OUT THE INVENTION

Hereinafter, the present invention will be described in more detail to help an understanding of the present invention. The terms or words used in the description and claims shall not be interpreted as being limited to ordinary or dictionary meanings and the terms or words should be interpreted as meanings and concepts consistent with the technical idea of the present invention, based on the principle that an inventor may properly define the concept of a term to explain his own invention in the best way.

In the definition of substituents of the compound of Formula 1 according to the present invention, the term “alkyl” means an aliphatic hydrocarbon radical. The alkyl may be “saturated alkyl” not including an alkenyl or alkynyl moiety, or “unsaturated alkyl” including at least one alkenyl or alkynyl moiety. “Alkenyl” means a group including at least one carbon-carbon double bond, and “alkynyl” means a group including at least one carbon-carbon triple bond. The alkyl may be a branch type or a linear type.

The alkyl may have 1 to 20 carbon atoms unless otherwise defined. The alkyl may be an alkyl having a medium size having 1 to 10 carbon atoms. The alkyl may be lower alkyl having 1 to 6 carbon atoms. Typical alkyl includes methyl, ethyl, propyl, isopropyl, butyl, isobutyl, t-butyl, pentyl, hexyl, ethenyl, propenyl, butenyl, or the like, but is not limited thereto. For example, C1-C4 alkyl has 1 to 4 carbon atoms in an alkyl chain and is selected from the group consisting of methyl, ethyl, propyl, iso-propyl, n-butyl, iso-butyl, sec-butyl and t-butyl.

The term “alkoxy” means alkyloxy having 1 to 10 carbon atoms, unless otherwise defined.

The term “cycloalkyl” means a saturated aliphatic 3- to 10-membered ring, unless otherwise defined. Typical cycloalkyl group includes cyclopropyl, cyclobutyl, cyclopentyl, cyclohexyl, or the like, but is not limited thereto.

The term “aryl” includes at least one ring having a covalent pi electron system and includes, for example, a monocyclic or fused-ring polycyclic (that is, rings sharing neighboring pairs of carbon atoms) group. That is, the aryl means 4- to 10-membered, preferably, 6- to 10-membered aromatic monocyclic or multicyclic ring including phenyl, naphthyl, or the like, unless otherwise defined.

The term “heteroaryl” means, unless otherwise defined, an aromatic 3- to 10-membered ring, preferably, 4- to 8-membered ring, more preferably, 5- to 6-membered ring which includes 1 to 3 heteroatoms selected from the group consisting of N, O and S, and is capable of being fused with benzo or C3-C8 cycloalkyl. Examples of monocyclic heteroaryl include thiazole, oxazole, thiophene, furan, pyrrole, imidazole, isoxazole, isothiazole, pyrazole, triazole, triazine, thiadiazole, tetrazole, oxadiazole, pyridine, pyridazine, pyrimidine, pyrazine and similar groups therewith, without limitation. Examples of bicyclic heteroaryl include indole, indoline, benzothiophene, benzofuran, benzimidazole, benzoxazole, benzisoxazole, benzthiazole, benzthiadiazole, benztriazole, quinoline, isoquionline, purine, puropyridine and similar groups therewith, without limitation.

The term “heterocycloalkyl” means, unless otherwise defined, 3- to 10-membered ring, preferably, 4- to 8-membered ring, more preferably, 5- to 6-membered ring which includes 1 to 3 heteroatoms selected from the group consisting of N, O and S, is capable of being fused with benzo or C3-C8 cycloalkyl, and is saturated or includes 1 or 2 double bonds. Examples of the heterocycloalkyl include pyrroline, pyrrolidine, imidazoline, imidazolidine, pyrazoline, pyrazolidine, pyrane, piperidine, morpholine, thiomorpholine, piperazine, hydrofuran or the like, without limitation.

The term “fused-bicyclo ring” means a cyclo ring in which two rings are fused, and includes a bridged bicyclo ring, a fused bicyclo ring, and a spirocyclo ring. The fused-bicyclo ring may also be used as the meaning including all of fused-bicycloalkyl, fused-bicycloaryl, and fused-bicycloheteroaryl, where for alkyl, aryl, and heteroaryl, the contents defined above may be applied. Specifically, the fused-bicyclo ring may be one in which a substituted or unsubstituted 4- to 8-membered aliphatic ring or 5- to 6-membered aromatic ring having 0 to 4 heteroatoms selected from the group consisting of O, N, and S, is fused to a substituted or unsubstituted 4- to 8-membered aliphatic ring or 5- to 6-membered aromatic ring having 0 to 4 heteroatoms selected from the group consisting of O, N, and S.

The term “direct linkage” means a case where a functional group such as hydrocarbon, does not exist in a corresponding substituent and may represent $-(CH_2)_k-$, where k may be 0.

The term “halogen” means one or more selected from the group consisting of F, Cl, Br, and I.

In the present invention, a wave “ ∫ ” or a small corner bracket “ ⌟ ” is used to indicate a bond in which the stereochemical relationship between substituents bonded to carbon or nitrogen forming a double bond, includes both E- and Z-isomers. Specifically,

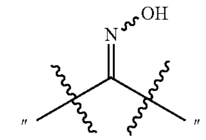 [SMILES: *C(*)=NO]

may mean that the bond between nitrogen, which forms a double bond with carbon, and an OH group includes both E- and Z-isomers.

Other terms and abbreviations used herein may be interpreted as meanings commonly understood by a person skilled in the art to which the present invention pertains unless otherwise defined.

An aspect of the present invention provides a compound represented by the following Formula 1, a pharmaceutically acceptable salt thereof, or an isomer thereof:

[Formula 1]

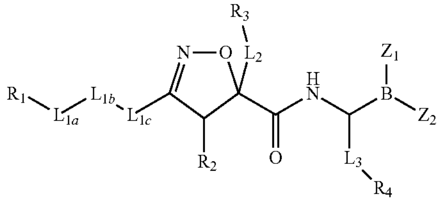

in the above formula, $R_1$ represents alkyl, cycloalkyl, aryl, heteroaryl, heterocycloalkyl, or a fused-bicyclo ring;

$R_2$ represents hydrogen or alkyl;

$R_3$ represents hydrogen, alkyl, cycloalkyl, aryl, or heteroaryl, or $R_2$ and $R_3$ may be combined with each other to form a 3- to 6-membered aliphatic ring, where $L_2$ is absent;

$R_4$ represents alkyl, cycloalkyl, or aryl;

$L_{1a}$ represents $(CH_2)_l$ (where l is an integer of 0 to 3) or $C(CH_2CH_2)$;

$L_{1b}$ is a direct linkage, or represents (C═O)NH, NH(C═O), NH, $(CH_2)_mO$ (where m is an integer of 0 to 3), $(C{=}O)N(CH_3)$, or $S(O_2)NH$;

$L_{1c}$ represents $(CH_2)_n$ (where n is an integer of 0 to 3), $CHR_5$, or $CR_6R_7$, where $R_5$, $R_6$, and $R_7$ are each independently C1-C4 heteroalkyl having 1 to 3 heteroatoms selected from the group consisting of 0, N, and S, or C1-C4 alkyl;

$L_2$ represents $(CH_2)_o$ (where o is an integer of 0 to 3), $(CH_2)_pO$ (where p is an integer of 1 to 3), $CHR_8$, $CX_1X_2$, or $C(CH_2CH_2)$, where $R_8$ is OH, halogen, or C1-C3 alkyl, and $X_1$ and $X_2$ are each independently halogen;

$L_3$ represents $(CH_2)_q$ (where q is an integer of 0 to 3) or $CHR_9$, where $R_9$ is C1-C3 alkyl; and $Z_1$ and $Z_2$ are each independently OH or $OR_{10}$, $R_{10}$ represents alkyl, cycloalkyl, aryl, heteroaryl, or heterocycloalkyl, or in the case where $Z_1$ and $Z_2$ are $OR_{10}$, the two $R_{10}$ together may form a C2-C20 cyclic boric acid ester having a saturated, unsaturated, or optionally fused-bicyclo ring, where the cyclic boric acid ester may be substituted with hydroxyl, substituted or unsubstituted alkyl, cycloalkyl, alkoxy, aryl, aryloxy, or heteroaryl or heterocycloalkyl containing in the ring 1 or 2 heteroatoms selected from N, O, and S atoms.

In an embodiment, $R_1$ represents C1-C6 alkyl, C3-C6 cycloalkyl, phenyl, 5- to 6-membered heteroaryl or heterocycloalkyl containing 1 or 2 heteroatoms selected from N, O, and S atoms, fused-bicycloalkyl, fused-bicycloaryl, or fused-bicycloheteroaryl containing 1 to 4 heteroatoms selected from N, O, and S atoms;

$R_2$ represents hydrogen or C1-C6 alkyl;

$R_3$ represents hydrogen, C1-C6 alkyl, C3-C6 cycloalkyl, phenyl, or 5- to 6-membered heteroaryl containing 1 or 2 heteroatoms selected from N, O, and S atoms, or $R_2$ and $R_3$ may be combined with each other to form a 3- to 6-membered aliphatic ring, where $L_2$ is absent;

$R_4$ represents C1-C6 alkyl, C3-C6 cycloalkyl, or phenyl;

$L_{1a}$ represents $(CH_2)_l$ (where l is an integer of 0 to 3) or $C(CH_2CH_2)$;

$L_{1b}$ is a direct linkage, or represents (C═O)NH, NH(C═O), NH, $(CH_2)_mO$ (where m is an integer of 0 to 3), $(C{=}O)N(CH_3)$, or $S(O_2)NH$;

$L_{1c}$ represents $(CH_2)_n$ (where n is an integer of 0 to 3), $CHR_5$, or $CR_6R_7$, where $R_5$ represents C1-C4 heteroalkyl having 1 to 3 heteroatoms selected from the group consisting of O, N, and S, or C1-C4 alkyl, and $R_6$ and $R_7$ are each independently C1-C4 alkyl;

$L_2$ represents $(CH_2)_o$ (where o is an integer of 0 to 3), $(CH_2)_pO$ (where p is an integer of 1 to 3), $CHR_5$, $CX_1X_2$, or $C(CH_2CH_2)$, where $R_8$ is OH, halogen, or C1-C3 alkyl, and $X_1$ and $X_2$ are each independently halogen;

$L_3$ represents $(CH_2)_q$ (where q is an integer of 0 to 3) or $CHR_9$, where $R_9$ is C1-C3 alkyl; and $Z_1$ and $Z_2$ are each independently OH, or together may form a cyclic boric acid ester of the following structure:

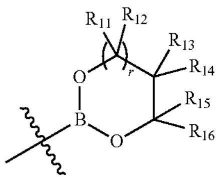

wherein r is 0 or 1, and $R_{11}$ to $R_{16}$ are each independently hydrogen, hydroxyl, substituted or unsubstituted alkyl, cycloalkyl, alkoxy, aryl, aryloxy, or heteroaryl or heterocycloalkyl, containing in the ring 1 or 2 heteroatoms selected from N, O, and S atoms, or $R_{13}$ and $R_{15}$ may be hydrogen, and $R_{14}$ and $R_{16}$ may be combined together to form substituted or unsubstituted cycloalkyl, or $R_{13}$ and $R_{15}$ may be absent, and $R_{14}$ and $R_{16}$ may be combined together to form substituted or unsubstituted aryl, or $R^{11}$ and $R^{12}$, or $R_{13}$ and $R_{14}$, or $R_{15}$ and $R_{16}$ may be combined together to form substituted or unsubstituted cycloalkyl.

In an embodiment, $R_1$ may represent phenyl, 5- to 6-membered heteroaryl containing 1 or 2 heteroatoms selected from N, O, and S atoms, fused-bicycloaryl, or fused-bicycloheteroaryl, $R_1$ may be substituted with one or more substituents selected from the group consisting of halogen, amine, nitro, nitrile, acetonitrile, ether, halogenated alkyl, C1-C6 alkyl, C3-C6 cycloalkyl, C1-C6 heteroalkyl having 1 or 2 heteroatoms selected from N, O, and S atoms, C1-C6 alkoxy, phenyl, phenoxy, 5- to 6-membered heteroaryl or heterocycloalkyl, containing 1 or 2 heteroatoms selected from N, O, and S atoms, or 5- to 6-membered heteroaryloxy or heterocycloalkyloxy, containing 1 or 2 heteroatoms selected from N, O, and S atoms, and $R_{12}(C{=}O)NH$, $R_{12}$ is hydrogen or C1-C3 alkyl, and the substituent may be substituted with one or more selected from the group consisting of halogen, C1-C3 alkyl, and C1-C3 alkoxy.

In an embodiment, $R_2$ may represent hydrogen.

In an embodiment, $R_3$ may represents hydrogen, C1-C3 alkyl, or phenyl, $R_3$ may be substituted with halogen, methyl halide, C1-C6 alkyl, C3-C6 cycloalkyl, phenyl, or C1-C3 alkoxy, and the substituent may be additionally substituted with halogen.

In an embodiment, $R_4$ may represent C1-C6 alkyl, C3-C6 cycloalkyl, or phenyl.

In an embodiment, $L_{1a}$ may represent $(CH_2)_l$ (where l is an integer of 0 to 3) or $C(CH_2CH_2)$.

In an embodiment, $L_{1b}$ may be a direct linkage, or represent (C═O)NH, NH(C═O), NH, $(CH_2)_mO$ (where m is an integer of 0 to 3), $(C{=}O)N(CH_3)$, or $S(O_2)NH$.

In an embodiment, $L_{1c}$ represents $(CH_2)_n$ (where n is an integer of 0 to 3), $CHR_5$, or $CR_6R_7$, where $R_5$ may be C1-C3 heteroalkyl having 1 or 2 heteroatoms selected from the group consisting of O, N, and S, or C1-C4 alkyl, and $R_6$ and $R_7$ may be each independently C1-C3 alkyl.

In an embodiment, $L_2$ represents $(CH_2)_o$ (where o is an integer of 0 to 3), $(CH_2)_pO$ (where p is an integer of 1 to 3), $CHR_5$, $CX_1X_2$, or $C(CH_2CH_2)$, where $R_8$ may be OH, halogen, or C1-C3 alkyl, and $X_1$ and $X_2$ may be each independently halogen.

In an embodiment, $L_3$ represents $(CH_2)_q$ (where q is an integer of 0 to 3) or $CHR_9$, where $R_9$ may be C1-C3 alkyl.

In an embodiment, $Z_1$ and $Z_2$ may be each independently OH, or together may form a cyclic boric acid ester of the following structure:

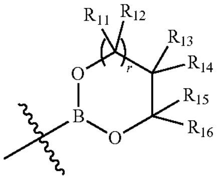

wherein r is 0 or 1, $R_{11}$ to $R_{16}$ are each independently hydrogen, hydroxyl, substituted or unsubstituted C1-C6 alkyl, C3-C6 cycloalkyl, C1-C6 alkoxy, C5-C6 aryl, C5-C6 aryloxy, heteroaryl or heterocycloalkyl containing in the ring 1 or 2 heteroatoms selected from N, O, and S atoms, where the substituent may be hydroxyl, C1-C6 alkyl, C3-C6 cycloalkyl, C1-C6 alkoxy, C5-C6 aryl, or C5-C6 aryloxy, or $R_{13}$ and $R_{15}$ may be hydrogen, and $R_{14}$ and $R_{16}$ may be combined together to form substituted or unsubstituted 4- to 8-membered cycloalkyl, where the substituent may be hydroxyl, substituted or unsubstituted C1-C6 alkyl, C3-C6 cycloalkyl, C1-C6 alkoxy, C5-C6 aryl, or C5-C6 aryloxy, or $R_{13}$ and $R_{15}$ may be absent, and $R_{14}$ and $R_{16}$ may be combined together to form substituted or unsubstituted 5- to 6-membered aryl, where the substituent may be hydroxyl, substituted or unsubstituted C1-C6 alkyl, C3-C6 cycloalkyl, C1-C6 alkoxy, C5-C6 aryl, or C5-C6 aryloxy, or $R_{11}$ and $R^{12}$, or $R_{13}$ and $R_{14}$, or $R_{15}$ and $R_{16}$ may be combined together to form substituted or unsubstituted 4- to 8-membered cycloalkyl, where the substituent may be hydroxyl, substituted or unsubstituted C1-C6 alkyl, C3-C6 cycloalkyl, C1-C6 alkoxy, C5-C6 aryl, or C5-C6 aryloxy.

In a preferred embodiment, $R_1$ may be selected from the group consisting of the following:

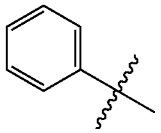
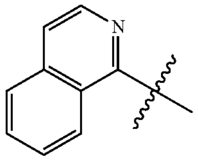
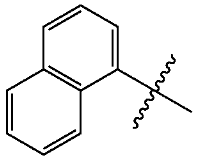
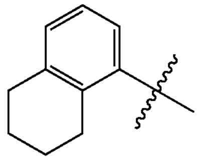
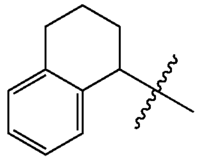
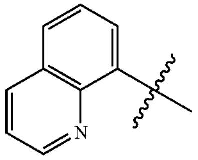
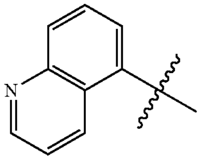

-continued

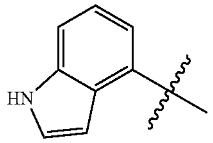
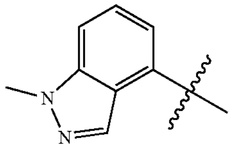
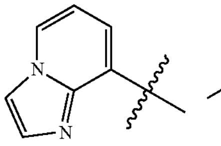
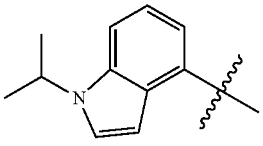
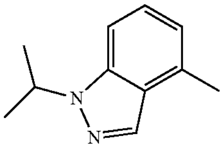
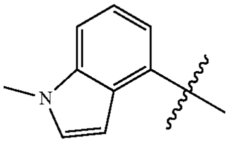
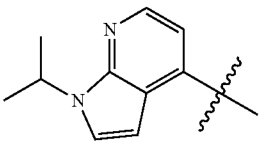
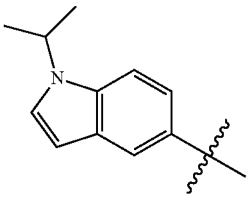
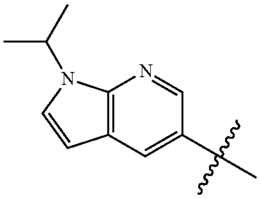
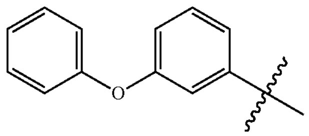
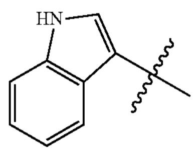
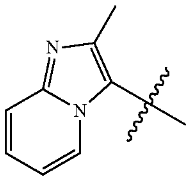
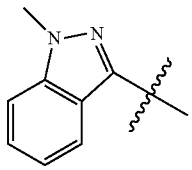
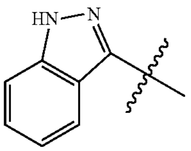
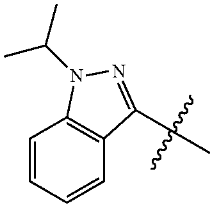
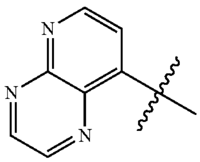
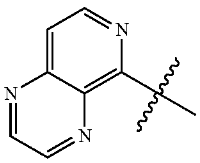
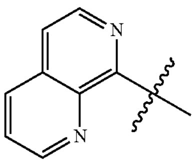
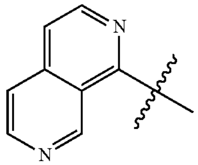
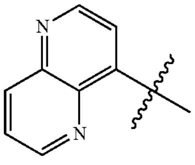

-continued
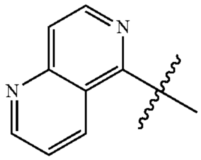
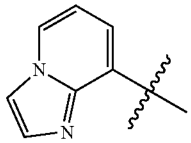
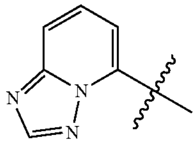
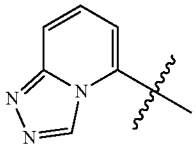
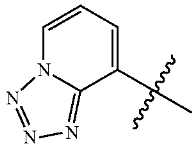
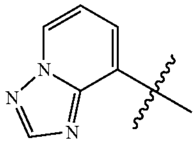
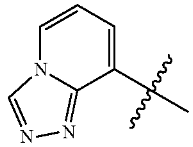
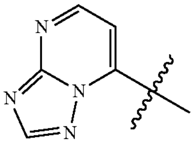
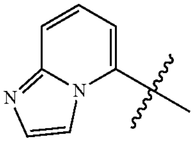
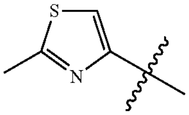
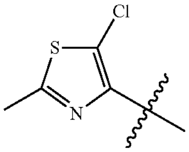
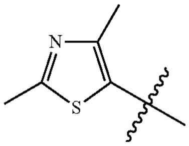
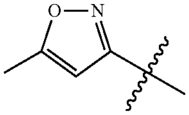
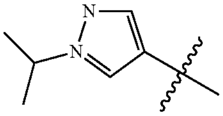
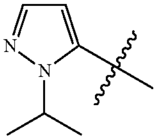
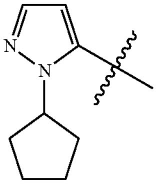
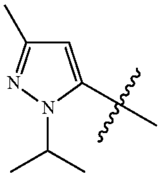
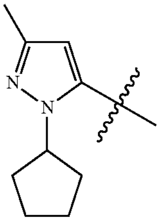
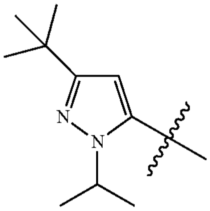
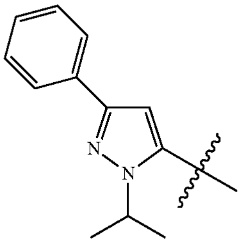
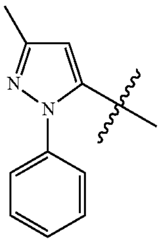
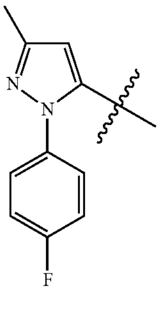
-continued
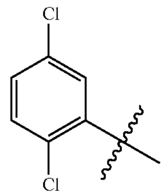
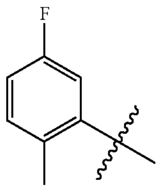
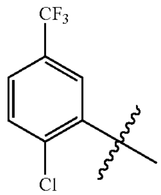
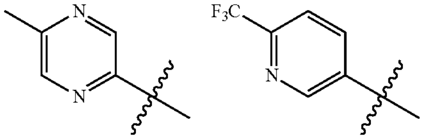
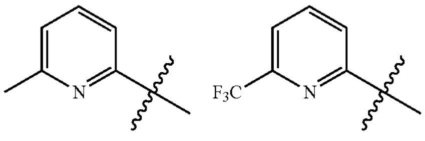
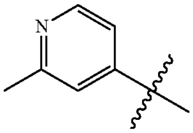
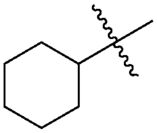
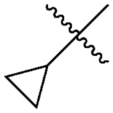
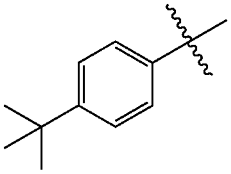
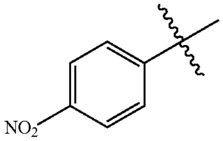
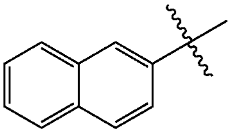
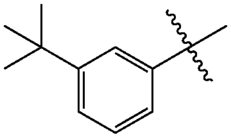
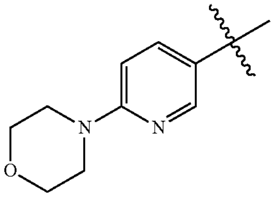
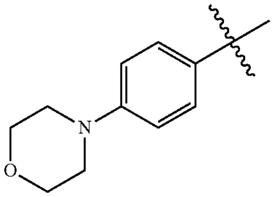
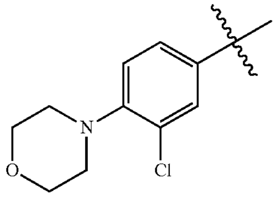
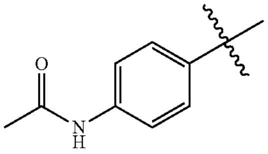
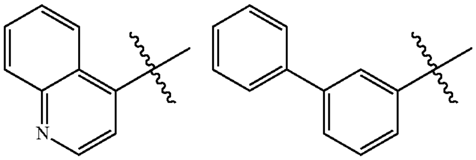
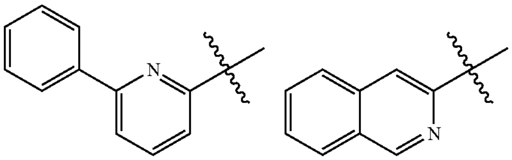

-continued
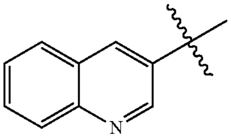
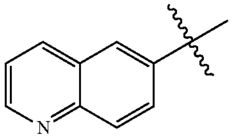
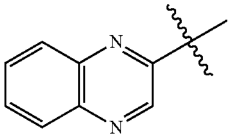
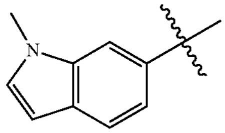
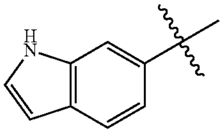
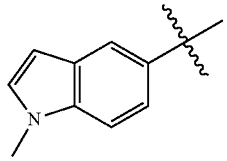
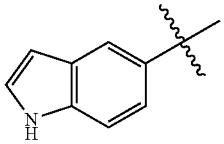
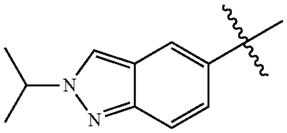
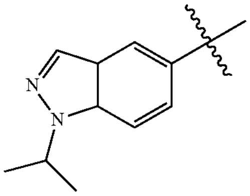
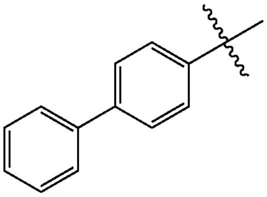
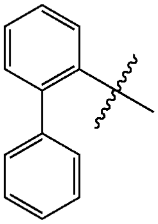
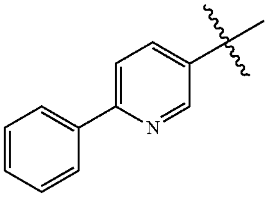
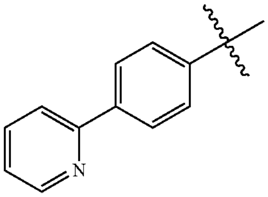
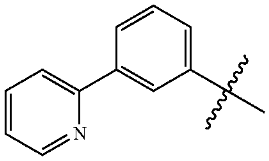
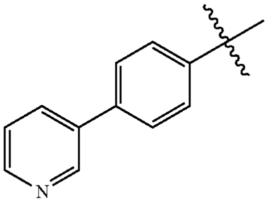
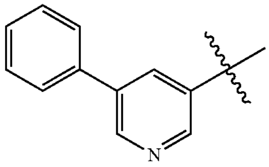
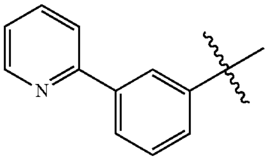
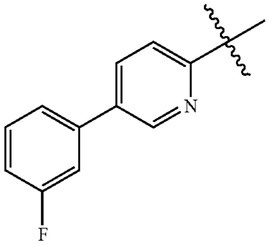
-continued
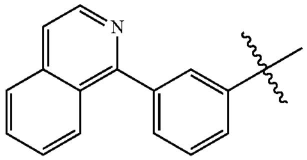
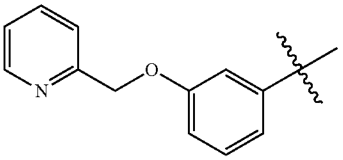
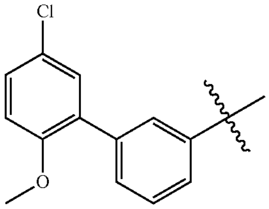
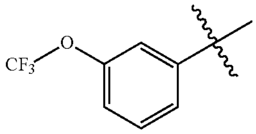
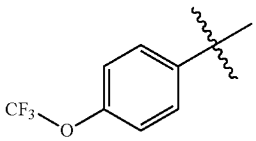
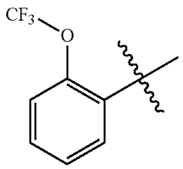
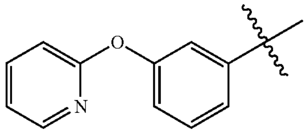
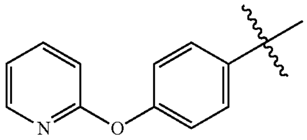
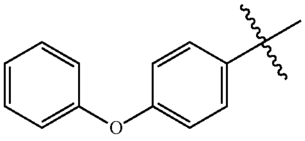
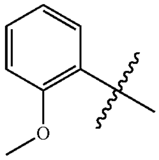
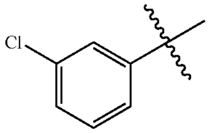
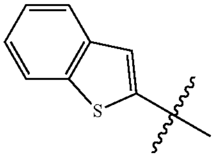
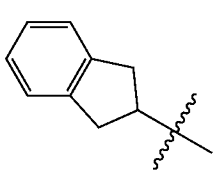
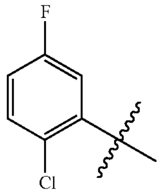
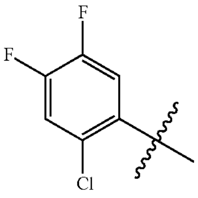
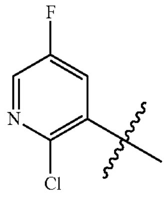
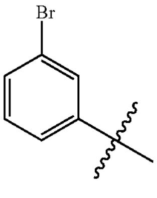

-continued
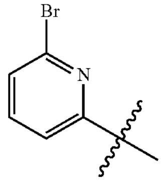
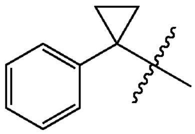
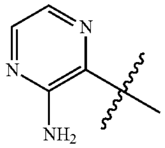
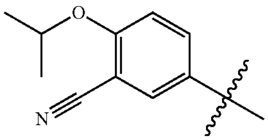
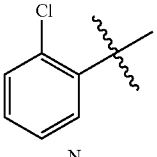
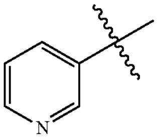
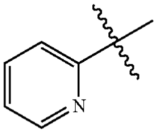
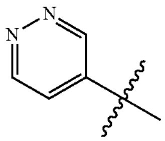
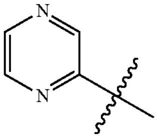
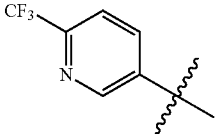
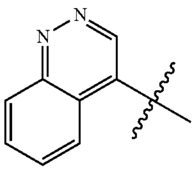
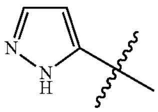
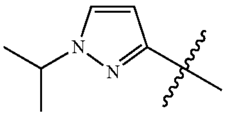
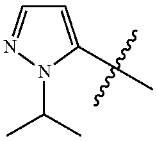
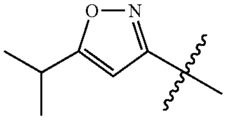
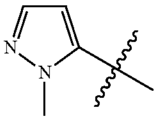
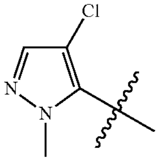
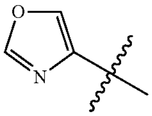
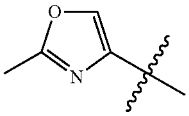
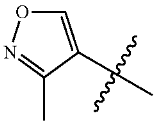
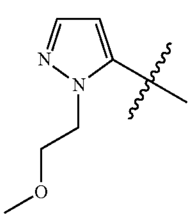
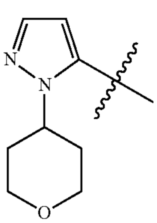
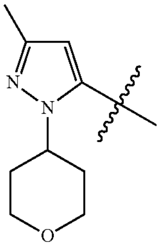
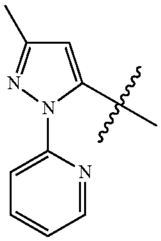
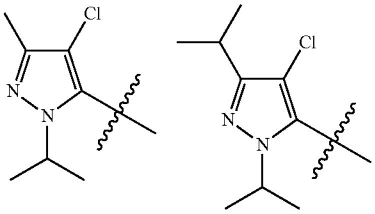
-continued
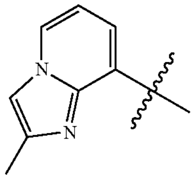
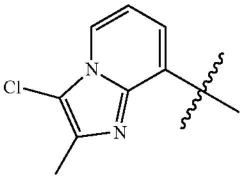
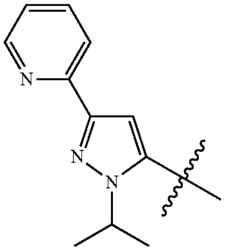
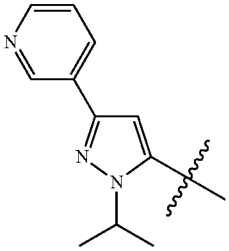
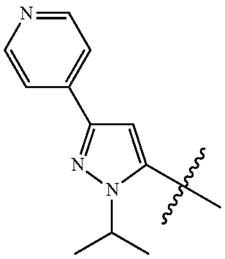
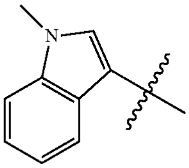
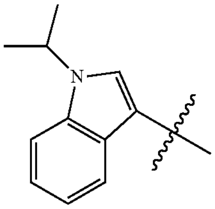
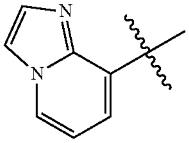
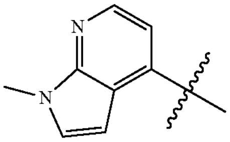
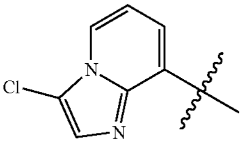
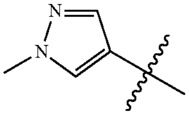
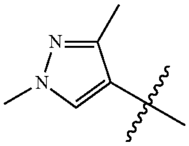
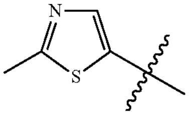
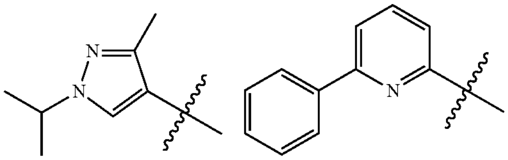
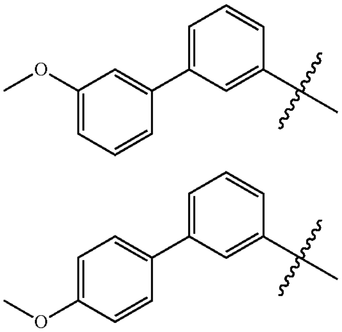

-continued

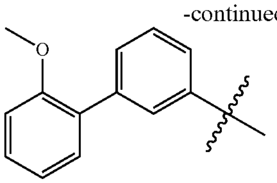
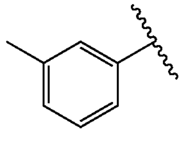
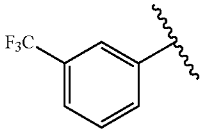
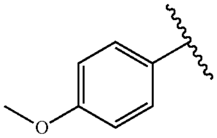
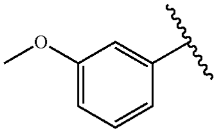
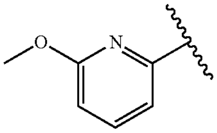
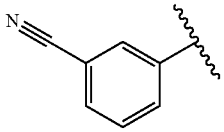
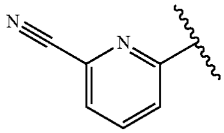
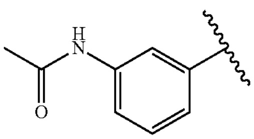
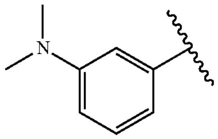
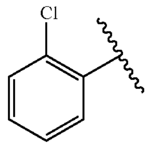
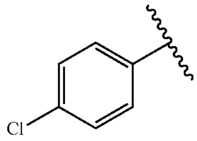
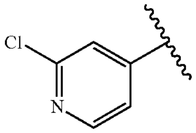
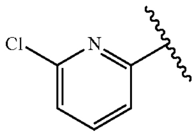

In addition, $R_2$ may represent hydrogen.

In addition, $R_3$ may represent hydrogen, C1-C3 alkyl, or phenyl, and may be substituted with halogen, C1-C3 alkyl, or C1-C3 alkoxy.

In addition, $R_4$ may represent C1-C6 branch type alkyl, or C3-C6 cycloalkyl.

In an embodiment, $L_{1a}$ may represent $(CH_2)_l$ (where l is an integer of 0 to 3), or $C(CH_2CH_2)$.

In an embodiment, $L_{1b}$ may be a direct linkage, or represent (C═O)NH, NH(C═O), NH, $(CH_2)_mO$ (where m is an integer of 0 to 3), $(C{=}O)N(CH_3)$, or $S(O_2)NH$.

In an embodiment, $L_{1c}$ may represent $(CH_2)_n$ (where n is an integer of 0 to 3) or $CHR_5$, where $R_5$ may be C1-C3 heteroalkyl having 1 or 2 heteroatoms selected from the group consisting of O, N, and S, or C1-C4 alkyl.

In an embodiment, $L_2$ represents $(CH_2)_o$ (where o is an integer of 0 to 3), $(CH_2)_pO$ (where p is an integer of 1 to 3), $CHR_5$, $CX_1X_2$, or $C(CH_2CH_2)$, where $R_8$ is OH, halogen, or C1-C3 alkyl, $X_1$ and $X_2$ may be each independently halogen.

In an embodiment, $L_3$ may represent $(CH_2)_q$ (where q is an integer of 0 to 3).

For example, $Z_1$ and $Z_2$ may be each independently OH, or together may form a cyclic boron acid ester including one or more selected from the following structure:

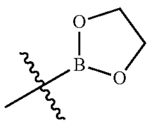
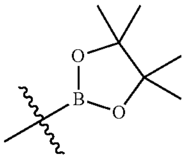
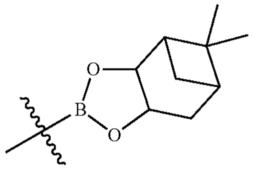
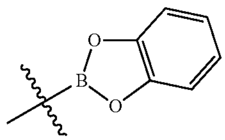
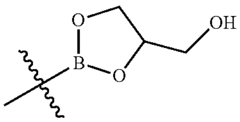
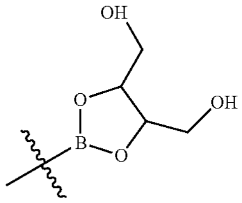
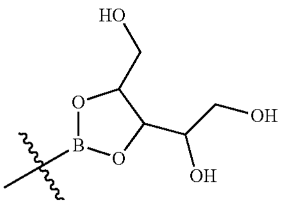
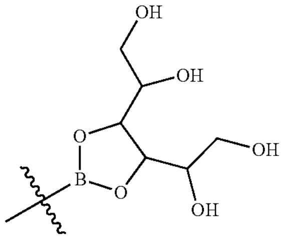
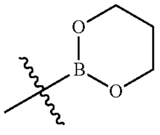
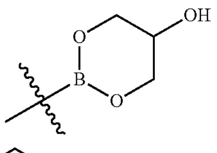
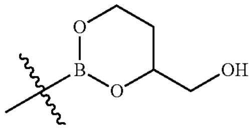

In an embodiment, $Z_1$ and $Z_2$ may be OH each.

In an aspect, the present invention provides a compound represented by the following Formula 2, a pharmaceutically acceptable salt thereof, or an isomer thereof:

[Formula 2]

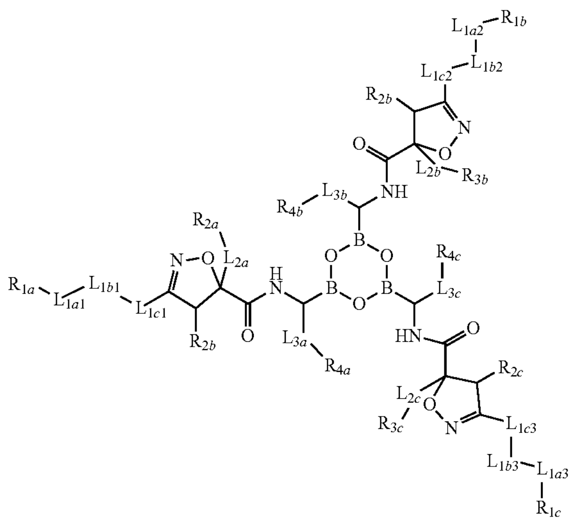

In the formula above, the same definition on $R_1$ above may be applied to Ria, Rib, and $R_{1c}$, each independently, The same definition on $R_2$ above may be applied to $R_{2a}$, $R_{2b}$, and $R_{2c}$, each independently, The same definition on $R_3$ above may be applied to $R_{3a}$, $R_{3b}$, and $R_{3c}$, each independently, The same definition on $R_4$ above may be applied to $R_{4a}$, $R_{4b}$, and $R_{4c}$, each independently, The same definition on $L_{1a}$ above may be applied to $L_{1a1}$, $L_{1a2}$, and $L_{1a3}$, each independently, The same definition on $L_{1b}$ above may be applied to $L_{1b1}$, $L_{1b2}$, and $L_{1b3}$, each independently, The same definition on $L_{1c}$ above may be applied to $L_{1c1}$, $L_{1c2}$, and $L_{1a3}$, each independently, The same definition on $L_2$ above may be applied to $L_{2a}$, $L_{2b}$, and $L_{2c}$, each independently, and The same definition on $L_3$ above may be applied to $L_{3a}$, $L_{3b}$, and $L_{3c}$, each independently.

The compound of Formula 1, the pharmaceutically acceptable salt thereof, or the isomer thereof, according to the present invention, inhibits the chymotrypsin-like activity within the proteasome.

The present invention provides a compound, which is used as an inhibitor of the chymotrypsin-like activity within the proteasome, a pharmaceutically acceptable salt thereof, or an isomer thereof.

The present invention provides a compound, a pharmaceutically acceptable salt thereof, or an isomer thereof, for use in the prevention or treatment of a proteasome-mediated disease.

The compound of Formula 1, the pharmaceutically acceptable salt thereof, or the isomer thereof, according to the present invention, is suitable for the prevention or treatment of a proteasome-mediated disease.

The present invention provides a pharmaceutical composition for inhibiting the chymotrypsin-like activity within the proteasome, the composition comprising: the compound of Formula 1, the pharmaceutically acceptable salt thereof, or the isomer thereof; and a pharmaceutically acceptable carrier.

In addition, various types of prodrugs that are converted to the compound of Formula 1, according to an intended purpose in vivo, are also included in the scope of the present invention.

The pharmaceutical composition, according to the present invention, may be used for the prevention or treatment of a proteasome-mediated disease. The proteasome-mediated disease may be, but is not limited to, cancer.

The cancer may be selected from the group consisting of brain tumor, benign astrocytoma, malignant astrocytoma, pituitary adenoma, intracranial meningioma, cerebral lymphoma, oligodendroglioma, craniopharyngioma, ependymoma, brain stem tumor, head and neck tumor, laryngeal cancer, oropharyngeal cancer, nasal cavity/sinus cancer, nasopharyngeal cancer, salivary gland cancer, hypopharyngeal cancer, thyroid cancer, neuroblastoma, chest tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary tract cancer, pancreatic cancer, small intestine cancer, colorectal cancer, anal cancer, bladder cancer, kidney cancer, male genital tumor, penile cancer, urethral cancer, prostate cancer, female genital tumor, cervical cancer, endometrial cancer, ovarian cancer, uterine sarcoma, vaginal cancer, external female genital cancer, female urethral cancer, skin cancer, myeloma, leukemia, lymphoma, and malignant lymphoma, and may preferably be multiple myeloma.

In addition, the present invention provides a use for preparing a drug for treating a proteasome-mediated disease of the compound of Formula 1, the pharmaceutically acceptable salt thereof, or the isomer thereof. The proteasome-mediated disease may be cancer, and particular examples are the same as described above.

In addition, the "pharmaceutical composition" may include the compound of the present invention and other chemical components such as diluents, carriers, etc. Accordingly, the pharmaceutical composition may include pharmaceutically acceptable carriers, diluents, excipients, or combinations thereof, as necessary. The pharmaceutical composition facilitates the administration of the compound into an organism. Various methods for administering the compound exist and include, but are not limited to, oral, injection, aerosol, parenteral, and local administration.

The term "carrier" means a compound that facilitates the introduction of the compound into a cell or tissue. For example, dimethylsulfoxide (DMSO) is a common carrier facilitating the introduction of many organic compounds into cells or tissues in an organism.

The term "diluent" is defined as a compound that not only stabilizes a biologically active form of a compound of interest but is also diluted in water dissolving the compound. Dissolved salts in a buffer solution are used as diluents in the present technical field. A commonly used buffer solution is phosphate buffered saline mimicking a salt form of the human body fluid. Since a buffer solution may control the pH of a solution at low concentration, a buffer diluent hardly modifies the biological activity of the compound.

The term "pharmaceutically acceptable" means properties that do not impair the biological activities and physical properties of the compound.

The compound according to the present invention may be formulated as various pharmaceutical dosage forms depending on the purpose. For the preparation of the pharmaceutical composition according to the present invention, the effective ingredient, particularly, the compound of Formula 1, the pharmaceutically acceptable salt thereof or the isomer thereof, is mixed together with various pharmaceutically acceptable carriers which may be selected according to the formulation to be prepared. For example, the pharmaceutical composition according to the present invention may be formulated as preparations for injection, oral preparations, and the like, depending on the purpose.

The compound of the present invention may be formulated by known methods using known pharmaceutical carriers and excipients, and inserted into a unit dose form or a multi-dose container. The preparation may be a solution, a suspension, or an emulsion in oil or aqueous medium and include conventional dispersing agents, suspending agents, or stabilizing agents. In addition, the preparation may be, for example, a dry powder form, which is used by dissolving in sterilized, pyrogen-free water before use. The compound of the present invention may be formulated into suppositories by using a conventional suppository base such as cocoa butter or other glycerides. As solid dosage forms for oral administration, capsules, tablets, pills, powders, and granules may be prepared, and capsules and tablets are especially useful. Tablets and pills are preferably enteric-coated. Solid dosage forms may be manufactured by mixing the compound of the present invention with at least one inert diluent(s), such as sucrose, lactose, and starch, and carriers, such as lubricants, e.g., magnesium stearate, disintegrating agents, binders, and the like. The compound or the pharmaceutical composition containing the same, according to the present invention, may be administered in combination with other drugs, for example, other diabetes treatment drugs, as required.

In addition, the present invention provides a method for preventing or treating a proteasome-mediated disease, the method comprising a step for administering the compound of Formula 1, the pharmaceutically acceptable salt thereof, or the isomer thereof, or the pharmaceutical composition containing the same to a subject.

The subject may be a human subject or a non-human mammalian subject in need of the treatment or prevention of the proteasome-mediated disease. The proteasome-mediated disease may be cancer.

In the disclosure, the term "treatment" means stopping, delaying or ameliorating the progress of diseases in a subject exhibiting symptoms of diseases. The term "prevention" means stopping, delaying or ameliorating the sign of diseases in a subject at risk of exhibiting symptoms of diseases, even if he or she does not exhibit the symptoms.

The dosage of the compound of Formula 1, the pharmaceutically acceptable salt thereof, or the isomer thereof, of the present invention, depends on the prescription of a physician, taking into account such factors as body weight and age of a patient, specific nature of the disease and severity of the disease, etc. However, a typical dosage for adults is in a range of about 1 to 500 mg per day according to the frequency and intensity of administration. For a typical daily dosage of intramuscular or intravenous administration for adults, which could be administered in divided unit dosages, a range of about 1 to 300 mg per day may be sufficient. For some patients, a higher daily dose may be preferred.

The present invention also provides a method for preparing the compound of Formula 1. Hereinafter, the method for preparing the compound of Formula 1 will be explained based on exemplary schemes to help understanding of the present invention. However, a person skilled in the art could prepare the compound of Formula 1 by various methods based on the structure of Formula 1, and such methods should be interpreted as being within the scope of the present invention. That is, the compound of Formula 1 may be prepared by the synthetic methods described herein or by optionally combining various synthetic methods disclosed in the prior art, which should be interpreted as being within the scope of the present invention. The method for preparing the compound of Formula 1 is not limited only to those described below.

When preparing the compound of the present invention, it is possible to appropriately change the reaction sequence. That is, it is possible to run first optional processes or insert optional processes to change substituents, and use any reagents other than the exemplified reagents as needed. Compounds obtained in each process could be separated or purified by conventional methods, such as recrystallization, distillation, or silica gel column chromatography. Furthermore, the compound obtained in each process could be used in the next step without further purification or separation.

In the schemes below, unless indicated otherwise, all substituents are as previously defined. Reagents and starting materials could be obtained readily commercially. Others could be produced by synthetic methods described in the Preparation Examples and Examples below, including known synthetic methods for structurally similar compounds. Unless otherwise noted, compounds used as starting materials are known ones or those which could be prepared by known synthetic methods or similar methods from known compounds.

Hereinafter, the present invention is explained in more detail through the Preparation Examples and Examples. However, the scope of the present invention is not limited by them.

EXAMPLES

Preparation Example 1: Preparation of ethyl 3-(((tert-butoxycarbonyl)amino)methyl)-4,5-dihydroisoxazol-5-carboxylate Through the processes (1) and (2) below, the title example was obtained.

(1) Preparation of tert-butyl (2-(hydroxyimino)ethyl)carbamate

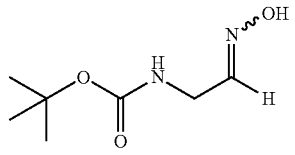

Tert-butyl (2-oxoethyl)carbamate (10.7 g, 67.2 mmol) was dissolved in methanol (50 ml), a 50% hydroxylamine aqueous solution (14.23 ml, 168 mmol) was added thereto at room temperature, and stirring was performed for 16 hours. The solvent was distilled under a reduced pressure to obtain the title compound (9.8 g, 84%), and this compound was used in the next reaction without purification.

(2) Preparation of ethyl 3-(((tert-butoxycarbonyl)amino)methyl)-4,5-dihydroisoxazol-5-carboxylate

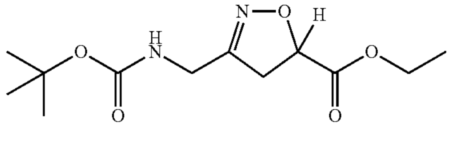 [SMILES: CCOC(=O)C1CC(CNC(=O)OC(C)(C)C)=NO1]

The tert-butyl (2-(hydroxyimino)ethyl)carbamate (1.09 g, 6.26 mmol) obtained in (1) above was dissolved in dichloromethane (40 ml), and ethyl acrylate (0.75 ml, 6.88 mmol) was added thereto at room temperature. A 4% sodium hypochlorite aqueous solution (21 ml, 13.5 mmol) was slowly added thereto at 0° C., and stirring was performed for 18 hours, while raising to room temperature. The solvent was distilled under a reduced pressure, a sodium bicarbonate aqueous solution was added, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.67 g, 39%).

NMR: $^1$H-NMR (400 MHz, $CDCl_3$); δ 5.04-4.99 (t, 3H), 4.91 (br s, 1H), 4.28-4.22 (q, 2H), 4.09-4.08 (d, 2H), 3.29-3.27 (d, 2H), 1.45 (s, 9H), 1.33-1.26 (t, 3H)

MS (m/z): 273[M+H], 173[M-$C_5H_7O_2$].

Preparation Example 2: Preparation of methyl 3-(((tert-butoxycarbonyl)amino)methyl)-4-methyl-4,5-dihydroisoxazol-5-carboxylate

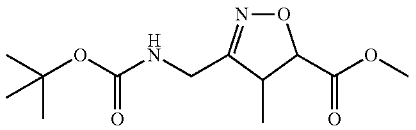 [SMILES: COC(=O)C1ON=C(CNC(=O)OC(C)(C)C)C1C]

The title compound (0.076 g, 9%) was obtained using crotonic acid methyl ester (0.48 ml, 4.5 mmol) and tert-butyl (2-(hydroxyimino)ethyl)carbamate (0.523 g, 3.00 mmol) obtained in Preparation Example 1-(1) by the preparation method of Preparation Example 1-(2).

NMR: $^1$H-NMR (400 MHz, $CDCl_3$); δ 5.33 and 5.10 (1H, 2 s), 4.63 and 4.55 (1H, 2 d), 4.17-4.02 (3H, m), 3.81 and 3.79 (3H, 2 s), 1.47-1.40 (12H, m)

Preparation Example 3: Preparation of ethyl 3-((S)-1-((tert-butoxycarbonyl)amino)-2-methylpropyl)-4,5-dihydroisoxazol-5-carboxylate Through the processes (1), (2) and (3) below, the title compound was obtained.

(1) Preparation of tert-butyl (S)-(3-methyl-1-oxobutan-2-yl)carbamate

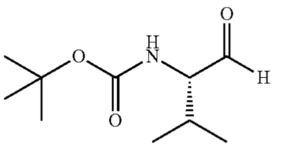

((S)-1-hydroxymethyl-2-methyl-propyl)-carbamic acid tert-butyl ester (1.5 g, 7.38 g) was dissolved in dimethylsulfoxide (10 ml), and 2-iodobenzoic acid (4.1 g, 14.76 mmol) was added thereto at 0° C. After stirring at room temperature for 18 hours, water was added, and extraction with diethyl ether was performed. The organic layer thus extracted was washed with brine, dried over anhydrous magnesium sulfate, and filtered. The filtrate was distilled under a reduced pressure and separated by column chromatography to obtain the title compound (1.01 g, 68%).

NMR: $^1$H-NMR (500 MHz, $CDCl_3$); δ 9.64 (s, 1H), 5.07 (br s, 1H), 4.24 (m, 1H), 2.28-2.27 (m, 1H), 1.44 (s, 9H), 1.03-1.01 (d, 3H), 0.94-0.93 (d, 3H)

(2) Preparation of tert-butyl (S)-(1-(hydroxyimino)-3-methylbutan-2-yl)carbamate

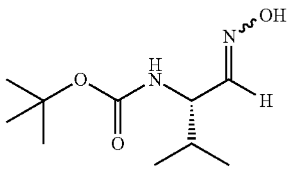

The title compound (1.09, 99%) was obtained using tert-butyl N-[(1S)-1-formyl-2-methyl-propyl]carbamate (1.01 g, 5.04 ml) obtained in (1) above by the preparation method of Preparation Example 1-(1).

(3) Preparation of ethyl 3-((S)-1-((tert-butoxycarbonyl)amino)-2-methylpropyl)-4,5-dihydroisoxazol-5-carboxylate

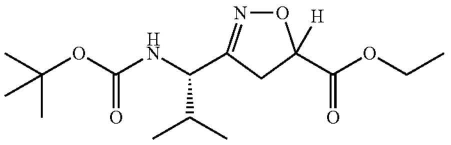 [SMILES: CCOC(=O)C1CC([C@@H](NC(=O)OC(C)(C)C)C(C)C)=NO1]

The title compound (0.72 g, 84%) was obtained using tert-butyl N-[(1S)-1-hydroxyiminomethyl-2-methyl-propyl] carbamate (0.59 g, 2.73 mmol) obtained (2) above and ethyl acrylate (0.36 ml, 3.27 mmol) by the preparation method of Preparation Example 1-(2).

NMR: $^1$H-NMR (400 MHz, $CDCl_3$); δ 5.02-4.97 (m, 1H), 4.37 (br s, 1H), 4.27-4.22 (m, 2H), 3.26-3.23 (m, 2H), 2.04-2.07 (m, 1H), 1.39 (s, 9H), 1.31-1.28 (t, 3H), 1.04-0.91 (m, 6H)

MS (m/z): 315[M+H]

Preparation Example 4: Preparation of ethyl 3-((S)-1-((tert-butoxycarbonyl)amino)-3-methylbutyl)-4,5-dihydroisoxazol-5-carboxylate Through the processes (1) and (2) below, the title compound was obtained.

(1) Preparation of tert-butyl (S)-(1-(hydroxyimino)-4-methylpentane-2-yl)carbamate

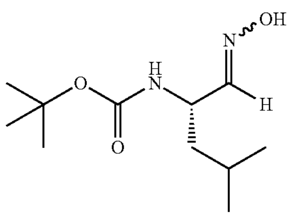 [SMILES: CC(C)C[C@@H](C=NO)NC(=O)OC(C)(C)C]

The title compound (0.42 g, 99%) was obtained using ((S)-1-formyl-3-methyl-butyl)-carbamic acid tert-butyl ester (0.39 g, 1.84 mmol) by the preparation method of Preparation Example 1-(1).

(2) Preparation of ethyl 3-((S)-1-((tert-butoxycarbonyl)amino)-3-methylbutyl)-4,5-dihydroisoxazol-5-carboxylate

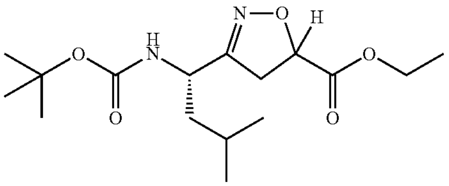 [SMILES: CCOC(=O)C1CC([C@H](CC(C)C)NC(=O)OC(C)(C)C)=NO1]

The title compound (0.3 g, 34%) was obtained using tert-butyl N-[(1S)-1-hydroxyiminomethyl-3-methyl-butyl] carbamate (0.61 g, 2.65 mmol) obtained (1) above and ethyl acrylate (0.35 ml, 3.18 mmol) by the preparation method of Preparation Example 1-(2).

NMR: $^{1}$H-NMR (400 MHz, $CDCl_3$); δ 5.01-4.93 (m, 1H), 4.72 (br s, 1H), 4.52 (br s, 1H), 4.03-4.22 (q, 2H), 3.34-3.22 (m, 2H), 1.78-1.53 (m, 3H), 1.32-1.29 (t, 3H), 0.96-0.91 (m, 6H)

MS (m/z): 329[M+H]

Preparation Example 5: Preparation of 5-(ethoxycarbonyl)-4,5-dihydroisoxazol-3-carboxylic acid Through the processes (1), (2) and (3) below, the title compound was obtained.

(1) Preparation of tert-butyl 2-chloro-2-(hydroxyimino)acetate

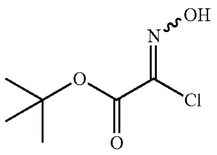

The title compound was obtained by the method described in WO200633551A1.

(2) Preparation of 3-(tert-butyl) 5-ethyl 4,5-dihydroisoxazol-3,5-dicarboxylate

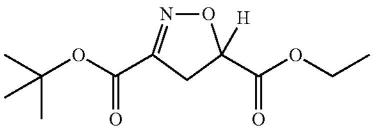 [SMILES: CCOC(=O)C1CC(C(=O)OC(C)(C)C)=NO1]

The title compound (1.05 g, 62%) was obtained using tert-butyl 2-chloro-2-(hydroxyimino)acetate (1.25 g, 6.96 mmol) obtained in (1) above by the preparation method of Preparation Example 1-(2).

NMR: $^{1}$H-NMR (400 MHz, $CDCl_3$); δ 5.18-5.13 (m, 1H), 4.38-4.24 (q, 2H), 3.52-3.40 (m, 2H), 1.55 (s, 9H), 1.34-1.30 (t, 3H)

MS (m/z): 244[M+H]

(3) Preparation of 5-(ethoxycarbonyl)-4,5-dihydroisoxazol-3-carboxylic acid

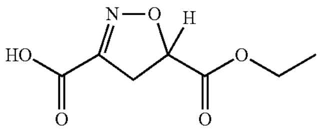

The 3-tert-butyl 5-ethyl 4,5-dihydro-1,2-oxazol-3,5-dicarboxylate (1.05 g, 4.32 mmol) obtained in (2) above was dissolved in dichloromethane (20 ml). A 4 N hydrochloric acid 1,4-dioxane solution (8.6 ml, 34.53 mmol) was slowly added thereto at 0° C., and stirring was performed for 5 hours, while raising to room temperature. The solvent was distilled under a reduced pressure, and separation by column chromatography was performed to obtain the title compound (0.87 g, 99%).

MS (m/z): 188[M+H]

Preparation Example 6: Preparation of methyl 5-benzyl-3-(((tert-butoxycarbonyl)amino)methyl)-4,5-dihydroisoxazol-5-carboxylate Through the processes (1) and (2) below, the title compound was obtained.

(1) Preparation of methyl 2-benzylacrylate

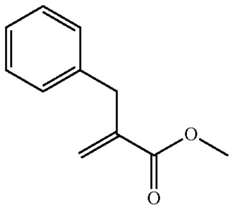

2-Benzoylacrylic acid (15 g, 92.5 mmol) was dissolved in methanol (100 ml). Thionyl chloride (20.15 ml, 27.75 mmol) was slowly added thereto at 0° C., and stirring was performed for 16 hours, while raising to room temperature. The solvent was distilled under a reduced pressure, ethyl acetate was added, and washing with a sodium bicarbonate aqueous solution was performed. An organic layer was dried over anhydrous magnesium sulfate, and filtered. The filtrate was distilled under a reduced pressure and dried under a reduced pressure to obtain the title compound (16.32 g, 99%).

NMR: $^{1}$H-NMR (400 MHz, $CDCl_3$); δ 7.17-7.35 (m, 5H), 6.23 (m, 1H), 5.47 (m, 1H), 3.74 (s, 3H), 3.63 (s, 2H)

(2) Preparation of methyl 5-benzyl-3-(((tert-butoxycarbonyl)amino)methyl)-4,5-dihydroisoxazol-5-carboxylate

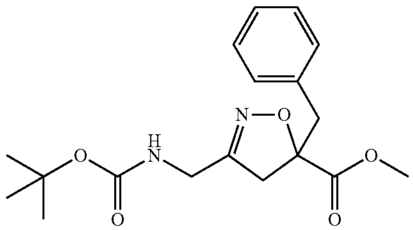 [SMILES: COC(=O)C1(Cc2ccccc2)CC(CNC(=O)OC(C)(C)C)=NO1]

The racemic mixture of the title compound (10.87 g, 56%) was obtained using methyl 2-benzylacrylate (10.77 g, 61.1 mmol) obtained in (1) above and tert-butyl (2-(hydroxyimino)ethyl)carbamate (9.68 g, 55.6 mmol) obtained in Preparation Example 1-(1) by the preparation method of Preparation Example 1-(2). Through HPLC utilizing a CHIRAL TECHNOLOGIES CHIRALPAK® IA chiral column and ethanol/hexane eluent, Isomer 1 which had a short retention time and Isomer 2 which had a long retention time were separated, and Isomer 2 was used for the synthesis of the title compound.

NMR: $^1$H-NMR (400 MHz, $CDCl_3$); δ 7.32-7.22 (m, 5H), 4.55 (br s, 1H), 3.89-3.83 (m, 2H), 3.78 (s, 3H), 3.40-3.36 (d, 1H), 3.33-3.29 (d, 1H), 3.13-3.10 (d, 1H), 2.98-2.94 (d, 1H), 1.44 (s, 9H)

MS (m/z): 349[M+H], 249[M-$C_5H_7O_2$].

Preparation Example 7: Preparation of ethyl 3-(((tert-butoxycarbonyl)amino)methyl)-5-methyl-4,5-dihydroisoxazol-5-carboxylate

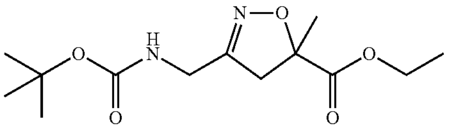 [SMILES: CCOC(=O)C1(C)CC(CNC(=O)OC(C)(C)C)=NO1]

The title compound (0.21 g, 31%) was obtained using tert-butyl (2-(hydroxyimino)ethyl)carbamate (0.41 g, 2.35 mmol) obtained in Preparation Example 1-(1) and 2-methyl-acrylic acid ethyl ester (0.35 ml, 2.82 mmol) by the preparation method of Preparation Example 1-(2).

NMR: $^1$H-NMR (400 MHz, $CDCl_3$); δ 4.91 (br s, 1H), 4.27-4.20 (q, 2H), 4.06-4.005 (d, 2H), 3.53-3.49 (d, 1H), 2.89-2.84 (d, 1H), 1.62 (s, 3H), 1.45 (s, 9H), 1.33-1.25 (t, 3H)

MS (m/z): 287[M+H]

Preparation Example 8: Preparation of ethyl 3-(((tert-butoxycarbonyl)amino)methyl)-5-ethyl-4,5-dihydroisoxazol-5-carboxylate

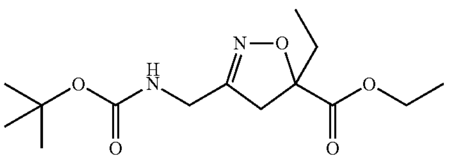 [SMILES: CCOC(=O)C1(CC)CC(CNC(=O)OC(C)(C)C)=NO1]

The title compound (0.25 g, 34%) was obtained using tert-butyl (2-(hydroxyimino)ethyl)carbamate (0.43 g, 2.47 mmol) obtained in Preparation Example 1-(1) and 2-methylene-butyric acid ethyl ester (0.51 g, 2.96 mmol) by the preparation method of Preparation Example 1-(2).

NMR: $^1$H-NMR (400 MHz, $CDCl_3$); δ 4.89 (br s, 1H), 4.29-4.19 (q, 2H), 4.03 (m, 2H), 3.45-3.41 (d, 1H), 2.91-2.87 (d, 1H), 1.96-1.91 (m, 2H), 1.44 (s, 9H), 1.31-1.25 (t, 3H), 0.94-0.91 (t, 3H)

MS (m/z): 301[M+H]

Preparation Example 9: Preparation of ethyl 3-(((tert-butoxycarbonyl)amino)methyl)-5-propyl-4,5-dihydroisoxazol-5-carboxylate

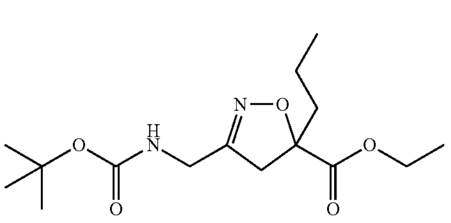 [SMILES: CCCC1(C(=O)OCC)CC(CNC(=O)OC(C)(C)C)=NO1]

The title compound (0.27 g, 37%) was obtained using tert-butyl (2-(hydroxyimino)ethyl)carbamate (0.4 g, 2.29 mmol) obtained in Preparation Example 1-(1) and 2-methylene-pentanoic acid ethyl ester (0.39 g, 2.75 mmol) by the preparation method of Preparation Example 1-(2).

NMR: $^1$H-NMR (500 MHz, $CDCl_3$); δ 4.88 (br s, 1H), 4.24-4.19 (m, 2H), 4.02 (m, 2H), 3.45-3.41 (d, 1H), 2.91-2.88 (d, 1H), 1.89-1.87 (m, 2H), 1.44 (s, 9H), 1.42-1.39 (m, 2H), 1.31-1.28 (t, 3H), 0.95-0.92 (t, 3H)

MS (m/z): 315[M+H]

Preparation Example 10: Preparation of ethyl 3-(((tert-butoxycarbonyl)amino)methyl)-5-isopropyl-4,5-dihydroisoxazol-5-carboxylate Through the processes (1) and (2) below, the title compound was obtained.

(1) Preparation of ethyl 3-methyl-2-methylenebutanoate

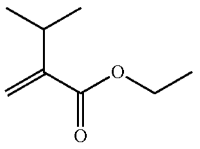

The title compound was obtained by the method described in Tetrahedron Letters, Vol. 24, No. 33, pp 3477-3480.

(2) Preparation of ethyl 3-(((tert-butoxycarbonyl) amino)methyl)-5-isopropyl-4,5-dihydroisoxazol-5-carboxylate

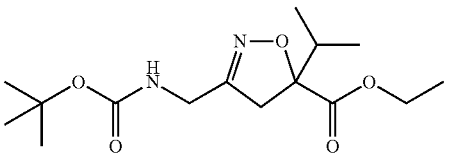 [SMILES: CCOC(=O)C1(C(C)C)CC(CNC(=O)OC(C)(C)C)=NO1]

The title compound (0.21 g, 30%) was obtained using tert-butyl (2-(hydroxyimino)ethyl)carbamate (0.38 g, 2.18 mmol) obtained in Preparation Example 1-(1) and ethyl 3-methyl-2-methylene-butanoate (0.44 g, 2.62 mmol) obtained in (1) above by the preparation method of Preparation Example 1-(2).

NMR: $^1$H-NMR (400 MHz, $CDCl_3$); δ 4.90 (br s, 1H), 4.32-4.15 (m, 2H), 4.04-3.99 (m, 2H), 3.43-3.39 (d, 1H), 2.94-2.90 (d, 1H), 2.40-2.30 (m, 1H), 1.46 (s, 9H), 1.33-1.29 (t, 3H), 0.97-0.94 (t, 3H), 0.90-0.88 (d, 3H)

MS (m/z): 315[M+H]

Preparation Example 11: Preparation of ethyl 3-(((tert-butoxycarbonyl)amino)methyl)-5-isobutyl-4,5-dihydroisoxazol-5-carboxylate Through the processes (1) and (2), the title compound was obtained.

(1) Preparation of ethyl 4-methyl-2-methylenepentanoate

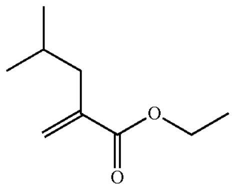

The title compound was obtained by the method described in Journal of Medicinal Chemistry, 2000, vol. 43 pp 1398-1408.

(2) Preparation of ethyl 3-(((tert-butoxycarbonyl) amino)methyl)-5-isobutyl-4,5-dihydroisoxazol-5-carboxylate

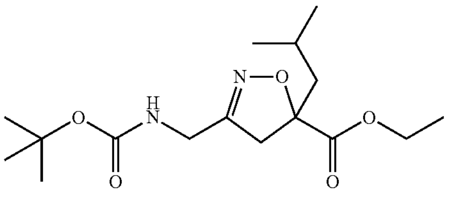 [SMILES: CCOC(=O)C1(CC(C)C)CC(CNC(=O)OC(C)(C)C)=NO1]

The title compound (0.41 g, 32%) was obtained using tert-butyl (2-(hydroxyimino)ethyl)carbamate (0.67 g, 3.90 mmol) obtained in Preparation Example 1-(1) and ethyl 4-methyl-2-methylenepentanoate (0.67 g, 4.29 mmol) obtained in (1) above by the preparation method of Preparation Example 1-(2).

NMR: $^1$H-NMR (400 MHz, $CDCl_3$); δ 4.89 (br s, 1H), 4.27-4.18 (m, 2H), 4.03-4.02 (m, 2H), 3.14-3.43 (d, 1H), 2.92-2.88 (d, 1H), 1.92-1.88 (m, 1H), 1.44 (s, 9H), 1.31-1.28 (t, 3H), 0.94-0.90 (dd, 6H)

MS (m/z): 329[M+H]

Preparation Example 12: Preparation of methyl 5-benzyl-3-(((tert-butoxycarbonyl)(methyl)amino) methyl)-4,5-dihydroisoxazol-5-carboxylate Through the processes (1) and (2) below, the title compound was obtained.

(1) Preparation of tert-butyl (2-(hydroxyimino)ethyl)(methyl)carbamate

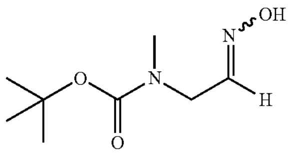

Methyl-(2-oxo-ethyl)-carbamic acid tert-butyl ester (0.17 g, 25%) was obtained using (2-hydroxy-ethyl)-methyl-carbamic acid tert-butyl ester (0.7 g, 3.99 mmol) by the preparation method of Preparation Example 3-(1). The title compound (0.16 g, 99%) was obtained using methyl-(2-oxo-ethyl)-carbamic acid tert-butyl ester (0.17 g, 0.98 mmol) by the preparation method of Preparation Example 1-(1).

(2) Preparation of methyl 5-benzyl-3-(((tert-butoxycarbonyl)(methyl)amino)methyl)-4,5-dihydroisoxazol-5-carboxylate

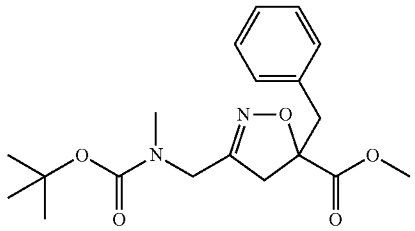 [SMILES: COC(=O)C1(Cc2ccccc2)CC(CN(C)C(=O)OC(C)(C)C)=NO1]

The title compound (0.24 g, 76%) was obtained using tert-butyl (2-(hydroxyimino)ethyl)(methyl)carbamate (0.16 g, 0.85 mmol) obtained in (1) above and methyl 2-benzylacrylate (0.18 g, 1.02 mmol) obtained in Preparation Example 1-(1) by the preparation method of Preparation Example 1-(2).

NMR: $^1$H-NMR (500 MHz, $CDCl_3$); δ 7.31-7.23 (m, 5H), 4.10-4.02 (m, 1H), 3.87-3.82 (m, 1H), 3.78 (s, 3H), 3.34-3.31 (d, 2H), 3.09-3.06 (d, 1H), 2.90-2.87 (d, 1H), 2.55-2.47 (d, 3H), 1.43 (s, 9H)

MS (m/z): 363[M+H]

Preparation Example 13: Preparation of ethyl 3-(((tert-butoxycarbonyl)amino)methyl)-5-(3-methoxybenzyl)-4,5-dihydroisoxazol-5-carboxylate Through the processes (1) and (2) below, the title compound was obtained.

(1) Preparation of ethyl 2-(3-methoxybenzyl)acrylate

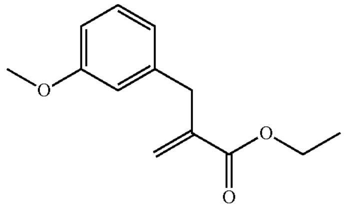

(Diethoxy-phosphoryl)-acetic acid ethyl ester (1.5 g, 6.69 mmol) was dissolved in dichloroformamide (15 ml). After slowly adding sodium hydride (0.29 g, 7.36 mmol) at 0° C., and after 30 minutes, 3-methoxybenzyl bromide (0.94 ml, 6.69 mmol) was added and stirred at room temperature for 18 hours. After finishing the reaction, water was added, and extraction with diethyl ether was performed. An organic layer was washed with brine, dried over anhydrous magnesium sulfate, and filtered. The filtrate was distilled under a reduced pressure and then, used in the next reaction without a purification process.

The product obtained above (2.3 g, 6.68 mmol) and a 37% formaldehyde aqueous solution (3.4 ml, 42.75 mmol) were dissolved in water (15 ml), and potassium carbonate (2.8 g, 20.04 mmol) dissolved in water (5 ml) was added thereto. After refluxing and stirring at 90° C. for 16 hours, water was added, and extraction with diethyl ether was performed. An organic layer was washed with brine and dried over anhydrous magnesium sulfate. The filtrate was distilled under a reduced pressure and separated by column chromatography to obtain the title compound (0.78 g, 53%, 2 steps).

NMR: $^{1}$H-NMR (400 MHz, $CDCl_3$); δ 7.23-7.19 (m, 1H), 6.80-6.75 (m, 3H), 6.23 (s, 1H), 5.47 (s, 1H), 4.21-4.09 (q, 2H), 3.79 (s, 3H), 3.61 (s, 2H), 1.29-1.24 (t, 3H)

(2) Preparation of ethyl 3-(((tert-butoxycarbonyl)amino)methyl)-5-(3-methoxybenzyl)-4,5-dihydroisoxazol-5-carboxylate

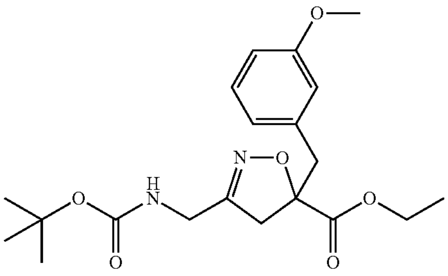 [SMILES: CCOC(=O)C1(Cc2cccc(OC)c2)CC(CNC(=O)OC(C)(C)C)=NO1]

The title compound (0.31 g, 44%) was obtained using ethyl 2-(3-methoxybenzyl)acrylate (0.36 g, 1.63 mmol) obtained in (1) above and tert-butyl (2-(hydroxyimino)ethyl) carbamate (0.31 g, 1.80 mmol) obtained in Preparation Example 1-(1) by the preparation method of Preparation Example 1-(2).

NMR: $^{1}$H-NMR (400 MHz, $CDCl_3$); δ 7.24-7.18 (m, 1H), 6.92-6.75 (m, 3H), 4.62 (br s, 1H), 4.27-4.17 (m, 2H), 3.89 (m, 2H), 3.78 (s, 3H), 3.46-2.94 (m, 4H), 1.44 (s, 9H), 1.31-1.26 (t, 3H)

MS (m/z): 393[M+H]

Preparation Example 14: Preparation of ethyl 3-(((tert-butoxycarbonyl)amino)methyl)-5-(4-chlorobenzyl)-4,5-dihydroisoxazol-5-carboxylate Through the processes (1) and (2) below, the title compound was obtained.

(1) Preparation of ethyl 2-(4-chlorobenzyl)acrylate

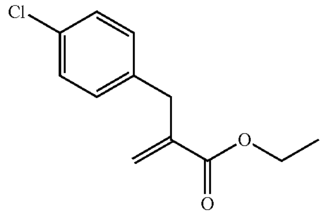

Under the charge of nitrogen, sodium (0.79 g, 34.34 mmol) was added to ethanol (40 ml). Malonic acid diethyl ester (5 g, 31.22 mmol) was slowly added thereto and stirred for 10 minutes, and 4-chlorobenzyl chloride (5.03 g, 31.22 mmol) dissolved in ethanol (10 ml) was slowly added thereto. After stirring for 16 hours, water was added, and extraction with ethyl acetate was performed. An organic layer was washed with brine, dried over anhydrous magnesium sulfate, and filtered. The filtrate was distilled under a reduced pressure and separated by column chromatography to obtain 2-(4-chloro-benzyl)-malonic acid diethyl ester (3.27 g, 37%).

NMR: $^{1}$H-NMR (400 MHz, $CDCl_3$); δ 7.26-7.24 (d, 2H), 7.15-7.13 (d, 2H), 4.22-4.12 (q, 2H), 3.62-3.60 (t, 1H), 3.19-3.17 (d, 2H), 1.23-1.20 (t, 3H)

2-(4-Chloro-benzyl)-malonic acid diethyl ester (3.3 g, 11.48 mmol) was dissolved in ethanol (20 ml). At 0° C., potassium hydroxide (0.61 g, 10.91 mmol) dissolved in ethanol (10 ml) was slowly added thereto, followed by stirring for 48 hours. After titrating pH 2 with 1 N hydrochloric acid, water was added, and the resultant product was extracted with ethyl acetate, dried over anhydrous magnesium sulfate, and filtered. The filtrate was distilled under a reduced pressure and separated by column chromatography to obtain 2-(4-chloro-benzyl)-malonic acid mono ethyl ester (2.10 g, 71%).

NMR: $^{1}$H-NMR (400 MHz, $CDCl_3$); δ 7.27-7.26 (d, 2H), 7.15-7.12 (d, 2H), 4.20-4.12 (q, 2H), 3.69-3.64 (t, 1H), 3.24-3.16 (dd, 2H), 1.26-1.20 (t, 3H)

The 2-(4-chloro-benzyl)-malonic acid monoethyl ester (2.1 g, 8.19 mmol) obtained above was dissolved in pyridine (15 ml). Paraformaldehyde (0.23 g, 7.78 mmol) and piperidine (0.081 ml, 0.82 mmol) were added in order, followed by refluxing and stirring at 120° C. for 3 hours. Water was added, and extraction with hexane was performed. Then, an organic layer was washed with water, 1 N hydrochloric acid, water, a sodium carbonate aqueous solution and brine in order, dried over anhydrous magnesium sulfate, and filtered. The filtrate was distilled under a reduced pressure and separated by column chromatography to obtain the title compound (1.29 g, 70%).

NMR: $^1$H-NMR (400 MHz, $CDCl_3$); δ 7.27-7.26 (d, 2H), 7.14-7.12 (d, 2H), 6.24 (s, 1H), 5.47 (s, 1H), 4.20-4.15 (q, 2H), 3.59 (s, 2H), 1.28-1.24 (t, 3H)

(2) Preparation of ethyl 3-(((tert-butoxycarbonyl) amino)methyl)-5-(4-chlorobenzyl)-4,5-dihydroisoxazol-5-carboxylate

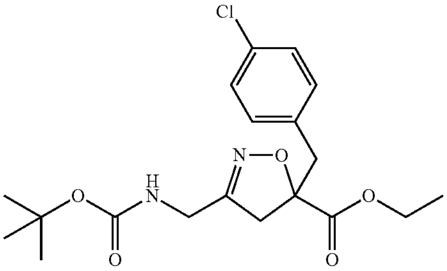 [SMILES: CCOC(=O)C1(Cc2ccc(Cl)cc2)CC(CNC(=O)OC(C)(C)C)=NO1]

The title compound (0.17 g, 19%) was obtained using ethyl 2-(4-chlorobenzyl)acrylate (0.57 g, 2.53 mmol) obtained in (1) above and tert-butyl (2-(hydroxyimino)ethyl) carbamate (0.4 g, 2.30 mmol) obtained in Preparation Example 1-(1) by the preparation method of Preparation Example 1-(2).

MS (m/z): 397[M+H]

Preparation Example 15: Preparation of ethyl 3-(((tert-butoxycarbonyl)amino)methyl)-5-(2-chlorobenzyl)-4,5-dihydroisoxazol-5-carboxylate

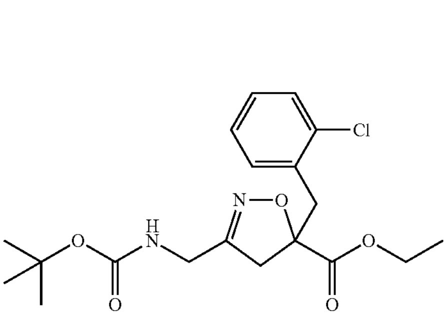 [SMILES: CCOC(=O)C1(Cc2ccccc2Cl)CC(CNC(=O)OC(C)(C)C)=NO1]

By the method described in WO2006134485A1, ethyl 2-(2-chlorobenzyl)acrylate was obtained. The title compound (0.4 g, 38%) was obtained using tert-butyl (2-(hydroxyimino)ethyl)carbamate (0.31 g, 1.76 mmol) obtained in Preparation Example 1-(1) and ethyl 2-(2-chlorobenzyl) acrylate (0.36 g, 1.6 mmol) by the preparation method of Preparation Example 1-(2).

MS (m/z): 397[M+H]

Preparation Example 16: Preparation of ethyl 3-(((tert-butoxycarbonyl)amino)methyl)-5-(3-chlorobenzyl)-4,5-dihydroisoxazol-5-carboxylate

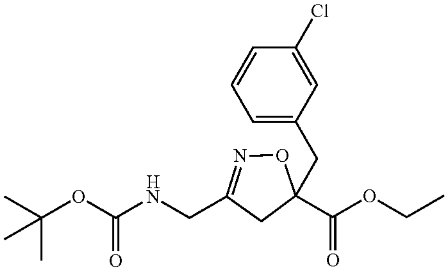

Ethyl 2-(3-chlorobenzyl)acrylate (0.96 g, 48%, 2 steps) was obtained using 3-chlorobenzyl bromide (1.17 ml, 8.92 mmol) by the preparation method of Preparation Example 13-(1). The title compound (0.4 g, 38%) was obtained using tert-butyl (2-(hydroxyimino)ethyl)carbamate (0.47 g, 2.67 mmol) obtained in Preparation Example 1-(1) by the preparation method of Preparation Example 1-(2).

NMR: $^1$H-NMR (400 MHz, $CDCl_3$); δ 7.25-7.14 (m, 5H), 4.68 (br s, 1H), 4.27-4.16 (q, 2H), 3.93-3.92 (d, 2H), 3.43-3.38 (d, 1H), 3.29-3.26 (d, 1H), 3.12-3.09 (d, 1H), 2.96-2.92 (d, 1H), 1.44 (s, 9H), 1.28-1.25 (t, 3H)

MS (m/z): 397[M+H]

Preparation Example 17: Preparation of ethyl 3-(((tert-butoxycarbonyl)amino)methyl)-5-(fluoro (phenyl)methyl)-4,5-dihydroisoxazol-5-carboxylate Through the processes (1) and (2) below, the title compound was obtained.

(1) Preparation of ethyl 2-(fluoro(phenyl)methyl)acrylate

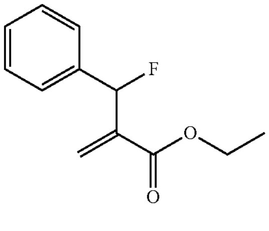

2-(Hydroxy-phenyl-methyl)-acrylic acid ethyl ester (0.412 g, 2.0 mmol) was dissolved in dichloromethane (10 ml), and diethylaminosulfur trifluoride (0.32 ml, 2.4 mmol) was added thereto at −78° C., followed by stirring for 2 hours. After quenching the reaction using a sodium bicarbonate aqueous solution, extraction with dichloromethane (20 ml) was performed twice, and an organic layer was dried over anhydrous magnesium sulfate, and filtered. The filtrate was distilled under a reduced pressure and separated by column chromatography to obtain the title compound (0.320 g, 77%).

NMR: $^1$H-NMR (500 MHz, $CDCl_3$); δ 7.49-7.30 (5H, m), 6.49 (1H, dd), 6.33 (1H, d), 6.05 (1H, s), 4.25-4.16 (2H, m), 1.27 (3H, t)

(2) Preparation of ethyl 3-(((tert-butoxycarbonyl) amino)methyl)-5-(fluoro(phenyl)methyl)-4,5-dihydroisoxazol-5-carboxylate

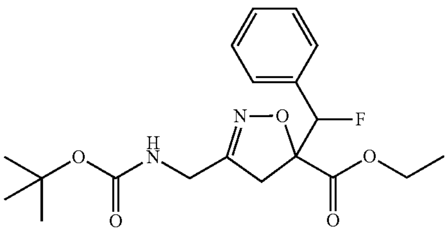 [SMILES: CCOC(=O)C1(C(F)c2ccccc2)CC(CNC(=O)OC(C)(C)C)=NO1]

Two types of the title compound of Isomer 1 having low polarity (0.089 g, 17%) and Isomer 2 having high polarity (0.100 g, 19%) were obtained using ethyl 2-(fluoro(phenyl) methyl)acrylate (0.244 g, 1.40 mmol) obtained in (1) above and tert-butyl (2-(hydroxyimino)ethyl)carbamate (0.320 g, 1.54 mmol) obtained in Preparation Example 1-(1) by the preparation method of Preparation Example 1-(2).

Isomer 1

NMR: $^1$H-NMR (500 MHz, $CDCl_3$); δ 7.42-7.35 (5H, m), 5.86 (1H, d), 4.81 (1H, br s), 4.30-4.20 (2H, m), 3.98-3.88 (2H, m), 3.40 (1H, d), 3.25 (1H, d), 1.46 (9H, s), 1.29 (3H, t)

Isomer 2

NMR: $^1$H-NMR (500 MHz, $CDCl_3$); δ 7.46-7.38 (5H, m), 5.95 (1H, d), 4.56 (1H, br s), 4.34-4.24 (2H, m), 3.91-3.78 (2H, m), 3.55 (1H, d), 3.25 (1H, d), 1.46 (9H, s), 1.31 (3H, t)

Preparation Example 18: Preparation of ethyl 3-(((tert-butoxycarbonyl)amino)methyl)-5-(3-methylbenzyl)-4,5-dihydroisoxazol-5-carboxylate

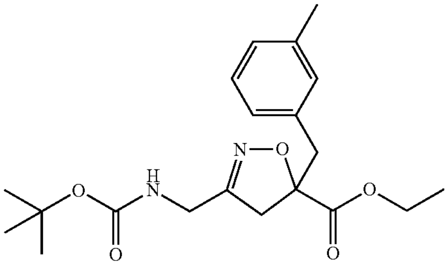 [SMILES: CCOC(=O)C1(Cc2cccc(C)c2)CC(CNC(=O)OC(C)(C)C)=NO1]

2-(3-Methyl-benzyl)-acrylic acid ethyl ester (0.7 g, 52%, 2 steps) was obtained using 3-methylbenzyl bromide (0.93 ml, 6.69 mmol) by the preparation method of Preparation Example 13-(1).

NMR: $^1$H-NMR (400 MHz, $CDCl_3$); δ 7.20-6.99 (m, 4H), 6.22 (s, 1H), 5.45 (s, 1H), 4.21-4.16 (q, 2H), 3.59 (s, 2H), 2.32 (s, 3H), 1.28-1.25 (t, 3H)

The title compound (0.38 g, 50%) was obtained using 2-(3-methyl-benzyl)-acrylic acid ethyl ester (0.37 g, 1.83 mmol) and tert-butyl (2-(hydroxyimino)ethyl)carbamate (0.35 g, 2.01 mmol) obtained in Preparation Example 1-(1) by the preparation method of Preparation Example 1-(2).

NMR: $^1$H-NMR (400 MHz, $CDCl_3$); δ 7.19-7.02 (m, 4H), 4.59 (br s, 1H), 4.27-4.18 (q, 2H), 3.89 (m, 2H), 3.40-3.35 (d, 1H), 3.27-3.23 (d, 1H), 3.11-3.08 (d, 1H), 2.98-2.93 (d, 1H), 2.32 (s, 3H), 1.43 (s, 9H), 1.29-1.24 (t, 3H)

MS (m/z): 377[M+H]

Preparation Example 19: Preparation of ethyl 3-(((tert-butoxycarbonyl)amino)methyl)-5-(phenoxymethyl)-4,5-dihydroisoxazol-5-carboxylate

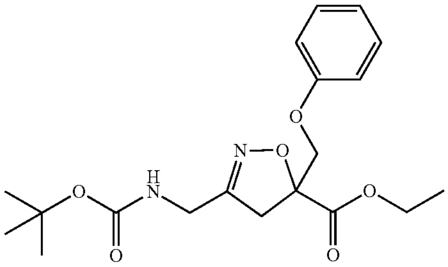

Ethyl 2-(phenoxymethyl)acrylate was obtained by the method described in U.S. Pat. No. 6,747,050. The title compound (0.59 g, 42%) was obtained using tert-butyl (2-(hydroxyimino)ethyl)carbamate (0.64 g, 3.67 mmol) obtained in Preparation Example 1-(1) and ethyl 2-(phenoxymethyl)acrylate (0.83 g, 4.04 mmol) by the preparation method of Preparation Example 1-(2).

NMR: $^1$H-NMR (400 MHz, $CDCl_3$); δ 7.31-7.28 (m, 2H), 7.00-6.89 (m, 3H), 4.93 (br s, 1H), 4.34-4.20 (m, 4H), 4.15-4.09 (d, 2H), 3.61-3.56 (d, 1H), 3.32-3.28 (d, 1H), 1.45 (s, 9H), 1.30-1.26 (t, 3H)

MS (m/z): 434[M+H]

Preparation Example 20: Preparation of ethyl 5-((1H-pyrazol-1-yl)methyl)-3-(((tert-butoxycarbonyl)amino)methyl)-4,5-dihydroisoxazol-5-carboxylate Through the processes (1) and (2) below, the title compound was obtained.

(1) Preparation of ethyl 2-((1H-pyrazol-1-yl)methyl)acrylate

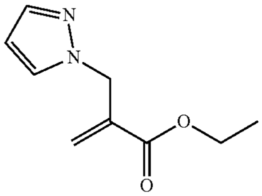

2-Hydroxymethyl-acrylic acid ethyl ester (2 g, 15.37 mmol) was dissolved in acetonitrile (20 ml). Potassium carbonate (38.42 mmol) and pyrazole (1.26 g, 18.44 mmol) were added thereto in order, followed by refluxing and stirring for 20 hours. Water was added, and extraction with ethyl acetate was performed. The organic layer thus extracted was washed with brine, dried over anhydrous magnesium sulfate, and filtered. The filtrate was distilled under a reduced pressure and separated by column chromatography to obtain the title compound (0.5 g, 18%).

NMR: $^1$H-NMR (400 MHz, $CDCl_3$); δ 7.54-7.53 (m, 1H), 7.47-7.46 (m, 1H), 6.34-6.33 (m, 1H), 6.28-6.26 (t, 1H), 5.46-5.45 (m, 1H), 5.00 (s, 2H), 4.33-4.20 (q, 2H), 1.34-1.28 (t, 3H)

(2) Preparation of ethyl 5-((1H-pyrazol-1-yl)methyl)-3-(((tert-butoxycarbonyl)amino)methyl)-4,5-dihydroisoxazol-5-carboxylate

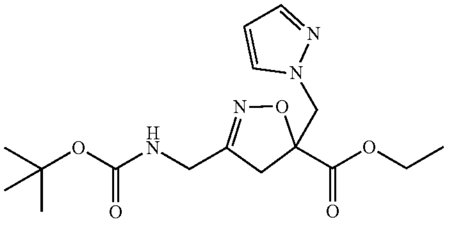 [SMILES: CCOC(=O)C1(Cn2cccn2)CC(CNC(=O)OC(C)(C)C)=NO1]

The title compound (0.58 g, 59%) was obtained using ethyl 2-((1H-pyrazol-1-yl)methyl)acrylate (0.5 g, 2.77 mmol) obtained in (1) above and tert-butyl (2-(hydroxyimino)ethyl)carbamate (0.73 g, 4.16 mmol) obtained in Preparation Example 1-(1) by the preparation method of Preparation Example 1-(2).

NMR: $^1$H-NMR (400 MHz, $CDCl_3$); δ 7.34-7.49 (m, 2H), 6.26-6.25 (m, 1H), 4.64-4.53 (m, 3H), 4.31-4.26 (q, 2H), 3.89-3.88 (m, 2H), 3.38 (s, 2H), 1.45 (s, 9H), 1.34-1.30 (t, 3H)

MS (m/z): 353[M+H]

Preparation Example 21: Preparation of ethyl 3-(((tert-butoxycarbonyl)amino)methyl)-5-(hydroxy(phenyl)methyl)-4,5-dihydroisoxazol-5-carboxylate

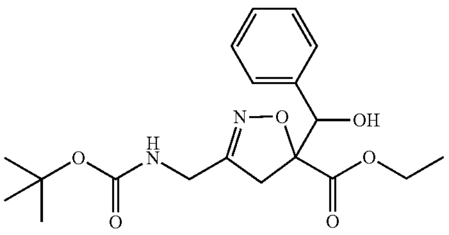 [SMILES: CCOC(=O)C1(C(O)c2ccccc2)CC(CNC(=O)OC(C)(C)C)=NO1]

The title compound (1.95 g, 64%) was obtained using 2-(hydroxy-phenyl-methyl)-acrylic acid ethyl ester (1.40 g, 8.0 mmol) and tert-butyl (2-(hydroxyimino)ethyl)carbamate (2.31 g, 11.2 mmol) obtained in Preparation Example 1-(1) by the preparation method of Preparation Example 1-(2).

NMR: $^1$H-NMR (500 MHz, $CDCl_3$); δ 7.44-7.26 (5H, m), 5.22 and 5.16 (1H, 2 d), 4.70 and 6.38 4.41 (1H, 2 s), 4.25-4.19 (2H, m), 3.95-3.73 (2H, m), 3.35-3.26 (2H, m), 2.85 and 2.80 (1H, 2 s), 1.45 and 1.44 (9H, 2 s), 1.29-1.24 (3H, m)

Preparation Example 22: Preparation of methyl 3-(((tert-butoxycarbonyl)amino)methyl)-5-(1-phenylethyl)-4,5-dihydroisoxazol-5-carboxylate Through the processes (1) and (2) below, the title compound was obtained.

(1) Preparation of methyl 2-methylene-3-phenylbutanoate

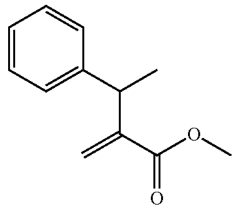

Palladium(II) acetate (0.045 g, 0.20 mmol) and 1,10-phenanthroline (0.040 g, 0.20 mmol) were dissolved in dimethylformamide (10 ml) and stirred for 30 minutes. To this solution, (E)-2-methyl-but-2-enoic acid methyl ester (0.72 ml, 6.00 mmol) and phenylboronic acid (0.488 g, 4.0 mmol) were added, followed by stirring at room temperature under an oxygen balloon for 16 hours. Diethyl ether (50 ml) was added thereto, and washing with a sodium bicarbonate aqueous solution and brine was performed. An organic layer was dried over anhydrous magnesium sulfate, and filtered. The filtrate was distilled under a reduced pressure and separated by column chromatography to obtain the title compound (0.546 g, 72%).

NMR: $^1$H-NMR (400 MHz, $CDCl_3$); δ 7.35-7.22 (5H, m), 6.33 (1H, s), 5.65 (1H, s), 3.72 (3H, s), 1.47 (2H, d)

(2) Preparation of methyl 3-(((tert-butoxycarbonyl)amino)methyl)-5-(1-phenylethyl)-4,5-dihydroisoxazol-5-carboxylate

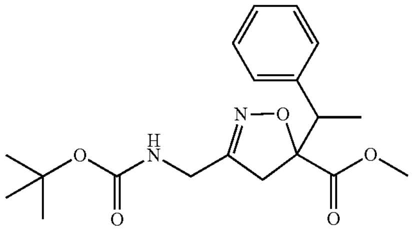 [SMILES: COC(=O)C1(C(C)c2ccccc2)CC(CNC(=O)OC(C)(C)C)=NO1]

The title compound (0.389 g, 52%) was obtained using methyl 2-methylene-3-phenylbutanoate (0.546 g, 2.87 mmol) obtained in (1) above and tert-butyl (2-(hydroxyimino)ethyl)carbamate (0.357 g, 2.05 mmol) obtained in Preparation Example 1-(1) by the preparation method of Preparation Example 1-(2).

NMR: $^1$H-NMR (400 MHz, $CDCl_3$); δ 7.35-7.27 (5H, m), 4.50-4.43 (1H, m), 3.89-3.81 (5H, m), 3.51-3.41 (1H, m), 3.24 (1H, d), 3.01 (1H, d), 1.47 (9H, s), 1.42 (3H, d)

Preparation Example 23: Preparation of ethyl 3-(((tert-butoxycarbonyl)amino)methyl)-5-(thiazol-4-ylmethyl)-4,5-dihydroisoxazol-5-carboxylate Through the processes (1) and (2) below, the title compound was obtained.

(1) Preparation of ethyl 2-(thiazol-4-ylmethyl)acrylate

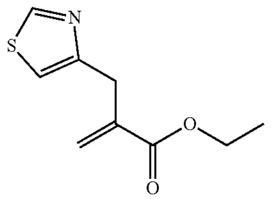

Malonic acid diethyl ester (0.59 ml, 3.85 mmol) was dissolved in dimethylamide (10 ml). At 0° C., sodium hydride (0.162 g, 4.05 mmol), and 4-chloromethyl-thiazole (0.52 g, 3.85 mmol) were added in order, followed by stirring at room temperature for 16 hours. The solvent was distilled under a reduced pressure, water was added, and extraction with ethyl acetate was performed twice. The organic layer thus extracted was washed with brine, dried over anhydrous magnesium sulfate, and filtered. The filtrate was distilled under a reduced pressure and separated by column chromatography to obtain 2-thiazol-4-ylmethyl-malonic acid diethyl ester (0.55 g, 56%).

NMR: $^1$H-NMR (400 MHz, $CDCl_3$); δ 8.74-8.73 (d, 1H), 7.06-7.05 (m, 1H), 4.24-4.11 (m, 2H), 3.95-3.91 (t, 1H), 3.43-3.41 (d, 2H), 1.24-1.21 (t, 3H)

The 2-thiazol-4-ylmethyl-malonic acid diethyl ester (0.55 g, 2.14 mmol) obtained above was dissolved in ethanol (20 ml). At 0° C., potassium hydroxide (0.114 g, 2.03 mmol) dissolved in ethanol (10 ml) was slowly added thereto and stirred for 48 hours. After titrating pH 2 with 1 N hydrochloric acid, water was added, and the resultant product was extracted with ethyl acetate, dried over anhydrous magnesium sulfate, and filtered. The filtrate was distilled under a reduced pressure and separated by column chromatography to obtain the title compound of 2-thiazol-4-ylmethyl-malonic acid monoethyl ester (0.36 g, 73%).

NMR: $^1$H-NMR (400 MHz, $CDCl_3$); δ 8.81 (d, 1H), 7.14-7.13 (m, 1H), 4.22-4.16 (q, 2H), 3.93-3.89 (t, 1H), 3.47-3.43 (m, 2H), 1.25-1.20 (t, 3H)

The 2-thiazol-4-ylmethyl-malonic acid monoethyl ester (0.36 g, 1.56 mmol) obtained above was dissolved in pyridine (10 ml). Paraformaldehyde (0.045 g, 1.48 mmol) and piperidine (0.015 ml, 0.16 mmol) were added thereto in order, followed by refluxing and stirring at 120° C. for 3 hours. After adding water and extracting with hexane, an organic layer was washed with water, 1 N hydrochloric acid, water, a sodium carbonate aqueous solution, and brine in order, dried over anhydrous magnesium sulfate, and filtered. The filtrate was distilled under a reduced pressure and separated by column chromatography to obtain the title compound (0.2 g, 65%).

NMR: $^1$H-NMR (500 MHz, $CDCl_3$); δ 8.75-8.73 (m, 1H), 7.04-7.00 (m, 1H), 6.29 (s, 1H), 5.60 (s, 1H), 4.21-4.16 (q, 2H), 3.86 (2H), 1.26-1.23 (t, 3H)

(2) Preparation of ethyl 3-(((tert-butoxycarbonyl)amino)methyl)-5-(thiazol-4-ylmethyl)-4,5-dihydroisoxazol-5-carboxylate

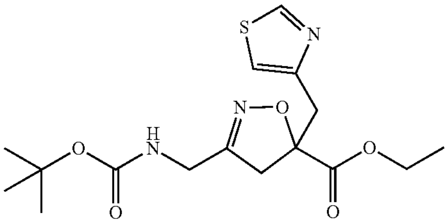 [SMILES: CCOC(=O)C1(Cc2cscn2)CC(CNC(=O)OC(C)(C)C)=NO1]

The title compound (0.30 g, 40%) was obtained using ethyl 2-(thiazol-4-ylmethyl)acrylate (0.2 g, 1.01 mmol) obtained in (1) above and tert-butyl (2-(hydroxyimino)ethyl) carbamate (0.35 g, 2.03 mmol) obtained in Preparation Example 1-(1) by the preparation method of Preparation Example 1-(2).

NMR: $^1$H-NMR (500 MHz, $CDCl_3$); δ 8.72 (d, 1H), 7.20 (d, 1H), 4.76 (br s, 1H), 4.28-4.22 (q, 2H), 3.92-3.94 (d, 2H), 3.49-3.27 (m, 4H), 1.45 (s, 9H), 1.31-1.27 (t, 3H)

MS (m/z): 370[M+H]

Preparation Example 24: Preparation of methyl 5-benzyl-3-((S)-1-((tert-butoxycarbonyl)amino)ethyl)-4,5-dihydroisoxazol-5-carboxylate

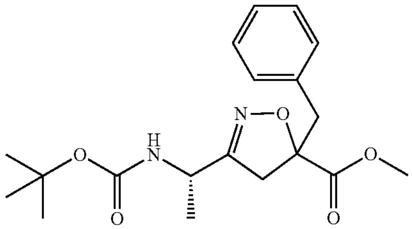 [SMILES: COC(=O)C1(Cc2ccccc2)CC([C@H](C)NC(=O)OC(C)(C)C)=NO1]

Tert-butyl (S)-(1-(hydroxyimino)propan-2-yl)carbamate (0.54 g, 99%) was obtained using (S)-1-methyl-2-oxo-ethyl)-carbamic acid tert-butyl ester (0.5 g, 2.89 mmol) by the preparation method of Preparation Example 1-(1). The title compound (0.36 g, 43%) was obtained using tert-butyl (S)-(1-(hydroxyimino)propan-2-yl)carbamate (0.44 g, 2.31 mmol) and methyl 2-benzylacrylate (0.45 g, 2.54 mmol) obtained in Preparation Example 6-(1) by the preparation method of Preparation Example 1-(2).

NMR: $^1$H-NMR (400 MHz, $CDCl_3$); δ 7.29-2.20 (m, 3H), 4.79 (m, 1H), 4.31 (br s, 1H), 3.78-3.77 (d, 3H), 3.39-3.28 (m, 2H), 3.11-3.05 (m, 1H), 2.95-2.92 (d, 1H), 1.43-1.41 (d, 9H), 1.14-1.13 (d, 3H)

MS (m/z): 363[M+H]

Preparation Example 25: Preparation of methyl 5-benzyl-3-((S)-1-((tert-butoxycarbonyl)amino)-2-methylpropyl)-4,5-dihydroisoxazol-5-carboxylate

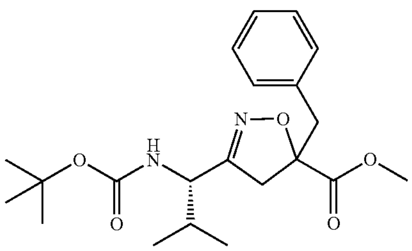 [SMILES: COC(=O)C1(Cc2ccccc2)CC([C@@H](NC(=O)OC(C)(C)C)C(C)C)=NO1]

The title compound (1.62 g, 82%) was obtained using tert-butyl (S)-(1-(hydroxyimino)-3-methylbutan-2-yl)carbamate (1.09 g, 5.04 mmol) obtained in Preparation Example 3-(2) and methyl 2-benzylacrylate (0.98 g, 5.54 mmol) obtained in Preparation Example 6-(1) by the preparation method of Preparation Example 1-(2).

NMR: $^1$H-NMR (500 MHz, $CDCl_3$); δ 7.31-7.23 (m, 5H), 4.85-4.4.59 (m, 1H), 4.22-4.13 (m 1H), 3.36-3.28 (m, 2H), 3.14-3.07 (m, 1H), 2.92-2.88 (m, 1H), 1.95-1.88 (m, 1H), 1.42-1.41 (d, 9H), 0.82-0.56 (m, 6H)

MS (m/z): 391[M+H]

Preparation Example 26: Preparation of methyl 5-benzyl-3-((S)-1-((tert-butoxycarbonyl)amino)-3-methylbutyl)-4,5-dihydroisoxazol-5-carboxylate

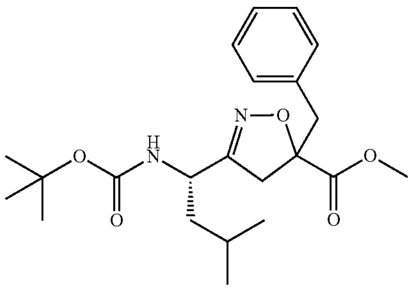 [SMILES: COC(=O)C1(Cc2ccccc2)CC([C@H](CC(C)C)NC(=O)OC(C)(C)C)=NO1]

The title compound (0.51 g, 67%) was obtained using tert-butyl (S)-(1-(hydroxyimino)-4-methylpentan-2-yl)carbamate (0.42 g, 1.84 mmol) obtained in Preparation Example 4-(1) and methyl 2-benzylacrylate (0.39 g, 2.21 mmol) obtained in Preparation Example 6-(1) by the preparation method of Preparation Example 1-(2).

NMR: $^1$H-NMR (500 MHz, $CDCl_3$); δ 7.31-7.23 (m, 5H), 4.58 (m, 1H), 4.30 (m, 1H), 3.40-3.29 (m, 2H), 3.28-2.90 (m, 2H), 1.43-1.42 (d, 9H), 1.37-1.31 (m, 3H), 0.86-0.81 (m, 6H)

MS (m/z): 405[M+H]

Preparation Example 27: Preparation of methyl 5-benzyl-3-((R)-1-((tert-butoxycarbonyl)amino)-2-methoxyethyl)-4,5-dihydroisoxazol-5-carboxylate Through the processes (1), (2), (3) and (4) below, the title compound was obtained.

(1) Preparation of methyl N-(tert-butoxycarbonyl)-O-methyl-L-serinate

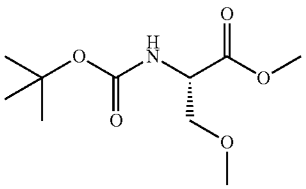 [SMILES: COC[C@H](NC(=O)OC(C)(C)C)C(=O)OC]

(S)-2-tert-butoxycarbonylamino-3-hydroxy-propionic acid methyl ester (1.5 g, 6.84 mmol) was dissolved in acetonitrile (20 ml), and silver(II) oxide (7.93 g, 34.21 mmol) and iodomethane (4.26 ml, 68.42 mmol) were added thereto in order. Stirring was performed at room temperature for 20 hours, while blocking the light. After filtering with celite, the resultant product was distilled under a reduced pressure and separated by column chromatography to obtain the title compound (0.58 g, 36%).

NMR: $^1$H-NMR (400 MHz, $CDCl_3$); δ 5.35 (m, 1H), 4.43-4.41 (m, 1H), 3.81-3.79 (m, 1H), 3.78 (s, 3H), 3.61-3.58 (m, 1H), 3.34 (s, 3H), 1.45 (s, 9H)

(2) Preparation of tert-butyl (S)-(1-methoxy-3-oxopropan-2-yl)carbamate

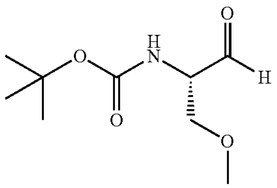

The methyl N-(tert-butoxycarbonyl)-O-methyl-L-serinate (0.58 g, 2.49 mmol) obtained in (1) above was dissolved in toluene (10 ml) under a nitrogen charge. At −78° C., a diisobutylaluminum hydride 1.5 M toluene solution (2.82 ml, 4.23 mmol) was added thereto, followed by stirring for 2 hours. After quenching with methanol (4 ml), a 1 N hydrochloric acid aqueous solution was added, and extraction with ethyl acetate was performed. The organic layer thus extracted was dried over anhydrous magnesium sulfate, filtered, and separated by column chromatography to obtain the title compound (0.42 g, 83%).

NMR: $^1$H-NMR (400 MHz, $CDCl_3$); δ 9.64 (s, 1H), 5.40 (br s, 1H), 4.29 (m, 1H), 3.92-3.90 (m, 1H), 3.64-3.61 (m, 1H), 3.34 (s, 3H), 1.46 (s, 9H)

(3) Preparation of tert-butyl (R)-(1-(hydroxyimino)-3-methoxypropan-2-yl)carbamate

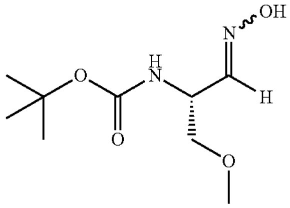

The title compound (0.45 g, 99%) was obtained using tert-butyl (S)-(1-methoxy-3-oxopropan-2-yl)carbamate (0.42 g, 2.07 mmol) obtained in (2) above by the preparation method of Preparation Example 1-(1).

(4) Preparation of methyl 5-benzyl-3-((R)-1-((tert-butoxycarbonyl)amino)-2-methoxyethyl)-4,5-dihydroisoxazol-5-carboxylate

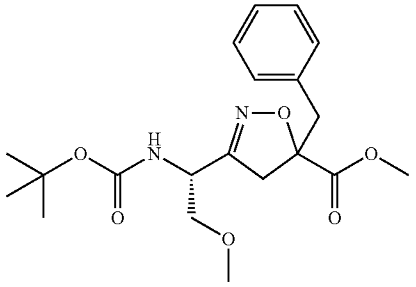 [SMILES: COC[C@H](NC(=O)OC(C)(C)C)C1=NOC(Cc2ccccc2)(C(=O)OC)C1]

The title compound (0.42 g, 52%) was obtained using tert-butyl (R)-(1-(hydroxyimino)-3-methoxypropan-2-yl) carbamate (0.45 g, 2.06 mmol) obtained in (3) above and methyl 2-benzylacrylate (0.44 g, 2.47 mmol) obtained in Preparation Example 6-(1) by the preparation method of Preparation Example 1-(2).

NMR: $^1$H-NMR (400 MHz, $CDCl_3$); δ 7.30-7.22 (m, 5H), 5.15-4.93 (m, 1H), 4.46 (m, 1H), 3.77 (dd, 3H), 3.50-3.27 (m, 4H), 3.26 (s, 3H), 3.17-2.95 (m, 2H), 1.43-1.42 (d, 9H)

MS (m/z): 393[M+H]

Preparation Example 28: Preparation of ethyl 3-(((tert-butoxycarbonyl)amino)methyl)-5-(2-methylbenzyl)-4,5-dihydroisoxazol-5-carboxylate

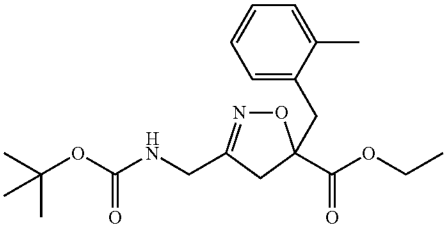 [SMILES: CCOC(=O)C1(Cc2ccccc2C)CC(CNC(=O)OC(C)(C)C)=NO1]

2-(2-Methyl-benzyl)-acrylic acid ethyl ester (0.84 g, 4.1 mmol) was obtained using 2-methylbenzyl bromide (1.0 g, 5.4 mmol) by the preparation method of Preparation Example 13-(1). The title compound (0.10 g, 68%) was obtained using 2-(2-methyl-benzyl)-acrylic acid ethyl ester (0.082 g, 0.40 mmol) and tert-butyl (2-(hydroxyimino)ethyl) carbamate (0.14 g, 0.80 mmol) obtained in Preparation Example 1-(1) by the preparation method of Preparation Example 1-(2).

MS (m/z): 377[M+H]

Preparation Example 29: Preparation of methyl 3-(((tert-butoxycarbonyl)amino)methyl)-5-(difluoro (phenyl)methyl)-4,5-dihydroisoxazol-5-carboxylate Through the processes (1), (2), (3), (4) and (5) below, the title compound was obtained.

(1) Preparation of 2,2-difluoro-2-phenylethan-1-ol

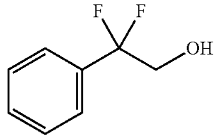 [SMILES: OCC(F)(F)c1ccccc1]

2-Bromoacetophenone (1.50 g, 7.54 mmol) was dissolved in benzene (15 ml), and at room temperature, diethylaminosulfur trifluoride (2.0 ml, 15.1 mmol) was added thereto, followed by stirring at 60° C. for 48 hours. After cooling the reaction product to room temperature, water was added, and extraction with diethyl ether (50 ml) was performed twice. An organic layer was dried over anhydrous magnesium sulfate, and filtered. The filtrate was distilled under a reduced pressure and separated by column chromatography to obtain (2-bromo-1,1-difluoro-ethyl)-benzene (1.12 g, 67%).

NMR: $^1$H-NMR (400 MHz, $CDCl_3$); δ 7.57-7.31 (5H, m), 3.81 (2H, dt)

(2-Bromo-1,1-difluoro-ethyl)-benzene (1.12 g, 5.07 mmol), potassium acetate (1.99 g, 20.3 mmol), and 18-C-6 crown ether (0.134 g, 0.507 mmol) were dissolved in dimethylacetamide (10 ml) and stirred at 150° C. for 18 hours. The reaction product was cooled to room temperature, water was added thereto, and extraction with diethyl ether (50 ml) was performed twice. An organic layer was dried over anhydrous magnesium sulfate, and filtered. The filtrate was distilled under a reduced pressure and separated by column chromatography to obtain acetic acid 2,2-difluoro-2-phenyl-ethyl ester (0.634 g, 62%).

NMR: $^1$H-NMR (400 MHz, $CDCl_3$); δ 7.57-7.47 (5H, m), 4.57 (2H, dt), 2.13 (3H, s)

Acetic acid 2,2-difluoro-2-phenyl-ethyl ester (0.634 g, 3.17 mmol) was dissolved in methanol (12 ml) and treated with 1 N NaOH (3.2 ml), followed by stirring at room temperature for 2 hours. Water was added to the reaction product, methanol was removed under a reduced pressure, and extraction with dichloromethane (20 ml) was performed twice. An organic layer was dried over anhydrous magnesium sulfate, and filtered. The filtrate was distilled under a reduced pressure and separated by column chromatography to obtain the title compound (0.489 g, 98%).

NMR: $^1$H-NMR (400 MHz, $CDCl_3$); δ 7.58-7.47 (5H, m), 4.02 (2H, t)

(2) Preparation of 3,3-difluoro-2-hydroxy-3-phenylpropanenitrile

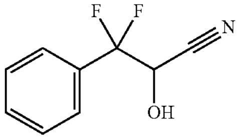 [SMILES: N#CC(O)C(F)(F)c1ccccc1]

Oxalyl chloride (0.29 ml, 3.38 mmol) was dissolved in dichloromethane (6 ml), the temperature was set to −78° C., and dimethyl sulfoxide (0.49 ml, 6.90 mmol) was slowly added thereto. After stirring the reactants for 30 minutes, a solution of 2,2-difluoro-2-phenylethan-1-ol (0.489 g, 3.09 mmol) obtained in (1) above dissolved in dichloromethane (2 ml) was added, followed by stirring for 30 minutes. After adding triethylamine (1.90 ml, 13.6 mmol) to the reaction product, the temperature was slowly raised to room temperature, and stirring was performed for 18 hours. Water was added, and extraction with dichloromethane (30 ml) was performed twice. An organic layer was dried over anhydrous magnesium sulfate, and filtered, and the filtrate was distilled under a reduced pressure to obtain the title compound of difluoro-phenyl-acetaldehyde (0.531 g).

The difluoro-phenyl-acetaldehyde (0.531 g) obtained above was dissolved in tetrahydrofuran (30 ml), and p-toluenesulfonic acid monohydrate (0.705 g, 3.71 mmol) and potassium cyanide (0.242 g, 3.72 mmol) were added in order, followed by stirring at 40° C. for 3 hours. The reaction product was cooled to room temperature, water was added thereto, the solvent was removed under a reduced pressure, and extraction with diethyl ether (20 ml) was performed three times. An organic layer was washed with a sodium disulfite aqueous solution, dried over anhydrous magnesium sulfate, and filtered. The filtrate was distilled under a reduced pressure and separated by column chromatography to obtain the title compound (0.327 g, 58%, 2 steps).

NMR: $^1$H-NMR (400 MHz, $CDCl_3$); δ 7.57-7.43 (5H, m), 4.80 (1H, t)

(3) Preparation of methyl 3,3-difluoro-2-hydroxy-3-phenylpropanoate

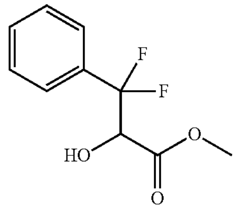

The 3,3-difluoro-2-hydroxy-3-phenylpropanenitrile (0.327 g, 1.79 mmol) obtained in (2) above was dissolved in MeOH (8 ml), and 4 N HCl (8.0 ml) was added thereto, followed by stirring at 65° C. for 48 hours. The reaction product was cooled to room temperature, water was added thereto, methanol was removed under a reduced pressure, and extraction with dichloromethane (20 ml) was performed twice. An organic layer was dried over anhydrous magnesium sulfate, and filtered. The filtrate was distilled under a reduced pressure and separated by column chromatography to obtain the title compound (0.318 g, 82%).

NMR: $^1$H-NMR (400 MHz, $CDCl_3$); δ 7.58-7.46 (5H, m), 4.60 (1H, dt), 3.87 (3H, s), 3.26 (1H, d)

(4) Preparation of methyl 2-(difluoro(phenyl)methyl)acrylate

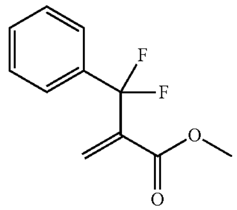

The methyl 3,3-difluoro-2-hydroxy-3-phenylpropanoate (0.419 g, 1.94 mmol) obtained in (3) above was dissolved in dimethylsulfoxide (15 ml), and 2-iodoxybenzoic acid (IBX, 1.29 g, 4.61 mmol) was added thereto, followed by stirring at room temperature for 2 hours. Water and ethyl acetate were added to the reaction product, the solid thus precipitated was removed under a reduced pressure, and the filtrate was extracted with ethyl acetate (30 ml) twice. An organic layer was dried over anhydrous magnesium sulfate, and filtered. The filtrate was distilled under a reduced pressure and separated by column chromatography to obtain 3,3-difluoro-2-oxo-3-phenyl-propionic acid methyl ester (0.282 g, 68%).

Methyltriphenylphosphonium bromide (1.18 g, 3.30 mmol) and potassium t-butoxide (0.356 g, 3.17 mmol) were dissolved in tetrahydrofuran (10 ml), followed by stirring at room temperature for 1 hour. The temperature of the reaction product was set to −30° C., and a solution of the 3,3-difluoro-2-oxo-3-phenyl-propionic acid methyl ester (0.282 g, 1.32 mmol) obtained above dissolved in tetrahydrofuran (2 ml) was added thereto. The temperature of the reaction product was slowly raised to room temperature, and stirring was performed at room temperature for 18 hours. After adding water, the resultant product was extracted with ethyl acetate (20 ml) twice, dried over anhydrous magnesium sulfate, and filtered. The filtrate was distilled under a reduced pressure and separated by column chromatography to obtain the title compound (0.114 g, 41%).

NMR: $^1$H-NMR (400 MHz, $CDCl_3$); δ 7.67-7.43 (5H, m), 6.68 (1H, s), 6.40 (1H, s), 3.74 (3H, s)

(5) Preparation of methyl 3-(((tert-butoxycarbonyl)amino)methyl)-5-(difluoro(phenyl)methyl)-4,5-dihydroisoxazol-5-carboxylate

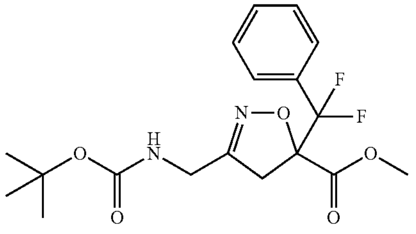 [SMILES: COC(=O)C1(C(F)(F)c2ccccc2)CC(CNC(=O)OC(C)(C)C)=NO1]

The title compound (0.173 g, 84%) was obtained using methyl 2-(difluoro(phenyl)methyl)acrylate (0.114 g, 0.537 mmol) obtained in (4) above and tert-butyl (2-(hydroxyimino)ethyl)carbamate (0.375 g, 2.15 mmol) obtained in Preparation Example 1-(1) by the preparation method of Preparation Example 1-(2).

NMR: $^1$H-NMR (400 MHz, $CDCl_3$); δ 7.61-7.45 (5H, m), 4.28 (1H, d), 4.01 (2H, s), 3.77 (3H, s), 3.60 (2H, d), 1.49 (9H, s)

Preparation Example 30: Preparation of methyl 5-benzyl-3-(2-((tert-butoxycarbonyl)amino)propan-2-yl)-4,5-dihydroisoxazol-5-carboxylate Through the processes (1) and (2) below, the title compound was obtained.

(1) Preparation of tert-butyl (1-(hydroxyimino)-2-methylpropan-2-yl)carbamate

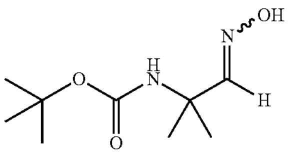

(1,1-Dimethyl-2-oxo-ethyl)-carbamic acid tert-butyl ester was obtained by the method described in EP2036896 A1. The title compound (1.07 g, 99%) was obtained using (1,1-dimethyl-2-oxo-ethyl)-carbamic acid tert-butyl ester (1 g, 5.34 mmol) by the preparation method of Preparation Example 1-(1).

(2) Preparation of methyl 5-benzyl-3-(2-((tert-butoxycarbonyl)amino)propan-2-yl)-4,5-dihydroisoxazol-5-carboxylate

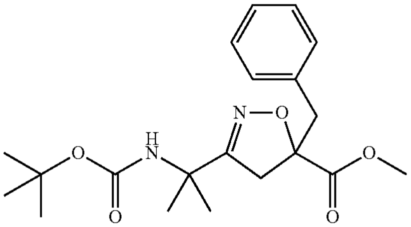 [SMILES: COC(=O)C1(Cc2ccccc2)CC(C(C)(C)NC(=O)OC(C)(C)C)=NO1]

The title compound (0.37 g, 18%) was obtained using tert-butyl (1-(hydroxyimino)-2-methylpropan-2-yl)carbamate (0.69 g, 3.41 mmol) obtained in (1) above and methyl 2-benzylacrylate (0.4 g, 2.27 mmol) obtained in Preparation Example 6-(1) by the preparation method of Preparation Example 1-(2).

NMR: $^1$H-NMR (500 MHz, $CDCl_3$); δ 7.29-7.22 (m, 5H), 4.77 (br s, 1H), 3.77 (s, 3H), 3.41-3.36 (d, 1H), 3.36-3.31 (d, 1H), 3.17-3.13 (d, 1H), 2.98-2.94 (d, 1H), 1.58 (s, 3H), 1.41 (s, 9H), 1.36 (s, 3H)

MS (m/z): 377[M+H]

Preparation Example 31: Preparation of ethyl 3-(((tert-butoxycarbonyl)amino)methyl)-5-penetyl-4,5-dihydroisoxazol-5-carboxylate Through the processes (1) and (2) below, the title compound was obtained.

(1) Preparation of ethyl 2-methylene-4-phenylbutanoate

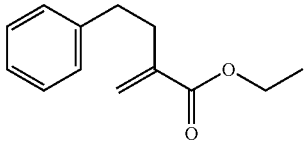

(Diethoxy-phosphoryl)-acetic acid ethyl ester (3.0 g, 13.38 mmol) was dissolved in dichloroformamide (30 ml). Sodium hydride (0.59 g, 14.72 mmol) was slowly added thereto at 0° C., and after 30 minutes, (2-bromo-ethyl)-benzene (1.83 ml, 13.38 mmol) was added thereto, followed by stirring at room temperature for 18 hours. After finishing the reaction, water was added, and extraction with diethyl ether was performed. An organic layer was washed with brine, dried over anhydrous magnesium sulfate, and filtered. The filtrate was distilled under a reduced pressure and used in the next reaction without separation.

The product (4.11 g, 12.50 mmol) obtained above and a 37% formaldehyde aqueous solution (6.3 ml, 80.01 mmol) were dissolved in water (30 ml), and potassium carbonate (5.2 g, 37.51 mmol) dissolved in water (10 ml) was added thereto. After refluxing and stirring at 90° C. for 16 hours, water was added, and extraction with diethyl ether was performed. An organic layer was washed with brine and dried over anhydrous magnesium sulfate. The filtrate was distilled under a reduced pressure and separated by column chromatography to obtain the title compound (1.39 g, 51%, 2 steps).

NMR: $^1$H-NMR (400 MHz, $CDCl_3$); δ 7.31-7.17 (m, 5H), 6.15 (s, 1H), 5.5 (s, 1H), 4.26-4.21 (q, 2H), 2.81-2.78 (t, 2H), 2.63-2.59 (t, 2H), 1.31-1.29 (t, 3H)

(2) Preparation of ethyl 3-(((tert-butoxycarbonyl)amino)methyl)-5-penetyl-4,5-dihydroisoxazol-5-carboxylate

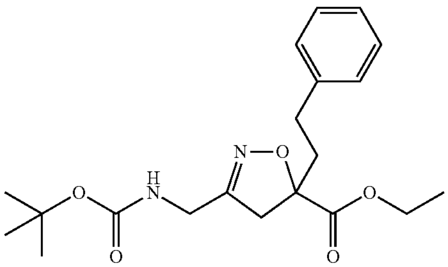 [SMILES: CCOC(=O)C1(CCc2ccccc2)CC(CNC(=O)OC(C)(C)C)=NO1]

The title compound (0.27 g, 30%) was obtained using ethyl 2-methylene-4-phenylbutanoate (0.5 g) obtained in (1) above and tert-butyl (2-(hydroxyimino)ethyl)carbamate (0.36 g) obtained in Preparation Example 1-(1) by the preparation method of Preparation Example 1-(2).

NMR: $^1$H-NMR (400 MHz, $CDCl_3$); δ 7.29-7.13 (m, 5H), 4.87 (br s, 1H), 4.23-4.21 (m, 2H), 3.45-4.43 (d, 1H), 2.96-2.94 (d, 1H), 2.71-2.59 (m, 2H), 2.31-2.21 (m, 2H), 1.45 (s, 9H), 1.31-1.29 (t, 3H)

MS (m/z): 377[M+H]

Preparation Example 32: Preparation of ethyl 3-(((tert-butoxycarbonyl)amino)methyl)-5-(2-(trifluoromethyl)benzyl)-4,5-dihydroisoxazol-5-carboxylate

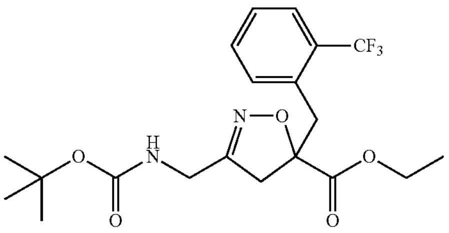 [SMILES: CCOC(=O)C1(Cc2ccccc2C(F)(F)F)CC(CNC(=O)OC(C)(C)C)=NO1]

2-(2-Trifluoromethyl-benzyl)-acrylic acid ethyl ester (0.24 g, 0.93 mmol) was obtained using 2-(trifluoromethyl) benzyl chloride (0.47 g, 2.42 mmol) by the preparation method of Preparation Example 13-(1). The title compound (0.09 g, 22%) was obtained using 2-(2-trifluoromethyl-benzyl)-acrylic acid ethyl ester (0.24 g, 0.93 mmol) and tert-butyl (2-(hydroxyimino)ethyl)carbamate (0.18 g, 1.02 mmol) obtained in Preparation Example 1-(1) by the preparation method of Preparation Example 1-(2).

MS (m/z): 431[M+H]

Preparation Example 33: Preparation of ethyl 3-(((tert-butoxycarbonyl)amino)methyl)-5-(2-fluorobenzyl)-4,5-dihydroisoxazol-5-carboxylate

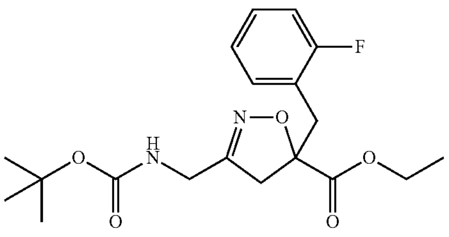 [SMILES: CCOC(=O)C1(Cc2ccccc2F)CC(CNC(=O)OC(C)(C)C)=NO1]

2-(2-Fluoro-benzyl)-acrylic acid ethyl ester (0.76 g, 3.65 mmol) was obtained using 2-fluorobenzyl bromide (1.0 g, 5.3 mmol) by the preparation method of Preparation Example 13-(1). The title compound (0.11 g, 30%) was obtained using 2-(2-fluoro-benzyl)-acrylic acid ethyl ester (0.21 g, 1.0 mmol) and tert-butyl (2-(hydroxyimino)ethyl) carbamate (0.17 g, 1.0 mmol) obtained in Preparation Example 1-(1) by the preparation method of Preparation Example 1-(2).

MS (m/z): 381[M+H]

Preparation Example 34: Preparation of ethyl 3-(((tert-butoxycarbonyl)amino)methyl)-5-(2,6-difluorobenzyl)-4,5-dihydroisoxazol-5-carboxylate

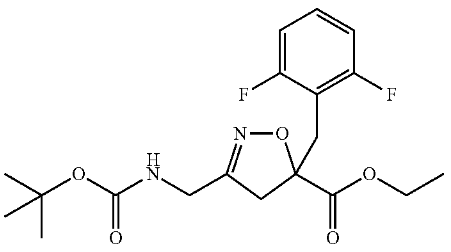 [SMILES: CCOC(=O)C1(Cc2c(F)cccc2F)CC(CNC(=O)OC(C)(C)C)=NO1]

2-(2,6-Difluoro-benzyl)-acrylic acid ethyl ester (0.79 g, 3.49 mmol) was obtained using 2,6-difluorobenzyl bromide (1.0 g, 4.83 mmol) by the preparation method of Preparation Example 13-(1). The title compound (0.476 g, 34%) was obtained using 2-(2,6-difluoro-benzyl)-acrylic acid ethyl ester (0.79 g, 3.49 mmol) and tert-butyl (2-(hydroxyimino) ethyl)carbamate (1.21 g, 6.38 mmol) obtained in Preparation Example 1-(1) by the preparation method of Preparation Example 1-(2).

MS (m/z): 399[M+H]

Preparation Example 35: Preparation of ethyl 3-(((tert-butoxycarbonyl)amino)methyl)-5-(2,4-difluorobenzyl)-4,5-dihydroisoxazol-5-carboxylate

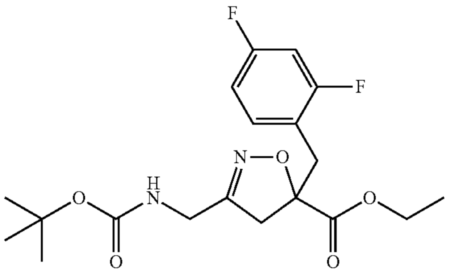 [SMILES: CCOC(=O)C1(Cc2ccc(F)cc2F)CC(CNC(=O)OC(C)(C)C)=NO1]

2-(2,4-Difluoro-benzyl)-acrylic acid ethyl ester (0.67 g, 3.0 mmol) was obtained using 2,4-difluorobenzyl bromide (1 g, 4.8 mmol) by the preparation method of Preparation Example 13-(1). The title compound (0.20 g, 37%) was obtained using 2-(2,4-difluoro-benzyl)-acrylic acid ethyl ester (0.30 g, 1.33 mmol) and tert-butyl (2-(hydroxyimino) ethyl)carbamate (0.28 g, 1.6 mmol) obtained in Preparation Example 1-(1) by the preparation method of Preparation Example 1-(2).

MS (m/z): 399[M+H]

Preparation Example 36: Preparation of methyl 3-(((tert-butoxycarbonyl)amino)methyl)-5-(1-phenylcyclopropyl)-4,5-dihydroisoxazol-5-carboxylate Through the processes of (2), (3), (4) and (5) below, the title compound was obtained.

(1) Preparation of 1-phenylcyclopropan-1-carbonitrile

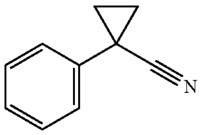 [SMILES: N#CC1(c2ccccc2)CC1]

Phenylacetonitrile (4.46 g, 40.0 mmol), tetra-butylammonium bromide (0.129 g, 0.40 mmol), and potassium hydroxide (22.4 g, 400 mmol) were dissolved in water, and 1,2-dibromoethane (6.90 ml, 80.0 mmol) was added thereto at 50° C., followed by stirring for 2 hours. The reaction product was cooled to room temperature, water was added thereto, and extraction with diethyl ether (100 ml) was performed twice. An organic layer was dried over anhydrous magnesium sulfate, and filtered. The filtrate was distilled under a reduced pressure and separated by column chromatography to obtain the title compound (3.61 g, 63%).

NMR: $^1$H-NMR (400 MHz, $CDCl_3$); δ 7.42-7.31 (5H, m), 1.79-1.76 (2H, m), 1.47-1.44 (2H, m)

(2) Preparation of 2-hydroxy-2-(1-phenylcyclopropyl)acetonitrile

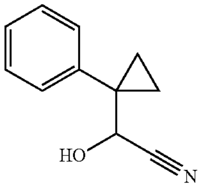 [SMILES: N#CC(O)C1(c2ccccc2)CC1]

The 1-phenylcyclopropan-1-carbonitrile (3.61 g, 25.2 mmol) obtained in (1) above was dissolved in dichloromethane (40 ml), a diisoaluminum hydride 1.5 M toluene solution (18.5 ml, 27.8 mmol) was slowly added thereto at 0° C., followed by stirring at room temperature for 2 hours. To the reaction product, 1 N HCl (150 ml) was slowly added at 0° C., and extraction with dichloromethane (100 ml) was performed twice. An organic layer was dried over anhydrous magnesium sulfate, and filtered. The filtrate was distilled under a reduced pressure to obtain 1-phenyl-cyclopropanecarbaldehyde (3.19 g, 87%). The title compound (2.69 g, 71%) was obtained using the 1-phenyl-cyclopropanecarbaldehyde (3.1 g, 21.8 mmol) obtained above by the preparation method of Preparation Example 29-(2).

NMR: $^1$H-NMR (400 MHz, $CDCl_3$); δ 7.53-7.36 (5H, m), 4.24 (1H, s), 2.46 (1H, br s), 1.19-1.06 (4H, m)

(3) Preparation of methyl 2-hydroxy-2-(1-phenylcyclopropyl)acetate

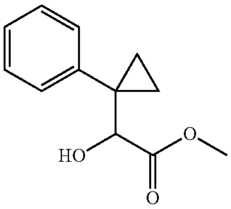

The title compound (0.986 g, 83%) was obtained using 2-hydroxy-2-(1-phenylcyclopropyl)acetonitrile (1.0 g, 5.77 mmol) obtained in (2) above by the preparation method of Preparation Example 29-(3).

NMR: $^1$H-NMR (400 MHz, $CDCl_3$); 7.37-7.27 (5H, m), 3.78 (3H, s), 3.74 (1H, d), 2.87 (1H, d), 1.31-0.94 (4H, m)

(4) Preparation of methyl 2-(1-phenylcyclopropyl)acrylate

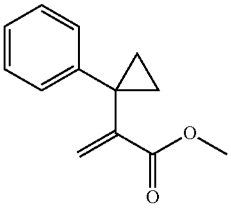

The title compound (0.209 g, 40%) was obtained using methyl 2-hydroxy-2-(1-phenylcyclopropyl)acetate (0.486 g, 2.36 mmol) obtained in (3) above by the preparation method of Preparation Example 29-(4).

NMR: $^1$H-NMR (400 MHz, $CDCl_3$); δ 7.33-7.18 (5H, m), 6.36 (1H, d), 5.88 (1H, d), 3.72 (3H, s), 1.23-1.13 (4H, m)

(5) Preparation of methyl 3-(((tert-butoxycarbonyl) amino)methyl)-5-(1-phenylcyclopropyl)-4,5-dihydroisoxazol-5-carboxylate

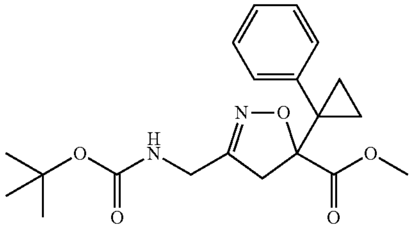 [SMILES: COC(=O)C1(C2(c3ccccc3)CC2)CC(CNC(=O)OC(C)(C)C)=NO1]

The title compound (0.277 g, 72%) was obtained using methyl 2-(1-phenylcyclopropyl)acrylate (0.209 g, 1.03 mmol) obtained in (4) above and tert-butyl (2-(hydroxyimino)ethyl)carbamate (0.359 g, 2.06 mmol) obtained in Preparation Example 1-(1) by the preparation method of Preparation Example 1-(2).

NMR: $^1$H-NMR (400 MHz, $CDCl_3$); δ 7.34-7.26 (5H, m), 4.28 (1H, d), 4.04 (2H, d), 3.79 (3H, s), 3.52 (1H, d), 3.22 (1H, d), 1.49-1.47 (10H, m), 0.95-0.83 (3H, m)

Preparation Example 37: Preparation of ethyl 3-(((tert-butoxycarbonyl)amino)methyl)-5-(3,5-difluorobenzyl)-4,5-dihydroisoxazol-5-carboxylate

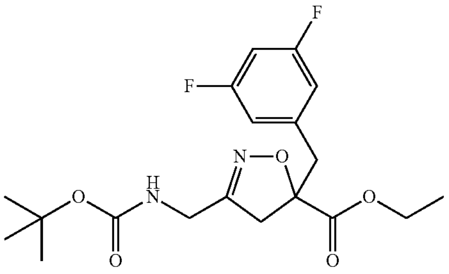 [SMILES: CCOC(=O)C1(Cc2cc(F)cc(F)c2)CC(CNC(=O)OC(C)(C)C)=NO1]

2-(3,5-Difluoro-benzyl)-acrylic acid ethyl ester (0.37 g, 24%, 2 steps) was obtained using 3,5-difluorobenzyl bromide (0.87 ml, 6.69 mmol) by the preparation method of Preparation Example 13-(1). NMR: $^1$H-NMR (400 MHz, $CDCl_3$); δ 6.76-6.63 (m, 3H), 6.29 (s, 1H), 5.54 (s, 1H), 4.21-4.09 (q, 2H), 3.61 (s, 2H), 1.28-1.24 (t, 3H)

The title compound (0.29, 41%) was obtained using 2-(3,5-difluoro-benzyl)-acrylic acid ethyl ester (0.36 g, 1.59 mmol) and tert-butyl (2-(hydroxyimino)ethyl)carbamate (0.30 g, 1.75 mmol) obtained in Preparation Example 1-(1) by the preparation method of Preparation Example 1-(2).

NMR: $^1$H-NMR (400 MHz, $CDCl_3$); δ 6.81-6.70 (m, 3H), 4.72 (br s, 1H), 4.27-4.19 (m, 2H), 3.95-3.94 (d, 2H), 3.43-3.39 (d, 1H), 3.30-3.27 (d, 1H), 3.12-3.08 (d, 1H), 2.96-2.92 (d, 1H), 1.44 (s, 9H), 1.29-1.25 (t, 3H)

MS (m/z): 399[M+H]

Preparation Example 38: Preparation of methyl 5-benzyl-3-((S)-1-((tert-butoxycarbonyl)amino)-2-methoxyethyl)-4,5-dihydroisoxazol-5-carboxylate Through the processes (1) and (2) below, the title compound was obtained.

(1) Preparation of tert-butyl (S)-(1-(hydroxyimino)-3-methoxypropan-2-yl)carbamate

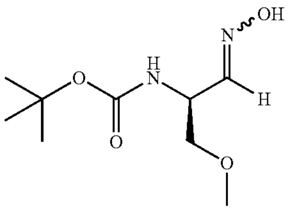

(R)-2-tert-butoxycarbonylamino-3-methoxy-propionic acid methyl ester (1.31 g, 54%) was obtained using (R)-2-tert-butoxycarbonylamino-3-hydroxy-propionic acid methyl ester (2.26 g, 10.31 mmol) by the preparation method of Preparation Example 27-(1). The title compound of ((R)-1-methoxymethyl-2-oxo-ethyl)-carbamic acid tert-butyl ester (0.89 g, 78%) was obtained using (R)-2-tert-butoxycarbonylamino-3-methoxy-propionic acid methyl ester (1.31 g, 5.62 mmol) by the preparation method of Preparation Example 27-(2). The title compound (0.96 g, 99%) was obtained using ((R)-1-methoxymethyl-2-oxo-ethyl)-carbamic acid tert-butyl ester (0.89 g, 4.38 mmol) by the preparation method of Preparation Example 1-(1).

(2) Preparation of methyl 5-benzyl-3-((S)-1-((tert-butoxycarbonyl)amino)-2-methoxyethyl)-4,5-dihydroisoxazol-5-carboxylate

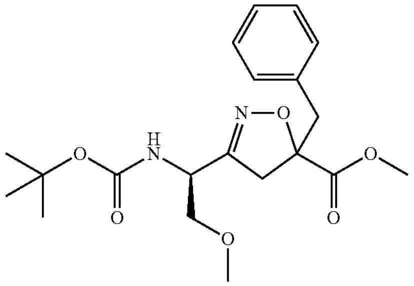 [SMILES: COC[C@@H](NC(=O)OC(C)(C)C)C1=NOC(Cc2ccccc2)(C(=O)OC)C1]

The title compound (0.93 g, 54%) was obtained using tert-butyl (S)-(1-(hydroxyimino)-3-methoxypropan-2-yl) carbamate (0.96 g, 4.39 mmol) obtained in (1) above and methyl 2-benzylacrylate (0.85 g, 4.84 mmol) obtained in Preparation Example 6-(1) by the preparation method of Preparation Example 1-(2).

NMR: $^1$H-NMR (400 MHz, $CDCl_3$); δ 7.31-7.22 (m, 5H), 5.15-4.93 (m, 1H), 4.46 (m, 1H), 3.77-3.76 (dd, 3H), 3.49-3.27 (m, 4H), 3.26 (s, 3H), 3.17-2.95 (m, 2H), 1.43-1.42 (d, 9H)

MS (m/z): 393[M+H]

Preparation Example 39: Preparation of ethyl 3-(((tert-butoxycarbonyl)amino)methyl)-5-(3-fluorobenzyl)-4,5-dihydroisoxazol-5-carboxylate

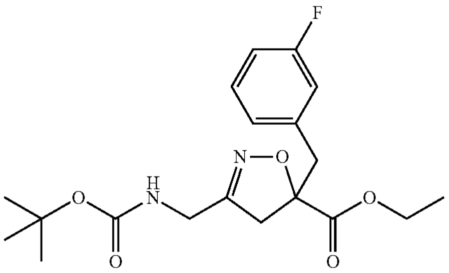 [SMILES: CCOC(=O)C1(Cc2cccc(F)c2)CC(CNC(=O)OC(C)(C)C)=NO1]

2-(3-Fluoro-benzyl)-acrylic acid ethyl ester (0.49 g, 2.35 mmol) was obtained using 3-fluorobenzyl bromide (1.0 g, 5.3 mmol) by the preparation method of Preparation Example 13-(1). The title compound (0.80 g, 80%) was obtained using 2-(3-fluoro-benzyl)-acrylic acid ethyl ester (0.49 g, 2.35 mmol) and tert-butyl (2-(hydroxyimino)ethyl) carbamate (0.82 g, 4.7 mmol) obtained in Preparation Example 1-(1) by the preparation method of Preparation Example 1-(2).

MS (m/z): 381[M+H]

Preparation Example 40: Preparation of methyl 3-(((tert-butoxycarbonyl)amino)methyl)-5-(methoxymethyl)-4,5-dihydroisoxazol-5-carboxylate Through the processes (1), (2), (3) and (4) below, the title compound was obtained.

(1) Preparation of methyl 2-(((tert-butyldimethylsilyl)oxy)methyl)acrylate

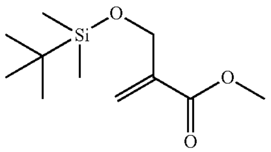

2-Hydroxymethyl-acrylic acid methyl ester (0.5 g, 4.31 mmol) was dissolved in dimethylamide (10 ml). At 0° C., imidazole (0.35 g, 5.17 mmol) and tert-butyl-chloro-dimethyl-silane (0.78 g, 5.17 mmol) were added thereto, followed by stirring at room temperature for 8 hours. The solvent was distilled under a reduced pressure, water was added, and extraction with ethyl acetate was performed. The organic layer thus extracted was washed with brine, dried over anhydrous magnesium sulfate, and filtered. The filtrate was distilled under a reduced pressure and separated by column chromatography to obtain the title compound (0.99 g, 99%).

NMR: $^1$H-NMR (400 MHz, $CDCl_3$); δ 6.18-6.17 (m, 1H), 5.84-5.85 (m, 1H), 4.29-4.28 (m, 2H), 3.67 (s, 3H), 0.84 (s, 9H), 0.09 (s, 6H)

(2) Preparation of methyl 3-(((tert-butoxycarbonyl)amino)methyl)-5-(((tert-butyldimethylsilyl)oxy)methyl)-4,5-dihydroisoxazol-5-carboxylate

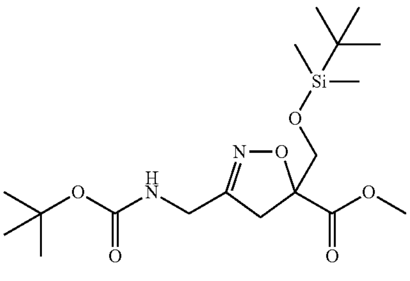 [SMILES: COC(=O)C1(CO[Si](C)(C)C(C)(C)C)CC(CNC(=O)OC(C)(C)C)=NO1]

The title compound (0.29 g, 31%) was obtained using methyl 2-(((tert-butyldimethylsilyl)oxy)methyl)acrylate (0.59 g, 2.56 mmol) obtained in (1) above and tert-butyl (2-(hydroxyimino)ethyl)carbamate (0.36 g) obtained in Preparation Example 1-(1) by the preparation method of Preparation Example 1-(2).

NMR: $^1$H-NMR (400 MHz, $CDCl_3$); δ 4.86 (br s, 1H), 4.05-4.04 (d, 2H), 3.92-6.84 (q, 2H), 3.79 (s, 3H), 3.44-3.39 (d, 1H), 3.21-3.17 (d, 1H), 1.45 (s, 9H), 0.86 (s, 9H), 0.06 (d, 6H)

MS (m/z): 403[M+H]

(3) Preparation of methyl 3-(((tert-butoxycarbonyl)amino)methyl)-5-(hydroxymethyl)-4,5-dihydroisoxazol-5-carboxylate

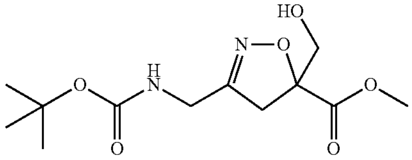 [SMILES: COC(=O)C1(CO)CC(CNC(=O)OC(C)(C)C)=NO1]

The methyl 3-(((tert-butoxycarbonyl)amino)methyl)-5-(((tert-butyldimethylsilyl)oxy)methyl)-4,5-dihydroisoxazol-5-carboxylate (0.29 g, 0.72 mmol) obtained in (2) above was dissolved in tetrahydrofuran (10 ml), and a 1 M tetrabutylammonium fluoride tetrahydrofuran solution (0.72 ml, 0.72 mmol) was added thereto. After stirring at room temperature for 18 hours, water was added, and extraction with ethyl acetate was performed. The organic layer thus extracted was washed with brine and dried over anhydrous magnesium sulfate, and the filtrate was distilled under a reduced pressure. The residue was separated by column chromatography to obtain the title compound (0.13 g, 62%).

MS (m/z): 289[M+H]

(4) Preparation of methyl 3-(((tert-butoxycarbonyl)amino)methyl)-5-(methoxymethyl)-4,5-dihydroisoxazol-5-carboxylate

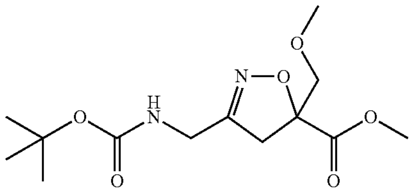 [SMILES: COCC1(C(=O)OC)CC(CNC(=O)OC(C)(C)C)=NO1]

The methyl 3-(((tert-butoxycarbonyl)amino)methyl)-5-(hydroxymethyl)-4,5-dihydroisoxazol-5-carboxylate (0.075 g, 0.26 mmol) obtained in (3) above was dissolved in acetonitrile (5 ml), and silver(II) oxide (0.60 g, 2.6 mmol) and iodomethane (0.08 ml, 1.30 mmol) were added thereto in order. Stirring was performed at room temperature for 20 hours, while blocking the light. After filtering using celite, the resultant product was distilled under a reduced pressure and separated by column chromatography to obtain the title compound (0.05 g, 64%).

NMR: $^1$H-NMR (400 MHz, $CDCl_3$); δ 4.94 (br s, 1H), 4.07-4.06 (m, 2H), 3.01 (s, 3H), 3.71-3.70 (m, 2H), 3.43-3.88 (d, 1H), 3.41 (s, 3H), 3.16-3.10 (d, 1H), 1.45 (s, 9H)

MS (m/z): 303[M+H]

Preparation Example 41: Preparation of ethyl 3-(((tert-butoxycarbonyl)amino)methyl)-5-(ethoxymethyl)-4,5-dihydroisoxazol-5-carboxylate Through the processes (1) and (2) below, the title compound was obtained.

(1) Preparation of ethyl 2-(ethoxymethyl)acrylate

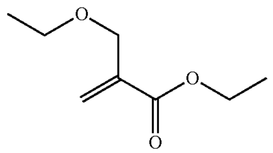

To a solution of 2-hydroxymethyl-acrylic acid ethyl ester (1.30 g, 10.0 mmol) dissolved in dichloromethane (20 ml), phosphorous tribromide (0.47 ml, 5.0 mmol) was added at 0° C., and then, the temperature was raised and stirring was performed at room temperature for 2 hours. To the reaction product, dichloromethane (50 ml) was added, and the resultant product was washed with water and brine, dried over anhydrous magnesium sulfate, and filtered. The filtrate was distilled under a reduced pressure to obtain 2-bromomethyl-acrylic acid ethyl ester (1.71 g, 91%).

Ethanol (0.046 g, 1.0 mmol) was dissolved in tetrahydrofuran (6 ml), and 0.5 M potassium bis(trimethylsilyl)amide (2.0 ml, 1.0 mmol) was slowly added thereto, followed by stirring at room temperature for 10 minutes. A solution of 2-bromomethyl-acrylic acid ethyl ester (0.193 g, 1.0 mmol) obtained above, dissolved in tetrahydrofuran (2 ml) was added to the solution, and stirring was performed for 1 hour at room temperature. To the reaction product, water (20 ml) was added, and extraction with dichloromethane (20 ml) was performed twice. The organic layer thus extracted was dried over anhydrous magnesium sulfate, and filtered. The filtrate was distilled under a reduced pressure and separated by column chromatography to obtain the title compound (0.118 g, 75%).

NMR: $^1$H-NMR (500 MHz, $CDCl_3$); δ 6.26 (1H, d), 5.83 (1H, d), 4.18 (2H, q), 4.15 (2H, d), 3.53 (2H, q), 1.27 (3H, t), 1.20 (3H, t)

(2) Preparation of ethyl 3-(((tert-butoxycarbonyl)amino)methyl)-5-(ethoxymethyl)-4,5-dihydroisoxazol-5-carboxylate

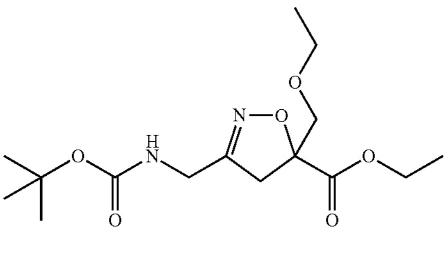 [SMILES: CCOCC1(C(=O)OCC)CC(CNC(=O)OC(C)(C)C)=NO1]

The title compound (0.051 g, 25%) was obtained using ethyl 2-(ethoxymethyl)acrylate (0.118 g, 0.75 mmol) obtained in (1) above and tert-butyl (2-(hydroxyimino)ethyl) carbamate (0.108 g, 0.62 mmol) obtained in Preparation Example 1-(1) by the preparation method of Preparation Example 1-(2).

NMR: $^1$H-NMR (500 MHz, $CDCl_3$); δ 4.96 (1H, s), 4.24-4.18 (2H, m), 4.04-4.02 (2H, m), 3.72-3.68 (2H, m), 3.55-3.51 (2H, m), 3.38 (1H, d), 3.14 (1H, d), 1.42 (9H, s), 1.27 (3H, t), 1.14 (3H, t)

MS (m/z): 331[M+H]

Preparation Example 42: Preparation of methyl 3-(((tert-butoxycarbonyl)amino)methyl)-3a,4,5,6-tetrahydro-6aH-cyclopenta[d]isoxazol-6a-carboxylate

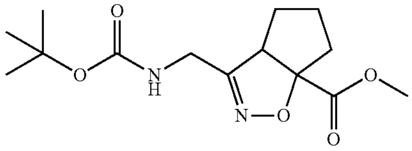 [SMILES: COC(=O)C12CCCC1C(CNC(=O)OC(C)(C)C)=NO2]

The title compound (0.148 g, 25%) was obtained using 1-cyclopentenecarboxylic acid methyl ester (0.252 g, 2.00 mmol) and tert-butyl (2-(hydroxyimino)ethyl)carbamate (0.523 g, 3.00 mmol) obtained in Preparation Example 1-(1) by the preparation method of Preparation Example 1-(2).

NMR: 1H-NMR (400 MHz, CDCl3); δ 5.02 (1H, s), 4.05-3.92 (2H, m), 3.78 (1H, d), 3.74 (3H, s), 2.22-1.79 (5H, m), 1.59-1.51 (1H, m), 1.40 (9H, s)

Preparation Example 43: Preparation of ethyl 3-(((tert-butoxycarbonyl)amino)methyl)-5-(2,3-difluorobenzyl)-4,5-dihydroisoxazol-5-carboxylate

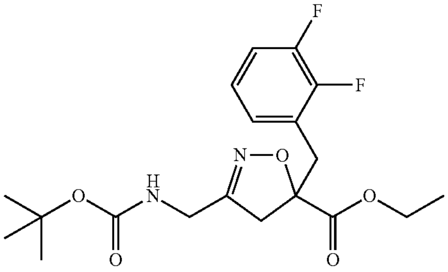 [SMILES: CCOC(=O)C1(Cc2cccc(F)c2F)CC(CNC(=O)OC(C)(C)C)=NO1]

2-(2,3-Difluoro-benzyl)-acrylic acid ethyl ester (0.92 g, 61%, 2 steps) was obtained using 2,3-difluorobenzyl bromide (0.84 ml, 6.69 mmol) by the preparation method of Preparation Example 13-(1).

NMR: $^1$H-NMR (400 MHz, $CDCl_3$); δ 7.07-6.95 (m, 3H), 6.28 (s, 1H), 5.49 (s, 1H), 4.23-4.18 (q, 2H), 3.69 (s, 2H), 1.30-1.26 (t, 3H)

The title compound (0.23 g, 37%) was obtained using 2-(2,3-difluoro-benzyl)-acrylic acid ethyl ester (0.35 g, 1.57 mmol) and tert-butyl (2-(hydroxyimino)ethyl)carbamate (0.3 g, 1.72 mmol) obtained in Preparation Example 1-(1) by the preparation method of Preparation Example 1-(2).

NMR: $^1$H-NMR (400 MHz, $CDCl_3$); δ 7.12-6.99 (m, 3H), 4.62 (br s, 1H), 4.29-4.21 (m, 2H), 3.94-3.90 (m, 2H0, 3.48-3.44 (d, 1H), 3.30 (s, 2H), 2.98-2.93 (d, 1H), 1.44 (s, 9H), 1.29-1.26 (t, 3H)

MS (m/z): 399[M+H]

Preparation Example 44: Preparation of ethyl 3-(((tert-butoxycarbonyl)amino)methyl)-5-((cyclohexyloxy)methyl)-4,5-dihydroisoxazol-5-carboxylate Through the processes (1) and (2) below, the title compound was obtained.

(1) Preparation of ethyl 2-((cyclohexyloxy)methyl)acrylate

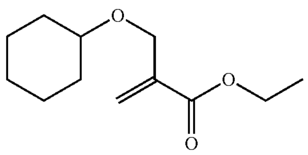

The title compound (0.20 g, 47%) was obtained using cyclohexanol (0.20 g, 2.0 mmol) by the preparation method of Preparation Example 41-(1).

NMR: $^1$H-NMR (500 MHz, $CDCl_3$); δ 6.26 (1H, d), 5.88 (1H, d), 4.26 (2H, q), 4.20 (2H, d), 3.31 (1H, q), 1.93-1.78 (4H, m), 1.53-1.49 (1H, m), 1.31-1.23 (8H, m)

(2) Preparation of ethyl 3-(((tert-butoxycarbonyl) amino)methyl)-5-((cyclohexyloxy)methyl)-4,5-dihydroisoxazol-5-carboxylate

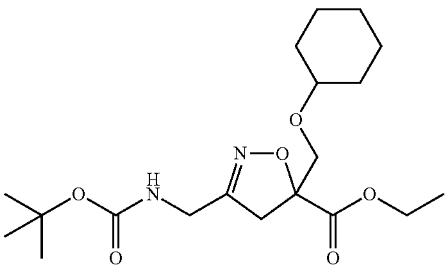 [SMILES: CCOC(=O)C1(COC2CCCCC2)CC(CNC(=O)OC(C)(C)C)=NO1]

The title compound (0.200 g, 55%) was obtained using tert-butyl (2-(hydroxyimino)ethyl)carbamate (0.330 g, 1.88 mmol) obtained in Preparation Example 1-(1) and ethyl 2-((cyclohexyloxy)methyl)acrylate (0.200 g, 0.94 mmol) obtained in (1) above by the preparation method of Preparation Example 1-(2).

NMR: $^1$H-NMR (500 MHz, $CDCl_3$); δ 5.03 (1H, t), 4.24-4.21 (2H, m), 4.02-3.99 (2H, m), 3.70 (1H, d), 3.66 (1H, d), 3.38 (1H, d), 3.29 (1H, t), 3.11 (1H, d), 1.78-1.60 (4H, m), 1.46-1.42 (10H, m), 1.29-1.18 (8H, m)

Preparation Example 45: Preparation of ethyl 3-(((tert-butoxycarbonyl)amino)methyl)-5-(3-(trifluoromethyl)benzyl)-4,5-dihydroisoxazol-5-carboxylate

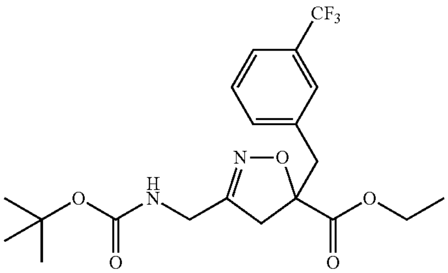 [SMILES: CCOC(=O)C1(Cc2cccc(C(F)(F)F)c2)CC(CNC(=O)OC(C)(C)C)=NO1]

2-(3-Trifluoromethyl-benzyl)-acrylic acid ethyl ester (0.49 g, 28%, 2 steps) was obtained using 3-trifluoromethylbenzyl bromide (1.02 ml, 6.69 mmol) by the preparation method of Preparation Example 13-(1).

NMR: $^1$H-NMR (400 MHz, $CDCl_3$); δ 4.79-7.39 (m, 4H), 6.28 (s, 1H), 5.51 (s, 1H), 4.21-4.15 (q, 2H), 3.69 (s, 2H), 1.28-1.24 (t, 3H)

The title compound (0.25 g, 42%) was obtained using 2-(3-trifluoromethyl-benzyl)-acrylic acid ethyl ester (0.36 g, 1.38 mmol) and tert-butyl (2-(hydroxyimino)ethyl)carbamate (0.24 g, 1.38 mmol) obtained in Preparation Example 1-(1) by the preparation method of Preparation Example 1-(2).

NMR: $^1$H-NMR (400 MHz, $CDCl_3$); δ 7.54-7.40 (m, 4H), 4.68 (br s, 1H), 4.24-4.19 (q, 2H), 3.93-3.92 (d, 2H), 3.44-3.40 (d, 1H), 3.38-3.35 (d, 1H), 3.21-3.17 (d, 1H), 2.96-2.92 (d, 1H), 1.45 (s, 9H), 1.28-1.22 (t, 3H)

MS (m/z): 431[M+H]

Preparation Example 46: Preparation of ethyl 3-(((tert-butoxycarbonyl)amino)methyl)-5-(3-(trifluoromethoxy)benzyl)-4,5-dihydroisoxazol-5-carboxylate

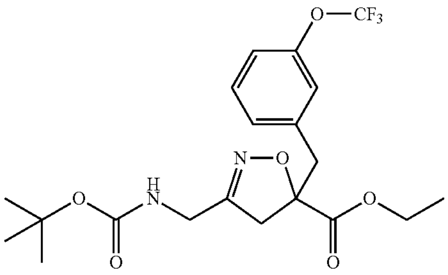 [SMILES: CCOC(=O)C1(Cc2cccc(OC(F)(F)F)c2)CC(CNC(=O)OC(C)(C)C)=NO1]

2-(3-Trifluoromethoxy-benzyl)-acrylic acid ethyl ester (0.33 g, 32%, 2 steps) was obtained using 3-trifluoromethoxybenzyl bromide (0.64 ml, 3.92 ml) by the preparation method of Preparation Example 13-(1).

NMR: $^1$H-NMR (400 MHz, $CDCl_3$); δ 7.33-7.29 (m, 1H), 7.15-7.06 (m, 3H), 6.27 (s, 1H), 5.51 (s, 1H), 4.21-4.16 (q, 2H), 3.65 (s, 2H), 1.27-1.24 (t, 3H)

The title compound (0.35 g, 67%) was obtained using 2-(3-trifluoromethoxy-benzyl)-acrylic acid ethyl ester (0.33 g, 1.19 mmol) and tert-butyl (2-(hydroxyimino)ethyl)carbamate (0.24 g, 1.38 mmol) obtained in Preparation Example 1-(1) by the preparation method of Preparation Example 1-(2).

NMR: $^1$H-NMR (400 MHz, $CDCl_3$); δ 7.34-7.30 (m, 1H), 7.21-7.13 (m, 3H), 4.67 (br s, 1H), 4.25-4.18 (q, 2H), 3.92-3.91 (d, 2H), 3.43-3.39 (d, 1H), 3.34-3.31 (d, 1H), 3.16-3.13 (d, 1H), 2.95-2.91 (d, 1H), 1.44 (s, 9H), 1.27-1.24 (t, 3H)

MS (m/z): 447[M+H]

Example 1: Preparation of ((1R)-3-methyl-1-(3-phenyl-4,5-dihydroisoxazol-5-carboxamido)butyl) boronic acid Through the processes (1), (2), (3) and (4) below, the title compound was obtained.

(1) Preparation of ethyl 3-phenyl-4,5-dihydroisoxazol-5-carboxylate

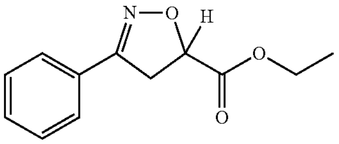 [SMILES: CCOC(=O)C1CC(c2ccccc2)=NO1]

N-hydroxybenzenecarbonimidoyl chloride (0.68 g, 4.3 mmol) was dissolved in tetrahydrofuran (20 ml), and ethyl acrylate (0.94 ml, 8.6 mmol) and diisopropylethylamine (1.5 ml, 8.6 mmol) were added thereto at 0° C. Stirring was performed for 18 hours, while raising to room temperature. The solvent was distilled under a reduced pressure, a sodium bicarbonate aqueous solution was added thereto, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.78 g, 82%).

MS (m/z): 220[M+H]

(2) Preparation of 3-phenyl-4,5-dihydroisoxazol-5-carboxylic acid

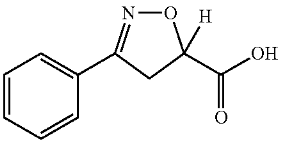 [SMILES: O=C(O)C1CC(c2ccccc2)=NO1]

The ethyl 3-phenyl-4,5-dihydroisoxazol-5-carboxylate (0.78 g, 3.6 mmol) obtained in (1) above was dissolved in methanol (5 ml), a 6 N sodium hydroxide aqueous solution (1.8 ml, 10.8 mmol) was added thereto, and stirring was performed for 5 hours at room temperature. After titrating pH 1 with a 1 N hydrochloric acid solution, extraction with ethyl acetate was performed twice. The organic layer thus extracted was dried over anhydrous magnesium sulfate, and the filtrate thus filtered was distilled under a reduced pressure to obtain the quantitative amount of the title compound without additional purification.

MS (m/z): 192[M+H]

(3) Preparation of N—((R)-3-methyl-1-((3aS,4S,6S,7aR)-3a,5,5-trimethylhexahydro-4,6-methanobenzo[d][1,3,2]dioxaborol-2-yl)butyl)-3-phenyl-4,5-dihydroisoxazol-5-carboxamide

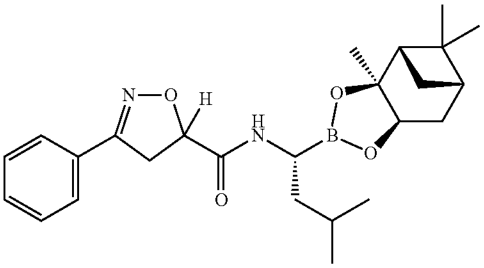 [SMILES: CC(C)C[C@H](NC(=O)C1CC(c2ccccc2)=NO1)B1O[C@@H]2C[C@@H]3C[C@@H](C3(C)C)[C@]2(C)O1]

3-Phenyl-4,5-dihydroisoxazol-5-carboxylic acid (0.11 g, 0.59 mmol) obtained in (2) above, (R)-3-methyl-1-((3aS,4S,6S,7aR)-3a,5,5-trimethylhexahydro-4,6-metanobenzo[d][1,3,2]dioxaborol-2-yl)butan-1-amine hydrochloride (0.18 g, 0.6 mmol), and 0-(benzotriazol-1-yl)-N,N,N',N'-tetramethyluronium tetrafluoroborate (0.21 g, 0.64 mmol) were dissolved at 0° C. in dimethylformamide (5 ml). While maintaining the temperature, diisopropylethylamine (0.31 ml, 1.78 mmol) was slowly added thereto, followed by stirring for 18 hours, while raising to room temperature. The solvent was distilled under a reduced pressure, a sodium bicarbonate aqueous solution was added thereto, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.19 g, 76%).

MS (m/z): 439[M+H]

(4) Preparation of ((1R)-3-methyl-1-(3-phenyl-4,5-dihydroisoxazol-5-carboxamido)butyl)boronic acid

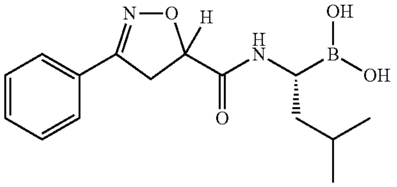 [SMILES: CC(C)C[C@H](NC(=O)C1CC(c2ccccc2)=NO1)B(O)O]

N—((R)-3-methyl-1-((3aS,4S,6S,7aR)-3a,5,5-trimethylhexahydro-4,6-metanobenzo[d][1,3,2]dioxaborol-2-yl)butyl)-3-phenyl-4,5-dihydroisoxazol-5-carboxamide (0.19 g, 0.44 mmol) obtained in (3) above was dissolved in methanol (5 ml) and hexane (5 ml). After adding isobutyl boronic acid (0.23 g, 2.2 mmol) and a 1 N hydrochloric acid aqueous solution (1.1 ml, 1.1 mmol) in order, stirring was performed for 18 hours at room temperature. Methanol (5 ml) and hexane (5 ml) were added thereto, and a methanol layer was separated. A hexane layer was extracted further with methanol (5 ml), and all methanol layers were distilled under a reduced pressure. Ethyl acetate was added, and the resultant product was washed with a sodium bicarbonate aqueous solution and brine in order, dried over anhydrous magnesium sulfate, and filtered. The filtrate was distilled under a reduced pressure and separated by column chromatography to obtain the title compound (0.052 g, 38%).

MS (m/z): 305[M+H], 287[M-OH]

Example 2: Preparation of ((1R)-3-methyl-1-(3-(pyrazin-2-yl)-4,5-dihydroisoxazol-5-carboxamido)butyl)boronic acid Through the processes (1), (2), (3), (4), (5) and (6) below, the title compound was obtained.

(1) Preparation of pyrazin-2-carboaldehyde

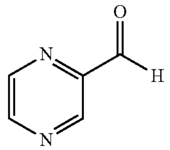

The title compound was obtained by the method described in WO200540159A1.

(2) Preparation of pyrazin-2-carboaldehyde oxime

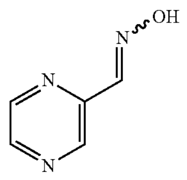

Pyrazin-2-carboaldehyde (0.53 g, 4.90 mmol) obtained in (1) above was dissolved in dichloromethane (10 ml). At 0° C., triethylamine (0.7 ml, 5.00 mmol) and a hydroxylamine hydrochloride (0.38 g, 5.39 mmol) were added thereto in order, followed by stirring for 2 hours at room temperature. After distilling the solvent under a reduced pressure, water was added, and extraction with diethyl ether was performed. After drying with anhydrous magnesium sulfate, the filtrate after filtering was separated by column chromatography to obtain the title compound (0.48 g, 79%).

NMR: $^1$H-NMR (400 MHz, $CDCl_3$); δ 12.06 (br s, 1H), 9.00 (d, 1H), 8.67-8.62 (m, 2H), 8.15 (s, 1H)

(3) Preparation of ethyl 3-(pyrazin-2-yl)-4,5-dihydro-1,2-oxazol-5-carboxylate

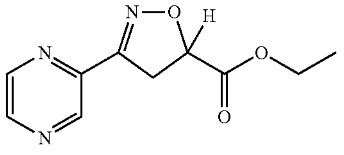 [SMILES: CCOC(=O)C1CC(c2cnccn2)=NO1]

Pyrazin-2-carboaldehyde oxime (0.12 g, 0.97 mmol) obtained in (2) above was dissolved in dichloromethane (10 ml), and acrylic acid ethyl ester (0.096 ml, 0.97 mmol) was added thereto at room temperature. A 4% sodium hypochlorite aqueous solution (2.97 ml, 1.75 mmol) was slowly added thereto at 0° C., and stirring was performed for 18 hours, while raising to room temperature. The solvent was distilled under a reduced pressure, a sodium bicarbonate aqueous solution was added thereto, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.14 g, 65%).

NMR: $^1$H-NMR (400 MHz, $CDCl_3$); δ 9.29 (d, 1H), 8.59-8.56 (m, 2H), 5.25-5.20 (m, 1H), 4.32-4.25 (q, 2H), 3.83-3.70 (m, 2H), 1.35-1.32 (t, 3H)

MS (m/z): 222[M+H]

(4) Preparation of 3-(pyrazin-2-yl)-4,5-dihydro-1,2-oxazol-5-carboxylic acid

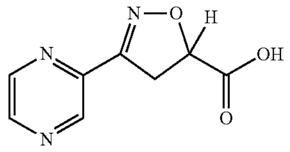 [SMILES: O=C(O)C1CC(c2cnccn2)=NO1]

The title compound (0.1 g, 82%) was obtained using ethyl 3-(pyrazin-2-yl)-4,5-dihydro-1,2-oxazol-5-carboxylate (0.14 g, 0.63 mmol) obtained in (3) above by the preparation method of Example 1-(2).

MS (m/z): 194[M+H]

(5) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(pyrazin-2-yl)-4,5-dihydroisoxazol-5-carboxamide

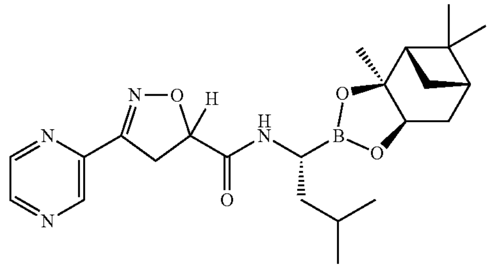 [SMILES: CC(C)C[C@H](NC(=O)C1CC(c2cnccn2)=NO1)B1O[C@@H]2C[C@@H]3C[C@@H](C3(C)C)[C@]2(C)O1]

The title compound (0.16 g, 70%) was obtained using 3-(pyrazin-2-yl)-4,5-dihydro-1,2-oxazol-5-carboxylic acid (0.1 g, 0.52 mmol) obtained in (4) above by the preparation method of Example 1-(3).

MS (m/z): 441[M+H]

(6) Preparation of ((1R)-3-methyl-1-(3-(pyrazin-2-yl)-4,5-dihydroisoxazol-5-carboxamido)butyl)boronic acid

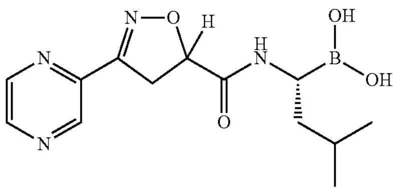 [SMILES: CC(C)C[C@H](NC(=O)C1CC(c2cnccn2)=NO1)B(O)O]

The title compound (0.067 g, 60%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(pyrazin-2-yl)-4,5-dihydroisoxazol-5-carboxamide (0.16 g, 0.36 mmol) obtained in (5) above by the preparation method of Example 1-(4).

NMR: $^1$H-NMR (400 MHz, MeOD-d4); δ 9.20-9.19 (d, 1H), 8.69-8.68 (dd, 1H), 8.64-8.64 (d, 1H), 5.49-5.43 (m, 1H), 3.95-3.84 (m, 1H), 3.81-3.74 (m, 1H), 2.95-2.90 (m, 1H), 1.69-1.63 (m, 1H), 1.44-1.37 (m, 2H), 0.94-0.92 (dd, 6H)

MS (m/z): 307[M+H], 289[M-OH]

Example 3: Preparation of ((1R)-1-(3-(2,5-dichlorophenyl)-4,5-dihydroisoxazol-5-carboxamido)-3-methylbutyl)boronic acid Through the processes (1), (2), (3), (4) and (5) below, the title compound was obtained.

(1) Preparation of 2,5-dichlorobenzaldehyde oxime

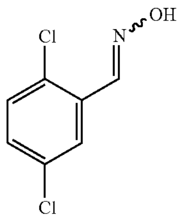 [SMILES: ON=Cc1cc(Cl)ccc1Cl]

2,5-Dichloro-benzaldehyde (0.3 g, 1.71 mmol) was dissolved in methanol (10 ml), and a 50% hydroxylamine aqueous solution (0.21 ml, 3.43 mmol) was added thereto at room temperature, followed by stirring for 16 hours. The title compound (0.32 g, 99%) was obtained by distilling the solvent under a reduced pressure and was immediately used in the next reaction without purification.

MS (m/z): 190[M+H]

(2) Preparation of ethyl 3-(2,5-dichlorophenyl)-4,5-dihydro-1,2-oxazol-5-carboxylate

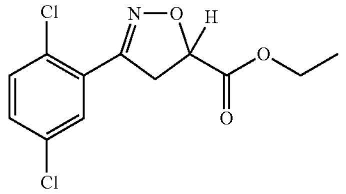 [SMILES: CCOC(=O)C1CC(c2cc(Cl)ccc2Cl)=NO1]

The title compound (0.42 g 87%) was obtained using 2,5-dichlorobenzaldehyde oxime (0.32 g, 1.68 mmol) obtained in (1) above by the preparation method of Example 2-(3).

MS (m/z): 288[M+H]

(3) Preparation of 3-(2,5-dichlorophenyl)-4,5-dihydro-1,2-oxazol-5-carboxylic acid

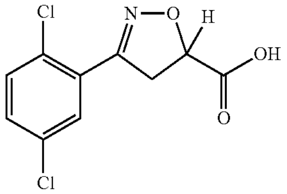 [SMILES: O=C(O)C1CC(c2cc(Cl)ccc2Cl)=NO1]

The title compound (0.37 g, 99%) was obtained using ethyl 3-(2,5-dichlorophenyl)-4,5-dihydro-1,2-oxazol-5-carboxylate (0.42 g, 1.46 mmol) obtained in (2) above by the preparation method of Example 1-(2).

MS (m/z): 260[M+H]

(4) Preparation of 3-(2,5-dichlorophenyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

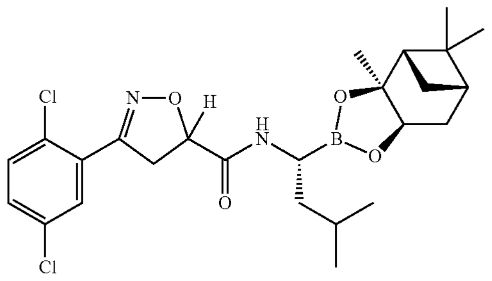 [SMILES: CC(C)C[C@H](NC(=O)C1CC(c2cc(Cl)ccc2Cl)=NO1)B1O[C@@H]2C[C@@H]3C[C@@H](C3(C)C)[C@]2(C)O1]

The title compound (0.16 g, 82%) was obtained using 3-(2,5-dichlorophenyl)-4,5-dihydro-1,2-oxazol-5-carboxylic acid (0.1 g, 0.38 mmol) obtained in (3) above by the preparation method of Example 1-(3).

MS (m/z): 507[M+H]

(5) Preparation of ((1R)-1-(3-(2,5-dichlorophenyl)-4,5-dihydroisoxazol-5-carboxamido)-3-methylbutyl) boronic acid

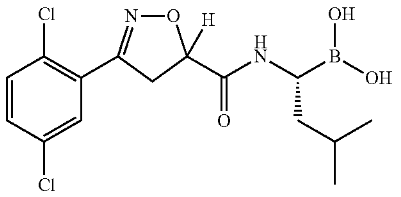 [SMILES: CC(C)C[C@H](NC(=O)C1CC(c2cc(Cl)ccc2Cl)=NO1)B(O)O]

The title compound (0.1 g, 85%) was obtained using 3-(2,5-dichlorophenyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.16 g, 0.32 mmol) obtained in (4) above by the preparation method of Example 1-(4).

NMR: $^1$H-NMR (400 MHz, MeOD-d4); δ 7.67-7.65 (dd, 1H), 7.55-7.48 (m, 2H), 5.47-5.41 (m, 1H), 3.96-3.89 (m, 1H), 3.79-3.72 (m, 1H), 2.96-2.93 (m, 1H), 1.71-1.65 (m, 1H), 1.44-1.38 (m, 2H), 0.95-0.93 (d, 6H)

MS (m/z): 373[M+H], 355[M-OH]

Example 4: Preparation of ((1R)-1-(5-ethyl-3-phenyl-4,5-dihydroisoxazol-5-carboxamido)-3-methylbutyl)boronic acid Through the processes (1), (2), (3) and (4) below, the title compound was obtained.

(1) Preparation of ethyl 5-ethyl-3-phenyl-4,5-dihydro-1,2-oxazol-5-carboxylate

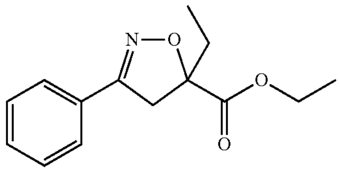 [SMILES: CCOC(=O)C1(CC)CC(c2ccccc2)=NO1]

The title compound (0.91 g, 80%) was obtained using N-hydroxybenzenecarbonimidoyl chloride (0.71 g, 4.6 mmol) and 2-methylene-butyric acid ethyl ester (1.19 g, 9.28 mmol) by the preparation method of Example 1-(1).

MS (m/z): 248[M+H]

(2) Preparation of 5-ethyl-3-phenyl-4,5-dihydro-1,2-oxazol-5-carboxylic acid

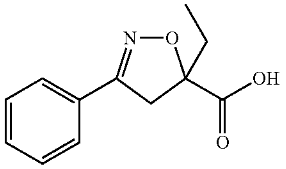 [SMILES: CCC1(C(=O)O)CC(c2ccccc2)=NO1]

The title compound (0.81 g, quant.) was obtained using ethyl 5-ethyl-3-phenyl-4,5-dihydro-1,2-oxazol-5-carboxylate (0.91 g, 3.7 mmol) obtained in (1) above by the preparation method of Example 1-(2).

MS (m/z): 220[M+H]

(3) Preparation of 5-ethyl-N—((R)-3-methyl-1-((3aS,4S,6S,7aR)-3a,5,5-trimethylhexahydro-4,6-metanobenzo[d][1,3,2]dioxaborol-2-yl)butyl)-3-phenyl-4,5-dihydroisoxazol-5-carboxamide

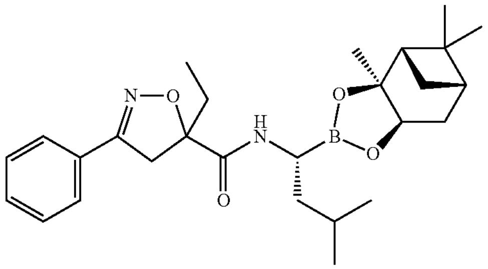 [SMILES: CCC1(C(=O)N[C@@H](CC(C)C)B2O[C@@H]3C[C@@H]4C[C@@H](C4(C)C)[C@]3(C)O2)CC(c2ccccc2)=NO1]

The title compound (0.21 g, 79%) was obtained using 5-ethyl-3-phenyl-4,5-dihydro-1,2-oxazol-5-carboxylic acid (0.12 g, 0.57 mmol) obtained in (2) above by the preparation method of Example 1-(3).

MS (m/z): 467[M+H]

(4) Preparation of ((1R)-1-(5-ethyl-3-phenyl-4,5-dihydroisoxazol-5-carboxamido)-3-methylbutyl) boronic acid

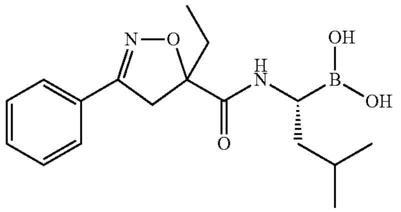 [SMILES: CCC1(C(=O)N[C@@H](CC(C)C)B(O)O)CC(c2ccccc2)=NO1]

The title compound (0.025 g, 57%) was obtained using 5-ethyl-N—((R)-3-methyl-1-((3aS,4S,6S,7aR)-3a,5,5-trimethylhexahydro-4,6-metanobenzo[d][1,3,2]dioxaborol-2-yl) butyl)-3-phenyl-4,5-dihydroisoxazol-5-carboxamide (0.062 g, 0.13 mmol) obtained in (3) above by the preparation method of Example 1-(4).

MS (m/z): 333[M+H], 315[M-OH]

Example 5: Preparation of ((1R)-3-methyl-1-(5-methyl-3-phenyl-4,5-dihydroisoxazol-5-carboxamido)butyl)boronic acid Through the processes (1), (2), (3) and (4) below, the title compound was obtained.

(1) Preparation of ethyl 5-methyl-3-phenyl-4,5-dihydro-1,2-oxazol-5-carboxylate

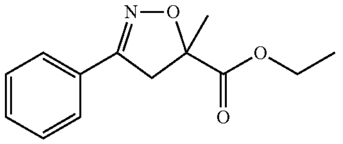 [SMILES: CCOC(=O)C1(C)CC(c2ccccc2)=NO1]

The title compound (1.0 g, 78%) was obtained using N-hydroxybenzenecarbonimidoyl chloride (0.89 g, 5.7 mmol) and 2-methylene-butyric acid ethyl ester (1.3 g, 11.5 mmol) by the preparation method of Example 2-(3).

MS (m/z): 234[M+H]

(2) Preparation of 5-methyl-3-phenyl-4,5-dihydro-1,2-oxazol-5-carboxylic acid

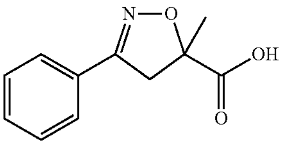

The title compound (0.83 g, 91%) was obtained using ethyl 5-methyl-3-phenyl-4,5-dihydro-1,2-oxazol-5-carboxylate (1.0 g, 4.45 mmol) obtained in (1) above by the preparation method of Example 1-(2).

MS (m/z): 206[M+H]

(3) Preparation of 5-methyl-N—((R)-3-methyl-1-((3aS,4S,6S,7aR)-3a,5,5-trimethylhexahydro-4,6-metanobenzo[d][1,3,2]dioxaborol-2-yl)butyl)-3-phenyl-4,5-dihydroisoxazol-5-carboxamide

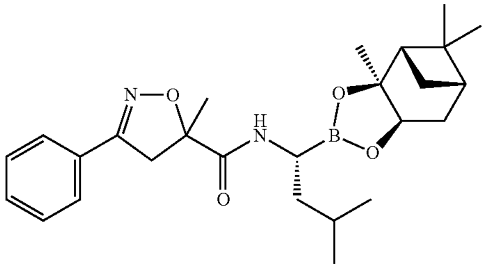 [SMILES: CC(C)C[C@H](NC(=O)C1(C)CC(c2ccccc2)=NO1)B1O[C@@H]2C[C@@H]3C[C@@H](C3(C)C)[C@]2(C)O1]

The title compound (0.19 g, 89%) was obtained using 5-methyl-3-phenyl-4,5-dihydro-1,2-oxazol-5-carboxylic acid (0.099 g, 0.48 mmol) obtained in (2) above by the preparation method of Example 1-(3).

MS (m/z): 453[M+H]

(4) Preparation of ((1R)-3-methyl-1-(5-methyl-3-phenyl-4,5-dihydroisoxazol-5-carboxamido)butyl) boronic acid

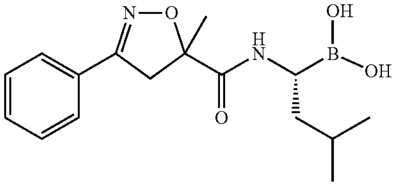 [SMILES: CC(C)C[C@H](NC(=O)C1(C)CC(c2ccccc2)=NO1)B(O)O]

The title compound (0.071 g, 52%) was obtained using 5-methyl-N—((R)-3-methyl-1-((3aS,4S,6S,7aR)-3a,5,5-trimethylhexahydro-4,6-metanobenzo[d][1,3,2]dioxaborol-2-yl)butyl)-3-phenyl-4,5-dihydroisoxazol-5-carboxamide (0.19 g, 0.43 mmol) obtained in (3) above by the preparation method of Example 1-(4).

MS (m/z): 319[M+H], 301[M-OH]

Example 6: Preparation of ((1R)-1-(5-ethyl-3-(pyrazin-2-yl)-4,5-dihydroisoxazol-5-carboxamido)-3-methylbutyl)boronic acid Through the processes (1), (2), (3) and (4) below, the title compound was obtained.

(1) Preparation of ethyl 5-ethyl-3-(pyrazin-2-yl)-4,5-dihydro-1,2-oxazol-5-carboxylate

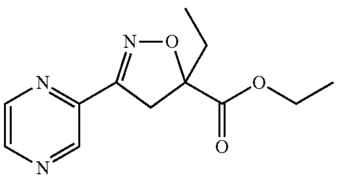 [SMILES: CCOC(=O)C1(CC)CC(c2cnccn2)=NO1]

The title compound (0.16 g, 56%) was obtained using pyrazin-2-carboaldehyde oxime (0.15 g, 1.22 mmol) obtained in Example 2-(2) and 2-methylene-butyric acid ethyl ester (0.19 g, 1.11 mmol) by the preparation method of Example 2-(3).

NMR: $^1$H-NMR (400 MHz, $CDCl_3$); δ 9.26 (d, 1H), 8.56-8.55 (d, 2H), 4.34-4.22 (m, 2H), 3.94-3.89 (d, 1H), 3.41-3.36 (d, 1H), 2.13-2.01 (m, 2H), 1.34-1.31 (t, 3H), 1.03-1.00 (t, 3H)

MS (m/z): 250[M+H]

(2) Preparation of 5-ethyl-3-(pyrazin-2-yl)-4,5-dihydro-1,2-oxazol-5-carboxylic acid

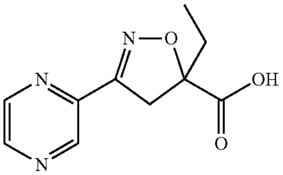 [SMILES: CCC1(C(=O)O)CC(c2cnccn2)=NO1]

The title compound (0.14 g, 99%) was obtained using ethyl 5-ethyl-3-(pyrazin-2-yl)-4,5-dihydro-1,2-oxazol-5-carboxylate (0.16 g, 0.62 mmol) obtained in (1) above by the preparation method of Example 1-(2).

MS (m/z): 222[M+H]

(3): Preparation of 5-ethyl-N—((R)-3-methyl-1-((3aS,4S,6S,7aR)-3a,5,5-trimethylhexahydro-4,6-metanobenzo[d][1,3,2]dioxaborol-2-yl)butyl)-3-(pyrazin-2-yl)-4,5-dihydroisoxazol-5-carboxamide

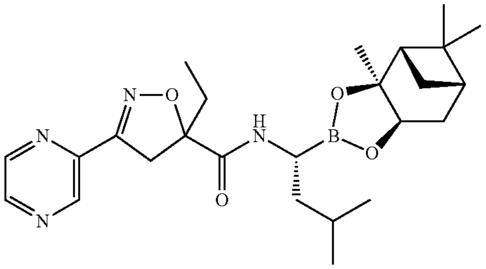 [SMILES: CCC1(C(=O)N[C@@H](CC(C)C)B2O[C@@H]3C[C@@H]4C[C@@H](C4(C)C)[C@]3(C)O2)CC(c2cnccn2)=NO1]

The title compound (0.23 g, 76%) was obtained using 5-ethyl-3-(pyrazin-2-yl)-4,5-dihydro-1,2-oxazol-5-carboxylic acid (0.14 g, 0.63 mmol) obtained in Example 6-(2) by the preparation method of Example 1-(3).

MS (m/z): 469[M+H]

(4): Preparation of ((1R)-1-(5-ethyl-3-(pyrazin-2-yl)-4,5-dihydroisoxazol-5-carboxamido)-3-methylbutyl)boronic acid

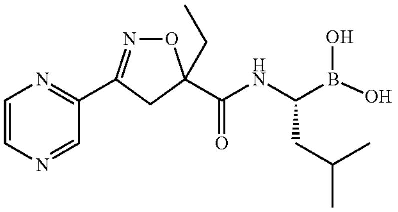 [SMILES: CCC1(C(=O)N[C@@H](CC(C)C)B(O)O)CC(c2cnccn2)=NO1]

The title compound (0.098 g, 60%) was obtained using 5-ethyl-N—((R)-3-methyl-1-((3aS,4S,6S,7aR)-3a,5,5-trimethylhexahydro-4,6-metanobenzo[d][1,3,2]dioxaborol-2-yl)butyl)-3-(pyrazin-2-yl)-4,5-dihydroisoxazol-5-carboxamide (0.23 g, 0.49 mmol) obtained in Example 6-(3) by the preparation method of Example 1-(4).

NMR: $^{1}$H-NMR (400 MHz, MeOD-d4); δ 9.17-9.16 (d, 1H), 8.68-8.67 (dd, 1H), 8.63-8.62 (d, 1H), 3.90-3.83 (m, 1H), 3.63-3.58 (m, 1H), 2.91-2.82 (m, 1H), 2.22-2.14 (m, 1H), 2.09-2.03 (m, 1H), 1.73-1.64 (m, 1H), 1.49-1.35 (m, 2H), 0.18-1.04 (m, 3H), 0.99-0.88 (m, 6H)

MS (m/z): 335[M+H], 317[M-OH]

Example 7: Preparation of ((R)-1-((S)-5-benzyl-3-phenyl-4,5-dihydroisoxazol-5-carboxamido)-3-methylbutyl)boronic acid Through the processes (1), (2) and (3) below, the title compound was obtained.

(1) Preparation of methyl 5-benzyl-3-phenyl-4,5-dihydro-1,2-oxazol-5-carboxylate

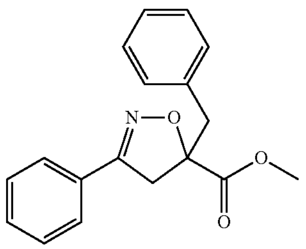 [SMILES: COC(=O)C1(Cc2ccccc2)CC(c2ccccc2)=NO1]

N-hydroxybenzenecarbonimidoyl chloride (0.58 g, 3.7 mmol) was dissolved in tetrahydrofuran (10 ml), and 2-benzoylacrylic acid (0.5 g, 3.1 mmol) and diisopropylethylamine (0.8 ml, 4.6 mmol) were added thereto at 0° C. After stirring for 18 hours, while raising to room temperature, 10 ml of a 1 N hydrochloric acid solution was added thereto, followed by stirring for 10 minutes. After distilling the tetrahydrofuran solvent under a reduced pressure, an aqueous solution layer was extracted with ethyl acetate twice. The organic layer thus extracted was washed with brine, dried over anhydrous magnesium sulfate, and filtered. The filtrate was distilled under a reduced pressure and separated by column chromatography to obtain the title compound (0.12 g, 13%).

NMR: $^{1}$H-NMR (400 MHz, DMSO-$d_6$); δ 7.59-7.17 (m, 10H), 3.74-3.70 (d, 1H), 3.34-3.17 (m, 4H)

MS (m/z): 296[M+H]

(2) Preparation of 5-benzyl-3-phenyl-4,5-dihydro-1,2-oxazol-5-carboxylic acid

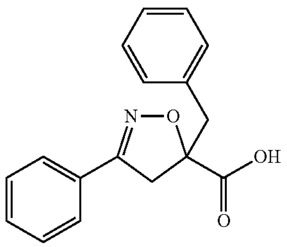 [SMILES: O=C(O)C1(Cc2ccccc2)CC(c2ccccc2)=NO1]

The title compound (0.12 g, quant.) was obtained using methyl 5-benzyl-3-phenyl-4,5-dihydro-1,2-oxazol-5-carboxylate (0.126 g, 0.43 mmol) obtained in (1) above by the preparation method of Example 1-(2).

MS (m/z): 282[M+H]

(3) Preparation of ((R)-1-((S)-5-benzyl-3-phenyl-4,5-dihydroisoxazol-5-carboxamido)-3-methylbutyl)boronic acid

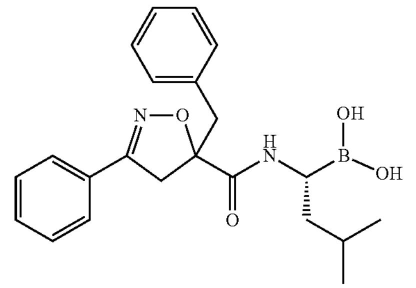 [SMILES: CC(C)C[C@H](NC(=O)C1(Cc2ccccc2)CC(c2ccccc2)=NO1)B(O)O]

5-Benzyl-3-phenyl-4,5-dihydro-1,2-oxazol-5-carboxylic acid (0.12 g, 0.41 mmol) obtained in (2) above, (R)-3-methyl-1-((3aS,4S,6S,7aR)-3a,5,5-trimethylhexahydro-4,6-metanobenzo[d][1,3,2]dioxaborol-2-yl)butan-1-amine hydrochloride (0.14 g, 0.45 mmol), and O-(benzotriazol-1-yl)-N,N,N',N'-tetramethyluronium tetrafluoroborate (0.14 g, 0.45 mmol) were dissolved at 0° C. in dimethylformamide (5 ml). While maintaining the temperature, diisopropylethylamine (0.21 ml, 1.3 mmol) was slowly added thereto, and stirring was performed for 18 hours, while raising to room temperature. The solvent was distilled under a reduced pressure, a sodium bicarbonate aqueous solution was added, and extraction with ethyl acetate was performed twice. The organic layer thus extracted was washed with brine, dried over anhydrous magnesium sulfate, and filtered. 5-Benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-phenyl-4,5-dihydroisoxazol-5-carboxamide obtained by distilling the filtrate under a reduced pressure, was dissolved in methanol (3 ml) and hexane (3 ml) without additional purification. Isobutyl boronic acid (0.060 g, 0.59 mmol) and 0.28 ml of a 1 N hydrochloric acid aqueous solution were added thereto in order, and stirring was performed at room temperature for 18 hours. Methanol (3 ml) and hexane (3 ml) were added thereto, and a methanol layer was separated. A hexane layer was extracted once more with methanol (3 ml), and all methanol layers were distilled under a reduced pressure. Ethyl acetate was added, and the resultant product was washed with a sodium bicarbonate aqueous solution and brine in order, dried over anhydrous magnesium sulfate, and filtered. The filtrate was distilled under a reduced pressure and separated by column chromatography to obtain two types of the title compound of Isomer 1 having low polarity (0.060 g, 37%, 2 steps) and Isomer 2 having high polarity (0.070 g, 44%, 2 steps).

Isomer 1

MS (m/z): 395[M+H], 377[M-OH]

Isomer 2

MS (m/z): 395[M+H], 377[M-OH]

Example 8: Preparation of ((1R)-1-(3-benzyl-4,5-dihydroisoxazol-5-carboxamido)-3-methylbutyl) boronic acid Through the processes (1), (2), (3), (4) and (5) below, the title compound was obtained.

(1) Preparation of phenyl-acetaldehyde oxime

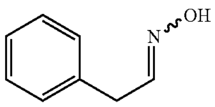

The title compound (1.11 g, 99%) was obtained using phenyl-acetaldehyde (1.0 g, 8.3 mmol) by the preparation method of Example 3-(1).

(2) Preparation of ethyl 3-benzyl-4,5-dihydro-1,2-oxazol-5-carboxylate

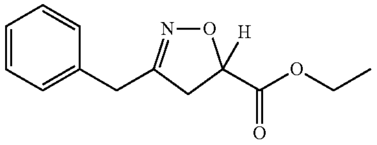 [SMILES: CCOC(=O)C1CC(Cc2ccccc2)=NO1]

The title compound (1.09 g 57%) was obtained using phenyl-acetaldehyde oxime (1.11 g, 8.2 mmol) obtained in (1) above by the preparation method of Example 2-(3).

MS (m/z): 234[M+H]

(3) Preparation of 3-benzyl-4,5-dihydro-1,2-oxazol-5-carboxylic acid

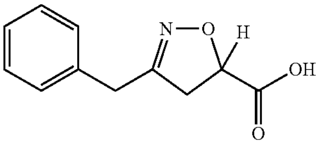 [SMILES: O=C(O)C1CC(Cc2ccccc2)=NO1]

The title compound (0.96 g, quant.) was obtained using ethyl 3-benzyl-4,5-dihydro-1,2-oxazol-5-carboxylate (1.09 g, 4.7 mmol) obtained in (2) above by the preparation method of Example 1-(2).

MS (m/z): 206[M+H]

(4) Preparation of 3-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

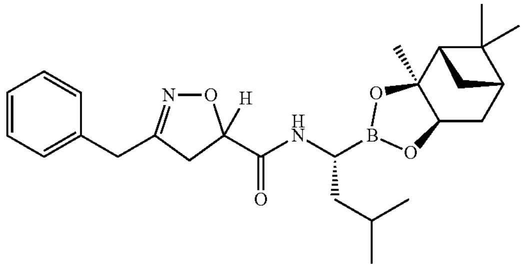 [SMILES: CC(C)C[C@H](NC(=O)C1CC(Cc2ccccc2)=NO1)B1O[C@@H]2C[C@@H]3C[C@@H](C3(C)C)[C@]2(C)O1]

The title compound (0.586 g, 28%) was obtained using 3-benzyl-4,5-dihydro-1,2-oxazol-5-carboxylic acid (0.96 g, 4.7 mmol) obtained in (3) above by the preparation method of Example 1-(3).

MS (m/z): 453[M+H]

(5) Preparation of ((1R)-1-(3-benzyl-4,5-dihydroisoxazol-5-carboxamido)-3-methylbutyl)boronic acid

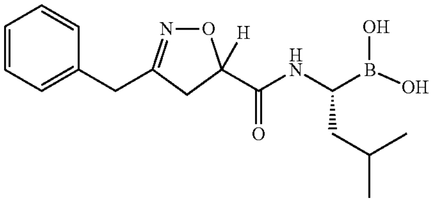 [SMILES: CC(C)C[C@H](NC(=O)C1CC(Cc2ccccc2)=NO1)B(O)O]

The title compound (0.031 g, 36%) was obtained using 3-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.122 g, 0.27 mmol) obtained in (4) above by the preparation method of Example 1-(4).

MS (m/z): 319[M+H], 301[M-OH]

Example 9: Preparation of ((1R)-1-(3-cyclohexyl-4,5-dihydroisoxazol-5-carboxamido)-3-methylbutyl) boronic acid Through the processes (1), (2), (3), (4) and (5) below, the title compound was obtained.

(1) Preparation of cyclohexanecarbaldehyde oxime

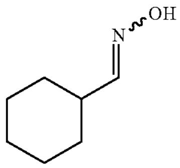

The title compound (1.38 g, 88%) was obtained using cyclohexanecarbaldehyde (1.5 ml, 12.4 mmol) by the preparation method of Example 3-(1).

(2) Preparation of ethyl 3-cyclohexyl-4,5-dihydroisoxazol-5-carboxylate

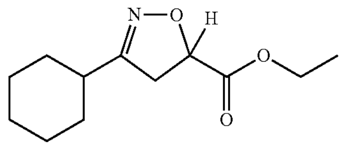 [SMILES: CCOC(=O)C1CC(C2CCCCC2)=NO1]

The title compound (1.17 g, 48%) was obtained using cyclohexanecarbaldehyde oxime (1.38 g, 10.9 mmol) obtained in (1) above by the preparation method of Preparation Example 1-(2).

MS (m/z): 226[M+H]

(3) Preparation of 3-cyclohexyl-4,5-dihydroisoxazol-5-carboxylic acid

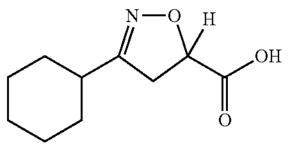 [SMILES: O=C(O)C1CC(C2CCCCC2)=NO1]

The title compound (1.02 g, quant.) was obtained using ethyl 3-cyclohexyl-4,5-dihydroisoxazol-5-carboxylate (1.17 g, 5.2 mmol) obtained in (2) above by the preparation method of Example 1-(2).

MS (m/z): 198[M+H]

(4) Preparation of 3-cyclohexyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

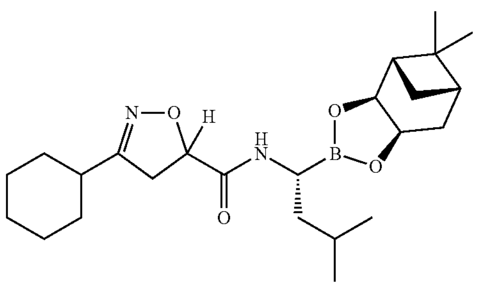 [SMILES: CC(C)C[C@H](NC(=O)C1CC(C2CCCCC2)=NO1)B1O[C@H]2[C@H]3C[C@@H](C[C@H]2O1)C3(C)C]

The title compound (0.26 g, 81%) was obtained using 3-cyclohexyl-4,5-dihydroisoxazol-5-carboxylic acid (0.14 g, 0.72 mmol) obtained in (3) above by the preparation method of Example 1-(3).

MS (m/z): 445[M+H]

(5) Preparation of ((1R)-1-(3-cyclohexyl-4,5-dihydroisoxazol-5-carboxamido)-3-methylbutyl)boronic acid

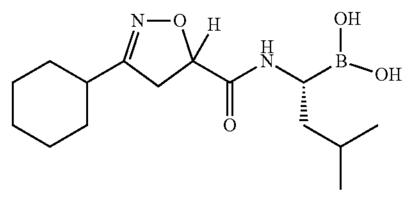 [SMILES: CC(C)C[C@H](NC(=O)C1CC(C2CCCCC2)=NO1)B(O)O]

The title compound (0.11 g, 62%) was obtained using 3-cyclohexyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.26 g, 0.58 mmol) obtained in (4) above by the preparation method of Example 1-(4).

MS (m/z): 311[M+H], 293[M-OH]

Example 10: Preparation of ((1R)-1-(3-cyclopropyl-4,5-dihydroisoxazol-5-carboxamido)-3-methylbutyl) boronic acid Through the processes (1), (2), (3), (4) and (5) below, the title compound was obtained.

(1) Preparation of cyclopropanecarbaldehyde oxime

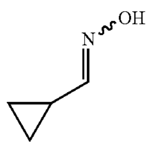

The title compound (0.37 g, 61%) was obtained using cyclopropanecarbaldehyde (0.5 g, 7.13 mmol) by the preparation method of Preparation Example 6-(1).

NMR: $^1$H-NMR (400 MHz, $CDCl_3$); δ 6.02-6.00 (d, 1H), 2.32-2.25 (m, 1H), 0.97-0.93 (m, 2H), 0.65-0.61 (m, 2H)

(2) Preparation of ethyl 3-cyclopropyl-4,5-dihydroisoxazol-5-carboxylate

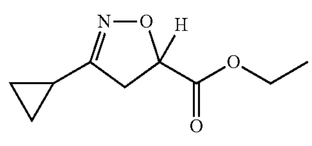

The title compound (0.33 g 41%) was obtained using cyclopropanecarbaldehyde oxime (0.37 g, 4.35 mmol) obtained in (1) above by the preparation method of Example 2-(3).

NMR: $^1$H-NMR (500 MHz, $CDCl_3$); δ 4.96-4.92 (t, 1H), 4.24-4.10 (m, 2H), 3.08-3.06 (d, 2H), 1.79-1.77 (m, 1H), 1.30-1.25 (m, 3H), 0.98-0.79 (m, 4H)

MS (m/z): 184[M+H]

(3) Preparation of 3-cyclopropyl-4,5-dihydroisoxazol-5-carboxylic acid

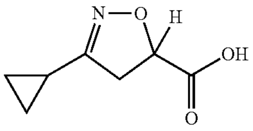 [SMILES: O=C(O)C1CC(C2CC2)=NO1]

The title compound (0.25 g, 90%) was obtained using ethyl 3-cyclopropyl-4,5-dihydroisoxazol-5-carboxylate (0.33 g, 1.80 mmol) obtained in (2) above by the preparation method of Example 1-(2).

MS (m/z): 156[M+H]

(4) Preparation of 3-cyclopropyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

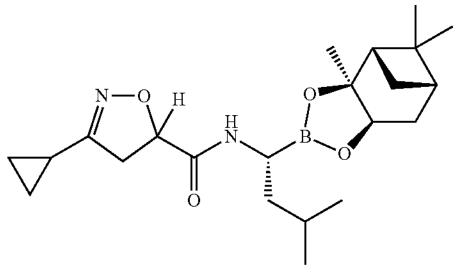 [SMILES: CC(C)C[C@H](NC(=O)C1CC(C2CC2)=NO1)B1O[C@@H]2C[C@@H]3C[C@@H](C3(C)C)[C@]2(C)O1]

The title compound (0.13 g, 72%) was obtained using 3-cyclopropyl-4,5-dihydroisoxazol-5-carboxylic acid (0.07 g, 0.45 mmol) obtained in (3) above by the preparation method of Example 1-(3).

MS (m/z): 403[M+H]

(5) Preparation of ((1R)-1-(3-cyclopropyl-4,5-dihydroisoxazol-5-carboxamido)-3-methylbutyl)boronic acid

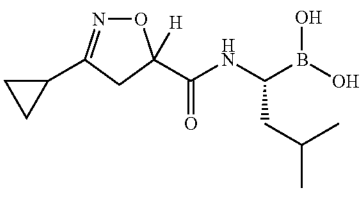 [SMILES: CC(C)C[C@H](NC(=O)C1CC(C2CC2)=NO1)B(O)O]

The title compound (0.07 g, 81%) was obtained using 3-cyclopropyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.13 g, 0.32 mmol) obtained in (4) above by the preparation method of Example 1-(4).

NMR: $^1$H-NMR (500 MHz, MeOD-d4); δ 5.16-5.12 (m, 1H), 3.27-3.24 (m, 1H), 3.07-3.02 (m, 1H), 2.83-2.78 (m, 1H), 1.82-1.77 (m, 1H), 1.65-1.60 (m, 1H), 1.36-1.32 (m, 2H), 0.95-0.92 (m, 2H), 0.91-0.88 (d, 6H), 0.80-0.76 (m, 2H)

MS (m/z): 269[M+H], 251[M-OH]

Example 11: Preparation of ((1R)-3-methyl-1-(3-penetyl-4,5-dihydroisoxazol-5-carboxamido)butyl) boronic acid Through the processes (1), (2), (3), (4) and (5) below, the title compound was obtained.

(1) Preparation of 3-phenyl-propionaldehyde oxime

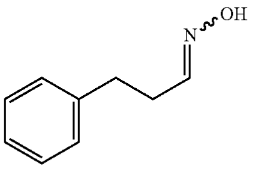 [SMILES: ON=CCCc1ccccc1]

The title compound (0.55 g, 99%) was obtained using 3-phenyl-propionaldehyde (0.5 g, 3.7 mmol) by the preparation method of Example 3-(1).

(2) Preparation of ethyl 3-(2-phenylethyl)-4,5-dihydro-1,2-oxazol-5-carboxylate

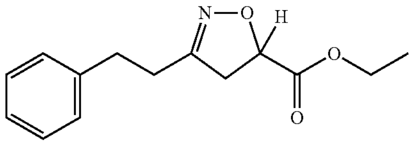 [SMILES: CCOC(=O)C1CC(CCc2ccccc2)=NO1]

The title compound (0.45 g 49%) was obtained using 3-phenyl-propionaldehyde oxime (0.55 g, 3.7 mmol) obtained in Example 11-(1) by the preparation method of Example 2-(3).

MS (m/z): 248[M+H]

(3) Preparation of 3-(2-phenylethyl)-4,5-dihydro-1,2-oxazol-5-carboxylic acid

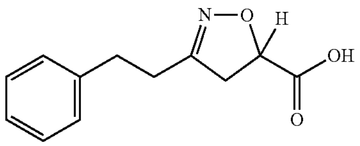 [SMILES: O=C(O)C1CC(CCc2ccccc2)=NO1]

The title compound (0.39 g, 98%) was obtained using ethyl 3-(2-phenylethyl)-4,5-dihydro-1,2-oxazol-5-carboxylate (0.45 g, 1.8 mmol) obtained in (2) above by the preparation method of Example 1-(2).

MS (m/z): 220[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-penetyl-4,5-dihydroisoxazol-5-carboxamide

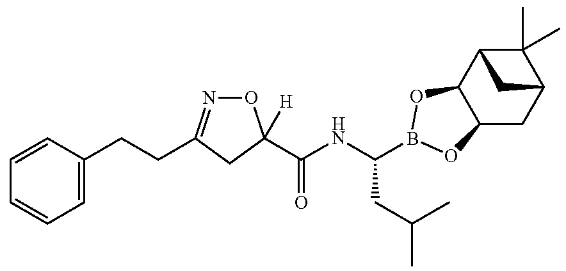 [SMILES: CC(C)C[C@H](NC(=O)C1CC(CCc2ccccc2)=NO1)B1O[C@H]2[C@H]3C[C@@H](C[C@H]2O1)C3(C)C]

The title compound (0.16 g, 19%) was obtained using 3-(2-phenylethyl)-4,5-dihydro-1,2-oxazol-5-carboxylic acid (0.39 g, 1.8 mmol) obtained in (3) above by the preparation method of Example 1-(3).

MS (m/z): 467[M+H]

(5) Preparation of ((1R)-3-methyl-1-(3-penetyl-4,5-dihydroisoxazol-5-carboxamido)butyl)boronic acid

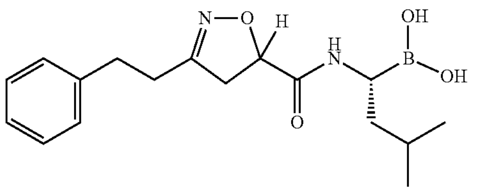 [SMILES: CC(C)C[C@H](NC(=O)C1CC(CCc2ccccc2)=NO1)B(O)O]

The title compound (0.045 g, 37%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-penetyl-4,5-dihydroisoxazol-5-carboxamide (0.16 g, 0.34 mmol) obtained in (4) above by the preparation method of Example 1-(4).

MS (m/z): 333[M+H], 315[M+H]

Example 12: Preparation of ((1R)-1-(3-(isoquinolin-1-yl)-4,5-dihydroisoxazol-5-carboxamido)-3-methylbutyl)boronic acid Through the processes (1), (2), (3), (4) and (5) below, the title compound was obtained.

(1) Preparation of isoquinolin-1-carbaldehyde oxime

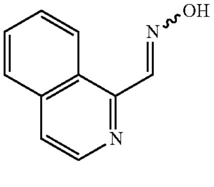 [SMILES: ON=Cc1nccc2ccccc12]

The title compound was obtained by the method described in WO200521516A1.

(2) Preparation of ethyl 3-(isoquinolin-1-yl)-4,5-dihydro-1,2-oxazol-5-carboxylate

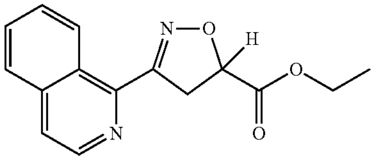 [SMILES: CCOC(=O)C1CC(c2nccc3ccccc23)=NO1]

The title compound (0.74 g, 91%) was obtained using isoquinolin-1-carbaldehyde oxime (0.52 g, 3.0 mmol) obtained in (1) above and acrylic acid ethyl ester (0.39 g, 3.9 mmol) by the preparation method of Example 2-(3).

NMR: $^1$H-NMR (500 MHz, $CDCl_3$); δ 9.25-9.24 (d, 1H), 8.55-8.54 (d, 1H), 7.86-7.85 (d, 1H), 7.74-7.66 (m, 3H), 5.21-5.17 (m, 1H), 4.31-4.25 (q, 2H), 4.10-3.97 (m, 2H), 1.34-1.31 (t, 3H)

MS (m/z): 271[M+H]

(3) Preparation of 3-(isoquinolin-1-yl)-4,5-dihydro-1,2-oxazol-5-carboxylic acid

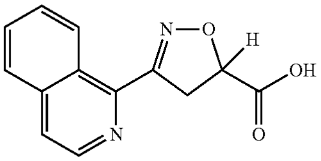 [SMILES: O=C(O)C1CC(c2nccc3ccccc23)=NO1]

The title compound (0.66 g, quant.) was obtained using ethyl 3-(isoquinolin-1-yl)-4,5-dihydro-1,2-oxazol-5-carboxylate (0.74 g, 2.7 mmol) obtained in (2) above by the preparation method of Example 1-(2).

MS (m/z): 243[M+H]

(4) Preparation of 3-(isoquinolin-1-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

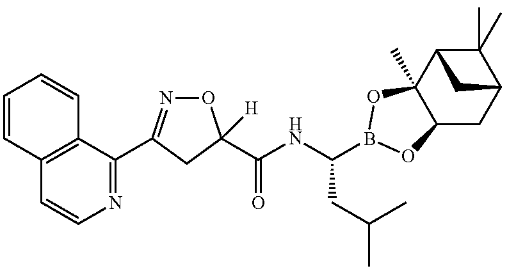 [SMILES: CC(C)C[C@H](NC(=O)C1CC(c2nccc3ccccc23)=NO1)B1O[C@@H]2C[C@@H]3C[C@@H](C3(C)C)[C@]2(C)O1]

The title compound (0.13 g, 81%) was obtained using 3-(isoquinolin-1-yl)-4,5-dihydro-1,2-oxazol-5-carboxylic acid (0.08 g, 0.33 mmol) obtained in (3) above by the preparation method of Example 1-(3).

MS (m/z): 490[M+H]

(5) Preparation of ((1R)-1-(3-(isoquinolin-1-yl)-4,5-dihydroisoxazol-5-carboxamido)-3-methylbutyl) boronic acid

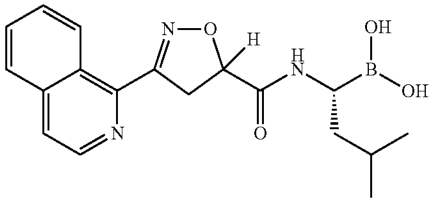 [SMILES: CC(C)C[C@H](NC(=O)C1CC(c2nccc3ccccc23)=NO1)B(O)O]

The title compound (0.045 g, 47%) was obtained using 3-(isoquinolin-1-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.13 g, 0.27 mmol) obtained in (4) above by the preparation method of Example 1-(4).

MS (m/z): 356[M+H], 338[M+H]

Example 13: Preparation of ((R)-1-((R)-5-isopropyl-3-(isoquinolin-1-yl)-4,5-dihydroisoxazol-5-carboxamido)-3-methylbutyl)boronic acid Through the processes (1), (2) and (3) below, the title compound was obtained.

(1) Preparation of 3-(isoquinolin-1-yl)-5-(propan-2-yl)-4,5-dihydro-1,2-oxazol-5-carboxylic acid

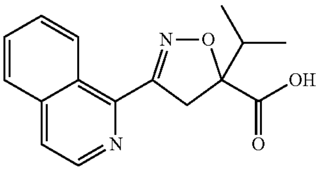 [SMILES: CC(C)C1(C(=O)O)CC(c2nccc3ccccc23)=NO1]

The title compound was obtained by the method described in WO2005021516A1.

(2) Preparation of 5-isopropyl-3-(isoquinolin-1-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

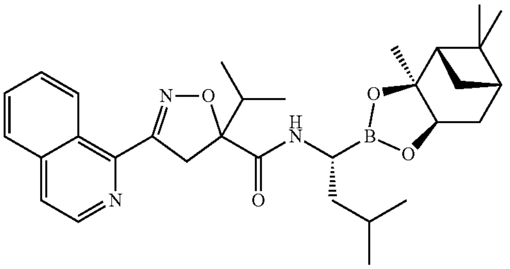 [SMILES: CC(C)C[C@H](NC(=O)C1(C(C)C)CC(c2nccc3ccccc23)=NO1)B1O[C@@H]2C[C@@H]3C[C@@H](C3(C)C)[C@]2(C)O1]

The title compound (0.075 g, 61%) was obtained using (R)-5-isopropyl-3-isoquinolin-1-yl-4,5-dihydro-isooxazol- 5-carboxylic acid (0.073 g, 0.14 mmol) obtained in (1) above by the preparation method of Example 1-(3).

MS (m/z): 490[M+H]

(3) Preparation of ((R)-1-((R)-5-isopropyl-3-(isoquinolin-1-yl)-4,5-dihydroisoxazol-5-carboxamido)-3-methylbutyl)boronic acid

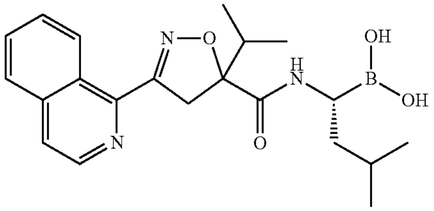 [SMILES: CC(C)C[C@H](NC(=O)C1(C(C)C)CC(c2nccc3ccccc23)=NO1)B(O)O]

The title compound (0.035 g, 63%) was obtained using 5-isopropyl-3-(isoquinolin-1-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.074 g, 0.14 mmol) obtained in (2) above by the preparation method of Example 1-(4).

NMR: $^1$H-NMR (400 MHz, $CDCl_3$); δ 9.14-9.12 (d, 1H), 8.57-8.56 (d, 1H), 7.90-7.88 (d, 1H), 7.76-7.67 (m, 3H), 7.50-7.49 (d, 1H), 4.09-4.04 (d, 1H), 3.88-3.84 (d, 1H), 3.005 (m, 1H), 2.47-2.40 (m, 1H), 1.72-1.43 (m, 3H), 1.67-1.10 (dd, 6H), 0.97-0.91 (dd, 6H)

MS (m/z): 398[M+H], 380[M-OH]

Example 14: Preparation of ((1R)-1-(3-(3-(3-(tert-butyl)phenyl)-4,5-dihydroisoxazol-5-carboxamido)-3-methylbutyl)boronic acid Through the processes (1), (2), (3), (4) and (5) below, the title compound was obtained.

(1) Preparation of 3-tert-butyl-benzaldehyde oxime

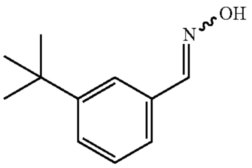

The title compound (0.54 g, 99%) was obtained using 3-tert-butyl-benzaldehyde (0.5 g, 3.08 mmol) by the preparation method of Example 3-(1).

(2) Preparation of ethyl 3-(3-tert-butylphenyl)-4,5-dihydro-1,2-oxazol-5-carboxylate

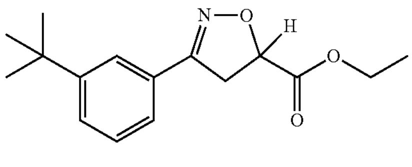 [SMILES: CCOC(=O)C1CC(c2cccc(C(C)(C)C)c2)=NO1]

The title compound (0.41 g 98%) was obtained using 3-tert-butyl-benzaldehyde oxime (0.27 g, 1.52 mmol) obtained in (1) above by the preparation method of Example 2-(3).

MS (m/z): 276[M+H]

(3) Preparation of 3-(3-tert-butylphenyl)-4,5-dihydro-1,2-oxazol-5-carboxylic acid

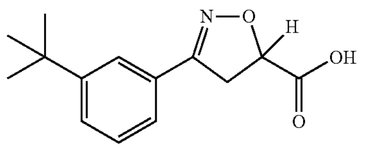 [SMILES: CC(C)(C)c1cccc(C2=NOC(C(=O)O)C2)c1]

The title compound (0.37 g, 99%) was obtained using ethyl 3-(3-tert-butylphenyl)-4,5-dihydro-1,2-oxazol-5-carboxylate (0.41 g, 1.49 mmol) obtained in (2) above by the preparation method of Example 1-(2).

MS (m/z): 248[M+H]

(4) Preparation of 3-(3-(tert-butyl)phenyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

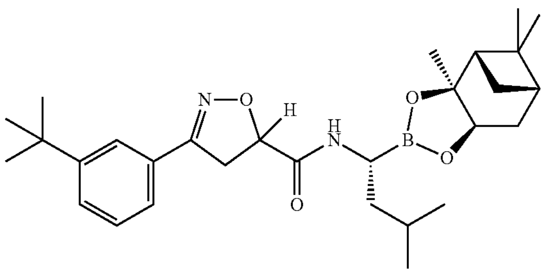 [SMILES: CC(C)C[C@H](NC(=O)C1CC(c2cccc(C(C)(C)C)c2)=NO1)B1O[C@@H]2C[C@@H]3C[C@@H](C3(C)C)[C@]2(C)O1]

The title compound (0.13 g, 66%) was obtained using 3-(3-tert-butylphenyl)-4,5-dihydro-1,2-oxazol-5-carboxylic acid (0.1 g, 0.40 mmol) obtained in Example 14-(3) by the preparation method of Example 1-(3).

MS (m/z): 495[M+H]

(5) Preparation of ((1R)-1-(3-(3-(tert-butyl)phenyl)-4,5-dihydroisoxazol-5-carboxamido)-3-methylbutyl)boronic acid

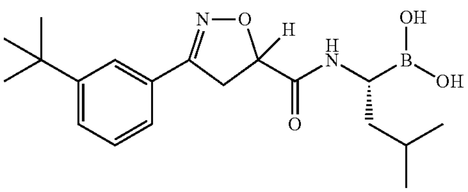 [SMILES: CC(C)C[C@H](NC(=O)C1CC(c2cccc(C(C)(C)C)c2)=NO1)B(O)O]

The title compound (0.06 g, 63%) was obtained using 3-(3-(tert-butyl)phenyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.13 g, 0.27 mmol) obtained in (4) above by the preparation method of Example 1-(4).

NMR: $^1$H-NMR (400 MHz, MeOD-d4); δ 7.79 (s, 1H), 7.57-7.38 (m, 3H), 5.41-5.38 (m, 1H), 3.90-3.74 (m, 1H), 3.74-3.67 (m, 1H), 2.90 (m, 1H), 1.67 (m, 1H), 1.43-1.38 (m, 2H), 1.36 (s, 9H), 0.94-0.91 (dd, 6H)

MS (m/z): 361[M+H], 343[M-OH]

Example 15: Preparation of ((1R)-1-(3-(4-(tert-butyl)phenyl)-4,5-dihydroisoxazol-5-carboxamido)-3-methylbutyl)boronic acid Through the processes (1), (2), (3), (4) and (5) below, the title compound was obtained.

(1) Preparation of 4-tert-butyl-benzaldehyde oxime

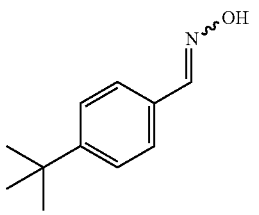

The title compound (0.46 g, quant.) was obtained using 4-tert-butyl-benzaldehyde (0.42 g, 2.6 mmol) by the preparation method of Example 3-(1).

(2) Preparation of ethyl 3-(4-tert-butylphenyl)-4,5-dihydro-1,2-oxazol-5-carboxylate

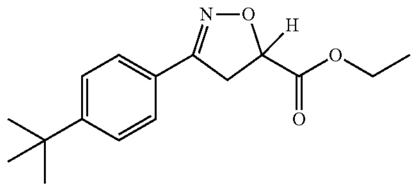 [SMILES: CCOC(=O)C1CC(c2ccc(C(C)(C)C)cc2)=NO1]

The title compound (0.12 g 17%) was obtained using 4-tert-butyl-benzaldehyde oxime (0.46 g, 2.6 mmol) obtained in (1) above by the preparation method of Example 2-(3).

MS (m/z): 276[M+H]

(3) Preparation of 3-(4-tert-butylphenyl)-4,5-dihydro-1,2-oxazol-5-carboxylic acid

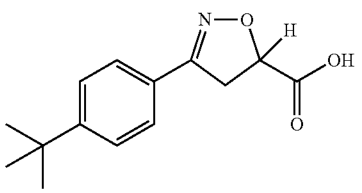 [SMILES: CC(C)(C)c1ccc(C2=NOC(C(=O)O)C2)cc1]

The title compound (0.11 g, quant.) was obtained using ethyl 3-(4-tert-butylphenyl)-4,5-dihydro-1,2-oxazol-5-carboxylate (0.12 g, 0.44 mmol) obtained in (2) above by the preparation method of Example 1-(2).

MS (m/z): 248[M+H]

(4) Preparation of 3-(4-(tert-butyl)phenyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

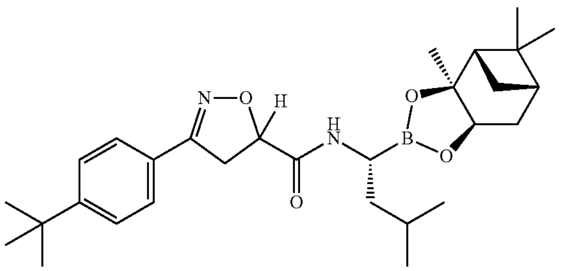 [SMILES: CC(C)C[C@H](NC(=O)C1CC(c2ccc(C(C)(C)C)cc2)=NO1)B1O[C@@H]2C[C@@H]3C[C@@H](C3(C)C)[C@]2(C)O1]

The title compound (0.15 g, 68%) was obtained using 3-(4-tert-butylphenyl)-4,5-dihydro-1,2-oxazol-5-carboxylic acid (0.11 g, 0.44 mmol) obtained in (3) above by the preparation method of Example 1-(3).

MS (m/z): 495[M+H]

(5) Preparation of ((1R)-1-(3-(4-(tert-butyl)phenyl)-4,5-dihydroisoxazol-5-carboxamido)-3-methylbutyl) boronic acid

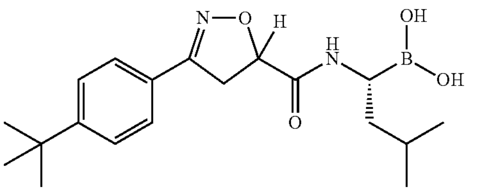 [SMILES: CC(C)C[C@H](NC(=O)C1CC(c2ccc(C(C)(C)C)cc2)=NO1)B(O)O]

The title compound (0.047 g, 44%) was obtained using 3-(4-(tert-butyl)phenyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.15 g, 0.30 mmol) obtained in (4) above by the preparation method of Example 1-(4).

MS (m/z): 361[M+H], 343[M-OH]

Example 16: Preparation of ((1R)-1-(3-(4-acetamidophenyl)-4,5-dihydroisoxazol-5-carboxamido)-3-methylbutyl)boronic acid Through the processes (1), (2), (3), (4) and (5) below, the title compound was obtained.

(1) Preparation of N-(4-formyl-phenyl)-acetamide oxime

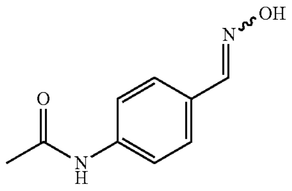

The title compound (0.99 g, quant.) was obtained using N-(4-formyl-phenyl)-acetamide (0.90 g, 5.5 mmol) by the preparation method of Example 3-(1).

MS (m/z): 179[M+H]

(2) Preparation of ethyl 3-(4-acetamidophenyl)-4,5-dihydro-1,2-oxazol-5-carboxylate

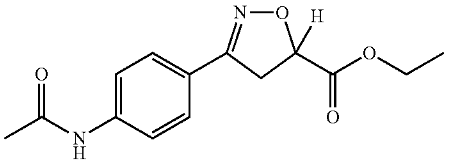 [SMILES: CCOC(=O)C1CC(c2ccc(NC(C)=O)cc2)=NO1]

The title compound (0.69 g 45%) was obtained using N-(4-formyl-phenyl)-acetamide oxime (0.99 g, 5.5 mmol) obtained in (1) above by the preparation method of Example 2-(3).

MS (m/z): 277[M+H]

(3) Preparation of 3-(4-acetamidophenyl)-4,5-dihydro-1,2-oxazol-5-carboxylic acid

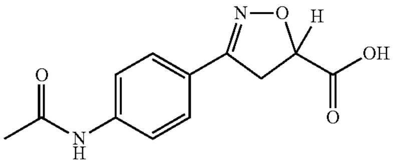 [SMILES: CC(=O)Nc1ccc(C2=NOC(C(=O)O)C2)cc1]

The title compound (0.12 g, quant.) was obtained using ethyl 3-(4-acetamidophenyl)-4,5-dihydro-1,2-oxazol-5-carboxylate (0.13 g, 0.46 mmol) obtained in (2) above by the preparation method of Example 1-(2).

MS (m/z): 249[M+H]

(4) Preparation of 3-(4-acetamidophenyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

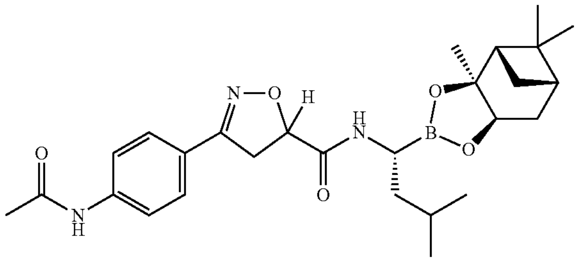 [SMILES: CC(=O)Nc1ccc(C2=NOC(C(=O)N[C@@H](CC(C)C)B3O[C@@H]4C[C@@H]5C[C@@H](C5(C)C)[C@]4(C)O3)C2)cc1]

The title compound (0.05 g, 22%) was obtained using 3-(4-acetamidophenyl)-4,5-dihydro-1,2-oxazol-5-carboxylic acid (0.11 g, 0.46 mmol) obtained in (3) above by the preparation method of Example 1-(3).

MS (m/z): 496[M+H]

(5) Preparation of ((1R)-1-(3-(4-acetamidophenyl)-4,5-dihydroisoxazol-5-carboxamido)-3-methylbutyl)boronic acid

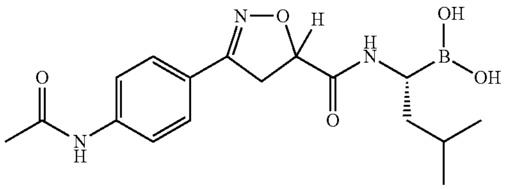 [SMILES: CC(=O)Nc1ccc(C2=NOC(C(=O)N[C@@H](CC(C)C)B(O)O)C2)cc1]

The title compound (0.022 g, 59%) was obtained using 3-(4-acetamidophenyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.050 g, 0.1 mmol) obtained in (4) above by the preparation method of Example 1-(4).

MS (m/z): 362[M+H], 344[M-OH]

Example 17: Preparation of ((1R)-3-methyl-1-(3-(naphthalen-2-yl)-4,5-dihydroisoxazol-5-carboxamido)butyl)boronic acid Through the processes (1), (2), (3), (4) and (5) below, the title compound was obtained.

(1) Preparation of naphthalen-2-carbaldehyde oxime

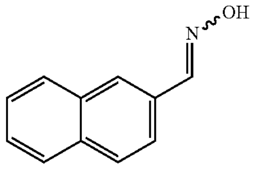 [SMILES: ON=Cc1ccc2ccccc2c1]

The title compound (1.70 g, 99%) was obtained using naphthalen-2-carbaldehyde (1.56 g, 9.99 mmol) by the preparation method of Example 3-(1).

(2) Preparation of ethyl 3-(naphthalen-2-yl)-4,5-dihydro-1,2-oxazol-5-carboxylate

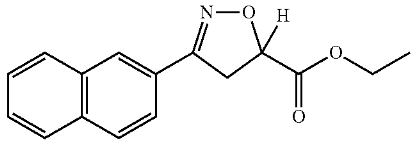 [SMILES: CCOC(=O)C1CC(c2ccc3ccccc3c2)=NO1]

The title compound (0.60 g 95%) was obtained using naphthalen-2-carbaldehyde oxime (0.40 g, 2.3 mmol) obtained in (1) above by the preparation method of Example 2-(3).

NMR: $^1$H-NMR (500 MHz, $CDCl_3$); δ 7.99-7.84 (m, 5H), 7.53-7.51 (m, 2H), 5.24-5.20 (m, 1H), 4.30-4.26 (m, 2H), 3.81-3.72 (m, 2H), 1.35-1.32 (t, 3H)

MS (m/z): 270[M+H]

(3) Preparation of 3-(naphthalen-2-yl)-4,5-dihydro-1,2-oxazol-5-carboxylic acid

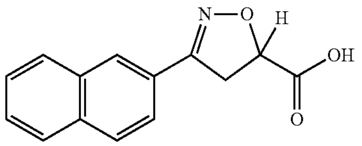 [SMILES: O=C(O)C1CC(c2ccc3ccccc3c2)=NO1]

The title compound (0.53 g, 99%) was obtained using ethyl 3-(naphthalen-2-yl)-4,5-dihydro-1,2-oxazol-5-carboxylate (0.60 g, 2.2 mmol) obtained in (2) above by the preparation method of Example 1-(2).

MS (m/z): 242[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(naphthalen-2-yl)-4,5-dihydroisoxazol-5-carboxamide

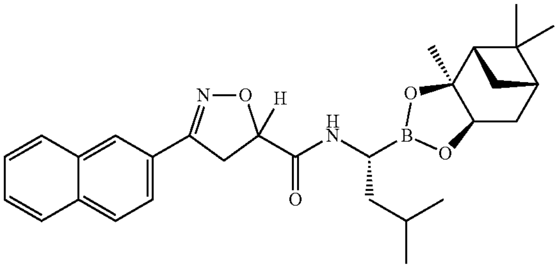 [SMILES: CC(C)C[C@H](NC(=O)C1CC(c2ccc3ccccc3c2)=NO1)B1O[C@@H]2C[C@@H]3C[C@@H](C3(C)C)[C@]2(C)O1]

The title compound (0.185 g, 91%) was obtained using 3-(naphthalen-2-yl)-4,5-dihydro-1,2-oxazol-5-carboxylic acid (0.10 g, 0.41 mmol) obtained in (3) above by the preparation method of Example 1-(3).

MS (m/z): 489[M+H]

(5) Preparation of ((1R)-3-methyl-1-(3-(naphthalen-2-yl)-4,5-dihydroisoxazol-5-carboxamido)butyl) boronic acid

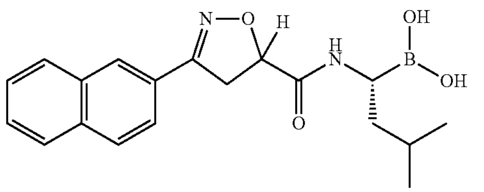 [SMILES: CC(C)C[C@H](NC(=O)C1CC(c2ccc3ccccc3c2)=NO1)B(O)O]

The title compound (0.083 g, 62%) was obtained using N—((R)-3-methyl-1-((3aS,4S,6S,7aR)-3a,5,5-trimethyl-hexahydro-4,6-metanobenzo[d][1,3,2]dioxaborol-2-yl) butyl)-3-(naphthalen-2-yl)-4,5-dihydroisoxazol-5-carboxamide (0.184 g, 0.38 mmol) obtained in (4) above by the preparation method of Example 1-(4).

NMR: $^1$H-NMR (500 MHz, $CDCl_3$); δ 7.99-7.81 (m, 5H), 7.54-7.51 (m, 2H), 7.31 (m, 1H), 5.32-5.17 (m, 1H), 3.88-3.66 (m, 2H), 3.09-2.79 (m, 1H), 1.62-1.28 (m, 3H), 0.89-0.79 (m, 6H)

MS (m/z): 355[M+H], 337[M-OH]

Example 18: Preparation of ((1R)-3-methyl-1-(3-(naphthalen-2-ylmethyl)-4,5-dihydroisoxazol-5-carboxamido)butyl)boronic acid Through the processes (1), (2), (3), (4) and (5) below, the title compound was obtained.

(1) Preparation of naphthalen-2-yl-acetaldehyde oxime

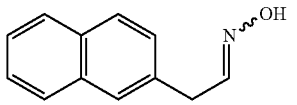 [SMILES: ON=CCc1ccc2ccccc2c1]

The title compound (0.24 g, quant.) was obtained using naphthalen-2-yl-acetaldehyde (0.22 g, 1.3 mmol) by the preparation method of Example 3-(1).

(2) Preparation of ethyl 3-[(naphthalen-2-yl) methyl]-4,5-dihydro-1,2-oxazol-5-carboxylate

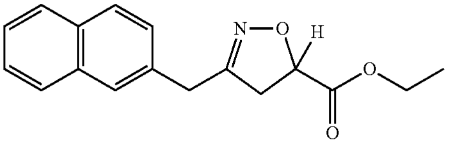 [SMILES: CCOC(=O)C1CC(Cc2ccc3ccccc3c2)=NO1]

The title compound (0.081 g 22%) was obtained using naphthalen-2-yl-acetaldehyde oxime (0.24 g, 1.3 mmol) obtained in (1) above by the preparation method of Example 2-(3).

MS (m/z): 284 [M+H]

(3) Preparation of 3-[(naphthalen-2-yl)methyl]-4,5-dihydro-1,2-oxazol-5-carboxylic acid

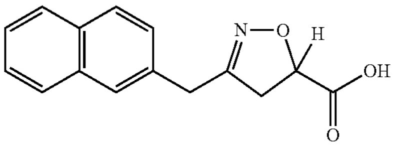 [SMILES: O=C(O)C1CC(Cc2ccc3ccccc3c2)=NO1]

The title compound (0.073 g, quant.) was obtained using ethyl 3-[(naphthalen-2-yl)methyl]-4,5-dihydro-1,2-oxazol-5-carboxylate (0.081 g, 0.29 mmol) obtained in (2) above by the preparation method of Example 1-(2).

MS (m/z): 256 [M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(naphthalen-2-ylmethyl)-4,5-dihydroisoxazol-5-carboxamide

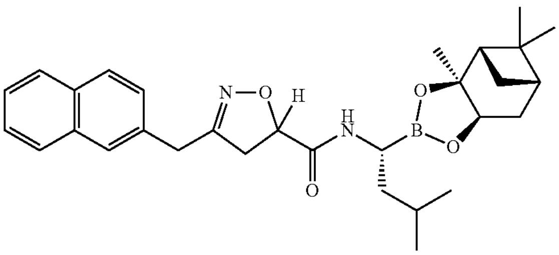 [SMILES: CC(C)C[C@H](NC(=O)C1CC(Cc2ccc3ccccc3c2)=NO1)B1O[C@@H]2C[C@@H]3C[C@@H](C3(C)C)[C@]2(C)O1]

The title compound (0.038 g, 26%) was obtained using 3-[(naphthalen-2-yl)methyl]-4,5-dihydro-1,2-oxazol-5-carboxylic acid (0.073 g, 0.29 mmol) obtained in (3) above by the preparation method of Example 1-(3).

MS (m/z): 503 [M+H]

(5) Preparation of ((1R)-3-methyl-1-(3-(naphthalen-2-ylmethyl)-4,5-dihydroisoxazol-5-carboxamido) butyl)boronic acid

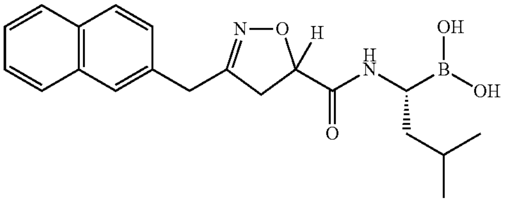 [SMILES: CC(C)C[C@H](NC(=O)C1CC(Cc2ccc3ccccc3c2)=NO1)B(O)O]

The title compound (0.008 g, 30%) was obtained using N—((R)-3-methyl-1-((3aS,4S,6S,7aR)-3a,5,5-trimethyl-hexahydro-4,6-metanobenzo[d][1,3,2]dioxaborol-2-yl) butyl)-3-(naphthalen-2-ylmethyl)-4,5-dihydroisoxazol-5-carboxamide (0.038 g, 0.08 mmol) obtained in (4) above by the preparation method of Example 1-(4).

MS (m/z): 369 [M+H], 351 [M-OH]

Example 19: Preparation of ((1R)-3-methyl-1-(3-(naphthalen-1-yl)-4,5-dihydroisoxazol-5-carboxamido)butyl)boronic acid Through the processes (1), (2), (3), (4) and (5) below, the title compound was obtained.

(1) Preparation of naphthalen-1-carbaldehyde oxime

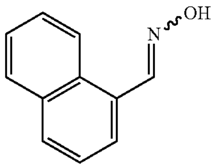

The title compound (1.71 g, 99%) was obtained using naphthalen-1-carbaldehyde (1.56 g, 9.99 mmol) by the preparation method of Example 3-(1).

MS (m/z): 172[M+H]

(2) Preparation of ethyl 3-(naphthalen-1-yl)-4,5-dihydro-1,2-oxazol-5-carboxylate

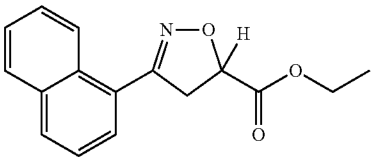

The title compound (0.53 g 85%) was obtained using naphthalen-1-carbaldehyde oxime (0.4 g, 2.34 mmol) obtained in (1) above by the preparation method of Example 2-(3).

MS (m/z): 270[M+H]

(3) Preparation of 3-(naphthalen-1-yl)-4,5-dihydro-1,2-oxazol-5-carboxylic acid

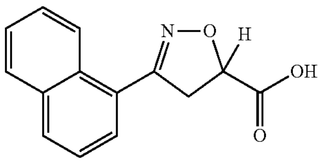 [SMILES: O=C(O)C1CC(c2cccc3ccccc23)=NO1]

The title compound (0.47 g, 99%) was obtained using ethyl 3-(naphthalen-1-yl)-4,5-dihydro-1,2-oxazol-5-carboxylate (0.53 g, 1.98 mmol) obtained in (2) above by the preparation method of Example 1-(2).

MS (m/z): 242[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(naphthalen-1-yl)-4,5-dihydroisoxazol-5-carboxamide

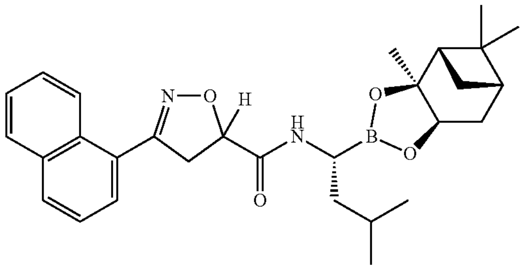 [SMILES: CC(C)C[C@H](NC(=O)C1CC(c2cccc3ccccc23)=NO1)B1O[C@@H]2C[C@@H]3C[C@@H](C3(C)C)[C@]2(C)O1]

The title compound (0.15 g, 70%) was obtained using 3-(naphthalen-1-yl)-4,5-dihydro-1,2-oxazol-5-carboxylic acid (0.1 g, 0.41 mmol) obtained in (3) above by the preparation method of Example 1-(3).

MS (m/z): 517[M+H]

(5) Preparation of ((1R)-3-methyl-1-(3-(naphthalen-1-yl)-4,5-dihydroisoxazol-5-carboxamido)butyl) boronic acid

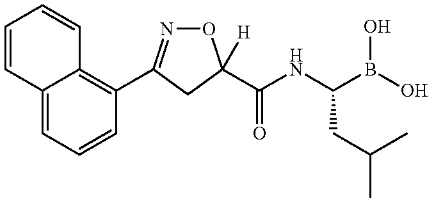 [SMILES: CC(C)C[C@H](NC(=O)C1CC(c2cccc3ccccc23)=NO1)B(O)O]

The title compound (0.07 g, 70%) was obtained using N—((R)-3-methyl-1-((3aS,4S,6S,7aR)-3a,5,5-trimethylhexahydro-4,6-metanobenzo[d][1,3,2]dioxaborol-2-yl) butyl)-3-(naphthalen-1-yl)-4,5-dihydroisoxazol-5-carboxamide (0.15 g, 0.29 mmol) obtained in (4) above by the preparation method of Example 1-(4).

NMR: $^1$H-NMR (400 MHz, MeOD-d4); δ 8.88-8.82 (m, 1H), 8.02-7.95 (m, 2H), 7.72-7.55 (m, 4H), 5.45-5.40 (m, 1H), 4.12-4.04 (m, 1H), 3.89-3.82 (m, 1H), 2.96-2.94 (m, 1H), 1.72-1.68 (m, 1H), 1.46-1.39 (m, 2H), 0.95-0.91 (m, 6H)

MS (m/z): 355[M+H]

Example 20: Preparation of ((1R)-1-(3-([1,1'-biphenyl]-3-yl)-4,5-dihydroisoxazol-5-carboxamido)-3-methylbutyl)boronic acid Through the processes (1), (2), (3), (4) and (5) below, the title compound was obtained.

(1) Preparation of biphenyl-3-carbaldehyde oxime

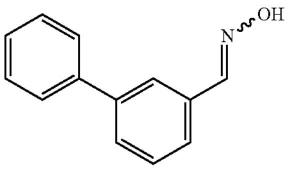 [SMILES: ON=Cc1cccc(-c2ccccc2)c1]

The title compound (0.54 g, 99%) was obtained using biphenyl-3-carbaldehyde (0.5 g, 2.74 mmol) by the preparation method of Example 3-(1).

MS (m/z): 198[M+H]

(2) Preparation of ethyl 3-(3-phenylphenyl)-4,5-dihydro-1,2-oxazol-5-carboxylate

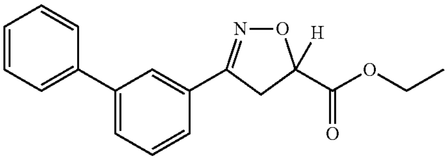 [SMILES: CCOC(=O)C1CC(c2cccc(-c3ccccc3)c2)=NO1]

The title compound (0.26 g 87%) was obtained using biphenyl-3-carbaldehyde oxime (0.2 g, 1.01 mmol) obtained in (1) above by the preparation method of Example 2-(3).

NMR: $^1$H-NMR (400 MHz, $CDCl_3$); δ 7.91-7.90 (m, 1H), 7.67-7.60 (m, 4H), 7.51-7.36 (m, 4H), 5.22-5.17 (m, 1H), 4.32-4.25 (q, 2H), 3.76-3.63 (m, 2H), 1.33-1.28 (t, 3H)

MS (m/z): 296[M+H]

(3) Preparation of 3-(3-phenylphenyl)-4,5-dihydro-1,2-oxazol-5-carboxylic acid

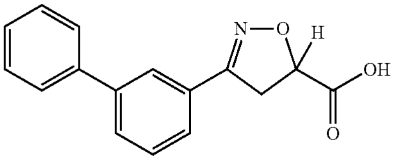

The title compound (0.23 g, 99%) was obtained using ethyl 3-(3-phenylphenyl)-4,5-dihydro-1,2-oxazol-5-carboxylate (0.26 g, 0.88 mmol) obtained in (2) above by the preparation method of Example 1-(2).

MS (m/z): 268[M+H]

(4) Preparation of 3-([1,1'-biphenyl]-3-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

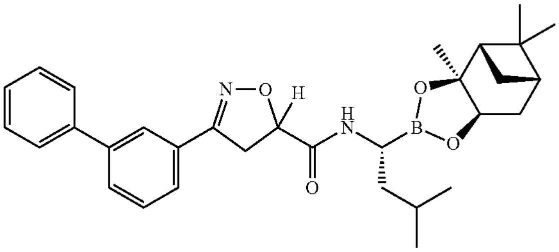

The title compound (0.17 g, 88%) was obtained using 3-(3-phenylphenyl)-4,5-dihydro-1,2-oxazol-5-carboxylic acid (0.1 g, 0.37 mmol) obtained in Example 20-(3) by the preparation method of Example 1-(3).

MS (m/z): 515[M+H]

(5) Preparation of ((1R)-1-(3-([1,1'-biphenyl]-3-yl)-4,5-dihydroisoxazol-5-carboxamido)-3-methylbutyl) boronic acid

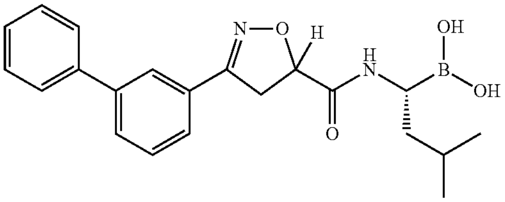

The title compound (0.089 g, 71%) was obtained using 3-([1,1'-biphenyl]-3-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.17 g, 0.33 mmol) obtained in (4) above by the preparation method of Example 1-(4).

NMR: $^1$H-NMR (500 MHz, MeOD-d4); δ 7.93-7.93 (m, 1H), 7.22-7.62 (m, 4H), 7.53-7.34 (m, 4H), 5.40-5.37 (m, 1H), 3.91-3.83 (m, 1H), 3.76-3.70 (m, 1H), 2.88-2.84 (m, 1H), 1.66-1.61 (m, 1H), 1.40-1.33 (m, 2H), 0.92-0.87 (dd, 6H)

MS (m/z): 381[M+H]

Example 21: Preparation of ((1R)-3-methyl-1-(3-(quinolin-2-yl)-4,5-dihydroisoxazol-5-carboxamido) butyl)boronic acid Through the processes (1), (2), (3), (4) and (5) below, the title compound was obtained.

(1) Preparation of quinolin-2-carbaldehyde oxime

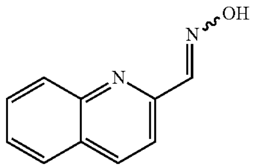 [SMILES: ON=Cc1ccc2ccccc2n1]

The title compound (1.72 g, quant.) was obtained using quinolin-2-carbaldehyde (1.57 g, 10.0 mmol) by the preparation method of Example 3-(1).

(2) Preparation of ethyl 3-(quinolin-2-yl)-4,5-dihydro-1,2-oxazol-5-carboxylate

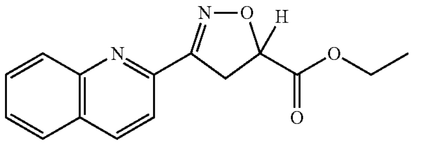 [SMILES: CCOC(=O)C1CC(c2ccc3ccccc3n2)=NO1]

The title compound (0.49 g, 78%) was obtained using quinolin-2-carbaldehyde oxime (0.40 g, 2.3 mmol) obtained in (1) above by the preparation method of Example 2-(3).

MS (m/z): 271[M+H]

(3) Preparation of 3-(quinolin-2-yl)-4,5-dihydro-1,2-oxazol-5-carboxylic acid

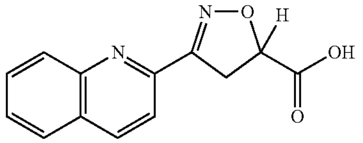 [SMILES: O=C(O)C1CC(c2ccc3ccccc3n2)=NO1]

The title compound (0.39 g, 89%) was obtained using ethyl 3-(quinolin-2-yl)-4,5-dihydro-1,2-oxazol-5-carboxylate (0.49 g, 1.8 mmol) obtained in (2) above by the preparation method of Example 1-(2).

MS (m/z): 243[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(quinolin-2-yl)-4,5-dihydroisoxazol-5-carboxamide

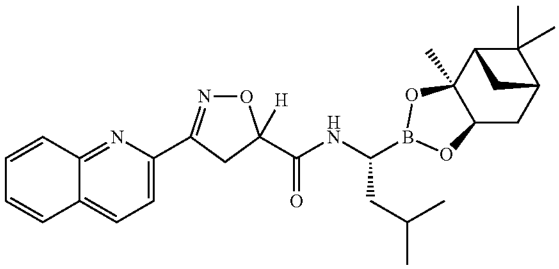 [SMILES: CC(C)C[C@H](NC(=O)C1CC(c2ccc3ccccc3n2)=NO1)B1O[C@@H]2C[C@@H]3C[C@@H](C3(C)C)[C@]2(C)O1]

The title compound (0.13 g, 82%) was obtained using 3-(quinolin-2-yl)-4,5-dihydro-1,2-oxazol-5-carboxylic acid (0.08 g, 0.33 mmol) obtained in (3) above by the preparation method of Example 1-(3).

MS (m/z): 490[M+H]

(5) Preparation of ((1R)-3-methyl-1-(3-(quinolin-2-yl)-4,5-dihydroisoxazol-5-carboxamido)butyl)boronic acid

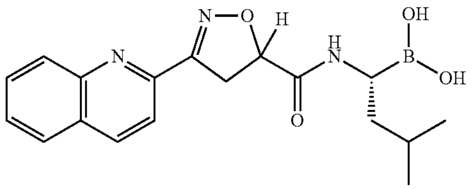 [SMILES: CC(C)C[C@H](NC(=O)C1CC(c2ccc3ccccc3n2)=NO1)B(O)O]

The title compound (0.045 g, 47%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(quinolin-2-yl)-4,5-dihydroisoxazol-5-carboxamide (0.13 g, 0.27 mmol) obtained in (4) above by the preparation method of Example 1-(4).

MS (m/z): 356[M+H]

Example 22: Preparation of ((1R)-1-(3-(isoquinolin-3-yl)-4,5-dihydroisoxazol-5-carboxamido)-3-methylbutyl)boronic acid Through the processes (1), (2), (3), (4) and (5) below, the title compound was obtained.

(1) Preparation of isoquinolin-3-carbaldehyde oxime

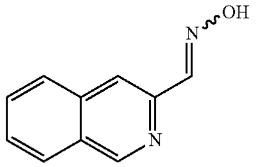 [SMILES: ON=Cc1cc2ccccc2cn1]

The title compound (0.39 g, 99%) was obtained using isoquinolin-3-carbaldehyde (0.36 g, 2.3 mmol) by the preparation method of Example 3-(1).

MS (m/z): 173[M+H]

(2) Preparation of ethyl 3-(isoquinolin-3-yl)-4,5-dihydro-1,2-oxazol-5-carboxylate

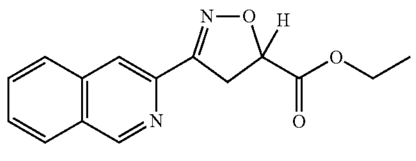 [SMILES: CCOC(=O)C1CC(c2cc3ccccc3cn2)=NO1]

The title compound (0.38 g 62%) was obtained using isoquinolin-3-carbaldehyde oxime (0.39 g, 2.3 mmol) obtained in (1) above by the preparation method of Example 2-(3).

MS (m/z): 271[M+H]

(3) Preparation of 3-(isoquinolin-3-yl)-4,5-dihydro-1,2-oxazol-5-carboxylic acid

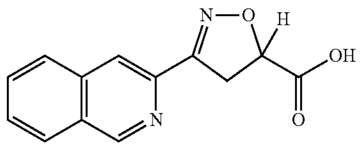 [SMILES: O=C(O)C1CC(c2cc3ccccc3cn2)=NO1]

The title compound (0.34 g, quant.) was obtained using ethyl 3-(isoquinolin-3-yl)-4,5-dihydro-1,2-oxazol-5-carboxylate (0.38 g, 1.41 mmol) obtained in (2) above by the preparation method of Example 1-(2).

MS (m/z): 243[M+H]

(4) Preparation of 3-(isoquinolin-3-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

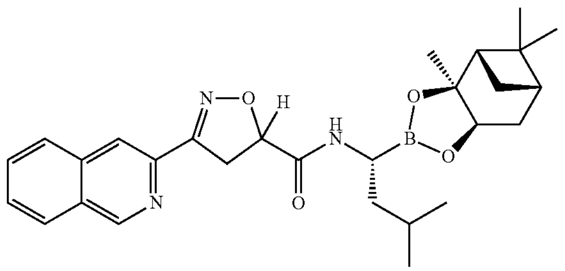 [SMILES: CC(C)C[C@H](NC(=O)C1CC(c2cc3ccccc3cn2)=NO1)B1O[C@@H]2C[C@@H]3C[C@@H](C3(C)C)[C@]2(C)O1]

The title compound (0.09 g, 56%) was obtained using 3-(isoquinolin-3-yl)-4,5-dihydro-1,2-oxazol-5-carboxylic acid (0.08 g, 0.33 mmol) obtained in (3) above by the preparation method of Example 1-(3).

MS (m/z): 490[M+H]

(5) Preparation of ((1R)-1-(3-(isoquinolin-3-yl)-4,5-dihydroisoxazol-5-carboxamido)-3-methylbutyl)boronic acid

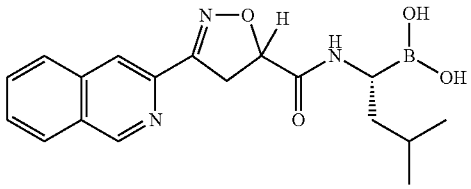 [SMILES: CC(C)C[C@H](NC(=O)C1CC(c2cc3ccccc3cn2)=NO1)B(O)O]

The title compound (0.043 g, 66%) was obtained using 3-(isoquinolin-3-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.09 g, 0.18 mmol) obtained in (4) above by the preparation method of Example 1-(4).

MS (m/z): 356[M+H]

Example 23: Preparation of ((1R)-3-methyl-1-(3-(quinolin-4-yl)-4,5-dihydroisoxazol-5-carboxamido)butyl)boronic acid Through the processes (1), (2), (3), (4) and (5) below, the title compound was obtained.

(1) Preparation of quinolin-4-carbaldehyde oxime

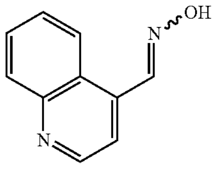 [SMILES: ON=Cc1ccnc2ccccc12]

The title compound (0.82 g, 99%) was obtained using quinolin-4-carbaldehyde (0.76 g, 4.8 mmol) by the preparation method of Example 3-(1).

(2) Preparation of ethyl 3-(quinolin-4-yl)-4,5-dihydro-1,2-oxazol-5-carboxylate

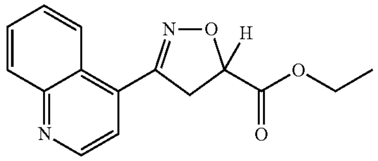 [SMILES: CCOC(=O)C1CC(c2ccnc3ccccc23)=NO1]

The title compound (0.87 g 67%) was obtained using quinolin-4-carbaldehyde oxime (0.82 g, 4.8 mmol) obtained in (1) above by the preparation method of Example 2-(3).

MS (m/z): 271[M+H]

(3) Preparation of 3-(quinolin-4-yl)-4,5-dihydro-1,2-oxazol-5-carboxylic acid

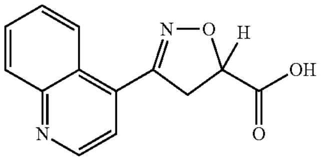 [SMILES: O=C(O)C1CC(c2ccnc3ccccc23)=NO1]

The title compound (0.77 g, 99%) was obtained using ethyl 3-(quinolin-4-yl)-4,5-dihydro-1,2-oxazol-5-carboxylate (0.87 g, 3.2 mmol) obtained in (2) above by the preparation method of Example 1-(2).

MS (m/z): 243[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(quinolin-4-yl)-4,5-dihydroisoxazol-5-carboxamide

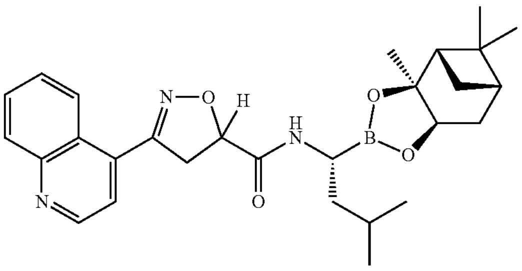 [SMILES: CC(C)C[C@H](NC(=O)C1CC(c2ccnc3ccccc23)=NO1)B1O[C@@H]2C[C@@H]3C[C@@H](C3(C)C)[C@]2(C)O1]

The title compound (0.092 g, 50%) was obtained using 3-(quinolin-4-yl)-4,5-dihydro-1,2-oxazol-5-carboxylic acid (0.091 g, 0.37 mmol) obtained in (3) above by the preparation method of Example 1-(3).

MS (m/z): 490[M+H]

(5) Preparation of ((1R)-3-methyl-1-(3-(quinolin-4-yl)-4,5-dihydroisoxazol-5-carboxamido)butyl)boronic acid

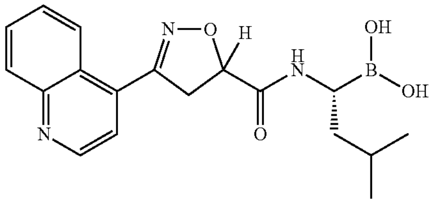 [SMILES: CC(C)C[C@H](NC(=O)C1CC(c2ccnc3ccccc23)=NO1)B(O)O]

The title compound (0.062 g, 93%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(quinolin-4-yl)-4,5-dihydroisoxazol-5-carboxamide (0.092 g, 0.19 mmol) obtained in (4) above by the preparation method of Example 1-(4).

MS (m/z): 356[M+H]

Example 24: Preparation of ((R)-1-((S)-5-benzyl-3-(3-(tert-butyl)phenyl)-4,5-dihydroisoxazol-5-carboxamido)-3-methylbutyl)boronic acid Through the processes (1), (2), (3) and (4) below, the title compound was obtained.

(1) Preparation of methyl 5-benzyl-3-(3-tert-butylphenyl)-4,5-dihydro-1,2-oxazol-5-carboxylate

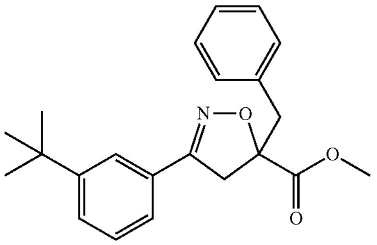 [SMILES: COC(=O)C1(Cc2ccccc2)CC(c2cccc(C(C)(C)C)c2)=NO1]

The title compound (0.37 g, 93%) was obtained using 3-tert-butyl-benzaldehyde oxime (0.2 g, 1.13 mmol) obtained in Example 14-(1) and methyl 2-benzylacrylate (0.37 g, 1.24 mmol) obtained in Preparation Example 6-(1) by the preparation method of Example 2-(3).

NMR: $^1$H-NMR (400 MHz, $CDCl_3$); δ 7.68-7.67 (d, 1H), 7.44-7.42 (m, 1H), 7.34-7.24 (7H), 3.82-3.75 (d, 1H), 3.77 (s, 3H), 3.41-3.38 (d, 1H), 3.32-3.27 (m, 2H), 1.31 (s, 9H)

MS (m/z): 352[M+H]

(2) Preparation of 5-benzyl-3-(3-tert-butylphenyl)-4,5-dihydro-1,2-oxazol-5-carboxylic acid

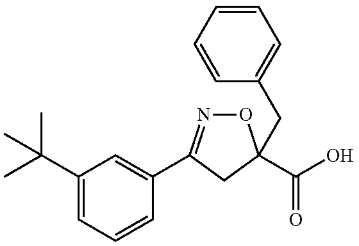 [SMILES: CC(C)(C)c1cccc(C2=NOC(Cc3ccccc3)(C(=O)O)C2)c1]

The title compound (0.35 g, 99%) was obtained using methyl 5-benzyl-3-(3-tert-butylphenyl)-4,5-dihydro-1,2-oxazol-5-carboxylate (0.37 g, 1.05 mmol) obtained in Example 24-(1) by the preparation method of Example 1-(2).

MS (m/z): 338[M+H]

(3) Preparation of 5-benzyl-3-(3-tert-butylphenyl)-N-[(1R)-3-methyl-1-[(1S,2S,6R,8S)-2,9,9-trimethyl-3,5-dioxa-4-boratricyclo[6.1.1.0$^{2,6}$]decan-4-yl]butyl]-4,5-dihydro-1,2-oxazol-5-carboxamide

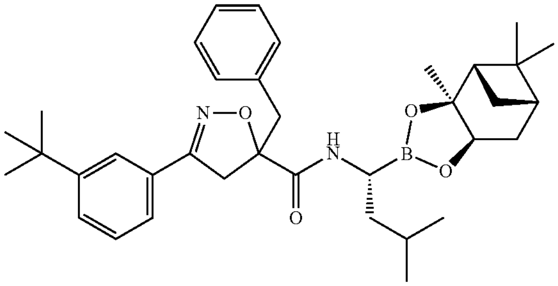 [SMILES: CC(C)C[C@H](NC(=O)C1(Cc2ccccc2)CC(c2cccc(C(C)(C)C)c2)=NO1)B1O[C@@H]2C[C@@H]3C[C@@H](C3(C)C)[C@]2(C)O1]

The title compound (0.1 g, 58%) was obtained using 5-benzyl-3-(3-tert-butylphenyl)-4,5-dihydro-1,2-oxazol-5-carboxylic acid (0.1 g, 0.30 mmol) obtained in (2) above by the preparation method of Example 1-(3).

MS (m/z): 585[M+H], 433[M-$C_{10}H_{15}O$]

(4) Preparation of ((R)-1-((S)-5-benzyl-3-(3-(tert-butyl)phenyl)-4,5-dihydroisoxazol-5-carboxamido)-3-methylbutyl)boronic acid

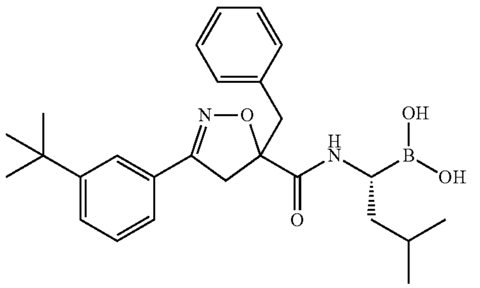 [SMILES: CC(C)C[C@H](NC(=O)C1(Cc2ccccc2)CC(c2cccc(C(C)(C)C)c2)=NO1)B(O)O]

The title compound (0.03 g, 80%) was obtained using 5-benzyl-3-(3-tert-butylphenyl)-N-[(1R)-3-methyl-1-[(1S,2S,6R,8S)-2,9,9-trimethyl-3,5-dioxa-4-boratricyclo[6.1.1.0$^{2,6}$]decan-4-yl]butyl]-4,5-dihydro-1,2-oxazol-5-carboxamide (0.05 g, 0.086 mmol) obtained in (3) above by the preparation method of Example 1-(4).

NMR: $^{1}$H-NMR (500 MHz, MeOD-d4); δ 7.67-7.66 (m, 1H), 7.50-7.49 (m, 1H), 7.40-7.22 (m, 7H), 3.82-3.79 (d, 1H), 3.58-3.55 (d, 1H), 3.43-3.40 (d, 1H), 3.27-3.24 (d, 1H), 2.74-2.41 (m, 1H), 1.48-1.43 (m, 1H), 1.31 (s, 9H), 1.28-1.21 (m, 2H), 0.81-0.79 (dd, 6H)

MS (m/z): 451[M+H], 433[M-OH]

Example 25: Preparation of ((1R)-3-methyl-1-(3-(6-phenylpyridin-2-yl)-4,5-dihydroisoxazol-5-carboxamido)butyl)boronic acid Through the processes (1), (2), (3), (4), (5) and (6) below, the title compound was obtained.

(1) Preparation of 6-phenyl-pyridin-2-carbaldehyde

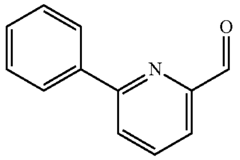 [SMILES: O=Cc1cccc(-c2ccccc2)n1]

The title compound was obtained by the method described in WO200982573A1.

(2) Preparation of 6-phenyl-pyridin-2-carbaldehyde oxime

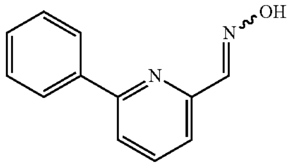 [SMILES: ON=Cc1cccc(-c2ccccc2)n1]

The title compound (0.36 g, 98%) was obtained using 6-phenyl-pyridin-2-carbaldehyde (0.34 g, 1.86 mmol) obtained in (1) above by the preparation method of Example 3-(1).

(3) Preparation of ethyl 3-(6-phenylpyridin-2-yl)-4,5-dihydro-1,2-oxazol-5-carboxylate

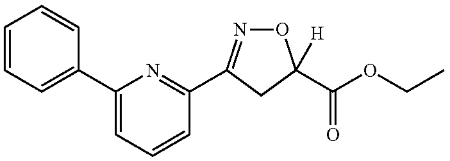 [SMILES: CCOC(=O)C1CC(c2cccc(-c3ccccc3)n2)=NO1]

The title compound (0.53 g, 99%) was obtained using 6-phenyl-pyridin-2-carbaldehyde oxime (0.36 g, 1.82 mmol) obtained in (2) above by the preparation method of Example 2-(3).

MS (m/z): 297[M+H]

(4) Preparation of 3-(6-phenylpyridin-2-yl)-4,5-dihydro-1,2-oxazol-5-carboxylic acid

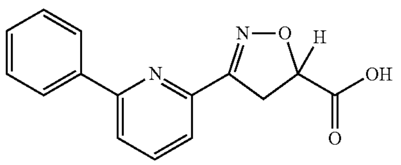 [SMILES: O=C(O)C1CC(c2cccc(-c3ccccc3)n2)=NO1]

The title compound (0.48 g, 99%) was obtained using ethyl 3-(6-phenylpyridin-2-yl)-4,5-dihydro-1,2-oxazol-5-carboxylate (0.53 g, 1.79 mmol) obtained in (3) above by the preparation method of Example 1-(2).

MS (m/z): 269[M+H]

(5) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(6-phenylpyridin-2-yl)-4,5-dihydroisoxazol-5-carboxamide

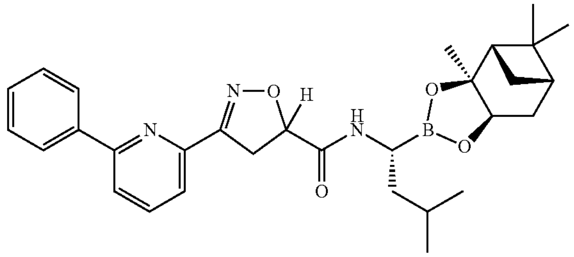 [SMILES: CC(C)C[C@H](NC(=O)C1CC(c2cccc(-c3ccccc3)n2)=NO1)B1O[C@@H]2C[C@@H]3C[C@@H](C3(C)C)[C@]2(C)O1]

The title compound (0.06 g, 52%) was obtained using 3-(6-phenylpyridin-2-yl)-4,5-dihydro-1,2-oxazol-5-carboxylic acid (0.06 g, 0.22 mmol) obtained in (4) above by the preparation method of Example 1-(3).

MS (m/z): 517[M+H]

(6) Preparation of ((1R)-3-methyl-1-(3-(6-phenylpyridin-2-yl)-4,5-dihydroisoxazol-5-carboxamido)butyl)boronic acid

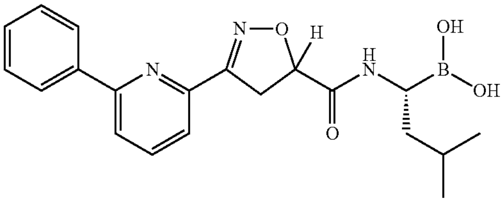 [SMILES: CC(C)C[C@H](NC(=O)C1CC(c2cccc(-c3ccccc3)n2)=NO1)B(O)O]

The title compound (0.03 g, 68%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(6-phenylpyridin-2-yl)-4,5-dihydroisoxazol-5-carboxamide (0.06 g, 0.12 mmol) obtained in Example 25-(5) by the preparation method of Example 1-(4).

NMR: $^1$H-NMR (500 MHz, MeOD-d4); δ 8.09-8.07 (m, 2H), 7.92-7.89 (m, 3H), 7.48-7.42 (m, 3H), 5.44-5.40 (m, 1H), 3.99-3.87 (m, 2H), 2.87-2.85 (m, 1H), 1.67-1.61 (m, 1H), 1.40-1.33 (m, 2H), 0.90-0.87 (m, 6H)

MS (m/z): 382[M+H], 365[M-OH]

Example 26: Preparation of ((1R)-3-methyl-1-(3-(4-(pyridin-2-yl)phenyl)-4,5-dihydroisoxazol-5-carboxamido)butyl)boronic acid Through the processes (1), (2), (3), (4), (5) and (6) below, the title compound was obtained.

(1) Preparation of 4-pyridin-2-yl-benzaldehyde

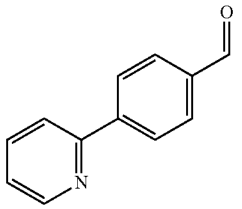 [SMILES: O=Cc1ccc(-c2ccccn2)cc1]

The title compound was obtained by the method described in European Journal of Organic Chemistry, 2008, #12 p. 2049-2055.

(2) Preparation of 4-pyridin-2-yl-benzaldehyde oxime

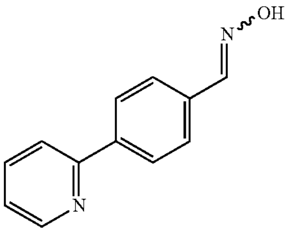 [SMILES: ON=Cc1ccc(-c2ccccn2)cc1]

The title compound (0.39 g, 99%) was obtained using 4-pyridin-2-yl-benzaldehyde (0.36 g, 1.97 mmol) obtained in (1) above by the preparation method of Example 3-(1).

MS (m/z): 199[M+H]

(3) Preparation of ethyl 3-[4-(pyridin-2-yl)phenyl]-4,5-dihydro-1,2-oxazol-5-carboxylate

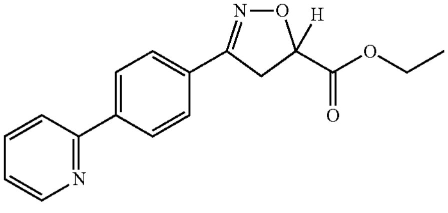 [SMILES: CCOC(=O)C1CC(c2ccc(-c3ccccn3)cc2)=NO1]

The title compound (0.42 g, 72%) was obtained using 4-pyridin-2-yl-benzaldehyde oxime (0.39 g, 1.97 mmol) obtained in (2) above by the preparation method of Example 2-(3).

MS (m/z): 297[M+H]

(4) Preparation of 3-[4-(pyridin-2-yl)phenyl]-4,5-dihydro-1,2-oxazol-5-carboxylic

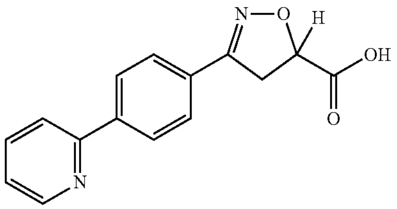 [SMILES: O=C(O)C1CC(c2ccc(-c3ccccn3)cc2)=NO1]

The title compound (0.38 g, 99%) was obtained using ethyl 3-[4-(pyridin-2-yl)phenyl]-4,5-dihydro-1,2-oxazol-5-carboxylate (0.42 g, 1.41 mmol) obtained in (3) above by the preparation method of Example 1-(2).

MS (m/z): 269[M+H]

(5) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(4-(pyridin-2-yl)phenyl)-4,5-dihydroisoxazol-5-carboxamide

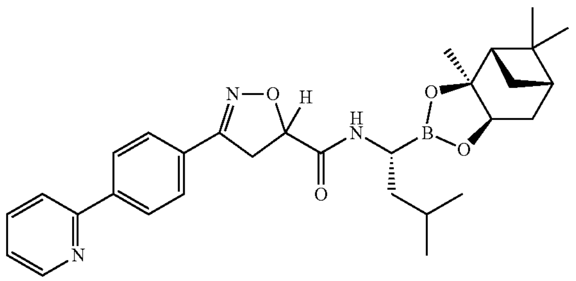 [SMILES: CC(C)C[C@H](NC(=O)C1CC(c2ccc(-c3ccccn3)cc2)=NO1)B1O[C@@H]2C[C@@H]3C[C@@H](C3(C)C)[C@]2(C)O1]

The title compound (0.13 g, 56%) was obtained using 3-[4-(pyridin-2-yl)phenyl]-4,5-dihydro-1,2-oxazol-5-carboxylic acid (0.12 g, 0.45 mmol) obtained in (4) above by the preparation method of Example 1-(3).

MS (m/z): 516[M+H], 364[M-$C_{10}H_{15}O$]

(6) Preparation of ((1R)-3-methyl-1-(3-(4-(pyridin-2-yl)phenyl)-4,5-dihydroisoxazol-5-carboxamido)butyl)boronic acid

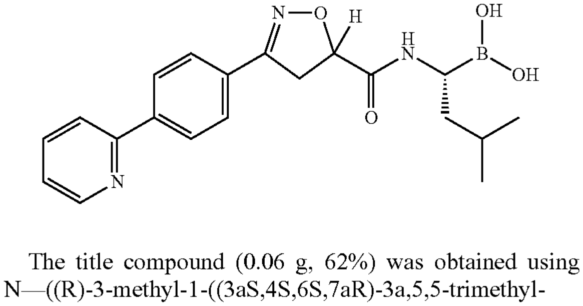

The title compound (0.06 g, 62%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(4-(pyridin-2-yl)phenyl)-4,5-dihydroisoxazol-5-carboxamide (0.13 g, 0.25 mmol) obtained in (5) above by the preparation method of Example 1-(4).

NMR: $^1$H-NMR (500 MHz, MeOD-d4); δ 8.63-8.62 (m, 1H0, 8.05-8.03 (m, 2H), 7.91-7.83 (m, 4H), 7.36-7.37 (m, 1H), 5.42-5.38 (m, 1H), 3.90-3.84 (m, 1H), 3.75-3.68 (m, 1H), 2.89-2.84 (m, 1H), 1.67-1.63 (m, 1H), 1.40-1.33 (m, 2H), 0.90-0.89 (dd, 6H)

MS (m/z): 382[M+H], 364[M-OH]

Example 27: Preparation of ((1R)-1-(3-([1,1'-biphenyl]-4-yl)-4,5-dihydroisoxazol-5-carboxamido)-3-methylbutyl)boronic acid Through the processes (1), (2), (3), (4) and (5) below, the title compound was obtained.

Preparation of (1) biphenyl-4-carbaldehyde oxime

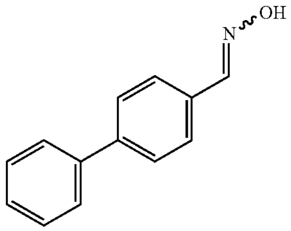 [SMILES: ON=Cc1ccc(-c2ccccc2)cc1]

The title compound (0.55 g, quant.) was obtained using biphenyl-4-carbaldehyde (0.51 g, 2.8 mmol) by the preparation method of Example 3-(1) Preparation Example 6-(1).

(2) Preparation of ethyl 3-(4-phenylphenyl)-4,5-dihydro-1,2-oxazol-5-carboxylate

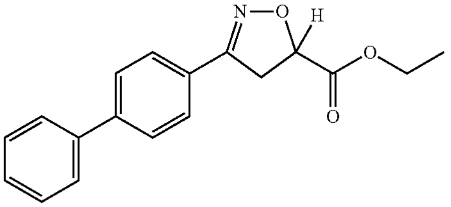 [SMILES: CCOC(=O)C1CC(c2ccc(-c3ccccc3)cc2)=NO1]

The title compound (0.62 g 75%) was obtained using biphenyl-4-carbaldehyde oxime (0.55 g, 2.8 mmol) obtained in (1) above by the preparation method of Example 2-(3).

MS (m/z): 297[M+H]

(3) Preparation of 3-(4-phenylphenyl)-4,5-dihydro-1,2-oxazol-5-carboxylic acid

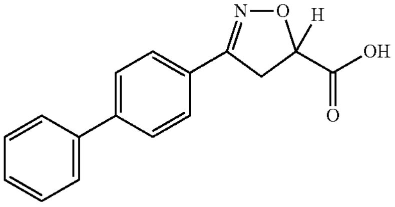

The title compound (0.43 g, 78%) was obtained using ethyl 3-(4-phenylphenyl)-4,5-dihydro-1,2-oxazol-5-carboxylate (0.62 g, 2.1 mmol) obtained in (2) above by the preparation method of Example 1-(2).

MS (m/z): 269[M+H]

(4) Preparation of 3-([1,1'-biphenyl]-4-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

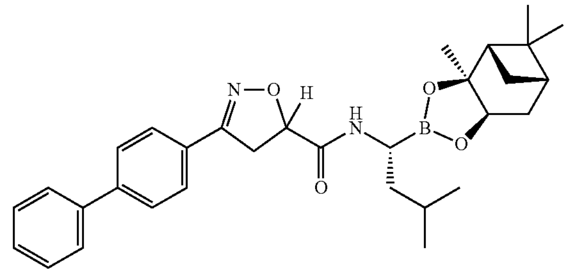

The title compound (0.11 g, 68%) was obtained using 3-(4-phenylphenyl)-4,5-dihydro-1,2-oxazol-5-carboxylic acid (0.083 g, 0.31 mmol) obtained in (3) above by the preparation method of Example 1-(3).

MS (m/z): 516[M+H]

(5) Preparation of ((1R)-1-(3-([1,1'-biphenyl]-4-yl)-4,5-dihydroisoxazol-5-carboxamido)-3-methylbutyl) boronic acid

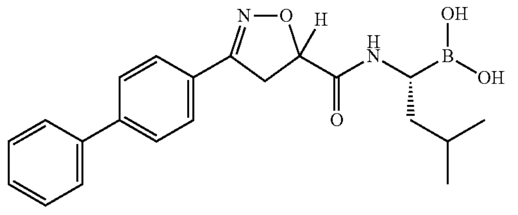

The title compound (0.041 g, 50%) was obtained using 3-([1,1'-biphenyl]-4-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.11 g, 0.21 mmol) obtained in (4) above by the preparation method of Example 1-(4).

MS (m/z): 381[M+H], 363[M-OH]

Example 28: Preparation of ((1R)-1-(3-(5-(3-fluorophenyl)pyridin-2-yl)-4,5-dihydroisoxazol-5-carboxamido)-3-methylbutyl)boronic acid Through the processes (1), (2), (3), (4), (5) and (6) below, the title compound was obtained.

(1) Preparation of 5-(3-fluoro-phenyl)-pyridin-2-carbaldehyde

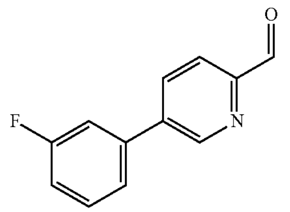 [SMILES: O=Cc1ccc(-c2cccc(F)c2)cn1]

The title compound was obtained by the method described in US2013/40981A1.

(2) Preparation of 5-(3-fluoro-phenyl)-pyridin-2-carbaldehyde oxime

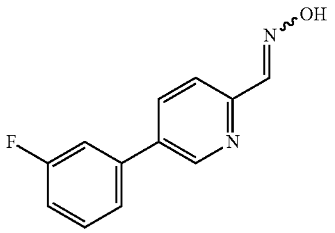 [SMILES: ON=Cc1ccc(-c2cccc(F)c2)cn1]

The title compound (0.17 g, 98%) was obtained using 5-(3-fluoro-phenyl)-pyridin-2-carbaldehyde (0.16 g, 0.80 mmol) obtained in (1) above by the preparation method of Example 3-(1).

MS (m/z): 217[M+H]

(3) Preparation of ethyl 3-[5-(3-fluorophenyl)pyridin-2-yl]-4,5-dihydro-1,2-oxazol-5-carboxylate

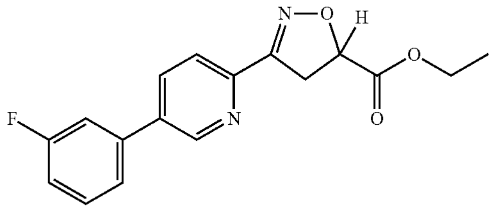 [SMILES: CCOC(=O)C1CC(c2ccc(-c3cccc(F)c3)cn2)=NO1]

The title compound (0.16 g, 64%) was obtained using 5-(3-fluoro-phenyl)-pyridin-2-carbaldehyde oxime (0.17 g, 0.80 mmol) obtained in (2) above by the preparation method of Example 2-(3).

NMR: $^1$H-NMR (400 MHz, $CDCl_3$); δ 8.82-8.81 (dd, 1H), 8.13-8.11 (dd, 1H), 7.93-7.91 (dd, 1H), 7.50-7.38 (m, 2H), 7.33-7.30 (m, 1H), 7.16-7.11 (m, 1H), 5.25-5.20 (m, 1H), 4.32-4.25 (q, 2H), 3.86-3.82 (d, 2H), 1.35-1.32 (t, 3H)

MS (m/z): 315[M+H]

(4) Preparation of 3-[5-(3-fluorophenyl)pyridin-2-yl]-4,5-dihydro-1,2-oxazol-5-carboxylic acid

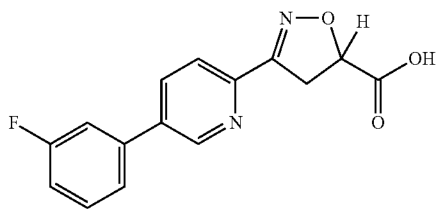 [SMILES: O=C(O)C1CC(c2ccc(-c3cccc(F)c3)cn2)=NO1]

The title compound (0.14 g, 99%) was obtained using ethyl 3-[5-(3-fluorophenyl)pyridin-2-yl]-4,5-dihydro-1,2-oxazol-5-carboxylate (0.16 g, 0.51 mmol) obtained in (3) above by the preparation method of Example 1-(2).

MS (m/z): 287[M+H]

(5) Preparation of 3-(5-(3-fluorophenyl)pyridin-2-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

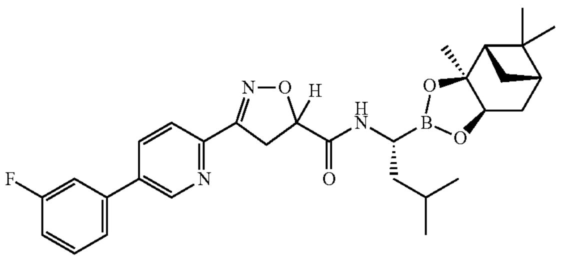 [SMILES: CC(C)C[C@H](NC(=O)C1CC(c2ccc(-c3cccc(F)c3)cn2)=NO1)B1O[C@@H]2C[C@@H]3C[C@@H](C3(C)C)[C@]2(C)O1]

The title compound (0.09 g, 69%) was obtained using 3-[5-(3-fluorophenyl)pyridin-2-yl]-4,5-dihydro-1,2-oxazol-5-carboxylic acid (0.07 g, 0.24 mmol) obtained in (4) above by the preparation method of Example 1-(3).

MS (m/z): 534[M+H]

(6) Preparation of ((1R)-1-(3-(5-(3-fluorophenyl) pyridin-2-yl)-4,5-dihydroisoxazol-5-carboxamido)-3-methylbutyl)boronic acid

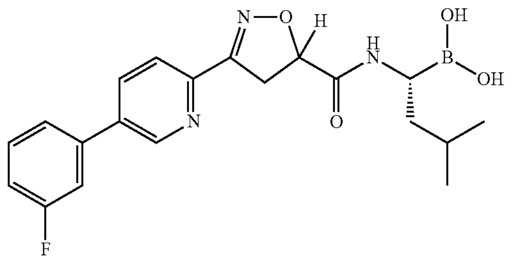 [SMILES: CC(C)C[C@H](NC(=O)C1CC(c2ccc(-c3cccc(F)c3)cn2)=NO1)B(O)O]

The title compound (0.045 g, 67%) was obtained using 3-(5-(3-fluorophenyl)pyridin-2-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.09 g, 0.17 mmol) obtained in (5) above by the preparation method of Example 1-(4).

NMR: $^1$H-NMR (500 MHz, MeOD-d4); δ 8.88-8.87 (d, 1H), 8.13-8.04 (m, 2H), 7.53-7.49 (m, 3H), 7.18-7.15 (m, 1H), 5.43-5.40 (m, 1H), 3.93-3.87 (m, 1H), 3.81-3.75 (m, 1H), 2.88-2.87 (m, 1H), 1.66-1.62 (m, 1H), 1.40-1.35 (m, 2H), 0.90-0.89 (dd, 6H)

MS (m/z): 400[M+H], 382[M-OH]

Example 29: Preparation of ((1R)-3-methyl-1-(3-(quinolin-3-yl)-4,5-dihydroisoxazol-5-carboxamido) butyl)boronic acid Through the processes (1), (2), (3), (4) and (5) below, the title compound was obtained.

(1) Preparation of quinolin-3-carbaldehyde oxime

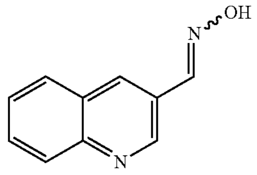 [SMILES: ON=Cc1cnc2ccccc2c1]

The title compound (0.48 g, quant.) was obtained using quinolin-3-carbaldehyde (0.44 g, 2.8 mmol) by the preparation method of Example 3-(1).

MS (m/z): 173[M+H]

(2) Preparation of ethyl 3-(quinolin-3-yl)-4,5-dihydro-1,2-oxazol-5-carboxylate

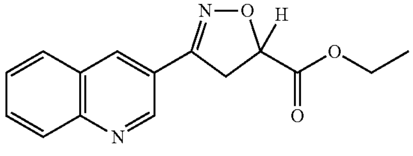 [SMILES: CCOC(=O)C1CC(c2cnc3ccccc3c2)=NO1]

The title compound (0.53 g 70%) was obtained using quinolin-3-carbaldehyde oxime (0.48 g, 2.8 mmol) obtained in (1) above by the preparation method of Example 2-(3).

NMR: $^1$H-NMR (400 MHz, $CDCl_3$); δ 8.17-8.06 (m, 3H), 7.84-7.56 (m, 3H), 5.26-5.23 (m, 1H), 4.30-4.27 (q, 2H), 3.95-3.93 (d, 2H), 1.34-1.32 (t, 3H)

MS (m/z): 271[M+H]

(3) Preparation of 3-(quinolin-3-yl)-4,5-dihydro-1,2-oxazol-5-carboxylic acid

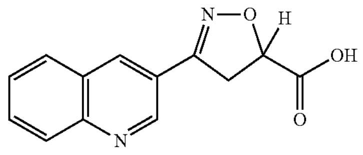 [SMILES: O=C(O)C1CC(c2cnc3ccccc3c2)=NO1]

The title compound (0.47 g, 99%) was obtained using ethyl 3-(quinolin-3-yl)-4,5-dihydro-1,2-oxazol-5-carboxylate (0.53 g, 2.0 mmol) obtained in (2) above by the preparation method of Example 1-(2).

MS (m/z): 243[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(quinolin-3-yl)-4,5-dihydroisoxazol-5-carboxamide

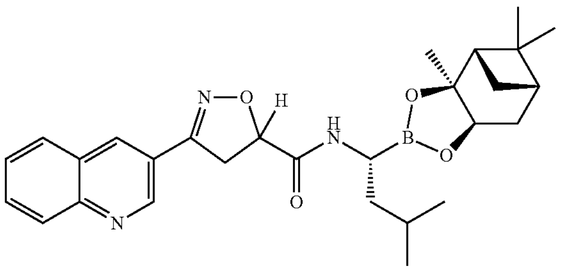 [SMILES: CC(C)C[C@H](NC(=O)C1CC(c2cnc3ccccc3c2)=NO1)B1O[C@@H]2C[C@@H]3C[C@@H](C3(C)C)[C@]2(C)O1]

The title compound (0.099 g, 39%) was obtained using 3-(quinolin-3-yl)-4,5-dihydro-1,2-oxazol-5-carboxylic acid (0.13 g, 0.52 mmol) obtained in (3) above by the preparation method of Example 1-(3).

MS (m/z): 490[M+H]

(5) Preparation of ((1R)-3-methyl-1-(3-(quinolin-3-yl)-4,5-dihydroisoxazol-5-carboxamido)butyl)boronic acid

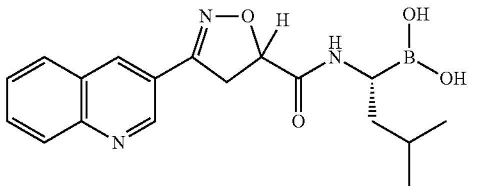 [SMILES: CC(C)C[C@H](NC(=O)C1CC(c2cnc3ccccc3c2)=NO1)B(O)O]

The title compound (0.039 g, 57%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(quinolin-3-yl)-4,5-dihydroisoxazol-5-carboxamide (0.094 g, 0.19 mmol) obtained in Example 29-(4) by the preparation method of Example 1-(4).

MS (m/z): 356[M+H], 338[M-OH]

Example 30: Preparation of ((1R)-3-methyl-1-(3-(quinolin-6-yl)-4,5-dihydroisoxazol-5-carboxamido)butyl)boronic acid Through the processes (1), (2), (3), (4) and (5) below, the title compound was obtained.

(1) Preparation of quinolin-6-carbaldehyde oxime

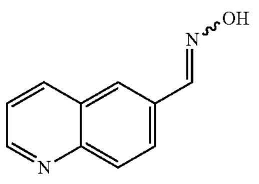 [SMILES: ON=Cc1ccc2ncccc2c1]

The title compound (0.60 g, quant.) was obtained using quinolin-6-carbaldehyde (0.55 g, 3.5 mmol) by the preparation method of Example 3-(1).

MS (m/z): 173[M+H]

(2) Preparation of ethyl 3-(quinolin-6-yl)-4,5-dihydro-1,2-oxazol-5-carboxylate

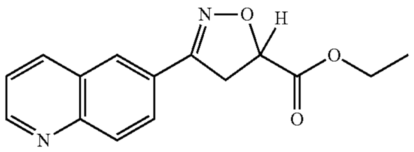 [SMILES: CCOC(=O)C1CC(c2ccc3ncccc3c2)=NO1]

The title compound (0.35 g 37%) was obtained using quinolin-6-carbaldehyde oxime (0.60 g, 3.5 mmol) obtained in (1) above by the preparation method of Example 2-(3).

MS (m/z): 271[M+H]

(3) Preparation of 3-(quinolin-6-yl)-4,5-dihydro-1,2-oxazol-5-carboxylic acid

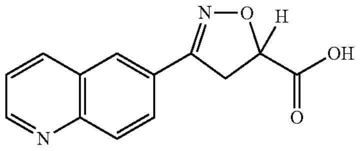 [SMILES: O=C(O)C1CC(c2ccc3ncccc3c2)=NO1]

The title compound (0.27 g, 84%) was obtained using ethyl 3-(quinolin-6-yl)-4,5-dihydro-1,2-oxazol-5-carboxylate (0.35 g, 1.3 mmol) obtained in (2) above by the preparation method of Example 1-(2).

MS (m/z): 243[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(quinolin-6-yl)-4,5-dihydroisoxazol-5-carboxamide

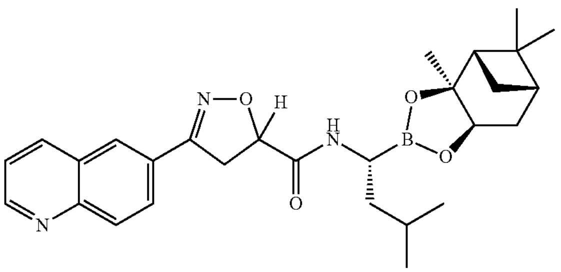 [SMILES: CC(C)C[C@H](NC(=O)C1CC(c2ccc3ncccc3c2)=NO1)B1O[C@@H]2C[C@@H]3C[C@@H](C3(C)C)[C@]2(C)O1]

The title compound (0.045 g, 22%) was obtained using 3-(quinolin-6-yl)-4,5-dihydro-1,2-oxazol-5-carboxylic acid (0.10 g, 0.42 mmol) obtained in (3) above by the preparation method of Example 1-(3).

MS (m/z): 490[M+H]

(5) Preparation of ((1R)-3-methyl-1-(3-(quinolin-6-yl)-4,5-dihydroisoxazol-5-carboxamido)butyl)boronic acid

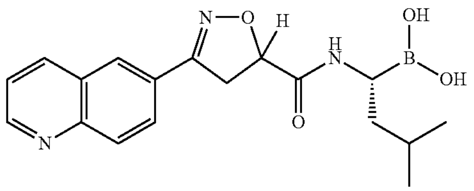 [SMILES: CC(C)C[C@H](NC(=O)C1CC(c2ccc3ncccc3c2)=NO1)B(O)O]

The title compound (0.014 g, 43%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(quinolin-6-yl)-4,5-dihydroisoxazol-5-carboxamide (0.045 g, 0.09 mmol) obtained in (4) above by the preparation method of Example 1-(4).

MS (m/z): 356[M+H], 338[M-OH]

Example 31: Preparation of ((1R)-3-methyl-1-(3-(4-(pyridin-3-yl)phenyl)-4,5-dihydroisoxazol-5-carboxamido)butyl)boronic acid Through the processes (1), (2), (3), (4), (5) and (6) below, the title compound was obtained.

(1) Preparation of 4-pyridin-3-yl-benzaldehyde

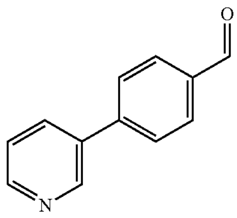 [SMILES: O=Cc1ccc(-c2cccnc2)cc1]

The title compound was obtained by the method described in Journal of Medicinal Chemistry, 2005, vol 48, pp. 224-239.

(2) Preparation of 4-pyridin-3-yl-benzaldehyde oxime

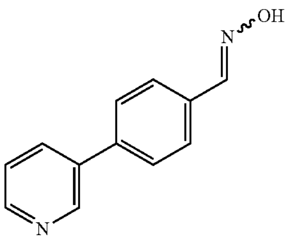 [SMILES: ON=Cc1ccc(-c2cccnc2)cc1]

The title compound (0.46 g, 99%) was obtained using 4-pyridin-3-yl-benzaldehyde (0.43 g, 2.34 mmol) obtained in (1) above by the preparation method of Example 3-(1).

MS (m/z): 199[M+H]

(3) Preparation of ethyl 3-[4-(pyridin-3-yl)phenyl]-4,5-dihydro-1,2-oxazol-5-carboxylate

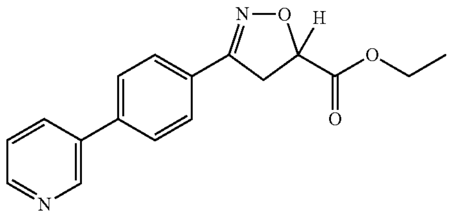 [SMILES: CCOC(=O)C1CC(c2ccc(-c3cccnc3)cc2)=NO1]

The title compound (0.42 g, 61%) was obtained using 4-pyridin-3-yl-benzaldehyde oxime (0.46 g, 2.32 mmol) obtained in (2) above by the preparation method of Example 2-(3).

MS (m/z): 297[M+H]

(4) Preparation of 3-[4-(pyridin-3-yl)phenyl]-4,5-dihydro-1,2-oxazol-5-carboxylic acid

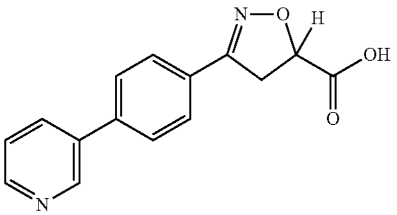 [SMILES: O=C(O)C1CC(c2ccc(-c3cccnc3)cc2)=NO1]

The title compound (0.37 g, 98%) was obtained using ethyl 3-[4-(pyridin-3-yl)phenyl]-4,5-dihydro-1,2-oxazol-5-carboxylate (0.42 g, 1.41 mmol) obtained in (3) above by the preparation method of Example 1-(2).

MS (m/z): 269[M+H]

(5) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(4-(pyridin-3-yl)phenyl)-4,5-dihydroisoxazol-5-carboxamide

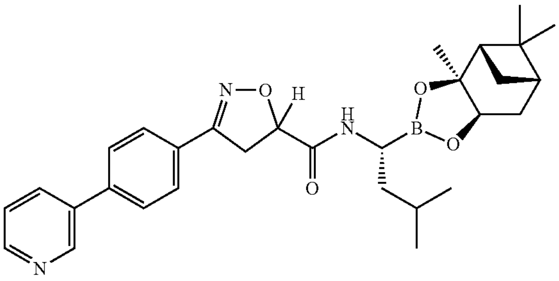 [SMILES: CC(C)C[C@H](NC(=O)C1CC(c2ccc(-c3cccnc3)cc2)=NO1)B1O[C@@H]2C[C@@H]3C[C@@H](C3(C)C)[C@]2(C)O1]

The title compound (0.13 g, 68%) was obtained using 3-[4-(pyridin-3-yl)phenyl]-4,5-dihydro-1,2-oxazol-5-carboxylic acid (0.1 g, 0.37 mmol) obtained in (4) above by the preparation method of Example 1-(3).

MS (m/z): 516[M+H]

(6) Preparation of ((1R)-3-methyl-1-(3-(4-(pyridin-3-yl)phenyl)-4,5-dihydroisoxazol-5-carboxamido)butyl)boronic acid

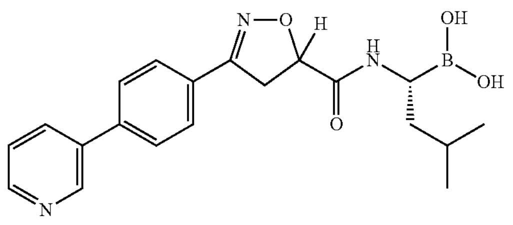 [SMILES: CC(C)C[C@H](NC(=O)C1CC(c2ccc(-c3cccnc3)cc2)=NO1)B(O)O]

The title compound (0.07 g, 73%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(4-(pyridin-3-yl)phenyl)-4,5-dihydroisoxazol-5-carboxamide (0.13 g, 0.25 mmol) obtained in (5) above by the preparation method of Example 1-(4).

NMR: $^{1}$H-NMR (500 MHz, MeOD-d4); δ 8.84 (d, 1H), 8.54-8.54 (m, 1H), 8.15-8.13 (m, 1H), 7.86-7.76 (m, 4H), 7.54-7.52 (m, 1H), 5.42-5.39 (m, 1H), 3.89-3.83 (m, 1H), 3.74-3.69 (m, 1H), 2.89-2.86 (m, 1H), 1.67-1.63 (m, 1H), 1.40-1.36 (m, 2H), 0.90-0.88 (dd, 6H)

MS (m/z): 382[M+H], 364[M-OH]

Example 32: Preparation of ((1R)-3-methyl-1-(3-(6-phenylpyridin-3-yl)-4,5-dihydroisoxazol-5-carboxamido)butyl)boronic acid Through the processes (1), (2), (3), (4), (5) and (6) below, the title compound was obtained.

(1) Preparation of 6-phenyl-pyridin-3-carbaldehyde

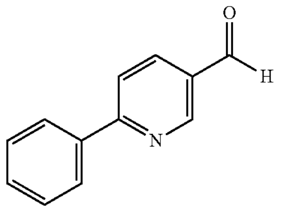 [SMILES: O=Cc1ccc(-c2ccccc2)nc1]

The title compound was obtained by the method described in Journal of Organic Chemistry, 2006, vol. 71, pp. 9589-9594.

(2) Preparation of 6-phenyl-pyridin-3-carbaldehyde oxime

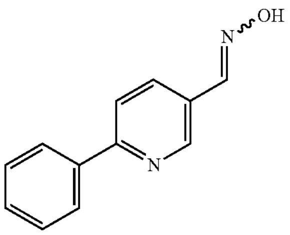 [SMILES: ON=Cc1ccc(-c2ccccc2)nc1]

The title compound (0.48 g, 99%) was obtained using 6-phenyl-pyridin-3-carbaldehyde (0.44 g, 2.40 mmol) obtained in (1) above by the preparation method of Preparation Example 6-(1).

MS (m/z): 199[M+H]

(3) Preparation of ethyl 3-(6-phenylpyridin-3-yl)-4,5-dihydro-1,2-oxazol-5-carboxylate

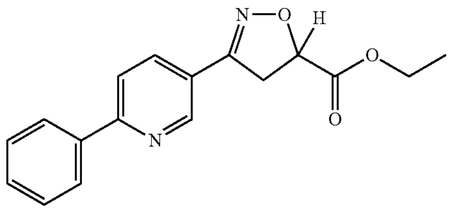 [SMILES: CCOC(=O)C1CC(c2ccc(-c3ccccc3)nc2)=NO1]

The title compound (0.5 g, 70%) was obtained using 6-phenyl-pyridin-3-carbaldehyde oxime (0.48 g, 2.42 mmol) obtained in (2) above by the preparation method of Preparation Example 1-(2).

NMR: $^{1}$H-NMR (400 MHz, $CDCl_3$); δ 8.89-8.88 (dd, 1H), 8.16-8.03 (m, 3H), 7.82-7.79 (d, 1H), 7.52-7.44 (m, 3H), 5.25-5.21 (m, 1H), 4.32-4.27 (q, 2H), 3.76-3.64 (m, 2H), 1.36-1.33 (t, 3H)

MS (m/z): 297[M+H]

(4) Preparation of 3-(6-phenylpyridin-3-yl)-4,5-dihydro-1,2-oxazol-5-carboxylic acid

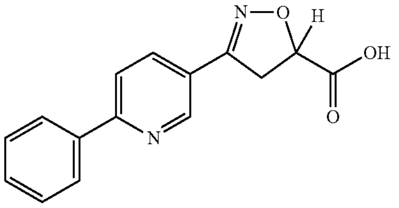 [SMILES: O=C(O)C1CC(c2ccc(-c3ccccc3)nc2)=NO1]

The title compound (0.25 g, 92%) was obtained using ethyl 3-(6-phenylpyridin-3-yl)-4,5-dihydro-1,2-oxazol-5-carboxylate (0.3 g, 1.01 mmol) obtained in (3) above by the preparation method of Example 1-(2).

MS (m/z): 269[M+H]

(5) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(6-phenylpyridin-3-yl)-4,5-dihydroisoxazol-5-carboxamide

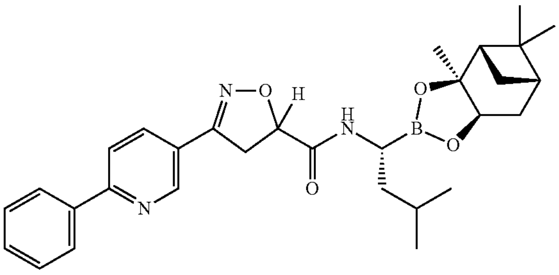 [SMILES: CC(C)C[C@H](NC(=O)C1CC(c2ccc(-c3ccccc3)nc2)=NO1)B1O[C@@H]2C[C@@H]3C[C@@H](C3(C)C)[C@]2(C)O1]

The title compound (0.13 g, 85%) was obtained using 3-(6-phenylpyridin-3-yl)-4,5-dihydro-1,2-oxazol-5-carboxylic acid (0.08 g, 0.30 mmol) obtained in (4) above by the preparation method of Example 1-(3).

MS (m/z): 516[M+H]

(6) Preparation of ((1R)-3-methyl-1-(3-(6-phenylpyridin-3-yl)-4,5-dihydroisoxazol-5-carboxamido)butyl)boronic acid

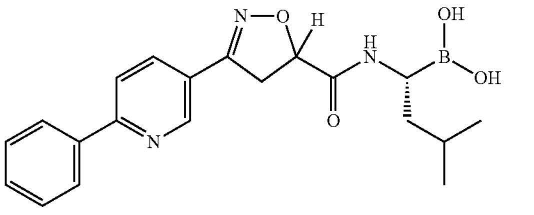 [SMILES: CC(C)C[C@H](NC(=O)C1CC(c2ccc(-c3ccccc3)nc2)=NO1)B(O)O]

The title compound (0.063 g, 65%) was obtained using N—((R)-3-methyl-1-((3aS,4S,6S,7aR)-3a,5,5-trimethyl-hexahydro-4,6-metanobenzo[d][1,3,2]dioxaborol-2-yl)butyl)-3-(6-phenylpyridin-3-yl)-4,5-dihydroisoxazol-5-carboxamide (0.13 g, 0.25 mmol) obtained in (5) above by the preparation method of Example 1-(2).

NMR: $^1$H-NMR (500 MHz, MeOD-d4); δ 8.91-8.90 (m, 1H), 8.18-8.17 (m, 1H), 8.03-8.01 (m, 3H), 7.51-7.43 (m, 3H), 5.44-5.40 (m, 1H), 3.90-3.84 (m, 1H), 3.79-3.70 (m, 1H), 2.90-2.85 (m, 1H), 1.67-1.63 (m, 1H), 1.40-4.35 (m, 2H), 0.91-0.89 (dd, 6H)

MS (m/z): 382[M+H], 364[M-OH]

Example 33: Preparation of ((1R)-3-methyl-1-(3-(5-phenylpyridin-3-yl)-4,5-dihydroisoxazol-5-carboxamido)butyl)boronic acid Through the processes (1), (2), (3), (4), (5) and (6) below, the title compound was obtained.

(1) Preparation of 5-phenyl-pyridin-3-carbaldehyde

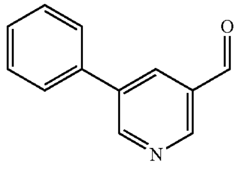 [SMILES: O=Cc1cncc(-c2ccccc2)c1]

The title compound was obtained by the method described in WO200770818A1.

(2) Preparation of 5-phenyl-pyridin-3-carbaldehyde oxime

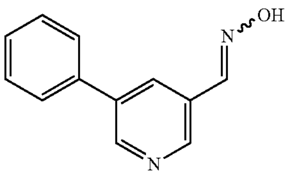 [SMILES: ON=Cc1cncc(-c2ccccc2)c1]

The title compound (0.51 g, 99%) was obtained using 5-phenyl-pyridin-3-carbaldehyde (0.47 g, 2.56 mmol) obtained in (1) above by the preparation method of Example 3-(1).

MS (m/z): 199[M+H]

(3) Preparation of ethyl 3-(5-phenylpyridin-3-yl)-4,5-dihydro-1,2-oxazol-5-carboxylate

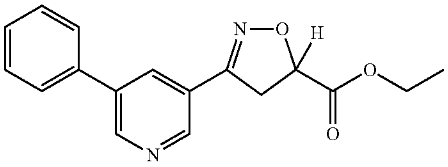 [SMILES: CCOC(=O)C1CC(c2cncc(-c3ccccc3)c2)=NO1]

The title compound (0.57 g, 83%) was obtained using 5-phenyl-pyridin-3-carbaldehyde oxime (0.51 g, 2.57 mmol) obtained in (2) above by the preparation method of Example 2-(3).

MS (m/z): 297[M+H]

(4) Preparation of 3-(5-phenylpyridin-3-yl)-4,5-dihydro-1,2-oxazol-5-carboxylic acid

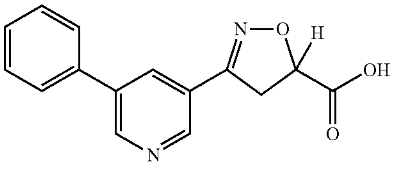 [SMILES: O=C(O)C1CC(c2cncc(-c3ccccc3)c2)=NO1]

The title compound (0.46 g, 89%) was obtained using ethyl 3-(5-phenylpyridin-3-yl)-4,5-dihydro-1,2-oxazol-5-carboxylate (0.57 g, 1.92 mmol) obtained in (3) above by the preparation method of Example 1-(2).

MS (m/z): 269[M+H]

(5) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(5-phenylpyridin-3-yl)-4,5-dihydroisoxazol-5-carboxamide

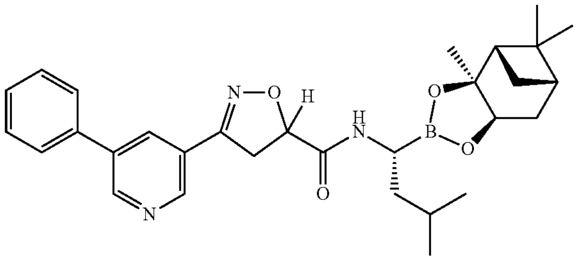 [SMILES: CC(C)C[C@H](NC(=O)C1CC(c2cncc(-c3ccccc3)c2)=NO1)B1O[C@@H]2C[C@@H]3C[C@@H](C3(C)C)[C@]2(C)O1]

The title compound (0.09 g, 59%) was obtained using 3-(5-phenylpyridin-3-yl)-4,5-dihydro-1,2-oxazol-5-carboxylic acid (0.08 g, 0.30 mmol) obtained in (4) above by the preparation method of Example 1-(3).

MS (m/z): 516[M+H]

(6) Preparation of ((1R)-3-methyl-1-(3-(5-phenylpyridin-3-yl)-4,5-dihydroisoxazol-5-carboxamido)butyl)boronic acid

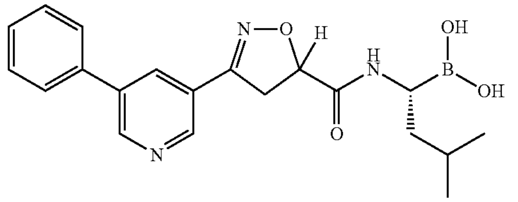 [SMILES: CC(C)C[C@H](NC(=O)C1CC(c2cncc(-c3ccccc3)c2)=NO1)B(O)O]

The title compound (0.054 g, 81%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(5-phenylpyridin-3-yl)-4,5-dihydroisoxazol-5-carboxamide (0.09 g, 0.17 mmol) obtained in (5) above by the preparation method of Example 1-(4).

NMR: $^1$H-NMR (500 MHz, MeOD-d4); δ 8.87-8.84 (dd, 2H), 8.34-8.33 (m, 1H), 7.70-7.69 (m, 2H), 7.53-7.42 (m, 3H), 5.45-5.41 (m, 1H), 3.94-3.88 (m, 1H), 3.80-3.74 (m, 1H), 2.90-2.85 (m, 1H), 1.67-1.61 (m, 1H), 1.40-1.34 (m, 2H), 0.91-0.88 (dd, 6H)

MS (m/z): 382[M+H], 364[M-OH]

Example 34: Preparation of ((1R)-3-methyl-1-(3-(3-(pyridin-2-yl)phenyl)-4,5-dihydroisoxazol-5-carboxamido)butyl)boronic acid Through the processes (1), (2), (3), (4), (5) and (6) below, the title compound was obtained.

(1) Preparation of 3-pyridin-2-yl-benzaldehyde

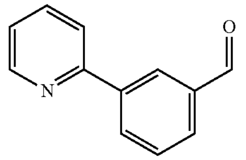 [SMILES: O=Cc1cccc(-c2ccccn2)c1]

The title compound was obtained by the method described in WO20032202772A1.

(2) Preparation of 3-pyridin-2-yl-benzaldehyde oxime

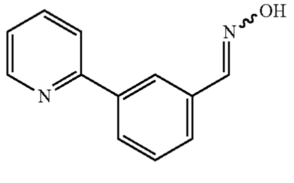 [SMILES: ON=Cc1cccc(-c2ccccn2)c1]

The title compound (0.55 g, 99%) was obtained using 3-pyridin-2-yl-benzaldehyde (0.51 g, 2.78 mmol) obtained in (1) above by the preparation method of Example 3-(1).

MS (m/z): 199[M+H]

(3) Preparation of ethyl 3-[3-(pyridin-2-yl)phenyl]-4,5-dihydro-1,2-oxazol-5-carboxylate

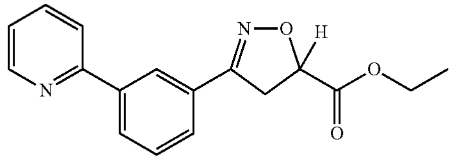 [SMILES: CCOC(=O)C1CC(c2cccc(-c3ccccn3)c2)=NO1]

The title compound (0.58 g, 70%) was obtained using 3-pyridin-2-yl-benzaldehyde oxime (0.55 g, 2.77 mmol) obtained in (2) above by the preparation method of Example 2-(3).

NMR: $^1$H-NMR (400 MHz, $CDCl_3$); δ 8.71-8.70 (d, 1H), 8.29-8.28 (d, 1H), 8.07-8.05 (dd, 1H), 7.81-7.77 (m, 3H), 7.55-7.51 (t, 1H), 7.27-7.26 (m, 1H), 5.23-5.18 (m, 1H), 4.31-4.26 (q, 2H), 3.80-3.68 (m, 2H), 1.35-1.32 (t, 3H)

MS (m/z): 297[M+H]

(4) Preparation of 3-[3-(pyridin-2-yl)phenyl]-4,5-dihydro-1,2-oxazol-5-carboxylic acid

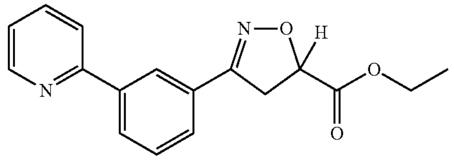 [SMILES: CCOC(=O)C1CC(c2cccc(-c3ccccn3)c2)=NO1]

The title compound (0.52 g, 98%) was obtained using ethyl 3-[3-(pyridin-2-yl)phenyl]-4,5-dihydro-1,2-oxazol-5-carboxylate (0.58 g, 1.95 mmol) obtained in (3) above by the preparation method of Example 1-(2).

MS (m/z): 269[M+H]

(5) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(3-(pyridin-2-yl)phenyl)-4,5-dihydroisoxazol-5-carboxamide

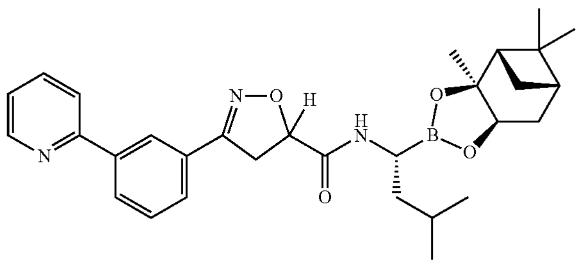 [SMILES: CC(C)C[C@H](NC(=O)C1CC(c2cccc(-c3ccccn3)c2)=NO1)B1O[C@@H]2C[C@@H]3C[C@@H](C3(C)C)[C@]2(C)O1]

The title compound (0.04 g, 26%) was obtained using 3-[3-(pyridin-2-yl)phenyl]-4,5-dihydro-1,2-oxazol-5-carboxylic acid (0.08 g, 0.30 mmol) obtained in Example 34-(4) by the preparation method of Example 1-(3).

MS (m/z): 516[M+H]

(6) Preparation of ((1R)-3-methyl-1-(3-(3-(pyridin-2-yl)phenyl)-4,5-dihydroisoxazol-5-carboxamido) butyl)boronic acid

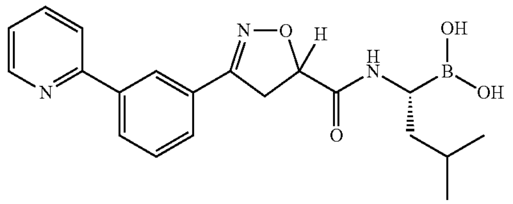 [SMILES: CC(C)C[C@H](NC(=O)C1CC(c2cccc(-c3ccccn3)c2)=NO1)B(O)O]

The title compound (0.021 g, 71%) was obtained using N—((R)-3-methyl-1-((3aS,4S,6S,7aR)-3a,5,5-trimethylhexahydro-4,6-metanobenzo[d][1,3,2]dioxaborol-2-yl) butyl)-3-(3-(pyridin-2-yl)phenyl)-4,5-dihydroisoxazol-5-carboxamide (0.04 g, 0.078 mmol) obtained in (5) above by the preparation method of Example 1-(4).

NMR: $^1$H-NMR (500 MHz, MeOD-d4); δ 8.63-8.62 (m, 1H), 8.29 (m, 1H), 8.05-8.04 (m, 1H), 7.35-7.89 (m, 2H), 7.81-7.79 (m, 1H), 7.59-7.56 (m, 1H), 7.40-7.37 (m, 1H), 5.43-5.40 (m, 1H), 3.93-3.87 (m, 1H), 3.78-3.71 (m, 1H), 2.87-2.85 (m, 1H), 1.66-1.63 (m, 1H), 1.40-1.33 (m, 2H), 0.90-0.88 (dd, 6H)

MS (m/z): 382[M+H], 364[M-OH]

Example 35: Preparation of ((1R)-1-(5-benzyl-3-(5'-chloro-2'-methoxy-[1,1'-biphenyl]-3-yl)-4,5-dihydroisoxazol-5-carboxamido)-3-methylbutyl)boronic acid Through the processes (1), (2), (3), (4) and (5) below, the title compound was obtained.

(1) Preparation of 3-bromo-benzaldehyde oxime

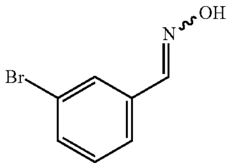

The title compound (2.03 g, 100%) was obtained using 3-bromo-benzaldehyde (1.85 g, 10.0 mmol) by the preparation method of Example 3-(1).

NMR: $^1$H-NMR (400 MHz, $CDCl_3$); δ 8.08 (1H, s), 7.81 (1H, s), 7.56-7.24 (4H, m)

(2) Preparation of methyl 5-benzyl-3-(3-bromophenyl)-4,5-dihydroisoxazol-5-carboxylate

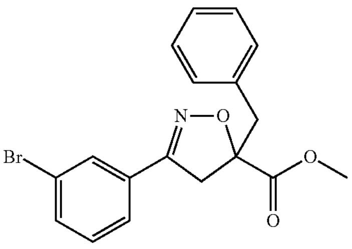 [SMILES: COC(=O)C1(Cc2ccccc2)CC(c2cccc(Br)c2)=NO1]

The title compound (1.01 g, 90%) was obtained using 3-bromo-benzaldehyde oxime (0.60 g, 3.0 mmol) obtained in (1) above and methyl 2-benzylacrylate (0.58 g, 3.3 mmol) obtained in Preparation Example 6-(1) by the preparation method of Example 2-(3).

NMR: $^1$H-NMR (400 MHz, $CDCl_3$); δ 7.70 (1H, s), 7.52-7.10 (8H, m), 3.79 (3H, s), 3.73 (1H, d), 3.39 (1H, d), 3.29-3.22 (2H, m)

MS (m/z): 374[M+H]

(3) Preparation of methyl 5-benzyl-3-(5'-chloro-2'-methoxy-[1,1'-biphenyl]-3-yl)-4,5-dihydroisoxazol-5-carboxylate

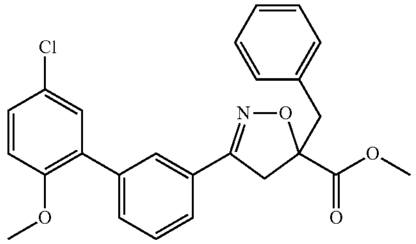 [SMILES: COC(=O)C1(Cc2ccccc2)CC(c2cccc(-c3cc(Cl)ccc3OC)c2)=NO1]

Methyl 5-benzyl-3-(3-bromophenyl)-4,5-dihydroisoxazol-5-carboxylate (0.154 g, 0.412 mmol) obtained in (2) above, 5-chloro-2-methoxyphenylboronic acid (0.093 g, 0.499 mmol), potassium carbonate (0.29 g, 2.06 mmol), [1,1'-bis(diphenylphosphino)ferrocene]dichloropalladium (II), and a dichloro complex (0.034 g, 0.042 mmol) were mixed with 1,4-dioxane (10 ml) and water (1 ml), followed by stirring at 80° C. for 3 hours. The solvent was distilled under a reduced pressure, and the residue remained was separated by column chromatography to obtain the title compound (0.189 g, 100%).

NMR: $^1$H-NMR (400 MHz, $CDCl_3$); δ 7.67 (1H, s), 7.57 (1H, d), 7.51 (1H, d), 7.42-7.24 (8H, m), 6.89 (1H, d), 3.78 (1H, d), 3.77 (3H, s), 3.41-3.27 (3H, m)

MS (m/z): 436[M+H]

(4) Preparation of 5-benzyl-3-[3-(5-chloro-2-methoxyphenyl)phenyl]-N-[(1R)-3-methyl-1-[(1S,2S,6R,8S)-2,9,9-trimethyl-3,5-dioxa-4-boratricyclo[6.1.1.0$^{2,6}$]decan-4-yl]butyl]-4,5-dihydro-1,2-oxazol-5-carboxamide

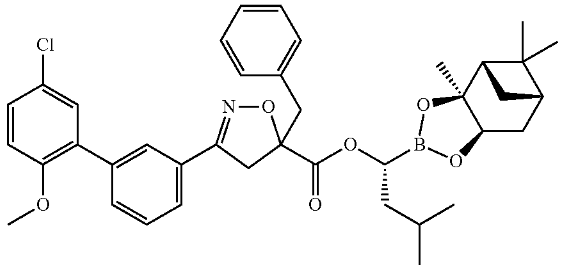 [SMILES: COc1ccc(Cl)cc1-c1cccc(C2=NOC(Cc3ccccc3)(C(=O)O[C@@H](CC(C)C)B3O[C@@H]4C[C@@H]5C[C@@H](C5(C)C)[C@]4(C)O3)C2)c1]

The title compound (0.163 g, 49%, 2 steps) was obtained using methyl 5-benzyl-3-(5'-chloro-2'-methoxy-[1,1'-biphenyl]-3-yl)-4,5-dihydroisoxazol-5-carboxylate (0.189 g, 0.434 mmol) obtained in (3) above by the preparation methods of Example 1-(2) and Example 1-(3).

MS (m/z): 669[M+H]

(5) Preparation of ((1R)-1-(5-benzyl-3-(5'-chloro-2'-methoxy-[1,1'-biphenyl]-3-yl)-4,5-dihydroisoxazol-5-carboxamido)-3-methylbutyl)boronic acid

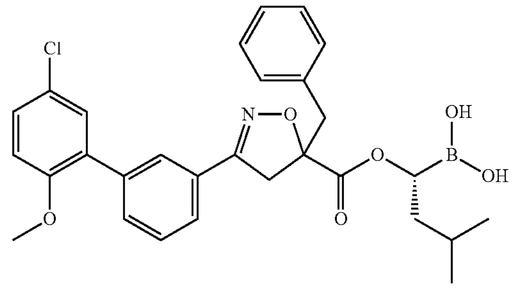 [SMILES: COc1ccc(Cl)cc1-c1cccc(C2=NOC(Cc3ccccc3)(C(=O)O[C@@H](CC(C)C)B(O)O)C2)c1]

The title compound (0.069 g, 72%) was obtained using 5-benzyl-3-[3-(5-chloro-2-methoxyphenyl)phenyl]-N-[(1R)-3-methyl-1-[(1S,2S,6R,8S)-2,9,9-trimethyl-3,5-dioxa-4-boratricyclo[6.1.1.$0^{2,6}$]decan-4-yl]butyl]-4,5-dihydro-1,2-oxazol-5-carboxamide (0.119 g, 0.180 mmol) obtained in (4) above by the preparation method of Example 1-(4).

NMR: $^1$H-NMR (400 MHz, $CDCl_3$); δ 7.79-6.91 (12H, m), 3.84-3.74 (4H, m), 3.53-3.26 (3H, m), 3.07-2.54 (1H, m), 1.42-0.83 (9H, m)

MS (m/z): 535[M+H]

Example 36: Preparation of ((1R)-1-(5-benzyl-3-(3-(isoquinolin-1-yl)phenyl)-4,5-dihydroisoxazol-5-carboxamido)-3-methylbutyl)boronic acid Through the processes (1), (2), (3) and (4) below, the title compound was obtained.

(1) Preparation of methyl 5-benzyl-3-[3-(4,4,5,5-tetramethyl-1,3,2-dioxaborolan-2-yl)phenyl]-4,5-dihydro-1,2-oxazol-5-carboxylate

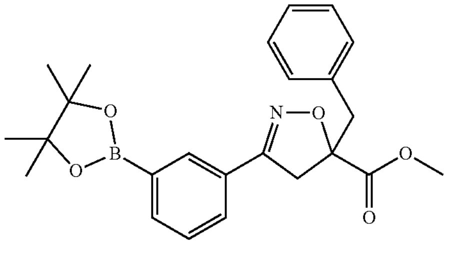

Methyl 5-benzyl-3-(3-bromophenyl)-4,5-dihydroisoxazol-5-carboxylate (0.655 g, 1.75 mmol) obtained in (2) above, bispinacolatodiborane (0.889 g, 3.50 mmol), potassium acetate (0.689 g, 7.02 mmol), [1,1'-bis(diphenylphosphino)ferrocene]dichloropalladium(II), and a dichloro complex (0.143 g, 0.175 mmol) were mixed with dimethylacetamide (15 ml), followed by stirring at 80° C. for 1 hour. The solvent was distilled under a reduced pressure, and the residue remained was separated by column chromatography to obtain the title compound (0.733 g, 100%).

NMR: $^1$H-NMR (400 MHz, $CDCl_3$); δ 7.92-7.84 (3H, m), 7.39 (1H, t), 7.34-7.26 (5H, m), 3.86 (1H, d), 3.82 (3H, s), 3.45-3.31 (3H, m), 1.38 (12H, s)

(2) Preparation of methyl 5-benzyl-3-[3-(isoquinolin-1-yl)phenyl]-4,5-dihydro-1,2-oxazol-5-carboxylate

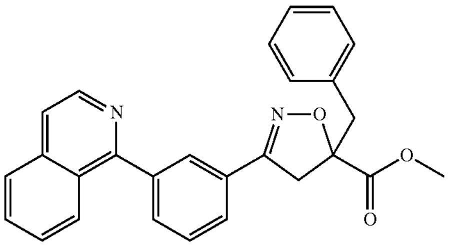 [SMILES: COC(=O)C1(Cc2ccccc2)CC(c2cccc(-c3nccc4ccccc34)c2)=NO1]

The title compound (0.101 g, 71%) was obtained using methyl 5-benzyl-3-[3-(4,4,5,5-tetramethyl-1,3,2-dioxaborolan-2-yl)phenyl]-4,5-dihydro-1,2-oxazol-5-carboxylate (0.142 g, 0.337 mmol) obtained in (1) above and 1-bromoisoquinoline by the preparation method of Example 35-(3).

NMR: $^1$H-NMR (400 MHz, $CDCl_3$); δ 8.60 (1H, d), 8.02-7.53 (9H, m), 7.29-7.25 (5H, m), 3.82 (1H, d), 3.78 (3H, s), 3.41-3.27 (3H, m)

(3) Preparation of 5-benzyl-3-(3-(isoquinolin-1-yl)phenyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

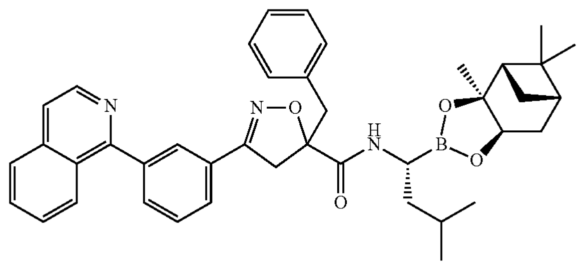 [SMILES: CC(C)C[C@H](NC(=O)C1(Cc2ccccc2)CC(c2cccc(-c3nccc4ccccc34)c2)=NO1)B1O[C@@H]2C[C@@H]3C[C@@H](C3(C)C)[C@]2(C)O1]

The title compound (0.076 g, 48%, 2 steps) was obtained using methyl 5-benzyl-3-[3-(isoquinolin-1-yl)phenyl]-4,5-dihydro-1,2-oxazol-5-carboxylate (0.101 g, 0.239 mmol) obtained in (2) above by the preparation methods of Example 1-(2) and Example 1-(3).

MS (m/z): 656[M+H]

(4) Preparation of ((1R)-1-(5-benzyl-3-(3-(isoquinolin-1-yl)phenyl)-4,5-dihydroisoxazol-5-carboxamido)-3-methylbutyl)boronic acid

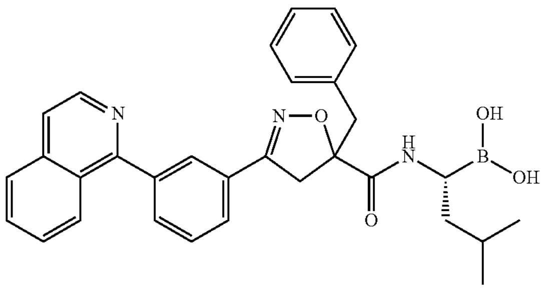 [SMILES: CC(C)C[C@H](NC(=O)C1(Cc2ccccc2)CC(c2cccc(-c3nccc4ccccc34)c2)=NO1)B(O)O]

The title compound (0.040 g, 66%) was obtained using 5-benzyl-3-(3-(isoquinolin-1-yl)phenyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.076 g, 0.239 mmol) obtained in (3) above by the preparation method of Example 1-(4).

NMR: $^{1}$H-NMR (500 MHz, $CD_3OD$); δ 8.48-8.47 (1H, m), 7.99-7.61 (9H, m), 7.33-7.22 (5H, m), 3.88-3.83 (1H, m), 3.67-3.59 (1H, m), 3.41 (1H, d), 3.29-3.26 (4H, m), 2.76-2.69 (1H, m), 1.41-1.06 (3H, m), 0.80-0.76 (6H, m)

MS (m/z): 522[M+H]

Example 37: Preparation of ((1R)-3-methyl-1-(3-(3-(trifluoromethoxy)phenyl)-4,5-dihydroisoxazol-5-carboxamido)butyl)boronic acid Through the processes (1), (2), (3), (4) and (5) below, the title compound was obtained.

(1) Preparation of 3-trifluoromethoxy-benzaldehyde oxime

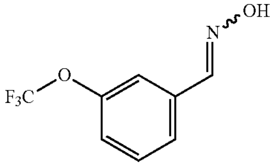 [SMILES: ON=Cc1cccc(OC(F)(F)F)c1]

The title compound (0.54 g, 99%) was obtained using 3-trifluoromethoxy-benzaldehyde (0.5 g, 2.63 mmol) by the preparation method of Example 3-(1).

MS (m/z): 206[M+H]

(2) Preparation of ethyl 3-[3-(trifluoromethoxy)phenyl]-4,5-dihydro-1,2-oxazol-5-carboxylate

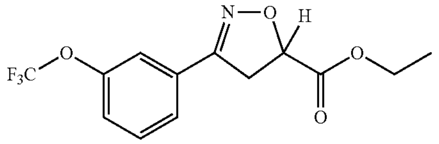 [SMILES: CCOC(=O)C1CC(c2cccc(OC(F)(F)F)c2)=NO1]

The title compound (0.63 g 79%) was obtained using 3-trifluoromethoxy-benzaldehyde oxime (0.54 g, 2.63 mmol) obtained in (1) above by the preparation method of Example 2-(3).

MS (m/z): 304[M+H]

(3) Preparation of 3-[3-(trifluoromethoxy)phenyl]-4,5-dihydro-1,2-oxazol-5-carboxylic acid

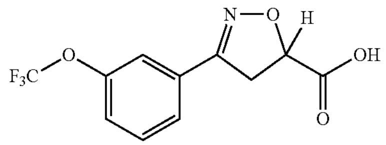 [SMILES: O=C(O)C1CC(c2cccc(OC(F)(F)F)c2)=NO1]

The title compound (0.57 g, 99%) was obtained using ethyl 3-[3-(trifluoromethoxy)phenyl]-4,5-dihydro-1,2-oxazol-5-carboxylate (0.63 g, 2.08 mmol) obtained in (2) above by the preparation method of Example 1-(2).

MS (m/z): 276[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(3-(trifluoromethoxy)phenyl)-4,5-dihydroisoxazol-5-carboxamide

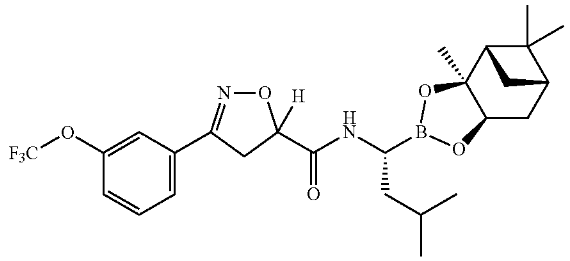 [SMILES: CC(C)C[C@H](NC(=O)C1CC(c2cccc(OC(F)(F)F)c2)=NO1)B1O[C@@H]2C[C@@H]3C[C@@H](C3(C)C)[C@]2(C)O1]

The title compound (0.11 g, 83%) was obtained using 3-[3-(trifluoromethoxy)phenyl]-4,5-dihydro-1,2-oxazol-5-carboxylic acid (0.07 g, 0.25 mmol) obtained in (3) above by the preparation method of Example 1-(3).

MS (m/z): 523[M+H]

(5) Preparation of ((1R)-3-methyl-1-(3-(3-(trifluoromethoxy)phenyl)-4,5-dihydroisoxazol-5-carboxamido)butyl)boronic acid

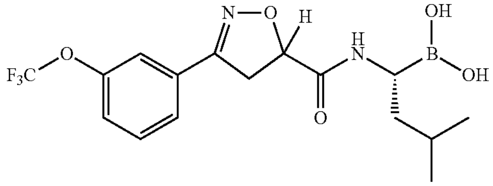 [SMILES: CC(C)C[C@H](NC(=O)C1CC(c2cccc(OC(F)(F)F)c2)=NO1)B(O)O]

The title compound (0.065 g, 80%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(3-(trifluoromethoxy)phenyl)-4,5-dihydroisoxazol- 5-carboxamide (0.11 g, 0.21 mmol) obtained in (4) above by the preparation method of Example 1-(4).

NMR: $^1$H-NMR (500 MHz, MeOD-d4); δ 7.68-7.64 (m, 2H), 7.56-7.53 (t, 1H), 7.38-7.37 (d, 1H), 5.41-5.37 (m, 1H), 3.85-3.79 (m, 1H), 3.70-3.63 (m, 1H), 2.88-2.84 (m, 1H), 1.65-1.61 (m, 1H), 1.39-1.34 (m, 2H), 0.89-0.88 (dd, 6H)

MS (m/z): 389[M+H], 371[M-OH]

Example 38: Preparation of ((1R)-3-methyl-1-(3-(4-(trifluoromethoxy)phenyl)-4,5-dihydroisoxazol-5-carboxamido)butyl)boronic acid Through the processes (1), (2), (3), (4) and (5) below, the title compound was obtained.

(1) Preparation of 4-trifluoromethoxy-benzaldehyde oxime

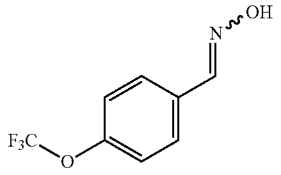

The title compound (1.0 g, quant.) was obtained using 4-trifluoromethoxy-benzaldehyde (0.93 g, 4.9 mmol) by the preparation method of Preparation Example 6-(1).

MS (m/z): 206[M+H]

(2) Preparation of ethyl 3-[4-(trifluoromethoxy)phenyl]-4,5-dihydro-1,2-oxazol-5-carboxylate

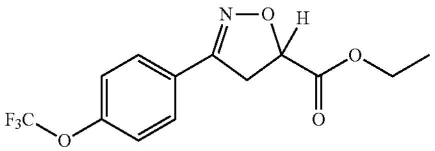 [SMILES: CCOC(=O)C1CC(c2ccc(OC(F)(F)F)cc2)=NO1]

The title compound (0.94 g, 64%) was obtained using 4-trifluoromethoxy-benzaldehyde oxime (1.0 g, 4.9 mmol) obtained in (1) above by the preparation method of Example 2-(3).

MS (m/z): 304[M+H]

(3) Preparation of 3-[4-(trifluoromethoxy)phenyl]-4,5-dihydro-1,2-oxazol-5-carboxylic acid

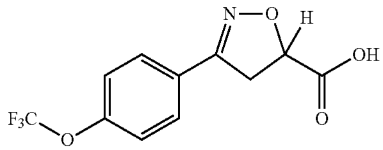 [SMILES: O=C(O)C1CC(c2ccc(OC(F)(F)F)cc2)=NO1]

The title compound (0.77 g, 90%) was obtained using ethyl 3-[4-(trifluoromethoxy)phenyl]-4,5-dihydro-1,2-oxazol-5-carboxylate (0.94 g, 3.1 mmol) obtained in (2) above by the preparation method of Example 1-(2).

MS (m/z): 276[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(4-(trifluoromethoxy)phenyl)-4,5-dihydroisoxazol-5-carboxamide

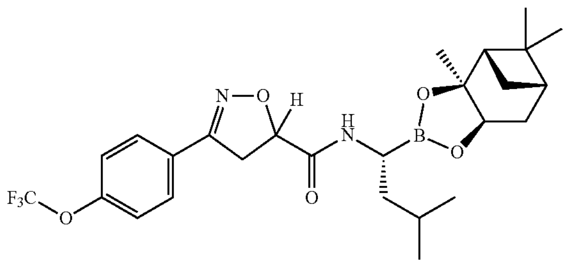 [SMILES: CC(C)C[C@H](NC(=O)C1CC(c2ccc(OC(F)(F)F)cc2)=NO1)B1O[C@@H]2C[C@@H]3C[C@@H](C3(C)C)[C@]2(C)O1]

The title compound (0.10 g, 54%) was obtained using 3-[4-(trifluoromethoxy)phenyl]-4,5-dihydro-1,2-oxazol-5-carboxylic acid (0.099 g, 0.36 mmol) obtained in (3) above by the preparation method of Example 1-(3).

MS (m/z): 523[M+H]

(5) Preparation of ((1R)-3-methyl-1-(3-(4-(trifluoromethoxy)phenyl)-4,5-dihydroisoxazol-5-carboxamido)butyl)boronic acid

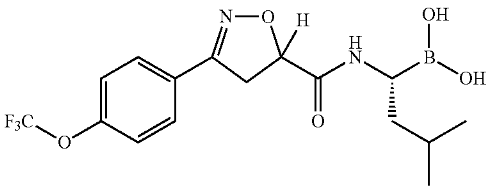 [SMILES: CC(C)C[C@H](NC(=O)C1CC(c2ccc(OC(F)(F)F)cc2)=NO1)B(O)O]

The title compound (0.014 g, 19%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(4-(trifluoromethoxy)phenyl)-4,5-dihydroisoxazol-5-carboxamide (0.10 g, 0.19 mmol) obtained in (4) above by the preparation method of Example 1-(4).

MS (m/z): 389[M+H], 371[M-OH]

Example 39: Preparation of ((1R)-3-methyl-1-(3-(2-(trifluoromethoxy)phenyl)-4,5-dihydroisoxazol-5-carboxamido)butyl)boronic acid Through the processes (1), (2), (3), (4) and (5) below, the title compound was obtained.

(1) Preparation of 2-trifluoromethoxy-benzaldehyde oxime

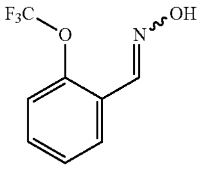 [SMILES: ON=Cc1ccccc1OC(F)(F)F]

The title compound (0.54 g, quant.) was obtained using 2-trifluoromethoxy-benzaldehyde (0.50 g, 2.6 mmol) by the preparation method of Example 3-(1).

MS (m/z): 206[M+H]

(2) Preparation of ethyl 3-[2-(trifluoromethoxy)phenyl]-4,5-dihydro-1,2-oxazol-5-carboxylate

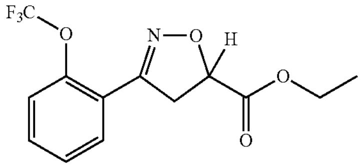 [SMILES: CCOC(=O)C1CC(c2ccccc2OC(F)(F)F)=NO1]

The title compound (0.60 g, 75%) was obtained using 2-trifluoromethoxy-benzaldehyde oxime (0.54 g, 2.6 mmol) obtained in (1) above by the preparation method of Example 2-(3).

MS (m/z): 304[M+H]

(3) Preparation of 3-[2-(trifluoromethoxy)phenyl]-4,5-dihydro-1,2-oxazol-5-carboxylic acid

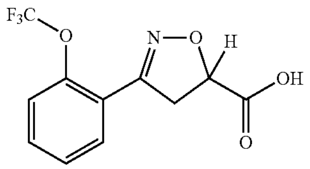 [SMILES: O=C(O)C1CC(c2ccccc2OC(F)(F)F)=NO1]

The title compound (0.55 g, quant.) was obtained using ethyl 3-[2-(trifluoromethoxy)phenyl]-4,5-dihydro-1,2-oxazol-5-carboxylate (0.60 g, 2.0 mmol) obtained in (2) above by the preparation method of Example 1-(2).

MS (m/z): 276[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(2-(trifluoromethoxy)phenyl)-4,5-dihydroisoxazol-5-carboxamide

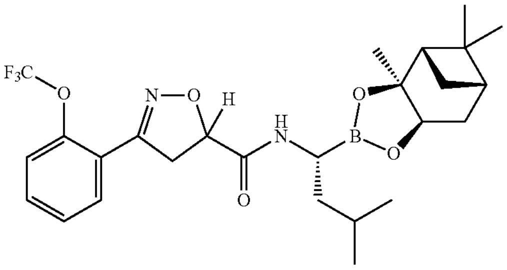 [SMILES: CC(C)C[C@H](NC(=O)C1CC(c2ccccc2OC(F)(F)F)=NO1)B1O[C@@H]2C[C@@H]3C[C@@H](C3(C)C)[C@]2(C)O1]

The title compound (0.12 g, 69%) was obtained using 3-[2-(trifluoromethoxy)phenyl]-4,5-dihydro-1,2-oxazol-5-carboxylic acid (0.091 g, 0.33 mmol) obtained in (3) above by the preparation method of Example 1-(3).

MS (m/z): 523[M+H]

(5) Preparation of ((1R)-3-methyl-1-(3-(2-(trifluoromethoxy)phenyl)-4,5-dihydroisoxazol-5-carboxamido)butyl)boronic acid

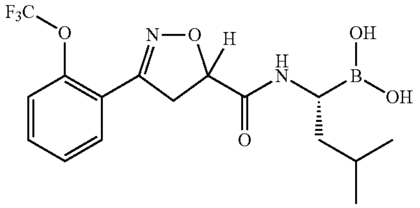 [SMILES: CC(C)C[C@H](NC(=O)C1CC(c2ccccc2OC(F)(F)F)=NO1)B(O)O]

The title compound (0.063 g, 71%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(2-(trifluoromethoxy)phenyl)-4,5-dihydroisoxazol-5-carboxamide (0.12 g, 0.23 mmol) obtained in (4) above by the preparation method of Example 1-(4).

MS (m/z): 389[M+H], 371[M-OH]

Example 40: Preparation of ((1R)-3-methyl-1-(3-(3-phenoxyphenyl)-4,5-dihydroisoxazol-5-carboxamido)butyl)boronic acid Through the processes (1), (2), (3), (4) and (5) below, the title compound was obtained.

(1) Preparation of 3-phenoxy-benzaldehyde oxime

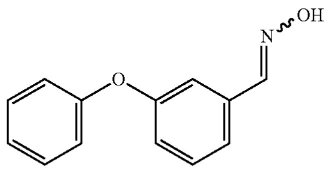 [SMILES: ON=Cc1cccc(Oc2ccccc2)c1]

The title compound (0.32 g, 99%) was obtained using 3-phenoxy-benzaldehyde (0.3 g, 1.51 mmol) by the preparation method of Example 3-(1).

MS (m/z): 214[M+H]

(2) Preparation of ethyl 3-(3-phenoxyphenyl)-4,5-dihydro-1,2-oxazol-5-carboxylate

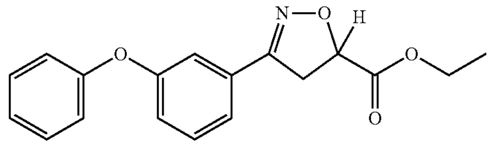 [SMILES: CCOC(=O)C1CC(c2cccc(Oc3ccccc3)c2)=NO1]

The title compound (0.44 g 93%) was obtained using 3-phenoxy-benzaldehyde oxime (0.32 g, 1.51 mmol) obtained in (1) above by the preparation method of Example 2-(3).

MS (m/z): 312[M+H]

(3) Preparation of 3-(3-phenoxyphenyl)-4,5-dihydro-1,2-oxazol-5-carboxylic acid

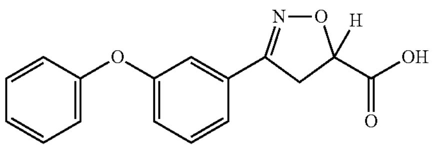 [SMILES: O=C(O)C1CC(c2cccc(Oc3ccccc3)c2)=NO1]

The title compound (0.4 g, 99%) was obtained using ethyl 3-(3-phenoxyphenyl)-4,5-dihydro-1,2-oxazol-5-carboxylate (0.44 g, 1.41 mmol) obtained in (2) above by the preparation method of Example 1-(2).

MS (m/z): 284[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(3-phenoxyphenyl)-4,5-dihydroisoxazol-5-carboxamide

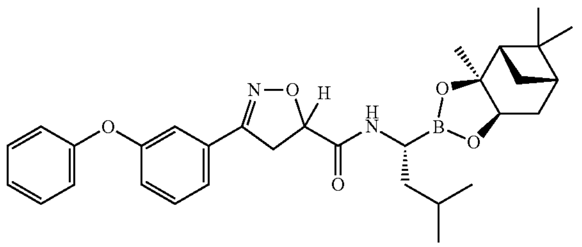 [SMILES: CC(C)C[C@H](NC(=O)C1CC(c2cccc(Oc3ccccc3)c2)=NO1)B1O[C@@H]2C[C@@H]3C[C@@H](C3(C)C)[C@]2(C)O1]

The title compound (0.12 g, 80%) was obtained using 3-(3-phenoxyphenyl)-4,5-dihydro-1,2-oxazol-5-carboxylic acid (0.08 g, 0.28 mmol) obtained in (3) above by the preparation method of Example 1-(3).

MS (m/z): 531[M+H]

(5) Preparation of ((1R)-3-methyl-1-(3-(3-phenoxyphenyl)-4,5-dihydroisoxazol-5-carboxamido)butyl) boronic acid

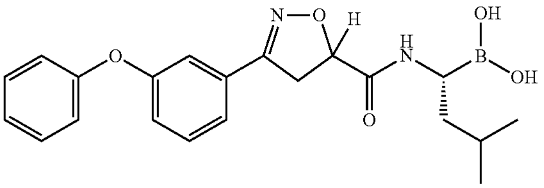 [SMILES: CC(C)C[C@H](NC(=O)C1CC(c2cccc(Oc3ccccc3)c2)=NO1)B(O)O]

The title compound (0.055 g, 61%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(3-phenoxyphenyl)-4,5-dihydroisoxazol-5-carboxamide (0.12 g, 0.23 mmol) obtained in (4) above by the preparation method of Example 1-(4).

NMR: $^1$H-NMR (500 MHz, MeOD-d4); δ 7.43-7.32 (m, 5H), 7.15-7.00 (m, 5H), 5.36-5.33 (m, 1H), 3.81-3.75 (m, 1H), 3.64-3.85 (m, 1H), 2.86-2.83 (m, 1H), 1.64-1.61 (m, 1H), 1.38-1.27 (m, 2H), 0.89-0.88 (dd, 6H)

MS (m/z): 397[M+H], 379[M-OH]

Example 41: Preparation of ((1R)-3-methyl-1-(3-(3-(pyridin-2-yloxy)phenyl)-4,5-dihydroisoxazol-5-carboxamido)butyl)boronic acid Through the processes (1), (2), (3), (4), (5) and (6) below, the title compound was obtained.

(1) Preparation of 3-(pyridin-2-yloxy)-benzaldehyde

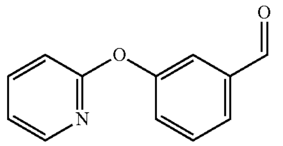 [SMILES: O=Cc1cccc(Oc2ccccn2)c1]

The title compound was obtained by the method described in EP1688138A1.

(2) Preparation of 3-(pyridin-2-yloxy)-benzaldehyde oxime

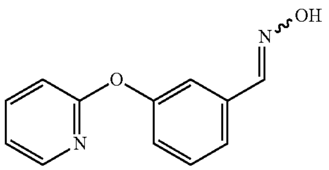 [SMILES: ON=Cc1cccc(Oc2ccccn2)c1]

The title compound (0.23 g, 99%) was obtained using 3-(pyridin-2-yloxy)-benzaldehyde (0.21 g, 1.05 mmol) obtained in (1) above by the preparation method of Example 3-(1).

MS (m/z): 215[M+H]

(3) Preparation of ethyl 3-[3-(pyridin-2-yloxy)phenyl]-4,5-dihydro-1,2-oxazol-5-carboxylate

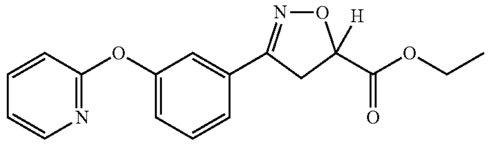 [SMILES: CCOC(=O)C1CC(c2cccc(Oc3ccccn3)c2)=NO1]

The title compound (0.3 g, 89%) was obtained using 3-(pyridin-2-yloxy)-benzaldehyde oxime (0.23 g, 1.07 mmol) obtained in (2) above by the preparation method of Example 2-(3).

MS (m/z): 313[M+H]

(4) Preparation of 3-[3-(pyridin-2-yloxy)phenyl]-4,5-dihydro-1,2-oxazol-5-carboxylic acid

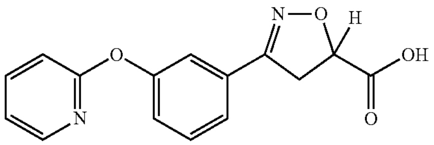 [SMILES: O=C(O)C1CC(c2cccc(Oc3ccccn3)c2)=NO1]

The title compound (0.27 g, 99%) was obtained using ethyl 3-[3-(pyridin-2-yloxy)phenyl]-4,5-dihydro-1,2-oxazol-5-carboxylate (0.3 g, 0.96 mmol) obtained in (3) above by the preparation method of Example 1-(2).

MS (m/z): 285[M+H]

(5) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(3-(pyridin-2-yloxy)phenyl)-4,5-dihydroisoxazol-5-carboxamide The title compound (0.1 g, 59%) was obtained using 3-[3-(pyridin-2-yloxy)phenyl]-4,5-dihydro-1,2-oxazol-5-carboxylic acid (0.09 g, 0.32 mmol) obtained in (4) above by the preparation method of Example 1-(3).

MS (m/z): 532[M+H]

(6) Preparation of ((1R)-3-methyl-1-(3-(3-(pyridin-2-yloxy)phenyl)-4,5-dihydroisoxazol-5-carboxamido)butyl)boronic acid

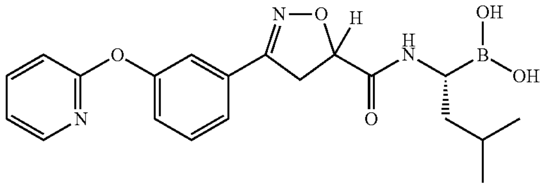 [SMILES: CC(C)C[C@H](NC(=O)C1CC(c2cccc(Oc3ccccn3)c2)=NO1)B(O)O]

The title compound (0.046 g, 62%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(3-(pyridin-2-yloxy)phenyl)-4,5-dihydroisoxazol-5-carboxamide (0.1 g, 0.19 mmol) obtained in (5) above by the preparation method of Example 1-(4).

NMR: $^1$H-NMR (500 MHz, MeOD-d4); δ 8.12-8.11 (m, 1H), 7.85-7.82 (m, 1H), 7.53-7.47 (m, 3H), 7.21-7.19 (m, 2H), 7.00-6.98 (m, 1H), 5.38-5.35 (m, 1H), 3.84-3.78 (m, 1H), 3.68-3.63 (m, 1H), 2.86-2.82 (m, 1H), 1.65-1.61 (m, 1H), 1.38-1.32 (m, 2H), 0.90-0.88 (dd, 6H)

MS (m/z): 398[M+H], 380[M-OH]

Example 42: Preparation of ((1R)-3-methyl-1-(3-(4-(pyridin-2-yloxy)phenyl)-4,5-dihydroisoxazol-5-carboxamido)butyl)boronic acid Through the processes of Example 42-(1), (2), (3), (4), (5) and (6), the title compound was obtained.

(1) Preparation of 3-(pyridin-2-yloxy)-benzaldehyde

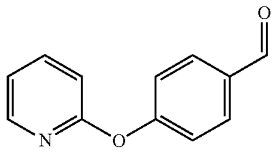 [SMILES: O=Cc1ccc(Oc2ccccn2)cc1]

The title compound was obtained by the method described in Synlett, 2008, #2 pp. 221-224.

(2) Preparation of 3-(pyridin-2-yloxy)-benzaldehyde oxime

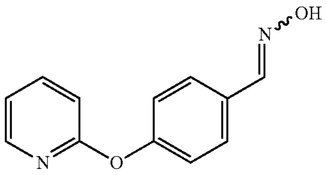 [SMILES: ON=Cc1ccc(Oc2ccccn2)cc1]

The title compound (0.19 g, 98%) was obtained using 3-(pyridin-2-yloxy)-benzaldehyde (0.18 g, 0.90 mmol) obtained in Example 42-(1) by the preparation method of Example 3-(1).

MS (m/z): 215[M+H]

(3) Preparation of ethyl 3-[4-(pyridin-2-yloxy)phenyl]-4,5-dihydro-1,2-oxazol-5-carboxylate

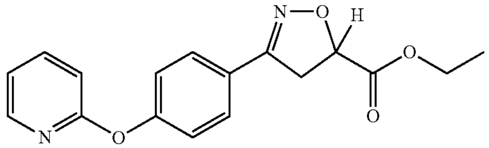 [SMILES: CCOC(=O)C1CC(c2ccc(Oc3ccccn3)cc2)=NO1]

The title compound (0.23 g, 83%) was obtained using 3-(pyridin-2-yloxy)-benzaldehyde oxime (0.19 g, 0.89 mmol) obtained in Example 42-(2) by the preparation method of Example 2-(3).

NMR: $^1$H-NMR (400 MHz, $CDCl_3$); δ 8.21-8.19 (m, 1H), 7.73-7.70 (m, 3H), 7.20-7.18 (m, 2H), 7.05-6.96 (m, 2H), 5.19-5.15 (m, 1H), 4.31-4.19 (q, 2H), 3.70-3.58 (m, 2H), 1.35-1.31 (t, 3H)

MS (m/z): 313[M+H]

(4) Preparation of 3-[4-(pyridin-2-yloxy)phenyl]-4,5-dihydro-1,2-oxazol-5-carboxylic acid

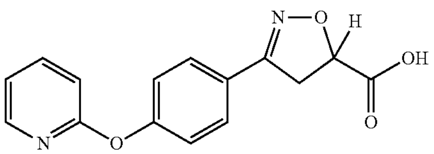 [SMILES: O=C(O)C1CC(c2ccc(Oc3ccccn3)cc2)=NO1]

The title compound (0.2 g, 99%) was obtained using ethyl 3-[4-(pyridin-2-yloxy)phenyl]-4,5-dihydro-1,2-oxazol-5-carboxylate (0.23 g, 0.74 mmol) obtained in Example 42-(3) by the preparation method of Example 1-(2).

MS (m/z): 284[M+H]

(5) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(4-(pyridin-2-yloxy)phenyl)-4,5-dihydroisoxazol-5-carboxamide

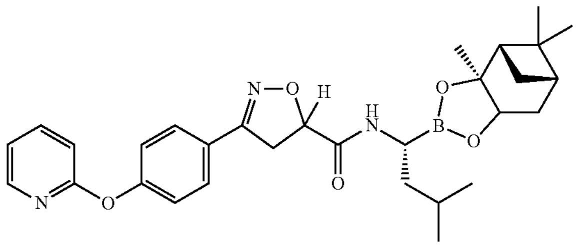 [SMILES: CC(C)C[C@H](NC(=O)C1CC(c2ccc(Oc3ccccn3)cc2)=NO1)B1OC2C[C@@H]3C[C@@H](C3(C)C)[C@]2(C)O1]

The title compound (0.11 g, 65%) was obtained using 3-[4-(pyridin-2-yloxy)phenyl]-4,5-dihydro-1,2-oxazol-5-carboxylic acid (0.09 g, 0.32 mmol) obtained in (4) above by the preparation method of Example 1-(3).

MS (m/z): 532[M+H]

(6) Preparation of ((1R)-3-methyl-1-(3-(4-(pyridin-2-yloxy)phenyl)-4,5-dihydroisoxazol-5-carboxamido)butyl)boronic acid

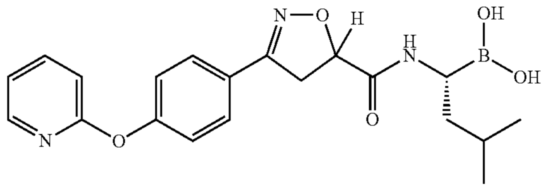 [SMILES: CC(C)C[C@H](NC(=O)C1CC(c2ccc(Oc3ccccn3)cc2)=NO1)B(O)O]

The title compound (0.054 g, 65%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(4-(pyridin-2-yloxy)phenyl)-4,5-dihydroisoxazol-5-carboxamide (0.11 g, 0.21 mmol) obtained in (5) above by the preparation method of Example 1-(4).

NMR: $^{1}$H-NMR (500 MHz, MeOD-d4); δ 8.15-8.14 (m, 1H), 7.87-7.83 (m, 1H), 7.77-7.75 (m, 2H), 7.17-7.14 (m, 3H), 7.02-7.00 (d, 1H), 5.38-5.35 (m, 1H), 3.86-3.80 (m, 1H), 3.70-3.64 (m, 1H), 2.87-2.83 (m, 1H), 1.66-1.62 (m, 1H), 1.39-1.33 (m, 2H), 0.90-0.88 (dd, 6H)

MS (m/z): 398[M+H], 380[M-OH]

Example 43: Preparation of ((1R)-3-methyl-1-(3-(3-(pyridin-2-ylmethoxy)phenyl)-4,5-dihydroisoxazol-5-carboxamido)butyl)boronic acid Through the processes (1), (2), (3), (4), (5) and (6) below, the title compound was obtained.

(1) Preparation of 3-(pyridin-2-ylmethoxy)-benzaldehyde

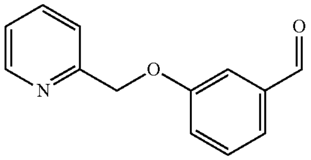 [SMILES: O=Cc1cccc(OCc2ccccn2)c1]

The title compound was obtained by the method described in WO2007105904A1.

(2) Preparation of 3-(pyridin-2-ylmethoxy)-benzaldehyde oxime

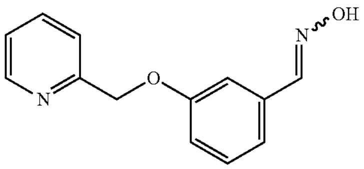 [SMILES: ON=Cc1cccc(OCc2ccccn2)c1]

The title compound (0.71 g, 99%) was obtained using 3-(pyridin-2-ylmethoxy)-benzaldehyde (0.66 g, 3.10 mmol) obtained in (1) above by the preparation method of Example 3-(1).

MS (m/z): 229[M+H]

(3) Preparation of ethyl 3-{3-[(pyridin-2-yl)methoxy]phenyl}-4,5-dihydro-1,2-oxazol-5-carboxylate

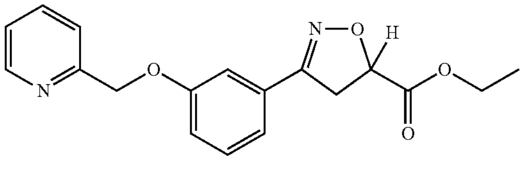 [SMILES: CCOC(=O)C1CC(c2cccc(OCc3ccccn3)c2)=NO1]

The title compound (0.9 g, 89%) was obtained using 3-(pyridin-2-ylmethoxy)-benzaldehyde oxime (0.71 g, 3.11 mmol) obtained in (2) above by the preparation method of Example 2-(3).

NMR: $^{1}$H-NMR (400 MHz, $CDCl_3$); δ 8.62-8.61 (d, 1H), 7.74-7.50 (m, 1H), 7.36-7.35 (d, 1H), 7.33-7.24 (m, 4H), 7.07-7.05 (m, 1H), 5.30 (s, 2H), 5.23-5.14 (m, 1H), 4.31-4.24 (q, 2H), 3.67-3.56 (m, 2H), 1.35-1.31 (t, 3H)

MS (m/z): 327[M+H]

(4) Preparation of 3-{3-[(pyridin-2-yl)methoxy]phenyl}-4,5-dihydro-1,2-oxazol-5-carboxylic acid

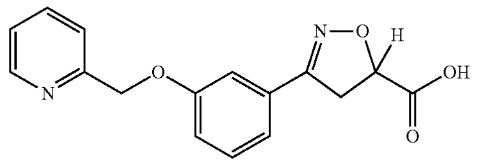 [SMILES: O=C(O)C1CC(c2cccc(OCc3ccccn3)c2)=NO1]

The title compound (0.82 g, 99%) was obtained using ethyl 3-{3-[(pyridin-2-yl)methoxy]phenyl}-4,5-dihydro-1,2-oxazol-5-carboxylate (0.9 g, 2.76 mmol) obtained in (3) above by the preparation method of Example 1-(2).

MS (m/z): 299[M+H]

(5) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(3-(pyridin-2-ylmethoxy)phenyl)-4,5-dihydroisoxazol-5-carboxamide

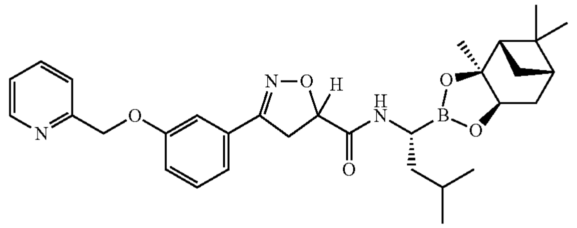 [SMILES: CC(C)C[C@H](NC(=O)C1CC(c2cccc(OCc3ccccn3)c2)=NO1)B1O[C@@H]2C[C@@H]3C[C@@H](C3(C)C)[C@]2(C)O1]

The title compound (0.05 g, 34%) was obtained using 3-{3-[(pyridin-2-yl)methoxy]phenyl}-4,5-dihydro-1,2-oxazol-5-carboxylic acid (0.08 g, 0.27 mmol) obtained in (4) above by the preparation method of Example 1-(3).

MS (m/z): 546[M+H]

(6) Preparation of ((1R)-3-methyl-1-(3-(3-(pyridin-2-ylmethoxy)phenyl)-4,5-dihydroisoxazol-5-carboxamido)butyl)boronic acid

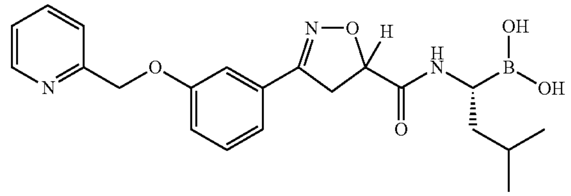 [SMILES: CC(C)C[C@H](NC(=O)C1CC(c2cccc(OCc3ccccn3)c2)=NO1)B(O)O]

The title compound (0.031 g, 82%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(3-(pyridin-2-ylmethoxy)phenyl)-4,5-dihydroisoxazol-5-carboxamide (0.05 g, 0.092 mmol) obtained in (5) above by the preparation method of Example 1-(4).

NMR: $^1$H-NMR (500 MHz, MeOD-d4); δ 8.54-8.53 (m, 1H), 7.88-7.84 (m, 1H), 7.61-7.59 (d, 1H), 7.38-7.28 (m, 4H), 7.13-7.12 (m, 1H), 5.37-5.33 (m, 1H), 5.21 (s, 2H), 3.83-3.77 (m, 1H), 3.67-3.61 (m, 1H), 2.85-2.82 (m, 1H), 1.65-1.62 (m, 1H), 1.39-1.32 (m, 2H), 0.90-0.87 (dd, 6H)

MS (m/z): 412[M+H], 394[M-OH]

Example 44: Preparation of ((1R)-3-methyl-1-(3-(4-phenoxyphenyl)-4,5-dihydroisoxazol-5-carboxamido)butyl)boronic acid Through the processes (1), (2), (3), (4) and (5) below, the title compound was obtained.

(1) Preparation of 4-phenoxy-benzaldehyde oxime

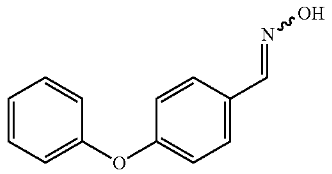 [SMILES: ON=Cc1ccc(Oc2ccccc2)cc1]

The title compound (0.38 g, quant.) was obtained using 4-phenoxy-benzaldehyde (0.35 g, 1.8 mmol) by the preparation method of Example 3-(1).

MS (m/z): 214[M+H]

(2) Preparation of ethyl 3-(4-phenoxyphenyl)-4,5-dihydro-1,2-oxazol-5-carboxylate

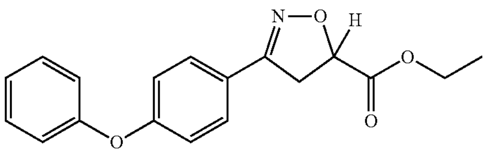 [SMILES: CCOC(=O)C1CC(c2ccc(Oc3ccccc3)cc2)=NO1]

The title compound (0.38 g 69%) was obtained using 4-phenoxy-benzaldehyde oxime (0.38 g, 1.8 mmol) obtained in (1) above by the preparation method of Example 2-(3).

MS (m/z): 312[M+H]

(3) Preparation of 3-(4-phenoxyphenyl)-4,5-dihydro-1,2-oxazol-5-carboxylic acid

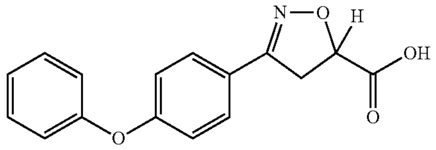 [SMILES: O=C(O)C1CC(c2ccc(Oc3ccccc3)cc2)=NO1]

The title compound (0.32 g, 94%) was obtained using ethyl 3-(4-phenoxyphenyl)-4,5-dihydro-1,2-oxazol-5-carboxylate (0.38 g, 1.2 mmol) obtained in (2) above by the preparation method of Example 1-(2).

MS (m/z): 284[M+H]

(4) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(4-phenoxyphenyl)-4,5-dihydroisoxazol-5-carboxamide

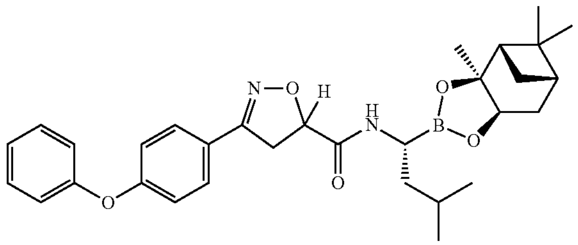 [SMILES: CC(C)C[C@H](NC(=O)C1CC(c2ccc(Oc3ccccc3)cc2)=NO1)B1O[C@@H]2C[C@@H]3C[C@@H](C3(C)C)[C@]2(C)O1]

The title compound (0.079 g, 43%) was obtained using 3-(4-phenoxyphenyl)-4,5-dihydro-1,2-oxazol-5-carboxylic acid (0.098 g, 0.35 mmol) obtained in (3) above by the preparation method of Example 1-(3).

MS (m/z): 531[M+H]

(5) Preparation of ((1R)-3-methyl-1-(3-(4-phenoxyphenyl)-4,5-dihydroisoxazol-5-carboxamido)butyl) boronic acid

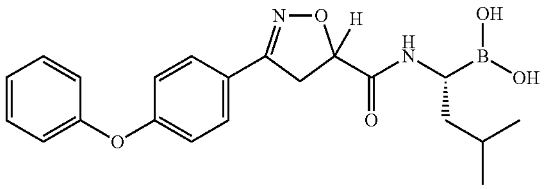 [SMILES: CC(C)C[C@H](NC(=O)C1CC(c2ccc(Oc3ccccc3)cc2)=NO1)B(O)O]

The title compound (0.018 g, 31%) was obtained using N—((R)-3-methyl-1-((3aS,4S,6S,7aR)-3a,5,5-trimethylhexahydro-4,6-metanobenzo[d][1,3,2]dioxaborol-2-yl) butyl)-3-(4-phenoxyphenyl)-4,5-dihydroisoxazol-5-carboxamide (0.079 g, 0.15 mmol) obtained in (4) above by the preparation method of Example 1-(4).

MS (m/z): 397[M+H], 379[M-OH]

Example 45: Preparation of ((1R)-1-(5-benzyl-3-(((2,5-dichlorobenzyl)oxy)methyl)-4,5-dihydroisoxazol-5-carboxamido)-3-methylbutyl)boronic acid Through the processes (1), (2), (3), (4) and (5) below, the title compound was obtained.

(1) Preparation of 1,4-dichloro-2-((2,2-diethoxyethoxy)methyl)benzene

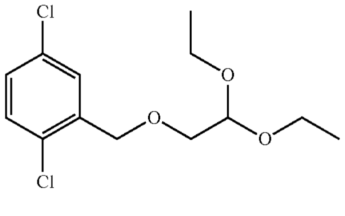 [SMILES: CCOC(COCc1cc(Cl)ccc1Cl)OCC]

2,2-Diethoxyethanol (0.268 g, 2.0 mmol) was dissolved in tetrahydrofuran (8 ml), and at 0° C., sodium hydride (0.088 g, 2.2 mmol) was added thereto, followed by stirring for 30 minutes. 2,5-Dichlorobenzyl bromide (0.48 g, 2.0 mmol) was added thereto, followed by stirring at room temperature for 1 hour. Water (20 ml) was added to quench the reaction, and extraction with dichloromethane (20 ml) was performed twice. The organic layer thus extracted was dried over anhydrous magnesium sulfate, and filtered. The filtrate was distilled under a reduced pressure and separated by column chromatography to obtain the title compound (0.416 g, 71%).

NMR: $^1$H-NMR (500 MHz, $CDCl_3$); δ 7.52 (1H, d), 7.26-7.24 (1H, m), 7.19-7.17 (1H, m), 4.70 (1H, t), 4.63 (2H, s), 3.76-3.70 (2H, m), 3.62-3.56 (4H, m), 1.24 (6H, t)

(2) Preparation of 2-((2,5-dichlorobenzyl)oxy)acetaldehyde oxime

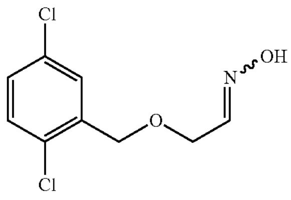 [SMILES: ON=CCOCc1cc(Cl)ccc1Cl]

1,4-Dichloro-2-((2,2-diethoxyethoxy)methyl)benzene (0.409 g, 1.39 mmol) obtained in (1) above was dissolved in methanol (10 ml), and a 50% hydroxylamine aqueous solution (0.26 ml, 4.24 mmol) and a 6 N hydrochloric acid solution (0.80 ml, 4.80 mmol) were added thereto, followed by stirring at room temperature for 18 hours. The solution thus obtained was neutralized with a sodium bicarbonate aqueous solution, methanol was removed by distilling under a reduced pressure, and the residue was extracted with dichloromethane (20 ml) three times. The organic layer thus extracted was dried over anhydrous magnesium sulfate, and filtered. The filtrate was distilled under a reduced pressure and separated by column chromatography to obtain the title compound (0.294 g, 90%).

MS (m/z): 234[M+H]

(3) Preparation of methyl 5-benzyl-3-(((2,5-dichlorobenzyl)oxy)methyl)-4,5-dihydroisoxazol-5-carboxylate

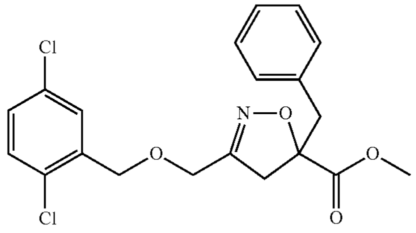 [SMILES: COC(=O)C1(Cc2ccccc2)CC(COCc2cc(Cl)ccc2Cl)=NO1]

The title compound (0.173 g, 76%) was obtained using ((2,5-dichloro-benzyloxy)-acetaldehyde oxime (0.130 g, 0.56 mmol) obtained in the process (2) above by the preparation method of Preparation Example 6-(2).

NMR: $^1$H-NMR (500 MHz, $CDCl_3$); δ 7.31-7.17 (8H, m), 4.34-4.15 (4H, m), 3.79 (3H, s), 3.41 (2H, dd), 3.09 (2H, dd)

MS (m/z): 408[M+H]

(4) Preparation of 5-benzyl-3-(((2,5-dichlorobenzyl) oxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

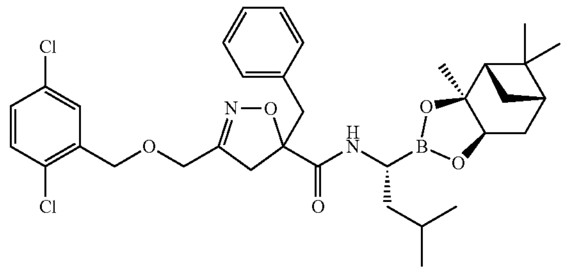 [SMILES: CC(C)C[C@H](NC(=O)C1(Cc2ccccc2)CC(COCc2cc(Cl)ccc2Cl)=NO1)B1O[C@@H]2C[C@@H]3C[C@@H](C3(C)C)[C@]2(C)O1]

The title compound (0.135 g, 79%, 2 steps) was obtained using methyl 5-benzyl-3-(((2,5-dichlorobenzyl)oxy) methyl)-4,5-dihydroisoxazol-5-carboxylate (0.173 g, 0.424 mmol) obtained in (3) above by the preparation methods of Examples 1-(2) and (3).

MS (m/z): 641[M+H]

(5) Preparation of ((1R)-1-(5-benzyl-3-(((2,5-dichlorobenzyl)oxy)methyl)-4,5-dihydroisoxazol-5-carboxamido)-3-methylbutyl)boronic acid

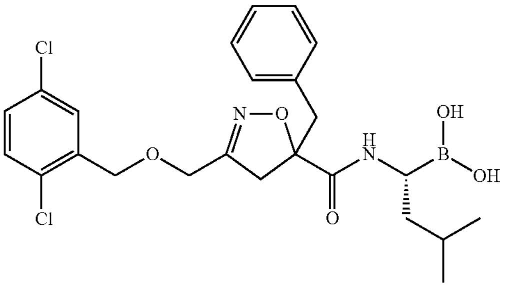 [SMILES: CC(C)C[C@H](NC(=O)C1(Cc2ccccc2)CC(COCc2cc(Cl)ccc2Cl)=NO1)B(O)O]

The title compound (0.076 g, 71%) was obtained using 5-benzyl-3-(((2,5-dichlorobenzyl)oxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.135 g, 0.21 mmol) obtained in (4) above by the preparation method of Example 1-(4).

NMR: $^1$H-NMR (500 MHz, $CD_3OD$); δ 7.41-7.18 (8H, m), 4.48-4.23 (4H, m), 3.47-3.14 (4H, m), 2.77-2.70 (1H, m), 1.49-1.06 (3H, m), 0.83-0.78 (6H, m)

MS (m/z): 507[M+H], 489[M-OH]

Example 46: Preparation of ((1R)-1-(5-benzyl-3-(((2-methylthiazol-4-yl)methoxy)methyl)-4,5-dihydroisoxazol-5-carboxamido)-3-methylbutyl)boronic acid Through the processes (1), (2), (3), (4) and (5) below, the title compound was obtained.

(1) Preparation of (2,2-diethoxy-ethoxymethyl)-2-methyl-thiazole

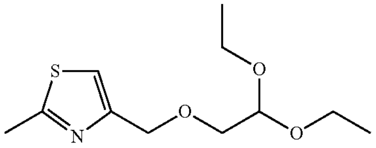 [SMILES: CCOC(COCc1csc(C)n1)OCC]

The title compound (0.396 g, 81%) was obtained using 4-chloromethyl-2-methyl-thiazole (0.296 g, 2.0 mmol) by the preparation method of Example 45-(1).

NMR: $^1$H-NMR (500 MHz, $CDCl_3$); δ 7.06 (1H, s), 4.67 (1H, t), 4.65 (2H, s), 3.72-3.66 (2H, m), 3.59-3.55 (m, 4H), 2.69 (3H, s), 1.22 (6H, t)

(2) Preparation of (2-methyl-thiazol-4-ylmethoxy)-acetaldehyde oxime

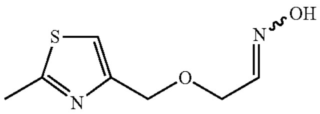

The title compound (0.267 g, 89%) was obtained using (2,2-diethoxy-ethoxymethyl)-2-methyl-thiazole (0.396 g, 1.61 mmol) obtained in (1) above by the preparation method of Example 45-(2).

(3) Preparation of methyl 5-benzyl-3-(((2-methylthiazol-4-yl)methoxy)methyl)-4,5-dihydroisoxazol-5-carboxylate

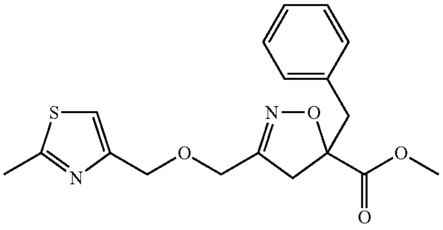

The title compound (0.104 g, 41%) was obtained using (2-methyl-thiazol-4-ylmethoxy)-acetaldehyde oxime (0.131 g, 0.70 mmol) obtained in (2) above by the preparation method of Preparation Example 6-(2).

NMR: $^1$H-NMR (500 MHz, $CDCl_3$); δ 7.28-7.22 (5H, m), 6.95 (1H, s), 4.32-4.26 (2H, dd), 4.23-4.13 (2H, dd), 3.77 (3H, s), 3.44 (1H, d), 3.33 (1H, d), 3.13 (1H, d), 3.05 (1H, d), 2.69 (3H, s)

MS (m/z): 361[M+H]

(4) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((2-methylthiazol-4-yl)methoxy)methyl)-4,5-dihydroisoxazol-5-carboxamide

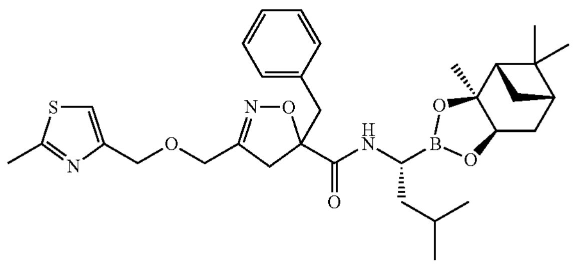

The title compound (0.063 g, 41%, 2 steps) was obtained using methyl 5-benzyl-3-(((2-methylthiazol-4-yl)methoxy) methyl)-4,5-dihydroisoxazol-5-carboxylate (0.104 g, 0.289 mmol) obtained in (3) above by the preparation methods of Examples 1-(2) and (3).

MS (m/z): 594[M+H]

(5) Preparation of ((1R)-1-(5-benzyl-3-(((2-methylthiazol-4-yl)methoxy)methyl)-4,5-dihydroisoxazol-5-carboxamido)-3-methylbutyl)boronic acid

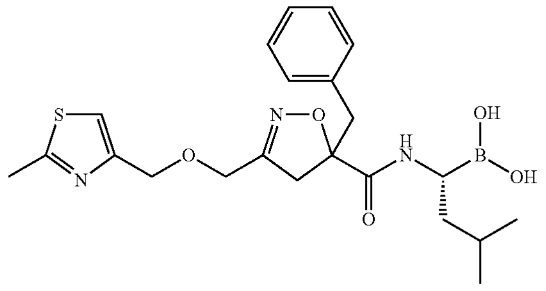 [SMILES: Cc1nc(COCC2=NOC(Cc3ccccc3)(C(=O)N[C@@H](CC(C)C)B(O)O)C2)cs1]

The title compound (0.028 g, 58%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((2-methylthiazol-4-yl)methoxy)methyl)-4,5-dihydroisoxazol-5-carboxamide (0.063 g, 0.106 mmol) obtained in the process (4) above by the preparation method of Example 1-(4).

NMR: $^1$H-NMR (500 MHz, $CD_3OD$); δ 7.17-7.11 (6H, m), 4.42 (2H, dd), 4.22 (2H, dd), 3.43 (1H, d), 3.33-3.22 (2H, m), 3.16 (1H, d), 1.41-1.03 (3H, m), 0.79 (6H, dd)

MS (m/z): 460[M+H], 442[M-OH]

Example 47: Preparation of ((1R)-1-(5-benzyl-3-(((6-methylpyridin-2-yl)methoxy)methyl)-4,5-dihydroisoxazol-5-carboxamido)-3-methylbutyl)boronic acid Through the processes (1), (2), (3), (4) and (5) below, the title compound was obtained.

(1) Preparation of 2-(2,2-diethoxy-ethoxymethyl)-6-methyl-pyridine

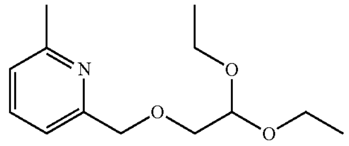 [SMILES: CCOC(COCc1cccc(C)n1)OCC]

The title compound (0.292 g, 61%) was obtained using 2-chloromethyl-6-methyl-pyridine (0.283 g, 2.0 mmol) by the preparation method of Example 45-(1).

NMR: $^1$H-NMR (500 MHz, $CDCl_3$); δ 7.57 (1H, t), 7.26 (1H, d), 7.03 (1H, d), 4.70 (1H, t), 4.66 (2H, s), 3.74-3.68 (2H, m), 3.60-3.55 (4H, m), 2.52 (3H, s), 1.22 (6H, t)

(2) Preparation of (6-methyl-pyridin-2-yl-methoxy)-acetaldehyde oxime

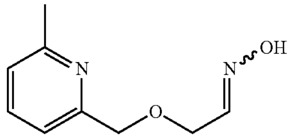

The title compound (0.189 g, 86%) was obtained using 2-(2,2-diethoxy-ethoxymethyl)-6-methyl-pyridine (0.29 g, 1.2 mmol) obtained in (1) above by the preparation method of Preparation Example 6-(2).

MS (m/z): 181[M+H]

(3) Preparation of methyl 5-benzyl-3-(((6-methylpyridin-2-yl)methoxy)methyl)-4,5-dihydroisoxazol-5-carboxylate

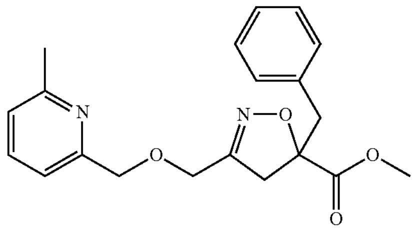 [SMILES: COC(=O)C1(Cc2ccccc2)CC(COCc2cccc(C)n2)=NO1]

The title compound (0.073 g, 36%) was obtained using (6-methyl-pyridin-2-yl-methoxy)-acetaldehyde oxime (0.104 g, 0.58 mmol) obtained in (2) above by the preparation method of Example 45-(3).

NMR: $^1$H-NMR (500 MHz, $CDCl_3$); δ 7.54 (1H, t), 7.25-7.21 (5H, m), 7.06 (1H, m), 7.03 (1H, d), 4.37 (2H, dd), 4.20 (2H, dd), 3.75 (3H, s), 3.46 (1H, d), 3.30 (1H, d), 3.13 (1H, d), 3.05 (1H, d), 2.51 (3H, s)

MS (m/z): 355[M+H]

(4) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((6-methylpyridin-2-yl)methoxy)methyl)-4,5-dihydroisoxazol-5-carboxamide

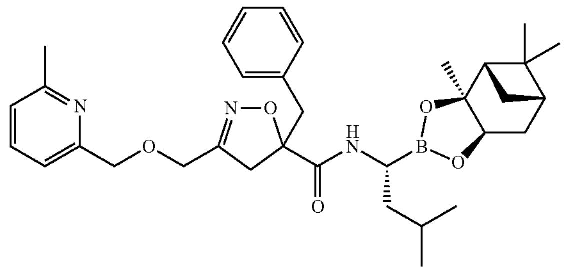 [SMILES: Cc1cccc(COCC2=NOC(Cc3ccccc3)(C(=O)N[C@@H](CC(C)C)B3O[C@@H]4C[C@@H]5C[C@@H](C5(C)C)[C@]4(C)O3)C2)n1]

The title compound (0.06 g, 56%, 2 steps) was obtained using methyl 5-benzyl-3-(((6-methylpyridin-2-yl)methoxy)methyl)-4,5-dihydroisoxazol-5-carboxylate (0.073 g, 0.21 mmol) obtained in (3) above by the preparation methods of Example 1-(2) and (3).

MS (m/z): 588[M+H]

(5) Preparation of ((1R)-1-(5-benzyl-3-(((6-methylpyridin-2-yl)methoxy)methyl)-4,5-dihydroisoxazol-5-carboxamido)-3-methylbutyl)boronic acid

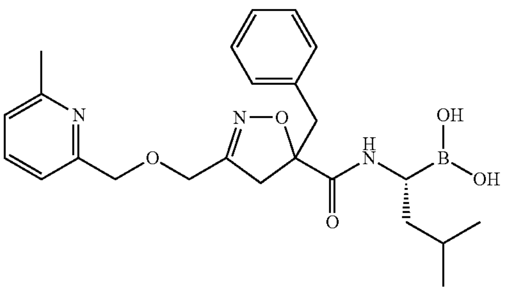 [SMILES: Cc1cccc(COCC2=NOC(Cc3ccccc3)(C(=O)N[C@@H](CC(C)C)B(O)O)C2)n1]

The title compound (0.014 g, 27%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((6-methylpyridin-2-yl)methoxy)methyl)-4,5-dihydroisoxazol-5-carboxamide (0.068 g, 0.116 mmol) obtained in (4) above by the preparation method of Example 1-(4).

NMR: $^1$H-NMR (500 MHz, $CD_3OD$); δ 7.74 (1H, dd), 7.29-7.22 (5H, m), 4.46 (2H, dd), 4.32 (2H, dd), 3.50 (1H, d), 3.37-3.28 (2H, m), 3.20 (1H, d), 2.73 (1H, t), 1.46-1.10 (3H, m), 0.83 (6H, dd)

MS (m/z): 454[M+H], 436[M-OH]

Example 48: Preparation of ((1R)-1-(5-benzyl-3-(((5-methylpyrazin-2-yl)methoxy)methyl)-4,5-dihydroisoxazol-5-carboxamido)-3-methylbutyl)boronic acid Through the processes (1), (2), (3), (4) and (5) below, the title compound was obtained.

(1) Preparation of 2-(2,2-diethoxy-ethoxymethyl)-5-methyl-pyrazine

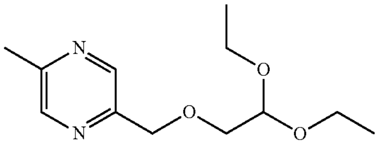 [SMILES: CCOC(COCc1cnc(C)cn1)OCC]

The title compound (0.168 g, 70%) was obtained using 2-chloromethyl-5-methyl-pyrazine (0.143 g, 1.0 mmol) by the preparation method of Example 45-(1).

NMR: $^1$H-NMR (500 MHz, $CDCl_3$); δ 8.59 (1H, s), 8.38 (1H, s), 4.70 (2H, s), 4.69 (1H, t), 3.74-3.68 (2H, m), 3.62-3.54 (4H, m), 2.55 (3H, s), 1.22 (6H, t)

(2) Preparation of (5-methyl-pyrazin-2-yl-methoxy)-acetaldehyde oxime

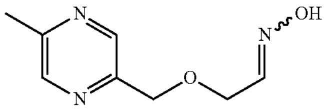

The title compound (0.112 g, 88%) was obtained using 2-(2,2-diethoxy-ethoxymethyl)-5-methyl-pyrazine (0.168 g, 0.70 mmol) obtained in (1) above by the preparation method of Example 45-(2).

MS (m/z): 182[M+H]

(3) Preparation of methyl 5-benzyl-3-(((5-methylpyrazin-2-yl)methoxy)methyl)-4,5-dihydroisoxazol-5-carboxylate

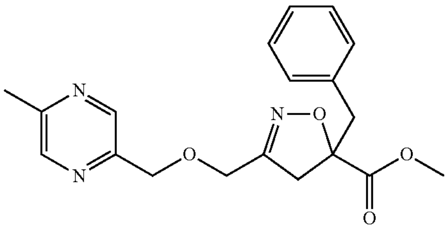

The title compound (0.079 g, 36%) was obtained using (5-methyl-pyrazin-2-yl-methoxy)-acetaldehyde oxime (0.112 g, 0.62 mmol) obtained in (2) above by the preparation method of Preparation Example 6-(2).

NMR: $^1$H-NMR (500 MHz, $CDCl_3$); δ 8.40 (1H, s), 8.38 (1H, s), 7.25-7.17 (5H, m), 4.37 (1H, d), 4.26 (2H, d), 4.18 (1H, d), 3.77 (3H, s), 3.44 (1H, d), 3.33 (1H, d), 3.11 (1H, d), 3.04 (1H, d), 2.55 (3H, s)

MS (m/z): 356[M+H]

(4) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((5-methylpyrazin-2-yl)methoxy)methyl)-4,5-dihydroisoxazol-5-carboxamide

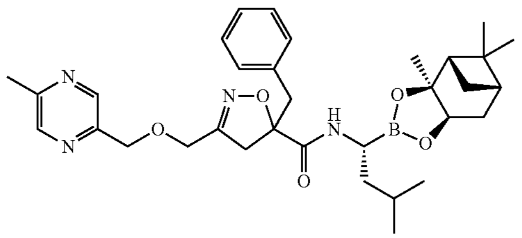

The title compound (0.071 g, 54%, 2 steps) was obtained using methyl 5-benzyl-3-(((5-methylpyrazin-2-yl)methoxy)methyl)-4,5-dihydroisoxazol-5-carboxylate (0.079 g, 0.22 mmol) obtained in (3) above by the preparation methods of Examples 1-(2) and (3).

MS (m/z): 589[M+H]

(5) Preparation of ((1R)-1-(5-benzyl-3-(((5-methylpyrazin-2-yl)methoxy)methyl)-4,5-dihydroisoxazol-5-carboxamido)-3-methylbutyl)boronic acid

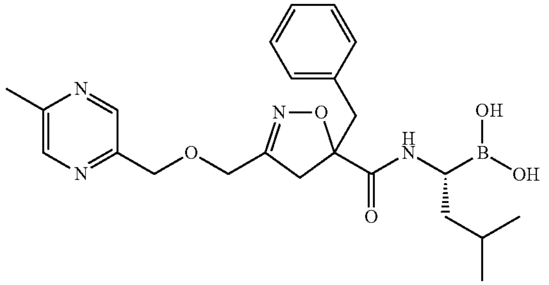 [SMILES: Cc1cnc(COCC2=NOC(Cc3ccccc3)(C(=O)N[C@@H](CC(C)C)B(O)O)C2)cn1]

The title compound (0.014 g, 26%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((5-methylpyrazin-2-yl)methoxy)methyl)-4,5-dihydroisoxazol-5-carboxamide (0.071 g, 0.121 mmol) obtained in (4) above by the preparation method of Example 1-(4).

NMR: $^1$H-NMR (500 MHz, $CD_3OD$); δ 8.47 (2H, s), 7.28-7.19 (5H, m), 4.50 (2H, dd), 4.31 (2H, dd), 3.46 (1H, d), 3.33-3.25 (2H, m), 3.17 (1H, d), 2.69 (1H, t), 1.43-1.05 (3H, m), 0.80 (6H, dd)

MS (m/z): 437 [M-OH]

Example 49: Preparation of ((1R)-1-(5-benzyl-3-((isoquinolin-1-ylmethoxy)methyl)-4,5-dihydroisoxazol-5-carboxamido)-3-methylbutyl)boronic acid Through the processes (1), (2), (3), (4) and (5) below, the title compound was obtained.

(1) Preparation of chloro-acetaldehyde oxime

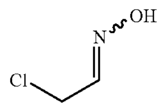

The title compound (0.650 g, 45%) was obtained using a 50% chloroacetaldehyde aqueous solution (2.4 g, 15.3 mmol) and a 50% hydroxylamine aqueous solution (1.2 g, 18.2 mmol) by the preparation method of Preparation Example 1-(1).

(2) Preparation of methyl 5-benzyl-3-(chloromethyl)-4,5-dihydroisoxazol-5-carboxylate

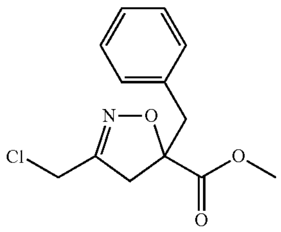 [SMILES: COC(=O)C1(Cc2ccccc2)CC(CCl)=NO1]

The title compound (0.351 g, 66%) was obtained using chloro-acetaldehyde oxime (0.281 g, 3.00 mmol) obtained in (1) above by the preparation method of Preparation Example 6-(2).

NMR: $^1$H-NMR (500 MHz, $CDCl_3$); δ 7.29-7.22 (5H, m), 4.13 (2H, dd), 3.78 (3H, s), 3.47 (1H, d), 3.32 (1H, d), 3.17 (1H, d), 3.07 (1H, d)

(3) Preparation of methyl 5-benzyl-3-((isoquinolin-1-ylmethoxy)methyl)-4,5-dihydroisoxazol-5-carboxylate

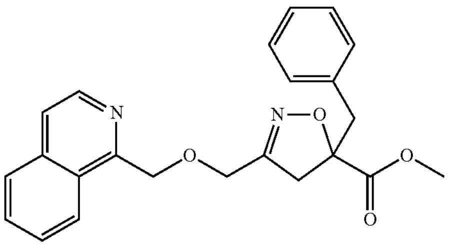 [SMILES: COC(=O)C1(Cc2ccccc2)CC(COCc2nccc3ccccc23)=NO1]

Isoquinolin-1-yl-methanol (0.064 g, 0.40 mmol) was dissolved in tetrahydrofuran (4 ml), and sodium hydride (0.040 g, 1.00 mmol) was added thereto, followed by stirring at room temperature for 30 minutes. To this solution, a solution of methyl 5-benzyl-3-(chloromethyl)-4,5-dihydroisoxazol-5-carboxylate (0.11 g, 0.44 mmol) obtained in (2) above, dissolved in tetrahydrofuran (2 ml) and tetrabutylammonium iodide (0.030 g, 0.08 mmol) were added in order, followed by stirring at room temperature for 4 hours. After adding water (10 ml) to the reaction product, extraction with dichloromethane (10 ml) was performed three times. The organic layer thus extracted was dried over anhydrous magnesium sulfate, and filtered. The filtrate was distilled under a reduced pressure and separated by column chromatography to obtain the title compound (0.042 g, 27%).

NMR: $^{1}$H-NMR (500 MHz, $CDCl_3$); δ 8.46 (1H, d), 8.18 (1H, d), 7.88 (1H, d), 7.76 (1H, t), 7.71 (1H, d), 7.66 (1H, t), 7.28-7.16 (5H, m), 5.01 (1H, d), 4.90 (1H, d), 4.23 (2H, dd), 3.72 (3H, s), 3.38-3.02 (4H, m)

MS (m/z): 391[M+H]

(4) Preparation of 5-benzyl-3-((isoquinolin-1-ylmethoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

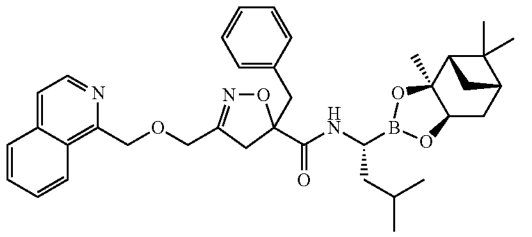 [SMILES: CC(C)C[C@H](NC(=O)C1(Cc2ccccc2)CC(COCc2nccc3ccccc23)=NO1)B1O[C@@H]2C[C@@H]3C[C@@H](C3(C)C)[C@]2(C)O1]

The title compound (0.043 g, 58%, 2 steps) was obtained using methyl 5-benzyl-3-((isoquinolin-1-ylmethoxy)methyl)-4,5-dihydroisoxazol-5-carboxylate (0.042 g, 0.112 mmol) obtained in (3) above by the preparation methods of Examples 1-(2) and (3).

(5) Preparation of ((1R)-1-(5-benzyl-3-((isoquinolin-1-ylmethoxy)methyl)-4,5-dihydroisoxazol-5-carboxamido)-3-methylbutyl)boronic acid

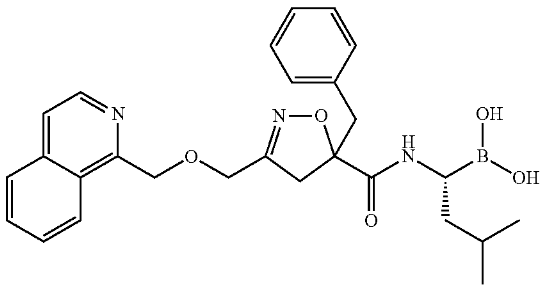 [SMILES: CC(C)C[C@H](NC(=O)C1(Cc2ccccc2)CC(COCc2nccc3ccccc23)=NO1)B(O)O]

The title compound (0.023 g, 68%) was obtained using 5-benzyl-3-((isoquinolin-1-ylmethoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.043 g, 0.069 mmol) obtained in (4) above by the preparation method of Example 1-(4).

NMR: $^{1}$H-NMR (500 MHz, $CD_3OD$); δ 8.38 (1H, d), 8.30 (1H, d), 7.95 (1H, d), 7.80-7.78 (2H, m), 7.70 (1H, t), 7.24-7.15 (5H, m), 5.08 (1H, d), 4.99 (1H, d), 4.34-4.28 (2H, m), 3.41-3.17 (3H, m), 3.08 (1H, d), 2.63 (1H, t), 1.38-1.03 (3H, m), 0.76 (6H, dd)

MS (m/z): 490[M+H], 472[M-OH]

Example 50: Preparation of ((1R)-1-(5-benzyl-3-(((5-chloro-2-methylthiazol-4-yl)methoxy)methyl)-4,5-dihydroisoxazol-5-carboxamido)-3-methylbutyl) boronic acid Through the processes (1), (2), (3), (4) and (5) below, the title compound was obtained.

(1) Preparation of 5-chloro-4-(2,2-diethoxy-ethoxymethyl)-2-methyl-thiazole

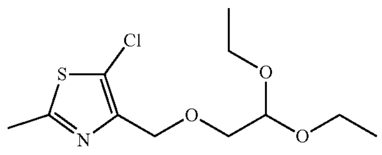 [SMILES: CCOC(COCc1nc(C)sc1Cl)OCC]

The title compound (0.352 g, 63%) was obtained using 5-chloro-4-chloromethyl-2-methylthiazole (0.362 g, 1.99 mmol) by the preparation method of Example 45-(1).

NMR: $^{1}$H-NMR (500 MHz, $CDCl_3$); δ 4.67 (1H, t), 4.60 (2H, s), 3.72-3.66 (2H, m), 3.59-3.53 (4H, m), 2.63 (3H, s), 1.21 (6H, t)

(2) Preparation of (5-chloro-2-methyl-thiazol-5-yl-methoxy)-acetaldehyde oxime

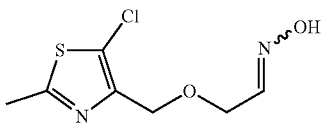

The title compound (0.209 g, 75%) was obtained using 5-chloro-4-(2,2-diethoxy-ethoxymethyl)-2-methyl-thiazole (0.352 g, 1.26 mmol) obtained in (1) above by the preparation method of Example 45-(2).

(3) Preparation of methyl 5-benzyl-3-(((5-chloro-2-methylthiazol-4-yl)methoxy)methyl)-4,5-dihydroisoxazol-5-carboxylate

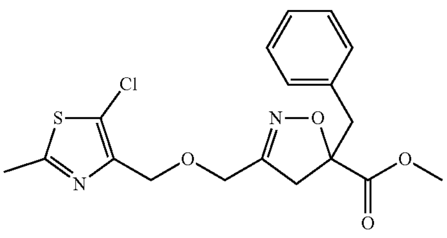

The title compound (0.264 g, 70%) was obtained using (5-chloro-2-methyl-thiazol-5-yl-methoxy)-acetaldehyde oxime (0.209 g, 0.95 mmol) obtained in (2) above by the preparation method of Preparation Example 6-(2).

NMR: $^{1}$H-NMR (500 MHz, $CDCl_3$); δ 7.25-7.18 (5H, m), 4.28 (2H, dd), 4.16 (2H, dd), 3.72 (3H, s), 3.43 (1H, d), 3.27 (1H, d), 3.13 (1H, d), 3.05 (1H, d), 2.59 (3H, s)

(4) Preparation of 5-benzyl-3-(((5-chloro-2-methylthiazol-4-yl)methoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

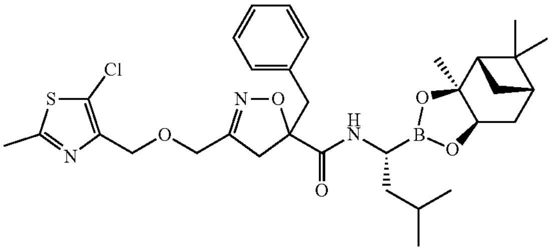

The title compound (0.217 g, 64%, 2 steps) was obtained using methyl 5-benzyl-3-(((5-chloro-2-methylthiazol-4-yl)methoxy)methyl)-4,5-dihydroisoxazol-5-carboxylate (0.264 g, 0.67 mmol) obtained in (3) above by the preparation methods of Examples 1-(2) and (3).

MS (m/z): 628[M+H]

(5) Preparation of ((1R)-1-(5-benzyl-3-(((5-chloro-2-methylthiazol-4-yl)methoxy)methyl)-4,5-dihydroisoxazol-5-carboxamido)-3-methylbutyl)boronic acid

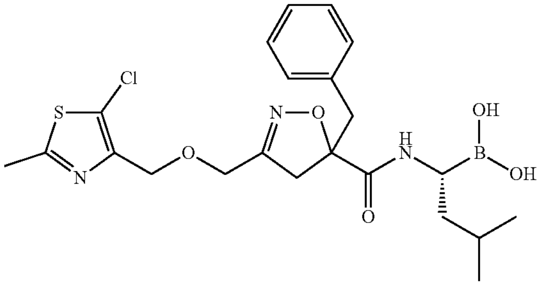 [SMILES: Cc1nc(COCC2=NOC(Cc3ccccc3)(C(=O)N[C@@H](CC(C)C)B(O)O)C2)c(Cl)s1]

The title compound (0.057 g, 33%) was obtained using 5-benzyl-3-(((5-chloro-2-methylthiazol-4-yl)methoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.21 g, 0.34 mmol) obtained in (4) above by the preparation method of Example 1-(4).

NMR: $^1$H-NMR (500 MHz, $CD_3OD$); δ 7.28-7.21 (5H, m), 4.43 (2H, dd), 4.23 (2H, dd), 3.42 (1H, d), 3.32-3.22 (2H, m), 3.16 (1H, d), 2.66 (1H, t), 2.62 (3H, s), 1.41-1.03 (3H, m), 0.79 (6H, dd)

MS (m/z): 476[M-OH]

Example 51: Preparation of ((1R)-1-(5-benzyl-3-(((2,4-dimethylthiazol-5-yl)methoxy)methyl)-4,5-dihydroisoxazol-5-carboxamido)-3-methylbutyl) boronic acid Through the processes (1), (2), (3), (4) and (5) below, the title compound was obtained.

(1) Preparation of 5-(2,2-diethoxy-ethoxymethyl)-2,4-dimethyl-thiazole

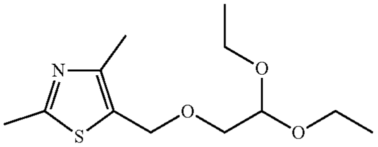 [SMILES: CCOC(COCc1sc(C)nc1C)OCC]

The title compound (0.162 g, 38%) was obtained using 5-chloromethyl-2,4-dimethyl-thiazole (0.264 g, 1.63 mmol) by the preparation method of Example 45-(1).

NMR: $^1$H-NMR (500 MHz, $CDCl_3$); δ 4.60 (2H, s), 4.52 (1H, t), 3.75-3.66 (2H, m), 3.56-3.51 (4H, m), 2.60 (3H, s), 2.42, (3H, s), 1.20 (6H, t)

(2) Preparation of (2,4-dimethyl-thiazol-5-yl-methoxy)-acetaldehyde oxime

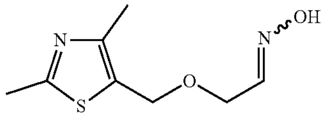

The title compound (0.055 g, 44%) was obtained using 5-(2,2-diethoxy-ethoxymethyl)-2,4-dimethyl-thiazole (0.162 g, 0.625 mmol) obtained in (1) above by the preparation method of Example 45-(2).

(3) Preparation of methyl 5-benzyl-3-(((2,4-dimethylthiazol-5-yl)methoxy)methyl)-4,5-dihydroisoxazol-5-carboxylate

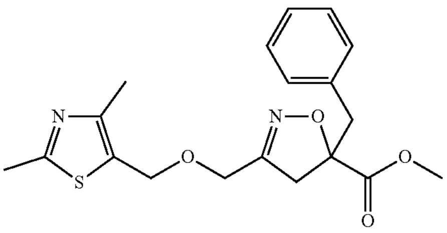

The title compound (0.040 g, 36%) was obtained using (2,4-dimethyl-thiazol-5-yl-methoxy)-acetaldehyde oxime (0.055 g, 0.275 mmol) obtained in (2) above by the preparation method of Preparation Example 6-(2).

NMR: $^1$H-NMR (500 MHz, $CDCl_3$); δ 7.27-7.21 (5H, m), 4.24 (2H, s), 4.07 (2H, dd), 3.76 (3H, s), 3.39 (1H, d), 3.32 (1H, d), 3.11 (1H, d), 2.99 (1H, d), 2.61 (3H, s), 2.27 (3H, s)

MS (m/z): 375[M+H]

(4) Preparation of 5-benzyl-3-(((2,4-dimethylthiazol-5-yl)methoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

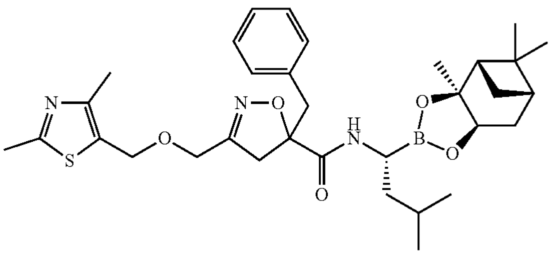

The title compound (0.055 g, 85%, 2 steps) was obtained using methyl 5-benzyl-3-(((2,4-dimethylthiazol-5-yl)methoxy)methyl)-4,5-dihydroisoxazol-5-carboxylate (0.040 g, 0.107 mmol) obtained in (3) above by the preparation methods of Examples 1-(2) and (3).

(5) Preparation of 5-benzyl-3-(2,4-dimethyl-thiazol-5-yl-methoxymethyl)-4,5-dihydro-isooxazol-5-carboxylic acid ((R)-1-boronic acid-3-methyl-butyl)-amide

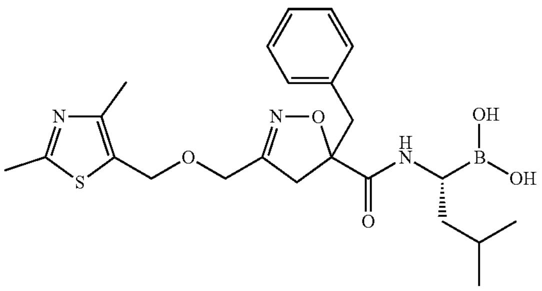 [SMILES: Cc1nc(C)c(COCC2=NOC(Cc3ccccc3)(C(=O)N[C@@H](CC(C)C)B(O)O)C2)s1]

The title compound (0.013 g, 30%) was obtained using 5-benzyl-3-(((2,4-dimethylthiazol-5-yl)methoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.055 g, 0.091 mmol) obtained in (4) above by the preparation method of Example 1-(4).

NMR: $^1$H-NMR (500 MHz, $CD_3OD$); δ 7.27-7.21 (5H, m), 4.47 (2H, s), 4.16 (2H, dd), 3.40 (1H, d), 3.32-3.20 (2H, m), 3.15 (1H, d), 2.68 (1H, t), 2.61 (3H, s), 2.27 (3H, s), 1.42-1.05 (3H, m), 0.80 (6H, dd)

MS (m/z): 456[M-OH]

Example 52: Preparation of ((1R)-1-(5-benzyl-3-(((3-bromobenzyl)oxy)methyl)-4,5-dihydroisoxazol-5-carboxamido)-3-methylbutyl)boronic acid Through the processes (1), (2), (3), (4) and (5) below, the title compound was obtained.

(1) Preparation of 1-bromo-3-(2,2-diethoxy-ethoxymethyl)-benzene

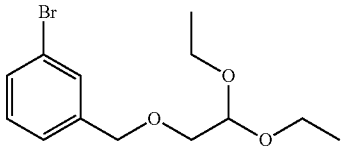 [SMILES: CCOC(COCc1cccc(Br)c1)OCC]

The title compound (0.841 g, 69%) was obtained using 3-bromo-benzyl bromide (1.00 g, 4.0 mmol) by the preparation method of Example 45-(1).

NMR: $^1$H-NMR (400 MHz, $CDCl_3$); δ 7.55 (1H, s), 7.45 (1H, dd), 7.31-7.23 (2H, m), 4.71 (1H, t), 4.60 (2H, s), 3.78-3.71 (2H, m), 3.65-3.55 (4H, m), 1.25 (6H, t)

(2) Preparation of (3-bromo-benzyloxy)-acetaldehyde oxime

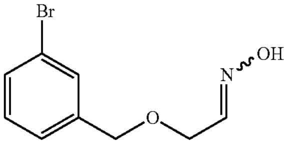 [SMILES: ON=CCOCc1cccc(Br)c1]

The title compound (0.647 g, 96%) was obtained using 1-bromo-3-(2,2-diethoxy-ethoxymethyl)-benzene (0.841 g, 2.77 mmol) obtained in (1) above by the preparation method of Example 45-(2).

(3) Preparation of methyl 5-benzyl-3-(((3-bromobenzyl)oxy)methyl)-4,5-dihydroisoxazol-5-carboxylate

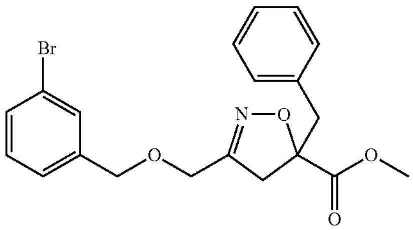 [SMILES: COC(=O)C1(Cc2ccccc2)CC(COCc2cccc(Br)c2)=NO1]

The title compound (0.641 g, 58%) was obtained using (3-bromo-benzyloxy)-acetaldehyde oxime (0.647 g, 2.65 mmol) obtained in the process (2) above by the preparation method of Preparation Example 6-(2).

NMR: $^1$H-NMR (400 MHz, $CDCl_3$); δ 7.42 (1H, d), 7.36 (1H, s), 7.29-7.19 (6H, m), 7.12 (1H, d), 4.18-4.07 (4H, m), 3.79 (3H, s), 3.39 (2H, dd), 3.07 (2H, dd)

(4) Preparation of 5-benzyl-3-(((3-bromobenzyl)oxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

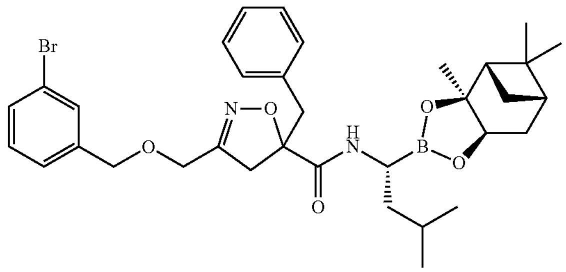 [SMILES: CC(C)C[C@H](NC(=O)C1(Cc2ccccc2)CC(COCc2cccc(Br)c2)=NO1)B1O[C@@H]2C[C@@H]3C[C@@H](C3(C)C)[C@]2(C)O1]

The title compound (0.050 g, 54%, 2 steps) was obtained using methyl 5-benzyl-3-(((3-bromobenzyl)oxy)methyl)-4,5-dihydroisoxazol-5-carboxylate (0.059 g, 0.14 mmol) obtained in (3) above by the preparation methods of Examples 1-(2) and (3).

MS (m/z): 651, 653 [M+H]

(5) Preparation of ((1R)-1-(5-benzyl-3-(((3-bromobenzyl)oxy)methyl)-4,5-dihydroisoxazol-5-carboxamido)-3-methylbutyl)boronic acid

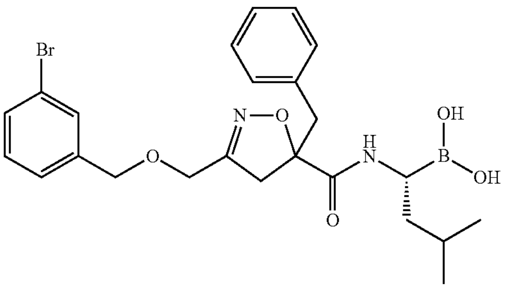 [SMILES: CC(C)C[C@H](NC(=O)C1(Cc2ccccc2)CC(COCc2cccc(Br)c2)=NO1)B(O)O]

The title compound (0.016 g, 40%) was obtained using 5-benzyl-3-(((3-bromobenzyl)oxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.050 g, 0.077 mmol) obtained in (4) above by the preparation method of Example 1-(4).

NMR: $^1$H-NMR (400 MHz, $CD_3OD$); δ 7.44 (1H, s), 7.43 (1H, d), 7.28-7.19 (7H, m), 4.33 (2H, dd), 4.20 (2H, dd), 3.42 (1H, d), 3.33-3.28 (1H, m), 3.23 (1H, d), 3.16 (1H, d), 2.69 (1H, dd), 1.44-1.04 (3H, m), 0.80 (6H, dd)

MS (m/z): 540, 542 (M+Na), 499, 501 [M-OH]

Example 53: Preparation of ((1R)-1-(5-benzyl-3-(((6-bromopyridin-2-yl)methoxy)methyl)-4,5-dihydroisoxazol-5-carboxamido)-3-methylbutyl)boronic acid Through the processes (1), (2), (3), (4) and (5) below, the title compound was obtained.

(1) Preparation of 2-bromo-6-(2,2-diethoxy-ethoxymethyl)-pyridine

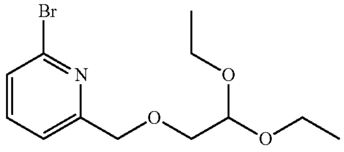 [SMILES: CCOC(COCc1cccc(Br)n1)OCC]

The title compound (0.196 g, 81%) was obtained using 2-bromo-6-chloromethyl-pyridine (0.191 g, 0.925 mmol) by the preparation method of Example 45-(1).

NMR: $^1$H-NMR (400 MHz, $CDCl_3$); δ 7.60-7.35 (3H, m), 4.72 (1H, t), 4.69 (2H, s), 3.81-3.67 (2H, m), 3.64-3.56 (4H, m), 1.24 (6H, t)

(2) Preparation of (6-bromo-pyridin-2-ylmethoxy)-acetaldehyde oxime

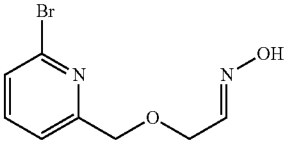 [SMILES: O/N=C/COCc1cccc(Br)n1]

The title compound (0.125 g, 79%) was obtained using 2-bromo-6-(2,2-diethoxy-ethoxymethyl)-pyridine (0.196 g, 0.644 mmol) obtained in (1) above by the preparation method of Example 45-(2).

(3) Preparation of methyl 5-benzyl-3-(((6-bromopyridin-2-yl)methoxy)methyl)-4,5-dihydroisoxazol-5-carboxylate

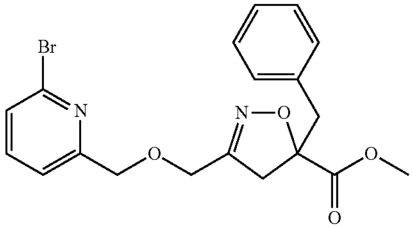 [SMILES: COC(=O)C1(Cc2ccccc2)CC(COCc2cccc(Br)n2)=NO1]

The title compound (0.125 g, 58%) was obtained using (6-bromo-pyridin-2-ylmethoxy)-acetaldehyde oxime (0.125 g, 0.51 mmol) obtained in (2) above by the preparation method of Preparation Example 6-(2).

NMR: $^1$H-NMR (400 MHz, $CDCl_3$); δ 7.58 (1H, t), 7.43 (1H, d), 7.30-7.24 (6H, m), 4.39 (2H, dd), 4.25 (2H, dd), 3.83 (3H, s), 3.45 (2H, dd), 3.14 (2H, dd)

(4) Preparation of 5-benzyl-3-(((6-bromopyridin-2-yl)methoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

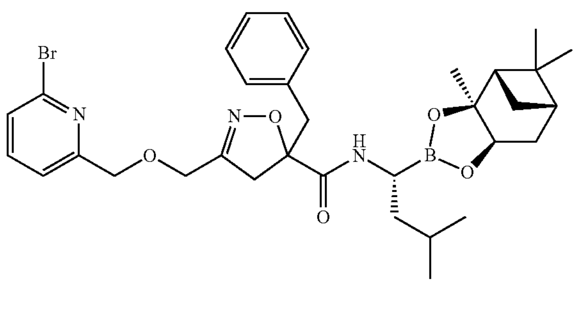

The title compound (0.039 g, 49%, 2 steps) was obtained using methyl 5-benzyl-3-(((6-bromopyridin-2-yl)methoxy)methyl)-4,5-dihydroisoxazol-5-carboxylate (0.052 g, 0.124 mmol) obtained in (3) above by the preparation methods of Examples 1-(2) and (3).

MS (m/z): 652, 654 [M+H]

(5) Preparation of ((1R)-1-(5-benzyl-3-(((6-bromopyridin-2-yl)methoxy)methyl)-4,5-dihydroisoxazol-5-carboxamido)-3-methylbutyl)boronic acid

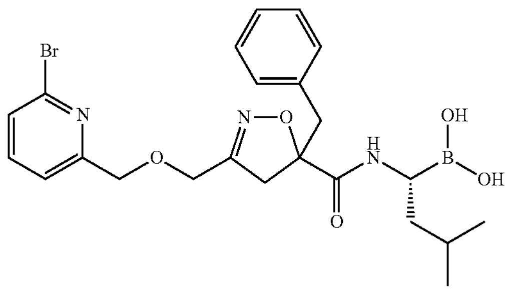 [SMILES: CC(C)C[C@H](NC(=O)C1(Cc2ccccc2)CC(COCc2cccc(Br)n2)=NO1)B(O)O]

The title compound (0.014 g, 45%) was obtained using 5-benzyl-3-(((6-bromopyridin-2-yl)methoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.039 g, 0.06 mmol) obtained in (4) above by the preparation method of Example 1-(4).

NMR: $^1$H-NMR (400 MHz, $CD_3OD$); δ 7.73 (1H, t), 7.53 (1H, d), 7.44 (1H, d), 7.32-7.22 (5H, m), 4.46 (2H, q), 4.34 (2H, dd), 3.50 (1H, d), 3.37-3.33 (2H, m), 3.21 (1H, d), 2.73 (1H, t), 1.48-1.07 (3H, m), 0.84 (6H, dd)

MS (m/z): 540, 542 (M+Na), 500, 502 [M-OH]

Example 54: Preparation of ((1R)-1-(3-(([1,1'-biphenyl]-3-ylmethoxy)methyl)-5-benzyl-4,5-dihydroisoxazol-5-carboxamido)-3-methylbutyl)boronic acid Through the processes (1), (2) and (3) below, the title compound was obtained.

(1) Preparation of methyl 3-(([1,1'-biphenyl]-3-ylmethoxy)methyl)-5-benzyl-4,5-dihydroisoxazol-5-carboxylate

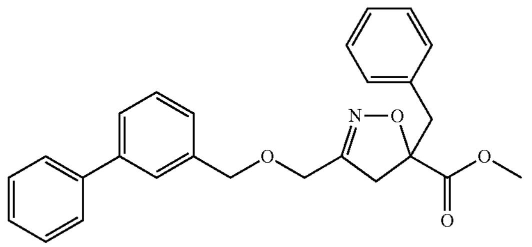 [SMILES: COC(=O)C1(Cc2ccccc2)CC(COCc2cccc(-c3ccccc3)c2)=NO1]

The title compound (0.064 g, 68%) was obtained using methyl 5-benzyl-3-(((3-bromobenzyl)oxy)methyl)-4,5-dihydroisoxazol-5-carboxylate (0.095 g, 0.227 mmol) obtained in Example 52-(3) and phenylboronic acid by the preparation method of Example 35-(3).

NMR: $^1$H-NMR (400 MHz, $CDCl_3$); δ 7.65-7.19 (14H, m), 4.34-4.13 (4H, m), 3.83 (3H, s), 3.45 (2H, dd), 3.14 (2H, dd)

MS (m/z): 416 [M+H]

(2) Preparation of 3-(([1,1'-biphenyl]-3-ylmethoxy)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

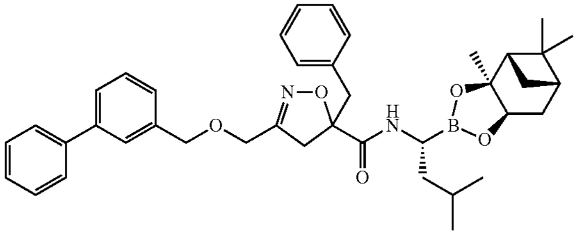 [SMILES: CC(C)C[C@H](NC(=O)C1(Cc2ccccc2)CC(COCc2cccc(-c3ccccc3)c2)=NO1)B1O[C@@H]2C[C@@H]3C[C@@H](C3(C)C)[C@]2(C)O1]

The title compound (0.069 g, 68%, 2 steps) was obtained using methyl 3-(([1,1'-biphenyl]-3-ylmethoxy)methyl)-5-benzyl-4,5-dihydroisoxazol-5-carboxylate (0.064 g, 0.154 mmol) obtained in (1) above by the preparation methods of Examples 1-(2) and (3).

MS (m/z): 649 [M+H]

(3) Preparation of ((1R)-1-(3-(([1,1'-biphenyl]-3-ylmethoxy)methyl)-5-benzyl-4,5-dihydroisoxazol-5-carboxamido)-3-methylbutyl)boronic acid

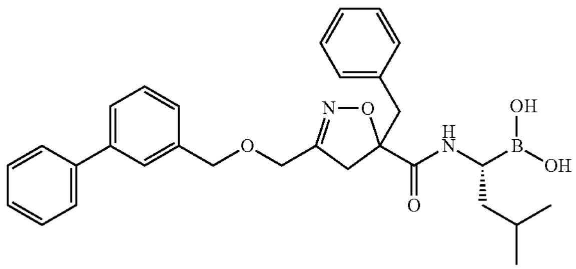 [SMILES: CC(C)C[C@H](NC(=O)C1(Cc2ccccc2)CC(COCc2cccc(-c3ccccc3)c2)=NO1)B(O)O]

The title compound (0.019 g, 35%) was obtained using 3-(([1,1'-biphenyl]-3-ylmethoxy)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.069 g, 0.106 mmol) obtained in (2) above by the preparation method of Example 1-(4).

NMR: $^1$H-NMR (400 MHz, $CD_3OD$); δ 7.64-7.24 (14H, m), 4.48-4.22 (4H, m), 3.47 (1H, d), 3.37-3.27 (1H, m), 3.23-3.14 (2H, m), 2.72 (1H, t), 1.47-1.10 (3H, m), 0.82 (6H, dd)

MS (m/z): 537 (M+Na), 497 [M-OH]

Example 55: Preparation of [(1R)-1-[[5-benzyl-3-[(6-phenyl-2-pyridyl)methoxymethyl]-4H-1,2-oxazol-5-carbonyl]amino]-3-methyl-butyl]boronic acid Through the processes (1), (2) and (3) below, the title compound was obtained.

(1) Preparation of methyl 5-benzyl-3-(((6-phenylpyridin-2-yl)methoxy)methyl)-4,5-dihydroisoxazol-5-carboxylate

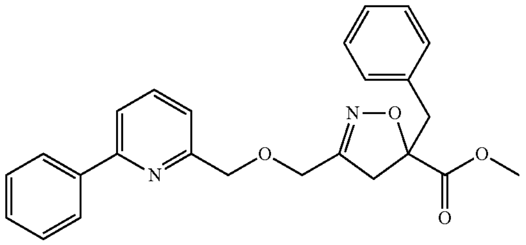 [SMILES: COC(=O)C1(Cc2ccccc2)CC(COCc2cccc(-c3ccccc3)n2)=NO1]

The title compound (0.041 g, 54%) was obtained using methyl 5-benzyl-3-(((6-bromopyridin-2-yl)methoxy)methyl)-4,5-dihydroisoxazol-5-carboxylate (0.076 g, 0.181 mmol) obtained in Example 53-(3) and phenylboronic acid by the preparation method of Example 35-(3).

NMR: $^1$H-NMR (400 MHz, $CDCl_3$); δ 8.04 (2H, dd), 7.79 (1H, t), 7.68 (1H, d), 7.53-7.46 (3H, m), 7.30-7.13 (6H, m), 4.55 (2H, dd), 4.32 (2H, dd), 3.82 (3H, s), 3.55 (1H, d), 3.39 (1H, d), 3.18 (2H, dd)

MS (m/z): 417 [M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((6-phenylpyridin-2-yl)methoxy)methyl)-4,5-dihydroisoxazol-5-carboxamide

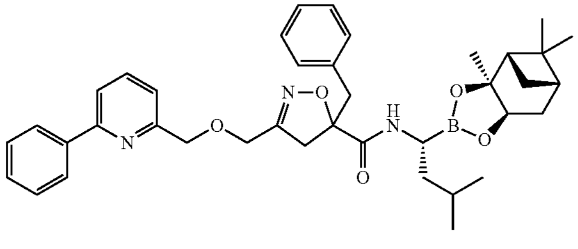

The title compound (0.036 g, 57%, 2 steps) was obtained using methyl 5-benzyl-3-(((6-phenylpyridin-2-yl)methoxy)methyl)-4,5-dihydroisoxazol-5-carboxylate (0.041 g, 0.098 mmol) obtained in (1) above by the preparation methods of Examples 1-(2) and (3).

MS (m/z): 650 [M+H]

(3) Preparation of ((1R)-1-(5-benzyl-3-(((6-phenylpyridin-2-yl)methoxy)methyl)-4,5-dihydroisoxazol-5-carboxamido)-3-methylbutyl)boronic acid

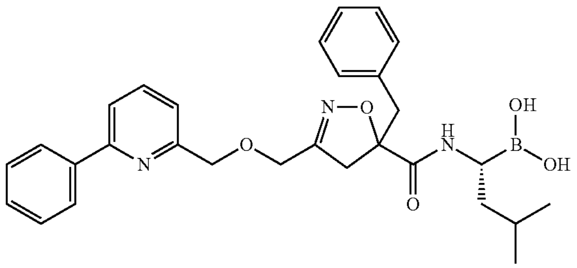 [SMILES: CC(C)C[C@H](NC(=O)C1(Cc2ccccc2)CC(COCc2cccc(-c3ccccc3)n2)=NO1)B(O)O]

The title compound (0.015 g, 53%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((6-phenylpyridin-2-yl)methoxy)methyl)-4,5-dihydroisoxazol-5-carboxamide (0.036 g, 0.055 mmol) in (2) above by the preparation method of Example 1-(4).

NMR: $^1$H-NMR (400 MHz, $CD_3OD$); δ 7.99 (2H, dd), 7.89 (1H, t), 7.77 (1H, d), 7.51-7.39 (4H, m), 7.29-7.24 (5H, m), 4.60 (2H, dd), 4.38 (2H, dd), 3.52 (1H, d), 3.37-3.30 (2H, m), 3.20 (1H, d), 2.72 (1H, t), 1.46-1.06 (3H, m), 0.82 (6H, dd)

MS (m/z): 498 [M-OH]

Example 56: Preparation of ((1R)-1-(5-benzyl-3-(((4'-methoxy-[1,1'-biphenyl]-3-yl)methoxy)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-(((4'-methoxy-[1,1'-biphenyl]-3-yl)methoxy)methyl)-4,5-dihydroisoxazol-5-carboxylate

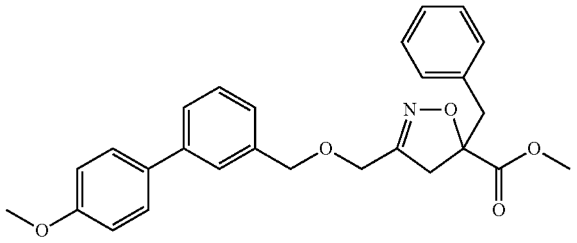

The title compound (0.047 g, 58%) was obtained using methyl 5-benzyl-3-(((3-bromobenzyl)oxy)methyl)-4,5-dihydroisoxazol-5-carboxylate (0.076 g, 0.182 mmol) obtained in Example 52-(3) and 4-methoxyphenylboronic acid by the preparation method of Example 35-(3).

NMR: $^1$H-NMR (400 MHz, $CDCl_3$); δ 7.59-7.41 (5H, m), 7.32-7.21 (6H, m), 7.03 (2H, dd), 4.32 (2H, dd), 4.18 (2H, dd), 3.90 (3H, s), 3.83 (3H, s), 3.51 (1H, d), 3.41 (1H, d), 3.18 (1H, d), 3.10 (1H, d)

MS (m/z): 446 [M+H]

(2) Preparation of 5-benzyl-3-(((4'-methoxy-[1,1'-biphenyl]-3-yl)methoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

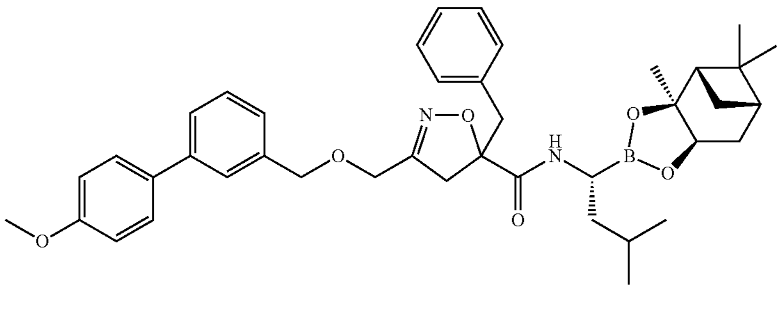

The title compound (0.043 g, 60%, 2 steps) was obtained using methyl 5-benzyl-3-(((4'-methoxy-[1,1'-biphenyl]-3-yl)methoxy)methyl)-4,5-dihydroisoxazol-5-carboxylate (0.047 g, 0.105 mmol) obtained in (1) above by the preparation methods of Examples 1-(2) and (3).

MS (m/z): 679 [M+H]

(3) Preparation of ((1R)-1-(5-benzyl-3-(((4'-methoxy-[1,1'-biphenyl]-3-yl)methoxy)methyl)-4,5-dihydroisoxazol-5-carboxamido)-3-methylbutyl) boronic acid

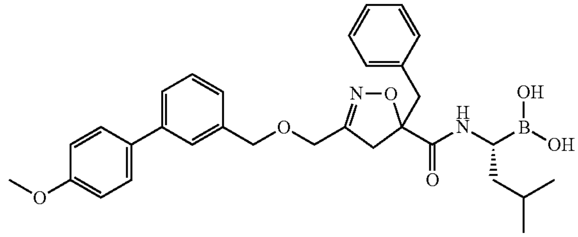 [SMILES: COc1ccc(-c2cccc(COCC3=NOC(Cc4ccccc4)(C(=O)N[C@@H](CC(C)C)B(O)O)C3)c2)cc1]

The title compound (0.015 g, 44%) was obtained using 5-benzyl-3-(((4'-methoxy-[1,1'-biphenyl]-3-yl)methoxy) methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.043 g, 0.063 mmol) obtained in (2) above by the preparation method of Example 1-(4).

NMR: $^1$H-NMR (400 MHz, $CD_3OD$); δ 7.58-7.39 (5H, m), 7.31-7.23 (6H, m), 7.03 (2H, dd), 4.46 (2H, dd), 4.26 (2H, dd), 3.85 (3H, s), 3.47 (1H, d), 3.37-3.27 (2H, m), 3.20 (1H, d), 2.72 (1H, t), 1.45-1.09 (3H, m), 0.82 (6H, dd)

MS (m/z): 545 [M+H], 527 [M-OH]

Example 57: Preparation of ((1R)-1-(5-benzyl-3-(((3'-methoxy-[1,1'-biphenyl]-3-yl)methoxy)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-(((3'-methoxy-[1,1'-biphenyl]-3-yl)methoxy)methyl)-4,5-dihydroisoxazol-5-carboxylate

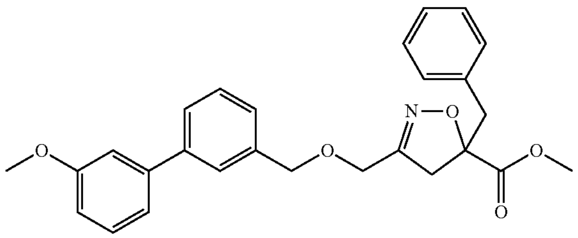

The title compound (0.046 g, 60%) was obtained using methyl 5-benzyl-3-(((3-bromobenzyl)oxy)methyl)-4,5-dihydroisoxazol-5-carboxylate (0.072 g, 0.172 mmol) obtained in Example 52-(3) and 3-methoxyphenylboronic acid by the preparation method of Example 35-(3).

NMR: $^1$H-NMR (400 MHz, $CDCl_3$); δ 7.56-7.40 (4H, m), 7.32-7.17 (8H, m), 6.98 (1H, d), 4.31 (2H, dd), 4.20 (2H, dd), 3.92 (3H, s), 3.83 (3H, s), 3.51 (1H, d), 3.39 (1H, d), 3.18 (1H, d), 3.10 (1H, d)

MS (m/z): 446 [M+H]

(2) Preparation of 5-benzyl-3-(((3'-methoxy-[1,1'-biphenyl]-3-yl)methoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

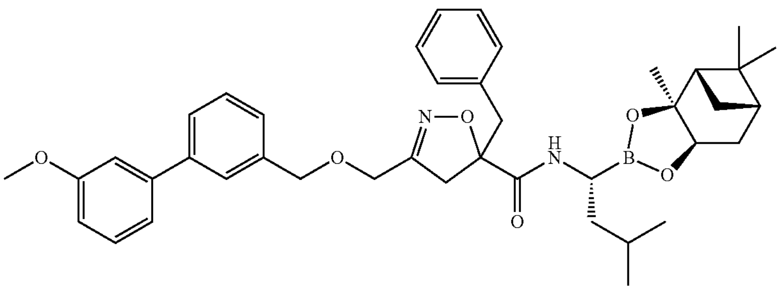

The title compound (0.035 g, 50%, 2 steps) was obtained using methyl 5-benzyl-3-(((3'-methoxy-[1,1'-biphenyl]-3-yl)methoxy)methyl)-4,5-dihydroisoxazol-5-carboxylate (0.046 g, 0.103 mmol) in (1) above by the preparation methods of Examples 1-(2) and (3).

MS (m/z): 679 [M+H]

(3) Preparation of ((1R)-1-(5-benzyl-3-(((3'-methoxy-[1,1'-biphenyl]-3-yl)methoxy)methyl)-4,5-dihydroisoxazol-5-carboxamido)-3-methylbutyl) boronic acid

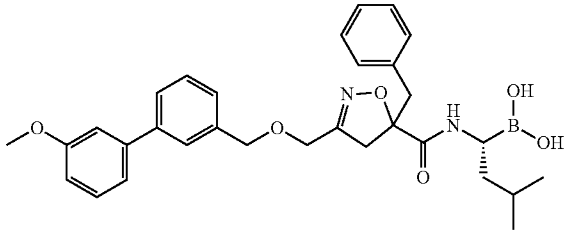 [SMILES: COc1cccc(-c2cccc(COCC3=NOC(Cc4ccccc4)(C(=O)N[C@@H](CC(C)C)B(O)O)C3)c2)c1]

The title compound (0.013 g, 46%) was obtained using 5-benzyl-3-(((3'-methoxy-[1,1'-biphenyl]-3-yl)methoxy) methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.035 g, 0.052 mmol) obtained in (2) above by the preparation method of Example 1-(4).

NMR: $^{1}$H-NMR (400 MHz, $CD_3OD$); δ 7.56-7.15 (12H, m), 6.95 (1H, dd), 4.48 (2H, dd), 4.27 (2H, dd), 3.87 (3H, s), 3.47 (1H, d), 3.37-3.23 (2H, m), 3.16 (1H, d), 2.72 (1H, t), 1.45-1.09 (3H, m), 0.82 (6H, dd)

MS (m/z): 545 [M+H], 527 [M-OH]

Example 58: Preparation of [(1R)-1-[[5-benzyl-3-[[3-(2-methoxyphenyl)phenyl]methoxymethyl]-4H-1,2-oxazol-5-carbonyl]amino]-3-methyl-butyl]boronic acid Through the processes (1), (2) and (3) below, the title compound was obtained.

(1) Preparation of methyl 5-benzyl-3-(((2'-methoxy-[1,1'-biphenyl]-3-yl)methoxy)methyl)-4,5-dihydroisoxazol-5-carboxylate

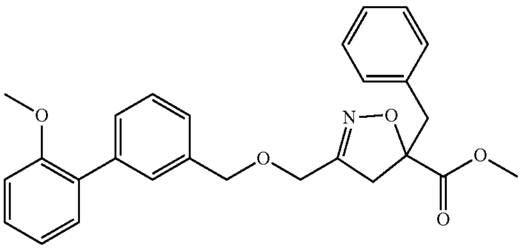 [SMILES: COC(=O)C1(Cc2ccccc2)CC(COCc2cccc(-c3ccccc3OC)c2)=NO1]

The title compound (0.052 g, 76%) was obtained using methyl 5-benzyl-3-(((3-bromobenzyl)oxy)methyl)-4,5-dihydroisoxazol-5-carboxylate (0.064 g, 0.153 mmol) obtained in Preparation Example 9 and 4-methoxyphenylboronic acid by the preparation method of Example 35-(3).

NMR: $^{1}$H-NMR (400 MHz, $CDCl_3$); δ 7.52-7.25 (11H, m), 7.11-7.04 (2H, m), 4.34 (2H, dd), 4.23 (2H, dd), 3.86 (3H, s), 3.83 (3H, s), 3.51 (1H, d), 3.39 (1H, d), 3.19 (1H, d), 3.11 (1H, d)

MS (m/z): 446 [M+H]

(2) Preparation of 5-benzyl-3-(((2'-methoxy-[1,1'-biphenyl]-3-yl)methoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

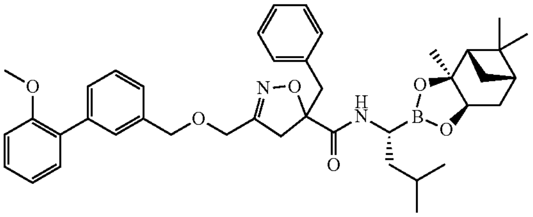 [SMILES: COc1ccccc1-c1cccc(COCC2=NOC(Cc3ccccc3)(C(=O)N[C@@H](CC(C)C)B3O[C@@H]4C[C@@H]5C[C@@H](C5(C)C)[C@]4(C)O3)C2)c1]

The title compound (0.042 g, 52%, 2 steps) was obtained using methyl 5-benzyl-3-(((2'-methoxy-[1,1'-biphenyl]-3- yl)methoxy)methyl)-4,5-dihydroisoxazol-5-carboxylate (0.052 g, 0.117 mmol) in (1) above by the preparation methods of Examples 1-(2) and (3).

MS (m/z): 679 [M+H]

(3) Preparation of 5-benzyl-3-(2'-methoxy-biphenyl-3-ylmethoxymethyl)-4,5-dihydro-isooxazol-5-carboxylic acid ((R)-1-boronic acid-3-methyl-butyl)-amide

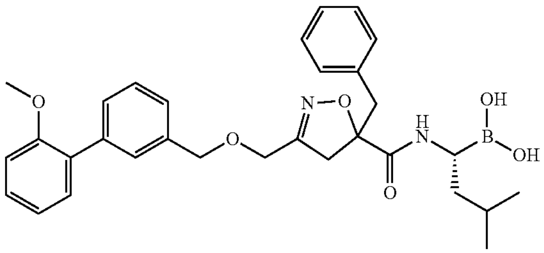 [SMILES: COc1ccccc1-c1cccc(COCC2=NOC(Cc3ccccc3)(C(=O)N[C@@H](CC(C)C)B(O)O)C2)c1]

The title compound (0.018 g, 53%) was obtained using 5-benzyl-3-(((2'-methoxy-[1,1'-biphenyl]-3-yl)methoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.042 g, 0.062 mmol) obtained in (2) above by the preparation method of Example 1-(4).

NMR: $^1$H-NMR (400 MHz, $CD_3OD$); δ 7.42-7.24 (11H, m), 7.10-7.03 (2H, m), 4.45 (2H, dd), 4.25 (2H, dd), 3.80 (3H, s), 3.46 (1H, d), 3.37-3.22 (2H, m), 3.15 (1H, d), 2.71 (1H, t), 1.45-1.09 (3H, m), 0.82 (6H, dd)

MS (m/z): 545 [M+H], 527 [M-OH]

Example 59: Preparation of ((1R)-1-(3-(benzamidomethyl)-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-4,5-dihydroisoxazol-5-carboxylate hydrochloride

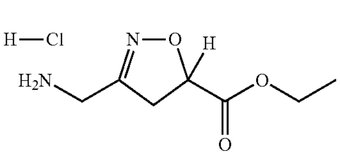

Ethyl 3-[(tert-butoxycarbonylamino)methyl]-4,5-dihydro-1,2-oxazol-5-carboxylate (0.67 g, 2.46 mmol) obtained in Preparation Example 1 was dissolved in dichloromethane (10 ml). A 4 N hydrochloric acid 1,4-dioxane solution (5 ml, 20 mmol) was slowly added thereto at 0° C., followed by stirring for 5 hours, while raising to room temperature. The solvent was distilled under a reduced pressure, and the resultant product was solidified with dichloromethane and hexane. The residual solvent was distilled under a reduced pressure, and drying was performed under a reduced pressure to obtain the title compound (0.48 g, 94%).

MS (m/z): 173 [M+H]

(2) Preparation of ethyl 3-(benzamidomethyl)-4,5-dihydroisoxazol-5-carboxylate

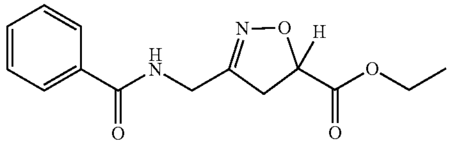 [SMILES: CCOC(=O)C1CC(CNC(=O)c2ccccc2)=NO1]

Ethyl 3-(aminomethyl)-4,5-dihydroisoxazol-5-carboxylate hydrochloride (0.15 g, 0.72 mmol) obtained in (1) above was dissolved in dimethylformamide (3 ml). 1-Ethyl-3-(3-dimethylaminopropyl)carbodiimide (0.18 g, 0.94 mmol), hydroxybenzotriazole (0.13 g, 0.94 mmol) and benzoic acid (0.11 g, 0.79 mmol) were added thereto in order. Diisopropylethylamine (0.38 ml, 2.16 mmol) was slowly added thereto, and stirring was performed at room temperature for 18 hours. The solvent was distilled under a reduced pressure, a sodium bicarbonate aqueous solution was added, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.07 g, 35%).

NMR: $^1$H-NMR (400 MHz, $CDCl_3$); δ 7.82-7.75 (dd, 2H), 7.54-7.40 (m, 3H), 6.90 (m, 1H), 5.06-5.02 (dd, 1H), 4.42-4.41 (d, 2H), 4.29-4.21 (q, 2H), 3.48-3.30 (m, 2H), 1.31-1.28 (t, 3H)

MS (m/z): 277[M+H]

(3) Preparation of 3-(benzamidomethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

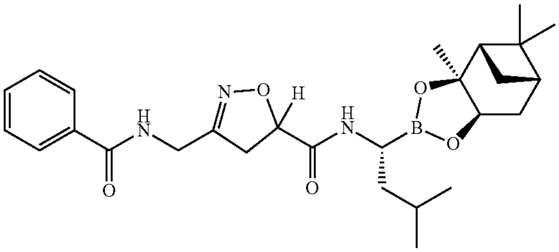 [SMILES: CC(C)C[C@H](NC(=O)C1CC(CNC(=O)c2ccccc2)=NO1)B1O[C@@H]2C[C@@H]3C[C@@H](C3(C)C)[C@]2(C)O1]

The title compound (0.08 g, 64%, 2 steps) was obtained using ethyl 3-(benzamidomethyl)-4,5-dihydroisoxazol-5-carboxylate (0.07 g, 0.26 mmol) obtained in (2) above by the preparation methods of Examples 1-(2) and (3).

MS (m/z): 496[M+H]

(4) Preparation of ((1R)-1-(3-(benzamidomethyl)-4,5-dihydroisoxazol-5-carboxamido)-3-methylbutyl) boronic acid

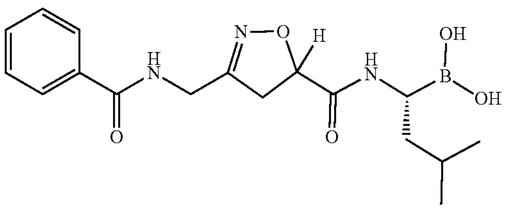 [SMILES: CC(C)C[C@H](NC(=O)C1CC(CNC(=O)c2ccccc2)=NO1)B(O)O]

The title compound (0.045 g, 78%) was obtained using 3-(benzamidomethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.08 g, 0.16 mmol) obtained in (3) above by the preparation method of Example 1-(4).

NMR: $^1$H-NMR (400 MHz, $CDCl_3$); δ 7.81-7.39 (m, 5H), 7.19 (m, 1H), 5.09-5.01 (m, 1H), 4.41-4.30 (m, 2H), 3.36-3.34 (m, 2H), 3.19-2.75 (m, 1H), 1.54-1.34 (m, 3H), 0.89-0.85 (m, 6H)

MS (m/z): 362[M+H], 344[M-OH]

Example 60: Preparation of ((1R)-3-methyl-1-(3-((pyridin-2-ylamino)methyl)-4,5-dihydroisoxazol-5-carboxamido)butyl)boronic acid Through the processes (1), (2) and (3) below, the title compound was obtained.

(1) Preparation of ethyl 3-[(pyridin-2-carbonylamino)methyl]-4,5-dihydroisoxazol-5-carboxylate

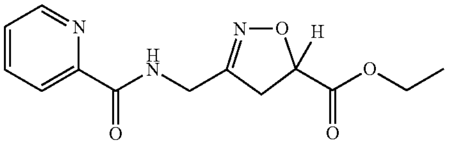 [SMILES: CCOC(=O)C1CC(CNC(=O)c2ccccn2)=NO1]

The title compound (0.09 g, 75%) was obtained using ethyl 3-(aminomethyl)-4,5-dihydroisoxazol-5-carboxylate hydrochloride (0.09 g, 0.43 mmol) obtained in Example 59-(1) and pyridin-2-carboxylic acid (0.059 g, 0.48 mmol) by the preparation method of Example 59-(2).

MS (m/z): 278[M+H]

(2) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-(picolinamidomethyl)-4,5-dihydroisoxazol-5-carboxamide

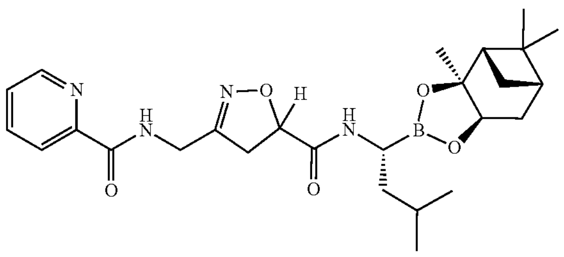 [SMILES: CC(C)C[C@H](NC(=O)C1CC(CNC(=O)c2ccccn2)=NO1)B1O[C@@H]2C[C@@H]3C[C@@H](C3(C)C)[C@]2(C)O1]

The title compound (0.052 g, 47%, 2 steps) was obtained using ethyl 3-[(pyridin-2-carbonylamino)methyl]-4,5-dihydroisoxazol-5-carboxylate (0.09 g, 0.32 mmol) obtained in (1) above by the preparation methods of Example 1-(2) and Example 1-(3).

MS (m/z): 497[M+H], 345[M-$C_{10}H_{15}O$]

(3) Preparation of ((1R)-3-methyl-1-(3-((pyridin-2-ylamino)methyl)-4,5-dihydroisoxazol-5-carboxamido)butyl)boronic acid

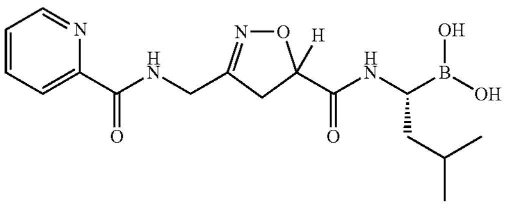 [SMILES: CC(C)C[C@H](NC(=O)C1CC(CNC(=O)c2ccccn2)=NO1)B(O)O]

The title compound (0.042 g, 75%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-(picolinamidomethyl)-4,5-dihydroisoxazol-5-carboxamide (0.077 g, 0.16 mmol) obtained in (2) above by the preparation method of Example 1-(4).

NMR: $^1$H-NMR (400 MHz, $CDCl_3$); δ 8.55-8.40 (m, 2H), 8.18-8.16 (t, 1H), 7.85-7.84 (m, 1H), 7.45-7.38 (m, 1H), 5.15-5.09 (m, 1H), 4.43-4.41 (m, 2H), 3.41-3.38 (m, 2H), 2.99-2.87 (m, 1H), 1.54-1.25 (m, 3H), 0.87-0.84 (m, 6H)

MS (m/z): 363[M+H], 345[M-OH]

Example 61: Preparation of ((1R)-1-(3-((isoquinolin-1-carboxamido)methyl)-4,5-dihydroisoxazol-5-carboxamido)-3-methylbutyl)boronic acid Through the processes (1), (2) and (3) below, the title compound was obtained.

(1) Preparation of ethyl 3-[(isoquinolin-1-carbonylamino)methyl]-4,5-dihydroisoxazol-5-carboxylate

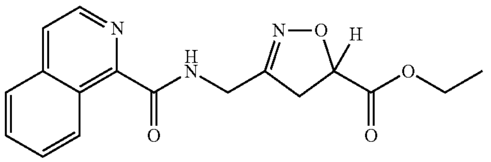 [SMILES: CCOC(=O)C1CC(CNC(=O)c2nccc3ccccc23)=NO1]

The title compound (0.107 g, 68%) was obtained using ethyl 3-(aminomethyl)-4,5-dihydroisoxazol-5-carboxylate hydrochloride (0.1 g, 0.48 mmol) obtained in Example 59-(1) and isoquinolin-1-carboxylic acid (0.083 g, 0.53 mmol) by the preparation method of Example 59-(2).

NMR: $^1$H-NMR (500 MHz, $CDCl_3$); δ 9.54-9.53 (d, 1H), 8.65 (br s, 1H), 8.45-8.44 (d, 1H), 7.85-7.55 (m, 4H), 5.05-5.01 (m, 1H), 4.49-4.47 (m, 2H), 4.24-4.19 (q, 2H), 3.38-3.36 (m, 2H), 1.29-1.26 (t, 3H)

MS (m/z): 328[M+H]

(2) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

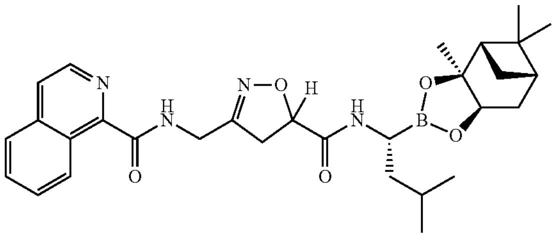 [SMILES: CC(C)C[C@H](NC(=O)C1CC(CNC(=O)c2nccc3ccccc23)=NO1)B1O[C@@H]2C[C@@H]3C[C@@H](C3(C)C)[C@]2(C)O1]

The title compound (0.116 g, 66%, 2 steps) was obtained using ethyl 3-[(isoquinolin-1-carbonylamino)methyl]-4,5-dihydroisoxazol-5-carboxylate (0.107 g, 0.33 mmol) obtained in (1) above by the preparation methods of Examples 1-(2) and (3).

MS (m/z): 547[M+H]

(3) Preparation of ((1R)-1-(3-((isoquinolin-1-carboxamido)methyl)-4,5-dihydroisoxazol-5-carboxamido)-3-methylbutyl)boronic acid

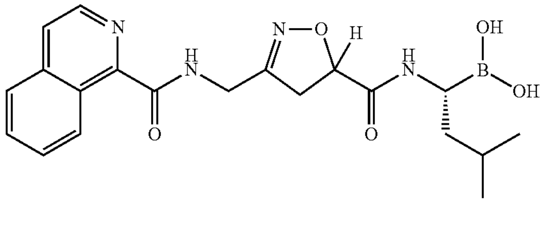 [SMILES: CC(C)C[C@H](NC(=O)C1CC(CNC(=O)c2nccc3ccccc23)=NO1)B(O)O]

The title compound (0.065 g, 74%) was obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.116 g, 0.21 mmol) obtained in (2) above by the preparation method of Example 1-(4).

NMR: $^1$H-NMR (400 MHz, $CDCl_3$); δ 9.51-9.46 (m, 1H), 8.68-8.50 (m, 1H), 8.47-8.38 (m, 1H), 7.83-7.60 (m, 4H), 7.50 (m, 1H), 5.12-5.06 (m, 1H), 4.49-4.41 (m, 2H), 3.49-3.39 (m, 2H), 2.98-2.87 (m, 1H), 1.59-1.27 (m, 3H), 0.88-0.82 (m, 6H)

MS (m/z): 413[M+H], 395[M-OH]

Example 62: Preparation of ((1R)-3-methyl-1-(3-((quinolin-5-carboxamido)methyl)-4,5-dihydroisoxazol-5-carboxamido)butyl)boronic acid Through the processes (1), (2) and (3) below, the title compound was obtained.

(1) Preparation of ethyl 3-((isoquinolin-1-carboxamido)methyl)-4,5-dihydroisoxazol-5-carboxylate

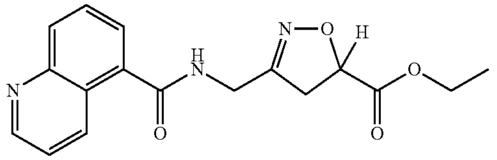 [SMILES: CCOC(=O)C1CC(CNC(=O)c2cccc3ncccc23)=NO1]

The title compound (0.19 g, 45%) was obtained using ethyl 3-(aminomethyl)-4,5-dihydroisoxazol-5-carboxylate hydrochloride (0.28 g, 1.3 mmol) obtained in Example 59-(1) and 5-quinolinecarboxylic acid (0.25 g, 1.5 mmol) by the preparation method of Example 59-(2).

MS (m/z): 314[M+H]

(2) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-((quinolin-5-carboxamido)methyl)-4,5-dihydroisoxazol-5-carboxamide

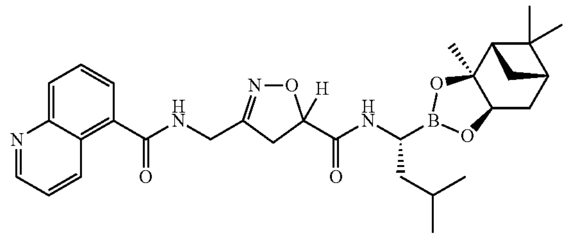 [SMILES: CC(C)C[C@H](NC(=O)C1CC(CNC(=O)c2cccc3ncccc23)=NO1)B1O[C@@H]2C[C@@H]3C[C@@H](C3(C)C)[C@]2(C)O1]

The title compound (0.092 g, 29%, 2 steps) was obtained using ethyl 3-[(isoquinolin-1-carbonylamino)methyl]-4,5-dihydroisoxazol-5-carboxylate (0.19 g, 0.59 mmol) obtained in (1) above by the preparation methods of Examples 1-(2) and (3).

MS (m/z): 547[M+H]

(3) Preparation of ((1R)-3-methyl-1-(3-((quinolin-5-carboxamido)methyl)-4,5-dihydroisoxazol-5-carboxamido)butyl)boronic acid

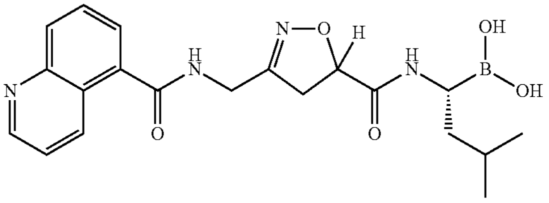 [SMILES: CC(C)C[C@H](NC(=O)C1CC(CNC(=O)c2cccc3ncccc23)=NO1)B(O)O]

The title compound (0.054 g, 77%) was obtained using N—((R)-3-methyl-1-((3aS,4S,6S,7aR)-3a,5,5-trimethyl-hexahydro-4,6-metanobenzo[d][1,3,2]dioxaborol-2-yl)butyl)-3-((quinolin-5-carboxamido)methyl)-4,5-dihydroisoxazol-5-carboxamide (0.092 g, 0.17 mmol) obtained in (2) above by the preparation method of Example 1-(4).

MS (m/z): 413[M+H], 395[M-OH]

Example 63: Preparation of ((1R)-3-methyl-1-(3-((5,6,7,8-tetrahydronaphthalen-1-carboxamido)methyl)-4,5-dihydroisoxazol-5-carboxamido)butyl)boronic acid Through the processes (1), (2) and (3) below, the title compound was obtained.

(1) Preparation of ethyl 3-[(tetralin-5-carbonylamino)methyl]-4,5-dihydroisoxazol-5-carboxylate

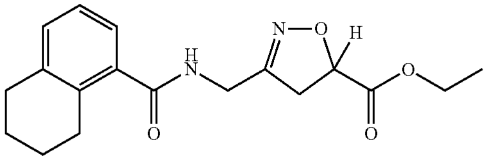 [SMILES: CCOC(=O)C1CC(CNC(=O)c2cccc3c2CCCC3)=NO1]

The title compound (0.114 g, 72%) was obtained using ethyl 3-(aminomethyl)-4,5-dihydroisoxazol-5-carboxylate hydrochloride (0.1 g, 0.48 mmol) obtained in Example 59-(1) and 5,6,7,8-tetrahydro-naphthalen-1-carboxylic acid (0.085 g, 0.53 mmol) by the preparation method of Example 59-(2).

MS (m/z): 331[M+H]

(2) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-((5,6,7,8-tetrahydronaphthalen-1-carboxamido)methyl)-4,5-dihydroisoxazol-5-carboxamide

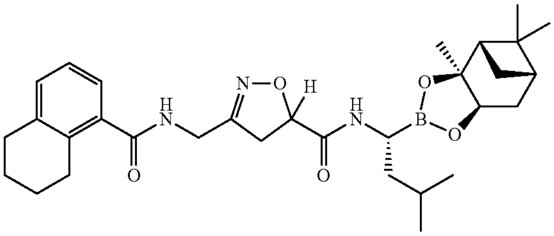 [SMILES: CC(C)C[C@H](NC(=O)C1CC(CNC(=O)c2cccc3c2CCCC3)=NO1)B1O[C@@H]2C[C@@H]3C[C@@H](C3(C)C)[C@]2(C)O1]

The title compound (0.13 g, 69%, 2 steps) was obtained using ethyl 3-[(tetralin-5-carbonylamino)methyl]-4,5-dihydroisoxazol-5-carboxylate (0.114 g, 0.35 mmol) obtained in (1) above by the preparation methods of Examples 1-(2) and (3).

MS (m/z): 550[M+H], 398[M+H]

(3) Preparation of ((1R)-3-methyl-1-(3-((5,6,7,8-tetrahydronaphthalen-1-carboxamido)methyl)-4,5-dihydroisoxazol-5-carboxamido)butyl)boronic acid

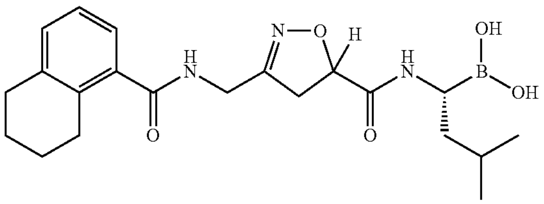 [SMILES: CC(C)C[C@H](NC(=O)C1CC(CNC(=O)c2cccc3c2CCCC3)=NO1)B(O)O]

The title compound (0.067 g, 68%) was obtained using N—((R)-3-methyl-1-((3aS,4S,6S,7aR)-3a,5,5-trimethyl-hexahydro-4,6-metanobenzo[d][1,3,2]dioxaborol-2-yl)butyl)-3-((5,6,7,8-tetrahydronaphthalen-1-carboxamido)methyl)-4,5-dihydroisoxazol-5-carboxamide (0.13 g, 0.24 mmol) obtained in (2) above by the preparation method of Example 1-(4).

NMR: $^1$H-NMR (500 MHz, $CD_3OD$); δ 7.14-7.11 (m, 3H), 5.26-5.22 (m, 1H), 4.30-4.23 (m, 2H), 3.52-3.46 (m, 1H), 3.33-3.30 (m, 1H), 2.81-2.78 (m, 5H), 1.79-1.77 (m, 4H), 1.64-1.62 (m, 1H), 1.37-1.33 (m, 2H), 0.90-0.88 (m, 6H)

MS (m/z): 416[M+H], 398[M-OH]

Example 64: Preparation of ((1R)-1-(3-((1-naphthamido)methyl)-4,5-dihydroisoxazol-5-carboxamido)-3-methylbutyl)boronic acid Through the processes (1), (2) and (3) below, the title compound was obtained.

(1) Preparation of ethyl 3-[(naphthalen-1-carbonylamino)methyl]-4,5-dihydroisoxazol-5-carboxylate

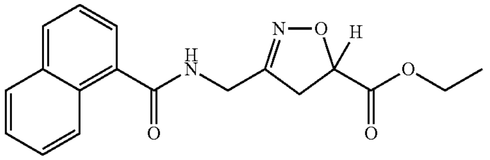 [SMILES: CCOC(=O)C1CC(CNC(=O)c2cccc3ccccc23)=NO1]

The title compound (0.09 g, 57%) was obtained using ethyl 3-(aminomethyl)-4,5-dihydroisoxazol-5-carboxylate hydrochloride (0.1 g, 0.48 mmol) obtained in Example 59-(1) and naphthalen-1-carboxylic acid (0.091 g, 0.53 mmol) by the preparation method of Example 59-(2).

NMR: $^1$H-NMR (400 MHz, $CDCl_3$); δ 8.28-8.27 (dd, 1H), 7.90-7.83 (m, 2H), 7.60-7.38 (m, 4H), 6.80-6.77 (m, 1H), 5.04-4.99 (t, 1H), 4.48-4.37 (m, 2H), 4.25-4.16 (q, 2H), 3.42-3.29 (d, 2H), 1.30-1.26 (t, 3H)

MS (m/z): 327[M+H]

(2) Preparation of 3-((1-naphthamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

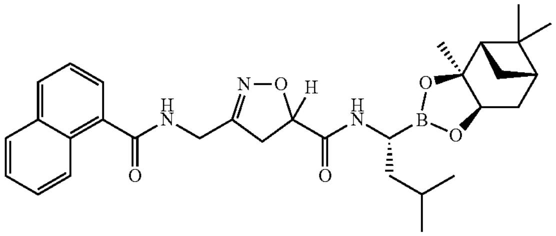 [SMILES: CC(C)C[C@H](NC(=O)C1CC(CNC(=O)c2cccc3ccccc23)=NO1)B1O[C@@H]2C[C@@H]3C[C@@H](C3(C)C)[C@]2(C)O1]

The title compound (0.114 g, 66%, 2 steps) was obtained using ethyl 3-[(naphthalen-1-carbonylamino)methyl]-4,5-dihydroisoxazol-5-carboxylate (0.09 g, 0.28 mmol) obtained in (1) above by the preparation methods of Examples 1-(2) and (3).

MS (m/z): 546[M+H], 394[M+H]

(3) Preparation of ((1R)-1-(3-((1-naphthamido)methyl)-4,5-dihydroisoxazol-5-carboxamido)-3-methylbutyl)boronic acid

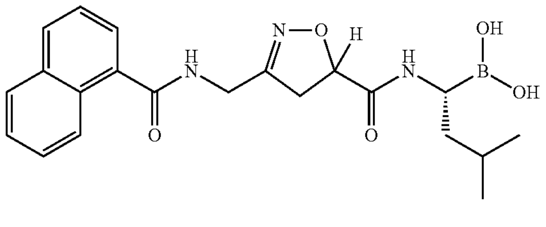 [SMILES: CC(C)C[C@H](NC(=O)C1CC(CNC(=O)c2cccc3ccccc23)=NO1)B(O)O]

The title compound (0.069 g, 80%) was obtained using 3-((1-naphthamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.114 g, 0.21 mmol) obtained in (2) above by the preparation method of Example 1-(4).

NMR: $^1$H-NMR (500 MHz, $CD_3OD$); δ 8.24-8.23 (d, 1H), 7.99-7.97 (d, 1H), 7.92-7.90 (m, 1H), 7.65-7.49 (m, 4H), 5.29-5.26 (m, 1H), 4.43-4.36 (m, 2H), 3.61-3.53 (m, 1H), 3.39-3.34 (m, 1H), 2.82-2.80 (m, 1H), 1.65-1.60 (m, 1H), 1.37-1.33 (m, 2H), 0.89-0.88 (dd, 6H)

MS (m/z): 412[M+H], 394[M+H]

Example 65: Preparation of ((1R)-1-(3-((isoquinolin-1-carboxamido)methyl)-4-methyl-4,5-dihydroisoxazol-5-carboxamido)-3-methylbutyl)boronic acid Through the processes (1), (2) and (3) below, the title compound was obtained.

(1) Preparation of methyl 3-((isoquinolin-1-carboxamido)methyl)-4-methyl-4,5-dihydroisoxazol-5-carboxylate

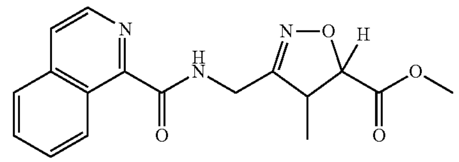 [SMILES: COC(=O)C1ON=C(CNC(=O)c2nccc3ccccc23)C1C]

Methyl 3-(((tert-butoxycarbonyl)amino)methyl)-4-methyl-4,5-dihydroisoxazol-5-carboxylate (0.076 g, 0.28 mmol) obtained in Preparation Example 2 was dissolved in dichloromethane (8 ml). A 4 N hydrochloric acid 1,4-dioxane solution (4 ml, 16 mmol) was slowly added thereto at 0° C., stirring was performed for 5 hours, while raising to room temperature, and the solvent was distilled under a reduced pressure. After adding dimethylformamide (4 ml) for dissolving, 1-ethyl-3-(3-dimethylaminopropyl)carbodiimide (0.081 g, 0.42 mmol), hydroxybenzotriazole (0.057 g, 0.42 mmol) and isoquinolin-1-carboxylic acid (0.063 g, 0.36 mmol) were added in order. Diisopropylethylamine (0.25 ml, 1.4 mmol) was slowly added thereto, followed by stirring at room temperature for 18 hours. The solvent was distilled under a reduced pressure, a sodium bicarbonate aqueous solution was added, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.025 g, 27%, 2 steps).

MS (m/z): 342[M+H]

(2) Preparation of 3-((isoquinolin-1-carboxamido)methyl)-4-methyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

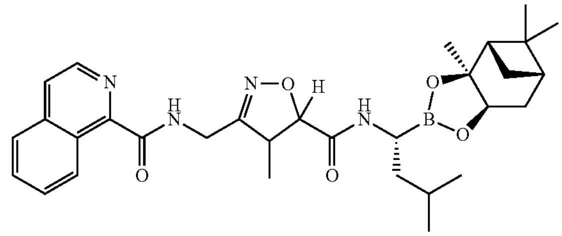 [SMILES: CC(C)C[C@H](NC(=O)C1ON=C(CNC(=O)c2nccc3ccccc23)C1C)B1O[C@@H]2C[C@@H]3C[C@@H](C3(C)C)[C@]2(C)O1]

The title compound (0.019 g, 44%, 2 steps) was obtained using ethyl 3-((isoquinolin-1-carboxamido)methyl)-4-methyl-4,5-dihydroisoxazol-5-carboxylate (0.025 g, 0.08 mmol) obtained in (1) above by the preparation methods of Examples 1-(2) and (3).

MS (m/z): 561[M+H]

(3) Preparation of ((1R)-1-(3-((isoquinolin-1-carboxamido)methyl)-4-methyl-4,5-dihydroisoxazol-5-carboxamido)-3-methylbutyl)boronic acid

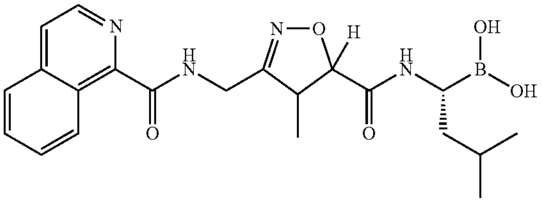 [SMILES: CC(C)C[C@H](NC(=O)C1ON=C(CNC(=O)c2nccc3ccccc23)C1C)B(O)O]

The title compound (0.003 g, 17%) was obtained using 3-((isoquinolin-1-carboxamido)methyl)-4-methyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.019 g, 0.03 mmol) obtained in (2) above by the preparation method of Example 1-(4).

MS (m/z): 427[M+H], 409[M-OH]

Example 66: Preparation of ((1R)-3-methyl-1-(3-((S)-2-methyl-1-(5,6,7,8-tetrahydronaphthalen-1-carboxamido)propyl)-4,5-dihydroisoxazol-5-carboxamido)butyl)boronic acid Through the processes (1), (2) and (3) below, the title compound was obtained.

(1) Preparation of ethyl 3-((S)-2-methyl-1-(5,6,7,8-tetrahydronaphthalen-1-carboxamido)propyl)-4,5-dihydroisoxazol-5-carboxylate

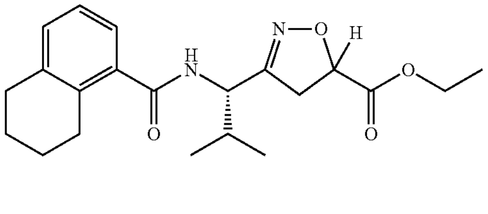 [SMILES: CCOC(=O)C1CC([C@@H](NC(=O)c2cccc3c2CCCC3)C(C)C)=NO1]

The title compound (0.13 g, 88%, 2 steps) was obtained using ethyl 3-((S)-1-((tert-butoxycarbonyl)amino)-2-methylpropyl)-4,5-dihydroisoxazol-5-carboxylate (0.13 g, 0.40 mmol) obtained in Preparation Example 3 and 5,6,7,8-tetrahydro-naphthalen-1-carboxylic acid (0.078, 0.44 mmol) by the preparation method of Example 65-(1).

MS (m/z): 373[M+H]

(2) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-((S)-2-methyl-1-(5,6,7,8-tetrahydronaphthalen-1-carboxamido)propyl)-4,5-dihydroisoxazol-5-carboxamide

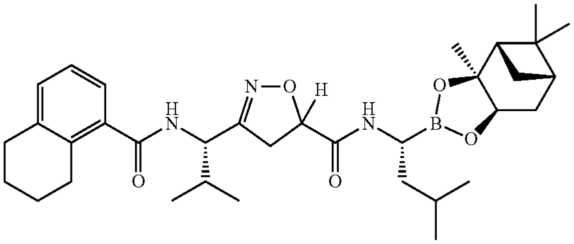 [SMILES: CC(C)C[C@H](NC(=O)C1CC([C@@H](NC(=O)c2cccc3c2CCCC3)C(C)C)=NO1)B1O[C@@H]2C[C@@H]3C[C@@H](C3(C)C)[C@]2(C)O1]

The title compound (0.15 g, 73%, 2 steps) was obtained using ethyl 3-((S)-2-methyl-1-(5,6,7,8-tetrahydronaphthalen-1-carboxamido)propyl)-4,5-dihydroisoxazol-5-carboxylate (0.13 g, 0.35 mmol) obtained in (1) above by the preparation methods of Examples 1-(2) and (3).

MS (m/z): 592[M+H]

(3) Preparation of ((1R)-3-methyl-1-(3-((S)-2-methyl-1-(5,6,7,8-tetrahydronaphthalen-1-carboxamido)propyl)-4,5-dihydroisoxazol-5-carboxamido)butyl)boronic acid

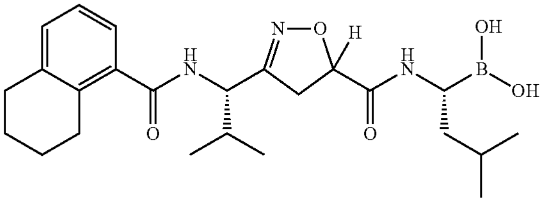 [SMILES: CC(C)C[C@H](NC(=O)C1CC([C@@H](NC(=O)c2cccc3c2CCCC3)C(C)C)=NO1)B(O)O]

The title compound (0.071 g, 61%) was obtained using 3-((S)-1-(isoquinolin-1-carboxamido)-2-methylpropyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.15 g, 0.25 mmol) obtained in (2) above by the preparation method of Example 1-(4).

MS (m/z): 458[M+H], 440[M-OH]

Example 67: Preparation of ((1R)-1-(3-((S)-1-(isoquinolin-1-carboxamido)-2-methylpropyl)-4,5-dihydroisoxazol-5-carboxamido)-3-methylbutyl)boronic acid Through the processes (1), (2) and (3) below, the title compound was obtained.

(1) Preparation of ethyl 3-((S)-1-(isoquinolin-1-carboxamido)-2-methylpropyl)-4,5-dihydroisoxazol-5-carboxylate

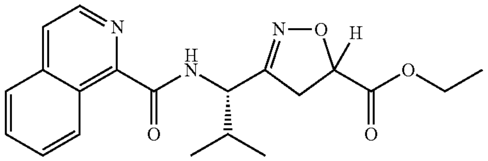 [SMILES: CCOC(=O)C1CC([C@@H](NC(=O)c2nccc3ccccc23)C(C)C)=NO1]

The title compound (0.12 g, 82%, 2 steps) was obtained using ethyl 3-((S)-1-((tert-butoxycarbonyl)amino)-2-methylpropyl)-4,5-dihydroisoxazol-5-carboxylate (0.13 g, 0.40 mmol) obtained in Preparation Example 3 and isoquinolin-1-carboxylic acid (0.076 g, 0.44 mmol) by the preparation method of Example 65-(1).

MS (m/z): 370[M+H]

(2) Preparation of 3-((S)-1-(isoquinolin-1-carboxamido)-2-methylpropyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

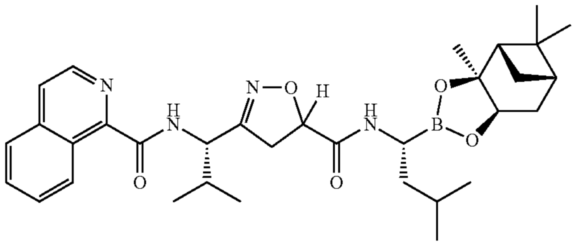 [SMILES: CC(C)C[C@H](NC(=O)C1CC([C@@H](NC(=O)c2nccc3ccccc23)C(C)C)=NO1)B1O[C@@H]2C[C@@H]3C[C@@H](C3(C)C)[C@]2(C)O1]

The title compound (0.13 g, 68%, 2 steps) was obtained using ethyl 3-((S)-1-(isoquinolin-1-carboxamido)-2-methylpropyl)-4,5-dihydroisoxazol-5-carboxylate (0.12 g, 0.32 mmol) obtained in (1) above by the preparation methods of Examples 1-(2) and (3).

MS (m/z): 589[M+H]

(3) Preparation of ((1R)-1-(3-((S)-1-(isoquinolin-1-carboxamido)-2-methylpropyl)-4,5-dihydroisoxazol-5-carboxamido)-3-methylbutyl)boronic acid

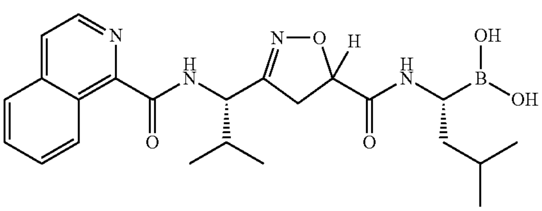 [SMILES: CC(C)C[C@H](NC(=O)C1CC([C@@H](NC(=O)c2nccc3ccccc23)C(C)C)=NO1)B(O)O]

The title compound (0.070 g, 70%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-((S)-2-methyl-1-(5,6,7,8-tetrahydronaphthalen-1-carboxamido)propyl)-4,5-dihydroisoxazol-5-carboxamide (0.13 g, 0.22 mmol) obtained in (2) above by the preparation method of Example 1-(4).

MS (m/z): 455[M+H], 437[M-OH]

Example 68: Preparation of ((1R)-1-(3-((2,5-dichlorobenzamido)methyl)-4,5-dihydroisoxazol-5-carboxamido)-3-methylbutyl)boronic acid Through the processes (1), (2) and (3) below, the title compound was obtained.

(1) Preparation of ethyl 3-[[(2,5-dichlorobenzoyl)amino]methyl]-4,5-dihydroisoxazol-5-carboxylate

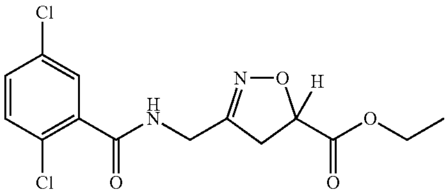 [SMILES: CCOC(=O)C1CC(CNC(=O)c2cc(Cl)ccc2Cl)=NO1]

The title compound (0.1 g, 60%) was obtained using ethyl 3-(aminomethyl)-4,5-dihydroisoxazol-5-carboxylate hydrochloride (0.1 g, 0.48 mmol) obtained in Example 59-(1) and 2,5-dichloro-benzoic acid (0.1 g, 0.53 mmol) by the preparation method of Example 59-(2).

MS (m/z): 345[M+H]

(2) Preparation of 3-((2,5-dichlorobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

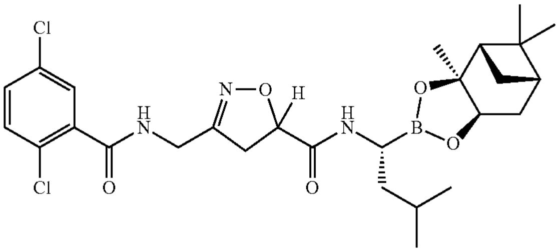 [SMILES: CC(C)C[C@H](NC(=O)C1CC(CNC(=O)c2cc(Cl)ccc2Cl)=NO1)B1O[C@@H]2C[C@@H]3C[C@@H](C3(C)C)[C@]2(C)O1]

The title compound (0.09 g, 55%, 2 steps) was obtained using ethyl 3-[[(2,5-dichlorobenzoyl)amino]methyl]-4,5-dihydroisoxazol-5-carboxylate (0.1 g, 0.29 mmol) obtained in (1) above by the preparation methods of Examples 1-(2) and (3).

MS (m/z): 564[M+H]

(3) Preparation of ((1R)-1-(3-((2,5-dichlorobenzamido)methyl)-4,5-dihydroisoxazol-5-carboxamido)-3-methylbutyl)boronic acid

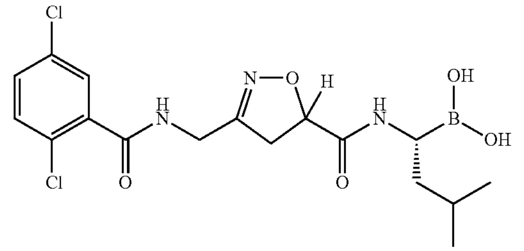

The title compound (0.048 g, 70%) was obtained using 3-((2,5-dichlorobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.09 g, 0.16 mmol) obtained in (2) above by the preparation method of Example 1-(4).

NMR: $^1$H-NMR (500 MHz, $CD_3OD$); δ 7.50-7.44 (m, 3H), 5.26-5.23 (m, 1H), 4.34-4.26 (m, 2H), 3.54-3.48 (m, 1H), 3.36-3.31 (m, 1H), 2.84-2.81 (m, 1H), 1.65-1.62 (m, 1H), 1.37-1.33 (m, 1H), 0.90-0.89 (d, 6H)

MS (m/z): 430[M+H], 412[M-OH]

Example 69: Preparation of [(1R)-3-methyl-1-[[3-[(naphthalen-2-carbonylamino)methyl]-4,5-dihydro-1,2-oxazol-5-carbonyl]amino]butyl]boronic acid Through the processes (1), (2) and (3) below, the title compound was obtained.

(1) Preparation of ethyl 3-((2-naphthamido)methyl)-4,5-dihydroisoxazol-5-carboxylate

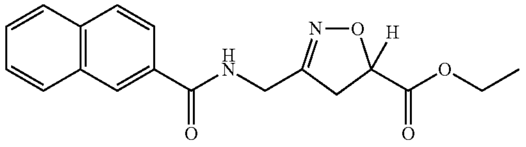 [SMILES: CCOC(=O)C1CC(CNC(=O)c2ccc3ccccc3c2)=NO1]

The title compound (0.12 g, 57%) was obtained using ethyl 3-(aminomethyl)-4,5-dihydroisoxazol-5-carboxylate hydrochloride (0.13 g, 0.62 mmol) obtained in Example 59-(1) and 2-naphthoic acid (0.18 g, 0.93 mmol) by the preparation method of Example 59-(2).

MS (m/z): 327[M+H]

(2) Preparation of 3-((2-naphthamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

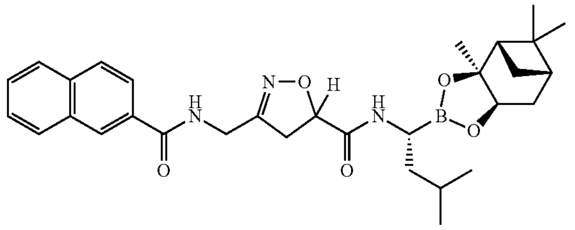 [SMILES: CC(C)C[C@H](NC(=O)C1CC(CNC(=O)c2ccc3ccccc3c2)=NO1)B1O[C@@H]2C[C@@H]3C[C@@H](C3(C)C)[C@]2(C)O1]

The title compound (0.074 g, 38%, 2 steps) was obtained using ethyl 3-((2-naphthamido)methyl)-4,5-dihydroisoxazol-5-carboxylate (0.12 g, 0.36 mmol) obtained in (1) above by the preparation methods of Examples 1-(2) and (3).

MS (m/z): 546[M+H]

(3) Preparation of ((1R)-1-(3-((2-naphthamido)methyl)-4,5-dihydroisoxazol-5-carboxamido)-3-methylbutyl)boronic acid

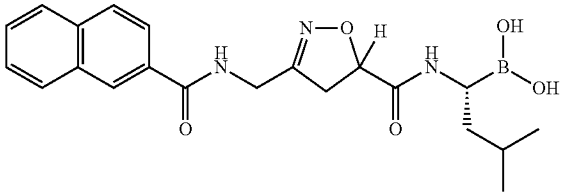 [SMILES: CC(C)C[C@H](NC(=O)C1CC(CNC(=O)c2ccc3ccccc3c2)=NO1)B(O)O]

The title compound (0.027 g, 49%) was obtained using 3-((2-naphthamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.074 g, 0.14 mmol) obtained in (2) above by the preparation method of Example 1-(4).

MS (m/z): 412[M+H], 394[M-OH]

Example 70: Preparation of ((1R)-1-(3-((4-(tert-butyl)benzamido)methyl)-4,5-dihydroisoxazol-5-carboxamido)-3-methylbutyl)boronic acid Through the processes (1), (2) and (3) below, the title compound was obtained.

(1) Preparation of ethyl 3-((4-(tert-butyl)benzamido)methyl)-4,5-dihydroisoxazol-5-carboxylate

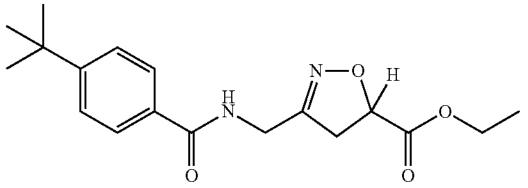 [SMILES: CCOC(=O)C1CC(CNC(=O)c2ccc(C(C)(C)C)cc2)=NO1]

The title compound (0.23 g, 50%, 2 steps) was obtained using ethyl 3-(aminomethyl)-4,5-dihydroisoxazol-5-carboxylate hydrochloride (0.28 g, 1.4 mmol) obtained in Example 59-(1) and 4-(tert-butyl)benzoic acid (0.27 g, 1.5 mmol) by the preparation method of Example 59-(2).

MS (m/z): 333[M+H]

(2) Preparation of 3-((4-(tert-butyl)benzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

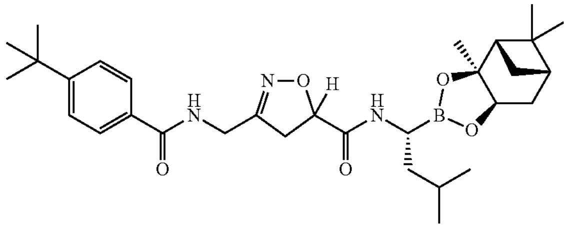 [SMILES: CC(C)C[C@H](NC(=O)C1CC(CNC(=O)c2ccc(C(C)(C)C)cc2)=NO1)B1O[C@@H]2C[C@@H]3C[C@@H](C3(C)C)[C@]2(C)O1]

The title compound (0.030 g, 17%, 2 steps) was obtained using ethyl 3-((4-(tert-butyl)benzamido)methyl)-4,5-dihydroisoxazol-5-carboxylate (0.11 g, 0.32 mmol) obtained in (1) above by the preparation methods of Examples 1-(2) and (3).

MS (m/z): 552[M+H]

(3) Preparation of ((1R)-1-(3-((4-(tert-butyl)benzamido)methyl)-4,5-dihydroisoxazol-5-carboxamido)-3-methylbutyl)boronic acid

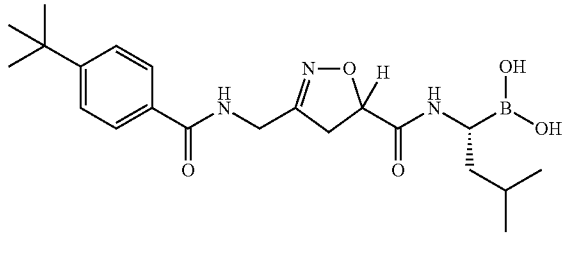 [SMILES: CC(C)C[C@H](NC(=O)C1CC(CNC(=O)c2ccc(C(C)(C)C)cc2)=NO1)B(O)O]

The title compound (0.007 g, 31%) was obtained using 3-((4-(tert-butyl)benzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.030 g, 0.05 mmol) obtained in (2) above by the preparation method of Example 1-(4).

MS (m/z): 418[M+H], 400[M+H]

Example 71: Preparation of ((1R)-3-methyl-1-(3-((3-phenoxybenzamido)methyl)-4,5-dihydroisoxazol-5-carboxamido)butyl)boronic acid Through the processes (1), (2) and (3) below, the title compound was obtained.

(1) Preparation of ethyl 3-[[(3-phenoxybenzoyl)amino]methyl]-4,5-dihydroisoxazol-5-carboxylate

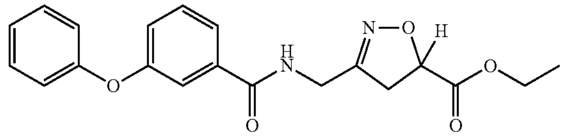 [SMILES: CCOC(=O)C1CC(CNC(=O)c2cccc(Oc3ccccc3)c2)=NO1]

The title compound (0.05 g, 28%) was obtained using ethyl 3-(aminomethyl)-4,5-dihydroisoxazol-5-carboxylate hydrochloride (0.1 g, 0.48 mmol) obtained in Example 59-(1) and 3-phenoxy-benzoic acid (0.114 g, 0.53 mmol) by the preparation method of Example 59-(2).

NMR: $^1$H-NMR (400 MHz, $CDCl_3$); δ 7.50-7.33 (m, 5H), 7.16-7.00 (m, 4H), 6.84 (t, 1H), 5.04-4.99 (m, 1H), 4.43-4.37 (d, 2H), 4.28-4.17 (q, 2H), 3.38-3.26 (m, 2H), 1.31-1.27 (t, 3H)

MS (m/z): 369[M+H]

(2) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-((3-phenoxybenzamido)methyl)-4,5-dihydroisoxazol-5-carboxamide

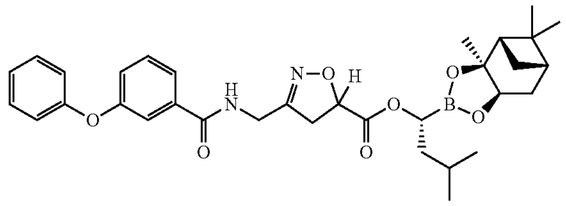 [SMILES: CC(C)C[C@H](OC(=O)C1CC(CNC(=O)c2cccc(Oc3ccccc3)c2)=NO1)B1O[C@@H]2C[C@@H]3C[C@@H](C3(C)C)[C@]2(C)O1]

The title compound (0.05 g, 69%, 2 steps) was obtained using ethyl 3-[[(3-phenoxybenzoyl)amino]methyl]-4,5-dihydroisoxazol-5-carboxylate (0.05 g, 0.14 mmol) obtained in Example 71-(1) by the preparation methods of Example 1-(2) and Example 1-(3).

MS (m/z): 588[M+H]

(3) Preparation of ((1R)-3-methyl-1-(3-((3-phenoxybenzamido)methyl)-4,5-dihydroisoxazol-5-carboxamido)butyl)boronic acid

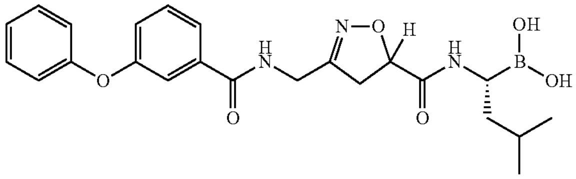 [SMILES: CC(C)C[C@H](NC(=O)C1CC(CNC(=O)c2cccc(Oc3ccccc3)c2)=NO1)B(O)O]

The title compound (0.025 g, 54%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-((3-phenoxybenzamido)methyl)-4,5-dihydroisoxazol-5-carboxamide (0.06 g, 0.10 mmol) obtained in Example 71-(2) by the preparation method of Example 1-(4).

NMR: $^1$H-NMR (500 MHz, $CD_3OD$); δ 7.57-7.55 (m, 1H), 7.46-7.42 (m, 2H), 7.38-7.35 (m, 2H), 7.16-7.12 (m,

2H), 7.01-7.00 (m, 2H), 5.23-5.20 (m, 1H), 4.27 (s, 2H), 3.48-3.42 (m, 1H), 3.26-3.22 (m, 1H), 2.78 (m, 1H), 1.63-1.60 (m, 1H), 1.35-1.31 (m, 2H), 0.89-0.87 (d, 6H)

MS (m/z): 454[M+H], 436[M-OH]

Example 72: Preparation of ((1R)-1-(3-((S)-1-(2,5-dichlorobenzamido)-2-methylpropyl)-4,5-dihydroisoxazol-5-carboxamido)-3-methylbutyl)boronic acid Through the processes (1), (2) and (3) below, the title compound was obtained.

(1) Preparation of ethyl 3-((S)-1-(2,5-dichlorobenzamido)-2-methylpropyl)-4,5-dihydroisoxazol-5-carboxylate

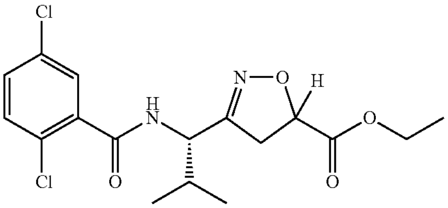 [SMILES: CCOC(=O)C1CC([C@@H](NC(=O)c2cc(Cl)ccc2Cl)C(C)C)=NO1]

The title compound (0.087 g, 39%) was obtained using ethyl 3-((S)-1-((tert-butoxycarbonyl)amino)-2-methylpropyl)-4,5-dihydroisoxazol-5-carboxylate (0.18 g, 0.57 mmol) obtained in Preparation Example 3 and 2,5-dichloro-benzoic acid (0.14 g, 0.74 mmol) by the preparation method of Example 65-(1).

MS (m/z): 387[M+H]

(2) Preparation of 3-((S)-1-(2,5-dichlorobenzamido)-2-methylpropyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

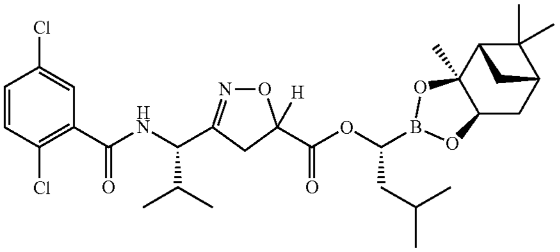 [SMILES: CC(C)C[C@H](OC(=O)C1CC([C@@H](NC(=O)c2cc(Cl)ccc2Cl)C(C)C)=NO1)B1O[C@@H]2C[C@@H]3C[C@@H](C3(C)C)[C@]2(C)O1]

The title compound (0.040 g, 29%, 2 steps) was obtained using ethyl 3-((S)-1-(2,5-dichlorobenzamido)-2-methylpropyl)-4,5-dihydroisoxazol-5-carboxylate (0.087 g, 0.22 mmol) obtained in (1) above by the preparation methods of Examples 1-(2) and (3).

MS (m/z): 606[M+H]

(3) Preparation of ((1R)-1-(3-((S)-1-(2,5-dichlorobenzamido)-2-methylpropyl)-4,5-dihydroisoxazol-5-carboxamido)-3-methylbutyl)boronic acid

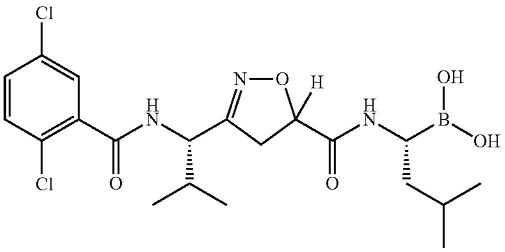 [SMILES: CC(C)C[C@H](NC(=O)C1CC([C@@H](NC(=O)c2cc(Cl)ccc2Cl)C(C)C)=NO1)B(O)O]

The title compound (0.004 g, 13%) was obtained using 3-((S)-1-(2,5-dichlorobenzamido)-2-methylpropyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.040 g, 0.07 mmol) obtained in (2) above by the preparation method of Example 1-(4).

MS (m/z): 472[M+H], 454[M-OH]

Example 73: Preparation of ((1R)-1-(3-((S)-1-(isoquinolin-1-carboxamido)-3-methylbutyl)-4,5-dihydroisoxazol-5-carboxamido)-3-methylbutyl)boronic acid Through the processes (1), (2), (3) and (4) below, the title compound was obtained.

(1) Preparation of ethyl 3-((S)-1-amino-3-methylbutyl)-4,5-dihydroisoxazol-5-carboxylate hydrochloride

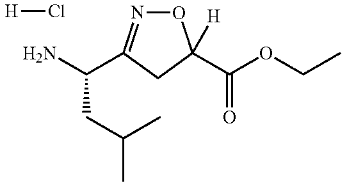

The title compound (0.41 g, quant.) was obtained using ethyl 3-((S)-1-((tert-butoxycarbonyl)amino)-3-methylbutyl)-4,5-dihydroisoxazol-5-carboxylate (0.51 g, 1.6 mmol) obtained in Preparation Example 4 by the preparation method of Example 59-(1).

(2) Preparation of ethyl 3-((S)-1-(isoquinolin-1-carboxamido)-3-methylbutyl)-4,5-dihydroisoxazol-5-carboxylate

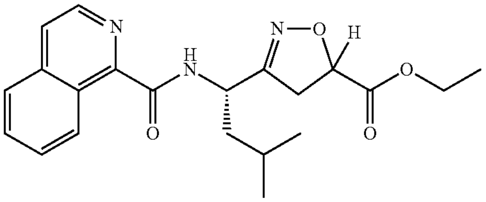 [SMILES: CCOC(=O)C1CC([C@H](CC(C)C)NC(=O)c2nccc3ccccc23)=NO1]

The title compound (0.10 g, 49%) was obtained using ethyl 3-((S)-1-amino-3-methylbutyl)-4,5-dihydroisoxazol-5-carboxylate hydrochloride (0.14 g, 0.53 mmol) obtained in (1) above and isoquinolin-1-carboxylic acid (0.092 g, 0.53 mmol) by the preparation method of Example 59-(2).

MS (m/z): 384[M+H]

(3) Preparation of 3-((S)-1-(isoquinolin-1-carboxamido)-3-methylbutyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

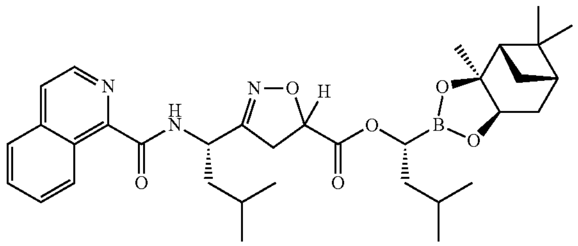 [SMILES: CC(C)C[C@H](OC(=O)C1CC([C@H](CC(C)C)NC(=O)c2nccc3ccccc23)=NO1)B1O[C@@H]2C[C@@H]3C[C@@H](C3(C)C)[C@]2(C)O1]

The title compound (0.11 g, 63%, 2 steps) was obtained using ethyl 3-((S)-1-(isoquinolin-1-carboxamido)-3-methylbutyl)-4,5-dihydroisoxazol-5-carboxylate (0.10 g, 0.26 mmol) obtained in (2) above by the preparation methods of Examples 1-(2) and (3).

MS (m/z): 603[M+H]

(4) Preparation of ((1R)-1-(3-((S)-1-(isoquinolin-1-carboxamido)-3-methylbutyl)-4,5-dihydroisoxazol-5-carboxamido)-3-methylbutyl)boronic acid

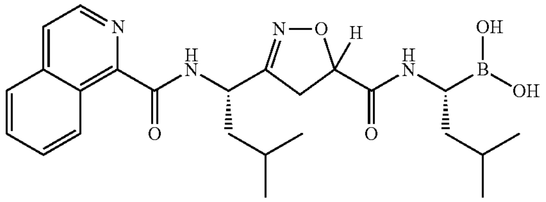 [SMILES: CC(C)C[C@H](NC(=O)C1CC([C@H](CC(C)C)NC(=O)c2nccc3ccccc23)=NO1)B(O)O]

The title compound (0.065 g, 76%) was obtained using 3-((S)-1-(isoquinolin-1-carboxamido)-3-methylbutyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.11 g, 0.18 mmol) obtained in (3) above by the preparation method of Example 1-(4).

MS (m/z): 469[M+H], 451[M-OH]

Example 74: Preparation of ((1R)-1-(3-((S)-1-(2,5-dichlorobenzamido)-3-methylbutyl)-4,5-dihydroisoxazol-5-carboxamido)-3-methylbutyl)boronic acid Through the processes (1), (2) and (3) below, the title compound was obtained.

(1) Preparation of ethyl 3-((S)-1-(2,5-dichlorobenzamido)-3-methylbutyl)-4,5-dihydroisoxazol-5-carboxylate

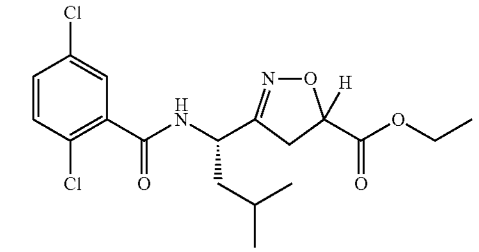 [SMILES: CCOC(=O)C1CC([C@H](CC(C)C)NC(=O)c2cc(Cl)ccc2Cl)=NO1]

The title compound (0.098 g, 54%) was obtained using ethyl 3-((S)-1-amino-3-methylbutyl)-4,5-dihydroisoxazol-5-carboxylate hydrochloride (0.12 g, 0.45 mmol) obtained in Example 73-(1) and 2,5-dichloro-benzoic acid (0.096 g, 0.50 mmol) by the preparation method of Example 59-(2).

MS (m/z): 401[M+H]

(2) Preparation of 3-((S)-1-(2,5-dichlorobenzamido)-3-methylbutyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

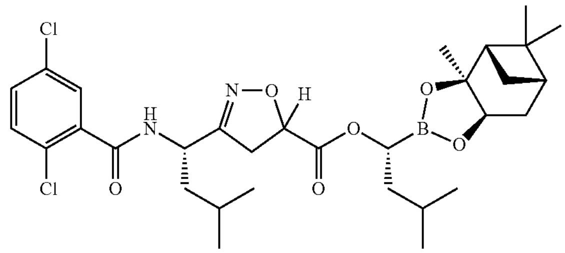 [SMILES: CC(C)C[C@H](OC(=O)C1CC([C@H](CC(C)C)NC(=O)c2cc(Cl)ccc2Cl)=NO1)B1O[C@@H]2C[C@@H]3C[C@@H](C3(C)C)[C@]2(C)O1]

The title compound (0.047 g, 31%, 2 steps) was obtained using ethyl 3-((S)-1-(2,5-dichlorobenzamido)-3-methylbutyl)-4,5-dihydroisoxazol-5-carboxylate (0.098 g, 0.24 mmol) obtained in (1) above by the preparation methods of Examples 1-(2) and (3).

MS (m/z): 620[M+H]

(3) Preparation of ((1R)-1-(3-((S)-1-(2,5-dichlorobenzamido)-3-methylbutyl)-4,5-dihydroisoxazol-5-carboxamido)-3-methylbutyl)boronic acid

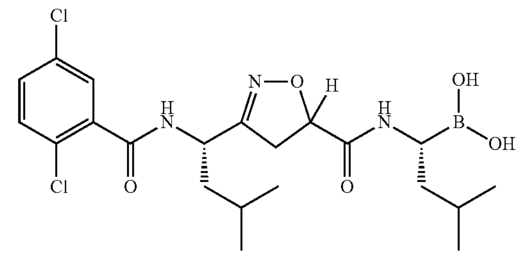 [SMILES: CC(C)C[C@H](NC(=O)C1CC([C@H](CC(C)C)NC(=O)c2cc(Cl)ccc2Cl)=NO1)B(O)O]

The title compound (0.006 g, 17%) was obtained using 3-((S)-1-(2,5-dichlorobenzamido)-3-methylbutyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.047 g, 0.08 mmol) obtained in (2) above by the preparation method of Example 1-(4).

MS (m/z): 486[M+H], 488[M+H], 468[M-OH], 470[M-OH]

Example 75: Preparation of ((1R)-1-(3-((2,5-dichlorobenzyl)carbamoyl)-4,5-dihydroisoxazol-5-carboxamido)-3-methylbutyl)boronic acid Through the processes (1), (2), (3) and (4) below, the title compound was obtained.

(1) Preparation of ethyl 3-{1[(2,5-dichlorophenyl)methyl]carbamoyl}-4,5-dihydro-1,2-oxazol-5-carboxylate

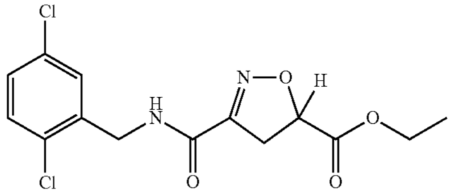 [SMILES: CCOC(=O)C1CC(C(=O)NCc2cc(Cl)ccc2Cl)=NO1]

5-(Ethoxycarbonyl)-4,5-dihydro-1,2-oxazol-3-carboxylic acid (0.15 g, 0.82 mmol) obtained in Preparation Example 5 was dissolved in dimethylformamide (5 ml). O-(7-azabenzotriazol-1-yl)-N,N,N',N'-tetramethyluronium hexafluorophosphate (0.4 g, 4.06 mmol), 2,5-dichlorobenzylamine (0.16 g, 0.90 mmol), and diisopropylethylamine (0.43 ml) were added in order, followed by stirring at room temperature for 16 hours. The solvent was distilled under a reduced pressure, a sodium bicarbonate aqueous solution was added, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.16 g, 57%).

NMR: $^1$H-NMR (400 MHz, $CDCl_3$); δ 7.53-7.21 (m, 3H), 7.11 (m, 1H), 5.19-5.15 (m, 1H), 4.63-4.53 (m, 2H), 4.30-4.23 (q, 2H), 3.57-3.48 (m, 2H), 1.35-1.32 (t, 3H)

MS (m/z): 345[M+H]

(2) Preparation of 3-{[(2,5-dichlorophenyl)methyl]carbamoyl}-4,5-dihydro-1,2-oxazol-5-carboxylic acid

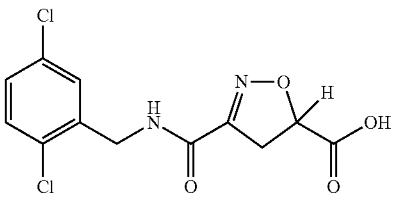 [SMILES: O=C(NCc1cc(Cl)ccc1Cl)C1=NOC(C(=O)O)C1]

The title compound (0.15 g, 99%) was obtained using ethyl 3-{[(2,5-dichlorophenyl)methyl]carbamoyl}-4,5-dihydro-1,2-oxazol-5-carboxylate (0.16 g, 0.46 mmol) obtained in (1) above by the preparation method of Example 1-(2).

MS (m/z): 317[M+H]

(3) Preparation of N3-(2,5-dichlorobenzyl)-N5-((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-3,5-dicarboxamide

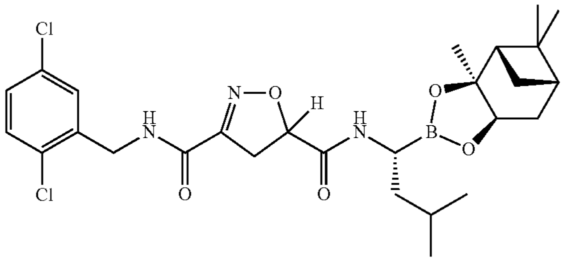 [SMILES: CC(C)C[C@H](NC(=O)C1CC(C(=O)NCc2cc(Cl)ccc2Cl)=NO1)B1O[C@@H]2C[C@@H]3C[C@@H](C3(C)C)[C@]2(C)O1]

The title compound (0.18 g, 69%) was obtained using 3-{[(2,5-dichlorophenyl)methyl]carbamoyl}-4,5-dihydro-1,2-oxazol-5-carboxylic acid (0.15 g, 0.47 mmol) obtained in (2) above by the preparation method of Example 1-(3).

MS (m/z): 564[M+H]

(4) Preparation of ((1R)-1-(3-((2,5-dichlorobenzyl)carbamoyl)-4,5-dihydroisoxazol-5-carboxamido)-3-methylbutyl)boronic acid

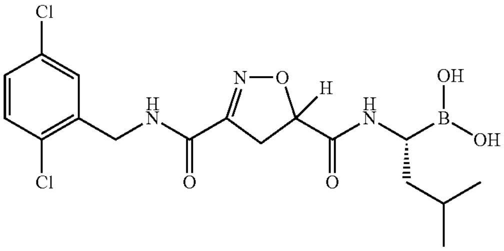 [SMILES: CC(C)C[C@H](NC(=O)C1CC(C(=O)NCc2cc(Cl)ccc2Cl)=NO1)B(O)O]

The title compound (0.092 g, 65%) was obtained using N3-(2,5-dichlorobenzyl)-N5-((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-3,5-dicarboxamide (0.18 g, 0.33 mmol) obtained in (3) above by the preparation method of Example 1-(4).

NMR: $^1$H-NMR (500 MHz, MeOD-d4); δ 7.38-7.23 (m, 3H), 5.38-5.34 (m, 1H), 4.52 (s, 2H), 3.65-3.59 (m, 1H), 3.49-3.42 (m, 1H), 2.91-2.88 (m, 1H), 1.65-1.60 (m, 1H), 1.39-1.36 (d, 6H)

MS (m/z): 430[M+H], 412[M-OH]

Example 76: Preparation of ((1R)-3-methyl-1-(3-(naphthalen-1-ylcarbamoyl)-4,5-dihydroisoxazol-5-carboxamido)butyl)boronic acid Through the processes (1), (2) and (3) below, the title compound was obtained.

(1) Preparation of ethyl 3-[(naphthalen-1-yl)carbamoyl]-4,5-dihydro-1,2-oxazol-5-carboxylate

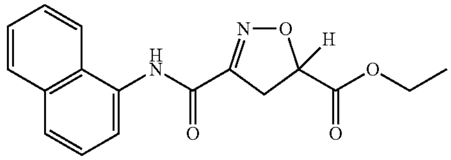 [SMILES: CCOC(=O)C1CC(C(=O)Nc2cccc3ccccc23)=NO1]

The title compound (0.15 g, 56%) was obtained using 5-(ethoxycarbonyl)-4,5-dihydro-1,2-oxazol-3-carboxylic acid (0.16 g, 0.85 mmol) obtained in Preparation Example 5 by the preparation method of Example 75-(1).

NMR: $^1$H-NMR (500 MHz, $CDCl_3$); δ 8.85 (br s, 1H), 8.07-8.05 (d, 1H), 7.90-7.88 (m, 2H), 7.74-7.72 (m, 1H), 7.58-7.48 (m, 3H), 5.29-5.27 (m, 1H), 4.33-4.30 (q, 2H), 3.67-3.65 (m, 2H), 1.36-1.33 (t, 3H)

MS (m/z): 313[M+H]

(2) Preparation of 3-[(naphthalen-1-yl)carbamoyl]-4,5-dihydro-1,2-oxazol-5-carboxylic acid

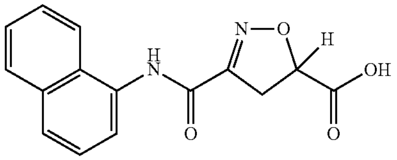 [SMILES: O=C(Nc1cccc2ccccc12)C1=NOC(C(=O)O)C1]

The title compound (0.14 g, 99%) was obtained using ethyl 3-[(naphthalen-1-yl)carbamoyl]-4,5-dihydro-1,2-oxazol-5-carboxylate (0.15 g, 0.49 mmol) obtained in (1) above by the preparation method of Example 1-(2).

MS (m/z): 285[M+H]

(3) Preparation of ((1R)-3-methyl-1-(3-(naphthalen-1-ylcarbamoyl)-4,5-dihydroisoxazol-5-carboxamido) butyl)boronic acid

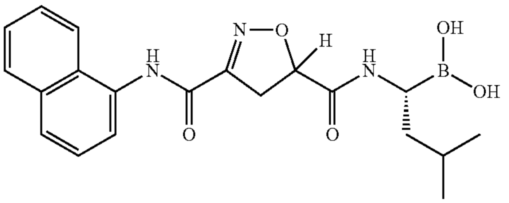 [SMILES: CC(C)C[C@H](NC(=O)C1CC(C(=O)Nc2cccc3ccccc23)=NO1)B(O)O]

The title compound (0.076 g, 38%, 2 steps) was obtained using 3-[(naphthalen-1-yl)carbamoyl]-4,5-dihydro-1,2-oxazol-5-carboxylic acid (0.14 g, 0.50 mmol) obtained in (2) above by the preparation methods of Examples 75-(3) and (4).

NMR: $^1$H-NMR (500 MHz, MeOD-d4); δ 7.97-7.95 (m, 1H), 7.92-7.90 (m, 1H), 7.83-7.81 (m, 1H), 7.64-7.63 (m, 1H), 7.55-7.48 (m, 3H), 5.46-5.43 (m, 1H), 3.76-3.70 (m, 1H), 3.60-3.53 (m, 1H), 2.96-2.93 (m, 1H), 1.68-1.64 (m, 1H), 1.42-1.39 (m, 2H), 0.94-0.90 (d, 6H)

MS (m/z): 398[M+H], 380[M-OH/]

Example 77: Preparation of ((1R)-1-(3-((3-chlorophenyl)carbamoyl)-4,5-dihydroisoxazol-5-carboxamido)-3-methylbutyl)boronic acid Through the processes (1), (2) and (3) below, the title compound was obtained.

(1) Preparation of ethyl 3-[(3-chlorophenyl)carbamoyl]-4,5-dihydro-1,2-oxazol-5-carboxylate

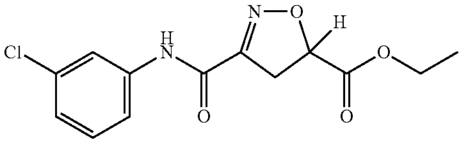 [SMILES: CCOC(=O)C1CC(C(=O)Nc2cccc(Cl)c2)=NO1]

The title compound (0.16 g, 56%) was obtained using 5-(ethoxycarbonyl)-4,5-dihydro-1,2-oxazol-3-carboxylic acid (0.17 g, 0.91 mmol) obtained in Preparation Example 5 by the preparation method of Example 75-(1).

NMR: $^1$H-NMR (400 MHz, $CDCl_3$); δ 8.40 (br s, 1H), 7.72-7.71 (d, 1H), 7.41-7.38 (m, 1H), 7.29-7.25 (t, 1H), 7.15-7.03 (m, 1H), 5.26-5.21 (m, 1H), 4.35-4.25 (q, 2H), 3.64-3.52 (m, 2H), 1.35-1.31 (t, 3H)

MS (m/z): 297[M+H]

(2) Preparation of 3-[(3-chlorophenyl)carbamoyl]-4,5-dihydro-1,2-oxazol-5-carboxylic acid

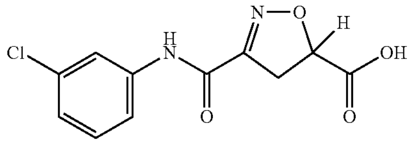 [SMILES: O=C(Nc1cccc(Cl)c1)C1=NOC(C(=O)O)C1]

The title compound (0.14 g, 99%) was obtained using ethyl 3-[(3-chlorophenyl)carbamoyl]-4,5-dihydro-1,2-oxazol-5-carboxylate (0.16 g, 0.52 mmol) obtained in (1) above by the preparation method of Example 1-(2).

MS (m/z): 269[M+H]

(3) Preparation of ((1R)-1-(3-((3-chlorophenyl)carbamoyl)-4,5-dihydroisoxazol-5-carboxamido)-3-methylbutyl)boronic acid

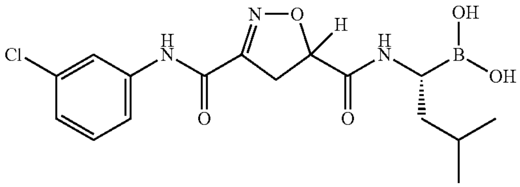 [SMILES: CC(C)C[C@H](NC(=O)C1CC(C(=O)Nc2cccc(Cl)c2)=NO1)B(O)O]

The title compound (0.081 g, 42%, 2 steps) was obtained using 3-[(3-chlorophenyl)carbamoyl]-4,5-dihydro-1,2-oxazol-5-carboxylic acid (0.14 g, 0.51 mmol) obtained in (2) above by the preparation methods of Examples 75-(3) and (4).

NMR: $^{1}$H-NMR (500 MHz, MeOD-d4); δ 7.81-7.80 (m, 1H), 7.54-7.52 (m, 1H), 7.31-728 (t, 1H), 7.14-7.12 (m, 1H), 5.42-5.38 (m, 1H), 3.67-3.48 (m, 2H), 2.92 (m, 1H), 1.65-1.63 (m, 1H), 1.40-1.36 (m, 2H), 0.92-0.90 (dd, 6H)

MS (m/z): 382[M+H], 364[M-OH]

Example 78: Preparation of ((1R)-1-(3-((2,3-dihydro-1H-inden-2-carboxamido)methyl)-4,5-dihydroisoxazol-5-carboxamido)-3-methylbutyl)boronic acid Through the processes (1), (2) and (3) below, the title compound was obtained.

(1) Preparation of ethyl 3-((2,3-dihydro-1H-inden-2-carboxamido)methyl)-4,5-dihydroisoxazol-5-carboxylate

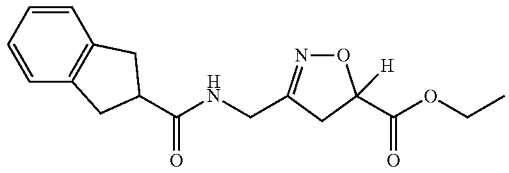 [SMILES: CCOC(=O)C1CC(CNC(=O)C2Cc3ccccc3C2)=NO1]

The title compound (0.15 g, 36%) was obtained using ethyl 3-(aminomethyl)-4,5-dihydroisoxazol-5-carboxylate hydrochloride (0.28 g, 1.4 mmol) obtained in Example 59-(1) and 2-indanecarboxylic acid (0.24 g, 1.5 mmol) by the preparation method of Example 59-(2).

MS (m/z): 317[M+H]

(2) Preparation of 3-((2,3-dihydro-1H-inden-2-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

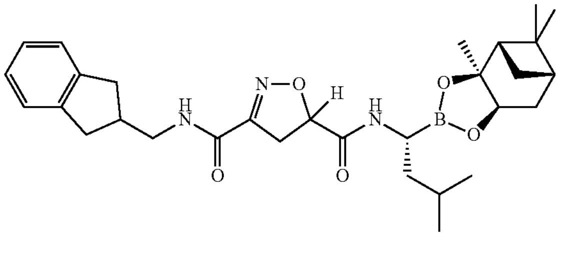 [SMILES: CC(C)C[C@H](NC(=O)C1CC(C(=O)NCC2Cc3ccccc3C2)=NO1)B1O[C@@H]2C[C@@H]3C[C@@H](C3(C)C)[C@]2(C)O1]

The title compound (0.10 g, 37%, 2 steps) was obtained using ethyl 3-((2,3-dihydro-1H-inden-2-carboxamido)methyl)-4,5-dihydroisoxazol-5-carboxylate (0.15 g, 0.48 mmol) obtained in (1) above by the preparation methods of Examples 1-(2) and (3).

MS (m/z): 536[M+H]

(3) Preparation of ((1R)-3-methyl-1-(3-((2-phenylacetamido)methyl)-4,5-dihydroisoxazol-5-carboxamido)butyl)boronic acid

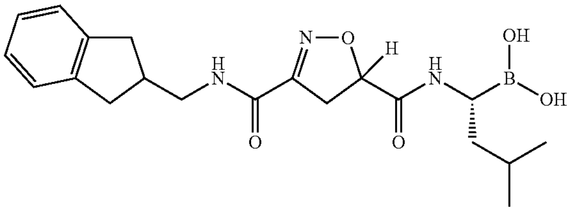 [SMILES: CC(C)C[C@H](NC(=O)C1CC(C(=O)NCC2Cc3ccccc3C2)=NO1)B(O)O]

The title compound (0.024 g, 32%) was obtained using 3-((2,3-dihydro-1H-inden-2-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.10 g, 0.19 mmol) obtained in (2) above by the preparation method of Example 1-(4).

MS (m/z): 402[M+H], 384[M-OH]

Example 79: Preparation of ((1R)-3-methyl-1-(3-((2-phenylacetamido)methyl)-4,5-dihydroisoxazol-5-carboxamido)butyl)boronic acid Through the processes (1), (2) and (3) below, the title compound was obtained.

(1) Preparation of ethyl 3-((2-phenylacetamido)methyl)-4,5-dihydroisoxazol-5-carboxylate

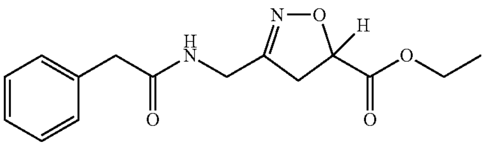 [SMILES: CCOC(=O)C1CC(CNC(=O)Cc2ccccc2)=NO1]

The title compound (0.19 g, 50%) was obtained using ethyl 3-(aminomethyl)-4,5-dihydroisoxazol-5-carboxylate hydrochloride (0.28 g, 1.3 mmol) obtained in Example 59-(1) and phenylacetic acid (0.2 g, 1.5 mmol) by the preparation method of Example 59-(2).

MS (m/z): 333[M+H]

(2) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-((2-phenylacetamido)methyl)-4,5-dihydroisoxazol-5-carboxamide

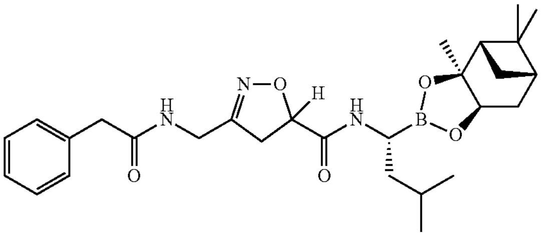 [SMILES: CC(C)C[C@H](NC(=O)C1CC(CNC(=O)Cc2ccccc2)=NO1)B1O[C@@H]2C[C@@H]3C[C@@H](C3(C)C)[C@]2(C)O1]

The title compound (0.042 g, 12%, 2 steps) was obtained using ethyl 3-((2-phenylacetamido)methyl)-4,5-dihydroisoxazol-5-carboxylate (0.19 g, 0.67 mmol) obtained in (1) above by the preparation methods of Examples 1-(2) and (3).

MS (m/z): 552[M+H]

(3) Preparation of ((1R)-3-methyl-1-(3-((2-phenylacetamido)methyl)-4,5-dihydroisoxazol-5-carboxamido)butyl)boronic acid

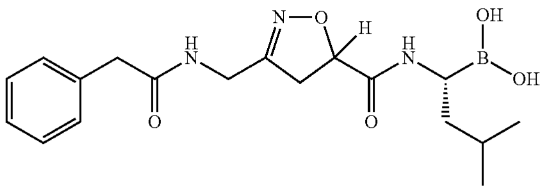 [SMILES: CC(C)C[C@H](NC(=O)C1CC(CNC(=O)Cc2ccccc2)=NO1)B(O)O]

The title compound (0.011 g, 36%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-((2-phenylacetamido)methyl)-4,5-dihydroisoxazol-5-carboxamide (0.042 g, 0.08 mmol) obtained in (2) above by the preparation method of Example 1-(4).

MS (m/z): 376[M+H], 358[M-OH]

Example 80: Preparation of ((1R)-3-methyl-1-(3-((1,2,3,4-tetrahydronaphthalen-1-carboxamido)methyl)-4,5-dihydroisoxazol-5-carboxamido)butyl)boronic acid Through the processes (1), (2) and (3) below, the title compound was obtained.

(1) Preparation of ethyl 3-[(1,2,3,4,4a,8a-hexahydronaphthalen-1-carbonylamino)methyl]-4,5-dihydroisoxazol-5-carboxylate

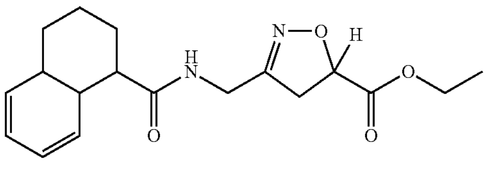 [SMILES: CCOC(=O)C1CC(CNC(=O)C2CCCC3C=CC=CC32)=NO1]

The title compound (0.11 g, 41%) was obtained using ethyl 3-(aminomethyl)-4,5-dihydroisoxazol-5-carboxylate hydrochloride (0.17 g, 0.82 mmol) obtained in Example 59-(1) and 1,2,3,4-tetrahydro-naphthalen-1-carboxylic acid (0.14 g, 0.90 mmol) by the preparation method of Example 59-(2).

NMR: $^1$H-NMR (500 MHz, $CDCl_3$); δ 7.19-7.07 (m, 4H), 5.85 (m, 1H), 4.99-1.95 (dd, 1H), 4.22-4.06 (m, 4H), 3.72-3.69 (m, 1H), 3.23-2.20 (m, 2H), 2.25-2.71 (m, 2H), 2.27-2.24 (m, 1H), 1.98-1.95 (m, 1H), 1.79-1.76 (m, 2H), 1.30-1.27 (t, 3H)

MS (m/z): 333[M+H]

(2) Preparation of 3-((1,2,3,4,4a,8a-hexahydronaphthalen-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

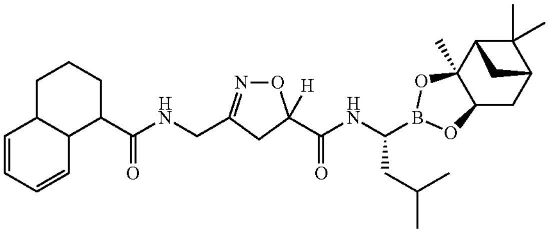 [SMILES: CC(C)C[C@H](NC(=O)C1CC(CNC(=O)C2CCCC3C=CC=CC32)=NO1)B1O[C@@H]2C[C@@H]3C[C@@H](C3(C)C)[C@]2(C)O1]

The title compound (0.073 g, 40%, 2 steps) was obtained using ethyl 3-[(1,2,3,4,4a,8a-hexahydronaphthalen-1-carbonylamino)methyl]-4,5-dihydroisoxazol-5-carboxylate (0.11 g, 0.33 mmol) obtained in (1) above by the preparation methods of Examples 1-(2) and (3).

MS (m/z): 550[M+H]

(3) Preparation of ((1R)-3-methyl-1-(3-((1,2,3,4-tetrahydronaphthalen-1-carboxamido)methyl)-4,5-dihydroisoxazol-5-carboxamido)butyl)boronic acid

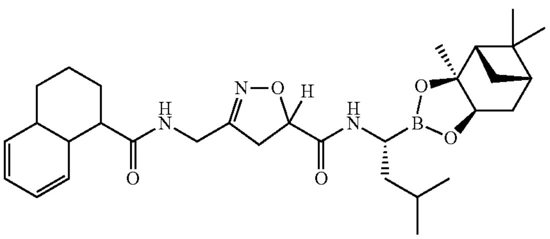 [SMILES: CC(C)C[C@H](NC(=O)C1CC(CNC(=O)C2CCCC3C=CC=CC32)=NO1)B1O[C@@H]2C[C@@H]3C[C@@H](C3(C)C)[C@]2(C)O1]

The title compound (0.025 g, 45%) was obtained using 3-((1,2,3,4,4a,8a-hexahydronaphthalen-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.073 g, 0.13 mmol) obtained in (2) above by the preparation method of Example 1-(4).

NMR: $^1$H-NMR (500 MHz, $CD_3OD$); δ 7.11-7.05 (m, 4H), 5.21-5.19 (m, 1H), 4.18-4.10 (m, 2H), 3.73-3.70 (m, 1H), 3.43-3.36 (m, 1H), 3.24-3.18 (m, 1H), 2.86-2.73 (m, 3H), 2.03-1.97 (m, 3H), 1.73-1.62 (m, 2H), 1.37-1.33 (m, 2H), 0.90-0.89 (d, 6H)

MS (m/z): 416[M+H], 398[M-OH]

Example 81: Preparation of ((1R)-3-methyl-1-(3-((5-methylisoxazol-3-carboxamido)methyl)-4,5-dihydroisoxazol-5-carboxamido)butyl)boronic acid Through the processes (1), (2) and (3) below, the title compound was obtained.

(1) Preparation of ethyl 3-[[(5-methylisoxazol-3-carbonyl)amino]methyl]-4,5-dihydroisoxazol-5-carboxylate

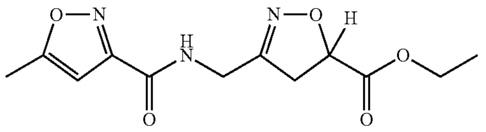 [SMILES: CCOC(=O)C1CC(CNC(=O)c2cc(C)on2)=NO1]

The title compound (0.07 g, 29%) was obtained using ethyl 3-(aminomethyl)-4,5-dihydroisoxazol-5-carboxylate hydrochloride (0.18 g, 0.87 mmol) obtained in Example 59-(1) and 5-methyl-isooxazol-3-carboxylic acid (0.11 g, 0.87 mmol) by the preparation method of Example 59-(2).

NMR: $^1$H-NMR (400 MHz, $CDCl_3$); δ 7.54 (br s, 1H), 6.45 (s, 1H), 5.09-5.02 (dd, 1H), 4.45-4.41 (d, 2H), 4.27-4.20 (q, 2H), 3.38-3.33 (m, 2H), 2.48 (s, 3H), 1.29-1.26 (t, 3H)

MS (m/z): 282[M+H]

(2) Preparation of 5-methyl-N-((5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)isoxazol-3-carboxamide

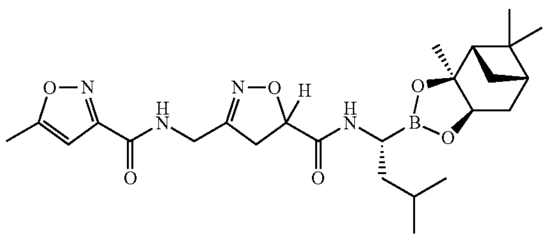

The title compound (0.04 g, 34%, 2 steps) was obtained using ethyl 3-[[(5-methylisoxazol-3-carbonyl)amino]methyl]-4,5-dihydroisoxazol-5-carboxylate (0.07 g, 0.25 mmol) obtained in (1) above by the preparation methods of Examples 1-(2) and (3).

MS (m/z): 501[M+H]

(3) Preparation of ((1R)-3-methyl-1-(3-((5-methylisoxazol-3-carboxamido)methyl)-4,5-dihydroisoxazol-5-carboxamido)butyl)boronic acid

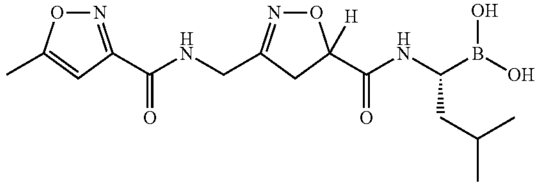 [SMILES: Cc1cc(C(=O)NCC2=NOC(C(=O)N[C@@H](CC(C)C)B(O)O)C2)no1]

The title compound (0.017 g, 59%) was obtained using 5-methyl-N-((5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)isoxazol-3-carboxamide (0.04 g, 0.08 mmol) obtained in Example 81-(2) by the preparation method of Example 1-(4).

NMR: $^1$H-NMR (500 MHz, $CD_3OD$); δ 6.44 (s, 1H), 5.24-5.21 (m, 1H), 4.28 (s, 2H), 3.48-3.43 (m, 1H), 3.27-3.22 (m, 1H), 2.81-2.78 (m, 1H), 2.46 (s, 3H), 1.66-1.60 (m, 1H), 1.36-1.32 (m, 2H), 0.89-0.88 (d, 6H)

MS (m/z): 367[M+H], 349[M-OH]

Example 82: Preparation of ((1R)-1-(3-((5-fluoro-2-methylbenzamido)methyl)-4,5-dihydroisoxazol-5-carboxamido)-3-methylbutyl)boronic acid Through the processes (1), (2) and (3) below, the title compound was obtained.

(1) Preparation of ethyl 3-[[(5-fluoro-2-methyl-benzoyl)amino]methyl]-4,5-dihydroisoxazol-5-carboxylate

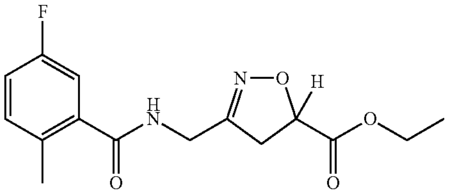 [SMILES: CCOC(=O)C1CC(CNC(=O)c2cc(F)ccc2C)=NO1]

The title compound (0.12 g, 58%) was obtained using ethyl 3-(aminomethyl)-4,5-dihydroisoxazol-5-carboxylate hydrochloride (0.14 g, 0.67 mmol) obtained in Example 59-(1) and 5-fluoro-2-methyl-benzoic acid (0.1 g, 0.67 mmol) by the preparation method of Example 59-(2).

NMR: $^1$H-NMR (400 MHz, $CDCl_3$); δ 7.20-7.01 (m, 3H) 6.62 (m, 1H), 5.06-5.02 (dd, 1H), 4.41-4.37 (d, 2H), 4.29-4.21 (q, 2H), 3.38-3.12 (m, 2H), 2.38 (s, 3H), 1.32-1.29 (t, 3H)

MS (m/z): 309[M+H]

(2) Preparation of 3-((5-fluoro-2-methylbenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

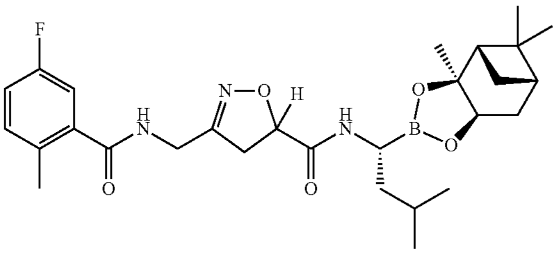 [SMILES: Cc1ccc(F)cc1C(=O)NCC1=NOC(C(=O)N[C@@H](CC(C)C)B2O[C@@H]3C[C@@H]4C[C@@H](C4(C)C)[C@]3(C)O2)C1]

The title compound (0.05 g, 27%, 2 steps) was obtained using ethyl 3-[[(5-fluoro-2-methyl-benzoyl)amino]methyl]-4,5-dihydroisoxazol-5-carboxylate (0.12 g, 0.39 mmol) obtained in (1) above by the preparation methods of Examples 1-(2) and (3).

MS (m/z): 528[M+H]

(3) Preparation of ((1R)-1-(3-((5-fluoro-2-methylbenzamido)methyl)-4,5-dihydroisoxazol-5-carboxamido)-3-methylbutyl)boronic acid

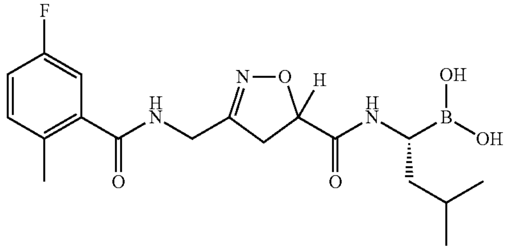 [SMILES: Cc1ccc(F)cc1C(=O)NCC1=NOC(C(=O)N[C@@H](CC(C)C)B(O)O)C1]

The title compound (0.019 g, 50%) was obtained using 3-((5-fluoro-2-methylbenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.05 g, 0.095 mmol) obtained in (2) above by the preparation method of Example 1-(4).

NMR: $^1$H-NMR (500 MHz, $CD_3OD$); δ 7.27-7.24 (dd, 1H), 7.14-7.05 (m, 2H), 5.28-5.23 (m, 1H), 4.28 (s, 2H), 3.52-3.46 (m, 1H), 3.33-3.29 (m, 1H), 2.83-2.80 (m, 1H), 2.34 (s, 3H), 1.66-1.62 (m, 1H), 1.37-1.33 (m, 2H), 0.90-0.88 (dd, 6H)

MS (m/z): 394[M+H], 376[M-OH]

Example 83: Preparation of ((1R)-3-methyl-1-(3-((pyrazin-2-carboxamido)methyl)-4,5-dihydroisoxazol-5-carboxamido)butyl)boronic acid Through the processes (1), (2) and (3) below, the title compound was obtained.

(1) Preparation of ethyl 3-((pyrazin-2-carboxamido)methyl)-4,5-dihydroisoxazol-5-carboxylate

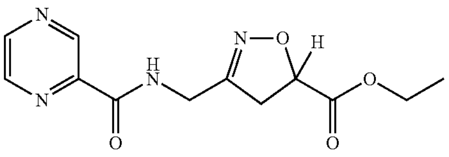 [SMILES: CCOC(=O)C1CC(CNC(=O)c2cnccn2)=NO1]

The title compound (0.07 g, 37%) was obtained using ethyl 3-(aminomethyl)-4,5-dihydroisoxazol-5-carboxylate hydrochloride (0.14 g, 0.67 mmol) obtained in Example 59-(1) and pyrazin-2-carboxylic acid (0.084 g, 0.67 mmol) by the preparation method of Example 59-(2).

NMR: $^1$H-NMR (400 MHz, $CDCl_3$); δ 9.43 (s, 1H), 8.79-8.77 (d, 1H), 8.57-8.56 (d, 1H), 8.25 (m, 1H), 5.11-5.04 (dd, 1H), 4.51-4.56 (dd, 2H), 4.29-4.22 (q, 2H), 3.36-3.29 (m, 2H), 1.32-1.29 (t, 3H)

MS (m/z): 279[M+H]

(2) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-((pyrazin-2-carboxamido)methyl)-4,5-dihydroisoxazol-5-carboxamide

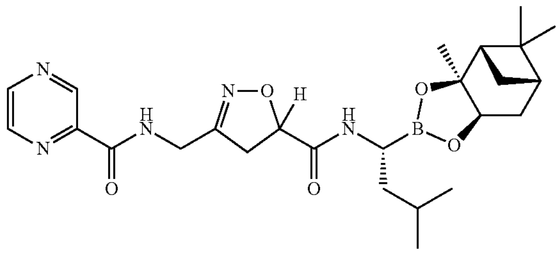 [SMILES: CC(C)C[C@H](NC(=O)C1CC(CNC(=O)c2cnccn2)=NO1)B1O[C@@H]2C[C@@H]3C[C@@H](C3(C)C)[C@]2(C)O1]

The title compound (0.02 g, 16%, 2 steps) was obtained using ethyl 3-((pyrazin-2-carboxamido)methyl)-4,5-dihydroisoxazol-5-carboxylate (0.07 g, 0.25 mmol) obtained in Example 83-(1) by the preparation methods of Examples 1-(2) and (3).

MS (m/z): 501[M+H], 349[M+H]

(3) Preparation of ((1R)-3-methyl-1-(3-((pyrazin-2-carboxamido)methyl)-4,5-dihydroisoxazol-5-carboxamido)butyl)boronic acid

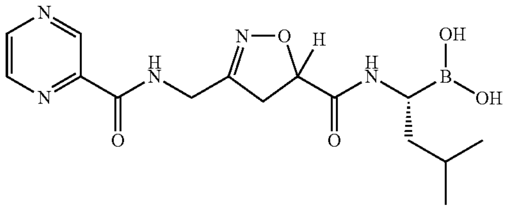 [SMILES: CC(C)C[C@H](NC(=O)C1CC(CNC(=O)c2cnccn2)=NO1)B(O)O]

The title compound (0.005 g, 33%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-((pyrazin-2-carboxamido)methyl)-4,5-dihydroisoxazol-5-carboxamide (0.02 g, 0.04 mmol) obtained in Example 83-(2) by the preparation method of Example 1-(4).

NMR: $^1$H-NMR (500 MHz, $CD_3OD$); δ 9.22 (s, 1H), 8.78-8.67 (m, 2H), 5.24-5.21 (m, 1H), 4.36 (s, 2H), 3.50-3.44 (m, 1H), 3.27-3.24 (m, 1H), 2.81-2.78 (m, 1H), 1.62-1.60 (m, 1H), 1.35-1.31 (m, 2H), 0.89-0.88 (d, 6H)

MS (m/z): 364[M+H], 349[M+H]

Example 84: Preparation of ((1R)-1-(5-benzyl-3-((isoquinolin-1-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of methyl 3-(aminomethyl)-5-benzyl-4,5-dihydroisoxazol-5-carboxylate hydrochloride

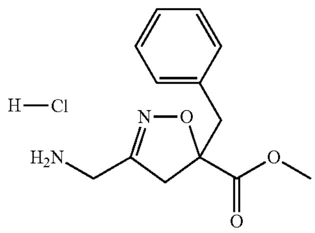

Methyl 5-benzyl-3-(((tert-butoxycarbonyl)amino)methyl)-4,5-dihydroisoxazol-5-carboxylate (2.6 g, 7.47 mmol) obtained in Preparation Example 6 was dissolved in dichloromethane (30 ml). A 4 N hydrochloric acid 1,4-dioxane solution (15 ml, 59.74 mmol) was slowly added thereto at 0° C., followed by stirring for 5 hours, while raising to room temperature. After distilling the solvent under a reduced pressure, the resultant product was solidified with dichloromethane and hexane. The residual solvent was distilled under a reduced pressure, and the resultant product was dried under a reduced pressure to obtain the title compound (2.1 g, 99%).

MS (m/z): 249[M+H]

(2) Preparation of methyl 5-benzyl-3-((isoquinolin-1-carboxamido)methyl)-4,5-dihydroisoxazol-5-carboxylate

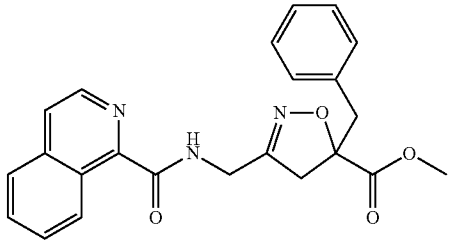 [SMILES: COC(=O)C1(Cc2ccccc2)CC(CNC(=O)c2nccc3ccccc23)=NO1]

Methyl 3-(aminomethyl)-5-benzyl-4,5-dihydroisoxazol-5-carboxylate hydrochloride (0.29 g, 1.02 mmol) obtained in (1) above was dissolved in dimethylformamide (5 ml). 1-Ethyl-3-(3-dimethylaminopropyl)carbodiimide (0.254 g, 1.32 mmol), hydroxybenzotriazole (0.179 g, 1.32 mmol) and isoquinolin-1-carboxylic acid (0.194 g, 1.12 mmol) were added thereto in order. Diisopropylethylamine (0.53 ml, 3.06 mmol) was slowly added thereto, and stirring was performed at room temperature for 18 hours. The solvent was distilled under a reduced pressure, a sodium bicarbonate aqueous solution was added, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.32 g, 78%).

NMR: $^1$H-NMR (400 MHz, $CDCl_3$); δ 9.55-9.52 (d, 1H), 8.48-8.47 (t, 1H), 8.39 (m, 1H), 7.88-7.83 (m, 2H), 7.76-7.68 (m, 2H), 7.22-7.14 (m, 5H), 4.35-4.24 (m, 2H), 3.76 (s, 3H), 3.50-3.46 (d, 1H), 3.33-3.29 (d, 1H), 3.14-3.11 (d, 1H), 3.10-3.06 (d, 1H)

MS (m/z): 404[M+H]

(3) Preparation of 5-benzyl-3-[(isoquinolin-1-carbonylamino)methyl]-4-1,2-oxazol-5-carboxylic acid

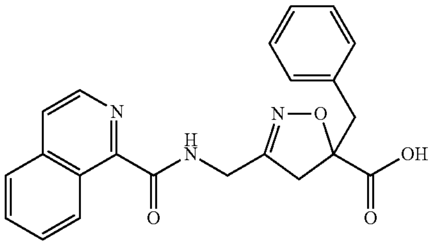

Methyl 5-benzyl-3-((isoquinolin-1-carboxamido)methyl)-4,5-dihydroisoxazol-5-carboxylate (0.32 g, 0.80 mmol) obtained in (2) above was dissolved in methanol (10 ml), a 1 N sodium hydroxide aqueous solution (4.0 ml, 4.0 mmol) was added thereto, and stirring was performed at room temperature for 5 hours. After titrating pH 1 with a 1 N hydrochloric acid solution, extraction with ethyl acetate was performed twice. The organic layer thus extracted was dried over anhydrous magnesium sulfate, and filtered, and the filtrate was distilled under a reduced pressure to obtain 5-benzyl-3-[(isoquinolin-1-carbonylamino)methyl]-4H-1,2-oxazol-5-carboxylic acid (0.31 g, 99%).

MS (m/z): 390[M+H]

(4) Preparation of 5-benzyl-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

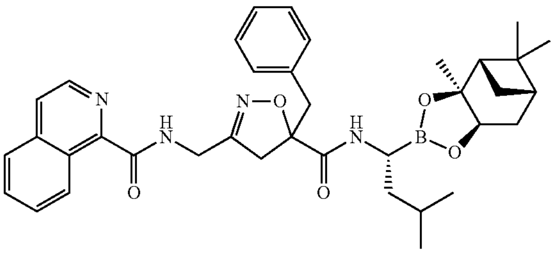

5-Benzyl-3-[(isoquinolin-1-carbonylamido)methyl]-4H-1,2-oxazol-5-carboxylic acid (0.31 g, 0.80 mmol) obtained in (3) above, (1R)-3-methyl-1-[(1S,2S,6R,8S)-2,9,9-trimethyl-3,5-dioxa-4-boratricyclo[6.1.1.0$^{2,6}$]decan-4-yl]butan-1-amine hydrochloride (0.24 g, 0.81 mmol), and O-(benzotriazol-1-yl)-N,N,N',N'-tetramethyluronium tetrafluoroborate (0.29 g, 0.89 mmol) were dissolved at 0° C. in dimethylformamide (5 ml). While maintaining 0° C., diisopropylethylamine (0.42 ml, 2.42 mmol) was slowly added thereto, followed by stirring for 18 hours, while raising to room temperature. The solvent was distilled under a reduced pressure, a sodium bicarbonate aqueous solution was added, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.41 g, 80%).

MS (m/z): 637[M+H]

(5) Preparation of ((1R)-1-(5-benzyl-3-((isoquinolin-1-carboxamido)methyl)-4,5-dihydroisoxazol-5-carboxamido)-3-methylbutyl)boronic acid

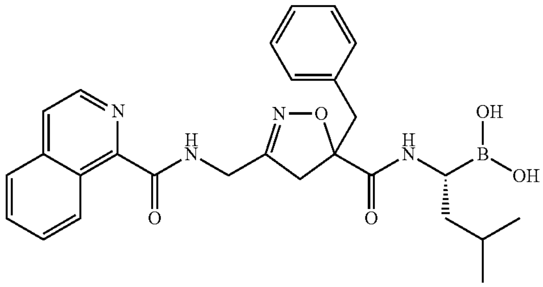

The title compound (0.24 g, 74%) was obtained using 5-benzyl-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.41 g, 0.65 mmol) obtained in (4) above by the preparation method of Example 1-(4).

NMR: $^1$H-NMR (400 MHz, MeOD-$d_4$); δ 9.11-9.10 (d, 1H), 8.54-8.53 (d, 1H), 8.02-7.97 (dd, 2H), 7.84-7.72 (m, 2H), 7.30-7.19 (m, 5H), 4.35 (s, 2H), 3.55-3.50 (d, 1H), 3.37-3.34 (dd, 2H), 3.25-3.22 (d, 1H), 2.71-2.67 (m, 1H), 1.45-1.31 (m, 1H), 1.21-1.03 (m, 2H), 0.83-0.78 (dd, 6H)

MS (m/z): 503[M+H], 485 [M-OH]

Example 85: Preparation of ((1R)-1-(5-benzyl-3-((2,5-dichlorobenzamido)methyl)-4,5-dihydroisoxazol-5-carboxamido)-3-methylbutyl)boronic acid Through the processes (1), (2), (3) and (4) below, the title compound was obtained.

(1) Preparation of methyl 5-benzyl-3-((2,5-dichlorobenzamido)methyl)-4,5-dihydroisoxazol-5-carboxylate

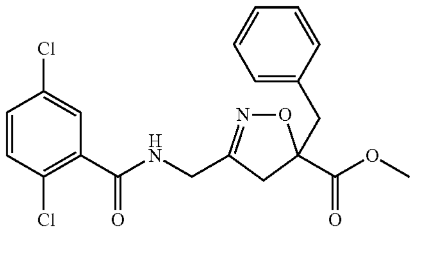

The title compound (0.20 g, 54%) was obtained using methyl 3-(aminomethyl)-5-benzyl-4,5-dihydroisoxazol-5-carboxylate hydrochloride (0.16 g, 0.56 mmol) obtained in Example 84-(1) and 2,5-dichlorobenzoic acid (0.12 g, 0.62 mmol) by the preparation method of Example 84-(2).

NMR: $^1$H-NMR (500 MHz, $CDCl_3$); δ 7.58-7.57 (d, 1H), 7.36-7.34 (m, 2H), 7.23-7.18 (m, 5H), 6.27 (m, 1H), 4.24-4.14 (m, 2H), 3.79 (s, 3H), 3.47-3.43 (d, 1H), 3.35-3.32 (d, 1H), 3.12-3.09 (d, 1H), 3.03-3.00 (d, 1H)

MS (m/z): 421[M+H]

(2) Preparation of 5-benzyl-3-((2,5-dichlorobenzamido)methyl)-4,5-dihydroisoxazol-5-carboxylic acid

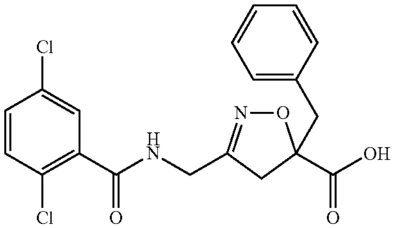 [SMILES: O=C(NCC1=NOC(Cc2ccccc2)(C(=O)O)C1)c1cc(Cl)ccc1Cl]

The quantitative amount of the title compound was obtained using methyl 5-benzyl-3-((2,5-dichlorobenzamido)methyl)-4,5-dihydroisoxazol-5-carboxylate (0.19 g, 0.47 mmol) obtained in (1) above by the preparation method of Example 84-(3).

MS (m/z): 407[M+H]

(3) Preparation of 5-benzyl-3-((2,5-dichlorobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

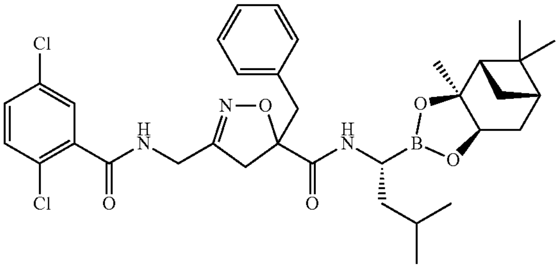 [SMILES: CC(C)C[C@H](NC(=O)C1(Cc2ccccc2)CC(CNC(=O)c2cc(Cl)ccc2Cl)=NO1)B1O[C@@H]2C[C@@H]3C[C@@H](C3(C)C)[C@]2(C)O1]

The title compound (0.12 g, 53%) was obtained using 5-benzyl-3-((2,5-dichlorobenzamido)methyl)-4,5-dihydroisoxazol-5-carboxylic acid (0.19 g, 0.47 mmol) obtained in (2) above by the preparation method of Example 84-(4).

MS (m/z): 654[M+H]

(4) Preparation of ((1R)-1-(5-benzyl-3-((2,5-dichlorobenzamido)methyl)-4,5-dihydroisoxazol-5-carboxamido)-3-methylbutyl)boronic acid

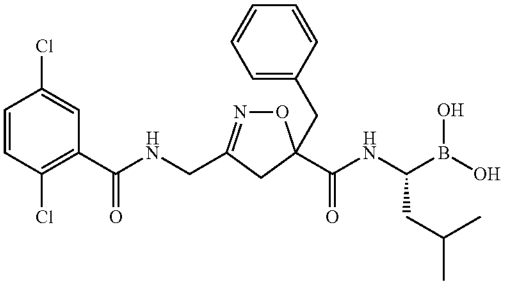 [SMILES: CC(C)C[C@H](NC(=O)C1(Cc2ccccc2)CC(CNC(=O)c2cc(Cl)ccc2Cl)=NO1)B(O)O]

The title compound (0.055 g, 59%) was obtained using 5-benzyl-3-{1[(2,5-dichlorophenyl)formamido]methyl}-N-[(1R)-3-methyl-1-[(1S,2S,6R,8S)-2,9,9-trimethyl-3,5-dioxa-4-boratricyclo[6.1.1.0$^{2,6}$]decan-4-yl]butyl]-4,5-dihydro-1,2-oxazol-5-carboxamide (0.12 g, 0.18 mmol) obtained in (3) above by the preparation method of Example 1-(4).

NMR: $^1$H-NMR (400 MHz, $CDCl_3$); δ 7.59 (d, 1H), 7.40-7.36 (m, 2H), 7.34-7.20 (m, 6H), 6.68 (m, 1H), 4.30-4.19 (m, 2H), 3.48-3.38 (m, 2H), 3.21-3.09 (m, 2H), 1.47-1.27 (m, 3H), 0.93-0.89 (m, 6H)

MS (m/z): 520[M+H], 502[M-OH]

Example 86: Preparation of ((1R)-1-(3-((2,5-dichlorobenzamido)methyl)-5-methyl-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-methyl-4,5-dihydroisoxazol-5-carboxylate hydrochloride

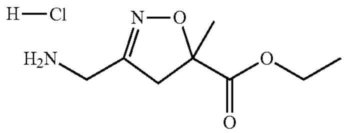

The title compound (0.167 g, 99%) was obtained using ethyl 3-(((tert-butoxycarbonyl)amino)methyl)-5-methyl-4,5-dihydroisoxazol-5-carboxylate (0.21 g, 0.73 mmol) obtained in Preparation Example 7 by the preparation method of Example 84-(1).

MS (m/z): 187[M+H]

(2) Preparation of ethyl 3-((2,5-dichlorobenzamido)methyl)-5-methyl-4,5-dihydroisoxazol-5-carboxylate

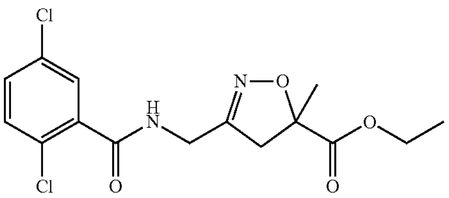 [SMILES: CCOC(=O)C1(C)CC(CNC(=O)c2cc(Cl)ccc2Cl)=NO1]

The title compound (0.2 g, 74%) was obtained using ethyl 3-(aminomethyl)-5-methyl-4,5-dihydroisoxazol-5-carboxylate hydrochloride (0.167 g, 0.75 mmol) obtained in (1) above and 2,5-dichloro-benzoic acid (0.158 g, 0.83 mmol) by the preparation method of Example 84-(2).

MS (m/z): 359[M+H]

(3) Preparation of 3-((2,5-dichlorobenzamido)methyl)-5-methyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

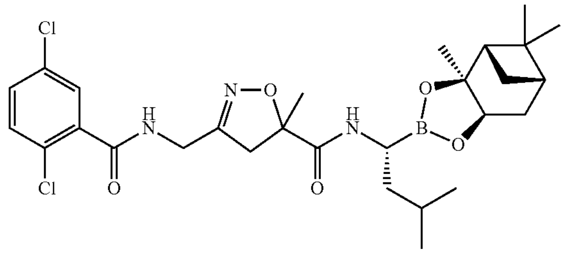 [SMILES: CC(C)C[C@H](NC(=O)C1(C)CC(CNC(=O)c2cc(Cl)ccc2Cl)=NO1)B1O[C@@H]2C[C@@H]3C[C@@H](C3(C)C)[C@]2(C)O1]

The title compound (0.1 g, 43%, 2 steps) was obtained using ethyl 3-((2,5-dichlorobenzamido)methyl)-5-methyl-4,5-dihydroisoxazol-5-carboxylate (0.2 g, 0.56 mmol) obtained in (2) above by the preparation methods of Example 1-(2) and Example 1-(3).

MS (m/z): 578[M+H]

(4) Preparation of ((1R)-1-(3-((2,5-dichlorobenzamido)methyl)-5-methyl-4,5-dihydroisoxazol-5-carboxamido)-3-methylbutyl)boronic acid

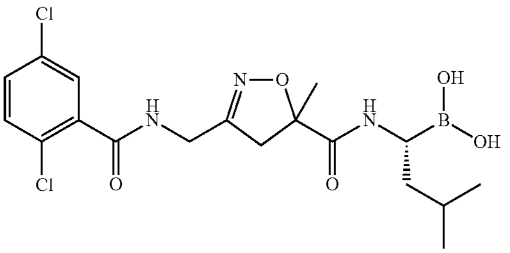

The title compound (0.058 g, 75%) was obtained using 3-((2,5-dichlorobenzamido)methyl)-5-methyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.1 g, 0.17 mmol) obtained in (3) above by the preparation method of Example 1-(4).

NMR: $^1$H-NMR (400 MHz, $CDCl_3$); δ 7.61-7.45 (m, 1H), 7.33-7.31 (m, 2H), 7.24 (m, 1H), 7.09 (m, 1H), 4.38-4.27 (m, 2H), 3.50-3.47 (m, 1H), 3.02-2.96 (m, 2H), 1.65 (m, 3H), 1.61-1.25 (m, 3H), 0.87-0.86 (m, 6H)

MS (m/z): 444[M+H], 426[M-OH]

Example 87: Preparation of ((1R)-1-(3-((2,5-dichlorobenzamido)methyl)-5-ethyl-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-ethyl-4,5-dihydroisoxazol-5-carboxylate hydrochloride

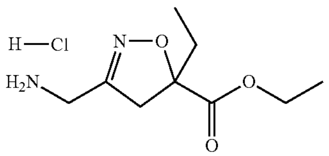

The title compound (0.21 g, 99%) was obtained using ethyl 3-(((tert-butoxycarbonyl)amino)methyl)-5-ethyl-4,5-dihydroisoxazol-5-carboxylate (0.25 g, 0. mmol) obtained in Preparation Example 8 by the preparation method of Example 84-(1).

MS (m/z): 201[M+H]

(2) Preparation of ethyl 3-((2,5-dichlorobenzamido)methyl)-5-ethyl-4,5-dihydroisoxazol-5-carboxylate

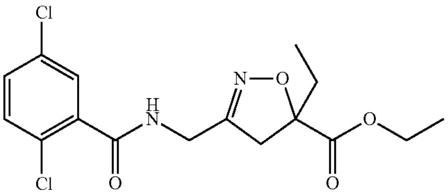

The title compound (0.26 g, 79%) was obtained using ethyl 3-(aminomethyl)-5-ethyl-4,5-dihydroisoxazol-5-carboxylate hydrochloride (0.21 g, 0.89 mmol) obtained in (1) above and 2,5-dichloro-benzoic acid (0.19 g, 0.98 mmol) by the preparation method of Example 84-(2).

MS (m/z): 373[M+H]

(3) Preparation of 3-((2,5-dichlorobenzamido)methyl)-5-ethyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

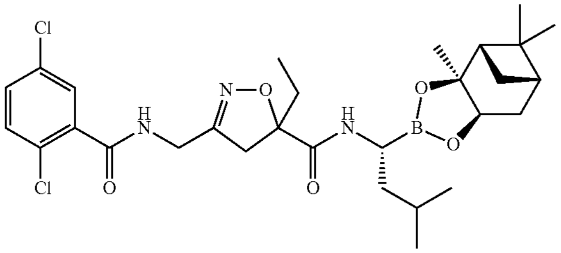 [SMILES: CCC1(C(=O)N[C@@H](CC(C)C)B2O[C@@H]3C[C@@H]4C[C@@H](C4(C)C)[C@]3(C)O2)CC(CNC(=O)c2cc(Cl)ccc2Cl)=NO1]

The title compound (0.1 g, 44%, 2 steps) was obtained using ethyl 3-((2,5-dichlorobenzamido)methyl)-5-ethyl-4,5-dihydroisoxazol-5-carboxylate (0.26 g, 6.70 mmol) obtained in Example 87-(2) by the preparation methods of Examples 1-(2) and Example 1-(3).

MS (m/z): 579[M+H], 427[M-$C_{10}H_{15}O$]

(4) Preparation of ((1R)-1-(3-((2,5-dichlorobenzamido)methyl)-5-ethyl-4,5-dihydroisoxazol-5-carboxamido)-3-methylbutyl)boronic acid

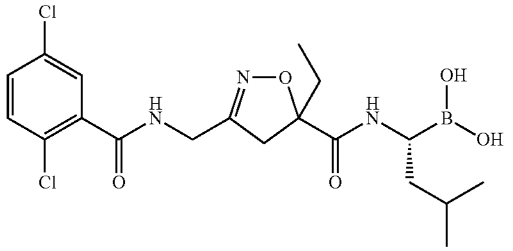

The title compound (0.058 g, 75%) was obtained using 3-((2,5-dichlorobenzamido)methyl)-5-ethyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.1 g, 0.17 mmol) obtained in Example 87-(3) by the preparation method of Example 1-(4).

NMR: $^1$H-NMR (400 MHz, $CDCl_3$); δ 7.61-7.55 (m, 1H), 7.46-7.31 (m, 2H), 7.21-7.11 (m, 1H), 4.41-4.24 (m, 2H), 3.46-3.65 (m, 1H), 3.03-2.87 (m, 2H), 2.11-1.82 (m, 2H), 1.58-1.27 (m, 3H), 0.95-0.86 (m, 9H)

MS (m/z): 445[M+H], 427[M-OH]

Example 88: Preparation of ((1R)-1-(3-((2,5-dichlorobenzamido)methyl)-5-propyl-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-propyl-4,5-dihydroisoxazol-5-carboxylate hydrochloride

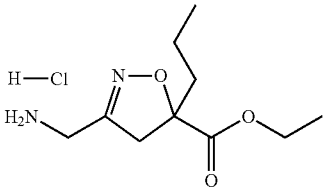

The title compound (0.22 g, 99%) was obtained using ethyl 3-[(tert-butoxycarbonylamino)methyl]-5-propyl-4H-1,2-oxazol-5-carboxylate (0.27 g, 0.86 mmol) obtained in Preparation Example 9 by the preparation method of Example 84-(1).

MS (m/z): 215[M+H]

(2) Preparation of ethyl 3-((2,5-dichlorobenzamido)methyl)-5-propyl-4,5-dihydroisoxazol-5-carboxylate

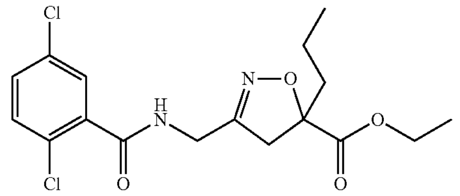 [SMILES: CCCC1(C(=O)OCC)CC(CNC(=O)c2cc(Cl)ccc2Cl)=NO1]

The title compound (0.21 g, 62%) was obtained using ethyl 3-(aminomethyl)-5-propyl-4,5-dihydroisoxazol-5-carboxylate hydrochloride (0.22 g, 0.88 mmol) obtained in (1) above and 2,5-dichloro-benzoic acid (0.18 g, 0.97 mmol) by the preparation method of Example 84-(2).

NMR: $^1$H-NMR (500 MHz, $CDCl_3$); δ 7.66 (s, 1H), 7.34 (d, 2H), 6.74 (br s, 1H), 4.37-4.36 (m, 2H), 4.25-4.18 (m, 2H), 3.53-3.49 (d, 1H), 2.99-2.96 (d, 1H), 1.94-1.89 (m, 2H), 1.37-1.33 (m, 2H), 1.31-1.28 (t, 3H), 0.95-0.92 (t, 3H)

MS (m/z): 387[M+H]

(3) Preparation of 3-((2,5-dichlorobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-propyl-4,5-dihydroisoxazol-5-carboxamide

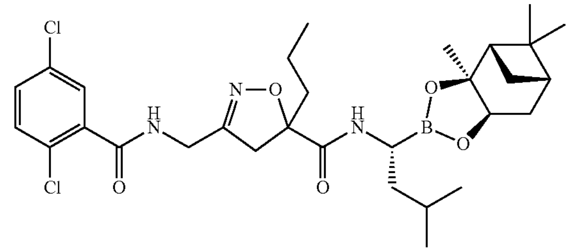 [SMILES: CCCC1(C(=O)N[C@@H](CC(C)C)B2O[C@@H]3C[C@@H]4C[C@@H](C4(C)C)[C@]3(C)O2)CC(CNC(=O)c2cc(Cl)ccc2Cl)=NO1]

The title compound (0.1 g, 58%, 2 steps) was obtained using ethyl 3-((2,5-dichlorobenzamido)methyl)-5-propyl-4,5-dihydroisoxazol-5-carboxylate (0.21 g, 0.54 mmol) obtained in (2) above by the preparation methods of Example 1-(2) and Example 1-(3).

MS (m/z): 606[M+H]

(4) Preparation of ((1R)-1-(3-((2,5-dichlorobenzamido)methyl)-5-propyl-4,5-dihydroisoxazol-5-carboxamido)-3-methylbutyl)boronic acid

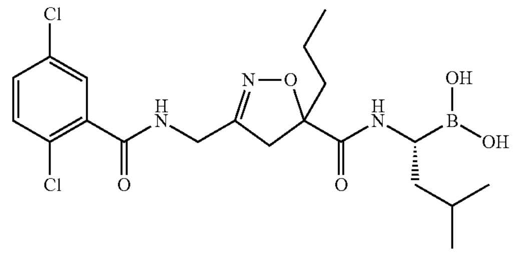 [SMILES: CCCC1(C(=O)N[C@@H](CC(C)C)B(O)O)CC(CNC(=O)c2cc(Cl)ccc2Cl)=NO1]

The title compound (0.052 g, 57%) was obtained using 3-((2,5-dichlorobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-propyl-4,5-dihydroisoxazol-5-carboxamide (0.1 g, 0.19 mmol) obtained in (3) above by the preparation method of Example 1-(4).

NMR: $^1$H-NMR (500 MHz, $CD_3OD$); δ 7.50-7.46 (m, 3H), 4.30-4.20 (m, 2H), 3.44-3.39 (m, 1H), 3.22-3.17 (m, 1H), 2.80-2.74 (m, 1H), 2.01-1.96 (m, 1H), 1.89-1.82 (m, 1H), 1.68-1.61 (m, 1H), 1.51-1.46 (m, 1H), 1.40-1.27 (m, 3H), 0.96-0.93 (t, 3H), 0.90-0.88 (m, 6H)

MS (m/z): 472[M+H], 454[M-OH]

Example 89: Preparation of ((1R)-1-(3-((2,5-dichlorobenzamido)methyl)-5-isopropyl-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-isopropyl-4,5-dihydroisoxazol-5-carboxylate hydrochloride

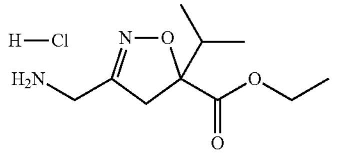

The title compound (0.17 g, 99%) was obtained using ethyl 3-[(tert-butoxycarbonylamino)methyl]-5-isopropyl-4H-1,2-oxazol-5-carboxylate (0.21 g, 0.66 mmol) obtained in Preparation Example 10 by the preparation method of Example 84-(1).

MS (m/z): 215[M+H]

(2) Preparation of ethyl 3-((2,5-dichlorobenzamido)methyl)-5-isopropyl-4,5-dihydroisoxazol-5-carboxylate

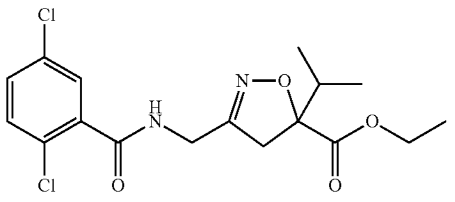 [SMILES: CCOC(=O)C1(C(C)C)CC(CNC(=O)c2cc(Cl)ccc2Cl)=NO1]

The title compound (0.23 g, 86%) was obtained using ethyl 3-(aminomethyl)-5-isopropyl-4,5-dihydroisoxazol-5-carboxylate hydrochloride (0.17 g, 0.68 mmol) obtained in (1) above and 2,5-dichloro-benzoic acid (0.14 g, 0.75 mmol) by the preparation method of Example 84-(2).

MS (m/z): 387[M+H]

(3) Preparation of 3-((2,5-dichlorobenzamido)methyl)-5-isopropyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

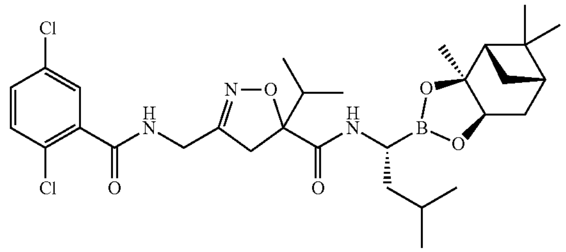 [SMILES: CC(C)C[C@H](NC(=O)C1(C(C)C)CC(CNC(=O)c2cc(Cl)ccc2Cl)=NO1)B1O[C@@H]2C[C@@H]3C[C@@H](C3(C)C)[C@]2(C)O1]

The title compound (0.11 g, 52%, 2 steps) was obtained using ethyl 3-((2,5-dichlorobenzamido)methyl)-5-isopropyl-4,5-dihydroisoxazol-5-carboxylate (0.23 g, 0.58 mmol) obtained in (2) above by the preparation methods of Example 1-(2) and Example 1-(3).

MS (m/z): 606[M+H]

(4) Preparation of ((1R)-1-(3-((2,5-dichlorobenzamido)methyl)-5-isopropyl-4,5-dihydroisoxazol-5-carboxamido)-3-methylbutyl)boronic acid

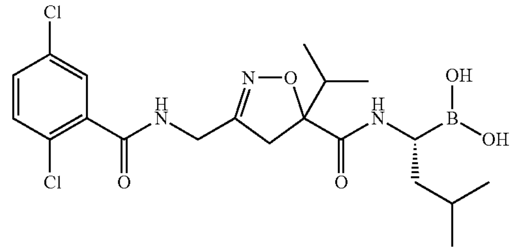 [SMILES: CC(C)C[C@H](NC(=O)C1(C(C)C)CC(CNC(=O)c2cc(Cl)ccc2Cl)=NO1)B(O)O]

The title compound (0.065 g, 80%) was obtained using 3-((2,5-dichlorobenzamido)methyl)-5-isopropyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.11 g, 0.17 mmol) obtained in Example 89-(3) above by the preparation method of Example 1-(4).

NMR: $^1$H-NMR (400 MHz, $CDCl_3$); δ 7.73-7.61 (m, 1H), 7.38-7.28 (m, 2H), 7.27-7.00 (m, 2H), 4.47-4.27 (m, 2H), 3.43-3.09 (m, 2H), 3.00-2.88 (m, 1H), 2.23-2.16 (m, 1H), 1.62-1.35 (m, 3H), 0.98-0.83 (m, 12H)

MS (m/z): 472[M+H], 454[M-OH]

Example 90: Preparation of ((1R)-1-(3-((2,5-dichlorobenzamido)methyl)-5-isobutyl-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-isobutyl-4,5-dihydroisoxazol-5-carboxylate hydrochloride

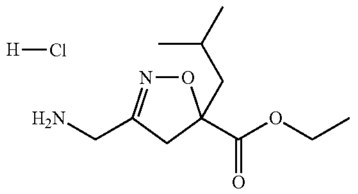 [SMILES: Cl ; CCOC(=O)C1(CC(C)C)CC(CN)=NO1]

The title compound (0.32 g, 95%) was obtained using ethyl 3-[(tert-butoxycarbonylamino)methyl]-5-isobutyl-4H-1,2-oxazol-5-carboxylate (0.41 g, 1.25 mmol) obtained in Preparation Example 11 by the preparation method of Example 84-(1).

MS (m/z): 229[M+H]

(2) Preparation of ethyl 3-((2,5-dichlorobenzamido)methyl)-5-isobutyl-4,5-dihydroisoxazol-5-carboxylate

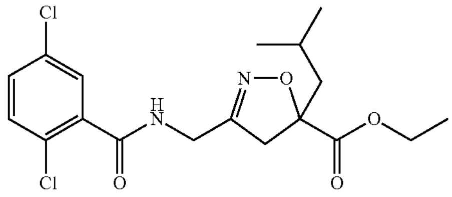 [SMILES: CCOC(=O)C1(CC(C)C)CC(CNC(=O)c2cc(Cl)ccc2Cl)=NO1]

The title compound (0.12 g, 73%) was obtained using ethyl 3-(aminomethyl)-5-isobutyl-4,5-dihydroisoxazol-5-carboxylate hydrochloride (0.11 g, 0.41 mmol) obtained in (1) above and 2,5-dichloro-benzoic acid (0.086 g, 0.45 mmol) by the preparation method of Example 84-(2).

MS (m/z): 401[M+H]

(3) Preparation of 3-((2,5-dichlorobenzamido)methyl)-5-isobutyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

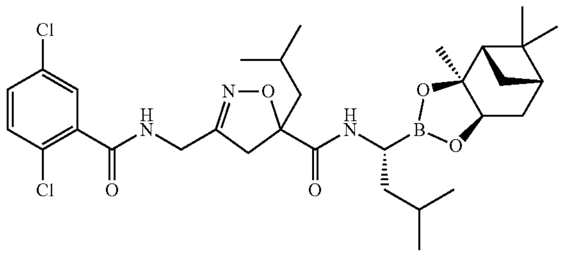 [SMILES: CC(C)C[C@H](NC(=O)C1(CC(C)C)CC(CNC(=O)c2cc(Cl)ccc2Cl)=NO1)B1O[C@@H]2C[C@@H]3C[C@@H](C3(C)C)[C@]2(C)O1]

The title compound (0.047 g, 57%, 2 steps) was obtained using ethyl 3-((2,5-dichlorobenzamido)methyl)-5-isobutyl-4,5-dihydroisoxazol-5-carboxylate (0.12 g, 0.30 mmol) obtained in (2) above by the preparation methods of Examples 1-(2) and (3).

MS (m/z): 620[M+H]

(4) Preparation of ((1R)-1-(3-((2,5-dichlorobenzamido)methyl)-5-isobutyl-4,5-dihydroisoxazol-5-carboxamido)-3-methylbutyl)boronic acid

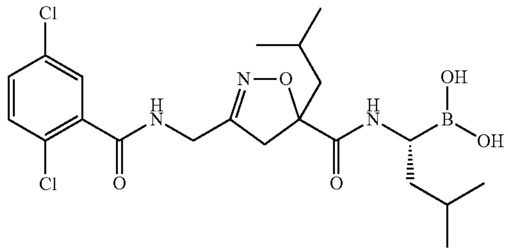 [SMILES: CC(C)C[C@H](NC(=O)C1(CC(C)C)CC(CNC(=O)c2cc(Cl)ccc2Cl)=NO1)B(O)O]

The title compound (0.027 g, 73%) was obtained using 3-((2,5-dichlorobenzamido)methyl)-5-isobutyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.047 g, 0.076 mmol) obtained in Example 90-(3) by the preparation method of Example 1-(4).

NMR: $^1$H-NMR (400 MHz, $CDCl_3$); δ 7.63-7.59 (m, 1H), 7.32-7.30 (m, 2H), 7.15-6.99 (m, 2H), 4.38-4.26 (m, 2H), 3.49-3.38 (m, 1H), 3.03-2.86 (m, 2H), 2.05-1.92 (m, 1H), 1.78-1.71 (m, 2H), 1.58-1.32 (m, 3H), 0.99-0.81 (m, 12H)

MS (m/z): 486[M+H], 468[M-OH]

Example 91: Preparation of ((1R)-1-(5-isobutyl-3-((isoquinolin-1-carboxamido)methyl)-4,5-dihydroisoxazol-5-carboxamido)-3-methylbutyl)boronic acid Through the processes (1), (2) and (3) below, the title compound was obtained.

(1) Preparation of ethyl 5-isobutyl-3-((isoquinolin-1-carboxamido)methyl)-4,5-dihydroisoxazol-5-carboxylate

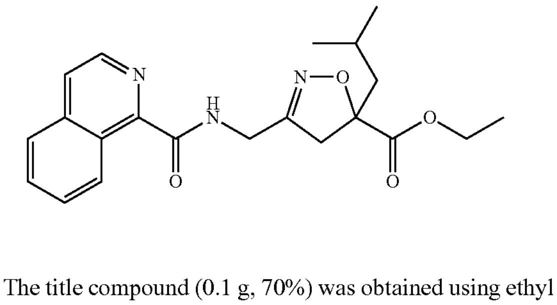

The title compound (0.1 g, 70%) was obtained using ethyl 3-(aminomethyl)-5-isobutyl-4,5-dihydroisoxazol-5-carboxylate hydrochloride (0.1 g, 0.38 mmol) obtained in Example 90-(1) and isoquinolin-1-carboxylic acid (0.072 g, 0.42 mmol) by the preparation method of Example 84-(2).

MS (m/z): 384[M+H]

(2) Preparation of 5-isobutyl-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

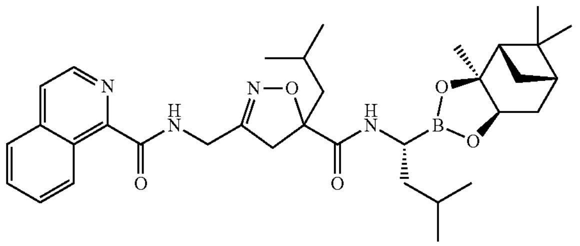 [SMILES: CC(C)C[C@H](NC(=O)C1(CC(C)C)CC(CNC(=O)c2nccc3ccccc23)=NO1)B1O[C@@H]2C[C@@H]3C[C@@H](C3(C)C)[C@]2(C)O1]

The title compound (0.017 g, 20%, 2 steps) was obtained using ethyl 5-isobutyl-3-((isoquinolin-1-carboxamido)methyl)-4,5-dihydroisoxazol-5-carboxylate (0.1 g, 0.26 mmol) obtained in (1) above by the preparation methods of Example 1-(2) and Example 1-(3).

MS (m/z): 603[M+H], 451[M-$C_{10}H_{15}O$]

(3) Preparation of ((1R)-1-(5-isobutyl-3-((isoquinolin-1-carboxamido)methyl)-4,5-dihydroisoxazol-5-carboxamido)-3-methylbutyl)boronic acid

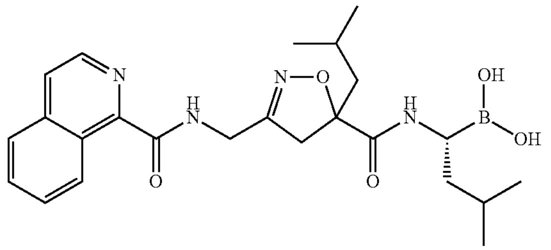 [SMILES: CC(C)C[C@H](NC(=O)C1(CC(C)C)CC(CNC(=O)c2nccc3ccccc23)=NO1)B(O)O]

The title compound (0.009 g, 70%) was obtained using 5-isobutyl-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.017 g, 0.028 mmol) obtained in Example 91-(2) above by the preparation method of Example 1-(4).

NMR: $^1$H-NMR (400 MHz, $CDCl_3$); δ 9.54-9.51 (m, 1H), 8.68-8.65 (m, 1H), 8.45-8.42 (m, 1H), 7.83-65 (m, 4H), 7.40-7.39 (m, 1H), 4.45-4.38 (m, 2H), 3.49-3.41 (m, 1H), 3.06-3.01 (m, 1H), 2.89-2.87 (m, 1H), 2.05-2.01 (m, 1H), 1.78-1.69 (m, 2H), 1.53-1.26 (m, 3H), 0.93-0.81 (m, 12H)

MS (m/z): 469[M+H], 451[M-OH]

Example 92: Preparation of ((1R)-1-(3-((1-naphthamido)methyl)-5-benzyl-4,5-dihydroisoxazol-5-carboxamido)-3-methylbutyl)boronic acid Through the processes (1), (2), (3) and (4) below, the title compound was obtained.

(1) Preparation of methyl 3-((1-naphthamido)methyl)-5-benzyl-4,5-dihydroisoxazol-5-carboxylate

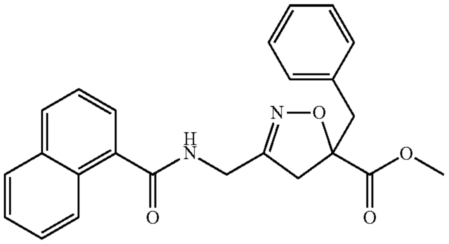 [SMILES: COC(=O)C1(Cc2ccccc2)CC(CNC(=O)c2cccc3ccccc23)=NO1]

The title compound (0.114 g, 73%) was obtained using methyl 3-(aminomethyl)-5-benzyl-4,5-dihydroisoxazol-5-carboxylate hydrochloride (0.11 g, 0.39 mmol) obtained in Example 84-(1) and naphthalen-1-carboxylic acid (0.073 g, 0.43 mmol) by the preparation method of Example 84-(2).

MS (m/z): 403[M+H]

(2) Preparation of 3-((1-naphthamido)methyl)-5-benzyl-4,5-dihydroisoxazol-5-carboxylic acid

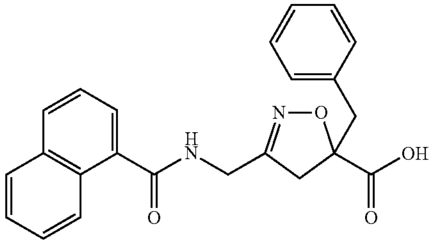 [SMILES: O=C(NCC1=NOC(Cc2ccccc2)(C(=O)O)C1)c1cccc2ccccc12]

The quantitative amount of the title compound was obtained using methyl 3-((1-naphthamido)methyl)-5-benzyl-4,5-dihydroisoxazol-5-carboxylate (0.11 g, 0.28 mmol) obtained in (1) above by the preparation method of Example 84-(3).

MS (m/z): 389[M+H]

(3) Preparation of 3-((1-naphthamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

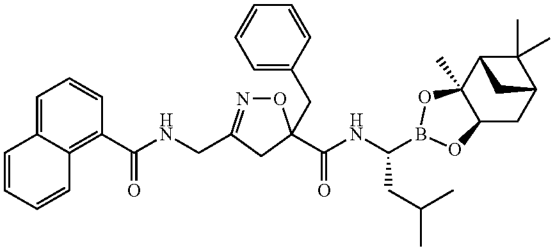 [SMILES: CC(C)C[C@H](NC(=O)C1(Cc2ccccc2)CC(CNC(=O)c2cccc3ccccc23)=NO1)B1O[C@@H]2C[C@@H]3C[C@@H](C3(C)C)[C@]2(C)O1]

The title compound (0.05 g, 28%) was obtained using methyl 3-((1-naphthamido)methyl)-5-benzyl-4,5-dihydroisoxazol-5-carboxylic acid (0.114 g, 0.28 mmol) obtained in (2) above by the preparation method of Example 84-(4).

MS (m/z): 654[M+H]

(4) Preparation of ((1R)-1-(3-((1-naphthamido)methyl)-5-benzyl-4,5-dihydroisoxazol-5-carboxamido)-3-methylbutyl)boronic acid

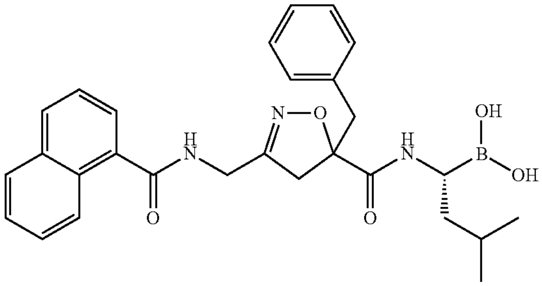

The title compound (0.037 g, 94%) was obtained using 3-((1-naphthamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.05 g, 0.078 mmol) obtained in (3) above by the preparation method of Example 1-(4).

NMR: $^1$H-NMR (400 MHz, $CDCl_3$); δ 8.24-8.23 (m, 1H), 7.90-7.84 (m, 2H), 7.52-7.38 (m, 4H), 7.24-7.14 (m, 6H), 6.27-6.25 (m, 1H), 4.25-4.23 (m, 2H), 3.44-3.40 (d, 1H), 3.33-3.30 (d, 1H), 3.13-3.06 (t, 2H), 2.85 (m, 1H), 1.42-1.22 (m, 3H), 0.83-0.81 (m, 6H)

MS (m/z): 502[M+H], 484[M-OH]

Example 93: Preparation of ((1R)-1-(3-((benzo[b]thiophen-2-carboxamido)methyl)-5-benzyl-4,5-dihydroisoxazol-5-carboxamido)-3-methylbutyl)boronic acid Through the processes (1), (2) and (3) below, the title compound was obtained.

(1) Preparation of methyl 3-((benzo[b]thiophen-2-carboxamido)methyl)-5-benzyl-4,5-dihydroisoxazol-5-carboxylate

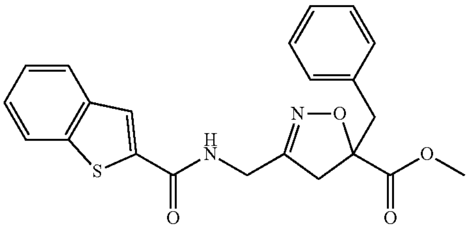 [SMILES: COC(=O)C1(Cc2ccccc2)CC(CNC(=O)c2cc3ccccc3s2)=NO1]

The title compound (0.10 g, 89%) was obtained using methyl 3-(aminomethyl)-5-benzyl-4,5-dihydroisoxazol-5-carboxylate hydrochloride (0.08 g, 0.28 mmol) obtained in Example 84-(1) and benzo[b]thiophen-2-carboxylic acid (0.05 g, 0.28 mmol) by the preparation method of Example 84-(2).

MS (m/z): 409[M+H]

(2) Preparation of 3-((benzo[b]thiophen-2-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

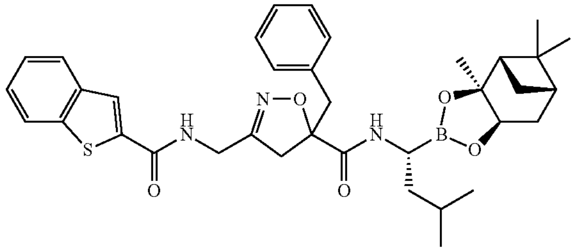 [SMILES: CC(C)C[C@H](NC(=O)C1(Cc2ccccc2)CC(CNC(=O)c2cc3ccccc3s2)=NO1)B1O[C@@H]2C[C@@H]3C[C@@H](C3(C)C)[C@]2(C)O1]

The title compound (0.11 g, 72%, 2 steps) was obtained using methyl 3-((benzo[b]thiophen-2-carboxamido)methyl)-5-benzyl-4,5-dihydroisoxazol-5-carboxylate (1 mmol) obtained in the process (1) above by the preparation method of Example 84-(3).

MS (m/z): 642[M+H]

(3) Preparation of ((1R)-1-(3-((benzo[b]thiophen-2-carboxamido)methyl)-5-benzyl-4,5-dihydroisoxazol-5-carboxamido)-3-methylbutyl)boronic acid

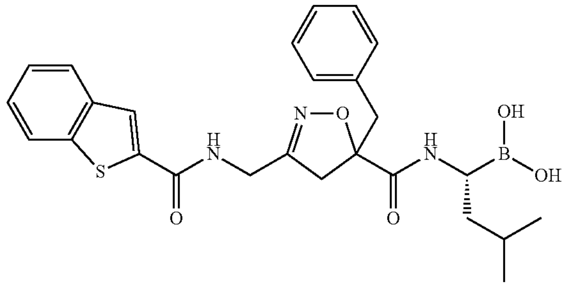 [SMILES: CC(C)C[C@H](NC(=O)C1(Cc2ccccc2)CC(CNC(=O)c2cc3ccccc3s2)=NO1)B(O)O]

The title compound (0.033 g, 36%) was obtained using 3-((benzo[b]thiophen-2-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (1 mmol) obtained in the process (2) above by the preparation method of Example 1-(4).

MS (m/z): 508[M+H], 490[M-OH]

Example 94: Preparation of ((1R)-1-(3-([1,1'-biphenyl]-4-carboxamidomethyl)-5-benzyl-4,5-dihydroisoxazol-5-carboxamido)-3-methylbutyl)boronic acid Through the processes (1), (2) and (3) below, the title compound was obtained.

(1) Preparation of methyl 3-([1,1'-biphenyl]-4-carboxamidomethyl)-5-benzyl-4,5-dihydroisoxazol-5-carboxylate

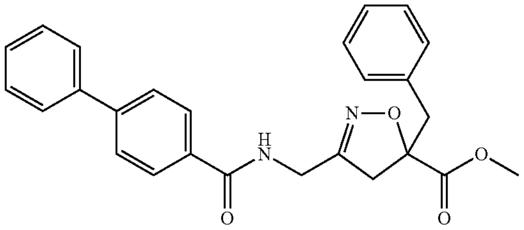 [SMILES: COC(=O)C1(Cc2ccccc2)CC(CNC(=O)c2ccc(-c3ccccc3)cc2)=NO1]

The title compound (0.07 g, 93%) was obtained using methyl 3-(aminomethyl)-5-benzyl-4,5-dihydroisoxazol-5-carboxylate hydrochloride (0.05 g, 0.18 mmol) obtained in Example 84-(1) and biphenyl-4-carboxylic acid (0.038 g, 0.19 mmol) by the preparation method of Example 84-(2).

MS (m/z): 429[M+H]

(2) Preparation of 3-([1,1'-biphenyl]-4-carboxamidomethyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

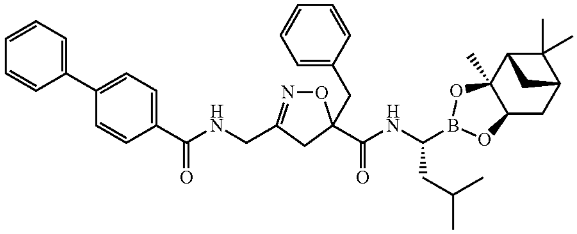 [SMILES: CC(C)C[C@H](NC(=O)C1(Cc2ccccc2)CC(CNC(=O)c2ccc(-c3ccccc3)cc2)=NO1)B1O[C@@H]2C[C@@H]3C[C@@H](C3(C)C)[C@]2(C)O1]

The title compound (0.068 g, 66%, 2 steps) was obtained using methyl 3-([1,1'-biphenyl]-4-carboxamidomethyl)-5-benzyl-4,5-dihydroisoxazol-5-carboxylate (0.07 g, 0.16 mmol) obtained in the process (1) above by the preparation method of Example 84-(3).

MS (m/z): 662[M+H]

(3) Preparation of ((1R)-1-(3-([1,1'-biphenyl]-4-carboxamidomethyl)-5-benzyl-4,5-dihydroisoxazol-5-carboxamido)-3-methylbutyl)boronic acid

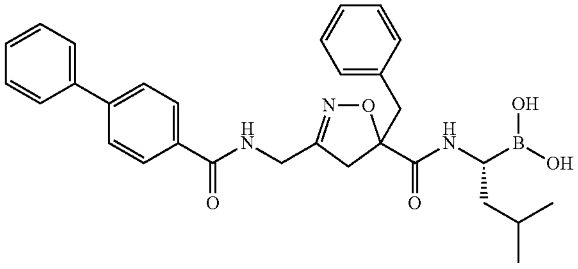 [SMILES: CC(C)C[C@H](NC(=O)C1(Cc2ccccc2)CC(CNC(=O)c2ccc(-c3ccccc3)cc2)=NO1)B(O)O]

The title compound (0.03 g, 55%) was obtained using 3-([1,1'-biphenyl]-4-carboxamidomethyl)-5-benzyl-N—

((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.068 g, 0.030 g, 0.10 mmol) obtained in the process (2) above by the preparation method of Example 1-(4).

NMR: 1H-NMR (400 MHz, MeOD-d4); δ 7.93-7.91 (m, 2H), 7.77-7.75 (m, 2H), 7.71-7.68 (m, 2H), 7.51-7.47 (m, 2H), 7.43-7.39 (m, 1H), 7.31-7.24 (m, 5H), 4.28 (s, 2H), 3.49-3.45 (d, 1H), 3.37-3.27 (m, 2H), 3.25-3.21 (d, 1H), 2.71-2.67 (m, 1H), 1.45-1.39 (m, 1H), 1.21-1.03 (m, 2H), 0.85-0.80 (dd, 6H)

MS (m/z): 528[M+H], 510[M-OH]

Example 95: Preparation of ((1R)-1-(3-([1,1'-biphenyl]-3-carboxamidomethyl)-5-benzyl-4,5-dihydroisoxazol-5-carboxamido)-3-methylbutyl)boronic acid Through the processes (1), (2) and (3) below, the title compound was obtained.

(1) Preparation of methyl 3-([1,1'-biphenyl]-3-carboxamidomethyl)-5-benzyl-4,5-dihydroisoxazol-5-carboxylate

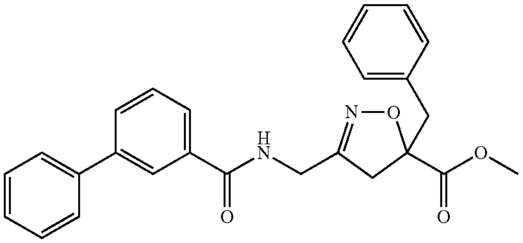 [SMILES: COC(=O)C1(Cc2ccccc2)CC(CNC(=O)c2cccc(-c3ccccc3)c2)=NO1]

The title compound (0.075 g, 99%) was obtained using methyl 3-(aminomethyl)-5-benzyl-4,5-dihydroisoxazol-5-carboxylate hydrochloride (0.05 g, 0.18 mmol) obtained in Example 84-(1) and biphenyl-4-carboxylic acid (0.038 g, 0.19 mmol) by the preparation method of Example 84-(2).

MS (m/z): 429[M+H]

(2) Preparation of 3-([1,1'-biphenyl]-3-carboxamidomethyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

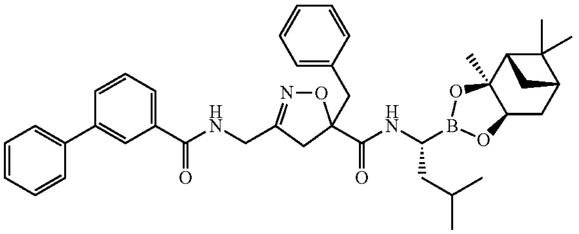 [SMILES: CC(C)C[C@H](NC(=O)C1(Cc2ccccc2)CC(CNC(=O)c2cccc(-c3ccccc3)c2)=NO1)B1O[C@@H]2C[C@@H]3C[C@@H](C3(C)C)[C@]2(C)O1]

The title compound (0.074 g, 66%, 2 steps) was obtained using methyl 3-([1,1'-biphenyl]-3-carboxamidomethyl)-5-benzyl-4,5-dihydroisoxazol-5-carboxylate (0.075 g, 0.18 mmol) obtained in (1) above by the preparation method of Example 84-(3).

MS (m/z): 662[M+H]

(3) Preparation of ((1R)-1-(3-([1,1'-biphenyl]-3-carboxamidomethyl)-5-benzyl-4,5-dihydroisoxazol-5-carboxamido)-3-methylbutyl)boronic acid

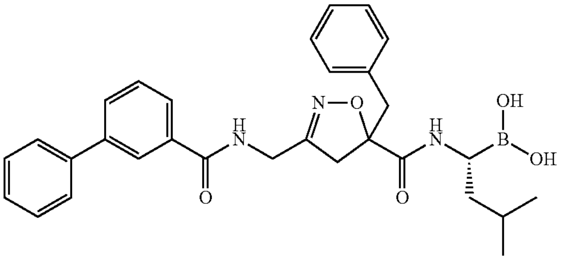 [SMILES: CC(C)C[C@H](NC(=O)C1(Cc2ccccc2)CC(CNC(=O)c2cccc(-c3ccccc3)c2)=NO1)B(O)O]

The title compound (0.034 g, 58%) was obtained using 3-([1,1'-biphenyl]-3-carboxamidomethyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.074 g, 0.11 mmol) obtained in (2) above by the preparation method of Example 1-(4).

NMR: $^1$H-NMR (400 MHz, MeOD-d4); δ 8.09 (m, 1H), 7.85-7.81 (m, 2H), 7.71-7.69 (m, 2H), 7.60-7.38 (m, 4H), 7.30-7.22 (m, 5H), 4.28 (s, 2H), 3.49-3.45 (d, 1H), 3.36-3.26 (m, 2H), 3.24-3.20 (d, 1H), 2.70-2.66 (m, 1H), 1.43-1.38 (m, 1H), 1.21-1.03 (m, 2H), 0.84-0.79 (dd, 6H)

MS (m/z): 528[M+H], 510[M-OH]

Example 96: Preparation of ((1R)-1-(5-benzyl-3-((6-phenylpicolinamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((6-phenylpicolinamido)methyl)-4,5-dihydroisoxazol-5-carboxylate

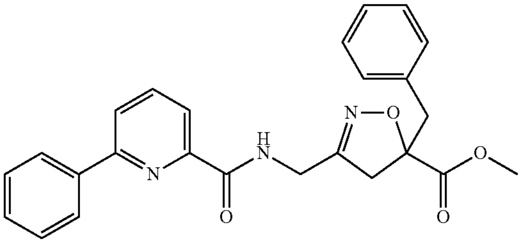 [SMILES: COC(=O)C1(Cc2ccccc2)CC(CNC(=O)c2cccc(-c3ccccc3)n2)=NO1]

The title compound (0.070 g, 90%) was obtained using methyl 3-(aminomethyl)-5-benzyl-4,5-dihydroisoxazol-5-carboxylate hydrochloride (0.06 g, 0.21 mmol) obtained in Example 84-(1) and 6-phenyl-pyridin-2-carboxylic acid (0.046 g, 0.23 mmol) by the preparation method of Example 84-(2).

MS (m/z): 430[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((6-phenylpicolinamido)methyl)-4,5-dihydroisoxazol-5-carboxamide

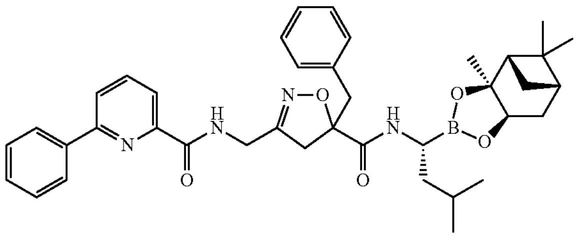 [SMILES: CC(C)C[C@H](NC(=O)C1(Cc2ccccc2)CC(CNC(=O)c2cccc(-c3ccccc3)n2)=NO1)B1O[C@@H]2C[C@@H]3C[C@@H](C3(C)C)[C@]2(C)O1]

The title compound (0.046 g, 42%, 2 steps) was obtained using methyl 5-benzyl-3-((6-phenylpicolinamido)methyl)-4,5-dihydroisoxazol-5-carboxylate (0.07 g, 0.16 mmol) obtained in (1) above by the preparation method of Example 84-(3).

MS (m/z): 663[M+H]

(3) Preparation of ((1R)-1-(5-benzyl-3-((6-phenylpicolinamido)methyl)-4,5-dihydroisoxazol-5-carboxamido)-3-methylbutyl)boronic acid

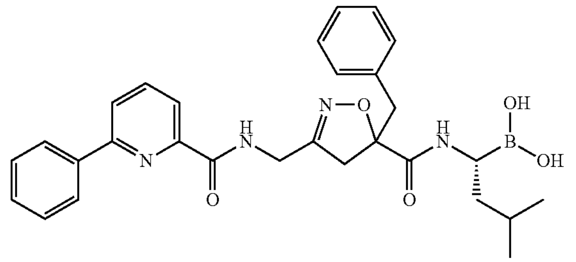 [SMILES: CC(C)C[C@H](NC(=O)C1(Cc2ccccc2)CC(CNC(=O)c2cccc(-c3ccccc3)n2)=NO1)B(O)O]

The title compound (0.020 g, 53%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((6-phenylpicolinamido)methyl)-4,5-dihydroisoxazol-5-carboxamide (0.046 g, 0.069 mmol) obtained in (2) above by the preparation method of Example 1-(4).

NMR: $^1$H-NMR (400 MHz, MeOD-$d_4$); δ 8.23-8.21 (m, 2H), 8.13-8.05 (m, 3H), 7.56-7.47 (m, 3H), 7.29-7.19 (m, 5H), 4.35 (s, 2H), 3.49-3.36 (m, 2H), 3.27-3.20 (m, 2H), 2.67-2.64 (m, 1H), 1.42-4.38 (m, 1H), 1.19-1.01 (m, 2H), 0.83-0.78 (dd, 6H)

MS (m/z): 529[M+H], 511[M-OH]

Example 97: Preparation of ((1R)-1-(3-([1,1'-biphenyl]-2-carboxamidomethyl)-5-benzyl-4,5-dihydroisoxazol-5-carboxamido)-3-methylbutyl)boronic acid Through the processes (1), (2) and (3) below, the title compound was obtained.

(1) Preparation of methyl 3-([1,1'-biphenyl]-2-carboxamidomethyl)-5-benzyl-4,5-dihydroisoxazol-5-carboxylate

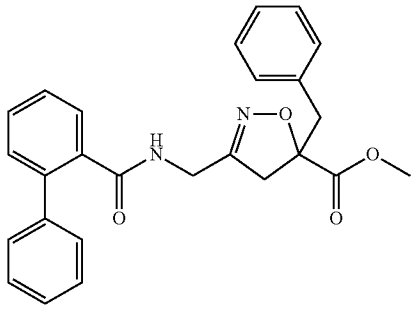 [SMILES: COC(=O)C1(Cc2ccccc2)CC(CNC(=O)c2ccccc2-c2ccccc2)=NO1]

The title compound (0.066 g, 73%) was obtained using methyl 3-(aminomethyl)-5-benzyl-4,5-dihydroisoxazol-5-carboxylate hydrochloride (0.06 g, 0.21 mmol) obtained in Example 84-(1) and biphenyl-2-carboxylic acid (0.046 g, 0.23 mmol) by the preparation method of Example 84-(2).

MS (m/z): 429[M+H]

(2) Preparation of 3-([1,1'-biphenyl]-2-carboxamidomethyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

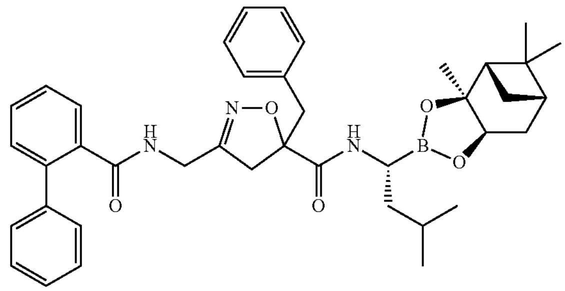 [SMILES: CC(C)C[C@H](NC(=O)C1(Cc2ccccc2)CC(CNC(=O)c2ccccc2-c2ccccc2)=NO1)B1O[C@@H]2C[C@@H]3C[C@@H](C3(C)C)[C@]2(C)O1]

The title compound (0.063 g, 63%, 2 steps) was obtained using methyl 3-([1,1'-biphenyl]-2-carboxamidomethyl)-5-benzyl-4,5-dihydroisoxazol-5-carboxylate (0.066 g, 0.15 mmol) obtained in (1) above by the preparation method of Example 84-(3).

MS (m/z): 662[M+H]

(3) Preparation of ((1R)-1-(3-([1,1'-biphenyl]-2-carboxamidomethyl)-5-benzyl-4,5-dihydroisoxazol-5-carboxamido)-3-methylbutyl)boronic acid

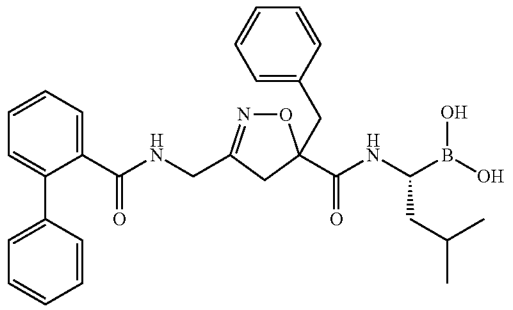 [SMILES: CC(C)C[C@H](NC(=O)C1(Cc2ccccc2)CC(CNC(=O)c2ccccc2-c2ccccc2)=NO1)B(O)O]

The title compound (0.029 g, 58%) was obtained using 3-([1,1'-biphenyl]-2-carboxamidomethyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.063 g, 0.095 mmol) obtained in (2) above by the preparation method of Example 1-(4).

NMR: $^1$H-NMR (400 MHz, MeOD-d4); δ 7.57-7.40 (m, 9H), 7.28-7.26 (m, 5H), 4.05 (s, 2H), 3.28-3.10 (m, 3H), 2.88-2.84 (d, 1H), 2.69-2.65 (t, 1H), 1.42-1.37 (m, 1H), 1.20-1.02 (m, 2H), 0.84-0.79 (dd, 6H)

MS (m/z): 528[M+H], 510[M-OH]

Example 98: Preparation of ((1R)-1-(5-benzyl-3-((3-(pyridin-2-yl)benzamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((3-(pyridin-2-yl)benzamido)methyl)-4,5-dihydroisoxazol-5-carboxylate

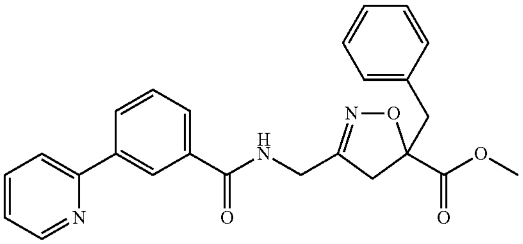 [SMILES: COC(=O)C1(Cc2ccccc2)CC(CNC(=O)c2cccc(-c3ccccn3)c2)=NO1]

The title compound (0.04 g, 44%) was obtained using methyl 3-(aminomethyl)-5-benzyl-4,5-dihydroisoxazol-5-carboxylate hydrochloride (0.06 g, 0.21 mmol) obtained in Example 84-(1) and 3-pyridin-2-yl-benzoic acid (0.046 g, 0.23 mmol) by the preparation method of Example 84-(2).

MS (m/z): 430[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-(pyridin-2-yl)benzamido)methyl)-4,5-dihydroisoxazol-5-carboxamide

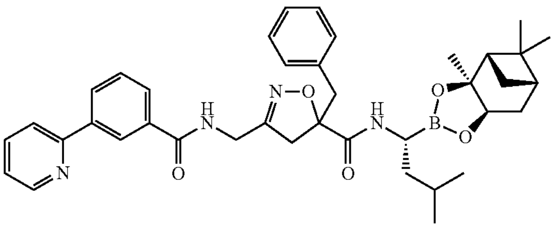 [SMILES: CC(C)C[C@H](NC(=O)C1(Cc2ccccc2)CC(CNC(=O)c2cccc(-c3ccccn3)c2)=NO1)B1O[C@@H]2C[C@@H]3C[C@@H](C3(C)C)[C@]2(C)O1]

The title compound (0.01 g, 19%, 2 steps) was obtained using methyl 5-benzyl-3-((3-(pyridin-2-yl)benzamido)methyl)-4,5-dihydroisoxazol-5-carboxylate (0.40 g, 0.093 mmol) obtained in the process (1) above by the preparation method of Example 84-(3).

MS (m/z): 663[M+H]

(3) Preparation of ((1R)-1-(5-benzyl-3-((3-(pyridin-2-yl)benzamido)methyl)-4,5-dihydroisoxazol-5-carboxamido)-3-methylbutyl)boronic acid

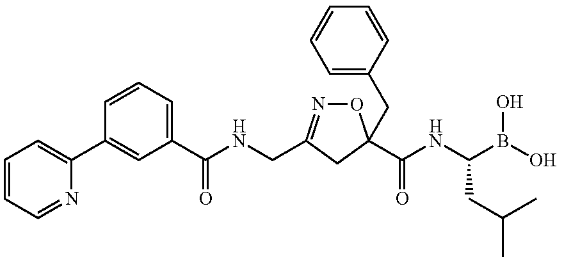 [SMILES: CC(C)C[C@H](NC(=O)C1(Cc2ccccc2)CC(CNC(=O)c2cccc(-c3ccccn3)c2)=NO1)B(O)O]

The title compound (0.005 g, 63%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-(pyridin-2-yl)benzamido)methyl)-4,5-dihydroisoxazol-5-carboxamide (0.01 g, 0.015 mmol) obtained in the process (2) above by the preparation method of Example 1-(4).

NMR: $^1$H-NMR (400 MHz, MeOD-d4); δ 8.69-8.67 (m, 1H), 8.45-8.44 (m, 1H), 8.20-8.17 (m, 1H), 7.97-7.90 (m, 3H), 7.66-7.62 (t, 1H), 7.44-7.41 (m, 1H), 7.30-7.22 (m, 5H), 4.29 (s, 2H), 3.50-3.46 (d, 1H), 3.37-3.28 (m, 2H), 3.24-3.21 (d, 1H), 2.70-2.66 (t, 1H), 1.45-1.38 (m, 1H), 1.21-1.03 (m, 3H), 0.84-0.79 (dd, 6H)

MS (m/z): 529[M+H], 511[M-OH]

Example 99: Preparation of ((1R)-1-(5-benzyl-3-((N-methylisoquinolin-1-carboxamido)methyl)-4,5-dihydroisoxazol-5-carboxamido)-3-methylbutyl) boronic acid Through the processes (1), (2), (3) and (4) below, the title compound was obtained.

(1) Preparation of methyl 5-benzyl-3-((methylamino)methyl)-4,5-dihydroisoxazol-5-carboxylate hydrochloride

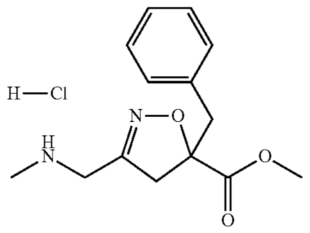

The title compound (0.19 g, 99%) was obtained using methyl 5-benzyl-3-(((tert-butoxycarbonyl)(methyl)amino)methyl)-4,5-dihydroisoxazol-5-carboxylate (0.24 g, 0.65 mmol) obtained in Preparation Example 12 by the preparation method of Example 84-(1).

MS (m/z): 263[M+H]

(2) Preparation of methyl 5-benzyl-3-((S)-1-(N-methylisoquinolin-1-carboxamido)ethyl)-4,5-dihydroisoxazol-5-carboxylate

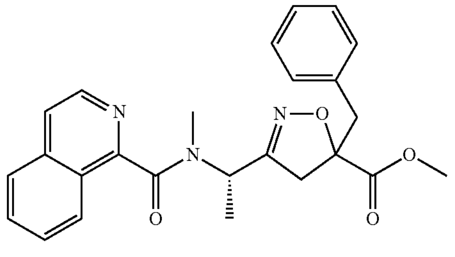 [SMILES: COC(=O)C1(Cc2ccccc2)CC([C@H](C)N(C)C(=O)c2nccc3ccccc23)=NO1]

The title compound (0.12 g, 86%) was obtained using methyl 5-benzyl-3-((methylamino)methyl)-4,5-dihydroisoxazol-5-carboxylate hydrochloride (0.1 g, 0.34 mmol) obtained in (1) above and isoquinolin-1-carboxylic acid (0.064 g, 0.37 mmol) by the preparation method of Example 84-(2).

NMR: $^{1}$H-NMR (500 MHz, $CDCl_3$); δ 8.52-8.51 (d, 1H), 7.98-7.96 (d, 1H), 7.89-7.87 (t, 1H), 7.75-7.66 (m, 4H), 7.30-7.17 (m, 5H), 4.59-4.56 (d, 1H), 4.31-4.28 (d, 1H), 3.82 (s, 3H), 3.61-3.57 (d, 1H), 3.40-3.37 (d, 1H), 3.19-3.14 (m, 2H), 2.48 (s, 3H)

MS (m/z): 432[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((N-methylisoquinolin-1-carboxamido)methyl)-4,5-dihydroisoxazol-5-carboxamide

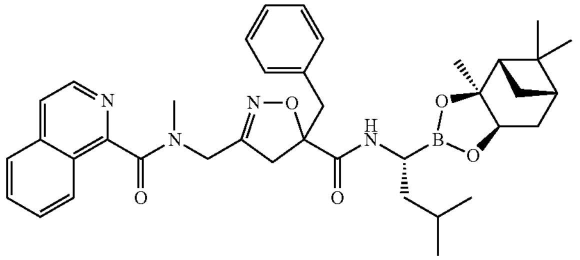 [SMILES: CC(C)C[C@H](NC(=O)C1(Cc2ccccc2)CC(CN(C)C(=O)c2nccc3ccccc23)=NO1)B1O[C@@H]2C[C@@H]3C[C@@H](C3(C)C)[C@]2(C)O1]

The title compound (0.048 g, 60%, 2 steps) was obtained using methyl 5-benzyl-3-((S)-1-(N-methylisoquinolin-1-carboxamido)ethyl)-4,5-dihydroisoxazol-5-carboxylate (0.12 g, 0.29 mmol) obtained in (2) above by the preparation method of Example 84-(3).

MS (m/z): 651[M+H]

(4) Preparation of ((1R)-1-(5-benzyl-3-((N-methylisoquinolin-1-carboxamido)methyl)-4,5-dihydroisoxazol-5-carboxamido)-3-methylbutyl)boronic acid

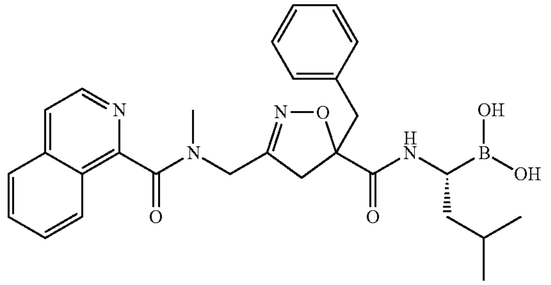 [SMILES: CC(C)C[C@H](NC(=O)C1(Cc2ccccc2)CC(CN(C)C(=O)c2nccc3ccccc23)=NO1)B(O)O]

The title compound (0.028 g, 73%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((N-methylisoquinolin-1-carboxamido)methyl)-4,5-dihydroisoxazol-5-carboxamide (0.048 g, 0.074 mmol) obtained in (3) above by the preparation method of Example 1-(4).

NMR: $^{1}$H-NMR (500 MHz, MeOD-d4); δ 8.49-8.45 (m, 1H), 8.05-8.00 (m, 2H), 7.92-7.71 (m, 3H), 7.32-7.17 (m, 5H), 4.60-4.46 (m, 2H), 3.56-3.34 (m, 2H), 3.27-3.20 (m, 2H), 3.07-3.01 (m, 1H), 2.74-2.58 (m, 3H), 1.45-1.39 (m, 1H), 1.27-1.10 (m, 2H), 0.82-0.77 (m, 6H)

MS (m/z): 517[M+H], 499[M-OH]

Example 100: Preparation of ((1R)-1-(3-((isoquinolin-1-carboxamido)methyl)-5-(3-methoxybenzyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(3-methoxybenzyl)-4,5-dihydroisoxazol-5-carboxylate hydrochloride

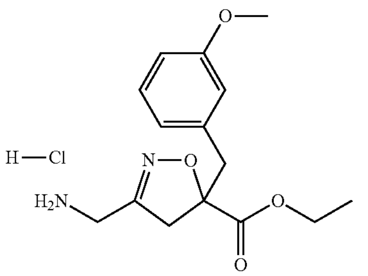

The title compound (0.26 g, 99%) was obtained using ethyl 3-(((tert-butoxycarbonyl)amino)methyl)-5-(3-methoxybenzyl)-4,5-dihydroisoxazol-5-carboxylate (0.31 g, 0.79 mmol) obtained in Preparation Example 13 by the preparation method of Example 84-(1).

MS (m/z): 293[M+H]

(2) Preparation of ethyl 3-((isoquinolin-1-carboxamido)methyl)-5-(3-methoxybenzyl)-4,5-dihydroisoxazol-5-carboxylate

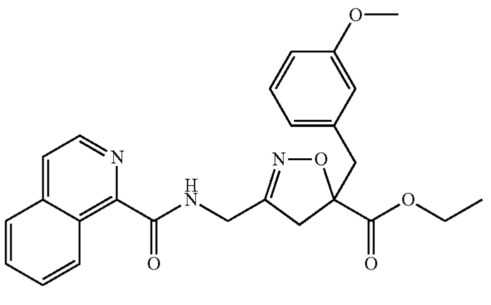 [SMILES: CCOC(=O)C1(Cc2cccc(OC)c2)CC(CNC(=O)c2nccc3ccccc23)=NO1]

The title compound (0.126 g, 71%) was obtained using ethyl 3-(aminomethyl)-5-(3-methoxybenzyl)-4,5-dihydroisoxazol-5-carboxylate hydrochloride (0.13 g, 0.40 mmol) obtained in (1) above and isoquinolin-1-carboxylic acid (0.075 g, 0.44 mmol) by the preparation method of Example 84-(2).

MS (m/z): 448[M+H]

(3) Preparation of 3-((isoquinolin-1-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

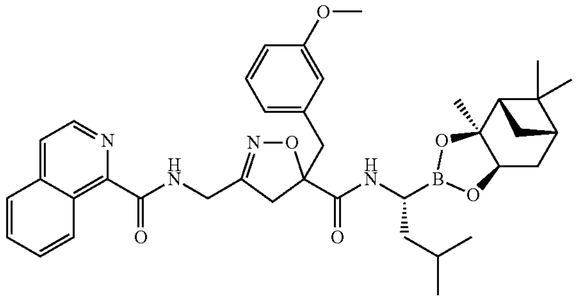 [SMILES: COc1cccc(CC2(C(=O)N[C@@H](CC(C)C)B3O[C@@H]4C[C@@H]5C[C@@H](C5(C)C)[C@]4(C)O3)CC(CNC(=O)c3nccc4ccccc34)=NO2)c1]

The title compound (0.116 g, 67%, 2 steps) was obtained using ethyl 3-((isoquinolin-1-carboxamido)methyl)-5-(3-methoxybenzyl)-4,5-dihydroisoxazol-5-carboxylate (0.126 g, 0.28 mmol) obtained in (2) above by the preparation method of Example 84-(3).

MS (m/z): 667[M+H]

(4) Preparation of ((1R)-1-(3-((isoquinolin-1-carboxamido)methyl)-5-(3-methoxybenzyl)-4,5-dihydroisoxazol-5-carboxamido)-3-methylbutyl)boronic acid

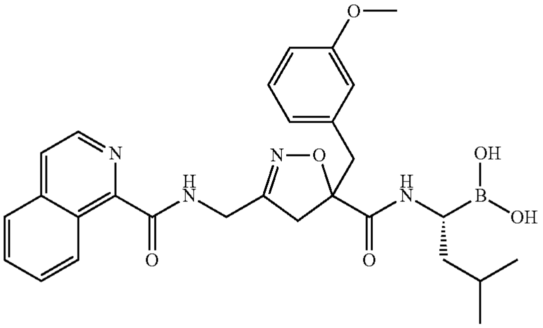 [SMILES: COc1cccc(CC2(C(=O)N[C@@H](CC(C)C)B(O)O)CC(CNC(=O)c3nccc4ccccc34)=NO2)c1]

The title compound (0.026 g, 28%) was obtained using 3-((isoquinolin-1-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.116 g, 0.17 mmol) obtained in (3) above by the preparation method of Example 1-(4).

NMR: $^1$H-NMR (400 MHz, $CDCl_3$); δ 9.51-9.49 (d, 1H), 8.50-8.49 (t, 1H), 8.39-8.38 (d, 1H), 7.84-7.65 (m, 4H), 7.18-7.14 (t, 1H), 6.85-6.72 (m, 4H) 4.35-4.26 (m, 2H), 3.72 (s, 3H), 3.45-3.29 (m, 2H), 3.13-3.09 (m, 2H), 2.79 (m, 1H), 1.33-1.19 (m, 3H), 0.78-0.76 (m, 6H)

MS (m/z): 533[M+H], 515[M-OH]

Example 101: Preparation of ((1R)-1-(5-(4-chlorobenzyl)-3-((isoquinolin-1-carboxamido)methyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(4-chlorobenzyl)-4,5-dihydroisoxazol-5-carboxylate hydrochloride

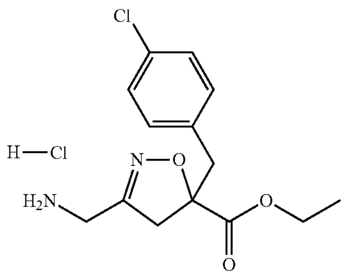

The title compound (0.14 g, 99%) was obtained using ethyl 3-(((tert-butoxycarbonyl)amino)methyl)-5-(4-chlorobenzyl)-4,5-dihydroisoxazol-5-carboxylate (0.17 g, 0.43 mmol) obtained in Preparation Example 14 by the preparation method of Example 84-(1).

MS (m/z): 297[M+H]

(2) Preparation of ethyl 5-(4-chlorobenzyl)-3-((isoquinolin-1-carboxamido)methyl)-4,5-dihydroisoxazol-5-carboxylate

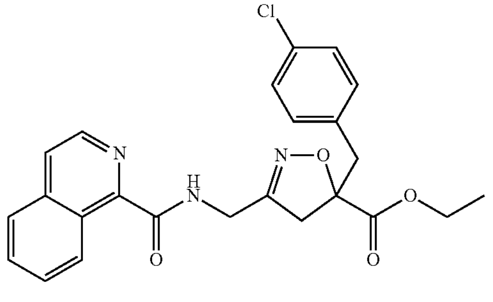 [SMILES: CCOC(=O)C1(Cc2ccc(Cl)cc2)CC(CNC(=O)c2nccc3ccccc23)=NO1]

The title compound (0.155 g, 82%) was obtained using ethyl 3-(aminomethyl)-5-(4-chlorobenzyl)-4,5-dihydroisoxazol-5-carboxylate hydrochloride (0.14 g, 0.42 mmol) obtained in (1) above and isoquinolin-1-carboxylic acid (0.080 g, 0.46 mmol) by the preparation method of Example 84-(2).

MS (m/z): 452[M+H]

(3) Preparation of 5-(4-chlorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

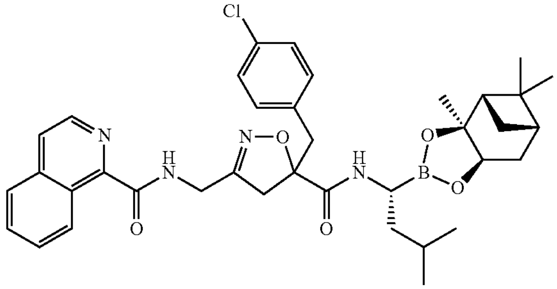 [SMILES: CC(C)C[C@H](NC(=O)C1(Cc2ccc(Cl)cc2)CC(CNC(=O)c2nccc3ccccc23)=NO1)B1O[C@@H]2C[C@@H]3C[C@@H](C3(C)C)[C@]2(C)O1]

The title compound (0.159 g, 69%, 2 steps) was obtained using ethyl 5-(4-chlorobenzyl)-3-((isoquinolin-1-carboxamido)methyl)-4,5-dihydroisoxazol-5-carboxylate (0.155 g, 0.27 mmol) obtained in (2) above by the preparation method of Example 84-(3).

MS (m/z): 671[M+H]

(4) Preparation of ((1R)-1-(5-(4-chlorobenzyl)-3-((isoquinolin-1-carboxamido)methyl)-4,5-dihydroisoxazol-5-carboxamido)-3-methylbutyl)boronic acid

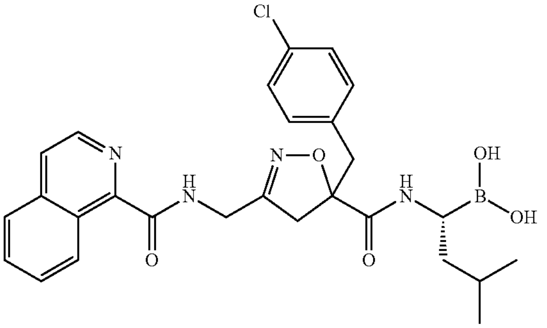 [SMILES: CC(C)C[C@H](NC(=O)C1(Cc2ccc(Cl)cc2)CC(CNC(=O)c2nccc3ccccc23)=NO1)B(O)O]

The title compound (0.089 g, 70%) was obtained using 5-(4-chlorobenzyl)-3-((isoquinolin-1-carboxamido) methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.159 g, 0.24 mmol) obtained in (3) above by the preparation method of Example 1-(4).

NMR: $^1$H-NMR (500 MHz, $CDCl_3$); δ 9.43-9.41 (d, 1H), 8.46-8.43 (t, 1H), 8.22-8.21 (d, 1H), 7.85-7.65 (m, 4H), 7.59 (m, 1H), 7.19-7.16 (m, 4H), 4.35-4.28 (m, 2H), 3.49-3.45 (d, 1H), 3.31-3.28 (d, 1H), 3.11-3.07 (d, 1H), 3.03-3.01 (d, 1H), 2.89 (m, 1H), 1.29-1.18 (m, 3H), 0.75-0.72 (m, 6H)

MS (m/z): 537[M+H], 519[M-OH]

Example 102: Preparation of ((1R)-1-(5-(2-chlorobenzyl)-3-((isoquinolin-1-carboxamido)methyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(2-chlorobenzyl)-4,5-dihydroisoxazol-5-carboxylate hydrochloride

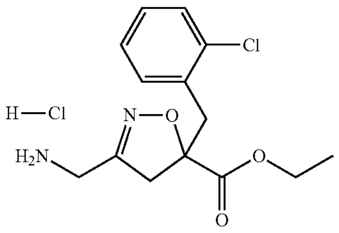

The title compound (0.13 g, 99%) was obtained using ethyl 3-(((tert-butoxycarbonyl)amino)methyl)-5-(2-chlorobenzyl)-4,5-dihydroisoxazol-5-carboxylate (0.16 g, 0.40 mmol) obtained in Preparation Example 15 by the preparation method of Example 84-(1).

MS (m/z): 297[M+H]

(2) Preparation of ethyl 5-(2-chlorobenzyl)-3-((isoquinolin-1-carboxamido)methyl)-4,5-dihydroisoxazol-5-carboxylate

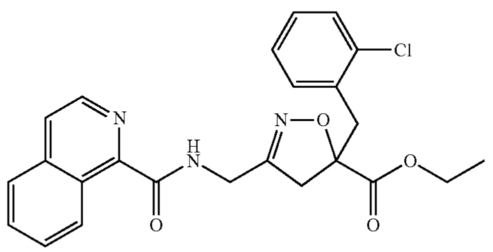 [SMILES: CCOC(=O)C1(Cc2ccccc2Cl)CC(CNC(=O)c2nccc3ccccc23)=NO1]

The title compound (0.10 g, 89%) was obtained using ethyl 3-(aminomethyl)-5-(2-chlorobenzyl)-4,5-dihydroisoxazol-5-carboxylate hydrochloride (0.13 g, 0.39 mmol) obtained in (1) above and isoquinolin-1-carboxylic acid (0.068 g, 0.39 mmol) by the preparation method of Example 84-(2).

MS (m/z): 452[M+H]

(3) Preparation of 5-(2-chlorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

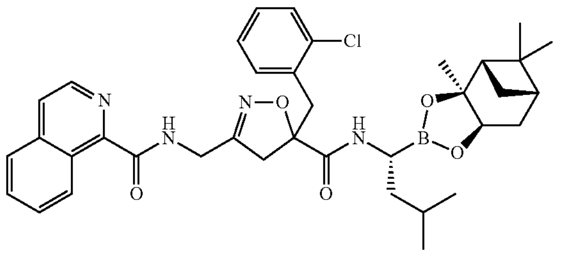 [SMILES: CC(C)C[C@H](NC(=O)C1(Cc2ccccc2Cl)CC(CNC(=O)c2nccc3ccccc23)=NO1)B1O[C@@H]2C[C@@H]3C[C@@H](C3(C)C)[C@]2(C)O1]

The title compound (0.11 g, 72%, 2 steps) was obtained using ethyl 5-(2-chlorobenzyl)-3-((isoquinolin-1-carboxamido)methyl)-4,5-dihydroisoxazol-5-carboxylate (0.10 g, 0.25 mmol) obtained in (2) above by the preparation method of Example 84-(3).

MS (m/z): 671[M+H]

(4) Preparation of ((1R)-1-(5-(2-chlorobenzyl)-3-((isoquinolin-1-carboxamido)methyl)-4,5-dihydroisoxazol-5-carboxamido)-3-methylbutyl)boronic acid

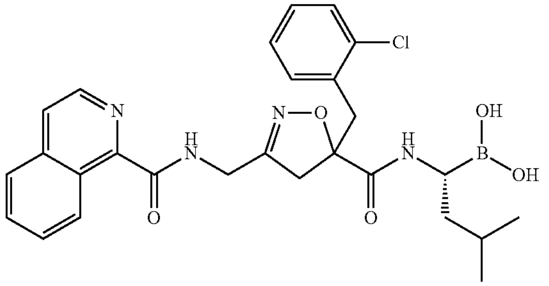 [SMILES: CC(C)C[C@H](NC(=O)C1(Cc2ccccc2Cl)CC(CNC(=O)c2nccc3ccccc23)=NO1)B(O)O]

The title compound (0.033 g, 36%) was obtained using 5-(2-chlorobenzyl)-3-((isoquinolin-1-carboxamido) methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.11 g, 0.18 mmol) obtained in (3) above by the preparation method of Example 1-(4).

MS (m/z): 537[M+H], 519[M-OH]

Example 103: Preparation of ((1R)-1-(3-((2-methoxybenzamido)methyl)-4,5-dihydroisoxazol-5-carboxamido)-3-methylbutyl)boronic acid Through the processes (1), (2) and (3) below, the title compound was obtained.

(1) Preparation of ethyl 3-((2-methoxybenzamido) methyl)-4,5-dihydroisoxazol-5-carboxylate

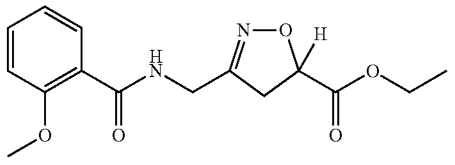 [SMILES: CCOC(=O)C1CC(CNC(=O)c2ccccc2OC)=NO1]

The title compound (0.17 g, 44%) was obtained using ethyl (aminomethyl)-4,5-dihydroisoxazol-5-carboxylate; hydrochloric acid salt (0.26 g, 1.2 mmol) obtained in Example 59-(1) and 2-methoxy-benzoic acid (0.23 g, 1.4 mol) by the preparation method of Example 59-(2).

MS (m/z): 307[M+H]

(2) Preparation of 3-((2-methoxybenzamido) methyl)-N—((R)-3-methyl-1-((3aS,4S,6S,7aR)-3a,5,5-trimethylhexahydro-4,6-metanobenzo[d][1,3,2] dioxaborol-2-yl)butyl)-4,5-dihydroisoxazol-5-carboxamide

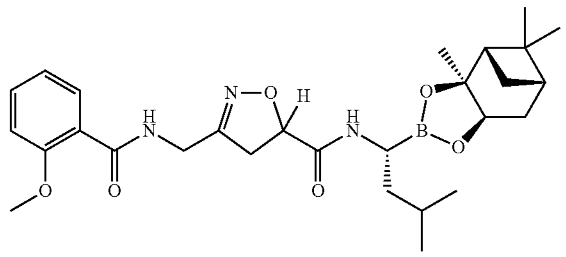 [SMILES: COc1ccccc1C(=O)NCC1=NOC(C(=O)N[C@@H](CC(C)C)B2O[C@@H]3C[C@@H]4C[C@@H](C4(C)C)[C@]3(C)O2)C1]

The title compound (0.12 g, 41%, 2 steps) was obtained using ethyl 3-((2-methoxybenzamido)methyl)-4,5-dihydroisoxazol-5-carboxylate (0.17 g, 0.54 mmol) obtained in (1) above by the preparation methods of Examples 1-(2) and (3).

MS (m/z): 526[M+H]

(3) Preparation of N-[(1R)-1-(dihydroxyboranyl)-3-methylbutyl]-3-{[(2-methoxyphenyl)formamido] methyl}-4,5-dihydro-1,2-oxazol-5-carboxamide

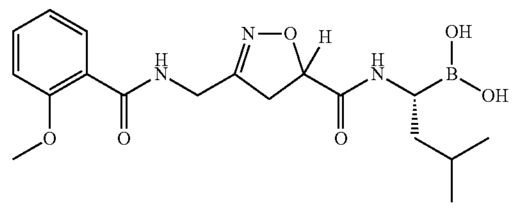 [SMILES: COc1ccccc1C(=O)NCC1=NOC(C(=O)N[C@@H](CC(C)C)B(O)O)C1]

The title compound (0.043 g, 50%) was obtained using 3-((2-methoxybenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.12 g, 0.22 mmol) obtained in (2) above by the preparation method of Example 1-(4).

MS (m/z): 392[M+H], 374[M-OH]

Example 104: Preparation of ((1R)-1-(3-((S)-1-benzamido-3-methylbutyl)-4,5-dihydroisoxazol-5-carboxamido)-3-methylbutyl)boronic acid Through the processes (1), (2) and (3) below, the title compound was obtained.

(1) Preparation of ethyl 3-((S)-1-benzamido-3-methylbutyl)-4,5-dihydroisoxazol-5-carboxylate

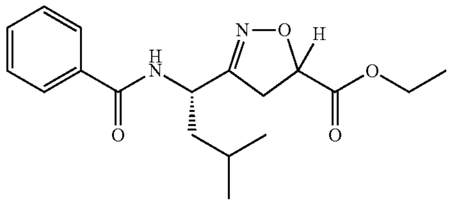 [SMILES: CCOC(=O)C1CC([C@H](CC(C)C)NC(=O)c2ccccc2)=NO1]

The title compound (0.30 g, 63%) was obtained using ethyl 3-((S)-1-amino-3-methylbutyl)-4,5-dihydroisoxazol-5-carboxylate hydrochloride (0.38 g, 1.44 mmol) obtained in Example 73-(1) and benzoic acid (0.19 g, 1.58 mmol) by the preparation method of Example 59-(2).

MS (m/z): 333[M+H]

(2) Preparation of 3-((S)-1-benzamido-3-methylbutyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

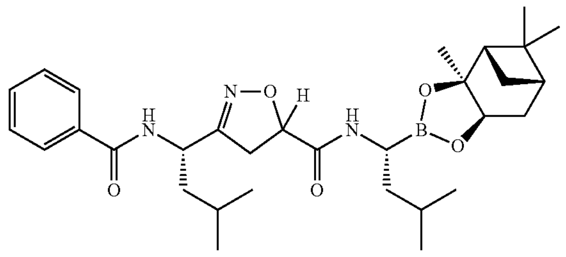 [SMILES: CC(C)C[C@H](NC(=O)C1CC([C@H](CC(C)C)NC(=O)c2ccccc2)=NO1)B1O[C@@H]2C[C@@H]3C[C@@H](C3(C)C)[C@]2(C)O1]

The title compound (0.096 g, 19%, 2 steps) was obtained using ethyl 3-((S)-1-benzamido-3-methylbutyl)-4,5-dihydroisoxazol-5-carboxylate (0.30 g, 0.90 mmol) obtained in (1) above by the preparation methods of Examples 1-(2) and (3).

MS (m/z): 552[M+H]

(3) Preparation of ((1R)-1-(3-((S)-1-benzamido-3-methylbutyl)-4,5-dihydroisoxazol-5-carboxamido)-3-methylbutyl)boronic acid

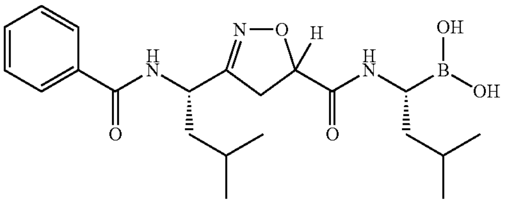

The title compound (0.012 g, 17%) was obtained using 3-((S)-1-benzamido-3-methylbutyl)-N—((R)-3-methyl-1-((3aS,4S,6S,7aR)-3a,5,5-trimethylhexahydro-4,6-metano-benzo[d][1,3,2]dioxaborol-2-yl)butyl)-4,5-dihydroisoxazol-5-carboxamide (0.096 g, 0.17 mmol) obtained in (2) above by the preparation method of Example 1-(4).

MS (m/z): 418[M+H], 400[M-OH]

Example 105: Preparation of ((1R)-3-methyl-1-(3-((S)-3-methyl-1-(2-phenylacetamido)butyl)-4,5-dihydroisoxazol-5-carboxamido)butyl)boronic acid Through the processes (1), (2) and (3) below, the title compound was obtained.

(1) Preparation of ethyl 3-((S)-3-methyl-1-(2-phenylacetamido)butyl)-4,5-dihydroisoxazol-5-carboxylate

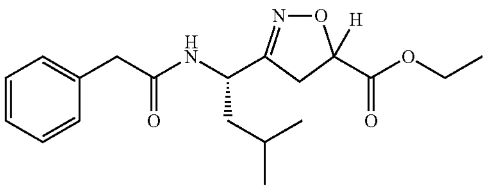 [SMILES: CCOC(=O)C1CC([C@H](CC(C)C)NC(=O)Cc2ccccc2)=NO1]

The title compound (0.275 g, 73%) was obtained using ethyl 3-((S)-1-amino-3-methylbutyl)-4,5-dihydroisoxazol-5-carboxylate hydrochloride (0.287 g, 1.08 mmol) obtained in Example 73-(1) and phenylacetic acid (0.16 g, 1.2 mmol) by the preparation method of Example 59-(2).

MS (m/z): 347[M+H]

(2) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-((S)-3-methyl-1-(2-phenylacetamido)butyl)-4,5-dihydroisoxazol-5-carboxamide

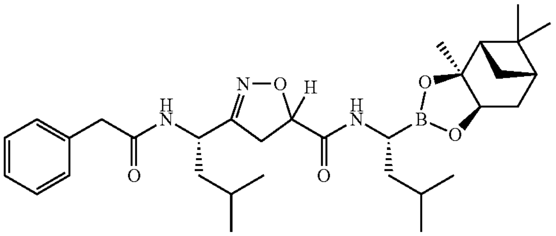 [SMILES: CC(C)C[C@H](NC(=O)C1CC([C@H](CC(C)C)NC(=O)Cc2ccccc2)=NO1)B1O[C@@H]2C[C@@H]3C[C@@H](C3(C)C)[C@]2(C)O1]

The title compound (0.09 g, 19%, 2 steps) was obtained using ethyl 3-((S)-3-methyl-1-(2-phenylacetamido)butyl)-4,5-dihydroisoxazol-5-carboxylate (0.275 g, 0.79 mmol) obtained in (1) above by the preparation methods of Examples 1-(2) and (3).

MS (m/z): 566[M+H]

(3) Preparation of ((1R)-3-methyl-1-(3-((S)-3-methyl-1-(2-phenylacetamido)butyl)-4,5-dihydroisoxazol-5-carboxamido)butyl)boronic acid

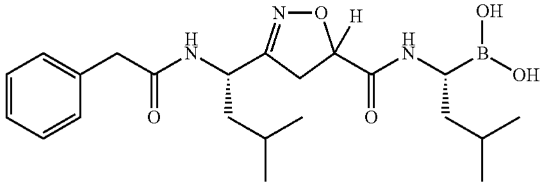 [SMILES: CC(C)C[C@H](NC(=O)C1CC([C@H](CC(C)C)NC(=O)Cc2ccccc2)=NO1)B(O)O]

The title compound (0.026 g, 38%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-((S)-3-methyl-1-(2-phenylacetamido)butyl)-4,5-dihydroisoxazol-5-carboxamide (0.09 g, 0.16 mmol) obtained in (2) above by the preparation method of Example 1-(4).

MS (m/z): 432[M+H], 414[M-OH]

Example 106: Preparation of ((1R)-1-(5-benzyl-3-((pyrazin-2-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((pyrazin-2-carboxamido)methyl)-4,5-dihydroisoxazol-5-carboxylate

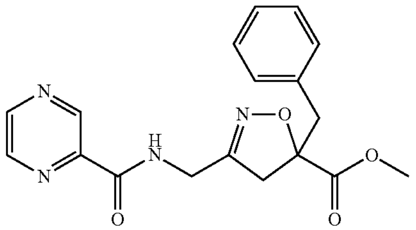 [SMILES: COC(=O)C1(Cc2ccccc2)CC(CNC(=O)c2cnccn2)=NO1]

The title compound (0.11 g, 74%) was obtained using methyl 3-(aminomethyl)-5-benzyl-4,5-dihydroisoxazol-5-carboxylate hydrochloride (0.056 g, 0.46 mmol) obtained in Example 84-(1) by the preparation method of Example 84-(2).

MS (m/z): 355[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((pyrazin-2-carboxamido)methyl)-4,5-dihydroisoxazol-5-carboxamide

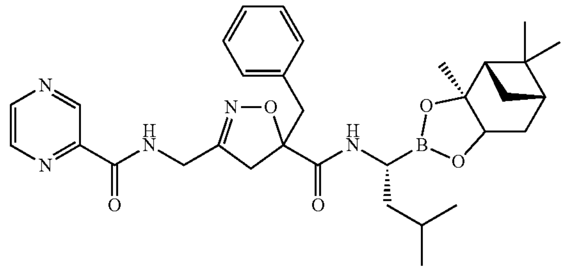 [SMILES: CC(C)C[C@H](NC(=O)C1(Cc2ccccc2)CC(CNC(=O)c2cnccn2)=NO1)B1OC2C[C@@H]3C[C@@H](C3(C)C)[C@]2(C)O1]

The title compound (0.11 g, 60%, 2 steps) was obtained using methyl 5-benzyl-3-((pyrazin-2-carboxamido)methyl)-4,5-dihydroisoxazol-5-carboxylate (0.11 g, 0.31 mmol) obtained in (1) above by the preparation method of Example 84-(3).

MS (m/z): 588[M+H]

(3) Preparation of ((1R)-1-(5-benzyl-3-((pyrazin-2-carboxamido)methyl)-4,5-dihydroisoxazol-5-carboxamido)-3-methylbutyl)boronic acid

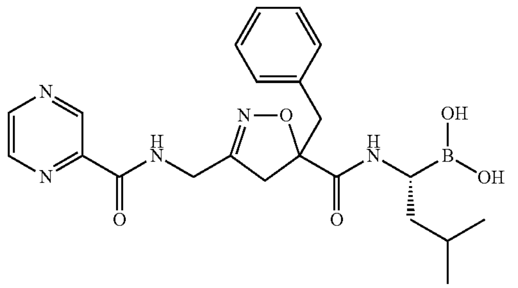 [SMILES: CC(C)C[C@H](NC(=O)C1(Cc2ccccc2)CC(CNC(=O)c2cnccn2)=NO1)B(O)O]

The title compound (0.018 g, 39%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((pyrazin-2-carboxamido)methyl)-4,5-dihydroisoxazol-5-carboxamide (0.06 g, 0.10 mmol) obtained in (2) above by the preparation method of Example 1-(4).

NMR: $^1$H-NMR (400 MHz, $CDCl_3$); δ 9.35-9.34 (d, 1H), 8.76-8.75 (d, 1H), 8.48-8.47 (d, 1H), 8.06-8.03 (m, 1H), 7.27-7.21 (m, 5H), 7.19 (m, 1H), 4.17-4.22 (m, 2H), 3.40-3.33 (m, 2H), 3.15-3.04 (m, 2H), 2.82 (m, 1H), 1.35-1.21 (m, 3H), 0.82-0.79 (m, 6H)

MS (m/z): 454[M+H], 436[M-OH]

Example 107: Preparation of ((1R)-1-(5-benzyl-3-((5-methylisoxazol-3-carboxamido)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-[[(5-methyl-isoxazol-3-carbonyl)amino]methyl]-4H-isoxazol-5-carboxylate

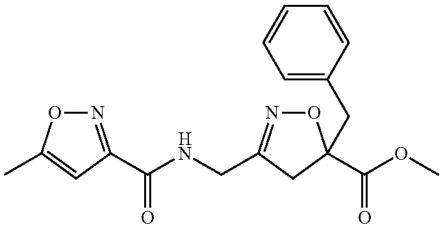

The title compound (0.087 g, 51%) was obtained using methyl 3-(aminomethyl)-5-benzyl-4,5-dihydroisoxazol-5-carboxylate hydrochloride (0.1 g, 0.35 mmol) obtained in Example 84-(1) and 5-methyl-isooxazol-3-carboxylic acid (0.049 g, 0.39 mmol) by the preparation method of Example 84-(2).

NMR: $^1$H-NMR (500 MHz, $CDCl_3$); δ 7.25-7.20 (m, 5H), 6.29 (m, 1H), 6.41 (s, 1H), 4.18-4.13 (m, 2H), 3.76 (s, 3H), 3.14-3.38 (d, 1H), 3.31-3.28 (d, 1H), 3.11-3.08 (d, 1H), 3.00-2.97 (d, 1H), 2.48 (s, 3H)

MS (m/z): 358[M+H]

(2) Preparation of N-((5-benzyl-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)-5-methylisoxazol-3-carboxamide

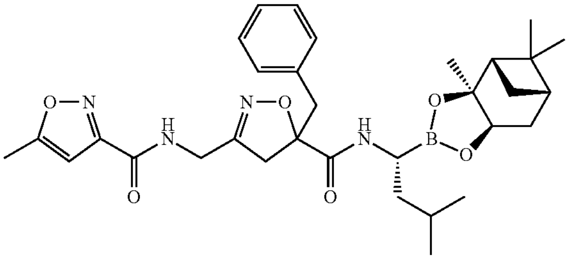

The title compound (0.042 g, 29%, 2 steps) was obtained using methyl 5-benzyl-3-[[(5-methylisoxazol-3-carbonyl) amino]methyl]-4H-isoxazol-5-carboxylate (0.087 g, 0.24 mmol) obtained in (1) above by the preparation method of Example 84-(3).

MS (m/z): 591[M+H]

(3) Preparation of ((1R)-1-(5-benzyl-3-((5-methylisoxazol-3-carboxamido)methyl)-4,5-dihydroisoxazol-5-carboxamido)-3-methylbutyl)boronic acid

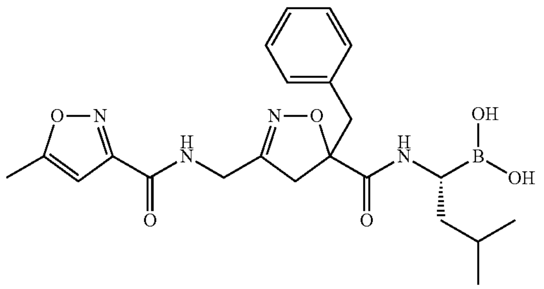 [SMILES: Cc1cc(C(=O)NCC2=NOC(Cc3ccccc3)(C(=O)N[C@@H](CC(C)C)B(O)O)C2)no1]

The title compound (0.016 g, 49%) was obtained using N-((5-benzyl-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)-5-methylisoxazol-3-carboxamide (0.042 g, 0.071 mmol) obtained in (2) above by the preparation method of Example 1-(4).

NMR: $^1$H-NMR (500 MHz, $CDCl_3$); δ 7.27-7.21 (m, 5H), 6.40 (s, 1H), 4.24-4.11 (m, 2H), 3.39-3.33 (t, 2H), 3.15-3.12 (d, 1H), 3.04-3.01 (d, 1H), 2.46 (s, 3H), 1.34-1.19 (m, 3H), 0.52-0.82 (d, 6H)

MS (m/z): 457[M+H], 439[M-OH]

Example 108: Preparation of ((1R)-1-(5-benzyl-3-((1,2,3,4-tetrahydronaphthalen-1-carboxamido) methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((1,2,3,4-tetrahydronaphthalen-1-carboxamido)methyl)-4,5-dihydroisoxazol-5-carboxylate

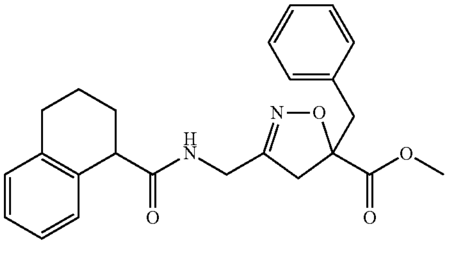 [SMILES: COC(=O)C1(Cc2ccccc2)CC(CNC(=O)C2CCCc3ccccc32)=NO1]

The title compound (0.063 g, 74%) was obtained using methyl 3-(aminomethyl)-5-benzyl-4,5-dihydroisoxazol-5-carboxylate hydrochloride (0.06 g, 0.21 mmol) obtained in Example 84-(1) and 1,2,3,4-tetrahydro-naphthalen-1-carboxylic acid (0.041 g, 0.23 mmol) by the preparation method of Example 84-(2).

MS (m/z): 407[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1,2,3,4-tetrahydronaphthalen-1-carboxamido)methyl)-4,5-dihydroisoxazol-5-carboxamide

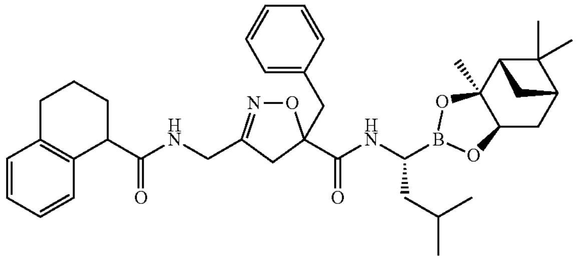 [SMILES: CC(C)C[C@H](NC(=O)C1(Cc2ccccc2)CC(CNC(=O)C2CCCc3ccccc32)=NO1)B1O[C@@H]2C[C@@H]3C[C@@H](C3(C)C)[C@]2(C)O1]

The title compound (0.059 g, 61%, 2 steps) was obtained using methyl 5-benzyl-3-((1,2,3,4-tetrahydronaphthalen-1-carboxamido)methyl)-4,5-dihydroisoxazol-5-carboxylate (0.063 g, 0.16 mmol) obtained in the process (1) above by the preparation method of Example 84-(3).

MS (m/z): 640[M+H]

(3) Preparation of ((1R)-1-(5-benzyl-3-((1,2,3,4-tetrahydronaphthalen-1-carboxamido)methyl)-4,5-dihydroisoxazol-5-carboxamido)-3-methylbutyl) boronic acid

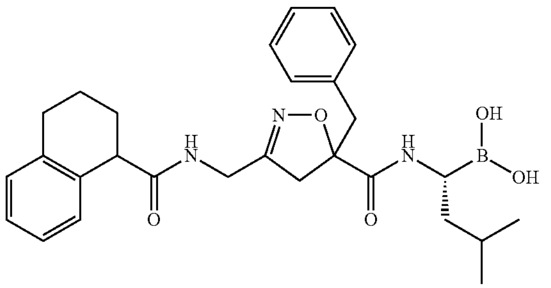 [SMILES: CC(C)C[C@H](NC(=O)C1(Cc2ccccc2)CC(CNC(=O)C2CCCc3ccccc32)=NO1)B(O)O]

The title compound (0.021 g, 45%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1,2,3,4-tetrahydronaphthalen-1-carboxamido)methyl)-4,5-dihydroisoxazol-5-carboxamide (0.059 g, 0.092 mmol) obtained in the process (2) above by the preparation method of Example 1-(4).

NMR: $^1$H-NMR (400 MHz, MeOD-d4); δ 7.29-7.28 (m, 5H), 7.16-7.08 (m, 4H), 4.10 (s, 2H), 3.74-3.71 (m, 1H), 3.42-3.17 (m, 4H), 2.87-2.69 (m, 3H), 2.03 (m, 3H), 1.76-1.74 (m, 1H), 1.45-1.41 (m, 1H), 1.19-1.10 (m, 2H), 0.86-0.81 (dd, 6H)

MS (m/z): 506[M+H], 488[M-OH]

Example 109: Preparation of ((1R)-1-(5-benzyl-3-((2-phenylacetamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((2-phenylacetamido)methyl)-4,5-dihydroisoxazol-5-carboxylate

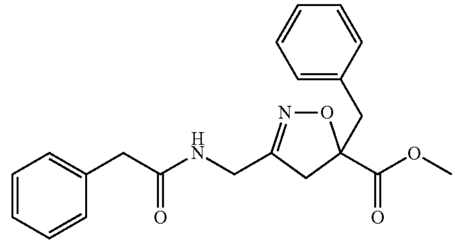 [SMILES: COC(=O)C1(Cc2ccccc2)CC(CNC(=O)Cc2ccccc2)=NO1]

Methyl 3-(aminomethyl)-5-benzyl-4,5-dihydroisoxazol-5-carboxylate hydrochloride (0.06 g, 0.21 mmol) obtained in Example 84-(1) was dissolved in dichloromethane (5 ml). At 0° C., triethylamine (0.059 ml, 0.42 mmol) and phenylacetyl chloride (0.03 ml, 0.24 mmol) were added in order, and stirring was performed at room temperature for 3 hours. Water was added thereto, and extraction with ethyl acetate was performed. An organic layer was dried over anhydrous magnesium sulfate, and filtered, and the filtrate was distilled under a reduced pressure and separated by column chromatography to obtain the title compound (0.058 g, 72%).

MS (m/z): 367[M+H], 385[M+$H_3$O]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-phenylacetamido)methyl)-4,5-dihydroisoxazol-5-carboxamide

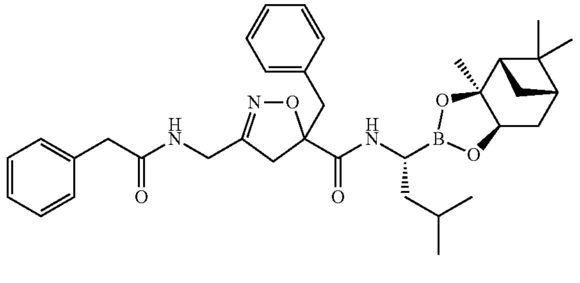 [SMILES: CC(C)C[C@H](NC(=O)C1(Cc2ccccc2)CC(CNC(=O)Cc2ccccc2)=NO1)B1O[C@@H]2C[C@@H]3C[C@@H](C3(C)C)[C@]2(C)O1]

The title compound (0.06 g, 66%, 2 steps) was obtained using methyl 5-benzyl-3-((2-phenylacetamido)methyl)-4,5-dihydroisoxazol-5-carboxylate (0.058 g, 0.15 mmol) obtained in (1) above by the preparation method of Example 84-(3).

MS (m/z): 600[M+H]

(3) Preparation of ((1R)-1-(5-benzyl-3-((2-phenylacetamido)methyl)-4,5-dihydroisoxazol-5-carboxamido)-3-methylbutyl)boronic acid

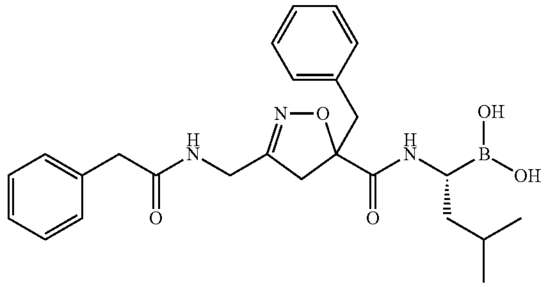 [SMILES: CC(C)C[C@H](NC(=O)C1(Cc2ccccc2)CC(CNC(=O)Cc2ccccc2)=NO1)B(O)O]

The title compound (0.025 g, 54%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-phenylacetamido)methyl)-4,5-dihydroisoxazol-5-carboxamide (0.06 g, 0.10 mmol) obtained in (2) above by the preparation method of Example 1-(4).

NMR: $^1$H-NMR (400 MHz, MeOD-d4); δ 7.36-7.25 (m, 10H), 4.05 (s, 2H), 3.53 (s, 2H), 3.36-3.09 (m, 4H), 2.70-2.66 (t, 1H), 1.43-1.38 (m, 1H), 1.21-1.03 (m, 2H), 0.85-0.80 (dd, 6H)

MS (m/z): 466[M+H], 448[M-OH]

Example 110: Preparation of ((1R)-1-(5-benzyl-3-((3-phenylpropanamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((3-phenylpropanamido)methyl)-4,5-dihydroisoxazol-5-carboxylate

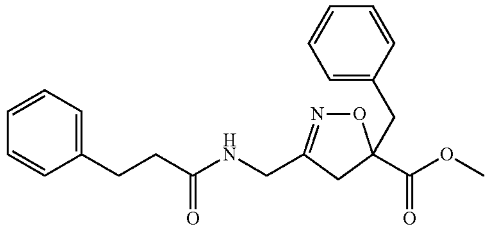 [SMILES: COC(=O)C1(Cc2ccccc2)CC(CNC(=O)CCc2ccccc2)=NO1]

The title compound (0.057 g, 68%) was obtained using methyl 3-(aminomethyl)-5-benzyl-4,5-dihydroisoxazol-5-carboxylate hydrochloride (0.06 g, 0.21 mmol) obtained in Example 84-(1) and 3-phenyl-propionyl chloride (0.036 ml, 0.24 mmol) by the preparation method of Example 109-(1).

MS (m/z): 381[M+H], 399[M+$H_3$O]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-phenylpropanamido)methyl)-4,5-dihydroisoxazol-5-carboxamide

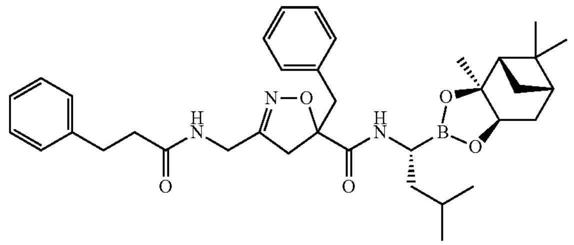 [SMILES: CC(C)C[C@H](NC(=O)C1(Cc2ccccc2)CC(CNC(=O)CCc2ccccc2)=NO1)B1O[C@@H]2C[C@@H]3C[C@@H](C3(C)C)[C@]2(C)O1]

The title compound (0.021 g, 25%) was obtained using methyl 5-benzyl-3-((3-phenylpropanamido)methyl)-4,5-dihydroisoxazol-5-carboxylate (0.057 g, 0.14 mmol) obtained in (1) above by the preparation method of Example 84-(3).

MS (m/z): 614[M+H]

(3) Preparation of ((1R)-1-(5-benzyl-3-((3-phenylpropanamido)methyl)-4,5-dihydroisoxazol-5-carboxamido)-3-methylbutyl)boronic acid

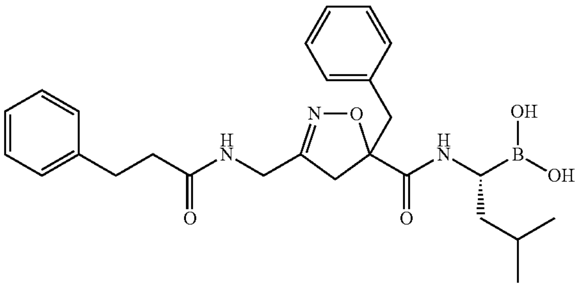 [SMILES: CC(C)C[C@H](NC(=O)C1(Cc2ccccc2)CC(CNC(=O)CCc2ccccc2)=NO1)B(O)O]

The title compound (0.015 g, 86%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-phenylpropanamido)methyl)-4,5-dihydroisoxazol-5-carboxamide (0.021 g, 0.14 mmol) obtained in (2) above by the preparation method of Example 1-(4).

NMR: $^1$H-NMR (400 MHz, MeOD-d4); δ 7.32-7.19 (m, 10H), 4.01 (s, 2H), 3.29-2.97 (m, 4H), 2.95-2.91 (t, 3H), 2.69-2.66 (t, 1H), 2.54-2.51 (t, 2H), 1.44-1.36 (m, 1H), 1.20-1.01 (m, 2H), 0.85-0.80 (dd, 6H)

MS (m/z): 480[M+H], 462[M-OH]

Example 111: Preparation of ((1R)-1-(5-benzyl-3-((5-fluoro-2-methylbenzamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((5-fluoro-2-methylbenzamido)methyl)-4,5-dihydroisoxazol-5-carboxylate

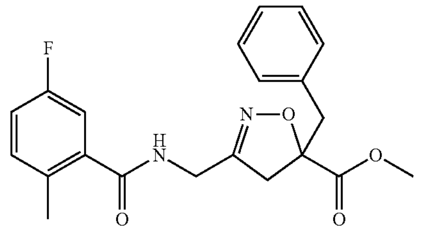 [SMILES: COC(=O)C1(Cc2ccccc2)CC(CNC(=O)c2cc(F)ccc2C)=NO1]

The title compound (0.10 g, 76%) was obtained using methyl 3-(aminomethyl)-5-benzyl-4,5-dihydroisoxazol-5-carboxylate hydrochloride (0.1 g, 0.35 mmol) obtained in Example 84-(1) and 5-fluoro-2-methylbenzoic acid (0.06 g, 0.39 mmol) by the preparation method of Example 84-(2).

NMR: $^1$H-NMR (500 MHz, $CDCl_3$); δ 7.25 (s, 1H), 7.24-7.17 (m, 5H), 7.02-6.98 (m, 2H), 5.84 (m, 1H), 4.22-4.11 (m, 2H), 3.79 (s, 3H), 3.15-3.42 (d, 1H), 3.36-3.33 (d, 1H), 3.11-3.09 (d, 1H), 3.01-2.98 (d, 1H), 2.36 (s, 3H)

MS (m/z): 385[M+H]

(2) Preparation of 5-benzyl-3-((5-fluoro-2-methylbenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

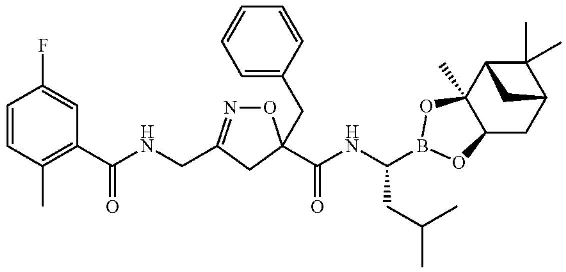

The title compound (0.061 g, 37%, 2 steps) was obtained using methyl 5-benzyl-3-((5-fluoro-2-methylbenzamido)methyl)-4,5-dihydroisoxazol-5-carboxylate (0.1 g, 0.27 mmol) obtained in (1) above by the preparation method of Example 84-(3).

MS (m/z): 618[M+H]

(3) Preparation of ((1R)-1-(5-benzyl-3-((5-fluoro-2-methylbenzamido)methyl)-4,5-dihydroisoxazol-5-carboxamido)-3-methylbutyl)boronic acid

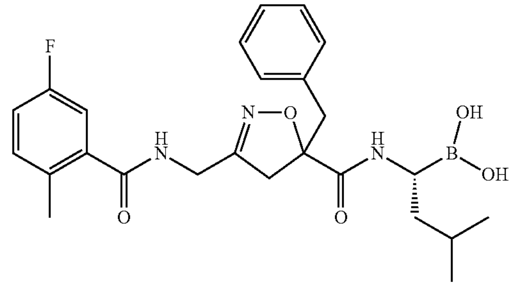 [SMILES: Cc1ccc(F)cc1C(=O)NCC1=NOC(Cc2ccccc2)(C(=O)N[C@@H](CC(C)C)B(O)O)C1]

The title compound (0.023 g, 49%) was obtained using 5-benzyl-3-((5-fluoro-2-methylbenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.061 g, 0.099 mmol) obtained in (2) above by the preparation method of Example 1-(4).

NMR: $^1$H-NMR (500 MHz, $CDCl_3$); δ 7.25-7.15 (m, 7H), 7.01-6.97 (m, 2H), 6.14-6.12 (m, 1H), 4.16-4.15 (d, 2H), 3.41-3.37 (d, 1H), 3.36-3.33 (d, 1H), 3.16-3.14 (d, 1H), 3.06-3.03 (d, 1H), 2.33 (s, 3H), 1.34-1.22 (m, 3H), 0.85-0.83 (m, 6H)

MS (m/z): 484[M+H], 466[M-OH]

Example 112: Preparation of ((1R)-1-(5-benzyl-3-((2-chloro-5-(trifluoromethyl)benzamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((2-chloro-5-(trifluoromethyl)benzamido)methyl)-4,5-dihydroisoxazol-5-carboxylate

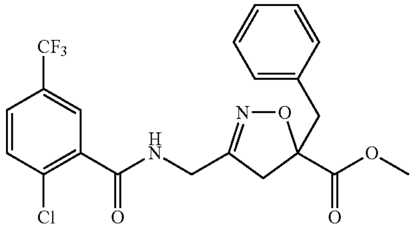 [SMILES: COC(=O)C1(Cc2ccccc2)CC(CNC(=O)c2cc(C(F)(F)F)ccc2Cl)=NO1]

The title compound (0.16 g, 83%) was obtained using methyl 3-(aminomethyl)-5-benzyl-4,5-dihydroisoxazol-5-carboxylate hydrochloride (0.12 g, 0.42 mmol) obtained in Example 84-(1) and 2-chloro-5-trifluoromethyl-benzoic acid (0.10 g, 0.46 mmol) by the preparation method of Example 84-(2).

MS (m/z): 455[M+H]

(2) Preparation of 5-benzyl-3-((2-chloro-5-(trifluoromethyl)benzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

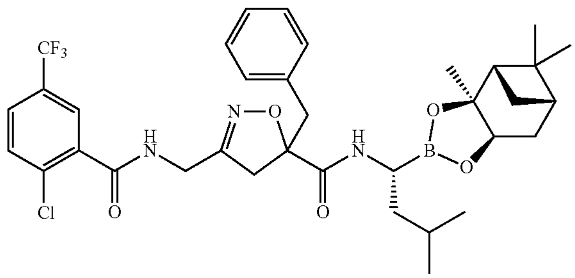 [SMILES: CC(C)C[C@H](NC(=O)C1(Cc2ccccc2)CC(CNC(=O)c2cc(C(F)(F)F)ccc2Cl)=NO1)B1O[C@@H]2C[C@@H]3C[C@@H](C3(C)C)[C@]2(C)O1]

The title compound (0.077 g, 41%, 2 steps) was obtained using methyl 5-benzyl-3-((2-chloro-5-(trifluoromethyl)benzamido)methyl)-4,5-dihydroisoxazol-5-carboxylate (0.16 g, 0.35 mmol) obtained in (1) above by the preparation method of Example 84-(3).

MS (m/z): 689[M+H]

(3) Preparation of ((1R)-1-(5-benzyl-3-((2-chloro-5-(trifluoromethyl)benzamido)methyl)-4,5-dihydroisoxazol-5-carboxamido)-3-methylbutyl)boronic acid

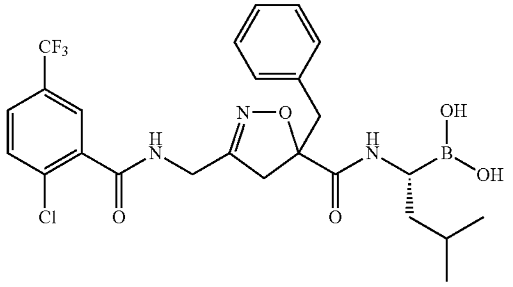

The title compound (0.025 g, 41%) was obtained using 5-benzyl-3-((2-chloro-5-(trifluoromethyl)benzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.077 g, 0.11 mmol) obtained in (2) above by the preparation method of Example 1-(4).

NMR: $^1$H-NMR (500 MHz, $CDCl_3$); δ 7.84 (d, 1H), 7.59 (m, 1H), 7.51-7.49 (m, 1H), 7.25-7.19 (m, 5H), 7.13 (m, 1H), 6.64-6.62 (m, 1H), 4.23-4.20 (m, 2H), 3.44-3.40 (d, 1H), 3.37-3.34 (d, 1H), 3.16-3.13 (d, 1H), 3.09-3.05 (d, 1H), 2.87 (m, 1H), 1.39-1.23 (m, 3H), 0.85-0.84 (m, 6H)

MS (m/z): 554[M+H], 537[M-OH]

Example 113: Preparation of ((1R)-1-(5-benzyl-3-((quinolin-8-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((quinolin-8-carboxamido)methyl)-4,5-dihydroisoxazol-5-carboxylate

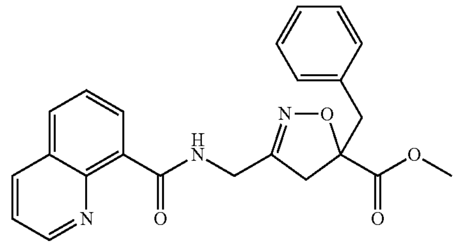 [SMILES: COC(=O)C1(Cc2ccccc2)CC(CNC(=O)c2cccc3cccnc23)=NO1]

The title compound (0.11 g, 65%) was obtained using methyl 3-(aminomethyl)-5-benzyl-4,5-dihydroisoxazol-5-carboxylate hydrochloride (0.12 g, 0.42 mmol) obtained in Example 84-(1) and quinolin-8-carboxylic acid (0.08 g, 0.46 mmol) by the preparation method of Example 84-(2).

MS (m/z): 404[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((quinolin-8-carboxamido)methyl)-4,5-dihydroisoxazol-5-carboxamide

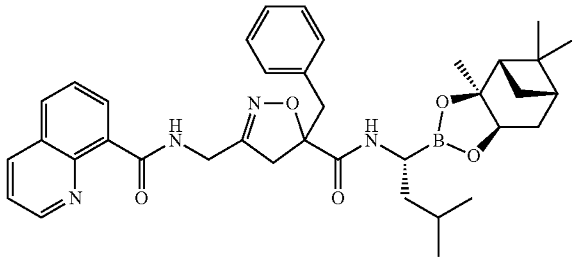

The title compound (0.06 g, 34%, 2 steps) was obtained using methyl 5-benzyl-3-((quinolin-8-carboxamido)methyl)-4,5-dihydroisoxazol-5-carboxylate (0.11 g, 0.27 mmol) obtained in (1) above by the preparation method of Example 84-(3).

MS (m/z): 637[M+H]

(3) Preparation of ((1R)-1-(5-benzyl-3-((quinolin-8-carboxamido)methyl)-4,5-dihydroisoxazol-5-carboxamido)-3-methylbutyl)boronic acid

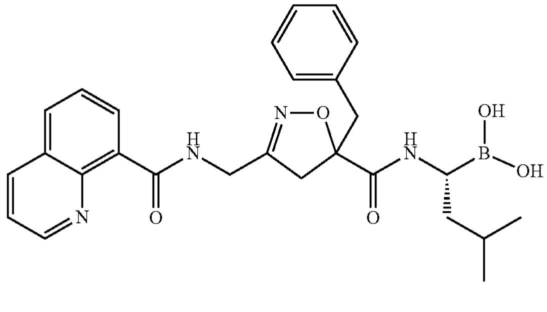 [SMILES: CC(C)C[C@H](NC(=O)C1(Cc2ccccc2)CC(CNC(=O)c2cccc3cccnc23)=NO1)B(O)O]

The title compound (0.03 g, 64%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((quinolin-8-carboxamido)methyl)-4,5-dihydroisoxazol-5-carboxamide (0.06 g, 0.094 mmol) obtained in (2) above by the preparation method of Example 1-(4).

NMR: $^{1}$H-NMR (500 MHz, MeOD-d4); δ 8.99-8.98 (dd, 1H), 8.66-8.64 (dd, 1H), 8.49-8.47 (dd, 1H), 8.16-8.14 (dd, 1H), 7.74-7.71 (t, 1H), 7.63-7.61 (dd, 1H), 7.25-7.11 (m, 5H), 4.41 (s, 2H), 3.50-3.47 (d, 1H), 3.33-3.28 (m, 2H), 3.20-3.17 (d, 1H), 2.62 (m, 1H), 1.36-1.33 (m, 1H), 1.41-4.00 (m, 2H), 0.78-0.73 (dd, 6H)

MS (m/z): 503[M+H], 485[M-OH]

Example 114: Preparation of ((1R)-1-(5-(fluoro(phenyl)methyl)-3-((isoquinolin-1-carboxamido)methyl)-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-(fluoro(phenyl)methyl)-4,5-dihydroisoxazol-5-carboxylate hydrochloride

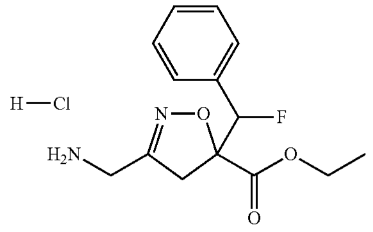

The title compounds of Isomer 1 (0.076 g, quant.) and Isomer 2 (0.084 g, quant.) were obtained using Isomer 1 (0.089 g, 0.234 mmol) and Isomer 2 (0.100 g, 0.263 mmol), obtained in Preparation Example 17, respectively, by the preparation method of Example 84-(1).

(2) Preparation of ethyl 5-(fluoro(phenyl)methyl)-3-((isoquinolin-1-carboxamido)methyl)-4,5-dihydroisoxazol-5-carboxylate

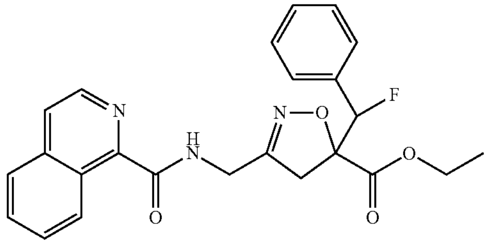 [SMILES: CCOC(=O)C1(C(F)c2ccccc2)CC(CNC(=O)c2nccc3ccccc23)=NO1]

The title compound of Isomer 1 (0.057 g, 56%) was obtained using ethyl 3-(aminomethyl)-5-(fluoro(phenyl)methyl)-4,5-dihydroisoxazol-5-carboxylate hydrochloride of Isomer 1 (0.076 g, 0.234 mmol) obtained in (1) above and isoquinolin-1-carboxylic acid (0.053 g, 0.306 mmol) by the preparation method of Example 84-(2).

NMR: $^1$H-NMR (400 MHz, $CDCl_3$); δ 9.56 (1H, t), 8.50-8.48 (2H, m), 7.91-7.71 (4H, m), 7.42-7.30 (4H, m), 5.86 (1H, d), 4.42-4.21 (4H, m), 3.52 (1H, d), 3.38 (1H, d), 1.28 (3H, t)

MS (m/z): 436[M+H]

The title compound of Isomer 2 (0.088 g, 86%) was obtained using ethyl 3-(aminomethyl)-5-(fluoro(phenyl)methyl)-4,5-dihydroisoxazol-5-carboxylate hydrochloride of Isomer 2 (0.084 g, 0.263 mmol) obtained in (1) above and isoquinolin-1-carboxylic acid (0.060 g, 0.346 mmol) by the preparation method of Example 84-(2).

NMR: $^1$H-NMR (400 MHz, $CDCl_3$); δ 9.58 (1H, d), 8.52 (1H, d), 8.33 (1H, t), 7.93-7.74 (4H, m), 7.46-7.27 (4H, m), 5.97 (1H, d), 4.37-4.15 (4H, m), 3.67 (1H, d), 3.38 (1H, d), 1.29 (3H, t)

MS (m/z): 436[M+H]

(3) Preparation of 5-(fluoro(phenyl)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

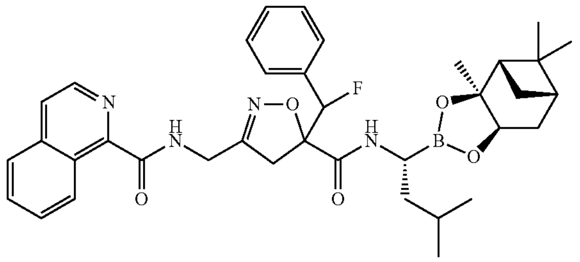 [SMILES: CC(C)C[C@H](NC(=O)C1(C(F)c2ccccc2)CC(CNC(=O)c2nccc3ccccc23)=NO1)B1O[C@@H]2C[C@@H]3C[C@@H](C3(C)C)[C@]2(C)O1]

The title compound of Isomer 1 (0.051 g, 59%, 2 steps) was obtained using ethyl 5-(fluoro(phenyl)methyl)-3-((isoquinolin-1-carboxamido)methyl)-4,5-dihydroisoxazol-5-carboxylate of Isomer 1 (0.057 g, 0.131 mmol) obtained in (2) above by the preparation method of Example 84-(3).

MS (m/z): 655[M+H]

The title compound of Isomer 2 (0.099 g, 75%, 2 steps) was obtained using ethyl 5-(fluoro(phenyl)methyl)-3-((isoquinolin-1-carboxamido)methyl)-4,5-dihydroisoxazol-5-carboxylate of Isomer 2 (0.088 g, 0.202 mmol) obtained in (2) above by the preparation method of Example 84-(3).

MS (m/z): 655[M+H]

(4) Preparation of ((1R)-1-(5-(fluoro(phenyl)methyl)-3-((isoquinolin-1-carboxamido)methyl)-4,5-dihydroisoxazol-5-carboxamido)-3-methylbutyl)boronic acid

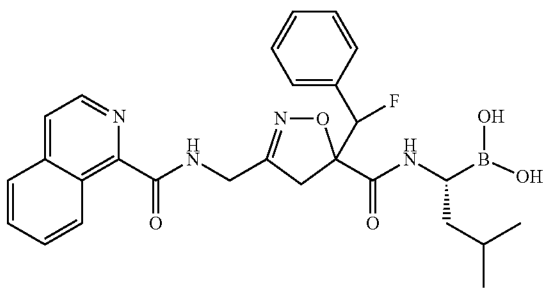 [SMILES: CC(C)C[C@H](NC(=O)C1(C(F)c2ccccc2)CC(CNC(=O)c2nccc3ccccc23)=NO1)B(O)O]

The title compound of Isomer 1 (0.021 g, 52%) was obtained using 5-(fluoro(phenyl)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide of Isomer 1 (0.051 g, 0.078 mmol) obtained in (3) above by the preparation method of Example 1-(4).

NMR: $^1$H-NMR (500 MHz, $CD_3OD$); δ 9.12 (1H, d), 8.54 (1H, d), 8.02-7.72 (4H, m), 7.47-7.36 (5H, m), 5.86 (1H, dd), 4.43 (2H, s), 3.78 (1H, dd), 3.56 (1H, d), 2.88-2.78 (1H, m), 1.47-1.03 (3H, m), 0.79-0.72 (6H, dd)

MS (m/z): 543 [M+Na], 503 [M-OH]

The title compound of Isomer 2 (0.049 g, 62%) was obtained using 5-(fluoro(phenyl)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide of Isomer 2 (0.099 g, 0.151 mmol) obtained in (3) above by the preparation method of Example 1-(4).

NMR: $^1$H-NMR (500 MHz, $CD_3OD$); δ 9.09 (1H, d), 8.51 (1H, dd), 8.01-7.72 (4H, m), 7.52-7.26 (5H, m), 5.89 (1H, d), 4.20-4.09 (2H, m), 3.48 (1H, dd), 3.35-3.25 (1H, m), 3.03-2.94 (1H, m), 1.66-1.30 (3H, m), 0.93-0.87 (6H, dd)

MS (m/z): 543[M+Na], 503[M-OH]

Example 115: Preparation of ((1R)-1-(5-benzyl-3-((5,6,7,8-tetrahydronaphthalen-1-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-[(tetralin-5-carbonylamino)methyl]-4H-isoxazol-5-carboxylate

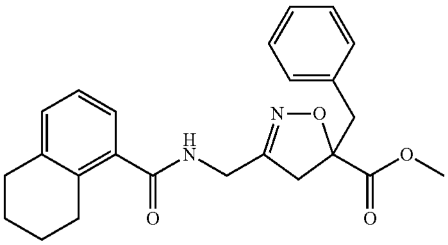 [SMILES: COC(=O)C1(Cc2ccccc2)CC(CNC(=O)c2cccc3c2CCCC3)=NO1]

The title compound (0.13 g, 73%) was obtained using methyl 3-(aminomethyl)-5-benzyl-4,5-dihydroisoxazol-5-carboxylate hydrochloride (0.12 g, 0.42 mmol) obtained in Example 84-(1) and 5,6,7,8-tetrahydro-naphthalen-1-carboxylic acid (0.082 g, 0.46 mmol) by the preparation method of Example 84-(2).

MS (m/z): 408[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((5,6,7,8-tetrahydronaphthalen-1-carboxamido)methyl)-4,5-dihydroisoxazol-5-carboxamide

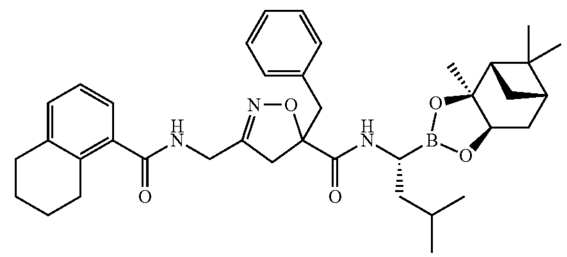

The title compound (0.08 g, 38%, 2 steps) was obtained using methyl 5-benzyl-3-[(tetralin-5-carbonylamino) methyl]-4H-isoxazol-5-carboxylate (0.13 g, 0.31 mmol) obtained in (1) above by the preparation method of Example 84-(3).

MS (m/z): 641[M+H], 489[M-$C_{10}H_{15}O$]

(3) Preparation of ((1R)-1-(5-benzyl-3-((5,6,7,8-tetrahydronaphthalen-1-carboxamido)methyl)-4,5-dihydroisoxazol-5-carboxamido)-3-methylbutyl) boronic acid

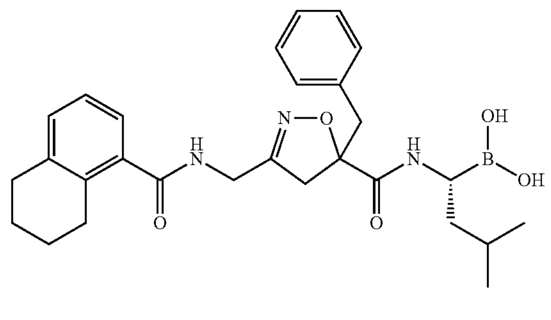 [SMILES: CC(C)C[C@H](NC(=O)C1(Cc2ccccc2)CC(CNC(=O)c2cccc3c2CCCC3)=NO1)B(O)O]

The title compound (0.039 g, 62%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((5,6,7,8-tetrahydronaphthalen-1-carboxamido)methyl)-4,5-dihydroisoxazol-5-carboxamide (0.08 g, 0.13 mmol) obtained in (2) above by the preparation method of Example 1-(4).

NMR: $^1$H-NMR (500 MHz, MeOD-d4); δ 7.27-7.09 (m, 8H), 4.21-4.14 (m, 2H), 3.46-3.42 (d, 1H), 3.33-3.18 (m, 3H), 2.79 (m, 4H), 2.67-2.64 (m, 1H), 1.79-1.77 (m, 4H), 1.41-1.37 (m, 1H), 1.17-1.03 (m, 2H), 0.81-0.77 (dd, 6H)

MS (m/z): 506[M+H], 408[M-OH]

Example 116: Preparation of ((1R)-1-(5-benzyl-3-((quinolin-5-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-[(quinolin-5-carbonylamino)methyl]-4H-isoxazol-5-carboxylate

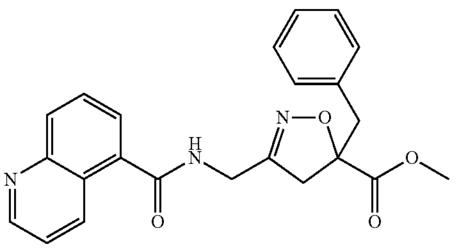 [SMILES: COC(=O)C1(Cc2ccccc2)CC(CNC(=O)c2cccc3ncccc23)=NO1]

The title compound (0.1 g, 58%) was obtained using methyl 3-(aminomethyl)-5-benzyl-4,5-dihydroisoxazol-5-carboxylate hydrochloride (0.12 g, 0.42 mmol) obtained in Example 84-(1) and quinolin-5-carboxylic acid (0.08 g, 0.46 mmol) by the preparation method of Example 84-(2).

MS (m/z): 404[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((quinolin-5-carboxamido)methyl)-4,5-dihydroisoxazol-5-carboxamide

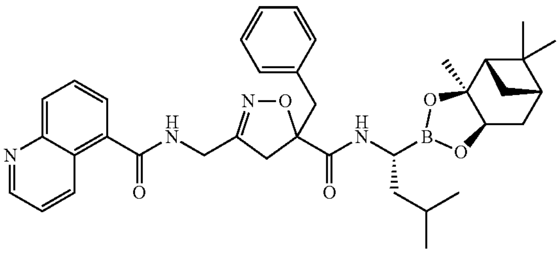 [SMILES: CC(C)C[C@H](NC(=O)C1(Cc2ccccc2)CC(CNC(=O)c2cccc3ncccc23)=NO1)B1O[C@@H]2C[C@@H]3C[C@@H](C3(C)C)[C@]2(C)O1]

The title compound (0.022 g, 14%, 2 steps) was obtained using methyl 5-benzyl-3-[(quinolin-5-carbonylamino) methyl]-4H-isoxazol-5-carboxylate (0.1 g, 0.25 mmol) obtained in (1) above by the preparation method of Example 84-(3).

MS (m/z): 637[M+H], 485[M-$C_{10}H_{15}O$]

(3) Preparation of ((1R)-1-(5-benzyl-3-((quinolin-5-carboxamido)methyl)-4,5-dihydroisoxazol-5-carboxamido)-3-methylbutyl)boronic acid

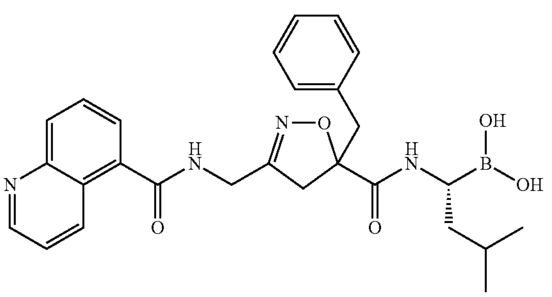 [SMILES: CC(C)C[C@H](NC(=O)C1(Cc2ccccc2)CC(CNC(=O)c2cccc3ncccc23)=NO1)B(O)O]

The title compound (0.006 g, 34%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((quinolin-5-carboxamido)methyl)-4,5-dihydroisoxazol-5-carboxamide (0.022 g, 0.035 mmol) obtained in (2) above by the preparation method of Example 1-(4).

NMR: $^1$H-NMR (500 MHz, MeOD-d4); δ 8.91-8.89 (m, 1H), 8.79-8.77 (d, 1H), 8.16-8.14 (d, 1H), 7.82-7.78 (m, 2H), 7.62-7.61 (dd, 1H), 7.29-7.24 (m, 5H), 4.31-7.29 (m, 2H), 3.52-3.48 (d, 1H), 3.36-3.30 (m, 2H), 3.24-3.21 (d, 1H), 2.67-2.64 (m, 1H), 1.41-1.36 (m, 1H), 1.17-1.11 (m, 2H), 0.80-0.76 (dd, 6H)

MS (m/z): 503[M+H], 485[M-OH]

Example 117: Preparation of ((1R)-1-(5-benzyl-3-((2-methylthiazol-4-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-[[(2-methylthiazol-4-carbonyl)amino]methyl]-4H-isoxazol-5-carboxylate

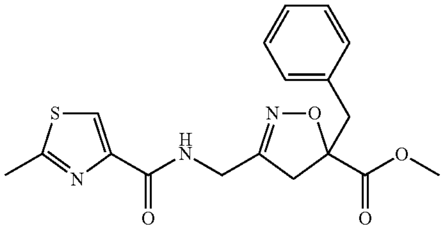

The title compound (0.114 g, 72%) was obtained using methyl 3-(aminomethyl)-5-benzyl-4,5-dihydroisoxazol-5-carboxylate hydrochloride (0.12, 0.42 mmol) obtained in Example 84-(1) and 2-methyl-thiazol-4-carboxylic acid (0.066 g, 0.46 mmol) by the preparation method of Example 84-(2).

MS (m/z): 374[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-methylthiazol-4-carboxamido)methyl)-4,5-dihydroisoxazol-5-carboxamide

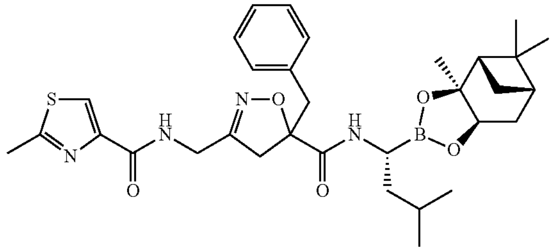

The title compound (0.065 g, 34%, 2 steps) was obtained using methyl 5-benzyl-3-[[(2-methylthiazol-4-carbonyl)amino]methyl]-4H-isoxazol-5-carboxylate (0.114 g, 0.31 mmol) obtained in (1) above by the preparation method of Example 84-(3).

MS (m/z): 607[M+H]

(3) Preparation of ((1R)-1-(5-benzyl-3-((2-methylthiazol-4-carboxamido)methyl)-4,5-dihydroisoxazol-5-carboxamido)-3-methylbutyl)boronic acid

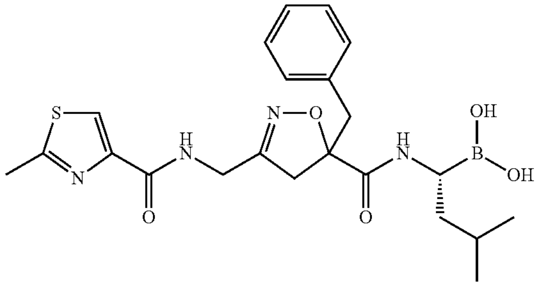 [SMILES: Cc1nc(C(=O)NCC2=NOC(Cc3ccccc3)(C(=O)N[C@@H](CC(C)C)B(O)O)C2)cs1]

The title compound (0.031 g, 62%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-methylthiazol-4-carboxamido)methyl)-4,5-dihydroisoxazol-5-carboxamide (0.065 g, 0.11 mmol) obtained in (2) above by the preparation method of Example 1-(4).

NMR: $^1$H-NMR (500 MHz, MeOD-d4); δ 8.03 (s, 1H), 7.24-7.19 (m, 5H), 4.21 (s, 2H), 3.42-3.38 (d, 1H), 3.31-3.16 (m, 3H), 2.71 (s, 3H), 2.64-2.61 (m, 1H), 1.38-1.33 (m, 1H), 1.14-0.98 (m, 2H), 0.80-0.75 (dd, 6H)

MS (m/z): 473[M+H], 455[M-OH]

Example 118: Preparation of ((1R)-1-(5-benzyl-3-((1-phenylcyclopropan-1-carboxamido)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-[[(1-phenylcyclopropanecarbonyl)amino]methyl]-4H-isoxazol-5-carboxylate

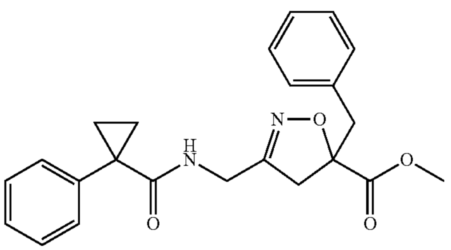 [SMILES: COC(=O)C1(Cc2ccccc2)CC(CNC(=O)C2(c3ccccc3)CC2)=NO1]

The title compound (0.124 g, 72%) was obtained using methyl 3-(aminomethyl)-5-benzyl-4,5-dihydroisoxazol-5-carboxylate hydrochloride (0.12, 0.42 mmol) obtained in Example 84-(1) and 1-phenyl-cyclopropanecarboxylic acid (0.075 g, 0.46 mmol) by the preparation method of Example 84-(2).

MS (m/z): 393[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-phenylcyclopropan-1-carboxamido)methyl)-4,5-dihydroisoxazol-5-carboxamide

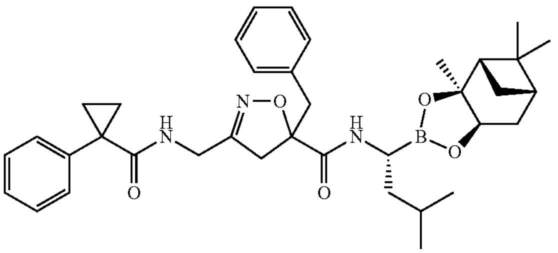 [SMILES: CC(C)C[C@H](NC(=O)C1(Cc2ccccc2)CC(CNC(=O)C2(c3ccccc3)CC2)=NO1)B1O[C@@H]2C[C@@H]3C[C@@H](C3(C)C)[C@]2(C)O1]

The title compound (0.06 g, 29%, 2 steps) was obtained using methyl 5-benzyl-3-[[(1-phenylcyclopropanecarbonyl) amino]methyl]-4H-isoxazol-5-carboxylate (0.124 g, 0.32 mmol) obtained in (1) above by the preparation method of Example 84-(3).

MS (m/z): 626[M+H]

(3) Preparation of ((1R)-1-(5-benzyl-3-((1-phenyl-cyclopropan-1-carboxamido)methyl)-4,5-dihydroisoxazol-5-carboxamido)-3-methylbutyl)boronic acid

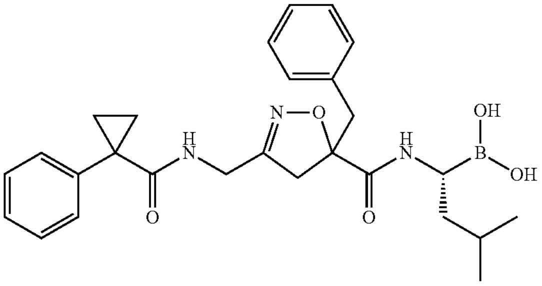 [SMILES: CC(C)C[C@H](NC(=O)C1(Cc2ccccc2)CC(CNC(=O)C2(c3ccccc3)CC2)=NO1)B(O)O]

The title compound (0.03 g, 64%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-phenylcyclopropan-1-carboxamido) methyl)-4,5-dihydroisoxazol-5-carboxamide (0.06 g, 0.096 mmol) obtained in (2) above by the preparation method of Example 1-(4).

NMR: $^1$H-NMR (500 MHz, MeOD-d4); δ 7.37-7.21 (m, 10H), 3.93 (s, 2H), 3.24-3.05 (m, 4H), 2.65-2.62 (m, 1H), 1.47-1.46 (m, 2H), 1.41-1.35 (m, 1H), 1.18-1.09 (m, 4H), 0.81-0.77 (dd, 6H)

MS (m/z): 492[M+H], 474[M-OH]

Example 119: Preparation of ((1R)-1-(5-benzyl-3-((5-chloro-2-methylthiazol-4-carboxamido)methyl)-4,5-dihydroisoxazol-5-carboxamido)-3-methylbutyl) boronic acid Through the processes (1), (2), (3), (4) and (5) below, the title compound was obtained.

(1) Preparation of ethyl 5-chloro-2-methyl-thiazol-4-carboxylate

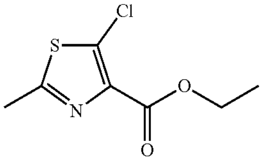

The title compound was obtained by the method described in US2012184521.

(2) Preparation of 5-chloro-2-methyl-thiazol-4-carboxylic acid

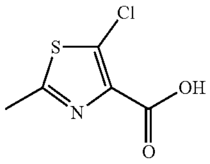

Ethyl 5-chloro-2-methyl-thiazol-4-carboxylate (0.15 g, 0.77 mmol) obtained in (1) above was dissolved in methanol (5 ml), a 1 N sodium hydroxide aqueous solution (2.3 ml, 2.3 mmol) was added thereto, and stirring was performed at room temperature for 5 hours. After titrating pH 1 with a 1 N hydrochloric acid solution, extraction with ethyl acetate was performed twice. The organic layer thus extracted was dried over anhydrous magnesium sulfate, and filtered, and the filtrate was distilled under a reduced pressure to obtain the title compound (0.14 g, 99%).

MS (m/z): 178[M+H]

(3) Preparation of methyl 5-benzyl-3-((5-chloro-2-methylthiazol-4-carboxamido)methyl)-4,5-dihydroisoxazol-5-carboxylate

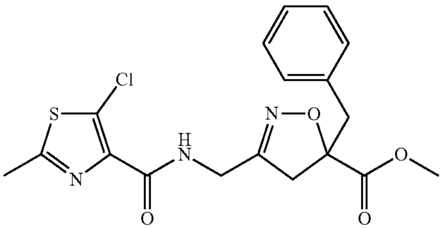

The title compound (0.176 g, 95%) was obtained using methyl 3-(aminomethyl)-5-benzyl-4,5-dihydroisoxazol-5-carboxylate hydrochloride (0.12 g, 0.42 mmol) obtained in Example 84-(1) and 5-chloro-2-methyl-thiazol-4-carboxylic acid (0.083 g, 0.46 mmol) obtained in (2) above by the preparation method of Example 84-(2).

MS (m/z): 408[M+H]

(4) Preparation of 5-benzyl-3-((5-chloro-2-methylthiazol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

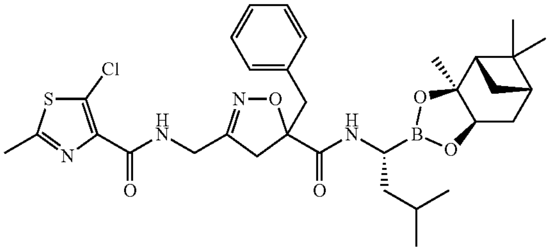

The title compound (0.085 g, 30%, 2 steps) was obtained using methyl 5-benzyl-3-((5-chloro-2-methylthiazol-4-carboxamido)methyl)-4,5-dihydroisoxazol-5-carboxylate (0.176 g, 0.43 mmol) obtained in (3) above by the preparation method of Example 84-(3).

MS (m/z): 641[M+H]

(5) Preparation of ((1R)-1-(5-benzyl-3-((5-chloro-2-methylthiazol-4-carboxamido)methyl)-4,5-dihydroisoxazol-5-carboxamido)-3-methylbutyl)boronic acid

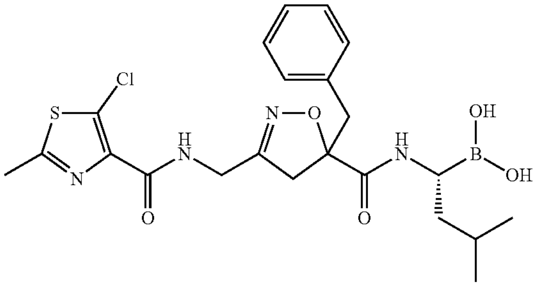 [SMILES: Cc1nc(C(=O)NCC2=NOC(Cc3ccccc3)(C(=O)N[C@@H](CC(C)C)B(O)O)C2)c(Cl)s1]

The title compound (0.039 g, 58%) was obtained using 5-benzyl-3-((5-chloro-2-methylthiazol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.085 g, 0.13 mmol) obtained in (4) above by the preparation method of Example 1-(4).

NMR: $^1$H-NMR (400 MHz, $CDCl_3$); δ 7.55-7.52 (m, 1H), 7.26-7.23 (m, 5H), 7.19-7.18 (m, 1H), 4.22-4.10 (m, 2H), 3.42-3.33 (t, 2H), 3.16-3.12 (d, 1H), 3.09-3.04 (d, 1H), 2.85 (m, 1H), 2.58 (s, 3H), 1.43-1.19 (m, 3H), 0.83-0.78 (m, 6H)

MS (m/z): 507[M+H], 490[M-OH]

Example 120: Preparation of ((1R)-1-(5-benzyl-3-((3-methylisoxazol-4-carboxamido)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-((3-methylisoxazol-4-carboxamido)methyl)-4,5-dihydroisoxazol-5-carboxylate

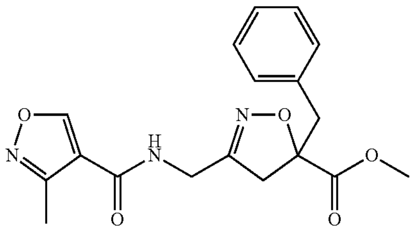 [SMILES: COC(=O)C1(Cc2ccccc2)CC(CNC(=O)c2conc2C)=NO1]

The title compound (0.15 g, 76%) was obtained using methyl 3-(aminomethyl)-5-benzyl-4,5-dihydroisoxazol-5-carboxylate hydrochloride (0.16 g, 0.56 mmol) obtained in Example 84-(1) and 4-methyl-isoxazol-3-carboxylic acid (0.08 g, 0.62 mmol) by the preparation method of Example 84-(2).

MS (m/z): 358[M+H]

(2) Preparation of N-((5-benzyl-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)-3-methylisoxazol-4-carboxamide

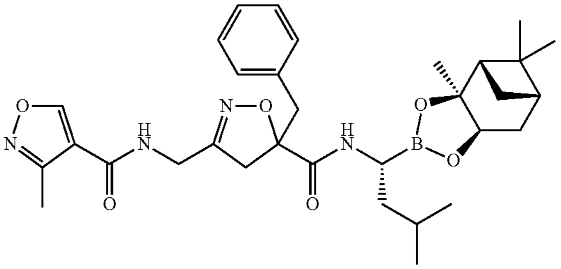 [SMILES: Cc1nocc1C(=O)NCC1=NOC(Cc2ccccc2)(C(=O)N[C@@H](CC(C)C)B2O[C@@H]3C[C@@H]4C[C@@H](C4(C)C)[C@]3(C)O2)C1]

The title compound (0.08 g, 31%, 2 steps) was obtained using methyl 5-benzyl-3-((3-methylisoxazol-4-carboxamido)methyl)-4,5-dihydroisoxazol-5-carboxylate (0.15 g, 0.43 mmol) obtained in (1) above by the preparation method of Example 84-(3).

MS (m/z): 591[M+H]

(3) Preparation of ((1R)-1-(5-benzyl-3-((3-methylisoxazol-4-carboxamido)methyl)-4,5-dihydroisoxazol-5-carboxamido)-3-methylbutyl)boronic acid

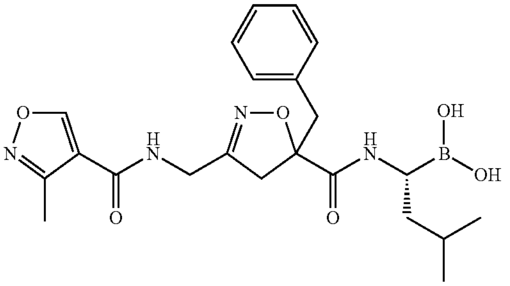 [SMILES: Cc1nocc1C(=O)NCC1=NOC(Cc2ccccc2)(C(=O)N[C@@H](CC(C)C)B(O)O)C1]

The title compound was obtained using N-((5-benzyl-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)-3-methylisoxazol-4-carboxamide (1 mmol) obtained in (2) above by the preparation method of Example 1-(4).

NMR: $^1$H-NMR (500 MHz, MeOD-d4); δ 8.96 (s, 1H), 7.25-7.19 (m, 5H), 4.15-4.14 (m, 2H), 3.43-3.39 (d, 1H), 3.32-3.16 (m, 3H), 2.66-2.63 (m, 1H), 2.42 (s, 3H), 1.39-1.35 (m, 1H), 1.16-0.99 (m, 2H), 0.81-0.77 (dd, 6H)

MS (m/z): 457[M+H], 439[M-OH].

Example 121: Preparation of ((1R)-1-(5-benzyl-3-((isoquinolin-3-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((isoquinolin-3-carboxamido)methyl)-4,5-dihydroisoxazol-5-carboxylate

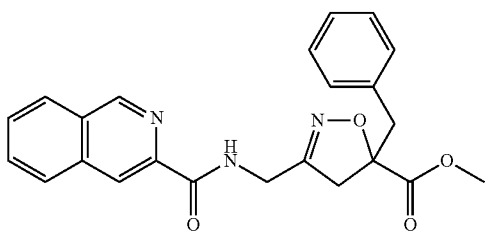 [SMILES: COC(=O)C1(Cc2ccccc2)CC(CNC(=O)c2cc3ccccc3cn2)=NO1]

The title compound (0.135 g, 80%) was obtained using methyl 3-aminomethyl-5-benzyl-4,5-dihydro-isoxazol-5-carboxylate; hydrochloric acid salt (0.12 g, 0.42 mmol) obtained in Example 84-(1) and isoquinolin-3-carboxylic acid (0.08 g, 0.46 mmol) by the preparation method of Example 84-(2).

MS (m/z): 404[M+H]

(2) Preparation of 5-benzyl-3-((isoquinolin-3-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

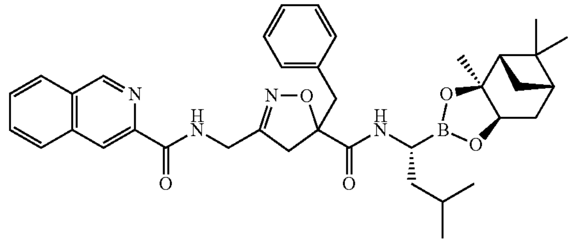 [SMILES: CC(C)C[C@H](NC(=O)C1(Cc2ccccc2)CC(CNC(=O)c2cc3ccccc3cn2)=NO1)B1O[C@@H]2C[C@@H]3C[C@@H](C3(C)C)[C@]2(C)O1]

The title compound (0.061 g, 29%, 2 steps) was obtained using methyl 5-benzyl-3-((isoquinolin-3-carboxamido)methyl)-4,5-dihydroisoxazol-5-carboxylate (0.135 g, 0.33 mmol) obtained in (1) above by the preparation method of Example 84-(3).

MS (m/z): 637[M+H]

(3) Preparation of ((1R)-1-(5-benzyl-3-((isoquinolin-3-carboxamido)methyl)-4,5-dihydroisoxazol-5-carboxamido)-3-methylbutyl)boronic acid

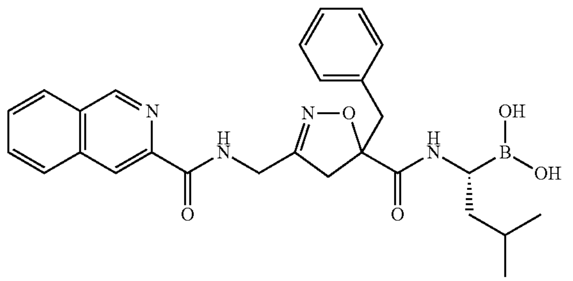 [SMILES: CC(C)C[C@H](NC(=O)C1(Cc2ccccc2)CC(CNC(=O)c2cc3ccccc3cn2)=NO1)B(O)O]

The title compound (0.025 g, 52%) was obtained using 5-benzyl-3-((isoquinolin-3-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.061 g, 0.096 mmol) obtained in (2) above by the preparation method of Example 1-(4).

NMR: $^1$H-NMR (500 MHz, MeOD-d4); δ 9.27 (s, 1H), 8.51 (s, 1H), 8.17-8.15 (d, 1H), 8.08-8.07 (d, 1H), 7.84-7.78 (m, 2H), 7.25-7.19 (m, 5H), 4.32 (s, 2H), 3.46-3.43 (d, 1H), 3.32-3.17 (m, 3H), 2.63-2.61 (m, 1H), 1.39-1.33 (m, 1H), 1.14-0.98 (m, 2H), 0.79-0.75 (dd, 6H)

MS (m/z): 503[M+H], 485[M-OH]

Example 122: Preparation of ((1R)-1-(5-benzyl-3-((quinoxalin-2-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((quinoxalin-2-carboxamido)methyl)-4,5-dihydroisoxazol-5-carboxylate

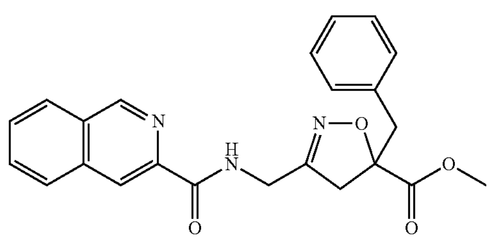 [SMILES: COC(=O)C1(Cc2ccccc2)CC(CNC(=O)c2cc3ccccc3cn2)=NO1]

The title compound (0.066 g, 77%) was obtained using methyl 3-(aminomethyl)-5-benzyl-4,5-dihydroisoxazol-5-carboxylate hydrochloride (0.06 g, 0.21 mmol) obtained in Example 84-(1) and quinoxalin-2-carboxylic acid (0.04 g, 0.23 mmol) by the preparation method of Example 84-(2).

MS (m/z): 405[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((quinoxalin-2-carboxamido)methyl)-4,5-dihydroisoxazol-5-carboxamide

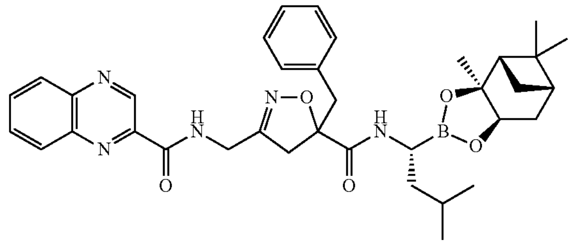 [SMILES: CC(C)C[C@H](NC(=O)C1(Cc2ccccc2)CC(CNC(=O)c2cnc3ccccc3n2)=NO1)B1O[C@@H]2C[C@@H]3C[C@@H](C3(C)C)[C@]2(C)O1]

The title compound (0.037 g, 35%, 2 steps) was obtained using methyl 5-benzyl-3-((quinoxalin-2-carboxamido)methyl)-4,5-dihydroisoxazol-5-carboxylate (0.066 g, 0.16 mmol) obtained in (1) above by the preparation method of Example 84-(3).

MS (m/z): 638[M+H]

(3) Preparation of ((1R)-1-(5-benzyl-3-((quinoxalin-2-carboxamido)methyl)-4,5-dihydroisoxazol-5-carboxamido)-3-methylbutyl)boronic acid

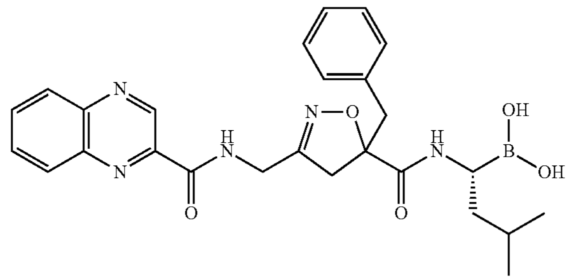 [SMILES: CC(C)C[C@H](NC(=O)C1(Cc2ccccc2)CC(CNC(=O)c2cnc3ccccc3n2)=NO1)B(O)O]

The title compound (0.016 g, 56%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((quinoxalin-2-carboxamido)methyl)-4,5-dihydroisoxazol-5-carboxamide (0.037 g, 0.058 mmol) obtained in (2) above by the preparation method of Example 1-(4).

NMR: $^1$H-NMR (400 MHz, MeOD-d4); δ 9.52 (s, 1H), 8.27-8.20 (m, 2H), 8.02-7.96 (m, 2H), 7.29-7.19 (m, 5H), 4.37 (s, 2H), 3.52-3.36 (m, 2H), 3.30-3.21 (m, 2H), 2.70-2.66 (m, 1H), 1.43-1.39 (m, 1H), 1.20-1.05 (m, 2H), 0.89-0.79 (dd, 6H)

MS (m/z): 504[M+H], 486[M-OH]

Example 123: [(1R)-1-[[5-benzyl-3-[[(3-cyano-4-isopropoxy-benzoyl)amino]methyl]-4H-1,2-oxazol-5-carbonyl]amino]-3-methyl-butyl]boronic acid Through the processes (1), (2), (3) and (4) below, the title compound was obtained.

(1) Preparation of 3-cyano-4-isopropoxy-benzoic acid

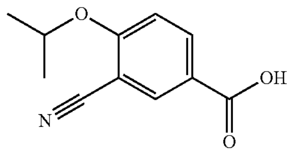

The title compound was obtained by the method described in US2010249071A1.

(2) Preparation of methyl 5-benzyl-3-((3-cyano-4-isopropoxybenzamido)methyl)-4,5-dihydroisoxazol-5-carboxylate

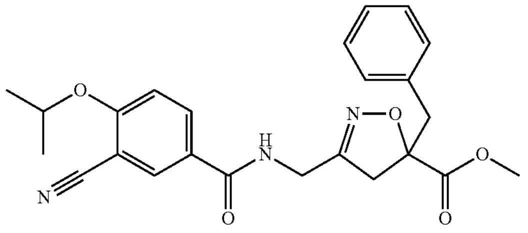 [SMILES: COC(=O)C1(Cc2ccccc2)CC(CNC(=O)c2ccc(OC(C)C)c(C#N)c2)=NO1]

The title compound (0.155 g, 85%) was obtained using methyl 3-(aminomethyl)-5-benzyl-4,5-dihydroisoxazol-5-carboxylate hydrochloride (0.12 g, 0.42 mmol) obtained in Example 84-(1) and 3-cyano-4-isopropoxy-benzoic acid (0.1 g, 0.46 mmol) obtained in the process (1) above by the preparation method of Example 84-(2).

MS (m/z): 436[M+H]

(3) Preparation of 5-benzyl-3-((3-cyano-4-isopropoxybenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

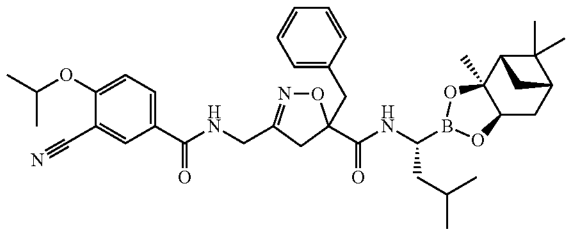 [SMILES: CC(C)C[C@H](NC(=O)C1(Cc2ccccc2)CC(CNC(=O)c2ccc(OC(C)C)c(C#N)c2)=NO1)B1O[C@@H]2C[C@@H]3C[C@@H](C3(C)C)[C@]2(C)O1]

The title compound (0.076 g, 32%, 2 steps) was obtained using methyl 5-benzyl-3-((3-cyano-4-isopropoxybenzamido)methyl)-4,5-dihydroisoxazol-5-carboxylate (0.155 g, 0.36 mmol) obtained in (2) above by the preparation method of Example 84-(3).

MS (m/z): 669[M+H]

(4) Preparation of ((1R)-1-(5-benzyl-3-((3-cyano-4-isopropoxybenzamido)methyl)-4,5-dihydroisoxazol-5-carboxamido)-3-methylbutyl)boronic acid

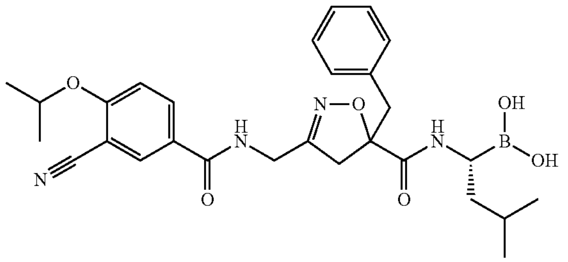 [SMILES: CC(C)C[C@H](NC(=O)C1(Cc2ccccc2)CC(CNC(=O)c2ccc(OC(C)C)c(C#N)c2)=NO1)B(O)O]

The title compound (0.037 g, 63%) was obtained using 5-benzyl-3-((3-cyano-4-isopropoxybenzamido)methyl)-N—((R)-3-methyl-1-((3aS,4S,6S,7aR)-3a,5,5-trimethyl-hexahydro-4,6-metanobenzo[d][1,3,2]dioxaborol-2-yl)butyl)-4,5-dihydroisoxazol-5-carboxamide (0.076 g, 0.11 mmol) obtained in the process (3) above by the preparation method of Example 1-(4).

NMR: $^1$H-NMR (500 MHz, MeOD-d4); δ 8.06-8.04 (m, 2H), 7.27-7.21 (m, 6H), 4.19 (s, 2H), 3.42-3.16 (m, 4H), 2.65-2.62 (m, 1H), 1.40-1.39 (d, 6H), 1.36 (m, 1H), 1.27 (m, 1H), 1.14-1.02 (m, 2H), 0.80-0.76 (dd, 6H)

MS (m/z): 535[M+H], 517[M-OH]

Example 124: Preparation of ((1R)-1-(3-((1H-indol-3-carboxamido)methyl)-5-benzyl-4,5-dihydroisoxazol-5-carboxamido)-3-methylbutyl)boronic acid Through the processes (1), (2) and (3) below, the title compound was obtained.

(1) Preparation of methyl 3-((1H-indol-3-carboxamido)methyl)-5-benzyl-4,5-dihydroisoxazol-5-carboxylate

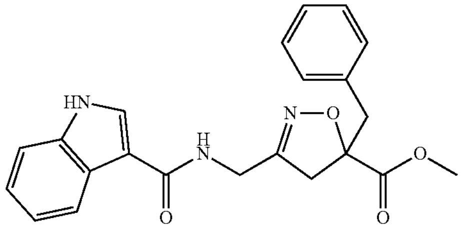 [SMILES: COC(=O)C1(Cc2ccccc2)CC(CNC(=O)c2c[nH]c3ccccc23)=NO1]

The title compound (0.08 g, 31%) was obtained using methyl 3-(aminomethyl)-5-benzyl-4,5-dihydroisoxazol-5-carboxylate hydrochloride (0.19 g, 0.67 mmol) obtained in Example 84-(1) and 1H-indol-3-carboxylic acid (0.12 g, 0.73 mmol) by the preparation method of Example 84-(2).

NMR: $^1$H-NMR (400 MHz, $CDCl_3$); δ 8.46 (br s, 1H), 7.56-7.54 (d, 1H), 7.48-7.46 (d, 1H), 7.35-7.34 (t, 1H), 7.24-7.13 (m, 6H), 6.92 (s, 1H), 6.38 (br s, 1H), 4.37-4.23 (m, 2H), 3.78 (s, 3H), 3.50-3.46 (d, 1H), 3.35-3.31 (d, 1H), 3.14-3.05 (m, 2H)

MS (m/z): 392[M+H]

(2) Preparation of 3-((1H-indol-3-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

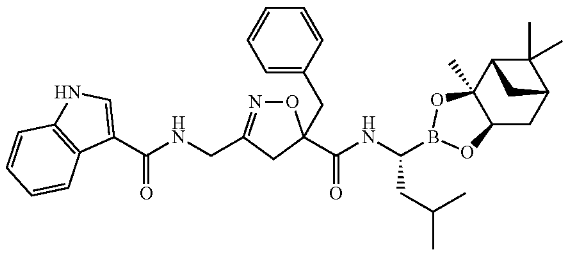 [SMILES: CC(C)C[C@H](NC(=O)C1(Cc2ccccc2)CC(CNC(=O)c2c[nH]c3ccccc23)=NO1)B1O[C@@H]2C[C@@H]3C[C@@H](C3(C)C)[C@]2(C)O1]

The title compound (0.03 g, 24%, 2 steps) was obtained using methyl 3-((1H-indol-3-carboxamido)methyl)-5-benzyl-4,5-dihydroisoxazol-5-carboxylate (0.08 g, 0.20 mmol) obtained in (1) above by the preparation method of Example 84-(3).

MS (m/z): 625[M+H]

(3) Preparation of ((1R)-1-(3-((1H-indol-3-carboxamido)methyl)-5-benzyl-4,5-dihydroisoxazol-5-carboxamido)-3-methylbutyl)boronic acid

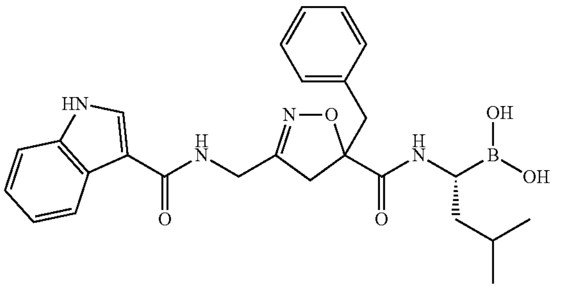

The title compound (0.016 g, 68%) was obtained using 3-((1H-indol-3-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.03 g, 0.048 mmol) obtained in (2) above by the preparation method of Example 1-(4).

NMR: $^1$H-NMR (500 MHz, MeOD-d4); δ 8.07-8.06 (d, 1H), 7.84 (s, 1H), 7.42-7.40 (d, 1H), 7.26-7.13 (m, 7H), 4.22 (s, 2H), 3.47-3.43 (m, 2H), 3.20-3.17 (m, 2H), 2.60 (m, 1H), 1.38-1.35 (m, 1H), 1.12-1.02 (m, 2H), 0.79-0.75 (dd, 6H)

MS (m/z): 491[M+H], 473[M-OH]

Example 125: Preparation of ((1R)-1-(3-((isoquinolin-1-carboxamido)methyl)-5-(3-methylbenzyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(3-methylbenzyl)-4,5-dihydroisoxazol-5-carboxylate hydrochloride

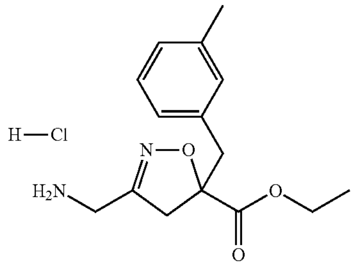

The title compound (0.32 g, 99%) was obtained using ethyl 3-(((tert-butoxycarbonyl)amino)methyl)-5-(3-methylbenzyl)-4,5-dihydroisoxazol-5-carboxylate (0.38 g, 1.01 mmol) obtained in Preparation Example 18 by the preparation method of Example 84-(1).

MS (m/z): 277[M+H]

(2) Preparation of ethyl 3-((isoquinolin-1-carboxamido)methyl)-5-(3-methylbenzyl)-4,5-dihydroisoxazol-5-carboxylate

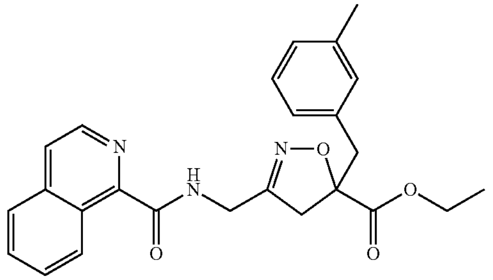 [SMILES: CCOC(=O)C1(Cc2cccc(C)c2)CC(CNC(=O)c2nccc3ccccc23)=NO1]

The title compound (0.10 g, 72%) was obtained using ethyl 3-(aminomethyl)-5-(3-methylbenzyl)-4,5-dihydroisoxazol-5-carboxylate hydrochloride (0.10 g, 0.32 mmol) obtained in (1) above and isoquinolin-1-carboxylic acid (0.061 g, 0.35 mmol) by the preparation method of Example 84-(2).

MS (m/z): 432[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide

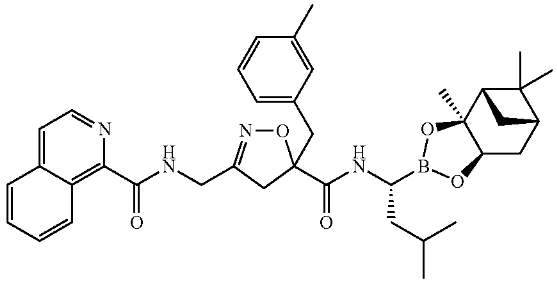 [SMILES: Cc1cccc(CC2(C(=O)N[C@@H](CC(C)C)B3O[C@@H]4C[C@@H]5C[C@@H](C5(C)C)[C@]4(C)O3)CC(CNC(=O)c3nccc4ccccc34)=NO2)c1]

The title compound (0.056 g, 37%, 2 steps) was obtained using ethyl 3-((isoquinolin-1-carboxamido)methyl)-5-(3-methylbenzyl)-4,5-dihydroisoxazol-5-carboxylate (0.1 g, 0.23 mmol) obtained in (2) above by the preparation method of Example 84-(3).

MS (m/z): 651[M+H], 499[M-$C_{10}H_{15}O$]

(4) Preparation of ((1R)-1-(3-((isoquinolin-1-carboxamido)methyl)-5-(3-methylbenzyl)-4,5-dihydroisoxazol-5-carboxamido)-3-methylbutyl)boronic acid

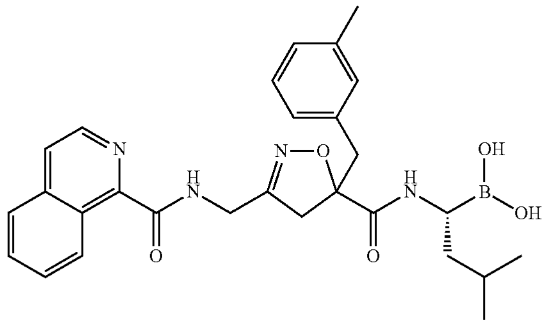

The title compound (0.029 g, 49%) was obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide (0.056 g, 0.086 mmol) obtained in (3) above by the preparation method of Example 1-(4).

NMR: $^1$H-NMR (400 MHz, $CDCl_3$); δ 9.52-9.49 (d, 1H), 8.50-8.47 (t, 1H), 8.39-8.37 (d, 1H), 7.84-7.64 (m, 4H), 7.25-7.24 (d, 1H), 7.15-6.98 (4H), 4.32-4.20 (m, 2H), 3.44-3.40 (d, 1H), 3.33-3.29 (d, 1H), 3.11-3.06 (dd, 2H), 2.80 (m, 1H), 2.26 (s, 3H), 1.34-1.14 (m, 3H), 0.78-0.76 (t, 6H)

MS (m/z): 517[M+H], 499[M-OH]

Example 126: Preparation of ((1R)-1-(3-((isoquinolin-1-carboxamido)methyl)-5-(phenoxymethyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(phenoxymethyl)-4,5-dihydroisoxazol-5-carboxylate hydrochloride

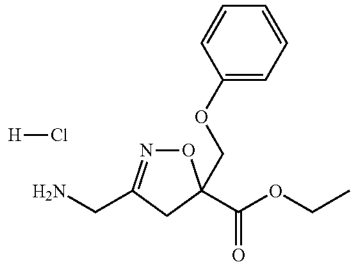

The title compound (0.46 g, 94%) was obtained using ethyl 3-(((tert-butoxycarbonyl)amino)methyl)-5-(phenoxymethyl)-4,5-dihydroisoxazol-5-carboxylate (0.59 g, 1.56 mmol) obtained in Preparation Example 19 by the preparation method of Example 84-(1).

MS (m/z): 279[M+H]

(2) Preparation of ethyl 3-((isoquinolin-1-carboxamido)methyl)-5-(phenoxymethyl)-4,5-dihydroisoxazol-5-carboxylate

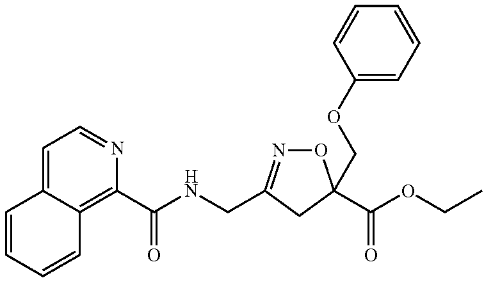 [SMILES: CCOC(=O)C1(COc2ccccc2)CC(CNC(=O)c2nccc3ccccc23)=NO1]

The title compound (0.16 g, 77%) was obtained using ethyl 3-(aminomethyl)-5-(phenoxymethyl)-4,5-dihydroisoxazol-5-carboxylate hydrochloride (0.15 g, 0.48 mmol) obtained in (1) above by the preparation method of Example 84-(2).

MS (m/z): 434[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(phenoxymethyl)-4,5-dihydroisoxazol-5-carboxamide

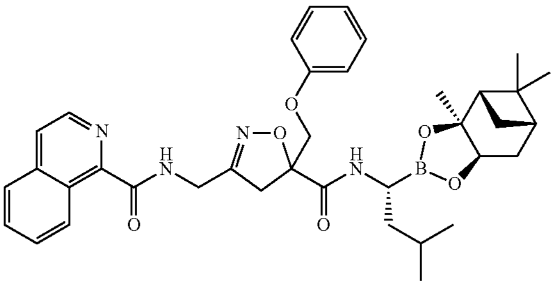 [SMILES: CC(C)C[C@H](NC(=O)C1(COc2ccccc2)CC(CNC(=O)c2nccc3ccccc23)=NO1)B1O[C@@H]2C[C@@H]3C[C@@H](C3(C)C)[C@]2(C)O1]

The title compound (0.053 g, 34%, 2 steps) was obtained using ethyl 3-((isoquinolin-1-carboxamido)methyl)-5-(phenoxymethyl)-4,5-dihydroisoxazol-5-carboxylate (0.16 g, 0.37 mmol) obtained in (2) above by the preparation method of Example 84-(3).

MS (m/z): 653[M+H], 675[M+Na]

(4) Preparation of ((1R)-1-(3-((isoquinolin-1-carboxamido)methyl)-5-(phenoxymethyl)-4,5-dihydroisoxazol-5-carboxamido)-3-methylbutyl)boronic acid

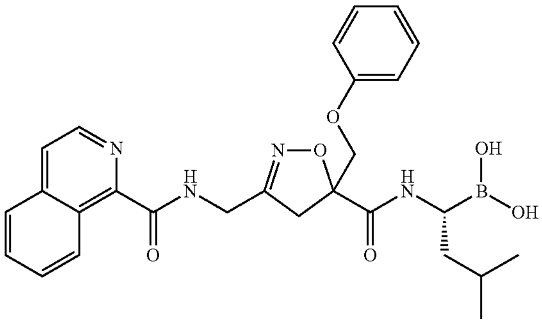

The title compound (0.025 g, 62%) was obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(phenoxymethyl)-4,5-dihydroisoxazol-5-carboxamide (0.053 g, 0.078 mmol) obtained in the process (3) above by the preparation method of Example 1-(4).

NMR: $^1$H-NMR (500 MHz, $CD_3OD$); δ 9.50-9.04 (d, 1H), 8.52-8.51 (d, 1H), 8.01-7.99 (m, 2H), 7.82-7.71 (m, 2H), 7.25-7.21 (m, 2H), 6.92-6.89 (m, 3H), 4.42-4.27 (m, 4H), 3.48-3.47 (d, 2H), 2.89-2.86 (m, 1H), 1.68-1.65 (m, 1H), 1.41-1.38 (m, 2H), 0.89-0.87 (dd, 6H)

MS (m/z): 519[M+H], 501[M-OH]

Example 127: Preparation of ((1R)-1-(3-((1H-indol-4-carboxamido)methyl)-5-benzyl-4,5-dihydroisoxazol-5-carboxamido)-3-methylbutyl)boronic acid Through the processes (1), (2) and (3) below, the title compound was obtained.

(1) Preparation of 5-benzyl-3-{[(1H-indol-4-carbonyl)-amino]-methyl}-4,5-dihydro-isoxazol-5-carboxylic acid methyl ester

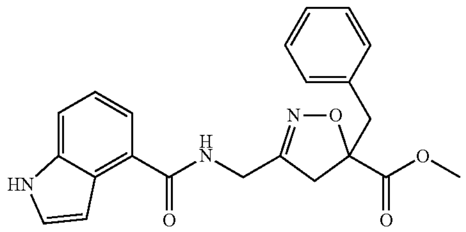 [SMILES: COC(=O)C1(Cc2ccccc2)CC(CNC(=O)c2cccc3[nH]ccc23)=NO1]

The title compound (0.21 g, 75%) was obtained using methyl 3-(aminomethyl)-5-benzyl-4,5-dihydroisoxazol-5-carboxylate hydrochloride (0.2 g, 0.70 mmol) obtained in Example 84-(1) and 1H-indol-4-carboxylic acid (0.125 g, 0.77 mmol) by the preparation method of Example 84-(2).

MS (m/z): 392[M+H]

(2) Preparation of 3-((1H-indol-4-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

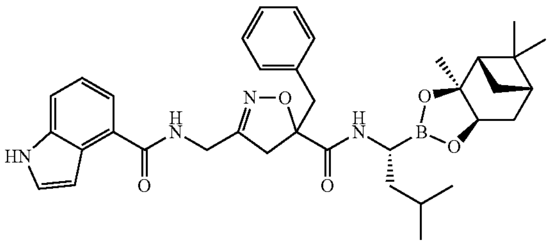 [SMILES: CC(C)C[C@H](NC(=O)C1(Cc2ccccc2)CC(CNC(=O)c2cccc3[nH]ccc23)=NO1)B1O[C@@H]2C[C@@H]3C[C@@H](C3(C)C)[C@]2(C)O1]

The title compound (0.06 g, 33%, 2 steps) was obtained using 5-benzyl-3-{[(1H-indol-4-carbonyl)-amino]-methyl}-4,5-dihydro-isoxazol-5-carboxylic acid methyl ester (0.21 g, 0.53 mmol) obtained in (1) above by the preparation method of Example 84-(3).

MS (m/z): 625[M+H]

(3) Preparation of ((1R)-1-(3-((1H-indol-4-carboxamido)methyl)-5-benzyl-4,5-dihydroisoxazol-5-carboxamido)-3-methylbutyl)boronic acid

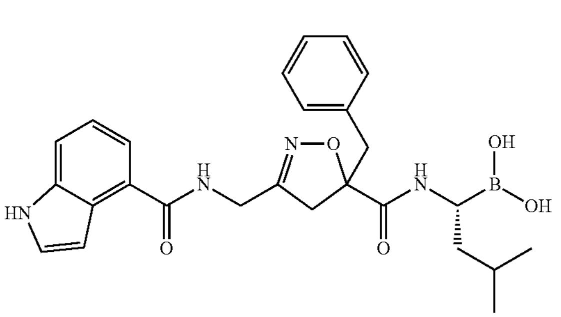

The title compound (0.033 g, 70%) was obtained using 3-((1H-indol-4-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.06 g, 0.096 mmol) obtained in (2) above by the preparation method of Example 1-(4).

NMR: $^1$H-NMR (500 MHz, MeOD-d4); δ 7.56-7.55 (d, 1H), 7.39-7.35 (m, 2H), 7.27-7.13 (m, 6H), 6.85-6.84 (d, 1H), 4.27 (s, 2H), 3.48-3.44 (d, 1H), 3.33-3.26 (m, 2H), 3.21-3.18 (d, 1H), 2.64-2.61 (m, 1H), 1.38-1.36 (m, 1H), 1.15-1.02 (m, 2H), 0.80-0.75 (dd, 6H)

MS (m/z): 491[M+H], 473[M-OH]

Example 128: Preparation of ((1R)-1-(5-((1H-pyrazol-1-yl)methyl)-3-((isoquinolin-1-carboxamido)methyl)-4,5-dihydroisoxazol-5-carboxamido)-3-methylbutyl)boronic acid Through the processes (1), (2), (3) and (4) below, the title compound was obtained.

(1) Preparation of ethyl 5-((1H-pyrazol-1-yl)methyl)-3-(aminomethyl)-4,5-dihydroisoxazol-5-carboxylate hydrochloride

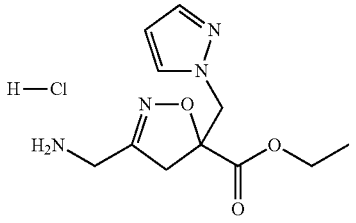

The title compound (0.47 g, 99%) was obtained using ethyl 5-((1H-pyrazol-1-yl)methyl)-3-(((tert-butoxycarbonyl)amino)methyl)-4,5-dihydroisoxazol-5-carboxylate (0.58 g, 1.64 mmol) obtained in Preparation Example 20 by the preparation method of Example 84-(1).

MS (m/z): 253[M+H]

(2) Preparation of ethyl 5-((1H-pyrazol-1-yl)methyl)-3-((isoquinolin-1-carboxamido)methyl)-4,5-dihydroisoxazol-5-carboxylate

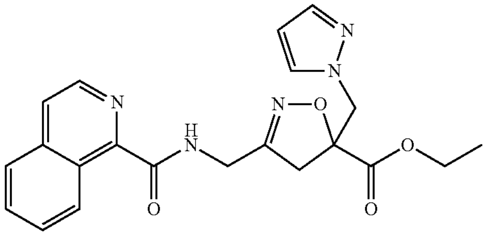 [SMILES: CCOC(=O)C1(Cn2cccn2)CC(CNC(=O)c2nccc3ccccc23)=NO1]

The title compound (0.117 g, 69%) was obtained using ethyl 5-((1H-pyrazol-1-yl)methyl)-3-(aminomethyl)-4,5-dihydroisoxazol-5-carboxylate hydrochloride (0.12 g, 0.42 mmol) obtained in (1) above and isoquinolin-1-carboxylic acid (0.079 g, 0.46 mmol) by the preparation method of Example 84-(2).

MS (m/z): 408[M+H]

(3) Preparation of 5-((1H-pyrazol-1-yl)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

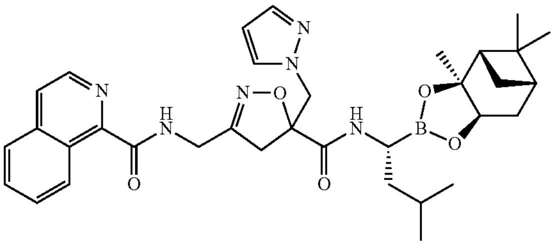 [SMILES: CC(C)C[C@H](NC(=O)C1(Cn2cccn2)CC(CNC(=O)c2nccc3ccccc23)=NO1)B1O[C@@H]2C[C@@H]3C[C@@H](C3(C)C)[C@]2(C)O1]

The title compound (0.1 g, 59%, 2 steps) was obtained using ethyl 5-((1H-pyrazol-1-yl)methyl)-3-((isoquinolin-1-carboxamido)methyl)-4,5-dihydroisoxazol-5-carboxylate (0.117 g, 0.29 mmol) obtained in (2) above by the preparation method of Example 84-(3).

MS (m/z): 627[M+H]

(4) Preparation of ((1R)-1-(5-((1H-pyrazol-1-yl)methyl)-3-((isoquinolin-1-carboxamido)methyl)-4,5-dihydroisoxazol-5-carboxamido)-3-methylbutyl)boronic acid

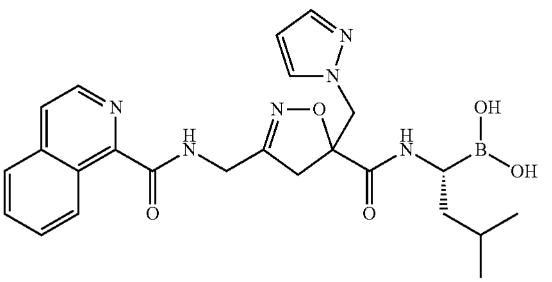 [SMILES: CC(C)C[C@H](NC(=O)C1(Cn2cccn2)CC(CNC(=O)c2nccc3ccccc23)=NO1)B(O)O]

The title compound (0.048 g, 61%) was obtained using 5-((1H-pyrazol-1-yl)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.1 g, 0.16 mmol) obtained in the process (3) above by the preparation method of Example 1-(4).

NMR: $^1$H-NMR (400 MHz, $CDCl_3$); δ 9.57-6.44 (m, 1H), 8.65-8.38 (m, 2H), 7.88-7.64 (m, 4H), 7.56-7.41 (m, 2H), 6.29-6.15 (m, 2H), 4.87-4.25 (4H), 3.64-3.15 (m, 2H), 2.85 (m, 1H), 1.46-1.30 (m, 3H), 0.87-0.83 (m, 6H)

MS (m/z): 493[M+H], 475[M-OH]

Example 129: Preparation of ((1R)-1-(5-benzyl-3-((1-isopropyl-1H-indol-5-carboxamido)methyl)-4,5-dihydroisoxazol-5-carboxamido)-3-methylbutyl)boronic acid Through the processes (1), (2), (3) and (4) below, the title compound was obtained.

(1) Preparation of 1-isopropyl-1H-indol-5-carboxylic acid

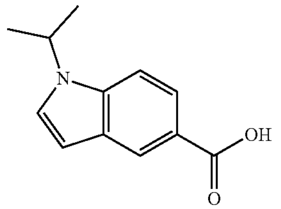

The title compound was obtained by the method described in WO2014129796A1.

(2) Preparation of methyl 5-benzyl-3-((1-isopropyl-1H-indol-5-carboxamido)methyl)-4,5-dihydroisoxazol-5-carboxylate

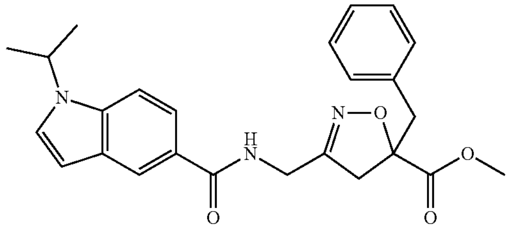 [SMILES: COC(=O)C1(Cc2ccccc2)CC(CNC(=O)c2ccc3c(ccn3C(C)C)c2)=NO1]

The title compound (0.138 g, 76%) was obtained using methyl 3-(aminomethyl)-5-benzyl-4,5-dihydroisoxazol-5-carboxylate hydrochloride (0.12 g, 0.42 mmol) obtained in Example 84-(1) and 1-isopropyl-1H-indol-5-carboxylic acid (0.094 g, 0.46 mmol) obtained in (1) above by the preparation method of Example 84-(2).

NMR: $^1$H-NMR (500 MHz, $CDCl_3$); δ 8.01-8.00 (d, 1H), 7.60-7.58 (dd, 1H), 7.40-7.38 (d, 1H), 7.30-7.29 (d, 1H), 7.23-7.22 (m, 5H), 6.60-6.59 (d, 1H), 6.27 (br s, 1H), 4.72-7.69 (m, 1H), 4.27-4.21 (m, 2H), 3.77 (s, 3H), 3.48-3.31 (m, 2H), 3.12-3.03 (m, 2H), 1.56-1.54 (dd, 6H)

MS (m/z): 434[M+H]

(3) Preparation of 5-benzyl-3-((1-isopropyl-1H-indol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

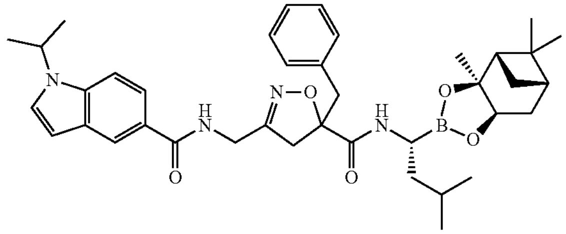 [SMILES: CC(C)C[C@H](NC(=O)C1(Cc2ccccc2)CC(CNC(=O)c2ccc3c(ccn3C(C)C)c2)=NO1)B1O[C@@H]2C[C@@H]3C[C@@H](C3(C)C)[C@]2(C)O1]

The title compound (0.075 g, 35%, 2 steps) was obtained using methyl 5-benzyl-3-((1-isopropyl-1H-indol-5-carboxamido)methyl)-4,5-dihydroisoxazol-5-carboxylate (0.138 g, 032 mmol) obtained in (2) above by the preparation method of Example 84-(3).

MS (m/z): 667[M+H]

(4) Preparation of ((1R)-1-(5-benzyl-3-((1-isopropyl-1H-indol-5-carboxamido)methyl)-4,5-dihydroisoxazol-5-carboxamido)-3-methylbutyl)boronic acid

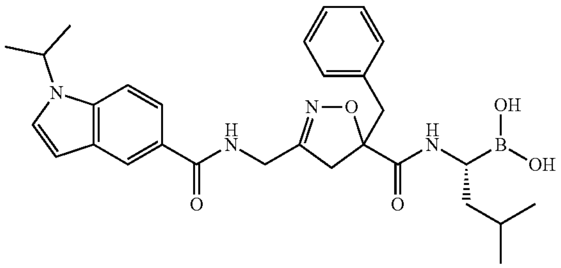

The title compound (0.038 g, 65%) was obtained using 5-benzyl-3-((1-isopropyl-1H-indol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.075 g, 0.11 mmol) obtained in (3) above by the preparation method of Example 1-(4).

NMR: $^1$H-NMR (500 MHz, MeOD-d4); δ 8.07 (d, 1H), 7.64-7.62 (dd, 1H), 7.49-7.44 (dd, 2H), 7.26-7.20 (m, 5H), 6.57-6.45 (d, 1H), 4.79-4.76 (m, 1H), 4.23 (s, 2H), 3.45-3.41 (d, 1H), 3.32-3.18 (m, 3H), 2.63-2.60 (m, 1H), 1.52-1.51 (d, 6H), 1.38-1.35 (m, 1H), 1.14-1.01 (m, 2H), 0.80-0.75 (dd, 6H)

MS (m/z): 533[M+H], 515[M-OH]

Example 130: Preparation of ((1R)-1-(5-benzyl-3-((2,4-dimethylthiazol-5-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((2,4-dimethylthiazol-5-carboxamido)methyl)-4,5-dihydroisoxazol-5-carboxylate

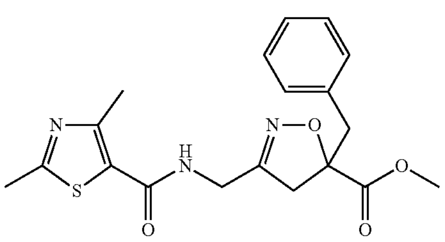

The title compound (0.13 g, 80%) was obtained using methyl 3-(aminomethyl)-5-benzyl-4,5-dihydroisoxazol-5-carboxylate hydrochloride (0.12 g, 0.42 mmol) obtained in Example 84-(1) and 2,4-dimethyl-thiazol-5-carboxylic acid (0.072 g, 0.46 mmol) by the preparation method of Example 84-(2).

MS (m/z): 388[M+H]

(2) Preparation of 5-benzyl-3-((2,4-dimethylthiazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

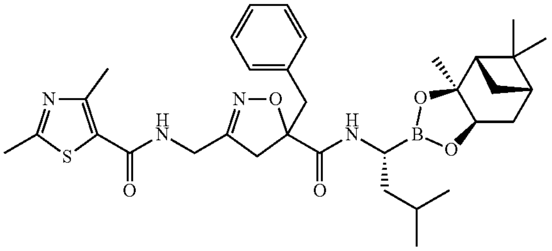

The title compound (0.093 g, 47%, 2 steps) was obtained using methyl 5-benzyl-3-((2,4-dimethylthiazol-5-carboxamido)methyl)-4,5-dihydroisoxazol-5-carboxylate (0.13 g, 0.34 mmol) obtained in (1) above by the preparation method of Example 84-(3).

MS (m/z): 621[M+H]

(3) Preparation of ((1R)-1-(5-benzyl-3-((2,4-dimethylthiazol-5-carboxamido)methyl)-4,5-dihydroisoxazol-5-carboxamido)-3-methylbutyl)boronic acid

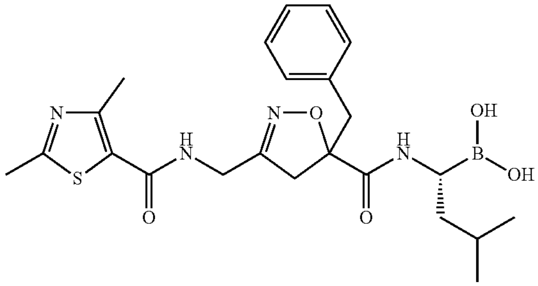 [SMILES: Cc1nc(C)c(C(=O)NCC2=NOC(Cc3ccccc3)(C(=O)N[C@@H](CC(C)C)B(O)O)C2)s1]

The title compound (0.035 g, 48%) was obtained using 5-benzyl-3-((2,4-dimethylthiazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.093 g, 0.15 mmol) obtained in (2) above by the preparation method of Example 1-(4).

NMR: $^1$H-NMR (500 MHz, MeOD-d4); δ 7.25-7.20 (m, 5H), 4.14 (s, 2H), 3.41-3.32 (m, 2H), 3.23-3.16 (m, 2H), 2.65 (s, 3H), 2.64-2.63 (m, 1H), 2.55 (s, 3H), 1.38 (m, 1H), 1.13-1.02 (m, 2H), 0.81-0.76 (dd, 6H)

MS (m/z): 487[M+H], 469[M-OH]

Example 131: Preparation of ((1R)-1-(5-(hydroxy(phenyl)methyl)-3-((isoquinolin-1-carboxamido)methyl)-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-(hydroxy(phenyl)methyl)-4,5-dihydroisoxazol-5-carboxylate hydrochloride

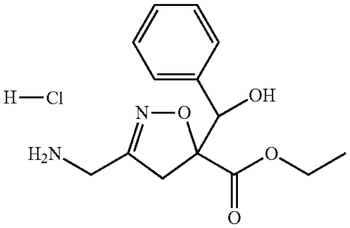

The title compound (1.65 g, quant.) was obtained using ethyl 3-(((tert-butoxycarbonyl)amino)methyl)-5-(hydroxy(phenyl)methyl)-4,5-dihydroisoxazol-5-carboxylate (1.95 g, 5.15 mmol) obtained in Preparation Example 21 by the preparation method of Example 84-(1).

(2) Preparation of ethyl 5-(hydroxy(phenyl)methyl)-3-((isoquinolin-1-carboxamido)methyl)-4,5-dihydroisoxazol-5-carboxylate

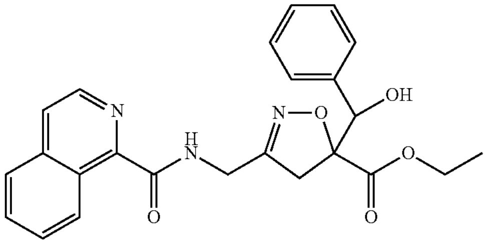 [SMILES: CCOC(=O)C1(C(O)c2ccccc2)CC(CNC(=O)c2nccc3ccccc23)=NO1]

The title compound (1.84 g, 82%) was obtained using ethyl 3-(aminomethyl)-5-(hydroxy(phenyl)methyl)-4,5-dihydroisoxazol-5-carboxylate hydrochloride (1.65 g, 5.15 mmol) obtained in (1) above and isoquinolin-1-carboxylic acid (0.892 g, 5.15 mmol) by the preparation method of Example 84-(2).

NMR: $^1$H-NMR (400 MHz, $CDCl_3$); δ 9.60 (1H, d), 8.53 (2H, t), 7.90-7.75 (4H, m), 7.46-7.27 (4H, m), 5.29 와 5.19 (1H, 2 s), 4.43-4.25 (3H, m), 3.50 과 3.42 (2H, 2 s), 2.85 와 2.77 (1H, 2 s), 1.30 (3H, t)

MS (m/z): 434[M+H]

(3) Preparation of 5-(hydroxy(phenyl)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

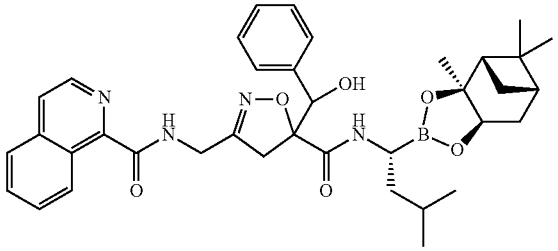 [SMILES: CC(C)C[C@H](NC(=O)C1(C(O)c2ccccc2)CC(CNC(=O)c2nccc3ccccc23)=NO1)B1O[C@@H]2C[C@@H]3C[C@@H](C3(C)C)[C@]2(C)O1]

The title compound (0.117 g, 43%, 2 steps) was obtained using ethyl 5-(hydroxy(phenyl)methyl)-3-((isoquinolin-1-carboxamido)methyl)-4,5-dihydroisoxazol-5-carboxylate (0.180 g, 0.415 mmol) obtained in (2) above by the preparation method of Example 84-(3).

MS (m/z): 653[M+H]

(4) Preparation of ((1R)-1-(5-(hydroxy(phenyl)methyl)-3-((isoquinolin-1-carboxamido)methyl)-4,5-dihydroisoxazol-5-carboxamido)-3-methylbutyl) boronic acid

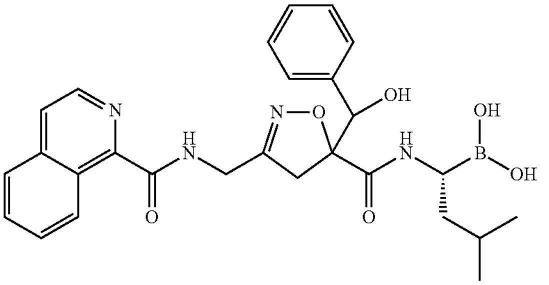

Two types of the title compound of Isomer 1 having low polarity (0.011 g, 12%) and Isomer 2 having high polarity (0.018 g, 19%) were obtained using 5-(hydroxy(phenyl)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.117 g, 0.179 mmol) obtained in (3) above by the preparation method of Example 1-(4).

Isomer 1

NMR: $^1$H-NMR (500 MHz, $CDCl_3$); δ 9.46 (1H, dd), 8.42-8.37 (2H, m), 7.81 (2H, dd), 7.71-7.64 (2H, m), 7.45 (2H, dd), 7.26-7.23 (2H, m), 5.08 (1H, s), 4.37 (1H, s), 4.11 (2H, d), 3.69 (1H, d), 3.34 (1H, d), 2.82 (1H, br s), 1.76 (2H, br s), 1.36-1.09 (3H, m), 0.79 (6H, dd)

MS (m/z): 541[M+Na], 501[M-OH]

Isomer 2

NMR: $^1$H-NMR (500 MHz, $CDCl_3$); δ 9.49-9.39 (1H, m), 8.50-8.36 (2H, m), 7.89-7.66 (4H, m), 7.55-7.16 (4H, m), 4.99-4.91 (1H, m), 4.35-4.09 (2H, m), 3.51-3.37 (2H, m), 3.00-2.92 (1H, m), 1.80 (2H, br s), 1.38-1.09 (3H, m), 0.98-0.80 (6H, dd)

MS (m/z): 541[M+Na], 501[M-OH]

Example 132: Preparation of ((1R)-1-(5-benzyl-3-((imidazo[1,2-a]pyridin-8-carboxamido)methyl)-4,5-dihydroisoxazol-5-carboxamido)-3-methylbutyl) boronic acid Through the processes (1), (2), (3), (4) and (5) below, the title compound was obtained.

(1) Preparation of imidazo[1,2-a]pyridin-8-carboxylic acid

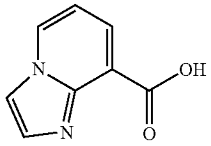 [SMILES: O=C(O)c1cccn2ccnc12]

The title compound was obtained by the method described in WO200923253A2.

(2) Preparation of methyl 5-benzyl-3-((imidazo[1,2-a]pyridin-8-carboxamido)methyl)-4,5-dihydroisoxazol-5-carboxylate

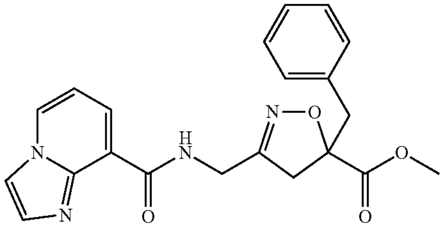 [SMILES: COC(=O)C1(Cc2ccccc2)CC(CNC(=O)c2cccn3ccnc23)=NO1]

The title compound (0.13 g, 78%) was obtained using methyl 3-(aminomethyl)-5-benzyl-4,5-dihydroisoxazol-5-carboxylate hydrochloride (0.12 g, 0.42 mmol) obtained in Example 84-(1) and imidazo[1,2-a]pyridin-8-carboxylic acid (0.075 g, 0.46 mmol) obtained in (1) by the preparation method of Example 84-(2).

NMR: $^1$H-NMR (400 MHz, $CDCl_3$); δ 10.52 (m, 1H), 8.29-8.21 (dd, 1H), 8.18-8.16 (dd, 1H), 7.67-7.64 (dd, 2H), 7.22-7.09 (m, 5H), 6.99-6.95 (t, 1H), 4.37-4.36 (d, 2H), 3.73 (s, 3H), 3.49-3.45 (d, 1H), 3.30-3.26 (d, 1H), 3.16-3.13 (d, 1H), 3.11-3.06 (d, 1H)

MS (m/z): 393[M+H]

(3) Preparation of 5-benzyl-3-((imidazo[1,2-a]pyridin-8-carboxamido)methyl)-4,5-dihydroisoxazol-5-carboxylic acid

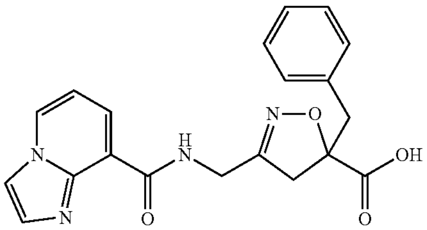 [SMILES: O=C(NCC1=NOC(Cc2ccccc2)(C(=O)O)C1)c1cccn2ccnc12]

The quantitative amount of the title compound was obtained using methyl 5-benzyl-3-((imidazo[1,2-a]pyridin-8-carboxamido)methyl)-4,5-dihydroisoxazol-5-carboxylate (0.128 g, 0.33 mmol) obtained in (2) above by the preparation method of Example 84-(3).

MS (m/z): 379[M+H]

(4) Preparation of 5-benzyl-3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

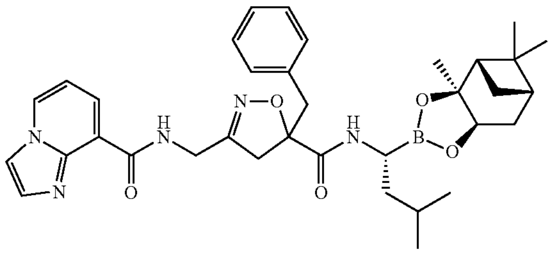 [SMILES: CC(C)C[C@H](NC(=O)C1(Cc2ccccc2)CC(CNC(=O)c2cccn3ccnc23)=NO1)B1O[C@@H]2C[C@@H]3C[C@@H](C3(C)C)[C@]2(C)O1]

The title compound (0.03 g, 17%) was obtained using 5-benzyl-3-((imidazo[1,2-a]pyridin-8-carboxamido)methyl)-4,5-dihydroisoxazol-5-carboxylic acid (0.12 g, 0.33 mmol) obtained in (3) above by the preparation method of Example 84-(4).

MS (m/z): 626[M+H]

(5) Preparation of ((1R)-1-(5-benzyl-3-((imidazo[1,2-a]pyridin-8-carboxamido)methyl)-4,5-dihydroisoxazol-5-carboxamido)-3-methylbutyl)boronic acid

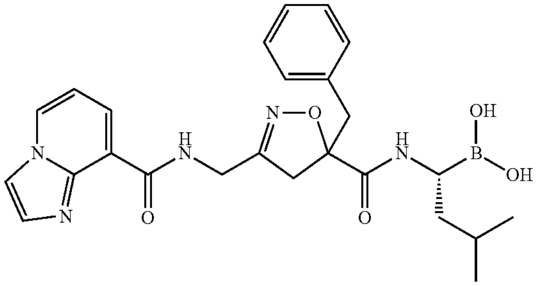 [SMILES: CC(C)C[C@H](NC(=O)C1(Cc2ccccc2)CC(CNC(=O)c2cccn3ccnc23)=NO1)B(O)O]

The title compound (0.009 g, 36%) was obtained using 5-benzyl-3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.03 g, 0.048 mmol) obtained in the process (4) above by the preparation method of Example 1-(4).

NMR: $^1$H-NMR (400 MHz, MeOD-$d_4$); δ 8.67-8.65 (dd, 1H), 8.11-8.09 (dd, 1H), 7.98-7.97 (d, 1H), 7.69-7.68 (d, 1H), 7.29-7.16 (m, 5H), 7.09-7.01 (t, 1H), 4.58 (s, 2H), 3.51-3.20 (m, 4H), 2.70-2.66 (t, 1H), 1.44-1.40 (m, 1H), 1.19-1.03 (m, 2H), 0.83-0.78 (dd, 6H)

MS (m/z): 492[M+H], 474[M-OH]

Example 133: Preparation of ((1R)-1-(5-benzyl-3-((2-methylimidazo[1,2-a]pyridin-3-carboxamido)methyl)-4,5-dihydroisoxazol-5-carboxamido)-3-methylbutyl)boronic acid Through the processes (1), (2), (3) and (4) below, the title compound was obtained.

(1) Preparation of 2-methyl-imidazo[1,2-a]pyridin-3-carboxylic acid

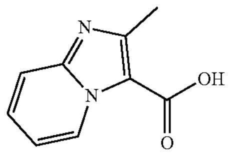

The title compound was obtained by the method described in Journal of Medicinal Chemistry, 2012, vol. 55, #17 p. 7525-7545.

(2) Preparation of methyl 5-benzyl-3-((2-methylimidazo[1,2-a]pyridin-3-carboxamido)methyl)-4,5-dihydroisoxazol-5-carboxylate

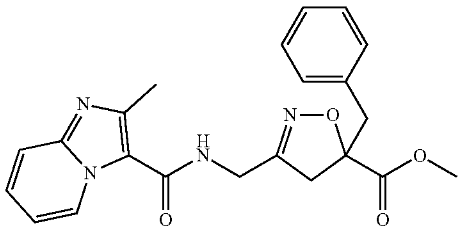 [SMILES: COC(=O)C1(Cc2ccccc2)CC(CNC(=O)c2c(C)nc3ccccn23)=NO1]

The title compound (0.133 g, 78%) was obtained using methyl 3-(aminomethyl)-5-benzyl-4,5-dihydroisoxazol-5-carboxylate hydrochloride (0.12 g, 0.42 mmol) obtained in Example 84-(1) and 2-methyl-imidazo[1,2-a]pyridin-3-carboxylic acid (0.081 g, 0.46 mmol) obtained in (1) above by the preparation method of Example 84-(2).

NMR: $^1$H-NMR (400 MHz, $CDCl_3$); δ 9.38-9.36 (m, 1H), 7.61-7.59 (m, 1H), 7.38-7.34 (m, 1H), 7.23-7.19 (m, 5H), 6.96-6.93 (m, 1H), 6.04 (m, 1H), 4.27-4.25 (m, 2H), 3.79 (s, 3H), 3.49-3.45 (d, 1H), 3.37-3.33 (d, 1H), 3.15-3.11 (d, 1H), 3.07-3.03 (d, 1H), 2.67 (s, 3H)

MS (m/z): 407[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-methylimidazo[1,2-a]pyridin-3-carboxamido)methyl)-4,5-dihydroisoxazol-5-carboxamide

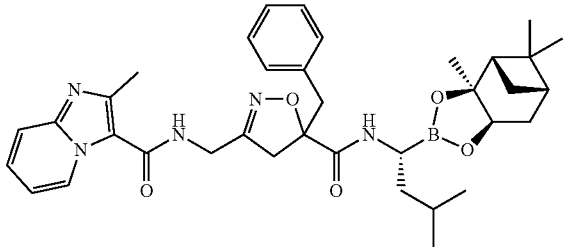 [SMILES: Cc1nc2ccccn2c1C(=O)NCC1=NOC(Cc2ccccc2)(C(=O)N[C@@H](CC(C)C)B2O[C@@H]3C[C@@H]4C[C@@H](C4(C)C)[C@]3(C)O2)C1]

The title compound (0.058 g, 27%, 2 steps) was obtained using methyl 5-benzyl-3-((2-methylimidazo[1,2-a]pyridin-3-carboxamido)methyl)-4,5-dihydroisoxazol-5-carboxylate (0.133 g, 0.33 mmol) obtained in (2) above by the preparation method of Example 84-(3).

MS (m/z): 640[M+H]

(4) Preparation of ((1R)-1-(5-benzyl-3-((2-methylimidazo[1,2-a]pyridin-3-carboxamido)methyl)-4,5-dihydroisoxazol-5-carboxamido)-3-methylbutyl) boronic acid

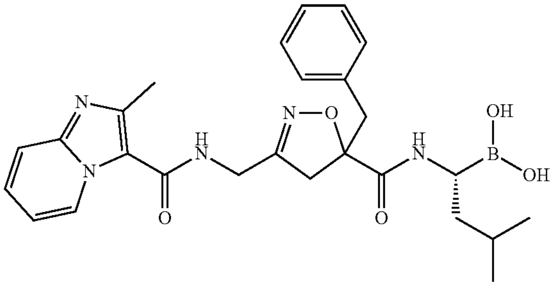 [SMILES: Cc1nc2ccccn2c1C(=O)NCC1=NOC(Cc2ccccc2)(C(=O)N[C@@H](CC(C)C)B(O)O)C1]

The title compound (0.013 g, 29%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-methylimidazo[1,2-a]pyridin-3-carboxamido)methyl)-4,5-dihydroisoxazol-5-carboxamide (0.058 g, 0.091 mmol) obtained in the process (3) above by the preparation method of Example 1-(4).

NMR: $^1$H-NMR (400 MHz, $CDCl_3$); δ 9.31-9.29 (m, 1H), 7.56-7.55 (m, 1H), 7.32 (m, 1H), 7.26-7.20 (m, 5H), 6.26-6.24 (m, 1H), 6.26-6.24 (m, 1H), 4.25-4.21 (m, 2H), 3.44-3.40 (d, 1H), 3.36-3.33 (d, 1H), 3.16-3.13 (d, 1H), 3.09-3.06 (d, 1H), 2.79 (m, 1H), 1.37-1.16 (m, 3H), 0.81-0.77 (m, 6H)

MS (m/z): 506[M+H], 488[M-OH]

Example 134: Preparation of ((1R)-1-(5-benzyl-3-((1-isopropyl-1H-indol-4-carboxamido)methyl)-4,5-dihydroisoxazol-5-carboxamido)-3-methylbutyl) boronic acid Through the processes (1), (2), (3), (4) and (5) below, the title compound was obtained.

(1) Preparation of 1-isopropyl-1H-indol-4-carboxylic acid methyl ester

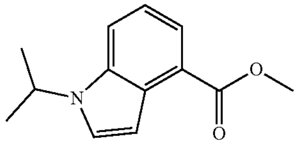 [SMILES: COC(=O)c1cccc2c1ccn2C(C)C]

1H-indol-4-carboxylic acid methyl ester (0.3 g, 1.71 mmol) was dissolved in dimethylformamide (10 ml). Sodium hydride (0.1 g, 2.57 mmol) and 2-iodopropane (0.34 ml, 3.42 mmol) were added in order, and stirring was performed at 60° C. for 4 hours. The solvent was distilled under a reduced pressure, water was added, and extraction with ethyl acetate was performed. An organic layer was dried over anhydrous magnesium sulfate, and filtered. The filtrate was distilled under a reduced pressure and separated by column chromatography to obtain the title compound (0.27 g, 72%).

NMR: $^1$H-NMR (400 MHz, $CDCl_3$); δ 7.91-7.89 (dd, 1H), 7.60-7.57 (d, 1H), 7.38-7.37 (d, 1H), 7.24-7.22 (d, 1H), 7.15-7.14 (d, 1H), 4.75-7.67 (m, 1H), 3.98 (s, 3H), 1.57-1.54 (s, 6H)

MS (m/z): 218[M+H]

(2) Preparation of 1-isopropyl-1H-indol-4-carboxylic acid

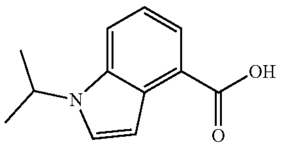

The title compound (0.25 g, 99%) was obtained using 1-isopropyl-1H-indol-4-carboxylic acid methyl ester (0.27 g, 1.24 mmol) obtained in (1) above by the preparation method of Example 119-(2).

MS (m/z): 204[M+H]

(3) Preparation of methyl 5-benzyl-3-((1-isopropyl-1H-indol-4-carboxamido)methyl)-4,5-dihydroisoxazol-5-carboxylate

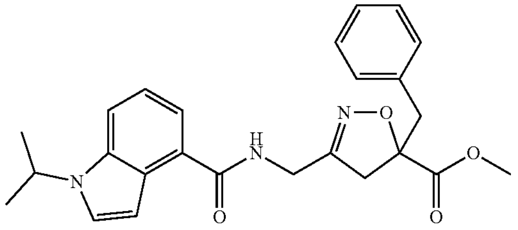 [SMILES: COC(=O)C1(Cc2ccccc2)CC(CNC(=O)c2cccc3c2ccn3C(C)C)=NO1]

The title compound (0.16 g, 88%) was obtained using methyl 3-(aminomethyl)-5-benzyl-4,5-dihydroisoxazol-5-carboxylate hydrochloride (0.12 g, 0.42 mmol) obtained in Example 84-(1) and 1-isopropyl-1H-indol-4-carboxylic acid (0.093 g, 0.46 mmol) obtained in (2) above by the preparation method of Example 84-(2).

NMR: $^1$H-NMR (400 MHz, $CDCl_3$); δ 7.54-7.52 (d, 1H), 7.46-7.44 (dd, 1H), 7.36-7.35 (dd, 1H), 7.25-7.12 (m, 6H), 6.86-6.85 (d, 1H), 6.44-6.41 (br s, 1H), 4.77-7.67 (m, 1H), 4.36-4.23 (m, 2H), 3.77 (s, 3H), 3.50-3.30 (m, 2H), 3.14-3.05 (m, 2H), 1.55-1.54 (d, 6H)

MS (m/z): 434[M+H]

(4) Preparation of 5-benzyl-3-((1-isopropyl-1H-indol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

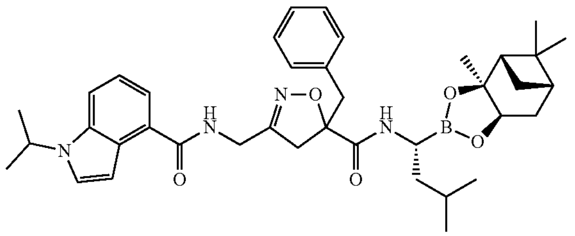 [SMILES: CC(C)C[C@H](NC(=O)C1(Cc2ccccc2)CC(CNC(=O)c2cccc3c2ccn3C(C)C)=NO1)B1O[C@@H]2C[C@@H]3C[C@@H](C3(C)C)[C@]2(C)O1]

The title compound (0.05 g, 31%, 2 steps) was obtained using methyl 5-benzyl-3-((1-isopropyl-1H-indol-4-carboxamido)methyl)-4,5-dihydroisoxazol-5-carboxylate (0.16 g, 0.37 mmol) obtained in (3) above by the preparation method of Example 84-(3).

MS (m/z): 667[M+H]

(5) Preparation of ((1R)-1-(5-benzyl-3-((1-isopropyl-1H-indol-4-carboxamido)methyl)-4,5-dihydroisoxazol-5-carboxamido)-3-methylbutyl)boronic acid

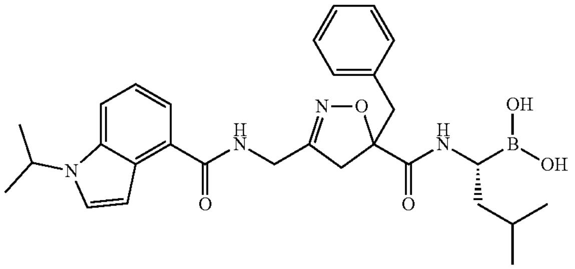

The title compound (0.023 g, 58%) was obtained using 5-benzyl-3-((1-isopropyl-1H-indol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.05 g, 0.075 mmol) obtained in (4) above by the preparation method of Example 1-(4).

NMR: $^1$H-NMR (500 MHz, MeOD-d4); δ 7.63-7.62 (d, 1H), 7.48-7.47 (d, 1H), 7.40-7.38 (d, 1H), 7.25-7.18 (m, 6H), 6.86-6.85 (d, 1H), 4.80-4.76 (m, 1H), 4.27 (s, 2H), 3.47-3.33 (m, 2H), 3.21-3.18 (m, 2H), 2.64-2.61 (m, 1H), 1.52-1.51 (d, 6H), 1.38-1.34 (m, 1H), 1.13-1.00 (m, 2H), 0.79-0.75 (dd, 6H)

MS (m/z): 533[M+H], 515[M-OH]

Example 135: Preparation of ((1R)-1-(3-((imidazo[1,2-a]pyridin-8-carboxamido)methyl)-5-(3-methoxybenzyl)-4,5-dihydroisoxazol-5-carboxamido)-3-methylbutyl)boronic acid Through the processes (1), (2) and (3) below, the title compound was obtained.

(1) Preparation of ethyl 3-((imidazo[1,2-a]pyridin-8-carboxamido)methyl)-5-(3-methoxybenzyl)-4,5-dihydroisoxazol-5-carboxylate

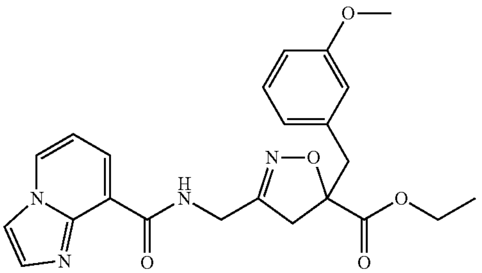 [SMILES: CCOC(=O)C1(Cc2cccc(OC)c2)CC(CNC(=O)c2cccn3ccnc23)=NO1]

The title compound (0.133 g, 74%) was obtained using ethyl 3-(aminomethyl)-5-(3-methoxybenzyl)-4,5-dihydroisoxazol-5-carboxylate hydrochloride (0.135 g, 0.411 mmol) obtained in Example 100-(1) and imidazo[1,2-a]pyridin-8-carboxylic acid (0.100 g, 0.620 mmol) obtained in Example 132-(1) by the preparation method of Example 84-(2).

NMR: $^1$H-NMR (400 MHz, $CDCl_3$); δ 10.56 (1H, t), 8.30 (1H, dd), 8.15 (1H, dd), 7.68 (1H, d), 7.62 (1H, d), 7.09 (1H, t), 6.95 (1H, t), 6.80 (1H, d), 6.79 (1H, s), 6.67 (1H, dd), 4.40 (2H, d), 4.24-4.17 (2H, m), 3.71 (3H, s), 3.49 (1H, d), 3.26 (1H, d), 3.15 (1H, d), 2.11 (1H, m), 1.24 (3H, t)

MS (m/z): 437[M+H]

(2) Preparation of 5-benzyl-3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

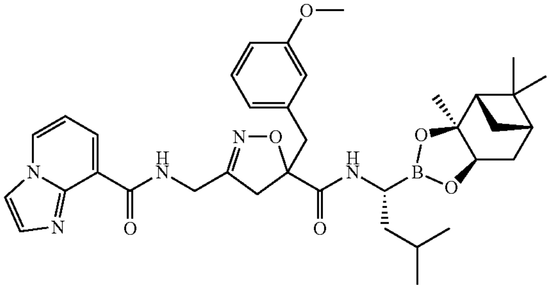 [SMILES: COc1cccc(CC2(C(=O)N[C@@H](CC(C)C)B3O[C@@H]4C[C@@H]5C[C@@H](C5(C)C)[C@]4(C)O3)CC(CNC(=O)c3cccn4ccnc34)=NO2)c1]

The title compound (0.043 g, 21%, 2 steps) was obtained using ethyl 3-((imidazo[1,2-a]pyridin-8-carboxamido)methyl)-5-(3-methoxybenzyl)-4,5-dihydroisoxazol-5-carboxylate (0.133 g, 0.305 mmol) obtained in (2) above by the preparation method of Example 84-(3).

MS (m/z): 626[M+H]

(3) Preparation of ((1R)-1-(3-((imidazo[1,2-a]pyridin-8-carboxamido)methyl)-5-(3-methoxybenzyl)-4,5-dihydroisoxazol-5-carboxamido)-3-methylbutyl)boronic acid

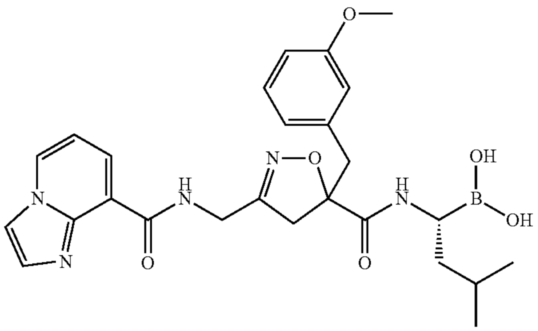 [SMILES: COc1cccc(CC2(C(=O)N[C@@H](CC(C)C)B(O)O)CC(CNC(=O)c3cccn4ccnc34)=NO2)c1]

The title compound (0.021 g, 61%) was obtained using 5-benzyl-3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.063 g, 0.0656 mmol) obtained in the process (2) above by the preparation method of Example 1-(4).

NMR: $^1$H-NMR (500 MHz, $CD_3OD$); δ 10.57 (1H, t), 8.28 (1H, d), 8.18 (1H, d), 7.66 (2H, dd), 7.21-7.17 (2H, m), 6.98 (1H, t), 6.89 (1H, d), 6.84 (1H, s), 6.74 (1H, d), 4.36 (2H, t), 3.78 (3H, s), 3.45 (1H, d), 3.34 (1H, d), 3.14 (1H, d), 3.13 (1H, d), 2.86 (1H, t), 1.62 (2H, br s), 1.41-1.21 (3H, m), 0.81 (6H, dd)

MS (m/z): 544[M+Na], 504[M-OH]

Example 136: Preparation of ((1R)-1-(3-((isoquinolin-1-carboxamido)methyl)-5-(1-phenylethyl)-4,5-dihydroisoxazol-5-carboxamido)-3-methylbutyl)boronic acid Through the processes (1), (2), (3) and (4) below, the title compound was obtained.

(1) Preparation of methyl 3-(aminomethyl)-5-(1-phenylethyl)-4,5-dihydroisoxazol-5-carboxylate hydrochloride

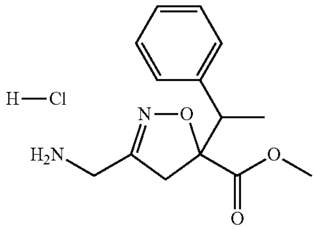

The title compound (0.276 g, quant.) was obtained using methyl 3-(((tert-butoxycarbonyl)amino)methyl)-5-(1-phenylethyl)-4,5-dihydroisoxazol-5-carboxylate (0.33 g, 0.9 mmol) obtained in Preparation Example 22 by the preparation method of Example 84-(1).

MS (m/z): 263[M+H]

(2) Preparation of methyl 3-((isoquinolin-1-carboxamido)methyl)-5-(1-phenylethyl)-4,5-dihydroisoxazol-5-carboxylate

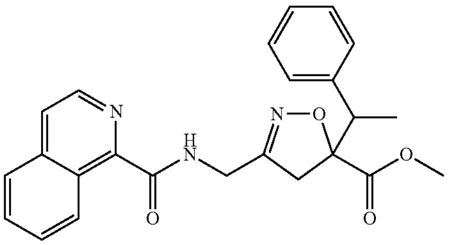 [SMILES: COC(=O)C1(C(C)c2ccccc2)CC(CNC(=O)c2nccc3ccccc23)=NO1]

The title compound (0.308 g, 81%) was obtained using methyl 3-(aminomethyl)-5-(1-phenylethyl)-4,5-dihydroisoxazol-5-carboxylate hydrochloride (0.276 g, 0.91 mmol) obtained in (1) above and isoquinolin-1-carboxylic acid (0.205 g, 1.18 mmol) by the preparation method of Example 84-(2).

NMR: $^1$H-NMR (400 MHz, $CDCl_3$); δ 9.55-9.53 (1H, m), 8.51-8.31 (2H, m), 7.91-7.72 (4H, m), 7.30-7.13 (5H, m), 4.37-4.22 (2H, m), 3.81 과 3.67 (3H, 2 s), 3.51-3.30 (3H, m), 1.43 (3H, d)

MS (m/z): 418[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(1-phenylethyl)-4,5-dihydroisoxazol-5-carboxamide

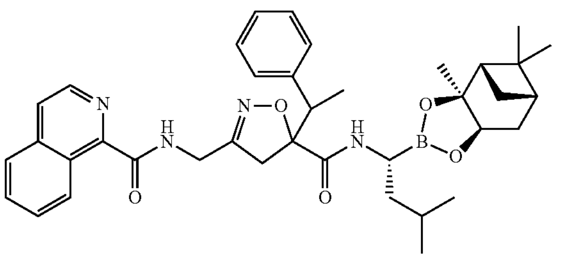 [SMILES: CC(C)C[C@H](NC(=O)C1(C(C)c2ccccc2)CC(CNC(=O)c2nccc3ccccc23)=NO1)B1O[C@@H]2C[C@@H]3C[C@@H](C3(C)C)[C@]2(C)O1]

The title compound (0.141 g, 68%, 2 steps) was obtained using methyl 3-((isoquinolin-1-carboxamido)methyl)-5-(1-phenylethyl)-4,5-dihydroisoxazol-5-carboxylate (0.308 g, 0.74 mmol) obtained in (3) above by the preparation method of Example 84-(3).

MS (m/z): 651[M+H]

(4) Preparation of ((1R)-1-(3-((isoquinolin-1-carboxamido)methyl)-5-(1-phenylethyl)-4,5-dihydroisoxazol-5-carboxamido)-3-methylbutyl)boronic acid

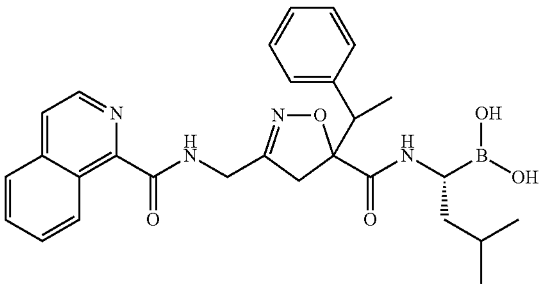

Isomer 1 having low polarity (0.025 g, 22%) and Isomer 2 having high polarity (0.0044 g, 4%) were obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(1-phenylethyl)-4,5-dihydroisoxazol-5-carboxamide (0.141 g, 0.217 mmol) obtained in the process (3) above by the preparation method of Example 1-(4).

Isomer 1

NMR: $^1$H-NMR (500 MHz, $CD_3OD$); δ 9.04 (1H, d), 8.47 (1H, d), 7.96 (1H, d), 7.93 (1H, d), 7.78 (1H, t), 7.70 (1H, t), 7.29 (2H, d), 7.14 (2H, dd), 7.04 (1H, t), 4.10 (2H, d), 3.37-3.29 (2H, m), 3.12 (1H, d), 2.77 (1H, t), 1.62-1.58 (1H, m), 1.49-1.27 (4H, m), 0.88 (6H, dd)

MS (m/z): 539[M+Na], 499[M-OH]

Isomer 2

NMR: $^1$H-NMR (500 MHz, $CD_3OD$); δ 9.07 (1H, d), 8.51 (1H, d), 7.97 (1H, d), 7.95 (1H, d), 7.78 (1H, t), 7.71 (1H, t), 7.31 (2H, d), 7.23-7.18 (2H, m), 4.39 (2H, d), 3.51 (2H, d), 3.36 (1H, dd), 2.45 (1H, dd), 1.37 (3H, d), 1.27-1.22 (1H, m), 0.86-0.79 (1H, m), 0.71 (6H, dd), 0.64-0.58 (1H, m)

MS (m/z): 539[M+Na], 499[M-OH]

Example 137: Preparation of ((1R)-1-(3-((isoquinolin-1-carboxamido)methyl)-5-(thiazol-4-ylmethyl)-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-(thiazol-4-ylmethyl)-4,5-dihydroisoxazol-5-carboxylate hydrochloride

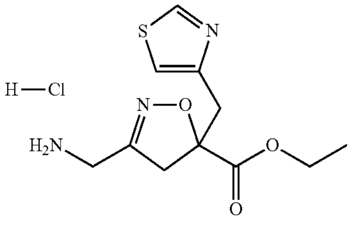

The title compound (0.25 g, 99%) was obtained using ethyl 3-(((tert-butoxycarbonyl)amino)methyl)-5-(thiazol-4-ylmethyl)-4,5-dihydroisoxazol-5-carboxylate (0.30 g, 0.81 mmol) obtained in Preparation Example 23 by the preparation method of Example 84-(1).

MS (m/z): 270[M+H]

(2) Preparation of ethyl 3-((isoquinolin-1-carboxamido)methyl)-5-(thiazol-4-ylmethyl)-4,5-dihydroisoxazol-5-carboxylate

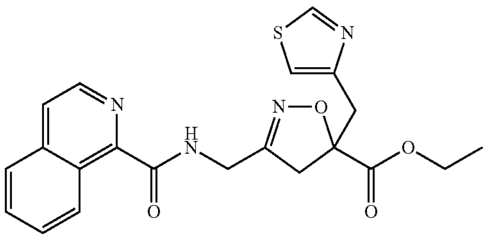 [SMILES: CCOC(=O)C1(Cc2cscn2)CC(CNC(=O)c2nccc3ccccc23)=NO1]

The title compound (0.113 g, 68%) was obtained using ethyl 3-(aminomethyl)-5-(thiazol-4-ylmethyl)-4,5-dihydroisoxazol-5-carboxylate hydrochloride (0.12 g, 0.39 mmol) obtained in (1) above and isoquinolin-1-carboxylic acid (0.075 g, 0.43 mmol) by the preparation method of Example 84-(2).

NMR: $^1$H-NMR (400 MHz, $CDCl_3$); δ 9.58-9.56 (d, 1H), 8.64-8.63 (d, 1H), 8.49-8.48 (m, 2H), 7.88-7.83 (m, 2H), 7.76-7.68 (m, 2H), 7.21 (d, 1H), 4.36-4.33 (m, 2H), 4.27-4.22 (q, 2H), 3.58-3.38 (m, 4H), 1.29-1.26 (t, 3H)

MS (m/z): 425[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(thiazol-4-ylmethyl)-4,5-dihydroisoxazol-5-carboxamide

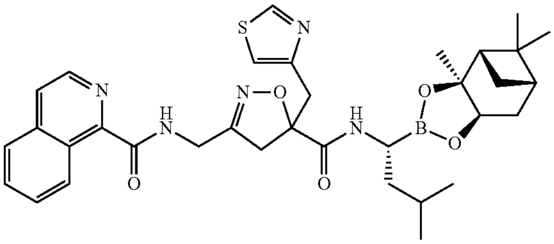 [SMILES: CC(C)C[C@H](NC(=O)C1(Cc2cscn2)CC(CNC(=O)c2nccc3ccccc23)=NO1)B1O[C@@H]2C[C@@H]3C[C@@H](C3(C)C)[C@]2(C)O1]

The title compound (0.083 g, 58%, 2 steps) was obtained using ethyl 3-((isoquinolin-1-carboxamido)methyl)-5-(thiazol-4-ylmethyl)-4,5-dihydroisoxazol-5-carboxylate (0.113 g, 0.27 mmol) obtained in the process (1) above by the preparation method of Example 84-(3).

MS (m/z): 644[M+H]

(4) Preparation of ((1R)-1-(3-((isoquinolin-1-carboxamido)methyl)-5-(thiazol-4-ylmethyl)-4,5-dihydroisoxazol-5-carboxamido)-3-methylbutyl)boronic acid

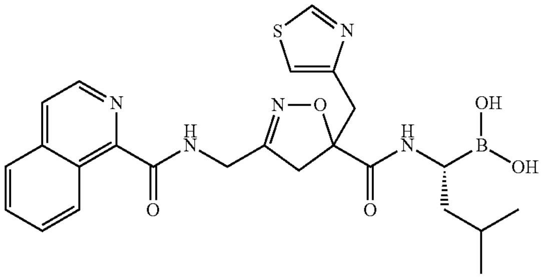 [SMILES: CC(C)C[C@H](NC(=O)C1(Cc2cscn2)CC(CNC(=O)c2nccc3ccccc23)=NO1)B(O)O]

The title compound (0.03 g, 41%) was obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(thiazol-4-ylmethyl)-4,5-dihydroisoxazol-5-carboxamide (0.083 g, 0.13 mmol) obtained in the process (3) above by the preparation method of Example 1-(4).

NMR: $^1$H-NMR (400 MHz, MeOD-d4); δ 9.11-9.09 (dd, 1H), 8.89-8.87 (m, 1H), 8.55-8.54 (d, 1H), 8.02-7.97 (m, 2H), 7.84-7.73 (m, 2H), 7.46 (m, 1H), 4.34 (s, 2H), 3.60-3.48 (m, 4H), 2.79 (m, 1H), 1.56 (m, 1H), 1.34-1.23 (m, 2H), 0.92-0.86 (m, 6H)

MS (m/z): 510[M+H], 492[M-OH]

Example 138: Preparation of ((1R)-1-(5-benzyl-3-((1-methyl-1H-indol-4-carboxamido)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-((1-methyl-1H-indol-4-carboxamido)methyl)-4,5-dihydroisoxazol-5-carboxylate

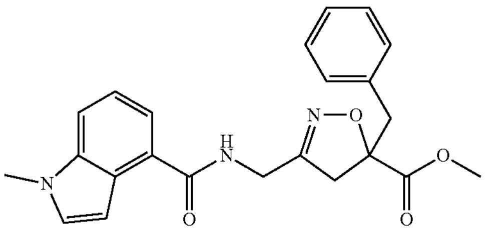

The title compound (0.17 g, 99%) was obtained using methyl 3-(aminomethyl)-5-benzyl-4,5-dihydroisoxazol-5-carboxylate hydrochloride (0.12 g, 0.42 mmol) obtained in Example 84-(1) and 1-methyl-1H-indol-4-carboxylic acid (0.081 g, 0.46 mmol) by the preparation method of Example 84-(2).

NMR: $^1$H-NMR (400 MHz, $CDCl_3$); δ 7.49-7.46 (m, 2H), 7.27-7.09 (m, 7H), 6.82-6.81 (d, 1H) 6.45 (br s, 1H), 4.35-4.22 (m, 2H), 3.84 (s, 3H), 3.77 (s, 3H), 3.49-3.30 (m, 2H), 2.95-2.88 (m, 2H)

MS (m/z): 406[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-indol-4-carboxamido)methyl)-4,5-dihydroisoxazol-5-carboxamide

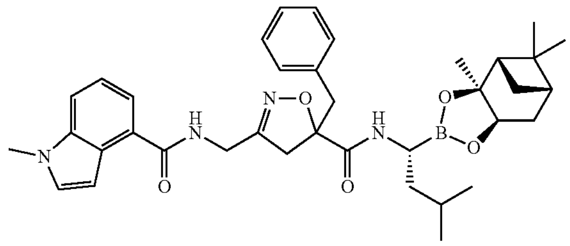

The title compound (0.051 g, 31%) was obtained using methyl 5-benzyl-3-((1-methyl-1H-indol-4-carboxamido) methyl)-4,5-dihydroisoxazol-5-carboxylate (0.17 g, 0.42 mmol) obtained in (1) above by the preparation method of Example 84-(3).

MS (m/z): 639[M+H]

(3) Preparation of ((1R)-1-(5-benzyl-3-((1-methyl-1H-indol-4-carboxamido)methyl)-4,5-dihydroisoxazol-5-carboxamido)-3-methylbutyl)boronic acid

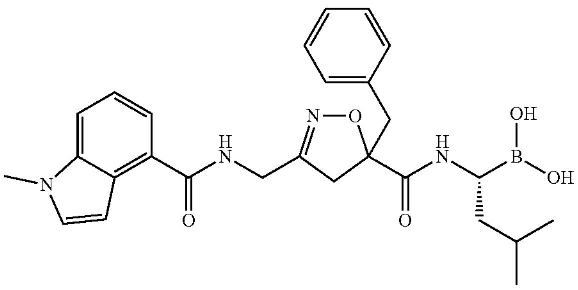

The title compound (0.025 g, 62%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-indol-4-carboxamido)methyl)-4,5-dihydroisoxazol-5-carboxamide (0.051 g, 0.08 mmol) obtained in (2) above by the preparation method of Example 1-(4).

NMR: $^1$H-NMR (500 MHz, MeOD-d4); δ 7.57-7.56 (d, 1H), 7.42-7.10 (d, 1H), 7.29-7.20 (m, 7H), 6.83-6.82 (d, 1H), 4.27 (s, 2H), 3.84 (s, 3H), 3.47-3.34 (m, 2H), 3.26-3.18 (m, 2H), 2.64-2.61 (m, 1H), 1.38-1.34 (m, 1H), 1.15-1.01 (m, 2H), 0.80-0.75 (dd, 6H)

MS (m/z): 505[M+H], 487[M-OH]

Example 139: Preparation of ((1R)-1-(5-benzyl-3-((2-methylimidazo[1,2-a]pyridin-8-carboxamido) methyl)-4,5-dihydroisoxazol-5-carboxamido)-3-methylbutyl)boronic acid Through the processes (1), (2), (3), (4) and (5) below, the title compound was obtained.

(1) Preparation of 2-methyl-imidazo[1,2-a]pyridin-8-carboxylic acid methyl ester

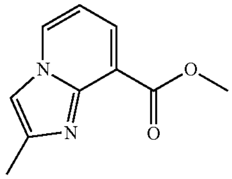

The title compound was obtained by the method described in U.S. Pat. No. 5,498,774A1.

(2) Preparation of 2-methyl-imidazo[1,2-a]pyridin-8-carboxylic acid

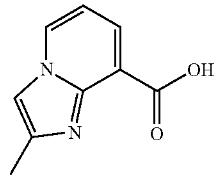

The title compound (0.45 g, 99%) was obtained using 2-methyl-imidazo[1,2-a]pyridin-8-carboxylic acid methyl ester (0.5 g, 2.63 mmol) obtained in (1) above by the preparation method of Example 119-(2).

MS (m/z): 177[M+H]

(3) Preparation of methyl 5-benzyl-3-((2-methylimidazo[1,2-a]pyridin-8-carboxamido)methyl)-4,5-dihydroisoxazol-5-carboxylate

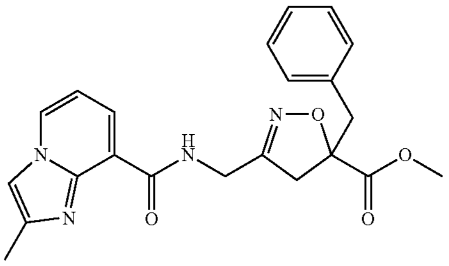

The title compound (0.13 g, 62%) was obtained using methyl 3-(aminomethyl)-5-benzyl-4,5-dihydroisoxazol-5-carboxylate hydrochloride (0.15 g, 0.53 mmol) obtained in Example 84-(1) and 2-methyl-imidazo[1,2-a]pyridin-8-carboxylic acid (0.18 g, 1.04 mmol) obtained in the process (2) above by the preparation method of Example 84-(2).

MS (m/z): 407[M+H]

(4) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-methylimidazo[1,2-a]pyridin-8-carboxamido)methyl)-4,5-dihydroisoxazol-5-carboxamide

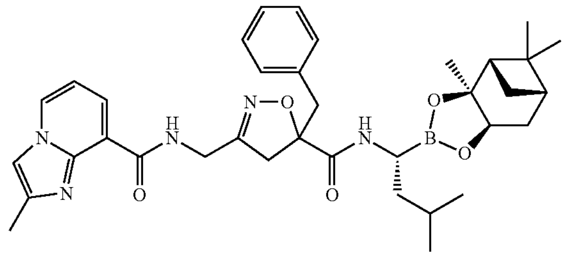

The title compound (0.10 g, 49%, 2 steps) was obtained using methyl 5-benzyl-3-((2-methylimidazo[1,2-a]pyridin-8-carboxamido)methyl)-4,5-dihydroisoxazol-5-carboxylate (0.13 g, 0.32 mmol) obtained in (3) above by the preparation method of Example 84-(3).

MS (m/z): 640[M+H]

(5) Preparation of ((1R)-1-(5-benzyl-3-((2-methylimidazo[1,2-a]pyridin-8-carboxamido)methyl)-4,5-dihydroisoxazol-5-carboxamido)-3-methylbutyl)boronic acid

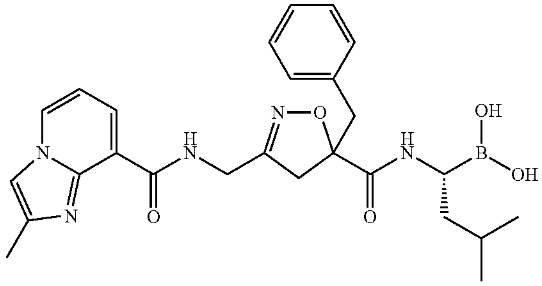 [SMILES: Cc1cn2cccc(C(=O)NCC3=NOC(Cc4ccccc4)(C(=O)N[C@@H](CC(C)C)B(O)O)C3)c2n1]

The title compound (0.033 g, 49%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-methylimidazo[1,2-a]pyridin-8-carboxamido)methyl)-4,5-dihydroisoxazol-5-carboxamide (0.10 g, 0.16 mmol) obtained in the process (4) above by the preparation method of Example 1-(4).

NMR: $^1$H-NMR (400 MHz, MeOD-d4); δ 8.55-8.53 (dd, 1H), 8.05-8.303 (dd, 1H), 7.71-7.70 (d, 1H), 7.29-7.14 (m, 5H), 7.02-6.99 (t, 3H), 4.41 (s, 2H), 3.51-3.46 (d, 1H), 3.35-3.29 (m, 2H), 3.23-3.20 (d, 1H), 2.69 (t, 1H), 2.47 (s, 3H), 1.47-1.37 (m, 1H), 1.20-1.06 (m, 2H), 0.83-0.78 (dd, 6H)

MS (m/z): 506[M+H], 488[M-OH]

Example 140: Preparation of ((1R)-1-(5-benzyl-3-((3-chloro-2-methylimidazo[1,2-a]pyridin-8-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of 3-chloro-2-methyl-imidazo[1,2-a]pyridin-8-carboxylic acid methyl ester

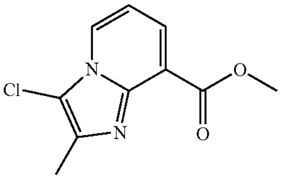

2-Methyl-imidazo[1,2-a]pyridin-8-carboxylic acid methyl ester (0.25 g, 1.31 mmol) obtained in Example 139-(1) was dissolved in acetonitrile (15 ml), and NCS (0.18 g, 1.31 mmol) was added thereto, followed by stirring at room temperature for 16 hours. Water was added, extraction with ethyl acetate was performed, and filtration with anhydrous magnesium sulfate was performed. The filtrate was separated by column chromatography to obtain the title compound (0.24 g, 82%).

NMR: $^1$H-NMR (400 MHz, $CDCl_3$); δ 8.20-8.18 (dd, 1H), 7.99-7.98 (dd, 1H), 7.00-6.96 (t, 1H), 4.04 (s, 3H), 2.54 (s, 3H)

(2) Preparation of 3-chloro-2-methyl-imidazo[1,2-a]pyridin-8-carboxylic acid

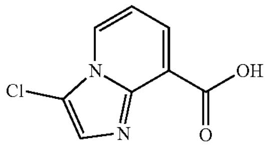 [SMILES: O=C(O)c1cccn2c(Cl)cnc12]

The title compound (0.23 g, 98%) was obtained using 3-chloro-2-methyl-imidazo[1,2-a]pyridin-8-carboxylic acid methyl ester (0.24 g, 1.08 mmol) obtained in the process (1) above by the preparation method of Example 119-(2).

(3) Preparation of methyl 5-benzyl-3-((3-chloro-2-methylimidazo[1,2-a]pyridin-8-carboxamido)methyl)-4,5-dihydroisoxazol-5-carboxylate

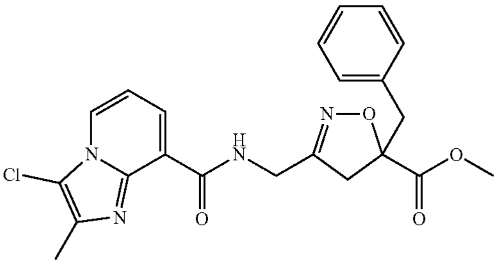 [SMILES: COC(=O)C1(Cc2ccccc2)CC(CNC(=O)c2cccn3c(Cl)c(C)nc23)=NO1]

The title compound (0.14 g, 68%) was obtained using methyl 3-(aminomethyl)-5-benzyl-4,5-dihydroisoxazol-5-carboxylate hydrochloride (0.13 g, 0.46 mmol) obtained in Example 84-(1) and 3-chloro-2-methyl-imidazo[1,2-a]pyridin-8-carboxylic acid (0.14 g, 0.68 mmol) by the preparation method of Example 84-(2).

MS (m/z): 441[M+H]

(4) Preparation of 5-benzyl-3-((3-chloro-2-methylimidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

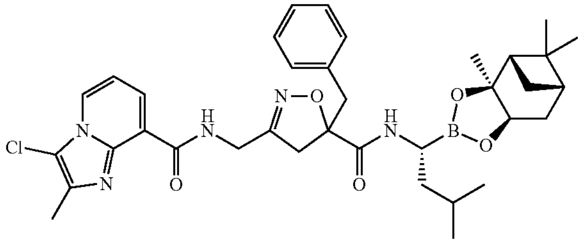 [SMILES: Cc1nc2c(C(=O)NCC3=NOC(Cc4ccccc4)(C(=O)N[C@@H](CC(C)C)B4O[C@@H]5C[C@@H]6C[C@@H](C6(C)C)[C@]5(C)O4)C3)cccn2c1Cl]

The title compound (0.11 g, 51%, 2 steps) was obtained using methyl 5-benzyl-3-((3-chloro-2-methylimidazo[1,2-a]pyridin-8-carboxamido)methyl)-4,5-dihydroisoxazol-5-carboxylate (0.14 g, 0.31 mmol) obtained in (3) above by the preparation method of Example 84-(3).

MS (m/z): 675[M+H], 523[M-$C_{10}H_{15}O$]

(5) Preparation of ((1R)-1-(5-benzyl-3-((3-chloro-2-methylimidazo[1,2-a]pyridin-8-carboxamido)methyl)-4,5-dihydroisoxazol-5-carboxamido)-3-methylbutyl)boronic acid

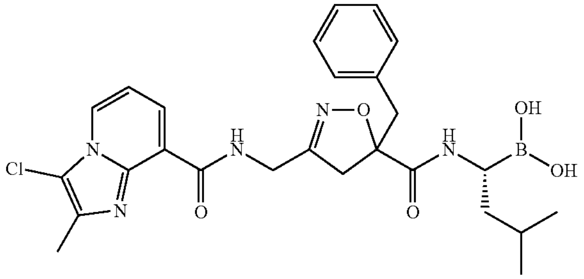 [SMILES: Cc1nc2c(C(=O)NCC3=NOC(Cc4ccccc4)(C(=O)N[C@@H](CC(C)C)B(O)O)C3)cccn2c1Cl]

The title compound (0.069 g, 82%) was obtained using 5-benzyl-3-((3-chloro-2-methylimidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.11 g, 0.16 mmol) obtained in (4) above by the preparation method of Example 1-(4).

NMR: $^1$H-NMR (400 MHz, MeOD-d4); δ 8.45-8.43 (dd, 1H), 8.14-8.12 (dd, 1H), 7.28-7.15 (m, 6H), 4.41 (s, 2H), 3.51-3.46 (d, 1H), 3.35-3.29 (m, 2H), 3.23-3.19 (d, 1H), 2.71-2.67 (t, 1H), 2.49 (s, 3H), 1.47-1.41 (m, 1H), 1.21-1.03 (m, 2H), 0.83-0.78 (dd, 6H)

MS (m/z): 540[M+H], 522[M-OH].

Example 141: Preparation of ((1R)-1-(3-((2,4-dimethylthiazol-5-carboxamido)methyl)-5-(phenoxymethyl)-4,5-dihydroisoxazol-5-carboxamido)-3-methylbutyl)boronic acid Through the processes (1), (2) and (3) below, the title compound was obtained.

(1) Preparation of 3-((2,4-dimethylthiazol-5-carboxamido)methyl)-N-ethyl-5-(phenoxymethyl)-4,5-dihydroisoxazol-5-carboxamide

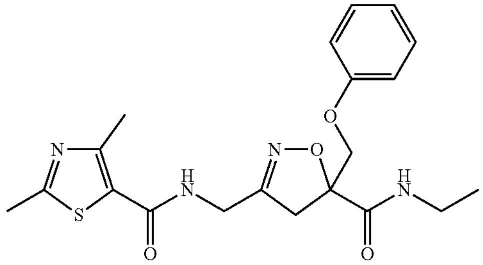 [SMILES: CCNC(=O)C1(COc2ccccc2)CC(CNC(=O)c2sc(C)nc2C)=NO1]

The title compound (0.13 g, 70%) was obtained using ethyl 3-(aminomethyl)-5-(phenoxymethyl)-4,5-dihydroisoxazol-5-carboxylate hydrochloride (0.12 g, 0.38 mmol) obtained in Example 126-(1) and 2,4-dimethyl-thiazol-5-carboxylic acid (0.066 g, 0.42 mmol) by the preparation method of Example 84-(2).

MS (m/z): 417[M+H]

(2) Preparation of 3-((2,4-dimethylthiazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(phenoxymethyl)-4,5-dihydroisoxazol-5-carboxamide

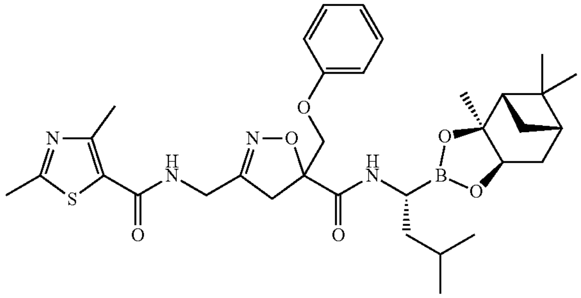

The title compound (0.09 g, 47%, 2 steps) was obtained using 3-((2,4-dimethylthiazol-5-carboxamido)methyl)-N-ethyl-5-(phenoxymethyl)-4,5-dihydroisoxazol-5-carboxamide (0.13 g, 0.31 mmol) obtained in (1) above by the preparation method of Example 84-(3).

MS (m/z): 637[M+H]

(3) Preparation of ((1R)-1-(3-((2,4-dimethylthiazol-5-carboxamido)methyl)-5-(phenoxymethyl)-4,5-dihydroisoxazol-5-carboxamido)-3-methylbutyl) boronic acid

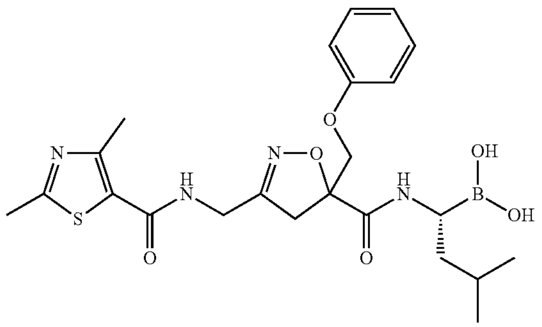 [SMILES: Cc1nc(C)c(C(=O)NCC2=NOC(COc3ccccc3)(C(=O)N[C@@H](CC(C)C)B(O)O)C2)s1]

The title compound (40 mg, 56%) was obtained using 3-((2,4-dimethylthiazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(phenoxymethyl)-4,5-dihydroisoxazol-5-carboxamide (0.09 g, 0.14 mmol) obtained in (2) above by the preparation method of Example 1-(4).

NMR: $^1$H-NMR (400 MHz, $CDCl_3$); δ 7.48-7.51 (m, 1H), 7.22-6.86 (m, 5H), 6.66-6.52 (m, 1H), 4.38-4.20 (m, 4H), 3.45-3.23 (m, 2H), 3.10-2.98 (m, 1H), 2.68-2.64 (m, 6H), 1.59-1.39 (m, 3H), 0.93-0.87 (m, 6H)

MS (m/z): 503[M+H], 485[M-OH]

Example 142: Preparation of ((1R)-1-(5-benzyl-3-((3-chloroimidazo[1,2-a]pyridin-8-carboxamido) methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((3-chloroimidazo[1,2-a]pyridin-8-carboxamido)methyl)-4,5-dihydroisoxazol-5-carboxylate

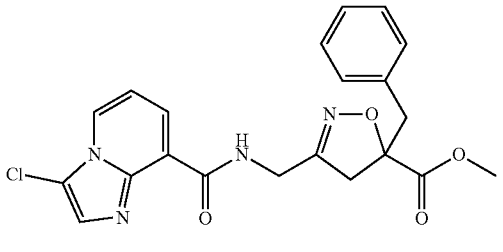 [SMILES: COC(=O)C1(Cc2ccccc2)CC(CNC(=O)c2cccn3c(Cl)cnc23)=NO1]

The title compound (0.076 g, 77%) was obtained using methyl 5-benzyl-3-((imidazo[1,2-a]pyridin-8-carboxamido) methyl)-4,5-dihydroisoxazol-5-carboxylate (0.051 g, 0.13 mmol) obtained in Example 132-(1) by the preparation method of Example 140-(1).

NMR: $^1$H-NMR (400 MHz, $CDCl_3$); δ 10.22 (br s, 1H), 8.25-8.22 (m, 2H), 7.58 (s, 1H), 7.20-7.11 (m, 6H), 4.37-4.35 (d, 2H), 3.74 (s, 3H), 3.48-3.44 (d, 1H), 3.30-3.27 (d, 1H), 3.16-3.05 (m, 2H)

MS (m/z): 427[M+H]

(2) Preparation of 5-benzyl-3-((3-chloroimidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl) butyl)-4,5-dihydroisoxazol-5-carboxamide

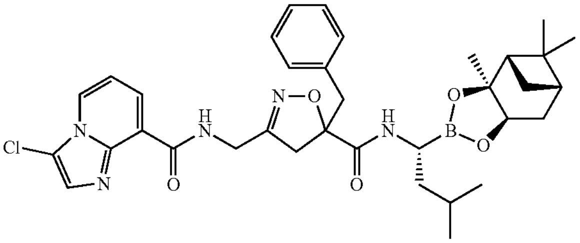 [SMILES: CC(C)C[C@H](NC(=O)C1(Cc2ccccc2)CC(CNC(=O)c2cccn3c(Cl)cnc23)=NO1)B1O[C@@H]2C[C@@H]3C[C@@H](C3(C)C)[C@]2(C)O1]

The title compound (0.065 g, 57%, 2 steps) was obtained using methyl 5-benzyl-3-((3-chloroimidazo[1,2-a]pyridin-8-carboxamido)methyl)-4,5-dihydroisoxazol-5-carboxylate (0.076 g, 0.18 mmol) obtained in (1) above by the preparation method of Example 84-(3).

MS (m/z): 660[M+H]

(3) Preparation of ((1R)-1-(5-benzyl-3-((3-chloroimidazo[1,2-a]pyridin-8-carboxamido)methyl)-4,5-dihydroisoxazol-5-carboxamido)-3-methylbutyl) boronic acid

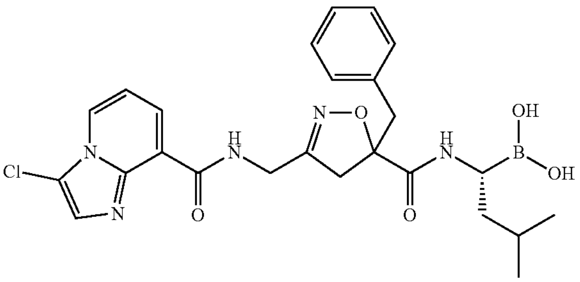 [SMILES: CC(C)C[C@H](NC(=O)C1(Cc2ccccc2)CC(CNC(=O)c2cccn3c(Cl)cnc23)=NO1)B(O)O]

The title compound (0.03 g, 58%) was obtained using 5-benzyl-3-((3-chloroimidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.065 g, 0.099 mmol) obtained in (2) above by the preparation method of Example 1-(4).

NMR: $^1$H-NMR (400 MHz, MeOD-d4); δ 8.55-8.53 (dd, 1H), 8.20-8.18 (dd, 1H), 7.71 (s, 1H), 7.29-7.18 (m, 6H), 4.41 (s, 2H), 3.50-3.46 (d, 1H), 3.35-3.32 (m, 2H), 3.23-3.19 (d, 1H), 2.69 (t, 3H), 1.47-1.39 (m, 1H), 1.19-1.07 (m, 2H), 0.83-0.75 (dd, 6H)

MS (m/z): 526[M+H], 508[M-OH]

Example 143: Preparation of ((1R)-1-(5-benzyl-3-(((2,5-dichlorophenyl)sulfonamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-(((2,5-dichlorophenyl)sulfonamido)methyl)-4,5-dihydroisoxazol-5-carboxylate

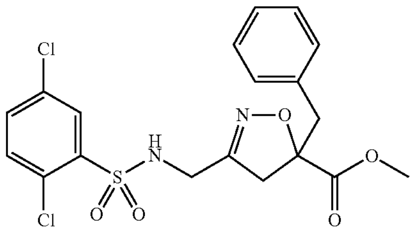 [SMILES: COC(=O)C1(Cc2ccccc2)CC(CNS(=O)(=O)c2cc(Cl)ccc2Cl)=NO1]

Methyl 3-(aminomethyl)-5-benzyl-4,5-dihydroisoxazol-5-carboxylate hydrochloride (0.061 g, 0.214 mmol) obtained in Example 84-(1), and 2,5-dichlorobenzenesulfonyl chloride (0.063 g, 0.257 mmol) were dissolved in dichloromethane (2.1 ml). Diisopropylethylamine (0.150 ml, 0.861 mmol) was slowly added thereto at 0° C., and stirring was performed for 5 hours, while raising to room temperature. The solvent was distilled under a reduced pressure, and the resultant product was separated by column chromatography to obtain the title compound (0.067 g, 68%).

NMR: $^1$H-NMR (400 MHz, $CDCl_3$); δ 8.02 (1H, d), 7.53-7.44 (2H, m), 7.32-7.21 (6H, m), 3.78 (3H, s), 3.74-3.59 (2H, m), 3.40-3.27 (2H, m), 3.10-2.98 (2H, m)

MS (m/z): 457[M+H]

(2) Preparation of 5-benzyl-3-(((2,5-dichlorophenyl)sulfonamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

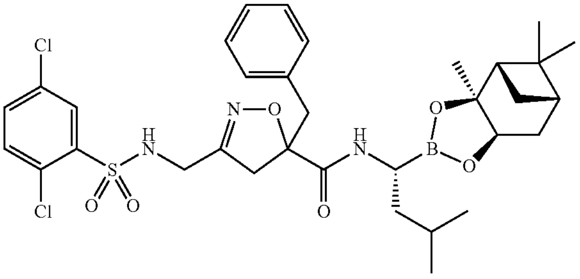 [SMILES: CC(C)C[C@H](NC(=O)C1(Cc2ccccc2)CC(CNS(=O)(=O)c2cc(Cl)ccc2Cl)=NO1)B1O[C@@H]2C[C@@H]3C[C@@H](C3(C)C)[C@]2(C)O1]

The title compound (0.051 g, 50%, 2 steps) was obtained using methyl 5-benzyl-3-(((2,5-dichlorophenyl)sulfonamido)methyl)-4,5-dihydroisoxazol-5-carboxylate (0.067 g, 0.146 mmol) obtained in (1) above by the preparation method of Example 84-(3).

MS (m/z): 690[M+H]

(3) Preparation of ((1R)-1-(5-benzyl-3-(((2,5-dichlorophenyl)sulfonamido)methyl)-4,5-dihydroisoxazol-5-carboxamido)-3-methylbutyl)boronic acid

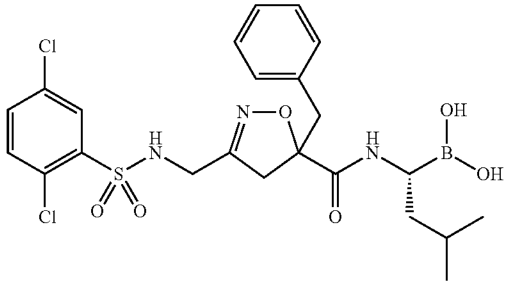 [SMILES: CC(C)C[C@H](NC(=O)C1(Cc2ccccc2)CC(CNS(=O)(=O)c2cc(Cl)ccc2Cl)=NO1)B(O)O]

The title compound (0.019 g, 46%) was obtained using 5-benzyl-3-(((2,5-dichlorophenyl)sulfonamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.051 g, 0.074 mmol) obtained in (2) above by the preparation method of Example 1-(4).

NMR: $^1$H-NMR (500 MHz, $CD_3OD$); δ 8.00 (1H, d), 7.61-7.58 (2H, m), 7.25-7.21 (6H, m), 3.89-3.80 (2H, m), 3.40-3.22 (2H, m), 3.14-2.99 (2H, m), 2.67-2.62 (1H, m), 1.38-0.98 (3H, m), 0.82-0.76 (6H, m)

MS (m/z): 556[M+H], 538[M-OH]

Example 144: Preparation of ((1R)-1-(5-benzyl-3-((quinolin-8-sulfonamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((quinolin-8-sulfonamido)methyl)-4,5-dihydroisoxazol-5-carboxylate

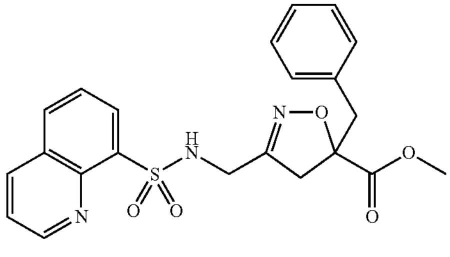 [SMILES: COC(=O)C1(Cc2ccccc2)CC(CNS(=O)(=O)c2cccc3cccnc23)=NO1]

The title compound (0.135 g, 88%) was obtained using methyl 3-(aminomethyl)-5-benzyl-4,5-dihydroisoxazol-5-carboxylate hydrochloride (0.100 g, 0.35 mmol) obtained in Example 84-(1) and quinolin-8-sulfonyl chloride (0.096 g, 0.42 mmol) by the preparation method of Example 143-(1).

NMR: $^1$H-NMR (400 MHz, $CDCl_3$); δ 9.00 (1H, d), 8.39 (1H, d), 8.29 (1H, d), 8.07 (1H, d), 7.66 (1H, t), 7.58 (1H, dd), 7.28-7.20 (5H, m), 6.52 (1H, t), 3.67-3.58 (1H, m), 3.46 (1H, d), 3.25 (1H, d), 3.12-3.08 (2H, m)

MS (m/z): 440[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((quinolin-8-sulfonamido)methyl)-4,5-dihydroisoxazol-5-carboxamide

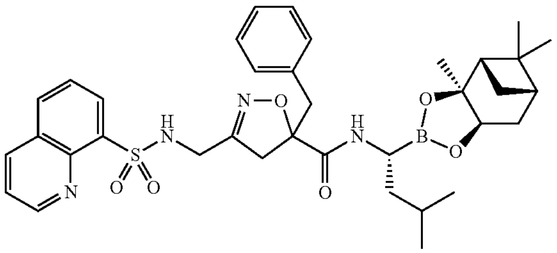 [SMILES: CC(C)C[C@H](NC(=O)C1(Cc2ccccc2)CC(CNS(=O)(=O)c2cccc3cccnc23)=NO1)B1O[C@@H]2C[C@@H]3C[C@@H](C3(C)C)[C@]2(C)O1]

The title compound (0.129 g, 62%, 2 steps) was obtained using methyl 5-benzyl-3-((quinolin-8-sulfonamido)methyl)-4,5-dihydroisoxazol-5-carboxylate (0.135 g, 0.31 mmol) obtained in (1) above by the preparation method of Example 84-(3).

MS (m/z): 673[M+H]

(3) Preparation of ((1R)-1-(5-benzyl-3-((quinolin-8-sulfonamido)methyl)-4,5-dihydroisoxazol-5-carboxamido)-3-methylbutyl)boronic acid

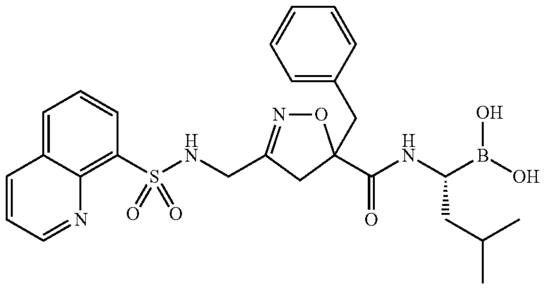 [SMILES: CC(C)C[C@H](NC(=O)C1(Cc2ccccc2)CC(CNS(=O)(=O)c2cccc3cccnc23)=NO1)B(O)O]

The title compound (0.067 g, 52%) was obtained using 5-benzyl-N—((R)-3-methyl-1-((3aS,4S,6S,7aR)-3a,5,5-trimethylhexahydro-4,6-metanobenzo[id][1,3,2]dioxaborol-2-yl)butyl)-3-((quinolin-8-sulfonamido)methyl)-4,5-dihydroisoxazol-5-carboxamide (0.129 g, 0.24 mmol) obtained in (2) above by the preparation method of Example 1-(4).

NMR: $^1$H-NMR (500 MHz, $CD_3OD$); δ 9.05-9.03 (1H, in), 8.46-8.44 (1H, in), 8.38-8.36 (1H, in), 8.23-8.21 (1H, in), 7.75-7.71 (1H, in), 7.67-7.64 (1H, dd), 7.23-7.15 (5H, in), 3.86-3.74 (2H, in), 3.38-3.33 (1H, in), 3.12 (1H, d), 3.06-3.01 (1H, in), 2.82 (1H, d), 2.67-2.61 (1H, in), 1.38-0.97 (3H, in), 0.81-0.75 (6H, m)

MS (m/z): 539[M+H]

Example 145: Preparation of ((1R)-1-(5-benzyl-3-((S)-1-(isoquinolin-1-carboxamido)ethyl)-4,5-dihydroisoxazol-5-carboxamido)-3-methylbutyl)boronic acid Through the processes (1), (2), (3) and (4) below, the title compound was obtained.

(1) Preparation of methyl 3-((S)-1-aminoethyl)-5-benzyl-4,5-dihydroisoxazol-5-carboxylate hydrochloride

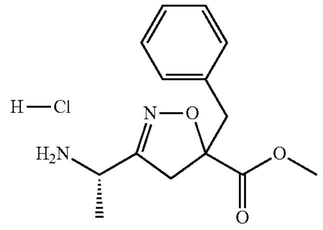

The title compound (0.29 g, 99%) was obtained using methyl 5-benzyl-3-((S)-1-((tert-butoxycarbonyl)amino)ethyl)-4,5-dihydroisoxazol-5-carboxylate (0.36 g, 1.00 mmol) obtained in Preparation Example 24 by the preparation method of Example 84-(1).

MS (m/z): 263[M+H]

(2) Preparation of methyl 5-benzyl-3-((S)-1-(isoquinolin-1-carboxamido)ethyl)-4,5-dihydroisoxazol-5-carboxylate

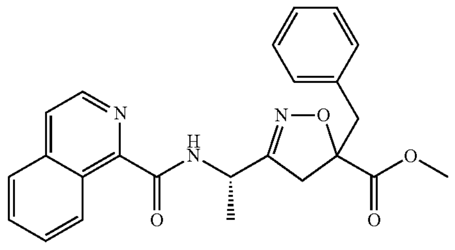

The title compound (0.12 g, 72%) was obtained using methyl 3-((S)-1-aminoethyl)-5-benzyl-4,5-dihydroisoxazol-5-carboxylate hydrochloride (0.12 g, 0.40 mmol) obtained in (1) above and isoquinolin-1-carboxylic acid (0.080 g, 0.44 mmol) by the preparation method of Example 84-(2).

NMR: $^1$H-NMR (500 MHz, $CDCl_3$); δ 9.55-9.52 (m, 1H), 8.49-8.45 (m, 1H), 8.18-8.16 (m, 1H), 7.86-7.69 (m, 4H), 7.25-1.13 (m, 5H), 4.95-4.88 (m, 1H), 3.78-3.75 (dd, 3H), 3.49-3.44 (m, 1H), 3.33-3.27 (t, 1H), 3.14-3.04 (m, 2H), 1.43-1.36 (dd, 3H)

MS (m/z): 418[M+H]

(3) Preparation of 5-benzyl-3-((S)-1-(isoquinolin-1-carboxamido)ethyl)-N—((R)-3-methyl-1-((3aS,4S,6S,7aR)-3a,5,5-trimethylhexahydro-4,6-metano-benzo[d][1,3,2]dioxaborol-2-yl)butyl)-4,5-dihydroisoxazol-5-carboxamide

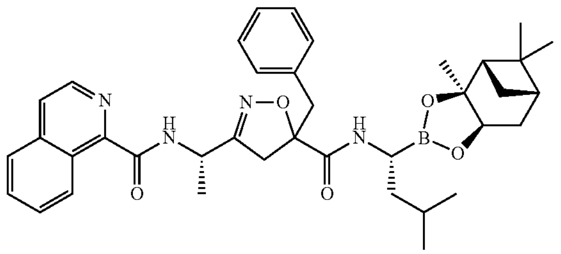 [SMILES: CC(C)C[C@H](NC(=O)C1(Cc2ccccc2)CC([C@H](C)NC(=O)c2nccc3ccccc23)=NO1)B1O[C@@H]2C[C@@H]3C[C@@H](C3(C)C)[C@]2(C)O1]

The title compound (0.055 g, 30%, 2 steps) was obtained using methyl 5-benzyl-3-((S)-1-(isoquinolin-1-carboxamido)ethyl)-4,5-dihydroisoxazol-5-carboxylate (0.12 g, 0.29 mmol) obtained in (2) above by the preparation method of Example 84-(3).

MS (m/z): 651[M+H], 499[M-$C_{10}H_{15}O$]

(4) Preparation of ((1R)-1-(5-benzyl-3-((S)-1-(isoquinolin-1-carboxamido)ethyl)-4,5-dihydroisoxazol-5-carboxamido)-3-methylbutyl)boronic acid

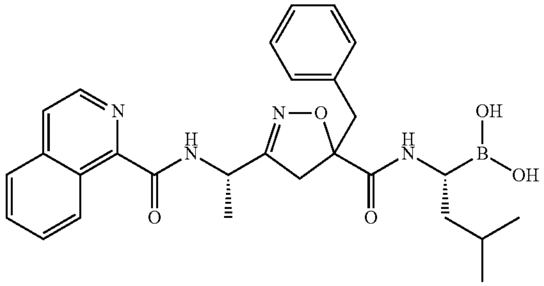 [SMILES: CC(C)C[C@H](NC(=O)C1(Cc2ccccc2)CC([C@H](C)NC(=O)c2nccc3ccccc23)=NO1)B(O)O]

The title compound (0.026 g, 59%) was obtained using 5-benzyl-3-((S)-1-(isoquinolin-1-carboxamido)ethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.055 g, 0.085 mmol) obtained in (3) above by the preparation method of Example 1-(4).

NMR: $^1$H-NMR (400 MHz, $CDCl_3$); δ 9.53-9.50 (d, 1H), 8.45-8.43 (d, 1H), 8.31-8.29 (d, 1H), 7.86-7.65 (m, 4H), 7.28-7.17 (m, 6H), 4.92-4.88 (m, 1H), 3.47-3.31 (m, 2H), 3.16-3.09 (m, 2H), 2.92 (m, 1H), 1.41-1.39 (d, 3H), 1.25-1.21 (m, 3H), 0.85-0.82 (m, 6H)

MS (m/z): 517[M+H], 499[M-OH]

Example 146: Preparation of ((1R)-1-(5-benzyl-3-(((2,5-dichlorobenzyl)amino)methyl)-4,5-dihydroisoxazol-5-carboxamido)-3-methylbutyl)boronic acid Through the processes (1), (2), (3), (4), (5) and (6) below, the title compound was obtained.

(1) Preparation of 2-(2,5-dichloro-benzylamino)-ethanol

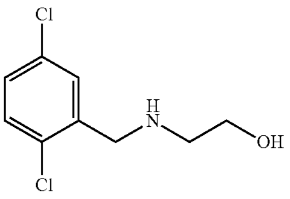 [SMILES: OCCNCc1cc(Cl)ccc1Cl]

2,2-Dichlorobenzaldehyde (0.175 g, 1.0 mmol) and ethanolamine (0.122 g, 2.0 mmol) were stirred in methanol (6 ml) for 16 hours. To the solution, sodium borohydride (0.076 g, 2.0 mmol) was added, followed by stirring at room temperature for 2 hours. Water (10 ml) was added to quench the reaction, and extraction was performed with dichloromethane (20 ml) three times. The organic layer thus extracted was dried over anhydrous magnesium sulfate, and filtered. The filtrate was distilled under a reduced pressure and separated by column chromatography to obtain the title compound (0.177 g, 80%).

NMR: 1H-NMR (500 MHz, $CDCl_3$); δ 7.38 (1H, d), 7.28-7.26 (1H, m), 7.18-7.16 (1H, m), 3.85 (3H, s), 3.67 (2H, t), 2.78 (2H, t), 2.12 (2H, br s)

(2) Preparation of (2,5-dichloro-benzyl)-(2-hydroxy-ethyl)-carbamic acid tert-butyl ester

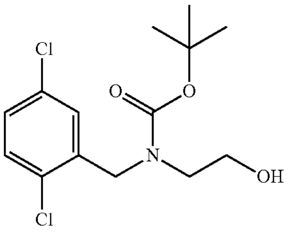 [SMILES: CC(C)(C)OC(=O)N(CCO)Cc1cc(Cl)ccc1Cl]

2-(2,5-Dichloro-benzylamino)-ethanol (0.177 g, 0.804 mmol) obtained in (1) above, di-tert-butyl dicarbonate (0.193 g, 0.884 mmol), and triethylamine (0.56 ml, 4.02 mmol) were dissolved in dichloromethane (6 ml), and stirring was performed at room temperature for 1 hour. A 0.1 N sodium hydroxide aqueous solution (10 ml) was added thereto, and extraction with dichloromethane (10 ml) was performed twice. The organic layer thus extracted was dried over anhydrous magnesium sulfate, and filtered, and the filtrate was distilled under a reduced pressure to obtain (2,5-dichloro-benzyl)-(2-hydroxy-ethyl)-carbamic acid tert-butyl ester (0.249 g, 97%).

MS (m/z): 320[M+H]

(3) Preparation of (2,5-dichloro-benzyl)-(2-hydroxyimino-ethyl)-carbamic acid tert-butyl ester

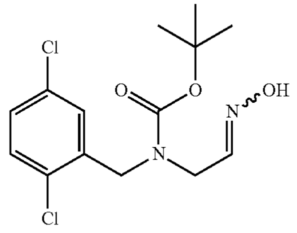 [SMILES: CC(C)(C)OC(=O)N(CC=NO)Cc1cc(Cl)ccc1Cl]

(2,5-Dichloro-benzyl)-(2-hydroxy-ethyl)-carbamic acid tert-butyl ester (0.249 g, 0.78 mmol) obtained in (3) above and iodoxybenzoic acid (0.654 g, 2.34 mmol) were dissolved in dimethylsulfoxide (10 ml) and stirred at room temperature for 4 hours. Water (10 ml) and ethyl acetate (20 ml) were added thereto, and a precipitate was filtered under a reduced pressure. The filtrate was washed with a sodium bicarbonate aqueous solution and brine in order, dried over anhydrous magnesium sulfate, and filtered. The filtrate was distilled under a reduced pressure to obtain (2,5-dichloro-benzyl)-(2-oxo-ethyl)-carbamic acid tert-butyl ester (0.316 g). The title compound (0.212 g, 82%, 2 steps) was obtained using (2,5-dichloro-benzyl)-(2-oxo-ethyl)-carbamic acid tert-butyl ester (0.316 g) obtained above by the preparation method of Preparation Example 1-(1).

NMR: $^1$H-NMR (500 MHz, $CDCl_3$); δ 8.48 (1H, s), 7.26-7.16 (3H, m), 4.20-3.88 (4H, m), 1.49 (9H, s)

MS (m/z): 333[M+H]

(4) Preparation of methyl 5-benzyl-3-(((tert-butoxycarbonyl)(2,5-dichlorobenzyl)amino)methyl)-4,5-dihydroisoxazol-5-carboxylate

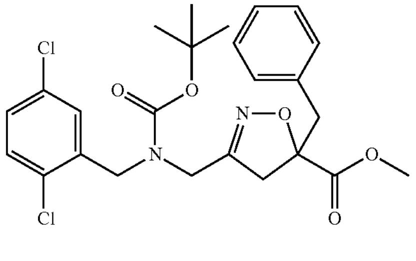 [SMILES: COC(=O)C1(Cc2ccccc2)CC(CN(Cc2cc(Cl)ccc2Cl)C(=O)OC(C)(C)C)=NO1]

The title compound (0.285 g, 88%) was obtained using (2,5-dichloro-benzyl)-(2-hydroxyimino-ethyl)-carbamic acid tert-butyl ester (0.212 g, 0.64 mmol) obtained in (3) above by the preparation method of Preparation Example 6-(2).

NMR: $^1$H-NMR (500 MHz, $CDCl_3$); δ 7.30-7.06 (8H, m), 4.13-3.78 (4H, m), 3.78 (3H, s), 3.38-3.30 (2H, m), 3.06 (1H, d), 2.94-2.91 (1H, m), 1.40 (9H, s)

(5) Preparation of tert-butyl ((5-benzyl-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)(2,5-dichlorobenzyl)carbamate

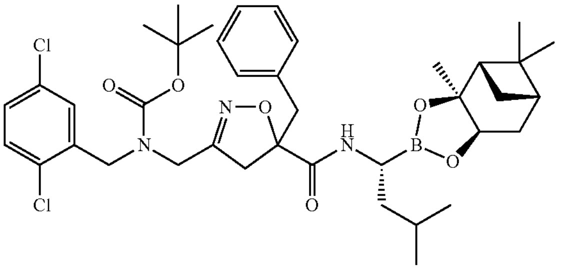 [SMILES: CC(C)C[C@H](NC(=O)C1(Cc2ccccc2)CC(CN(Cc2cc(Cl)ccc2Cl)C(=O)OC(C)(C)C)=NO1)B1O[C@@H]2C[C@@H]3C[C@@H](C3(C)C)[C@]2(C)O1]

The title compound (0.217 g, 52%, 2 steps) was obtained using methyl 5-benzyl-3-(((tert-butoxycarbonyl)(2,5-dichlorobenzyl)amino)methyl)-4,5-dihydroisoxazol-5-carboxylate (0.285 g, 0.56 mmol) obtained in (4) above by the preparation method of Example 84-(3).

MS (m/z): 740[M+H]

(6) Preparation of ((1R)-1-(5-benzyl-3-(((2,5-dichlorobenzyl)amino)methyl)-4,5-dihydroisoxazol-5-carboxamido)-3-methylbutyl)boronic acid

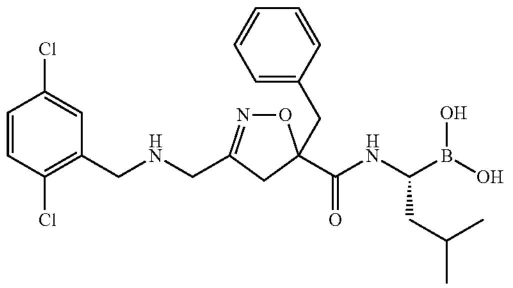 [SMILES: CC(C)C[C@H](NC(=O)C1(Cc2ccccc2)CC(CNCc2cc(Cl)ccc2Cl)=NO1)B(O)O]

The title compound (0.135 g, 84%) was obtained using tert-butyl ((5-benzyl-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)(2,5-dichlorobenzyl)carbamate (0.217 g, 0.293 mmol) obtained in (5) above by the preparation method of Example 1-(4).

NMR: $^1$H-NMR (500 MHz, $CD_3OD$); δ 7.66 (1H, dd), 7.54-7.48 (2H, m), 7.29-7.22 (6H, m), 4.36 (2H, d), 4.11-4.03 (2H, m), 3.52-3.46 (1H, m), 3.36-3.20 (3H, m), 2.79-2.71 (1H, m), 1.46-1.06 (3H, m), 0.83-0.78 (6H, m)

MS (m/z): 506[M+H], 488[M-OH]

Example 147: Preparation of ((1R)-1-(5-benzyl-3-(((isoquinolin-1-ylmethyl)amino)methyl)-4,5-dihydroisoxazol-5-carboxamido)-3-methylbutyl)boronic acid Through the processes (1), (2), (3) and (4) below, the title compound was obtained.

(1) Preparation of methyl 5-benzyl-3-(((isoquinolin-1-ylmethyl)amino)methyl)-4,5-dihydroisoxazol-5-carboxylate

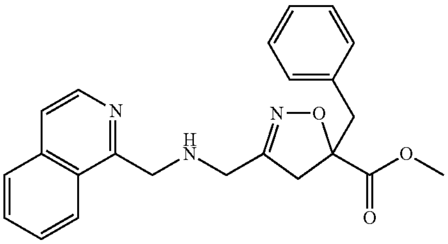 [SMILES: COC(=O)C1(Cc2ccccc2)CC(CNCc2nccc3ccccc23)=NO1]

Methyl 3-(aminomethyl)-5-benzyl-4,5-dihydroisoxazol-5-carboxylate hydrochloride (0.063 g, 0.22 mmol) in Example 84-(1) and isoquinolin-1-carbaldehyde (0.039 g, 0.25 mmol) were mixed with dichloromethane (6 ml), and stirred for 1 hour at room temperature. After adding a sodium triacetoxyborohydride (0.070 g, 0.33 mmol) to the solution, stirring was performed for 16 hours at room temperature. A sodium bicarbonate aqueous solution (10 ml) was added to quench the reaction, and extraction with dichloromethane (10 ml) was performed three times. The organic layer thus extracted was dried over anhydrous magnesium sulfate, and filtered. The filtrate was distilled under a reduced pressure and separated by column chromatography to obtain the title compound (0.072 g, 84%).

NMR: $^1$H-NMR (400 MHz, $CDCl_3$); δ 8.43 (1H, d), 8.01 (1H, d), 7.82 (1H, d), 7.69 (1H, t), 7.62 (1H, t), 7.55 (1H, d), 7.26-7.06 (5H, m), 4.23 (1H, d), 4.07 (1H, d), 3.75 (3H, s), 3.58 (2H, d), 3.47 (1H, d), 3.32 (1H, d), 3.13-3.08 (2H, m)

MS (m/z): 390[M+H]

(2) Preparation of methyl 5-benzyl-3-(((tert-butoxycarbonyl)(isoquinolin-1-ylmethyl)amino)methyl)-4,5-dihydroisoxazol-5-carboxylate

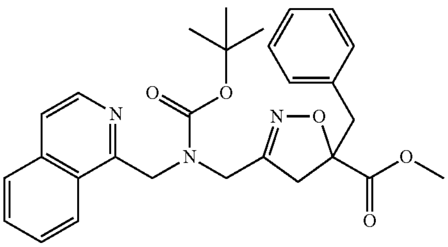 [SMILES: COC(=O)C1(Cc2ccccc2)CC(CN(Cc2nccc3ccccc23)C(=O)OC(C)(C)C)=NO1]

The title compound (0.076 g, 84%) was obtained using methyl 5-benzyl-3-(((isoquinolin-1-ylmethyl)amino)methyl)-4,5-dihydroisoxazol-5-carboxylate (0.072 g, 0.185 mmol) in (1) above by the preparation method of Example 146-(2).

MS (m/z): 490[M+H]

(3) Preparation of tert-butyl ((5-benzyl-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)(isoquinolin-1-ylmethyl)carbamate

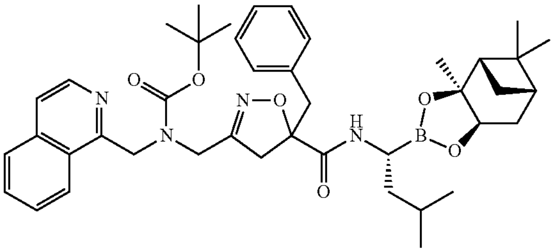 [SMILES: CC(C)C[C@H](NC(=O)C1(Cc2ccccc2)CC(CN(Cc2nccc3ccccc23)C(=O)OC(C)(C)C)=NO1)B1O[C@@H]2C[C@@H]3C[C@@H](C3(C)C)[C@]2(C)O1]

The title compound (0.075 g, 67%, 2 steps) was obtained using methyl 5-benzyl-3-(((tert-butoxycarbonyl)(isoquinolin-1-ylmethyl)amino)methyl)-4,5-dihydroisoxazol-5-carboxylate (0.076 g, 0.155 mmol) obtained in (2) above by the preparation method of Example 84-(3).

MS (m/z): 723[M+H]

(4) Preparation of ((1R)-1-(5-benzyl-3-(((isoquinolin-1-ylmethyl)amino)methyl)-4,5-dihydroisoxazol-5-carboxamido)-3-methylbutyl)boronic acid

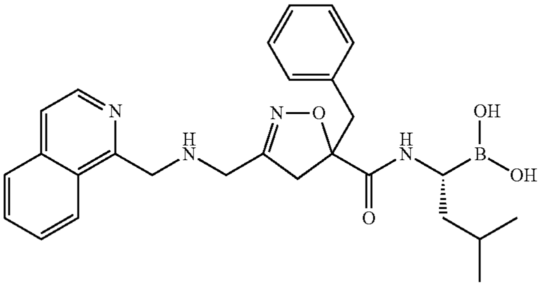

The title compound (0.042 g, 69%) was obtained using tert-butyl ((5-benzyl-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)(isoquinolin-1-ylmethyl)carbamate (0.075 g, 0.104 mmol) obtained in the process (2) above by the preparation method of Example 1-(4).

NMR: $^1$H-NMR (500 MHz, $CD_3OD$); δ 7.66 (1H, dd), 7.54-7.48 (2H, m), 7.29-7.22 (6H, m), 4.36 (2H, d), 4.11-4.03 (2H, m), 3.52-3.46 (1H, m), 3.36-3.20 (3H, m), 2.79-2.71 (1H, m), 1.46-1.06 (3H, m), 0.83-0.78 (6H, m)

MS (m/z): 489[M+H]

Example 148: Preparation of ((1R)-1-(5-benzyl-3-((S)-1-(isoquinolin-1-carboxamido)-2-methylpropyl)-4,5-dihydroisoxazol-5-carboxamido)-3-methylbutyl)boronic acid Through the processes (1), (2), (3) and (4) below, the title compound was obtained.

(1) Preparation of methyl 3-((S)-1-amino-2-methylpropyl)-5-benzyl-4,5-dihydroisoxazol-5-carboxylate hydrochloride

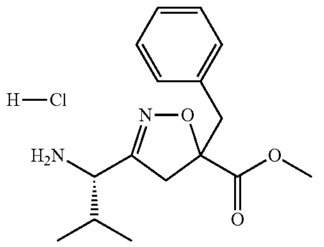

The title compound (1.34 g, 99%) was obtained using methyl 5-benzyl-3-((S)-1-((tert-butoxycarbonyl)amino)-2-methylpropyl)-4,5-dihydroisoxazol-5-carboxylate (1.62 g, 4.15 mmol) obtained in Preparation Example 25 by the preparation method of Example 84-(1).

MS (m/z): 291[M+H]

(2) Preparation of methyl 5-benzyl-3-((S)-1-(isoquinolin-1-carboxamido)-2-methylpropyl)-4,5-dihydroisoxazol-5-carboxylate

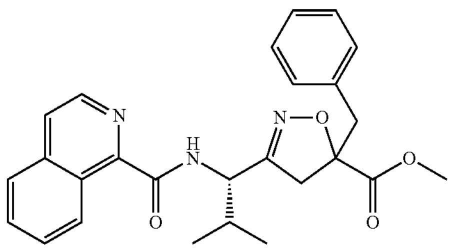 [SMILES: COC(=O)C1(Cc2ccccc2)CC([C@@H](NC(=O)c2nccc3ccccc23)C(C)C)=NO1]

The title compound (0.138 g, 84%) was obtained using methyl 3-((S)-1-amino-2-methylpropyl)-5-benzyl-4,5-dihydroisoxazol-5-carboxylate hydrochloride (0.12 g, 0.37 mmol) obtained in (1) above and isoquinolin-1-carboxylic acid (0.07 g, 0.40 mmol) by the preparation method of Example 84-(2).

NMR: $^1$H-NMR (500 MHz, $CDCl_3$); δ 9.57-9.54 (m, 1H), 8.52-8.38 (m, 2H), 7.87-7.68 (m, 4H), 7.24-7.11 (m, 5H), 4.78-4.74 (m, 1H), 3.76 (s, 3H), 3.47-3.28 (m, 2H), 3.12-3.02 (m, 2H), 2.18-2.14 (m, 1H), 0.94-0.91 (dd, 6H)

MS (m/z): 446[M+H]

(3) Preparation of 5-benzyl-3-((S)-1-(isoquinolin-1-carboxamido)-2-methylpropyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

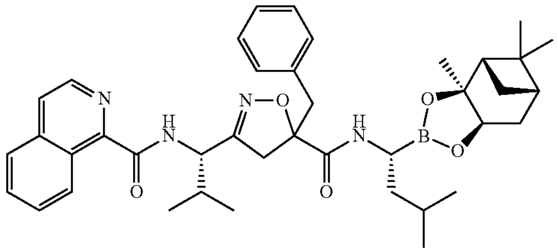 [SMILES: CC(C)C[C@H](NC(=O)C1(Cc2ccccc2)CC([C@@H](NC(=O)c2nccc3ccccc23)C(C)C)=NO1)B1O[C@@H]2C[C@@H]3C[C@@H](C3(C)C)[C@]2(C)O1]

The title compound (0.05 g, 26%, 2 steps) was obtained using methyl 5-benzyl-3-((S)-1-(isoquinolin-1-carboxamido)-2-methylpropyl)-4,5-dihydroisoxazol-5-carboxylate (0.138 g, 0.31 mmol) obtained in (2) above by the preparation method of Example 84-(3).

MS (m/z): 679[M+H]

(4) Preparation of ((1R)-1-(5-benzyl-3-((S)-1-(isoquinolin-1-carboxamido)-2-methylpropyl)-4,5-dihydroisoxazol-5-carboxamido)-3-methylbutyl)boronic acid

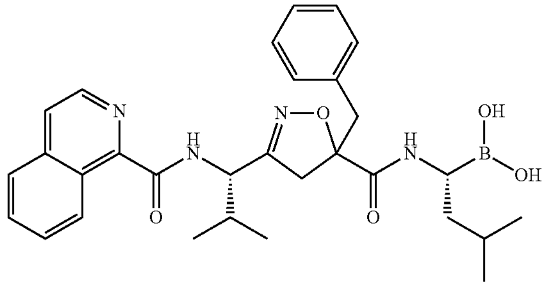 [SMILES: CC(C)C[C@H](NC(=O)C1(Cc2ccccc2)CC([C@@H](NC(=O)c2nccc3ccccc23)C(C)C)=NO1)B(O)O]

The title compound (0.032 g, 80%) was obtained using 5-benzyl-3-((S)-1-(isoquinolin-1-carboxamido)-2-methylpropyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.05 g, 0.074 mmol) obtained in (3) above by the preparation method of Example 1-(4).

NMR: $^1$H-NMR (500 MHz, MeOD-d4); δ 8.95-8.93 (d, 1H), 8.52-8.51 (d, 1H), 7.98-7.94 (dd, 2H), 7.79-7.68 (m, 2H), 7.28-7.21 (m, 5H), 4.69-4.68 (d, 1H), 3.47-3.32 (m, 2H), 3.25-3.16 (m, 2H), 2.65-2.61 (m, 1H), 2.07-2.03 (m, 1H), 1.41-1.37 (m, 1H), 1.17-1.05 (m, 2H), 1.02-1.00 (d, 3H), 0.79-0.76 (dd, 6H), 0.73-0.72 (d, 3H)

MS (m/z): 545[M+H], 527[M-OH]

Example 149: Preparation of ((1R)-1-(5-((1H-pyrazol-1-yl)methyl)-3-((imidazo[1,2-a]pyridin-8-carboxamido)methyl)-4,5-dihydroisoxazol-5-carboxamido)-3-methylbutyl)boronic acid Through the processes (1), (2) and (3) below, the title compound was obtained.

(1) Preparation of ethyl 5-((1H-pyrazol-1-yl)methyl)-3-((imidazo[1,2-a]pyridin-8-carboxamido)methyl)-4,5-dihydroisoxazol-5-carboxylate

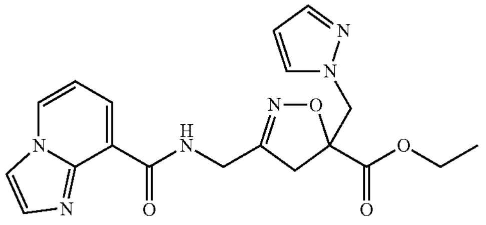 [SMILES: CCOC(=O)C1(Cn2cccn2)CC(CNC(=O)c2cccn3ccnc23)=NO1]

The title compound (0.078 g, 44%) was obtained using ethyl 5-((1H-pyrazol-1-yl)methyl)-3-(aminomethyl)-4,5-dihydroisoxazol-5-carboxylate hydrochloride (0.13 g, 0.45 mmol) obtained in Example 128-(1) and imidazo[1,2-a]pyridin-8-carboxylic acid (0.098 g, 0.50 mmol) obtained in Example 132-(1) by the preparation method of Example 84-(2).

MS (m/z): 397[M+H]

(2) Preparation of 5-((1H-pyrazol-1-yl)methyl)-3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

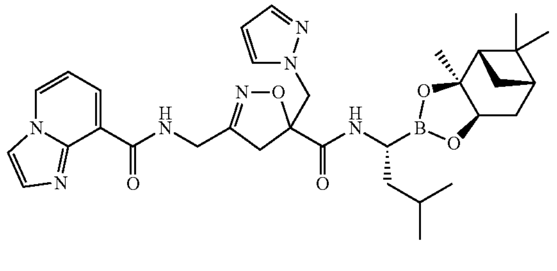 [SMILES: CC(C)C[C@H](NC(=O)C1(Cn2cccn2)CC(CNC(=O)c2cccn3ccnc23)=NO1)B1O[C@@H]2C[C@@H]3C[C@@H](C3(C)C)[C@]2(C)O1]

The title compound (0.062 g, 52%, 2 steps) was obtained using ethyl 5-((1H-pyrazol-1-yl)methyl)-3-((imidazo[1,2-a]pyridin-8-carboxamido)methyl)-4,5-dihydroisoxazol-5-carboxylate (0.078 g, 0.20 mmol) obtained in (1) above by the preparation method of Example 84-(3).

MS (m/z): 616[M+H]

(3) Preparation of ((1R)-1-(5-((1H-pyrazol-1-yl)methyl)-3-((imidazo[1,2-a]pyridin-8-carboxamido)methyl)-4,5-dihydroisoxazol-5-carboxamido)-3-methylbutyl)boronic acid

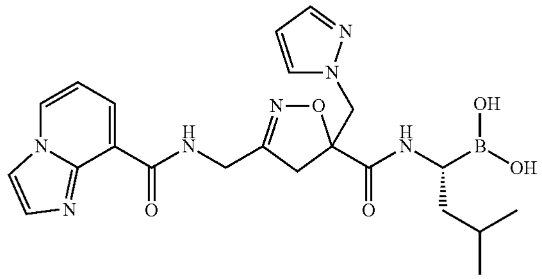 [SMILES: CC(C)C[C@H](NC(=O)C1(Cn2cccn2)CC(CNC(=O)c2cccn3ccnc23)=NO1)B(O)O]

The title compound (0.017 g, 34%) was obtained using 5-((1H-pyrazol-1-yl)methyl)-3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.062 g, 0.10 mmol) obtained in (2) above by the preparation method of Example 1-(4).

NMR: $^1$H-NMR (400 MHz, MeOD-$d_4$); δ 8.67-8.65 (dd, 1H), 8.11-8.10 (dd, 1H), 7.98 (d, 1H), 7.70-7.66 (m, 2H), 7.39-7.38 (dd, 1H), 1.09-7.06 (t, 1H), 6.27-6.25 (m, 1H), 4.75-4.60 (m, 2H), 4.38 (s, 2H), 3.43 (s, 2H), 2.93-2.91 (m, 1H), 1.53-1.50 (m, 1H), 1.35-1.27 (m, 2H), 0.88-0.84 (m, 6H)

MS (m/z): 482[M+H], 464[M-OH]

Example 150: Preparation of ((1R)-1-(3-((imidazo[1,2-a]pyridin-8-carboxamido)methyl)-5-(thiazol-4-ylmethyl)-4,5-dihydroisoxazol-5-carboxamido)-3-methylbutyl)boronic acid Through the processes (1), (2) and (3) below, the title compound was obtained.

(1) Preparation of ethyl 3-((imidazo[1,2-a]pyridin-8-carboxamido)methyl)-5-(thiazol-4-ylmethyl)-4,5-dihydroisoxazol-5-carboxylate

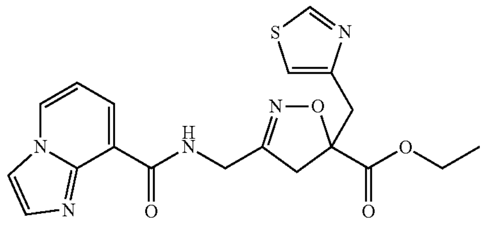 [SMILES: CCOC(=O)C1(Cc2cscn2)CC(CNC(=O)c2cccn3ccnc23)=NO1]

The title compound (0.077 g, 47%) was obtained using ethyl 3-(aminomethyl)-5-(thiazol-4-ylmethyl)-4,5-dihydroisoxazol-5-carboxylate hydrochloride (0.12 g, 0.39 mmol) obtained in Example 137-(1) and imidazo[1,2-a]pyridin-8-carboxylic acid (0.086 g, 0.43 mmol) obtained in Example 132-(1) by the preparation method of Example 84-(2).

MS (m/z): 414[M+H]

(2) Preparation of 3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(thiazol-4-ylmethyl)-4,5-dihydroisoxazol-5-carboxamide

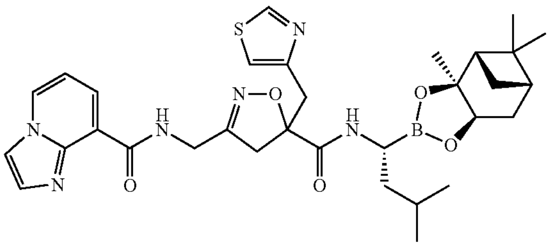 [SMILES: CC(C)C[C@H](NC(=O)C1(Cc2cscn2)CC(CNC(=O)c2cccn3ccnc23)=NO1)B1O[C@@H]2C[C@@H]3C[C@@H](C3(C)C)[C@]2(C)O1]

The title compound (0.066 g, 57%, 2 steps) was obtained using ethyl 3-((imidazo[1,2-a]pyridin-8-carboxamido)methyl)-5-(thiazol-4-ylmethyl)-4,5-dihydroisoxazol-5-carboxylate (0.077 g, 0.19 mmol) obtained in (1) above by the preparation method of Example 84-(3).

MS (m/z): 633[M+H]

(3) Preparation of ((1R)-1-(3-((imidazo[1,2-a]pyridin-8-carboxamido)methyl)-5-(thiazol-4-ylmethyl)-4,5-dihydroisoxazol-5-carboxamido)-3-methylbutyl)boronic acid

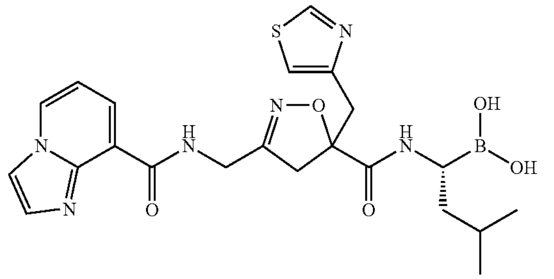 [SMILES: CC(C)C[C@H](NC(=O)C1(Cc2cscn2)CC(CNC(=O)c2cccn3ccnc23)=NO1)B(O)O]

The title compound (0.014 g, 26%) was obtained using 3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(thiazol-4-ylmethyl)-4,5-dihydroisoxazol-5-carboxamide (0.066 g, 0.10 mmol) obtained in (2) above by the preparation method of Example 1-(4).

NMR: $^1$H-NMR (400 MHz, MeOD-d4); δ 0.85-8.84 (dd, 1H), 8.67-8.65 (d, 1H), 8.12-8.10 (dd, 1H), 7.99-7.98 (d, 1H), 7.70-7.69 (t, 1H), 7.45-7.44 (t, 1H), 7.09-7.06 (t, 1H), 4.41-4.40 (d, 2H), 3.58-3.46 (m, 4H), 2.81-2.77 (m, 1H), 1.56 (m, 1H), 1.35-1.23 (m, 2H), 0.89-0.86 (m, 6H)

MS (m/z): 499[M+H], 481[M-OH]

Example 151: Preparation of [(1R)-1-[[5-benzyl-3-[[(5-methylpyrazin-2-carbonyl)amino]methyl]-4H-1,2-oxazol-5-carbonyl]amino]-3-methyl-butyl]boronic acid Through the processes (1), (2) and (3) below, the title compound was obtained.

(1) Preparation of methyl 5-benzyl-3-((5-methylpyrazin-2-carboxamido)methyl)-4,5-dihydroisoxazol-5-carboxylate

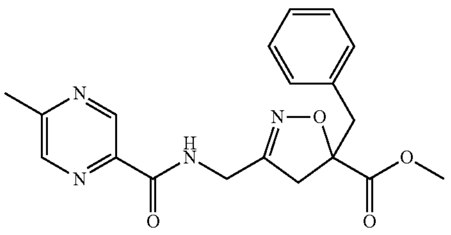

The title compound (0.15 g, 97%) was obtained using methyl 3-(aminomethyl)-5-benzyl-4,5-dihydroisoxazol-5-carboxylate hydrochloride (0.12 g, 0.42 mmol) obtained in Example 84-(1) and 5-methyl-pyrazin-2-carboxylic acid (0.064 g, 0.46 mmol) by the preparation method of Example 84-(2).

MS (m/z): 369[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((5-methylpyrazin-2-carboxamido)methyl)-4,5-dihydroisoxazol-5-carboxamide

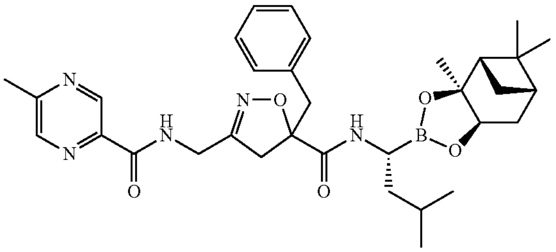

The title compound (0.05 g, 24%, 2 steps) was obtained using methyl 5-benzyl-3-((5-methylpyrazin-2-carboxamido)methyl)-4,5-dihydroisoxazol-5-carboxylate (0.15 g, 0.41 mmol) obtained in (1) above by the preparation method of Example 84-(3).

MS (m/z): 602[M+H]

(3) Preparation of ((1R)-1-(5-benzyl-3-((5-methylpyrazin-2-carboxamido)methyl)-4,5-dihydroisoxazol-5-carboxamido)-3-methylbutyl)boronic acid

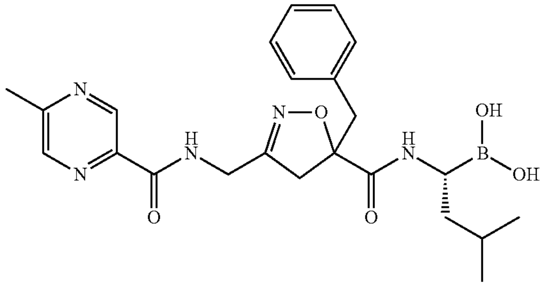 [SMILES: Cc1cnc(C(=O)NCC2=NOC(Cc3ccccc3)(C(=O)N[C@@H](CC(C)C)B(O)O)C2)cn1]

The title compound (0.025 g, 64%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((5-methylpyrazin-2-carboxamido)methyl)-4,5-dihydroisoxazol-5-carboxamide (0.05 g, 0.083 mmol) obtained in (2) above by the preparation method of Example 1-(4).

NMR: $^1$H-NMR (400 MHz, $CDCl_3$); δ 9.22-9.21 (d, 1H), 8.31 (d, 1H), 8.02-7.99 (m, 1H), 7.27-7.22 (m, 6H), 4.27-4.22 (m, 2H), 3.42-3.33 (m, 2H), 3.16-3.04 (m, 2H), 2.80 (m, 1H), 2.64 (s, 3H), 1.38-1.18 (m, 3H), 0.82-0.78 (m, 6H)

MS (m/z): 468[M+H], 450[M-OH]

Example 152: Preparation of ((1R)-1-(5-benzyl-3-((S)-1-(isoquinolin-1-carboxamido)-3-methylbutyl)-4,5-dihydroisoxazol-5-carboxamido)-3-methylbutyl) boronic acid Through the processes (1), (2), (3) and (4) below, the title compound was obtained.

(1) Preparation of methyl 3-((S)-1-amino-3-methylbutyl)-5-benzyl-4,5-dihydroisoxazol-5-carboxylate hydrochloride

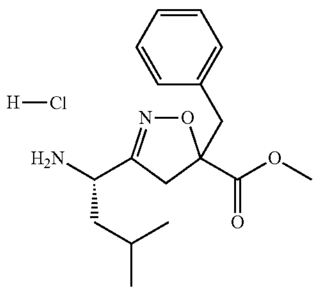

The title compound (0.41 g, 95%) was obtained using methyl 5-benzyl-3-((S)-1-((tert-butoxycarbonyl)amino)-3-methylbutyl)-4,5-dihydroisoxazol-5-carboxylate (0.51 g, 1.26 mmol) obtained in Preparation Example 26 by the preparation method of Example 84-(1).

MS (m/z): 305[M+H]

(2) Preparation of methyl 5-benzyl-3-((S)-1-(isoquinolin-1-carboxamido)-3-methylbutyl)-4,5-dihydroisoxazol-5-carboxylate

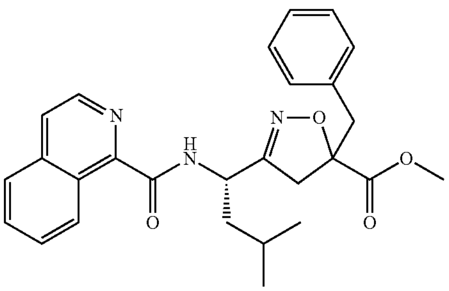 [SMILES: COC(=O)C1(Cc2ccccc2)CC([C@H](CC(C)C)NC(=O)c2nccc3ccccc23)=NO1]

The title compound (0.11 g, 96%) was obtained using methyl 3-((S)-1-amino-3-methylbutyl)-5-benzyl-4,5-dihydroisoxazol-5-carboxylate hydrochloride (0.12 g, 0.35 mmol) obtained in (1) above and isoquinolin-1-carboxylic acid (0.068 g, 0.39 mmol) by the preparation method of Example 84-(2).

MS (m/z): 460[M+H]

(3) Preparation of 5-benzyl-3-((S)-1-(isoquinolin-1-carboxamido)-3-methylbutyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

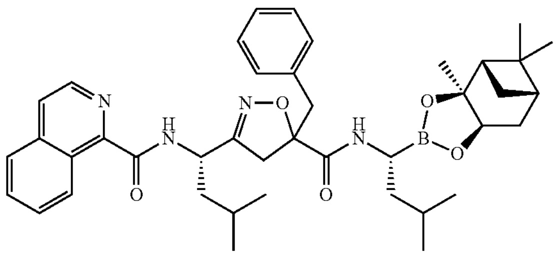 [SMILES: CC(C)C[C@H](NC(=O)C1(Cc2ccccc2)CC([C@H](CC(C)C)NC(=O)c2nccc3ccccc23)=NO1)B1O[C@@H]2C[C@@H]3C[C@@H](C3(C)C)[C@]2(C)O1]

The title compound (0.038 g, 16%, 2 steps) was obtained using methyl 5-benzyl-3-((S)-1-(isoquinolin-1-carboxamido)-3-methylbutyl)-4,5-dihydroisoxazol-5-carboxylate (0.11 g, 0.34 mmol) obtained in (2) above by the preparation method of Example 84-(3).

MS (m/z): 693[M+H]

(4) Preparation of ((1R)-1-(5-benzyl-3-((S)-1-(isoquinolin-1-carboxamido)-3-methylbutyl)-4,5-dihydroisoxazol-5-carboxamido)-3-methylbutyl)boronic acid

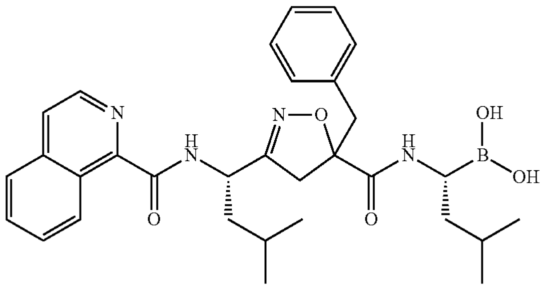 [SMILES: CC(C)C[C@H](NC(=O)C1(Cc2ccccc2)CC([C@H](CC(C)C)NC(=O)c2nccc3ccccc23)=NO1)B(O)O]

The title compound (0.020 g, 65%) was obtained using 5-benzyl-3-((S)-1-(isoquinolin-1-carboxamido)-3-methylbutyl)-N—((R)-3-methyl-1-((3aS,4S,6S,7aR)-3a,5,5-trimethylhexahydro-4,6-metanobenzo[d][1,3,2]dioxaborol-2-yl) butyl)-4,5-dihydroisoxazol-5-carboxamide (0.038 g, 0.055 mmol) obtained in (3) above by the preparation method of Example 1-(4).

NMR: $^1$H-NMR (400 MHz, $CDCl_3$); δ 9.55-9.53 (d, 1H), 8.44-8.43 (d, 1H), 8.20-8.17 (d, 1H), 7.85-7.64 (m, 4H), 7.27-7.14 (m, 6H), 4.92 (m, 1H), 3.43-3.06 (m, 4H), 2.90 (m, 1H), 1.49-1.21 (m, 6H), 0.89-0.79 (m, 12H)

MS (m/z): 559[M+H], 541[M-OH]

Example 153: Preparation of ((1R)-1-(5-benzyl-3-((R)-1-(isoquinolin-1-carboxamido)-2-methoxyethyl)-4,5-dihydroisoxazol-5-carboxamido)-3-methylbutyl)boronic acid Through the processes (1), (2), (3) and (4) below, the title compound was obtained.

(1) Preparation of methyl 3-((R)-1-amino-2-methoxyethyl)-5-benzyl-4,5-dihydroisoxazol-5-carboxylate hydrochloride

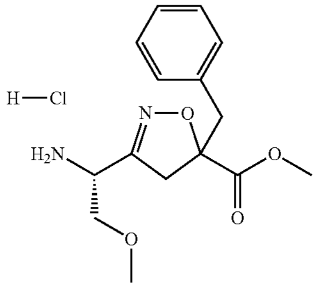

The title compound (0.41 g, 95%) was obtained using methyl 5-benzyl-3-((R)-1-((tert-butoxycarbonyl)amino)-2-methoxyethyl)-4,5-dihydroisoxazol-5-carboxylate (0.42 g, 1.08 mmol) obtained in Preparation Example 27 by the preparation method of Example 84-(1).

MS (m/z): 293[M+H]

(2) Preparation of methyl 5-benzyl-3-((R)-1-(isoquinolin-1-carboxamido)-2-methoxyethyl)-4,5-dihydroisoxazol-5-carboxylate

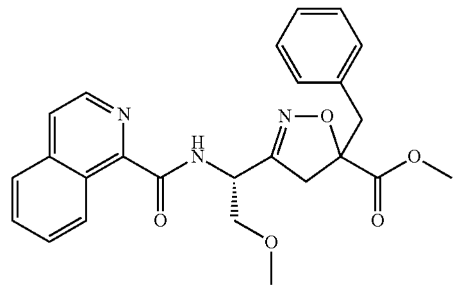 [SMILES: COC[C@H](NC(=O)c1nccc2ccccc12)C1=NOC(Cc2ccccc2)(C(=O)OC)C1]

The title compound (0.11 g, 73%) was obtained using methyl 3-((R)-1-amino-2-methoxyethyl)-5-benzyl-4,5-dihydroisoxazol-5-carboxylate hydrochloride (0.12 g, 0.37 mmol) obtained in (1) above and isoquinolin-1-carboxylic acid (0.69 g, 0.40 mmol) by the preparation method of Example 84-(2).

MS (m/z): 418[M+H]

(3) Preparation of 5-benzyl-3-((R)-1-(isoquinolin-1-carboxamido)-2-methoxyethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

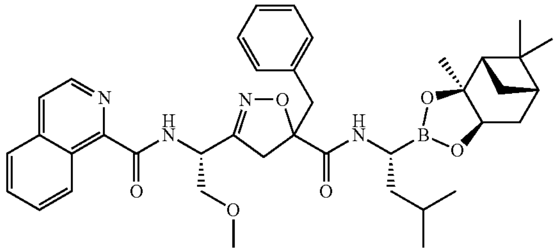 [SMILES: COC[C@H](NC(=O)c1nccc2ccccc12)C1=NOC(Cc2ccccc2)(C(=O)N[C@@H](CC(C)C)B2O[C@@H]3C[C@@H]4C[C@@H](C4(C)C)[C@]3(C)O2)C1]

The title compound (0.13 g, 56%, 2 steps) was obtained using methyl 5-benzyl-3-((R)-1-(isoquinolin-1-carboxamido)-2-methoxyethyl)-4,5-dihydroisoxazol-5-carboxylate (0.1 g, 0.32 mmol) obtained in (2) above by the preparation method of Example 84-(3).

MS (m/z): 681[M+H]

(4) Preparation of ((1R)-1-(5-benzyl-3-((R)-1-(isoquinolin-1-carboxamido)-2-methoxyethyl)-4,5-dihydroisoxazol-5-carboxamido)-3-methylbutyl)boronic acid

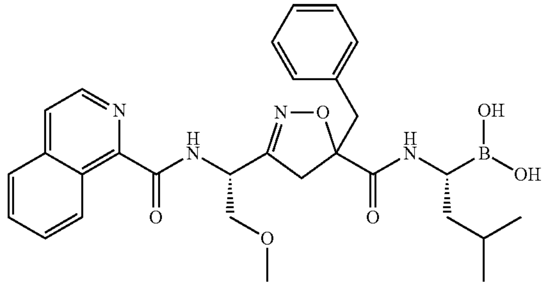 [SMILES: COC[C@H](NC(=O)c1nccc2ccccc12)C1=NOC(Cc2ccccc2)(C(=O)N[C@@H](CC(C)C)B(O)O)C1]

The title compound (0.073 g, 71%) was obtained using 5-benzyl-3-((R)-1-(isoquinolin-1-carboxamido)-2-methoxyethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.13 g, 0.19 mmol) obtained in (3) above by the preparation method of Example 1-(4).

NMR: $^1$H-NMR (400 MHz, $CDCl_3$); δ 9.53-9.51 (m, 1H), 8.79-8.69 (m, 1H), 8.45-8.41 (m, 1H), 7.84-7.65 (m, 4H), 7.31-7.15 (m, 6H), 5.08-5.01 (m, 1H), 3.63-3.32 (m, 4H), 3.30 (d, 3H), 3.17-3.10 (m, 2H), 2.90 (m, 1H), 1.48-1.23 (m, 3H), 0.79-0.78 (m, 6H)

MS (m/z): 547[M+H], 529[M-OH]

Example 154: Preparation of ((1R)-1-(3-((isoquinolin-1-carboxamido)methyl)-5-(2-methylbenzyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(2-methylbenzyl)-4,5-dihydroisoxazol-5-carboxylate hydrochloride

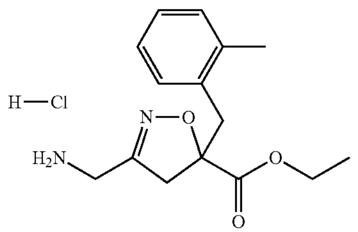

The title compound (0.085 g, quant.) was obtained using ethyl 3-(((tert-butoxycarbonyl)amino)methyl)-5-(2-methylbenzyl)-4,5-dihydroisoxazol-5-carboxylate (0.10 g, 0.27 mmol) obtained in Preparation Example 28 by the preparation method of Example 84-(1).

MS (m/z): 277[M+H]

(2) Preparation of ethyl 3-((isoquinolin-1-carboxamido)methyl)-5-(2-methylbenzyl)-4,5-dihydroisoxazol-5-carboxylate

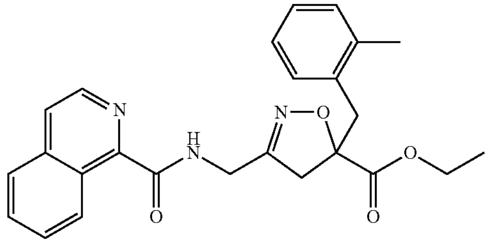 [SMILES: CCOC(=O)C1(Cc2ccccc2C)CC(CNC(=O)c2nccc3ccccc23)=NO1]

The title compound (0.056 g, 65%) was obtained using ethyl 3-(aminomethyl)-5-(2-methylbenzyl)-4,5-dihydroisoxazol-5-carboxylate hydrochloride (0.063 g, 0.20 mmol) obtained in (1) above and isoquinolin-1-carboxylic acid (0.038 g, 0.22 mmol) by the preparation method of Example 84-(2).

NMR: $^1$H-NMR (500 MHz, $CDCl_3$); δ 9.52 (1H, d), 8.46 (1H, d), 8.37 (1H, t), 7.86 (1H, d), 7.82 (1H, d), 7.74-7.69 (2H, m), 7.20-7.18 (1H, m), 7.04-7.00 (3H, m), 4.2 (2H, q), 4.24-4.19 (2H, m), 3.50 (1H, d), 3.34 (2H, d), 3.17 (1H, d), 3.03 (1H, d), 2.30 (3H, s), 1.24 (3H, t)

MS (m/z): 432[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(2-methylbenzyl)-4,5-dihydroisoxazol-5-carboxamide

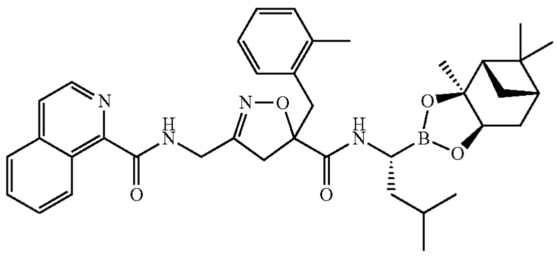 [SMILES: Cc1ccccc1CC1(C(=O)N[C@@H](CC(C)C)B2O[C@@H]3C[C@@H]4C[C@@H](C4(C)C)[C@]3(C)O2)CC(CNC(=O)c2nccc3ccccc23)=NO1]

The title compound (0.046 g, 49%, 2 steps) was obtained using ethyl 3-((isoquinolin-1-carboxamido)methyl)-5-(2-methylbenzyl)-4,5-dihydroisoxazol-5-carboxylate (0.056 g, 0.13 mmol) obtained in (2) above by the preparation method of Example 84-(3).

MS (m/z): 651[M+H]

(4) Preparation of ((1R)-1-(3-((isoquinolin-1-carboxamido)methyl)-5-(2-methylbenzyl)-4,5-dihydroisoxazol-5-carboxamido)-3-methylbutyl)boronic acid

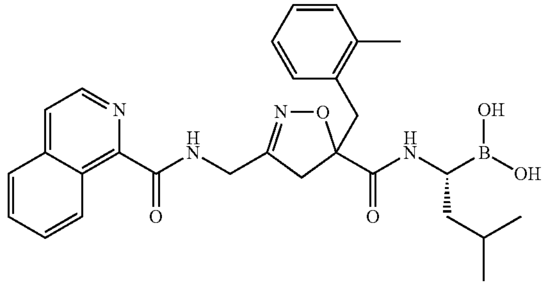 [SMILES: Cc1ccccc1CC1(C(=O)N[C@@H](CC(C)C)B(O)O)CC(CNC(=O)c2nccc3ccccc23)=NO1]

The title compound (0.013 g, 35%) was obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(2-methylbenzyl)-4,5-dihydroisoxazol-5-carboxamide (0.046 g, 0.071 mmol) obtained in (3) above by the preparation method of Example 1-(4).

NMR: $^1$H-NMR (500 MHz, $CD_3OD$); δ 9.06 (1H, d), 8.50 (1H, d), 7.98 (1H, d), 7.95 (1H, d), 7.79 (1H, t), 7.71 (1H, t), 7.22 (1H, d), 7.08-7.04 (3H, m), 4.32 (2H, s), 3.50 (1H, d), 3.33-3.29 (3H, m), 2.65 (1H, t), 1.41-1.06 (3H, m), 0.79 (6H, dd)

MS (m/z): 539[M+Na], 499[M-OH]

Example 155: Preparation of ((1R)-1-(5-(difluoro(phenyl)methyl)-3-((isoquinolin-1-carboxamido)methyl)-4,5-dihydroisoxazol-5-carboxamido)-3-methylbutyl)boronic acid Through the processes (1), (2), (3) and (4) below, the title compound was obtained.

(1) Preparation of methyl 3-(aminomethyl)-5-(difluoro(phenyl)methyl)-4,5-dihydroisoxazol-5-carboxylate hydrochloride

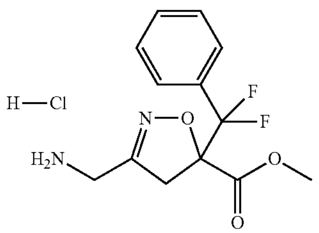

The title compound (0.146 g, quant.) was obtained using methyl 3-(((tert-butoxycarbonyl)amino)methyl)-5-(difluoro(phenyl)methyl)-4,5-dihydroisoxazol-5-carboxylate (0.173 g, 0.45 mmol) obtained in Preparation Example 29 by the preparation method of Example 84-(1).

MS (m/z): 285[M+H]

(2) Preparation of methyl 5-(difluoro(phenyl)methyl)-3-((isoquinolin-1-carboxamido)methyl)-4,5-dihydroisoxazol-5-carboxylate

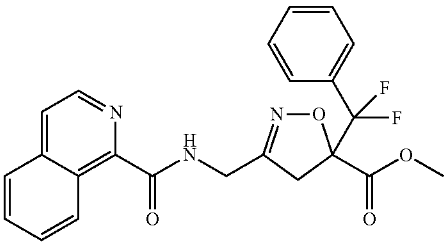 [SMILES: COC(=O)C1(C(F)(F)c2ccccc2)CC(CNC(=O)c2nccc3ccccc23)=NO1]

The title compound (0.071 g, 76%) was obtained using methyl 3-(aminomethyl)-5-(difluoro(phenyl)methyl)-4,5-dihydroisoxazol-5-carboxylate hydrochloride (0.068 g, 0.212 mmol) obtained in (1) above and isoquinolin-1-carboxylic acid (0.048 g, 0.277 mmol) by the preparation method of Example 84-(2).

NMR: $^1$H-NMR (400 MHz, $CDCl_3$); δ 9.60 (1H, dd), 8.53 (1H, t), 8.50 (1H, d), 7.91-7.74 (4H, m), 7.60-7.30 (5H, m), 4.48-4.35 (2H, m), 3.76 (3H, s), 3.70 (2H, d)

MS (m/z): 440[M+H]

(3) Preparation of 5-(difluoro(phenyl)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

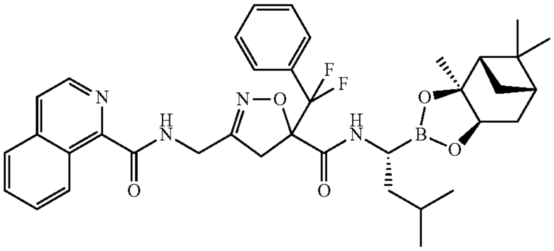 [SMILES: CC(C)C[C@H](NC(=O)C1(C(F)(F)c2ccccc2)CC(CNC(=O)c2nccc3ccccc23)=NO1)B1O[C@@H]2C[C@@H]3C[C@@H](C3(C)C)[C@]2(C)O1]

The title compound (0.037 g, 42%, 2 steps) was obtained using methyl 5-(difluoro(phenyl)methyl)-3-((isoquinolin-1-carboxamido)methyl)-4,5-dihydroisoxazol-5-carboxylate (0.071 g, 0.161 mmol) obtained in (2) above by the preparation method of Example 84-(3).

MS (m/z): 673[M+H]

(4) Preparation of ((1R)-1-(5-(difluoro(phenyl)methyl)-3-((isoquinolin-1-carboxamido)methyl)-4,5-dihydroisoxazol-5-carboxamido)-3-methylbutyl)boronic acid

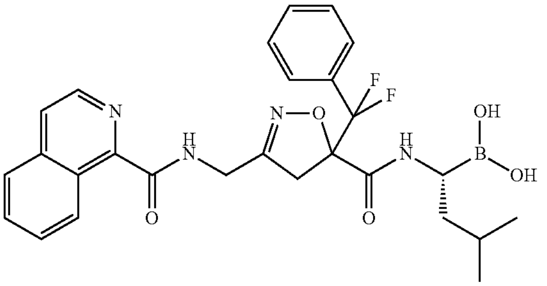 [SMILES: CC(C)C[C@H](NC(=O)C1(C(F)(F)c2ccccc2)CC(CNC(=O)c2nccc3ccccc23)=NO1)B(O)O]

Two types of the title compound of Isomer 1 having low polarity (0.00147 g, 50%) and Isomer 2 having high polarity (0.0021 g, 7%) were obtained using 5-(difluoro(phenyl)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.037 g, 0.055 mmol) obtained in (3) above by the preparation method of Example 1-(4).

Isomer 1

NMR: $^1$H-NMR (400 MHz, $CD_3OD$); δ 9.10 (1H, d), 8.54 (1H, d), 8.02-7.97 (2H, m), 7.84-7.72 (2H, m), 7.57 (1H, d), 7.49-7.43 (2H, m), 4.40 (2H, s), 3.86 (1H, d), 3.64 (1H, d), 2.86 (1H, t), 1.36-1.06 (3H, m), 0.79 (6H, dd)

MS (m/z): 561[M+Na], 521[M-OH]

Isomer 2

NMR: $^1$H-NMR (400 MHz, $CD_3OD$); δ 9.09 (1H, d), 8.55 (1H, d), 8.00 (2H, dd), 7.83 (1H, t), 7.75 (1H, t), 7.59 (2H, d), 7.48-7.42 (3H, m), 4.60 (2H, s), 3.82 (1H, d), 3.62 (1H, dd), 2.96 (1H, t), 1.55-0.92 (3H, m), 0.82-0.78 (6H, m)

MS (m/z): 561[M+Na], 521[M-OH]

Example 156: Preparation of ((1R)-1-(5-(difluoro(phenyl)methyl)-3-((imidazo[1,2-a]pyridin-8-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-(difluoro(phenyl)methyl)-3-((imidazo[1,2-a]pyridin-8-carboxamido)methyl)-4,5-dihydroisoxazol-5-carboxylate

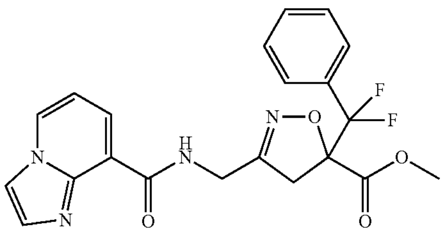 [SMILES: COC(=O)C1(C(F)(F)c2ccccc2)CC(CNC(=O)c2cccn3ccnc23)=NO1]

The title compound (0.046 g, 48%) was obtained using methyl 3-(aminomethyl)-5-(difluoro(phenyl)methyl)-4,5-dihydroisoxazol-5-carboxylate hydrochloride (0.072 g, 0.224 mmol) obtained in Example 155-(1) and imidazo[1,2-a]pyridin-8-carboxylic acid (0.058 g, 0.293 mmol) obtained in Example 132-(1) by the preparation method of Example 84-(2).

NMR: $^1$H-NMR (400 MHz, $CDCl_3$); δ 10.64 (1H, t), 8.34 (1H, dd), 8.22 (1H, dd), 7.69 (2H, dd), 7.58 (2H, dd), 7.43-7.35 (3H, m), 7.01 (1H, t), 4.52-4.42 (2H, m), 3.75 (3H, s), 3.72 (2H, d)

MS (m/z): 429[M+H]

(2) Preparation of 5-(difluoro(phenyl)methyl)-3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

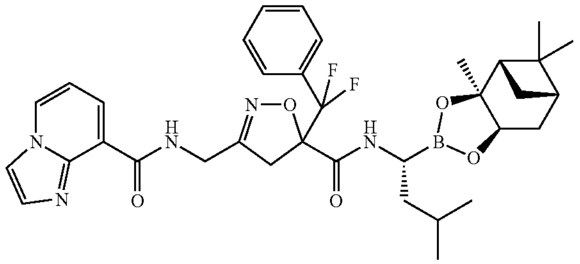 [SMILES: CC(C)C[C@H](NC(=O)C1(C(F)(F)c2ccccc2)CC(CNC(=O)c2cccn3ccnc23)=NO1)B1O[C@@H]2C[C@@H]3C[C@@H](C3(C)C)[C@]2(C)O1]

The title compound (0.051 g, 72%, 2 steps) was obtained using methyl 5-(difluoro(phenyl)methyl)-3-((imidazo[1,2-a]pyridin-8-carboxamido)methyl)-4,5-dihydroisoxazol-5-carboxylate (0.046 g, 0.107 mmol) obtained in (1) above by the preparation method of Example 84-(3).

MS (m/z): 662[M+H]

(3) Preparation of ((1R)-1-(5-(difluoro(phenyl)methyl)-3-((imidazo[1,2-a]pyridin-8-carboxamido)methyl)-4,5-dihydroisoxazol-5-carboxamido)-3-methylbutyl)boronic acid

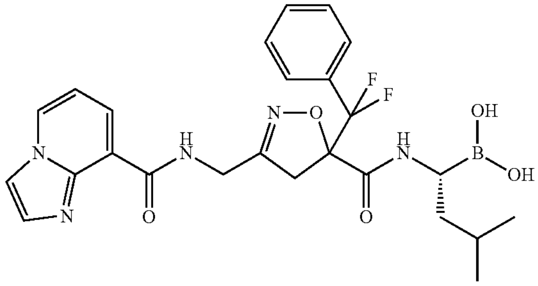 [SMILES: CC(C)C[C@H](NC(=O)C1(C(F)(F)c2ccccc2)CC(CNC(=O)c2cccn3ccnc23)=NO1)B(O)O]

The title compound (0.025 g, 61%) was obtained using 5-(difluoro(phenyl)methyl)-3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.051 g, 0.077 mmol) obtained in (2) above by the preparation method of Example 1-(4).

NMR: $^1$H-NMR (400 MHz, $CD_3OD$); δ 8.65 (1H, d), 8.10 (1H, dd), 7.98 (1H, d), 7.69 (1H, d), 7.54 (2H, d), 7.48-7.38 (3H, m), 7.07 (1H, t), 4.42 (2H, s), 3.81 (1H, d), 3.58 (1H, d), 2.88 (1H, t), 1.30-1.12 (4H, m), 0.79-0.74 (6H, m)

MS (m/z): 550[M+Na], 510[M-OH]

Example 157: Preparation of [(1R)-1-[[5-benzyl-3-[1-(isoquinolin-1-carbonylamino)-1-methyl-ethyl]-4H-1,2-oxazol-5-carbonyl]amino]-3-methyl-butyl]boronic acid Through the processes (1), (2), (3) and (4) below, the title compound was obtained.

(1) Preparation of methyl 3-(2-aminopropan-2-yl)-5-benzyl-4,5-dihydroisoxazol-5-carboxylate hydrochloride

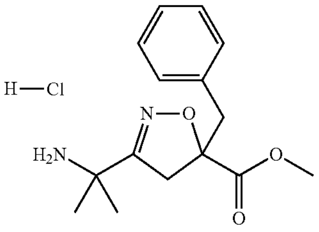 [SMILES: Cl ; COC(=O)C1(Cc2ccccc2)CC(C(C)(C)N)=NO1]

The title compound (0.31 g, 99%) was obtained using methyl 5-benzyl-3-(2-((tert-butoxycarbonyl)amino)propan-2-yl)-4,5-dihydroisoxazol-5-carboxylate (0.37 g, 98 mmol) obtained in Preparation Example 30, preparation of methyl 5-benzyl-3-(2-((tert-butoxycarbonyl)amino)propan-2-yl)-4,5-dihydroisoxazol-5-carboxylate, by the preparation method of Example 84-(1).

MS (m/z): 277[M+H]

(2) Preparation of methyl 5-benzyl-3-(2-(isoquinolin-1-carboxamido)propan-2-yl)-4,5-dihydroisoxazol-5-carboxylate

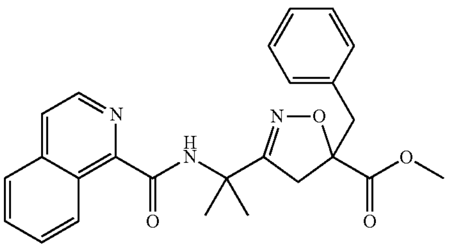 [SMILES: COC(=O)C1(Cc2ccccc2)CC(C(C)(C)NC(=O)c2nccc3ccccc23)=NO1]

The title compound (0.094 g, 76%) was obtained using methyl 3-(2-aminopropan-2-yl)-5-benzyl-4,5-dihydroisoxazol-5-carboxylate hydrochloride (0.09 g, 0.29 mmol) obtained in (1) above and isoquinolin-1-carboxylic acid (0.055 g, 0.32 mmol) by the preparation method of Example 84-(2).

MS (m/z): 432[M+H]

(3) Preparation of 5-benzyl-3-(2-(isoquinolin-1-carboxamido)propan-2-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

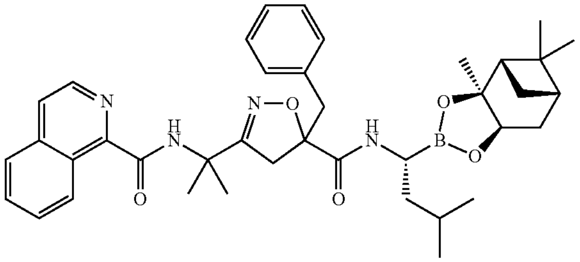 [SMILES: CC(C)C[C@H](NC(=O)C1(Cc2ccccc2)CC(C(C)(C)NC(=O)c2nccc3ccccc23)=NO1)B1O[C@@H]2C[C@@H]3C[C@@H](C3(C)C)[C@]2(C)O1]

The title compound (0.089 g, 61%, 2 steps) was obtained using methyl 5-benzyl-3-(2-(isoquinolin-1-carboxamido)propan-2-yl)-4,5-dihydroisoxazol-5-carboxylate (0.094 g, 0.22 mmol) obtained in (2) above by the preparation method of Example 84-(3).

MS (m/z): 665[M+H]

(4) Preparation of ((1R)-1-(5-benzyl-3-(2-(isoquinolin-1-carboxamido)propan-2-yl)-4,5-dihydroisoxazol-5-carboxamido)-3-methylbutyl)boronic acid

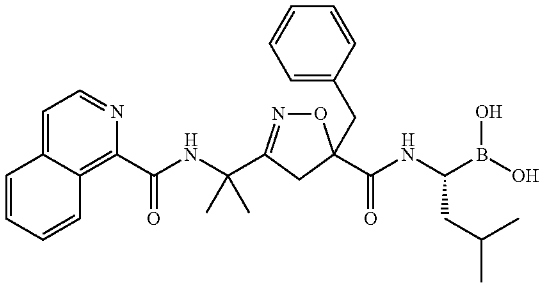 [SMILES: CC(C)C[C@H](NC(=O)C1(Cc2ccccc2)CC(C(C)(C)NC(=O)c2nccc3ccccc23)=NO1)B(O)O]

The title compound (0.024 g, 34%) was obtained using 5-benzyl-3-(2-(isoquinolin-1-carboxamido)propan-2-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.089 g, 0.14 mmol) obtained in (3) above by the preparation method of Example 1-(4).

MS (m/z): 531[M+H], 513[M-OH]

Example 158: Preparation of ((1R)-1-(5-benzyl-3-(2-(imidazo[1,2-a]pyridin-8-carboxamido)propan-2-yl)-4,5-dihydroisoxazol-5-carboxamido)-3-methylbutyl)boronic acid Through the processes (1), (2) and (3) below, the title compound was obtained.

(1) Preparation of methyl 5-benzyl-3-(2-(imidazo[1,2-a]pyridin-8-carboxamido)propan-2-yl)-4,5-dihydroisoxazol-5-carboxylate

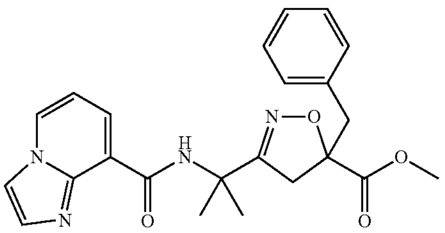 [SMILES: COC(=O)C1(Cc2ccccc2)CC(C(C)(C)NC(=O)c2cccn3ccnc23)=NO1]

The title compound (0.073 g, 60%) was obtained using methyl 3-(2-aminopropan-2-yl)-5-benzyl-4,5-dihydroisoxazol-5-carboxylate hydrochloride (0.093 g, 0.29 mmol) obtained in Example 157-(1) and imidazo[1,2-a]pyridin-8-carboxylic acid (0.063 g, 0.32 mmol) obtained in Example 132-(1) by the preparation method of Example 84-(2).

MS (m/z): 419[M+H]

(2) Preparation of 5-benzyl-3-(2-(imidazo[1,2-a]pyridin-8-carboxamido)propan-2-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

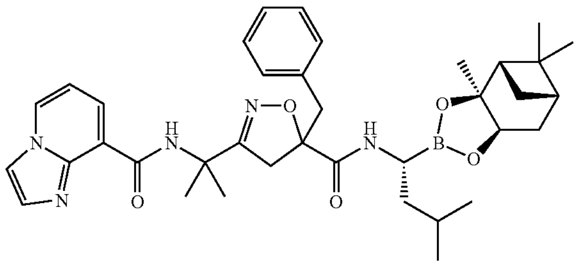 [SMILES: CC(C)C[C@H](NC(=O)C1(Cc2ccccc2)CC(C(C)(C)NC(=O)c2cccn3ccnc23)=NO1)B1O[C@@H]2C[C@@H]3C[C@@H](C3(C)C)[C@]2(C)O1]

The title compound (0.079 g, 69%, 2 steps) was obtained using methyl 5-benzyl-3-(2-(imidazo[1,2-a]pyridin-8-carboxamido)propan-2-yl)-4,5-dihydroisoxazol-5-carboxylate (0.073 g, 0.17 mmol) obtained in (1) above by the preparation method of Example 84-(3).

MS (m/z): 654[M+H]

(3) Preparation of ((1R)-1-(5-benzyl-3-(2-(imidazo[1,2-a]pyridin-8-carboxamido)propan-2-yl)-4,5-dihydroisoxazol-5-carboxamido)-3-methylbutyl)boronic acid

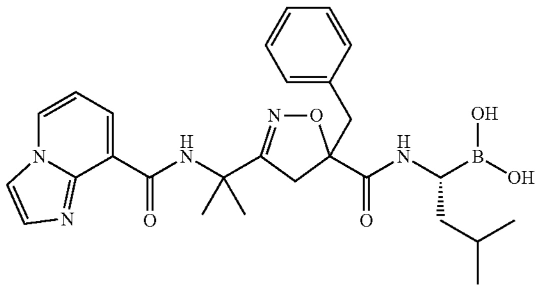 [SMILES: CC(C)C[C@H](NC(=O)C1(Cc2ccccc2)CC(C(C)(C)NC(=O)c2cccn3ccnc23)=NO1)B(O)O]

The title compound (0.028 g, 49%) was obtained using 5-benzyl-3-(2-(imidazo[1,2-a]pyridin-8-carboxamido)propan-2-yl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.079 g, 0.12 mmol) obtained in (2) above by the preparation method of Example 1-(4).

MS (m/z): 520[M+H], 502[M-OH]

Example 159: Preparation of ((1R)-1-(5-benzyl-3-((3-methylpicolinamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((3-methylpicolinamido)methyl)-4,5-dihydroisoxazol-5-carboxylate

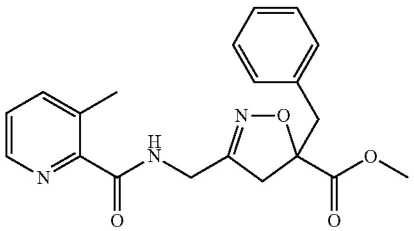 [SMILES: COC(=O)C1(Cc2ccccc2)CC(CNC(=O)c2ncccc2C)=NO1]

The title compound (0.12 g, 78%) was obtained using methyl 3-(aminomethyl)-5-benzyl-4,5-dihydroisoxazol-5-carboxylate hydrochloride (0.12 g, 0.42 mmol) obtained in Example 84-(1) and 3-methyl-pyridin-2-carboxylic acid (0.063 g, 0.46 mmol) by the preparation method of Example 84-(2).

MS (m/z): 368[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-methylpicolinamido)methyl)-4,5-dihydroisoxazol-5-carboxamide

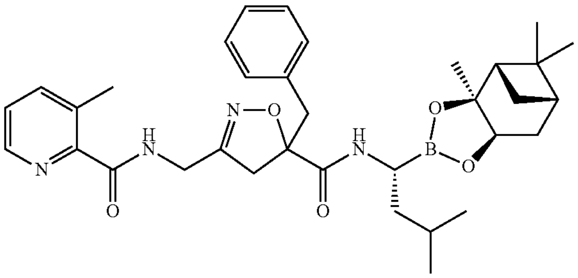 [SMILES: Cc1cccnc1C(=O)NCC1=NOC(Cc2ccccc2)(C(=O)N[C@@H](CC(C)C)B2O[C@@H]3C[C@@H]4C[C@@H](C4(C)C)[C@]3(C)O2)C1]

The title compound (0.11 g, 61%, 2 steps) was obtained using methyl 5-benzyl-3-((3-methylpicolinamido)methyl)-4,5-dihydroisoxazol-5-carboxylate (0.12 g, 0.33 mmol) obtained in (1) above by the preparation method of Example 84-(3).

MS (m/z): 601[M+H]

(3) Preparation of ((1R)-1-(5-benzyl-3-((3-methylpicolinamido)methyl)-4,5-dihydroisoxazol-5-carboxamido)-3-methylbutyl)boronic acid

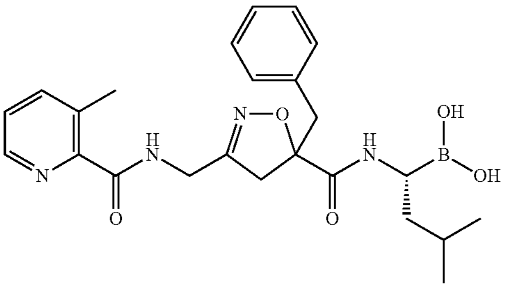 [SMILES: Cc1cccnc1C(=O)NCC1=NOC(Cc2ccccc2)(C(=O)N[C@@H](CC(C)C)B(O)O)C1]

The title compound (0.043 g, 49%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-methylpicolinamido)methyl)-4,5-dihydroisoxazol-5-carboxamide (0.11 g, 0.31 mmol) obtained in (2) above by the preparation method of Example 1-(4).

NMR: $^1$H-NMR (500 MHz, MeOD-d4); δ 8.42-8.41 (d, 1H), 7.72-7.70 (d, 1H), 7.42-7.40 (m, 1H), 7.26-7.19 (m, 5H), 4.22 (s, 2H), 3.44-3.32 (m, 2H), 3.24-3.17 (m, 2H), 2.64-2.61 (m, 1H), 2.60 (s, 3H), 1.38-1.34 (m, 1H), 1.15-0.99 (m, 2H), 0.82-0.75 (dd, 6H)

MS (m/z): 467[M+H], 449[M-OH]

Example 160: Preparation of ((1R)-1-(5-benzyl-3-((6-methylpicolinamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((6-methylpicolinamido)methyl)-4,5-dihydroisoxazol-5-carboxylate

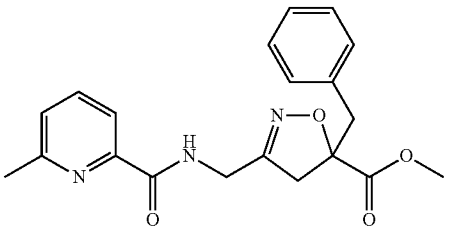

The title compound (0.1 g, 65%) was obtained using methyl 3-(aminomethyl)-5-benzyl-4,5-dihydroisoxazol-5-carboxylate hydrochloride (0.12 g, 0.42 mmol) obtained in Example 84-(1) and 6-methyl-pyridin-2-carboxylic acid (0.063 g, 0.46 mmol) by the preparation method of Example 84-(2).

MS (m/z): 368[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((6-methylpicolinamido)methyl)-4,5-dihydroisoxazol-5-carboxamide

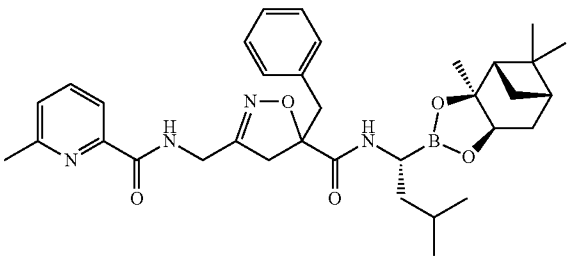

The title compound (0.1 g, 59%, 2 steps) was obtained using methyl 5-benzyl-3-((6-methylpicolinamido)methyl)-4,5-dihydroisoxazol-5-carboxylate (0.1 g, 0.27 mmol) obtained in (1) above by the preparation method of Example 84-(3).

MS (m/z): 601[M+H]

(3) Preparation of ((1R)-1-(5-benzyl-3-((6-methylpicolinamido)methyl)-4,5-dihydroisoxazol-5-carboxamido)-3-methylbutyl)boronic acid

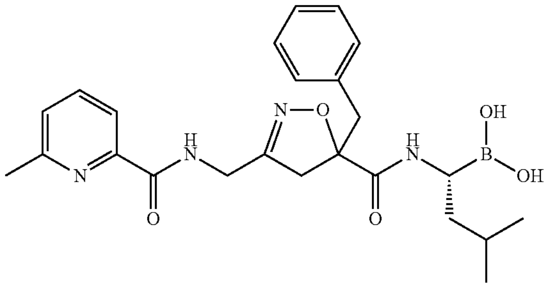 [SMILES: Cc1cccc(C(=O)NCC2=NOC(Cc3ccccc3)(C(=O)N[C@@H](CC(C)C)B(O)O)C2)n1]

The title compound (0.047 g, 60%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((6-methylpicolinamido)methyl)-4,5-dihydroisoxazol-5-carboxamide (0.1 g, 0.17 mmol) obtained in (2) above by the preparation method of Example 1-(4).

NMR: $^1$H-NMR (500 MHz, MeOD-d4); δ 7.88-7.80 (m, 2H), 7.43-7.41 (d, 1H), 7.25-7.19 (m, 5H), 4.25 (s, 2H), 3.42-3.39 (d, 1H), 3.31-3.18 (m, 3H), 2.63-2.60 (m, 1H), 2.58 (s, 3H), 1.38-1.33 (m, 1H), 1.14-0.98 (m, 2H), 0.79-0.75 (dd, 6H)

MS (m/z): 467[M+H], 449[M-OH].

Example 161: Preparation of ((1R)-1-(3-((3-aminopyrazin-2-carboxamido)methyl)-5-benzyl-4,5-dihydroisoxazol-5-carboxamido)-3-methylbutyl)boronic acid Through the processes (1), (2) and (3) below, the title compound was obtained.

(1) Preparation of methyl 3-((3-aminopyrazin-2-carboxamido)methyl)-5-benzyl-4,5-dihydroisoxazol-5-carboxylate

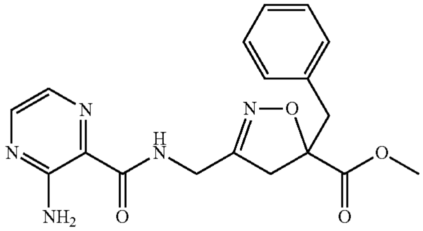 [SMILES: COC(=O)C1(Cc2ccccc2)CC(CNC(=O)c2nccnc2N)=NO1]

The title compound (0.091 g, 70%) was obtained using methyl 3-(aminomethyl)-5-benzyl-4,5-dihydroisoxazol-5-carboxylate hydrochloride (0.100 g, 0.35 mmol) obtained in Example 84-(1) and 3-amino-pyrazin-2-carboxylic acid (0.059 g, 0.42 mmol) by the preparation method of Example 84-(2).

NMR: $^1$H-NMR (500 MHz, $CDCl_3$); δ 8.15 (1H, d), 8.01 (1H, t), 7.78 (1H, d), 7.23-7.17 (5H, m), 4.16 (2H, dd), 3.75 (3H, s), 3.40 (1H, d), 3.29 (1H, d), 3.10 (1H, d), 2.99 (1H, d)

MS (m/z): 370[M+H]

(2) Preparation of 3-((3-aminopyrazin-2-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

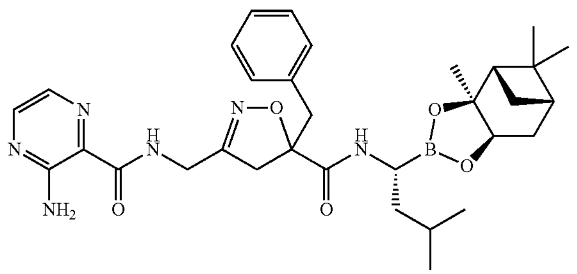 [SMILES: CC(C)C[C@H](NC(=O)C1(Cc2ccccc2)CC(CNC(=O)c2nccnc2N)=NO1)B1O[C@@H]2C[C@@H]3C[C@@H](C3(C)C)[C@]2(C)O1]

The title compound (0.131 g, 88%, 2 steps) was obtained using methyl 3-((3-aminopyrazin-2-carboxamido)methyl)-5-benzyl-4,5-dihydroisoxazol-5-carboxylate (0.091 g, 0.246 mmol) obtained in (1) above by the preparation method of Example 84-(3).

MS (m/z): 603[M+H]

(3) Preparation of ((1R)-1-(3-((3-aminopyrazin-2-carboxamido)methyl)-5-benzyl-4,5-dihydroisoxazol-5-carboxamido)-3-methylbutyl)boronic acid

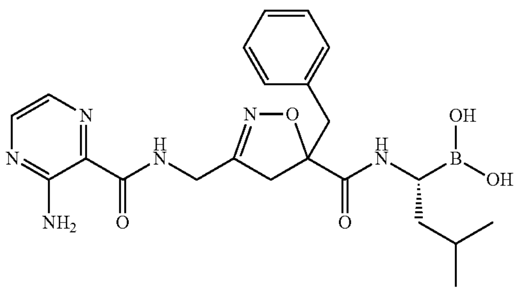 [SMILES: CC(C)C[C@H](NC(=O)C1(Cc2ccccc2)CC(CNC(=O)c2nccnc2N)=NO1)B(O)O]

The title compound (0.032 g, 31%) was obtained using 3-((3-aminopyrazin-2-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.131 g, 0.217 mmol) obtained in (2) above by the preparation method of Example 1-(4).

NMR: $^1$H-NMR (500 MHz, $CD_3OD$); δ 8.12 (1H, d), 7.81 (1H, d), 7.24-7.19 (5H, m), 4.19 (2H, s), 3.40 (1H, d), 3.29-3.22 (2H, m), 3.18 (1H, d), 2.63 (1H, t), 1.36-0.99 (3H, m), 0.78 (6H, dd)

MS (m/z): 491[M+Na], 451[M-OH]

Example 162: Preparation of ((1R)-1-(3-((isoquinolin-1-carboxamido)methyl)-5-penetyl-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-penetyl-4,5-dihydroisoxazol-5-carboxylate hydrochloride

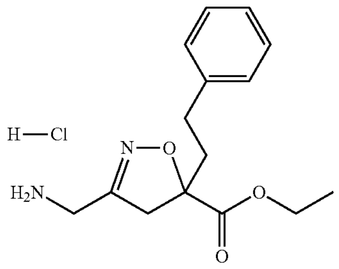 [SMILES: Cl ; CCOC(=O)C1(CCc2ccccc2)CC(CN)=NO1]

The title compound (0.22 g, 99%) was obtained using ethyl 3-(((tert-butoxycarbonyl)amino)methyl)-5-penetyl-4,5-dihydroisoxazol-5-carboxylate (0.27 g, 0.72 mmol) obtained in Preparation Example 31 by the preparation method of Example 84-(1).

MS (m/z): 277[M+H]

(2) Preparation of ethyl 3-((isoquinolin-1-carboxamido)methyl)-5-penetyl-4,5-dihydroisoxazol-5-carboxylate

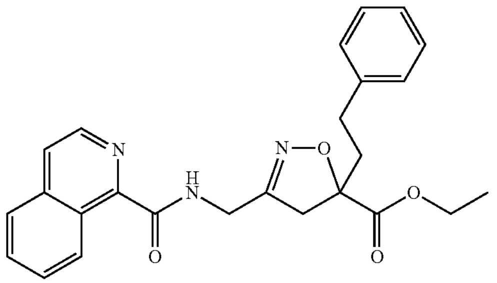 [SMILES: CCOC(=O)C1(CCc2ccccc2)CC(CNC(=O)c2nccc3ccccc23)=NO1]

The title compound (0.12 g, 70%) was obtained using ethyl 3-(aminomethyl)-5-penetyl-4,5-dihydroisoxazol-5-carboxylate hydrochloride (0.12 g, 0.38 mmol) obtained in (1) above and isoquinolin-1-carboxylic acid (0.073 g, 0.42 mmol) by the preparation method of Example 84-(2).

MS (m/z): 432[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-penetyl-4,5-dihydroisoxazol-5-carboxamide

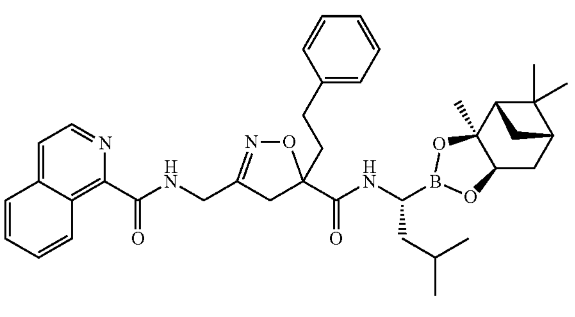 [SMILES: CC(C)C[C@H](NC(=O)C1(CCc2ccccc2)CC(CNC(=O)c2nccc3ccccc23)=NO1)B1O[C@@H]2C[C@@H]3C[C@@H](C3(C)C)[C@]2(C)O1]

The title compound (0.068 g, 39%, 2 steps) was obtained using ethyl 3-((isoquinolin-1-carboxamido)methyl)-5-penetyl-4,5-dihydroisoxazol-5-carboxylate (0.12 g, 0.27 mmol) obtained in (2) above by the preparation method of Example 84-(3).

MS (m/z): 651[M+H]

(4) Preparation of ((1R)-1-(3-((isoquinolin-1-carboxamido)methyl)-5-penetyl-4,5-dihydroisoxazol-5-carboxamido)-3-methylbutyl)boronic acid

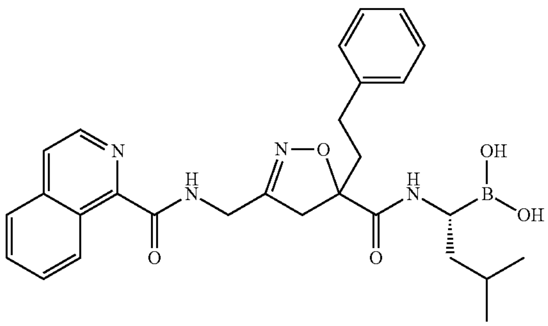 [SMILES: CC(C)C[C@H](NC(=O)C1(CCc2ccccc2)CC(CNC(=O)c2nccc3ccccc23)=NO1)B(O)O]

The title compound (0.025 g, 46%) was obtained using 3-((isoquinolin-1-carboxamido)methyl)-N—((R)-3-methyl-1-((3aS,4S,6S,7aR)-3a,5,5-trimethylhexahydro-4,6-metano-benzo[d][1,3,2]dioxaborol-2-yl)butyl)-5-penetyl-4,5-dihydroisoxazol-5-carboxamide (0.068 g, 0.11 mmol) obtained in (3) above by the preparation method of Example 1-(4).

NMR: $^1$H-NMR (400 MHz, $CDCl_3$); δ 9.54-9.50 (m, 1H), 8.69-8.58 (m, 1H), 8.46-8.41 (1H), 7.85-7.65 (m, 4H), 7.48-7.42 (m, 1H), 7.21-7.13 (m, 5H), 4.37-4.29 (m, 2H), 3.49-3.34 (m, 1H), 3.05-2.96 (m, 2H), 2.74-2.60 (m, 2H), 2.33-2.10 (m, 2H), 1.49-1.27 (m, 3H), 0.84-0.81 (m, 6H)

MS (m/z): 517[M+H], 499[M-OH]

Example 163: Preparation of ((1R)-1-(5-benzyl-3-((2-chloro-4,5-difluorobenzamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((2-chloro-4,5-difluorobenzamido)methyl)-4,5-dihydroisoxazol-5-carboxylate

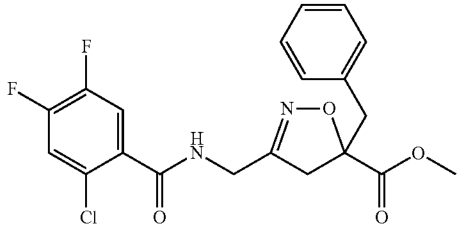 [SMILES: COC(=O)C1(Cc2ccccc2)CC(CNC(=O)c2cc(F)c(F)cc2Cl)=NO1]

The title compound (0.135 g, 76%) was obtained using methyl 3-(aminomethyl)-5-benzyl-4,5-dihydroisoxazol-5-carboxylate hydrochloride (0.12 g, 0.42 mmol) obtained in Example 84-(1) and 2-chloro-4,5-difluoro-benzoic acid (0.089 g, 0.46 mmol) by the preparation method of Example 84-(2).

MS (m/z): 423[M+H]

(2) Preparation of 5-benzyl-3-((2-chloro-4,5-difluorobenzamido)methyl)-N—((R)-3-methyl-1-((3aS,4S,6S,7aR)-3a,5,5-trimethylhexahydro-4,6-metano-benzo[d][1,3,2]dioxaborol-2-yl)butyl)-4,5-dihydroisoxazol-5-carboxamide

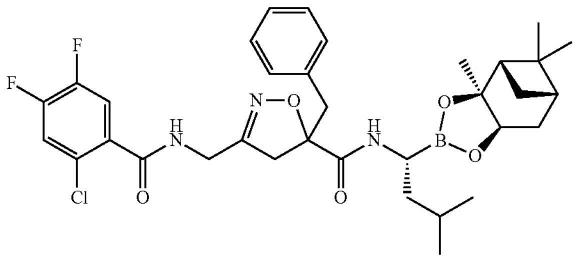 [SMILES: CC(C)C[C@H](NC(=O)C1(Cc2ccccc2)CC(CNC(=O)c2cc(F)c(F)cc2Cl)=NO1)B1O[C@@H]2C[C@@H]3C[C@@H](C3(C)C)[C@]2(C)O1]

The title compound (0.162 g, 84%, 2 steps) was obtained using methyl 5-benzyl-3-((2-chloro-4,5-difluorobenzamido)methyl)-4,5-dihydroisoxazol-5-carboxylate (0.135 g, 0.32 mmol) obtained in (1) above by the preparation method of Example 84-(3).

MS (m/z): 656[M+H]

(3) Preparation of ((1R)-1-(5-benzyl-3-((2-chloro-4,5-difluorobenzamido)methyl)-4,5-dihydroisoxazol-5-carboxamido)-3-methylbutyl)boronic acid

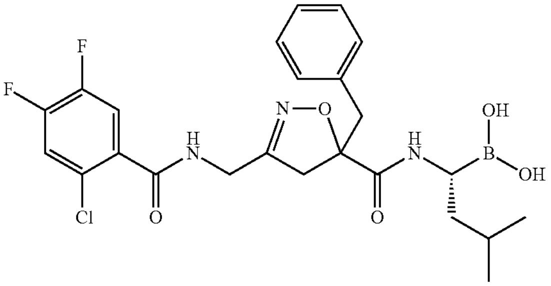 [SMILES: CC(C)C[C@H](NC(=O)C1(Cc2ccccc2)CC(CNC(=O)c2cc(F)c(F)cc2Cl)=NO1)B(O)O]

The title compound (0.046 g, 36%) was obtained using 5-benzyl-3-((2-chloro-4,5-difluorobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.162 g, 0.25 mmol) obtained in (2) above by the preparation method of Example 1-(4).

NMR: $^1$H-NMR (500 MHz, MeOD-d4); δ 7.53-7.44 (m, 2H), 7.26-7.22 (m, 5H), 4.20 (s, 2H), 3.48-3.44 (d, 1H), 3.33-3.18 (m, 3H), 2.68-2.65 (m, 1H), 1.41-1.36 (m, 1H), 1.18-1.02 (m, 2H), 0.83-0.77 (dd, 6H)

MS (m/z): 522[M+H], 504[M-OH]

Example 164: Preparation of ((1R)-1-(5-benzyl-3-((2-chloro-5-fluoronicotinamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((2-chloro-5-fluoronicotinamido)methyl)-4,5-dihydroisoxazol-5-carboxylate

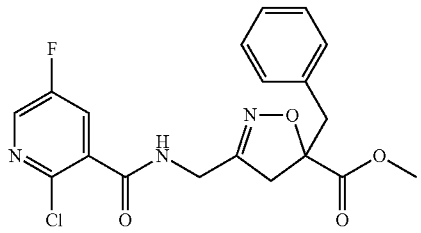 [SMILES: COC(=O)C1(Cc2ccccc2)CC(CNC(=O)c2cc(F)cnc2Cl)=NO1]

The title compound (0.12 g, 70%) was obtained using methyl 3-(aminomethyl)-5-benzyl-4,5-dihydroisoxazol-5-carboxylate hydrochloride (0.12, 0.42 mmol) obtained in Example 84-(1) and 2-chloro-5-fluoro-nicotinic acid (0.081 g, 0.46 mmol) by the preparation method of Example 84-(2).

MS (m/z): 407[M+H]

(2) Preparation of 5-benzyl-3-((2-chloro-5-fluoronicotinamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

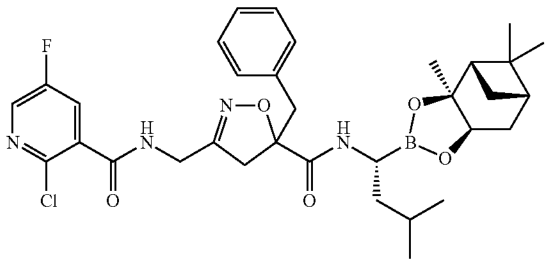 [SMILES: CC(C)C[C@H](NC(=O)C1(Cc2ccccc2)CC(CNC(=O)c2cc(F)cnc2Cl)=NO1)B1O[C@@H]2C[C@@H]3C[C@@H](C3(C)C)[C@]2(C)O1]

The title compound (0.132 g, 73%, 2 steps) was obtained using methyl 5-benzyl-3-((2-chloro-5-fluoronicotinamido)methyl)-4,5-dihydroisoxazol-5-carboxylate (0.12 g, 0.30 mmol) obtained in (1) above by the preparation method of Example 84-(3).

MS (m/z): 639[M+H]

(3) Preparation of ((1R)-1-(5-benzyl-3-((2-chloro-5-fluoronicotinamido)methyl)-4,5-dihydroisoxazol-5-carboxamido)-3-methylbutyl)boronic acid

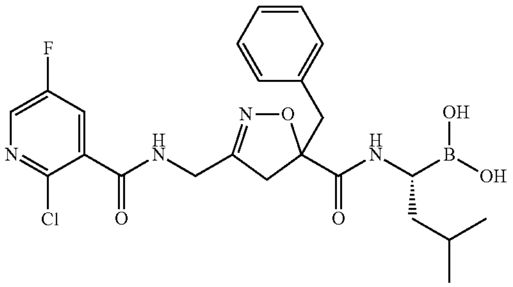 [SMILES: CC(C)C[C@H](NC(=O)C1(Cc2ccccc2)CC(CNC(=O)c2cc(F)cnc2Cl)=NO1)B(O)O]

The title compound (0.038 g, 35%) was obtained using 5-benzyl-3-((2-chloro-5-fluoronicotinamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.132 g, 0.21 mmol) obtained in (2) above by the preparation method of Example 1-(4).

NMR: $^1$H-NMR (500 MHz, MeOD-d4); δ 8.41-8.40 (d, 1H), 7.80-7.78 (m, 1H), 7.27-7.22 (m, 5H), 4.22 (s, 2H), 3.51-3.46 (d, 1H), 3.33-3.18 (m, 3H), 2.68-2.65 (m, 1H), 1.41-1.38 (m, 1H), 1.17-1.04 (m, 2H), 0.82-0.77 (dd, 6H)

MS (m/z): 505[M+H], 487[M-OH]

Example 165: Preparation of ((1R)-1-(5-benzyl-3-((cinnolin-4-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((cinnolin-4-carboxamido)methyl)-4,5-dihydroisoxazol-5-carboxylate

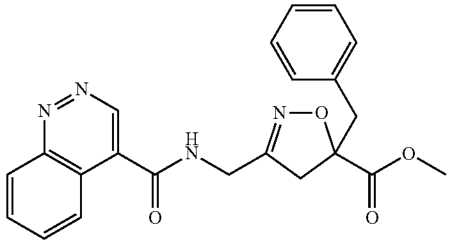 [SMILES: COC(=O)C1(Cc2ccccc2)CC(CNC(=O)c2cnnc3ccccc23)=NO1]

The title compound (0.07 g, 62%) was obtained using methyl 3-(aminomethyl)-5-benzyl-4,5-dihydroisoxazol-5-carboxylate hydrochloride (0.08 g, 0.28 mmol) obtained in Example 84-(1) and cinnolin-4-carboxylic acid (0.054 g, 0.31 mmol) by the preparation method of Example 84-(2).

MS (m/z): 405[M+H]

(2) Preparation of 5-benzyl-3-((cinnolin-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

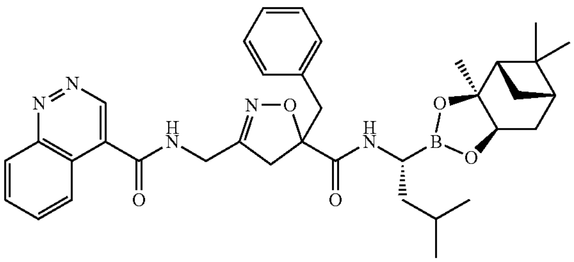 [SMILES: CC(C)C[C@H](NC(=O)C1(Cc2ccccc2)CC(CNC(=O)c2cnnc3ccccc23)=NO1)B1O[C@@H]2C[C@@H]3C[C@@H](C3(C)C)[C@]2(C)O1]

The title compound (0.06 g, 61%, 2 steps) was obtained using methyl 5-benzyl-3-((cinnolin-4-carboxamido)methyl)-4,5-dihydroisoxazol-5-carboxylate (0.07 g, 0.17 mmol) obtained in (1) above by the preparation method of Example 84-(3).

MS (m/z): 638[M+H]

(3) Preparation of ((1R)-1-(5-benzyl-3-((cinnolin-4-carboxamido)methyl)-4,5-dihydroisoxazol-5-carboxamido)-3-methylbutyl)boronic acid

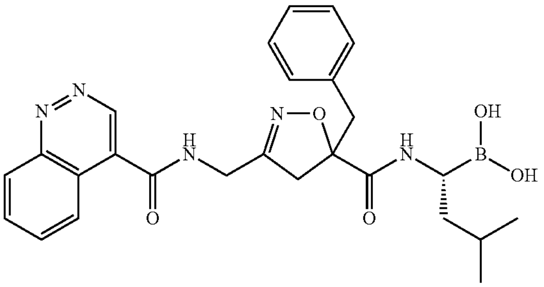 [SMILES: CC(C)C[C@H](NC(=O)C1(Cc2ccccc2)CC(CNC(=O)c2cnnc3ccccc23)=NO1)B(O)O]

The title compound (0.016 g, 34%) was obtained using 5-benzyl-3-((cinnolin-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.06 g, 0.094 mmol) obtained in (2) above by the preparation method of Example 1-(4).

NMR: $^{1}$H-NMR (500 MHz, MeOD-d4); δ 9.34 (s, 1H), 8.55-8.53 (d, 1H), 8.36-8.34 (d, 1H), 8.04-7.94 (m, 2H), 7.29-7.19 (m, 5H), 4.34 (s, 2H), 3.53-3.50 (d, 1H), 3.39-3.32 (m, 2H), 3.24-3.20 (d, 1H), 2.68-2.65 (m, 1H), 1.41-1.36 (m, 1H), 1.18-1.11 (m, 2H), 0.81-0.76 (dd, 6H)

MS (m/z): 504[M+H], 486[M-OH]

Example 166: Preparation of ((1R)-1-(5-benzyl-3-((pyridazin-4-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((pyridazin-4-carboxamido)methyl)-4,5-dihydroisoxazol-5-carboxylate

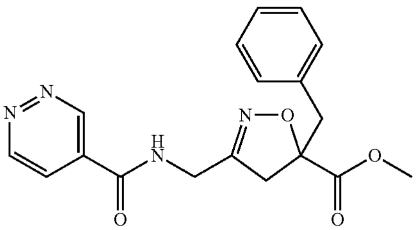 [SMILES: COC(=O)C1(Cc2ccccc2)CC(CNC(=O)c2ccnnc2)=NO1]

The title compound (0.063 g, 60%) was obtained using methyl 3-(aminomethyl)-5-benzyl-4,5-dihydroisoxazol-5-carboxylate hydrochloride (0.08 g, 0.28 mmol) obtained in Example 84-(1) and pyridazin-4-carboxylic acid (0.04 g, 0.31 mmol) by the preparation method of Example 84-(2).

MS (m/z): 355[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((pyridazin-4-carboxamido)methyl)-4,5-dihydroisoxazol-5-carboxamide

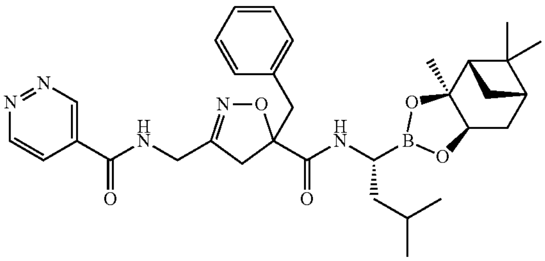 [SMILES: CC(C)C[C@H](NC(=O)C1(Cc2ccccc2)CC(CNC(=O)c2ccnnc2)=NO1)B1O[C@@H]2C[C@@H]3C[C@@H](C3(C)C)[C@]2(C)O1]

The title compound (0.035 g, 39%, 2 steps) was obtained using methyl 5-benzyl-3-((pyridazin-4-carboxamido)methyl)-4,5-dihydroisoxazol-5-carboxylate (0.063 g, 0.18 mmol) obtained in (1) above by the preparation method of Example 84-(3).

MS (m/z): 588[M+H]

(3) Preparation of ((1R)-1-(5-benzyl-3-((pyridazin-4-carboxamido)methyl)-4,5-dihydroisoxazol-5-carboxamido)-3-methylbutyl)boronic acid

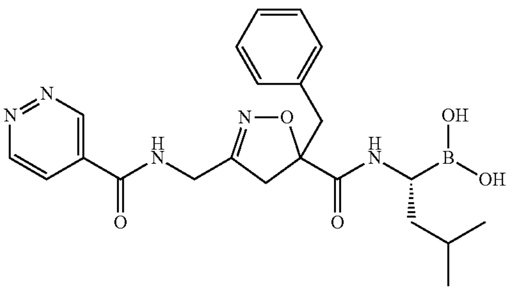 [SMILES: CC(C)C[C@H](NC(=O)C1(Cc2ccccc2)CC(CNC(=O)c2ccnnc2)=NO1)B(O)O]

The title compound (0.010 g, 37%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((pyridazin-4-carboxamido)methyl)-4,5-dihydroisoxazol-5-carboxamide (0.035 g, 0.059 mmol) obtained in (2) above by the preparation method of Example 1-(4).

NMR: $^1$H-NMR (500 MHz, MeOD-d4); δ 9.49 (m, 1H), 9.38-9.37 (m, 1H), 8.01-7.92 (m, 1H), 7.26-7.18 (m, 5H), 4.25 (s, 2H), 3.47-3.42 (d, 1H), 3.32-3.18 (m, 3H), 2.66-2.63 (m, 1H), 1.40-1.36 (m, 1H), 1.28-1.01 (m, 2H), 0.81-0.77 (dd, 6H)

MS (m/z): 454[M+H], 436[M-OH]

Example 167: Preparation of ((1R)-1-(3-((isoquinolin-1-carboxamido)methyl)-5-(2-(trifluoromethyl)benzyl)-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-(2-(trifluoromethyl)benzyl)-4,5-dihydroisoxazol-5-carboxylate hydrochloride

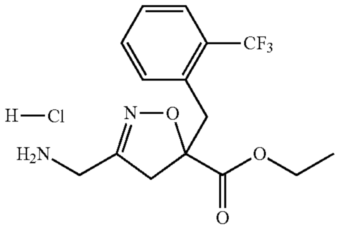

The title compound (0.12 g, quant.) was obtained using ethyl 3-(((tert-butoxycarbonyl)amino)methyl)-5-(2-(trifluoromethyl)benzyl)-4,5-dihydroisoxazol-5-carboxylate (0.142 g, 0.33 mmol) obtained in Preparation Example 32 by the preparation method of Example 84-(1).

MS (m/z): 331[M+H]

(2) Preparation of ethyl 3-((isoquinolin-1-carboxamido)methyl)-5-(2-(trifluoromethyl)benzyl)-4,5-dihydroisoxazol-5-carboxylate

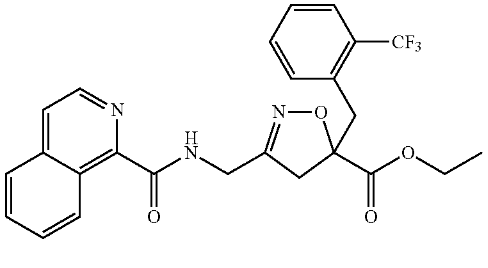

The title compound (0.089 g, 55%) was obtained using ethyl 3-(aminomethyl)-5-(2-(trifluoromethyl)benzyl)-4,5-dihydroisoxazol-5-carboxylate hydrochloride (0.12 g, 0.33 mmol) obtained in (1) above and isoquinolin-1-carboxylic acid (0.057 g, 0.33 mmol) by the preparation method of Example 84-(2).

MS (m/z): 486[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(2-(trifluoromethyl)benzyl)-4,5-dihydroisoxazol-5-carboxamide

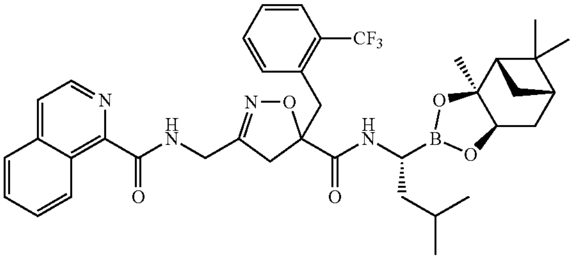 [SMILES: CC(C)C[C@H](NC(=O)C1(Cc2ccccc2C(F)(F)F)CC(CNC(=O)c2nccc3ccccc23)=NO1)B1O[C@@H]2C[C@@H]3C[C@@H](C3(C)C)[C@]2(C)O1]

The title compound (0.070 g, 54%, 2 steps) was obtained using ethyl 3-((isoquinolin-1-carboxamido)methyl)-5-(2-(trifluoromethyl)benzyl)-4,5-dihydroisoxazol-5-carboxylate (0.089 g, 0.18 mmol) obtained in (2) above by the preparation method of Example 84-(3).

MS (m/z): 705[M+H]

(4) Preparation of ((1R)-1-(3-((isoquinolin-1-carboxamido)methyl)-5-(2-(trifluoromethyl)benzyl)-4,5-dihydroisoxazol-5-carboxamido)-3-methylbutyl)boronic acid

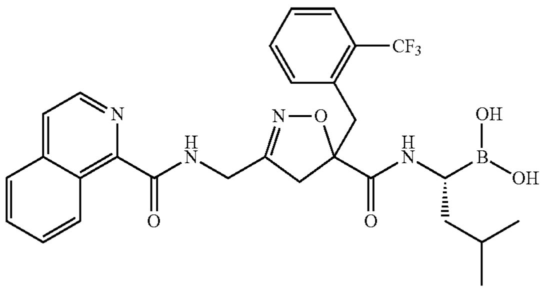 [SMILES: CC(C)C[C@H](NC(=O)C1(Cc2ccccc2C(F)(F)F)CC(CNC(=O)c2nccc3ccccc23)=NO1)B(O)O]

The title compound (0.011 g, 19%) was obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(2-(trifluoromethyl)benzyl)-4,5-dihydroisoxazol-5-carboxamide (0.070 g, 0.10 mmol) obtained in (3) above by the preparation method of Example 1-(4).

MS (m/z): 571[M+H], 553[M-OH]

Example 168: Preparation of ((1R)-1-(5-benzyl-3-((oxazol-4-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((oxazol-4-carboxamido)methyl)-4,5-dihydroisoxazol-5-carboxylate

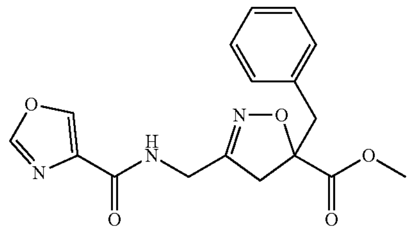 [SMILES: COC(=O)C1(Cc2ccccc2)CC(CNC(=O)c2cocn2)=NO1]

The title compound (0.09 g, 62%) was obtained using methyl 3-(aminomethyl)-5-benzyl-4,5-dihydroisoxazol-5-carboxylate hydrochloride (0.12 g, 0.42 mmol) obtained in Example 84-(1) and isoxazol-4-carboxylic acid (0.052 g, 0.46 mmol) by the preparation method of Example 84-(2).

MS (m/z): 344[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((oxazol-4-carboxamido)methyl)-4,5-dihydroisoxazol-5-carboxamide

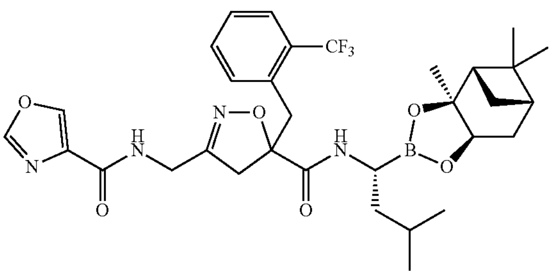 [SMILES: CC(C)C[C@H](NC(=O)C1(Cc2ccccc2C(F)(F)F)CC(CNC(=O)c2cocn2)=NO1)B1O[C@@H]2C[C@@H]3C[C@@H](C3(C)C)[C@]2(C)O1]

The title compound (0.105 g, 67%, 2 steps) was obtained using methyl 5-benzyl-3-((oxazol-4-carboxamido)methyl)-4,5-dihydroisoxazol-5-carboxylate (0.09 g, 0.26 mmol) obtained in (1) above by the preparation method of Example 84-(3).

MS (m/z): 577[M+H]

(3) Preparation of ((1R)-1-(5-benzyl-3-((oxazol-4-carboxamido)methyl)-4,5-dihydroisoxazol-5-carboxamido)-3-methylbutyl)boronic acid

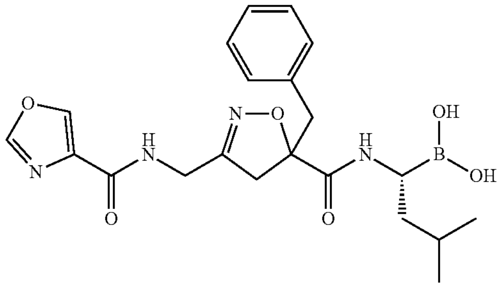 [SMILES: CC(C)C[C@H](NC(=O)C1(Cc2ccccc2)CC(CNC(=O)c2cocn2)=NO1)B(O)O]

The title compound (0.02 g, 25%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((oxazol-4-carboxamido)methyl)-4,5-dihydroisoxazol-5-carboxamide (0.105 g, 0.18 mmol) obtained in (2) above by the preparation method of Example 1-(4).

NMR: $^1$H-NMR (400 MHz, $CDCl_3$); δ 8.23-8.22 (d, 1H), 7.84 (d, 1H), 7.29-7.27 (m, 5H), 4.26-4.13 (m, 2H), 3.46-3.02 (m, 4H), 2.81 (m, 1H), 1.27-1.19 (m, 3H), 0.82-0.79 (m, 6H)

MS (m/z): 443[M+H], 425[M-OH]

Example 169: Preparation of ((1R)-1-(3-((1H-pyrazol-5-carboxamido)methyl)-5-benzyl-4,5-dihydroisoxazol-5-carboxamido)-3-methylbutyl)boronic acid Through the processes (1), (2) and (3) below, the title compound was obtained.

(1) Preparation of methyl 3-((1H-pyrazol-5-carboxamido)methyl)-5-benzyl-4,5-dihydroisoxazol-5-carboxylate

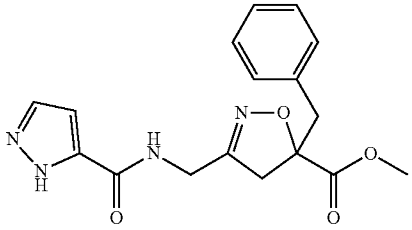 [SMILES: COC(=O)C1(Cc2ccccc2)CC(CNC(=O)c2ccn[nH]2)=NO1]

The title compound (0.086 g, 77%) was obtained using methyl 3-(aminomethyl)-5-benzyl-4,5-dihydroisoxazol-5-carboxylate hydrochloride (0.093 g, 0.327 mmol) obtained in Example 84-(1) and 2H-pyrazol-3-carboxylic acid (0.040 g, 0.357 mmol) by the preparation method of Example 84-(2).

NMR: $^1$H-NMR (500 MHz, $CDCl_3$); δ 8.00 (1H, s), 7.57 (1H, d), 7.18-7.13 (5H, m), 6.81 (1H, d), 4.22-4.15 (2H, m), 3.70 (3H, s), 3.43 (1H, d), 3.25 (1H, d), 3.09 (2H, d)

MS (m/z): 343[M+H]

(2) Preparation of 3-((1H-pyrazol-5-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

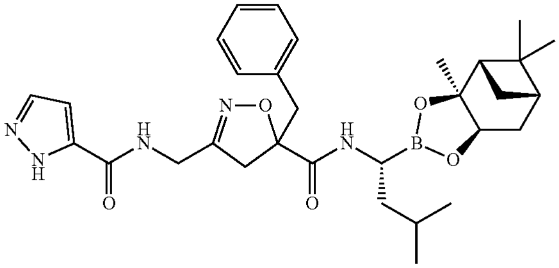 [SMILES: CC(C)C[C@H](NC(=O)C1(Cc2ccccc2)CC(CNC(=O)c2ccn[nH]2)=NO1)B1O[C@@H]2C[C@@H]3C[C@@H](C3(C)C)[C@]2(C)O1]

The title compound (0.110 g, 75%, 2 steps) was obtained using methyl 3-((1H-pyrazol-5-carboxamido)methyl)-5-benzyl-4,5-dihydroisoxazol-5-carboxylate (0.086 g, 0.251 mmol) obtained in (1) above by the preparation method of Example 84-(3).

MS (m/z): 576[M+H]

(3) Preparation of ((1R)-1-(3-((1H-pyrazol-5-carboxamido)methyl)-5-benzyl-4,5-dihydroisoxazol-5-carboxamido)-3-methylbutyl)boronic acid

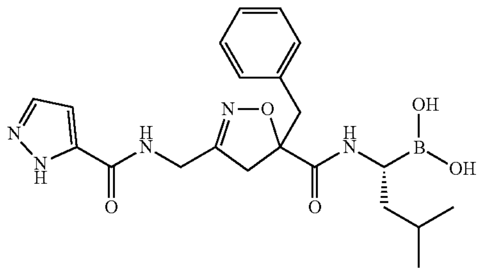 [SMILES: CC(C)C[C@H](NC(=O)C1(Cc2ccccc2)CC(CNC(=O)c2ccn[nH]2)=NO1)B(O)O]

The title compound (0.012 g, 14%) was obtained using 3-((1H-pyrazol-5-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.110 g, 0.191 mmol) obtained in (2) above by the preparation method of Example 1-(4).

NMR: $^1$H-NMR (500 MHz, $CD_3OD$); δ 7.70 (1H, s), 7.25-7.20 (5H, m), 6.75 (1H, d), 4.21 (2H, s), 3.41 (1H, d), 3.33-3.23 (2H, m), 3.19 (1H, d), 2.60 (1H, t), 1.38-0.99 (3H, m), 0.77 (6H, dd)

MS (m/z): 464[M+Na], 424[M-OH]

Example 170: Preparation of ((1R)-1-(5-(2-fluorobenzyl)-3-((isoquinolin-1-carboxamido)methyl)-4,5-dihydroisoxazol-5-carboxamido)-3-methylbutyl) boronic acid Through the processes (1), (2) and (3) below, the title compound was obtained.

(1) Preparation of ethyl 3-(aminomethyl)-5-(2-fluorobenzyl)-4,5-dihydroisoxazol-5-carboxylate hydrochloride

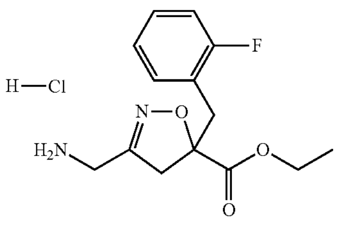 [SMILES: Cl ; CCOC(=O)C1(Cc2ccccc2F)CC(CN)=NO1]

The title compound (0.093 g, quant.) was obtained using ethyl 3-(((tert-butoxycarbonyl)amino)methyl)-5-(2-fluorobenzyl)-4,5-dihydroisoxazol-5-carboxylate (0.11 g, 0.294 mmol) obtained in Preparation Example 33 by the preparation method of Example 84-(1).

MS (m/z): 281[M+H]

(2) Preparation of ethyl 5-(2-fluorobenzyl)-3-((isoquinolin-1-carboxamido)methyl)-4,5-dihydroisoxazol-5-carboxylate

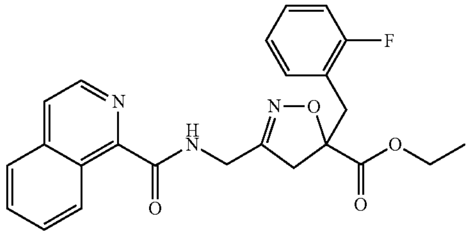 [SMILES: CCOC(=O)C1(Cc2ccccc2F)CC(CNC(=O)c2nccc3ccccc23)=NO1]

The title compound (0.073 g, 59%) was obtained using ethyl 3-(aminomethyl)-5-(2-fluorobenzyl)-4,5-dihydroisoxazol-5-carboxylate hydrochloride (0.093 g, 0.294 mmol) obtained in (1) above and isoquinolin-1-carboxylic acid (0.056 g, 0.326 mmol) by the preparation method of Example 84-(2).

NMR: $^1$H-NMR (500 MHz, $CDCl_3$); δ 9.53 (1H, d), 8.45 (1H, d), 8.42 (1H, t), 7.86-7.81 (2H, m), 7.74-7.69 (2H, m), 7.32 (1H, dd), 7.13 (1H, dd), 7.02 (1H, t), 6.85 (1H, t), 4.32-4.28 (2H, m), 4.25-4.19 (2H, m), 3.52 (1H, d), 3.28 (2H, d), 3.07 (1H, d), 1.26 (3H, t)

MS (m/z): 436[M+H]

(3) Preparation of 5-(2-fluorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

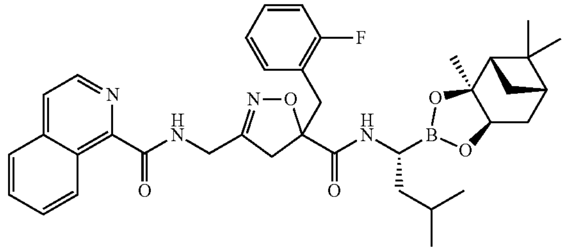 [SMILES: CC(C)C[C@H](NC(=O)C1(Cc2ccccc2F)CC(CNC(=O)c2nccc3ccccc23)=NO1)B1O[C@@H]2C[C@@H]3C[C@@H](C3(C)C)[C@]2(C)O1]

The title compound (0.083 g, 73%, 2 steps) was obtained using ethyl 5-(2-fluorobenzyl)-3-((isoquinolin-1-carboxamido)methyl)-4,5-dihydroisoxazol-5-carboxylate (0.073 g, 0.173 mmol) obtained in (2) above by the preparation method of Example 84-(3).

MS (m/z): 655[M+H]

(4) Preparation of ((1R)-1-(5-(2-fluorobenzyl)-3-((isoquinolin-1-carboxamido)methyl)-4,5-dihydroisoxazol-5-carboxamido)-3-methylbutyl)boronic acid

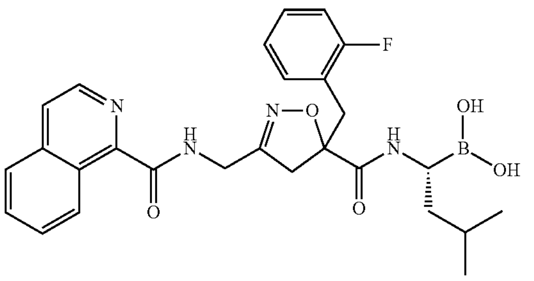 [SMILES: CC(C)C[C@H](NC(=O)C1(Cc2ccccc2F)CC(CNC(=O)c2nccc3ccccc23)=NO1)B(O)O]

The title compound (0.024 g, 36%) was obtained using 5-(2-fluorobenzyl)-3-((isoquinolin-1-carboxamido)methyl)-N—((R)-3-methyl-1-((3aS,4S,6S,7aR)-3a,5,5-trimethyl-hexahydro-4,6-metanobenzo[d][1,3,2]dioxaborol-2-yl)butyl)-4,5-dihydroisoxazol-5-carboxamide (0.083 g, 0.127 mmol) obtained in (3) above by the preparation method of Example 1-(4).

NMR: $^1$H-NMR (500 MHz, $CD_3OD$); δ 9.06 (1H, d), 8.49 (1H, d), 7.97-7.93 (2H, m), 7.78 (1H, t), 7.70 (1H, t), 7.35 (1H, t), 7.20 (1H, dd), 7.06 (1H, d), 6.97 (1H, d), 4.31 (2H, s), 3.51 (1H, d), 3.30 (1H, d), 3.29 (2H, s), 2.70 (1H, t), 1.47-1.10 (3H, m), 0.80 (6H, dd)

MS (m/z): 503[M-OH]

Example 171: Preparation of ((1R)-1-(5-benzyl-3-((1-isopropyl-1H-pyrazol-5-carboxamido)methyl)-4,5-dihydroisoxazol-5-carboxamido)-3-methylbutyl) boronic acid Through the processes (1), (2), (3), (4) and (5) below, the title compound was obtained.

(1) Preparation of 2-isopropyl-2H-pyrazol-3-carboxylic acid ethyl ester

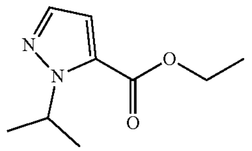

The title compound was obtained by the method described in WO2009147188A1.

(2) Preparation of 2-isopropyl-2H-pyrazol-3-carboxylic acid

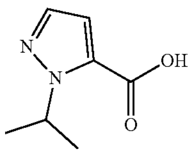

The title compound (0.17 g, 94%) was obtained using 2-isopropyl-2H-pyrazol-3-carboxylic acid ethyl ester (0.19 g, 1.18 mmol) obtained in (1) above by the preparation method of Example 119-(2).

(3) Preparation of methyl 5-benzyl-3-((1-isopropyl-1H-pyrazol-5-carboxamido)methyl)-4,5-dihydroisoxazol-5-carboxylate

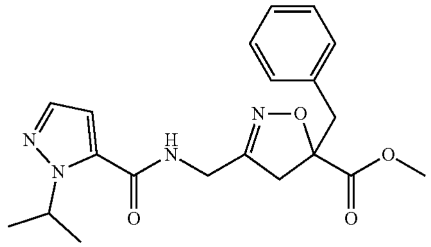 [SMILES: COC(=O)C1(Cc2ccccc2)CC(CNC(=O)c2ccnn2C(C)C)=NO1]

The title compound (0.113 g, 84%) was obtained using methyl 3-(aminomethyl)-5-benzyl-4,5-dihydroisoxazol-5-carboxylate hydrochloride (0.100 g, 0.35 mmol) obtained in Example 84-(1) and 2-isopropyl-2H-pyrazol-3-carboxylic acid (0.060 g, 0.39 mmol) obtained in (2) above by the preparation method of Example 84-(2).

NMR: $^1$H-NMR (500 MHz, $CDCl_3$); δ 7.46 (1H, d), 7.26-7.20 (5H, m), 6.45-6.44 (2H, m), 5.43 (1H, dt), 4.12 (2H, d), 3.75 (3H, s), 3.40 (1H, d), 3.30 (1H, d), 3.10 (1H, d), 2.99 (1H, d), 2.89 (1H, d), 1.47 (6H, dd)

MS (m/z): 385[M+H]

(4) Preparation of 5-benzyl-3-((1-isopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

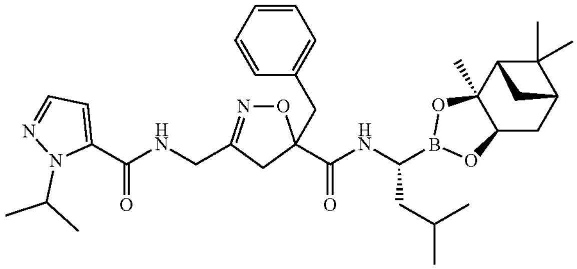 [SMILES: CC(C)C[C@H](NC(=O)C1(Cc2ccccc2)CC(CNC(=O)c2ccnn2C(C)C)=NO1)B1O[C@@H]2C[C@@H]3C[C@@H](C3(C)C)[C@]2(C)O1]

The title compound (0.123 g, 68%, 2 steps) was obtained using methyl 5-benzyl-3-((1-isopropyl-1H-pyrazol-5-carboxamido)methyl)-4,5-dihydroisoxazol-5-carboxylate (0.113 g, 0.293 mmol) obtained in (3) above by the preparation method of Example 84-(3).

MS (m/z): 618[M+H]

(5) Preparation of ((1R)-1-(5-benzyl-3-((1-isopropyl-1H-pyrazol-5-carboxamido)methyl)-4,5-dihydroisoxazol-5-carboxamido)-3-methylbutyl)boronic acid

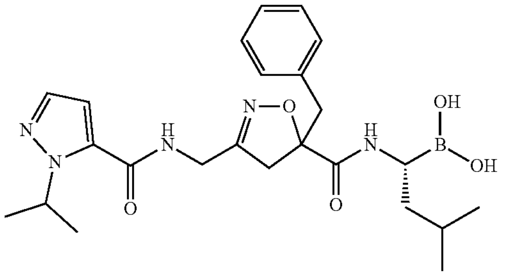 [SMILES: CC(C)C[C@H](NC(=O)C1(Cc2ccccc2)CC(CNC(=O)c2ccnn2C(C)C)=NO1)B(O)O]

The title compound (0.037 g, 38%) was obtained using 5-benzyl-3-((1-isopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.123 g, 0.199 mmol) obtained in (4) above by the preparation method of Example 1-(4).

NMR: $^{1}$H-NMR (500 MHz, $CD_3OD$); δ 7.48 (1H, s), 7.25-7.20 (5H, m), 6.67 (1H, s), 5.47 (1H, dt), 4.19-4.12 (2H, m), 3.42 (1H, d), 3.33-3.18 (3H, m), 2.64 (1H, t), 1.43 (6H, d), 1.39-1.03 (3H, m), 0.78 (6H, dd)

MS (ES+): 484[M+H], 466[M-OH]

Example 172: Preparation of ((1R)-1-(5-benzyl-3-((1-isopropyl-1H-pyrazol-3-carboxamido)methyl)-4,5-dihydroisoxazol-5-carboxamido)-3-methylbutyl) boronic acid Through the processes (1), (2), (3), (4) and (5) below, the title compound was obtained.

(1) Preparation of 1-isopropyl-1H-pyrazol-3-carboxylic acid ethyl ester

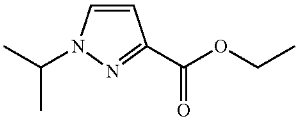

The title compound was obtained by the method described in WO2009147188A1.

(2) Preparation of 1-isopropyl-1H-pyrazol-3-carboxylic acid

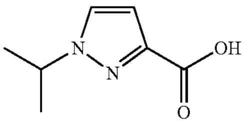

The title compound (0.22 g, 99%) was obtained using 2-isopropyl-2H-pyrazol-3-carboxylic acid ethyl ester (0.24 g, 1.41 mmol) obtained in (1) above by the preparation method of Example 119-(2).

(3) Preparation of methyl 5-benzyl-3-((1-isopropyl-1H-pyrazol-3-carboxamido)methyl)-4,5-dihydroisoxazol-5-carboxylate

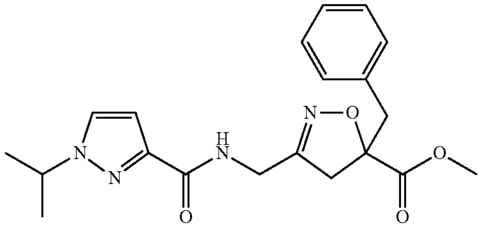 [SMILES: COC(=O)C1(Cc2ccccc2)CC(CNC(=O)c2ccn(C(C)C)n2)=NO1]

The title compound (0.102 g, 76%) was obtained using methyl 3-(aminomethyl)-5-benzyl-4,5-dihydroisoxazol-5-carboxylate hydrochloride (0.100 g, 0.35 mmol) obtained in Example 84-(1) and 1-isopropyl-1H-pyrazol-3-carboxylic acid (0.060 g, 0.39 mmol) obtained in (2) above by the preparation method of Example 84-(2).

NMR: $^{1}$H-NMR (500 MHz, $CDCl_3$); δ 7.40 (1H, d), 7.22-7.17 (5H, m), 7.03 (1H, t), 6.73 (1H, d), 4.46 (1H, dt), 4.18-4.13 (2H, m), 3.72 (3H, s), 3.41 (1H, d), 3.26 (1H, d), 3.10 (1H, d), 3.03 (1H, d), 1.48 (6H, d)

MS (m/z): 385[M+H]

(4) Preparation of 5-benzyl-3-((1-isopropyl-1H-pyrazol-3-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

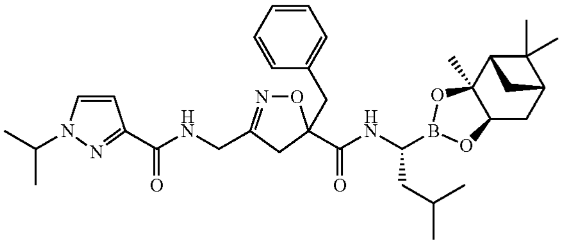 [SMILES: CC(C)C[C@H](NC(=O)C1(Cc2ccccc2)CC(CNC(=O)c2ccn(C(C)C)n2)=NO1)B1O[C@@H]2C[C@@H]3C[C@@H](C3(C)C)[C@]2(C)O1]

The title compound (0.093 g, 57%, 2 steps) was obtained using methyl 5-benzyl-3-((1-isopropyl-1H-pyrazol-3-carboxamido)methyl)-4,5-dihydroisoxazol-5-carboxylate (0.102 g, 0.26 mmol) obtained in (3) above by the preparation method of Example 84-(3).

MS (m/z): 618[M+H]

(5) Preparation of ((1R)-1-(5-benzyl-3-((1-isopropyl-1H-pyrazol-3-carboxamido)methyl)-4,5-dihydroisoxazol-5-carboxamido)-3-methylbutyl)boronic acid

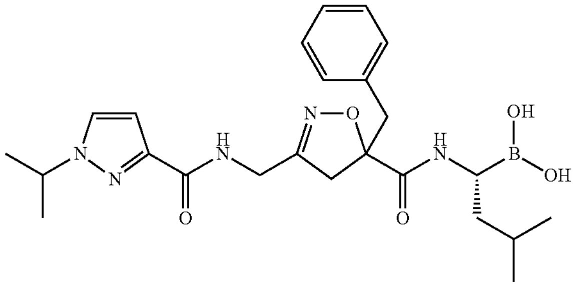

The title compound (0.032 g, 44%) was obtained using 5-benzyl-3-((1-isopropyl-1H-pyrazol-3-carboxamido) methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.093 g, 0.151 mmol) obtained in (4) above by the preparation method of Example 1-(4).

NMR: $^1$H-NMR (500 MHz, $CD_3OD$); δ 7.69 (1H, s), 7.24-7.20 (5H, m), 6.69 (1H, d), 4.56 (1H, dt), 4.20 (2H, s), 3.41 (1H, d), 3.33-3.24 (2H, m), 3.20 (1H, d), 2.62 (1H, dd), 1.51 (6H, d), 1.37-0.98 (3H, m), 0.77 (6H, dd)

MS (ES+): 484[M+H], 466[M-OH]

Example 173: Preparation of ((1R)-1-(5-benzyl-3-((2-methyloxazol-4-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((2-methyloxazol-4-carboxamido)methyl)-4,5-dihydroisoxazol-5-carboxylate

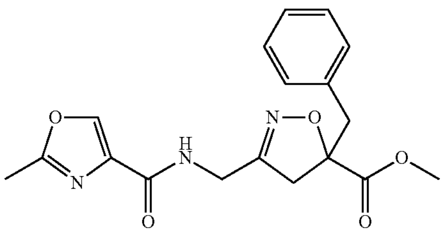

The title compound (0.1 g, 67%) was obtained using methyl 3-(aminomethyl)-5-benzyl-4,5-dihydroisoxazol-5-carboxylate hydrochloride (0.12 g, 0.42 mmol) obtained in Example 84-(1) and 2-methyl-oxazol-4-carboxylic acid (0.059 g, 0.46 mmol) by the preparation method of Example 84-(2).

MS (m/z): 358[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-methyloxazol-4-carboxamido)methyl)-4,5-dihydroisoxazol-5-carboxamide

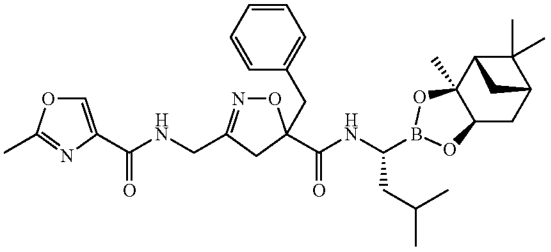

The title compound (0.013 g, 76%, 2 steps) was obtained using methyl 5-benzyl-3-((2-methyloxazol-4-carboxamido) methyl)-4,5-dihydroisoxazol-5-carboxylate (0.1 g, 0.29 mmol) obtained in (1) above by the preparation method of Example 84-(3).

MS (m/z): 591[M+H]

(3) Preparation of ((1R)-1-(5-benzyl-3-((2-methyloxazol-4-carboxamido)methyl)-4,5-dihydroisoxazol-5-carboxamido)-3-methylbutyl)boronic acid

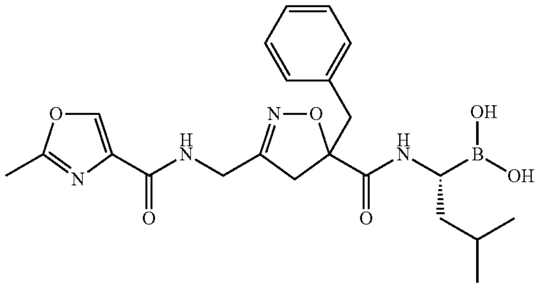 [SMILES: Cc1nc(C(=O)NCC2=NOC(Cc3ccccc3)(C(=O)N[C@@H](CC(C)C)B(O)O)C2)co1]

The title compound (0.026 g, 26%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-methyloxazol-4-carboxamido)methyl)-4,5-dihydroisoxazol-5-carboxamide (0.13 g, 0.22 mmol) obtained in (2) above by the preparation method of Example 1-(4).

NMR: $^1$H-NMR (400 MHz, MeOD-d4); δ 8.27 (s, 1H), 7.28-7.25 (m, 5H), 4.61 (s, 2H), 3.45-3.34 (m, 2H), 3.27-3.19 (m, 2H), 2.69-2.65 (m, 1H), 2.49 (s, 3H), 1.42-1.39 (m, 1H), 1.19-1.05 (m, 2H), 0.82-0.79 (dd, 6H)

MS (m/z): 457[M+H], 439[M-OH]

Example 174: Preparation of ((1R)-1-(5-(2,6-difluorobenzyl)-3-((isoquinolin-1-carboxamido)methyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(2,6-difluorobenzyl)-4,5-dihydroisoxazol-5-carboxylate hydrochloride

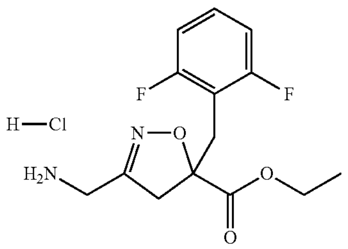

The title compound (0.37 g, 94%) was obtained using ethyl 3-(((tert-butoxycarbonyl)amino)methyl)-5-(2,6-difluorobenzyl)-4,5-dihydroisoxazol-5-carboxylate (0.48 g, 1.2 mmol) obtained in Preparation Example 34 by the preparation method of Example 84-(1).

MS (m/z): 299[M+H]

(2) Preparation of ethyl 5-(2,6-difluorobenzyl)-3-((isoquinolin-1-carboxamido)methyl)-4,5-dihydroisoxazol-5-carboxylate

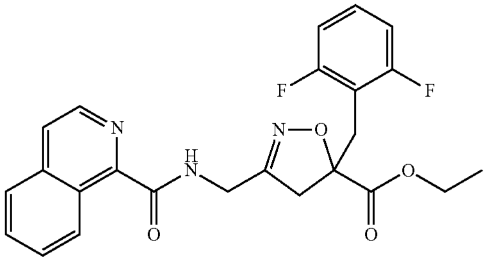 [SMILES: CCOC(=O)C1(Cc2c(F)cccc2F)CC(CNC(=O)c2nccc3ccccc23)=NO1]

The title compound (0.27 g, 54%) was obtained using ethyl 3-(aminomethyl)-5-(2,6-difluorobenzyl)-4,5-dihydroisoxazol-5-carboxylate hydrochloride (0.37 g, 1.1 mmol) obtained in (1) above and isoquinolin-1-carboxylic acid (0.19 g, 1.1 mmol) by the preparation method of Example 84-(2).

MS (m/z): 454[M+H]

(3) Preparation of 5-(2,6-difluorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

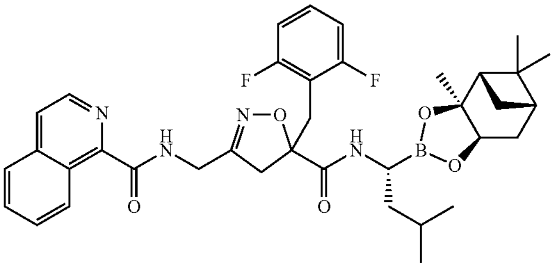 [SMILES: CC(C)C[C@H](NC(=O)C1(Cc2c(F)cccc2F)CC(CNC(=O)c2nccc3ccccc23)=NO1)B1O[C@@H]2C[C@@H]3C[C@@H](C3(C)C)[C@]2(C)O1]

The title compound (0.23 g, 56%, 2 steps) was obtained using ethyl 5-(2,6-difluorobenzyl)-3-((isoquinolin-1-carboxamido)methyl)-4,5-dihydroisoxazol-5-carboxylate (0.27 g, 0.6 mmol) obtained in (2) above by the preparation method of Example 84-(3).

MS (m/z): 673[M+H]

(4) Preparation of ((1R)-1-(5-(2,6-difluorobenzyl)-3-((isoquinolin-1-carboxamido)methyl)-4,5-dihydroisoxazol-5-carboxamido)-3-methylbutyl)boronic acid

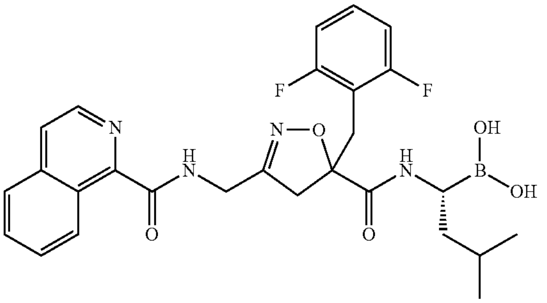 [SMILES: CC(C)C[C@H](NC(=O)C1(Cc2c(F)cccc2F)CC(CNC(=O)c2nccc3ccccc23)=NO1)B(O)O]

The title compound (0.063 g, 35%) was obtained using 5-(2,6-difluorobenzyl)-3-((isoquinolin-1-carboxamido) methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.23 g, 0.34 mmol) obtained in (3) above by the preparation method of Example 1-(4).

MS (m/z): 539[M+H], 521[M-OH]

Example 175: Preparation of ((1R)-1-(5-(3-chlorobenzyl)-3-((isoquinolin-1-carboxamido)methyl)-4,5-dihydroisoxazol-5-carboxamido)-3-methylbutyl) boronic acid Through the processes (1), (2) and (3) below, the title compound was obtained.

(1) Preparation of ethyl 3-(aminomethyl)-5-(3-chlorobenzyl)-4,5-dihydroisoxazol-5-carboxylate hydrochloride

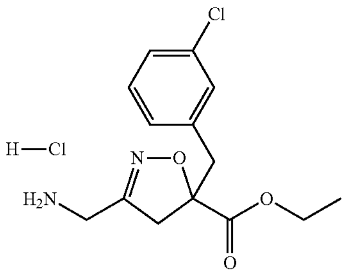

The title compound (0.34 g, 99%) was obtained using ethyl 3-(((tert-butoxycarbonyl)amino)methyl)-5-(3-chlorobenzyl)-4,5-dihydroisoxazol-5-carboxylate (0.4 g, 1.02 mmol) obtained in Preparation Example 16 by the preparation method of Example 84-(1).

MS (m/z): 297[M+H]

(2) Preparation of ethyl 5-(3-chlorobenzyl)-3-((isoquinolin-1-carboxamido)methyl)-4,5-dihydroisoxazol-5-carboxylate

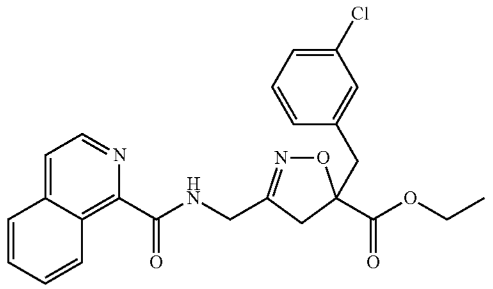

The title compound (0.12 g, 66%) was obtained using ethyl 3-(aminomethyl)-5-(3-chlorobenzyl)-4,5-dihydroisoxazol-5-carboxylate hydrochloride (0.13 g, 0.39 mmol) obtained in (1) above and isoquinolin-1-carboxylic acid (0.075 g, 0.43 mmol) by the preparation method of Example 84-(2).

MS (m/z): 452[M+H]

(3) Preparation of 5-(3-chlorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

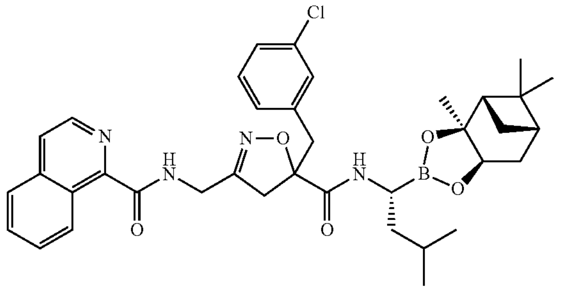

The title compound (0.12 g, 69%, 2 steps) was obtained using ethyl 5-(3-chlorobenzyl)-3-((isoquinolin-1-carboxamido)methyl)-4,5-dihydroisoxazol-5-carboxylate (0.12 g, 0.26 mmol) obtained in (2) above by the preparation method of Example 84-(3).

MS (m/z): 671[M+H]

(4) Preparation of ((1R)-1-(5-(3-chlorobenzyl)-3-((isoquinolin-1-carboxamido)methyl)-4,5-dihydroisoxazol-5-carboxamido)-3-methylbutyl)boronic acid

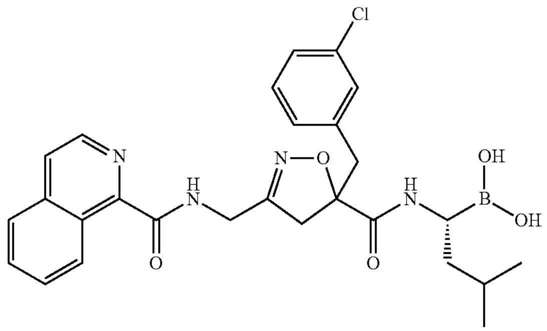

The title compound (0.033 g, 34%) was obtained using 5-(3-chlorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.12 g, 0.18 mmol) obtained in (3) above by the preparation method of Example 1-(4).

NMR: $^1$H-NMR (400 MHz, MeOD-d4); δ 9.12-9.01 (d, 1H), 8.55-8.54 (d, 1H), 8.03-7.98 (m, 2H), 7.84-7.73 (m, 2H), 7.33 (s, 1H), 7.25 (m, 3H), 4.38 (s, 2H), 3.57-3.38 (m, 2H), 3.35-3.23 (m, 2H), 2.70-2.67 (m, 1H), 1.43-1.40 (m, 1H), 1.19-1.03 (m, 2H), 0.84-0.79 (dd, 6H)

MS (m/z): 537[M+H], 519[M-OH]

Example 176: Preparation of ((1R)-1-(5-benzyl-3-((1-methyl-1H-pyrazol-5-carboxamido)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-((1-methyl-1H-pyrazol-5-carboxamido)methyl)-4,5-dihydroisoxazol-5-carboxylate

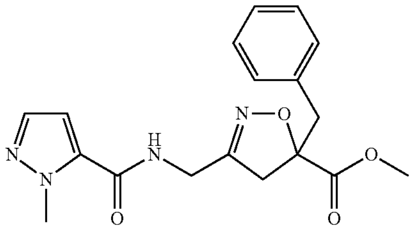 [SMILES: COC(=O)C1(Cc2ccccc2)CC(CNC(=O)c2ccnn2C)=NO1]

The title compound (0.039 g, 57%) was obtained using methyl 3-(aminomethyl)-5-benzyl-4,5-dihydroisoxazol-5-carboxylate hydrochloride (0.055 g, 0.193 mmol) obtained in Example 84-(1) and 2-methyl-2H-pyrazol-3-carboxylic acid (0.027 g, 0.214 mmol) by the preparation method of Example 84-(2).

NMR: $^1$H-NMR (400 MHz, $CDCl_3$); δ 7.43 (1H, d), 7.28-7.20 (5H, m), 6.53 (1H, t), 6.50 (1H, d), 4.15 (3H, s), 4.13 (2H, s), 3.76 (3H, s), 3.42 (1H, d), 3.33 (1H, d), 3.12 (1H, d), 3.02 (1H, d)

MS (m/z): 357[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-pyrazol-5-carboxamido)methyl)-4,5-dihydroisoxazol-5-carboxamide

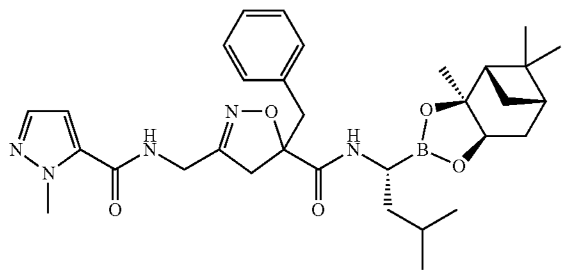 [SMILES: CC(C)C[C@H](NC(=O)C1(Cc2ccccc2)CC(CNC(=O)c2ccnn2C)=NO1)B1O[C@@H]2C[C@@H]3C[C@@H](C3(C)C)[C@]2(C)O1]

The title compound (0.052 g, 81%, 2 steps) was obtained using methyl 5-benzyl-3-((1-methyl-1H-pyrazol-5-carboxamido)methyl)-4,5-dihydroisoxazol-5-carboxylate (0.039 g, 0.109 mmol) obtained in (1) above by the preparation method of Example 84-(3).

MS (m/z): 590[M+H]

(3) Preparation of ((1R)-1-(5-benzyl-3-((1-methyl-1H-pyrazol-5-carboxamido)methyl)-4,5-dihydroisoxazol-5-carboxamido)-3-methylbutyl)boronic acid

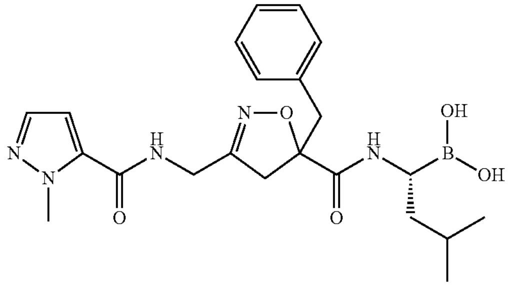 [SMILES: CC(C)C[C@H](NC(=O)C1(Cc2ccccc2)CC(CNC(=O)c2ccnn2C)=NO1)B(O)O]

The title compound (0.025 g, 62%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-pyrazol-5-carboxamido)methyl)-4,5-dihydroisoxazol-5-carboxamide (0.052 g, 0.088 mmol) obtained in (2) above by the preparation method of Example 1-(4).

NMR: $^1$H-NMR (400 MHz, $CD_3OD$); δ 7.48 (1H, d), 7.28-7.22 (5H, m), 6.77 (1H, d), 4.17 (2H, s), 4.13 (3H, s), 3.44 (1H, d), 3.37-3.27 (2H, m), 3.21 (1H, d), 2.70 (1H, dd), 1.44-1.05 (3H, m), 0.82 (6H, dd)

MS (m/z): 478[M+Na], 438[M-OH]

Example 177: Preparation of ((1R)-1-(5-(3-chlorobenzyl)-3-((imidazo[1,2-a]pyridin-8-carboxamido)methyl)-4,5-dihydroisoxazol-5-carboxamido)-3-methylbutyl)boronic acid Through the processes (1), (2) and (3) below, the title compound was obtained.

(1) Preparation of ethyl 5-(3-chlorobenzyl)-3-((imidazo[1,2-a]pyridin-8-carboxamido)methyl)-4,5-dihydroisoxazol-5-carboxylate

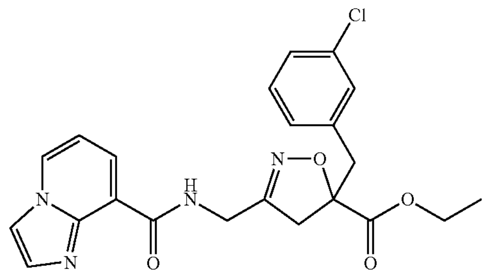 [SMILES: CCOC(=O)C1(Cc2cccc(Cl)c2)CC(CNC(=O)c2cccn3ccnc23)=NO1]

The title compound (0.13 g, 66%) was obtained using ethyl 3-(aminomethyl)-5-(3-chlorobenzyl)-4,5-dihydroisoxazol-5-carboxylate hydrochloride (0.15 g, 0.45 mmol) obtained in Example 175-(1) and imidazo[1,2-a]pyridin-8-carboxylic acid (0.080 g, 0.50 mmol) obtained in Example 132-(1) by the preparation method of Example 84-(2).

MS (m/z): 441[M+H]

(2) Preparation of 5-(3-chlorobenzyl)-3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

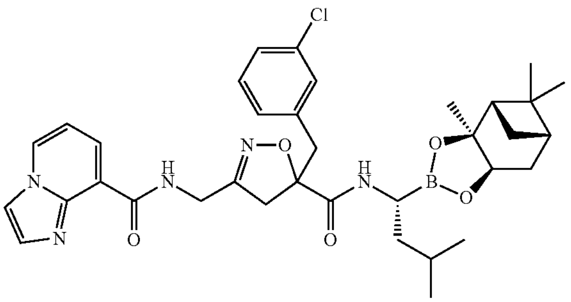 [SMILES: CC(C)C[C@H](NC(=O)C1(Cc2cccc(Cl)c2)CC(CNC(=O)c2cccn3ccnc23)=NO1)B1O[C@@H]2C[C@@H]3C[C@@H](C3(C)C)[C@]2(C)O1]

The title compound (0.063 g, 30%, 2 steps) was obtained using ethyl 5-(3-chlorobenzyl)-3-((imidazo[1,2-a]pyridin-8-carboxamido)methyl)-4,5-dihydroisoxazol-5-carboxylate (0.13 g, 0.36 mmol) obtained in (1) above by the preparation method of Example 84-(3).

MS (m/z): 660[M+H]

(3) Preparation of ((1R)-1-(5-(3-chlorobenzyl)-3-((imidazo[1,2-a]pyridin-8-carboxamido)methyl)-4,5-dihydroisoxazol-5-carboxamido)-3-methylbutyl) boronic acid

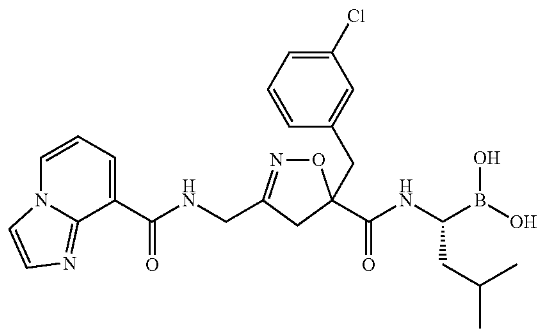 [SMILES: CC(C)C[C@H](NC(=O)C1(Cc2cccc(Cl)c2)CC(CNC(=O)c2cccn3ccnc23)=NO1)B(O)O]

The title compound (0.040 g, 74%) was obtained using 5-(3-chlorobenzyl)-3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.063 g, 0.095 mmol) obtained in (2) above by the preparation method of Example 1-(4).

NMR: $^1$H-NMR (500 MHz, $CDCl_3$); δ 10.56-10.54 (t, 1H), 8.25-8.24 (d, 1H), 8.14-8.13 (d, 1H), 7.64-7.61 (m, 2H), 7.24-7.01 (m, 5H), 6.95-6.93 (t, 3H), 4.36-4.34 (m, 2H), 3.45-3.41 (d, 1H), 3.30-3.27 (d, 1H), 3.11-3.04 (m, 2H), 2.82-2.80 (m, 1H), 1.34-1.28 (m, 2H), 1.16-1.12 (m, 1H), 0.78-0.76 (t, 6H)

MS (m/z): 526[M+H], 508[M-OH]

Example 178: Preparation of ((1R)-1-(5-(2,4-difluorobenzyl)-3-((isoquinolin-1-carboxamido)methyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(2,4-difluorobenzyl)-4,5-dihydroisoxazol-5-carboxylate hydrochloride

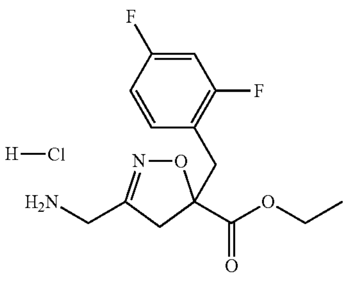

The title compound (0.17 g, quant.) was obtained using ethyl 3-(((tert-butoxycarbonyl)amino)methyl)-5-(2,4-difluorobenzyl)-4,5-dihydroisoxazol-5-carboxylate (0.20 g, 0.50 mmol) obtained in Preparation Example 35 by the preparation method of Example 84-(1).

MS (m/z): 299[M+H]

(2) Preparation of ethyl 5-(2,4-difluorobenzyl)-3-((isoquinolin-1-carboxamido)methyl)-4,5-dihydroisoxazol-5-carboxylate

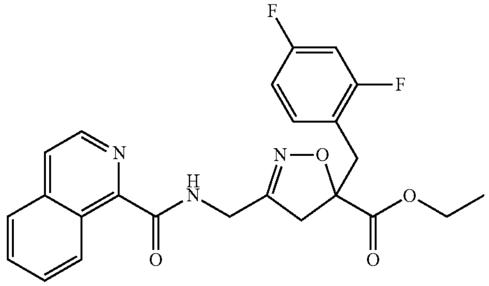 [SMILES: CCOC(=O)C1(Cc2ccc(F)cc2F)CC(CNC(=O)c2nccc3ccccc23)=NO1]

The title compound (0.17 g, 74%) was obtained using ethyl 3-(aminomethyl)-5-(2,4-difluorobenzyl)-4,5-dihydroisoxazol-5-carboxylate hydrochloride (0.17 g, 0.50 mmol) obtained in (1) above and isoquinolin-1-carboxylic acid (0.087 g, 0.50 mmol) by the preparation method of Example 84-(2).

MS (m/z): 454[M+H]

(3) Preparation of 5-(2,4-difluorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

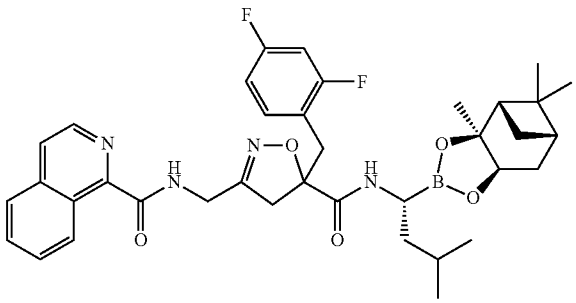 [SMILES: CC(C)C[C@H](NC(=O)C1(Cc2ccc(F)cc2F)CC(CNC(=O)c2nccc3ccccc23)=NO1)B1O[C@@H]2C[C@@H]3C[C@@H](C3(C)C)[C@]2(C)O1]

The title compound (0.12 g, 45%, 2 steps) was obtained using ethyl 5-(2,4-difluorobenzyl)-3-((isoquinolin-1-carboxamido)methyl)-4,5-dihydroisoxazol-5-carboxylate (0.17 g, 0.37 mmol) obtained in (2) above by the preparation method of Example 84-(3).

MS (m/z): 673[M+H]

(4) Preparation of ((1R)-1-(5-(2,4-difluorobenzyl)-3-((isoquinolin-1-carboxamido)methyl)-4,5-dihydroisoxazol-5-carboxamido)-3-methylbutyl)boronic acid

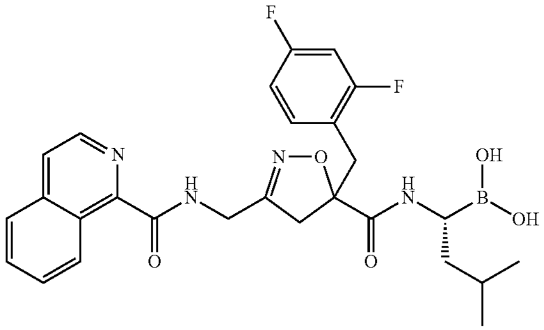 [SMILES: CC(C)C[C@H](NC(=O)C1(Cc2ccc(F)cc2F)CC(CNC(=O)c2nccc3ccccc23)=NO1)B(O)O]

The title compound (0.040 g, 42%) was obtained using 5-(2,4-difluorobenzyl)-3-((isoquinolin-1-carboxamido) methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.12 g, 0.18 mmol) obtained in (3) above by the preparation method of Example 1-(4).

MS (m/z): 539[M+H], 521[M-OH]

Example 179: Preparation of ((1R)-1-(5-benzyl-3-((6-(trifluoromethyl)nicotinamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((6-(trifluoromethyl)nicotinamido)methyl)-4,5-dihydroisoxazol-5-carboxylate

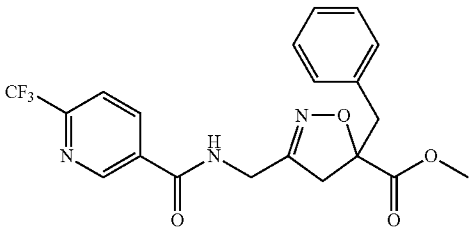 [SMILES: COC(=O)C1(Cc2ccccc2)CC(CNC(=O)c2ccc(C(F)(F)F)nc2)=NO1]

The title compound (0.66 g, 75%) was obtained using methyl 3-(aminomethyl)-5-benzyl-4,5-dihydroisoxazol-5-carboxylate hydrochloride (0.06 g, 0.21 mmol) obtained in Example 84-(1) and 6-trifluoromethyl-nicotinic acid (0.044 g, 0.23 mmol) by the preparation method of Example 84-(2).

MS (m/z): 422[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((6-(trifluoromethyl)nicotinamido)methyl)-4,5-dihydroisoxazol-5-carboxamide

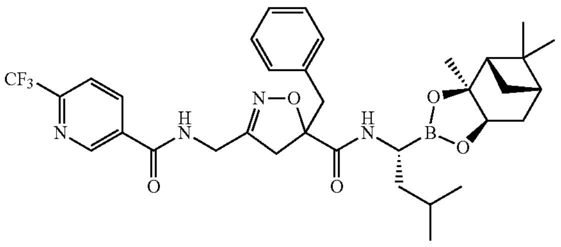 [SMILES: CC(C)C[C@H](NC(=O)C1(Cc2ccccc2)CC(CNC(=O)c2ccc(C(F)(F)F)nc2)=NO1)B1O[C@@H]2C[C@@H]3C[C@@H](C3(C)C)[C@]2(C)O1]

The title compound (0.072 mg, 70%, 2 steps) was obtained using methyl 5-benzyl-3-((6-(trifluoromethyl)nicotinamido)methyl)-4,5-dihydroisoxazol-5-carboxylate (1 mmol) obtained in (1) above by the preparation method of Example 84-(3).

MS (m/z): 655[M+H], 503[M-$C_{10}H_{15}O$]

(3) Preparation of ((1R)-1-(5-benzyl-3-((6-(trifluoromethyl)nicotinamido)methyl)-4,5-dihydroisoxazol-5-carboxamido)-3-methylbutyl)boronic acid

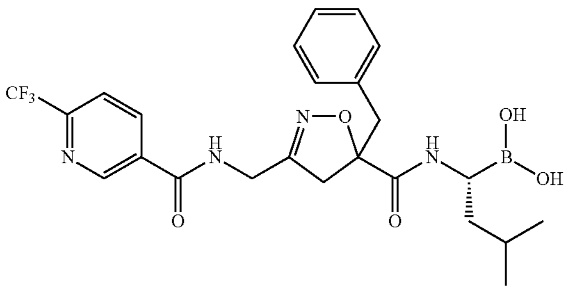 [SMILES: CC(C)C[C@H](NC(=O)C1(Cc2ccccc2)CC(CNC(=O)c2ccc(C(F)(F)F)nc2)=NO1)B(O)O]

The title compound (0.035 g, 61%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((6-(trifluoromethyl)nicotinamido)methyl)-4,5-dihydroisoxazol-5-carboxamide (0.072 g, 0.11 mmol) obtained in (2) above by the preparation method of Example 1-(4).

NMR: $^1$H-NMR (400 MHz, MeOD-d4); δ 9.11 (s, 1H), 8.43-8.41 (m, 1H), 7.98-7.96 (d, 1H), 7.28-7.23 (m, 5H), 4.29 (s, 2H), 3.49-3.36 (m, 2H), 3.26-3.20 (m, 2H), 2.70 (m, 1H), 1.44-1.40 (m, 1H), 1.22-1.07 (m, 2H), 0.85-0.80 (dd, 6H)

MS (m/z): 521[M+H], 503[M-OH]

Example 180: Preparation of ((1R)-1-(3-((isoquinolin-1-carboxamido)methyl)-5-(1-phenylcyclopropyl)-4,5-dihydroisoxazol-5-carboxamido)-3-methylbutyl)boronic acid Through the processes (1), (2), (3) and (4) below, the title compound was obtained.

(1) Preparation of methyl 3-(aminomethyl)-5-(1-phenylcyclopropyl)-4,5-dihydroisoxazol-5-carboxylate hydrochloride

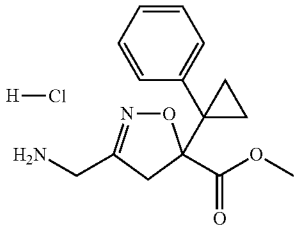 [SMILES: Cl ; COC(=O)C1(C2(c3ccccc3)CC2)CC(CN)=NO1]

The title compound (0.239 g, quant.) was obtained using methyl 3-(((tert-butoxycarbonyl)amino)methyl)-5-(1-phenylcyclopropyl)-4,5-dihydroisoxazol-5-carboxylate (0.277 g, 0.74 mmol) obtained in Preparation Example 36, preparation of methyl 3-(((tert-butoxycarbonyl)amino)methyl)-5-(1-phenylcyclopropyl)-4,5-dihydroisoxazol-5-carboxylate, by the preparation method of Example 84-(1).

MS (m/z): 275[M+H]

(2) Preparation of methyl 3-((isoquinolin-1-carboxamido)methyl)-5-(1-phenylcyclopropyl)-4,5-dihydroisoxazol-5-carboxylate

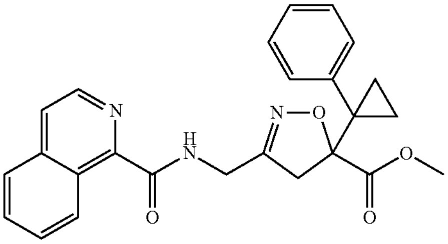 [SMILES: COC(=O)C1(C2(c3ccccc3)CC2)CC(CNC(=O)c2nccc3ccccc23)=NO1]

The title compound (0.089 g, 79%) was obtained using methyl 3-(aminomethyl)-5-(1-phenylcyclopropyl)-4,5-dihydroisoxazol-5-carboxylate hydrochloride (0.081 g, 0.261 mmol) obtained in (1) above and isoquinolin-1-carboxylic acid (0.059 g, 0.341 mmol) by the preparation method of Example 84-(2).

NMR: $^1$H-NMR (400 MHz, $CDCl_3$); δ 9.60 (1H, d), 8.63 (1H, t), 8.50 (1H, d), 7.91-7.73 (4H, m), 7.33-7.23 (5H, m), 4.50-4.40 (2H, m), 3.77 (3H, s), 3.62 (1H, d), 3.32 (1H, d), 1.53-1.49 (1H, m), 1.14-0.85 (3H, m)

MS (m/z): 430[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(1-phenylcyclopropyl)-4,5-dihydroisoxazol-5-carboxamide

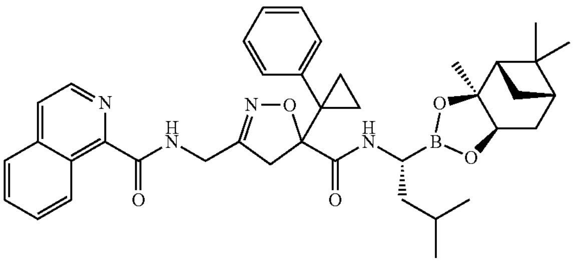 [SMILES: CC(C)C[C@H](NC(=O)C1(C2(c3ccccc3)CC2)CC(CNC(=O)c2nccc3ccccc23)=NO1)B1O[C@@H]2C[C@@H]3C[C@@H](C3(C)C)[C@]2(C)O1]

The title compound (0.059 g, 44%, 2 steps) was obtained using methyl 3-((isoquinolin-1-carboxamido)methyl)-5-(1-phenylcyclopropyl)-4,5-dihydroisoxazol-5-carboxylate (0.089 g, 0.201 mmol) obtained in (2) above by the preparation method of Example 84-(3).

MS (m/z): 663[M+H]

(4) Preparation of ((1R)-1-(3-((isoquinolin-1-carboxamido)methyl)-5-(1-phenylcyclopropyl)-4,5-dihydroisoxazol-5-carboxamido)-3-methylbutyl)boronic acid

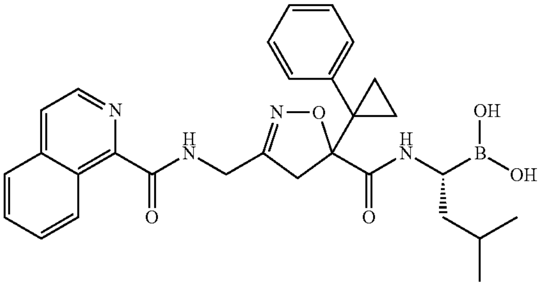 [SMILES: CC(C)C[C@H](NC(=O)C1(C2(c3ccccc3)CC2)CC(CNC(=O)c2nccc3ccccc23)=NO1)B(O)O]

The title compound (0.021 g, 45%) was obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(1-phenylcyclopropyl)-4,5-dihydroisoxazol-5-carboxamide (0.059 g, 0.089 mmol) obtained in (3) above by the preparation method of Example 1-(4).

NMR: $^1$H-NMR (400 MHz, $CD_3OD$); δ 9.09 (1H, d), 8.53 (1H, d), 7.99-7.96 (2H, m), 7.81 (1H, dt), 7.73 (1H, dt), 7.43 (2H, d), 7.27-7.21 (3H, m), 4.40 (2H, s), 3.37 (1H, dd), 3.22 (1H, d), 2.65 (1H, t), 1.45-1.00 (7H, m), 0.83 (6H, dd)

MS (m/z): 551[M+Na], 511[M-OH].

Example 181: Preparation of ((1R)-1-(3-((imidazo[1,2-a]pyridin-8-carboxamido)methyl)-5-(1-phenylcyclopropyl)-4,5-dihydroisoxazol-5-carboxamido)-3-methylbutyl)boronic acid Through the processes (1), (2) and (3) below, the title compound was obtained.

(1) Preparation of methyl 3-((imidazo[1,2-a]pyridin-8-carboxamido)methyl)-5-(1-phenylcyclopropyl)-4,5-dihydroisoxazol-5-carboxylate

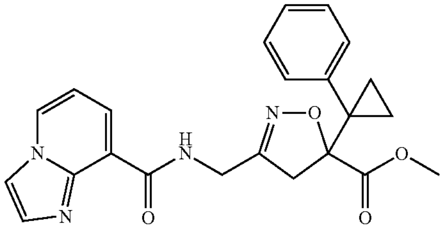 [SMILES: COC(=O)C1(C2(c3ccccc3)CC2)CC(CNC(=O)c2cccn3ccnc23)=NO1]

The title compound (0.098 g, 83%) was obtained using methyl 3-(aminomethyl)-5-(1-phenylcyclopropyl)-4,5-dihydroisoxazol-5-carboxylate hydrochloride (0.088 g, 0.283 mmol) obtained in Example 181-(1) and imidazo[1,2-a]pyridin-8-carboxylic acid (0.074 g, 0.373 mmol) by the preparation method of Example 84-(2).

NMR: 1H-NMR (400 MHz, CDCl3); δ 10.70 (1H, t), 8.32 (1H, dd), 8.21 (1H, dd), 7.69 (2H, dd), 7.32-7.21 (5H, m), 6.99 (1H, t), 4.51 (2H, dd), 3.75 (3H, s), 3.59 (1H, d), 3.32 (1H, d), 1.53-1.50 (1H, m), 1.13-0.84 (3H, m)

MS (m/z): 419[M+H]

(2) Preparation of 3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(1-phenylcyclopropyl)-4,5-dihydroisoxazol-5-carboxamide

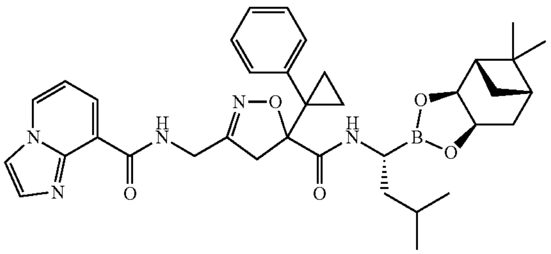 [SMILES: CC(C)C[C@H](NC(=O)C1(C2(c3ccccc3)CC2)CC(CNC(=O)c2cccn3ccnc23)=NO1)B1O[C@H]2[C@H]3C[C@@H](C[C@H]2O1)C3(C)C]

The title compound (0.116 g, 76%, 2 steps) was obtained using methyl 3-((imidazo[1,2-a]pyridin-8-carboxamido)methyl)-5-(1-phenylcyclopropyl)-4,5-dihydroisoxazol-5-carboxylate (0.098 g, 0.234 mmol) obtained in (1) above by the preparation method of Example 84-(3).

MS (m/z): 652[M+H]

(3) Preparation of ((1R)-1-(3-((imidazo[1,2-a]pyridin-8-carboxamido)methyl)-5-(1-phenylcyclopropyl)-4,5-dihydroisoxazol-5-carboxamido)-3-methylbutyl)boronic acid

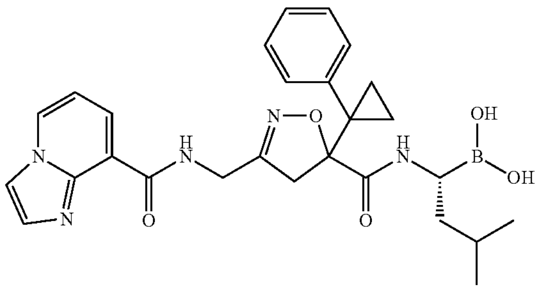 [SMILES: CC(C)C[C@H](NC(=O)C1(C2(c3ccccc3)CC2)CC(CNC(=O)c2cccn3ccnc23)=NO1)B(O)O]

The title compound (0.024 g, 26%) was obtained using 3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(1-phenylcyclopropyl)-4,5-dihydroisoxazol-5-carboxamide (0.116 g, 0.178 mmol) obtained in (2) above by the preparation method of Example 1-(4).

NMR: 1H-NMR (400 MHz, CD3OD); δ 8.65 (1H, d), 8.09 (1H, dd), 7.97 (1H, d), 7.68 (1H, d), 7.41 (2H, d), 7.23-7.04 (4H, m), 4.41 (2H, s), 3.33 (2H, d), 2.64 (1H, t), 1.41-0.99 (7H, m), 0.83-0.79 (6H, m)

MS (m/z): 540 [M+Na], 500 [M-OH]

Example 182: Preparation of ((1R)-1-(5-benzyl-3-((5-isopropylisoxazol-3-carboxamido)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-((5-isopropylisoxazol-3-carboxamido)methyl)-4,5-dihydroisoxazol-5-carboxylate

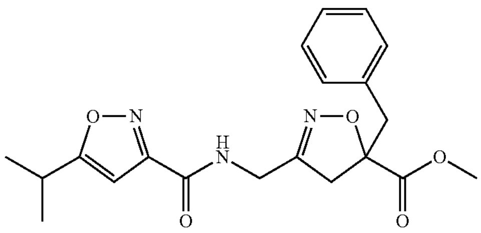 [SMILES: COC(=O)C1(Cc2ccccc2)CC(CNC(=O)c2cc(C(C)C)on2)=NO1]

The title compound (0.053 g, 65%) was obtained using methyl 3-(aminomethyl)-5-benzyl-4,5-dihydroisoxazol-5-carboxylate hydrochloride (0.06 g, 0.21 mmol) obtained in Example 84-(1) and 5-isopropyl-isoxazol-3-carboxylic acid (0.036 g, 0.23 mmol) by the preparation method of Example 84-(2).

MS (m/z): 386[M+H]

(2) Preparation of N-((5-benzyl-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)-5-isopropylisoxazol-3-carboxamide

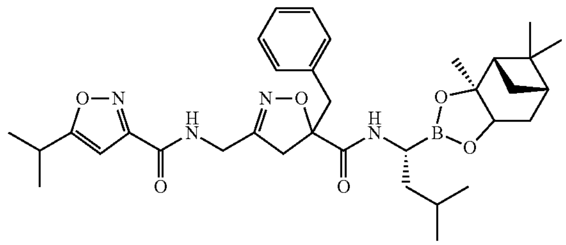 [SMILES: CC(C)C[C@H](NC(=O)C1(Cc2ccccc2)CC(CNC(=O)c2cc(C(C)C)on2)=NO1)B1OC2C[C@@H]3C[C@@H](C3(C)C)[C@]2(C)O1]

The title compound (0.066 g, 77%, 2 steps) was obtained using methyl 5-benzyl-3-((5-isopropylisoxazol-3-carboxamido)methyl)-4,5-dihydroisoxazol-5-carboxylate (0.053 g, 0.14 mmol) obtained in (1) above by the preparation method of Example 84-(3).

MS (m/z): 619[M+H]

(3) Preparation of ((1R)-1-(5-benzyl-3-((5-isopropylisoxazol-3-carboxamido)methyl)-4,5-dihydroisoxazol-5-carboxamido)-3-methylbutyl)boronic acid

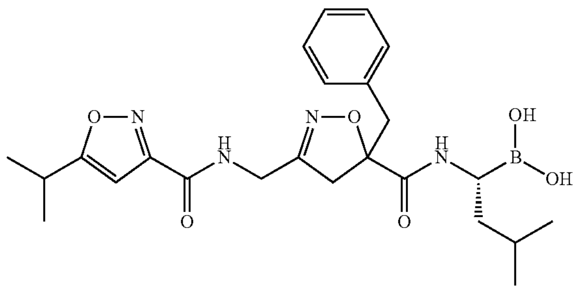 [SMILES: CC(C)C[C@H](NC(=O)C1(Cc2ccccc2)CC(CNC(=O)c2cc(C(C)C)on2)=NO1)B(O)O]

The title compound (0.028 g, 41%) was obtained using N-((5-benzyl-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)-5-isopropylisoxazol-3-carboxamide (0.066 g, 0.14 mmol) obtained in (2) above by the preparation method of Example 1-(4).

NMR: $^1$H-NMR (400 MHz, MeOD-d4); δ 7.28-7.24 (m, 5H), 6.47 (s, 1H), 4.23 (s, 2H), 3.46-3.41 (d, 1H), 3.28-3.14 (m, 3H), 2.70-2.66 (m, 1H), 1.42-1.39 (m, 1H), 1.37-1.35 (d, 6H), 1.20-1.01 (m, 2H), 0.84-0.79 (dd, 6H)

MS (m/z): 485[M+H], 467[M-OH]

Example 183: Preparation of ((1R)-1-(5-(3,5-difluorobenzyl)-3-((isoquinolin-1-carboxamido)methyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(3,5-difluorobenzyl)-4,5-dihydroisoxazol-5-carboxylate hydrochloride

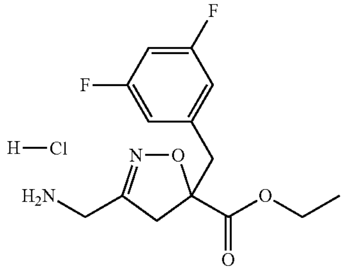

The title compound (0.24 g, 99%) was obtained using ethyl 3-(((tert-butoxycarbonyl)amino)methyl)-5-(3,5-difluorobenzyl)-4,5-dihydroisoxazol-5-carboxylate (0.29 g, 0.72 mmol) obtained in Preparation Example 37 by the preparation method of Example 84-(1).

MS (m/z): 299[M+H]

(2) Preparation of ethyl 5-(3,5-difluorobenzyl)-3-((isoquinolin-1-carboxamido)methyl)-4,5-dihydroisoxazol-5-carboxylate

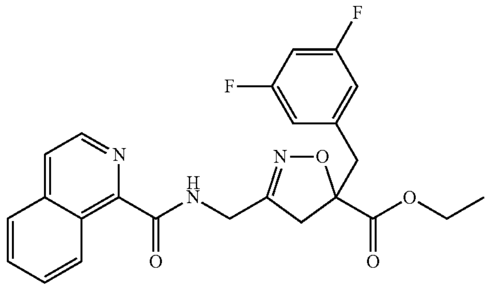 [SMILES: CCOC(=O)C1(Cc2cc(F)cc(F)c2)CC(CNC(=O)c2nccc3ccccc23)=NO1]

The title compound (0.12 g, 72%) was obtained using ethyl 3-(aminomethyl)-5-(3,5-difluorobenzyl)-4,5-dihydroisoxazol-5-carboxylate hydrochloride (0.12 g, 0.36 mmol) obtained in (1) above and isoquinolin-1-carboxylic acid (0.068 g, 0.39 mmol) by the preparation method of Example 84-(2).

NMR: $^1$H-NMR (400 MHz, $CDCl_3$); δ 9.56-9.54 (d, 1H), 8.26 (t, 1H), 8.49-8.47 (d, 1H), 7.89-7.69 (m, 4H), 6.80-6.78 (m, 2H), 6.67-6.62 (m, 1H), 4.42-4.31 (m, 2H), 4.26-4.18 (m, 2H), 3.53-3.48 (d, 1H), 3.31-3.27 (d, 1H), 3.13-3.09 (d, 1H), 3.08-3.04 (d, 1H), 1.27-1.23 (t, 3H)

MS (m/z): 454[M+H]

(3) Preparation of 5-(3,5-difluorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

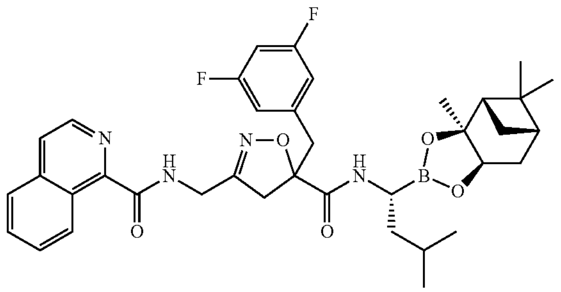 [SMILES: CC(C)C[C@H](NC(=O)C1(Cc2cc(F)cc(F)c2)CC(CNC(=O)c2nccc3ccccc23)=NO1)B1O[C@@H]2C[C@@H]3C[C@@H](C3(C)C)[C@]2(C)O1]

The title compound (0.10 g, 59%, 2 steps) was obtained using ethyl 5-(3,5-difluorobenzyl)-3-((isoquinolin-1-carboxamido)methyl)-4,5-dihydroisoxazol-5-carboxylate (0.12 g, 0.26 mmol) obtained in (2) above by the preparation method of Example 84-(3).

MS (m/z): 673[M+H]

(4) Preparation of ((1R)-1-(5-(3,5-difluorobenzyl)-3-((isoquinolin-1-carboxamido)methyl)-4,5-dihydroisoxazol-5-carboxamido)-3-methylbutyl)boronic acid

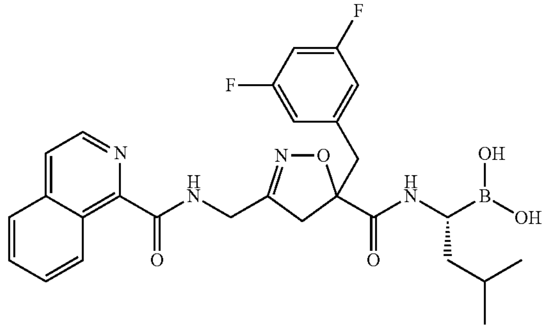 [SMILES: CC(C)C[C@H](NC(=O)C1(Cc2cc(F)cc(F)c2)CC(CNC(=O)c2nccc3ccccc23)=NO1)B(O)O]

The title compound (0.025 g, 31%) was obtained using 5-(3,5-difluorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.10 g, 0.15 mmol) obtained in (3) above by the preparation method of Example 1-(4).

NMR: $^1$H-NMR (400 MHz, $CDCl_3$); δ 9.51-9.49 (d, 1H), 8.60 (t, 1H), 8.41-8.40 (d, 1H), 7.85-7.65 (m, 4H), 7.17 (d, 1H), 6.81-6.79 (m, 2H), 6.64 (m, 1H), 4.40-4.30 (m, 2H), 3.49-3.45 (d, 1H), 3.34-3.31 (d, 1H), 3.13-3.09 (d, 1H), 3.05-3.01 (d, 1H), 2.77 (m, 1H), 1.30-1.15 (m, 3H), 0.77-0.76 (m, 6H)

MS (m/z): 539[M+H], 521[M-OH]

Example 184: Preparation of ((1R)-1-(5-benzyl-3-((4-chloro-1-methyl-1H-pyrazol-5-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((4-chloro-1-methyl-1H-pyrazol-5-carboxamido)methyl)-4,5-dihydroisoxazol-5-carboxylate

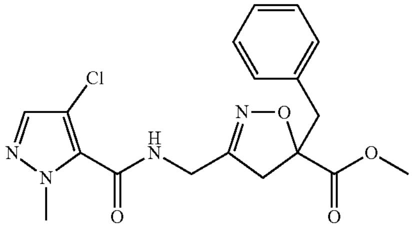 [SMILES: COC(=O)C1(Cc2ccccc2)CC(CNC(=O)c2c(Cl)cnn2C)=NO1]

The title compound (0.051 g, 77%) was obtained using methyl 3-(aminomethyl)-5-benzyl-4,5-dihydroisoxazol-5-carboxylate hydrochloride (0.048 g, 0.169 mmol) obtained in Example 84-(1) and 4-chloro-2-methyl-2H-pyrazol-3-carboxylic acid (0.033 g, 0.206 mmol) by the preparation method of Example 84-(2).

NMR: $^1$H-NMR (400 MHz, $CDCl_3$); δ 7.43 (1H, d), 7.26-7.17 (5H, m), 6.92 (1H, t), 4.20 (2H, t), 4.14 (3H, s), 3.78 (3H, s), 3.43 (1H, d), 3.34 (1H, d), 3.13 (1H, d), 2.99 (1H, d)

MS (m/z): 391[M+H]

(2) Preparation of 5-benzyl-3-((4-chloro-1-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

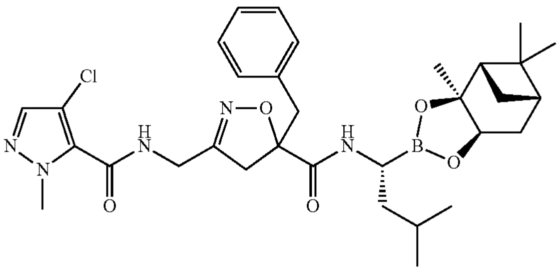 [SMILES: CC(C)C[C@H](NC(=O)C1(Cc2ccccc2)CC(CNC(=O)c2c(Cl)cnn2C)=NO1)B1O[C@@H]2C[C@@H]3C[C@@H](C3(C)C)[C@]2(C)O1]

The title compound (0.068 g, 84%, 2 steps) was obtained using methyl 5-benzyl-3-((4-chloro-1-methyl-1H-pyrazol-5-carboxamido)methyl)-4,5-dihydroisoxazol-5-carboxylate (0.051 g, 0.130 mmol) obtained in (1) above by the preparation method of Example 84-(3).

MS (m/z): 624[M+H]

(3) Preparation of ((1R)-1-(5-benzyl-3-((4-chloro-1-methyl-1H-pyrazol-5-carboxamido)methyl)-4,5-dihydroisoxazol-5-carboxamido)-3-methylbutyl) boronic acid

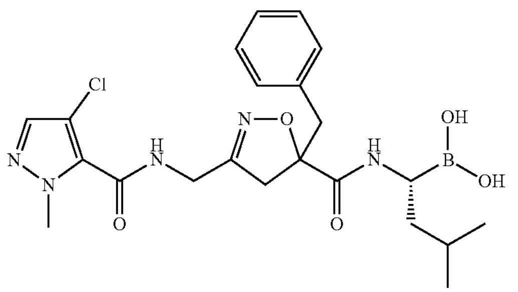 [SMILES: CC(C)C[C@H](NC(=O)C1(Cc2ccccc2)CC(CNC(=O)c2c(Cl)cnn2C)=NO1)B(O)O]

The title compound (0.035 g, 66%) was obtained using 5-benzyl-3-((4-chloro-1-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.068 g, 0.109 mmol) obtained in (2) above by the preparation method of Example 1-(4).

NMR: $^1$H-NMR (400 MHz, $CD_3OD$); δ 7.52 (1H, s), 7.29-7.23 (5H, m), 4.27 (2H, s), 4.02 (3H, s), 3.48 (1H, d), 3.37-3.25 (2H, m), 3.22 (1H, d), 2.72 (1H, dd), 1.45-1.06 (3H, m), 0.83 (6H, dd)

MS (ES+): 512[M+Na], 472[M-OH]

Example 185: Preparation of ((1R)-1-(5-benzyl-3-((S)-1-(isoquinolin-1-carboxamido)-2-methoxyethyl)-4,5-dihydroisoxazol-5-carboxamido)-3-methylbutyl)boronic acid Through the processes (1), (2), (3) and (4) below, the title compound was obtained.

(1) Preparation of methyl 3-((S)-1-amino-2-methoxyethyl)-5-benzyl-4,5-dihydroisoxazol-5-carboxylate hydrochloride

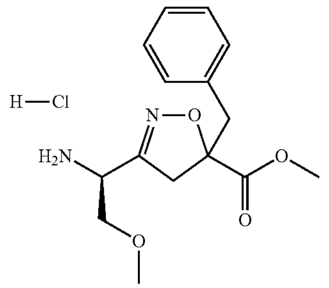

The title compound (0.77 g, 99%) was obtained using methyl 5-benzyl-3-((S)-1-((tert-butoxycarbonyl)amino)-2-methoxyethyl)-4,5-dihydroisoxazol-5-carboxylate (0.93 g, 2.38 mmol) obtained in Preparation Example 38 by the preparation method of Example 84-(1).

MS (m/z): 293[M+H]

(2) Preparation of methyl 5-benzyl-3-((S)-1-(isoquinolin-1-carboxamido)-2-methoxyethyl)-4,5-dihydroisoxazol-5-carboxylate

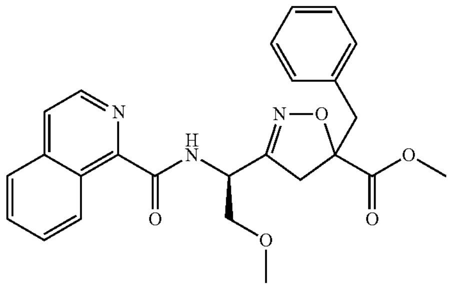 [SMILES: COC[C@@H](NC(=O)c1nccc2ccccc12)C1=NOC(Cc2ccccc2)(C(=O)OC)C1]

The title compound (0.11 g, 58%) was obtained using methyl 3-((S)-1-amino-2-methoxyethyl)-5-benzyl-4,5-dihydroisoxazol-5-carboxylate hydrochloride (0.15 g, 0.47 mmol) obtained in (1) above and isoquinolin-1-carboxylic acid (0.087 g, 0.50 mmol) by the preparation method of Example 84-(2).

MS (m/z): 448[M+H]

(3) Preparation of 5-benzyl-3-((S)-1-(isoquinolin-1-carboxamido)-2-methoxyethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

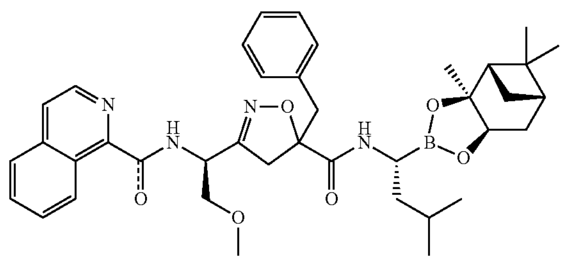

The title compound (0.14 g, 82%, 2 steps) was obtained using methyl 5-benzyl-3-((S)-1-(isoquinolin-1-carboxamido)-2-methoxyethyl)-4,5-dihydroisoxazol-5-carboxylate (0.11 g, 0.26 mmol) obtained in (2) above by the preparation method of Example 84-(3).

MS (m/z): 681[M+H]

(4) Preparation of ((1R)-1-(5-benzyl-3-((S)-1-(isoquinolin-1-carboxamido)-2-methoxyethyl)-4,5-dihydroisoxazol-5-carboxamido)-3-methylbutyl)boronic acid

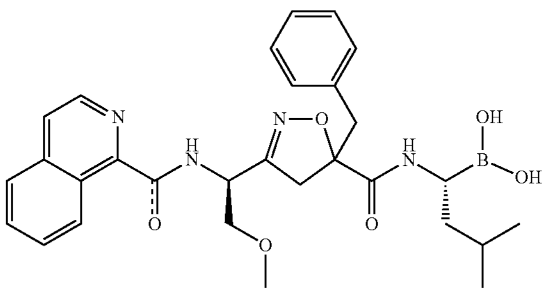

The title compound (0.057 g, 52%) was obtained using 5-benzyl-3-((S)-1-(isoquinolin-1-carboxamido)-2-methoxyethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.14 g, 0.20 mmol) obtained in (3) above by the preparation method of Example 1-(4).

NMR: $^1$H-NMR (400 MHz, MeOD-d4); δ 9.10-9.08 (m, 1H), 8.55-8.53 (m, 1H), 8.03-7.98 (m, 2H), 7.84-7.72 (m, 2H), 7.30-7.18 (m, 5H), 5.16 (m, 1H), 3.77-3.71 (m, 2H), 3.57-3.50 (m, 1H), 3.40-3.36 (m, 4H), 3.24-3.21 (m, 1H), 2.74-2.67 (m, 1H), 1.45-1.40 (m, 1H), 1.19-1.07 (m, 2H), 0.85-0.76 (m, 6H)

MS (m/z): 547[M+H], 529[M-OH]

Example 186: Preparation of ((1R)-1-(5-benzyl-3-((6-(trifluoromethyl)picolinamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((6-(trifluoromethyl)picolinamido)methyl)-4,5-dihydroisoxazol-5-carboxylate

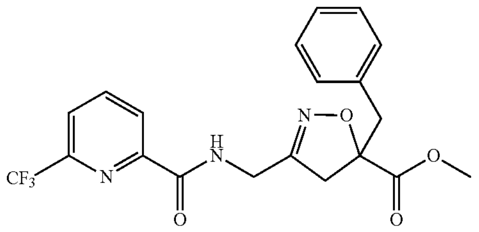 [SMILES: COC(=O)C1(Cc2ccccc2)CC(CNC(=O)c2cccc(C(F)(F)F)n2)=NO1]

The title compound (0.05 g, 57%) was obtained using methyl 3-(aminomethyl)-5-benzyl-4,5-dihydroisoxazol-5-carboxylate hydrochloride (0.06 g, 0.21 mmol) obtained in Example 84-(1) and 6-trifluoromethyl-pyridin-2-carboxylic acid (0.044 g, 0.23 mmol) by the preparation method of Example 84-(2).

MS (m/z): 422[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((6-(trifluoromethyl)picolinamido)methyl)-4,5-dihydroisoxazol-5-carboxamide

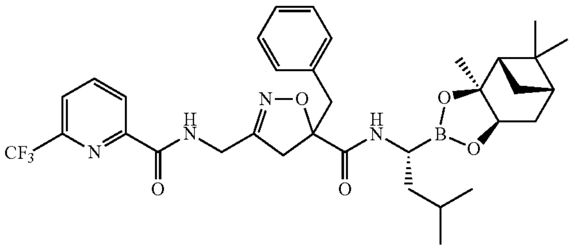 [SMILES: CC(C)C[C@H](NC(=O)C1(Cc2ccccc2)CC(CNC(=O)c2cccc(C(F)(F)F)n2)=NO1)B1O[C@@H]2C[C@@H]3C[C@@H](C3(C)C)[C@]2(C)O1]

The title compound (0.075 g, 96%, 2 steps) was obtained using methyl 5-benzyl-3-((6-(trifluoromethyl)picolinamido)methyl)-4,5-dihydroisoxazol-5-carboxylate (0.05 g, 0.16 mmol) obtained in (1) above by the preparation method of Example 84-(3).

MS (m/z): 655[M+H]

(3) Preparation of ((1R)-1-(5-benzyl-3-((6-(trifluoromethyl)picolinamido)methyl)-4,5-dihydroisoxazol-5-carboxamido)-3-methylbutyl)boronic acid

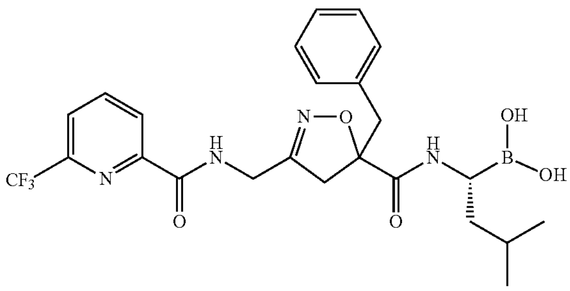 [SMILES: CC(C)C[C@H](NC(=O)C1(Cc2ccccc2)CC(CNC(=O)c2cccc(C(F)(F)F)n2)=NO1)B(O)O]

The title compound (0.046 g, 77%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((6-(trifluoromethyl)picolinamido)methyl)-4,5-dihydroisoxazol-5-carboxamide (0.075 g, 0.11 mmol) obtained in (2) above by the preparation method of Example 1-(4).

NMR: $^1$H-NMR (400 MHz, MeOD-d4); δ 8.37-8.25 (m, 2H), 8.05-8.03 (m, 1H), 7.29-7.21 (m, 5H), 4.31 (s, 2H), 3.47-3.43 (d, 1H), 3.32-3.19 (m, 3H), 2.69-2.65 (m, 1H), 1.42-4.37 (m, 1H), 1.19-1.02 (m, 2H), 0.84-0.79 (dd, 6H)

MS (m/z): 521[M+H], 503[M-OH]

Example 187: Preparation of ((1R)-1-(5-(3-fluorobenzyl)-3-((isoquinolin-1-carboxamido)methyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(3-fluorobenzyl)-4,5-dihydroisoxazol-5-carboxylate hydrochloride

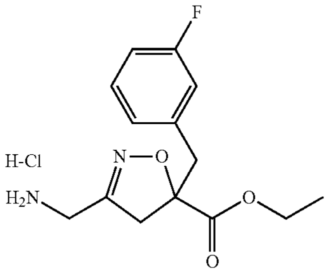

The title compound (0.20 g, quant.) was obtained using ethyl 3-(((tert-butoxycarbonyl)amino)methyl)-5-(3-fluorobenzyl)-4,5-dihydroisoxazol-5-carboxylate (0.24 g, 0.62 mmol) obtained in Preparation Example 39 by the preparation method of Example 84-(1).

MS (m/z): 281[M+H]

(2) Preparation of ethyl 5-(3-fluorobenzyl)-3-((isoquinolin-1-carboxamido)methyl)-4,5-dihydroisoxazol-5-carboxylate

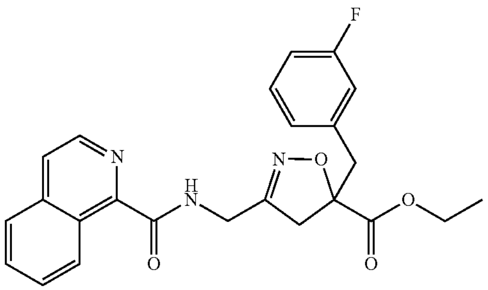

The title compound (0.22 g, 80%) was obtained using ethyl 3-(aminomethyl)-5-(3-fluorobenzyl)-4,5-dihydroisoxazol-5-carboxylate hydrochloride (0.20 g, 0.62 mmol) obtained in (1) above and isoquinolin-1-carboxylic acid (0.10 g, 0.62 mmol) by the preparation method of Example 84-(2).

MS (m/z): 346[M+H]

(3) Preparation of 5-(3-fluorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

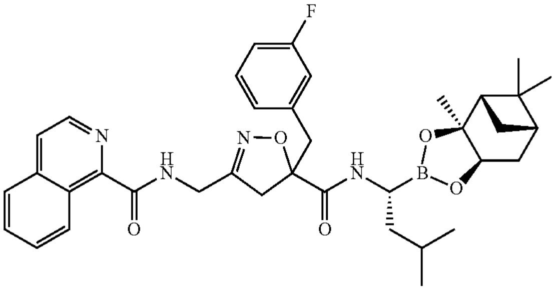 [SMILES: CC(C)C[C@H](NC(=O)C1(Cc2cccc(F)c2)CC(CNC(=O)c2nccc3ccccc23)=NO1)B1O[C@@H]2C[C@@H]3C[C@@H](C3(C)C)[C@]2(C)O1]

The title compound (0.11 g, 35%, 2 steps) was obtained using ethyl 5-(3-fluorobenzyl)-3-((isoquinolin-1-carboxamido)methyl)-4,5-dihydroisoxazol-5-carboxylate (0.22 g, 0.49 mmol) obtained in (2) above by the preparation method of Example 84-(3).

MS (m/z): 655[M+H]

(4) Preparation of ((1R)-1-(5-(3-fluorobenzyl)-3-((isoquinolin-1-carboxamido)methyl)-4,5-dihydroisoxazol-5-carboxamido)-3-methylbutyl)boronic acid

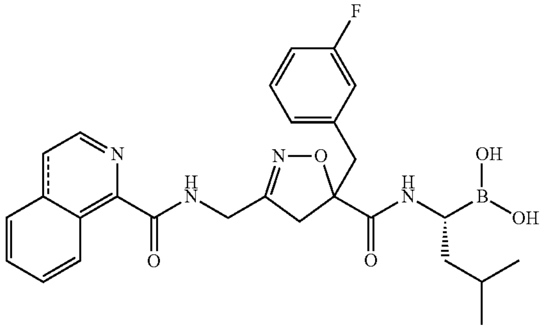

The title compound (0.040 g, 45%) was obtained using 5-(3-fluorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.11 g, 0.17 mmol) obtained in (3) above by the preparation method of Example 1-(4).

MS (m/z): 521[M+H], 503[M-OH]

Example 188: Preparation of ((1R)-1-(5-benzyl-3-((1-isopropyl-1H-pyrazol-4-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of 1-isopropyl-1H-pyrazol-4-carboxylic acid ethyl ester

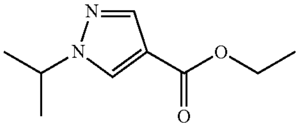

1H-pyrazol-4-carboxylic acid ethyl ester (0.19 g, 1.36 mmol) was dissolved in acetonitrile (10 ml), and cesium carbonate (1.1 g, 3.39 mmol) and iodopropane (0.27 ml, 2.71 mmol) were added in order. After stirring at room temperature for 18 hours, water was added, and extraction with ethyl acetate was performed. The resultant product was washed with brine, dried over magnesium sulfate, and filtered. The filtrate was distilled under a reduced pressure and separated by column chromatography to obtain the title compound of 1-isopropyl-1H-pyrazol-4-carboxylic acid ethyl ester (0.23 g, 94%).

MS (m/z): 183[M+H]

(2) Preparation of 1-isopropyl-1H-pyrazol-4-carboxylic acid

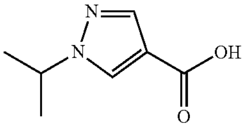

The title compound (0.18 g, 91%) was obtained using 1-isopropyl-1H-pyrazol-4-carboxylic acid ethyl ester (0.23 g, 1.28 mmol) obtained above by the preparation method of Example 119-(2).

(3) Preparation of methyl 5-benzyl-3-((1-isopropyl-1H-pyrazol-4-carboxamido)methyl)-4,5-dihydroisoxazol-5-carboxylate

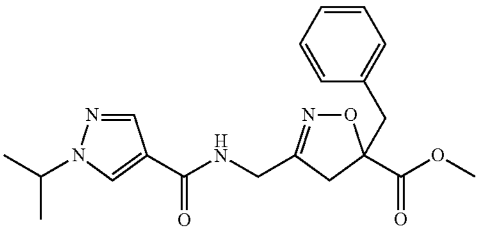 [SMILES: COC(=O)C1(Cc2ccccc2)CC(CNC(=O)c2cnn(C(C)C)c2)=NO1]

The title compound (0.06 g, 89%) was obtained using methyl 3-(aminomethyl)-5-benzyl-4,5-dihydroisoxazol-5-carboxylate hydrochloride (0.05 g, 0.18 mmol) obtained in Example 84-(1) and 1-isopropyl-1H-pyrazol-4-carboxylic acid (0.03 g, 0.19 mmol) obtained in (2) above by the preparation method of Example 84-(2).

MS (m/z): 385[M+H]

(4) Preparation of 5-benzyl-3-((1-isopropyl-1H-pyrazol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

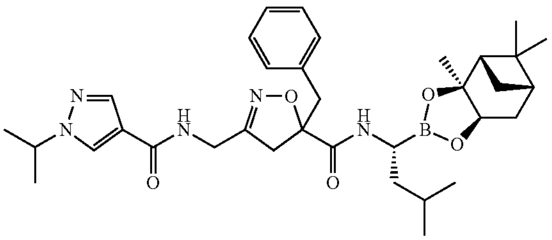 [SMILES: CC(C)C[C@H](NC(=O)C1(Cc2ccccc2)CC(CNC(=O)c2cnn(C(C)C)c2)=NO1)B1O[C@@H]2C[C@@H]3C[C@@H](C3(C)C)[C@]2(C)O1]

The title compound (0.06 g, 62%, 2 steps) was obtained using methyl 5-benzyl-3-((1-isopropyl-1H-pyrazol-4-carboxamido)methyl)-4,5-dihydroisoxazol-5-carboxylate (0.06 g, 0.16 mmol) obtained in (3) above by the preparation method of Example 84-(3).

MS (m/z): 618[M+H]

(5) Preparation of ((1R)-1-(5-benzyl-3-((1-isopropyl-1H-pyrazol-4-carboxamido)methyl)-4,5-dihydroisoxazol-5-carboxamido)-3-methylbutyl)boronic acid

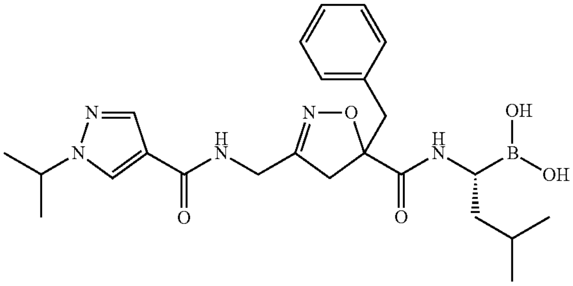 [SMILES: CC(C)C[C@H](NC(=O)C1(Cc2ccccc2)CC(CNC(=O)c2cnn(C(C)C)c2)=NO1)B(O)O]

The title compound (0.028 g, 60%) was obtained using 5-benzyl-3-((1-isopropyl-1H-pyrazol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.06 g, 0.097 mmol) obtained in (4) above by the preparation method of Example 1-(4).

NMR: $^1$H-NMR (400 MHz, MeOD-d4); δ 8.13 (s, 1H), 7.89 (s, 1H), 7.28-7.24 (m, 5H), 4.62-4.54 (m, 1H), 4.19 (s, 2H), 3.45-3.41 (d, 1H), 3.35-3.19 (m, 3H), 2.69-2.65 (m, 1H), 1.53-1.52 (d, 6H), 1.43-1.38 (m, 1H), 1.20-1.01 (m, 2H), 0.84-0.79 (dd, 6H)

MS (m/z): 484[M+H], 466[M-OH]

Example 189: Preparation of ((1R)-1-(5-benzyl-3-((1-cyclopentyl-1H-pyrazol-5-carboxamido)methyl)-4,5-dihydroisoxazol-5-carboxamido)-3-methylbutyl) boronic acid Through the processes (1), (2), (3), (4) and (5) below, the title compound was obtained.

(1) Preparation of 2-cyclopentyl-2H-pyrazol-3-carboxylic acid ethyl ester

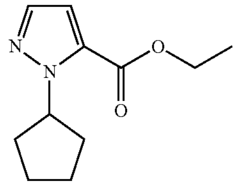

The title compound (0.031 g, 26%) was obtained using 2H-pyrazol-3-carboxylic acid ethyl ester (0.078 g, 0.62 mmol) and bromo-cyclopentane (0.13 ml, 1.2 mmol) by the preparation method of Example 188-(1).

MS (m/z): 209[M+H]

(2) Preparation of 2-cyclopentyl-2H-pyrazol-3-carboxylic acid

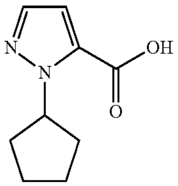 [SMILES: O=C(O)c1ccnn1C1CCCC1]

The title compound (0.03 g, 99%) was obtained using 2-cyclopentyl-2H-pyrazol-3-carboxylic acid ethyl ester (0.031 g, 0.16 mmol) obtained in (1) above by the preparation method of Example 119-(2).

(3) Preparation of 5-benzyl-3-1{[(2-cyclopentyl-2H-pyrazol-3-carbonyl)-amino]-methyl}-4,5-dihydro-isoxazol-5-carboxylic acid methyl ester

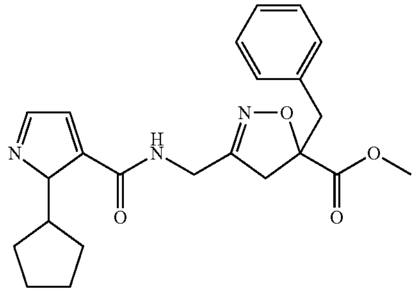 [SMILES: COC(=O)C1(Cc2ccccc2)CC(CNC(=O)C2=CC=NC2C2CCCC2)=NO1]

The title compound (0.044 g, 67%) was obtained using methyl 3-(aminomethyl)-5-benzyl-4,5-dihydroisoxazol-5-carboxylate hydrochloride (0.046 g, 0.16 mmol) obtained in Example 84-(1) and 2-cyclopentyl-2H-pyrazol-3-carboxylic acid (0.030 g, 0.16 mmol) obtained in (2) above by the preparation method of Example 84-(2).

NMR: $^1$H-NMR (500 MHz, $CDCl_3$); δ 7.46 (1H, d), 7.28-7.20 (5H, m), 6.43 (1H, d), 6.25 (1H, t), 5.55 (1H, q), 4.15-4.09 (2H, m), 3.78 (3H, s), 3.42 (1H, d), 3.33 (1H, d), 3.12 (1H, d), 3.01 (1H, d), 2.12-1.65 (8H, m)

MS (m/z): 411[M+H]

(4) Preparation of 5-benzyl-3-1{[(1-cyclopentyl-1H-pyrazol-5-yl)formamido]methyl}-N-[(1R)-3-methyl-1-[(1S,2S,6R,8S)-2,9,9-trimethyl-3,5-dioxa-4-boratricyclo[6.1.1.0$^{2,6}$]decan-4-yl]butyl]-4,5-dihydro-1,2-oxazol-5-carboxamide

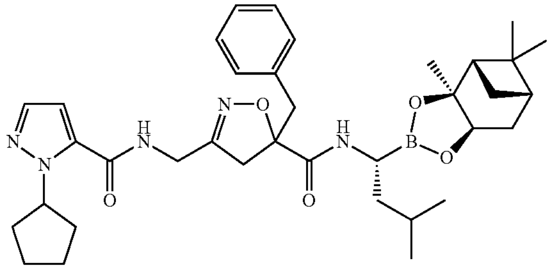 [SMILES: CC(C)C[C@H](NC(=O)C1(Cc2ccccc2)CC(CNC(=O)c2ccnn2C2CCCC2)=NO1)B1O[C@@H]2C[C@@H]3C[C@@H](C3(C)C)[C@]2(C)O1]

The title compound (0.043 g, 62%, 2 steps) was obtained using 5-benzyl-3-{[(2-cyclopentyl-2H-pyrazol-3-carbonyl)-amino]-methyl}-4,5-dihydro-isoxazol-5-carboxylic acid methyl ester (0.044 g, 0.107 mmol) obtained in (3) above by the preparation method of Example 84-(3).

MS (m/z): 644[M+H]

(5) Preparation of 5-benzyl-3-{[(1-cyclopentyl-1H-pyrazol-5-yl)formamido]methyl}-N-[(1R)-1-(□lhydroxyboranyl)-3-methylbutyl]-4,5-dihydro-1,2-oxazol-5-carboxamide

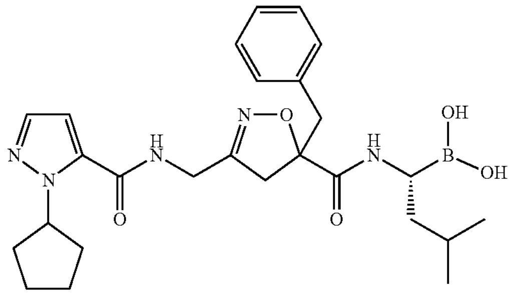 [SMILES: CC(C)C[C@H](NC(=O)C1(Cc2ccccc2)CC(CNC(=O)c2ccnn2C2CCCC2)=NO1)B(O)O]

The title compound (0.026 g, 76%) was obtained using 5-benzyl-3-{1[(1-cyclopentyl-1H-pyrazol-5-yl)formamido]methyl}-N-[(1R)-3-methyl-1-[(1S,2S,6R,8S)-2,9,9-trimethyl-3,5-dioxa-4-boratricyclo[6.1.1.0$^{2,6}$]decan-4-yl]butyl]-4,5-dihydro-1,2-oxazol-5-carboxamide (0.043 g, 0.067 mmol) obtained in (4) above by the preparation method of Example 1-(4).

NMR: $^1$H-NMR (500 MHz, $CD_3OD$); δ 7.46 (1H, d), 7.25-7.20 (5H, m), 6.67 (1H, d), 5.58 (1H, q), 4.15 (2H, d), 3.40 (1H, d), 3.33-3.20 (2H, m), 3.18 (1H, d), 2.64 (1H, dd), 2.12-1.65 (8H, m), 1.38-0.99 (3H, m), 0.78 (6H, dd)

MS (ES+): 532 [M+Na], 492 [M-OH]

Example 190: Preparation of ((1R)-1-(5-benzyl-3-((1-isopropyl-3-methyl-1H-pyrazol-5-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of 2-isopropyl-5-methyl-2H-pyrazol-3-carboxylic acid ethyl ester

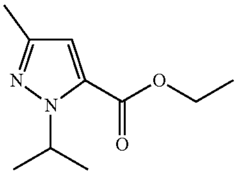

The title compound (0.29 g, 49%) was obtained using 5-methyl-2H-pyrazol-3-carboxylic acid ethyl ester (0.46 g, 3.0 mmol) by the preparation method of Example 188-(1).

(2) Preparation of 2-isopropyl-5-methyl-2H-pyrazol-3-carboxylic acid

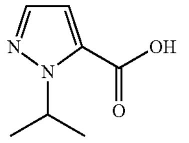

The title compound (0.12 g, 95%) was obtained using 2-isopropyl-5-methyl-2H-pyrazol-3-carboxylic acid ethyl ester (0.15 g, 0.76 mmol) obtained in (1) above by the preparation method of Example 119-(2).

(3) Preparation of methyl 5-benzyl-3-((1-isopropyl-3-methyl-1H-pyrazol-5-carboxamido)methyl)-4,5-dihydroisoxazol-5-carboxylate

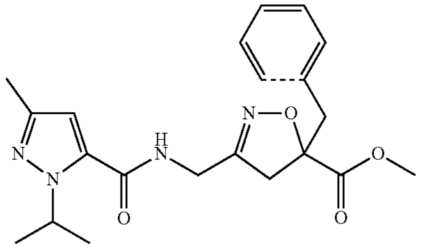

The title compound (0.056 g, 79%) was obtained using methyl 3-(aminomethyl)-5-benzyl-4,5-dihydroisoxazol-5-carboxylate hydrochloride (0.051 g, 0.179 mmol) obtained in Example 84-(1) and 2-isopropyl-5-methyl-2H-pyrazol-3-carboxylic acid (0.039 g, 0.232 mmol) obtained in (2) above by the preparation method of Example 84-(2).

NMR: $^1$H-NMR (400 MHz, $CDCl_3$); δ 7.24-7.20 (5H, m), 6.23 (1H, t), 6.19 (1H, s), 5.35 (1H, t), 4.11 (2H, d), 3.76 (3H, s), 3.40 (1H, d), 3.31 (1H, d), 3.11 (1H, d), 2.99 (1H, d), 2.26 (3H, s), 1.44 (6H, dd)

MS (m/z): 399[M+H]

(4) Preparation of 5-benzyl-3-((1-isopropyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

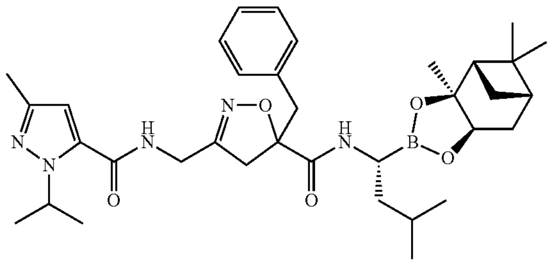

The title compound (0.066 g, 75%, 2 steps) was obtained using methyl 5-benzyl-3-((1-isopropyl-3-methyl-1H-pyrazol-5-carboxamido)methyl)-4,5-dihydroisoxazol-5-carboxylate (0.056 g, 0.140 mmol) obtained in (3) above by the preparation method of Example 84-(3).

MS (m/z): 632[M+H]

(5) Preparation of ((1R)-1-(5-benzyl-3-((1-isopropyl-3-methyl-1H-pyrazol-5-carboxamido)methyl)-4,5-dihydroisoxazol-5-carboxamido)-3-methylbutyl)boronic acid

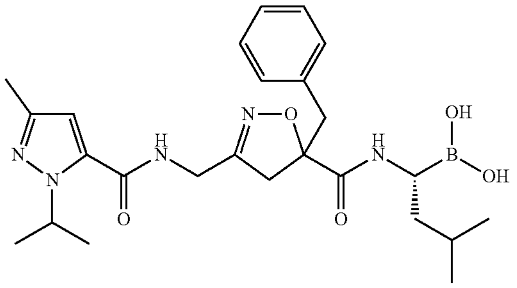 [SMILES: Cc1cc(C(=O)NCC2=NOC(Cc3ccccc3)(C(=O)N[C@@H](CC(C)C)B(O)O)C2)n(C(C)C)n1]

The title compound (0.040 g, 77%) was obtained using 5-benzyl-3-((1-isopropyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.066 g, 0.104 mmol) obtained in (4) above by the preparation method of Example 1-(4).

NMR: $^1$H-NMR (500 MHz, $CD_3OD$); δ 7.25-7.20 (5H, m), 6.43 (1H, s), 5.39 (1H, dt), 4.13 (2H, d), 3.39 (1H, d), 3.33-3.29 (2H, m), 3.18 (1H, d), 2.64 (1H, dd), 1.42-1.38 (7H, m), 1.16-1.00 (2H, m), 0.78 (6H, dd)

MS (m/z): 498[M+H], 480[M-OH]

Example 191: Preparation of ((1R)-1-(5-benzyl-3-((1-(2-methoxyethyl)-1H-pyrazol-5-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of 2-(2-methoxy-ethyl)-2H-pyrazol-3-carboxylic acid ethyl ester

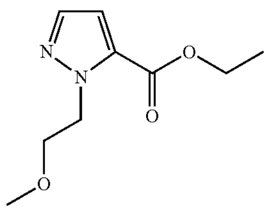

The title compound was obtained by the method described in US2007105872A1.

(2) Preparation of 2-(2-methoxy-ethyl)-2H-pyrazol-3-carboxylic acid

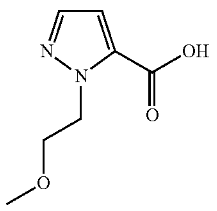

The title compound (0.055 g, 99%) was obtained using 2-(2-methoxy-ethyl)-2H-pyrazol-3-carboxylic acid ethyl ester (0.059 g, 0.32 mmol) obtained in (1) above by the preparation method of Example 119-(2).

(3) Preparation of methyl 5-benzyl-3-((1-(2-methoxyethyl)-1H-pyrazol-5-carboxamido)methyl)-4,5-dihydroisoxazol-5-carboxylate

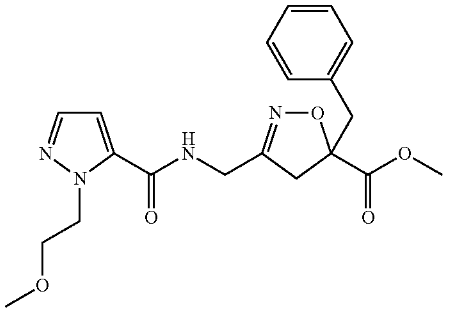

The title compound (0.034 g, 61%) was obtained using methyl 3-(aminomethyl)-5-benzyl-4,5-dihydroisoxazol-5-carboxylate hydrochloride (0.040 g, 0.14 mmol) obtained in Example 84-(1) and 2-(2-methoxy-ethyl)-2H-pyrazol-3-carboxylic acid (0.027 g, 0.16 mmol) obtained in (2) above by the preparation method of Example 84-(2).

NMR: $^1$H-NMR (500 MHz, $CDCl_3$); δ 7.47 (1H, d), 7.25-7.20 (5H, m), 6.99 (1H, t), 6.52 (1H, d), 4.64 (2H, t), 4.14 (2H, d), 3.76 (2H, d), 3.75 (3H, s), 3.40 (1H, d), 3.30 (1H, d), 3.28 (3H, s), 3.12 (1H, d), 3.00 (1H, d)

MS (m/z): 401[M+H]

(4) Preparation of 5-benzyl-3-((1-(2-methoxyethyl)-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

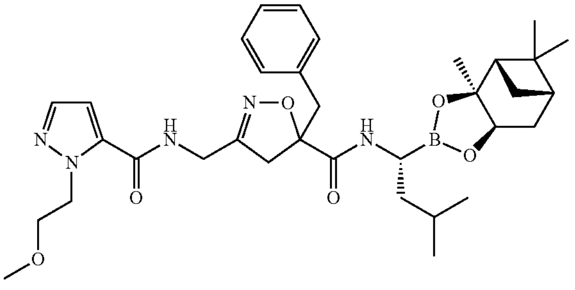

The title compound (0.038 g, 70%, 2 steps) was obtained using methyl 5-benzyl-3-((1-(2-methoxyethyl)-1H-pyrazol-5-carboxamido)methyl)-4,5-dihydroisoxazol-5-carboxylate (0.034 g, 0.085 mmol) obtained in (3) above by the preparation method of Example 84-(3).

MS (m/z): 634[M+H]

(5) Preparation of ((1R)-1-(5-benzyl-3-((1-(2-methoxyethyl)-1H-pyrazol-5-carboxamido)methyl)-4,5-dihydroisoxazol-5-carboxamido)-3-methylbutyl) boronic acid

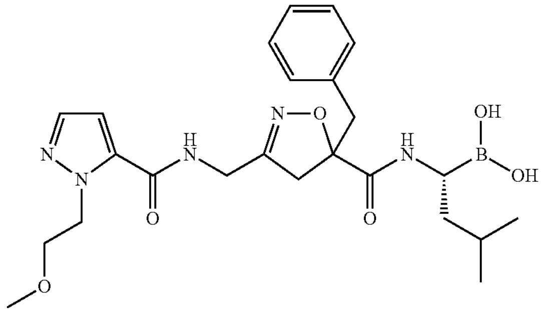

The title compound (0.020 g, 67%) was obtained using 5-benzyl-3-((1-(2-methoxyethyl)-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.038 g, 0.060 mmol) obtained in (4) above by the preparation method of Example 1-(4).

NMR: $^1$H-NMR (500 MHz, $CD_3OD$); δ 7.49 (1H, d), 7.25-7.20 (5H, m), 6.72 (1H, d), 4.73-4.67 (2H, m), 4.16 (2H, dd), 3.69 (2H, d), 3.41 (1H, d), 3.31-3.22 (2H, m), 3.18 (1H, d), 2.63 (1H, dd), 1.38-0.99 (3H, m), 0.79 (6H, dd)

MS (ES+): 522 [M+Na], 482 [M-OH]

Example 192: Preparation of ((1R)-1-(3-((isoquinolin-1-carboxamido)methyl)-5-(methoxymethyl)-4,5-dihydroisoxazol-5-carboxamido)-3-methylbutyl) boronic acid Through the processes (1), (2), (3) and (4) below, the title compound was obtained.

(1) Preparation of methyl 3-(aminomethyl)-5-(methoxymethyl)-4,5-dihydroisoxazol-5-carboxylate hydrochloride

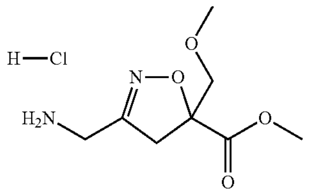

The title compound (0.058 g, 99%) was obtained using methyl 3-(((tert-butoxycarbonyl)amino)methyl)-5-(methoxymethyl)-4,5-dihydroisoxazol-5-carboxylate (0.074 g, 0.24 mmol) obtained in Preparation Example 40 by the preparation method of Example 84-(1).

MS (m/z): 203[M+H]

(2) Preparation of methyl 3-((isoquinolin-1-carboxamido)methyl)-5-(methoxymethyl)-4,5-dihydroisoxazol-5-carboxylate

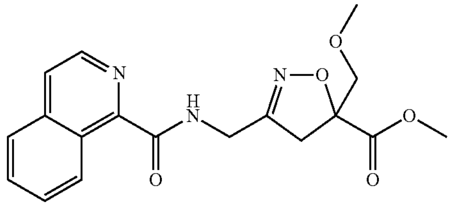 [SMILES: COCC1(C(=O)OC)CC(CNC(=O)c2nccc3ccccc23)=NO1]

The title compound (0.06 g, 69%) was obtained using methyl 3-(aminomethyl)-5-(methoxymethyl)-4,5-dihydroisoxazol-5-carboxylate hydrochloride (0.058 g, 0.24 mmol) obtained in (1) above and isoquinolin-1-carboxylic acid (0.073 g, 0.42 mmol) by the preparation method of Example 84-(2).

MS (m/z): 358[M+H]

(3) Preparation of 3-((isoquinolin-1-carboxamido)methyl)-5-(methoxymethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

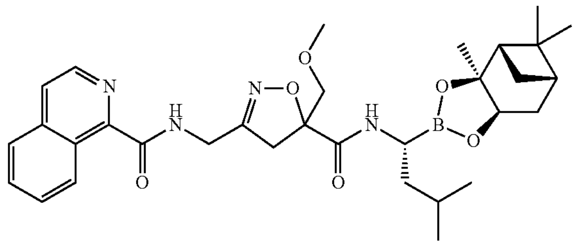 [SMILES: COCC1(C(=O)N[C@@H](CC(C)C)B2O[C@@H]3C[C@@H]4C[C@@H](C4(C)C)[C@]3(C)O2)CC(CNC(=O)c2nccc3ccccc23)=NO1]

The title compound (0.06 g, 64%, 2 steps) was obtained using methyl 3-((isoquinolin-1-carboxamido)methyl)-5-(methoxymethyl)-4,5-dihydroisoxazol-5-carboxylate (0.06 g, 0.17 mmol) obtained in (2) above by the preparation method of Example 84-(3).

MS (m/z): 591[M+H]

(4) Preparation of ((1R)-1-(3-((isoquinolin-1-carboxamido)methyl)-5-(methoxymethyl)-4,5-dihydroisoxazol-5-carboxamido)-3-methylbutyl)boronic acid

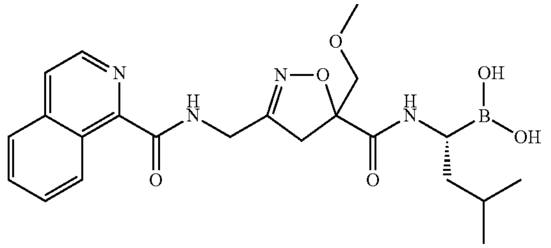 [SMILES: COCC1(C(=O)N[C@@H](CC(C)C)B(O)O)CC(CNC(=O)c2nccc3ccccc23)=NO1]

The title compound (0.032 g, 69%) was obtained using 3-((isoquinolin-1-carboxamido)methyl)-5-(methoxymethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.06 g, 0.10 mmol) obtained in (3) above by the preparation method of Example 1-(4).

NMR: $^1$H-NMR (400 MHz, MeOD-d4); δ 9.10-9.08 (d, 1H), 8.54-8.53 (d, 1H), 8.02-7.97 (m, 2H), 7.84-7.72 (m, 2H), 4.40 (s, 2H), 3.87-3.83 (m, 1H), 3.73-3.69 (m, 1H), 3.45-3.35 (m, 5H), 2.89-2.83 (m, 1H), 1.66 (m, 1H), 1.41-1.35 (m, 2H), 0.92-0.89 (dd, 6H)

MS (m/z): 457[M+H], 439[M-OH]

Example 193: Preparation of ((1R)-1-(5-(ethoxymethyl)-3-((isoquinolin-1-carboxamido)methyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(ethoxymethyl)-4,5-dihydroisoxazol-5-carboxylate hydrochloride

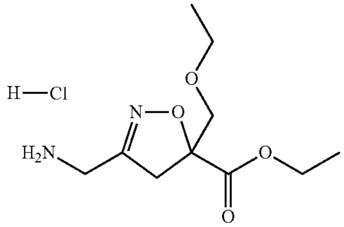 [SMILES: Cl ; CCOCC1(C(=O)OCC)CC(CN)=NO1]

The title compound (0.042 g, quant.) was obtained using ethyl 3-(((tert-butoxycarbonyl)amino)methyl)-5-(ethoxymethyl)-4,5-dihydroisoxazol-5-carboxylate (0.051 g, 0.20 mmol) obtained in Preparation Example 41 by the preparation method of Example 84-(1).

MS (m/z): 231[M+H]

(2) Preparation of ethyl 5-(ethoxymethyl)-3-((isoquinolin-1-carboxamido)methyl)-4,5-dihydroisoxazol-5-carboxylate

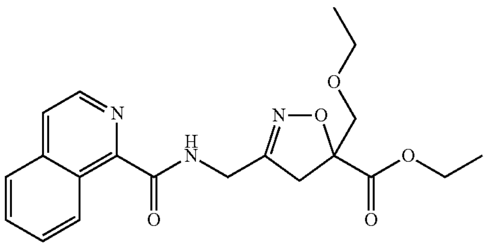 [SMILES: CCOCC1(C(=O)OCC)CC(CNC(=O)c2nccc3ccccc23)=NO1]

The title compound (0.017 g, 44%) was obtained using ethyl 3-(aminomethyl)-5-(ethoxymethyl)-4,5-dihydroisoxazol-5-carboxylate hydrochloride (0.027 g, 0.10 mmol) obtained in (1) above and isoquinolin-1-carboxylic acid (0.019 g, 0.11 mmol) by the preparation method of Example 84-(2).

NMR: $^1$H-NMR (500 MHz, $CDCl_3$); δ 9.57 (1H, d), 8.65 (1H, t), 8.47 (1H, d), 7.86 (1H, d), 7.82 (1H, d), 7.74-7.69 (2H, m), 4.46 (2H, d), 4.25-4.20 (2H, m), 3.75 (2H, s), 3.56-3.51 (2H, m), 3.50 (1H, d), 3.26 (1H, d), 1.28 (3H, t), 1.14 (3H, t)

MS (m/z): 386[M+H]

(3) Preparation of 5-(ethoxymethyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

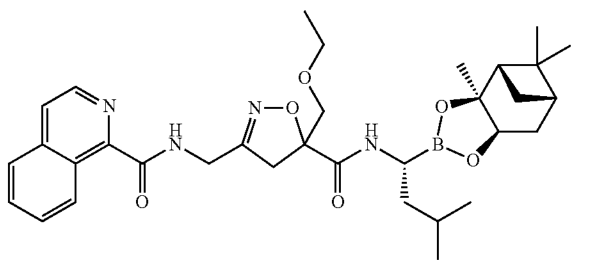 [SMILES: CCOCC1(C(=O)N[C@@H](CC(C)C)B2O[C@@H]3C[C@@H]4C[C@@H](C4(C)C)[C@]3(C)O2)CC(CNC(=O)c2nccc3ccccc23)=NO1]

The title compound (0.011 g, 41%, 2 steps) was obtained using ethyl 5-(ethoxymethyl)-3-((isoquinolin-1-carboxamido)methyl)-4,5-dihydroisoxazol-5-carboxylate (0.017 g, 0.044 mmol) obtained in (2) above by the preparation method of Example 84-(3).

MS (m/z): 605 [M+H]

(4) Preparation of ((1R)-1-(5-(ethoxymethyl)-3-((isoquinolin-1-carboxamido)methyl)-4,5-dihydroisoxazol-5-carboxamido)-3-methylbutyl)boronic acid

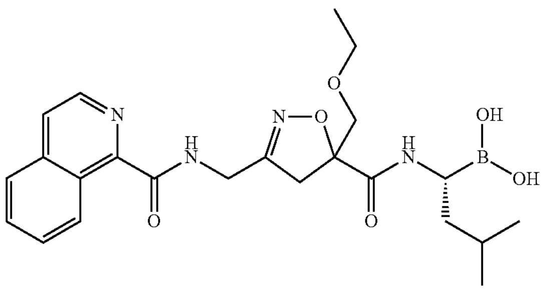 [SMILES: CCOCC1(C(=O)N[C@@H](CC(C)C)B(O)O)CC(CNC(=O)c2nccc3ccccc23)=NO1]

The title compound (0.0044 g, 52%) was obtained using 5-(ethoxymethyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.011 g, 0.018 mmol) obtained in (3) above by the preparation method of Example 1-(4).

NMR: $^1$H-NMR (500 MHz, $CD_3OD$); δ 9.06 (1H, d), 8.49 (1H, d), 7.96 (1H, d), 7.93 (1H, d), 7.77 (1H, t), 7.69 (1H, dd), 4.37 (2H, s), 3.85 (1H, dd), 3.71 (1H, dd), 3.59-3.51 (2H, m), 3.40-3.26 (2H, m), 2.86-2.77 (1H, m), 1.66-1.62 (1H, m), 1.37-1.32 (2H, m), 1.14-1.10 (3H, m), 0.87-0.85 (6H, m)

MS (m/z): 493 [M+Na], 453 [M-OH]

Example 194: Preparation of ((1R)-1-(5-benzyl-3-((S)-3-methyl-1-(6-methylpicolinamido)butyl)-4,5-dihydroisoxazol-5-carboxamido)-3-methylbutyl) boronic acid Through the processes (1), (2) and (3) below, the title compound was obtained.

(1) Preparation of methyl 5-benzyl-3-((S)-3-methyl-1-(6-methylpicolinamido)butyl)-4,5-dihydroisoxazol-5-carboxylate

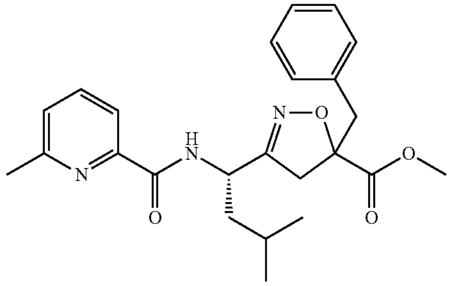

The title compound (0.12 g, 77%) was obtained using methyl 3-((S)-1-amino-3-methylbutyl)-5-benzyl-4,5-dihydroisoxazol-5-carboxylate hydrochloride (0.12 g, 0.35 mmol) obtained in Example 152-(1) and 6-methyl-pyridin-2-carboxylic acid (0.053 g, 0.39 mmol) by the preparation method of Example 84-(2).

MS (m/z): 424[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((S)-3-methyl-1-(6-methylpicolinamido)butyl)-4,5-dihydroisoxazol-5-carboxamide

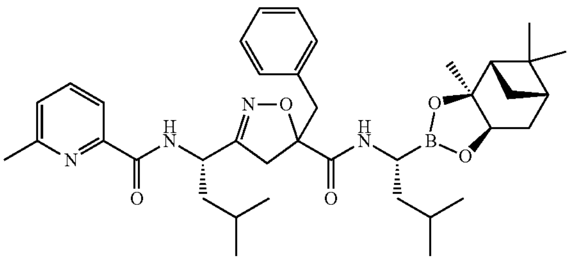

The title compound (0.093 g, 68%, 2 steps) was obtained using methyl 5-benzyl-3-((S)-3-methyl-1-(6-methylpicolinamido)butyl)-4,5-dihydroisoxazol-5-carboxylate (0.12 g, 0.27 mmol) obtained in (1) above by the preparation method of Example 84-(3).

MS (m/z): 657[M+H]

(3) Preparation of ((1R)-1-(5-benzyl-3-((S)-3-methyl-1-(6-methylpicolinamido)butyl)-4,5-dihydroisoxazol-5-carboxamido)-3-methylbutyl)boronic acid

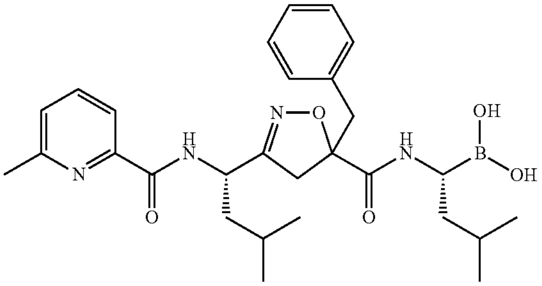 [SMILES: Cc1cccc(C(=O)N[C@@H](CC(C)C)C2=NOC(Cc3ccccc3)(C(=O)N[C@@H](CC(C)C)B(O)O)C2)n1]

The title compound (0.028 g, 29%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((S)-3-methyl-1-(6-methylpicolinamido)butyl)-4,5-dihydroisoxazol-5-carboxamide (0.093 g, 0.91 mmol) obtained in (2) above by the preparation method of Example 1-(4).

NMR: $^{1}$H-NMR (400 MHz, MeOD-d4); δ 7.89-7.83 (m, 2H), 7.47-7.45 (m, 1H), 7.29-7.24 (m, 5H), 5.00-4.96 (m, 1H), 3.43-3.17 (m, 4H), 2.722-2.68 (m, 1H), 2.63 (s, 3H), 1.73-1.69 (m, 1H), 1.58-1.43 (m, 3H), 1.21-1.10 (m, 2H), 0.95-0.87 (dd, 6H), 0.85-0.79 (dd, 6H)

MS (m/z): 523[M+H], 505[M-OH]

Example 195: Preparation of ((1R)-1-(5-benzyl-3-((R)-2-methoxy-1-(6-methylpicolinamido)ethyl)-4,5-dihydroisoxazol-5-carboxamido)-3-methylbutyl) boronic acid Through the processes (1), (2) and (3) below, the title compound was obtained.

(1) Preparation of methyl 5-benzyl-3-((R)-2-methoxy-1-(6-methylpicolinamido)ethyl)-4,5-dihydroisoxazol-5-carboxylate

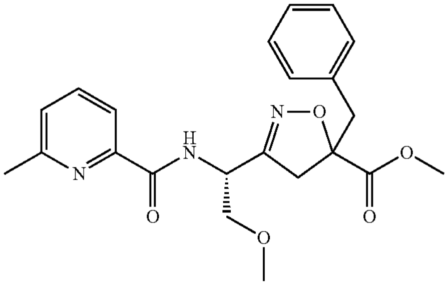

The title compound (0.074 g, 59%) was obtained using methyl 3-((R)-1-amino-2-methoxyethyl)-5-benzyl-4,5-dihydroisoxazol-5-carboxylate hydrochloride (0.1 g, 0.31 mmol) obtained in Example 153-(1) and 6-methyl-pyridin-2-carboxylic acid (0.046 g, 0.34 mmol) by the preparation method of Example 84-(2).

MS (m/z): 412[M+H]

(2) Preparation of 5-benzyl-3-((R)-2-methoxy-1-(6-methylpicolinamido)ethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

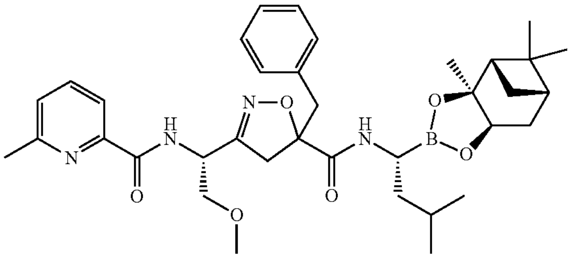

The title compound (0.085 g, 63%, 2 steps) was obtained using methyl 5-benzyl-3-((R)-2-methoxy-1-(6-methylpicolinamido)ethyl)-4,5-dihydroisoxazol-5-carboxylate (0.074 g, 0.18 mmol) obtained in (1) above by the preparation method of Example 84-(3).

MS (m/z): 645[M+H]

(3) Preparation of ((1R)-1-(5-benzyl-3-((R)-2-methoxy-1-(6-methylpicolinamido)ethyl)-4,5-dihydroisoxazol-5-carboxamido)-3-methylbutyl)boronic acid

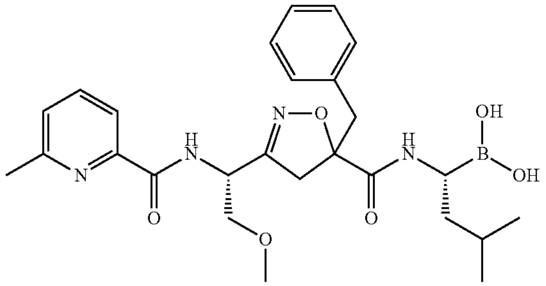 [SMILES: COC[C@H](NC(=O)c1cccc(C)n1)C1=NOC(Cc2ccccc2)(C(=O)N[C@@H](CC(C)C)B(O)O)C1]

The title compound (0.025 g, 39%) was obtained using 5-benzyl-3-((R)-2-methoxy-1-(6-methylpicolinamido)ethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.085 g, 0.13 mmol) obtained in (2) above by the preparation method of Example 1-(4).

NMR: $^1$H-NMR (400 MHz, MeOD-d4); δ 7.92-7.84 (m, 2H), 7.48-7.46 (d, 1H), 7.29-7.24 (m, 5H), 5.06-5.04 (m, 1H), 3.77-3.67 (m, 2H), 3.50-3.44 (m, 1H), 3.38 (s, 3H), 3.37-3.18 (m, 3H), 2.72-2.69 (m, 1H), 2.62 (s, 3H), 1.41-1.40 (m, 1H), 1.19-1.07 (m, 2H), 0.86-0.79 (m, 6H)

MS (m/z): 511[M+H], 493[M-OH]

Example 196: Preparation of ((1R)-1-(5-benzyl-3-((1-cyclopentyl-3-methyl-1H-pyrazol-5-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of 2-cyclopentyl-5-methyl-2H-pyrazol-3-carboxylic acid ethyl ester

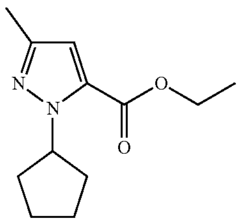 [SMILES: CCOC(=O)c1cc(C)nn1C1CCCC1]

The title compound (0.24 g, 51%) was obtained using 5-methyl-2H-pyrazol-3-carboxylic acid ethyl ester (0.31 g, 2.0 mmol) and bromo-cyclopentane (0.51 g, 3.0 mmol) by the preparation method of Example 188-(1).

(2) Preparation of 2-cyclopentyl-5-methyl-2H-pyrazol-3-carboxylic acid

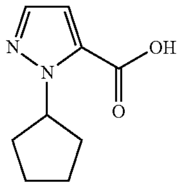 [SMILES: O=C(O)c1ccnn1C1CCCC1]

The title compound (0.19 g, 98%) was obtained using 2-cyclopentyl-5-methyl-2H-pyrazol-3-carboxylic acid ethyl ester (0.24 g, 1.02 mmol) obtained in (1) above by the preparation method of Example 119-(2).

(3) Preparation of methyl 5-benzyl-3-((1-cyclopentyl-3-methyl-1H-pyrazol-5-carboxamido)methyl)-4,5-dihydroisoxazol-5-carboxylate

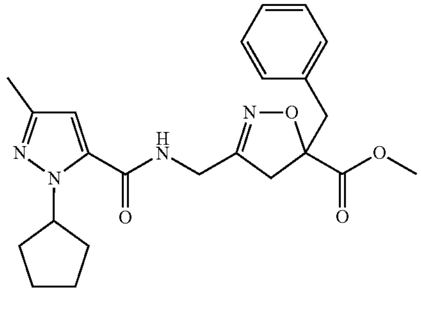

The title compound (0.061 g, 80%) was obtained using methyl 3-(aminomethyl)-5-benzyl-4,5-dihydroisoxazol-5-carboxylate hydrochloride (0.051 g, 0.18 mmol) obtained in Example 84-(1) and 2-cyclopentyl-5-methyl-2H-pyrazol-3-carboxylic acid (0.039 g, 0.20 mmol) obtained in (2) above by the preparation method of Example 84-(2).

NMR: $^1$H-NMR (400 MHz, $CDCl_3$); δ 7.28-7.20 (5H, m), 6.23 (1H, br s), 6.20 (1H, s), 5.46 (1H, q), 4.17-4.11 (2H, m), 3.77 (3H, s), 3.41 (1H, d), 3.32 (1H, d), 3.12 (1H, d), 3.00 (1H, d), 2.26 (3H, s), 2.06-1.99 (4H, m), 1.93-1.86 (2H, m), 1.68-1.60 (2H, m)

MS (m/z): 425[M+H]

(4) Preparation of 5-benzyl-3-((1-cyclopentyl-3-methyl-1H-pyrazol-5-carboxamido)methyl)-N—((R)-3-methyl-1-((3aS,4S,6S,7aR)-3a,5,5-trimethyl-hexahydro-4,6-metanobenzo[d][1,3,2]dioxaborol-2-yl)butyl)-4,5-dihydroisoxazol-5-carboxamide N, 6

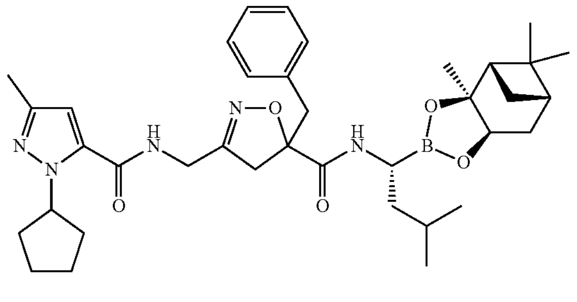

The title compound (0.073 g, 78%, 2 steps) was obtained using methyl 5-benzyl-3-((1-cyclopentyl-3-methyl-1H-pyrazol-5-carboxamido)methyl)-4,5-dihydroisoxazol-5-carboxylate (0.061 g, 0.144 mmol) obtained in (3) above by the preparation method of Example 84-(3).

MS (m/z): 658[M+H]

(5) Preparation of ((1R)-1-(5-benzyl-3-((1-cyclopentyl-3-methyl-1H-pyrazol-5-carboxamido)methyl)-4,5-dihydroisoxazol-5-carboxamido)-3-methylbutyl)boronic acid

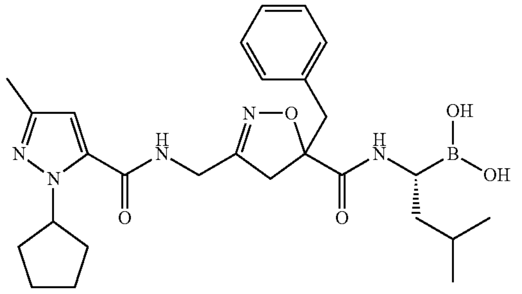 [SMILES: Cc1cc(C(=O)NCC2=NOC(Cc3ccccc3)(C(=O)N[C@@H](CC(C)C)B(O)O)C2)n(C2CCCC2)n1]

The title compound (0.037 g, 64%) was obtained using 5-benzyl-3-((1-cyclopentyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.073 g, 0.111 mmol) obtained in (4) above by the preparation method of Example 1-(4).

NMR: $^1$H-NMR (500 MHz, $CD_3OD$); δ 7.29-7.23 (5H, m), 6.42 (1H, s), 5.48 (1H, q), 5.47 (1H, s), 4.14 (2H, d), 3.37 (1H, d), 3.33-3.23 (2H, m), 3.19 (1H, d), 2.64 (1H, dd), 2.22 (3H, s), 2.06-1.87 (6H, m), 1.66-1.63 (2H, m), 1.37-0.99 (3H, m), 0.78 (6H, dd)

MS (ES+): 546 [M+Na], 506 [M-OH]

Example 197: Preparation of ((1R)-1-(5-benzyl-3-((1-(tetrahydro-2H-pyran-4-yl)-1H-pyrazol-5-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of 2-(tetrahydro-pyran-4-yl)-2H-pyrazol-3-carboxylic acid ethyl ester

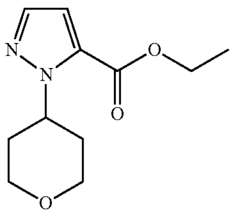 [SMILES: CCOC(=O)c1ccnn1C1CCOCC1]

The title compound (0.02 g, 16%) was obtained using 2H-pyrazol-3-carboxylic acid ethyl ester (0.12 g, 0.5 mmol), methanesulfonic acid tetrahydro-pyran-4-yl ester (0.09 g, 0.5 mmol), and iodo tetrabutylammonium salt (0.037 g, 0.2 mmol) by the preparation method of Example 188-(1).

(2) Preparation of 2-(tetrahydro-pyran-4-yl)-2H-pyrazol-3-carboxylic acid

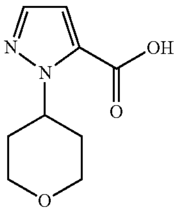 [SMILES: O=C(O)c1ccnn1C1CCOCC1]

The title compound (0.014 g, 88%) was obtained using 2-(tetrahydro-pyran-4-yl)-2H-pyrazol-3-carboxylic acid ethyl ester (0.02 g, 0.081 mmol) obtained in (1) above by the preparation method of Example 119-(2).

(3) Preparation of methyl 5-benzyl-3-((1-(tetrahydro-2H-pyran-4-yl)-1H-pyrazol-5-carboxamido)methyl)-4,5-dihydroisoxazol-5-carboxylate

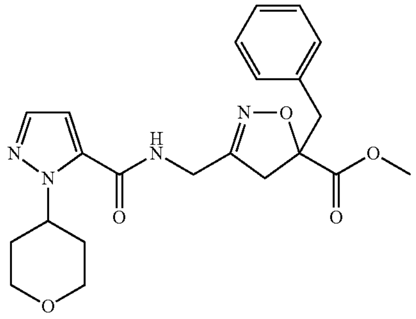 [SMILES: COC(=O)C1(Cc2ccccc2)CC(CNC(=O)c2ccnn2C2CCOCC2)=NO1]

The title compound (0.015 g, 50%) was obtained using methyl 3-(aminomethyl)-5-benzyl-4,5-dihydroisoxazol-5-carboxylate hydrochloride (0.021 g, 0.074 mmol) obtained in Example 84-(1) and 2-(tetrahydro-pyran-4-yl)-2H-pyrazol-3-carboxylic acid (0.014 g, 0.071 mmol) obtained in (2) above by the preparation method of Example 84-(2).

NMR: $^1$H-NMR (500 MHz, $CDCl_3$); δ 7.49 (1H, d), 7.25-7.21 (5H, m), 6.46 (1H, d), 6.30 (1H, t), 5.28-5.24 (1H, m), 4.14 (2H, d), 4.11-4.07 (2H, m), 3.78 (3H, s), 3.57-3.52 (2H, m), 3.41 (1H, d), 3.33 (1H, d), 3.12 (1H, d), 2.99 (1H, d), 2.31-2.25 (2H, m), 1.93-1.89 (2H, m)

MS (m/z): 427[M+H]

(4) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-(tetrahydro-2H-pyran-4-yl)-1H-pyrazol-5-carboxamido)methyl)-4,5-dihydroisoxazol-5-carboxamide

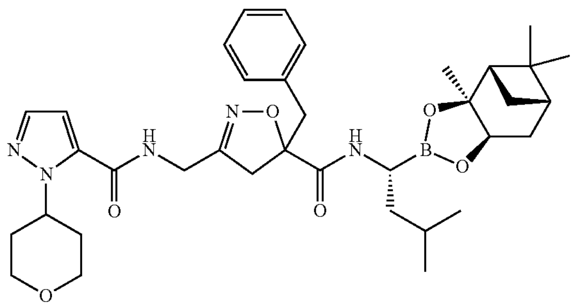 [SMILES: CC(C)C[C@H](NC(=O)C1(Cc2ccccc2)CC(CNC(=O)c2ccnn2C2CCOCC2)=NO1)B1O[C@@H]2C[C@@H]3C[C@@H](C3(C)C)[C@]2(C)O1]

The title compound (0.012 g, 51%, 2 steps) was obtained using methyl 5-benzyl-3-((1-(tetrahydro-2H-pyran-4-yl)-1H-pyrazol-5-carboxamido)methyl)-4,5-dihydroisoxazol-5-carboxylate (0.015 g, 0.035 mmol) obtained in (3) above by the preparation method of Example 84-(3).

MS (m/z): 660[M+H]

(5) Preparation of ((1R)-1-(5-benzyl-3-((1-(tetrahydro-2H-pyran-4-yl)-1H-pyrazol-5-carboxamido)methyl)-4,5-dihydroisoxazol-5-carboxamido)-3-methylbutyl)boronic acid

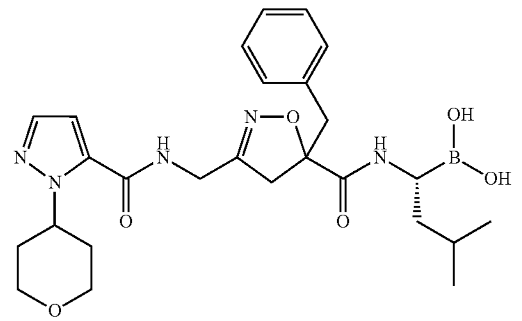 [SMILES: CC(C)C[C@H](NC(=O)C1(Cc2ccccc2)CC(CNC(=O)c2ccnn2C2CCOCC2)=NO1)B(O)O]

The title compound (0.0042 g, 44%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-(tetrahydro-2H-pyran-4-yl)-1H-pyrazol-5-carboxamido)methyl)-4,5-dihydroisoxazol-5-carboxamide (0.012 g, 0.018 mmol) obtained in (4) above by the preparation method of Example 1-(4).

NMR: $^1$H-NMR (400 MHz, $CD_3OD$); δ 7.53 (1H, d), 7.29-7.24 (5H, m), 6.74 (1H, d), 5.40-5.35 (1H, m), 4.20 (2H, d), 4.09-4.05 (2H, m), 3.61-3.54 (2H, m), 3.45 (1H, d), 3.37-3.28 (2H, m), 3.22 (1H, d), 2.68 (1H, t), 2.25-2.20 (2H, m), 1.95-1.91 (2H, m), 1.42-1.05 (3H, m), 0.82 (6H, dd)

MS (ES+): 548 [M+Na], 508 [M-OH]

Example 198: Preparation of ((1R)-1-(3-((isoquinolin-1-carboxamido)methyl)-3a,5,6,6a-tetrahydro-4H-cyclopenta[d]isoxazol-6a-carboxamido)-3-methylbutyl)boronic acid Through the processes (1), (2), (3) and (4) below, the title compound was obtained.

(1) Preparation of methyl 3-(aminomethyl)-3a,4,5,6-tetrahydro-6aH-cyclopenta[d]isoxazol-6a-carboxylate hydrochloride

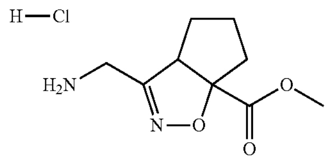

The title compound (0.115 g, quant.) was obtained using methyl 3-(((tert-butoxycarbonyl)amino)methyl)-3a,4,5,6-tetrahydro-6aH-cyclopenta[d]isoxazol-6a-carboxylate (0.148 g, 0.496 mmol) obtained in Preparation Example 42 by the preparation method of Example 84-(1).

(2) Preparation of methyl 3-((isoquinolin-1-carboxamido)methyl)-3a,4,5,6-tetrahydro-6aH-cyclopenta[d]isoxazol-6a-carboxylate

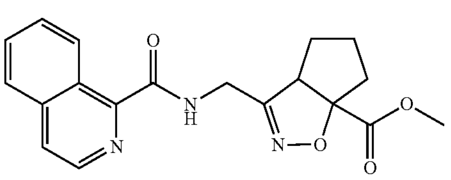 [SMILES: COC(=O)C12CCCC1C(CNC(=O)c1nccc3ccccc13)=NO2]

The title compound (0.085 g, 49%) was obtained using methyl 3-(aminomethyl)-3a,4,5,6-tetrahydro-6aH-cyclopenta[d]isoxazol-6a-carboxylate hydrochloride (0.115 g, 0.49 mmol) obtained in (1) above and isoquinolin-1-carboxylic acid (0.110 g, 0.64 mmol) by the preparation method of Example 84-(2).

NMR: $^1$H-NMR (400 MHz, $CDCl_3$); δ 9.54 (1H, d), 8.65 (1H, t), 8.45 (1H, d), 7.83-7.68 (4H, m), 4.50 (1H, dd), 4.35 (1H, dd), 3.90 (1H, d), 3.76 (3H, s), 2.28-1.62 (6H, m)

MS (m/z): 354[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-3a,4,5,6-tetrahydro-6aH-cyclopenta[d]isoxazol-6a-carboxamide

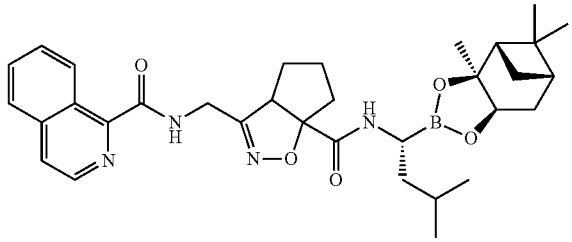 [SMILES: CC(C)C[C@H](NC(=O)C12CCCC1C(CNC(=O)c1nccc3ccccc13)=NO2)B1O[C@@H]2C[C@@H]3C[C@@H](C3(C)C)[C@]2(C)O1]

The title compound (0.090 g, 64%, 2 steps) was obtained using methyl 3-((isoquinolin-1-carboxamido)methyl)-3a,4,5,6-tetrahydro-6aH-cyclopenta[d]isoxazol-6a-carboxylate (0.085 g, 0.24 mmol) obtained in (2) above by the preparation method of Example 84-(3).

MS (m/z): 587[M+H]

(4) Preparation of ((1R)-1-(3-((isoquinolin-1-carboxamido)methyl)-3a,5,6,6a-tetrahydro-4H-cyclopenta[d]isoxazol-6a-carboxamido)-3-methylbutyl)boronic acid

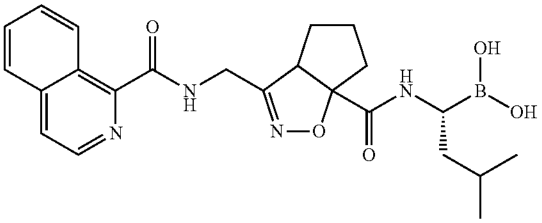 [SMILES: CC(C)C[C@H](NC(=O)C12CCCC1C(CNC(=O)c1nccc3ccccc13)=NO2)B(O)O]

The title compound (0.04 g, 58%) was obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-3a,4,5,6-tetrahydro-6aH-cyclopenta[d]isoxazol-6a-carboxamide (0.09 g, 0.153 mmol) obtained in (3) above by the preparation method of Example 1-(4).

NMR: $^1$H-NMR (400 MHz, $CD_3OD$); δ 9.09 (1H, dd), 8.53 (1H, d), 7.98 (2H, dd), 7.83 (1H, dt), 7.73 (1H, dt), 4.43 (1H, dd), 4.37 (1H, d), 3.98 (1H, t), 2.79 (1H, q), 2.25-1.35 (9H, m), 0.91-0.88 (6H, m)

MS (ES+): 475[M+Na], 435[M-OH]

Example 199: Preparation of ((1R)-1-(3-((imidazo[1,2-a]pyridin-8-carboxamido)methyl)-3a,5,6,6a-tetrahydro-4H-cyclopenta[d]isoxazol-6a-carboxamido)-3-methylbutyl)boronic acid Through the processes (1), (2) and (3) below, the title compound was obtained.

(1) Preparation of methyl 3-((imidazo[1,2-a]pyridin-8-carboxamido)methyl)-3a,4,5,6-tetrahydro-6aH-cyclopenta[d]isoxazol-6a-carboxylate

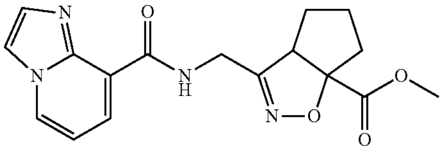 [SMILES: COC(=O)C12CCCC1C(CNC(=O)c1cccn3ccnc13)=NO2]

The title compound (0.037 g, 54%) was obtained using methyl 3-(aminomethyl)-3a,4,5,6-tetrahydro-6aH-cyclopenta[d]isoxazol-6a-carboxylate hydrochloride (0.047 g, 0.20 mmol) obtained in Example 198-(1) and imidazo[1,2-a]pyridin-8-carboxylic acid (0.052 g, 0.26 mmol) by the preparation method of Example 84-(2).

NMR: $^1$H-NMR (400 MHz, $CDCl_3$); δ 10.68 (1H, s), 8.27 (1H, dd), 8.16 (1H, dd), 7.64-7.60 (2H, m), 6.93 (1H, t), 4.52 (1H, dd), 4.41 (1H, dd), 3.89 (1H, d), 3.74 (3H, s), 2.26-1.59 (6H, m)

MS (m/z): 354[M+H]

(2) Preparation of 3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-3a,4,5,6-tetrahydro-6aH-cyclopenta[d]isoxazol-6a-carboxamide

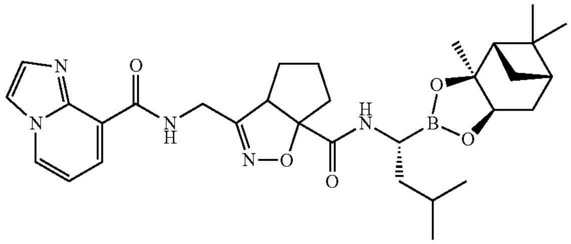 [SMILES: CC(C)C[C@H](NC(=O)C12CCCC1C(CNC(=O)c1cccn3ccnc13)=NO2)B1O[C@@H]2C[C@@H]3C[C@@H](C3(C)C)[C@]2(C)O1]

The title compound (0.024 g, 38%, 2 steps) was obtained using methyl 3-((imidazo[1,2-a]pyridin-8-carboxamido)methyl)-3a,4,5,6-tetrahydro-6aH-cyclopenta[d]isoxazol-6a-carboxylate (0.037 g, 0.11 mmol) obtained in (1) above by the preparation method of Example 84-(3).

MS (m/z): 587[M+H]

(3) Preparation of ((1R)-1-(3-((imidazo[1,2-a]pyridin-8-carboxamido)methyl)-3a,5,6,6a-tetrahydro-4H-cyclopenta[d]isoxazol-6a-carboxamido)-3-methylbutyl)boronic acid

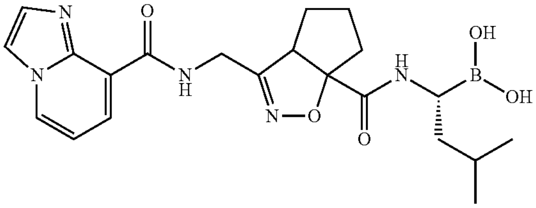 [SMILES: CC(C)C[C@H](NC(=O)C12CCCC1C(CNC(=O)c1cccn3ccnc13)=NO2)B(O)O]

The title compound (0.007 g, 38%) was obtained using 3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-3a,4,5,6-tetrahydro-6aH-cyclopenta[d]isoxazol-6a-carboxamide (0.024 g, 0.042 mmol) obtained in (2) above by the preparation method of Example 1-(4).

NMR: $^1$H-NMR (400 MHz, $CD_3OD$); δ 8.66 (1H, d), 8.11 (1H, d), 7.98 (1H, s), 7.69 (1H, s), 7.08 (1H, t), 4.48 (2H, q), 3.94 (1H, dd), 2.79 (1H, q), 2.18-1.31 (9H, m), 0.89 (6H, dd)

MS (m/z): 464[M+Na], 424[M-OH]

Example 200: Preparation of ((1R)-1-(3-((1H-indazol-3-carboxamido)methyl)-5-benzyl-4,5-dihydroisoxazol-5-carboxamido)-3-methylbutyl)boronic acid Through the processes (1), (2) and (3) below, the title compound was obtained.

(1) Preparation of methyl 3-((1H-indazol-3-carboxamido)methyl)-5-benzyl-4,5-dihydroisoxazol-5-carboxylate

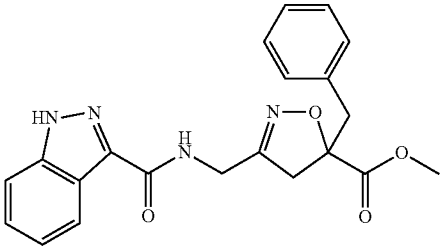 [SMILES: COC(=O)C1(Cc2ccccc2)CC(CNC(=O)c2n[nH]c3ccccc23)=NO1]

The title compound (0.058 g, 84%) was obtained using methyl 3-(aminomethyl)-5-benzyl-4,5-dihydroisoxazol-5-carboxylate hydrochloride (0.05 g, 0.18 mmol) obtained in Example 84-(1) and 1H-indazol-3-carboxylic acid (1.1 mmol) by the preparation method of Example 84-(2).

NMR: $^1$H-NMR (400 MHz, $CDCl_3$); δ 11.19 (br s, 1H), 8.36-8.34 (dd, 1H), 7.68-7.65 (t, 1H), 7.56-7.54 (d, 1H), 7.46-7.42 (m, 1H) 7.32-7.28 (m, 1H), 7.21-7.09 (m, 5H), 4.36-4.22 (m, 2H), 3.76 (s, 3H), 3.56-3.12 (m, 4H)

MS (m/z): 393[M+H]

(2) Preparation of 3-((1H-indazol-3-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

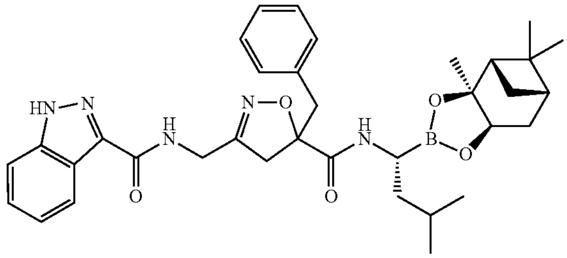 [SMILES: CC(C)C[C@H](NC(=O)C1(Cc2ccccc2)CC(CNC(=O)c2n[nH]c3ccccc23)=NO1)B1O[C@@H]2C[C@@H]3C[C@@H](C3(C)C)[C@]2(C)O1]

The title compound (0.04 g, 43%, 2 steps) was obtained using methyl 3-((1H-indazol-3-carboxamido)methyl)-5-benzyl-4,5-dihydroisoxazol-5-carboxylate (0.058 g, 0.15 mmol) obtained in (1) above by the preparation method of Example 84-(3).

MS (m/z): 626[M+H]

(3) Preparation of ((1R)-1-(3-((1H-indazol-3-carboxamido)methyl)-5-benzyl-4,5-dihydroisoxazol-5-carboxamido)-3-methylbutyl)boronic acid

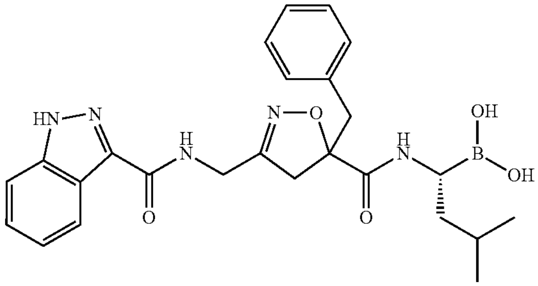 [SMILES: CC(C)C[C@H](NC(=O)C1(Cc2ccccc2)CC(CNC(=O)c2n[nH]c3ccccc23)=NO1)B(O)O]

The title compound (0.015 g, 48%) was obtained using 3-((1H-indazol-3-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.04 g, 0.064 mmol) obtained in (2) above by the preparation method of Example 1-(4).

NMR: $^1$H-NMR (400 MHz, $CDCl_3$); δ 11.52 (br s, 1H), 8.32-8.30 (d, 1H), 7.72 (m, 1H), 7.52-7.50 (d, 1H), 7.41-7.37 (m, 1H), 7.27-7.21 (m, 7H), 4.44 (m, 1H), 4.13-4.09 (m, 1H), 3.42-3.02 (m, 4H), 2.66 (m, 1H), 1.21-1.02 (m, 3H), 0.65 (m, 6H)

MS (m/z): 492[M+H], 474[M-OH].

Example 201: Preparation of ((1R)-1-(5-benzyl-3-((1-methyl-1H-indazol-3-carboxamido)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-((1-methyl-1H-indazol-3-carboxamido)methyl)-4,5-dihydroisoxazol-5-carboxylate

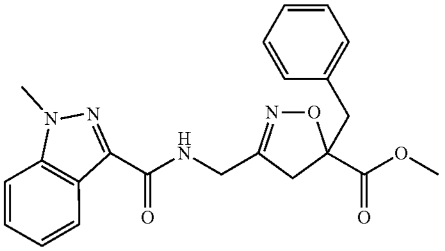 [SMILES: COC(=O)C1(Cc2ccccc2)CC(CNC(=O)c2nn(C)c3ccccc23)=NO1]

The title compound (0.047 g, 66%) was obtained using methyl 3-(aminomethyl)-5-benzyl-4,5-dihydroisoxazol-5-carboxylate hydrochloride (0.05 g, 0.18 mmol) obtained in Example 84-(1) and 1-methyl-1H-indazol-3-carboxylic acid (0.034 g, 0.19 mmol) by the preparation method of Example 84-(2).

NMR: $^1$H-NMR (400 MHz, $CDCl_3$); δ 8.33-8.31 (dd, 1H), 7.47-7.41 (m, 2H), 7.32-7.29 (m, 1H), 7.24-7.19 (m, 5H), 7.17-7.14 (m, 1H), 4.28-4.26 (m, 2H), 4.11 (s, 3H), 3.76 (s, 3H), 3.49-3.45 (d, 1H), 3.23-3.28 (d, 1H), 3.15-3.05 (m, 2H)

MS (m/z): 407[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-indazol-3-carboxamido)methyl)-4,5-dihydroisoxazol-5-carboxamide

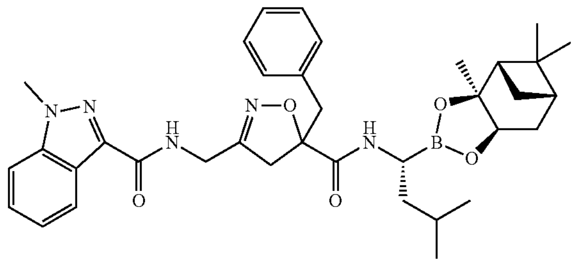 [SMILES: CC(C)C[C@H](NC(=O)C1(Cc2ccccc2)CC(CNC(=O)c2nn(C)c3ccccc23)=NO1)B1O[C@@H]2C[C@@H]3C[C@@H](C3(C)C)[C@]2(C)O1]

The title compound (0.048 g, 66%, 2 steps) was obtained using methyl 5-benzyl-3-((1-methyl-1H-indazol-3-carboxamido)methyl)-4,5-dihydroisoxazol-5-carboxylate (0.047 g, 0.12 mmol) obtained in (1) above by the preparation method of Example 84-(3).

MS (m/z): 640[M+H]

(3) Preparation of ((1R)-1-(5-benzyl-3-((1-methyl-1H-indazol-3-carboxamido)methyl)-4,5-dihydroisoxazol-5-carboxamido)-3-methylbutyl)boronic acid

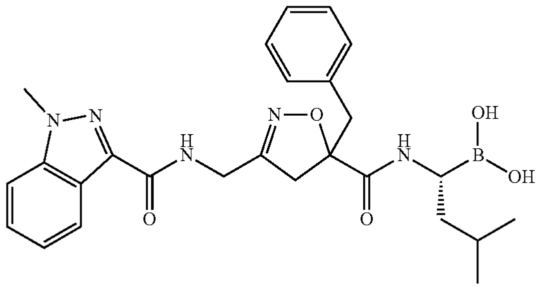 [SMILES: CC(C)C[C@H](NC(=O)C1(Cc2ccccc2)CC(CNC(=O)c2nn(C)c3ccccc23)=NO1)B(O)O]

The title compound (0.021 g, 55%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-indazol-3-carboxamido)methyl)-4,5-dihydroisoxazol-5-carboxamide (0.048 g, 0.075 mmol) obtained in (2) above by the preparation method of Example 1-(4).

NMR: $^1$H-NMR (400 MHz, $CDCl_3$); δ 8.31-8.29 (dd, 1H), 7.44-7.36 (m, 2H), 7.31-7.21 (m, 8H), 4.35-4.20 (m, 2H), 4.00 (s, 3H), 3.46-3.33 (m, 2H), 3.14-3.08 (m, 2H0, 2.78 (m, 1H), 1.32-1.16 (m, 3H), 0.77-0.76 (d, 6H)

MS (m/z): 506[M+H], 488[M-OH]

Example 202: Preparation of ((1R)-1-(5-benzyl-3-((1-isopropyl-1H-indazol-3-carboxamido)methyl)-4,5-dihydroisoxazol-5-carboxamido)-3-methylbutyl) boronic acid Through the processes (1), (2), (3) and (4) below, the title compound was obtained.

(1) Preparation of 1-isopropyl-1H-indazol-3-carboxylic acid

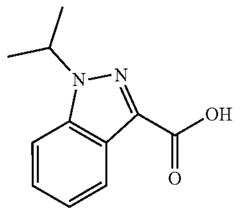

1H-indazol-3-carboxylic acid methyl ester (0.5 g, 2.84 mmol) was dissolved in dimethylformamide (10 ml). At 0° C., sodium hydride (0.15 g, 3.69 mmol) and iodopropane (0.34 ml) were added in order, followed by stirring at room temperature for 16 hours. The solvent was distilled under a reduced pressure, water was added, and extraction with ethyl acetate was performed. The resultant product was washed with brine, dried over anhydrous magnesium sulfate, and filtered. The filtrate was distilled under a reduced pressure and separated by column chromatography to obtain 1-isopropyl-1H-indazol-3-carboxylic acid methyl ester (0.24 g, 39%).

The title compound (0.21 g, 95%) was obtained using 1-isopropyl-1H-indazol-3-carboxylic acid methyl ester (0.24 g, 1.10 mmol) obtained above by the preparation method of Example 119-(2).

MS (m/z): 205[M+H]

(2) Preparation of methyl 5-benzyl-3-((1-isopropyl-1H-indazol-3-carboxamido)methyl)-4,5-dihydroisoxazol-5-carboxylate

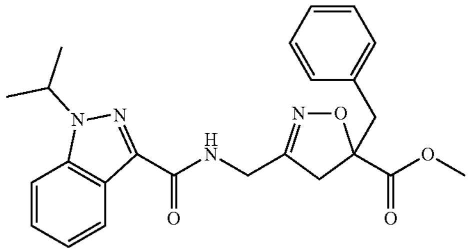 [SMILES: COC(=O)C1(Cc2ccccc2)CC(CNC(=O)c2nn(C(C)C)c3ccccc23)=NO1]

The title compound (0.059 g, 77%) was obtained using methyl 3-(aminomethyl)-5-benzyl-4,5-dihydroisoxazol-5-carboxylate hydrochloride (0.05 g, 0.18 mmol) obtained in Example 84-(1) and 1-isopropyl-1H-indazol-3-carboxylic acid (0.039 g, 0.19 mmol) obtained in (1) above by the preparation method of Example 84-(2).

NMR: $^1$H-NMR (400 MHz, $CDCl_3$); δ 8.35-8.33 (d, 1H), 7.84-7.40 (m, 2H), 7.31-7.27 (m, 1H), 7.23-7.19 (m, 6H), 4.20-4.85 (m, 1H), 4.33-4.23 (m, 2H), 3.76 (s, 3H), 3.50-3.46 (d, 1H), 3.33-3.29 (d, 1H), 3.15-3.08 (m, 2H), 1.63-1.59 (t, 3H)

MS (m/z): 435[M+H]

(3) Preparation of 5-benzyl-3-((1-isopropyl-1H-indazol-3-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

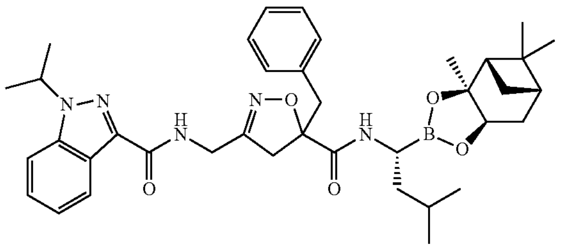 [SMILES: CC(C)C[C@H](NC(=O)C1(Cc2ccccc2)CC(CNC(=O)c2nn(C(C)C)c3ccccc23)=NO1)B1O[C@@H]2C[C@@H]3C[C@@H](C3(C)C)[C@]2(C)O1]

The title compound (0.067 g, 74%, 2 steps) was obtained using methyl 5-benzyl-3-((1-isopropyl-1H-indazol-3-carboxamido)methyl)-4,5-dihydroisoxazol-5-carboxylate (0.059 g, 0.14 mmol) obtained in (2) above by the preparation method of Example 84-(3).

MS (m/z): 668[M+H]

(4) Preparation of ((1R)-1-(5-benzyl-3-((1-isopropyl-1H-indazol-3-carboxamido)methyl)-4,5-dihydroisoxazol-5-carboxamido)-3-methylbutyl)boronic acid

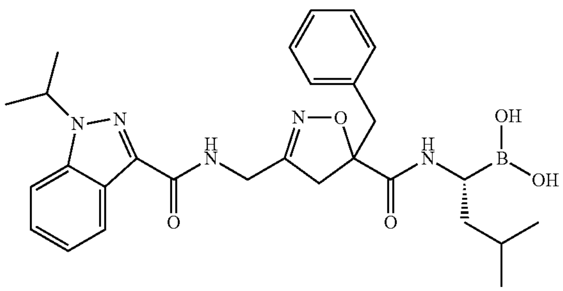 [SMILES: CC(C)C[C@H](NC(=O)C1(Cc2ccccc2)CC(CNC(=O)c2nn(C(C)C)c3ccccc23)=NO1)B(O)O]

The title compound (0.032 g, 60%) was obtained using 5-benzyl-3-((1-isopropyl-1H-indazol-3-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.067 g, 0.1 mmol) obtained in (3) above by the preparation method of Example 1-(4).

NMR: $^1$H-NMR (400 MHz, $CDCl_3$); δ 8.33-8.30 (m, 1H), 7.46-7.38 (m, 2H), 7.28-7.21 (m, 7H), 7.16-7.15 (m, 1H), 4.89-4.82 (m, 1H), 4.26-4.24 (d, 2H), 3.46-3.42 (d, 1H), 3.35-3.32 (d, 1H), 3.15-3.10 (m, 2H), 2.85 (m, 1H), 1.59-1.57 (t, 3H), 1.36-1.20 (m, 3H), 0.82-0.79 (m, 6H)

MS (m/z): 534[M+H], 516[M-OH]

Example 203: Preparation of ((1R)-1-(5-(2,3-difluorobenzyl)-3-((isoquinolin-1-carboxamido)methyl)-4,5-dihydroisoxazol-5-carboxamido)-3-methylbutyl) boronic acid Through the processes (1), (2), (3) and (4) below, the title compound was obtained.

(1) Preparation of ethyl 3-(aminomethyl)-5-(2,3-difluorobenzyl)-4,5-dihydroisoxazol-5-carboxylate hydrochloride

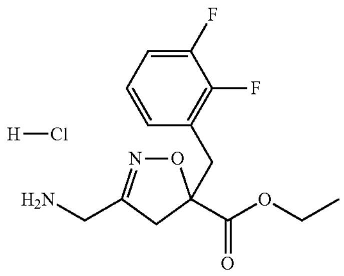 [SMILES: Cl ; CCOC(=O)C1(Cc2cccc(F)c2F)CC(CN)=NO1]

The title compound (0.19 g, 99%) was obtained using ethyl 3-(((tert-butoxycarbonyl)amino)methyl)-5-(2,3-difluorobenzyl)-4,5-dihydroisoxazol-5-carboxylate (0.23 g, 0.57 mmol) obtained in Preparation Example 43 by the preparation method of Example 84-(1).

MS (m/z): 299[M+H]

(2) Preparation of ethyl 5-(2,3-difluorobenzyl)-3-((isoquinolin-1-carboxamido)methyl)-4,5-dihydroisoxazol-5-carboxylate

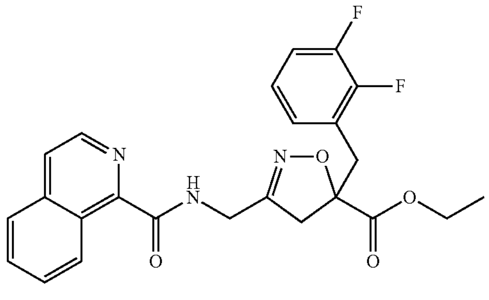 [SMILES: CCOC(=O)C1(Cc2cccc(F)c2F)CC(CNC(=O)c2nccc3ccccc23)=NO1]

The title compound (0.09 g, 70%) was obtained using ethyl 3-(aminomethyl)-5-(2,3-difluorobenzyl)-4,5-dihydroisoxazol-5-carboxylate hydrochloride (0.095 g, 0.28 mmol) obtained in (1) above and isoquinolin-1-carboxylic acid (0.054 g, 0.31 mmol) by the preparation method of Example 84-(2).

MS (m/z): 454[M+H]

(3) Preparation of 5-(2,3-difluorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

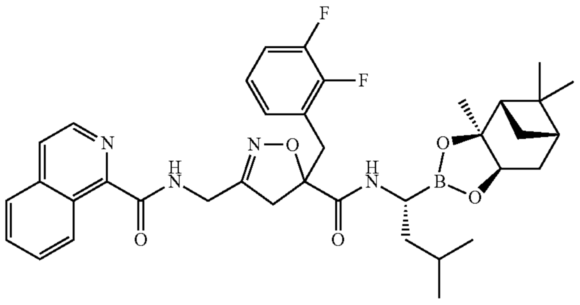 [SMILES: CC(C)C[C@H](NC(=O)C1(Cc2cccc(F)c2F)CC(CNC(=O)c2nccc3ccccc23)=NO1)B1O[C@@H]2C[C@@H]3C[C@@H](C3(C)C)[C@]2(C)O1]

The title compound (0.047 g, 35%, 2 steps) was obtained using ethyl 5-(2,3-difluorobenzyl)-3-((isoquinolin-1-carboxamido)methyl)-4,5-dihydroisoxazol-5-carboxylate (0.09 g, 0.20 mmol) obtained in (2) above by the preparation method of Example 84-(3).

MS (m/z): 673[M+H]

(4) Preparation of ((1R)-1-(5-(2,3-difluorobenzyl)-3-((isoquinolin-1-carboxamido)methyl)-4,5-dihydroisoxazol-5-carboxamido)-3-methylbutyl)boronic acid

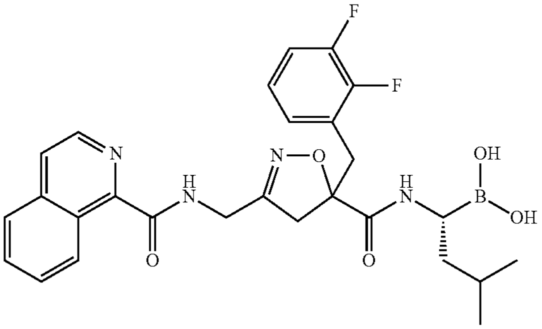 [SMILES: CC(C)C[C@H](NC(=O)C1(Cc2cccc(F)c2F)CC(CNC(=O)c2nccc3ccccc23)=NO1)B(O)O]

The title compound (0.021 g, 56%) was obtained using 5-(2,3-difluorobenzyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.047 g, 0.070 mmol) obtained in (3) above by the preparation method of Example 1-(4).

NMR: $^1$H-NMR (400 MHz, $CDCl_3$); δ 9.50-9.48 (d, 1H), 8.59-8.56 (t, 1H), 8.40-8.38 (d, 1H), 7.84-7.64 (m, 4H), 7.27 (m, 1H), 7.07-6.98 (m, 3H) 4.42-4.27 (m, 2H), 3.51-3.47 (d, 1H), 3.38-3.26 (dd, 2H), 3.19-3.15 (d, 1H), 1.43-1.22 (m, 3H), 0.80-0.78 (d, 6H)

MS (m/z): 539[M+H], 521[M-OH]

Example 204: Preparation of ((1R)-1-(5-benzyl-3-((1-methyl-1H-indazol-4-carboxamido)methyl)-4,5-dihydroisoxazol-5-carboxamido)-3-methylbutyl) boronic acid Through the processes (1), (2), (3) and (4) below, the title compound was obtained.

(1) Preparation of 1-methyl-1H-indazol-4-carboxylic acid

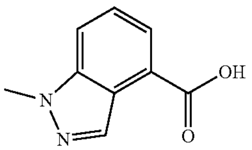

The title compound (0.29 g, 58%, 2 steps) was obtained using 1H-indazol-4-carboxylic acid methyl ester (0.5 g, 2.84 mmol) and iodomethane (0.21 ml) by the preparation method of Example 202-(1).

(2) Preparation of methyl 5-benzyl-3-((1-methyl-1H-indazol-4-carboxamido)methyl)-4,5-dihydroisoxazol-5-carboxylate

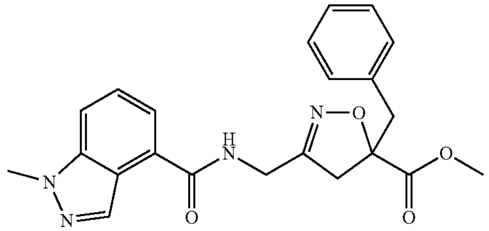

The title compound (0.063 g, 88%) was obtained using methyl 3-(aminomethyl)-5-benzyl-4,5-dihydroisoxazol-5-carboxylate hydrochloride (0.05 g, 0.18 mmol) obtained in Example 84-(1) and 1-methyl-1H-indazol-4-carboxylic acid (0.034, 0.19 mmol) obtained in (1) above by the preparation method of Example 84-(2).

MS (m/z): 407[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-indazol-4-carboxamido)methyl)-4,5-dihydroisoxazol-5-carboxamide

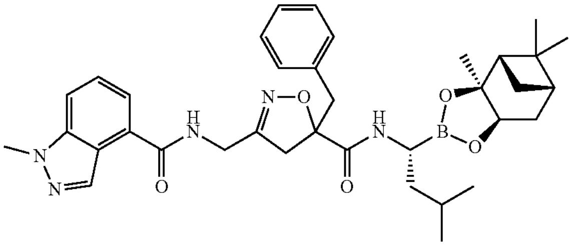

The title compound (0.070 g, 66%, 2 steps) was obtained using methyl 5-benzyl-3-((1-methyl-1H-indazol-4-carboxamido)methyl)-4,5-dihydroisoxazol-5-carboxylate (0.063 g, 0.16 mmol) obtained in (2) above by the preparation method of Example 84-(3).

MS (m/z): 640[M+H]

(4) Preparation of ((1R)-1-(5-benzyl-3-((1-methyl-1H-indazol-4-carboxamido)methyl)-4,5-dihydroisoxazol-5-carboxamido)-3-methylbutyl)boronic acid

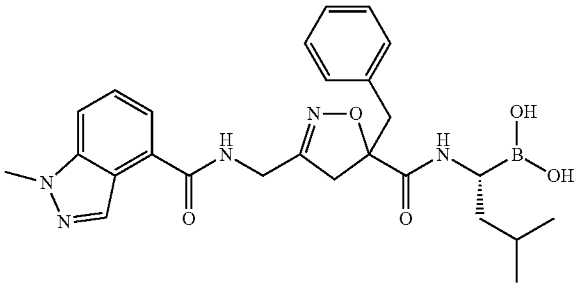 [SMILES: CC(C)C[C@H](NC(=O)C1(Cc2ccccc2)CC(CNC(=O)c2cccc3c2cnn3C)=NO1)B(O)O]

The title compound (0.029 g, 53%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-indazol-4-carboxamido) methyl)-4,5-dihydroisoxazol-5-carboxamide (0.070 g, 0.11 mmol) obtained in (3) above by the preparation method of Example 1-(4).

NMR: $^1$H-NMR (400 MHz, $CDCl_3$); δ 8.28-8.26 (d, 1H), 7.52-7.28 (m, 4H), 7.27-7.22 (m, 5H), 6.79 (m, 1H), 4.40-4.15 (m, 2H), 4.08 (s, 3H), 3.46-6.42 (d, 1H), 3.38-3.35 (d, 1H), 3.19-3.15 (d, 1H), 3.11-3.07 (d, 1H), 2.82 (m, 1H), 1.39-1.23 (m, 3H), 0.81-0.78 (t, 3H)

MS (m/z): 506[M+H], 488[M-OH]

Example 205: Preparation of ((1R)-1-(5-benzyl-3-((1-isopropyl-1H-indazol-4-carboxamido)methyl)-4,5-dihydroisoxazol-5-carboxamido)-3-methylbutyl) boronic acid Through the processes (1), (2), (3) and (4) below, the title compound was obtained.

(1) Preparation of 1-isopropyl-1H-indazol-4-carboxylic acid

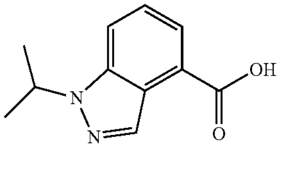

The title compound (0.23 g, 40%, 2 steps) was obtained using 1H-indazol-4-carboxylic acid methyl ester (0.5 g, 2.84 mmol) by the preparation method of Example 202-(1).

(2) Preparation of methyl 5-benzyl-3-((1-isopropyl-1H-indazol-4-carboxamido)methyl)-4,5-dihydroisoxazol-5-carboxylate

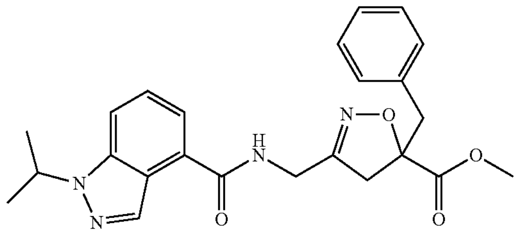 [SMILES: COC(=O)C1(Cc2ccccc2)CC(CNC(=O)c2cccc3c2cnn3C(C)C)=NO1]

The title compound (0.063 g, 82%) was obtained using methyl 3-(aminomethyl)-5-benzyl-4,5-dihydroisoxazol-5-carboxylate hydrochloride (0.05 g, 0.18 mmol) obtained in Example 84-(1) and 1-isopropyl-1H-indazol-4-carboxylic acid (0.039 g, 0.19 mmol) by the preparation method of Example 84-(2).

MS (m/z): 435[M+H]

(3) Preparation of 5-benzyl-3-((1-isopropyl-1H-indazol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

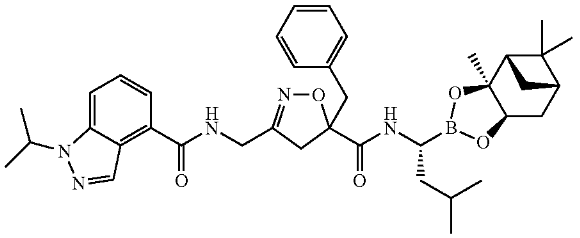 [SMILES: CC(C)C[C@H](NC(=O)C1(Cc2ccccc2)CC(CNC(=O)c2cccc3c2cnn3C(C)C)=NO1)B1O[C@@H]2C[C@@H]3C[C@@H](C3(C)C)[C@]2(C)O1]

The title compound (0.068 g, 63%, 2 steps) was obtained using methyl 5-benzyl-3-((1-isopropyl-1H-indazol-4-carboxamido)methyl)-4,5-dihydroisoxazol-5-carboxylate (0.063 g, 0.15 mmol) obtained in (2) above by the preparation method of Example 84-(3).

MS (m/z): 668[M+H]

(4) Preparation of ((1R)-1-(5-benzyl-3-((1-isopropyl-1H-indazol-4-carboxamido)methyl)-4,5-dihydroisoxazol-5-carboxamido)-3-methylbutyl)boronic acid

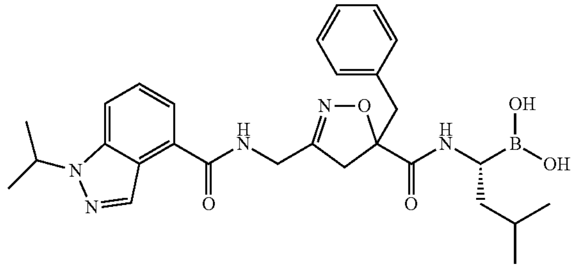 [SMILES: CC(C)C[C@H](NC(=O)C1(Cc2ccccc2)CC(CNC(=O)c2cccc3c2cnn3C(C)C)=NO1)B(O)O]

The title compound (0.029 g, 53%) was obtained using 5-benzyl-3-((1-isopropyl-1H-indazol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.068 g, 0.10 mmol) obtained in (3) above by the preparation method of Example 1-(4).

NMR: $^1$H-NMR (400 MHz, $CDCl_3$); δ 8.31 (s, 1H), 7.52-7.50 (m, 2H), 7.34-7.21 (7H), 6.77 (m, 1H), 4.86-4.82 (m, 1H), 4.36-4.17 (m, 2H), 3.46-3.35 (m, 2H), 3.18-3.06 (m, 2H), 1.60-1.56 (t, 3H), 1.39-1.21 (m, 3H), 0.80-0.79 (d, 6H)

MS (m/z): 534[M+H], 516[M-OH]

Example 206: Preparation of ((1R)-1-(5-benzyl-3-((1-isopropyl-3-methyl-1H-pyrazol-4-carboxamido)methyl)-4,5-dihydroisoxazol-5-carboxamido)-3-methylbutyl)boronic acid Through the processes (1), (2), (3) and (4) below, the title compound was obtained.

(1) Preparation of 1-isopropyl-3-methyl-1H-pyrazol-4-carboxylic acid

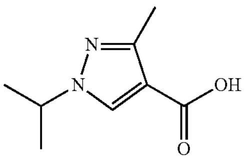

The title compound (0.15 g, 65%, 2 steps) was obtained using 3-methyl-1H-pyrazol-4-carboxylic acid ethyl ester (0.2 g, 1.29 mmol) by the preparation methods of Examples 188-(1) and (2) in order.

(2) Preparation of methyl 5-benzyl-3-((1-isopropyl-3-methyl-1H-pyrazol-4-carboxamido)methyl)-4,5-dihydroisoxazol-5-carboxylate

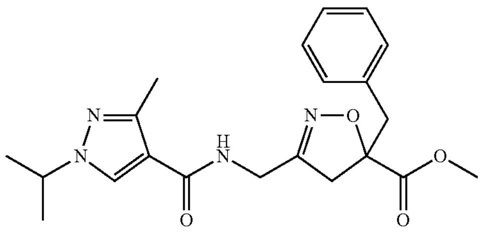 [SMILES: COC(=O)C1(Cc2ccccc2)CC(CNC(=O)c2cn(C(C)C)nc2C)=NO1]

The title compound (0.054 g, 77%) was obtained using methyl 3-(aminomethyl)-5-benzyl-4,5-dihydroisoxazol-5-carboxylate hydrochloride (0.05 g, 0.18 mmol) obtained in Example 84-(1) and 1-isopropyl-3-methyl-1H-pyrazol-4-carboxylic acid (0.033 g, 0.19 mmol) obtained in (1) above by the preparation method of Example 84-(2).

MS (m/z): 399[M+H]

(3) Preparation of 5-benzyl-3-((1-isopropyl-3-methyl-1H-pyrazol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

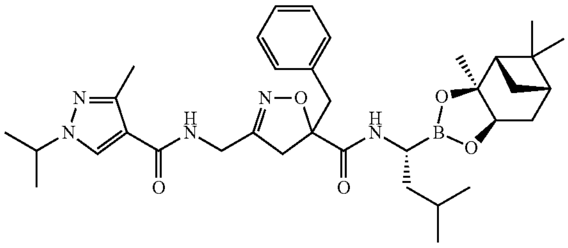 [SMILES: Cc1nn(C(C)C)cc1C(=O)NCC1=NOC(Cc2ccccc2)(C(=O)N[C@@H](CC(C)C)B2O[C@@H]3C[C@@H]4C[C@@H](C4(C)C)[C@]3(C)O2)C1]

The title compound (0.038 g, 45%, 2 steps) was obtained using methyl 5-benzyl-3-((1-isopropyl-3-methyl-1H-pyrazol-4-carboxamido)methyl)-4,5-dihydroisoxazol-5-carboxylate (0.054 g, 0.11 mmol) obtained in (2) above by the preparation method of Example 84-(3).

MS (m/z): 632[M+H], 480[M-$C_{10}H_{15}O$]

(4) Preparation of ((1R)-1-(5-benzyl-3-((1-isopropyl-3-methyl-1H-pyrazol-4-carboxamido)methyl)-4,5-dihydroisoxazol-5-carboxamido)-3-methylbutyl)boronic acid

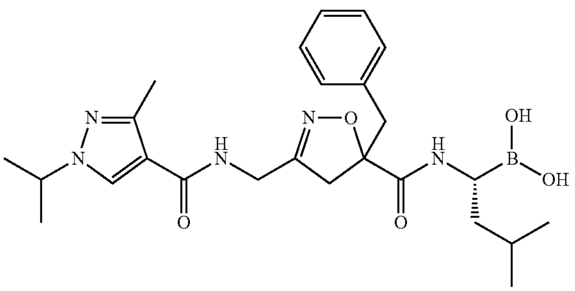 [SMILES: Cc1nn(C(C)C)cc1C(=O)NCC1=NOC(Cc2ccccc2)(C(=O)N[C@@H](CC(C)C)B(O)O)C1]

The title compound (0.029 g, 85%) was obtained using 5-benzyl-3-((1-isopropyl-3-methyl-1H-pyrazol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.038 g, 0.060 mmol) obtained in (3) above by the preparation method of Example 1-(4).

NMR: $^1$H-NMR (400 MHz, $CDCl_3$); δ 7.79 (s, 1H), 7.28-7.22 (m, 5H), 7.14 (m, 1H), 6.13 (m, 1H), 4.41-4.34 (m, 1H), 4.16-4.15 (d, 2H), 3.43-3.33 (m, 2H), 3.16-3.04 (m, 2H), 2.84 (m, 1H), 2.42 (s, 3H), 1.47-1.45 (d, 6H), 1.38-1.23 (m, 3H), 0.85-0.82 (m, 6H)

MS (m/z): 498[M+H], 480[M+H]

Example 207: Preparation of ((1R)-1-(5-benzyl-3-((1-isopropyl-3-phenyl-1H-pyrazol-5-carboxamido)methyl)-4,5-dihydroisoxazol-5-carboxamido)-3-methylbutyl)boronic acid Through the processes (1), (2), (3), (4), (5) and (6) below, the title compound was obtained.

(1) Preparation of 5-phenyl-2H-pyrazol-3-carboxylic acid ethyl ester

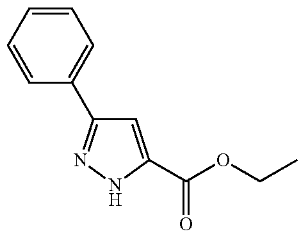 [SMILES: CCOC(=O)c1cc(-c2ccccc2)n[nH]1]

The title compound was obtained by the method described in Medicinal Chemistry Letters, 2012, 3, 678-682.

(2) Preparation of 2-isopropyl-5-phenyl-2H-pyrazol-3-carboxylic acid ethyl ester

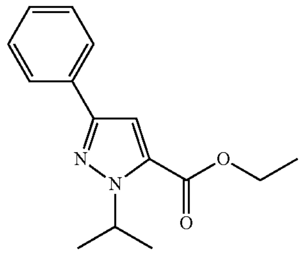 [SMILES: CCOC(=O)c1cc(-c2ccccc2)nn1C(C)C]

The title compound (0.22 g, 84%) was obtained using 5-phenyl-2H-pyrazol-3-carboxylic acid ethyl ester (0.22 g, 1.0 mmol) obtained in (1) above by the preparation method of Example 188-(1).

(3) Preparation of 2-isopropyl-5-phenyl-2H-pyrazol-3-carboxylic acid

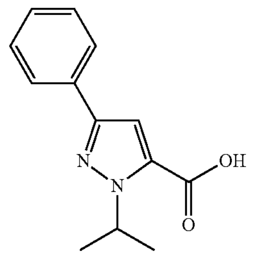 [SMILES: CC(C)n1nc(-c2ccccc2)cc1C(=O)O]

The title compound (0.19 g, 97%) was obtained using 2-isopropyl-5-phenyl-2H-pyrazol-3-carboxylic acid ethyl ester (0.22 g, 0.84 mmol) obtained in (2) above by the preparation method of Example 119-(2).

(4) Preparation of methyl 5-benzyl-3-((1-isopropyl-3-phenyl-1H-pyrazol-5-carboxamido)methyl)-4,5-dihydroisoxazol-5-carboxylate

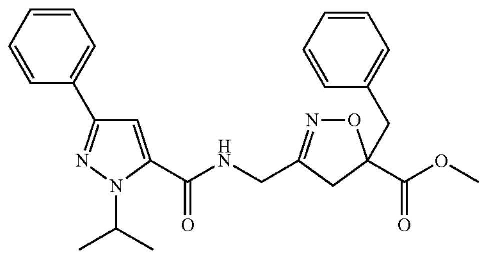 [SMILES: COC(=O)C1(Cc2ccccc2)CC(CNC(=O)c2cc(-c3ccccc3)nn2C(C)C)=NO1]

The title compound (0.063 g, 75%) was obtained using methyl 3-(aminomethyl)-5-benzyl-4,5-dihydroisoxazol-5-carboxylate hydrochloride (0.052 g, 0.183 mmol) obtained in Example 84-(1) and 2-isopropyl-5-phenyl-2H-pyrazol-3-carboxylic acid (0.050 g, 0.217 mmol) obtained in (3) above by the preparation method of Example 84-(2).

NMR: $^1$H-NMR (500 MHz, $CDCl_3$); δ 7.79 (1H, d), 7.40 (2H, dd), 7.31 (1H, dd), 7.26-7.21 (5H, m), 6.39 (1H, t), 5.44 (1H, q), 4.18-4.12 (2H, m), 3.77 (3H, s), 3.43 (1H, d), 3.33 (1H, d), 3.12 (1H, d), 3.02 (1H, d), 1.53 (6H, dd)

MS (m/z): 461[M+H]

(5) Preparation of 5-benzyl-3-((1-isopropyl-3-phenyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

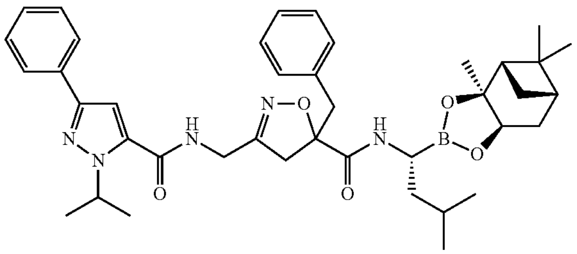 [SMILES: CC(C)C[C@H](NC(=O)C1(Cc2ccccc2)CC(CNC(=O)c2cc(-c3ccccc3)nn2C(C)C)=NO1)B1O[C@@H]2C[C@@H]3C[C@@H](C3(C)C)[C@]2(C)O1]

The title compound (0.074 g, 78%, 2 steps) was obtained using methyl 5-benzyl-3-((1-isopropyl-3-phenyl-1H-pyrazol-5-carboxamido)methyl)-4,5-dihydroisoxazol-5-carboxylate (0.063 g, 0.137 mmol) obtained in (4) above by the preparation method of Example 84-(3).

MS (m/z): 694[M+H]

(6) Preparation of ((1R)-1-(5-benzyl-3-((1-isopropyl-3-phenyl-1H-pyrazol-5-carboxamido)methyl)-4,5-dihydroisoxazol-5-carboxamido)-3-methylbutyl) boronic acid

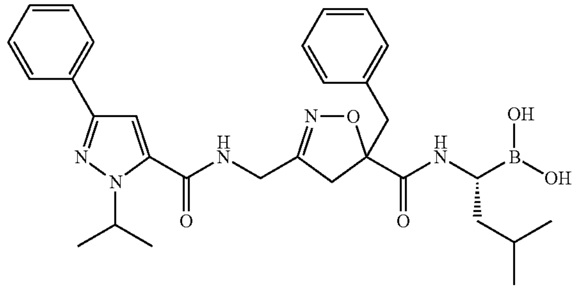 [SMILES: CC(C)C[C@H](NC(=O)C1(Cc2ccccc2)CC(CNC(=O)c2cc(-c3ccccc3)nn2C(C)C)=NO1)B(O)O]

The title compound (0.034 g, 57%) was obtained using 5-benzyl-3-((1-isopropyl-3-phenyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.074 g, 0.107 mmol) obtained in (5) above by the preparation method of Example 1-(4).

NMR: $^1$H-NMR (500 MHz, $CD_3OD$); δ 7.78 (2H, d), 7.38 (2H, dd), 7.30-7.21 (6H, m), 7.00 (1H, s), 5.48 (1H, q), 4.22-4.15 (2H, m), 3.42 (1H, d), 3.33-3.21 (2H, m), 3.18 (1H, d), 2.65 (1H, dd), 1.50 (6H, dd), 1.41-1.01 (3H, m), 0.78 (6H, dd)

MS (ES+): 582 [M+Na], 542 [M-OH]

Example 208: Preparation of ((1R)-1-(5-benzyl-3-((1-methyl-1H-indol-3-carboxamido)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-((1-methyl-1H-indol-3-carboxamido)methyl)-4,5-dihydroisoxazol-5-carboxylate

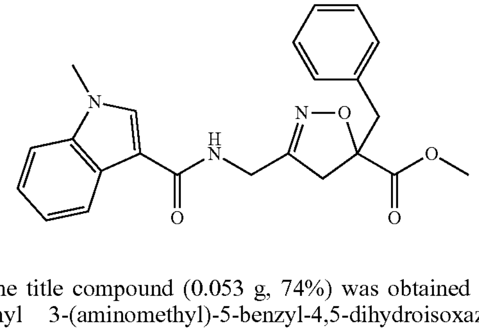

The title compound (0.053 g, 74%) was obtained using methyl 3-(aminomethyl)-5-benzyl-4,5-dihydroisoxazol-5-carboxylate hydrochloride (0.05 g, 0.18 mmol) obtained in Example 84-(1) and 1-methyl-1H-indol-3-carboxylic acid (0.034 g, 0.19 mmol) by the preparation method of Example 84-(2).

MS (m/z): 406[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-indol-3-carboxamido)methyl)-4,5-dihydroisoxazol-5-carboxamide

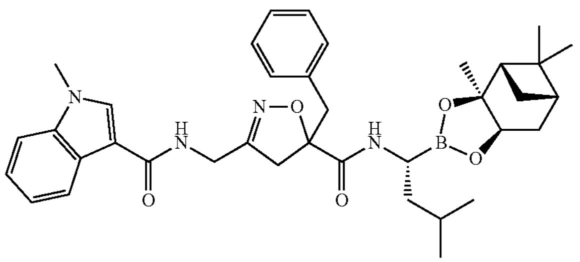 [SMILES: CC(C)C[C@H](NC(=O)C1(Cc2ccccc2)CC(CNC(=O)c2cn(C)c3ccccc23)=NO1)B1O[C@@H]2C[C@@H]3C[C@@H](C3(C)C)[C@]2(C)O1]

The title compound (0.058 g, 66%, 2 steps) was obtained using methyl 5-benzyl-3-((1-methyl-1H-indol-3-carboxamido)methyl)-4,5-dihydroisoxazol-5-carboxylate (0.053 g, 0.13 mmol) obtained in (1) above by the preparation method of Example 84-(3).

MS (m/z): 639[M+H]

(3) Preparation of ((1R)-1-(5-benzyl-3-((1-methyl-1H-indol-3-carboxamido)methyl)-4,5-dihydroisoxazol-5-carboxamido)-3-methylbutyl)boronic acid

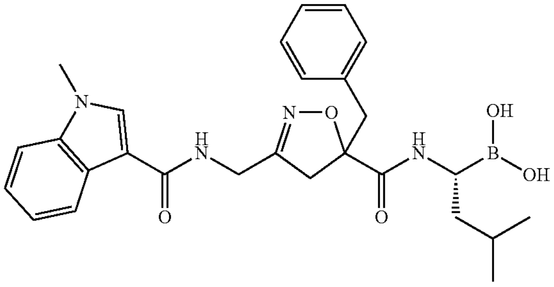 [SMILES: CC(C)C[C@H](NC(=O)C1(Cc2ccccc2)CC(CNC(=O)c2cn(C)c3ccccc23)=NO1)B(O)O]

The title compound (0.025 g, 55%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-indol-3-carboxamido)methyl)-4,5-dihydroisoxazol-5-carboxamide (0.058 g, 0.091 mmol) obtained in (2) above by the preparation method of Example 1-(4).

NMR: $^1$H-NMR (400 MHz, $CDCl_3$); δ 7.96-7.94 (dd, 1H), 7.57 (s, 1H), 7.29-7.21 (8H), 7.12 (m, 1H), 6.44 (m, 1H), 4.28 (m, 2H), 3.70 (s, 3H), 3.47-3.42 (d, 1H), 3.36-3.33 (d, 1H), 3.14-3.08 (m, 2H), 2.79 (m, 1H), 1.33-1.19 (m, 3H), 0.80-0.79 (d, 6H)

MS (m/z): 505[M+H], 487[M-OH]

Example 209: Preparation of ((1R)-1-(5-benzyl-3-((1-isopropyl-1H-indol-3-carboxamido)methyl)-4,5-dihydroisoxazol-5-carboxamido)-3-methylbutyl) boronic acid Through the processes (1), (2), (3) and (4) below, the title compound was obtained.

(1) Preparation of 1-isopropyl-1H-indol-3-carboxylic acid

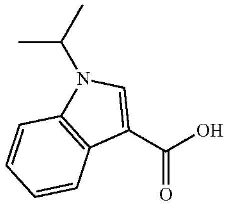

The title compound (0.19 g, 97%, 2 steps) was obtained using 1H-indol-3-carboxylic acid methyl ester (0.3 g, 1.71 mmol) by the preparation method of Example 202-(1).

(2) Preparation of methyl 5-benzyl-3-((1-isopropyl-1H-indol-3-carboxamido)methyl)-4,5-dihydroisoxazol-5-carboxylate

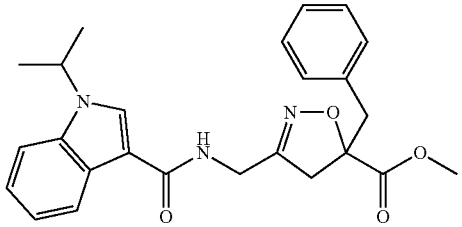 [SMILES: COC(=O)C1(Cc2ccccc2)CC(CNC(=O)c2cn(C(C)C)c3ccccc23)=NO1]

The title compound (0.058 g, 76%) was obtained using methyl 3-(aminomethyl)-5-benzyl-4,5-dihydroisoxazol-5-carboxylate hydrochloride (0.05 g, 0.18 mmol) obtained in Example 84-(1) and 1-isopropyl-1H-indol-3-carboxylic acid (0.040 g, 0.19 mmol) obtained in (1) above by the preparation method of Example 84-(2).

MS (m/z): 434[M+H]

(3) Preparation of 5-benzyl-3-((1-isopropyl-1H-indol-3-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

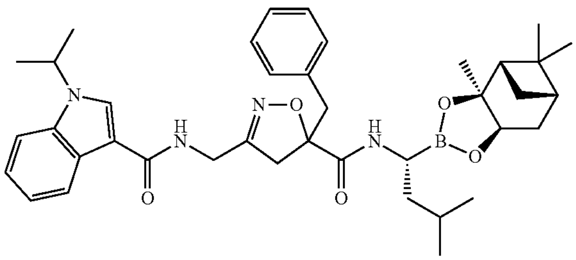 [SMILES: CC(C)C[C@H](NC(=O)C1(Cc2ccccc2)CC(CNC(=O)c2cn(C(C)C)c3ccccc23)=NO1)B1O[C@@H]2C[C@@H]3C[C@@H](C3(C)C)[C@]2(C)O1]

The title compound (0.051 g, 54%, 2 steps) was obtained using methyl 5-benzyl-3-((1-isopropyl-1H-indol-3-carboxamido)methyl)-4,5-dihydroisoxazol-5-carboxylate (0.058 g, 0.13 mmol) obtained in (2) above by the preparation method of Example 84-(3).

MS (m/z): 667[M+H]

(4) Preparation of ((1R)-1-(5-benzyl-3-((1-isopropyl-1H-indol-3-carboxamido)methyl)-4,5-dihydroisoxazol-5-carboxamido)-3-methylbutyl)boronic acid

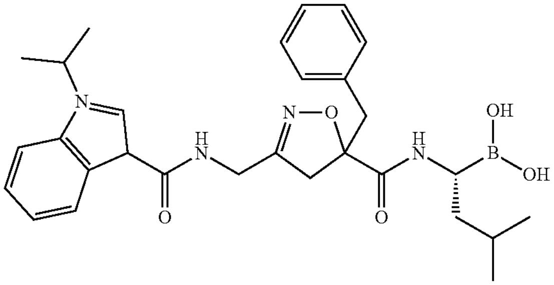

The title compound (0.022 g, 53%) was obtained using 5-benzyl-3-((1-isopropyl-1H-indol-3-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.051 g, 0.077 mmol) obtained in (3) above by the preparation method of Example 1-(4).

NMR: $^1$H-NMR (400 MHz, $CDCl_3$); δ 7.91-7.89 (d, 1H), 7.82 (s, 1H), 7.41-7.39 (d, 1H), 7.27-7.20 (m, 7H), 7.15 (m, 1H), 6.35 (m, 1H), 4.67-4.63 (m, 1H), 4.27-4.26 (d, 2H), 3.47-3.42 (d, 1H), 3.36-3.33 (d, 1H), 3.15-3.09 (m, 2H), 2.83 (m, 1H), 1.51-1.50 (d, 6H), 1.36-1.21 (m, 3H), 0.82-0.80 (m, 6H)

MS (m/z): 533[M+H], 515[M-OH]

Example 210: Preparation of ((1R)-1-(5-benzyl-3-((1-methyl-1H-pyrrolo[2,3-b]pyridin-4-carboxamido)methyl)-4,5-dihydroisoxazol-5-carboxamido)-3-methylbutyl)boronic acid Through the processes (1), (2), (3) and (4) below, the title compound was obtained.

(1) Preparation of 1-methyl-1H-pyrrolo[2,3-b]pyridin-4-carboxylic acid

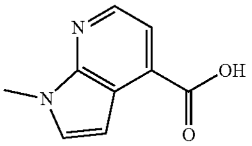

The title compound (0.075 g, 65%, 2 steps) was obtained using 1H-pyrrolo[2,3-b]pyridin-4-carboxylic acid methyl ester (0.1 g, 0.57 mmol) by the preparation method of Example 204-(1).

(2) Preparation of methyl 5-benzyl-3-((1-methyl-1H-pyrrolo[2,3-b]pyridin-4-carboxamido)methyl)-4,5-dihydroisoxazol-5-carboxylate

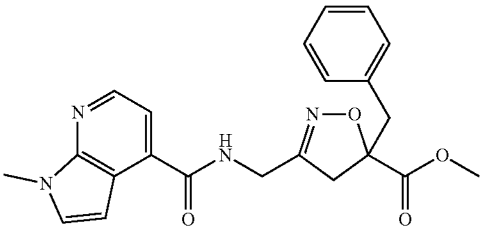

The title compound (0.051 g, 71%) was obtained using methyl 3-(aminomethyl)-5-benzyl-4,5-dihydroisoxazol-5-carboxylate hydrochloride (0.05 g, 0.18 mmol) obtained in Example 84-(1) and 1-methyl-1H-pyrrolo[2,3-b]pyridin-4-carboxylic acid (0.034 g, 0.19 mmol) obtained in (1) above by the preparation method of Example 84-(2).

MS (m/z): 407[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-pyrrolo[2,3-b]pyridin-4-carboxamido)methyl)-4,5-dihydroisoxazol-5-carboxamide

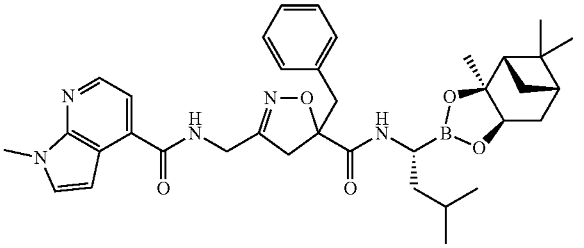

The title compound (0.043 g, 54%, 2 steps) was obtained using methyl 5-benzyl-3-((1-methyl-1H-pyrrolo[2,3-b]pyridin-4-carboxamido)methyl)-4,5-dihydroisoxazol-5-carboxylate (0.051 g, 0.13 mmol) obtained in (2) above by the preparation method of Example 84-(3).

MS (m/z): 640[M+H]

(4) Preparation of ((1R)-1-(5-benzyl-3-((1-methyl-1H-pyrrolo[2,3-b]pyridin-4-carboxamido)methyl)-4,5-dihydroisoxazol-5-carboxamido)-3-methylbutyl)boronic acid

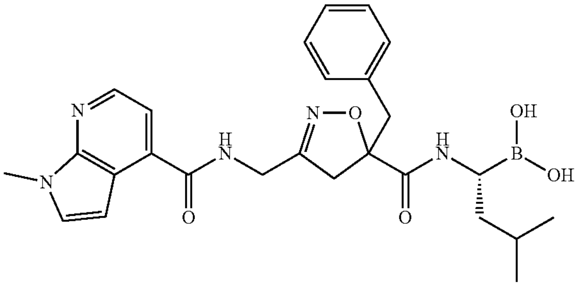 [SMILES: CC(C)C[C@H](NC(=O)C1(Cc2ccccc2)CC(CNC(=O)c2ccnc3c2ccn3C)=NO1)B(O)O]

The title compound (0.019 g, 55%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-pyrrolo[2,3-b]pyridin-4-carboxamido)methyl)-4,5-dihydroisoxazol-5-carboxamide (0.043 g, 0.067 mmol) obtained in (3) above by the preparation method of Example 1-(4).

NMR: $^1$H-NMR (400 MHz, $CDCl_3$); δ 8.41-8.39 (d, 1H), 7.36-7.28 (m, 7H), 7.20 (m, 1H), 6.85 (m, 1H), 6.79-6.78 (m, 1H), 4.32-4.31 (m, 2H), 3.94 (s, 3H), 3.50-3.38 (m, 2H), 3.21-3.11 (m, 2H), 2.88 (m, 1H), 1.47-1.31 (m, 3H), 0.87-0.86 (m, 6H)

MS (m/z): 506[M+H], 488[M-OH]

Example 211: Preparation of ((1R)-1-(5-benzyl-3-((1-isopropyl-1H-pyrrolo[2,3-b]pyridin-4-carboxamido)methyl)-4,5-dihydroisoxazol-5-carboxamido)-3-methylbutyl)boronic acid Through the processes (1), (2), (3) and (4) below, the title compound was obtained.

(1) Preparation of 1-isopropyl-1H-pyrrolo[2,3-b]pyridin-4-carboxylic acid

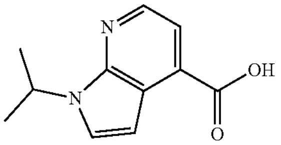

The title compound (0.08 g, 87%, 2 steps) was obtained using 1H-pyrrolo[2,3-b]pyridin-4-carboxylic acid methyl ester (0.1 g, 0.57 mmol) by the preparation method of Example 202-(1).

(2) Preparation of methyl 5-benzyl-3-((1-isopropyl-1H-pyrrolo[2,3-b]pyridin-4-carboxamido)methyl)-4,5-dihydroisoxazol-5-carboxylate

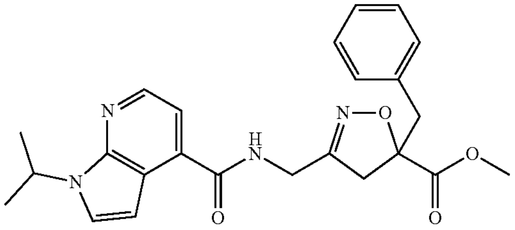 [SMILES: COC(=O)C1(Cc2ccccc2)CC(CNC(=O)c2ccnc3c2ccn3C(C)C)=NO1]

The title compound (0.065 g, 85%) was obtained using methyl 3-(aminomethyl)-5-benzyl-4,5-dihydroisoxazol-5-carboxylate hydrochloride (0.05 g, 0.18 mmol) obtained in Example 84-(1) and 1-isopropyl-1H-pyrrolo[2,3-b]pyridin-4-carboxylic acid (0.040 g, 0.19 mmol) by the preparation method of Example 84-(2).

MS (m/z): 435[M+H]

(3) Preparation of 5-benzyl-3-((1-isopropyl-1H-pyrrolo[2,3-b]pyridin-4-carboxamido)methyl)-N—((R)-3-methyl-1-((3aS,4S,6S,7aR)-3a,5,5-trimethyl-hexahydro-4,6-metanobenzo[d][1,3,2]dioxaborol-2-yl)butyl)-4,5-dihydroisoxazol-5-carboxamide

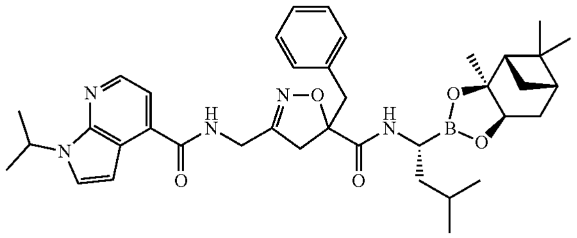 [SMILES: CC(C)C[C@H](NC(=O)C1(Cc2ccccc2)CC(CNC(=O)c2ccnc3c2ccn3C(C)C)=NO1)B1O[C@@H]2C[C@@H]3C[C@@H](C3(C)C)[C@]2(C)O1]

The title compound (0.058 g, 65%, 2 steps) was obtained using methyl 5-benzyl-3-((1-isopropyl-1H-pyrrolo[2,3-b]pyridin-4-carboxamido)methyl)-4,5-dihydroisoxazol-5-carboxylate (0.065 g, 0.13 mmol) obtained in (2) above by the preparation method of Example 84-(3).

MS (m/z): 668[M+H]

(4) Preparation of ((1R)-1-(5-benzyl-3-((1-isopropyl-1H-pyrrolo[2,3-b]pyridin-4-carboxamido)methyl)-4,5-dihydroisoxazol-5-carboxamido)-3-methylbutyl)boronic acid

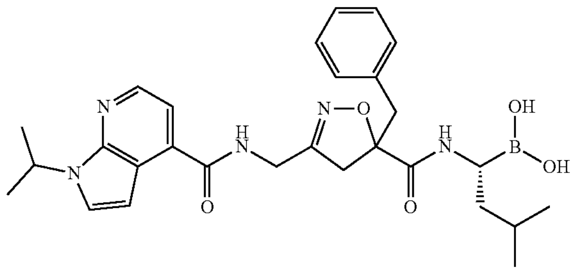 [SMILES: CC(C)C[C@H](NC(=O)C1(Cc2ccccc2)CC(CNC(=O)c2ccnc3c2ccn3C(C)C)=NO1)B(O)O]

The title compound (0.020 g, 42%) was obtained using 5-benzyl-3-((1-isopropyl-1H-pyrrolo[2,3-b]pyridin-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.058 g, 0.09 mmol) obtained in (3) above by the preparation method of Example 1-(4).

NMR: $^1$H-NMR (400 MHz, $CDCl_3$); δ 8.35-8.34 (d, 1H), 7.43-7.42 (d, 1H), 7.21-7.30 (d, 1H), 7.27-7.19 (m, 5H), 7.17-7.16 (m, 1H), 6.79 (m, 1H), 6.77-6.76 (d, 1H), 5.23-5.20 (m, 1H), 4.29-4.27 (d, 2H), 3.46-3.34 (m, 2H), 3.17-3.06 (m, 2H), 2.84 (m, 1H), 1.52-1.50 (d, 6H), 1.37-1.21 (m, 3H), 0.82-0.81 (m, 6H)

MS (m/z): 534[M+H], 516[M-OH]

Example 212: Preparation of ((1R)-1-(5-benzyl-3-((1-isopropyl-1H-pyrrolo[2,3-b]pyridin-5-carboxamido)methyl)-4,5-dihydroisoxazol-5-carboxamido)-3-methylbutyl)boronic acid Through the processes (1), (2) and (3) below, the title compound was obtained.

(1) Preparation of 1-isopropyl-1H-pyrrolo[2,3-b]pyridin-5-carboxylic acid

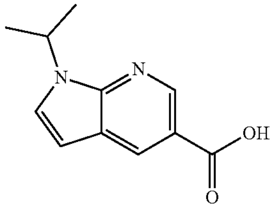

The title compound was obtained by the method described in WO2014129796A1.

(2) Preparation of methyl 5-benzyl-3-((1-isopropyl-1H-pyrrolo[2,3-b]pyridin-5-carboxamido)methyl)-4,5-dihydroisoxazol-5-carboxylate

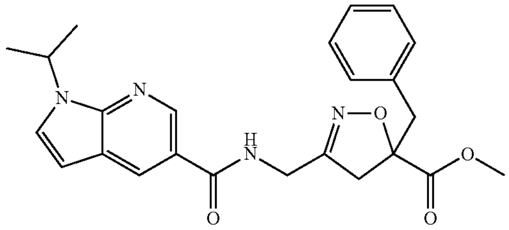 [SMILES: COC(=O)C1(Cc2ccccc2)CC(CNC(=O)c2cnc3c(ccn3C(C)C)c2)=NO1]

The title compound (0.062 g, 81%) was obtained using methyl 3-(aminomethyl)-5-benzyl-4,5-dihydroisoxazol-5-carboxylate hydrochloride (0.05 g, 0.18 mmol) obtained in Example 84-(1) and 1-isopropyl-1H-pyrrolo[2,3-b]pyridin-5-carboxylic acid (0.04 g, 0.19 mmol) obtained in (1) above by the preparation method of Example 84-(2).

MS (m/z): 435[M+H]

(3) Preparation of 5-benzyl-3-((1-isopropyl-1H-pyrrolo[2,3-b]pyridin-5-carboxamido)methyl)-N—((R)-3-methyl-1-((3aS,4S,6S,7aR)-3a,5,5-trimethyl-hexahydro-4,6-metanobenzo[d][1,3,2]dioxaborol-2-yl)butyl)-4,5-dihydroisoxazol-5-carboxamide

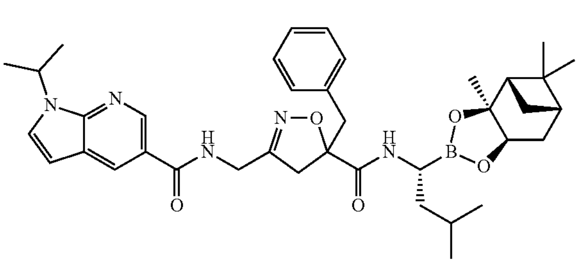 [SMILES: CC(C)C[C@H](NC(=O)C1(Cc2ccccc2)CC(CNC(=O)c2cnc3c(ccn3C(C)C)c2)=NO1)B1O[C@@H]2C[C@@H]3C[C@@H](C3(C)C)[C@]2(C)O1]

The title compound (0.054 g, 53%) was obtained using methyl 5-benzyl-3-((1-isopropyl-1H-pyrrolo[2,3-b]pyridin-5-carboxamido)methyl)-4,5-dihydroisoxazol-5-carboxylate (0.062 g, 0.14 mmol) obtained in (2) above by the preparation method of Example 84-(3).

MS (m/z): 668[M+H]

(4) Preparation of ((1R)-1-(5-benzyl-3-((1-isopropyl-1H-pyrrolo[2,3-b]pyridin-5-carboxamido)methyl)-4,5-dihydroisoxazol-5-carboxamido)-3-methylbutyl)boronic acid

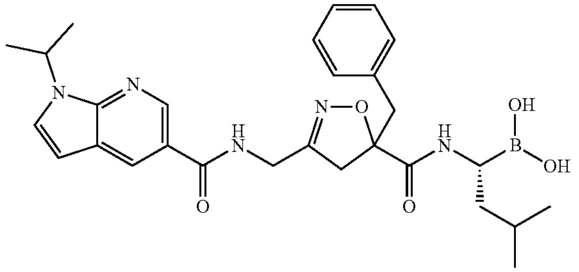 [SMILES: CC(C)C[C@H](NC(=O)C1(Cc2ccccc2)CC(CNC(=O)c2cnc3c(ccn3C(C)C)c2)=NO1)B(O)O]

The title compound (0.021 g, 49%) was obtained using 5-benzyl-3-((1-isopropyl-1H-pyrrolo[2,3-b]pyridin-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.054 g, 0.081 mmol) obtained in (3) above by the preparation method of Example 1-(4).

NMR: $^1$H-NMR (400 MHz, $CDCl_3$); δ 8.62-8.61 (d, 1H), 8.24-8.23 (d, 1H), 8.16 (m, 1H), 7.38-7.37 (d, 1H), 7.29-7.23 (m, 5H), 6.98 (m, 1H), 6.51-6.50 (d, 1H), 5.18-5.14 (m, 1H), 4.31-4.11 (m, 2H), 3.49-3.36 (m, 2H), 3.18-3.02 (m, 2H), 2.81 (m, 1H), 1.53-1.46 (dd, 6H), 1.32-1.15 (m, 3H), 0.75-0.69 (dd, 6H)

MS (m/z): 534[M+H], 516[M-OH]

Example 213: Preparation of ((1R)-1-(5-benzyl-3-((3-methyl-1-(pyridin-2-yl)-1H-pyrazol-5-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of 5-methyl-2-pyridin-2-yl-2H-pyrazol-3-carboxylic acid ethyl ester

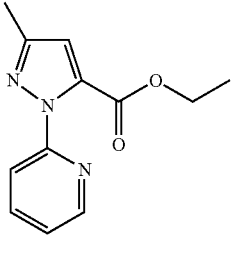 [SMILES: CCOC(=O)c1cc(C)nn1-c1ccccn1]

The title compound was obtained by the method described in EP946508B1.

(2) Preparation of 5-methyl-2-pyridin-2-yl-2H-pyrazol-3-carboxylic acid

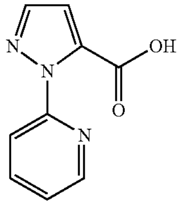 [SMILES: O=C(O)c1ccnn1-c1ccccn1]

The title compound (0.059 g, 93%) was obtained using 5-methyl-2-pyridin-2-yl-2H-pyrazol-3-carboxylic acid ethyl ester (0.072 g, 0.31 mmol) obtained in (1) above by the preparation method of Example 119-(2).

(3) Preparation of methyl 5-benzyl-3-((3-methyl-1-(pyridin-2-yl)-1H-pyrazol-5-carboxamido)methyl)-4,5-dihydroisoxazol-5-carboxylate

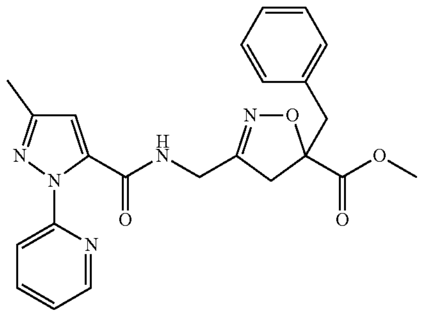

The title compound (0.058 g, 79%) was obtained using methyl 3-(aminomethyl)-5-benzyl-4,5-dihydroisoxazol-5-carboxylate hydrochloride (0.048 g, 0.169 mmol) obtained in Example 84-(1) and 5-methyl-2-pyridin-2-yl-2H-pyrazol-3-carboxylic acid (0.038 g, 0.186 mmol) obtained in (2) above by the preparation method of Example 84-(2).

NMR: $^1$H-NMR (500 MHz, $CDCl_3$); δ 8.46 (1H, d), 7.84 (2H, d), 7.27-7.13 (6H, m), 6.68 (1H, s), 4.23-4.19 (2H, m), 3.73 (3H, s), 3.42 (1H, d), 3.28 (1H, d), 3.11 (1H, d), 3.03 (1H, d), 2.67 (3H, s)

MS (m/z): 434[M+H]

(4) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-methyl-1-(pyridin-2-yl)-1H-pyrazol-5-carboxamido)methyl)-4,5-dihydroisoxazol-5-carboxamide

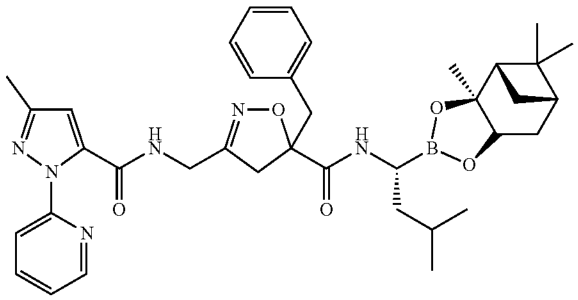

The title compound (0.055 g, 62%, 2 steps) was obtained using methyl 5-benzyl-3-((3-methyl-1-(pyridin-2-yl)-1H-pyrazol-5-carboxamido)methyl)-4,5-dihydroisoxazol-5-carboxylate (0.058 g, 0.134 mmol) obtained in (3) above by the preparation method of Example 84-(3).

MS (m/z): 667[M+H]

(5) Preparation of ((1R)-1-(5-benzyl-3-((3-methyl-1-(pyridin-2-yl)-1H-pyrazol-5-carboxamido)methyl)-4,5-dihydroisoxazol-5-carboxamido)-3-methylbutyl)boronic acid

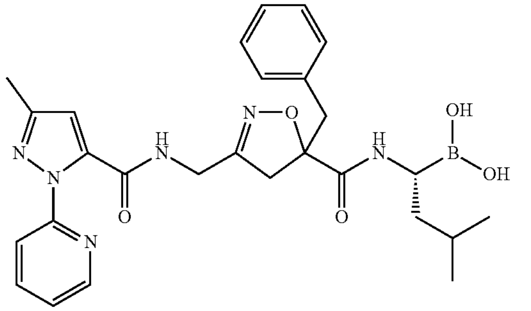 [SMILES: Cc1cc(C(=O)NCC2=NOC(Cc3ccccc3)(C(=O)N[C@@H](CC(C)C)B(O)O)C2)n(-c2ccccn2)n1]

The title compound (0.029 g, 66%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-methyl-1-(pyridin-2-yl)-1H-pyrazol-5-carboxamido)methyl)-4,5-dihydroisoxazol-5-carboxamide (0.055 g, 0.0825 mmol) obtained in (4) above by the preparation method of Example 1-(4).

NMR: $^1$H-NMR (400 MHz, $CD_3OD$); δ 8.52 (1H, d), 8.02-7.96 (2H, m), 7.43-7.39 (1H, m), 7.28-7.22 (5H, m), 6.70 (1H, s), 4.26 (2H, s), 3.46 (1H, d), 3.37-3.25 (2H, m), 3.21 (1H, d), 2.68 (3H, s), 2.65 (1H, dd), 1.41-1.04 (3H, m), 0.81 (6H, dd)

MS (m/z): 555[M+Na], 515[M-OH]

Example 214: Preparation of ((1R)-1-(5-((cyclohexyloxy)methyl)-3-((isoquinolin-1-carboxamido)methyl)-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-((cyclohexyloxy)methyl)-4,5-dihydroisoxazol-5-carboxylate hydrochloride

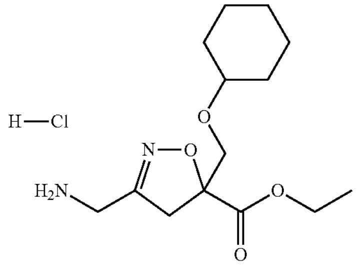 [SMILES: Cl ; CCOC(=O)C1(COC2CCCCC2)CC(CN)=NO1]

The title compound (0.165 g, 99%) was obtained using ethyl 3-(((tert-butoxycarbonyl)amino)methyl)-5-((cyclohexyloxy)methyl)-4,5-dihydroisoxazol-5-carboxylate (0.200 g, 0.52 mmol) obtained in Preparation Example 44 by the preparation method of Example 84-(1).

MS (m/z): 285[M+H]

(2) Preparation of ethyl 5-((cyclohexyloxy)methyl)-3-((isoquinolin-1-carboxamido)methyl)-4,5-dihydroisoxazol-5-carboxylate

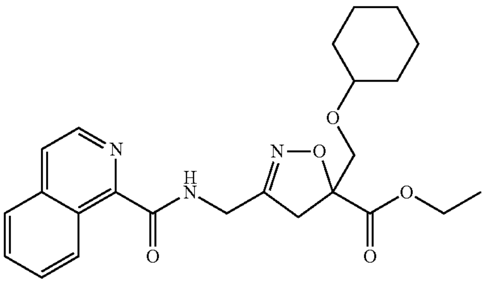 [SMILES: CCOC(=O)C1(COC2CCCCC2)CC(CNC(=O)c2nccc3ccccc23)=NO1]

The title compound (0.024 g, 11%) was obtained using ethyl 3-(aminomethyl)-5-((cyclohexyloxy)methyl)-4,5-dihydroisoxazol-5-carboxylatehydrochloride (0.165 g, 0.514 mmol) obtained in (1) above and isoquinolin-1-carboxylic acid (0.099 g, 0.572 mmol) by the preparation method of Example 84-(2).

NMR: $^1$H-NMR (400 MHz, $CDCl_3$); δ 9.58 (1H, dd), 8.67-8.62 (1H, m), 8.48 (1H, dd), 7.88-7.82 (2H, m), 7.75-7.70 (2H, m), 4.49-4.46 (2H, m), 4.30-4.23 (2H, m), 3.82-3.73 (2H, m), 3.62-3.50 (1H, m), 3.31-3.25 (2H, m), 1.81-1.45 (5H, m), 1.33-1.11 (8H, m)

MS (m/z): 440[M+H]

(3) Preparation of 5-((cyclohexyloxy)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

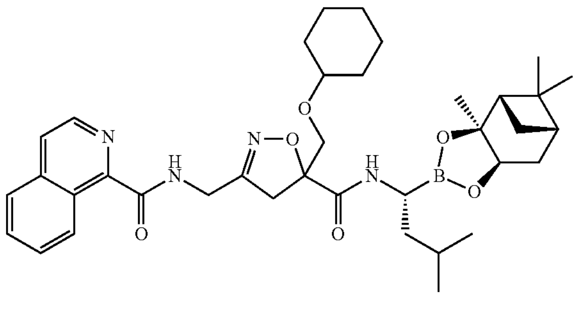 [SMILES: CC(C)C[C@H](NC(=O)C1(COC2CCCCC2)CC(CNC(=O)c2nccc3ccccc23)=NO1)B1O[C@@H]2C[C@@H]3C[C@@H](C3(C)C)[C@]2(C)O1]

The title compound (0.014 g, 38%, 2 steps) was obtained using ethyl 5-((cyclohexyloxy)methyl)-3-((isoquinolin-1-carboxamido)methyl)-4,5-dihydroisoxazol-5-carboxylate (0.024 g, 0.0546 mmol) obtained in (2) above by the preparation method of Example 84-(3).

MS (m/z): 659[M+H]

(4) Preparation of ((1R)-1-(5-((cyclohexyloxy)methyl)-3-((isoquinolin-1-carboxamido)methyl)-4,5-dihydroisoxazol-5-carboxamido)-3-methylbutyl)boronic acid

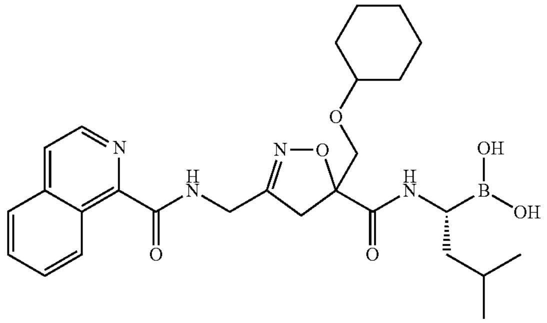 [SMILES: CC(C)C[C@H](NC(=O)C1(COC2CCCCC2)CC(CNC(=O)c2nccc3ccccc23)=NO1)B(O)O]

The title compound (0.006 g, 54%) was obtained using 5-((cyclohexyloxy)methyl)-3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.014 g, 0.0213 mmol) obtained in (3) above by the preparation method of Example 1-(4).

NMR: $^1$H-NMR (400 MHz, $CD_3OD$); δ 9.07 (1H, d), 8.50 (1H, d), 7.97 (1H, d), 7.94 (1H, d), 7.77 (1H, t), 7.70 (1H, t), 4.36 (2H, s), 3.87 (1H, dd), 3.74 (1H, dd), 3.42-3.28 (2H, m), 2.84-2.76 (1H, m), 1.83-1.46 (5H, m), 1.35-1.20 (5H, m), 1.14-1.10 (3H, m), 0.87-0.85 (6H, m)

MS (ES+): 547[M+Na], 507[M-OH]

Example 215: Preparation of ((1R)-1-(3-((isoquinolin-1-carboxamido)methyl)-5-(3-(trifluoromethyl)benzyl)-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-(3-(trifluoromethyl)benzyl)-4,5-dihydroisoxazol-5-carboxylate hydrochloride

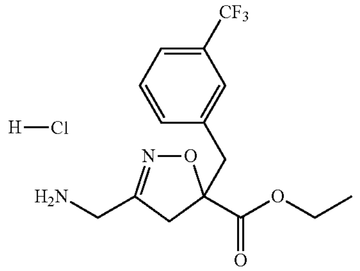 [SMILES: Cl ; CCOC(=O)C1(Cc2cccc(C(F)(F)F)c2)CC(CN)=NO1]

The title compound (0.19 g, 99%) was obtained using ethyl 3-(((tert-butoxycarbonyl)amino)methyl)-5-(3-(trifluoromethyl)benzyl)-4,5-dihydroisoxazol-5-carboxylate (0.25 g, 0.58 mmol) obtained in Preparation Example 45 by the preparation method of Example 84-(1).

MS (m/z): 331[M+H]

(2) Preparation of ethyl 3-((isoquinolin-1-carboxamido)methyl)-5-(3-(trifluoromethyl)benzyl)-4,5-dihydroisoxazol-5-carboxylate

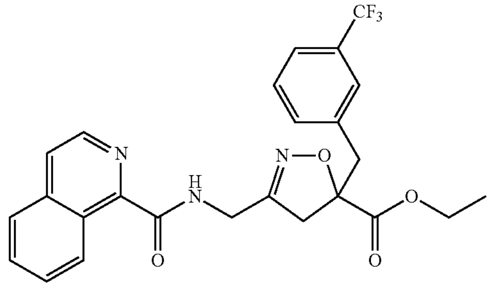 [SMILES: CCOC(=O)C1(Cc2cccc(C(F)(F)F)c2)CC(CNC(=O)c2nccc3ccccc23)=NO1]

The title compound (0.096 g, 73%) was obtained using ethyl 3-(aminomethyl)-5-(3-(trifluoromethyl)benzyl)-4,5-dihydroisoxazol-5-carboxylate hydrochloride (0.10 g, 0.27 mmol) obtained in (1) above and isoquinolin-1-carboxylic acid (0.052 g, 0.030 mmol) by the preparation method of Example 84-(2).

MS (m/z): 486[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-(trifluoromethyl)benzyl)-4,5-dihydroisoxazol-5-carboxamide

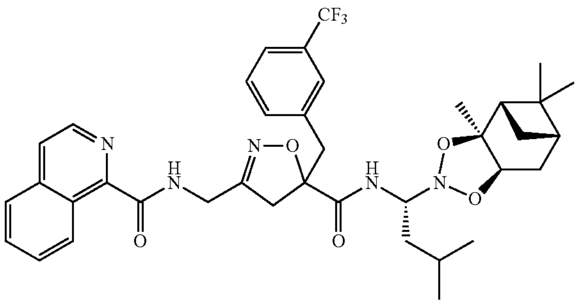 [SMILES: CC(C)C[C@H](NC(=O)C1(Cc2cccc(C(F)(F)F)c2)CC(CNC(=O)c2nccc3ccccc23)=NO1)N1O[C@@H]2C[C@@H]3C[C@@H](C3(C)C)[C@]2(C)O1]

The title compound (0.043 g, 31%, 2 steps) was obtained using ethyl 3-((isoquinolin-1-carboxamido)methyl)-5-(3-(trifluoromethyl)benzyl)-4,5-dihydroisoxazol-5-carboxylate (0.096 g, 0.20 mmol) obtained in (2) above by the preparation method of Example 84-(3).

MS (m/z): 705[M+H]

(4) Preparation of ((1R)-1-(3-((isoquinolin-1-carboxamido)methyl)-5-(3-(trifluoromethyl)benzyl)-4,5-dihydroisoxazol-5-carboxamido)-3-methylbutyl)boronic acid

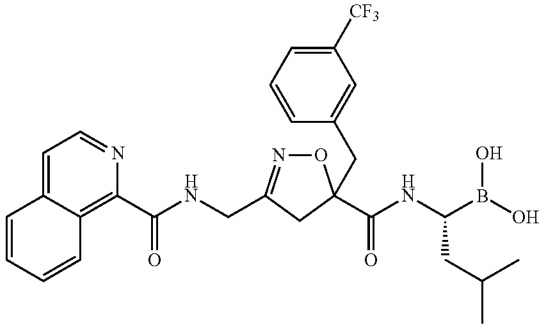 [SMILES: CC(C)C[C@H](NC(=O)C1(Cc2cccc(C(F)(F)F)c2)CC(CNC(=O)c2nccc3ccccc23)=NO1)B(O)O]

The title compound (0.026 g, 75%) was obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-(trifluoromethyl)benzyl)-4,5-dihydroisoxazol-5-carboxamide (0.043 g, 0.061 mmol) obtained in (3) above by the preparation method of Example 1-(4).

NMR: $^{1}$H-NMR (400 MHz, $CDCl_3$); δ 9.51-9.49 (d, 1H), 8.56 (t, 1H), 8.38-8.36 (d, 1H), 7.84-7.38 (m, 8H), 7.22 (d, 1H), 4.38-4.30 (m, 2H), 3.48-3.44 (d, 1H), 3.41-3.38 (d, 1H), 3.17-3.09 (dd, 2H), 2.76 (m, 1H), 1.27-1.08 (m, 3H), 0.75-0.72 (dd, 6H)

MS (m/z): 571[M+H], 553[M-OH]

Example 216: Preparation of ((1R)-1-(3-((isoquinolin-1-carboxamido)methyl)-5-(3-(trifluoromethoxy)benzyl)-4,5-dihydroisoxazol-5-carboxamido)-3-methylbutyl)boronic acid Through the processes (1), (2), (3) and (4) below, the title compound was obtained.

(1) Preparation of ethyl 3-(aminomethyl)-5-(3-(trifluoromethoxy)benzyl)-4,5-dihydroisoxazol-5-carboxylate hydrochloride

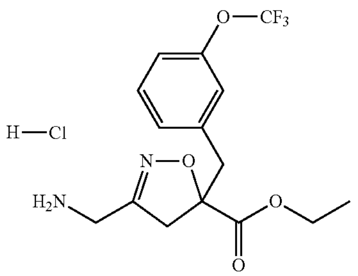 [SMILES: Cl ; CCOC(=O)C1(Cc2cccc(OC(F)(F)F)c2)CC(CN)=NO1]

The title compound (0.29 g, 99%) was obtained using ethyl 3-(((tert-butoxycarbonyl)amino)methyl)-5-(3-(trifluoromethoxy)benzyl)-4,5-dihydroisoxazol-5-carboxylate (0.35 g, 0.79 mmol) obtained in Preparation Example 46 by the preparation method of Example 84-(1).

MS (m/z): 347[M+H]

(2) Preparation of ethyl 3-((isoquinolin-1-carboxamido)methyl)-5-(3-(trifluoromethoxy)benzyl)-4,5-dihydroisoxazol-5-carboxylate

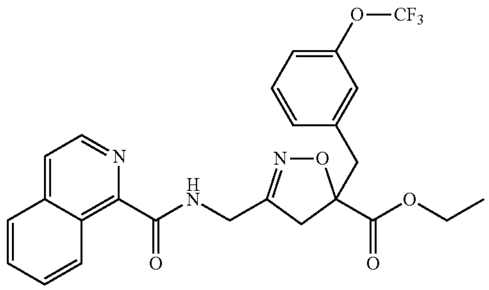 [SMILES: CCOC(=O)C1(Cc2cccc(OC(F)(F)F)c2)CC(CNC(=O)c2nccc3ccccc23)=NO1]

The title compound (0.10 g, 70%) was obtained using ethyl 3-(aminomethyl)-5-(3-(trifluoromethoxy)benzyl)-4,5-dihydroisoxazol-5-carboxylate hydrochloride (0.11 g, 0.29 mmol) obtained in (1) above and isoquinolin-1-carboxylic acid (0.055 g, 0.32 mmol) by the preparation method of Example 84-(2).

MS (m/z): 502[M+H]

(3) Preparation of 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-(trifluoromethoxy)benzyl)-4,5-dihydroisoxazol-5-carboxamide

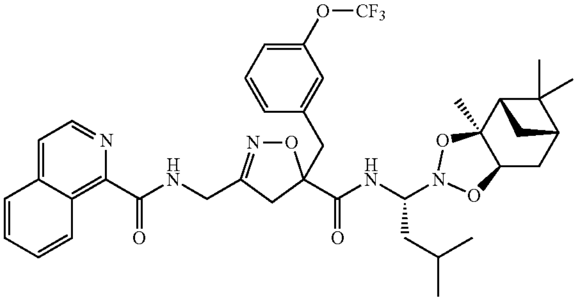 [SMILES: CC(C)C[C@H](NC(=O)C1(Cc2cccc(OC(F)(F)F)c2)CC(CNC(=O)c2nccc3ccccc23)=NO1)N1O[C@@H]2C[C@@H]3C[C@@H](C3(C)C)[C@]2(C)O1]

The title compound (0.054 g, 38%, 2 steps) was obtained using ethyl 3-((isoquinolin-1-carboxamido)methyl)-5-(3-(trifluoromethoxy)benzyl)-4,5-dihydroisoxazol-5-carboxylate (0.10 g, 0.20 mmol) obtained in (2) above by the preparation method of Example 84-(3).

MS (m/z): 721[M+H]

(4) Preparation of ((1R)-1-(3-((isoquinolin-1-carboxamido)methyl)-5-(3-(trifluoromethoxy)benzyl)-4,5-dihydroisoxazol-5-carboxamido)-3-methylbutyl)boronic acid

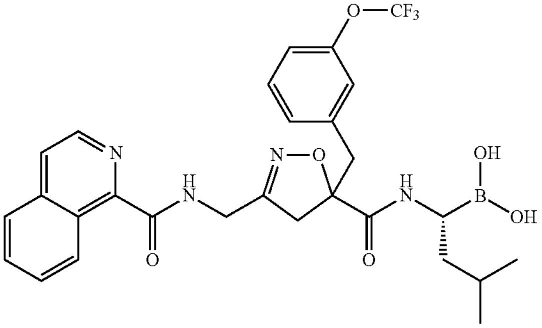 [SMILES: CC(C)C[C@H](NC(=O)C1(Cc2cccc(OC(F)(F)F)c2)CC(CNC(=O)c2nccc3ccccc23)=NO1)B(O)O]

The title compound (0.03 g, 69%) was obtained using 3-((isoquinolin-1-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-(trifluoromethoxy)benzyl)-4,5-dihydroisoxazol-5-carboxamide (0.054 g, 0.075 mmol) obtained in (3) above by the preparation method of Example 1-(4).

NMR: $^1$H-NMR (400 MHz, $CDCl_3$); δ 9.52-9.50 (d, 1H), 8.54-8.53 (t, 1H), 8.39-8.38 (d, 1H), 7.85-7.64 (m, 4H), 7.28-7.16 (m, 4H), 7.08-7.06 (d, 1H), 4.32-4.28 (m, 2H), 3.47-3.42 (d, 1H), 3.36-3.07 (d, 1H), 3.13-3.07 (m, 2H), 2.79 (m, 1H), 1.31-1.13 (m, 3H), 0.77-0.75 (dd, 6H)

MS (m/z): 587[M+H], 569[M-OH]

Example 217: Preparation of ((1R)-1-(3-((2,4-dimethylthiazol-5-carboxamido)methyl)-5-(3-methylbenzyl)-4,5-dihydroisoxazol-5-carboxamido)-3-methylbutyl)boronic acid Through the processes (1), (2) and (3) below, the title compound was obtained.

(1) Preparation of ethyl 3-((2,4-dimethylthiazol-5-carboxamido)methyl)-5-(3-methylbenzyl)-4,5-dihydroisoxazol-5-carboxylate

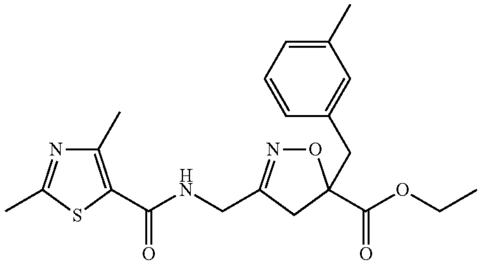 [SMILES: CCOC(=O)C1(Cc2cccc(C)c2)CC(CNC(=O)c2sc(C)nc2C)=NO1]

The title compound (0.12 g, 76%) was obtained using ethyl 3-(aminomethyl)-5-(3-methylbenzyl)-4,5-dihydroisoxazol-5-carboxylate hydrochloride (0.12 g, 0.38 mmol) obtained in Example 125-(1) and 2,4-dimethyl-thiazol-5-carboxylic acid (0.066 g, 0.42 mmol) by the preparation method of Example 84-(2).

MS (m/z): 416[M+H]

(2) Preparation of 3-((2,4-dimethylthiazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide

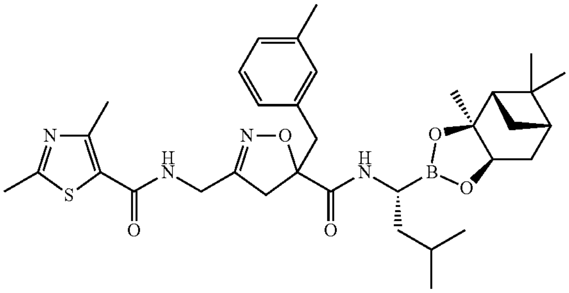

The title compound (0.086 g, 48%, 2 steps) was obtained using ethyl 3-((2,4-dimethylthiazol-5-carboxamido)methyl)-5-(3-methylbenzyl)-4,5-dihydroisoxazol-5-carboxylate (0.12 g, 0.29 mmol) obtained in (1) above by the preparation method of Example 84-(3).

MS (m/z): 635[M+H]

(3) Preparation of ((1R)-1-(3-((2,4-dimethylthiazol-5-carboxamido)methyl)-5-(3-methylbenzyl)-4,5-dihydroisoxazol-5-carboxamido)-3-methylbutyl) boronic acid

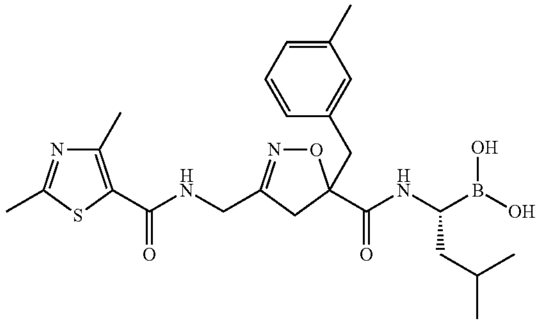 [SMILES: Cc1cccc(CC2(C(=O)N[C@@H](CC(C)C)B(O)O)CC(CNC(=O)c3sc(C)nc3C)=NO2)c1]

The title compound (0.03 g, 44%) was obtained using 3-((2,4-dimethylthiazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide (0.086 g, 0.14 mmol) obtained in (2) above by the preparation method of Example 1-(4).

NMR: $^1$H-NMR (400 MHz, $CDCl_3$); δ 7.20-7.04 (m, 5H), 6.13 (t, 1H), 4.13-4.12 (d, 2H), 3.40-3.30 (m, 2H), 3.12-3.01 (m, 2H), 2.66 (s, 3H), 2.61 (s, 3H), 2.31 (s, 3H), 1.43-1.21 (m, 3H), 0.86-0.82 (t, 6H)

MS (m/z): 501[M+H], 483[M-OH]

Example 218: Preparation of ((1R)-1-(5-benzyl-3-((3-methyl-1-(tetrahydro-2H-pyran-4-yl)-1H-pyrazol-5-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of ethyl 3-methyl-1-(tetrahydro-2H-pyran-4-yl)-1H-pyrazol-5-carboxylate

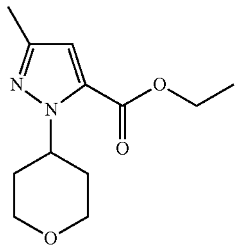 [SMILES: CCOC(=O)c1cc(C)nn1C1CCOCC1]

The title compound (0.2 g, 42%) was obtained using 5-methyl-2H-pyrazol-3-carboxylic acid ethyl ester (0.21 g, 2.0 mmol), methanesulfonic acid tetrahydro-pyran-4-yl ester (0.22 g, 2.6 mmol), and iodo tetrabutylammonium salt (0.74 g, 2.0 mmol) by the preparation method of Example 188-(1).

(2) Preparation of 3-methyl-1-(tetrahydro-2H-pyran-4-yl)-1H-pyrazol-5-carboxylic acid

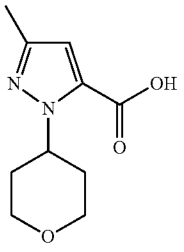

The title compound (0.17 g, 97%) was obtained using ethyl 3-methyl-1-(tetrahydro-2H-pyran-4-yl)-1H-pyrazol-5-carboxylate (0.2 g, 0.84 mmol) obtained in (1) above by the preparation method of Example 119-(2).

(3) Preparation of methyl 5-benzyl-3-((3-methyl-1-(tetrahydro-2H-pyran-4-yl)-1H-pyrazol-5-carboxamido)methyl)-4,5-dihydroisoxazol-5-carboxylate

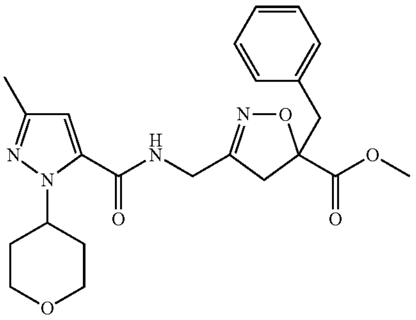

The title compound (0.056 g, 72%) was obtained using methyl 3-(aminomethyl)-5-benzyl-4,5-dihydroisoxazol-5-carboxylate hydrochloride (0.050 g, 0.176 mmol) obtained in Example 84-(1) and 3-methyl-1-(tetrahydro-2H-pyran-4-yl)-1H-pyrazol-5-carboxylic acid (0.041 g, 0.195 mmol) obtained in (2) above by the preparation method of Example 84-(2).

NMR: $^1$H-NMR (500 MHz, $CDCl_3$); δ 7.27-7.19 (5H, m), 6.31 (1H, t), 6.23 (1H, d), 5.22-5.17 (1H, m), 4.11-4.04 (4H, m), 3.76 (3H, s), 3.54-3.47 (2H, m), 3.40 (1H, d), 3.31 (1H, d), 3.12 (1H, d), 2.98 (1H, d), 2.29-2.23 (5H, m), 1.88-1.85 (2H, m)

MS (m/z): 441[M+H]

(4) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-methyl-1-(tetrahydro-2H-pyran-4-yl)-1H-pyrazol-5-carboxamido)methyl)-4,5-dihydroisoxazol-5-carboxamide

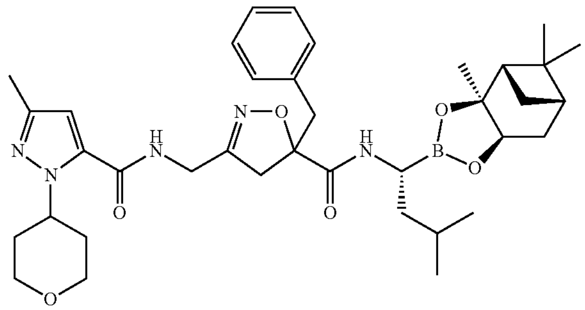

The title compound (0.055 g, 64%, 2 steps) was obtained using methyl 5-benzyl-3-((3-methyl-1-(tetrahydro-2H-pyran-4-yl)-1H-pyrazol-5-carboxamido)methyl)-4,5-dihydroisoxazol-5-carboxylate (0.056 g, 0.127 mmol) obtained in (3) above by the preparation method of Example 84-(3).

MS (m/z): 674[M+H]

(5) Preparation of ((1R)-1-(5-benzyl-3-((3-methyl-1-(tetrahydro-2H-pyran-4-yl)-1H-pyrazol-5-carboxamido)methyl)-4,5-dihydroisoxazol-5-carboxamido)-3-methylbutyl)boronic acid

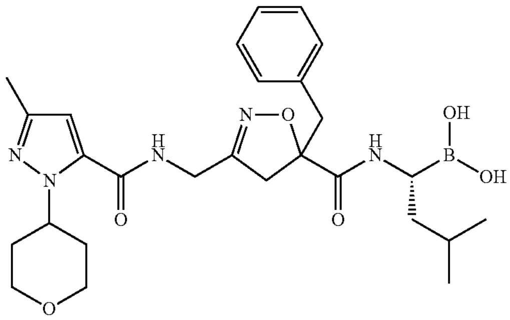 [SMILES: Cc1cc(C(=O)NCC2=NOC(Cc3ccccc3)(C(=O)N[C@@H](CC(C)C)B(O)O)C2)n(C2CCOCC2)n1]

The title compound (0.025 g, 57%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-methyl-1-(tetrahydro-2H-pyran-4-yl)-1H-pyrazol-5-carboxamido)methyl)-4,5-dihydroisoxazol-5-carboxamide (0.055 g, 0.082 mmol) obtained in (4) above by the preparation method of Example 1-(4).

NMR: $^1$H-NMR (500 MHz, $CD_3OD$); δ 7.25-7.20 (5H, m), 6.46 (1H, s), 5.28-5.22 (1H, m), 4.18-4.12 (2H, m), 4.05-4.01 (2H, m), 3.51 (2H, t), 3.40 (1H, d), 3.32-3.24 (2H, m), 3.17 (1H, d), 2.65 (1H, t), 2.23 (3H, s), 2.22-2.16 (2H, m), 1.86-1.82 (2H, m), 1.39-0.99 (3H, m), 0.79 (6H, dd)

MS (m/z): 562 [M+Na], 522 [M-OH]

Example 219: Preparation of ((1R)-1-(5-(3-chlorobenzyl)-3-((2,4-dimethylthiazol-5-carboxamido)methyl)-4,5-dihydroisoxazol-5-carboxamido)-3-methylbutyl)boronic acid Through the processes (1), (2) and (3) below, the title compound was obtained.

(1) Preparation of ethyl 5-(3-chlorobenzyl)-3-((2,4-dimethylthiazol-5-carboxamido)methyl)-4,5-dihydroisoxazol-5-carboxylate

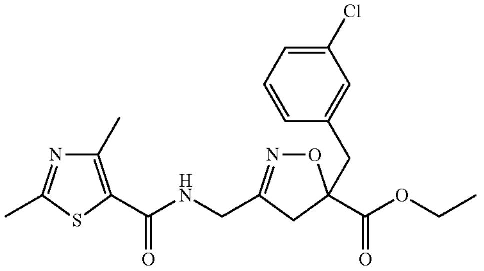 [SMILES: CCOC(=O)C1(Cc2cccc(Cl)c2)CC(CNC(=O)c2sc(C)nc2C)=NO1]

The title compound (0.12 g, 71%) was obtained using ethyl 3-(aminomethyl)-5-(3-chlorobenzyl)-4,5-dihydroisoxazol-5-carboxylate hydrochloride (0.12 g, 0.36 mmol) obtained in Example 175-(1) and 2,4-dimethyl-thiazol-5-carboxylic acid (0.06 g, 0.40 mmol) by the preparation method of Example 84-(2).

MS (m/z): 436[M+H]

(2) Preparation of 5-(3-chlorobenzyl)-3-((2,4-dimethylthiazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

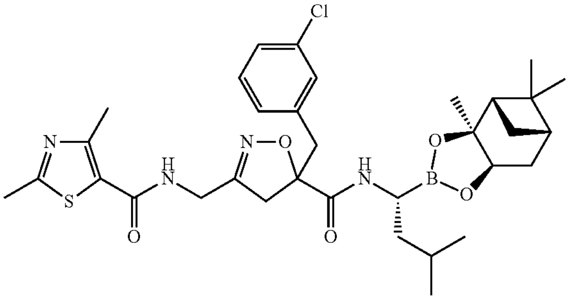

The title compound (0.071 g, 41%, 2 steps) was obtained using ethyl 5-(3-chlorobenzyl)-3-((2,4-dimethylthiazol-5-carboxamido)methyl)-4,5-dihydroisoxazol-5-carboxylate (0.112 g, 0.26 mmol) obtained in (1) above by the preparation method of Example 84-(3).

MS (m/z): 655[M+H]

(3) Preparation of ((1R)-1-(5-(3-chlorobenzyl)-3-((2,4-dimethylthiazol-5-carboxamido)methyl)-4,5-dihydroisoxazol-5-carboxamido)-3-methylbutyl) boronic acid

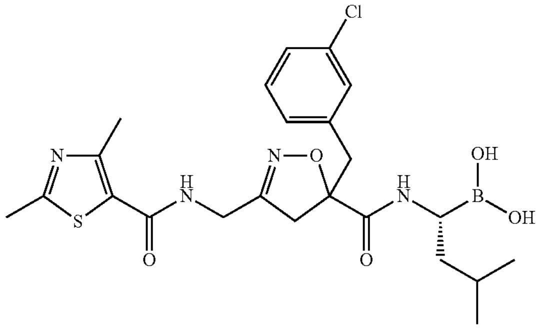 [SMILES: Cc1nc(C)c(C(=O)NCC2=NOC(Cc3cccc(Cl)c3)(C(=O)N[C@@H](CC(C)C)B(O)O)C2)s1]

The title compound (0.025 g, 44%) was obtained using 5-(3-chlorobenzyl)-3-((2,4-dimethylthiazol-5-carboxamido) methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.071 g, 0.11 mmol) obtained in (2) above by the preparation method of Example 1-(4).

NMR: $^1$H-NMR (400 MHz, MeOD-d4); δ 7.32-7.23 (m, 4H), 4.62 (s, 2H), 3.47-3.36 (m, 2H), 3.31-3.19 (m, 2H), 2.68 (m, 1H), 2.69 (s, 3H), 2.60 (s, 3H), 1.47-1.41 (m, 1H), 1.23-1.04 (m, 2H), 0.85-0.81 (dd, 6H)

MS (m/z): 521[M+H], 503[M-OH]

Example 220: Preparation of ((1R)-1-(5-benzyl-3-((1-methyl-1H-pyrazol-4-carboxamido)methyl)-4,5-dihydroisoxazol-5-carboxamido)-3-methylbutyl) boronic acid Through the processes (1), (2) and (3) below, the title compound was obtained.

(1) Preparation of methyl 5-benzyl-3-((1-methyl-1H-pyrazol-4-carboxamido)methyl)-4,5-dihydroisoxazol-5-carboxylate

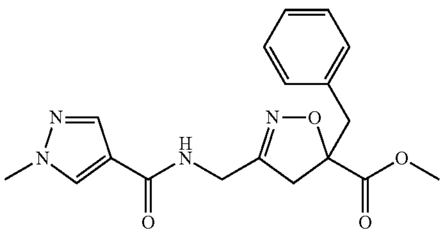

The title compound (0.051 g, 81%) was obtained using methyl 3-(aminomethyl)-5-benzyl-4,5-dihydroisoxazol-5-carboxylate hydrochloride (0.05 g, 0.18 mmol) obtained in Example 84-(1) and 1-methyl-1H-pyrazol-4-carboxylic acid (0.024 g, 0.19 mmol) by the preparation method of Example 84-(2).

MS (m/z): 357[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-pyrazol-4-carboxamido)methyl)-4,5-dihydroisoxazol-5-carboxamide

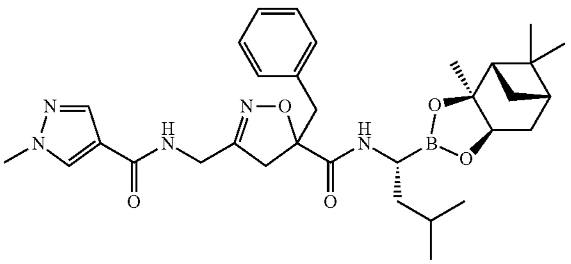

The title compound (0.037 g, 44%, 2 steps) was obtained using methyl 5-benzyl-3-((1-methyl-1H-pyrazol-4-carboxamido)methyl)-4,5-dihydroisoxazol-5-carboxylate (0.051 g, 0.14 mmol) obtained in (1) above by the preparation method of Example 84-(3).

MS (m/z): 590[M+H]

(3) Preparation of ((1R)-1-(5-benzyl-3-((1-methyl-1H-pyrazol-4-carboxamido)methyl)-4,5-dihydroisoxazol-5-carboxamido)-3-methylbutyl)boronic acid

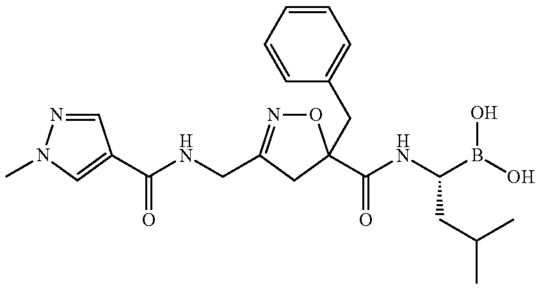 [SMILES: CC(C)C[C@H](NC(=O)C1(Cc2ccccc2)CC(CNC(=O)c2cnn(C)c2)=NO1)B(O)O]

The title compound (0.016 g, 56%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((1-methyl-1H-pyrazol-4-carboxamido) methyl)-4,5-dihydroisoxazol-5-carboxamide (0.037 g, 0.063 mmol) obtained in (2) above by the preparation method of Example 1-(4).

NMR: $^1$H-NMR (400 MHz, $CDCl_3$); δ 7.78 (s, 1H), 7.70 (s, 1H), 7.31-7.24 (m, 5H), 7.21-7.20 (m, 1H), 6.46 (m, 1H), 4.24-4.10 (m, 2H), 3.89 (s, 3H), 3.41-3.29 (m, 2H), 3.15-3.02 (m, 2H), 2.78 (m, 1H), 1.35-1.18 (m, 3H), 0.82-0.81 (d, 6H)

MS (m/z): 456[M+H], 438[M-OH].

Example 221: Preparation of ((1R)-1-(5-benzyl-3-((1-isopropyl-3-(pyridin-2-yl)-1H-pyrazol-5-carboxamido)methyl)-4,5-dihydroisoxazol-5-carboxamido)-3-methylbutyl)boronic acid Through the processes (1), (2), (3), (4), (5) and (6) below, the title compound was obtained.

(1) Preparation of 5-pyridin-2-yl-2H-pyrazol-3-carboxylic acid ethyl ester

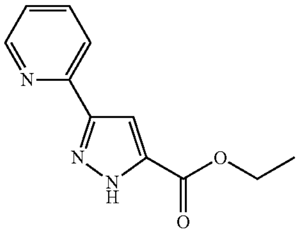

The title compound was obtained by the method described in Medicinal Chemistry Letters, 2012, 3, 678-682.

(2) Preparation of 2-isopropyl-5-pyridin-2-yl-2H-pyrazol-3-carboxylic acid ethyl ester

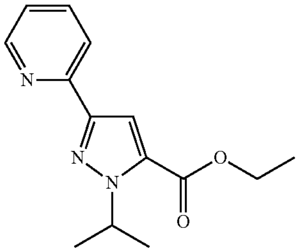 [SMILES: CCOC(=O)c1cc(-c2ccccn2)nn1C(C)C]

The title compound (0.35 g, 83%) was obtained using 5-pyridin-2-yl-2H-pyrazol-3-carboxylic acid ethyl ester (0.35 g, 1.6 mmol) obtained in (1) above by the preparation method of Example 188-(1).

MS (m/z): 260[M+H]

(3) Preparation of 2-isopropyl-5-pyridin-2-yl-2H-pyrazol-3-carboxylic acid

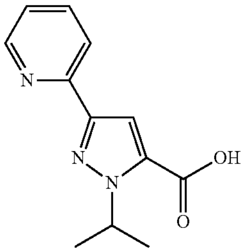 [SMILES: CC(C)n1nc(-c2ccccn2)cc1C(=O)O]

The title compound (0.30 g, 98%) was obtained using 2-isopropyl-5-pyridin-2-yl-2H-pyrazol-3-carboxylic acid ethyl ester (0.35 g, 1.33 mmol) obtained in (2) above by the preparation method of Example 119-(2).

(4) Preparation of methyl 5-benzyl-3-((1-isopropyl-3-(pyridin-2-yl)-1H-pyrazol-5-carboxamido)methyl)-4,5-dihydroisoxazol-5-carboxylate

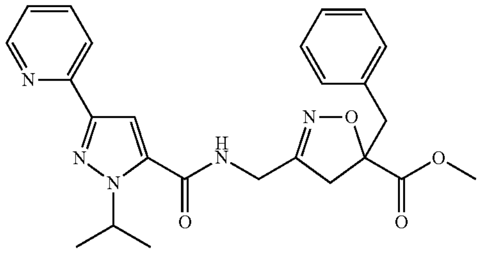 [SMILES: COC(=O)C1(Cc2ccccc2)CC(CNC(=O)c2cc(-c3ccccn3)nn2C(C)C)=NO1]

The title compound (0.07 g, 86%) was obtained using methyl 3-(aminomethyl)-5-benzyl-4,5-dihydroisoxazol-5-carboxylate hydrochloride (0.053 g, 0.186 mmol) obtained in Example 84-(1) and 2-isopropyl-5-pyridin-2-yl-2H-pyrazol-3-carboxylic acid (0.056 g, 0.242 mmol) obtained in (3) above by the preparation method of Example 84-(2).

NMR: $^1$H-NMR (400 MHz, $CDCl_3$); δ 8.60-8.58 (1H, m), 8.02 (1H, dd), 7.72 (1H, dd), 7.27-7.20 (5H, m), 7.13 (1H, s), 6.47 (1H, t), 5.49 (1H, q), 4.21-4.15 (2H, m), 3.78 (3H, s), 3.43 (1H, d), 3.34 (1H, d), 3.12 (1H, d), 3.01 (1H, d), 1.56 (6H, dd)

MS (m/z): 462[M+H]

(5) Preparation of 5-benzyl-3-((1-isopropyl-3-(pyridin-2-yl)-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

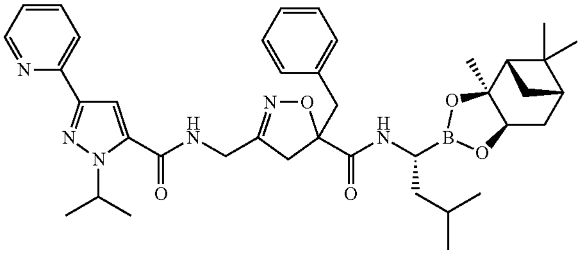

The title compound (0.066 g, 59%, 2 steps) was obtained using methyl 5-benzyl-3-((1-isopropyl-3-(pyridin-2-yl)-1H-pyrazol-5-carboxamido)methyl)-4,5-dihydroisoxazol-5-carboxylate (0.074 g, 0.160 mmol) obtained in (4) above by the preparation method of Example 84-(3).

MS (m/z): 695[M+H]

(6) Preparation of ((1R)-1-(5-benzyl-3-((1-isopropyl-3-(pyridin-2-yl)-1H-pyrazol-5-carboxamido)methyl)-4,5-dihydroisoxazol-5-carboxamido)-3-methylbutyl)boronic acid

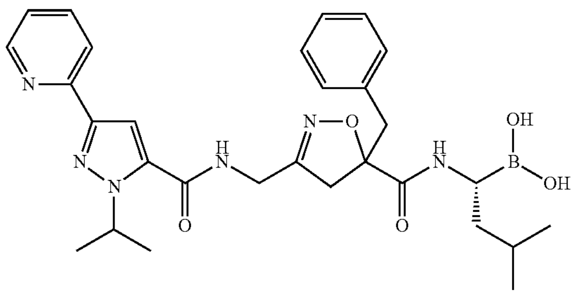

The title compound (0.032 g, 60%) was obtained using 5-benzyl-3-((1-isopropyl-3-(pyridin-2-yl)-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.066 g, 0.095 mmol) obtained in (5) above by the preparation method of Example 1-(4).

NMR: $^1$H-NMR (400 MHz, $CD_3OD$); δ 8.58-8.56 (1H, m), 8.07 (1H, s), 7.91-7.87 (1H, m), 7.38-7.34 (1H, m), 7.29-7.25 (5H, m), 7.21 (1H, s), 5.53 (1H, q), 4.23 (2H, s), 3.47 (1H, d), 3.37-3.26 (2H, m), 3.22 (1H, d), 2.71 (1H, t), 1.55 (6H, dd), 1.44-1.08 (3H, m), 0.82 (6H, dd)

MS (m/z): 583[M+Na], 543[M-OH]

Example 222: Preparation of ((1R)-1-(5-benzyl-3-((4-chloro-1-isopropyl-3-methyl-1H-pyrazol-5-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of 4-chloro-2-isopropyl-5-methyl-2H-pyrazol-3-carboxylic acid ethyl ester

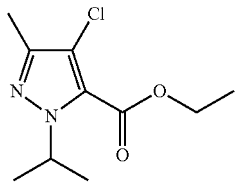

The title compound (0.11 g, 92%) was obtained using 2-isopropyl-5-methyl-2H-pyrazol-3-carboxylic acid ethyl ester (0.1 g, 0.51 mmol) obtained in Example 190-(1) by the preparation method of Example 140-(1).

MS (m/z): 231[M+H]

(2) Preparation of 4-chloro-2-isopropyl-5-methyl-2H-pyrazol-3-carboxylic acid

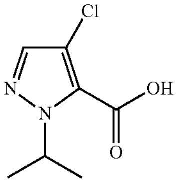

The title compound (0.091 g, 96%) was obtained using 4-chloro-2-isopropyl-5-methyl-2H-pyrazol-3-carboxylic acid ethyl ester (0.11 g, 0.47 mmol) obtained in (1) above by the preparation method of Example 119-(2).

(3) Preparation of methyl 5-benzyl-3-((4-chloro-1-isopropyl-3-methyl-1H-pyrazol-5-carboxamido)methyl)-4,5-dihydroisoxazol-5-carboxylate

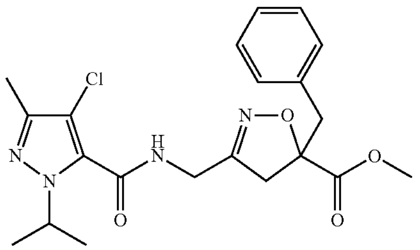

The title compound (0.048 g, 72%) was obtained using methyl 3-(aminomethyl)-5-benzyl-4,5-dihydroisoxazol-5-carboxylate hydrochloride (0.044 g, 0.155 mmol) obtained in Example 84-(1) and 4-chloro-2-isopropyl-5-methyl-2H-pyrazol-3-carboxylic acid (0.041 g, 0.202 mmol) obtained in (2) above by the preparation method of Example 84-(2).

NMR: $^1$H-NMR (400 MHz, $CDCl_3$); δ 7.27-7.18 (5H, m), 6.80 (1H, t), 5.42 (1H, q), 4.25-4.15 (2H, m), 3.78 (3H, s), 3.43 (1H, d), 3.33 (1H, d), 3.13 (1H, d), 3.00 (1H, d), 2.25 (3H, s), 1.45 (6H, dd)

MS (m/z): 433[M+H]

(4) Preparation of 5-benzyl-3-((4-chloro-1-isopropyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

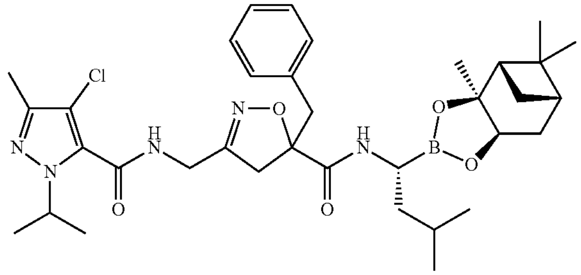

The title compound (0.050 g, 69%, 2 steps) was obtained using methyl 5-benzyl-3-((4-chloro-1-isopropyl-3-methyl-1H-pyrazol-5-carboxamido)methyl)-4,5-dihydroisoxazol-5-carboxylate (0.048 g, 0.11 mmol) obtained in (3) above by the preparation method of Example 84-(3).

MS (m/z): 666[M+H]

(5) Preparation of ((1R)-1-(5-benzyl-3-((4-chloro-1-isopropyl-3-methyl-1H-pyrazol-5-carboxamido)methyl)-4,5-dihydroisoxazol-5-carboxamido)-3-methylbutyl)boronic acid

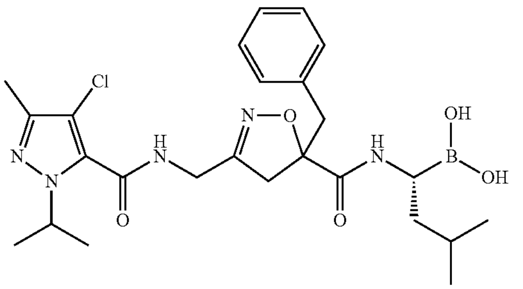 [SMILES: Cc1nn(C(C)C)c(C(=O)NCC2=NOC(Cc3ccccc3)(C(=O)N[C@@H](CC(C)C)B(O)O)C2)c1Cl]

The title compound (0.027 g, 68%) was obtained using 5-benzyl-3-((4-chloro-1-isopropyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.050 g, 0.075 mmol) obtained in (4) above by the preparation method of Example 1-(4).

NMR: $^{1}$H-NMR (400 MHz, $CD_3OD$); δ 7.29-7.25 (5H, m), 4.95 (1H, q), 4.26 (2H, s), 3.47 (1H, d), 3.37-3.24 (2H, m), 3.21 (1H, d), 2.73 (1H, dd), 2.23 (3H, s), 1.45-1.39 (7H, m), 1.23-1.05 (2H, m), 0.83 (6H, dd)

MS (ES+): 554[M+Na], 514[M-OH]

Example 223: Preparation of ((1R)-1-(5-(3-chlorobenzyl)-3-((5-isopropylisoxazol-3-carboxamido)methyl)-4,5-dihydroisoxazol-5-carboxamido)-3-methylbutyl)boronic acid Through the processes (1), (2) and (3) below, the title compound was obtained.

(1) Preparation of ethyl 5-(3-chlorobenzyl)-3-((5-isopropylisoxazol-3-carboxamido)methyl)-4,5-dihydroisoxazol-5-carboxylate

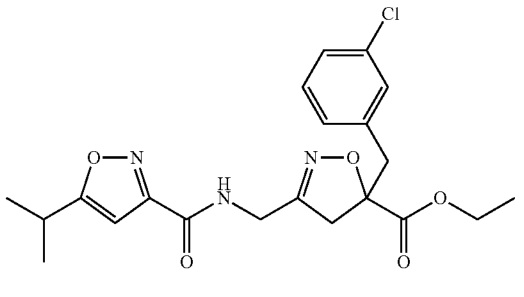 [SMILES: CCOC(=O)C1(Cc2cccc(Cl)c2)CC(CNC(=O)c2cc(C(C)C)on2)=NO1]

The title compound (0.079 g, 51%) was obtained using ethyl 3-(aminomethyl)-5-(3-chlorobenzyl)-4,5-dihydroisoxazol-5-carboxylate hydrochloride (0.12 g, 0.36 mmol) obtained in Example 175-(1) and 5-isopropyl-isoxazol-3-carboxylic acid (0.062 g, 0.40 mmol) by the preparation method of Example 84-(2).

MS (m/z): 434[M+H]

(2) Preparation of N-((5-(3-chlorobenzyl)-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)-5-isopropylisoxazol-3-carboxamide

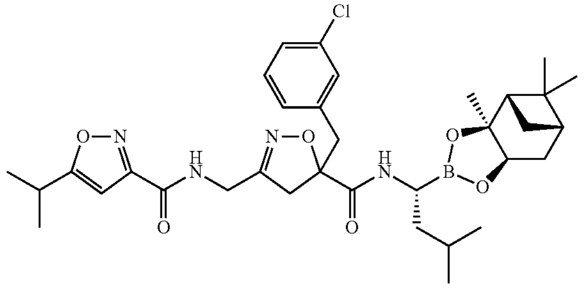 [SMILES: CC(C)C[C@H](NC(=O)C1(Cc2cccc(Cl)c2)CC(CNC(=O)c2cc(C(C)C)on2)=NO1)B1O[C@@H]2C[C@@H]3C[C@@H](C3(C)C)[C@]2(C)O1]

The title compound (0.047 g, 37%, 2 steps) was obtained using ethyl 5-(3-chlorobenzyl)-3-((5-isopropylisoxazol-3-carboxamido)methyl)-4,5-dihydroisoxazol-5-carboxylate (0.079 g, 0.18 mmol) obtained in (1) above by the preparation method of Example 84-(3).

MS (m/z): 653[M+H]

(3) Preparation of ((1R)-1-(5-(3-chlorobenzyl)-3-((5-isopropylisoxazol-3-carboxamido)methyl)-4,5-dihydroisoxazol-5-carboxamido)-3-methylbutyl)boronic acid

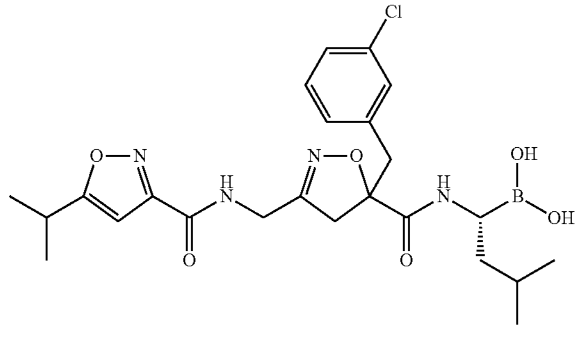 [SMILES: CC(C)C[C@H](NC(=O)C1(Cc2cccc(Cl)c2)CC(CNC(=O)c2cc(C(C)C)on2)=NO1)B(O)O]

The title compound (0.018 g, 48%) was obtained using N-((5-(3-chlorobenzyl)-5-(((R)-3-methyl-1-((3aS,4S,6S,7aR)-3a,5,5-trimethylhexahydro-4,6-metanobenzo[d][1,3,2]dioxaborol-2-yl)butyl)carbamoyl)-4,5-dihydroisoxazol-3-yl)methyl)-5-isopropylisoxazol-3-carboxamide (0.047 g, 0.072 mmol) obtained in (2) above by the preparation method of Example 1-(4).

NMR: $^{1}$H-NMR (400 MHz, MeOD-d4); δ 7.32-7.23 (m, 4H), 6.48 (d, 1H), 4.26 (s, 2H), 3.48-3.36 (m, 2H), 3.29-3.14 (m, 3H), 2.71-2.67 (m, 1H), 1.43-4.40 (m, 1H), 1.37-1.35 (d, 6H), 1.22-1.15 (m, 1H), 1.07-1.03 (m, 1H), 0.85-0.80 (dd, 6H)

MS (m/z): 519[M+H], 501[M-OH]

Example 224: Preparation of ((1R)-1-(5-benzyl-3-((3-(tert-butyl)-1-isopropyl-1H-pyrazol-5-carboxamido)methyl)-4,5-dihydroisoxazol-5-carboxamido)-3-methylbutyl)boronic acid Through the processes (1), (2), (3) and (4) below, the title compound was obtained.

(1) Preparation of 5-tert-butyl-2-isopropyl-2H-pyrazol-3-carboxylic acid

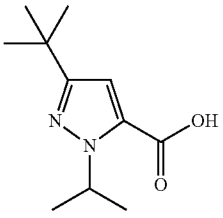

The title compound was obtained by the method described in US2012202856A1.

(2) Preparation of methyl 5-benzyl-3-((3-(tert-butyl)-1-isopropyl-1H-pyrazol-5-carboxamido)methyl)-4,5-dihydroisoxazol-5-carboxylate

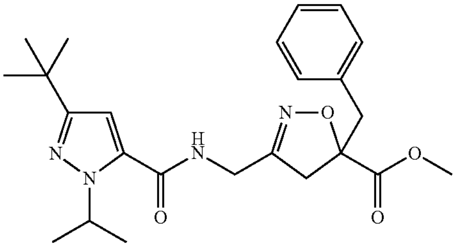 [SMILES: COC(=O)C1(Cc2ccccc2)CC(CNC(=O)c2cc(C(C)(C)C)nn2C(C)C)=NO1]

The title compound (0.086 g, 84%) was obtained using methyl 3-(aminomethyl)-5-benzyl-4,5-dihydroisoxazol-5-carboxylate hydrochloride (0.066 g, 0.232 mmol) obtained in Example 84-(1) and 5-tert-butyl-2-isopropyl-2H-pyrazol-3-carboxylic acid (0.064 g, 0.304 mmol) obtained in (1) above by the preparation method of Example 84-(2).

NMR: $^1$H-NMR (500 MHz, $CDCl_3$); δ 7.24-7.20 (5H, m), 6.24 (1H, s), 6.15 (1H, t), 5.32 (1H, q), 4.16-4.08 (2H, m), 3.77 (3H, s), 3.40 (1H, d), 3.32 (1H, d), 3.10 (1H, d), 3.00 (1H, d), 1.43 (6H, dd), 1.27 (9H, s)

MS (m/z): 441[M+H]

(3) Preparation of 5-benzyl-3-((3-(tert-butyl)-1-isopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

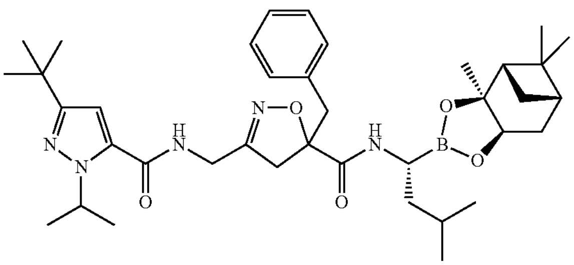 [SMILES: CC(C)C[C@H](NC(=O)C1(Cc2ccccc2)CC(CNC(=O)c2cc(C(C)(C)C)nn2C(C)C)=NO1)B1O[C@@H]2C[C@@H]3C[C@@H](C3(C)C)[C@]2(C)O1]

The title compound (0.088 g, 67%, 2 steps) was obtained using methyl 5-benzyl-3-((3-(tert-butyl)-1-isopropyl-1H-pyrazol-5-carboxamido)methyl)-4,5-dihydroisoxazol-5-carboxylate (0.086 g, 0.195 mmol) obtained in (2) above by the preparation method of Example 84-(3).

MS (m/z): 674[M+H]

(4) Preparation of ((1R)-1-(5-benzyl-3-((3-(tert-butyl)-1-isopropyl-1H-pyrazol-5-carboxamido) methyl)-4,5-dihydroisoxazol-5-carboxamido)-3-methylbutyl)boronic acid

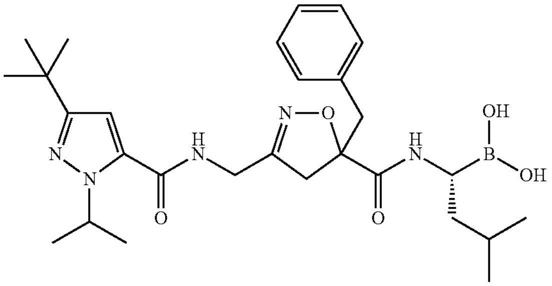 [SMILES: CC(C)C[C@H](NC(=O)C1(Cc2ccccc2)CC(CNC(=O)c2cc(C(C)(C)C)nn2C(C)C)=NO1)B(O)O]

The title compound (0.043 g, 61%) was obtained using 5-benzyl-3-((3-(tert-butyl)-1-isopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.088 g, 0.131 mmol) obtained in (3) above by the preparation method of Example 1-(4).

NMR: $^1$H-NMR (400 MHz, $CD_3OD$); δ 7.29-7.23 (5H, m), 6.56 (1H, s), 5.41 (1H, q), 4.12 (2H, d), 3.43 (1H, d), 3.37-3.23 (2H, m), 3.21 (1H, d), 2.69 (1H, dd), 1.47-1.40 (7H, m), 1.32 (9H, s), 1.20-1.06 (2H, m), 0.82 (6H, dd)

MS (ES+): 562[M+Na], 522[M-OH]

Example 225: Preparation of ((1R)-1-(5-(3-chlorobenzyl)-3-((1-isopropyl-3-methyl-1H-pyrazol-5-carboxamido)methyl)-4,5-dihydroisoxazol-5-carboxamido)-3-methylbutyl)boronic acid Through the processes (1), (2) and (3) below, the title compound was obtained.

(1) Preparation of ethyl 5-(3-chlorobenzyl)-3-((1-isopropyl-3-methyl-1H-pyrazol-5-carboxamido)methyl)-4,5-dihydroisoxazol-5-carboxylate

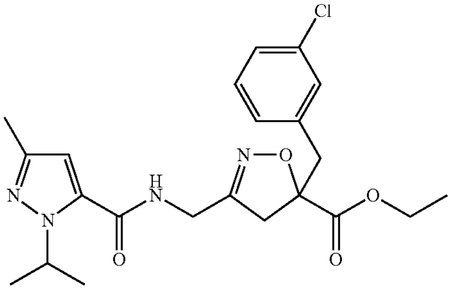 [SMILES: CCOC(=O)C1(Cc2cccc(Cl)c2)CC(CNC(=O)c2cc(C)nn2C(C)C)=NO1]

The title compound (0.12 g, 75%) was obtained using ethyl 3-(aminomethyl)-5-(3-chlorobenzyl)-4,5-dihydroisoxazol-5-carboxylate hydrochloride (0.12 g, 0.36 mmol) obtained in Example 175-(1) and 2-isopropyl-5-methyl-2H-pyrazol-3-carboxylic acid (0.067 g, 0.40 mmol) obtained in Example 190-(2) by the preparation method of Example 84-(2).

MS (m/z): 447[M+H]

(2) Preparation of 5-(3-chlorobenzyl)-3-((1-isopropyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

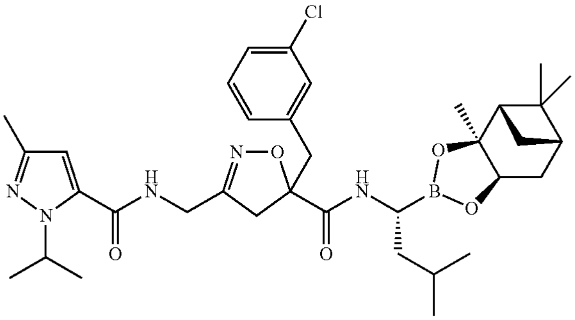

The title compound (0.115 g, 23%, 2 steps) was obtained using ethyl 5-(3-chlorobenzyl)-3-((1-isopropyl-3-methyl-1H-pyrazol-5-carboxamido)methyl)-4,5-dihydroisoxazol-5-carboxylate (0.12 g, 0.27 mmol) obtained in (1) above by the preparation method of Example 84-(3).

MS (m/z): 666[M+H]

(3) Preparation of ((1R)-1-(5-(3-chlorobenzyl)-3-((1-isopropyl-3-methyl-1H-pyrazol-5-carboxamido)methyl)-4,5-dihydroisoxazol-5-carboxamido)-3-methylbutyl)boronic acid

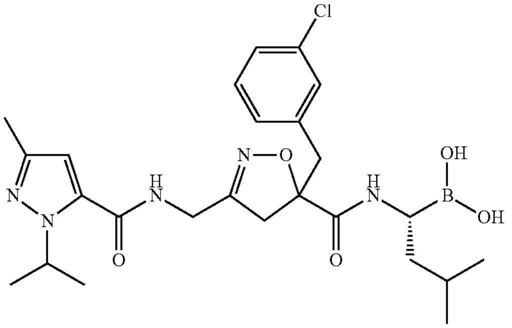 [SMILES: Cc1cc(C(=O)NCC2=NOC(Cc3cccc(Cl)c3)(C(=O)N[C@@H](CC(C)C)B(O)O)C2)n(C(C)C)n1]

The title compound (0.020 g, 59%) was obtained using 5-(3-chlorobenzyl)-3-((1-isopropyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.042 g, 0.063 mmol) obtained in (2) above by the preparation method of Example 1-(4).

NMR: $^1$H-NMR (400 MHz, MeOD-d4); δ 7.32-7.22 (m, 4H), 6.47 (s, 1H), 5.46-5.39 (m, 1H), 4.21-4.20 (d, 2H), 3.47-3.34 (m, 2H), 3.32-3.20 (m, 2H), 2.70 (m, 1H), 2.27 (m, 3H), 1.46-1.44 (d, 6H), 1.40-1.39 (m, 1H), 1.23-1.04 (m, 2H), 0.85-0.80 (dd, 6H)

MS (m/z): 532[M+H], 514[M-OH]

Example 226: Preparation of ((1R)-1-(5-benzyl-3-((1,3-dimethyl-1H-pyrazol-4-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((1,3-dimethyl-1H-pyrazol-4-carboxamido)methyl)-4,5-dihydroisoxazol-5-carboxylate

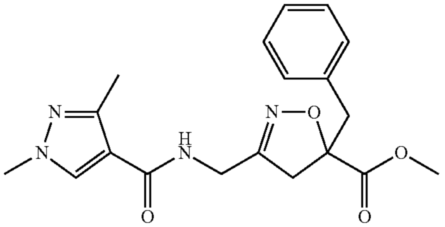

The title compound (0.063 g, 97%) was obtained using methyl 3-(aminomethyl)-5-benzyl-4,5-dihydroisoxazol-5-carboxylate hydrochloride (0.05 g, 0.18 mmol) obtained in Example 84-(1) and 1,3-dimethyl-1H-pyrazol-4-carboxylic acid (0.027 g, 0.19 mmol) by the preparation method of Example 84-(2).

MS (m/z): 371[M+H]

(2) Preparation of 5-benzyl-3-((1,3-dimethyl-1H-pyrazol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

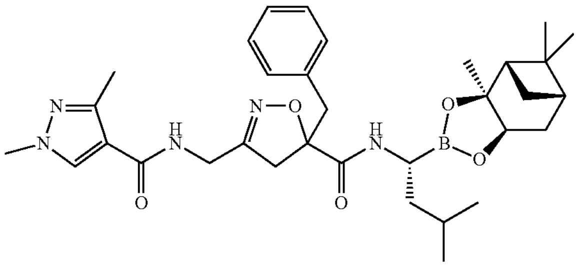

The title compound (0.023 g, 26%, 2 steps) was obtained using methyl 5-benzyl-3-((1,3-dimethyl-1H-pyrazol-4-carboxamido)methyl)-4,5-dihydroisoxazol-5-carboxylate (0.063 g, 0.17 mmol) obtained in (1) above by the preparation method of Example 84-(3).

MS (m/z): 604[M+H]

(3) Preparation of ((1R)-1-(5-benzyl-3-((1,3-dimethyl-1H-pyrazol-4-carboxamido)methyl)-4,5-dihydroisoxazol-5-carboxamido)-3-methylbutyl)boronic acid

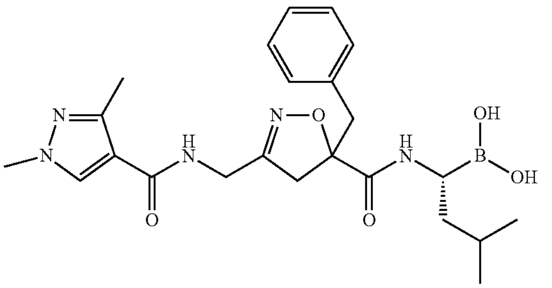 [SMILES: Cc1nn(C)cc1C(=O)NCC1=NOC(Cc2ccccc2)(C(=O)N[C@@H](CC(C)C)B(O)O)C1]

The title compound (0.012 g, 67%) was obtained using 5-benzyl-3-((1,3-dimethyl-1H-pyrazol-4-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.023 g, 0.038 mmol) obtained in (2) above by the preparation method of Example 1-(4).

NMR: $^1$H-NMR (400 MHz, MeOD-d4); δ 7.91 (s, 1H), 7.29-7.25 (m, 5H), 4.16 (s, 2H), 3.85 (s, 3H), 3.45-3.34 (m, 2H), 3.32-3.19 (m, 2H), 2.69-2.65 (m, 1H), 2.41 (s, 3H), 1.43-1.40 (m, 1H), 1.20-1.05 (m, 2H), 0.84-0.80 (dd, 6H)

MS (m/z): 470[M+H], 452[M-OH]

Example 227: Preparation of ((1R)-1-(5-benzyl-3-((1,3-diisopropyl-1H-pyrazol-5-carboxamido)methyl)-4,5-dihydroisoxazol-5-carboxamido)-3-methylbutyl)boronic acid Through the processes (1), (2), (3), (4) and (5) below, the title compound was obtained.

(1) Preparation of 2,5-diisopropyl-2H-pyrazol-3-carboxylic acid ethyl ester

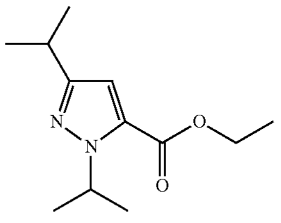 [SMILES: CCOC(=O)c1cc(C(C)C)nn1C(C)C]

The title compound was obtained by the method described in WO200718314A2.

(2) Preparation of 2,5-diisopropyl-2H-pyrazol-3-carboxylic acid

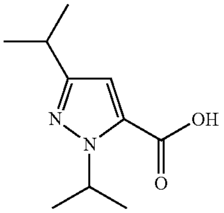

The title compound (0.33 g, 98%) was obtained using 2,5-diisopropyl-2H-pyrazol-3-carboxylic acid ethyl ester (0.39 g, 1.73 mmol) obtained in (1) above by the preparation method of Example 119-(2).

(3) Preparation of methyl 5-benzyl-3-((1,3-diisopropyl-1H-pyrazol-5-carboxamido)methyl)-4,5-dihydroisoxazol-5-carboxylate

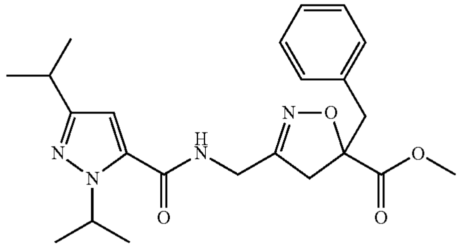 [SMILES: COC(=O)C1(Cc2ccccc2)CC(CNC(=O)c2cc(C(C)C)nn2C(C)C)=NO1]

The title compound (0.088 g, 82%) was obtained using methyl 3-(aminomethyl)-5-benzyl-4,5-dihydroisoxazol-5-carboxylate hydrochloride (0.047 g, 0.165 mmol) obtained in Example 84-(1) and 2,5-diisopropyl-2H-pyrazol-3-carboxylic acid (0.043 g, 0.219 mmol) obtained in (2) above by the preparation method of Example 84-(2).

NMR: $^1$H-NMR (400 MHz, $CDCl_3$); δ 7.30-7.23 (5H, m), 6.31 (1H, t), 6.28 (1H, s), 5.41 (1H, q), 4.21-4.09 (2H, m), 3.80 (3H, s), 3.45 (1H, d), 3.36 (1H, d), 3.15 (1H, d), 3.11-3.00 (2H, m), 1.49 (6H, dd), 1.32 (6H, dd)

MS (m/z): 427[M+H]

(4) Preparation of 5-benzyl-3-((1,3-diisopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

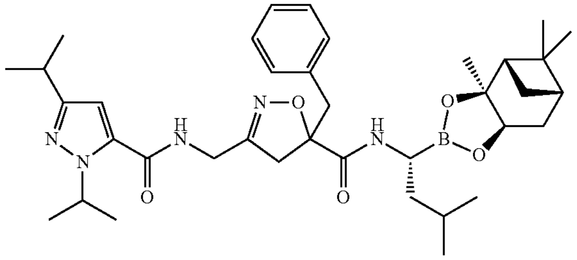 [SMILES: CC(C)C[C@H](NC(=O)C1(Cc2ccccc2)CC(CNC(=O)c2cc(C(C)C)nn2C(C)C)=NO1)B1O[C@@H]2C[C@@H]3C[C@@H](C3(C)C)[C@]2(C)O1]

The title compound (0.051 g, 57%, 2 steps) was obtained using methyl 5-benzyl-3-((1,3-diisopropyl-1H-pyrazol-5-carboxamido)methyl)-4,5-dihydroisoxazol-5-carboxylate (0.058 g, 0.136 mmol) obtained in (3) above by the preparation method of Example 84-(3).

MS (m/z): 660[M+H]

(5) Preparation of ((1R)-1-(5-benzyl-3-((1,3-diisopropyl-1H-pyrazol-5-carboxamido)methyl)-4,5-dihydroisoxazol-5-carboxamido)-3-methylbutyl)boronic acid

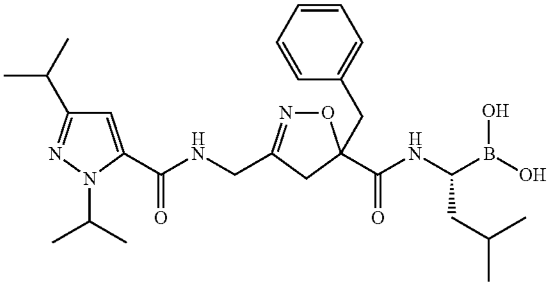 [SMILES: CC(C)C[C@H](NC(=O)C1(Cc2ccccc2)CC(CNC(=O)c2cc(C(C)C)nn2C(C)C)=NO1)B(O)O]

The title compound (0.023 g, 57%) was obtained using 5-benzyl-3-((1,3-diisopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.051 g, 0.077 mmol) obtained in (4) above by the preparation method of Example 1-(4).

NMR: $^1$H-NMR (400 MHz, $CD_3OD$); δ 7.28-7.25 (5H, m), 6.54 (1H, s), 5.43 (1H, q), 4.17 (2H, s), 3.43 (1H, d), 3.37-3.23 (2H, m), 3.21 (1H, d), 2.99 (1H, dt), 2.69 (1H, dd), 1.46-1.41 (7H, m), 1.27 (6H, d), 1.20-1.07 (2H, m), 0.82 (6H, dd)

MS (m/z): 548[M+Na], 508[M-OH]

Example 228: Preparation of ((1R)-1-(5-benzyl-3-((1-isopropyl-3-(pyridin-3-yl)-1H-pyrazol-5-carboxamido)methyl)-4,5-dihydroisoxazol-5-carboxamido)-3-methylbutyl)boronic acid Through the processes (1), (2), (3), (4), (5) and (6) below, the title compound was obtained.

(1) Preparation of 5-pyridin-3-yl-2H-pyrazol-3-carboxylic acid ethyl ester

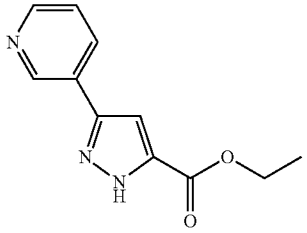 [SMILES: CCOC(=O)c1cc(-c2cccnc2)n[nH]1]

The title compound was obtained using 1-pyridin-3-yl-ethanone by the method described in Medicinal Chemistry Letters, 2012, 3, 678-682.

(2) Preparation of 2-isopropyl-5-pyridin-3-yl-2H-pyrazol-3-carboxylic acid ethyl ester

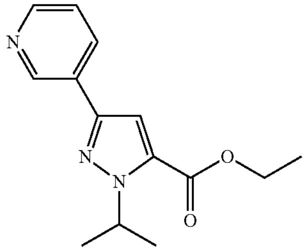 [SMILES: CCOC(=O)c1cc(-c2cccnc2)nn1C(C)C]

The title compound (0.48 g, 92%) was obtained using 5-pyridin-3-yl-2H-pyrazol-3-carboxylic acid ethyl ester (0.44 g, 2.0 mmol) obtained in (1) above by the preparation method of Example 188-(1).

MS (m/z): 244[M+H]

(3) Preparation of 2-isopropyl-5-pyridin-3-yl-2H-pyrazol-3-carboxylic acid

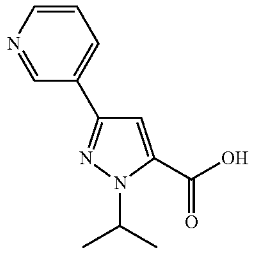 [SMILES: CC(C)n1nc(-c2cccnc2)cc1C(=O)O]

The title compound (0.37 g, 87%) was obtained using 2-isopropyl-5-pyridin-3-yl-2H-pyrazol-3-carboxylic acid ethyl ester (0.48 g, 1.84 mmol) obtained in (2) above by the preparation method of Example 119-(2).

(4) Preparation of methyl 5-benzyl-3-((1-isopropyl-3-(pyridin-3-yl)-1H-pyrazol-5-carboxamido)methyl)-4,5-dihydroisoxazol-5-carboxylate

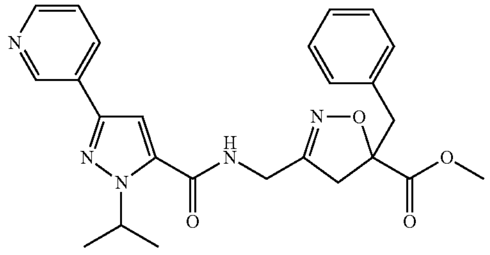 [SMILES: COC(=O)C1(Cc2ccccc2)CC(CNC(=O)c2cc(-c3cccnc3)nn2C(C)C)=NO1]

The title compound (0.067 g, 88%) was obtained using methyl 3-(aminomethyl)-5-benzyl-4,5-dihydroisoxazol-5-carboxylate hydrochloride (0.047 g, 0.165 mmol) obtained in Example 84-(1) and 2-isopropyl-5-pyridin-3-yl-2H-pyrazol-3-carboxylic acid (0.050 g, 0.216 mmol) obtained in (3) above by the preparation method of Example 84-(2).

NMR: $^1$H-NMR (400 MHz, $CDCl_3$); δ 8.99 (1H, d), 8.54 (1H, dd), 8.19-8.17 (1H, m), 7.37-7.34 (2H, m), 7.24-7.20 (5H, m), 6.95 (1H, s), 5.52 (1H, q), 4.20 (2H, m), 3.77 (3H, s), 3.49 (1H, d), 3.34 (1H, d), 3.16 (1H, d), 3.08 (1H, d), 1.56 (6H, dd)

MS (m/z): 462[M+H]

(5) Preparation of 5-benzyl-3-((1-isopropyl-3-(pyridin-3-yl)-1H-pyrazol-5-carboxamido)methyl)-N—((R)-3-methyl-1-((3aS,4S,6S,7aR)-3a,5,5-trimethyl-hexahydro-4,6-metanobenzo[d][1,3,2]dioxaborol-2-yl)butyl)-4,5-dihydroisoxazol-5-carboxamide

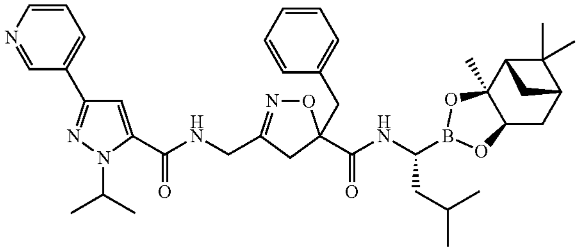 [SMILES: CC(C)C[C@H](NC(=O)C1(Cc2ccccc2)CC(CNC(=O)c2cc(-c3cccnc3)nn2C(C)C)=NO1)B1O[C@@H]2C[C@@H]3C[C@@H](C3(C)C)[C@]2(C)O1]

The title compound (0.048 g, 48%, 2 steps) was obtained using methyl 5-benzyl-3-((1-isopropyl-3-(pyridin-3-yl)-1H-pyrazol-5-carboxamido)methyl)-4,5-dihydroisoxazol-5-carboxylate (0.067 g, 0.145 mmol) obtained in (4) above by the preparation method of Example 84-(3).

MS (m/z): 695[M+H]

(6) Preparation of ((1R)-1-(5-benzyl-3-((1-isopropyl-3-(pyridin-3-yl)-1H-pyrazol-5-carboxamido)methyl)-4,5-dihydroisoxazol-5-carboxamido)-3-methylbutyl)boronic acid

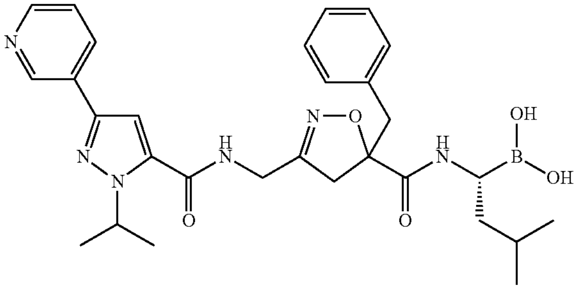 [SMILES: CC(C)C[C@H](NC(=O)C1(Cc2ccccc2)CC(CNC(=O)c2cc(-c3cccnc3)nn2C(C)C)=NO1)B(O)O]

The title compound (0.019 g, 47%) was obtained using 5-benzyl-3-((1-isopropyl-3-(pyridin-3-yl)-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.048 g, 0.069 mmol) obtained in (5) above by the preparation method of Example 1-(4).

NMR: $^1$H-NMR (500 MHz, $CD_3OD$); δ 9.00 (1H, s), 8.51 (1H, s), 8.27 (1H, d), 7.52 (1H, dd), 7.29-7.23 (5H, m), 7.14 (1H, s), 5.52 (1H, q), 4.23 (2H, s), 3.47 (1H, d), 3.37-3.26 (2H, m), 3.22 (1H, d), 2.71 (1H, t), 1.55 (6H, dd), 1.44-1.07 (3H, m), 0.82 (6H, dd)

MS (m/z): 583[M+Na], 543[M-OH]

Example 229: Preparation of ((1R)-1-(5-benzyl-3-((1-isopropyl-3-(pyridin-4-yl)-1H-pyrazol-5-carboxamido)methyl)-4,5-dihydroisoxazol-5-carboxamido)-3-methylbutyl)boronic acid Through the processes (1), (2), (3), (4), (5) and (6) below, the title compound was obtained.

(1) Preparation of 5-pyridin-4-yl-2H-pyrazol-3-carboxylic acid ethyl ester

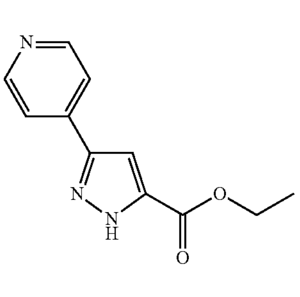 [SMILES: CCOC(=O)c1cc(-c2ccncc2)n[nH]1]

The title compound was obtained using 1-pyridin-4-yl-ethanone by the same method as described in Medicinal Chemistry Letters, 2012, 3, 678-682.

(2) Preparation of 2-isopropyl-5-pyridin-4-yl-2H-pyrazol-3-carboxylic acid ethyl ester

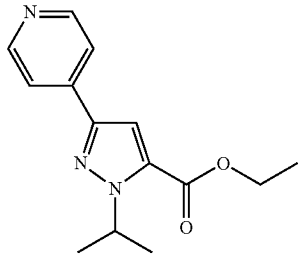 [SMILES: CCOC(=O)c1cc(-c2ccncc2)nn1C(C)C]

The title compound (0.42 g, 81%) was obtained using 5-pyridin-4-yl-2H-pyrazol-3-carboxylic acid ethyl ester (0.44 g, 2.0 mmol) obtained in (1) above by the preparation method of Example 188-(1).

MS (m/z): 260[M+H]

(3) Preparation of 2-isopropyl-5-pyridin-4-yl-2H-pyrazol-3-carboxylic acid

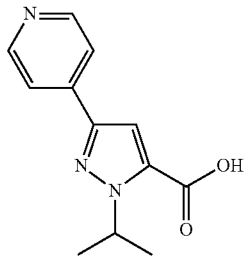 [SMILES: CC(C)n1nc(-c2ccncc2)cc1C(=O)O]

The title compound (0.31 g, 82%) was obtained using 2-isopropyl-5-pyridin-4-yl-2H-pyrazol-3-carboxylic acid ethyl ester (0.42 g, 1.62 mmol) obtained in (2) above by the preparation method of Example 119-(2).

(4) Preparation of methyl 5-benzyl-3-((1-isopropyl-3-(pyridin-4-yl)-1H-pyrazol-5-carboxamido)methyl)-4,5-dihydroisoxazol-5-carboxylate

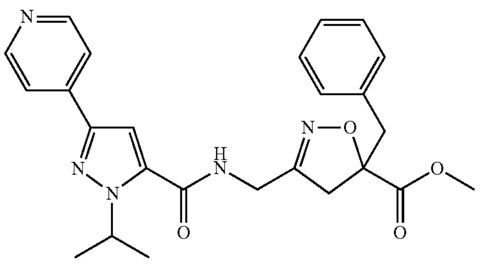 [SMILES: COC(=O)C1(Cc2ccccc2)CC(CNC(=O)c2cc(-c3ccncc3)nn2C(C)C)=NO1]

The title compound (0.063 g, 83%) was obtained using methyl 3-(aminomethyl)-5-benzyl-4,5-dihydroisoxazol-5-carboxylate hydrochloride (0.047 g, 0.165 mmol) obtained in Example 84-(1) and 2-isopropyl-5-pyridin-4-yl-2H-pyrazol-3-carboxylic acid (0.050 g, 0.216 mmol) obtained in (3) above by the preparation method of Example 84-(2).

NMR: $^1$H-NMR (400 MHz, $CDCl_3$); δ 8.61 (2H, dd), 7.70 (2H, dd), 7.30-7.20 (5H, m), 7.09 (1H, t), 6.96 (1H, d), 5.51

(1H, q), 4.20 (2H, d), 3.78 (3H, s), 3.48 (1H, d), 3.35 (1H, d), 3.17 (1H, d), 3.07 (1H, d), 1.56 (6H, dd)

MS (m/z): 462[M+H]

(5) Preparation of 5-benzyl-3-((1-isopropyl-3-(pyridin-4-yl)-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

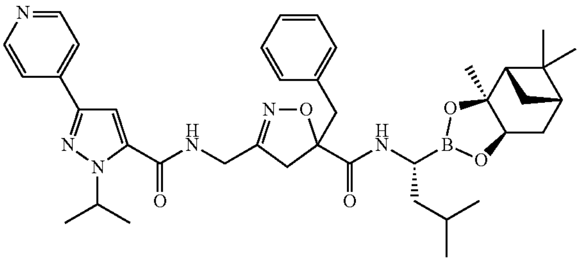 [SMILES: CC(C)C[C@H](NC(=O)C1(Cc2ccccc2)CC(CNC(=O)c2cc(-c3ccncc3)nn2C(C)C)=NO1)B1O[C@@H]2C[C@@H]3C[C@@H](C3(C)C)[C@]2(C)O1]

The title compound (0.020 g, 20%, 2 steps) was obtained using methyl 5-benzyl-3-((1-isopropyl-3-(pyridin-4-yl)-1H-pyrazol-5-carboxamido)methyl)-4,5-dihydroisoxazol-5-carboxylate (0.063 g, 0.137 mmol) obtained in (4) above by the preparation method of Example 84-(3).

MS (m/z): 695[M+H]

(6) Preparation of ((1R)-1-(5-benzyl-3-((1-isopropyl-3-(pyridin-4-yl)-1H-pyrazol-5-carboxamido)methyl)-4,5-dihydroisoxazol-5-carboxamido)-3-methylbutyl)boronic acid

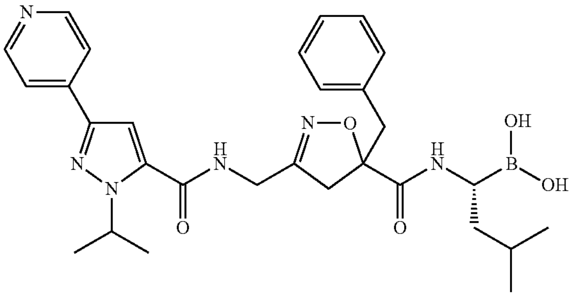 [SMILES: CC(C)C[C@H](NC(=O)C1(Cc2ccccc2)CC(CNC(=O)c2cc(-c3ccncc3)nn2C(C)C)=NO1)B(O)O]

The title compound (0.009 g, 55%) was obtained using 5-benzyl-3-((1-isopropyl-3-(pyridin-4-yl)-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.020 g, 0.029 mmol) obtained in (5) above by the preparation method of Example 1-(4).

NMR: $^1$H-NMR (500 MHz, $CD_3OD$); δ 8.57 (2H, d), 7.87 (2H, dd), 7.29-7.22 (5H, m), 7.21 (1H, s), 5.53 (1H, q), 4.24-4.19 (2H, m), 3.47 (1H, d), 3.37-3.26 (2H, m), 3.22 (1H, d), 2.71 (1H, t), 1.55 (6H, dd), 1.44-1.08 (3H, m), 0.82 (6H, dd)

MS (m/z): 583[M+Na], 543[M-OH]

Example 230: Preparation of ((1R)-1-(3-((1-isopropyl-3-phenyl-1H-pyrazol-5-carboxamido)methyl)-5-(3-methoxybenzyl)-4,5-dihydroisoxazol-5-carboxamido)-3-methylbutyl)boronic acid Through the processes (1), (2) and (3) below, the title compound was obtained.

(1) Preparation of ethyl 3-((1-isopropyl-3-phenyl-1H-pyrazol-5-carboxamido)methyl)-5-(3-methoxybenzyl)-4,5-dihydroisoxazol-5-carboxylate

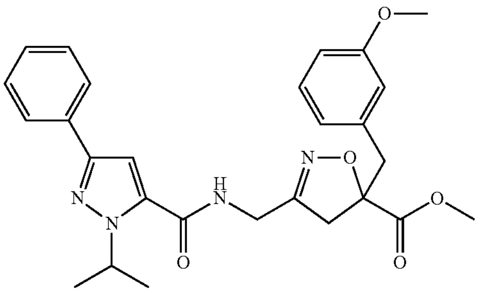 [SMILES: COC(=O)C1(Cc2cccc(OC)c2)CC(CNC(=O)c2cc(-c3ccccc3)nn2C(C)C)=NO1]

The title compound (0.145 g, 80%) was obtained using ethyl 3-(aminomethyl)-5-(3-methoxybenzyl)-4,5-dihydroisoxazol-5-carboxylate hydrochloride (0.120 g, 0.36 mmol) obtained in Example 100-(1) and 2-isopropyl-5-phenyl-2H-pyrazol-3-carboxylic acid (0.114 g, 0.50 mmol) obtained in Example 207-(3) by the preparation method of Example 84-(2).

NMR: $^1$H-NMR (400 MHz, $CDCl_3$); δ 7.85 (2H, dd), 7.45 (2H, dd), 7.37 (1H, dd), 7.19 (1H, t), 6.85-6.79 (4H, m), 6.47 (1H, t), 5.49 (1H, q), 4.31-4.15 (4H, m), 3.76 (3H, s), 3.48 (1H, d), 3.35 (1H, d), 3.15 (1H, d), 3.07 (1H, m), 1.58 (6H, dd), 1.32 (3H, t)

MS (m/z): 505[M+H]

(2) Preparation of 3-((1-isopropyl-3-phenyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

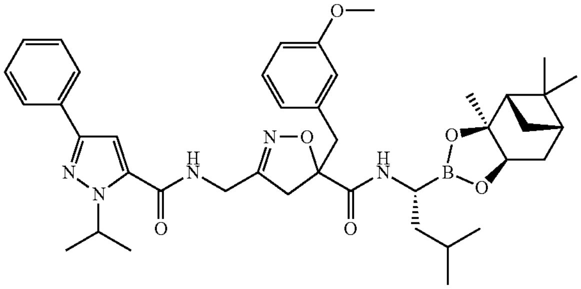 [SMILES: COc1cccc(CC2(C(=O)N[C@@H](CC(C)C)B3O[C@@H]4C[C@@H]5C[C@@H](C5(C)C)[C@]4(C)O3)CC(CNC(=O)c3cc(-c4ccccc4)nn3C(C)C)=NO2)c1]

The title compound (0.074 g, 36%, 2 steps) was obtained using ethyl 3-((1-isopropyl-3-phenyl-1H-pyrazol-5-carboxamido)methyl)-5-(3-methoxybenzyl)-4,5-dihydroisoxazol-5-carboxylate (0.145 g, 0.29 mmol) obtained in (1) above by the preparation method of Example 84-(3).

MS (m/z): 724[M+H]

(3) Preparation of ((1R)-1-(3-((1-isopropyl-3-phenyl-1H-pyrazol-5-carboxamido)methyl)-5-(3-methoxybenzyl)-4,5-dihydroisoxazol-5-carboxamido)-3-methylbutyl)boronic acid

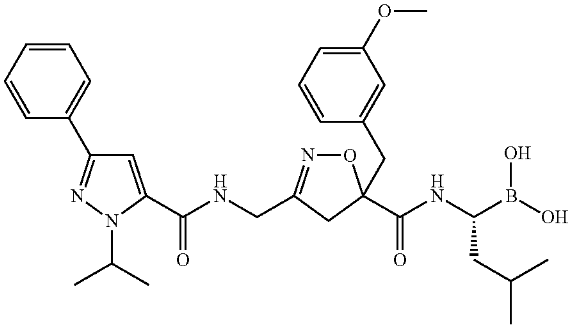

The title compound (0.031 g, 52%) was obtained using 3-((1-isopropyl-3-phenyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.074 g, 0.102 mmol) obtained in (2) above by the preparation method of Example 1-(4).

NMR: $^1$H-NMR (500 MHz, $CD_3OD$); δ 7.79 (2H, dd), 7.37 (2H, dd), 7.28 (1H, dd), 7.14 (1H, dd), 7.00 (1H, s), 6.83-6.75 (3H, m), 5.47 (1H, q), 4.22-4.16 (2H, m), 3.74 (3H, s), 3.43 (1H, d), 3.33-3.23 (2H, m), 3.16 (1H, d), 2.65 (1H, t), 1.50 (6H, dd), 1.41-1.01 (3H, m), 0.78 (6H, dd)

MS (m/z): 612[M+Na], 572[M-OH]

Example 231: Preparation of ((1R)-1-(3-((3-(tert-butyl)-1-isopropyl-1H-pyrazol-5-carboxamido)methyl)-5-(3-methoxybenzyl)-4,5-dihydroisoxazol-5-carboxamido)-3-methylbutyl)boronic acid Through the processes (1), (2) and (3) below, the title compound was obtained.

(1) Preparation of ethyl 3-((3-(tert-butyl)-1-isopropyl-1H-pyrazol-5-carboxamido)methyl)-5-(3-methoxybenzyl)-4,5-dihydroisoxazol-5-carboxylate

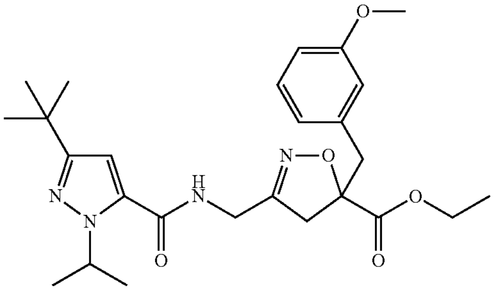 [SMILES: CCOC(=O)C1(Cc2cccc(OC)c2)CC(CNC(=O)c2cc(C(C)(C)C)nn2C(C)C)=NO1]

The title compound (0.148 g, 85%) was obtained using ethyl 3-(aminomethyl)-5-(3-methoxybenzyl)-4,5-dihydroisoxazol-5-carboxylate hydrochloride (0.120 g, 0.36 mmol) obtained in Example 100-(1) and 5-tert-butyl-2- isopropyl-2H-pyrazol-3-carboxylic acid (0.104 g, 0.49 mmol) obtained in Example 224-(1) by the preparation method of Example 84-(2).

NMR: $^1$H-NMR (500 MHz, $CDCl_3$); δ 7.13 (1H, t), 6.79-6.76 (3H, m), 6.28-6.26 (2H, m), 5.34 (1H, q), 4.24-4.10 (4H, m), 3.73 (3H, s), 3.40 (1H, d), 3.28 (1H, d), 3.10 (1H, d), 2.98 (1H, m), 1.43 (6H, dd), 1.27 (9H, s), 1.25 (3H, t)

MS (m/z): 485[M+H]

(2) Preparation of 3-((3-(tert-butyl)-1-isopropyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

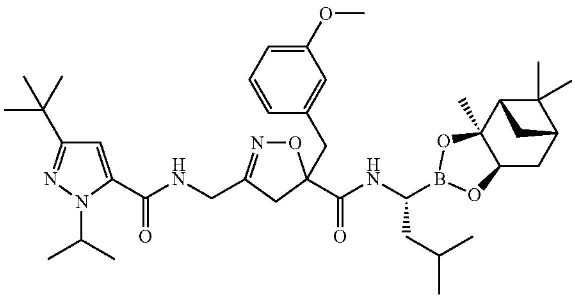 [SMILES: COc1cccc(CC2(C(=O)N[C@@H](CC(C)C)B3O[C@@H]4C[C@@H]5C[C@@H](C5(C)C)[C@]4(C)O3)CC(CNC(=O)c3cc(C(C)(C)C)nn3C(C)C)=NO2)c1]

The title compound (0.096 g, 44%, 2 steps) was obtained using ethyl 3-((3-(tert-butyl)-1-isopropyl-1H-pyrazol-5-carboxamido)methyl)-5-(3-methoxybenzyl)-4,5-dihydroisoxazol-5-carboxylate (0.148 g, 0.31 mmol) obtained in (1) above by the preparation method of Example 84-(3).

MS (m/z): 704[M+H]

(3) Preparation of ((1R)-1-(3-((3-(tert-butyl)-1-isopropyl-1H-pyrazol-5-carboxamido)methyl)-5-(3-methoxybenzyl)-4,5-dihydroisoxazol-5-carboxamido)-3-methylbutyl)boronic acid

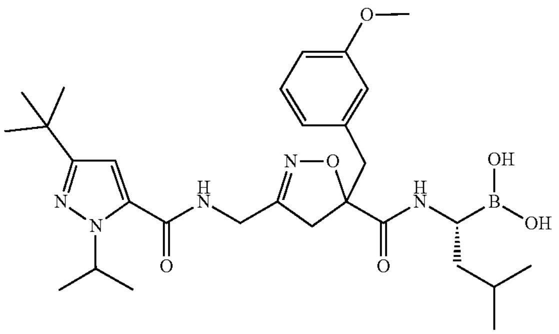 [SMILES: COc1cccc(CC2(C(=O)N[C@@H](CC(C)C)B(O)O)CC(CNC(=O)c3cc(C(C)(C)C)nn3C(C)C)=NO2)c1]

The title compound (0.030 g, 61%) was obtained using 3-((3-(tert-butyl)-1-isopropyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.062 g, 0.094 mmol) obtained in (2) above by the preparation method of Example 1-(4).

NMR: $^1$H-NMR (500 MHz, $CD_3OD$); δ 7.14 (1H, t), 6.83-6.76 (3H, m), 6.53 (1H, s), 5.37 (1H, q), 4.18-4.10 (2H, m), 3.75 (3H, s), 3.40 (1H, d), 3.33-3.18 (2H, m), 3.16 (1H, d), 2.64 (1H, t), 1.42-1.39 (7H, m), 1.27 (9H, s), 1.19-0.98 (2H, m), 0.78 (6H, dd)

MS (m/z): 592[M+Na], 552[M-OH]

Example 232: Preparation of ((1R)-1-(3-((1-isopropyl-3-methyl-1H-pyrazol-5-carboxamido)methyl)-5-(3-methoxybenzyl)-4,5-dihydroisoxazol-5-carboxamido)-3-methylbutyl)boronic acid Through the processes (1), (2) and (3) below, the title compound was obtained.

(1) Preparation of ethyl 3-((1-isopropyl-3-methyl-1H-pyrazol-5-carboxamido)methyl)-5-(3-methoxybenzyl)-4,5-dihydroisoxazol-5-carboxylate

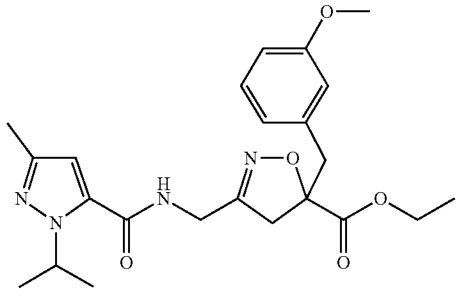 [SMILES: CCOC(=O)C1(Cc2cccc(OC)c2)CC(CNC(=O)c2cc(C)nn2C(C)C)=NO1]

The title compound (0.130 g, 82%) was obtained using ethyl 3-(aminomethyl)-5-(3-methoxybenzyl)-4,5-dihydroisoxazol-5-carboxylate hydrochloride (0.120 g, 0.36 mmol) obtained in Example 100-(1) and 2-isopropyl-5-methyl-2H-pyrazol-3-carboxylic acid (0.083 g, 0.49 mmol) obtained in Example 190-(2) by the preparation method of Example 84-(2).

NMR: $^1$H-NMR (500 MHz, $CDCl_3$); δ 7.13 (1H, t), 6.78-6.76 (3H, m), 6.38 (1H, t), 6.21 (1H, s), 5.35 (1H, q), 4.22-4.08 (4H, m), 3.72 (3H, s), 3.39 (1H, d), 3.27 (1H, d), 3.09 (1H, d), 2.98 (1H, m), 2.24 (3H, s), 1.43 (6H, dd), 1.25 (3H, t)

MS (m/z): 443[M+H]

(2) Preparation of 3-((1-isopropyl-3-methyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

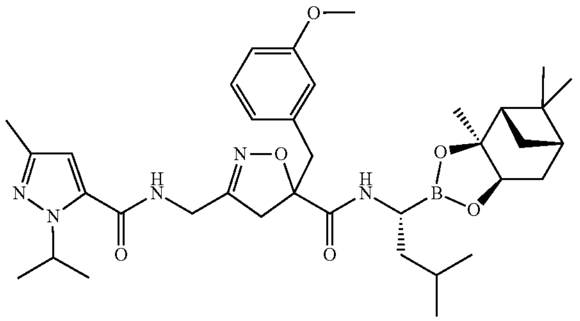

The title compound (0.062 g, 32%, 2 steps) was obtained using ethyl 3-((1-isopropyl-3-methyl-1H-pyrazol-5-carboxamido)methyl)-5-(3-methoxybenzyl)-4,5-dihydroisoxazol-5-carboxylate (0.130 g, 0.294 mmol) obtained in (1) above by the preparation method of Example 84-(3).

MS (m/z): 662[M+H]

(3) Preparation of ((1R)-1-(3-((1-isopropyl-3-methyl-1H-pyrazol-5-carboxamido)methyl)-5-(3-methoxybenzyl)-4,5-dihydroisoxazol-5-carboxamido)-3-methylbutyl)boronic acid

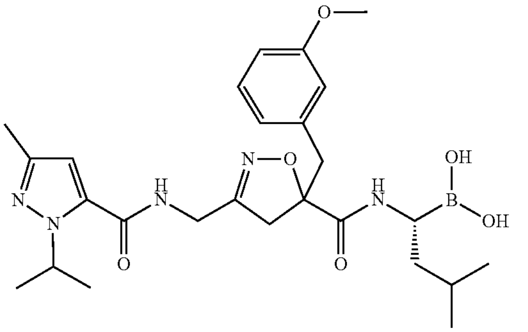 [SMILES: COc1cccc(CC2(C(=O)N[C@@H](CC(C)C)B(O)O)CC(CNC(=O)c3cc(C)nn3C(C)C)=NO2)c1]

The title compound (0.030 g, 61%) was obtained using 3-((1-isopropyl-3-methyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.062 g, 0.094 mmol) obtained in (2) above by the preparation method of Example 1-(4).

NMR: $^1$H-NMR (500 MHz, $CD_3OD$); δ 7.14 (1H, t), 6.83-6.78 (3H, m), 6.43 (1H, s), 5.38 (1H, q), 4.18-4.11 (2H, m), 3.75 (3H, s), 3.39 (1H, d), 3.33-3.19 (2H, m), 3.16 (1H, d), 2.65 (1H, t), 2.23 (3H, s), 1.41-1.35 (7H, m), 1.17-0.98 (2H, m), 0.78 (6H, dd)

MS (m/z): 550[M+Na], 510[M-OH]

Example 233: Preparation of ((1R)-1-(3-((4-chloro-1-isopropyl-3-methyl-1H-pyrazol-5-carboxamido)methyl)-5-(3-methoxybenzyl)-4,5-dihydroisoxazol-5-carboxamido)-3-methylbutyl)boronic acid Through the processes (1), (2) and (3) below, the title compound was obtained.

(1) Preparation of ethyl 3-((4-chloro-1-isopropyl-3-methyl-1H-pyrazol-5-carboxamido)methyl)-5-(3-methoxybenzyl)-4,5-dihydroisoxazol-5-carboxylate

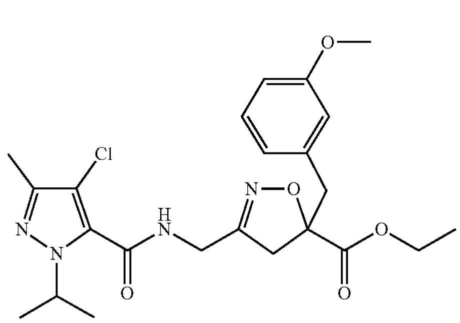 [SMILES: CCOC(=O)C1(Cc2cccc(OC)c2)CC(CNC(=O)c2c(Cl)c(C)nn2C(C)C)=NO1]

The title compound (0.139 g, 81%) was obtained using ethyl 3-(aminomethyl)-5-(3-methoxybenzyl)-4,5-dihydroisoxazol-5-carboxylate hydrochloride (0.120 g, 0.36 mmol) obtained in Example 100-(1) and 4-chloro-2-isopropyl-5-methyl-2H-pyrazol-3-carboxylic acid (0.100 g, 0.49 mmol) obtained in Example 222-(2) by the preparation method of Example 84-(2).

NMR: $^1$H-NMR (500 MHz, $CDCl_3$); δ 7.12 (1H, t), 6.85 (1H, t), 6.78-6.73 (3H, m), 5.38 (1H, q), 4.24-4.15 (4H, m), 3.73 (3H, s), 3.41 (1H, d), 3.27 (1H, d), 3.10 (1H, d), 2.99 (1H, m), 2.24 (3H, s), 1.42 (6H, dd), 1.26 (3H, t)

MS (m/z): 477[M+H]

(2) Preparation of 3-((4-chloro-1-isopropyl-3-methyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

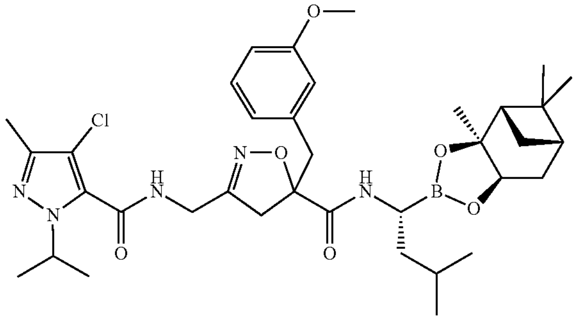

The title compound (0.067 g, 33%, 2 steps) was obtained using ethyl 3-((4-chloro-1-isopropyl-3-methyl-1H-pyrazol-5-carboxamido)methyl)-5-(3-methoxybenzyl)-4,5-dihydroisoxazol-5-carboxylate (0.139 g, 0.291 mmol) obtained in (1) above by the preparation method of Example 84-(3).

MS (m/z): 696[M+H]

(3) Preparation of ((1R)-1-(3-((4-chloro-1-isopropyl-3-methyl-1H-pyrazol-5-carboxamido)methyl)-5-(3-methoxybenzyl)-4,5-dihydroisoxazol-5-carboxamido)-3-methylbutyl)boronic acid

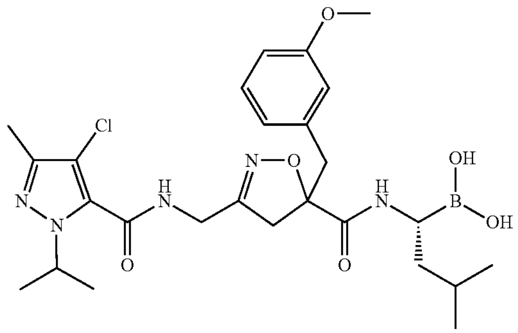 [SMILES: COc1cccc(CC2(C(=O)N[C@@H](CC(C)C)B(O)O)CC(CNC(=O)c3c(Cl)c(C)nn3C(C)C)=NO2)c1]

The title compound (0.034 g, 63%) was obtained using 3-((4-chloro-1-isopropyl-3-methyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.067 g, 0.096 mmol) obtained in (2) above by the preparation method of Example 1-(4).

NMR: $^1$H-NMR (500 MHz, $CD_3OD$); δ 7.15 (1H, t), 6.83-6.77 (3H, m), 4.93 (1H, q), 4.23 (2H, s), 3.76 (3H, s), 3.42 (1H, d), 3.33-3.21 (2H, m), 3.15 (1H, d), 2.68 (1H, t), 1.41-1.37 (7H, m), 1.19-1.01 (2H, m), 0.79 (6H, dd)

MS (m/z): 584[M+Na], 544[M-OH]

Example 234: Preparation of ((1R)-1-(3-((1-isopropyl-3-methyl-1H-pyrazol-5-carboxamido)methyl)-5-(3-methylbenzyl)-4,5-dihydroisoxazol-5-carboxamido)-3-methylbutyl)boronic acid Through the processes (1), (2) and (3) below, the title compound was obtained.

(1) Preparation of ethyl 3-((1-isopropyl-3-methyl-1H-pyrazol-5-carboxamido)methyl)-5-(3-methylbenzyl)-4,5-dihydroisoxazol-5-carboxylate

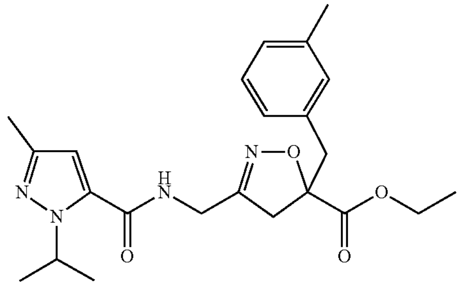 [SMILES: CCOC(=O)C1(Cc2cccc(C)c2)CC(CNC(=O)c2cc(C)nn2C(C)C)=NO1]

The title compound (0.11 g, 66%) was obtained using ethyl 3-(aminomethyl)-5-(3-methylbenzyl)-4,5-dihydroisoxazol-5-carboxylate hydrochloride (0.12 g, 0.38 mmol) obtained in Example 125-(1) and 2-isopropyl-5-methyl-2H-pyrazol-3-carboxylic acid (0.071 g, 0.42 mmol) obtained in Example 190-(2) by the preparation method of Example 84-(2).

MS (m/z): 427[M+H]

(2) Preparation of 3-((1-isopropyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide

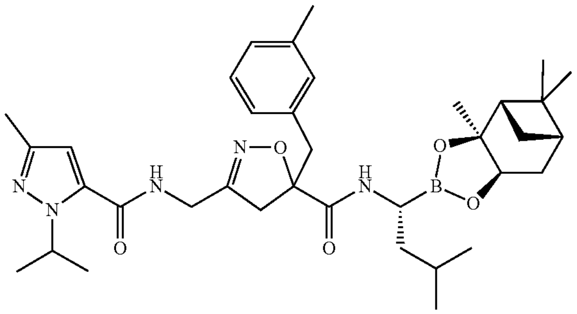

The title compound (0.066 g, 39%, 2 steps) was obtained using ethyl 3-((1-isopropyl-3-methyl-1H-pyrazol-5-carboxamido)methyl)-5-(3-methylbenzyl)-4,5-dihydroisoxazol-5-carboxylate (0.11 g, 0.25 mmol) obtained in (1) above by the preparation method of Example 84-(3).

MS (m/z): 646[M+H]

(3) Preparation of ((1R)-1-(3-((1-isopropyl-3-methyl-1H-pyrazol-5-carboxamido)methyl)-5-(3-methylbenzyl)-4,5-dihydroisoxazol-5-carboxamido)-3-methylbutyl)boronic acid

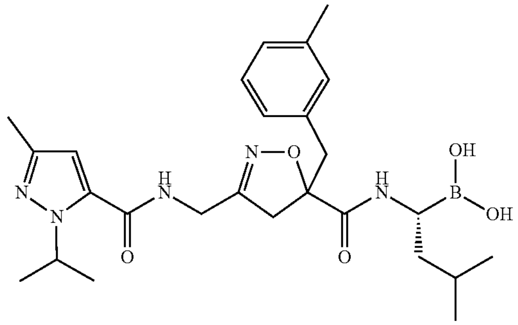 [SMILES: Cc1cccc(CC2(C(=O)N[C@@H](CC(C)C)B(O)O)CC(CNC(=O)c3cc(C)nn3C(C)C)=NO2)c1]

The title compound (0.034 g, 66%) was obtained using 3-((1-isopropyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide (0.066 g, 0.10 mmol) obtained in (2) above by the preparation method of Example 1-(4).

NMR: $^1$H-NMR (500 MHz, $CDCl_3$); δ 7.18-7.05 (m, 5H), 6.34-6.32 (t, 1H), 6.18 (s, 1H), 5.36-5.33 (m, 1H), 4.12-4.11 (dd, 2H), 3.39-3.35 (d, 1H), 3.32-3.29 (d, 1H), 3.11-3.08 (d, 1H), 3.03-2.99 (d, 1H), 2.85 (m, 1H), 2.30 (s, 3H), 2.24 (s, 3H), 1.44-1.42 (t, 6H), 1.29-1.19 (m, 3H), 0.84-0.82 (t, 6H)

MS (m/z): 512[M+H], 494[M-OH]

Example 235: Preparation of ((1R)-1-(5-benzyl-3-((2-methylthiazol-5-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((2-methylthiazol-5-carboxamido)methyl)-4,5-dihydroisoxazol-5-carboxylate

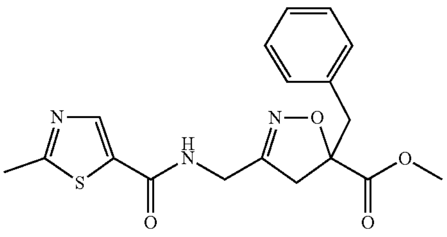

The title compound (0.12 g, 74%) was obtained using methyl 3-(aminomethyl)-5-benzyl-4,5-dihydroisoxazol-5-carboxylate hydrochloride (0.12 g, 0.42 mmol) obtained in Example 84-(1) and 2-methyl-thiazol-5-carboxylic acid (0.066 g, 0.46 mmol) by the preparation method of Example 84-(2).

MS (m/z): 374[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-methylthiazol-5-carboxamido)methyl)-4,5-dihydroisoxazol-5-carboxamide

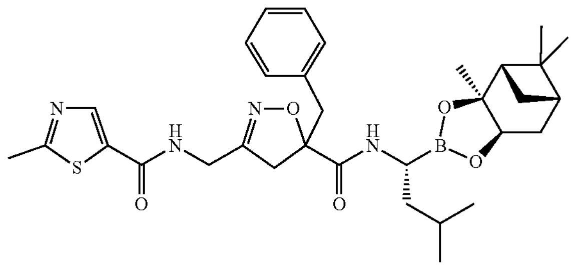

The title compound (0.069 g, 38%, 2 steps) was obtained using methyl 5-benzyl-3-((2-methylthiazol-5-carboxamido)methyl)-4,5-dihydroisoxazol-5-carboxylate (0.12 g, 0.31 mmol) obtained in (1) above by the preparation method of Example 84-(3).

MS (m/z): 607[M+H]

(3) Preparation of ((1R)-1-(5-benzyl-3-((2-methylthiazol-5-carboxamido)methyl)-4,5-dihydroisoxazol-5-carboxamido)-3-methylbutyl)boronic acid

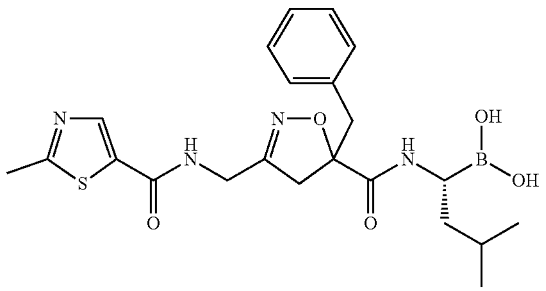 [SMILES: Cc1ncc(C(=O)NCC2=NOC(Cc3ccccc3)(C(=O)N[C@@H](CC(C)C)B(O)O)C2)s1]

The title compound (0.029 g, 54%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((2-methylthiazol-5-carboxamido)methyl)-4,5-dihydroisoxazol-5-carboxamide (0.069 g, 0.11 mmol) obtained in (2) above by the preparation method of Example 1-(4).

NMR: 1H-NMR (500 MHz, CDCl3); δ 7.94 (s, 1H), 7.38 (m, 1H), 7.30-7.26 (m, 5H), 6.80 (m, 1H), 4.28-4.08 (m, 2H), 3.41-3.32 (m, 2H), 3.17-3.14 (d, 1H), 3.05-3.01 (d, 1H), 2.75-2.73 (m, 1H), 2.70 (s, 3H), 1.34-1.17 (m, 3H), 0.81-0.79 (m, 6H)

MS (m/z): 473[M+H], 455[M-OH]

Example 236: Preparation of ((1R)-1-(3-((1-isopropyl-3-phenyl-1H-pyrazol-5-carboxamido)methyl)-5-(3-methylbenzyl)-4,5-dihydroisoxazol-5-carboxamido)-3-methylbutyl)boronic acid Through the processes (1), (2) and (3) below, the title compound was obtained.

(1) Preparation of ethyl 3-((1-isopropyl-3-phenyl-1H-pyrazol-5-carboxamido)methyl)-5-(3-methylbenzyl)-4,5-dihydroisoxazol-5-carboxylate

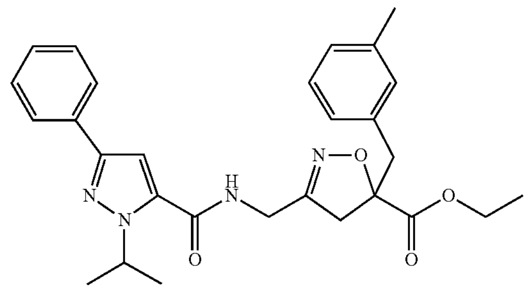 [SMILES: CCOC(=O)C1(Cc2cccc(C)c2)CC(CNC(=O)c2cc(-c3ccccc3)nn2C(C)C)=NO1]

The title compound (0.15 g, 78%) was obtained using ethyl 3-(aminomethyl)-5-(3-methylbenzyl)-4,5-dihydroisoxazol-5-carboxylate hydrochloride (0.12 g, 0.38 mmol) obtained in Example 125-(1) and 2-isopropyl-5-phenyl-2H-pyrazol-3-carboxylic acid (0.097 g, 0.42 mmol) obtained in Example 207-(3) by the preparation method of Example 84-(2).

MS (m/z): 489[M+H]

(2) Preparation of 3-((1-isopropyl-3-phenyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide

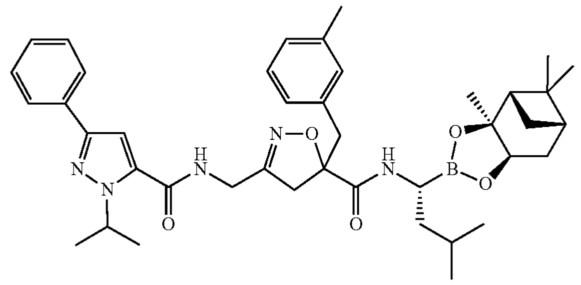 [SMILES: Cc1cccc(CC2(C(=O)N[C@@H](CC(C)C)B3O[C@@H]4C[C@@H]5C[C@@H](C5(C)C)[C@]4(C)O3)CC(CNC(=O)c3cc(-c4ccccc4)nn3C(C)C)=NO2)c1]

The title compound (0.079 g, 43%, 2 steps) was obtained using ethyl 3-((1-isopropyl-3-phenyl-1H-pyrazol-5-carboxamido)methyl)-5-(3-methylbenzyl)-4,5-dihydroisoxazol-5-carboxylate (0.15 g, 0.30 mmol) obtained in (1) above by the preparation method of Example 84-(3).

MS (m/z): 708[M+H]

(3) Preparation of ((1R)-1-(3-((1-isopropyl-3-phenyl-1H-pyrazol-5-carboxamido)methyl)-5-(3-methylbenzyl)-4,5-dihydroisoxazol-5-carboxamido)-3-methylbutyl)boronic acid

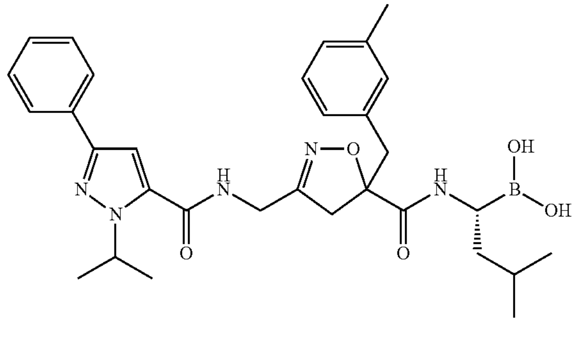 [SMILES: Cc1cccc(CC2(C(=O)N[C@@H](CC(C)C)B(O)O)CC(CNC(=O)c3cc(-c4ccccc4)nn3C(C)C)=NO2)c1]

The title compound (0.042 g, 66%) was obtained using 3-((1-isopropyl-3-phenyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide (0.079 g, 0.11 mmol) obtained in (2) above by the preparation method of Example 1-(4).

NMR: $^{1}$H-NMR (500 MHz, $CDCl_3$); δ 7.76-7.75 (d, 2H), 7.39-7.36 (t, 2H), 7.30-7.28 (m, 1H), 7.18-7.13 (m, 2H), 7.06-7.03 (m, 3H), 6.70 (s, 1H), 6.52-6.50 (t, 1H), 5.45-5.39 (m, 1H), 4.19-4.13 (m, 2H), 3.41-3.38 (d, 1H), 3.31-3.29 (d, 1H), 3.12-3.09 (d, 1H), 3.05-3.02 (d, 1H), 2.83 (m, 1H), 2.29 (s, 3H), 1.50-1.48 (t, 6H), 1.37-1.16 (m, 3H), 0.82-0.78 (dd, 6H)

MS (m/z): 574[M+H], 556[M-OH]

Example 237: Preparation of ((1R)-1-(3-((3-(tert-butyl)-1-isopropyl-1H-pyrazol-5-carboxamido)methyl)-5-(3-methylbenzyl)-4,5-dihydroisoxazol-5-carboxamido)-3-methylbutyl)boronic acid Through the processes (1), (2) and (3) below, the title compound was obtained.

(1) Preparation of ethyl 3-((3-(tert-butyl)-1-isopropyl-1H-pyrazol-5-carboxamido)methyl)-5-(3-methylbenzyl)-4,5-dihydroisoxazol-5-carboxylate

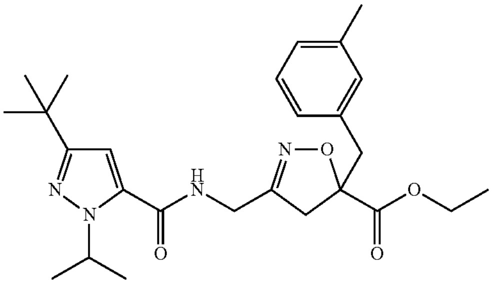 [SMILES: CCOC(=O)C1(Cc2cccc(C)c2)CC(CNC(=O)c2cc(C(C)(C)C)nn2C(C)C)=NO1]

The title compound (0.152 g, 85%) was obtained using ethyl 3-(aminomethyl)-5-(3-methylbenzyl)-4,5-dihydroisoxazol-5-carboxylate hydrochloride (0.12 g, 0.38 mmol) obtained in Example 125-(1) and 5-tert-butyl-2-isopropyl-2H-pyrazol-3-carboxylic acid (0.089 g, 0.42 mmol) obtained in Example 224-(1) by the preparation method of Example 84-(2).

MS (m/z): 469[M+H]

(2) Preparation of 3-((3-(tert-butyl)-1-isopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide

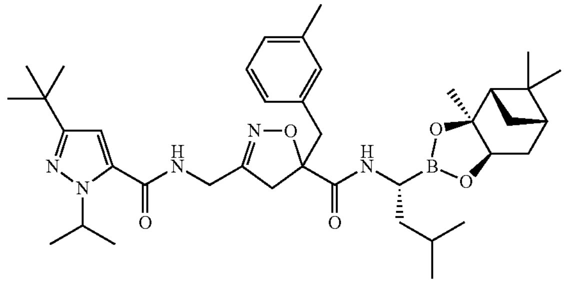 [SMILES: Cc1cccc(CC2(C(=O)N[C@@H](CC(C)C)B3O[C@@H]4C[C@@H]5C[C@@H](C5(C)C)[C@]4(C)O3)CC(CNC(=O)c3cc(C(C)(C)C)nn3C(C)C)=NO2)c1]

The title compound (0.09 g, 48%, 2 steps) was obtained using ethyl 3-((3-(tert-butyl)-1-isopropyl-1H-pyrazol-5-carboxamido)methyl)-5-(3-methylbenzyl)-4,5-dihydroisoxazol-5-carboxylate (0.152 g, 0.32 mmol) obtained in (1) above by the preparation method of Example 84-(3).

MS (m/z): 688[M+H]

(3) Preparation of ((1R)-1-(3-((3-(tert-butyl)-1-isopropyl-1H-pyrazol-5-carboxamido)methyl)-5-(3-methylbenzyl)-4,5-dihydroisoxazol-5-carboxamido)-3-methylbutyl)boronic acid

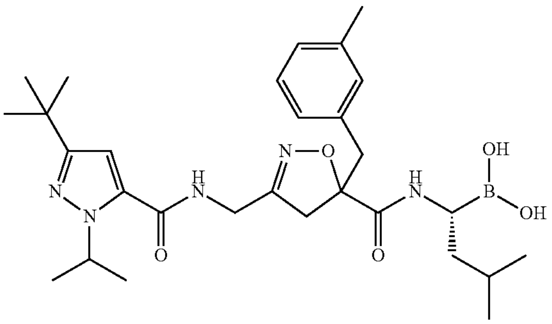 [SMILES: Cc1cccc(CC2(C(=O)N[C@@H](CC(C)C)B(O)O)CC(CNC(=O)c3cc(C(C)(C)C)nn3C(C)C)=NO2)c1]

The title compound (0.043 g, 59%) was obtained using 3-((3-(tert-butyl)-1-isopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide (0.09 g, 0.13 mmol) obtained in (2) above by the preparation method of Example 1-(4).

NMR: $^{1}$H-NMR (500 MHz, $CDCl_3$); δ 7.18-7.03 (m, 5H), 6.24 (t, 1H), 6.23 (s, 1H), 5.34-5.29 (m, 1H), 4.11-4.08 (m, 2H), 3.39-3.35 (d, 1H), 3.33-3.30 (d, 1H), 3.11-3.08 (d, 1H), 3.05-3.01 (d, 1H), 2.87 (m, 1H), 2.29 (s, 3H), 1.45-1.38 (m, 9H), 1.26 (s, 9H), 0.85-0.82 (dd, 6H)

MS (m/z): 554[M+H], 536[M-OH]

Example 238: Preparation of ((1R)-1-(3-((imidazo[1,2-a]pyridin-8-carboxamido)methyl)-5-(3-methylbenzyl)-4,5-dihydroisoxazol-5-carboxamido)-3-methylbutyl)boronic acid Through the processes (1), (2) and (3) below, the title compound was obtained.

(1) Preparation of ethyl 3-((imidazo[1,2-a]pyridin-8-carboxamido)methyl)-5-(3-methylbenzyl)-4,5-dihydroisoxazol-5-carboxylate

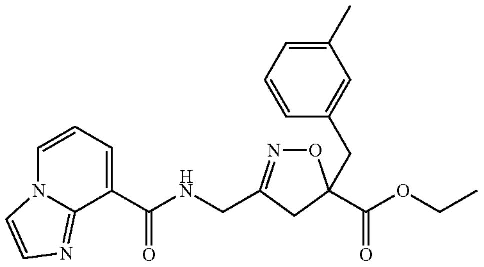 [SMILES: CCOC(=O)C1(Cc2cccc(C)c2)CC(CNC(=O)c2cccn3ccnc23)=NO1]

The title compound (0.115 g, 71%) was obtained using ethyl 3-(aminomethyl)-5-(3-methylbenzyl)-4,5-dihydroisoxazol-5-carboxylate hydrochloride (0.12 g, 0.38 mmol) obtained in Example 125-(1) and imidazo[1,2-a]pyridin-8-carboxylic acid (0.068 g, 0.42 mmol) obtained in Example 132-(1) by the preparation method of Example 84-(2).

MS (m/z): 421[M+H]

(2) Preparation of 3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide

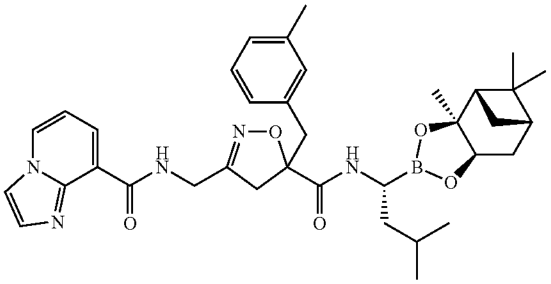 [SMILES: Cc1cccc(CC2(C(=O)N[C@@H](CC(C)C)B3O[C@@H]4C[C@@H]5C[C@@H](C5(C)C)[C@]4(C)O3)CC(CNC(=O)c3cccn4ccnc34)=NO2)c1]

The title compound (0.074 g, 32%, 2 steps) was obtained using ethyl 3-((imidazo[1,2-a]pyridin-8-carboxamido)methyl)-5-(3-methylbenzyl)-4,5-dihydroisoxazol-5-carboxylate (0.115 g, 0.27 mmol) obtained in (1) above by the preparation method of Example 84-(3).

MS (m/z): 640[M+H]

(3) Preparation of ((1R)-1-(3-((imidazo[1,2-a]pyridin-8-carboxamido)methyl)-5-(3-methylbenzyl)-4,5-dihydroisoxazol-5-carboxamido)-3-methylbutyl) boronic acid

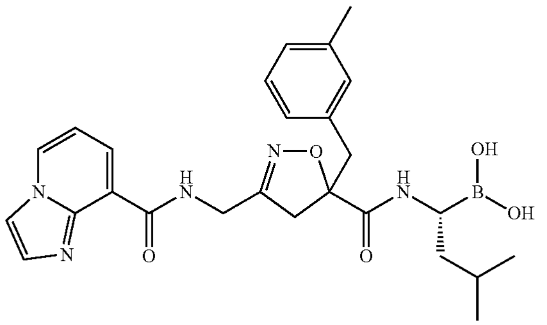 [SMILES: Cc1cccc(CC2(C(=O)N[C@@H](CC(C)C)B(O)O)CC(CNC(=O)c3cccn4ccnc34)=NO2)c1]

The title compound (0.022 g, 38%) was obtained using 3-((imidazo[1,2-a]pyridin-8-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide (0.074 g, 0.12 mmol) obtained in (2) above by the preparation method of Example 1-(4).

NMR: $^1$H-NMR (500 MHz, $CDCl_3$); δ 10.52-10.50 (t, 1H), 8.24-8.23 (d, 1H), 8.14-8.13 (d, 1H), 7.62-7.60 (d, 2H), 7.15-6.92 (m, 6H), 4.29-4.27 (m, 2H), 3.42-3.38 (d, 1H), 3.30-3.27 (d, 1H), 3.09-3.03 (dd, 2H), 2.25 (s, 3H), 1.34-1.26 (m, 3H), 0.79-0.75 (dd, 6H)

MS (m/z): 506[M+H], 488[M-OH]

Example 239: Preparation of ((1R)-1-(3-((1-isopropyl-1H-pyrazol-5-carboxamido)methyl)-5-(3-methoxybenzyl)-4,5-dihydroisoxazol-5-carboxamido)-3-methylbutyl)boronic acid Through the processes (1), (2) and (3) below, the title compound was obtained.

(1) Preparation of ethyl 3-((1-isopropyl-1H-pyrazol-5-carboxamido)methyl)-5-(3-methoxybenzyl)-4,5-dihydroisoxazol-5-carboxylate

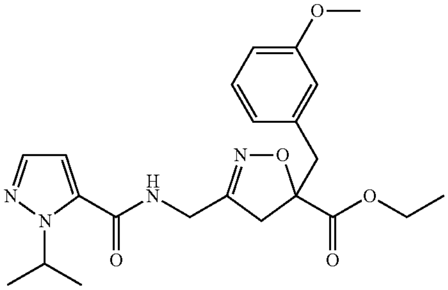 [SMILES: CCOC(=O)C1(Cc2cccc(OC)c2)CC(CNC(=O)c2ccnn2C(C)C)=NO1]

The title compound (0.134 g, 75%) was obtained using ethyl 3-(aminomethyl)-5-(3-methoxybenzyl)-4,5-dihydroisoxazol-5-carboxylate hydrochloride (0.138 g, 0.419 mmol) obtained in Example 100-(1) and 2-isopropyl-2H-pyrazol-3-carboxylic acid (0.084 g, 0.545 mmol) obtained in Example 171-(2) by the preparation method of Example 84-(2).

NMR: $^1$H-NMR (400 MHz, $CDCl_3$); δ 7.49 (1H, d), 7.19 (1H, t), 6.83-6.78 (3H, m), 6.56-6.50 (2H, m), 5.48 (1H, q), 4.30-4.13 (4H, m), 3.77 (3H, s), 3.45 (1H, d), 3.31 (1H, d), 3.13 (1H, d), 3.05 (1H, m), 1.51 (6H, dd), 1.28 (3H, t)

MS (m/z): 429[M+H]

(2) Preparation of 3-((1-isopropyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

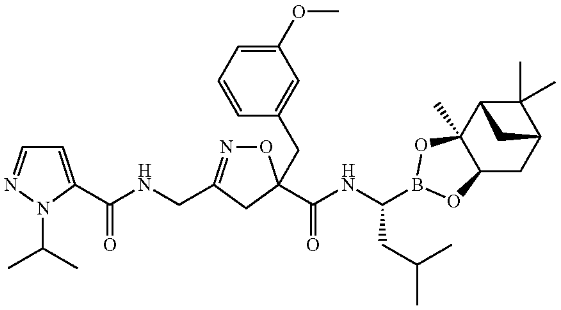 [SMILES: COc1cccc(CC2(C(=O)N[C@@H](CC(C)C)B3O[C@@H]4C[C@@H]5C[C@@H](C5(C)C)[C@]4(C)O3)CC(CNC(=O)c3ccnn3C(C)C)=NO2)c1]

The title compound (0.049 g, 24%, 2 steps) was obtained using ethyl 3-((1-isopropyl-1H-pyrazol-5-carboxamido)methyl)-5-(3-methoxybenzyl)-4,5-dihydroisoxazol-5-carboxylate (0.134 g, 0.313 mmol) obtained in (1) above by the preparation method of Example 84-(3).

MS (m/z): 648[M+H]

(3) Preparation of ((1R)-1-(3-((1-isopropyl-1H-pyrazol-5-carboxamido)methyl)-5-(3-methoxybenzyl)-4,5-dihydroisoxazol-5-carboxamido)-3-methylbutyl)boronic acid

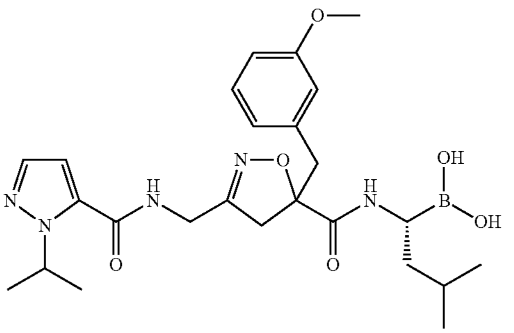 [SMILES: COc1cccc(CC2(C(=O)N[C@@H](CC(C)C)B(O)O)CC(CNC(=O)c3ccnn3C(C)C)=NO2)c1]

The title compound (0.020 g, 51%) was obtained using 3-((1-isopropyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.049 g, 0.0757 mmol) obtained in (2) above by the preparation method of Example 1-(4).

NMR: $^1$H-NMR (500 MHz, $CDCl_3$); δ 7.45 (1H, dd), 7.19 (1H, t), 7.14 (1H, d), 6.85 (1H, d), 6.81-6.77 (2H, m), 6.46 (1H, t), 6.44 (1H, s), 5.42 (1H, q), 4.16-4.13 (2H, m), 3.76 (3H, s), 3.38 (1H, d), 3.31 (1H, d), 3.12 (1H, d), 3.05 (1H, d), 1.60 (2H, s), 1.47-1.22 (9H, m), 0.82 (6H, dd)

MS (m/z): 536[M+Na], 496[M-OH]

Example 240: Preparation of ((1R)-1-(3-((1-cyclopentyl-3-methyl-1H-pyrazol-5-carboxamido)methyl)-5-(3-methoxybenzyl)-4,5-dihydroisoxazol-5-carboxamido)-3-methylbutyl)boronic acid Through the processes (1), (2) and (3) below, the title compound was obtained.

(1) Preparation of ethyl 3-((1-cyclopentyl-3-methyl-1H-pyrazol-5-carboxamido)methyl)-5-(3-methoxybenzyl)-4,5-dihydroisoxazol-5-carboxylate

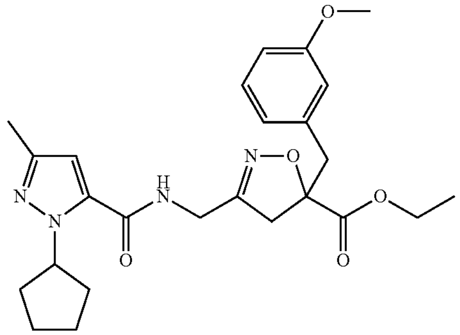 [SMILES: CCOC(=O)C1(Cc2cccc(OC)c2)CC(CNC(=O)c2cc(C)nn2C2CCCC2)=NO1]

The title compound (0.146 g, 83%) was obtained using ethyl 3-(aminomethyl)-5-(3-methoxybenzyl)-4,5-dihydroisoxazol-5-carboxylate hydrochloride (0.124 g, 0.377 mmol) obtained in Example 100-(1) and 2-cyclopentyl-5-methyl-2H-pyrazol-3-carboxylic acid (0.096 g, 0.494 mmol) obtained in Example 196-(2) by the preparation method of Example 84-(2).

NMR: $^1$H-NMR (400 MHz, $CDCl_3$); δ 7.17 (1H, t), 6.83-6.77 (3H, m), 6.43 (1H, t), 6.26 (1H, s), 5.48 (1H, q), 4.28-4.13 (4H, m), 3.76 (3H, s), 3.43 (1H, d), 3.30 (1H, d), 3.13 (1H, d), 3.03 (1H, m), 2.28 (3H, s), 2.08-1.31 (8H, m), 1.27 (3H, t)

MS (m/z): 469[M+H]

(2) Preparation of 3-((1-cyclopentyl-3-methyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

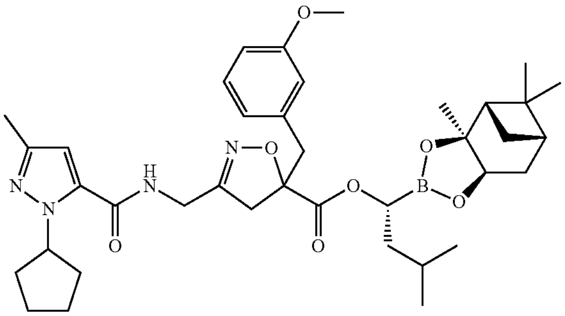

The title compound (0.072 g, 33%, 2 steps) was obtained using ethyl 3-((1-cyclopentyl-3-methyl-1H-pyrazol-5-carboxamido)methyl)-5-(3-methoxybenzyl)-4,5-dihydroisoxazol-5-carboxylate (0.161 g, 0.318 mmol) obtained in (1) above by the preparation method of Example 84-(3).

MS (m/z): 688[M+H]

(3) Preparation of ((1R)-1-(3-((1-cyclopentyl-3-methyl-1H-pyrazol-5-carboxamido)methyl)-5-(3-methoxybenzyl)-4,5-dihydroisoxazol-5-carboxamido)-3-methylbutyl)boronic acid

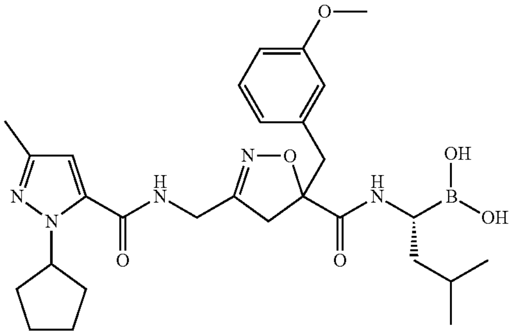 [SMILES: COc1cccc(CC2(C(=O)N[C@@H](CC(C)C)B(O)O)CC(CNC(=O)c3cc(C)nn3C3CCCC3)=NO2)c1]

The title compound (0.025 g, 43%) was obtained using 3-((1-cyclopentyl-3-methyl-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.072 g, 0.105 mmol) obtained in (2) above by the preparation method of Example 1-(4).

NMR: $^1$H-NMR (500 MHz, $CD_3OD$); δ 7.21-7.15 (2H, m), 6.85-6.77 (3H, m), 6.35 (1H, t), 5.44 (1H, q), 4.14-4.11 (2H, m), 3.76 (3H, s), 3.37 (1H, d), 3.31 (1H, d), 3.12 (1H, d), 3.04 (1H, d), 2.86 (1H, br s), 2.23 (3H, s), 2.03-1.22 (13H, m), 0.83 (6H, dd)

MS (m/z): 576[M+Na], 536[M-OH].

Example 241: Preparation of ((1R)-1-(3-((1-isopropyl-3-(pyridin-2-yl)-1H-pyrazol-5-carboxamido)methyl)-5-(3-methoxybenzyl)-4,5-dihydroisoxazol-5-carboxamido)-3-methylbutyl)boronic acid Through the processes (1), (2) and (3) below, the title compound was obtained.

(1) Preparation of ethyl 3-((1-isopropyl-3-(pyridin-2-yl)-1H-pyrazol-5-carboxamido)methyl)-5-(3-methoxybenzyl)-4,5-dihydroisoxazol-5-carboxylate

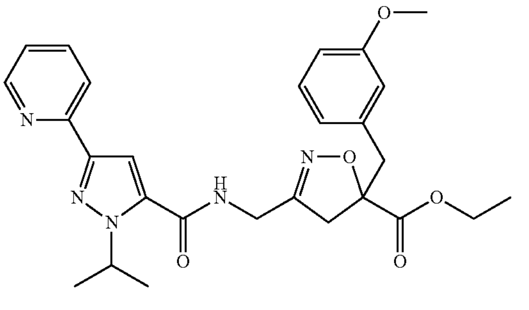 [SMILES: CCOC(=O)C1(Cc2cccc(OC)c2)CC(CNC(=O)c2cc(-c3ccccn3)nn2C(C)C)=NO1]

The title compound (0.161 g, 77%) was obtained using ethyl 3-(aminomethyl)-5-(3-methoxybenzyl)-4,5-dihydroisoxazol-5-carboxylate hydrochloride (0.135 g, 0.411 mmol) obtained in Example 100-(1) and 2-isopropyl-5-pyridin-2-yl-2H-pyrazol-3-carboxylic acid (0.124 g, 0.536 mmol) obtained in Example 221-(3) by the preparation method of Example 84-(2).

NMR: 1H-NMR (400 MHz, CDCl3); δ 8.57 (1H, dd), 8.00 (1H, dd), 7.72 (1H, dd), 7.21-7.14 (3H, m), 6.82-6.77 (4H, m), 5.52 (1H, q), 4.27-4.16 (4H, m), 3.73 (3H, s), 3.45 (1H, d), 3.30 (1H, d), 3.13 (1H, d), 3.05 (1H, m), 1.55 (6H, dd), 1.27 (3H, t)

MS (m/z): 506[M+H]

(2) Preparation of 3-((1-isopropyl-3-(pyridin-2-yl)-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

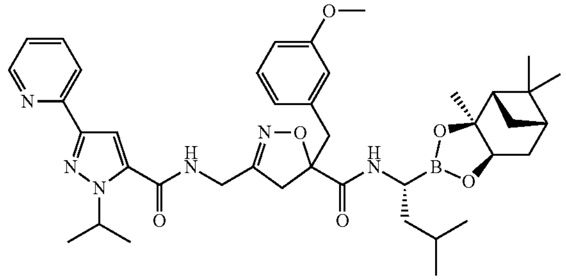 [SMILES: COc1cccc(CC2(C(=O)N[C@@H](CC(C)C)B3O[C@@H]4C[C@@H]5C[C@@H](C5(C)C)[C@]4(C)O3)CC(CNC(=O)c3cc(-c4ccccn4)nn3C(C)C)=NO2)c1]

The title compound (0.095 g, 41%, 2 steps) was obtained using ethyl 3-((1-isopropyl-3-(pyridin-2-yl)-1H-pyrazol-5-carboxamido)methyl)-5-(3-methoxybenzyl)-4,5-dihydroisoxazol-5-carboxylate (0.161 g, 0.318 mmol) obtained in (1) above by the preparation method of Example 84-(3).

MS (m/z): 725[M+H]

(3) Preparation of ((1R)-1-(3-((1-isopropyl-3-(pyridin-2-yl)-1H-pyrazol-5-carboxamido)methyl)-5-(3-methoxybenzyl)-4,5-dihydroisoxazol-5-carboxamido)-3-methylbutyl)boronic acid

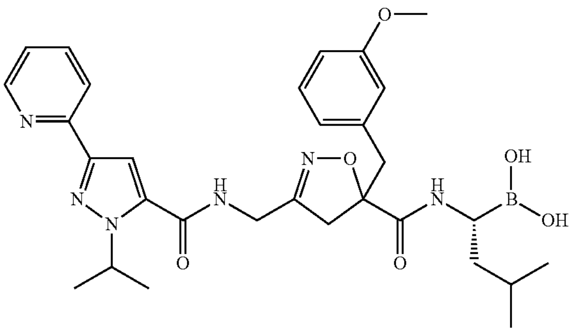 [SMILES: COc1cccc(CC2(C(=O)N[C@@H](CC(C)C)B(O)O)CC(CNC(=O)c3cc(-c4ccccn4)nn3C(C)C)=NO2)c1]

The title compound (0.038 g, 49%) was obtained using 3-((1-isopropyl-3-(pyridin-2-yl)-1H-pyrazol-5-carboxamido)methyl)-5-(3-methoxybenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.095 g, 0.131 mmol) obtained in (2) above by the preparation method of Example 1-(4).

NMR: 1H-NMR (400 MHz, CD3OD); δ 8.48 (1H, d), 8.21 (1H, s), 8.03 (1H, d), 7.74 (1H, t), 7.27-7.19 (2H, m), 7.08 (1H, s), 6.99 (1H, t), 6.91-6.83 (2H, m), 5.46 (1H, q), 4.39 (2H, dd), 4.07 (1H, dd), 3.81 (3H, s), 3.46 (1H, d), 3.42 (1H, d), 3.21 (1H, d), 3.12 (1H, d), 2.84 (1H, br s), 1.83 (2H, br s), 1.52-1.13 (9H, m), 0.77 (6H, dd)

MS (m/z): 613[M+Na], 573[M-OH]

Example 242: Preparation of ((1R)-1-(3-((1-isopropyl-1H-pyrazol-5-carboxamido)methyl)-5-(3-methylbenzyl)-4,5-dihydroisoxazol-5-carboxamido)-3-methylbutyl)boronic acid Through the processes (1), (2) and (3) below, the title compound was obtained.

(1) Preparation of ethyl 3-((1-isopropyl-1H-pyrazol-5-carboxamido)methyl)-5-(3-methylbenzyl)-4,5-dihydroisoxazol-5-carboxylate

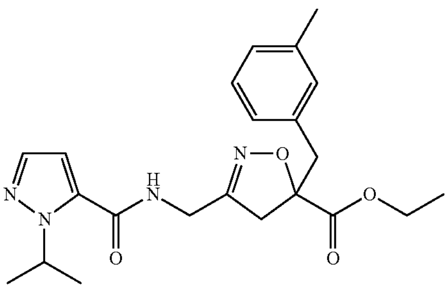 [SMILES: CCOC(=O)C1(Cc2cccc(C)c2)CC(CNC(=O)c2ccnn2C(C)C)=NO1]

The title compound (0.15 g, 76%) was obtained using ethyl 3-(aminomethyl)-5-(3-methylbenzyl)-4,5-dihydroisoxazol-5-carboxylate hydrochloride (0.15 g, 0.48 mmol) obtained in Example 125-(1) and 2-isopropyl-2H-pyrazol-3-carboxylic acid (0.081 g, 0.53 mmol) obtained in Example 171-(2) by the preparation method of Example 84-(2).

MS (m/z): 413[M+H]

(2) Preparation of 3-((1-isopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide

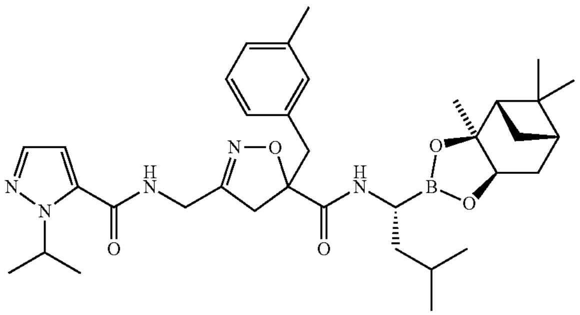 [SMILES: Cc1cccc(CC2(C(=O)N[C@@H](CC(C)C)B3O[C@@H]4C[C@@H]5C[C@@H](C5(C)C)[C@]4(C)O3)CC(CNC(=O)c3ccnn3C(C)C)=NO2)c1]

The title compound (0.072 g, 32%, 2 steps) was obtained using ethyl 3-((1-isopropyl-1H-pyrazol-5-carboxamido)methyl)-5-(3-methylbenzyl)-4,5-dihydroisoxazol-5-carboxylate (0.15 g, 0.37 mmol) obtained in (1) above by the preparation method of Example 84-(3).

MS (m/z): 632[M+H]

(3) Preparation of ((1R)-1-(3-((1-isopropyl-1H-pyrazol-5-carboxamido)methyl)-5-(3-methylbenzyl)-4,5-dihydroisoxazol-5-carboxamido)-3-methylbutyl) boronic acid

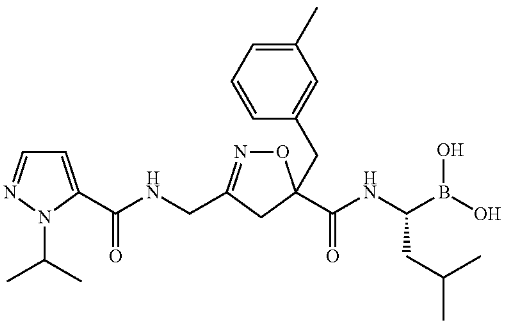 [SMILES: Cc1cccc(CC2(C(=O)N[C@@H](CC(C)C)B(O)O)CC(CNC(=O)c3ccnn3C(C)C)=NO2)c1]

The title compound (0.03 g, 50%) was obtained using 3-((1-isopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide (0.072 g, 0.11 mmol) obtained in (2) above by the preparation method of Example 1-(4).

NMR: $^1$H-NMR (500 MHz, $CDCl_3$); δ 7.45 (s, 1H), 7.19-7.04 (m, 5H), 6.49-6.47 (t, 1H), 6.43 (s, 1H), 5.45-5.41 (m, 1H), 4.15-4.12 (m, 2H), 3.40-3.36 (d, 1H), 3.32-3.29 (d, 1H), 3.11-3.08 (d, 1H), 3.04-3.00 (d, 1H), 2.83 (m, 1H), 2.30 (s, 3H), 1.46-1.44 (t, 6H), 1.38-1.20 (m, 3H), 0.82-0.80 (t, 6H)

MS (m/z): 498[M+H], 480[M-OH]

Example 243: Preparation of ((1R)-1-(3-((1-cyclopentyl-3-methyl-1H-pyrazol-5-carboxamido)methyl)-5-(3-methylbenzyl)-4,5-dihydroisoxazol-5-carboxamido)-3-methylbutyl)boronic acid Through the processes (1), (2) and (3) below, the title compound was obtained.

(1) Preparation of ethyl 3-((1-cyclopentyl-3-methyl-1H-pyrazol-5-carboxamido)methyl)-5-(3-methylbenzyl)-4,5-dihydroisoxazol-5-carboxylate

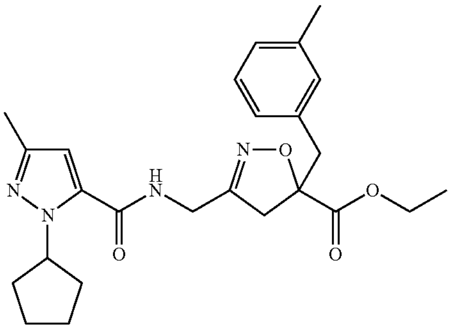 [SMILES: CCOC(=O)C1(Cc2cccc(C)c2)CC(CNC(=O)c2cc(C)nn2C2CCCC2)=NO1]

The title compound (0.157 g, 72%) was obtained using ethyl 3-(aminomethyl)-5-(3-methylbenzyl)-4,5-dihydroisoxazol-5-carboxylate hydrochloride (0.15 g, 0.48 mmol) obtained in Example 125-(1) and 2-cyclopentyl-5-methyl-2H-pyrazol-3-carboxylic acid (0.10 g, 0.53 mmol) obtained in Example 196-(2) by the preparation method of Example 84-(2).

MS (m/z): 453[M+H]

(2) Preparation of 3-((1-cyclopentyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide

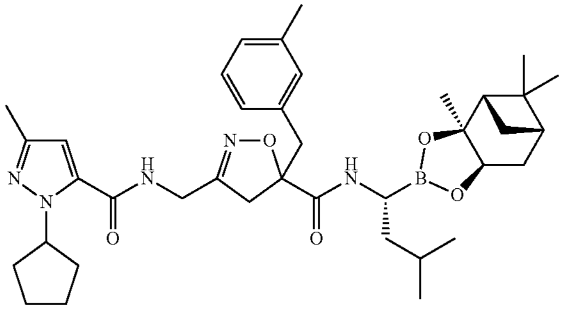

The title compound (0.076 g, 40%, 2 steps) was obtained using ethyl 3-((1-cyclopentyl-3-methyl-1H-pyrazol-5-carboxamido)methyl)-5-(3-methylbenzyl)-4,5-dihydroisoxazol-5-carboxylate (0.157 g, 0.35 mmol) obtained in (1) above by the preparation method of Example 84-(3).

MS (m/z): 672[M+H]

(3) Preparation of ((1R)-1-(3-((1-cyclopentyl-3-methyl-1H-pyrazol-5-carboxamido)methyl)-5-(3-methylbenzyl)-4,5-dihydroisoxazol-5-carboxamido)-3-methylbutyl)boronic acid

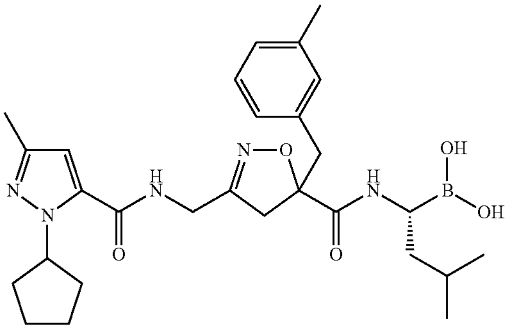 [SMILES: Cc1cccc(CC2(C(=O)N[C@@H](CC(C)C)B(O)O)CC(CNC(=O)c3cc(C)nn3C3CCCC3)=NO2)c1]

The title compound (0.029 g, 49%) was obtained using 3-((1-cyclopentyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide (0.076 g, 0.11 mmol) obtained in (2) above by the preparation method of Example 1-(4).

NMR: $^1$H-NMR (500 MHz, $CDCl_3$); δ 7.19-7.04 (m, 5H), 6.34-6.33 (t, 1H), 6.18 (s, 1H), 5.46-5.43 (m, 1H), 4.12-4.10 (m, 2H), 3.39-3.35 (d, 1H), 3.32-3.29 (d, 1H), 3.11-3.08 (d, 1H), 3.03-3.00 (d, 1H), 2.85 (m, 1H), 2.29 (s, 3H), 2.28 (s, 3H), 2.05-1.87 (m, 7H), 1.62-1.61 (m, 1H), 1.42-1.18 (m, 3H), 0.84-0.82 (t, 6H)

MS (m/z): 538[M+H], 520[M-OH]

Example 244: Preparation of ((1R)-1-(3-((4-chloro-1-isopropyl-3-methyl-1H-pyrazol-5-carboxamido)methyl)-5-(3-methylbenzyl)-4,5-dihydroisoxazol-5-carboxamido)-3-methylbutyl)boronic acid Through the processes (1), (2) and (3) below, the title compound was obtained.

(1) Preparation of ethyl 3-((4-chloro-1-isopropyl-3-methyl-1H-pyrazol-5-carboxamido)methyl)-5-(3-methylbenzyl)-4,5-dihydroisoxazol-5-carboxylate

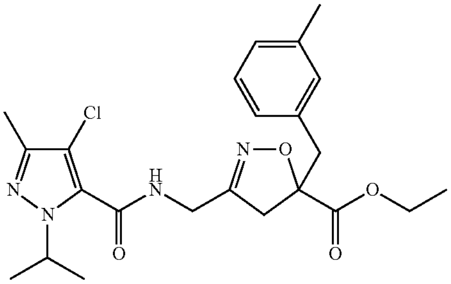 [SMILES: CCOC(=O)C1(Cc2cccc(C)c2)CC(CNC(=O)c2c(Cl)c(C)nn2C(C)C)=NO1]

The title compound (0.162 g, 73%) was obtained using ethyl 3-(aminomethyl)-5-(3-methylbenzyl)-4,5-dihydroisoxazol-5-carboxylate hydrochloride (0.15 g, 0.48 mmol) obtained in Example 125-(1) and 4-chloro-2-isopropyl-5-methyl-2H-pyrazol-3-carboxylic acid (0.107 g, 0.53 mmol) obtained in Example 222-(2) by the preparation method of Example 84-(2).

MS (m/z): 461[M+H]

(2) Preparation of 3-((4-chloro-1-isopropyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide

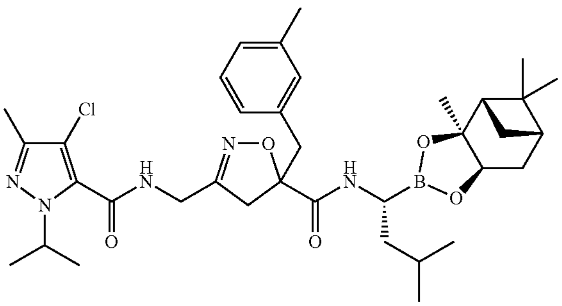

The title compound (0.065 g, 32%, 2 steps) was obtained using ethyl 3-((4-chloro-1-isopropyl-3-methyl-1H-pyrazol-5-carboxamido)methyl)-5-(3-methylbenzyl)-4,5-dihydroisoxazol-5-carboxylate (0.162 g, 0.35 mmol) obtained in (1) above by the preparation method of Example 84-(3).

MS (m/z): 680[M+H]

(3) Preparation of ((1R)-1-(3-((4-chloro-1-isopropyl-3-methyl-1H-pyrazol-5-carboxamido)methyl)-5-(3-methylbenzyl)-4,5-dihydroisoxazol-5-carboxamido)-3-methylbutyl)boronic acid

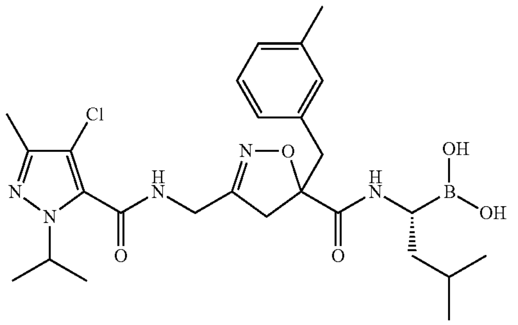 [SMILES: Cc1cccc(CC2(C(=O)N[C@@H](CC(C)C)B(O)O)CC(CNC(=O)c3c(Cl)c(C)nn3C(C)C)=NO2)c1]

The title compound (0.029 g, 55%) was obtained using 3-((4-chloro-1-isopropyl-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide (0.065 g, 0.096 mmol) obtained in (2) above by the preparation method of Example 1-(4).

NMR: $^1$H-NMR (500 MHz, $CDCl_3$); δ 7.17-7.02 (m, 5H), 6.89-6.87 (t, 1H), 5.43-5.38 (m, 1H), 4.19-4.07 (m, 2H), 3.38-3.35 (d, 1H), 3.34-3.31 (d, 1H), 3.11-3.08 (d, 1H), 3.04-3.00 (d, 1H), 2.88 (m, 1H), 2.31 (s, 3H), 2.23 (s, 3H), 1.431.40 (t, 6H), 1.39-1.21 (m, 3H), 0.85-0.82 (t, 6H)

MS (m/z): 546[M+H], 528[M-OH]

Example 245: Preparation of ((1R)-1-(3-((1-isopropyl-3-(pyridin-2-yl)-1H-pyrazol-5-carboxamido)methyl)-5-(3-methylbenzyl)-4,5-dihydroisoxazol-5-carboxamido)-3-methylbutyl)boronic acid Through the processes (1), (2) and (3) below, the title compound was obtained.

(1) Preparation of ethyl 3-((1-isopropyl-3-(pyridin-2-yl)-1H-pyrazol-5-carboxamido)methyl)-5-(3-methylbenzyl)-4,5-dihydroisoxazol-5-carboxylate

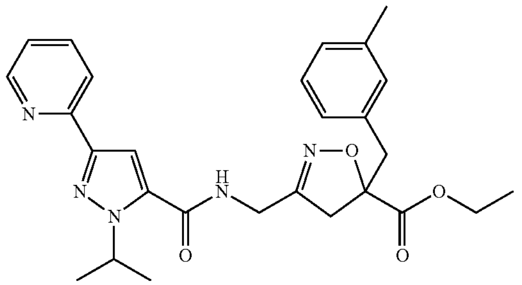 [SMILES: CCOC(=O)C1(Cc2cccc(C)c2)CC(CNC(=O)c2cc(-c3ccccn3)nn2C(C)C)=NO1]

The title compound (0.188 g, 80%) was obtained using ethyl 3-(aminomethyl)-5-(3-methylbenzyl)-4,5-dihydroisoxazol-5-carboxylate hydrochloride (0.15 g, 0.48 mmol) obtained in Example 125-(1) and 2-isopropyl-5-pyridin-2-yl-2H-pyrazol-3-carboxylic acid (0.122 g, 0.53 mmol) obtained in Example 221-(3) by the preparation method of Example 84-(2).

MS (m/z): 490[M+H]

(2) Preparation of 3-((1-isopropyl-3-(pyridin-2-yl)-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide

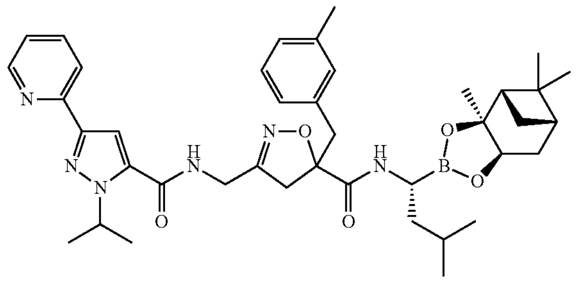 [SMILES: Cc1cccc(CC2(C(=O)N[C@@H](CC(C)C)B3O[C@@H]4C[C@@H]5C[C@@H](C5(C)C)[C@]4(C)O3)CC(CNC(=O)c3cc(-c4ccccn4)nn3C(C)C)=NO2)c1]

The title compound (0.092 g, 46%, 2 steps) was obtained using ethyl 3-((1-isopropyl-3-(pyridin-2-yl)-1H-pyrazol-5-carboxamido)methyl)-5-(3-methylbenzyl)-4,5-dihydroisoxazol-5-carboxylate (0.188 g, 0.38 mmol) obtained in (1) above by the preparation method of Example 84-(3).

MS (m/z): 709[M+H]

(3) Preparation of ((1R)-1-(3-((1-isopropyl-3-(pyridin-2-yl)-1H-pyrazol-5-carboxamido)methyl)-5-(3-methylbenzyl)-4,5-dihydroisoxazol-5-carboxamido)-3-methylbutyl)boronic acid

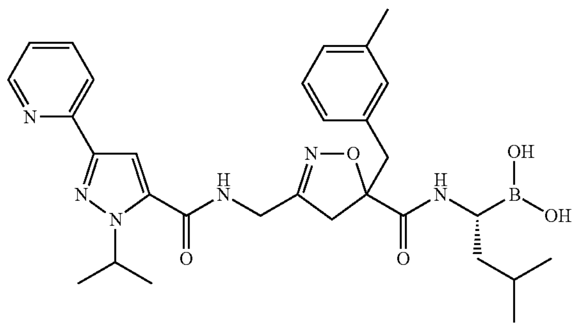

The title compound (0.034 g, 46%) was obtained using 3-((1-isopropyl-3-(pyridin-2-yl)-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-5-(3-methylbenzyl)-4,5-dihydroisoxazol-5-carboxamide (0.092 g, 0.13 mmol) obtained in (2) above by the preparation method of Example 1-(4).

NMR: $^1$H-NMR (500 MHz, $CDCl_3$); δ 8.39-8.38 (d, 1H), 8.23 (br s, 1H), 8.00-7.99 (d, 1H), 7.71-7.68 (t, 1H), 7.20-7.01 (m, 7H), 5.47-5.42 (m, 1H), 4.40-4.35 (m, 1H), 4.05-4.00 (m, 1H), 3.42-3.36 (t, 2H), 3.14-3.11 (d, 1H), 3.05-3.01 (d, 1H), 2.77 (m, 1H), 2.30 (s, 3H), 1.48-1.45 (t, 6H), 1.41-1.26 (m, 2H), 1.07-1.02 (m, 1H), 0.73-0.67 (dd, 6H)

MS (m/z): 575[M+H], 557[M-OH]

Example 246: Preparation of ((1R)-1-(5-benzyl-3-((3-methyl-1-phenyl-1H-pyrazol-5-carboxamido)methyl)-4,5-dihydroisoxazol-5-carboxamido)-3-methylbutyl)boronic acid Through the processes (1), (2) and (3) below, the title compound was obtained.

(1) Preparation of methyl 5-benzyl-3-((3-methyl-1-phenyl-1H-pyrazol-5-carboxamido)methyl)-4,5-dihydroisoxazol-5-carboxylate

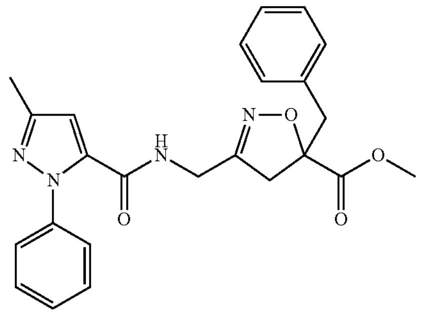

The title compound (0.102 g, 72%) was obtained using methyl 3-(aminomethyl)-5-benzyl-4,5-dihydroisoxazol-5-carboxylate hydrochloride (0.093 g, 0.327 mmol) obtained in Example 84-(1) and 5-methyl-2-phenyl-2H-pyrazol-3-carboxylic acid (0.073 g, 0.361 mmol) by the preparation method of Example 84-(2).

NMR: $^1$H-NMR (500 MHz, $CDCl_3$); δ 7.43-7.37 (5H, m), 7.28-7.21 (5H, m), 6.48 (1H, s), 5.99 (1H, t), 4.06 (2H, d), 3.78 (3H, s), 3.34 (1H, d), 3.30 (1H, d), 3.10 (1H, d), 2.91 (1H, d), 2.35 (3H, s)

MS (m/z): 433[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-methyl-1-phenyl-1H-pyrazol-5-carboxamido)methyl)-4,5-dihydroisoxazol-5-carboxamide

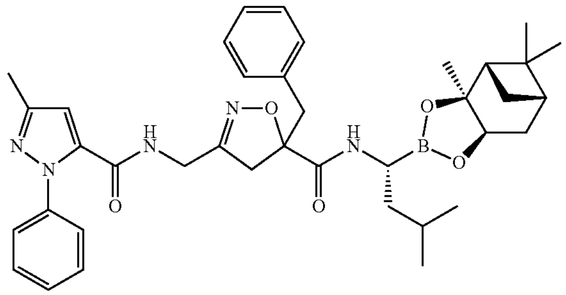

The title compound (0.107 g, 68%, 2 steps) was obtained using methyl 5-benzyl-3-((3-methyl-1-phenyl-1H-pyrazol-5-carboxamido)methyl)-4,5-dihydroisoxazol-5-carboxylate (0.102 g, 0.236 mmol) obtained in (1) above by the preparation method of Example 84-(3).

MS (m/z): 666[M+H]

(3) Preparation of ((1R)-1-(5-benzyl-3-((3-methyl-1-phenyl-1H-pyrazol-5-carboxamido)methyl)-4,5-dihydroisoxazol-5-carboxamido)-3-methylbutyl) boronic acid

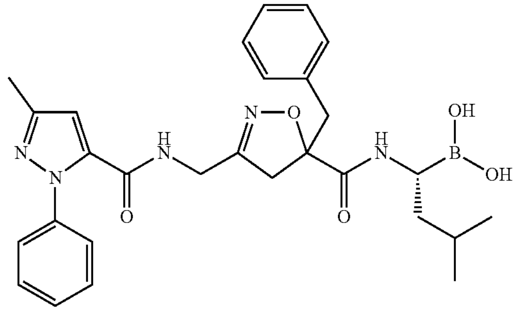 [SMILES: Cc1cc(C(=O)NCC2=NOC(Cc3ccccc3)(C(=O)N[C@@H](CC(C)C)B(O)O)C2)n(-c2ccccc2)n1]

The title compound (0.033 g, 39%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-methyl-1-phenyl-1H-pyrazol-5-carboxamido)methyl)-4,5-dihydroisoxazol-5-carboxamide (0.107 g, 0.161 mmol) obtained in (2) above by the preparation method of Example 1-(4).

NMR: $^1$H-NMR (500 MHz, $CD_3OD$); δ 7.46-7.38 (5H, m), 7.25-7.20 (5H, m), 6.62 (1H, s), 4.10 (2H, d), 3.37-3.27 (2H, m), 3.14 (1H, d), 3.12 (1H, d), 2.64 (1H, t), 1.39-1.02 (3H, m), 0.78 (6H, dd)

MS (m/z): 554[M+Na], 514[M-OH]

Example 247: Preparation of ((1R)-1-(5-benzyl-3-((1-(4-fluorophenyl)-3-methyl-1H-pyrazol-5-carboxamido)methyl)-4,5-dihydroisoxazol-5-carboxamido)-3-methylbutyl)boronic acid Through the processes (1), (2), (3) and (4) below, the title compound was obtained.

(1) Preparation of 2-(4-fluoro-phenyl)-5-methyl-2H-pyrazol-3-carboxylic acid

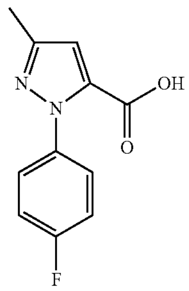 [SMILES: Cc1cc(C(=O)O)n(-c2ccc(F)cc2)n1]

The title compound was obtained by the method described in EP1176140A1.

(2) Preparation of methyl 5-benzyl-3-((1-(4-fluoro-phenyl)-3-methyl-1H-pyrazol-5-carboxamido) methyl)-4,5-dihydroisoxazol-5-carboxylate

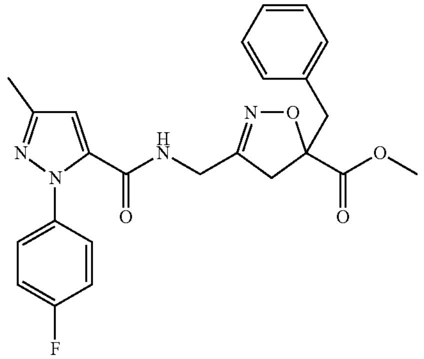

The title compound (0.113 g, 77%) was obtained using methyl 3-(aminomethyl)-5-benzyl-4,5-dihydroisoxazol-5-carboxylate hydrochloride (0.093 g, 0.327 mmol) obtained in Example 84-(1) and 2-(4-fluoro-phenyl)-5-methyl-2H-pyrazol-3-carboxylic acid (0.079 g, 0.359 mmol) obtained in (1) above by the preparation method of Example 84-(2).

NMR: $^1$H-NMR (500 MHz, $CDCl_3$); δ 7.37 (2H, dd), 7.27-7.18 (5H, m), 7.09 (2H, dd), 6.45 (1H, d), 6.25 (1H, t), 4.07-4.02 (2H, m), 3.77 (3H, s), 3.35 (1H, d), 3.30 (1H, d), 3.11 (1H, d), 2.93 (1H, d), 2.33 (3H, s)

MS (m/z): 451[M+H]

(3) Preparation of 5-benzyl-3-((1-(4-fluorophenyl)-3-methyl-1H-pyrazol-5-carboxamido)methyl)-N—((R)-3-methyl-1-((3aS,4S,6S,7aR)-3a,5,5-trimethyl-hexahydro-4,6-metanobenzo[d][1,3,2]dioxaborol-2-yl)butyl)-4,5-dihydroisoxazol-5-carboxamide

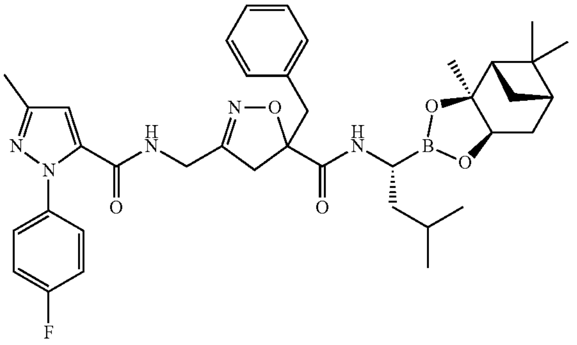

The title compound (0.103 g, 60%, 2 steps) was obtained using methyl 5-benzyl-3-((1-(4-fluorophenyl)-3-methyl-1H-pyrazol-5-carboxamido)methyl)-4,5-dihydroisoxazol-5-carboxylate (0.113 g, 0.259 mmol) obtained in (2) above by the preparation method of Example 84-(3).

MS (m/z): 684[M+H]

(4) Preparation of ((1R)-1-(5-benzyl-3-((1-(4-fluorophenyl)-3-methyl-1H-pyrazol-5-carboxamido) methyl)-4,5-dihydroisoxazol-5-carboxamido)-3-methylbutyl)boronic acid

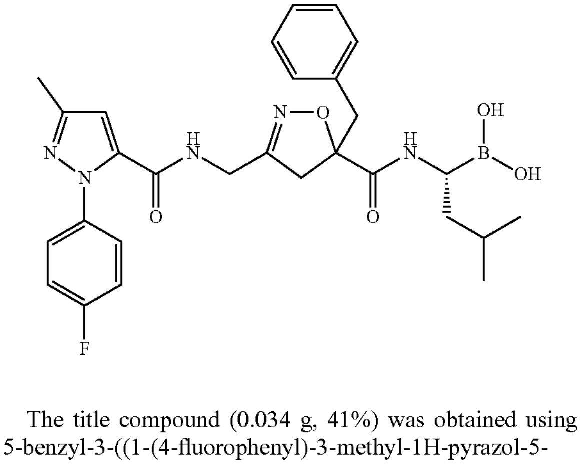

The title compound (0.034 g, 41%) was obtained using 5-benzyl-3-((1-(4-fluorophenyl)-3-methyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.103 g, 0.151 mmol) obtained in (3) above by the preparation method of Example 1-(4).

NMR: $^1$H-NMR (500 MHz, $CD_3OD$); δ 7.39 (2H, dd), 7.25-7.20 (5H, m), 7.18 (1H, dd), 6.63 (1H, s), 4.13-4.05 (2H, m), 3.37-3.27 (2H, m), 3.17 (1H, d), 3.12 (1H, d), 2.64 (1H, t), 2.30 (3H, s), 1.55 (6H, dd), 1.39-1.02 (3H, m), 0.78 (6H, dd)

MS (ES+): 572[M+Na], 532[M-OH]

Example 248: Preparation of ((1R)-1-(3-((4-chloro-1-isopropyl-3-methyl-1H-pyrazol-5-carboxamido)methyl)-5-(3-chlorobenzyl)-4,5-dihydroisoxazol-5-carboxamido)-3-methylbutyl)boronic acid Through the processes (1), (2) and (3) below, the title compound was obtained.

(1) Preparation of ethyl 3-((4-chloro-1-isopropyl-3-methyl-1H-pyrazol-5-carboxamido)methyl)-5-(3-chlorobenzyl)-4,5-dihydroisoxazol-5-carboxylate

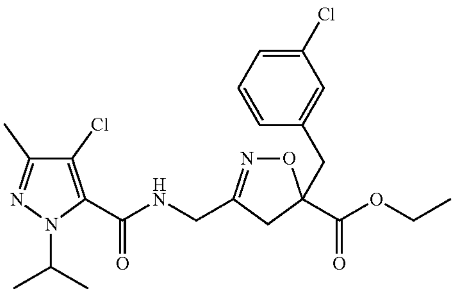 [SMILES: CCOC(=O)C1(Cc2cccc(Cl)c2)CC(CNC(=O)c2c(Cl)c(C)nn2C(C)C)=NO1]

The title compound (0.158 g, 73%) was obtained using ethyl 3-(aminomethyl)-5-(3-chlorobenzyl)-4,5-dihydroisoxazol-5-carboxylate hydrochloride (0.15 g, 0.45 mmol) obtained in Example 175-(1) and 4-chloro-2-isopropyl-5-methyl-2H-pyrazol-3-carboxylic acid (0.1 g, 0.50 mmol) obtained in Example 222-(2) by the preparation method of Example 84-(2).

MS (m/z): 481[M+H], 483[M-OH]

(2) Preparation of 3-((4-chloro-1-isopropyl-3-methyl-1H-pyrazol-5-carboxamido)methyl)-5-(3-chlorobenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

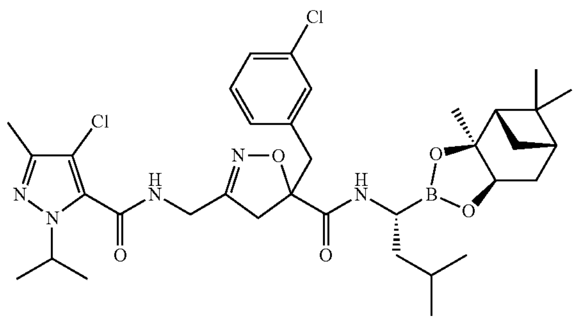

The title compound (0.053 g, 26%, 2 steps) was obtained using ethyl 3-((4-chloro-1-isopropyl-3-methyl-1H-pyrazol-5-carboxamido)methyl)-5-(3-chlorobenzyl)-4,5-dihydroisoxazol-5-carboxylate (0.158 g, 0.27 mmol) obtained in (1) above by the preparation method of Example 84-(3).

MS (m/z): 700[M+H]

(3) Preparation of ((1R)-1-(3-((4-chloro-1-isopropyl-3-methyl-1H-pyrazol-5-carboxamido)methyl)-5-(3-chlorobenzyl)-4,5-dihydroisoxazol-5-carboxamido)-3-methylbutyl)boronic acid

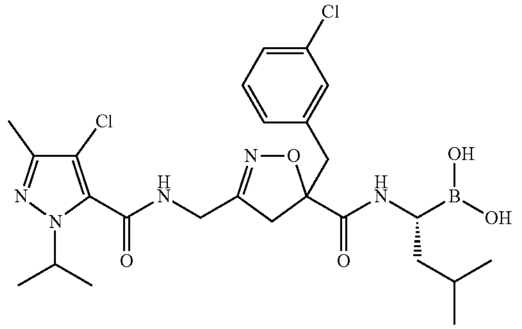 [SMILES: Cc1nn(C(C)C)c(C(=O)NCC2=NOC(Cc3cccc(Cl)c3)(C(=O)N[C@@H](CC(C)C)B(O)O)C2)c1Cl]

The title compound (0.034 g, 74%) was obtained using 3-((4-chloro-1-isopropyl-3-methyl-1H-pyrazol-5-carboxamido)methyl)-5-(3-chlorobenzyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.053 g, 0.076 mmol) obtained in (2) above by the preparation method of Example 1-(4).

NMR: $^1$H-NMR (500 MHz, $CDCl_3$); δ 7.29-7.14 (m, 5H), 6.98-6.96 (t, 1H), 5.42-5.38 (m, 1H), 4.25-4.17 (m, 2H), 3.43-3.33 (m, 2H), 3.12-3.03 (m, 2H), 2.88 (m, 1H), 2.23 (s, 3H), 1.44-1.42 (d, 6H), 1.40-1.21 (m, 3H), 0.84-0.82 (t, 6H)

MS (m/z): 566[M+H], 548[M-OH]

Example 249: Preparation of ((1R)-1-(5-(3-chlorobenzyl)-3-((1-isopropyl-3-phenyl-1H-pyrazol-5-carboxamido)methyl)-4,5-dihydroisoxazol-5-carboxamido)-3-methylbutyl)boronic acid Through the processes (1), (2) and (3) below, the title compound was obtained.

(1) Preparation of ethyl 5-(3-chlorobenzyl)-3-((1-isopropyl-3-phenyl-1H-pyrazol-5-carboxamido)methyl)-4,5-dihydroisoxazol-5-carboxylate

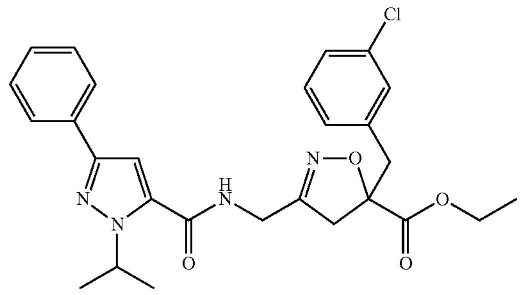 [SMILES: CCOC(=O)C1(Cc2cccc(Cl)c2)CC(CNC(=O)c2cc(-c3ccccc3)nn2C(C)C)=NO1]

The title compound (0.163 g, 80%) was obtained using ethyl 3-(aminomethyl)-5-(3-chlorobenzyl)-4,5-dihydroisoxazol-5-carboxylate hydrochloride (0.133 g, 0.40 mmol) obtained in Example 175-(1) and 2-isopropyl-5-phenyl-2H-pyrazol-3-carboxylic acid (0.120 g, 0.52 mmol) obtained in Example 207-(3) by the preparation method of Example 84-(2).

NMR: $^1$H-NMR (400 MHz, $CDCl_3$); δ 7.84 (2H, dd), 7.44 (2H, dd), 7.36-7.15 (5H, m), 6.81 (1H, s), 6.59 (1H, t), 5.49 (1H, q), 4.29-4.21 (4H, m), 3.50 (1H, d), 3.34 (1H, d), 3.21 (1H, d), 3.05 (1H, m), 1.57 (6H, dd), 1.30 (3H, t)

MS (m/z): 509[M+H]

(2) Preparation of 5-(3-chlorobenzyl)-3-((1-isopropyl-3-phenyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

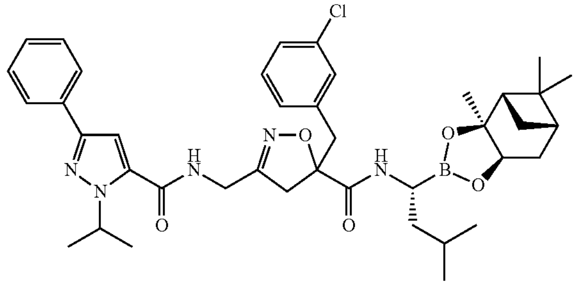 [SMILES: CC(C)C[C@H](NC(=O)C1(Cc2cccc(Cl)c2)CC(CNC(=O)c2cc(-c3ccccc3)nn2C(C)C)=NO1)B1O[C@@H]2C[C@@H]3C[C@@H](C3(C)C)[C@]2(C)O1]

The title compound (0.087 g, 37%, 2 steps) was obtained using ethyl 5-(3-chlorobenzyl)-3-((1-isopropyl-3-phenyl-1H-pyrazol-5-carboxamido)methyl)-4,5-dihydroisoxazol-5-carboxylate (0.163 g, 0.32 mmol) obtained in (1) above by the preparation method of Example 84-(3).

MS (m/z): 728[M+H]

(3) Preparation of ((1R)-1-(5-(3-chlorobenzyl)-3-((1-isopropyl-3-phenyl-1H-pyrazol-5-carboxamido)methyl)-4,5-dihydroisoxazol-5-carboxamido)-3-methylbutyl)boronic acid

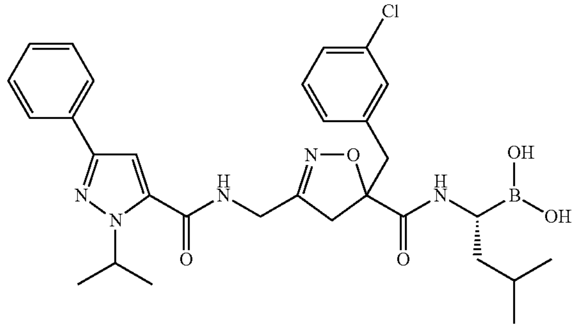

The title compound (0.044 g, 6%) was obtained using 5-(3-chlorobenzyl)-3-((1-isopropyl-3-phenyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.087 g, 0.119 mmol) obtained in (2) above by the preparation method of Example 1-(4).

NMR: $^1$H-NMR (500 MHz, $CDCl_3$); δ 7.83 (2H, dd), 7.43 (2H, t), 7.39-7.22 (5H, m), 7.04 (1H, s), 5.50 (1H, q), 4.25 (2H, d), 3.48 (1H, d), 3.37-3.26 (2H, m), 3.22 (1H, d), 2.72 (1H, t), 1.54 (6H, dd), 1.44-1.02 (3H, m), 0.83 (6H, dd)

MS (m/z): 616[M+Na], 576[M-OH]

Example 250: Preparation of ((1R)-1-(5-(3-chlorobenzyl)-3-((1-isopropyl-1H-pyrazol-5-carboxamido)methyl)-4,5-dihydroisoxazol-5-carboxamido)-3-methylbutyl)boronic acid Through the processes (1), (2) and (3) below, the title compound was obtained.

(1) Preparation of ethyl 5-(3-chlorobenzyl)-3-((1-isopropyl-1H-pyrazol-5-carboxamido)methyl)-4,5-dihydroisoxazol-5-carboxylate

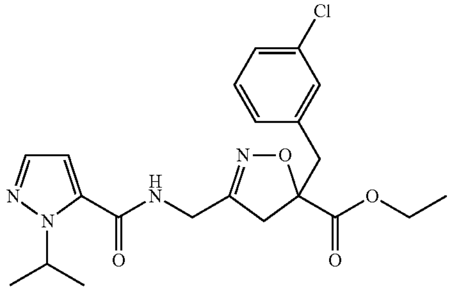 [SMILES: CCOC(=O)C1(Cc2cccc(Cl)c2)CC(CNC(=O)c2ccnn2C(C)C)=NO1]

The title compound (0.123 g, 73%) was obtained using ethyl 3-(aminomethyl)-5-(3-chlorobenzyl)-4,5-dihydroisoxazol-5-carboxylate hydrochloride (0.13 g, 0.39 mmol) obtained in Example 175-(1) and 2-isopropyl-2H-pyrazol-3-carboxylic acid (0.066 g, 0.43 mmol) obtained in Example 171-(2) by the preparation method of Example 84-(2).

MS (m/z): 433[M+H]

(2) Preparation of 5-(3-chlorobenzyl)-3-((1-isopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

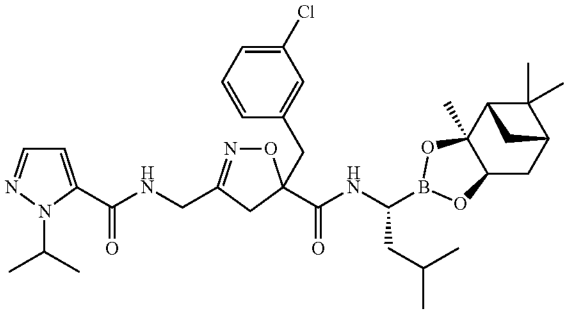 [SMILES: CC(C)C[C@H](NC(=O)C1(Cc2cccc(Cl)c2)CC(CNC(=O)c2ccnn2C(C)C)=NO1)B1O[C@@H]2C[C@@H]3C[C@@H](C3(C)C)[C@]2(C)O1]

The title compound (0.049 g, 30%, 2 steps) was obtained using ethyl 5-(3-chlorobenzyl)-3-((1-isopropyl-1H-pyrazol-5-carboxamido)methyl)-4,5-dihydroisoxazol-5-carboxylate (0.123 g, 0.28 mmol) obtained in (1) above by the preparation method of Example 84-(3).

MS (m/z): 652[M+H]

(3) Preparation of ((1R)-1-(5-(3-chlorobenzyl)-3-((1-isopropyl-1H-pyrazol-5-carboxamido)methyl)-4,5-dihydroisoxazol-5-carboxamido)-3-methylbutyl) boronic acid

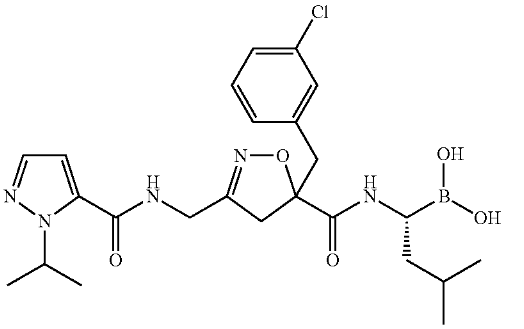 [SMILES: CC(C)C[C@H](NC(=O)C1(Cc2cccc(Cl)c2)CC(CNC(=O)c2ccnn2C(C)C)=NO1)B(O)O]

The title compound (0.023 g, 59%) was obtained using 5-(3-chlorobenzyl)-3-((1-isopropyl-1H-pyrazol-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.049 g, 0.075 mmol) obtained in (2) above by the preparation method of Example 1-(4).

NMR: $^1$H-NMR (400 MHz, $CDCl_3$); δ 7.46-7.45 (d, 1H), 7.28-7.13 (m, 6H), 6.58-6.57 (t, 1H), 6.48-6.47 (d, 1H), 5.47-5.40 (m, 1H), 4.26-4.13 (m, 2H), 3.46-3.41 (d, 1H), 3.36-3.33 (d, 1H), 3.13-3.04 (m, 2H), 2.83 (m, 1H), 1.48-1.45 (dd, 6H0, 1.37-1.21 (m, 3H), 0.84-0.82 (dd, 6H)

MS (m/z): 518[M+H], 500[M-OH]

Example 251: Preparation of ((1R)-3-methyl-1-(3-((3-methyl-1-(tetrahydro-2H-pyran-4-yl)-1H-pyrazol-5-carboxamido)methyl)-5-(3-methylbenzyl)-4,5-dihydroisoxazol-5-carboxamido)butyl)boronic acid Through the processes (1), (2) and (3) below, the title compound was obtained.

(1) Preparation of ethyl 3-((3-methyl-1-(tetrahydro-2H-pyran-4-yl)-1H-pyrazol-5-carboxamido)methyl)-5-(3-methylbenzyl)-4,5-dihydroisoxazol-5-carboxylate

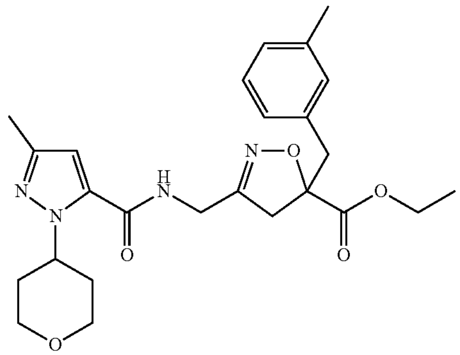 [SMILES: CCOC(=O)C1(Cc2cccc(C)c2)CC(CNC(=O)c2cc(C)nn2C2CCOCC2)=NO1]

The title compound (0.12 g, 64%) was obtained using ethyl 3-(aminomethyl)-5-(3-methylbenzyl)-4,5-dihydroisoxazol-5-carboxylate hydrochloride (0.13 g, 0.42 mmol) obtained in Example 125-(1) and 3-methyl-1-(tetrahydro-2H-pyran-4-yl)-1H-pyrazol-5-carboxylic acid (0.096 g, 0.46 mmol) obtained in Example 218-(2) by the preparation method of Example 84-(2).

MS (m/z): 469[M+H]

(2) Preparation of N—((R)-3-methyl-1-((3aS,4S,6S,7aR)-3a,5,5-trimethylhexahydro-4,6-metanobenzo[d][1,3,2]dioxaborol-2-yl)butyl)-3-((3-methyl-1-(tetrahydro-2H-pyran-4-yl)-1H-pyrazol-5-carboxamido)methyl)-5-(3-methylbenzyl)-4,5-dihydroisoxazol-5-carboxamide

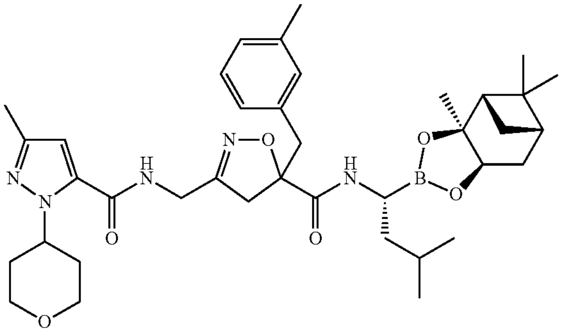

The title compound (0.06 g, 32%, 2 steps) was obtained using ethyl 3-((3-methyl-1-(tetrahydro-2H-pyran-4-yl)-1H-pyrazol-5-carboxamido)methyl)-5-(3-methylbenzyl)-4,5-dihydroisoxazol-5-carboxylate (0.12 g, 0.26 mmol) obtained in (1) above by the preparation method of Example 84-(3).

MS (m/z): 688[M+H]

(3) Preparation of ((1R)-3-methyl-1-(3-((3-methyl-1-(tetrahydro-2H-pyran-4-yl)-1H-pyrazol-5-carboxamido)methyl)-5-(3-methylbenzyl)-4,5-dihydroisoxazol-5-carboxamido)butyl)boronic acid

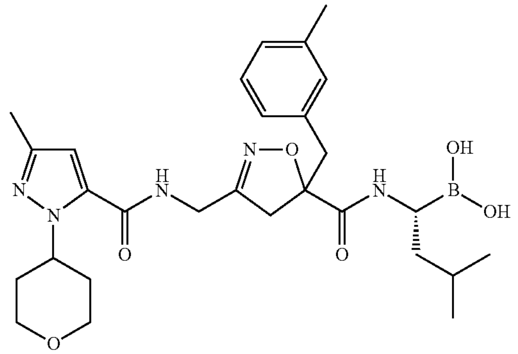 [SMILES: Cc1cccc(CC2(C(=O)N[C@@H](CC(C)C)B(O)O)CC(CNC(=O)c3cc(C)nn3C3CCOCC3)=NO2)c1]

The title compound (0.027 g, 56%) was obtained using N—((R)-3-methyl-1-((3aS,4S,6S,7aR)-3a,5,5-trimethylhexahydro-4,6-metanobenzo[d][1,3,2]dioxaborol-2-yl)butyl)-3-((3-methyl-1-(tetrahydro-2H-pyran-4-yl)-1H-pyrazol-5-carboxamido)methyl)-5-(3-methylbenzyl)-4,5-dihydroisoxazol-5-carboxamide (0.06 g, 0.087 mmol) obtained in (2) above by the preparation method of Example 1-(4).

NMR: $^1$H-NMR (400 MHz, $CDCl_3$); δ 7.19-7.05 (m, 5H), 6.41 (t, 1H), 6.23 (s, 1H), 5.20 (m, 1H), 4.13-4.07 (m, 4H), 3.54-3.48 (m, 2H), 3.41-3.36 (d, 1H), 3.33-3.29 (d, 1H), 3.12-3.08 (d, 1H), 3.05-3.00 (d, 1H), 2.85 (m, 1H), 2.30 (s, 3H), 2.28-2.25 (m, 5H), 1.87 (m, 2H), 1.43-1.21 (m, 3H), 0.85-0.82 (t, 6H)

MS (m/z): 554[M+H], 536[M-OH]

Example 252: Preparation of ((1R)-1-(3-((benzyloxy)methyl)-4,5-dihydroisoxazol-5-carboxamido)-3-methylbutylboronic acid Through the processes (1), (2), (3) and (4) below, the title compound was obtained.

(1) Preparation of 2-(benzyloxy)acetaldehyde oxime

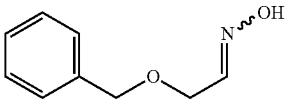 [SMILES: ON=CCOCc1ccccc1]

The title compound (1.18 g, quant.) was obtained using 2-(benzyloxy)acetaldehyde (1.0 ml, 7.1 mmol) by the preparation method of Example 3-(1).

MS (m/z): 166[M+H]

(2) Preparation of ethyl 3-((benzyloxy)methyl)-4,5-dihydroisoxazol-5-carboxylate

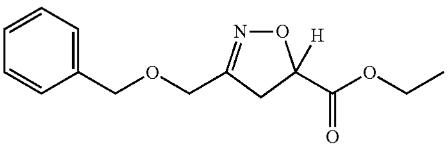 [SMILES: CCOC(=O)C1CC(COCc2ccccc2)=NO1]

The title compound (1.19 g, 63%) was obtained using 2-(benzyloxy)acetaldehyde oxime (1.18 g, 7.1 mmol) obtained in (1) above by the preparation method of Example 2-(3).

MS (m/z): 264[M+H]

(3) Preparation of 3-((benzyloxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

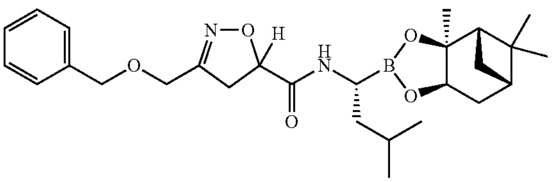 [SMILES: CC(C)C[C@H](NC(=O)C1CC(COCc2ccccc2)=NO1)B1O[C@@H]2C[C@@H]3C[C@@H](C3(C)C)[C@]2(C)O1]

The title compound (0.205 g, 54%) was obtained using ethyl 3-((benzyloxy)methyl)-4,5-dihydroisoxazol-5-carboxylate (0.209 g, 0.79 mmol) obtained in (2) above by the preparation methods of Example 1-(2) and Example 1-(3).

MS (m/z): 483[M+H]

(4) Preparation of ((1R)-1-(3-((benzyloxy)methyl)-4,5-dihydroisoxazol-5-carboxamido)-3-methylbutylboronic acid

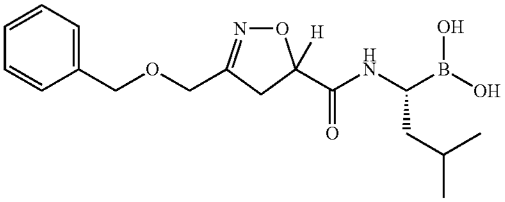 [SMILES: CC(C)C[C@H](NC(=O)C1CC(COCc2ccccc2)=NO1)B(O)O]

The title compound (0.042 g, 63%) was obtained using 3-((benzyloxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.205 g, 0.43 mmol) obtained in (3) above by the preparation method of Example 1-(4).

MS (m/z): 349[M+H], 331[M-OH]

Example 253: Preparation of ((1R)-1-(5-benzyl-3-(2-(isoquinolin-1-carboxamido)ethyl)-4,5-dihydroisoxazol-5-carboxamido)-3-methylbutylboronic acid Through the processes (1), (2), (3), (4) and (5) below, the title compound was obtained.

(1) Preparation of methyl 5-benzyl-3-(2-((tert-butoxycarbonyl)amino)ethyl)-4,5-dihydroisoxazol-5-carboxylate

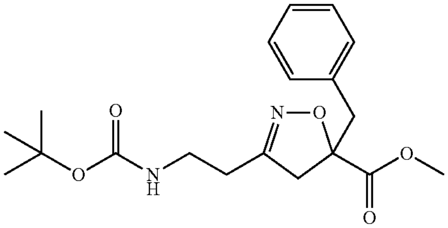 [SMILES: COC(=O)C1(Cc2ccccc2)CC(CCNC(=O)OC(C)(C)C)=NO1]

The title compound (0.56 g, 53%) was obtained using tert-butyl (3-(hydroxyimino)propyl)carbamate (0.65 g, 2.89 mmol) and methyl 2-benzylacrylate (0.56 g, 3.18 mmol) obtained in Preparation Example 6-(1) by the preparation method of Preparation Example 1-(2).

MS (m/z): 363[M+H]

(2) Preparation of methyl 3-(2-aminoethyl)-5-benzyl-4,5-dihydroisoxazol-5-carboxylate hydrochloride

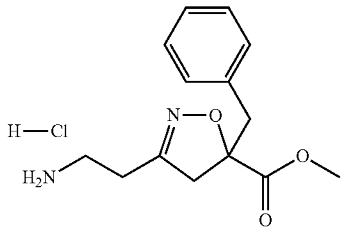

The title compound (0.42 g, 91%) was obtained using methyl 5-benzyl-3-(2-((tert-butoxycarbonyl)amino)ethyl)-4,5-dihydroisoxazol-5-carboxylate (0.56 g, 1.5 mmol) obtained in the process (1) above by the preparation method of Example 84-(1).

MS (m/z): 299[M+H]

(3) Preparation of methyl 5-benzyl-3-(2-(isoquinolin-1-carboxamido)ethyl)-4,5-dihydroisoxazol-5-carboxylate

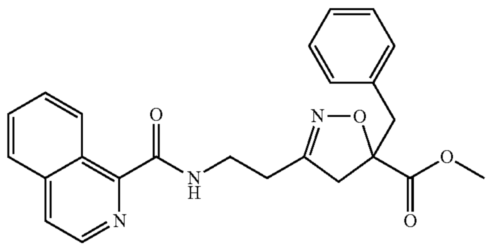 [SMILES: COC(=O)C1(Cc2ccccc2)CC(CCNC(=O)c2nccc3ccccc23)=NO1]

The title compound (0.104 g, 86%) was obtained using methyl 3-(2-aminoethyl)-5-benzyl-4,5-dihydroisoxazol-5-carboxylate hydrochloride (0.087 g, 0.29 mmol) obtained in the process (2) above by the preparation method of Example 84-(2).

MS (m/z): 418[M+H]

(4) Preparation of 5-benzyl-3-(2-(isoquinolin-1-carboxamido)ethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

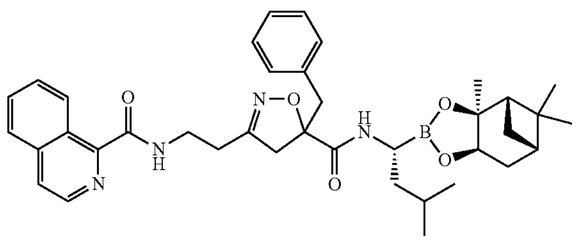 [SMILES: CC(C)C[C@H](NC(=O)C1(Cc2ccccc2)CC(CCNC(=O)c2nccc3ccccc23)=NO1)B1O[C@@H]2C[C@@H]3C[C@@H](C3(C)C)[C@]2(C)O1]

The title compound (0.058 g, 37%) was obtained using methyl 5-benzyl-3-(2-(isoquinolin-1-carboxamido)ethyl)-4,5-dihydroisoxazol-5-carboxylate (0.1 g, 0.24 mmol) obtained in the process (3) above by the preparation method of Example 84-(3).

MS (m/z): 651[M+H]

(5) Preparation of ((1R)-1-(5-benzyl-3-(2-(isoquinolin-1-carboxamido)ethyl)-4,5-dihydroisoxazol-5-carboxamido)-3-methylbutylboronic acid

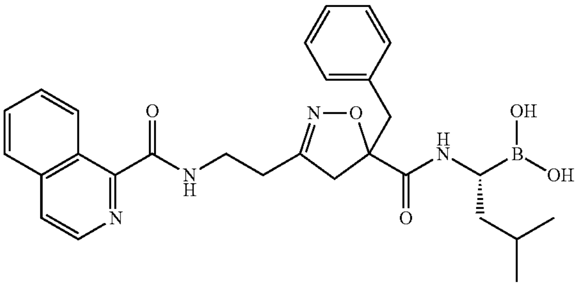 [SMILES: CC(C)C[C@H](NC(=O)C1(Cc2ccccc2)CC(CCNC(=O)c2nccc3ccccc23)=NO1)B(O)O]

The title compound (0.018 g, 38%) was obtained using 5-benzyl-3-(2-(isoquinolin-1-carboxamido)ethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.058 g, 0.09 mmol) obtained in the process (4) above by the preparation method of Example 1-(4).

MS (m/z): 517[M+H], 499[M-OH]

Example 254: Preparation of ((1R)-1-(5-benzyl-3-(phenoxymethyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-(phenoxymethyl)-4,5-dihydroisoxazol-5-carboxylate

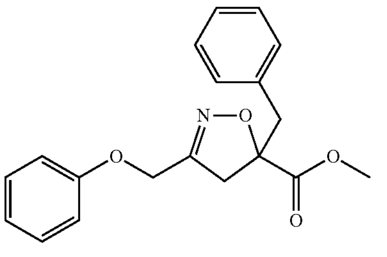 [SMILES: COC(=O)C1(Cc2ccccc2)CC(COc2ccccc2)=NO1]

Methyl 5-benzyl-3-(chloromethyl)-4,5-dihydroisoxazol-5-carboxylate (1.7 g, 6.4 mmol) obtained in Example 49-(2) was dissolved in dimethylformamide (64 ml). Potassium carbonate (1.3 g, 9.5 mmol) and phenol (0.84 ml, 9.5 mmol) were added thereto, followed by stirring at 30° C. for 8 hours. Water and diethyl ether were added thereto, an organic layer was separated, and an aqueous solution layer was extracted with diethyl ether twice. The organic layer was washed with brine and dried over anhydrous magnesium sulfate. The filtrate was distilled under a reduced pressure and separated by column chromatography to obtain the title compound (2.0 g, 98%).

MS (m/z): 326[M+H]

(2) Preparation of 5-benzyl-3-(phenoxymethyl)-4,5-dihydroisoxazol-5-carboxylic acid

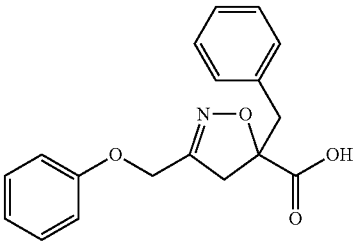 [SMILES: O=C(O)C1(Cc2ccccc2)CC(COc2ccccc2)=NO1]

The quantitative amount of the title compound was obtained using methyl 5-benzyl-3-(phenoxymethyl)-4,5-dihydroisoxazol-5-carboxylate (2.03 g, 6.2 mmol) obtained in (1) above by the preparation method of Example 84-(3).

MS (m/z): 312[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(phenoxymethyl)-4,5-dihydroisoxazol-5-carboxamide

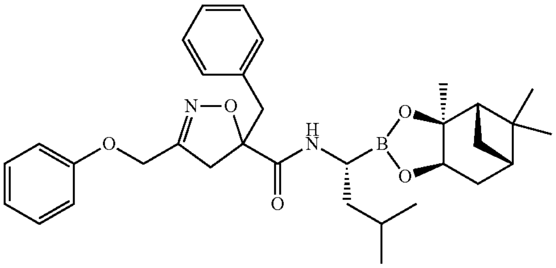 [SMILES: CC(C)C[C@H](NC(=O)C1(Cc2ccccc2)CC(COc2ccccc2)=NO1)B1O[C@@H]2C[C@@H]3C[C@@H](C3(C)C)[C@]2(C)O1]

5-Benzyl-3-(phenoxymethyl)-4,5-dihydroisoxazol-5-carboxylic acid (0.70 g, 2.25 mmol) obtained in (2) above, (R)-3-methyl-1-((3aS,4S,6S,7aR)-3a,5,5-trimethylhexahydro-4,6-metanobenzo[d][1,3,2]dioxaborol-2-yl)butan-1-amine 2,2,2-trifluoroacetate (0.90 g, 2.36 mmol), and O-(benzotriazol-1-yl)-N,N,N',N'-tetramethyluronium tetrafluoroborate (0.79 g, 2.47 mmol) were dissolved at 0° C. in dichloromethane (8 ml). While maintaining 0° C., diisopropylethylamine (1.17 ml, 6.75 mmol) was slowly added thereto, followed by stirring for 18 hours, while raising to room temperature. A sodium bicarbonate aqueous solution (5 ml) was added to quench the reaction, an organic layer and an aqueous solution layer were separated, and the aqueous solution layer was extracted with dichloromethane twice. Organic layers were collected and washed with brine, dried over anhydrous magnesium sulfate, and filtered. The filtrate was distilled under a reduced pressure and separated by column chromatography to obtain the title compound (0.32 g, 25%).

MS (m/z): 559[M+H]

(4) Preparation of ((1R)-1-(5-benzyl-3-(phenoxymethyl)-4,5-dihydroisoxazol-5-carboxamido)-3-methylbutylboronic acid

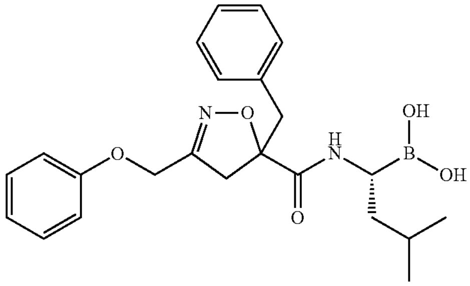 [SMILES: CC(C)C[C@H](NC(=O)C1(Cc2ccccc2)CC(COc2ccccc2)=NO1)B(O)O]

The title compound (0.040 g, 16%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(phenoxymethyl)-4,5-dihydroisoxazol-5-carboxamide (0.32 g, 0.57 mmol) obtained in (3) above by the preparation method of Example 1-(4).

NMR: 1H NMR (400 MHz, METHANOL-d4) δ ppm 0.68-0.76 (6H, m), 0.84-1.01 (1H, m), 1.11-1.17 (1H, m), 1.26-1.43 (1H, m), 2.52-2.67 (1H, m), 2.96-3.19 (2H, m), 3.25 (1H, m), 3.31-3.44 (1H, m), 4.63-4.71 (2H, m), 6.76-6.89 (3H, m), 7.08-7.23 (8H, m)

MS (m/z): 425[M+H], 407[M-OH]

Example 255: Preparation of ((1R)-1-(5-benzyl-3-(phenoxymethyl)-4,5-dihydroisoxazol-5-carboxamido)-2-phenylethyl)boronic acid Through the processes (1) and (2) below, the title compound was obtained.

(1) Preparation of 5-benzyl-3-(phenoxymethyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

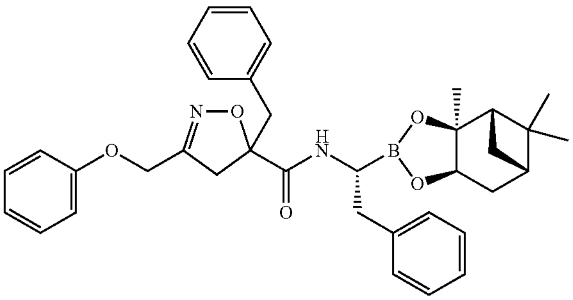 [SMILES: CC1(C)[C@@H]2C[C@H]3OB([C@H](Cc4ccccc4)NC(=O)C4(Cc5ccccc5)CC(COc5ccccc5)=NO4)O[C@@]3(C)[C@H]1C2]

1,1'-Carbonyldiimidazole (0.34 g, 2.1 mmol) was dissolved in acetonitrile (5 ml), and at 0° C., 5-benzyl-3-(phenoxymethyl)-4,5-dihydroisoxazol-5-carboxylic acid (0.40 g, 1.6 mmol) obtained in Example 254-(2) was added thereto, followed by stirring for 1 hour. (R)-2-phenyl-1-((3aS,4S,6S,7aR)-3a,5,5-trimethylhexahydro-4,6-metanobenzo[d][1,3,2]dioxaborol-2-yl)ethan-1-amine hydrochloride (0.57 g, 1.7 mmol) was added thereto, and stirring was performed at room temperature for 16 hours. Through distillation under a reduced pressure, the acetonitrile solvent was removed, and then, ethyl acetate was added. An organic layer was washed with a sodium bicarbonate aqueous solution, dried over anhydrous magnesium sulfate, and filtered. The filtrate of an organic layer was distilled under a reduced pressure and separated by column chromatography to obtain the title compound (0.75 g, 79%).

MS (m/z): 593[M+H]

(2) Preparation of ((1R)-1-(5-benzyl-3-(phenoxymethyl)-4,5-dihydroisoxazol-5-carboxamido)-2-phenylethyl)boronic acid

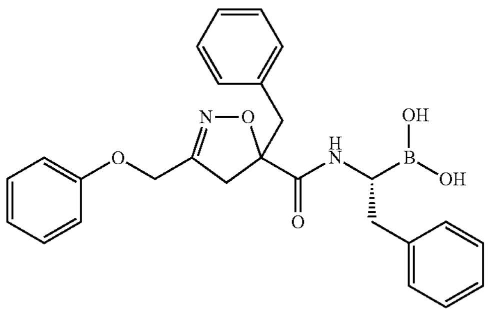 [SMILES: O=C(N[C@@H](Cc1ccccc1)B(O)O)C1(Cc2ccccc2)CC(COc2ccccc2)=NO1]

The title compound (0.234 g, 40%) was obtained using 5-benzyl-3-(phenoxymethyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.75 g, 1.3 mmol) obtained in (1) above by the preparation method of Example 1-(4).

NMR: 1H NMR (400 MHz, METHANOL-d4) δ ppm 2.28-2.76 (2H, m), 2.81-2.97 (1H, m), 3.06-3.18 (1H, m), 3.21-3.29 (1H, m), 3.32-3.49 (2H, m), 4.69-4.84 (2H, m), 6.81-7.02 (4H, m), 7.03-7.41 (12H, m)

MS (m/z): 459[M+H], 441[M-OH]

Example 256: Preparation of ((1R)-1-(5-benzyl-3-((benzyloxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((benzyloxy)methyl)-4,5-dihydroisoxazol-5-carboxylate

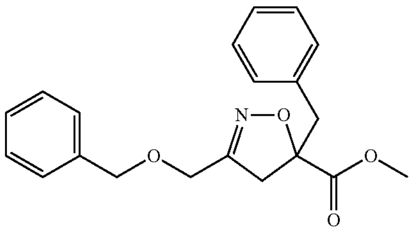 [SMILES: COC(=O)C1(Cc2ccccc2)CC(COCc2ccccc2)=NO1]

The title compound (1.65 g, 65%) was obtained using methyl 5-benzyl-3-(chloromethyl)-4,5-dihydroisoxazol-5-carboxylate (2.0 g, 7.5 mmol) obtained in Example 49-(2) and phenylmethanol (0.77 ml, 7.5 mmol) by the preparation method of Example 49-(3).

MS (m/z): 340[M+H]

(2) Preparation of 5-benzyl-3-((benzyloxy)methyl)-4,5-dihydroisoxazol-5-carboxylic acid

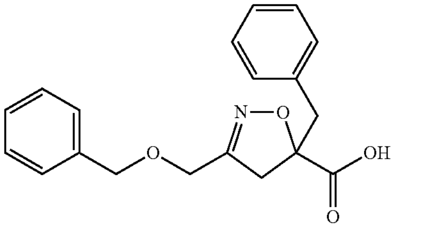 [SMILES: O=C(O)C1(Cc2ccccc2)CC(COCc2ccccc2)=NO1]

The title compound (1.39 g, 88%) was obtained using methyl 5-benzyl-3-((benzyloxy)methyl)-4,5-dihydroisoxazol-5-carboxylate (1.65 g, 4.8 mmol) obtained in (1) above by the preparation method of Example 84-(3).

MS (m/z): 326[M+H]

(3) Preparation of 5-benzyl-3-((benzyloxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

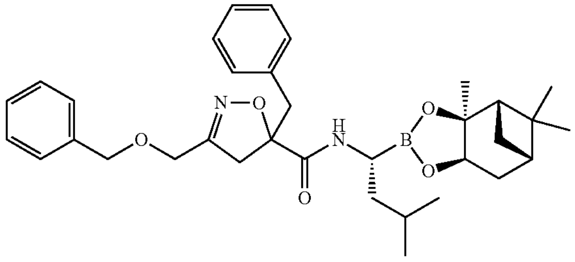

1,1'-Carbonyldiimidazole (0.32 g, 2.00 mmol) was dissolved in acetonitrile (5 ml), and at 0° C., 5-benzyl-3-((benzyloxy)methyl)-4,5-dihydroisoxazol-5-carboxylic acid (0.50 g, 1.54 mmol) obtained in (2) above was added thereto, followed by stirring for 1 hour. (R)-3-methyl-1-((3aS,4S,6S,7aR)-3a,5,5-trimethylhexahydro-4,6-metanobenzo[d][1,3,2]dioxaborol-2-yl)butan-1-amine 2,2,2-trifluoroacetate (0.61 g, 1.61 mmol) was added thereto, and stirring was performed at room temperature for 16 hours. Through distillation under a reduced pressure, the acetonitrile solvent was removed, ethyl acetate was added, and an organic layer was washed with a sodium bicarbonate aqueous solution, dried over anhydrous magnesium sulfate, and filtered. The filtrate of an organic layer was distilled under a reduced pressure and separated by column chromatography to obtain the title compound (0.22 g, 25%).

MS (m/z): 573[M+H]

(4) Preparation of ((1R)-1-(5-benzyl-3-((benzyloxy)methyl)-4,5-dihydroisoxazol-5-carboxamido)-3-methylbutylboronic acid

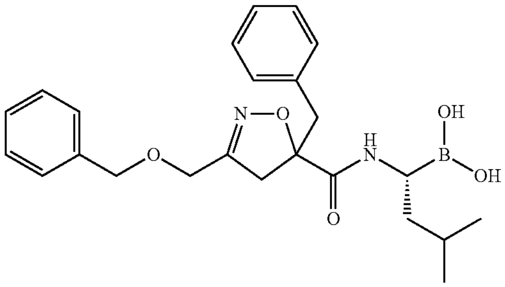

The title compound (0.037 g, 22%) was obtained using 5-benzyl-3-((benzyloxy)methyl)-N—((R)-3-methyl-1-((3aS,4S,6S,7aR)-3a,5,5-trimethylhexahydro-4,6-metano-benzo[d][1,3,2]dioxaborol-2-yl)butyl)-4,5-dihydroisoxazol-5-carboxamide (0.22 g, 0.38 mmol) obtained in (3) above by the preparation method of Example 1-(4).

NMR: 1H NMR (400 MHz, METHANOL-d4) δ ppm 0.77-0.88 (6H, m), 1.03-1.23 (1H, m), 1.24-1.35 (1H, m), 1.36-1.58 (1H, m), 2.65-2.83 (1H, m), 3.10-3.28 (2H, m), 3.31-3.36 (1H, m), 3.44 (1H, dd), 4.11-4.25 (2H, m), 4.28-4.45 (2H, m), 7.12-7.40 (10H, m).

MS (m/z): 439[M+H], 421[M-OH]

Example 257: Preparation of ((1R)-1-(5-benzyl-3-((benzyloxy)methyl)-4,5-dihydroisoxazol-5-carboxamido)-2-phenylethyl)boronic acid Through the processes (1) and (2) below, the title compound was obtained.

(1) Preparation of 5-benzyl-3-((benzyloxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

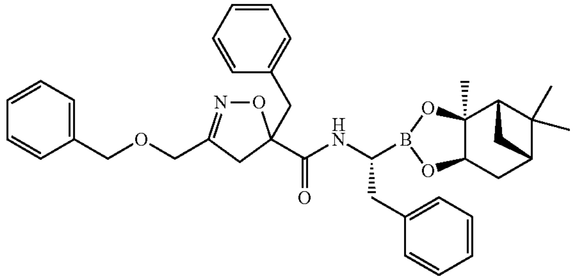 [SMILES: CC1(C)[C@@H]2C[C@H]3OB([C@H](Cc4ccccc4)NC(=O)C4(Cc5ccccc5)CC(COCc5ccccc5)=NO4)O[C@@]3(C)[C@H]1C2]

The title compound (0.40 g, 43%) was obtained using 5-benzyl-3-((benzyloxy)methyl)-4,5-dihydroisoxazol-5-carboxylic acid (0.50 g, 1.5 mmol) obtained in Example 256-(2) by the method of Example 255-(1).

MS (m/z): 607[M+H]

(2) Preparation of ((1R)-1-(5-benzyl-3-((benzyloxy)methyl)-4,5-dihydroisoxazol-5-carboxamido)-2-phenylethyl)boronic acid

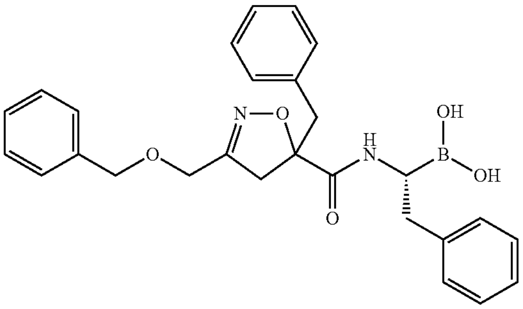 [SMILES: O=C(N[C@@H](Cc1ccccc1)B(O)O)C1(Cc2ccccc2)CC(COCc2ccccc2)=NO1]

The title compound (0.126 g, 40%) was obtained using 5-benzyl-3-((benzyloxy)methyl)-N—((R)-2-phenyl-1-((3aS,4S,6S,7aR)-3a,5,5-trimethylhexahydro-4,6-metano-benzo[d][1,3,2]dioxaborol-2-yl)ethyl)-4,5-dihydroisoxazol-5-carboxamide (0.40 g, 0.27 mmol) obtained in (1) above by the preparation method of Example 1-(4).

NMR: 1H NMR (400 MHz, METHANOL-d4) δ ppm 2.32-2.79 (2H, m), 2.88-3.03 (1H, m), 3.07-3.30 (3H, m), 3.37 (1H, m), 4.05-4.24 (2H, m), 4.25-4.42 (2H, m), 6.92 (1H, d), 7.00-7.44 (14H, m)

MS (m/z): 473[M+H], 455[M-OH]

Example 258: Preparation of ((1R)-1-(5-benzyl-3-((3-chlorophenoxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((3-chlorophenoxy)methyl)-4,5-dihydroisoxazol-5-carboxylate

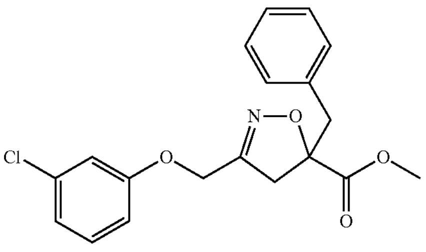 [SMILES: COC(=O)C1(Cc2ccccc2)CC(COc2cccc(Cl)c2)=NO1]

3-Chlorophenol (0.96 g, 7.5 mmol) was dissolved in tetrahydrofuran (38 ml), and at 0° C., sodium hydride (0.75 g, 18.8 mmol) was added thereto. After stirring at room temperature for 30 minutes, methyl 5-benzyl-3-(chloromethyl)-4,5-dihydroisoxazol-5-carboxylate (2.0 g, 7.5 mmol) obtained in Example 49-(2) was added thereto, and stirring was performed for 4 hours. After finishing the reaction, water was added, and extraction with diethyl ether was performed. An organic layer was washed with brine and dried over anhydrous magnesium sulfate. The filtrate was distilled under a reduced pressure and separated by column chromatography to obtain the title compound (2.34 g, 87%).

MS (m/z): 360[M+H]

(2) Preparation of 5-benzyl-3-((3-chlorophenoxy)methyl)-4,5-dihydroisoxazol-5-carboxylic acid

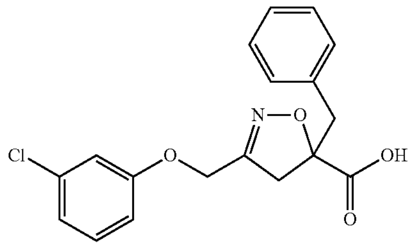 [SMILES: O=C(O)C1(Cc2ccccc2)CC(COc2cccc(Cl)c2)=NO1]

The title compound (2.2 g, 98%) was obtained using methyl 5-benzyl-3-((3-chlorophenoxy)methyl)-4,5-dihydroisoxazol-5-carboxylate (2.34 g, 6.5 mmol) obtained in (1) above by the preparation method of Example 84-(3).

MS (m/z): 346[M+H]

(3) Preparation of 5-benzyl-3-((3-chlorophenoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

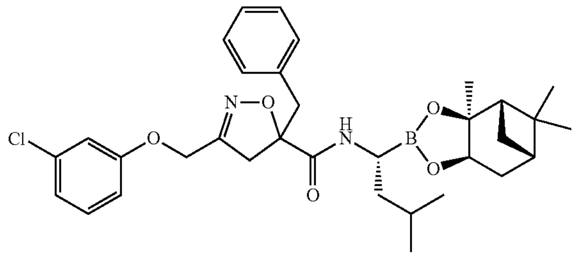 [SMILES: CC(C)C[C@H](NC(=O)C1(Cc2ccccc2)CC(COc2cccc(Cl)c2)=NO1)B1O[C@@H]2C[C@@H]3C[C@@H](C3(C)C)[C@]2(C)O1]

The title compound (0.9 g, 52%) was obtained using 5-benzyl-3-((3-chlorophenoxy)methyl)-4,5-dihydroisoxazol-5-carboxylic acid (1.0 g, 2.9 mmol) obtained in (2) above by the preparation method of Example 84-(4).

MS (m/z): 593[M+H]

(4) Preparation of ((1R)-1-(5-benzyl-3-((3-chlorophenoxy)methyl)-4,5-dihydroisoxazol-5-carboxamido)-3-methylbutylboronic acid

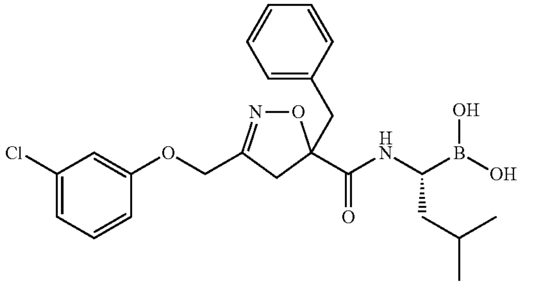 [SMILES: CC(C)C[C@H](NC(=O)C1(Cc2ccccc2)CC(COc2cccc(Cl)c2)=NO1)B(O)O]

The title compound (0.025 g, 4%) was obtained using 5-benzyl-3-((3-chlorophenoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.9 g, 1.5 mmol) obtained in (3) above by the preparation method of Example 1-(4).

NMR: 1H NMR (400 MHz, METHANOL-d4) δ ppm 0.79-0.85 (m, 6H), 1.03-1.50 (m, 3H), 2.67-2.75 (m, 1H), 3.18-3.26 (m, 2H), 3.35 (m, 1H), 3.44-3.50 (m, 1H), 4.79-4.81 (m, 2H), 6.86-6.97 (m, 3H), 7.22-7.27 (m, 6H)

MS (m/z): 459[M+H], 441[M-OH]

Example 259: Preparation of ((1R)-1-(5-benzyl-3-((3-chlorophenoxy)methyl)-4,5-dihydroisoxazol-5-carboxamido)-2-phenylethyl)boronic acid Through the processes (1) and (2) below, the title compound was obtained.

(1) Preparation of 5-benzyl-3-((3-chlorophenoxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

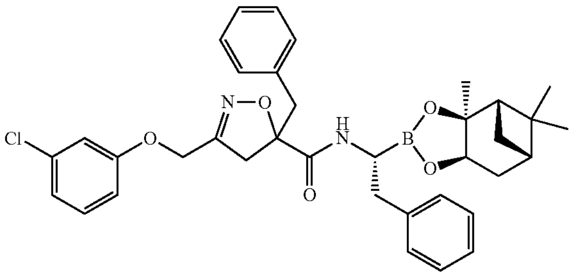 [SMILES: CC1(C)[C@@H]2C[C@H]3OB([C@H](Cc4ccccc4)NC(=O)C4(Cc5ccccc5)CC(COc5cccc(Cl)c5)=NO4)O[C@@]3(C)[C@H]1C2]

The title compound (0.75 g, 83%) was obtained using 5-benzyl-3-((3-chlorophenoxy)methyl)-4,5-dihydroisoxazol-5-carboxylic acid (0.50 g, 1.4 mmol) obtained in Example 258-(2) by the method of Example 255-(1).

MS (m/z): 627[M+H]

(2) Preparation of ((1R)-1-(5-benzyl-3-((3-chlorophenoxy)methyl)-4,5-dihydroisoxazol-5-carboxamido)-2-phenylethyl)boronic acid

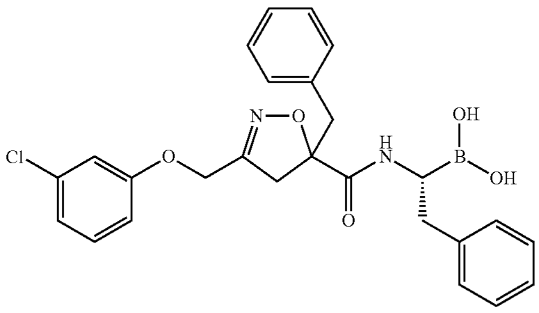 [SMILES: O=C(N[C@@H](Cc1ccccc1)B(O)O)C1(Cc2ccccc2)CC(COc2cccc(Cl)c2)=NO1]

The title compound (0.013 g, 2%) was obtained using 5-benzyl-3-((3-chlorophenoxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.75 g, 1.2 mmol) obtained in (1) above by the preparation method of Example 1-(4).

NMR: 1H NMR (400 MHz, METHANOL-d4) δ ppm 2.38 (br dd, 1H), 2.58-2.77 (m, 2H) 2.85-3.02 (m, 1H) 3.05-3.29 (m, 3H) 3.33-3.46 (m, 1H) 4.66-4.80 (m, 2H) 6.80-6.89 (m, 1H) 6.89-7.02 (m, 3H) 7.04-7.37 (m, 10H)

MS (m/z): 493[M+H], 475[M-OH]

Example 260: Preparation of ((1R)-1-(5-benzyl-3-(((3-chlorobenzyl)oxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-(((3-chlorobenzyl)oxy)methyl)-4,5-dihydroisoxazol-5-carboxylate

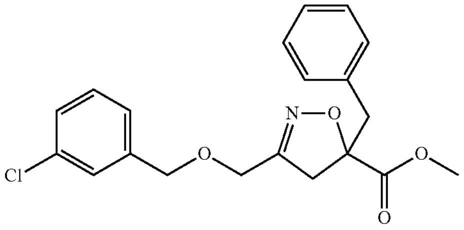 [SMILES: COC(=O)C1(Cc2ccccc2)CC(COCc2cccc(Cl)c2)=NO1]

The title compound (1.6 g, 57%) was obtained using methyl 5-benzyl-3-(chloromethyl)-4,5-dihydroisoxazol-5-carboxylate (2.0 g, 7.5 mmol) obtained in Example 49-(2) and (3-chlorophenyl)methanol (1.1 g, 7.5 mmol) by the preparation method of Example 49-(3).

MS (m/z): 374[M+H]

(2) Preparation of 5-benzyl-3-(((3-chlorobenzyl)oxy)methyl)-4,5-dihydroisoxazol-5-carboxylic acid

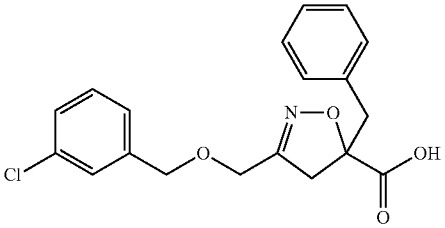 [SMILES: O=C(O)C1(Cc2ccccc2)CC(COCc2cccc(Cl)c2)=NO1]

The title compound (1.3 g, 3.6 mmol) was obtained using methyl 5-benzyl-3-(((3-chlorobenzyl)oxy)methyl)-4,5-dihydroisoxazol-5-carboxylate (1.6 g, 4.3 mmol) obtained in (1) above by the preparation method of Example 84-(3).

MS (m/z): 360[M+H]

(3) Preparation of 5-benzyl-3-(((3-chlorobenzyl)oxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

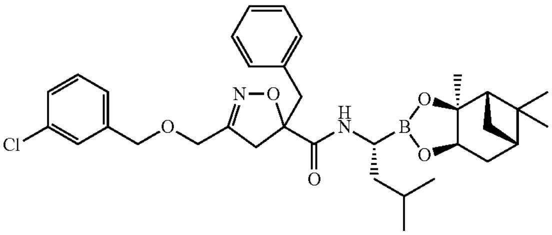 [SMILES: CC(C)C[C@H](NC(=O)C1(Cc2ccccc2)CC(COCc2cccc(Cl)c2)=NO1)B1O[C@@H]2C[C@@H]3C[C@@H](C3(C)C)[C@]2(C)O1]

The title compound (0.090 g, 31%) was obtained using 5-benzyl-3-(((3-chlorobenzyl)oxy)methyl)-4,5-dihydroisoxazol-5-carboxylic acid (0.17 g, 0.47 mmol) obtained in (2) above by the preparation method of Example 84-(4).

MS (m/z): 607[M+H]

(4) Preparation of ((1R)-1-(5-benzyl-3-(((3-chlorobenzyl)oxy)methyl)-4,5-dihydroisoxazol-5-carboxamido)-3-methylbutylboronic acid

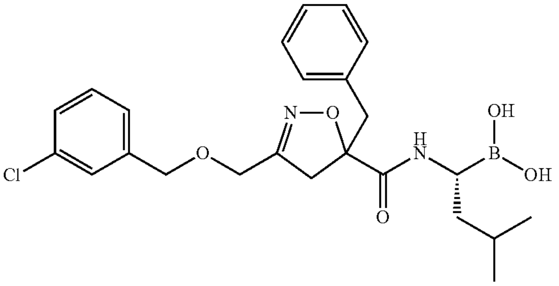 [SMILES: CC(C)C[C@H](NC(=O)C1(Cc2ccccc2)CC(COCc2cccc(Cl)c2)=NO1)B(O)O]

The title compound (0.011 g, 15%) was obtained using 5-benzyl-3-(((3-chlorobenzyl)oxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.090 g, 0.15 mmol) obtained in (3) above by the preparation method of Example 1-(4).

NMR: 1H NMR (400 MHz, METHANOL-d4) δ ppm 0.77-0.89 (6H, m), 1.04-1.25 (1H, m), 1.27-1.33 (1H, m), 1.37-1.57 (1H, m), 2.69-2.80 (1H, m), 3.17 (1H, d), 3.20 (1H, m), 3.32-3.38 (1H, m), 3.45 (1H, dd), 4.15-4.28 (2H, m), 4.29-4.41 (2H, m), 7.14-7.38 (9H, m)

MS (m/z): 473[M+H], 455[M-OH].

Example 261: Preparation of ((1R)-1-(5-benzyl-3-(((3-chlorobenzyl)oxy)methyl)-4,5-dihydroisoxazol-5-carboxamido)-2-phenylethyl)boronic acid Through the processes (1) and (2) below, the title compound was obtained.

(1) Preparation of 5-benzyl-3-(((3-chlorobenzyl)oxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

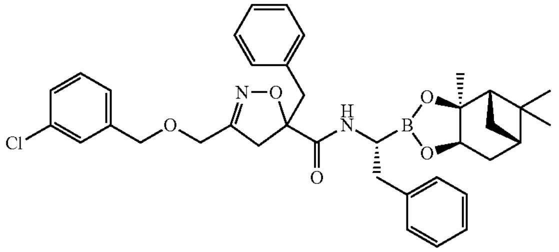 [SMILES: CC1(C)[C@@H]2C[C@H]3OB([C@H](Cc4ccccc4)NC(=O)C4(Cc5ccccc5)CC(COCc5cccc(Cl)c5)=NO4)O[C@@]3(C)[C@H]1C2]

5-Benzyl-3-(((3-chlorobenzyl)oxy)methyl)-4,5-dihydroisoxazol-5-carboxylic acid (0.50 g, 1.39 mmol) obtained in Example 260-(2), (R)-2-phenyl-1-((3aS,4S,6S,7aR)-3a,5,5-trimethylhexahydro-4,6-metanobenzo[d][1,3,2]dioxaborol-2-yl)ethan-1-amine hydrochloride (0.49 g, 1.46 mmol), and O-(benzotriazol-1-yl)-N,N,N',N'-tetramethyluronium tetrafluoroborate (0.49 g, 1.53 mmol) were dissolved at 0° C. in dichloromethane (4.4 ml). While maintaining 0° C., diisopropylethylamine (0.73 ml, 4.17 mmol) was slowly added thereto, followed by stirring for 18 hours, while raising to room temperature. A sodium bicarbonate aqueous solution (4 ml) was added to quench the reaction, an organic layer and an aqueous solution layer were separated, and the aqueous solution layer was extracted with dichloromethane twice. Organic layers were collected, washed with brine, dried over anhydrous magnesium sulfate, and filtered. The filtrate was distilled under a reduced pressure and separated by column chromatography to obtain the title compound (0.46 g, 52%).

MS (m/z): 641[M+H]

(2) Preparation of ((1R)-1-(5-benzyl-3-(((3-chlorobenzyl)oxy)methyl)-4,5-dihydroisoxazol-5-carboxamido)-2-phenylethyl)boronic acid

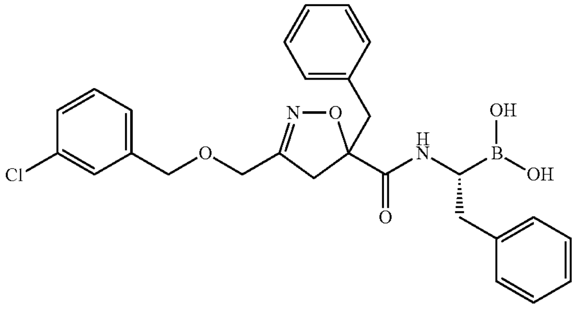 [SMILES: O=C(N[C@@H](Cc1ccccc1)B(O)O)C1(Cc2ccccc2)CC(COCc2cccc(Cl)c2)=NO1]

The title compound (0.144 g, 40%) was obtained using 5-benzyl-3-(((3-chlorobenzyl)oxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.46 g, 0.72 mmol) obtained in (1) above by the preparation method of Example 1-(4).

NMR: 1H NMR (400 MHz, METHANOL-d4) δ ppm 2.34-2.79 (2H, m), 2.89-3.04 (1H, m), 3.06-3.25 (2H, m), 3.37 (1H, m), 4.08-4.41 (4H, m), 6.93 (1H, br d), 7.05-7.39 (13H, m)

MS (m/z): 507[M+H], 489[M-OH]

Example 262: Preparation of ((1R)-1-(5-benzyl-3-((naphthalen-2-yloxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((naphthalen-2-yloxy)methyl)-4,5-dihydroisoxazol-5-carboxylate

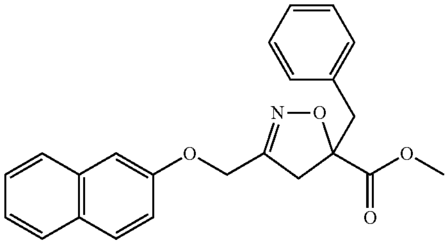 [SMILES: COC(=O)C1(Cc2ccccc2)CC(COc2ccc3ccccc3c2)=NO1]

The title compound (2.42 g, 86%) was obtained using methyl 5-benzyl-3-(chloromethyl)-4,5-dihydroisoxazol-5-carboxylate (2.0 g, 7.5 mmol) obtained in Example 49-(2) and naphthalen-2-ol (1.1 g, 7.5 mmol) by the preparation method of Example 254-(1).

MS (m/z): 376[M+H]

(2) Preparation of 5-benzyl-3-((naphthalen-2-yloxy)methyl)-4,5-dihydroisoxazol-5-carboxylic acid

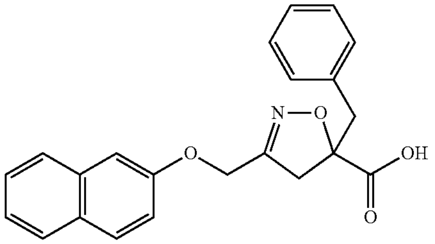 [SMILES: O=C(O)C1(Cc2ccccc2)CC(COc2ccc3ccccc3c2)=NO1]

The title compound (2.18 g, 6.0 mmol) was obtained using methyl 5-benzyl-3-((naphthalen-2-yloxy)methyl)-4,5-dihydroisoxazol-5-carboxylate (2.42 g, 6.4 mmol) obtained in (1) above by the preparation method of Example 84-(3).

MS (m/z): 362[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((naphthalen-2-yloxy)methyl)-4,5-dihydroisoxazol-5-carboxamide

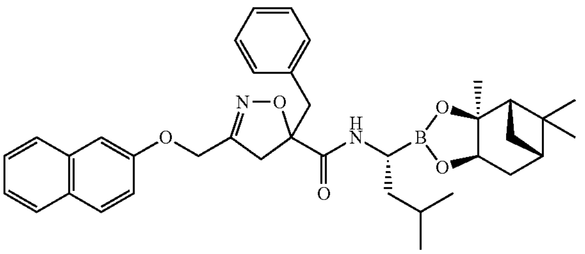 [SMILES: CC(C)C[C@H](NC(=O)C1(Cc2ccccc2)CC(COc2ccc3ccccc3c2)=NO1)B1O[C@@H]2C[C@@H]3C[C@@H](C3(C)C)[C@]2(C)O1]

The title compound (0.42 g, 50%) was obtained using 5-benzyl-3-((naphthalen-2-yloxy)methyl)-4,5-dihydroisoxazol-5-carboxylic acid (0.50 g, 1.38 mmol) obtained in (2) above by the preparation method of Example 254-(3).

MS (m/z): 609[M+H]

(4) Preparation of ((1R)-1-(5-benzyl-3-((naphthalen-2-yloxy)methyl)-4,5-dihydroisoxazol-5-carboxamido)-3-methylbutylboronic acid

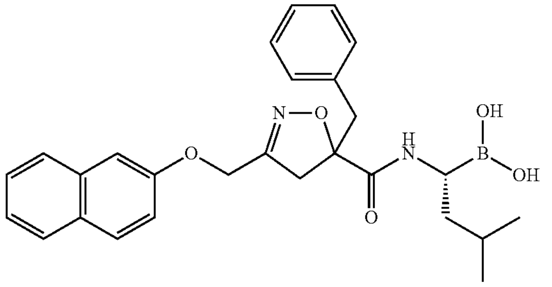 [SMILES: CC(C)C[C@H](NC(=O)C1(Cc2ccccc2)CC(COc2ccc3ccccc3c2)=NO1)B(O)O]

The title compound (0.096 g, 29%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((naphthalen-2-yloxy)methyl)-4,5-dihydroisoxazol-5-carboxamide (0.42 g, 0.69 mmol) obtained in (3) above by the preparation method of Example 1-(4).

NMR: 1H NMR (400 MHz, METHANOL-d4) δ ppm 0.72-0.85 (m, 6H), 0.98-1.18 (m, 1H), 1.16-1.24 (m, 1H), 1.31-1.49 (m, 1H), 2.56 (t, 0.5H), 2.69 (t, 0.5H), 3.12-3.22 (m, 1H), 3.35 (m, 2H), 3.44-3.57 (m, 1H), 4.89-5.00 (m, 2H), 7.07-7.30 (m, 5H), 7.30-7.38 (m, 1H), 7.43 (t, 1H), 7.70-7.80 (m, 3H)

MS (m/z): 475[M+H], 457[M-OH]

Example 263: Preparation of ((1R)-1-(5-benzyl-3-((naphthalen-2-yloxy)methyl)-4,5-dihydroisoxazol-5-carboxamido)-2-phenylethyl)boronic acid Through the processes (1) and (2) below, the title compound was obtained.

(1) Preparation of 5-benzyl-3-((naphthalen-2-yloxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

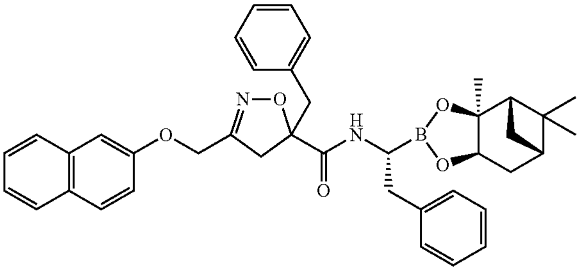 [SMILES: CC1(C)[C@@H]2C[C@H]3OB([C@H](Cc4ccccc4)NC(=O)C4(Cc5ccccc5)CC(COc5ccc6ccccc6c5)=NO4)O[C@@]3(C)[C@H]1C2]

The title compound (0.56 g, 63%) was obtained using 5-benzyl-3-((naphthalen-2-yloxy)methyl)-4,5-dihydroisoxazol-5-carboxylic acid (0.50 g, 1.38 mmol) obtained in Example 262-(2) by the preparation method of Example 255-(1).

MS (m/z): 643[M+H]

(2) Preparation of ((1R)-1-(5-benzyl-3-((naphthalen-2-yloxy)methyl)-4,5-dihydroisoxazol-5-carboxamido)-2-phenylethyl)boronic acid

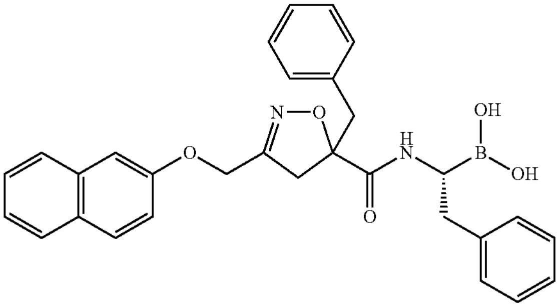 [SMILES: O=C(N[C@@H](Cc1ccccc1)B(O)O)C1(Cc2ccccc2)CC(COc2ccc3ccccc3c2)=NO1]

The title compound (0.099 g, 22%) was obtained using 5-benzyl-3-((naphthalen-2-yloxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.56 g, 0.87 mmol) obtained in (1) above by the preparation method of Example 1-(4).

NMR: 1H NMR (400 MHz, METHANOL-d4) δ ppm 1.93-2.42 (m, 1H), 2.52-2.68 (m, 2H), 2.68-2.80 (m, 0.5H), 2.85-2.95 (m, 0.5H), 3.10-3.18 (m, 1H), 3.23-3.29 (m, 1H), 3.38-3.50 (m, 1H), 4.62 (s, 1H), 6.88 (br d, 1H), 7.04-7.07 (br d, 1H), 7.09-7.30 (m, 10H), 7.31-7.37 (t, 1H), 7.40-7.46 (t, 1H), 7.67-7.84 (m, 3H)

MS (m/z): 509[M+H], 491[M-OH]

Example 264: Preparation of ((1R)-1-(5-benzyl-3-(((3-cyanobenzyl)oxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-(((3-cyanobenzyl)oxy)methyl)-4,5-dihydroisoxazol-5-carboxylate

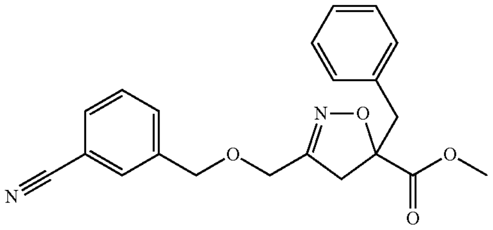 [SMILES: COC(=O)C1(Cc2ccccc2)CC(COCc2cccc(C#N)c2)=NO1]

The title compound (1.56 g, 57%) was obtained using methyl 5-benzyl-3-(chloromethyl)-4,5-dihydroisoxazol-5-carboxylate (2.0 g, 7.5 mmol) obtained in Example 49-(2) and 3-(hydroxymethyl)benzonitrile (0.99 g, 7.5 mmol) by the preparation method of Example 258-(1).

MS (m/z): 365[M+H]

(2) Preparation of 5-benzyl-3-(((3-cyanobenzyl)oxy)methyl)-4,5-dihydroisoxazol-5-carboxylic acid

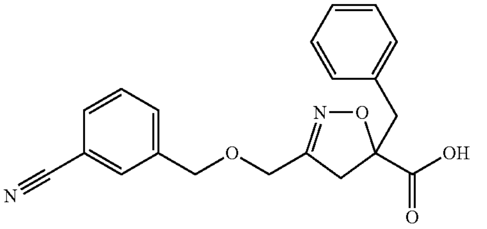 [SMILES: N#Cc1cccc(COCC2=NOC(Cc3ccccc3)(C(=O)O)C2)c1]

The title compound (1.39 g, 93%) was obtained using methyl 5-benzyl-3-(((3-cyanobenzyl)oxy)methyl)-4,5-dihydroisoxazol-5-carboxylate (1.56 g, 4.28 mmol) obtained in (1) above by the preparation method of Example 84-(3).

MS (m/z): 351[M+H]

(3) Preparation of 5-benzyl-3-(((3-cyanobenzyl)oxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

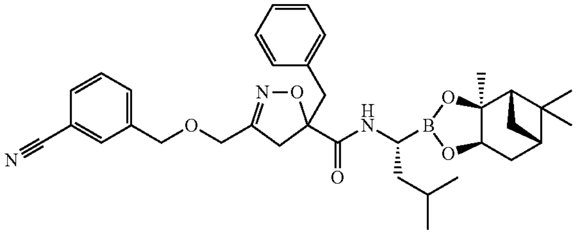 [SMILES: CC(C)C[C@H](NC(=O)C1(Cc2ccccc2)CC(COCc2cccc(C#N)c2)=NO1)B1O[C@@H]2C[C@@H]3C[C@@H](C3(C)C)[C@]2(C)O1]

The title compound (0.210 g, 18%) was obtained using 5-benzyl-3-(((3-cyanobenzyl)oxy)methyl)-4,5-dihydroisoxazol-5-carboxylic acid (0.70 g, 2.0 mmol) obtained in (2) above by the method of Example 254-(3).

MS (m/z): 598[M+H]

(4) Preparation of ((1R)-1-(5-benzyl-3-(((3-cyanobenzyl)oxy)methyl)-4,5-dihydroisoxazol-5-carboxamido)-3-methylbutylboronic acid

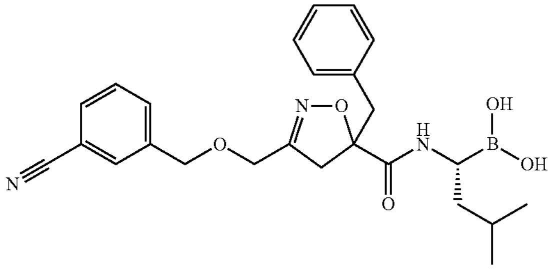 [SMILES: CC(C)C[C@H](NC(=O)C1(Cc2ccccc2)CC(COCc2cccc(C#N)c2)=NO1)B(O)O]

The title compounds of Isomer 1 having low polarity and Isomer 2 having high polarity (0.014 g, 8%) were obtained using 5-benzyl-3-(((3-cyanobenzyl)oxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.21 g, 0.35 mmol) obtained in (3) above by the preparation method of Example 1-(4).

Isomer 1

NMR: 1H NMR (400 MHz, METHANOL-d4) δ ppm 0.79-0.86 (6H, m), 1.05-1.26 (1H, m), 1.28-1.37 (1H, m), 1.39-1.57 (1H, m), 2.68-2.81 (1H, m), 3.18 (1H, m), 3.21 (1H, m), 3.32-3.38 (1H, m), 3.41-3.51 (1H, dd), 4.17-4.30 (2H, m), 4.31-4.49 (2H, m), 7.20-7.33 (5H, m), 7.46-7.72 (4H, m)

MS (m/z): 464[M+H], 446[M-OH]

Isomer 2

NMR: 1H NMR (400 MHz, METHANOL-d4) δ ppm 0.82 (6H, dd), 1.05-1.17 (1H, m), 1.17-1.26 (1H, m), 1.36-1.51 (1H, m), 2.73 (1H, t), 3.08-3.28 (2H, m), 3.35 (1H, m), 3.46 (1H, d), 4.18-4.31 (2H, m), 4.34-4.48 (2H, m), 7.20-7.31 (5H, m), 7.48-7.71 (4H, m)

MS (m/z): 464[M+H], 446[M-OH]

Example 265: Preparation of ((1R)-1-(5-benzyl-3-(((3-cyanobenzyl)oxy)methyl)-4,5-dihydroisoxazol-5-carboxamido)-2-phenylethyl)boronic acid Through the processes (1) and (2) below, the title compound was obtained.

(1) Preparation of 5-benzyl-3-(((3-cyanobenzyl)oxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

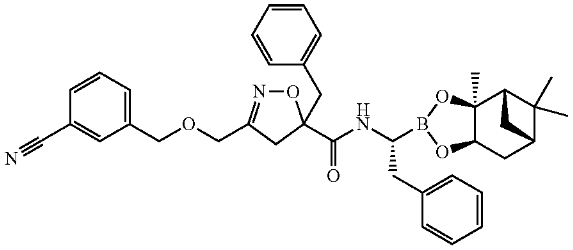 [SMILES: CC1(C)[C@@H]2C[C@H]3OB([C@H](Cc4ccccc4)NC(=O)C4(Cc5ccccc5)CC(COCc5cccc(C#N)c5)=NO4)O[C@@]3(C)[C@H]1C2]

The title compound (0.255 g, 28%) was obtained using 5-benzyl-3-(((3-cyanobenzyl)oxy)methyl)-4,5-dihydroisoxazol-5-carboxylic acid (0.50 g, 1.4 mmol) obtained in Example 264-(2) by the method of Example 261-(1).

MS (m/z): 632[M+H]

(2) Preparation of ((1R)-1-(5-benzyl-3-(((3-cyanobenzyl)oxy)methyl)-4,5-dihydroisoxazol-5-carboxamido)-2-phenylethyl)boronic acid

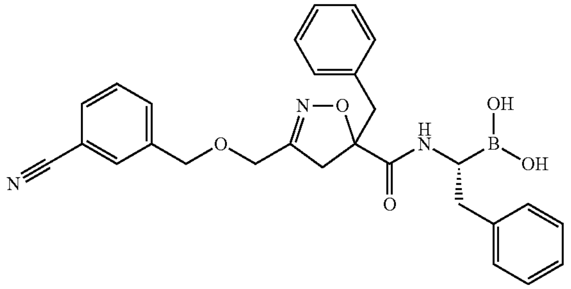 [SMILES: N#Cc1cccc(COCC2=NOC(Cc3ccccc3)(C(=O)N[C@@H](Cc3ccccc3)B(O)O)C2)c1]

The title compound (0.065 g, 33%) was obtained using 5-benzyl-3-(((3-cyanobenzyl)oxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.255 g, 0.40 mmol) obtained in (1) above by the preparation method of Example 1-(4).

NMR: 1H NMR (400 MHz, METHANOL-d4) δ ppm 2.33-2.75 (m, 2H), 2.87-3.04 (m, 1H), 3.06-3.30 (m, 3H), 3.34 (m, 1H), 4.10-4.45 (m, 4H), 6.94 (br d, 1H), 7.02-7.40 (m, 9H), 7.42-7.74 (m, 4H)

MS (m/z): 498[M+H], 480[M-OH]

Example 266: Preparation of ((1R)-1-(5-benzyl-3-((imidazo[1,2-a]pyridin-8-ylmethoxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((imidazo[1,2-a]pyridin-8-ylmethoxy)methyl)-4,5-dihydroisoxazol-5-carboxylate

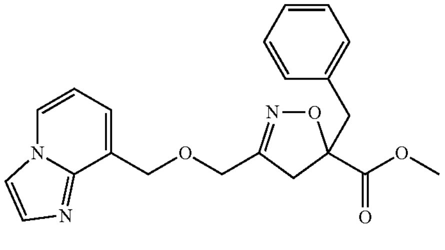 [SMILES: COC(=O)C1(Cc2ccccc2)CC(COCc2cccn3ccnc23)=NO1]

The title compound (1.64 g, 58%) was obtained using methyl 5-benzyl-3-(chloromethyl)-4,5-dihydroisoxazol-5-carboxylate (2.0 g, 7.5 mmol) obtained in Example 49-(2) and imidazo[1,2-a]pyridin-8-ylmethanol (1.11 g, 7.5 mmol) by the preparation method of Example 258-(1).

MS (m/z): 380[M+H]

(2) Preparation of 5-benzyl-3-((imidazo[1,2-a]pyridin-8-ylmethoxy)methyl)-4,5-dihydroisoxazol-5-carboxylic acid

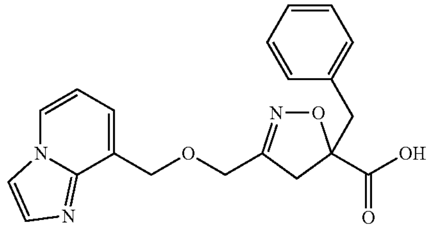 [SMILES: O=C(O)C1(Cc2ccccc2)CC(COCc2cccn3ccnc23)=NO1]

The title compound (1.4 g, 89%) was obtained using methyl 5-benzyl-3-((imidazo[1,2-a]pyridin-8-ylmethoxy)methyl)-4,5-dihydroisoxazol-5-carboxylate (1.64 g, 4.3 mmol) obtained in (1) above by the preparation method of Example 84-(3).

MS (m/z): 366[M+H]

(3) Preparation of 5-benzyl-3-((imidazo[1,2-a]pyridin-8-ylmethoxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

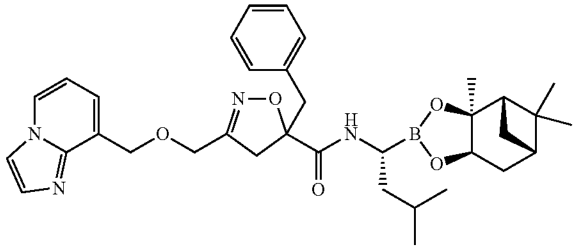 [SMILES: CC(C)C[C@H](NC(=O)C1(Cc2ccccc2)CC(COCc2cccn3ccnc23)=NO1)B1O[C@@H]2C[C@@H]3C[C@@H](C3(C)C)[C@]2(C)O1]

The title compound (0.23 g, 39%) was obtained using 5-benzyl-3-((imidazo[1,2-a]pyridin-8-ylmethoxy)methyl)-4,5-dihydroisoxazol-5-carboxylic acid (0.35 g, 0.96 mmol) obtained in (2) above by the method of Example 256-(3).

MS (m/z): 613[M+H]

(4) Preparation of ((1R)-1-(5-benzyl-3-((imidazo[1,2-a]pyridin-8-ylmethoxy)methyl)-4,5-dihydroisoxazol-5-carboxamido)-3-methylbutylboronic acid

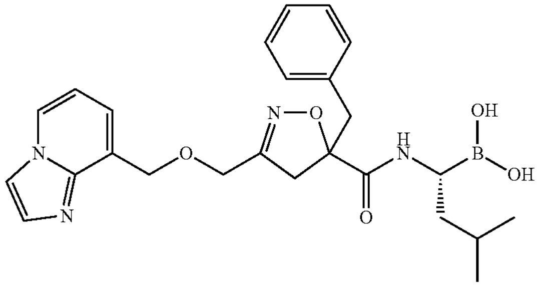 [SMILES: CC(C)C[C@H](NC(=O)C1(Cc2ccccc2)CC(COCc2cccn3ccnc23)=NO1)B(O)O]

The title compound (0.030 g, 15%) was obtained using 5-benzyl-3-((imidazo[1,2-a]pyridin-8-ylmethoxy)methyl)-N—((R)-3-methyl-1-((3aS,4S,6S,7aR)-3a,5,5-trimethyl-hexahydro-4,6-metanobenzo[d][1,3,2]dioxaborol-2-yl)butyl)-4,5-dihydroisoxazol-5-carboxamide (0.26 g, 0.42 mmol) obtained in (3) above by the preparation method of Example 1-(4).

NMR: 1H NMR (400 MHz, METHANOL-d4) δ ppm 0.77-0.82 (m, 6H), 1.23-1.43 (m, 3H), 2.68-2.75 (m, 1H), 3.14-3.29 (m, 2H), 3.34-3.48 (m, 2H), 4.33-4.36 (m, 2H), 4.71-4.77 (m, 2H), 6.92-6.94 (m, 1H), 7.17-7.29 (m, 6H), 7.56-7.61 (m, 1H), 7.87 (s, 1H), 8.39-8.41 (d, 1H)

MS (m/z): 479[M+H], 461[M-OH]

Example 267: Preparation of ((1R)-1-(5-benzyl-3-((imidazo[1,2-a]pyridin-8-ylmethoxy)methyl)-4,5-dihydroisoxazol-5-carboxamido)-2-phenylethyl) boronic acid Through the processes (1) and (2) below, the title compound was obtained.

(1) Preparation of 5-benzyl-3-((imidazo[1,2-a]pyridin-8-ylmethoxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

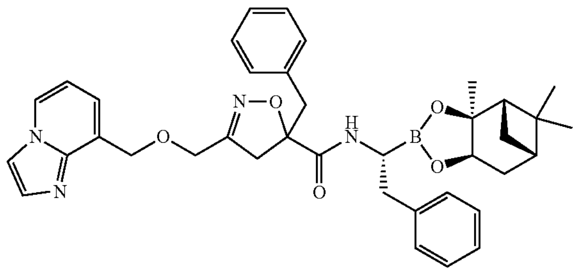 [SMILES: CC1(C)[C@@H]2C[C@H]3OB([C@H](Cc4ccccc4)NC(=O)C4(Cc5ccccc5)CC(COCc5cccn6ccnc56)=NO4)O[C@@]3(C)[C@H]1C2]

The title compound (0.7 g, 40%) was obtained using 5-benzyl-3-((imidazo[1,2-a]pyridin-8-ylmethoxy)methyl)-4,5-dihydroisoxazol-5-carboxylic acid (1.0 g, 2.7 mmol) obtained in Example 266-(2) by the method of Example 261-(1).

MS (m/z): 647[M+H]

(2) Preparation of ((1R)-1-(5-benzyl-3-((imidazo[1,2-a]pyridin-8-ylmethoxy)methyl)-4,5-dihydroisoxazol-5-carboxamido)-2-phenylethyl)boronic acid

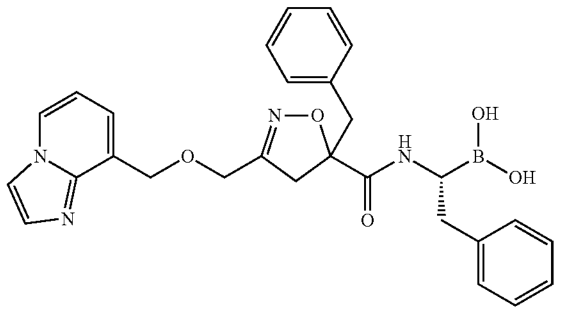 [SMILES: O=C(N[C@@H](Cc1ccccc1)B(O)O)C1(Cc2ccccc2)CC(COCc2cccn3ccnc23)=NO1]

The title compound (0.021 g, 3%) was obtained using 5-benzyl-3-((imidazo[1,2-a]pyridin-8-ylmethoxy)methyl)-N—((R)-2-phenyl-1-((3aS,4S,6S,7aR)-3a,5,5-trimethyl-hexahydro-4,6-metanobenzo[d][1,3,2]dioxaborol-2-yl)ethyl)-4,5-dihydroisoxazol-5-carboxamide (0.79 g, 1.2 mmol) obtained in (1) above by the preparation method of Example 1-(4).

NMR: 1H NMR (400 MHz, METHANOL-d4) δ ppm 2.34-2.71 (m, 2H), 2.91-2.99 (m, 1H), 3.10-3.26 (m, 2H), 3.35-3.48 (m, 2H), 4.28-4.37 (m, 2H), 4.71-4.76 (m, 2H), 6.90-6.95 (m, 2H), 7.07-7.30 (m, 11H), 7.56-7.57 (dd, 1H), 7.86-7.87 (dd, 1H), 8.39-8.41 (dd, 1H)

MS (m/z): 513[M+H], 495[M-OH]

Example 268: Preparation of ((1R)-1-(5-benzyl-3-((pyridin-2-ylmethoxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((pyridin-2-ylmethoxy)methyl)-4,5-dihydroisoxazol-5-carboxylate

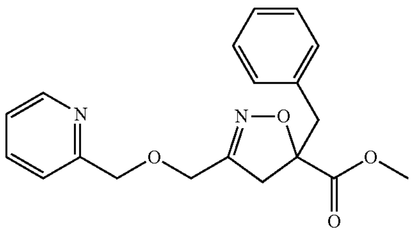 [SMILES: COC(=O)C1(Cc2ccccc2)CC(COCc2ccccn2)=NO1]

The title compound (1.32 g, 52%) was obtained using methyl 5-benzyl-3-(chloromethyl)-4,5-dihydroisoxazol-5-carboxylate (2.0 g, 7.5 mmol) obtained in Example 49-(2) and pyridin-2-ylmethanol (0.72 ml, 7.5 mmol) by the preparation method of Example 49-(3).

MS (m/z): 341[M+H]

(2) Preparation of 5-benzyl-3-((pyridin-2-ylmethoxy)methyl)-4,5-dihydroisoxazol-5-carboxylic acid

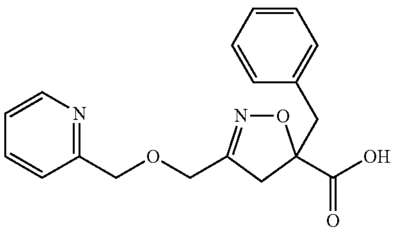 [SMILES: O=C(O)C1(Cc2ccccc2)CC(COCc2ccccn2)=NO1]

The title compound (0.83 g, 66%) was obtained using methyl 5-benzyl-3-((pyridin-2-ylmethoxy)methyl)-4,5-dihydroisoxazol-5-carboxylate (1.32 g, 3.9 mmol) obtained in (1) above by the preparation method of Example 84-(3).

MS (m/z): 327[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((pyridin-2-ylmethoxy)methyl)-4,5-dihydroisoxazol-5-carboxamide

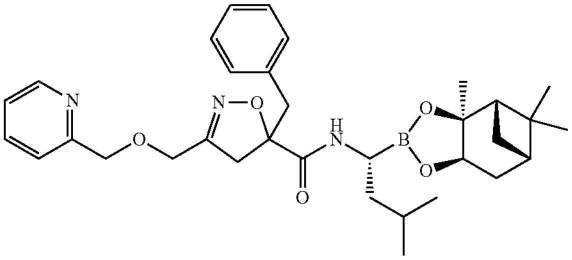 [SMILES: CC(C)C[C@H](NC(=O)C1(Cc2ccccc2)CC(COCc2ccccn2)=NO1)B1O[C@@H]2C[C@@H]3C[C@@H](C3(C)C)[C@]2(C)O1]

The title compound (0.33 g, 47%) was obtained using 5-benzyl-3-((pyridin-2-ylmethoxy)methyl)-4,5-dihydroisoxazol-5-carboxylic acid (0.40 g, 1.2 mmol) obtained in (2) above by the method of Example 256-(3).

MS (m/z): 574[M+H]

(4) Preparation of ((1R)-1-(5-benzyl-3-((pyridin-2-ylmethoxy)methyl)-4,5-dihydroisoxazol-5-carboxamido)-3-methylbutylboronic acid

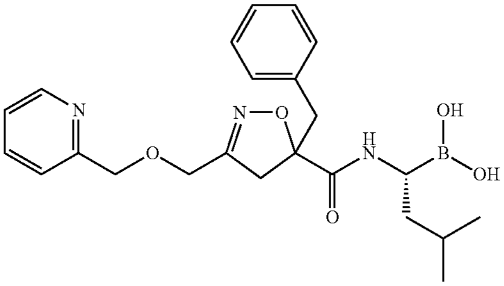 [SMILES: CC(C)C[C@H](NC(=O)C1(Cc2ccccc2)CC(COCc2ccccn2)=NO1)B(O)O]

The title compound (0.079 g, 31%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((pyridin-2-ylmethoxy)methyl)-4,5-dihydroisoxazol-5-carboxamide (0.33 g, 0.58 mmol) obtained in (3) above by the preparation method of Example 1-(4).

NMR: 1H NMR (400 MHz, METHANOL-d4) δ ppm 0.74-0.87 (6H, m), 1.03-1.34 (2H, m), 1.42 (1H, m), 2.66-2.92 (1H, m), 3.13-3.30 (2H, m), 3.31-3.37 (1H, m), 3.40-3.56 (1H, m), 4.22-4.37 (2H, m), 4.40-4.57 (2H, m), 7.16-7.31 (5H, m), 7.31-7.37 (1H, m), 7.44 (1H, dd), 7.84 (1H, tt), 8.49 (1H, d)

MS (m/z): 440[M+H], 422[M-OH]

Example 269: Preparation of ((1R)-1-(5-benzyl-3-((pyridin-2-ylmethoxy)methyl)-4,5-dihydroisoxazol-5-carboxamido)-2-phenylethyl)boronic acid Through the processes (1) and (2) below, the title compound was obtained.

(1) Preparation of 5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-3-((pyridin-2-ylmethoxy)methyl)-4,5-dihydroisoxazol-5-carboxamide

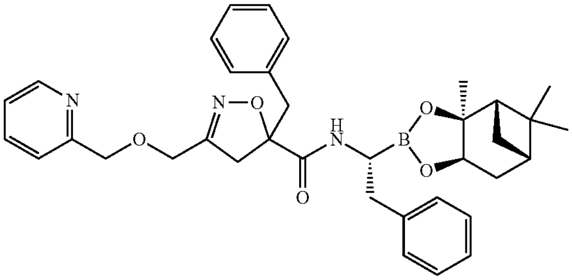 [SMILES: CC1(C)[C@@H]2C[C@H]3OB([C@H](Cc4ccccc4)NC(=O)C4(Cc5ccccc5)CC(COCc5ccccn5)=NO4)O[C@@]3(C)[C@H]1C2]

The title compound (0.39 g, 52%) was obtained using 5-benzyl-3-((pyridin-2-ylmethoxy)methyl)-4,5-dihydroisoxazol-5-carboxylic acid (0.40 g, 1.2 mmol) obtained in Example 268-(2) by the method of Example 255-(1).

MS (m/z): 608[M+H]

(2) Preparation of ((1R)-1-(5-benzyl-3-((pyridin-2-ylmethoxy)methyl)-4,5-dihydroisoxazol-5-carboxamido)-2-phenylethyl)boronic acid

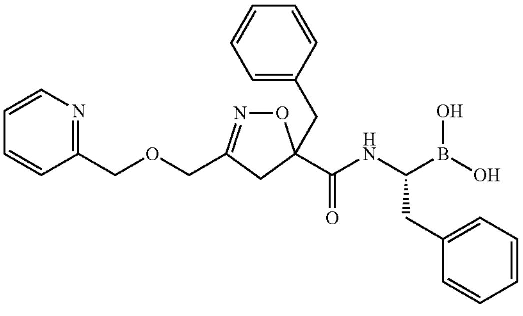 [SMILES: O=C(N[C@@H](Cc1ccccc1)B(O)O)C1(Cc2ccccc2)CC(COCc2ccccn2)=NO1]

The title compound (0.086 g, 28%) was obtained using 5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-3-((pyridin-2-ylmethoxy)methyl)-4,5-dihydroisoxazol-5-carboxamide (0.39 g, 0.64 mmol) obtained in (3) above by the preparation method of Example 1-(4).

NMR: 1H NMR (400 MHz, METHANOL-d4) δ ppm 2.36-2.84 (2H, m), 2.94-3.17 (2H, m), 3.18-3.29 (1H, m), 3.31-3.51 (2H, m), 4.20-4.35 (2H, m), 4.37-4.58 (2H, m), 6.94 (1H, d), 7.07-7.35 (10H, m), 7.44 (1H, d), 7.76-7.89 (1H, m), 8.43-8.54 (1H, m)

MS (m/z): 474[M+H], 456[M-OH]

Example 270: Preparation of ((1R)-1-(5-benzyl-3-(((3-methylbenzyl)oxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-(((3-methylbenzyl)oxy)methyl)-4,5-dihydroisoxazol-5-carboxylate

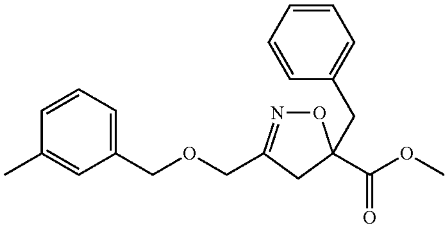

The title compound (1.77 g, 67%) was obtained using methyl 5-benzyl-3-(chloromethyl)-4,5-dihydroisoxazol-5-carboxylate (2.0 g, 7.5 mmol) obtained in Example 49-(2) and 3-methylbenzyl alcohol (0.90 ml, 7.5 mmol) by the preparation method of Example 49-(3).

MS (m/z): 354[M+H]

(2) Preparation of 5-benzyl-3-(((3-methylbenzyl)oxy)methyl)-4,5-dihydroisoxazol-5-carboxylic acid

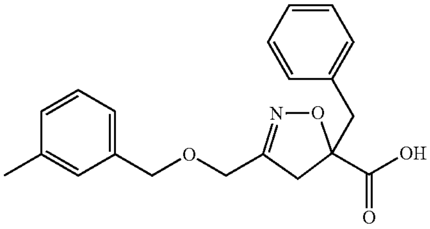 [SMILES: Cc1cccc(COCC2=NOC(Cc3ccccc3)(C(=O)O)C2)c1]

The title compound (0.90 g, 53%) was obtained using methyl 5-benzyl-3-(((3-methylbenzyl)oxy)methyl)-4,5-dihydroisoxazol-5-carboxylate (1.77 g, 5.0 mmol) obtained in (1) above by the preparation method of Example 84-(3).

MS (m/z): 340[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((3-methylbenzyl)oxy)methyl)-4,5-dihydroisoxazol-5-carboxamide

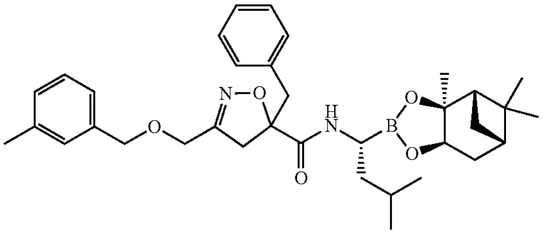

The title compound (0.25 g, 48%) was obtained using 5-benzyl-3-(((3-methylbenzyl)oxy)methyl)-4,5-dihydroisoxazol-5-carboxylic acid (0.30 g, 0.88 mmol) obtained in (2) above by the method of Example 256-(3).

MS (m/z): 587[M+H]

(4) Preparation of ((1R)-1-(5-benzyl-3-(((3-methylbenzyl)oxy)methyl)-4,5-dihydroisoxazol-5-carboxamido)-3-methylbutylboronic acid

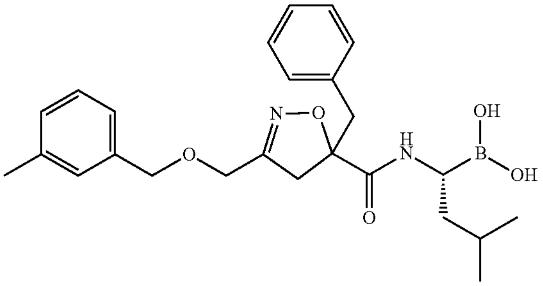 [SMILES: Cc1cccc(COCC2=NOC(Cc3ccccc3)(C(=O)N[C@@H](CC(C)C)B(O)O)C2)c1]

The title compound (0.0094 g, 5%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((3-methylbenzyl)oxy)methyl)-4,5-dihydroisoxazol-5-carboxamide (0.25 g, 0.43 mmol) obtained in (3) above by the preparation method of Example 1-(4).

NMR: 1H NMR (400 MHz, METHANOL-d4) δ ppm 0.76-0.90 (m, 6H) 1.14-1.47 (m, 3H) 2.28-2.44 (m, 3H) 2.61-2.78 (m, 1H) 3.10-3.25 (m, 2H) 3.34-3.56 (m, 2H) 4.11-4.40 (m, 4H) 7.03-7.34 (m, 9H)

MS (m/z): 453[M+H], 435[M-OH]

Example 271: Preparation of ((1R)-1-(5-benzyl-3-(((3-methylbenzyl)oxy)methyl)-4,5-dihydroisoxazol-5-carboxamido)-2-phenylethyl)boronic acid Through the processes (1) and (2) below, the title compound was obtained.

(1) Preparation of 5-benzyl-3-(((3-methylbenzyl)oxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

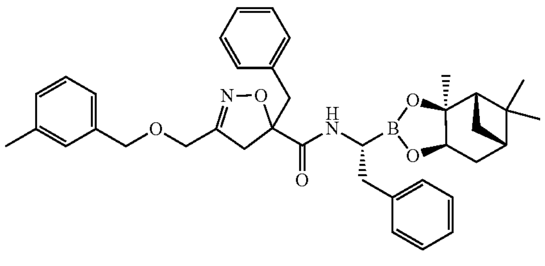

The title compound (0.21 g, 38%) was obtained using 5-benzyl-3-(((3-methylbenzyl)oxy)methyl)-4,5-dihydroisoxazol-5-carboxylic acid (0.30 g, 0.88 mmol) obtained in Example 270-(2) by the method of Example 261-(1).

MS (m/z): 621[M+H]

(2) Preparation of ((1R)-1-(5-benzyl-3-(((3-methylbenzyl)oxy)methyl)-4,5-dihydroisoxazol-5-carboxamido)-2-phenylethyl)boronic acid

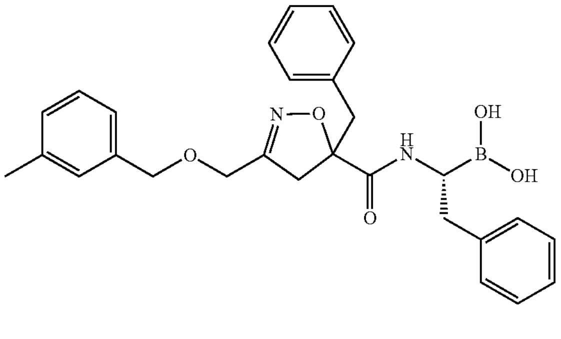 [SMILES: Cc1cccc(COCC2=NOC(Cc3ccccc3)(C(=O)N[C@@H](Cc3ccccc3)B(O)O)C2)c1]

The title compound (0.024 g, 15%) was obtained using 5-benzyl-3-(((3-methylbenzyl)oxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.21 g, 0.34 mmol) obtained in (1) above by the preparation method of Example 1-(4).

NMR: 1H NMR (400 MHz, METHANOL-d4) δ ppm 2.33 (d, 3H) 2.60-2.84 (m, 2H) 2.88-2.99 (m, 1H) 3.06-3.24 (m, 3H) 4.08-4.21 (m, 2H) 4.26-4.38 (m, 2H) 6.83-7.40 (m, 15H)

MS (m/z): 487[M+H], 469[M-OH]

Example 272: Preparation of ((1R)-1-(5-benzyl-3-(((3-methoxybenzyl)oxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-(((3-methoxybenzyl)oxy)methyl)-4,5-dihydroisoxazol-5-carboxylate

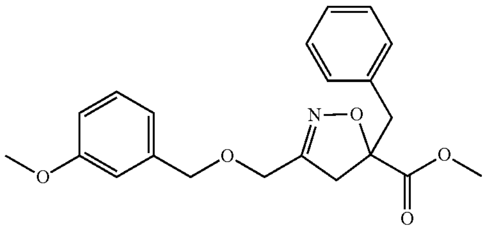

The title compound (2.25 g, 82%) was obtained using methyl 5-benzyl-3-(chloromethyl)-4,5-dihydroisoxazol-5-carboxylate (2.0 g, 7.5 mmol) obtained in Example 49-(2) and (3-methoxybenzyl)methanol (1.03 g, 7.5 mmol) by the preparation method of Example 49-(3).

MS (m/z): 370[M+H]

(2) Preparation of 5-benzyl-3-(((3-methoxybenzyl)oxy)methyl)-4,5-dihydroisoxazol-5-carboxylic acid

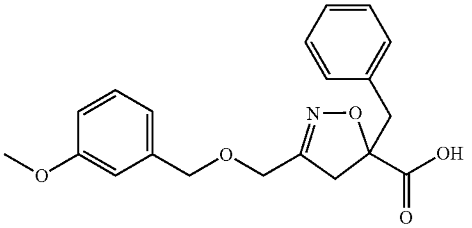 [SMILES: COc1cccc(COCC2=NOC(Cc3ccccc3)(C(=O)O)C2)c1]

The title compound (1.45 g, 75%) was obtained using methyl 5-benzyl-3-(((3-methoxybenzyl)oxy)methyl)-4,5-dihydroisoxazol-5-carboxylate (2.0 g, 5.4 mmol) obtained in (1) above by the preparation method of Example 84-(3).

MS (m/z): 356[M+H]

(3) Preparation of 5-benzyl-3-(((3-methoxybenzyl)oxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

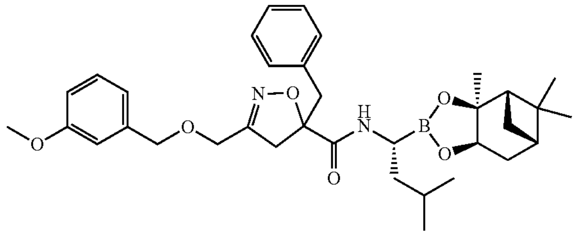

The title compound (0.35 g, 41%) was obtained using 5-benzyl-3-(((3-methoxybenzyl)oxy)methyl)-4,5-dihydroisoxazol-5-carboxylic acid (0.50 g, 1.4 mmol) obtained in (2) above by the method of Example 254-(3).

MS (m/z): 603[M+H]

(4) Preparation of ((1R)-1-(5-benzyl-3-(((3-methoxybenzyl)oxy)methyl)-4,5-dihydroisoxazol-5-carboxamido)-3-methylbutylboronic acid

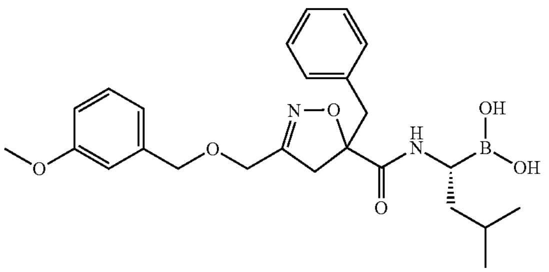 [SMILES: COc1cccc(COCC2=NOC(Cc3ccccc3)(C(=O)N[C@@H](CC(C)C)B(O)O)C2)c1]

The title compound (0.028 g, 10%) was obtained using 5-benzyl-3-(((3-methoxybenzyl)oxy)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.35 g, 0.58 mmol) obtained in (1) above by the preparation method of Example 1-(4).

NMR: 1H NMR (400 MHz, METHANOL-d4) δ ppm 0.73-0.92 (6H, m), 1.07-1.33 (2H, m), 1.35-1.59 (1H, m), 2.64-2.89 (1H, m), 2.95-3.30 (3H, m), 3.43 (1H, m), 3.77 (3H, s), 4.05-4.24 (2H, m), 4.25-4.42 (2H, m), 6.84 (3H, m), 7.17-7.35 (6H, m)

MS (m/z): 469[M+H], 451[M-OH]

Example 273: Preparation of ((1R)-1-(5-benzyl-3-(((3-methoxybenzyl)oxy)methyl)-4,5-dihydroisoxazol-5-carboxamido)-2-phenylethyl)boronic acid Through the processes (1) and (2) below, the title compound was obtained.

(1) Preparation of 5-benzyl-3-(((3-methoxybenzyl)oxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

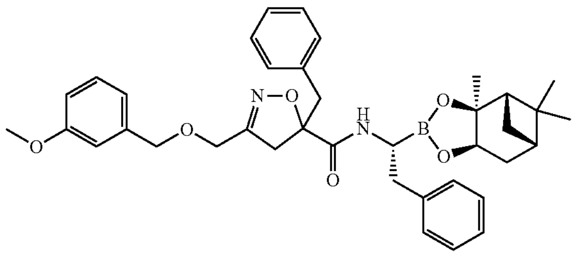

The title compound (0.45 g, 50%) was obtained using 5-benzyl-3-(((3-methoxybenzyl)oxy)methyl)-4,5-dihydroisoxazol-5-carboxylic acid (0.50 g, 1.4 mmol) obtained in Example 272-(2) by the method of Example 261-(1).

MS (m/z): 637[M+H]

(2) Preparation of ((1R)-1-(5-benzyl-3-(((3-methoxybenzyl)oxy)methyl)-4,5-dihydroisoxazol-5-carboxamido)-2-phenylethyl)boronic acid

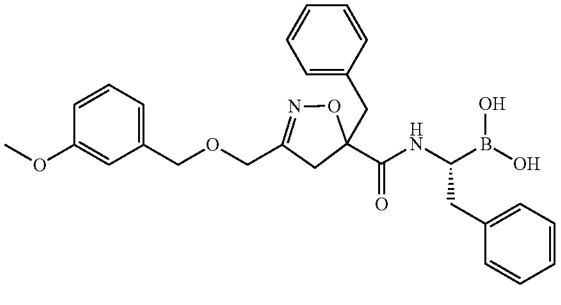 [SMILES: COc1cccc(COCC2=NOC(Cc3ccccc3)(C(=O)N[C@@H](Cc3ccccc3)B(O)O)C2)c1]

The title compound (0.10 g, 28%) was obtained using 5-benzyl-3-(((3-methoxybenzyl)oxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.45 g, 0.71 mmol) obtained in (1) above by the preparation method of Example 1-(4).

NMR: 1H NMR (400 MHz, METHANOL-d4) δ ppm 2.33-2.78 (2H, m), 2.89-3.03 (1H, m), 3.05-3.23 (2H, m), 3.25-3.31 (1H, m), 3.32-3.40 (1H, m), 3.78 (3H, s), 4.07-4.23 (2H, m), 4.24-4.40 (2H, m), 6.74-6.89 (3H, m), 6.92 (1H, br d), 7.05-7.36 (10H, m)

MS (m/z): 503[M+H], 485[M-OH]

Example 274: Preparation of ((1R)-1-(5-benzyl-3-(((4-methoxybenzyl)oxy)methyl)-4,5-dihydroisoxazol-5-carboxamido)-3-methylbutylboronic acid Through the processes (1), (2) and (3) below, the title compound was obtained.

(1) Preparation of methyl 5-benzyl-3-(((4-methoxybenzyl)oxy)methyl)-4,5-dihydroisoxazol-5-carboxylate

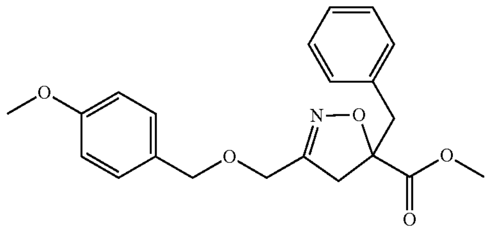

The title compound (2.2 g, 80%) was obtained using methyl 5-benzyl-3-(chloromethyl)-4,5-dihydroisoxazol-5-carboxylate (2.0 g, 7.5 mmol) obtained in Example 49-(2) and (4-methoxybenzyl)methanol (1.03 g, 7.5 mmol) by the preparation method of Example 49-(3).

MS (m/z): 370[M+H]

(2) Preparation of 5-benzyl-3-(((4-methoxybenzyl)oxy)methyl)-4,5-dihydroisoxazol-5-carboxylic acid

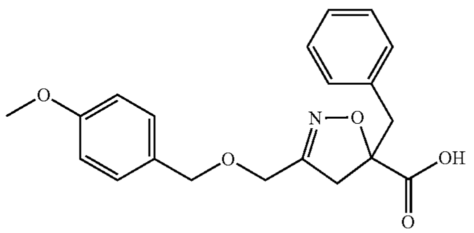 [SMILES: COc1ccc(COCC2=NOC(Cc3ccccc3)(C(=O)O)C2)cc1]

The quantitative amount of the title compound was obtained using methyl 5-benzyl-3-(((4-methoxybenzyl)oxy)methyl)-4,5-dihydroisoxazol-5-carboxylate (2.2 g, 6.0 mmol) obtained in (1) above by the preparation method of Example 84-(3).

MS (m/z): 356[M+H]

(3) Preparation of ((1R)-1-(5-benzyl-3-(((4-methoxybenzyl)oxy)methyl)-4,5-dihydroisoxazol-5-carboxamido)-3-methylbutylboronic acid

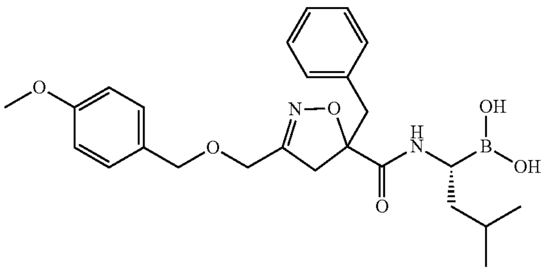 [SMILES: COc1ccc(COCC2=NOC(Cc3ccccc3)(C(=O)N[C@@H](CC(C)C)B(O)O)C2)cc1]

The title compound (0.0072 g, 0.7%, 2 steps) was obtained using 5-benzyl-3-(((4-methoxybenzyl)oxy) methyl)-4,5-dihydroisoxazol-5-carboxylic acid (0.80 g, 2.3 mmol) obtained in (2) above by the methods of Example 254-(3) and Example 1-(4).

NMR: 1H NMR (400 MHz, METHANOL-d4) δ ppm 0.79-0.84 (m, 6H), 1.17-1.42 (m, 3H) 2.69-2.77 (m, 1H), 3.14-3.24 (m, 2H), 3.34-3.45 (m, 2H), 3.78 (s, 3H), 4.14-4.32 (m, 4H), 6.88-6.91 (dd, 2H), 7.19-7.32 (m, 7H)

MS (m/z): 469[M+H], 451[M-OH]

Example 275: Preparation of ((1R)-1-(5-benzyl-3-(((4-methoxybenzyl)oxy)methyl)-4,5-dihydroisoxazol-5-carboxamido)-2-phenylethyl)boronic acid

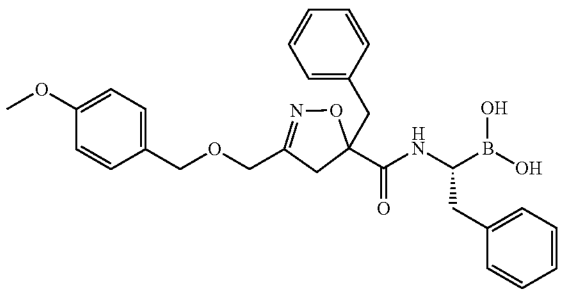 [SMILES: COc1ccc(COCC2=NOC(Cc3ccccc3)(C(=O)N[C@@H](Cc3ccccc3)B(O)O)C2)cc1]

The title compound (0.007 g, 0.6%, 2 steps) was obtained using 5-benzyl-3-(((4-methoxybenzyl)oxy)methyl)-4,5-dihydroisoxazol-5-carboxylic acid (0.80 g, 2.3 mmol) obtained in Example 274-(2) by the methods of Example 261-(1) and Example 1-(4).

NMR: 1H NMR (400 MHz, METHANOL-d4) δ ppm 2.59-2.80 (m, 2H) 2.92-3.02 (m, 1H) 3.07-3.15 (m, 2H) 3.38-3.55 (m, 1H) 3.75-3.82 (m, 3H) 4.08-4.20 (m, 2H) 4.22-4.34 (m, 2H) 6.84-6.98 (m, 3H) 7.06-7.35 (m, 12H)

MS (m/z): 503[M+H], 485[M-OH]

Example 276: Preparation of ((1R)-1-(5-benzyl-3-(((2-methylpyridin-4-yl)methoxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-(((2-methylpyridin-4-yl)methoxy)methyl)-4,5-dihydroisoxazol-5-carboxylate

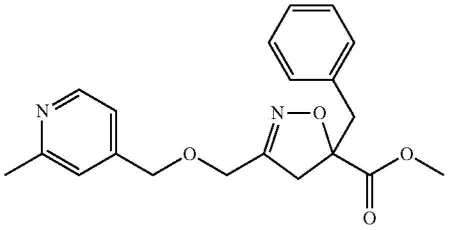

The title compound (1.25 g, 47%) was obtained using methyl 5-benzyl-3-(chloromethyl)-4,5-dihydroisoxazol-5-carboxylate (2.0 g, 7.5 mmol) obtained in Example 49-(2) and (2-methylpyridin-4-yl)methanol (0.92 g, 7.5 mmol) by the preparation method of Example 258-(1).

MS (m/z): 355[M+H]

(2) Preparation of 5-benzyl-3-(((2-methylpyridin-4-yl)methoxy)methyl)-4,5-dihydroisoxazol-5-carboxylic acid

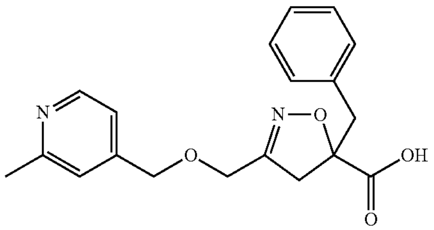 [SMILES: Cc1cc(COCC2=NOC(Cc3ccccc3)(C(=O)O)C2)ccn1]

The title compound (0.68 g, 57%) was obtained using methyl 5-benzyl-3-(((2-methylpyridin-4-yl)methoxy) methyl)-4,5-dihydroisoxazol-5-carboxylate (1.25 g, 3.5 mmol) obtained in (1) above by the preparation method of Example 84-(3).

MS (m/z): 341[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((2-methylpyridin-4-yl)methoxy)methyl)-4,5-dihydroisoxazol-5-carboxamide

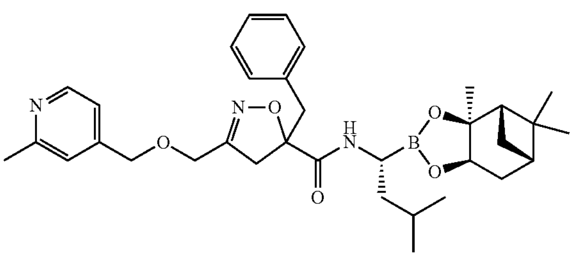

The title compound (0.17 g, 33%) was obtained using 5-benzyl-3-(((2-methylpyridin-4-yl)methoxy)methyl)-4,5- dihydroisoxazol-5-carboxylic acid (0.30 g, 0.88 mmol) obtained in (2) above by the method of Example 256-(3).

MS (m/z): 588[M+H]

(4) Preparation of ((1R)-1-(5-benzyl-3-(((2-methylpyridin-4-yl)methoxy)methyl)-4,5-dihydroisoxazol-5-carboxamido)-3-methylbutylboronic acid

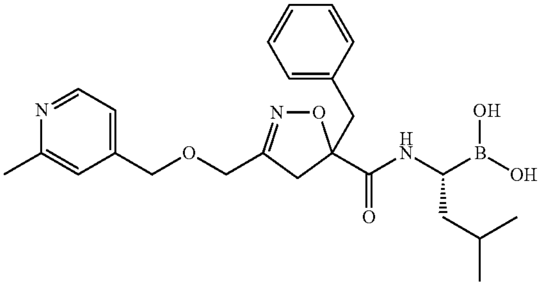 [SMILES: Cc1cc(COCC2=NOC(Cc3ccccc3)(C(=O)N[C@@H](CC(C)C)B(O)O)C2)ccn1]

The title compound (0.045 g, 35%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-(((2-methylpyridin-4-yl)methoxy)methyl)-4,5-dihydroisoxazol-5-carboxamide (0.17 g, 0.29 mmol) obtained in (3) above by the preparation method of Example 1-(4).

NMR: 1H NMR (400 MHz, METHANOL-d4) δ ppm 0.76-0.88 (6H, m), 1.02-1.60 (4H, m), 2.53 (3H, s), 3.06-3.27 (2H, m), 3.34-3.54 (2H, m), 4.16-4.48 (4H, m), 7.02-7.36 (7H, m), 8.21-8.41 (1H, m)

MS (m/z): 454[M+H], 436[M-OH]

Example 277: Preparation of ((1R)-1-(5-benzyl-3-(((2-methylpyridin-4-yl)methoxy)methyl)-4,5-dihydroisoxazol-5-carboxamido)-2-phenylethyl)boronic acid Through the processes (1) and (2) below, the title compound was obtained.

(1) Preparation of 5-benzyl-3-(((2-methylpyridin-4-yl)methoxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

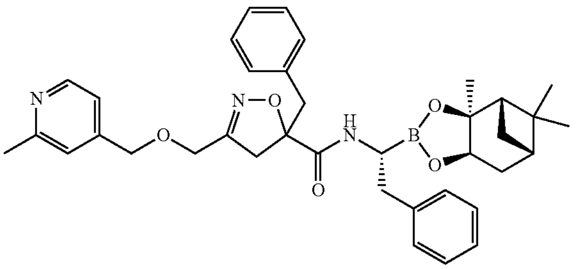

The title compound (0.10 g, 18%) was obtained using 5-benzyl-3-(((2-methylpyridin-4-yl)methoxy)methyl)-4,5-dihydroisoxazol-5-carboxylic acid (0.30 g, 0.88 mmol) obtained in Example 276-(2) by the method of Example 255-(1).

MS (m/z): 622[M+H]

(2) Preparation of ((1R)-1-(5-benzyl-3-(((2-methylpyridin-4-yl)methoxy)methyl)-4,5-dihydroisoxazol-5-carboxamido)-2-phenylethyl)boronic acid

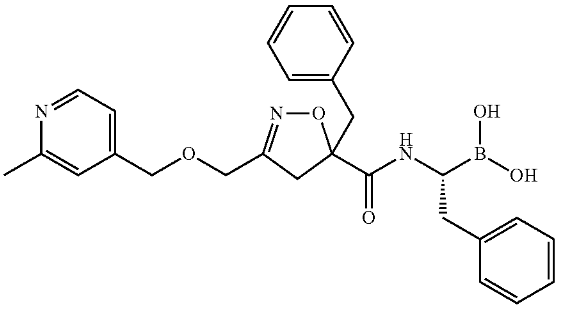 [SMILES: Cc1cc(COCC2=NOC(Cc3ccccc3)(C(=O)N[C@@H](Cc3ccccc3)B(O)O)C2)ccn1]

The title compound (0.018 g, 23%) was obtained using 5-benzyl-3-(((2-methylpyridin-4-yl)methoxy)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.10 g, 0.16 mmol) obtained in (1) above by the preparation method of Example 1-(4).

NMR: 1H NMR (400 MHz, METHANOL-d4) δ ppm 2.37-2.45 (1H, m), 2.53 (3H, d), 2.65-2.78 (2H, m), 2.87-3.03 (1H, m), 3.07-3.29 (3H, m), 3.34-3.42 (1H, m), 4.17-4.45 (4H, m), 6.89-6.97 (1H, m), 7.10-7.33 (11H, m), 8.29-8.41 (1H, m)

MS (m/z): 488[M+H], 470[M-OH]

Example 278: Preparation of ((1R)-1-(5-benzyl-3-((naphthalen-1-yloxy)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((naphthalen-1-yloxy)methyl)-4,5-dihydroisoxazol-5-carboxylate

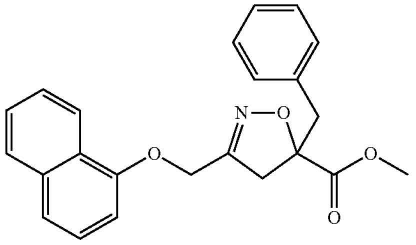 [SMILES: COC(=O)C1(Cc2ccccc2)CC(COc2cccc3ccccc23)=NO1]

The title compound (2.27 g, 81%) was obtained using methyl 5-benzyl-3-(chloromethyl)-4,5-dihydroisoxazol-5-carboxylate (2.0 g, 7.5 mmol) obtained in Example 49-(2) and naphthalen-1-ol (1.08 g, 7.5 mmol) by the preparation method of Example 254-(1).

MS (m/z): 376[M+H]

(2) Preparation of 5-benzyl-3-((naphthalen-1-yloxy) methyl)-4,5-dihydroisoxazol-5-carboxylic acid

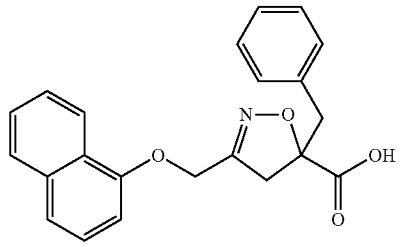 [SMILES: O=C(O)C1(Cc2ccccc2)CC(COc2cccc3ccccc23)=NO1]

The title compound (1.97 g, 90%) was obtained using methyl 5-benzyl-3-((naphthalen-1-yloxy)methyl)-4,5-dihydroisoxazol-5-carboxylate (2.25 g, 6.05 mmol) obtained in (1) above by the preparation method of Example 84-(3).

MS (m/z): 362[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((naphthalen-1-yloxy)methyl)-4,5-dihydroisoxazol-5-carboxamide

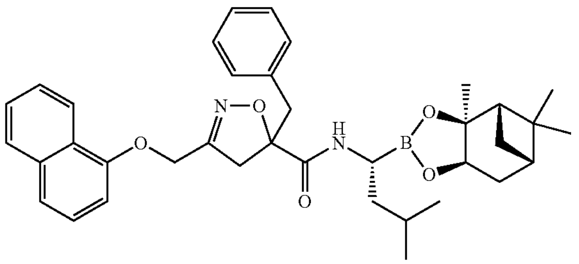 [SMILES: CC(C)C[C@H](NC(=O)C1(Cc2ccccc2)CC(COc2cccc3ccccc23)=NO1)B1O[C@@H]2C[C@@H]3C[C@@H](C3(C)C)[C@]2(C)O1]

The title compound (0.35 g, 42%) was obtained using 5-benzyl-3-((naphthalen-1-yloxy)methyl)-4,5-dihydroisoxazol-5-carboxylic acid (0.50 g, 1.4 mmol) obtained in (2) above by the method of Example 256-(3).

MS (m/z): 609[M+H]

(4) Preparation of ((1R)-1-(5-benzyl-3-((naphthalen-1-yloxy)methyl)-4,5-dihydroisoxazol-5-carboxamido)-3-methylbutylboronic acid

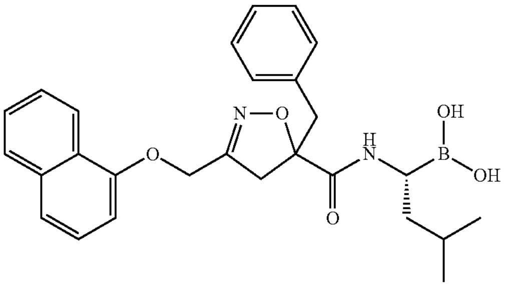 [SMILES: CC(C)C[C@H](NC(=O)C1(Cc2ccccc2)CC(COc2cccc3ccccc23)=NO1)B(O)O]

The title compound (0.041 g, 15%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((naphthalen-1-yloxy)methyl)-4,5-dihydroisoxazol-5-carboxamide (0.35 g, 0.58 mmol) obtained in (3) above by the preparation method of Example 1-(4).

NMR: 1H NMR (400 MHz, METHANOL-d4) δ ppm 0.77-0.85 (6H, m), 1.01-1.58 (4H, m), 2.58-2.76 (1H, m), 3.15-3.25 (1H, m), 3.32-3.43 (2H, m), 3.46-3.64 (1H, m), 4.97-5.07 (2H, m), 6.86-6.95 (1H, m), 7.16-7.31 (5H, m), 7.32-7.40 (1H, m), 7.41-7.56 (3H, m), 7.81 (1H, d), 8.04-8.20 (1H, m)

MS (m/z): 475[M+H], 457[M-OH]

Example 279: Preparation of ((1R)-1-(5-benzyl-3-((naphthalen-1-yloxy)methyl)-4,5-dihydroisoxazol-5-carboxamido)-2-phenylethyl)boronic acid Through the processes (1) and (2) below, the title compound was obtained.

(1) Preparation of 5-benzyl-3-((naphthalen-1-yloxy) methyl)-N—((R)-2-phenyl-1-((3aS,4S,6S,7aR)-3a,5,5-trimethylhexahydro-4,6-metanobenzo[d][1,3,2] dioxaborol-2-yl)ethyl)-4,5-dihydroisoxazol-5-carboxamide

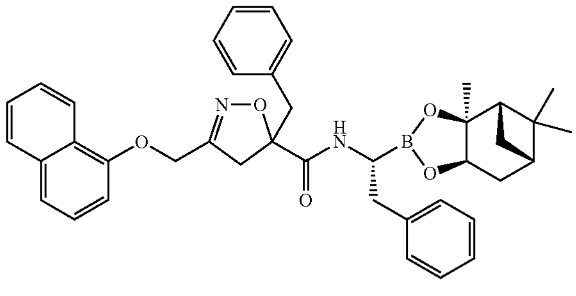 [SMILES: CC1(C)[C@@H]2C[C@H]3OB([C@H](Cc4ccccc4)NC(=O)C4(Cc5ccccc5)CC(COc5cccc6ccccc56)=NO4)O[C@@]3(C)[C@H]1C2]

The title compound (0.684 g, 77%) was obtained using 5-benzyl-3-((naphthalen-1-yloxy)methyl)-4,5-dihydroisoxazol-5-carboxylic acid (0.50 g, 1.4 mmol) obtained in Example 278-(2) by the method of Example 255-(1).

MS (m/z): 643[M+H]

(2) Preparation of ((1R)-1-(5-benzyl-3-((naphthalen-1-yloxy)methyl)-4,5-dihydroisoxazol-5-carboxamido)-2-phenylethyl)boronic acid

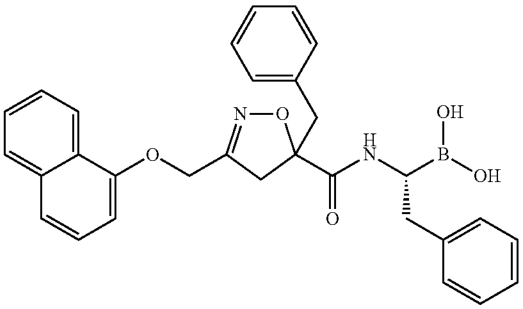 [SMILES: O=C(N[C@@H](Cc1ccccc1)B(O)O)C1(Cc2ccccc2)CC(COc2cccc3ccccc23)=NO1]

The title compound (0.213 g, 39%) was obtained using 5-benzyl-3-((naphthalen-1-yloxy)methyl)-N—((R)-2-phenyl-1-((3aS,4S,6S,7aR)-3a,5,5-trimethylhexahydro-4,6- metanobenzo[d][1,3,2]dioxaborol-2-yl)ethyl)-4,5-dihydroisoxazol-5-carboxamide (0.684 g, 4.18 mmol) obtained in (1) above by the preparation method of Example 1-(4).

NMR: 1H NMR (400 MHz, METHANOL-d4) δ ppm 2.28-2.75 (2H, m), 2.79-2.99 (1H, m), 3.08-3.19 (1H, m), 3.28 (1H, br s), 3.35 (1H, br s), 3.40-3.55 (1H, m), 4.95 (2H, m), 6.83-6.95 (2H, m), 7.02-7.38 (10H, m), 7.40-7.54 (3H, m), 7.74-7.86 (1H, m), 8.12 (1H, br d)

MS (m/z): 509[M+H], 491[M-OH]

Example 280: Preparation of ((1R)-1-(5-benzyl-3-((3-(trifluoromethyl)benzamido)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((3-(trifluoromethyl)benzamido)methyl)-4,5-dihydroisoxazol-5-carboxylate

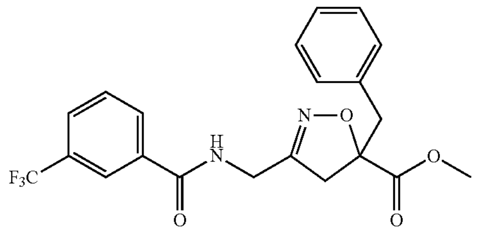 [SMILES: COC(=O)C1(Cc2ccccc2)CC(CNC(=O)c2cccc(C(F)(F)F)c2)=NO1]

The title compound (1.2 g, 81%) was obtained using methyl 3-(aminomethyl)-5-benzyl-4,5-dihydroisoxazol-5-carboxylate hydrochloride (1 g, 3.5 mmol) obtained in Example 84-(1) and 3-(trifluoromethyl)benzoic acid (0.73 g, 3.9 mmol) by the preparation method of Example 84-(2).

MS (m/z): 421[M+H]

(2) Preparation of 5-benzyl-3-((3-(trifluoromethyl)benzamido)methyl)-4,5-dihydroisoxazol-5-carboxylic acid

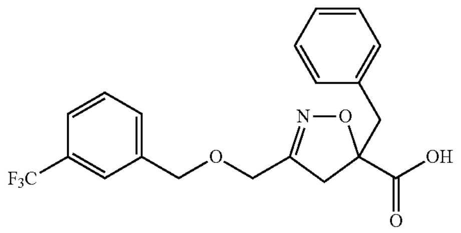 [SMILES: O=C(O)C1(Cc2ccccc2)CC(COCc2cccc(C(F)(F)F)c2)=NO1]

The quantitative amount of the title compound was obtained using methyl 5-benzyl-3-((3-(trifluoromethyl)benzamido)methyl)-4,5-dihydroisoxazol-5-carboxylate (1.2 g, 2.9 mmol) obtained in (1) above by the preparation method of Example 84-(3).

MS (m/z): 407[M+H]

(3) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-(trifluoromethyl)benzamido)methyl)-4,5-dihydroisoxazol-5-carboxamide

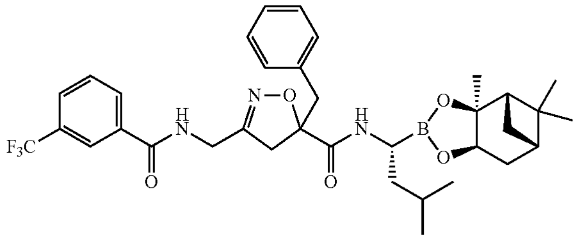 [SMILES: CC(C)C[C@H](NC(=O)C1(Cc2ccccc2)CC(CNC(=O)c2cccc(C(F)(F)F)c2)=NO1)B1O[C@@H]2C[C@@H]3C[C@@H](C3(C)C)[C@]2(C)O1]

The title compound (0.2 g, 25%) was obtained using 5-benzyl-3-((3-(trifluoromethyl)benzamido)methyl)-4,5-dihydroisoxazol-5-carboxylic acid (0.5 g, 1.2 mmol) obtained in (2) above by the preparation method of Example 256-(3).

MS (m/z): 654[M+H]

(4) Preparation of ((1R)-1-(5-benzyl-3-((3-(trifluoromethyl)benzamido)methyl)-4,5-dihydroisoxazol-5-carboxamido)-3-methylbutylboronic acid

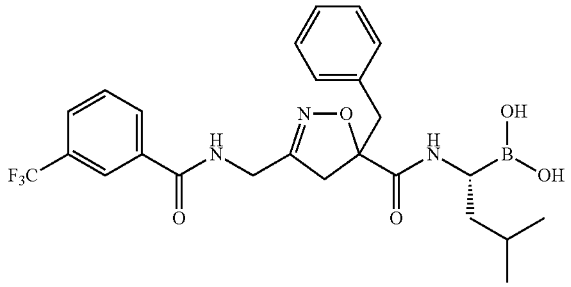 [SMILES: CC(C)C[C@H](NC(=O)C1(Cc2ccccc2)CC(CNC(=O)c2cccc(C(F)(F)F)c2)=NO1)B(O)O]

The title compound (0.014 g, 9%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-(trifluoromethyl)benzamido)methyl)-4,5-dihydroisoxazol-5-carboxamide (0.2 g, 0.31 mmol) obtained in (3) above by the preparation method of Example 1-(4).

NMR: 1H NMR (400 MHz, METHANOL-d4) δ ppm 0.68-0.92 (m, 6H) 0.99-1.08 (m, 1H) 1.10-1.21 (m, 1H) 1.24-1.56 (m, 2H) 2.56-2.77 (m, 1H) 3.06-3.28 (m, 2H) 3.40-3.48 (d, 1H) 4.24 (s, 2H) 7.06-7.40 (m, 5H) 7.66-7.74 (m, 1H) 7.85-7.91 (m, 1H) 8.05-8.10 (m, 1H) 8.12-8.18 (m, 1H)

MS (m/z): 520[M+H], 502[M-OH].

Example 281: Preparation of ((1R)-1-(5-benzyl-3-((3-(trifluoromethyl)benzamido)methyl)-4,5-dihydroisoxazol-5-carboxamido)-2-phenylethyl)boronic acid Through the processes (1) and (2) below, the title compound was obtained.

(1) Preparation of 5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-3-((3-(trifluoromethyl)benzamido)methyl)-4,5-dihydroisoxazol-5-carboxamide

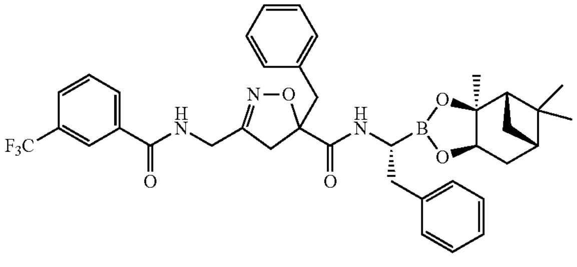 [SMILES: CC1(C)[C@@H]2C[C@H]3OB([C@H](Cc4ccccc4)NC(=O)C4(Cc5ccccc5)CC(CNC(=O)c5cccc(C(F)(F)F)c5)=NO4)O[C@@]3(C)[C@H]1C2]

The title compound (0.196 g, 58%) was obtained using 5-benzyl-3-((3-(trifluoromethyl)benzamido)methyl)-4,5-dihydroisoxazol-5-carboxylic acid (0.20 g, 0.49 mmol) obtained in Example 280-(2) by the method of Example 261-(1).

MS (m/z): 688[M+H]

(2) Preparation of ((1R)-1-(5-benzyl-3-((3-(trifluoromethyl)benzamido)methyl)-4,5-dihydroisoxazol-5-carboxamido)-2-phenylethyl)boronic acid

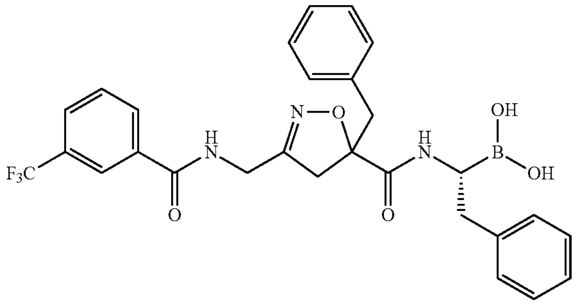 [SMILES: O=C(NCC1=NOC(Cc2ccccc2)(C(=O)N[C@@H](Cc2ccccc2)B(O)O)C1)c1cccc(C(F)(F)F)c1]

The title compound (0.014 g, 9%) was obtained using 5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-3-((3-(trifluoromethyl)benzamido)methyl)-4,5-dihydroisoxazol-5-carboxamide (0.196 g, 0.285 mmol) obtained in (1) above by the preparation method of Example 1-(4).

NMR: 1H NMR (400 MHz, METHANOL-d4) δ ppm 2.16-2.43 (m, 1H) 2.57-2.74 (m, 1H) 2.79-2.95 (m, 1H) 3.10-3.23 (m, 2H) 3.35-3.39 (m, 1H) 4.22 (s, 2H) 6.80-6.95 (m, 2H) 7.01-7.39 (m, 9H) 7.61-7.75 (m, 1H) 7.79-7.95 (m, 1H) 8.02-8.09 (m, 1H) 8.10-8.17 (m, 1H)

MS (m/z): 554[M+H], 536[M-OH]

Example 282: Preparation of ((1R)-1-(5-benzyl-3-((4-methoxybenzamido)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((4-methoxybenzamido)methyl)-4,5-dihydroisoxazol-5-carboxylate

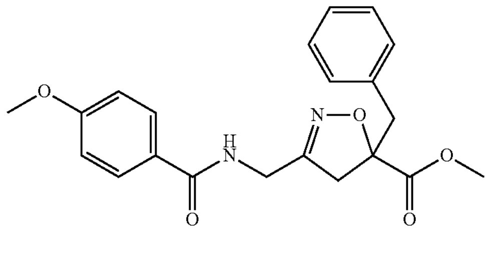

The title compound (2.7 g, 86%) was obtained using methyl 3-(aminomethyl)-5-benzyl-4,5-dihydroisoxazol-5-carboxylate hydrochloride (2.3 g, 8.0 mmol) obtained in Example 84-(1) and 4-methoxybenzoic acid (1.2 g, 8.0 mmol) by the preparation method of Example 84-(2).

MS (m/z): 383[M+H]

(2) Preparation of 5-benzyl-3-((4-methoxybenzamido)methyl)-4,5-dihydroisoxazol-5-carboxylic acid

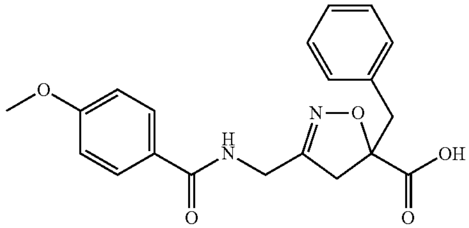 [SMILES: COc1ccc(C(=O)NCC2=NOC(Cc3ccccc3)(C(=O)O)C2)cc1]

The title compound (2.2 g, 85%) was obtained using methyl 5-benzyl-3-((4-methoxybenzamido)methyl)-4,5-dihydroisoxazol-5-carboxylate (2.7 g, 7.1 mmol) obtained in (1) above by the preparation method of Example 84-(3).

MS (m/z): 369[M+H]

(3) Preparation of 5-benzyl-3-((4-methoxybenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

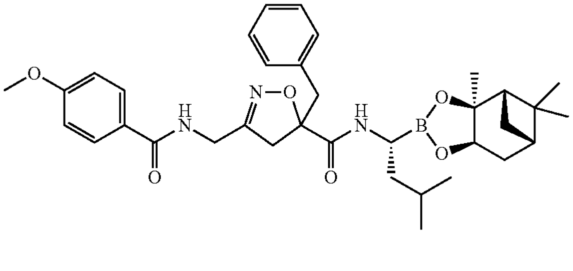

The title compound (0.25 g, 30%) was obtained using 5-benzyl-3-((4-methoxybenzamido)methyl)-4,5-dihydroisoxazol-5-carboxylic acid (0.5 g, 1.4 mmol) obtained in (2) above by the preparation method of Example 256-(3).

MS (m/z): 616[M+H]

(4) Preparation of ((1R)-1-(5-benzyl-3-((4-methoxybenzamido)methyl)-4,5-dihydroisoxazol-5-carboxamido)-3-methylbutylboronic acid

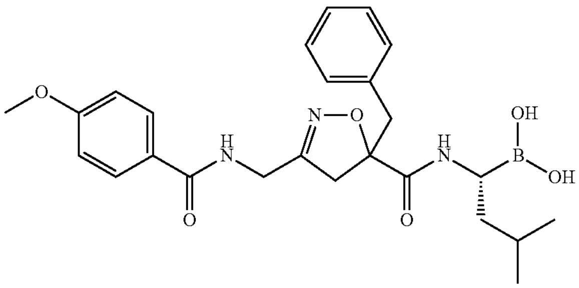 [SMILES: COc1ccc(C(=O)NCC2=NOC(Cc3ccccc3)(C(=O)N[C@@H](CC(C)C)B(O)O)C2)cc1]

The title compound (0.047 g, 40%) was obtained using 5-benzyl-3-((4-methoxybenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.15 g, 0.24 mmol) obtained in (3) above by the preparation method of Example 1-(4).

NMR: 1H NMR (400 MHz, METHANOL-d4) δ ppm 0.72-0.90 (m, 6H) 0.98-1.09 (m, 1H) 1.10-1.20 (m, 1H) 1.24-1.54 (m, 2H) 2.57-2.69 (m, 1H) 3.15-3.28 (m, 2H) 3.37-3.49 (d, 1H) 3.85 (s, 3H) 4.21 (s, 2H) 6.91-7.09 (m, 2H) 7.12-7.41 (m, 5H) 7.67-7.87 (m, 2H)

MS (m/z): 482[M+H], 464[M-OH]

Example 283: Preparation of ((1R)-1-(5-benzyl-3-((4-methoxybenzamido)methyl)-4,5-dihydroisoxazol-5-carboxamido)-2-phenylethyl)boronic acid Through the processes (1) and (2) below, the title compound was obtained.

(1) Preparation of 5-benzyl-3-((4-methoxybenzamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

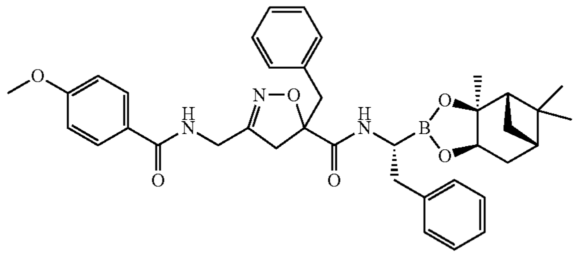

The title compound (0.27 g, 77%) was obtained using 5-benzyl-3-((4-methoxybenzamido)methyl)-4,5-dihydroisoxazol-5-carboxylic acid (0.20 g, 0.54 mmol) obtained in Example 282-(2) by the method of Example 261-(1).

MS (m/z): 650[M+H]

(2) Preparation of ((1R)-1-(5-benzyl-3-((4-methoxybenzamido)methyl)-4,5-dihydroisoxazol-5-carboxamido)-2-phenylethyl)boronic acid

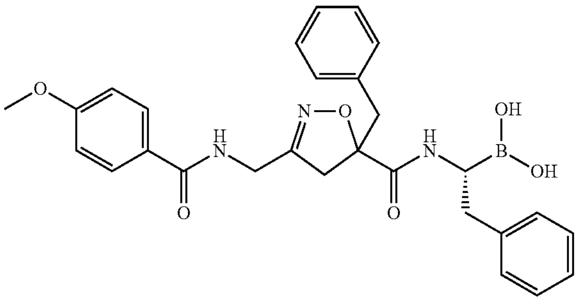 [SMILES: COc1ccc(C(=O)NCC2=NOC(Cc3ccccc3)(C(=O)N[C@@H](Cc3ccccc3)B(O)O)C2)cc1]

The title compound (0.057 g, 72%) was obtained using 5-benzyl-3-((4-methoxybenzamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.10 g, 0.15 mmol) obtained in (1) above by the preparation method of Example 1-(4).

NMR: 1H NMR (400 MHz, METHANOL-d4) δ ppm 2.20-2.41 (m, 1H) 2.61-2.74 (m, 1H) 2.77-2.91 (m, 1H) 3.10-3.26 (m, 2H) 3.32-3.40 (m, 1H) 3.83 (s, 3H) 4.17 (s, 2H) 6.79-6.92 (m, 2H) 6.94-7.04 (m, 2H) 7.05-7.22 (m, 3H) 7.23-7.42 (m, 5H) 7.66-7.88 (m, 2H)

MS (m/z): 516[M+H], 498[M-OH]

Example 284: Preparation of ((1R)-1-(5-benzyl-3-((3-methoxybenzamido)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((3-methoxybenzamido)methyl)-4,5-dihydroisoxazol-5-carboxylate

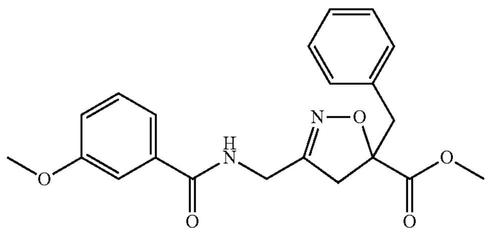

The title compound (0.75 g, 56%) was obtained using methyl 3-(aminomethyl)-5-benzyl-4,5-dihydroisoxazol-5-carboxylate hydrochloride (1.0 g, 3.5 mmol) obtained in Example 84-(1) and 3-methoxybenzoic acid (0.59 g, 3.9 mmol) by the preparation method of Example 84-(2).

MS (m/z): 383[M+H]

(2) Preparation of 5-benzyl-3-((3-methoxybenzamido)methyl)-4,5-dihydroisoxazol-5-carboxylic acid

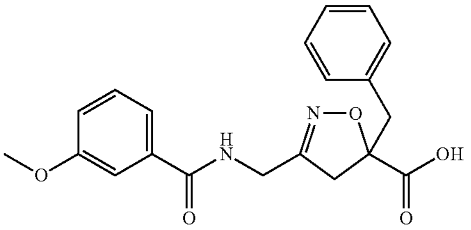 [SMILES: COc1cccc(C(=O)NCC2=NOC(Cc3ccccc3)(C(=O)O)C2)c1]

The quantitative amount of the title compound was obtained using methyl 5-benzyl-3-((3-methoxybenzamido)methyl)-4,5-dihydroisoxazol-5-carboxylate (0.75 g, 2.0 mmol) obtained in (1) above by the preparation method of Example 84-(3).

MS (m/z): 369[M+H]

(3) Preparation of 5-benzyl-3-((3-methoxybenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

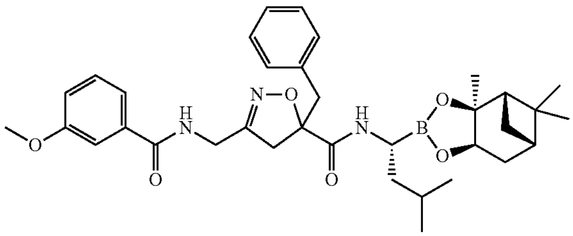

The title compound (0.27 g, 32%) was obtained using 5-benzyl-3-((3-methoxybenzamido)methyl)-4,5-dihydroisoxazol-5-carboxylic acid (0.5 g, 1.4 mmol) obtained in (2) above by the preparation method of Example 256-(3).

MS (m/z): 616[M+H]

(4) Preparation of ((1R)-1-(5-benzyl-3-((3-methoxybenzamido)methyl)-4,5-dihydroisoxazol-5-carboxamido)-3-methylbutylboronic acid

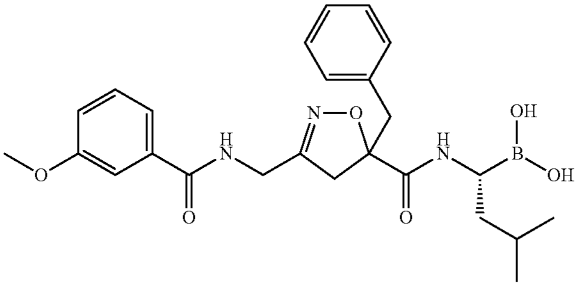 [SMILES: COc1cccc(C(=O)NCC2=NOC(Cc3ccccc3)(C(=O)N[C@@H](CC(C)C)B(O)O)C2)c1]

The title compound (0.083 g, 39%) was obtained using 5-benzyl-3-((3-methoxybenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.27 g, 0.44 mmol) obtained in (3) above by the preparation method of Example 1-(4).

NMR: 1H NMR (400 MHz, METHANOL-d4) δ ppm 0.66-0.85 (m, 6H) 0.98-1.09 (m, 1H) 1.10-1.21 (m, 1H) 1.25-1.49 (m, 2H) 2.58-2.71 (m, 1H) 3.16-3.27 (m, 2H) 3.37-3.46 (d, 1H) 3.84 (s, 3H) 4.22 (s, 2H) 7.07-7.15 (m, 1H) 7.16-7.31 (m, 5H) 7.31-7.42 (m, 3H)

MS (m/z): 482[M+H], 464[M-OH]

Example 285: Preparation of ((1R)-1-(5-benzyl-3-((3-methoxybenzamido)methyl)-4,5-dihydroisoxazol-5-carboxamido)-2-phenylethyl)boronic acid Through the processes (1) and (2) below, the title compound was obtained.

(1) Preparation of 5-benzyl-3-((3-methoxybenzamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

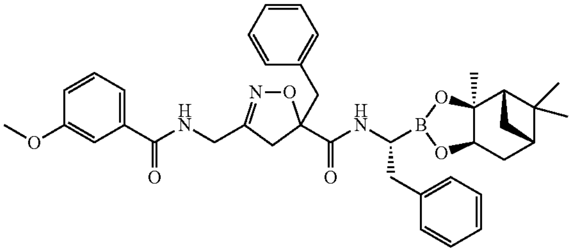

The title compound (0.27 g, 77%) was obtained using 5-benzyl-3-((3-methoxybenzamido)methyl)-4,5-dihydroisoxazol-5-carboxylic acid (0.20 g, 0.54 mmol) obtained in Example 284-(2) by the method of Example 261-(1).

MS (m/z): 650[M+H]

(2) Preparation of ((1R)-1-(5-benzyl-3-((3-methoxybenzamido)methyl)-4,5-dihydroisoxazol-5-carboxamido)-2-phenylethyl)boronic acid

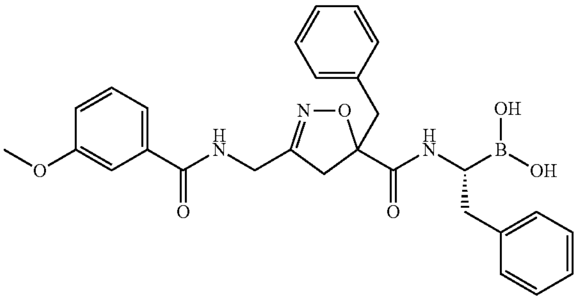 [SMILES: COc1cccc(C(=O)NCC2=NOC(Cc3ccccc3)(C(=O)N[C@@H](Cc3ccccc3)B(O)O)C2)c1]

The title compound (0.10 g, 47%) was obtained using 5-benzyl-3-((3-methoxybenzamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.27 g, 0.42 mmol) obtained in (1) above by the preparation method of Example 1-(4).

NMR: 1H NMR (400 MHz, METHANOL-d4) δ ppm 2.26-2.42 (m, 1H) 2.61-2.73 (m, 1H) 2.79-2.90 (m, 1H) 3.08-3.26 (m, 2H) 3.34-3.40 (m, 1H) 3.83 (s, 3H) 4.19 (s, 2H) 6.83-6.93 (m, 2H) 7.04-7.22 (m, 4H) 7.23-7.43 (m, 8H)

MS (m/z): 516[M+H], 498[M-OH]

Example 286: Preparation of ((1R)-1-(5-benzyl-3-((2-chlorobenzamido)methyl)-4,5-dihydroisoxazol-5-carboxamido)-3-methylbutylboronic acid Through the processes (1), (2) and (3) below, the title compound was obtained.

(1) Preparation of methyl 5-benzyl-3-((2-chlorobenzamido)methyl)-4,5-dihydroisoxazol-5-carboxylate

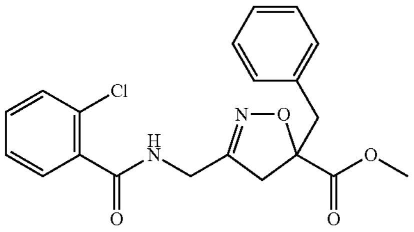 [SMILES: COC(=O)C1(Cc2ccccc2)CC(CNC(=O)c2ccccc2Cl)=NO1]

The title compound (0.55 g, 81%) was obtained using methyl 3-(aminomethyl)-5-benzyl-4,5-dihydroisoxazol-5-carboxylate hydrochloride (0.5 g, 1.8 mmol) obtained in Example 84-(1) and 2-chlorobenzoic acid (0.30 g, 1.9 mmol) by the preparation method of Example 84-(2).

MS (m/z): 387[M+H]

(2) Preparation of 5-benzyl-3-((2-chlorobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

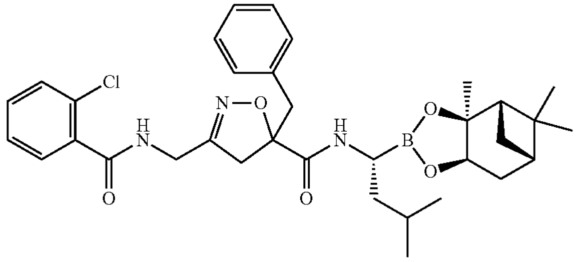 [SMILES: CC(C)C[C@H](NC(=O)C1(Cc2ccccc2)CC(CNC(=O)c2ccccc2Cl)=NO1)B1O[C@@H]2C[C@@H]3C[C@@H](C3(C)C)[C@]2(C)O1]

The title compound (0.045 g, 5%, 2 steps) was obtained using methyl 5-benzyl-3-((2-chlorobenzamido)methyl)-4,5-dihydroisoxazol-5-carboxylate (0.045 g, 0.073 mmol) obtained in (1) above by the preparation methods of Example 84-(3) and Example 256-(3).

MS (m/z): 620[M+H]

(3) Preparation of ((1R)-1-(5-benzyl-3-((2-chlorobenzamido)methyl)-4,5-dihydroisoxazol-5-carboxamido)-3-methylbutylboronic acid

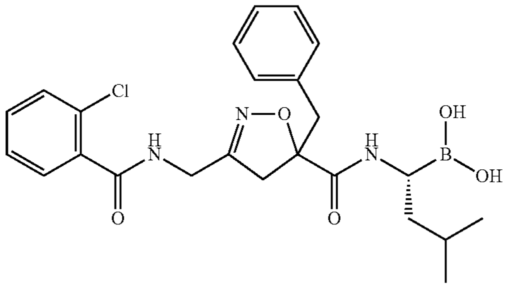 [SMILES: CC(C)C[C@H](NC(=O)C1(Cc2ccccc2)CC(CNC(=O)c2ccccc2Cl)=NO1)B(O)O]

The title compound (0.014 g, 39%) was obtained using 5-benzyl-3-((2-chlorobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.45 g, 0.073 mmol) obtained in (3) above by the preparation method of Example 1-(4).

NMR: 1H NMR (400 MHz, METHANOL-d4) δ ppm 0.71-0.91 (m, 6H) 1.00-1.10 (m, 1H) 1.12-1.21 (m, 1H) 1.33-1.46 (m, 2H) 2.56-2.75 (m, 1H) 3.16-3.30 (m, 2H) 3.48-3.52 (d, 1H) 4.23 (s, 2H) 7.20-7.34 (m, 5H) 7.35-7.53 (m, 4H)

MS (m/z): 486[M+H], 468[M-OH]

Example 287: Preparation of ((1R)-1-(5-benzyl-3-((4-chlorobenzamido)methyl)-4,5-dihydroisoxazol-5-carboxamido)-3-methylbutylboronic acid Through the processes (1), (2) and (3) below, the title compound was obtained.

(1) Preparation of methyl 5-benzyl-3-((4-chlorobenzamido)methyl)-4,5-dihydroisoxazol-5-carboxylate

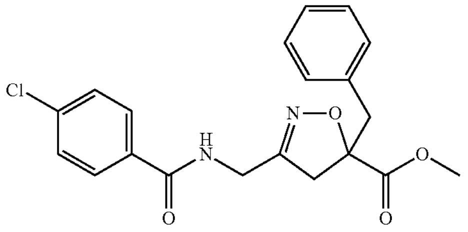 [SMILES: COC(=O)C1(Cc2ccccc2)CC(CNC(=O)c2ccc(Cl)cc2)=NO1]

The title compound (0.57 g, 84%) was obtained using methyl 3-(aminomethyl)-5-benzyl-4,5-dihydroisoxazol-5-carboxylate hydrochloride (0.5 g, 1.8 mmol) obtained in Example 84-(1) and 4-chlorobenzoic acid (0.30 g, 1.9 mmol) by the preparation method of Example 84-(2).

MS (m/z): 387[M+H]

(2) Preparation of 5-benzyl-3-((4-chlorobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

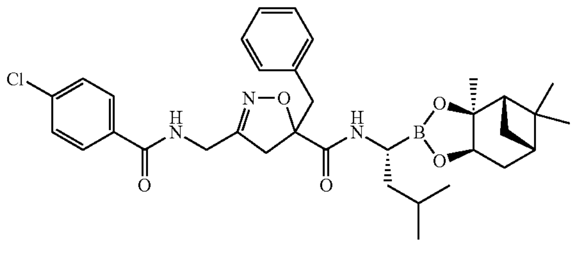 [SMILES: CC(C)C[C@H](NC(=O)C1(Cc2ccccc2)CC(CNC(=O)c2ccc(Cl)cc2)=NO1)B1O[C@@H]2C[C@@H]3C[C@@H](C3(C)C)[C@]2(C)O1]

The title compound (0.11 g, 12%, 2 steps) was obtained using methyl 5-benzyl-3-((4-chlorobenzamido)methyl)-4,5-dihydroisoxazol-5-carboxylate (0.57 g, 1.5 mmol) obtained in (1) above by the preparation methods of Example 84-(3) and Example 256-(3).

MS (m/z): 620[M+H]

(3) Preparation of ((1R)-1-(5-benzyl-3-((4-chlorobenzamido)methyl)-4,5-dihydroisoxazol-5-carboxamido)-3-methylbutylboronic acid

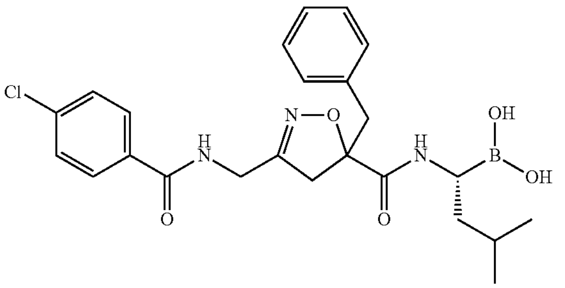 [SMILES: CC(C)C[C@H](NC(=O)C1(Cc2ccccc2)CC(CNC(=O)c2ccc(Cl)cc2)=NO1)B(O)O]

The title compound (0.013 g, 15%) was obtained using 5-benzyl-3-((4-chlorobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.11 g, 0.18 mmol) obtained in (3) above by the preparation method of Example 1-(4).

NMR: 1H NMR (400 MHz, METHANOL-d4) δ ppm 0.70-0.85 (m, 6H) 0.99-1.08 (m, 1H) 1.09-1.20 (m, 1H) 1.32-1.48 (m, 2H) 2.57-2.74 (m, 1H) 3.17-3.29 (m, 2H) 3.40-3.46 (d, 1H) 4.22 (s, 2H) 7.11-7.33 (m, 5H) 7.41-7.58 (m, 2H) 7.68-7.90 (m, 2H)

MS (m/z): 486[M+H], 468[M-OH]

Example 288: Preparation of ((1R)-1-(5-benzyl-3-((isoquinolin-1-carboxamido)methyl)-4,5-dihydroisoxazol-5-carboxamido)-2-phenylethyl)boronic acid Through the processes (1) and (2) below, the title compound was obtained.

(1) Preparation of 5-benzyl-3-((isoquinolin-1-carboxamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

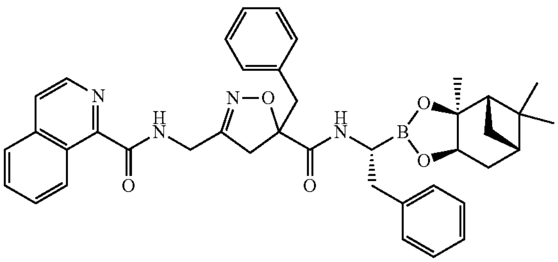 [SMILES: CC1(C)[C@@H]2C[C@H]3OB([C@H](Cc4ccccc4)NC(=O)C4(Cc5ccccc5)CC(CNC(=O)c5nccc6ccccc56)=NO4)O[C@@]3(C)[C@H]1C2]

The title compound (0.20 g, 58%) was obtained using 5-benzyl-3-[(isoquinolin-1-carbonylamino)methyl]-4H-1,2-oxazol-5-carboxylic acid (0.20 g, 0.51 mmol) obtained in Example 84-(3) by the method of Example 261-(1).

MS (m/z): 671[M+H]

(2) Preparation of ((1R)-1-(5-benzyl-3-((isoquinolin-1-carboxamido)methyl)-4,5-dihydroisoxazol-5-carboxamido)-2-phenylethyl)boronic acid

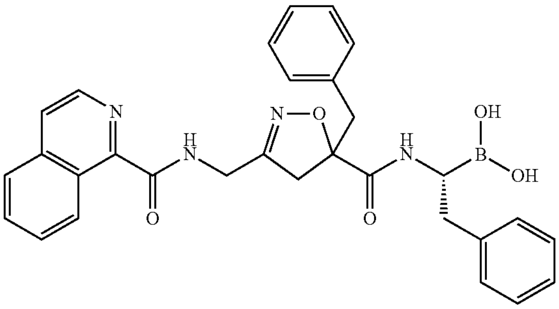 [SMILES: O=C(NCC1=NOC(Cc2ccccc2)(C(=O)N[C@@H](Cc2ccccc2)B(O)O)C1)c1nccc2ccccc12]

The title compound (0.047 g, 29%) was obtained using 5-benzyl-3-((isoquinolin-1-carboxamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.20 g, 0.30 mmol) obtained in (1) above by the preparation method of Example 1-(4).

NMR: 1H NMR (400 MHz, METHANOL-d4) δ ppm 2.27-2.39 (m, 1H) 2.63-2.90 (m, 2H) 3.29 (s, 2H) 3.33-3.51 (m, 2H) 4.31 (s, 2H) 6.82-6.93 (m, 2H) 7.07-7.13 (m, 1H) 7.14-7.21 (m, 2H) 7.23-7.35 (m, 5H) 7.68-7.83 (m, 2H) 7.93-8.02 (m, 2H) 8.48-8.54 (m, 1H) 9.03-9.11 (m, 1H)

MS (m/z): 537[M+H], 519[M-OH]

Example 289: Preparation of ((1R)-1-(5-benzyl-3-((isoquinolin-1-carboxamido)methyl)-4,5-dihydroisoxazol-5-carboxamido)propyl)boronic acid Through the processes (1) and (2) below, the title compound was obtained.

(1) Preparation of 5-benzyl-3-((isoquinolin-1-carboxamido)methyl)-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

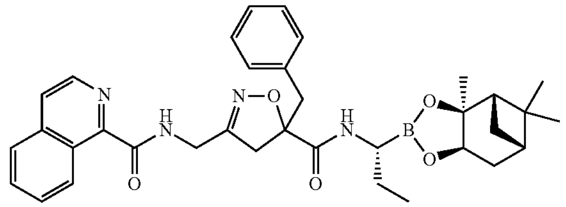

1,1'-Carbonyldiimidazole (0.42 g, 2.57 mmol) was dissolved in acetonitrile (3 ml), and at 0° C., 5-benzyl-3-[(isoquinolin-1-carbonylamino)methyl]-4H-1,2-oxazol-5-carboxylic acid (0.50 g, 1.28 mmol) obtained in Example 84-(3) was added thereto, followed by stirring for 1 hour. (R)-1-((3aS,4S,6S,7aR)-3a,5,5-trimethylhexahydro-4,6-metanobenzo[d][1,3,2]dioxaborol-2-yl)propan-1-amine hydrochloride (0.42 g, 1.54 mmol) was added thereto, and stirring was performed at room temperature for 16 hours. Through distillation under a reduced pressure, the acetonitrile solvent was removed, ethyl acetate was added, and an organic layer was washed with a sodium bicarbonate aqueous solution, dried over anhydrous magnesium sulfate, and filtered. The filtrate of the organic layer was distilled under a reduced pressure and separated by column chromatography to obtain the title compound (0.47 g, 60%).

MS (m/z): 609[M+H]

(2) Preparation of ((1R)-1-(5-benzyl-3-((isoquinolin-1-carboxamido)methyl)-4,5-dihydroisoxazol-5-carboxamido)propyl)boronic acid

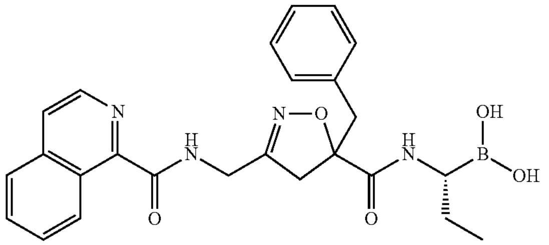

The title compound (0.069 g, 19%) was obtained using 5-benzyl-3-((isoquinolin-1-carboxamido)methyl)-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.47 g, 0.77 mmol) obtained in (1) above by the preparation method of Example 1-(4).

NMR: 1H NMR (400 MHz, METHANOL-d4) δ ppm 0.67-0.78 (m, 3H) 1.15-1.46 (m, 2H) 2.42-2.50 (m, 1H) 3.12-3.30 (m, 2H) 3.34-3.55 (d, 2H) 4.33 (s, 2H) 7.15-7.31 (m, 5H) 7.69-7.84 (m, 2H) 7.93-8.03 (m, 2H) 8.49-8.55 (m, 1H) 9.03-9.11 (m, 1H)

MS (m/z): 475[M+H], 457[M-OH]

Example 290: Preparation of ((1R)-1-(5-benzyl-3-((isoquinolin-1-carboxamido)methyl)-4,5-dihydroisoxazol-5-carboxamido)-2-methylpropyl)boronic acid Through the processes (1) and (2) below, the title compound was obtained.

(1) Preparation of 5-benzyl-3-((isoquinolin-1-carboxamido)methyl)-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

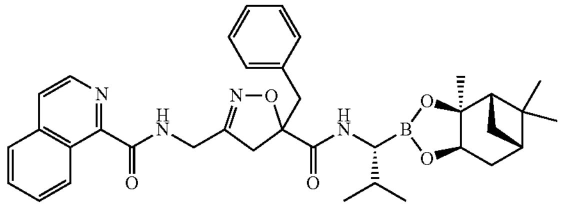 [SMILES: CC(C)[C@H](NC(=O)C1(Cc2ccccc2)CC(CNC(=O)c2nccc3ccccc23)=NO1)B1O[C@@H]2C[C@@H]3C[C@@H](C3(C)C)[C@]2(C)O1]

1,1'-Carbonyldiimidazole (0.58 g, 3.60 mmol) was dissolved in acetonitrile (5 ml), and at 0° C., 5-benzyl-3-[(isoquinolin-1-carbonylamino)methyl]-4H-1,2-oxazol-5-carboxylic acid (0.70 g, 1.80 mmol) obtained in Example 84-(3) was added thereto, followed by stirring for 1 hour. After adding (R)-2-methyl-1-((3aS,4S,6S,7aR)-3a,5,5-trimethylhexahydro-4,6-metanobenzo[d][1,3,2]dioxaborol-2-yl)propan-1-amine hydrochloride (0.62 g, 2.16 mmol), stirring was performed at room temperature for 16 hours. After removing the acetonitrile solvent through distillation under a reduced pressure, ethyl acetate was added, and an organic layer was washed with a sodium bicarbonate aqueous solution, dried over anhydrous magnesium sulfate, and filtered. The filtrate of the organic layer was distilled under a reduced pressure and separated by column chromatography to obtain the title compound (0.78 g, 70%).

MS (m/z): 623[M+H]

(2) Preparation of ((1R)-1-(5-benzyl-3-((isoquinolin-1-carboxamido)methyl)-4,5-dihydroisoxazol-5-carboxamido)-2-methylpropyl)boronic acid

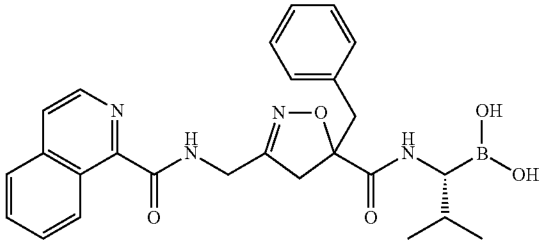 [SMILES: CC(C)[C@H](NC(=O)C1(Cc2ccccc2)CC(CNC(=O)c2nccc3ccccc23)=NO1)B(O)O]

The title compound (0.061 g, 10%) was obtained using 5-benzyl-3-((isoquinolin-1-carboxamido)methyl)-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.78 g, 1.25 mmol) obtained in (1) above by the preparation method of Example 1-(4).

NMR: 1H NMR (400 MHz, METHANOL-d4) δ ppm 0.61-0.67 (m, 3H) 0.75-0.82 (m, 3H) 1.54-1.67 (m, 1H) 2.39-2.44 (m, 1H) 3.17-3.30 (m, 2H) 3.18-3.24 (m, 1H) 3.32-3.54 (m, 2H) 3.33-3.35 (m, 1H) 3.47-3.54 (m, 1H) 4.33 (s, 2H) 7.17-7.29 (m, 5H) 7.68-7.84 (m, 2H) 7.93-8.02 (m, 2H) 8.48-8.54 (m, 1H) 9.03-9.13 (m, 1H)

MS (m/z): 489[M+H], 471[M-OH]

Example 291: Preparation of ((1R)-1-(3-(benzamidomethyl)-5-benzyl-4,5-dihydroisoxazol-5-carboxamido)-3-methylbutylboronic acid Through the processes (1), (2), (3) and (4) below, the title compound was obtained.

(1) Preparation of methyl 3-(benzamidomethyl)-5-benzyl-4,5-dihydroisoxazol-5-carboxylate

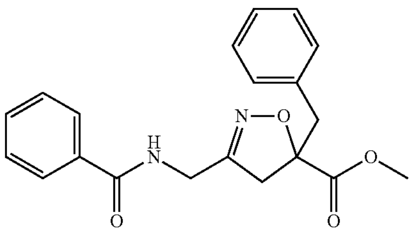 [SMILES: COC(=O)C1(Cc2ccccc2)CC(CNC(=O)c2ccccc2)=NO1]

The title compound (2.2 g, 74%) was obtained using methyl 3-(aminomethyl)-5-benzyl-4,5-dihydroisoxazol-5-carboxylate hydrochloride (2.4 g, 8.4 mmol) obtained in Example 84-(1) and benzoic acid (1.1 g, 9.3 mmol) by the preparation method of Example 84-(2).

MS (m/z): 353[M+H]

(2) Preparation of 3-(benzamidomethyl)-5-benzyl-4,5-dihydroisoxazol-5-carboxylic acid

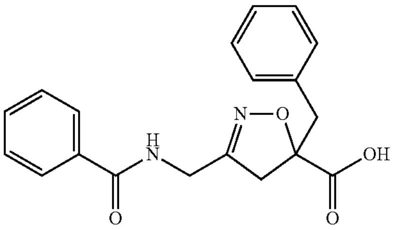 [SMILES: O=C(NCC1=NOC(Cc2ccccc2)(C(=O)O)C1)c1ccccc1]

The title compound (2.0 g, 95%) was obtained using methyl 3-(benzamidomethyl)-5-benzyl-4,5-dihydroisoxazol-5-carboxylate (2.2 g, 6.2 mmol) obtained in (1) above by the preparation method of Example 84-(3).

MS (m/z): 339[M+H]

(3) Preparation of 3-(benzamidomethyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

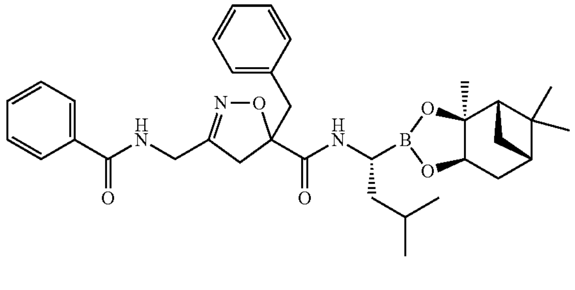 [SMILES: CC(C)C[C@H](NC(=O)C1(Cc2ccccc2)CC(CNC(=O)c2ccccc2)=NO1)B1O[C@@H]2C[C@@H]3C[C@@H](C3(C)C)[C@]2(C)O1]

The title compound (0.51 g, 59%) was obtained using 3-(benzamidomethyl)-5-benzyl-4,5-dihydroisoxazol-5-carboxylic acid (0.50 g, 1.5 mmol) obtained in (2) above by the preparation method of Example 256-(3).

MS (m/z): 586[M+H]

(4) Preparation of ((1R)-1-(3-(benzamidomethyl)-5-benzyl-4,5-dihydroisoxazol-5-carboxamido)-3-methylbutylboronic acid

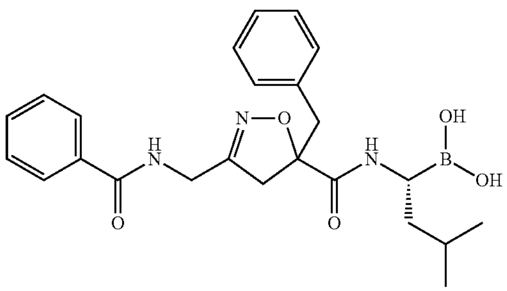 [SMILES: CC(C)C[C@H](NC(=O)C1(Cc2ccccc2)CC(CNC(=O)c2ccccc2)=NO1)B(O)O]

The title compound (0.060 g, 15%) was obtained using 3-(benzamidomethyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.51 g, 0.88 mmol) obtained in (3) above by the preparation method of Example 1-(4).

NMR: 1H NMR (400 MHz, METHANOL-d4) δ ppm 0.72-0.89 (m, 6H) 0.99-1.11 (m, 1H) 1.11-1.23 (m, 1H) 1.34-1.49 (m, 1H) 2.61-2.72 (m, 1H) 3.18-3.27 (m, 2H) 3.42-3.47 (d, 1H) 4.25 (s, 2H) 7.19-7.32 (m, 5H) 7.43-7.53 (m, 2H) 7.54-7.63 (m, 1H) 7.77-7.89 (m, 2H)

MS (m/z): 452[M+H], 434[M-OH]

Example 292: Preparation of ((1R)-1-(3-(benzamidomethyl)-5-benzyl-4,5-dihydroisoxazol-5-carboxamido)-2-phenylethyl)boronic acid Through the processes (1) and (2) below, the title compound was obtained.

(1) Preparation of 3-(benzamidomethyl)-5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

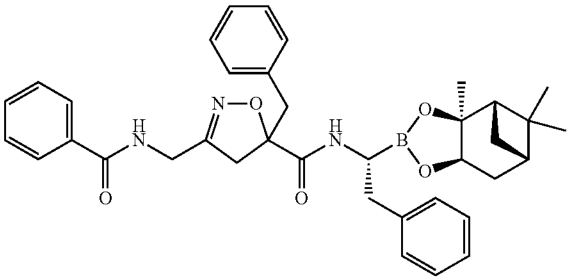 [SMILES: CC1(C)[C@@H]2C[C@H]3OB([C@H](Cc4ccccc4)NC(=O)C4(Cc5ccccc5)CC(CNC(=O)c5ccccc5)=NO4)O[C@@]3(C)[C@H]1C2]

The title compound (0.25 g, 68%) was obtained using 3-(benzamidomethyl)-5-benzyl-4,5-dihydroisoxazol-5-carboxylic acid (0.20 g, 0.59 mmol) obtained in Example 291-(2) by the method of Example 255-(1).

MS (m/z): 620[M+H]

(2) Preparation of ((1R)-1-(3-(benzamidomethyl)-5-benzyl-4,5-dihydroisoxazol-5-carboxamido)-2-phenylethyl)boronic acid

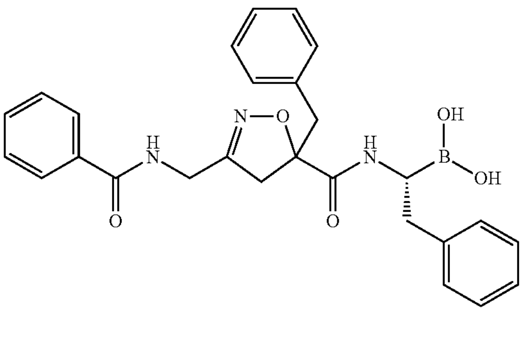 [SMILES: O=C(NCC1=NOC(Cc2ccccc2)(C(=O)N[C@@H](Cc2ccccc2)B(O)O)C1)c1ccccc1]

The title compound (0.051 g, 26%) was obtained using 3-(benzamidomethyl)-5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.25 g, 0.40 mmol) obtained in (1) above by the preparation method of Example 1-(4).

NMR: 1H NMR (400 MHz, METHANOL-d4) δ ppm 2.24-2.41 (m, 1H) 2.56-2.75 (m, 1H) 2.78-2.92 (m, 1H) 3.08-3.26 (m, 2H) 3.33-3.41 (m, 1H) 4.14-4.26 (m, 2H) 6.75-6.96 (m, 2H) 7.06-7.38 (m, 8H) 7.41-7.51 (m, 2H) 7.51-7.62 (m, 1H) 7.74-7.86 (m, 2H)

MS (m/z): 486[M+H], 468[M-OH]

Example 293: Preparation of ((1R)-1-(3-(benzamidomethyl)-5-benzyl-4,5-dihydroisoxazol-5-carboxamido)propyl)boronic acid Through the processes (1) and (2) below, the title compound was obtained.

(1) Preparation of 3-(benzamidomethyl)-5-benzyl-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

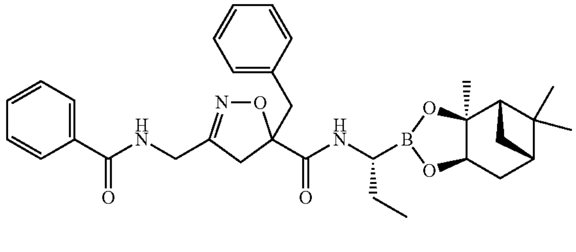 [SMILES: CC[C@H](NC(=O)C1(Cc2ccccc2)CC(CNC(=O)c2ccccc2)=NO1)B1O[C@@H]2C[C@@H]3C[C@@H](C3(C)C)[C@]2(C)O1]

The title compound (0.48 g, 59%) was obtained using 3-(benzamidomethyl)-5-benzyl-4,5-dihydroisoxazol-5-carboxylic acid (0.49 g, 1.4 mmol) obtained in Example 291-(2) by the method of Example 289-(1).

MS (m/z): 558[M+H]

(2) Preparation of ((1R)-1-(3-(benzamidomethyl)-5-benzyl-4,5-dihydroisoxazol-5-carboxamido)propyl)boronic acid

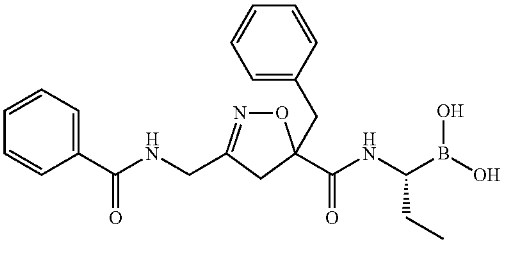 [SMILES: CC[C@H](OC(=O)C1(Cc2ccccc2)CC(CNC(=O)c2ccccc2)=NO1)B(O)O]

The title compound (0.069 g, 19%) was obtained using 3-(benzamidomethyl)-5-benzyl-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.48 g, 0.86 mmol) obtained in (1) above by the preparation method of Example 1-(4).

NMR: 1H NMR (400 MHz, METHANOL-d4) δ ppm 0.65-0.82 (m, 3H) 1.11-1.29 (m, 1H) 1.30-1.47 (m, 1H) 2.39-2.54 (m, 1H) 3.09-3.26 (m, 2H) 3.42-3.47 (d, 1H) 4.25 (s, 2H) 7.19-7.30 (m, 5H) 7.44-7.53 (m, 2H) 7.54-7.62 (m, 1H) 7.77-7.89 (m, 2H)

MS (m/z): 424[M+H], 406[M-OH]

Example 294: Preparation of ((1R)-1-(3-(benzamidomethyl)-5-benzyl-4,5-dihydroisoxazol-5-carboxamido)-2-methylpropyl)boronic acid Through the processes (1) and (2) below, the title compound was obtained.

(1) Preparation of 3-(benzamidomethyl)-5-benzyl-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

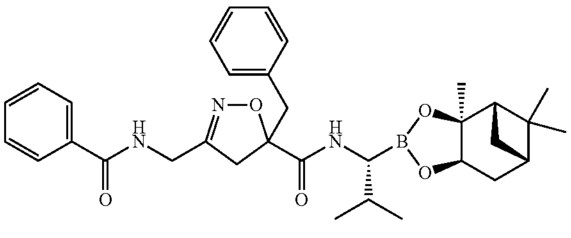 [SMILES: CC(C)[C@H](NC(=O)C1(Cc2ccccc2)CC(CNC(=O)c2ccccc2)=NO1)B1O[C@@H]2C[C@@H]3C[C@@H](C3(C)C)[C@]2(C)O1]

The title compound (0.5 g, 93%) was obtained using 3-(benzamidomethyl)-5-benzyl-4,5-dihydroisoxazol-5-carboxylic acid (0.32 g, 0.95 mmol) obtained in Example 291-(2) by the method of Example 290-(1).

MS (m/z): 572[M+H]

(2) Preparation of ((1R)-1-(3-(benzamidomethyl)-5-benzyl-4,5-dihydroisoxazol-5-carboxamido)-2-methylpropyl)boronic acid

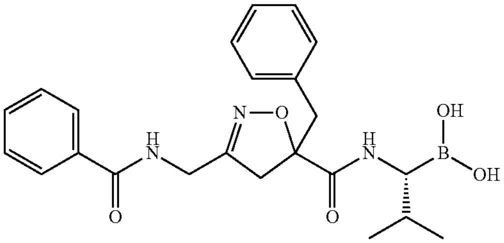 [SMILES: CC(C)[C@H](NC(=O)C1(Cc2ccccc2)CC(CNC(=O)c2ccccc2)=NO1)B(O)O]

The title compound (0.057 g, 15%) was obtained using 3-(benzamidomethyl)-5-benzyl-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.5 g, 0.87 mmol) obtained in (1) above by the preparation method of Example 1-(4).

NMR: 1H NMR (400 MHz, METHANOL-d4) δ ppm 0.61-0.68 (m, 3H) 0.76-0.83 (m, 3H) 1.55-1.69 (m, 1H) 2.41-2.46 (m, 1H) 3.13-3.27 (m, 2H) 3.31-3.47 (m, 2H) 4.19-4.25 (m, 2H) 7.19-7.28 (m, 5H) 7.44-7.50 (m, 2H) 7.51-7.58 (m, 1H) 7.76-7.85 (m, 2H)

MS (m/z): 438[M+H], 420[M-OH]

Example 295: Preparation of cyclic boronic acid ester of ((1R)-1-(3-(benzamidomethyl)-5-benzyl-4,5-dihydroisoxazol-5-carboxamido)-3-methylbutylboronic acid combined with mannitol ((1R)-1-(3-(benzamidomethyl)-5-benzyl-4,5-dihydroisoxazol-5-carboxamido)-3-methylbutylboronic acid (0,010 g, 0.022 mmol) obtained in Example 291-(4) was dissolved in tetrahydrofuran (0.44 ml), and mannitol (0.004 g, 0,023 mmol) was added thereto. Stirring was performed at room temperature for 2 hours. After finishing the reaction, the reaction solution was passed through celite. The filtrate was distilled under a reduced pressure to obtain a cyclic boronic acid ester mixture having a cyclic structure with a pentagonal, hexagonal or higher size, including (a), (b), (c), (d), and (e) below (0.012 g, 91%).

MS (m/z): 620[M+Na]

(a) 3-(benzamidomethyl)-5-benzyl-N-((1R)-1-(4,5-bis(1,2-dihydroxyethyl)-1,3,2-dioxaborolan-2-yl)-3-methylbutyl-4,5-dihydroisoxazol-5-carboxamide

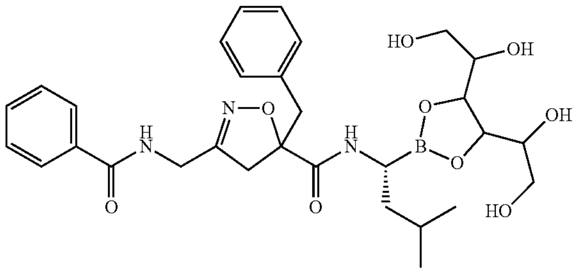 [SMILES: CC(C)C[C@H](NC(=O)C1(Cc2ccccc2)CC(CNC(=O)c2ccccc2)=NO1)B1OC(C(O)CO)C(C(O)CO)O1]

(b) 3-(benzamidomethyl)-5-benzyl-N-((1R)-1-(4-(hydroxymethyl)-5-(1,2,3-triihydroxypropyl)-1,3,2-dioxaborolan-2-yl)-3-methylbutyl-4,5-dihydroisoxazol-5-carboxamide

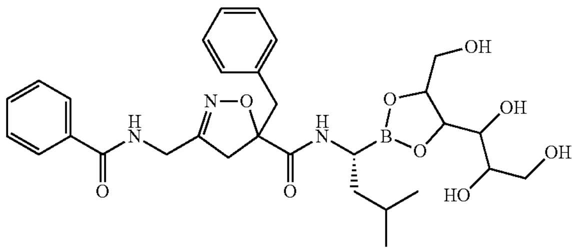 [SMILES: CC(C)C[C@H](NC(=O)C1(Cc2ccccc2)CC(CNC(=O)c2ccccc2)=NO1)B1OC(CO)C(C(O)C(O)CO)O1]

(c) 3-(benzamidomethyl)-5-benzyl-N-((1R)-3-methyl-1-(4-(1,2,3,4-tetrahydroxybutyl)-1,3,2-dioxaborolan-2-yl)butyl)-4,5-dihydroisoxazol-5-carboxamide

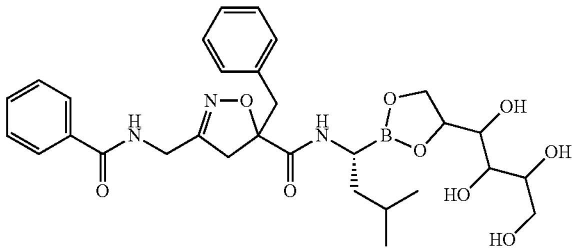 [SMILES: CC(C)C[C@H](NC(=O)C1(Cc2ccccc2)CC(CNC(=O)c2ccccc2)=NO1)B1OCC(C(O)C(O)C(O)CO)O1]

(d) 3-(benzamidomethyl)-5-benzyl-N-((1R)-1-(4-(1,2-dihydroxyethyl)-5-hydroxy-6-(hydroxymethyl)-1,3,2-dioxaborinan-2-yl)-3-methylbutyl-4,5-dihydroisoxazol-5-carboxamide

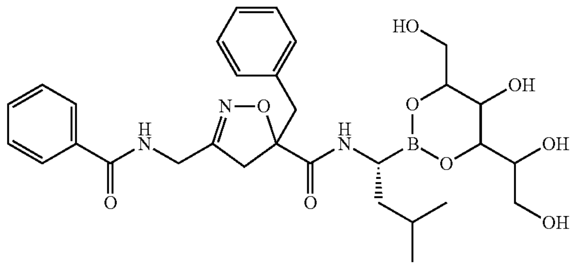 [SMILES: CC(C)C[C@H](NC(=O)C1(Cc2ccccc2)CC(CNC(=O)c2ccccc2)=NO1)B1OC(CO)C(O)C(C(O)CO)O1]

(e) 3-(benzamidomethyl)-5-benzyl-N-((1R)-1-(5-hydroxy-4-(1,2,3-triihydroxypropyl)-1,3,2-dioxaborinan-2-yl)-3-methylbutyl-4,5-dihydroisoxazol-5-carboxamide

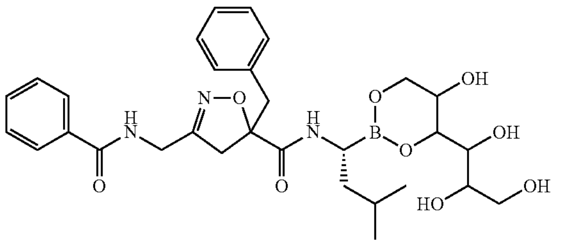 [SMILES: CC(C)C[C@H](NC(=O)C1(Cc2ccccc2)CC(CNC(=O)c2ccccc2)=NO1)B1OCC(O)C(C(O)C(O)CO)O1]

Example 296: Preparation of ((1R)-1-(5-benzyl-3-((2,5-dichlorobenzamido)methyl)-4,5-dihydroisoxazol-5-carboxamido)-2-phenylethyl)boronic acid Through the processes (1) and (2) below, the title compound was obtained.

(1) Preparation of 5-benzyl-3-((2,5-dichlorobenzamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

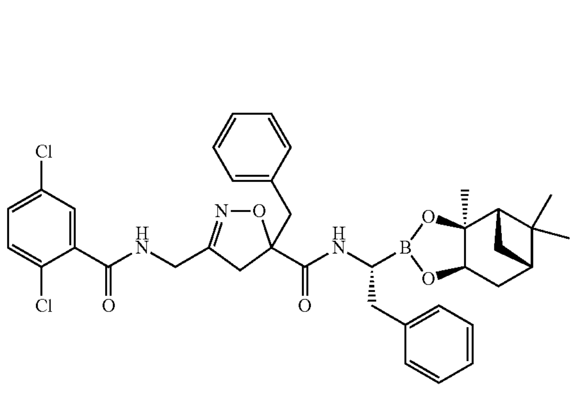 [SMILES: CC1(C)[C@@H]2C[C@H]3OB([C@H](Cc4ccccc4)NC(=O)C4(Cc5ccccc5)CC(CNC(=O)c5cc(Cl)ccc5Cl)=NO4)O[C@@]3(C)[C@H]1C2]

The title compound (0.52 g, 51%) was obtained using 5-benzyl-3-((2,5-dichlorobenzamido)methyl)-4,5-dihydroisoxazol-5-carboxylic acid (0.60 g, 1.5 mmol) obtained in Example 85-(2) by the method of Example 261-(1).

MS (m/z): 688[M+H]

(2) Preparation of ((1R)-1-(5-benzyl-3-((2,5-dichlorobenzamido)methyl)-4,5-dihydroisoxazol-5-carboxamido)-2-phenylethyl)boronic acid

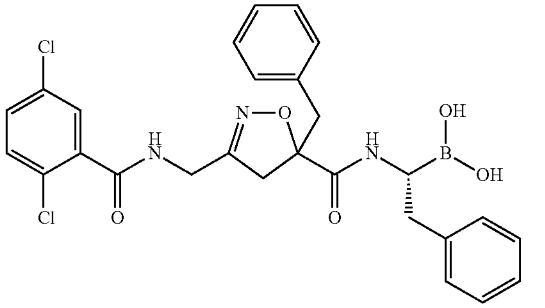 [SMILES: O=C(NCC1=NOC(Cc2ccccc2)(C(=O)N[C@@H](Cc2ccccc2)B(O)O)C1)c1cc(Cl)ccc1Cl]

The title compound (0.040 g, 34%) was obtained using 5-benzyl-3-((2,5-dichlorobenzamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.145 g, 0.21 mmol) obtained in (1) above by the preparation method of Example 1-(4).

NMR: 1H NMR (400 MHz, METHANOL-d4) δ ppm 2.32-2.48 (m, 1H) 2.70 (br dd, 1H) 2.91 (br s, 1H) 3.09-3.29 (m, 2H) 3.31-3.45 (m, 2H) 4.19 (s, 2H) 6.92 (br d, 2H) 7.08-7.22 (m, 3H) 7.32 (br s, 5H) 7.46 (s, 3H)

MS (m/z): 554[M+H], 536[M-OH]

Example 297: Preparation of ((1R)-1-(5-benzyl-3-((imidazo[1,2-a]pyridin-8-carboxamido)methyl)-4,5-dihydroisoxazol-5-carboxamido)propyl)boronic acid Through the processes (1) and (2) below, the title compound was obtained.

(1) Preparation of 5-benzyl-3-((imidazo[1,2-a]pyridin-8-carboxamido)methyl)-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

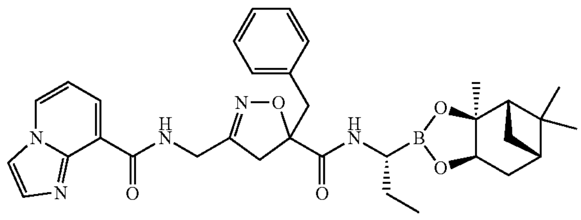 [SMILES: CC[C@H](NC(=O)C1(Cc2ccccc2)CC(CNC(=O)c2cccn3ccnc23)=NO1)B1O[C@@H]2C[C@@H]3C[C@@H](C3(C)C)[C@]2(C)O1]

5-Benzyl-3-((imidazo[1,2-a]pyridin-8-carboxamido)methyl)-4,5-dihydroisoxazol-5-carboxylic acid (0.20 g, 0.53 mmol) obtained in Example 132-(3), (R)-1-((3aS,4S,6S,7aR)-3a,5,5-trimethylhexahydro-4,6-metanobenzo[d][1,3,2]dioxaborol-2-yl)propan-1-amine hydrochloride (0.205 g, 0.75 mmol), and O-(benzotriazol-1-yl)-N,N,N',N'-tetramethyluronium tetrafluoroborate (0.22 g, 0.69 mmol) were dissolved at 0° C. in dimethylformamide (3 ml). A solution of diisopropylethylamine (0.28 ml, 1.6 mmol) dissolved in dimethylformamide (1 ml) was slowly added thereto at 0° C., and stirring was performed for 16 hours, while raising to room temperature. The solvent was distilled under a reduced pressure, a sodium bicarbonate aqueous solution was added, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.255 g, 81%).

MS (m/z): 598[M+H]

(2) Preparation of ((1R)-1-(5-benzyl-3-((imidazo[1,2-a]pyridin-8-carboxamido)methyl)-4,5-dihydroisoxazol-5-carboxamido)propyl)boronic acid

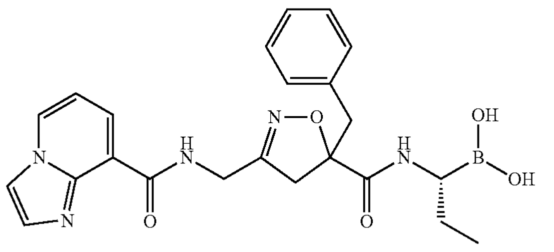 [SMILES: CC[C@H](NC(=O)C1(Cc2ccccc2)CC(CNC(=O)c2cccn3ccnc23)=NO1)B(O)O]

The title compound (0.005 g, 3%) was obtained using 5-benzyl-3-((imidazo[1,2-a]pyridin-8-carboxamido)methyl)-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.255 g, 0.43 mmol) obtained in (1) above by the preparation method of Example 1-(4).

NMR: 1H NMR (400 MHz, METHANOL-d4) δ ppm 0.72 (t, 3H) 1.19 (dt, 1H) 1.35 (br dd, 1H) 2.45 (br t, 1H) 3.13-3.26 (m, 2H) 3.46 (br d, 2H) 4.39 (s, 2H) 7.05 (t, 1H) 7.11-7.32 (m, 5H) 7.66 (d, 1H) 7.96 (d, 1H) 8.08 (dd, 1H) 8.64 (dd, 1H)

MS (m/z): 464[M+H], 446[M-OH]

Example 298: Preparation of ((1R)-1-(5-benzyl-3-((imidazo[1,2-a]pyridin-8-carboxamido)methyl)-4,5-dihydroisoxazol-5-carboxamido)-2-methylpropyl)boronic acid Through the processes (1) and (2) below, the title compound was obtained.

(1) Preparation of 5-benzyl-3-((imidazo[1,2-a]pyridin-8-carboxamido)methyl)-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

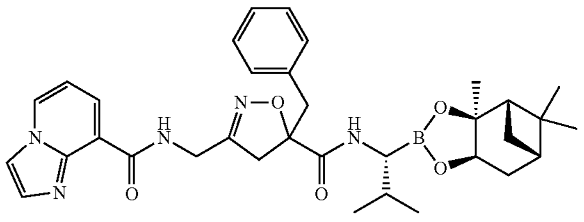 [SMILES: CC(C)[C@H](NC(=O)C1(Cc2ccccc2)CC(CNC(=O)c2cccn3ccnc23)=NO1)B1O[C@@H]2C[C@@H]3C[C@@H](C3(C)C)[C@]2(C)O1]

5-Benzyl-3-((imidazo[1,2-a]pyridin-8-carboxamido)methyl)-4,5-dihydroisoxazol-5-carboxylic acid (0.20 g, 0.53 mmol) obtained in Example 132-(3), (R)-2-methyl-1-((3aS,4S,6S,7aR)-3a,5,5-trimethylhexahydro-4,6-metanobenzo[d][1,3,2]dioxaborol-2-yl)propan-1-amine hydrochloride (0.216 g, 0.75 mmol), and O-(benzotriazol-1-yl)-N,N,N',N'-tetramethyluronium tetrafluoroborate (0.22 g, 0.69 mmol) were dissolved at 0° C. in dimethylformamide (3 ml). A solution of diisopropylethylamine (0.28 ml, 1.6 mmol) dissolved in dimethylformamide (1 ml) was slowly added thereto at 0° C., and stirring was performed for 16 hours, while raising to room temperature. The solvent was distilled under a reduced pressure, a sodium bicarbonate aqueous solution was added, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.262 g, 81%).

MS (m/z): 612[M+H]

(2) Preparation of ((1R)-1-(5-benzyl-3-((imidazo[1,2-a]pyridin-8-carboxamido)methyl)-4,5-dihydroisoxazol-5-carboxamido)-2-methylpropyl)boronic acid

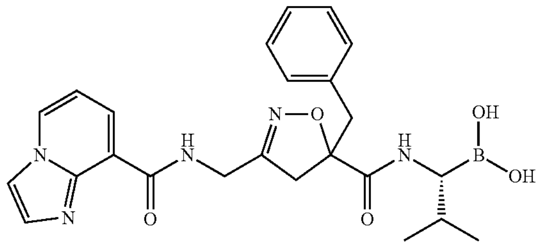 [SMILES: CC(C)[C@H](NC(=O)C1(Cc2ccccc2)CC(CNC(=O)c2cccn3ccnc23)=NO1)B(O)O]

The title compound (0.010 g, 5%) was obtained using 5-benzyl-3-((imidazo[1,2-a]pyridin-8-carboxamido)methyl)-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.262 g, 0.43 mmol) obtained in (1) above by the preparation method of Example 1-(4).

NMR: 1H NMR (400 MHz, METHANOL-d4) δ ppm 0.63 (d, 3H) 0.72-0.84 (m, 3H) 1.61 (br dd, 1H) 2.41 (d, 1H) 3.14-3.22 (m, 1H) 3.23-3.30 (m, 2H) 3.40-3.53 (m, 1H) 4.35-4.42 (m, 2H) 6.96-7.33 (m, 6H) 7.66 (s, 1H) 7.92-8.13 (m, 2H) 8.57-8.70 (m, 1H)

MS (m/z): 478[M+H], 460[M-OH]

Example 299: Preparation of ((1R)-1-(3-((1-naphthamido)methyl)-5-benzyl-4,5-dihydroisoxazol-5-carboxamido)-2-phenylethyl)boronic acid Through the processes (1) and (2) below, the title compound was obtained.

(1) Preparation of 3-((1-naphthamido)methyl)-5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

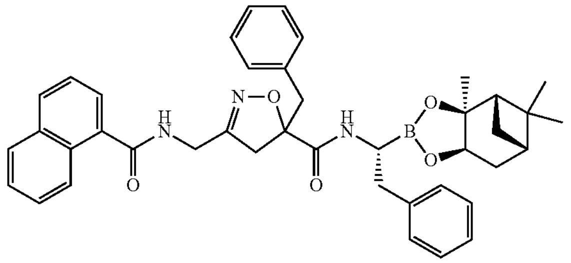

The title compound (0.30 g, 86%) was obtained using 3-((1-naphthamido)methyl)-5-benzyl-4,5-dihydroisoxazol-5-carboxylic acid (0.20 g, 0.51 mmol) obtained in Example 92-(2) by the method of Example 261-(1).

MS (m/z): 670[M+H]

(2) Preparation of ((1R)-1-(3-((1-naphthamido)methyl)-5-benzyl-4,5-dihydroisoxazol-5-carboxamido)-2-phenylethyl)boronic acid

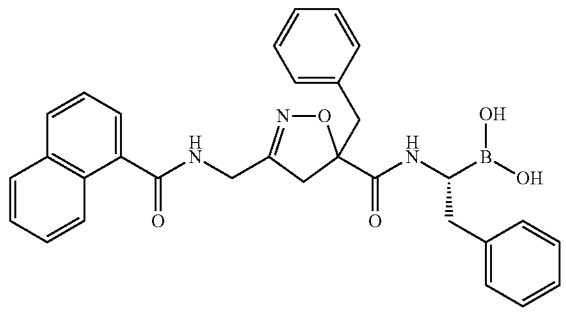 [SMILES: O=C(NCC1=NOC(Cc2ccccc2)(C(=O)N[C@@H](Cc2ccccc2)B(O)O)C1)c1cccc2ccccc12]

The title compound (0.024 g, 11%) was obtained using 3-((1-naphthamido)methyl)-5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.27 g, 0.40 mmol) obtained in (1) above by the preparation method of Example 1-(4).

NMR: 1H NMR (400 MHz, METHANOL-d4) δ ppm 2.29-2.43 (m, 1H) 2.62-2.77 (m, 1H) 2.83-2.97 (m, 1H) 3.13-3.30 (m, 2H) 3.40-3.53 (m, 1H) 4.29 (s, 2H) 6.81-6.97 (m, 2H) 7.05-7.22 (m, 3H) 7.22-7.39 (m, 5H) 7.45-7.67 (m, 4H) 7.89-7.94 (m, 1H) 7.97-8.01 (m, 1H) 8.14-8.27 (m, 1H)

MS (m/z): 536[M+H], 518[M-OH]

Example 300: Preparation of ((1R)-1-(5-benzyl-3-((imidazo[1,2-a]pyridin-8-carboxamido)methyl)-4,5-dihydroisoxazol-5-carboxamido)-2-phenylethyl) boronic acid Through the processes (1) and (2) below, the title compound was obtained.

(1) Preparation of 5-benzyl-3-((imidazo[1,2-a]pyridin-8-carboxamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

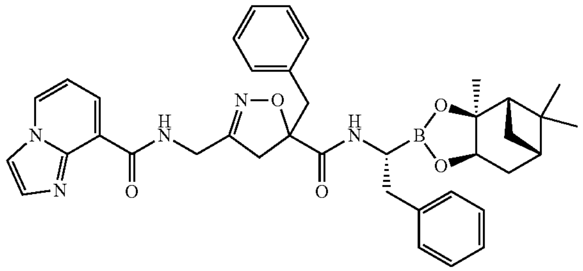

The title compound (0.35 g, quant.) was obtained using 5-benzyl-3-((imidazo[1,2-a]pyridin-8-carboxamido) methyl)-4,5-dihydroisoxazol-5-carboxylic acid (0.20 g, 0.0 mmol) obtained in Example 132-(3) by the method of Example 261-(1).

MS (m/z): 660[M+H]

(2) Preparation of ((1R)-1-(5-benzyl-3-((imidazo[1,2-a]pyridin-8-carboxamido)methyl)-4,5-dihydroisoxazol-5-carboxamido)-2-phenylethyl)boronic acid

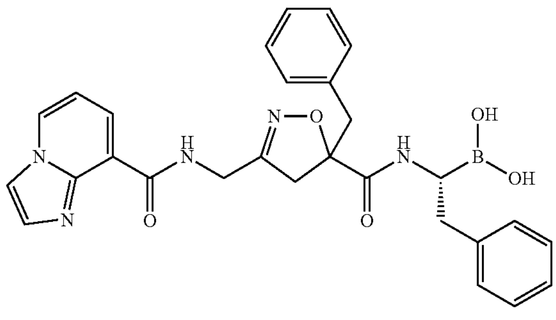 [SMILES: O=C(NCC1=NOC(Cc2ccccc2)(C(=O)N[C@@H](Cc2ccccc2)B(O)O)C1)c1cccn2ccnc12]

The title compound (0.008 g, 3%) was obtained using 5-benzyl-3-((imidazo[1,2-a]pyridin-8-carboxamido) methyl)-N—((R)-2-phenyl-1-((3aS,4S,6S,7aR)-3a,5,5-trimethylhexahydro-4,6-metanobenzo[d][1,3,2]dioxaborol-2-yl) ethyl)-4,5-dihydroisoxazol-5-carboxamide (0.35 g, 0.54 mmol) obtained in (1) above by the preparation method of Example 1-(4).

NMR: 1H NMR (400 MHz, METHANOL-d4) δ ppm 2.33 (br s, 1H) 2.60-2.75 (m, 1H) 2.78-2.95 (m, 1H) 3.08-3.23 (m, 2H) 4.36 (br s, 2H) 4.58 (s, 8H) 6.88 (br d, 2H) 6.96-7.43 (m, 11H) 7.65 (d, 1H) 7.95 (d, 1H) 8.07 (dd, 1H) 8.63 (dd, 1H)

MS (m/z): 526[M+H], 508[M-OH].

Example 301: Preparation of ((1R)-1-(5-benzyl-3-((imidazo[1,2-a]pyridin-5-carboxamido)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((imidazo[1,2-a]pyridin-5-carboxamido)methyl)-4,5-dihydroisoxazol-5-carboxylate

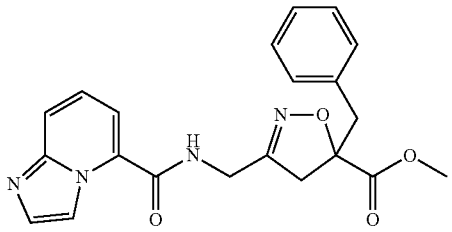 [SMILES: COC(=O)C1(Cc2ccccc2)CC(CNC(=O)c2cccc3nccn23)=NO1]

The title compound (0.84 g, 61%) was obtained using methyl 3-(aminomethyl)-5-benzyl-4,5-dihydroisoxazol-5-carboxylate hydrochloride (1.0 g, 3.5 mmol) obtained in Example 84-(1) and imidazo[1,2-a]pyridin-5-carboxylic acid (0.63 g, 3.9 mmol) by the preparation method of Example 84-(2).

MS (m/z): 393[M+H]

(2) Preparation of 5-benzyl-3-((imidazo[1,2-a]pyridin-5-carboxamido)methyl)-4,5-dihydroisoxazol-5-carboxylic acid

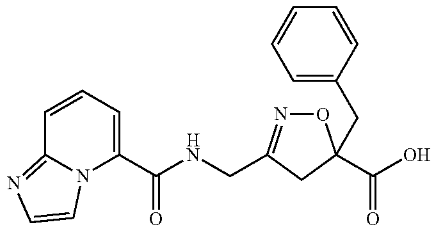 [SMILES: O=C(NCC1=NOC(Cc2ccccc2)(C(=O)O)C1)c1cccc2nccn12]

The title compound (0.81 g, quant.) was obtained using methyl 5-benzyl-3-((imidazo[1,2-a]pyridin-5-carboxamido) methyl)-4,5-dihydroisoxazol-5-carboxylate (0.84 g, 2.14 mmol) obtained in (1) above by the preparation method of Example 84-(3).

MS (m/z): 379[M+H]

(3) Preparation of 5-benzyl-3-((imidazo[1,2-a]pyridin-5-carboxamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

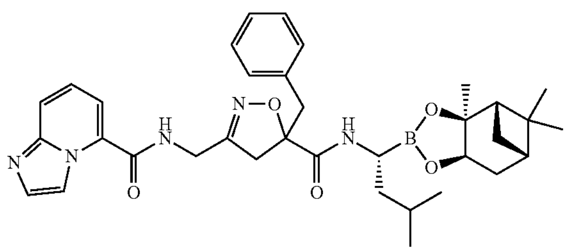 [SMILES: CC(C)C[C@H](NC(=O)C1(Cc2ccccc2)CC(CNC(=O)c2cccc3nccn23)=NO1)B1O[C@@H]2C[C@@H]3C[C@@H](C3(C)C)[C@]2(C)O1]

The title compound (0.49 g, quant.) was obtained using 5-benzyl-3-((imidazo[1,2-a]pyridin-5-carboxamido) methyl)-4,5-dihydroisoxazol-5-carboxylic acid (0.30 g, 0.79 mmol) obtained in (2) above by the preparation method of Example 84-(4).

MS (m/z): 626[M+H]

(4) Preparation of ((1R)-1-(5-benzyl-3-((imidazo[1,2-a]pyridin-5-carboxamido)methyl)-4,5-dihydroisoxazol-5-carboxamido)-3-methylbutylboronic acid

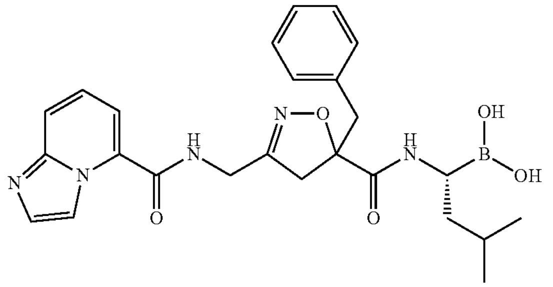 [SMILES: CC(C)C[C@H](NC(=O)C1(Cc2ccccc2)CC(CNC(=O)c2cccc3nccn23)=NO1)B(O)O]

The title compound (0.019 g, 5%) was obtained using 5-benzyl-3-((imidazo[1,2-a]pyridin-5-carboxamido) methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.49 g, 0.78 mmol) obtained in (3) above by the preparation method of Example 1-(4).

NMR: 1H NMR (400 MHz, METHANOL-d4) δ ppm 0.76-0.83 (m, 6H) 1.00-1.26 (m, 2H) 1.34-1.45 (m, 1H) 2.63-2.79 (m, 1H) 3.10-3.29 (m, 2H) 3.32-3.53 (m, 2H) 4.22-4.34 (m, 2H) 7.16-7.29 (m, 5H) 7.36-7.44 (m, 2H) 7.65-7.71 (m, 1H) 7.74-7.81 (m, 1H) 8.50-8.57 (m, 1H)

MS (m/z): 492[M+H], 474[M-OH]

Example 302: Preparation of ((1R)-1-(5-benzyl-3-((imidazo[1,2-a]pyridin-5-carboxamido)methyl)-4,5-dihydroisoxazol-5-carboxamido)-2-phenylethyl) boronic acid Through the processes (1) and (2) below, the title compound was obtained.

(1) Preparation of 5-benzyl-3-((imidazo[1,2-a]pyridin-5-carboxamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

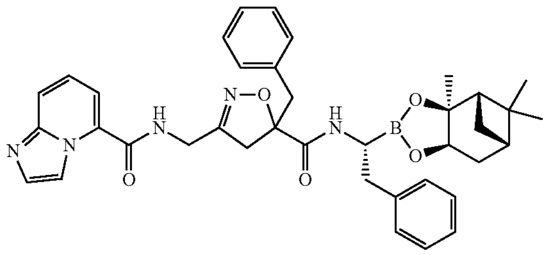 [SMILES: CC1(C)[C@@H]2C[C@H]3OB([C@H](Cc4ccccc4)NC(=O)C4(Cc5ccccc5)CC(CNC(=O)c5cccc6nccn56)=NO4)O[C@@]3(C)[C@H]1C2]

5-Benzyl-3-((imidazo[1,2-a]pyridin-5-carboxamido) methyl)-4,5-dihydroisoxazol-5-carboxylic acid (0.30 g, 0.79 mmol) obtained in Example 301-(2), (R)-2-phenyl-1-((3aS,4S,6S,7aR)-3a,5,5-trimethylhexahydro-4,6-metanobenzo[d][1,3,2]dioxaborol-2-yl)ethan-1-amine hydrochloride (0.378 g, 1.13 mmol), and O-(benzotriazol-1-yl)-N,N,N',N'-tetramethyluronium tetrafluoroborate (0.33 g, 1.03 mmol) were dissolved at 0° C. in dimethylformamide (3 ml). A solution of diisopropylethylamine (0.41 ml, 2.38 mmol) dissolved in dimethylformamide (1 ml) was slowly added thereto at 0° C., and stirring was performed for 16 hours, while raising to room temperature. The solvent was distilled under a reduced pressure, a sodium bicarbonate aqueous solution was added, and extraction with ethyl acetate was performed twice. The organic layer thus extracted was washed with brine, dried over anhydrous magnesium sulfate, and filtered. The filtrate was distilled under a reduced pressure and separated by column chromatography to obtain the title compound (0.40 g, 76%).

MS (m/z): 660[M+H]

(2) Preparation of ((1R)-1-(5-benzyl-3-((imidazo[1,2-a]pyridin-5-carboxamido)methyl)-4,5-dihydroisoxazol-5-carboxamido)-2-phenylethyl)boronic acid

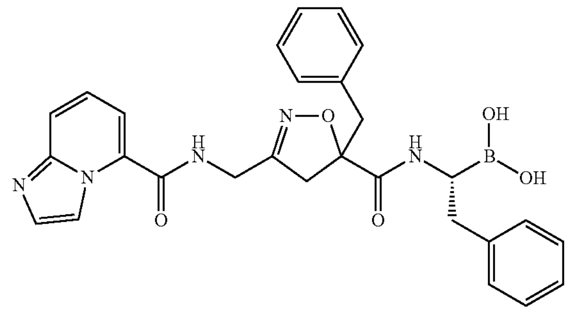 [SMILES: O=C(NCC1=NOC(Cc2ccccc2)(C(=O)N[C@@H](Cc2ccccc2)B(O)O)C1)c1cccc2nccn12]

The title compound (0.014 g, 4%) was obtained using 5-benzyl-3-((imidazo[1,2-a]pyridin-5-carboxamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.40 g, 0.61 mmol) obtained in (1) above by the preparation method of Example 1-(4).

NMR: 1H NMR (400 MHz, METHANOL-d4) δ ppm 2.32-2.49 (m, 1H) 2.64-2.79 (m, 1H) 2.85-3.02 (m, 1H) 3.11-3.28 (m, 2H) 3.32-3.43 (m, 2H) 4.20-4.29 (m, 2H) 6.88-6.96 (m, 2H) 7.07-7.14 (m, 1H) 7.15-7.20 (m, 2H) 7.21-7.33 (m, 5H) 7.36-7.43 (m, 2H) 7.65-7.71 (m, 1H) 7.73-7.80 (m, 1H) 8.50-8.56 (m, 1H)

MS (m/z): 526[M+H], 508[M-OH]

Example 303: Preparation of ((1R)-1-(3-((1-naphthamido)methyl)-5-benzyl-4,5-dihydroisoxazol-5-carboxamido)propyl)boronic acid Through the processes (1) and (2) below, the title compound was obtained.

(1) Preparation of 3-((1-naphthamido)methyl)-5-benzyl-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

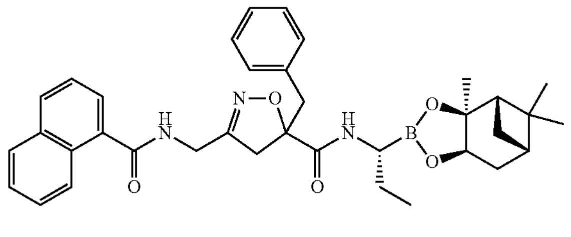 [SMILES: CC[C@H](NC(=O)C1(Cc2ccccc2)CC(CNC(=O)c2cccc3ccccc23)=NO1)B1O[C@@H]2C[C@@H]3C[C@@H](C3(C)C)[C@]2(C)O1]

The title compound (0.50 g, 66%) was obtained using 3-((1-naphthamido)methyl)-5-benzyl-4,5-dihydroisoxazol-5-carboxylic acid (0.48 g, 1.24 mmol) obtained in Example 92-(2) by the method of Example 289-(1).

MS (m/z): 608[M+H]

(2) Preparation of ((1R)-1-(3-((1-naphthamido)methyl)-5-benzyl-4,5-dihydroisoxazol-5-carboxamido)propyl)boronic acid

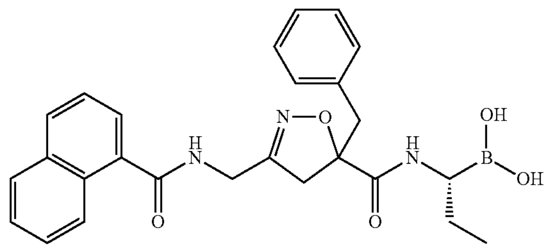 [SMILES: CC[C@H](NC(=O)C1(Cc2ccccc2)CC(CNC(=O)c2cccc3ccccc23)=NO1)B(O)O]

The title compound (0.092 g, 49%) was obtained using 3-((1-naphthamido)methyl)-5-benzyl-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.24 g, 0.39 mmol) obtained in (1) above by the preparation method of Example 1-(4).

NMR: 1H NMR (400 MHz, METHANOL-d4) δ ppm 0.56-0.84 (m, 3H) 1.12-1.28 (m, 1H) 1.30-1.45 (m, 1H) 2.28-2.68 (m, 1H) 3.17-3.29 (m, 2H) 3.34-3.39 (m, 1H) 3.41-3.62 (d, 1H) 4.31 (s, 2H) 7.03-7.34 (m, 5H) 7.44-7.70 (m, 4H) 7.88-8.03 (m, 2H) 8.11-8.33 (m, 1H)

MS (m/z): 474[M+H], 456[M-OH]

Example 304: Preparation of ((1R)-1-(3-((1-naphthamido)methyl)-5-benzyl-4,5-dihydroisoxazol-5-carboxamido)-2-methylpropyl)boronic acid Through the processes (1) and (2) below, the title compound was obtained.

(1) Preparation of 3-((1-naphthamido)methyl)-5-benzyl-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

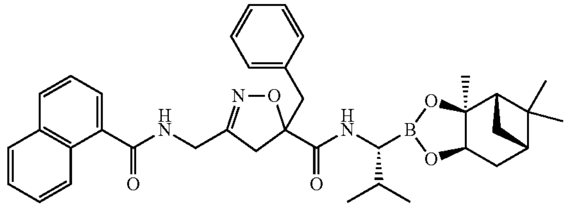

The title compound (0.35 g, 71%) was obtained using 3-((1-naphthamido)methyl)-5-benzyl-4,5-dihydroisoxazol-5-carboxylic acid (0.31 g, 0.80 mmol) obtained in Example 92-(2) by the method of Example 290-(1).

MS (m/z): 622[M+H]

(2) Preparation of ((1R)-1-(3-((1-naphthamido)methyl)-5-benzyl-4,5-dihydroisoxazol-5-carboxamido)-2-methylpropyl)boronic acid

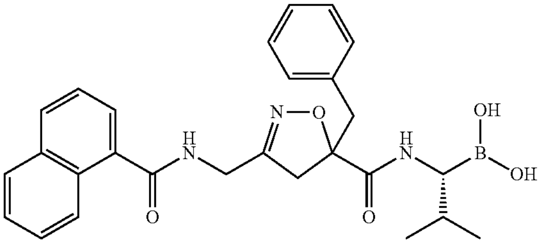 [SMILES: CC(C)[C@H](NC(=O)C1(Cc2ccccc2)CC(CNC(=O)c2cccc3ccccc23)=NO1)B(O)O]

The title compound (0.022 g, 8%) was obtained using 3-((1-naphthamido)methyl)-5-benzyl-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.35 g, 0.57 mmol) obtained in (1) above by the preparation method of Example 1-(4).

NMR: 1H NMR (400 MHz, METHANOL-d4) δ ppm 0.67 (d, 3H) 0.81 (d, 3H) 1.64 (br dd, 1H) 2.46 (d, 1H) 3.09-3.18 (m, 1H) 3.18-3.29 (m, 1H) 3.37 (s, 1H) 3.44-3.59 (m, 1H) 4.23-4.37 (m, 2H) 7.14-7.36 (m, 5H) 7.44-7.68 (m, 4H) 7.86-8.07 (m, 2H) 8.17-8.31 (m, 1H)

MS (m/z): 488[M+H], 470[M-OH]

Example 305: Preparation of ((1R)-1-(3-(([1,2,4]triazolo[4,3-a]pyridin-8-carboxamido)methyl)-5-benzyl-4,5-dihydroisoxazol-5-carboxamido)-3-methylbutylboronic acid Through the processes (1), (2), (3) and (4) below, the title compound was obtained.

(1) Preparation of methyl 3-(([1,2,4]triazolo[4,3-a]pyridin-8-carboxamido)methyl)-5-benzyl-4,5-dihydroisoxazol-5-carboxylate

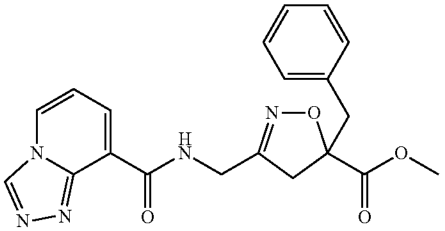 [SMILES: COC(=O)C1(Cc2ccccc2)CC(CNC(=O)c2cccn3cnnc23)=NO1]

The title compound (0.50 g, 72%) was obtained using methyl 3-(aminomethyl)-5-benzyl-4,5-dihydroisoxazol-5-carboxylate hydrochloride (0.50 g, 1.8 mmol) obtained in Example 84-(1) and [1,2,4]triazolo[4,3-a]pyridin-8-carboxylic acid (0.32 g, 1.9 mmol) by the preparation method of Example 84-(2).

MS (m/z): 394[M+H]

(2) Preparation of 3-(([1,2,4]triazolo[4,3-a]pyridin-8-carboxamido)methyl)-5-benzyl-4,5-dihydroisoxazol-5-carboxylic acid

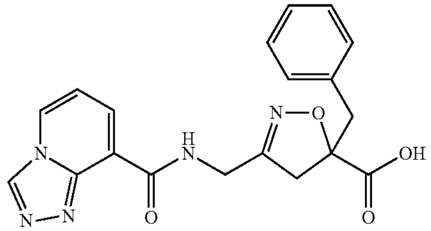 [SMILES: O=C(NCC1=NOC(Cc2ccccc2)(C(=O)O)C1)c1cccn2cnnc12]

The title compound (0.49 g, 83%) was obtained using methyl 3-(([1,2,4]triazolo[4,3-a]pyridin-8-carboxamido)methyl)-5-benzyl-4,5-dihydroisoxazol-5-carboxylate (0.50 g, 1.27 mmol) obtained in (1) above by the preparation method of Example 84-(3).

MS (m/z): 380[M+H]

(3) Preparation of 3-(([1,2,4]triazolo[4,3-a]pyridin-8-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

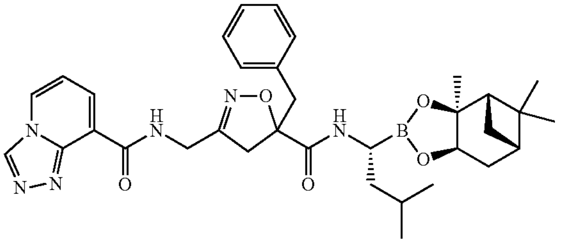 [SMILES: CC(C)C[C@H](NC(=O)C1(Cc2ccccc2)CC(CNC(=O)c2cccn3cnnc23)=NO1)B1O[C@@H]2C[C@@H]3C[C@@H](C3(C)C)[C@]2(C)O1]

The title compound (0.11 g, 35%) was obtained using 3-(([1,2,4]triazolo[4,3-a]pyridin-8-carboxamido)methyl)-5-benzyl-4,5-dihydroisoxazol-5-carboxylic acid (0.19 g, 0.50 mmol) obtained in (2) above by the method of Example 256-(3).

MS (m/z): 627[M+H]

(4) Preparation of ((1R)-1-(3-(([1,2,4]triazolo[4,3-a]pyridin-8-carboxamido)methyl)-5-benzyl-4,5-dihydroisoxazol-5-carboxamido)-3-methylbutylboronic acid

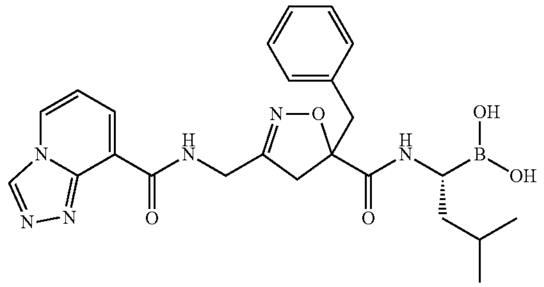 [SMILES: CC(C)C[C@H](NC(=O)C1(Cc2ccccc2)CC(CNC(=O)c2cccn3cnnc23)=NO1)B(O)O]

The title compound (0.032 g, 37%) was obtained using 3-(([1,2,4]triazolo[4,3-a]pyridin-8-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.11 g, 0.18 mmol) obtained in (3) above by the preparation method of Example 1-(4).

NMR: 1H NMR (400 MHz, METHANOL-d4) δ ppm 0.76-0.82 (m, 6H) 1.00-1.19 (m, 2H) 1.33-1.44 (m, 1H) 2.61-2.72 (m, 1H) 3.16-3.29 (m, 2H) 3.42-3.52 (m, 1H) 4.38-4.44 (m, 2H) 4.60-4.62 (m, 1H) 7.13-7.27 (m, 5H) 7.33-7.40 (m, 1H) 8.38-8.43 (m, 1H) 8.50-8.54 (m, 1H) 8.97-9.02 (m, 1H)

MS (m/z): 4931[M+H], 475[M-OH]

Example 306: Preparation of ((1R)-1-(3-(([1,2,4]triazolo[4,3-a]pyridin-8-carboxamido)methyl)-5-benzyl-4,5-dihydroisoxazol-5-carboxamido)-2-phenylethyl)boronic acid Through the processes (1) and (2) below, the title compound was obtained.

(1) Preparation of 3-(([1,2,4]triazolo[4,3-a]pyridin-8-carboxamido)methyl)-5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

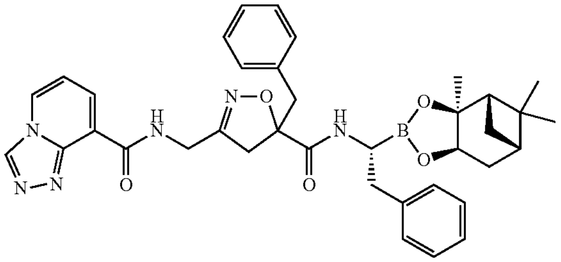 [SMILES: CC1(C)[C@@H]2C[C@H]3OB([C@H](Cc4ccccc4)NC(=O)C4(Cc5ccccc5)CC(CNC(=O)c5cccn6cnnc56)=NO4)O[C@@]3(C)[C@H]1C2]

The title compound (0.13 g, 37%) was obtained using 3-(([1,2,4]triazolo[4,3-a]pyridin-8-carboxamido)methyl)-5-benzyl-4,5-dihydroisoxazol-5-carboxylic acid (0.20 g, 0.53 mmol) obtained in Example 305-(2) by the method of Example 261-(1).

MS (m/z): 661[M+H]

(2) Preparation of ((1R)-1-(3-(([1,2,4]triazolo[4,3-a]pyridin-8-carboxamido)methyl)-5-benzyl-4,5-dihydroisoxazol-5-carboxamido)-2-phenylethyl)boronic acid

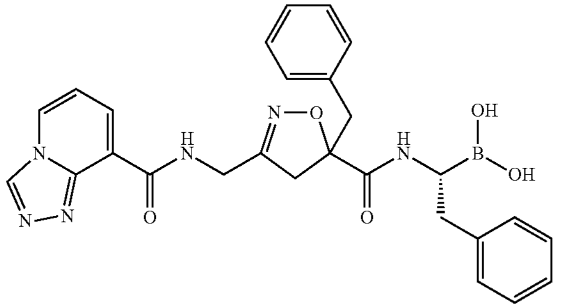 [SMILES: O=C(NCC1=NOC(Cc2ccccc2)(C(=O)N[C@@H](Cc2ccccc2)B(O)O)C1)c1cccn2cnnc12]

The title compound (0.031 g, 30%) was obtained using 3-(([1,2,4]triazolo[4,3-a]pyridin-8-carboxamido)methyl)-5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.13 g, 0.20 mmol) obtained in (1) above by the preparation method of Example 1-(4).

NMR: 1H NMR (400 MHz, METHANOL-d4) δ ppm 2.29-2.45 (m, 1H) 2.63-2.77 (m, 1H) 2.86-2.94 (m, 1H) 3.10-3.28 (m, 2H) 3.39-3.52 (m, 1H) 4.40 (s, 2H) 6.86-6.96 (m, 2H) 7.14-7.42 (m, 9H) 8.35-8.47 (m, 1H) 8.49-8.58 (m, 1H) 8.94-9.08 (m, 1H)

MS (m/z): 527[M+H], 509[M-OH]

Example 307: Preparation of ((1R)-1-(5-benzyl-3-((3-methylbenzamido)methyl)-4,5-dihydroisoxazol-5-carboxamido)-3-methylbutylboronic acid Through the processes (1), (2) and (3) below, the title compound was obtained.

(1) Preparation of methyl 5-benzyl-3-((3-methylbenzamido)methyl)-4,5-dihydroisoxazol-5-carboxylate

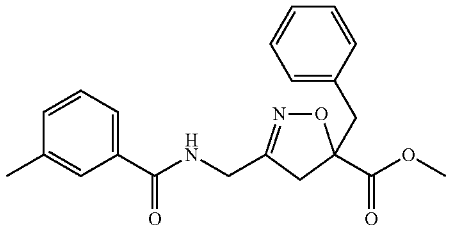

The title compound (0.50 g, 77%) was obtained using methyl 3-(aminomethyl)-5-benzyl-4,5-dihydroisoxazol-5-carboxylate hydrochloride (0.50 g, 1.8 mmol) obtained in Example 84-(1) and 3-methylbenzoic acid (0.26 g, 1.9 mmol) by the preparation method of Example 84-(2).

MS (m/z): 367[M+H]

(2) Preparation of 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-methylbenzamido)methyl)-4,5-dihydroisoxazol-5-carboxamide

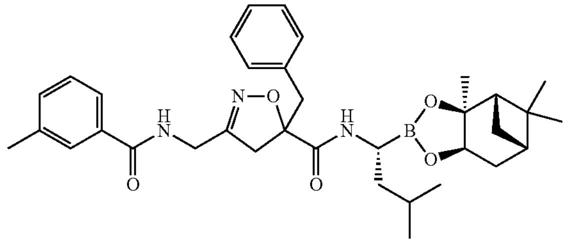

The title compound (0.52 g, 64%, 2 steps) was obtained using methyl 5-benzyl-3-((3-methylbenzamido)methyl)-4,5-dihydroisoxazol-5-carboxylate (0.50 g, 1.36 mmol) obtained in (1) above by the preparation methods of Example 84-(3) and Example 256-(3).

MS (m/z): 600[M+H]

(3) Preparation of ((1R)-1-(5-benzyl-3-((3-methylbenzamido)methyl)-4,5-dihydroisoxazol-5-carboxamido)-3-methylbutylboronic acid

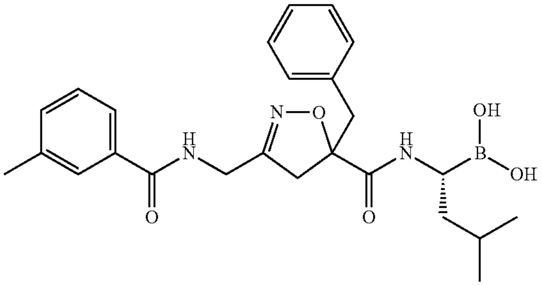 [SMILES: Cc1cccc(C(=O)NCC2=NOC(Cc3ccccc3)(C(=O)N[C@@H](CC(C)C)B(O)O)C2)c1]

The title compound (0.139 g, 34%) was obtained using 5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-3-((3-methylbenzamido)methyl)-4,5-dihydroisoxazol-5-carboxamide (0.52 g, 0.87 mmol) obtained in (3) above by the preparation method of Example 1-(4).

NMR: 1H NMR (400 MHz, METHANOL-d4) δ ppm 0.69-0.83 (m, 6H) 0.99-1.09 (m, 1H) 1.10-1.21 (m, 1H) 1.22-1.52 (m, 2H) 2.30-2.49 (m, 3H) 2.61-2.69 (m, 1H) 3.15-3.29 (m, 2H) 3.38-3.47 (d, 1H) 4.22 (s, 2H) 7.16-7.29 (m, 5H) 7.30-7.45 (m, 2H) 7.56-7.69 (m, 2H)

MS (m/z): 466[M+H], 448[M-OH]

Example 308: Preparation of ((1R)-1-(5-benzyl-3-((6-chloropicolinamido)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((6-chloropicolinamido)methyl)-4,5-dihydroisoxazol-5-carboxylate

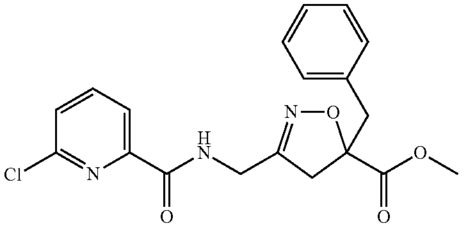 [SMILES: COC(=O)C1(Cc2ccccc2)CC(CNC(=O)c2cccc(Cl)n2)=NO1]

The title compound (0.69 g, 51%) was obtained using methyl 3-(aminomethyl)-5-benzyl-4,5-dihydroisoxazol-5-carboxylate hydrochloride (1.0 g, 3.5 mmol) obtained in Example 84-(1) and 6-chloropicolinic acid (0.61 g, 3.9 mmol) by the preparation method of Example 84-(2).

MS (m/z): 388[M+H]

(2) Preparation of 5-benzyl-3-((6-chloropicolinamido)methyl)-4,5-dihydroisoxazol-5-carboxylic acid

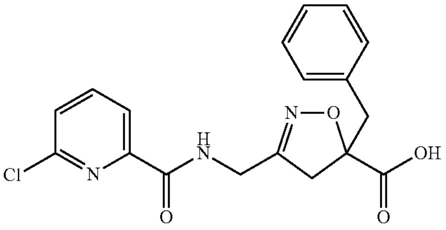 [SMILES: O=C(NCC1=NOC(Cc2ccccc2)(C(=O)O)C1)c1cccc(Cl)n1]

The title compound (0.60 g, 90%) was obtained using methyl 5-benzyl-3-((6-chloropicolinamido)methyl)-4,5-dihydroisoxazol-5-carboxylate (0.69 g, 1.77 mmol) obtained in (1) above by the preparation method of Example 84-(3).

MS (m/z): 374[M+H]

(3) Preparation of 5-benzyl-3-((6-chloropicolinamido)methyl)-N—((R)-3-methyl-1-((3aS,4S,6S,7aR)-3a,5,5-trimethylhexahydro-4,6-metanobenzo[d][1,3,2]dioaborol-2-yl)butyl)-4,5-dihydroisoxazol-5-carboxamide

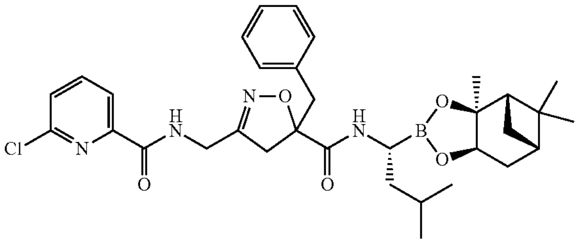 [SMILES: CC(C)C[C@H](NC(=O)C1(Cc2ccccc2)CC(CNC(=O)c2cccc(Cl)n2)=NO1)B1O[C@@H]2C[C@@H]3C[C@@H](C3(C)C)[C@]2(C)O1]

The title compound (0.15 g, 23%) was obtained using 5-benzyl-3-((6-chloropicolinamido)methyl)-4,5-dihydroisoxazol-5-carboxylic acid (0.40 g, 1.1 mmol) obtained in (2) above by the preparation method of Example 256-(3).

MS (m/z): 621[M+H]

(4) Preparation of ((1R)-1-(5-benzyl-3-((6-chloropicolinamido)methyl)-4,5-dihydroisoxazol-5-carboxamido)-3-methylbutylboronic acid

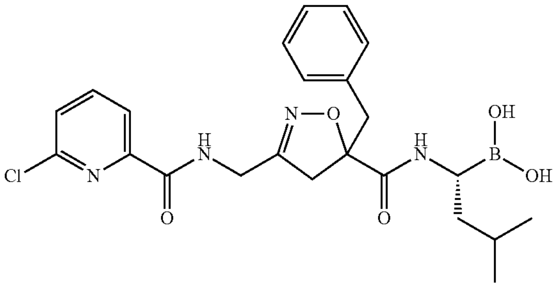 [SMILES: CC(C)C[C@H](NC(=O)C1(Cc2ccccc2)CC(CNC(=O)c2cccc(Cl)n2)=NO1)B(O)O]

The title compound (0.025 g, 21%) was obtained using 5-benzyl-3-((6-chloropicolinamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.15 g, 0.024 mmol) obtained in (3) above by the preparation method of Example 1-(4).

NMR: 1H NMR (400 MHz, METHANOL-d4) δ ppm 0.72-0.86 (m, 6H) 0.97-1.09 (m, 1H) 1.11-1.21 (m, 1H) 1.30-1.44 (m, 2H) 2.55-2.75 (m, 1H) 3.15-3.28 (m, 2H) 3.35-3.56 (d, 1H) 4.25 (s, 2H) 7.03-7.39 (m, 5H) 7.57-7.78 (m, 1H) 7.86-8.17 (m, 2H)

MS (m/z): 487[M+H], 469[M-OH]

Example 309: Preparation of cyclic boronic acid ester of ((1R)-1-(5-benzyl-3-((6-chloropicolinamido)methyl)-4,5-dihydroisoxazol-5-carboxamido)-3-methylbutylboronic acid combined with mannitol A cyclic boronic acid ester mixture with a size of pentagonal, hexagonal, or higher, including (a), (b), (c), (d) and (e) below (0.012 g, 95%), was obtained using ((1R)-1-(5-benzyl-3-((6-chloropicolinamido)methyl)-4,5-dihydroisoxazol-5-carboxamido)-3-methylbutylboronic acid (0.010 g, 0.020 mmol) obtained in Example 308-(4) by the method of Example 295.

MS (m/z): 655[M+Na]

(a) 5-benzyl-N-((1R)-1-(4,5-bis(1,2-dihydroxyethyl)-1,3,2-dioxaborolan-2-yl)-3-methylbutyl-3-((6-chloropicolinamido)methyl)-4,5-dihydroisoxazol-5-carboxamide

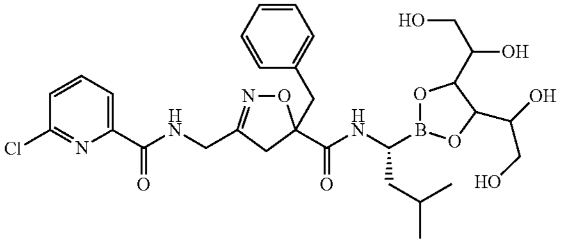 [SMILES: CC(C)C[C@H](NC(=O)C1(Cc2ccccc2)CC(CNC(=O)c2cccc(Cl)n2)=NO1)B1OC(C(O)CO)C(C(O)CO)O1]

(b) 5-benzyl-3-((6-chloropicolinamido)methyl)-N-((1R)-1-(4-(hydroxymethyl)-5-(1,2,3-trihydroxypropyl)-1,3,2-dioxaborolan-2-yl)-3-methylbutyl-4,5-dihydroisoxazol-5-carboxamide

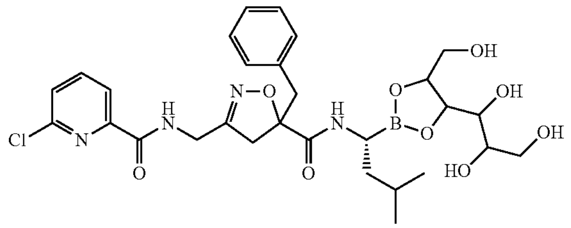 [SMILES: CC(C)C[C@H](NC(=O)C1(Cc2ccccc2)CC(CNC(=O)c2cccc(Cl)n2)=NO1)B1OC(CO)C(C(O)C(O)CO)O1]

(c) 5-benzyl-3-((6-chloropicolinamido)methyl)-N-((1R)-3-methyl-1-(4-(1,2,3,4-tetrahydroxybutyl)-1,3,2-dioxaborolan-2-yl)butyl)-4,5-dihydroisoxazol-5-carboxamide

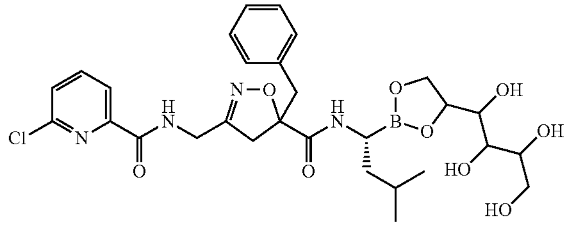 [SMILES: CC(C)C[C@H](NC(=O)C1(Cc2ccccc2)CC(CNC(=O)c2cccc(Cl)n2)=NO1)B1OCC(C(O)C(O)C(O)CO)O1]

(d) 5-benzyl-3-((6-chloropicolinamido)methyl)-N-((1R)-1-(4-(1,2-dihydroxyethyl)-5-hydroxy-6-(hydroxymethyl)-1,3,2-dioxaborinan-2-yl)-3-methylbutyl-4,5-dihydroisoxazol-5-carboxamide

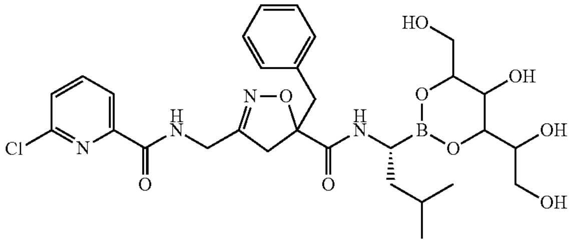 [SMILES: CC(C)C[C@H](NC(=O)C1(Cc2ccccc2)CC(CNC(=O)c2cccc(Cl)n2)=NO1)B1OC(CO)C(O)C(C(O)CO)O1]

(e) 5-benzyl-3-((6-chloropicolinamido)methyl)-N-((1R)-1-(5-hydroxy-4-(1,2,3-triihydroxypropyl)-1,3,2-dioxaborinan-2-yl)-3-methylbutyl-4,5-dihydroisoxazol-5-carboxamide

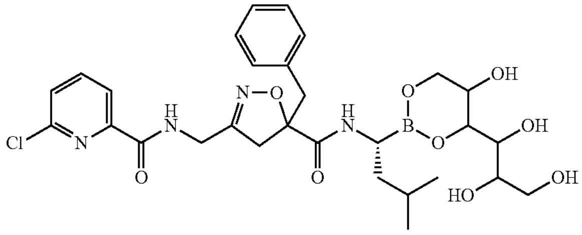 [SMILES: CC(C)C[C@H](NC(=O)C1(Cc2ccccc2)CC(CNC(=O)c2cccc(Cl)n2)=NO1)B1OCC(O)C(C(O)C(O)CO)O1]

Example 310: Preparation of ((1R)-1-(5-benzyl-3-((6-chloropicolinamido)methyl)-4,5-dihydroisoxazol-5-carboxamido)-2-phenylethyl)boronic acid Through the processes (1) and (2) below, the title compound was obtained.

(1) Preparation of 5-benzyl-3-((6-chloropicolinamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

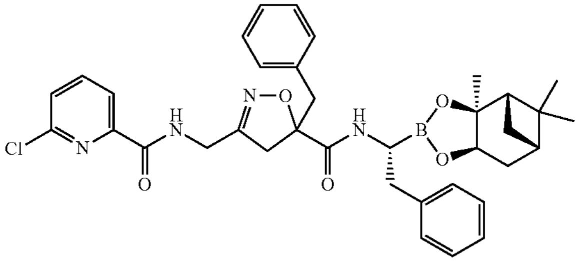 [SMILES: CC1(C)[C@@H]2C[C@H]3OB([C@H](Cc4ccccc4)NC(=O)C4(Cc5ccccc5)CC(CNC(=O)c5cccc(Cl)n5)=NO4)O[C@@]3(C)[C@H]1C2]

The title compound (0.27 g, 78%) was obtained using 5-benzyl-3-((6-chloropicolinamido)methyl)-4,5-dihydroisoxazol-5-carboxylic acid (0.20 g, 0.54 mmol) obtained in Example 308-(2) by the method of Example 261-(1).

MS (m/z): 655[M+H]

(2) Preparation of ((1R)-1-(5-benzyl-3-((6-chloropicolinamido)methyl)-4,5-dihydroisoxazol-5-carboxamido)-2-phenylethyl)boronic acid

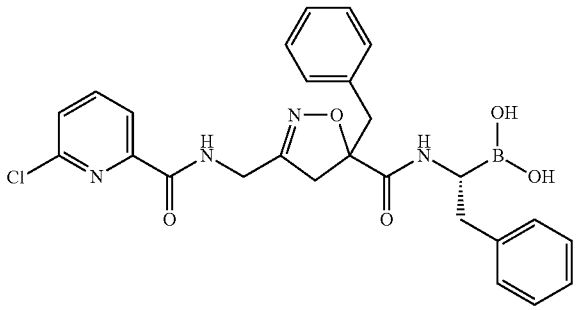 [SMILES: O=C(NCC1=NOC(Cc2ccccc2)(C(=O)N[C@@H](Cc2ccccc2)B(O)O)C1)c1cccc(Cl)n1]

The title compound (0.042 g, 19%) was obtained using 5-benzyl-3-((6-chloropicolinamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.27 g, 0.42 mmol) obtained in (1) above by the preparation method of Example 1-(4).

NMR: 1H NMR (400 MHz, METHANOL-d4) δ ppm 2.24-2.39 (m, 1H) 2.61-2.75 (m, 1H) 2.80-2.93 (m, 1H) 3.09-3.26 (m, 2H) 3.33-3.44 (m, 1H) 4.22 (s, 2H) 6.81-6.94 (m, 2H) 7.00-7.42 (m, 8H) 7.56-7.73 (m, 1H) 7.88-8.17 (m, 2H)

MS (m/z): 521[M+H], 503[M-OH]

Example 311: Preparation of ((1R)-1-(5-benzyl-3-((2-chloroisonicotinamido)methyl)-4,5-dihydroisoxazol-5-carboxamido)-3-methylbutylboronic acid Through the processes (1), (2) and (3) below, the title compound was obtained.

(1) Preparation of methyl 5-benzyl-3-((2-chloroisonicotinamido)methyl)-4,5-dihydroisoxazol-5-carboxylate

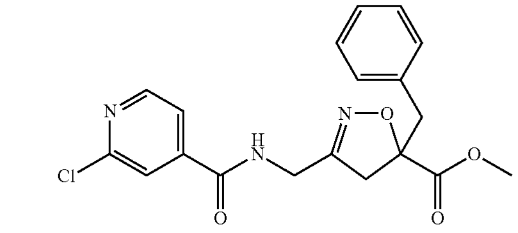 [SMILES: COC(=O)C1(Cc2ccccc2)CC(CNC(=O)c2ccnc(Cl)c2)=NO1]

The title compound (0.55 g, 80%) was obtained using methyl 3-(aminomethyl)-5-benzyl-4,5-dihydroisoxazol-5-carboxylate hydrochloride (0.5 g, 1.8 mmol) obtained in Example 84-(1) and 2-chloroisonicotinic acid (0.30 g, 1.9 mmol) by the preparation method of Example 84-(2).

MS (m/z): 388[M+H]

(2) Preparation of 5-benzyl-3-((2-chloroisonicotinamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

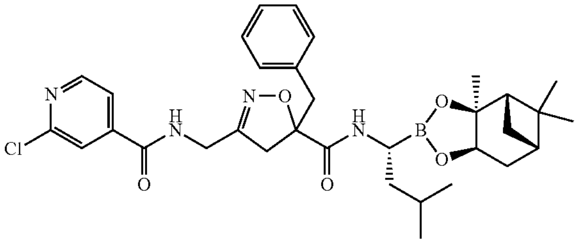 [SMILES: CC(C)C[C@H](NC(=O)C1(Cc2ccccc2)CC(CNC(=O)c2ccnc(Cl)c2)=NO1)B1O[C@@H]2C[C@@H]3C[C@@H](C3(C)C)[C@]2(C)O1]

The title compound (0.20 g, 23%, 2 steps) was obtained using methyl 5-benzyl-3-((2-chloroisonicotinamido)methyl)-4,5-dihydroisoxazol-5-carboxylate (0.55 g, 1.4 mmol) obtained in (1) above by the preparation methods of Example 84-(3) and Example 256-(3).

MS (m/z): 621[M+H]

(3) Preparation of ((1R)-1-(5-benzyl-3-((2-chloroisonicotinamido)methyl)-4,5-dihydroisoxazol-5-carboxamido)-3-methylbutylboronic acid

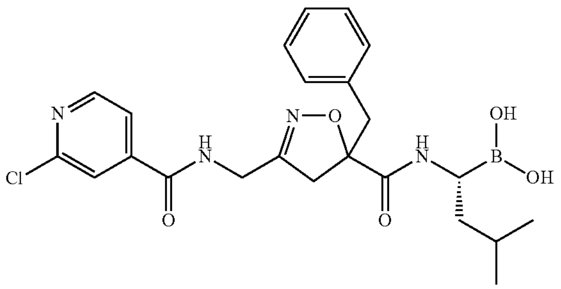 [SMILES: CC(C)C[C@H](NC(=O)C1(Cc2ccccc2)CC(CNC(=O)c2ccnc(Cl)c2)=NO1)B(O)O]

The title compound (0.046 g, 29%) was obtained using 5-benzyl-3-((2-chloroisonicotinamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.20 g, 0.32 mmol) obtained in (3) above by the preparation method of Example 1-(4).

NMR: 1H NMR (400 MHz, METHANOL-d4) δ ppm 0.77-0.86 (m, 6H) 1.02-1.11 (m, 1H) 1.14-1.23 (m, 1H) 1.28-1.48 (m, 2H) 2.61-2.75 (m, 1H) 3.19-3.31 (m, 2H) 3.42-3.47 (d, 1H) 4.25 (s, 2H) 7.20-7.32 (m, 5H) 7.68-7.74 (m, 1H) 7.79-7.85 (m, 1H) 8.50-8.59 (m, 1H)

MS (m/z): 487[M+H], 469[M-OH]

Example 312: Preparation of ((1R)-1-(3-(([1,2,4]triazolo[1,5-a]pyridin-5-carboxamido)methyl)-5-benzyl-4,5-dihydroisoxazol-5-carboxamido)-3-methylbutylboronic acid Through the processes (1), (2), (3) and (4) below, the title compound was obtained.

(1) Preparation of methyl 3-(([1,2,4]triazolo[1,5-a]pyridin-5-carboxamido)methyl)-5-benzyl-4,5-dihydroisoxazol-5-carboxylate

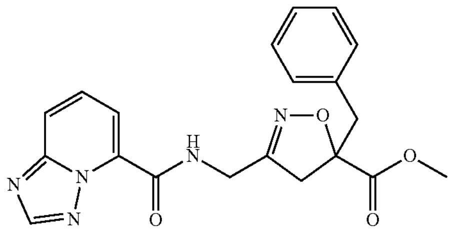

The title compound (0.20 g, 32%) was obtained using methyl 3-(aminomethyl)-5-benzyl-4,5-dihydroisoxazol-5-carboxylate hydrochloride (0.45 g, 1.58 mmol) obtained in Example 84-(1) and [1,2,4]triazolo[1,5-a]pyridin-5-carboxylic acid (0.28 g, 1.74 mmol) by the preparation method of Example 84-(2).

MS (m/z): 394[M+H]

(2) Preparation of 3-(([1,2,4]triazolo[1,5-a]pyridin-5-carboxamido)methyl)-5-benzyl-4,5-dihydroisoxazol-5-carboxylic acid

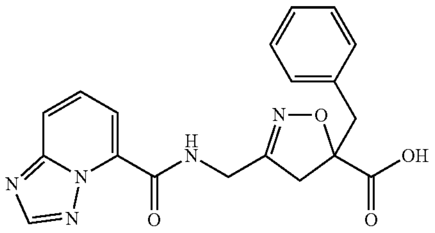 [SMILES: O=C(NCC1=NOC(Cc2ccccc2)(C(=O)O)C1)c1cccc2ncnn12]

The title compound (0.17 g, 88%) was obtained using methyl 3-(([1,2,4]triazolo[1,5-a]pyridin-5-carboxamido)methyl)-5-benzyl-4,5-dihydroisoxazol-5-carboxylate (0.20 g, 0.51 mmol) obtained in (1) above by the preparation method of Example 84-(3).

MS (m/z): 380[M+H]

(3) Preparation of 3-(([1,2,4]triazolo[1,5-a]pyridin-5-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

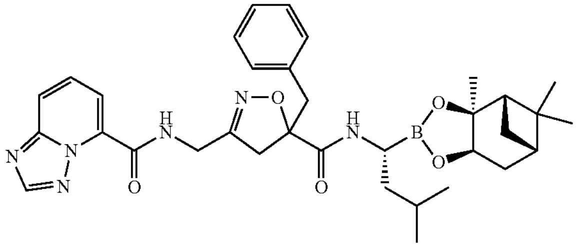 [SMILES: CC(C)C[C@H](NC(=O)C1(Cc2ccccc2)CC(CNC(=O)c2cccc3ncnn23)=NO1)B1O[C@@H]2C[C@@H]3C[C@@H](C3(C)C)[C@]2(C)O1]

The title compound (0.10 g, 36%) was obtained using 3-(([1,2,4]triazolo[1,5-a]pyridin-5-carboxamido)methyl)-5-benzyl-4,5-dihydroisoxazol-5-carboxylic acid (0.17 g, 0.45 mmol) obtained in (2) above by the method of Example 256-(3).

MS (m/z): 627[M+H]

(4) Preparation of ((1R)-1-(3-(([1,2,4]triazolo[1,5-a]pyridin-5-carboxamido)methyl)-5-benzyl-4,5-dihydroisoxazol-5-carboxamido)-3-methylbutylboronic acid

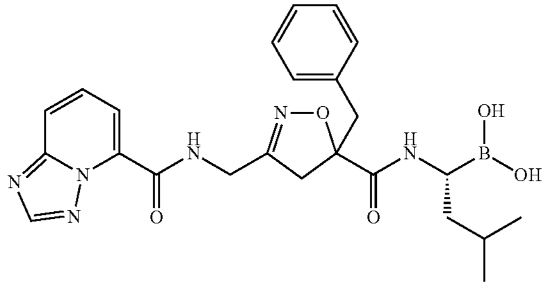 [SMILES: CC(C)C[C@H](NC(=O)C1(Cc2ccccc2)CC(CNC(=O)c2cccc3ncnn23)=NO1)B(O)O]

The title compound (0.024 g, 31%) was obtained using 3-(([1,2,4]triazolo[1,5-a]pyridin-5-carboxamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.10 g, 0.16 mmol) obtained in (3) above by the preparation method of Example 1-(4).

NMR: 1H NMR (400 MHz, METHANOL-d4) δ ppm 0.77-0.83 (m, 6H) 1.00-1.22 (m, 2H) 1.32-1.49 (m, 1H) 2.61-2.75 (m, 1H) 3.17-3.24 (m, 1H) 3.33-3.36 (m, 1H) 3.45-3.54 (m, 1H) 4.40-4.49 (m, 2H) 4.56-4.66 (m, 1H) 7.10-7.16 (m, 1H) 7.17-7.23 (m, 2H) 7.24-7.29 (m, 2H) 7.85-7.93 (m, 1H) 8.04-8.11 (m, 2H) 8.60-8.65 (m, 1H)

MS (m/z): 493[M+H], 475[M-OH]

Example 313: Preparation of ((1R)-1-(3-(([1,2,4]triazolo[1,5-a]pyridin-5-carboxamido)methyl)-5-benzyl-4,5-dihydroisoxazol-5-carboxamido)-2-phenylethyl)boronic acid Through the processes (1) and (2) below, the title compound was obtained.

(1) Preparation of 3-(([1,2,4]triazolo[1,5-a]pyridin-5-carboxamido)methyl)-5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

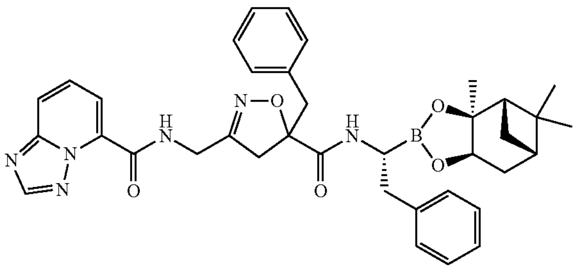

The title compound (0.28 g, 80%) was obtained using 3-(([1,2,4]triazolo[1,5-a]pyridin-5-carboxamido)methyl)-5-benzyl-4,5-dihydroisoxazol-5-carboxylic acid (0.20 g, 0.53 mmol) obtained in Example 312-(2) by the method of Example 261-(1).

MS (m/z): 661[M+H]

(2) Preparation of ((1R)-1-(3-(([1,2,4]triazolo[1,5-a]pyridin-5-carboxamido)methyl)-5-benzyl-4,5-dihydroisoxazol-5-carboxamido)-2-phenylethyl)boronic acid

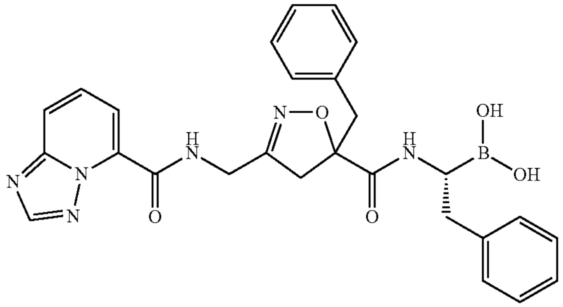 [SMILES: O=C(NCC1=NOC(Cc2ccccc2)(C(=O)N[C@@H](Cc2ccccc2)B(O)O)C1)c1cccc2ncnn12]

The title compound (0.080 g, 34%) was obtained using 3-(([1,2,4]triazolo[1,5-a]pyridin-5-carboxamido)methyl)-5-benzyl-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.30 g, 0.45 mmol) obtained in (1) above by the preparation method of Example 1-(4).

NMR: 1H NMR (400 MHz, METHANOL-d4) δ ppm 2.31-2.44 (m, 1H) 2.63-2.77 (m, 1H) 2.87-2.96 (m, 1H) 3.11-3.28 (m, 2H) 3.37-3.52 (m, 1H) 4.42 (s, 2H) 6.93 (br d, 2H) 7.08-7.36 (m, 8H) 7.84-7.96 (m, 1H) 8.02-8.16 (m, 2H) 8.59-8.67 (m, 1H)

MS (m/z): 527[M+H], 509[M-OH]

Example 314: Preparation of ((1R)-1-(5-benzyl-3-((2,5-dichlorobenzamido)methyl)-4,5-dihydroisoxazol-5-carboxamido)propyl)boronic acid Through the processes (1) and (2) below, the title compound was obtained.

(1) Preparation of 5-benzyl-3-((2,5-dichlorobenzamido)methyl)-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

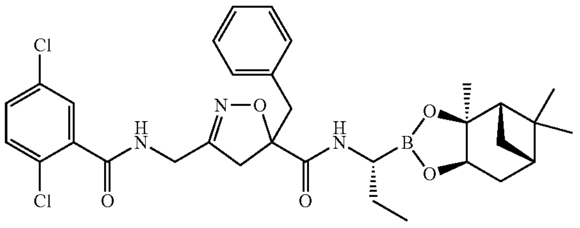 [SMILES: CC[C@H](NC(=O)C1(Cc2ccccc2)CC(CNC(=O)c2cc(Cl)ccc2Cl)=NO1)B1O[C@@H]2C[C@@H]3C[C@@H](C3(C)C)[C@]2(C)O1]

The title compound (0.35 g, 46%) was obtained using 5-benzyl-3-((2,5-dichlorobenzamido)methyl)-4,5-dihydroisoxazol-5-carboxylic acid (0.50 g, 1.2 mmol) obtained in Example 85-(2) by the method of Example 289-(1).

MS (m/z): 626[M+H]

(2) Preparation of ((1R)-1-(5-benzyl-3-((2,5-dichlorobenzamido)methyl)-4,5-dihydroisoxazol-5-carboxamido)propyl)boronic acid

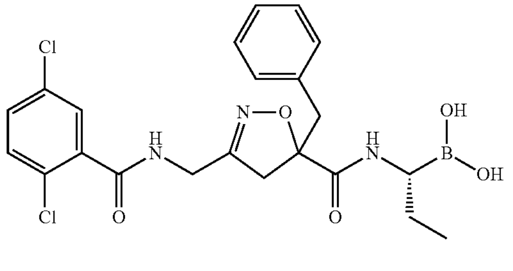 [SMILES: CC[C@H](NC(=O)C1(Cc2ccccc2)CC(CNC(=O)c2cc(Cl)ccc2Cl)=NO1)B(O)O]

The title compound (0.060 g, 22%) was obtained using 5-benzyl-3-((2,5-dichlorobenzamido)methyl)-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.35 g, 0.56 mmol) obtained in (1) above by the preparation method of Example 1-(4).

NMR: 1H NMR (400 MHz, METHANOL-d4) δ ppm 0.82 (br t, 1H) 0.76 (t, 2H) 1.24 (dt, 1H) 1.30-1.46 (m, 1H) 1.46-1.60 (m, 1H) 2.46-2.62 (m, 1H) 3.28 (br s, 2H) 3.44-3.53 (m, 1H) 4.19-4.25 (m, 2H) 7.23-7.33 (m, 5H) 7.40-7.54 (m, 3H)

MS (m/z): 492[M+H], 474[M-OH]

Example 315: Preparation of ((1R)-1-(5-benzyl-3-((2,5-dichlorobenzamido)methyl)-4,5-dihydroisoxazol-5-carboxamido)-2-methylpropyl)boronic acid Through the processes (1) and (2) below, the title compound was obtained.

(1) Preparation of 5-benzyl-3-((2,5-dichlorobenzamido)methyl)-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

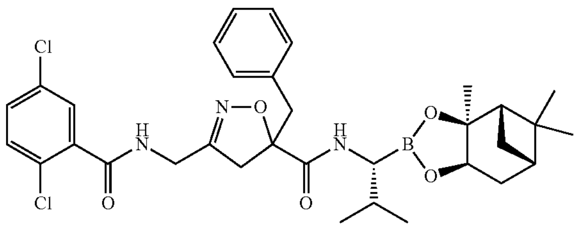 [SMILES: CC(C)[C@H](NC(=O)C1(Cc2ccccc2)CC(CNC(=O)c2cc(Cl)ccc2Cl)=NO1)B1O[C@@H]2C[C@@H]3C[C@@H](C3(C)C)[C@]2(C)O1]

The title compound (0.378 g, 75%) was obtained using 5-benzyl-3-((2,5-dichlorobenzamido)methyl)-4,5-dihydroisoxazol-5-carboxylic acid (0.32 g, 0.79 mmol) obtained in Example 85-(2) by the method of Example 290-(1).

MS (m/z): 640[M+H]

(2) Preparation of ((1R)-1-(5-benzyl-3-((2,5-dichlorobenzamido)methyl)-4,5-dihydroisoxazol-5-carboxamido)-2-methylpropyl)boronic acid

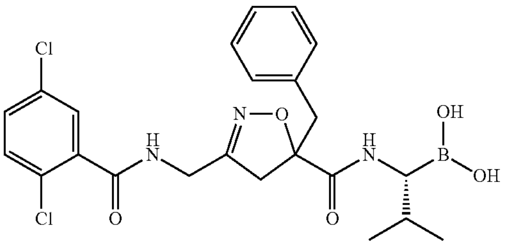 [SMILES: CC(C)[C@H](NC(=O)C1(Cc2ccccc2)CC(CNC(=O)c2cc(Cl)ccc2Cl)=NO1)B(O)O]

The title compound (0.040 g, 13%) was obtained using 5-benzyl-3-((2,5-dichlorobenzamido)methyl)-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.378 g, 0.59 mmol) obtained in (1) above by the preparation method of Example 1-(4).

NMR: 1H NMR (400 MHz, METHANOL-d4) δ ppm 0.67 (d, 3H) 0.82 (d, 3H) 1.59-1.69 (m, 1H) 2.46 (d, 1H) 3.17-3.26 (m, 1H) 3.28 (s, 1H) 3.31-3.38 (m, 1H) 3.49 (d, 1H) 4.22 (s, 2H) 7.22-7.31 (m, 5H) 7.50 (s, 3H)

MS (m/z): 506[M+H], 488[M-OH]

Example 316: Preparation of ((1R)-1-(5-benzyl-3-((3-cyanobenzamido)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((3-cyanobenzamido)methyl)-4,5-dihydroisoxazol-5-carboxylate

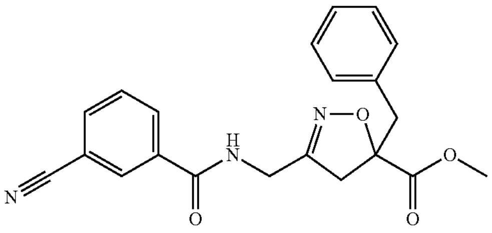 [SMILES: COC(=O)C1(Cc2ccccc2)CC(CNC(=O)c2cccc(C#N)c2)=NO1]

The title compound (1.19 g, 89%) was obtained using methyl 3-(aminomethyl)-5-benzyl-4,5-dihydroisoxazol-5-carboxylate hydrochloride (1.0 g, 3.5 mmol) obtained in Example 84-(1) and 3-cyanobenzoic acid (0.57 g, 3.9 mmol) by the preparation method of Example 84-(2).

MS (m/z): 378[M+H]

(2) Preparation of 5-benzyl-3-((3-cyanobenzamido)methyl)-4,5-dihydroisoxazol-5-carboxylic acid

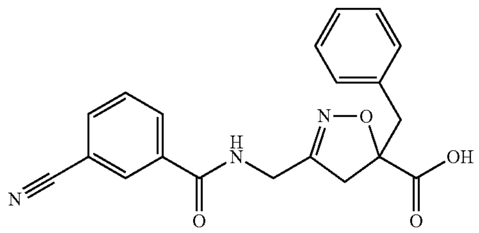 [SMILES: N#Cc1cccc(C(=O)NCC2=NOC(Cc3ccccc3)(C(=O)O)C2)c1]

The title compound (1.0 g, 87%) was obtained using methyl 5-benzyl-3-((3-cyanobenzamido)methyl)-4,5-dihydroisoxazol-5-carboxylate (1.19 g, 3.2 mmol) obtained in (1) above by the preparation method of Example 84-(3).

MS (m/z): 364[M+H]

(3) Preparation of 5-benzyl-3-((3-cyanobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

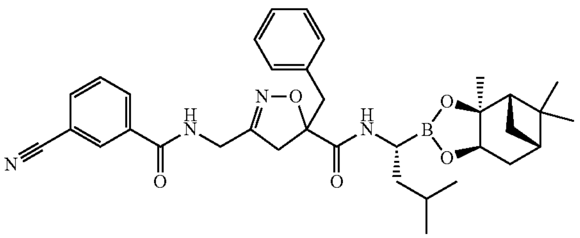 [SMILES: CC(C)C[C@H](NC(=O)C1(Cc2ccccc2)CC(CNC(=O)c2cccc(C#N)c2)=NO1)B1O[C@@H]2C[C@@H]3C[C@@H](C3(C)C)[C@]2(C)O1]

The title compound (0.38 g, 45%) was obtained using 5-benzyl-3-((3-cyanobenzamido)methyl)-4,5-dihydroisoxazol-5-carboxylic acid (0.50 g, 1.4 mmol) obtained in (2) above by the method of Example 256-(3).

MS (m/z): 611[M+H]

(4) Preparation of ((1R)-1-(5-benzyl-3-((3-cyanobenzamido)methyl)-4,5-dihydroisoxazol-5-carboxamido)-3-methylbutylboronic acid

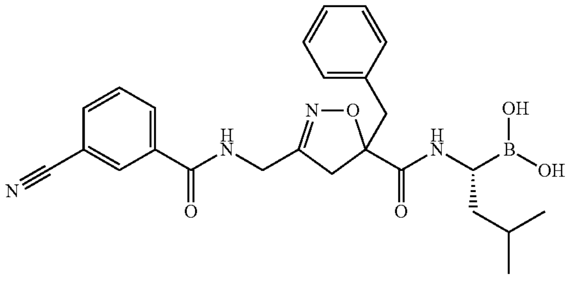 [SMILES: CC(C)C[C@H](NC(=O)C1(Cc2ccccc2)CC(CNC(=O)c2cccc(C#N)c2)=NO1)B(O)O]

The title compound (0.051 g, 17%) was obtained using 5-benzyl-3-((3-cyanobenzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.38 g, 0.62 mmol) obtained in (3) above by the preparation method of Example 1-(4).

NMR: 1H NMR (400 MHz, METHANOL-d4) δ ppm 0.75-0.86 (m, 6H) 0.99-1.12 (m, 1H) 1.12-1.25 (m, 1H) 1.36-1.48 (m, 1H) 2.61-2.76 (m, 1H) 3.17-3.31 (m, 2H) 3.41-3.54 (d, 1H) 4.26 (s, 2H) 7.22-7.32 (m, 5H) 7.62-7.78 (m, 1H) 7.90-7.99 (m, 1H) 8.07-8.20 (m, 2H)

MS (m/z): 477[M+H], 459[M-OH]

Example 317: Preparation of ((1R)-1-(5-benzyl-3-((3-cyanobenzamido)methyl)-4,5-dihydroisoxazol-5-carboxamido)-2-phenylethyl)boronic acid Through the processes (1) and (2) below, the title compound was obtained.

(1) Preparation of 5-benzyl-3-((3-cyanobenzamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide

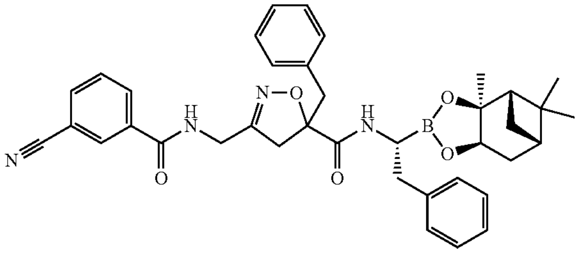 [SMILES: CC1(C)[C@@H]2C[C@H]3OB([C@H](Cc4ccccc4)NC(=O)C4(Cc5ccccc5)CC(CNC(=O)c5cccc(C#N)c5)=NO4)O[C@@]3(C)[C@H]1C2]

The title compound (0.25 g, 70%) was obtained using 5-benzyl-3-((3-cyanobenzamido)methyl)-4,5-dihydroisoxazol-5-carboxylic acid (0.20 g, 0.55 mmol) obtained in Example 316-(2) by the method of Example 261-(1).

MS (m/z): 645[M+H]

(2) Preparation of ((1R)-1-(5-benzyl-3-((3-cyanobenzamido)methyl)-4,5-dihydroisoxazol-5-carboxamido)-2-phenylethyl)boronic acid

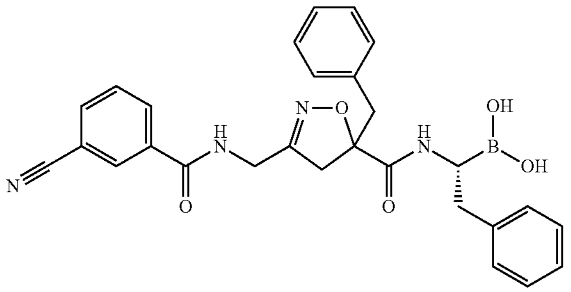 [SMILES: N#Cc1cccc(C(=O)NCC2=NOC(Cc3ccccc3)(C(=O)N[C@@H](Cc3ccccc3)B(O)O)C2)c1]

The title compound (0.023 g, 12%) was obtained using 5-benzyl-3-((3-cyanobenzamido)methyl)-N—((R)-2-phenyl-1-((3aS,4S,6S,7aR)-3a,5,5-trimethylhexahydro-4,6-metanobenzo[d][1,3,2]dioxaborol-2-yl)ethyl)-4,5-dihydroisoxazol-5-carboxamide (0.25 g, 0.39 mmol) obtained in (1) above by the preparation method of Example 1-(4).

NMR: 1H NMR (400 MHz, METHANOL-d4) δ ppm 2.28-2.44 (m, 1H) 2.62-2.80 (m, 1H) 2.83-2.99 (m, 1H) 3.08-3.26 (m, 2H) 3.35-3.44 (m, 1H) 4.32 (s, 2H) 6.85-7.00 (m, 2H) 7.05-7.48 (m, 8H) 7.63-7.80 (m, 1H) 7.86-8.00 (m, 1H) 8.04-8.28 (m, 2H)

MS (m/z): 511[M+H], 493[M-OH]

Example 318: Preparation of ((1R)-1-(5-benzyl-3-((6-chloropicolinamido)methyl)-4,5-dihydroisoxazol-5-carboxamido)propyl)boronic acid Through the processes (1) and (2) below, the title compound was obtained.

(1) Preparation of 5-benzyl-3-((6-chloropicolinamido)methyl)-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

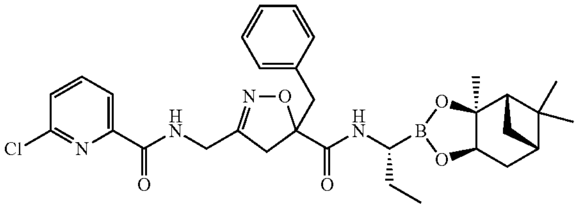 [SMILES: CC[C@H](NC(=O)C1(Cc2ccccc2)CC(CNC(=O)c2cccc(Cl)n2)=NO1)B1O[C@@H]2C[C@@H]3C[C@@H](C3(C)C)[C@]2(C)O1]

The title compound (0.20 g, 63%) was obtained using 5-benzyl-3-((6-chloropicolinamido)methyl)-4,5-dihydroisoxazol-5-carboxylic acid (0.20 g, 0.54 mmol) obtained in Example 308-(2) by the method of Example 289-(1).

MS (m/z): 593[M+H]

(2) Preparation of ((1R)-1-(5-benzyl-3-((6-chloropicolinamido)methyl)-4,5-dihydroisoxazol-5-carboxamido)propyl)boronic acid

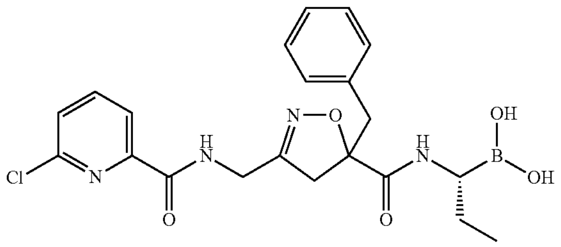 [SMILES: CC[C@H](NC(=O)C1(Cc2ccccc2)CC(CNC(=O)c2cccc(Cl)n2)=NO1)B(O)O]

The title compound (0.022 g, 14%) was obtained using 5-benzyl-3-((6-chloropicolinamido)methyl)-N—((R)-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.20 g, 0.34 mmol) obtained in (1) above by the preparation method of Example 1-(4).

NMR: 1H NMR (400 MHz, METHANOL-d4) δ ppm 0.69-0.76 (m, 3H) 1.12-1.25 (m, 1H) 1.29-1.42 (m, 1H) 2.41-2.49 (m, 1H) 3.15-3.28 (m, 2H) 3.32-3.45 (m, 2H) 4.21-4.28 (m, 2H) 7.18-7.28 (m, 5H) 7.62-7.67 (m, 1H) 7.95-8.08 (m, 2H)

MS (m/z): 459[M+H], 441[M-OH]

Example 319: Preparation of ((1R)-1-(5-benzyl-3-((6-chloropicolinamido)methyl)-4,5-dihydroisoxazol-5-carboxamido)-2-methylpropyl)boronic acid Through the processes (1) and (2) below, the title compound was obtained.

(1) Preparation of 5-benzyl-3-((6-chloropicolinamido)methyl)-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide

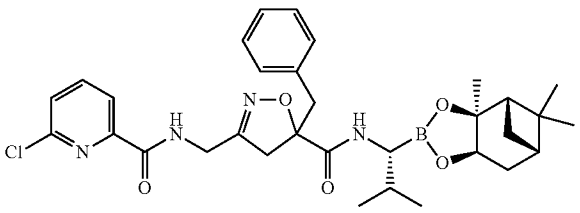 [SMILES: CC(C)[C@H](NC(=O)C1(Cc2ccccc2)CC(CNC(=O)c2cccc(Cl)n2)=NO1)B1O[C@@H]2C[C@@H]3C[C@@H](C3(C)C)[C@]2(C)O1]

The title compound (0.22 g, 68%) was obtained using 5-benzyl-3-((6-chloropicolinamido)methyl)-4,5-dihydroisoxazol-5-carboxylic acid (0.20 g, 0.54 mmol) obtained in Example 308-(2) by the method of Example 290-(1).

MS (m/z): 607[M+H]

(2) Preparation of ((1R)-1-(5-benzyl-3-((6-chloropicolinamido)methyl)-4,5-dihydroisoxazol-5-carboxamido)-2-methylpropyl)boronic acid

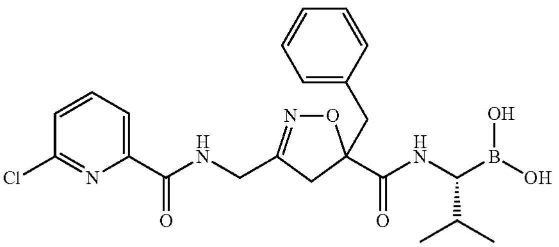 [SMILES: CC(C)[C@H](NC(=O)C1(Cc2ccccc2)CC(CNC(=O)c2cccc(Cl)n2)=NO1)B(O)O]

The title compound (0.023 g, 13%) was obtained using 5-benzyl-3-((6-chloropicolinamido)methyl)-N—((R)-2-methyl-1-((3aS,4S,6S,7aR)-3a,5,5-trimethylhexahydro-4,6-metanobenzo[d][1,3,2]dioxaborol-2-yl)propyl)-4,5-dihydroisoxazol-5-carboxamide (0.22 g, 0.36 mmol) obtained in (1) above by the preparation method of Example 1-(4).

NMR: 1H NMR (400 MHz, METHANOL-d4) δ ppm 0.63-0.69 (m, 3H) 0.79-0.85 (m, 3H) 1.57-1.69 (m, 1H) 2.38-2.46 (m, 1H) 3.15-3.31 (m, 3H) 3.38-3.48 (m, 1H) 4.23-4.31 (m, 2H) 7.20-7.29 (m, 5H) 7.64-7.69 (m, 1H) 7.98-8.08 (m, 2H)

MS (m/z): 473[M+H], 455[M-OH]

Example 320: Preparation of ((1R)-1-(3-((3-acetamidobenzamido)methyl)-5-benzyl-4,5-dihydroisoxazol-5-carboxamido)-3-methylbutylboronic acid Through the processes (1), (2), (3) and (4) below, the title compound was obtained.

(1) Preparation of methyl 3-((3-acetamidobenzamido)methyl)-5-benzyl-4,5-dihydroisoxazol-5-carboxylate

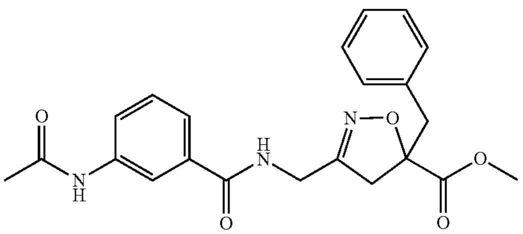 [SMILES: COC(=O)C1(Cc2ccccc2)CC(CNC(=O)c2cccc(NC(C)=O)c2)=NO1]

The title compound (0.54 g, 75%) was obtained using methyl 3-(aminomethyl)-5-benzyl-4,5-dihydroisoxazol-5-carboxylate hydrochloride (0.50 g, 1.8 mmol) obtained in Example 84-(1) and 3-acetamidobenzoic acid (0.34 g, 1.9 mmol) by the preparation method of Example 84-(2).

MS (m/z): 410[M+H]

(2) Preparation of 3-((3-acetamidobenzamido)methyl)-5-benzyl-4,5-dihydroisoxazol-5-carboxylic acid

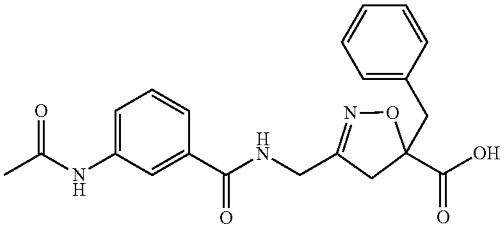 [SMILES: CC(=O)Nc1cccc(C(=O)NCC2=NOC(Cc3ccccc3)(C(=O)O)C2)c1]

The title compound (0.40 g, 76%) was obtained using methyl 3-((3-acetamidobenzamido)methyl)-5-benzyl-4,5-dihydroisoxazol-5-carboxylate (0.54 g, 1.3 mmol) obtained in (1) above by the preparation method of Example 84-(3).

MS (m/z): 396[M+H]

(3) Preparation of 3-((3-acetamidobenzamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

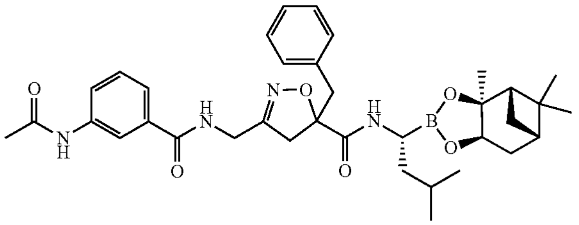 [SMILES: CC(=O)Nc1cccc(C(=O)NCC2=NOC(Cc3ccccc3)(C(=O)N[C@@H](CC(C)C)B3O[C@@H]4C[C@@H]5C[C@@H](C5(C)C)[C@]4(C)O3)C2)c1]

The title compound (0.51 g, 79%) was obtained using 3-((3-acetamidobenzamido)methyl)-5-benzyl-4,5-dihydroisoxazol-5-carboxylic acid (0.40 g, 1.0 mmol) obtained in (2) above by the method of Example 256-(3).

MS (m/z): 643[M+H]

(4) Preparation of ((1R)-1-(3-((3-acetamidobenzamido)methyl)-5-benzyl-4,5-dihydroisoxazol-5-carboxamido)-3-methylbutylboronic acid

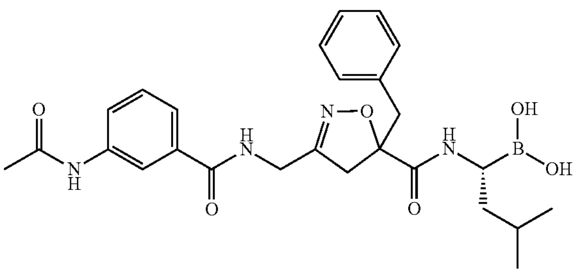 [SMILES: CC(=O)Nc1cccc(C(=O)NCC2=NOC(Cc3ccccc3)(C(=O)N[C@@H](CC(C)C)B(O)O)C2)c1]

The title compound (0.11 g, 28%) was obtained using 3-((3-acetamidobenzamido)methyl)-5-benzyl-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.51 g, 0.80 mmol) obtained in (3) above by the preparation method of Example 1-(4).

NMR: 1H NMR (400 MHz, METHANOL-d4) δ ppm 0.75-0.86 (m, 6H) 0.98-1.09 (m, 1H) 1.09-1.20 (m, 1H) 1.26-1.45 (m, 1H) 2.04-2.25 (m, 3H) 2.57-2.73 (m, 1H) 3.17-3.28 (m, 2H) 3.40-3.45 (d, 1H) 4.22 (s, 2H) 7.16-7.30 (m, 5H) 7.37-7.45 (m, 1H) 7.48-7.57 (m, 1H) 7.66-7.77 (m, 1H) 7.97-8.06 (m, 1H)

MS (m/z): 509[M+H], 491[M-OH].

Example 321: Preparation of ((1R)-1-(5-benzyl-3-((3-(dimethylamino)benzamido)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((3-(dimethylamino)benzamido)methyl)-4,5-dihydroisoxazol-5-carboxylate

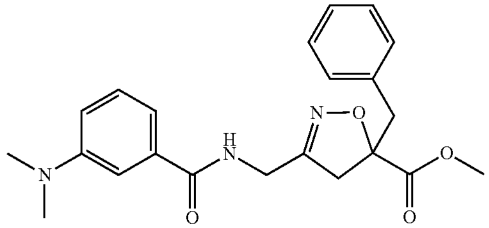

The title compound (0.6 g, 86%) was obtained using methyl 3-(aminomethyl)-5-benzyl-4,5-dihydroisoxazol-5-carboxylate hydrochloride (0.50 g, 1.8 mmol) obtained in Example 84-(1) and 3-(dimethylamino)benzoic acid (0.38 g, 2.3 mmol) by the preparation method of Example 84-(2).

MS (m/z): 396[M+H]

(2) Preparation of 5-benzyl-3-((3-(dimethylamino)benzamido)methyl)-4,5-dihydroisoxazol-5-carboxylic acid

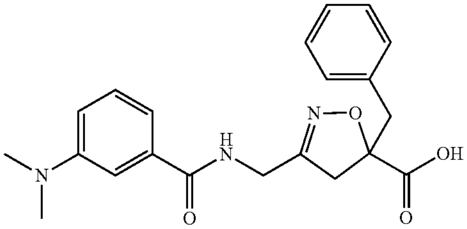 [SMILES: CN(C)c1cccc(C(=O)NCC2=NOC(Cc3ccccc3)(C(=O)O)C2)c1]

The title compound (0.55 g, 95%) was obtained using methyl 5-benzyl-3-((3-(dimethylamino)benzamido)methyl)-4,5-dihydroisoxazol-5-carboxylate (0.6 g, 1.5 mmol) obtained in (1) above by the preparation method of Example 84-(3).

MS (m/z): 382[M+H]

(3) Preparation of 5-benzyl-3-((3-(dimethylamino)benzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

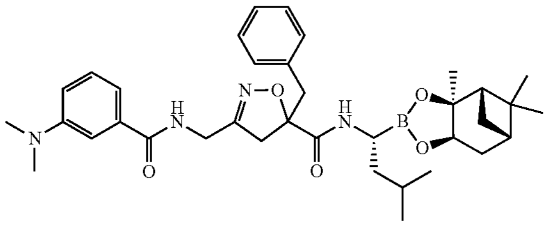

The title compound (0.8 g, 88%) was obtained using 5-benzyl-3-((3-(dimethylamino)benzamido)methyl)-4,5-dihydroisoxazol-5-carboxylic acid (0.55 g, 1.4 mmol) obtained in (2) above by the method of Example 256-(3).

MS (m/z): 629[M+H]

(4) Preparation of ((1R)-1-(5-benzyl-3-((3-(dimethylamino)benzamido)methyl)-4,5-dihydroisoxazol-5-carboxamido)-3-methylbutylboronic acid

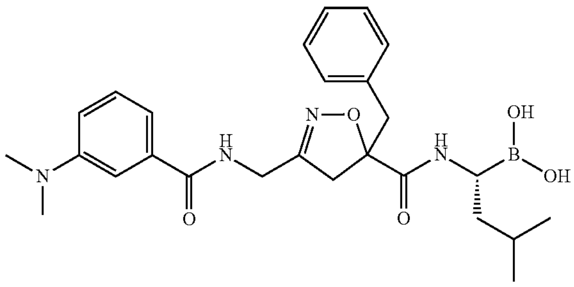 [SMILES: CC(C)C[C@H](NC(=O)C1(Cc2ccccc2)CC(CNC(=O)c2cccc(N(C)C)c2)=NO1)B(O)O]

The title compound (0.107 g, 27%) was obtained using 5-benzyl-3-((3-(dimethylamino)benzamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.50 g, 0.80 mmol) obtained in (3) above by the preparation method of Example 1-(4).

NMR: 1H NMR (400 MHz, METHANOL-d4) δ ppm 0.66-0.81 (m, 6H) 1.02-1.04 (m, 1H) 1.11-1.15 (m, 1H) 1.19-1.46 (m, 2H) 2.61-2.62 (m, 1H) 3.00 (s, 6H) 3.21-3.29 (m, 2H) 3.41-2.96 (d, 1H) 4.22 (s, 2H) 6.94-6.95 (m, 1H) 7.18-7.20 (m, 1H) 7.23-7.32 (m, 5H)

MS (m/z): 495[M+H], 477[M-OH]

Example 322: Preparation of ((1R)-1-(5-benzyl-3-((6-methoxypicolinamidomethyl)-4,5-dihydroisoxazol-5-carboxamido)-3-methylbutylboronic acid Through the processes (1), (2) and (3) below, the title compound was obtained.

(1) Preparation of methyl 5-benzyl-3-((6-methoxypicolinamidomethyl)-4,5-dihydroisoxazol-5-carboxylate

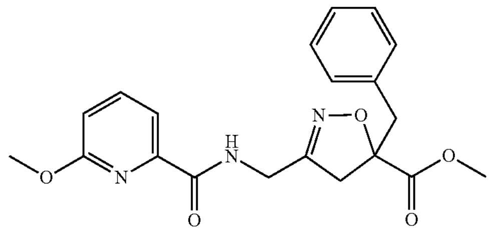

The title compound (0.60 g, 89%) was obtained using methyl 3-(aminomethyl)-5-benzyl-4,5-dihydroisoxazol-5-carboxylate hydrochloride (0.50 g, 1.8 mmol) obtained in Example 84-(1) and 6-methoxypicolinic acid (0.34 g, 2.2 mmol) by the preparation method of Example 84-(2).

MS (m/z): 384[M+H]

(2) Preparation of 5-benzyl-3-((6-methoxypicolinamidomethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

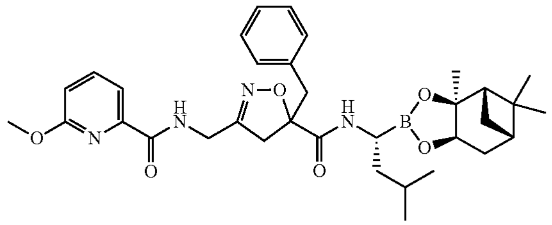

The title compound (0.90 g, 93%, 2 steps) was obtained using methyl 5-benzyl-3-((6-methoxypicolinamidomethyl)-4,5-dihydroisoxazol-5-carboxylate (0.60 g, 1.56 mmol) obtained in (1) above by the preparation methods of Example 84-(3) and Example 256-(3).

MS (m/z): 617[M+H]

(3) Preparation of ((1R)-1-(5-benzyl-3-((6-methoxypicolinamidomethyl)-4,5-dihydroisoxazol-5-carboxamido)-3-methylbutylboronic acid

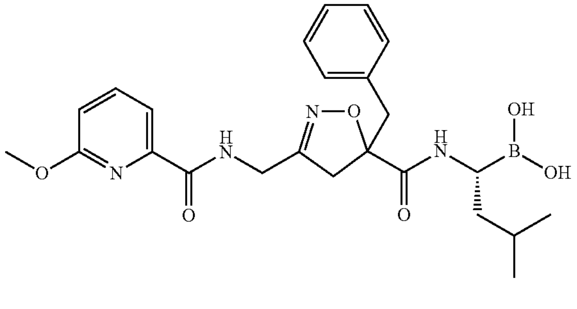 [SMILES: COc1cccc(C(=O)NCC2=NOC(Cc3ccccc3)(C(=O)N[C@@H](CC(C)C)B(O)O)C2)n1]

The title compound (0.033 g, 4.6%) was obtained using 5-benzyl-3-((6-methoxypicolinamidomethyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.90 g, 1.46 mmol) obtained in (2) above by the preparation method of Example 1-(4).

NMR: 1H NMR (400 MHz, METHANOL-d4) δ ppm 0.76-0.84 (m, 6H) 0.98-1.21 (m, 2H) 1.33-1.45 (m, 1H) 2.62-2.69 (m, 1H) 3.28 (s, 2H) 3.32-3.48 (m, 2H) 3.98-4.02 (m, 3H) 4.25-4.31 (m, 2H) 6.94-7.05 (m, 1H) 7.18-7.29 (m, 5H) 7.63-7.73 (m, 1H) 7.79-7.85 (m, 1H)

MS (m/z): 483[M+H], 465[M-OH]

Example 323: Preparation of ((1R)-1-(5-benzyl-3-((6-cyanopicolinamido)methyl)-4,5-dihydroisoxazol-5-carboxamido)-3-methylbutylboronic acid Through the processes (1), (2), (3) and (4) below, the title compound was obtained.

(1) Preparation of methyl 5-benzyl-3-((6-cyanopicolinamido)methyl)-4,5-dihydroisoxazol-5-carboxylate

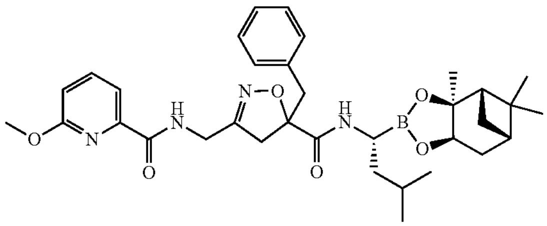

The title compound (1.1 g, 83%) was obtained using methyl 3-(aminomethyl)-5-benzyl-4,5-dihydroisoxazol-5-carboxylate hydrochloride (1.0 g, 3.5 mmol) obtained in Example 84-(1) and 6-cyanopicolinic acid (0.57 g, 3.9 mmol) by the preparation method of Example 84-(2).

MS (m/z): 379[M+H]

(2) Preparation of 5-benzyl-3-((6-cyanopicolinamido)methyl)-4,5-dihydroisoxazol-5-carboxylic acid

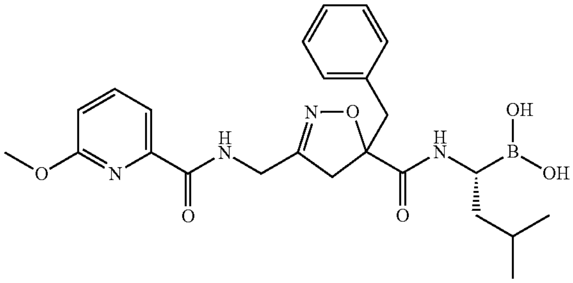 [SMILES: COc1cccc(C(=O)NCC2=NOC(Cc3ccccc3)(C(=O)N[C@@H](CC(C)C)B(O)O)C2)n1]

Methyl 5-benzyl-3-((6-cyanopicolinamido)methyl)-4,5-dihydroisoxazol-5-carboxylate (0.50 g, 1.32 mmol) obtained in (1) above was dissolved in acetonitrile (5 ml), and triethylamine (0.55 ml, 3.96 mmol) and lithium bromide (1.15 g, 13.2 mmol) were added thereto in order, followed by stirring at room temperature for 16 hours. The solvent was distilled under a reduced pressure and separated by prep-HPLC to obtain the title compound (0.15 g, 31%).

MS (m/z): 365[M+H]

(3) Preparation of 5-benzyl-3-((6-cyanopicolinamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide

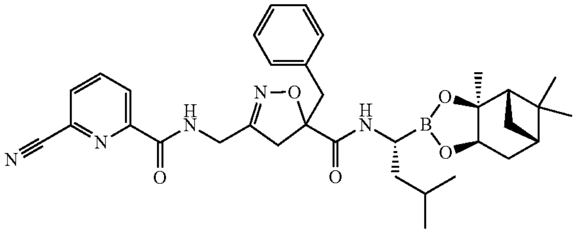 [SMILES: CC(C)C[C@H](NC(=O)C1(Cc2ccccc2)CC(CNC(=O)c2cccc(C#N)n2)=NO1)B1O[C@@H]2C[C@@H]3C[C@@H](C3(C)C)[C@]2(C)O1]

The title compound (0.28 g, 93%) was obtained using 5-benzyl-3-((6-cyanopicolinamido)methyl)-4,5-dihydroisoxazol-5-carboxylic acid (0.18 g, 0.49 mmol) obtained in (2) above by the preparation method of Example 84-(4).

MS (m/z): 612[M+H]

(4) Preparation of ((1R)-1-(5-benzyl-3-((6-cyanopicolinamido)methyl)-4,5-dihydroisoxazol-5-carboxamido)-3-methylbutylboronic acid

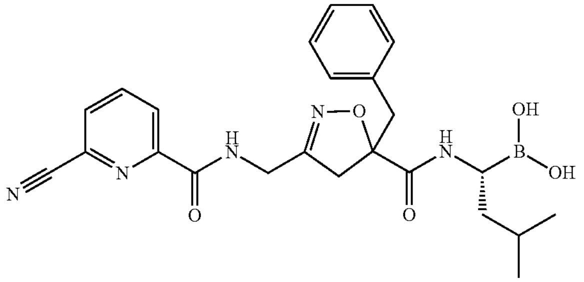 [SMILES: CC(C)C[C@H](NC(=O)C1(Cc2ccccc2)CC(CNC(=O)c2cccc(C#N)n2)=NO1)B(O)O]

The title compound (0.062 g, 28%) was obtained using 5-benzyl-3-((6-cyanopicolinamido)methyl)-N—((R)-3-methyl-1-((3aS,4S,6S,7aR)-3a,5,5-trimethylhexahydro-4,6-metanobenzo[d][1,3,2]dioxaborol-2-yl)butyl)-4,5-dihydroisoxazol-5-carboxamide (0.28 g, 0.46 mmol) obtained in (3) above by the preparation method of Example 1-(4).

NMR: 1H NMR (400 MHz, METHANOL-d4) δ ppm 0.80 (dd, 6H) 0.98-1.09 (m, 1H) 1.15 (dt, 1H) 1.39 (dt, 1H) 2.67 (br t, 1H) 3.15-3.28 (m, 2H) 3.31-3.49 (m, 2H) 4.27 (s, 2H) 7.16-7.31 (m, 5H) 8.06 (dd, 1H) 8.20 (t, 1H) 8.34 (dd, 1H)

MS (m/z): 478[M+H], 460[M-OH].

Experimental Examples

The abilities to inhibit the proteasome activity of the compounds described in the Examples of the present invention and boronic acid drugs were evaluated as follows.

RPMI8226 cells, which is a multiple myeloma cell line, were cultured and then separated by a centrifuge, and washed twice with phosphate buffered saline (PBS). 20 mM of a tris-HCl (pH 8.0) buffer solution was added to the washed cells, and the cells were disrupted by a homogenizer and centrifuged to obtain S26 protein from the supernatant. Suc-Leu-Leu-Val-Tyr-AMC, for a fluorogenic substrate for the chymotrypsin-like activity of the proteasome, and Z-Leu-Leu-Glu-AMC, for a fluorogenic substrate for the caspase-like activity, were purchased from Calbiochem, EMD Millipore and used. Into each well of a 96-well plate (opaque, black round bottom), 20 ul of the S26 protein (final RPMI8226 cell extract concentration: 2 ug/well), 10 ul of S26 proteasome inhibitor serially diluted from 10 uM (final DMSO concentration: 0.5%), and 20 ul of the fluorogenic substrate for the proteasome chymotrypsin-like or caspase-like activity (final concentration: 20 uM) were added and mixed and allowed to react in a 37° C. incubator for 90 minutes. The fluorescence of the fluorogenic substrate was measured by FlexStation II Fluorometer (Molecular Devices). The fluorescence inhibited by the compound diluted at each concentration was measured as the relative percentage value for the amount obtained from the treatment only with the S26 protein and the fluorogenic substrate. IC50 (inhibitory concentration 50) was expressed in terms of a concentration that inhibits 50% of the maximum fluorescence induced by the fluorogenic substrate.

TABLE 1

| Compounds | Proteasome chymotrypsin-like activity inhibition IC50 (nM) | Proteasome caspase-like activity inhibition IC50 (nM) |
|---|---|---|
| Example 1 | <500 | |
| Example 2 | <1000 | |
| Example 3 | <250 | |
| Example 4 | >1000 | |
| Example 5 | >1000 | |
| Example 6 | >1000 | |
| Example 7 | <500 | |
| Example 8 | <250 | |
| Example 9 | <500 | |
| Example 10 | <500 | |
| Example 11 | <250 | |
| Example 12 | <250 | |
| Example 13 | >1000 | |
| Example 14 | <250 | |
| Example 15 | <250 | |
| Example 16 | <250 | |
| Example 17 | <500 | |
| Example 18 | <500 | |
| Example 19 | <100 | |
| Example 20 | <250 | |
| Example 21 | <250 | |
| Example 22 | <250 | |
| Example 23 | <250 | |
| Example 24 | <500 | |
| Example 25 | <100 | |
| Example 26 | <50 | |
| Example 27 | <250 | |
| Example 28 | <250 | |
| Example 29 | <500 | |
| Example 30 | <1000 | |
| Example 31 | <50 | |
| Example 32 | <100 | |
| Example 33 | <100 | |
| Example 34 | <100 | |
| Example 35 | <500 | |
| Example 36 | <250 | |
| Example 37 | <500 | |
| Example 38 | <500 | |
| Example 39 | <500 | |
| Example 40 | <500 | |
| Example 41 | <250 | |
| Example 42 | <250 | |
| Example 43 | <250 | |
| Example 44 | <500 | |
| Example 45 | <10 | |

TABLE 1-continued

| Compounds | Proteasome chymotrypsin-like activity inhibition IC50 (nM) | Proteasome caspase-like activity inhibition IC50 (nM) |
|---|---|---|
| Example 46 | <10 | >250 |
| Example 47 | <10 | >250 |
| Example 48 | <25 | >250 |
| Example 49 | <10 | >1000 |
| Example 50 | <10 | |
| Example 51 | <10 | >500 |
| Example 52 | <10 | |
| Example 53 | <10 | |
| Example 54 | <10 | |
| Example 55 | <10 | |
| Example 56 | <10 | |
| Example 57 | <25 | |
| Example 58 | <25 | |
| Example 59 | <100 | >500 |
| Example 60 | <250 | |
| Example 61 | <10 | >500 |
| Example 62 | <25 | |
| Example 63 | <10 | >500 |
| Example 64 | <10 | >250 |
| Example 65 | <250 | |
| Example 66 | <25 | |
| Example 67 | <25 | |
| Example 68 | <10 | >500 |
| Example 69 | <25 | |
| Example 70 | <100 | |
| Example 71 | <25 | >250 |
| Example 72 | <10 | >100 |
| Example 73 | <25 | >100 |
| Example 74 | <25 | >500 |
| Example 75 | <100 | |
| Example 76 | <50 | |
| Example 77 | <250 | |
| Example 78 | <50 | |
| Example 79 | <100 | |
| Example 80 | <25 | >500 |
| Example 81 | <250 | |
| Example 82 | <50 | >500 |
| Example 83 | <250 | |
| Example 84 | <10 | >1000 |
| Example 85 | <10 | >1000 |
| Example 86 | <50 | >2500 |
| Example 87 | <50 | >2500 |
| Example 88 | <25 | >2500 |
| Example 89 | <100 | |
| Example 90 | <25 | |
| Example 91 | <25 | |
| Example 92 | <10 | >500 |
| Example 93 | <10 | |
| Example 94 | <10 | |
| Example 95 | <10 | |
| Example 96 | <10 | |
| Example 97 | <10 | |
| Example 98 | <10 | |
| Example 99 | <25 | |
| Example 100 | <10 | >1000 |
| Example 101 | <10 | |
| Example 102 | <10 | |
| Example 103 | <50 | |
| Example 104 | <100 | |
| Example 105 | <100 | |
| Example 106 | <10 | |
| Example 107 | <10 | >500 |
| Example 108 | <10 | |
| Example 109 | <10 | |
| Example 110 | <25 | |
| Example 111 | <10 | |
| Example 112 | <10 | >2500 |
| Example 113 | <10 | >500 |
| Example 114 | <10 | |
| Example 115 | <10 | >1000 |
| Example 116 | <10 | >2500 |
| Example 117 | <10 | >1000 |
| Example 118 | <25 | |
| Example 119 | <10 | >1000 |
| Example 120 | <10 | |
| Example 121 | <10 | |

TABLE 1-continued

| Compounds | Proteasome chymotrypsin-like activity inhibition IC50 (nM) | Proteasome caspase-like activity inhibition IC50 (nM) |
|---|---|---|
| Example 122 | <10 | |
| Example 123 | <10 | |
| Example 124 | <10 | >500 |
| Example 125 | <10 | >500 |
| Example 126 | <10 | >500 |
| Example 127 | <10 | >500 |
| Example 128 | <10 | |
| Example 129 | <10 | >250 |
| Example 130 | <10 | >500 |
| Example 131 | <10 | |
| Example 132 | <10 | >250 |
| Example 133 | <10 | >500 |
| Example 134 | <10 | >500 |
| Example 135 | <10 | |
| Example 136 | <10 | |
| Example 137 | <10 | |
| Example 138 | <10 | >500 |
| Example 139 | <10 | |
| Example 140 | <10 | |
| Example 141 | <10 | >500 |
| Example 142 | <10 | |
| Example 143 | <10 | >500 |
| Example 144 | <10 | |
| Example 145 | <10 | >2500 |
| Example 146 | <25 | |
| Example 147 | <25 | |
| Example 148 | <25 | >1000 |
| Example 149 | <10 | |
| Example 150 | <10 | |
| Example 151 | <10 | >250 |
| Example 152 | <10 | >1000 |
| Example 153 | <10 | >500 |
| Example 154 | <10 | >500 |
| Example 155 | <25 | |
| Example 156 | <25 | |
| Example 157 | <10 | |
| Example 158 | <100 | |
| Example 159 | <10 | |
| Example 160 | <10 | >500 |
| Example 161 | <10 | |
| Example 162 | <25 | >1000 |
| Example 163 | <10 | |
| Example 164 | <10 | |
| Example 165 | <10 | |
| Example 166 | <25 | |
| Example 167 | <10 | |
| Example 168 | <25 | |
| Example 169 | <25 | |
| Example 170 | <10 | >1000 |
| Example 171 | <10 | >500 |
| Example 172 | <10 | |
| Example 173 | <25 | |
| Example 174 | <10 | |
| Example 175 | <10 | |
| Example 176 | <25 | |
| Example 177 | <10 | |
| Example 178 | <10 | >1000 |
| Example 179 | <10 | >500 |
| Example 180 | <50 | |
| Example 181 | <50 | |
| Example 182 | <10 | |
| Example 183 | <10 | |
| Example 184 | <10 | |
| Example 185 | <10 | |
| Example 186 | <10 | >1000 |
| Example 187 | <10 | >500 |
| Example 188 | <10 | >1000 |
| Example 189 | <10 | >1000 |
| Example 190 | <10 | >2500 |
| Example 191 | <25 | |
| Example 192 | <10 | |
| Example 193 | <10 | |
| Example 194 | <250 | |
| Example 195 | <50 | |
| Example 196 | <10 | >1000 |
| Example 197 | <10 | |

TABLE 1-continued

| Compounds | Proteasome chymotrypsin-like activity inhibition IC50 (nM) | Proteasome caspase-like activity inhibition IC50 (nM) |
|---|---|---|
| Example 198 | <100 | |
| Example 199 | <1000 | |
| Example 200 | <10 | >100 |
| Example 201 | <10 | >250 |
| Example 202 | <10 | >500 |
| Example 203 | <10 | |
| Example 204 | <10 | >500 |
| Example 205 | <10 | >500 |
| Example 206 | <10 | |
| Example 207 | <10 | >250 |
| Example 208 | <10 | |
| Example 209 | <10 | |
| Example 210 | <10 | |
| Example 211 | <10 | >500 |
| Example 212 | <10 | >100 |
| Example 213 | <10 | |
| Example 214 | <10 | |
| Example 215 | <10 | |
| Example 216 | <10 | |
| Example 217 | <10 | |
| Example 218 | <10 | |
| Example 219 | <10 | |
| Example 220 | <10 | |
| Example 221 | <10 | |
| Example 222 | <10 | |
| Example 223 | <10 | |
| Example 224 | <10 | >2500 |
| Example 225 | <10 | |
| Example 226 | <25 | |
| Example 227 | <10 | |
| Example 228 | <10 | |
| Example 229 | <10 | |
| Example 230 | <10 | |
| Example 231 | <10 | |
| Example 232 | <10 | |
| Example 233 | <10 | |
| Example 234 | <10 | |
| Example 235 | <10 | |
| Example 236 | <10 | |
| Example 237 | <10 | |
| Example 238 | <10 | |
| Example 239 | <10 | |
| Example 240 | <10 | |
| Example 241 | <10 | |
| Example 242 | <10 | |
| Example 243 | <10 | |
| Example 244 | <10 | |
| Example 245 | <10 | |
| Example 246 | <10 | >1000 |
| Example 247 | <10 | >1000 |
| Example 248 | <10 | |
| Example 249 | <10 | |
| Example 250 | <10 | |
| Example 251 | <10 | |
| Example 252 | <100 | >500 |
| Example 253 | <10 | |
| Example 254 | <10 | |
| Example 255 | <25 | |
| Example 256 | <10 | >1000 |
| Example 257 | <10 | >2500 |
| Example 258 | <10 | |
| Example 259 | <50 | |
| Example 260 | <50 | |
| Example 261 | <25 | |
| Example 262 | <100 | |
| Example 263 | <50 | |
| Example 264 | <10 | |
| Example 265 | <10 | |
| Example 266 | <10 | |
| Example 267 | <10 | |
| Example 268 | <10 | |
| Example 269 | <25 | |
| Example 270 | <10 | |
| Example 271 | <10 | |
| Example 272 | <10 | |
| Example 273 | <10 | |

TABLE 1-continued

| Compounds | Proteasome chymotrypsin-like activity inhibition IC50 (nM) | Proteasome caspase-like activity inhibition IC50 (nM) |
|---|---|---|
| Example 274 | <100 | |
| Example 275 | <50 | |
| Example 276 | <10 | |
| Example 277 | <10 | |
| Example 278 | <10 | |
| Example 279 | <10 | |
| Example 280 | <10 | |
| Example 281 | <10 | |
| Example 282 | <10 | |
| Example 283 | <10 | |
| Example 284 | <10 | |
| Example 285 | <10 | |
| Example 286 | <10 | |
| Example 287 | <10 | |
| Example 288 | <10 | |
| Example 289 | <25 | |
| Example 290 | <10 | |
| Example 291 | <10 | >250 |
| Example 292 | <10 | >1000 |
| Example 293 | <25 | >500 |
| Example 294 | <10 | >1000 |
| Example 296 | <10 | |
| Example 297 | <25 | |
| Example 298 | <10 | |
| Example 299 | <10 | |
| Example 300 | <10 | |
| Example 301 | <10 | |
| Example 302 | <10 | |
| Example 303 | <10 | |
| Example 304 | <10 | |
| Example 305 | <10 | |
| Example 306 | <10 | |
| Example 307 | <10 | |
| Example 308 | <10 | >500 |
| Example 309 | <10 | |
| Example 311 | <10 | |
| Example 312 | <25 | |
| Example 313 | <10 | |
| Example 314 | <10 | |
| Example 315 | <10 | |
| Example 316 | <10 | |
| Example 317 | <10 | |
| Example 318 | <25 | |
| Example 319 | <10 | |
| Example 320 | <10 | |
| Example 321 | <10 | |
| Example 322 | <10 | |
| Example 323 | <10 | |
| bortezomib CAS: 179324-69-7 | 3 | 24 |
| ixazomib CAS: 1072833-77-2 | 4 | 7 |

As confirmed in Table 1 above, it could be found that the compounds of the present invention have excellent ability to selectively bind to and inhibit the proteasome chymotrypsin-like activity.

The invention claimed is:

1. A compound represented by the following Formula 1, a pharmaceutically acceptable salt thereof, or isomers thereof:

[Formula 1]

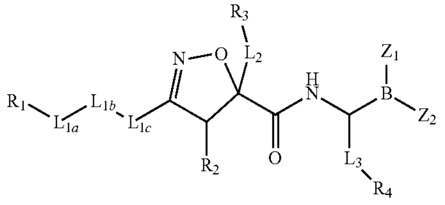

in the above formula, $R_1$ represents alkyl, cycloalkyl, aryl, heteroaryl, heterocycloalkyl, or a fused-bicyclo ring;

$R_2$ represents hydrogen or alkyl;

$R_3$ represents hydrogen, alkyl, cycloalkyl, aryl, or heteroaryl, or $R_2$ and $R_3$ optionally are combined with each other to form a 3- to 6-membered aliphatic ring, where $L_2$ is absent;

$R_4$ represents alkyl, cycloalkyl, or aryl;

$L_{1a}$ represents $(CH_2)_l$ (where l is an integer of 0 to 3) or $C(CH_2CH_2)$;

$L_{1b}$ is a direct linkage, or represents (C═O)NH, NH(C═O), NH, $(CH_2)_mO$ (where m is an integer of 0 to 3), $(C═O)N(CH_3)$, or $S(O_2)NH$;

$L_{1c}$ represents $(CH_2)_n$ (where n is an integer of 0 to 3), $CHR_5$, or $CR_6R_7$, where $R_5$, $R_6$, and $R_7$ are each independently C1-C4 heteroalkyl having 1 to 3 heteroatoms selected from the group consisting of O, N, and S, or C1-C4 alkyl;

$L_2$ represents $(CH_2)_o$ (where o is an integer of 0 to 3), $(CH_2)_pO$ (where p is an integer of 1 to 3), $CHR_8$, $CX_1X_2$, or $C(CH_2CH_2)$, where $R_8$ is OH, halogen, or C1-C3 alkyl, and $X_1$ and $X_2$ are each independently halogen;

$L_3$ represents $(CH_2)_q$ (where q is an integer of 0 to 3) or $CHR_9$, where $R_9$ is C1-C3 alkyl; and $Z_1$ and $Z_2$ are each independently OH or $OR_{10}$, $R_{10}$ represents alkyl, cycloalkyl, aryl, heteroaryl, or heterocycloalkyl, or in the case where $Z_1$ and $Z_2$ are $OR_{10}$, the two $R_{10}$ together optionally form a C2-C20 cyclic boric acid ester having a saturated, unsaturated, or optionally fused-bicyclo ring, where the cyclic boric acid ester optionally is substituted with hydroxyl, substituted or unsubstituted alkyl, cycloalkyl, alkoxy, aryl, aryloxy, or heteroaryl or heterocycloalkyl containing in the ring 1 or 2 heteroatoms selected from N, O, and S atoms.

2. The compound, the pharmaceutically acceptable salt thereof, or the isomer thereof according to claim 1, wherein $R_1$ represents C1-C6 alkyl, C3-C6 cycloalkyl, phenyl, 5- to 6-membered heteroaryl or heterocycloalkyl containing 1 or 2 heteroatoms selected from N, O, and S atoms, fused-bicyclo alkyl, fused-bicycloaryl, or fused-bicycloheteroaryl containing 1 to 4 heteroatoms selected from N, O, and S atoms;

$R_2$ represents hydrogen or C1-C6 alkyl;

$R_3$ represents hydrogen, C1-C6 alkyl, C3-C6 cycloalkyl, phenyl, or 5- to 6-membered heteroaryl containing 1 or 2 heteroatoms selected from N, O, and S atoms, or $R_2$ and $R_3$ optionally are combined with each other to form a 3- to 6-membered aliphatic ring, where $L_2$ is absent;

$R_4$ represents C1-C6 alkyl, C3-C6 cycloalkyl, or phenyl;

$L_{1a}$ represents $(CH_2)_l$ (where l is an integer of 0 to 3) or $C(CH_2CH_2)$;

$L_{1b}$ is a direct linkage, or represents (C═O)NH, NH(C═O), NH, $(CH_2)_mO$ (where m is an integer of 0 to 3), (C═O)N($CH_3$), or S($O_2$)NH;

$L_{1c}$ represents $(CH_2)_n$ (where n is an integer of 0 to 3), $CHR_5$, or $CR_6R_7$, where $R_5$ represents C1-C4 heteroalkyl having 1 to 3 heteroatoms selected from the group consisting of O, N, and S, or C1-C4 alkyl, and $R_6$ and $R_7$ are each independently C1-C4 alkyl;

$L_2$ represents $(CH_2)_o$ (where o is an integer of 0 to 3), $(CH_2)_pO$ (where p is an integer of 1 to 3), $CHR_8$, $CX_1X_2$, or C($CH_2CH_2$), where $R_8$ is OH, halogen, or C1-C3 alkyl, and $X_1$ and $X_2$ are each independently halogen;

$L_3$ represents $(CH_2)_q$ (where q is an integer of 0 to 3) or $CHR_9$, where $R_9$ is C1-C3 alkyl; and $Z_1$ and $Z_2$ are each independently OH, or together optionally form a cyclic boric acid ester of the following structure:

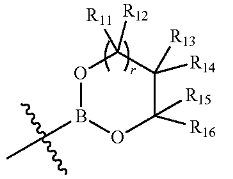

wherein r is 0 or 1, and $R_{11}$ to $R_{16}$ are each independently hydrogen, hydroxyl, substituted or unsubstituted alkyl, cycloalkyl, alkoxy, aryl, aryloxy, or heteroaryl or heterocycloalkyl containing in the ring 1 or 2 heteroatoms selected from N, O, and S atoms, or $R_{13}$ and $R_{15}$ optionally are hydrogen, and $R_{14}$ and $R_{16}$ optionally are combined together to form substituted or unsubstituted cycloalkyl, or $R_{13}$ and $R_{15}$ optionally are absent, and $R_{14}$ and $R_{16}$ optionally are combined together to form substituted or unsubstituted aryl, or $R_{11}$ and $R_{12}$, or $R_{13}$ and $R_{14}$, or $R_{15}$ and $R_{16}$ optionally are combined together to form substituted or unsubstituted cycloalkyl.

3. The compound, the pharmaceutically acceptable salt thereof, or the isomer thereof according to claim 1, wherein $R_1$ is C1-C6 alkyl, C3-C6 cycloalkyl, phenyl, 5- to 6-membered heteroaryl or heterocycloalkyl containing 1 or 2 heteroatoms selected from N, O, and S atoms, or a fused-bicyclo ring, where a substituted or unsubstituted 4- to 8-membered aliphatic ring or 5- to 6-membered aromatic ring having 0 to 4 heteroatoms selected from the group consisting of O, N, and S, is fused to a substituted or unsubstituted 4- to 8-membered aliphatic ring or 5- to 6-membered aromatic ring having 0 to 4 heteroatoms selected from the group consisting of O, N, and S, $R_1$ optionally is substituted with one or more substituents selected from the group consisting of halogen, amine, nitro, nitrile, acetonitrile, ether, halogenated alkyl, C1-C6 alkyl, C3-C6 cycloalkyl, C1-C6 heteroalkyl having 1 or 2 heteroatoms selected from N, O, and S atoms, C1-C6 alkoxy, phenyl, phenoxy, 5- to 6-membered heteroaryl or heterocycloalkyl containing 1 or 2 heteroatoms selected from N, O, and S atoms, or 5- to 6-membered heteroaryloxy or heterocycloalkyloxy containing 1 or 2 heteroatoms selected from N, O, and S atoms, and $R_{12}$ (C═O)NH, $R_{12}$ is hydrogen or C1-C3 alkyl, and the substituent is optionally be substituted with one or more selected from the group consisting of halogen, C1-C3 alkyl, and C1-C3 alkoxy, $R_2$ represents hydrogen;

$R_3$ represents hydrogen, C1-C6 alkyl, C3-C6 cycloalkyl, phenyl, or 5- to 6-membered heteroaryl containing 1 or 2 heteroatoms selected from N, O, and S atoms, or $R_2$ and $R_3$ are optionally combined with each other to form a 3- to 6-membered aliphatic ring, where $L_2$ is absent, $R_3$ optionally is substituted with halogen, methyl halide, C1-C3 alkyl, phenyl, or C1-C3 alkoxy;

$R_4$ represents C1-C6 alkyl, C3-C6 cycloalkyl, or phenyl;

$L_{1a}$ represents $(CH_2)_l$ (where l is an integer of 0 to 3) or C($CH_2CH_2$);

$L_{1b}$ is a direct linkage, or represents (C═O)NH, NH(C═O), NH, $(CH_2)_mO$ (where m is an integer of 0 to 3), (C═O)N($CH_3$), or S($O_2$)NH;

$L_{1c}$ represents $(CH_2)_n$ (where n is an integer of 0 to 3), $CHR_5$, or $CR_6R_7$, where $R_5$ represents C1-C3 heteroalkyl having 1 or 2 heteroatoms selected from the group consisting of O, N, and S, or C1-C4 alkyl, and $R_6$ and $R_7$ are each independently C1-C3 alkyl;

$L_2$ represents $(CH_2)_o$ (where o is an integer of 0 to 3), $(CH_2)_pO$ (where p is an integer of 1 to 3), $CHR_8$, $CX_1X_2$, or C($CH_2CH_2$), where $R_8$ is OH, halogen, or C1-C3 alkyl, and $X_1$ and $X_2$ are each independently halogen;

$L_3$ represents $(CH_2)_q$ (where q is an integer of 0 to 3) or $CHR_9$, where $R_9$ is C1-C3 alkyl; and $Z_1$ and $Z_2$ are each independently OH, or together optionally form a cyclic boric acid ester of the following structure:

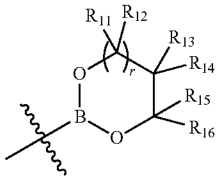

wherein r is 0 or 1, $R_{11}$ to $R_{16}$ are each independently hydrogen, hydroxyl, substituted or unsubstituted C1-C6 alkyl, C3-C6 cycloalkyl, C1-C6 alkoxy, C5-C6 aryl, C5-C6 aryloxy, heteroaryl or heterocycloalkyl containing in the ring 1 or 2 heteroatoms selected from N, O, and S atoms, where the substituent optionally is hydroxyl, C1-C6 alkyl, C3-C6 cycloalkyl, C1-C6 alkoxy, C5-C6 aryl, or C5-C6 aryloxy, or $R_{13}$ and $R_{15}$ optionally are hydrogen, and $R_{14}$ and $R_{16}$ optionally are combined together to form substituted or unsubstituted 4- to 8-membered cycloalkyl, where the substituent optionally is hydroxyl, substituted or unsubstituted C1-C6 alkyl, C3-C6 cycloalkyl, C1-C6 alkoxy, C5-C6 aryl, or C5-C6 aryloxy, or $R_{13}$ and $R_{15}$ optionally are absent, and $R_{14}$ and $R_{16}$ optionally are combined together to form substituted or unsubstituted 5- to 6-membered aryl, where the substituent optionally is hydroxyl, substituted or unsubstituted C1-C6 alkyl, C3-C6 cycloalkyl, C1-C6 alkoxy, C5-C6 aryl, or C5-C6 aryloxy, or $R_{11}$ and $R_{12}$, or $R_{13}$ and $R_{14}$, or $R_{15}$ and $R_{16}$ optionally are combined together to form substituted or unsubstituted 4- to 8-membered cycloalkyl, where the substituent optionally is hydroxyl, substituted or unsubstituted C1-C6 alkyl, C3-C6 cycloalkyl, C1-C6 alkoxy, C5-C6 aryl, or C5-C6 aryloxy.

4. The compound, the pharmaceutically acceptable salt thereof, or the isomer thereof according to claim 1, being used as an inhibitor of the chymotrypsin-like activity within the proteasome.

5. The compound, the pharmaceutically acceptable salt thereof, or the isomer thereof according to claim 1, being used for the prevention or treatment of a proteasome-mediated disease.

6. A pharmaceutical composition comprising: the compound, the pharmaceutically acceptable salt thereof, or the isomer thereof according to claim 1; and a pharmaceutically acceptable carrier.

7. A method for preventing or treating a proteasome-mediated disease, the method comprising administering the compound, the pharmaceutically acceptable salt thereof, or the isomer thereof according to claim 1 to a subject in need thereof.

8. The method according to claim 7, wherein the proteasome-mediated disease is cancer.

9. The method according to claim 8, wherein the cancer is selected from the group consisting of brain tumor, benign astrocytoma, malignant astrocytoma, pituitary adenoma, intracranial meningioma, cerebral lymphoma, oligodendroglioma, craniopharyngioma, ependymoma, brain stem tumor, head and neck tumor, laryngeal cancer, oropharyngeal cancer, nasal cavity/sinus cancer, nasopharyngeal cancer, salivary gland cancer, hypopharyngeal cancer, thyroid cancer, neuroblastoma, chest tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary tract cancer, pancreatic cancer, small intestine cancer, colorectal cancer, anal cancer, bladder cancer, kidney cancer, male genital tumor, penile cancer, urethral cancer, prostate cancer, female genital tumor, cervical cancer, endometrial cancer, ovarian cancer, uterine sarcoma, vaginal cancer, external female genital cancer, female urethral cancer, skin cancer, myeloma, leukemia, lymphoma, and malignant lymphoma.

10. The method according to claim 7, wherein the preventing or treating a proteasome-mediated disease is inhibiting chymotrypsin-like activity within proteasome.

11. A pharmaceutical composition comprising: the compound, the pharmaceutically acceptable salt thereof, or the isomer thereof according to claim 2; and a pharmaceutically acceptable carrier.

12. A pharmaceutical composition comprising: the compound, the pharmaceutically acceptable salt thereof, or the isomer thereof according to claim 3; and a pharmaceutically acceptable carrier.

13. A method for preventing or treating a proteasome-mediated disease, the method comprising administering the compound, the pharmaceutically acceptable salt thereof, or the isomer thereof according to claim 2 to a subject in need thereof.

14. A method for preventing or treating a proteasome-mediated disease, the method comprising administering the compound, the pharmaceutically acceptable salt thereof, or the isomer thereof according to claim 3 to a subject in need thereof.

15. The method according to claim 13, wherein the proteasome-mediated disease is cancer.

16. The method according to claim 15, wherein the cancer is selected from the group consisting of brain tumor, benign astrocytoma, malignant astrocytoma, pituitary adenoma, intracranial meningioma, cerebral lymphoma, oligodendroglioma, craniopharyngioma, ependymoma, brain stem tumor, head and neck tumor, laryngeal cancer, oropharyngeal cancer, nasal cavity/sinus cancer, nasopharyngeal cancer, salivary gland cancer, hypopharyngeal cancer, thyroid cancer, neuroblastoma, chest tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary tract cancer, pancreatic cancer, small intestine cancer, colorectal cancer, anal cancer, bladder cancer, kidney cancer, male genital tumor, penile cancer, urethral cancer, prostate cancer, female genital tumor, cervical cancer, endometrial cancer, ovarian cancer, uterine sarcoma, vaginal cancer, external female genital cancer, female urethral cancer, skin cancer, myeloma, leukemia, lymphoma, and malignant lymphoma.

17. The method according to claim 14, wherein the proteasome-mediated disease is cancer.

18. The method according to claim 17, wherein the cancer is selected from the group consisting of brain tumor, benign astrocytoma, malignant astrocytoma, pituitary adenoma, intracranial meningioma, cerebral lymphoma, oligodendroglioma, craniopharyngioma, ependymoma, brain stem tumor, head and neck tumor, laryngeal cancer, oropharyngeal cancer, nasal cavity/sinus cancer, nasopharyngeal cancer, salivary gland cancer, hypopharyngeal cancer, thyroid cancer, neuroblastoma, chest tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary tract cancer, pancreatic cancer, small intestine cancer, colorectal cancer, anal cancer, bladder cancer, kidney cancer, male genital tumor, penile cancer, urethral cancer, prostate cancer, female genital tumor, cervical cancer, endometrial cancer, ovarian cancer, uterine sarcoma, vaginal cancer, external female genital cancer, female urethral cancer, skin cancer, myeloma, leukemia, lymphoma, and malignant lymphoma.

* * * * *